US011591619B2

(12) United States Patent
Jooss et al.

(10) Patent No.: US 11,591,619 B2
(45) Date of Patent: Feb. 28, 2023

(54) MODIFIED ADENOVIRUSES

(71) Applicant: Gritstone bio, Inc., Emeryville, CA (US)

(72) Inventors: Karin Jooss, Emeryville, CA (US); Ciaran Daniel Scallan, Emeryville, CA (US); Leonid Gitlin, Foster City, CA (US)

(73) Assignee: GRITSTONE BIO, INC., Emeryville, CA (US)

( * ) Notice: Subject to any disclaimer, the term of this patent is extended or adjusted under 35 U.S.C. 154(b) by 0 days.

(21) Appl. No.: 17/538,716

(22) Filed: Nov. 30, 2021

(65) Prior Publication Data

US 2022/0090138 A1 Mar. 24, 2022

Related U.S. Application Data

(63) Continuation of application No. PCT/US2020/035591, filed on Jun. 1, 2020.

(60) Provisional application No. 62/854,865, filed on May 30, 2019.

(51) Int. Cl.

| | |
|---|---|
| ***C12N 15/86*** | (2006.01) |
| ***A61P 37/04*** | (2006.01) |
| ***A61P 35/00*** | (2006.01) |
| ***A61K 39/00*** | (2006.01) |
| ***A61K 39/395*** | (2006.01) |
| ***C07K 14/74*** | (2006.01) |
| ***A61K 38/00*** | (2006.01) |

(52) U.S. Cl.

CPC ...... *C12N 15/86* (2013.01); *A61K 39/001114* (2018.08); *A61K 39/3955* (2013.01); *A61P 35/00* (2018.01); *A61P 37/04* (2018.01); *C07K 14/70539* (2013.01); *A61K 38/00* (2013.01); *C12N 2710/10343* (2013.01); *C12N 2710/10352* (2013.01); *C12N 2710/10371* (2013.01); *C12N 2830/006* (2013.01); *C12N 2830/50* (2013.01); *C12N 2840/203* (2013.01)

(58) Field of Classification Search

CPC .......... C12N 15/86; C12N 2710/10343; C12N 2710/10352; C12N 2710/10371; C12N 2830/006; C12N 2830/50; C12N 2840/203; C12N 2710/10334; C12N 2830/003; A61K 39/001114; A61K 39/3955; A61K 38/00; A61K 39/00; A61K 39/0011; A61K 2039/5256; A61K 39/001189; A61P 35/00; A61P 37/04; A61P 37/00; C07K 14/70539; C07K 14/005

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,656,127 | A | 4/1987 | Mundy |
| 4,722,848 | A | 2/1988 | Paoletti et al. |
| 4,837,028 | A | 6/1989 | Allen |
| 5,019,369 | A | 5/1991 | Presant et al. |
| 5,204,253 | A | 4/1993 | Sanford et al. |
| 5,217,879 | A | 6/1993 | Huang et al. |
| 5,279,833 | A | 1/1994 | Rose |
| 5,505,947 | A | 4/1996 | Johnston et al. |
| 5,580,859 | A | 12/1996 | Felgner et al. |
| 5,589,466 | A | 12/1996 | Felgner et al. |
| 5,622,931 | A | 4/1997 | Edgington et al. |
| 5,643,576 | A | 7/1997 | Johnston et al. |
| 5,662,907 | A | 9/1997 | Kubo et al. |
| 5,814,482 | A | 9/1998 | Dubensky, Jr. et al. |
| 5,843,723 | A | 12/1998 | Dubensky, Jr. et al. |
| 5,849,561 | A | 12/1998 | Falck-Pedersen |
| 5,849,589 | A | 12/1998 | Tedder et al. |
| 5,851,796 | A | 12/1998 | Schatz |
| 6,015,686 | A | 1/2000 | Dubensky, Jr. et al. |
| 6,037,135 | A | 3/2000 | Kubo et al. |
| 6,083,716 | A | 7/2000 | Wilson et al. |
| 6,090,406 | A | 7/2000 | Popescu et al. |
| 6,296,854 | B1 | 10/2001 | Pushko et al. |
| 6,312,946 | B1 | 11/2001 | Yeh et al. |
| 6,365,394 | B1 | 4/2002 | Gao et al. |
| 6,376,236 | B1 | 4/2002 | Dubensky, Jr. et al. |
| 6,413,935 | B1 | 7/2002 | Sette et al. |
| 6,531,135 | B1 | 3/2003 | Johnston et al. |
| 6,610,321 | B2 | 8/2003 | Huang et al. |
| 6,770,283 | B1 | 8/2004 | Garoff et al. |
| 6,783,939 | B2 | 8/2004 | Olmsted et al. |
| 7,078,218 | B2 | 7/2006 | Smith et al. |
| 7,202,351 | B1 | 4/2007 | Sette et al. |
| 7,283,337 | B2 | 10/2007 | Sakai et al. |

(Continued)

FOREIGN PATENT DOCUMENTS

| | | | |
|---|---|---|---|
| CA | 2705787 | A1 | 6/2009 |
| CN | 101579528 | A | 11/2009 |

(Continued)

OTHER PUBLICATIONS

Alvira MR. .Simian adenovirus 25, complete genome. GenBank: AF394196.1; Dep. Nov. 27, 2001. (Year: 2001).*

(Continued)

*Primary Examiner* — Rachel B Gill

(74) *Attorney, Agent, or Firm* — Goodwin Procter LLP

(57) ABSTRACT

Compositions include modified adenoviruses. Nucleotides, cells, and methods associated with the compositions, including their use as vaccines. Viral vectors using a TET promoter system and methods of producing viruses having the same.

41 Claims, 65 Drawing Sheets

Specification includes a Sequence Listing.

(56) References Cited

U.S. PATENT DOCUMENTS 7,285,265 B2 10/2007 Vogels et al.
7,291,498 B2 11/2007 Roy et al.
7,344,872 B2 3/2008 Gao et al.
7,468,181 B2 12/2008 Vogels et al.
7,531,180 B2 5/2009 Polo et al.
7,541,038 B2 6/2009 Kovacs et al.
7,557,200 B2 7/2009 Wu et al.
7,572,453 B2 8/2009 Polo et al.
7,572,628 B2 8/2009 Dubensky, Jr. et al.
7,605,235 B2 10/2009 Anderson et al.
7,732,129 B1 6/2010 Zhang et al.
7,744,900 B2 6/2010 Dubensky, Jr. et al.
7,771,979 B2 8/2010 Polo et al.
7,820,440 B2 10/2010 Vogels et al.
7,820,441 B2 10/2010 Chamberlain et al.
7,838,277 B2 11/2010 Gao et al.
7,850,977 B2 12/2010 Kamrud et al.
7,888,472 B2 2/2011 Sette et al.
8,052,967 B2 11/2011 Vogels et al.
8,093,021 B2 1/2012 Hurtado et al.
8,119,336 B2 2/2012 Sampath et al.
8,158,418 B2 4/2012 Polo et al.
8,216,834 B2 7/2012 Colloca et al.
8,252,574 B2 8/2012 Mason et al.
8,426,188 B2 4/2013 Weaver et al.
8,460,913 B2 6/2013 Kamrud et al.
8,614,082 B2 12/2013 Frolov et al.
8,617,533 B2 12/2013 Smith et al.
8,637,313 B2 1/2014 Chamberlain et al.
8,647,864 B2 2/2014 Polo et al.
8,673,319 B2 3/2014 Colloca et al.
8,680,258 B2 3/2014 Coffield et al.
8,691,563 B2 4/2014 Pushko et al.
8,722,044 B2 5/2014 Almagro et al.
8,951,525 B2 2/2015 Almagro et al.
8,961,995 B2 2/2015 Frolov et al.
8,999,333 B2 4/2015 Almagro et al.
9,017,696 B2 4/2015 Draper et al.
9,024,001 B2 5/2015 Tang et al.
9,101,572 B2 8/2015 Pushko et al.
9,115,402 B2 8/2015 Hacohen et al.
9,192,661 B2 11/2015 Jain et al.
9,217,159 B2 12/2015 Roy et al.
9,234,181 B2 1/2016 Tang et al.
9,249,191 B2 2/2016 Ueno et al.
9,254,265 B2 2/2016 Geall et al.
9,255,126 B2 2/2016 Polo et al.
9,273,288 B2 3/2016 Mason et al.
9,295,646 B2 3/2016 Brito et al.
9,340,830 B2 5/2016 Lipson et al.
9,353,353 B2 5/2016 Nabel et al.
9,402,888 B2 8/2016 Ertl et al.
9,416,370 B2 8/2016 Smith et al.
9,453,240 B2 9/2016 Chamberlain et al.
9,486,519 B2 11/2016 Sahin et al.
9,487,563 B2 11/2016 Nabel et al.
9,512,190 B2 12/2016 Ueno et al.
9,580,690 B2 2/2017 Weaver et al.
9,714,435 B2 7/2017 Dicks et al.
9,770,463 B2 9/2017 Geall et al.
9,795,668 B2 10/2017 Jain et al.
9,801,897 B2 10/2017 Geall et al.
10,092,636 B2 10/2018 Binder
10,238,733 B2 3/2019 Brito et al.
10,240,128 B2 3/2019 Thirion et al.
10,487,332 B2 11/2019 Geall
10,532,067 B2 1/2020 Geall et al.
2002/0065241 A1 5/2002 Shankara
2002/0119127 A1 8/2002 Sette et al.
2002/0137081 A1 9/2002 Bandman
2003/0044774 A1 3/2003 Valenzuela et al.
2003/0072767 A1 4/2003 Gaiger et al.
2003/0148262 A1 8/2003 Polo et al.
2004/0037843 A1 2/2004 Fikes et al.
2004/0115625 A1 6/2004 Ebner
2004/0248113 A1 12/2004 Sette et al.
2005/0003505 A1 1/2005 Marasco et al.
2005/0123555 A1 6/2005 Olmsted et al.
2005/0196754 A1 9/2005 Drmanac et al.
2005/0271676 A1 12/2005 Sette et al.
2006/0051405 A1 3/2006 MacLachlan et al.
2006/0093623 A1 5/2006 Andrieu et al.
2006/0198854 A1 9/2006 Pushko
2006/0252077 A1 11/2006 Buzby
2006/0292175 A1 12/2006 Polo et al.
2007/0031442 A1 2/2007 Sewell
2007/0055049 A1 3/2007 Grey et al.
2007/0224201 A1 9/2007 Wu et al.
2007/0231347 A1 10/2007 Wilson et al.
2008/0050393 A1 2/2008 Tang et al.
2008/0206837 A1 8/2008 Vogels et al.
2008/0241189 A1 10/2008 Wilson
2009/0075384 A1 3/2009 Kamrud et al.
2009/0081200 A1 3/2009 Wang
2009/0093050 A1 4/2009 Wu et al.
2009/0118181 A1 5/2009 Walker et al.
2009/0253184 A1 10/2009 Clarke et al.
2009/0305344 A1 12/2009 Polo et al.
2010/0041737 A1 2/2010 Naldini et al.
2010/0068218 A1 3/2010 Sette et al.
2010/0120897 A1 5/2010 Hurtado et al.
2010/0183665 A1 7/2010 Kamrud et al.
2010/0286070 A1 11/2010 Verheyden et al.
2010/0330121 A1 12/2010 Dubensky, Jr. et al.
2011/0052634 A1 3/2011 Weaver et al.
2011/0091496 A1 4/2011 Graham et al.
2011/0129498 A1 6/2011 Cortese et al.
2011/0142880 A1 6/2011 Lemiale et al.
2011/0217332 A1 9/2011 Colloca et al.
2011/0293637 A1 12/2011 Hacohen et al.
2012/0027788 A1* 2/2012 Colloca ................ C12N 15/861 435/235.1
2012/0258126 A1 10/2012 Scholler et al.
2012/0282290 A1 11/2012 Spencer et al.
2012/0328651 A1 12/2012 Colloca et al.
2013/0011426 A1 1/2013 Tureci et al.
2013/0123199 A1 5/2013 Lee
2013/0149375 A1 6/2013 Geall
2013/0171241 A1 7/2013 Geall
2013/0177639 A1 7/2013 Geall et al.
2013/0177640 A1 7/2013 Geall et al.
2013/0189351 A1 7/2013 Geall
2013/0195968 A1 8/2013 Geall et al.
2013/0195969 A1 8/2013 Geall et al.
2013/0202684 A1 8/2013 Geall et al.
2014/0010841 A1 1/2014 Weaver et al.
2014/0141070 A1 5/2014 Geall et al.
2014/0178438 A1 6/2014 Sahin et al.
2014/0227346 A1 8/2014 Geall et al.
2014/0234304 A1 8/2014 Almagro et al.
2014/0242152 A1 8/2014 Geall et al.
2014/0248314 A1 9/2014 Swanson et al.
2014/0255472 A1 9/2014 Geall et al.
2014/0271724 A1 9/2014 Ertl et al.
2014/0271829 A1 9/2014 Lilja et al.
2015/0001108 A1 1/2015 Lee et al.
2015/0110831 A1 4/2015 Gilbert et al.
2015/0125465 A1 5/2015 Binder et al.
2015/0125477 A1 5/2015 Kuttruff-Coqui et al.
2015/0140068 A1 5/2015 Barnett et al.
2015/0167003 A1 6/2015 Naldini et al.
2015/0307897 A1 10/2015 Soden et al.
2016/0008447 A1 1/2016 Hacohen et al.
2016/0074506 A1 3/2016 Jain et al.
2016/0101170 A1 4/2016 Hacohen et al.
2016/0199513 A1 7/2016 Bancel et al.
2016/0289674 A1 10/2016 Bancel et al.
2016/0331822 A1 11/2016 Hacohen et al.
2016/0339090 A1 11/2016 Hacohen et al.
2016/0354409 A1 12/2016 Wang et al.
2017/0028044 A1 2/2017 Soon-Shiong et al.
2017/0212984 A1 7/2017 Yelensky et al.
2017/0340721 A1 11/2017 Volkmann et al.
2018/0000913 A1 1/2018 Hacohen et al.

(56) References Cited

U.S. PATENT DOCUMENTS

2018/0050059 A1 2/2018 Geall et al.
2018/0055922 A1 3/2018 Hacohen et al.
2018/0153975 A1 6/2018 Fritsch et al.
2018/0363066 A1 12/2018 Chalmers et al.
2019/0025308 A1 1/2019 Cummings et al.
2019/0060432 A1 2/2019 Hacohen et al.
2019/0134184 A1 5/2019 Yu et al.
2019/0256924 A1 8/2019 Vogelstein et al.
2019/0270766 A1 9/2019 Hogrefe et al.
2020/0010849 A1 1/2020 Blair et al.
2020/0197500 A1 6/2020 Blair et al.
2021/0213122 A1 7/2021 Blair et al.
2022/0125919 A1 4/2022 Jooss et al.
2022/0226453 A1 7/2022 Blair et al.
2022/0265797 A1 8/2022 Jooss et al.

FOREIGN PATENT DOCUMENTS

EP 1585812 A2 10/2005
EP 2044947 A1 4/2009
EP 2370584 A1 10/2011
EP 2590670 A2 5/2013
EP 2590676 A2 5/2013
EP 2917353 A1 9/2015
EP 2947149 A1 11/2015
FR 2650840 A1 2/1991
JP 2007-534295 A 11/2007
JP 2011-504724 A 2/2011
JP 2014-209917 A 11/2014
KR 20060017635 A 2/2006
RU 2206329 C2 6/2003
WO 1991/02087 A1 2/1991
WO 1991/06309 A1 5/1991
WO 1992/15712 A1 9/1992
WO 1993/24640 A2 12/1993
WO 1995/07994 A2 3/1995
WO 1995/13392 A1 5/1995
WO 1996/13597 A2 5/1996
WO 1996/18373 A1 6/1996
WO 1997/41241 A1 11/1997
WO 2000/018433 A2 4/2000
WO 2001/055177 A2 8/2001
WO 2001/073027 A2 10/2001
WO 2004/023973 A2 3/2004
WO 2004/055166 A2 7/2004
WO 2005/016961 A1 2/2005
WO 2005/033265 A2 4/2005
WO 2005/071093 A2 8/2005
WO 2006/078294 A2 7/2006
WO 2006/090090 A2 8/2006
WO 2007/024708 A2 3/2007
WO 2007/047749 A1 4/2007
WO 2008/122811 A2 10/2008
WO 2008/145685 A1 12/2008
WO 2009/079185 A2 6/2009
WO 2011/128704 A1 10/2011
WO 2011/143656 A2 11/2011
WO 2012/006359 A1 1/2012
WO 2012/006377 A2 1/2012
WO 2012/006376 A3 4/2012
WO 2012/172058 A1 12/2012
WO 2012/172277 A1 12/2012
WO 2014/072929 A1 5/2014
WO 2014/168874 A2 10/2014
WO 2015/085233 A1 6/2015
WO 2015/095811 A2 6/2015
WO 2016/085904 A1 6/2016
WO 2016/100975 A1 6/2016
WO 2016/100977 A1 6/2016
WO 2016/122414 A1 8/2016
WO 2016/124670 A1 8/2016
WO 2016/154047 A2 9/2016
WO 2016/154246 A1 9/2016
WO 2016/187508 A3 1/2017
WO 2017/106638 A1 6/2017
WO 2017/151940 A2 9/2017
WO 2017/173321 A1 10/2017
WO 2017/184590 A1 10/2017
WO 2017/192924 A1 11/2017
WO 2017/220463 A1 12/2017
WO 2018/028438 A1 2/2018
WO 2018/039131 A1 3/2018
WO 2018/098362 A1 5/2018
WO 2018/102585 A1 6/2018
WO 2018/104911 A1 6/2018
WO 2018/116193 A1 6/2018
WO 2018/119115 A1 6/2018
WO 2018/187356 A2 10/2018
WO 2018/208856 A1 11/2018
WO 2018/227030 A1 12/2018
WO 2018/232330 A1 12/2018
WO 2019/090156 A1 5/2019
WO 2019/170773 A1 9/2019
WO 2019/226939 A1 11/2019
WO 2019/226941 A1 11/2019
WO 2020/097393 A1 5/2020
WO 2021/003348 A1 1/2021
WO 2021/092095 A1 5/2021
WO 2021/119545 A1 6/2021
WO 2021/142437 A1 7/2021
WO 2021216775 A2 10/2021
WO 2022/032196 A2 2/2022

OTHER PUBLICATIONS

Sakuma et al., "Lentiviral vectors: basic to translational," Biochemical Journal 443, No. 3 (2012): 603-618.

Cooper et al., "Rescue of splicing-mediated intron loss maximizes expression in lentiviral vectors containing the human ubiquitin C promoter," Nucleic Acids Research vol. 43, No. 1, pp. 682-690, Dec. 17, 2014.

Zufferey et al., "Self-Inactivating Lentivirus Vector for Safe and Efficient In Vivo Gene Delivery," Journal of Virology vol. 72, No. 12, pp. 9873-9880, 1998.

Gros et al., "Prospective identification of neoantigen-specific lymphocytes in the peripheral blood of melanoma patients," Nature Medicine vol. 22, Issue 4, pp. 433-438, Feb. 22, 2016.

Strønen et al., "Targeting of cancer neoantigens with donor-derived T cell receptor repertoires," Science 352, No. 6291 (May 19, 2016): 1337-1341.

Lu et al., "Efficient identification of mutated cancer antigens recognized by T cells associated with durable tumor regressions," Clinical Cancer Research vol. 20, No. 13, pp. 3401-3410, 2014.

Stover et al., "New use of BCG for recombinant vaccines," Nature vol. 351, No. 6326, pp. 456-460, 1991.

Boshart et al., "A Very Strong Enhancer is Located Upstream of an Immediate Early Gene of Human Cytomegalovirus," Cell vol. 41, No. 2, 521-530, 1985.

Kost et al., "The nucleotide sequence of the chick cytoplasmic b-actin gene," Nucleic Acids Research vol. 11, No. 23, pp. 8287-8301,1983.

Shukla et al., "Comprehensive analysis of cancer-associated somatic mutations in class I HLA genes," Nature Biotechnology vol. 33, No. 11. pp. 1152-1158, Nov. 2015.

McGranahan et al., "Allele-specific HLA loss and immune escape in lung cancer evolution," Cell vol. 171, No. 6, pp. 1259-1271, 2017.

Van Loo et al., "Allele-specific copy number analysis of tumors," Proceedings of the National Academy of Sciences, vol. 107, No. 39, pp. 16910-16915, 2010.

Desrichard et al., "Cancer neoantigens and applications for immunotherapy," Clinical Cancer Research vol. 22, No. 4, pp. 807-812, Feb. 15, 2016.

Gubin et al., "Tumor neoantigens: Building a framework for personalized cancer immunotherapy," The Journal of Clinical Investigation, vol. 125, No. 9, pp. 3413-3421, Sep. 2015.

Rizvi et al., "Mutational landscape determines sensitivity to PD-1 blockade in non-small cell lung cancer," Science vol. 348, No. p. 6230, Apr. 3, 2015.

(56) References Cited

OTHER PUBLICATIONS

Snyder et al., "Genetic Basis for Clinical Response to CTLA-4 Blockade in Melanoma," New England Journal of Medicine, vol. 371, No. 23, pp. 2189-2199, 2014.
Carreno et al., "A dendritic cell vaccine increases the breadth and diversity of melanoma neoantigen-specific T cells." Science 348, No. 6236 (Apr. 2, 2015): 9 pages.
Tran et al., "Cancer Immunotherapy Based on Mutation-Specific CD4+ T Cells in a Patient with Epithelial Cancer," Science vol. 344, No. 6184, pp. 641-645, 2014.
Lundegaard et al., "State of the art and challenges in sequence based T-cell epitope prediction," Immunome Research vol. 6, No. 2, pp. 1-14, 2010.
Yadav et al., "Predicting immunogenic tumour mutations by combining mass spectrometry and exome sequencing," Nature, vol. 515, No. 7528, pp. 572-576, 2014.
Bassani-Sternberg et al., "Mass Spectrometry of Human Leukocyte Antigen Class I Peptidomes Reveals Strong Effects of Protein Abundance and Turnover on Antigen Presentation," Molecular & Cellular Proteomics Vo. 14, Issue 3, 658-673, Mar. 1, 2015.
Van Allen et al., "Genomic correlates of response to CTLA-4 blockade in metastatic melanoma," Science vol. 350, No. 6257, pp. 207-211, Nov. 11, 2015.
Yoshida et al., "Splicing factor mutations and cancer," Wiley Interdisciplinary Reviews: RNA 5, No. 4 (2014): 445-459.
Cancer Genome Atlas Research Network, "Comprehensive molecular profiling of lung adenocarcinoma," Nature, vol. 511, pp. 543-550, 2014.
Rajasagi et al., "Systematic identification of personal tumor-specific neoantigens in chronic lymphocytic leukemia," Blood, vol. 124, No. 3, pp. 453-462, 2014.
Cieslik et al., "The use of exome capture RNA-seq for highly degraded RNA with application to clinical cancer sequencing," Genome Research vol. 25, No. 9, 1372-1381, Sep. 1, 2015.
Bodini et al., "The hidden genomic landscape of acute myeloid leukemia: subclonal structure revealed by undetected mutations," Blood, The Journal of the American Society of Hematology vol. 125, No. 4 (Jan. 22, 2015): 600-605.
Saunders et al., Strelka: accurate somatic small-variant calling from sequenced tumor-normal sample pairs, Bioinformatics vol. 28, No. 14, pp. 1811-1817, 2012.
Cibulskis et al., "Sensitive detection of somatic point mutations in impure and heterogeneous cancer samples," Nature Biotechnology vol. 31, No. 3, pp. 213-219, 2013.
Wilkerson et al., "Integrated RNA and DNA sequencing improves mutation detection in low purity tumors," Nucleic Acids Research, vol. 42, p. e107, 2014.
Mose et al., "ABRA: improved coding indel detection via assembly-based realignment," Bioinformatics, vol. 30, No. 19, pp. 2813-2815, 2014.
Ye et al., "Pindel: a pattern growth approach to detect break points of large deletions and medium sized insertions from paired-end short reads," Bioinformatics vol. 25, No. 21, pp. 2865-2871, 2009.
Lam et al., "Nucleotide-resolution analysis of structural variants using BreakSeq and a breakpoint library," Nature Biotechnology vol. 28, No. 1, pp. 47-55 2010.
Frampton et al., "Development and validation of a clinical cancer genomic profiling test based on massively parallel DNA sequencing," Nature Biotechnology vol. 31, No. 11, 2013.
Boegel et al., "HLA typing from RNA-Seq sequence reads," Genome Medicine vol. 4, Issue 12, 2013.
Liu et al., "ATHLATES: accurate typing of human leukocyte antigen through exome sequencing," Nucleic Acids Research vol. 41, No. 14, 2013.
Mayor et al., "HLA typing for the next generation," PLoS One vol. 10, No. 5, May 27, 2015.
Roy et al., "Assessing long-distance RNA sequence connectivity via RNA-templated DNA-DNA ligation," Elife vol. 4, p. e03700, Apr. 13, 2015.
Song et al., "CLASS: constrained transcript assembly of RNA-seq reads," BMC Bioinformatics, vol. 14, Supp. 5, S14, BioMed Central, 2013.
Maretty et al. "Bayesian transcriptome assembly," Genome Biology vol. 15, No. 10, Oct. 2014.
Pertea et al., "StringTie enables improved reconstruction of a transcriptome from RNA-seq reads," Nature Biotechnology vol. 33, No. 3, pp. 290-295, Mar. 2015.
Roberts et al., "Identification of novel transcripts in annotated genomes using RNA-Seq," Bioinformatics vol. 27, No. 17, pp. 2325-2329, 2011.
Vitting-Seerup et al., "spliceR: an R package for classification of alternative splicing and prediction of coding potential from RNA-seq data," BMC Bioinformatics, vol. 15, Issue 1, pp. 1-7, 2014.
Skelly et al., "A powerful and flexible statistical framework for testing hypotheses of allele-specific gene expression from RNA-seq data," Genome Research vol. 21, No. 10, pp. 1728-1737, 2011.
Anders et al., "HTSeq-a Python framework to work with high-throughput sequencing data." Bioinformatics vol. 31, No. 2 (Jan. 15, 2015): 166-169.
Furney et al., "SF3B1 Mutations are Associated with Alternative Splicing in Uveal Melanoma," Cancer Discovery vol. 3, Issue 10, pp. 1122-1129, 2013.
Zhou et al., "A Chemical Genetics Approach for the Functional Assessment of Novel Cancer Genes," Cancer Research vol. 75, No. 10, pp. 1949-1958, May 15, 2015.
Maguire et al., "SF3B1 mutations constitute a novel therapeutic target in breast cancer," The Journal of Pathology vol. 235, No. 4 pp. 571-580, Mar. 2015.
Carithers et al., "A Novel Approach to High-Quality Postmortem Tissue Procurement: The GTEx Project," Biopreservation and Biobanking, vol. 13, No. 5, 311-319, Oct. 1, 2015.
Xu et al., "RNA CoMPASS: A Dual Approach for Pathogen and Host Transcriptome Analysis of RNA-Seq Datasets," PloS One, vol. 9, Issue 2, p. e89445, 2014.
PCT/US2020/035591—International Preliminary Report on Patentability, dated Nov. 16, 2021.
Nezafat et al., "A novel multi-epitope peptide vaccine against cancer: an in silico approach." Journal of theoretical biology 349 (2014): 121-134.
Mohammed et al., "Phosphorylation-dependent interaction between antigenic peptides and MHC class I: a molecular basis for the presentation of transformed self" Nature immunology 9, No. 11 (2008): 1236-1243.
Toes et al., "Protective anti-tumor immunity induced by vaccination with recombinant adenoviruses encoding multiple tumor-associated cytotoxic T lymphocyte epitopes in a string-of-beads fashion." Proceedings of the National Academy of Sciences 94, No. 26 (1997): 14660-14665.
Wei et al., "Dendritic cells expressing a combined PADRE/MUC4-derived polyepitope DNA vaccine induce multiple cytotoxic T-cell responses." Cancer biotherapy & radiopharmaceuticals 23, No. 1 (2008): 121-128.
Meko'o et al., "Immunopreventive effects against murine H22 hepatocellular carcinoma in vivo by a DNA vaccine targeting a gastrin-releasing peptide." Asian Pacific Journal of Cancer Prevention 15, No. 20 (2014): 9039-9043.
Huang et al., "DNA vaccines for cervical cancer." American journal of translational research 2, No. 1 (2010): 75, 13 pages.
Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs," Molecular Pharmaceutics 12 (11) ( ): 3986-3998, Nov. 2, 2015.
Koizume et al., "Tissue Factor—Factor VII Complex as a Key Regulator of Ovarian Cancer Phenotypes," Biomarkers in Cancer vol. 7, pp. 1-13, Aug. 5, 2015.
Schumacher et al., "Neoantigens in cancer immunotherapy," Science vol. 348, Issue 6230, pp. 69-74, Apr. 3, 2015.
Rivas et al., "Effect of predicted protein-truncating genetic variants on the human transcriptome," Science vol. 348, No. 6235, pp. 666-669, May 8, 2015.

(56) References Cited

OTHER PUBLICATIONS

Andreatta et al., "Gapped sequence alignment using artificial neural networks: application to the MHC class I system," Bioinformatics 1 (Feb. 15, 2015): 7 pages.
Jørgensen et al., "NETMHCSTAB-predicting stability of peptide—MHC-I complexes; impacts for cytotoxic T lymphocyte epitope discovery," Immunology vol. 141, No. 1, pp. 18-26, 2014.
Larsen et al., "An integrative approach to CTL epitope prediction: a combined algorithm integrating MHC class I binding, TAP transport efficiency, and proteasomal cleavage predictions," European Journal of Immunology, vol. 35, No. 8, pp. 2295-2303, 2005.
Nielsen et al., "The role of the proteasome in generating cytotoxic T-cell epitopes: insights obtained from improved predictions of proteasomal cleavage," Immunogenetics vol. 57, No. 1-2, pp. 33-41, 2005.
Boisvert et al., "A Quantitative Spatial Proteomics Analysis of Proteome Turnover in Human Cells," Molecular & Cellular Proteomics, vol. 11, Issue. 3, Mar. 1, 2012.
Duan et al., "Genomic and bioinformatic profiling of mutational neoepitopes reveals new rules to predict anticancer immunogenicity," Journal of Experimental Medicine vol. 211, No. 11, Oct. 20, 2014.
Calis et al., "Properties of MHC Class I Presented Peptides That enhance immunogenicity." PLoS Comput Biol. vol. 9, Issue 10 (Oct. 24, 2013): e1003266, 13 pages.
Zhang et al., "Intra-tumor Heterogeneity in Localized Lung Adenocarcinomas Delineated by Multi-region Sequencing," Science vol. 346, No. 6206, pp. 256-259, 2014.
Walter et al., "Clonal Architecture of Secondary Acute Myeloid Leukemia," New England Journal of Medicine, vol. 366, Issue 12, pp. 1090-1098, 2012.
Hunt et al., "Characterization of Peptides Bound to the Class I MHC Molecule HLA-A2. 1 by Mass Spectrometry," Science vol. 255, pp. 1261-1263, 1992.
Zarling et al., "Identification of class I MHC-associated phosphopeptides as targets for cancer immunotherapy," Proceedings of the National Academy of Sciences, vol. 103, No. 40, pp. 14889-14894, 2006.
Abelin et al., "Complementary IMAC enrichment methods for HLA-associated phosphopeptide identification by mass spectrometry," Nature Protocols 10(9) (2015): 1308-1318.
Barnstable et al., "Production of Monoclonal Antibodies to Group A Erythrocytes, HLA and Other Human Cell Surface Antigens—New Tools for Genetic Analysis," Cell vol. 14, 9-20, 1978.
Goldman et al, "HLA-DA monoclonal antibodies inhibit the proliferation of normal and chronic granulocytic leukaemia myeloid progenitor cell," British Journal of Haematology 52, No. 3 (1982): 411-420.
Eng et al., "Comet: An open-source MS/MS sequence database search tool," Proteomics vol. 13, No. 1, pp. 22-24, 2013.
Eng et al., "A Deeper Look into Comet—Implementation and Features," Journal of the American Society for Mass Spectrometry vol. 26, No. 11, pp. 1865-1874, 2015.
Käll et al., "Semi-supervised learning for peptide identification from shotgun proteomics datasets," Nature Methods vol. 4, No. 11, pp. 923-925, 2007.
Käll et al., "Assigning Significance to Peptides Identified by Tandem Mass Spectrometry Using Decoy Databases," Journal of Proteome Research vol. 7, No. 01, pp. 29-34, 2008.
Käll et al., "Non-parametric estimation of posterior error probabilities associated with peptides identified by tandem mass spectrometry," Bioinformatics vol. 24, No. 16, pp. i42-i48, 2008.
Kinney et al., "Nucleotide sequence of the 26 S mRNA of the virulent Trinidad donkey strain of Venezuelan equine encephalitis virus and deduced sequence of the encoded structural proteins," Virology 152, No. 2 (1986): 400-413.
Slansky et al., "Enhanced Antigen-Specific Antitumor Immunity with Altered Peptide Ligands that Stabilize the MHC-Peptide-TCR Complex," Immunity vol. 13, No. 4, pp. 529-538, 2000.
Huang et al., "The immunodominant major histocompatibility complex class I-restricted antigen of a murine colon tumor derives from an endogenous retroviral gene product," Proceedings of the National Academy of Sciences vol. 93, No. 18, pp. 9730-9735, 1996.
Johnson et al., "Molecular Determinants of Alphavirus Neurovirulence: Nucleotide and Deduced Protein Sequence Changes during Attenuation of Venezuelan Equine Encephalitis Virus," Journal of General Virology vol. 67, Issue 9, pp. 1951-1960, 1986.
Aarnoudse et al., "TCR Reconstitution in Jurkat Reporter Cells Facilitates the Identification of Novel Tumor Antigens by CDNA Expression Cloning," International Journal of Vancer 99, 7013 (2002).
Alexander et al., "Development of High Potency Universal DR-Restricted Helper Epitopes by Modification of High Affinity DR-Blocking Peptides." Immunity vol. 1, Issue 9 (1994): 751-761.
Banu et al., "Building and Optimizing a Virus-specific T Cell Receptor Library for Targeted Immunotherapy in Viral Infections." Scientific Reports vol. 4, pp. 4166, 2014.
Cornet et al., "Optimal organization of a polypeptide-based candidate cancer vaccine composed of cryptic tumor peptides with enhanced immunogenicity," Vaccine vol. 24, No. 12, pp. 2102-2109, 2006.
Depla et al., "Rational Design of a Multiepitope Vaccine Encoding T-Lymphocyte Epitopes for Treatment of Chronic Hepatitis B Virus Infections," Journal of Virology vol. 82, No. 1, pp. 435-450, 2008.
Ishioka et al., "Utilization of MHC Class I Transgenic Mice for Development of Minigene DNA Vaccines Encoding Multiple HLA-Restricted CTL Epitopes," The Journal of Immunology vol. 162, No. 7, pp. 3915-3925, 1999.
Janetzki et al., "Guidelines for the automated evaluation of Elispot assays," Nature Protocols vol. 10, No. 7, pp. 1098-1115, Jul. 2015.
Lyons et al., "Influence of Human CD8 on Antigen Recognition by T-Cell Receptor-Transduced Cells," Cancer Research vol. 66, No. 23, pp. 11455-11461, 2006.
Nagai et al., "Aurora kinase A-specific T-cell receptor gene transfer redirects T lymphocytes to display effective antileukemia reactivity," Blood, The Journal of the American Society of Hematology, vol. 119, No. 2, pp. 368-376, 2012.
Panina-Bordignon et al., "Universally immunogenic T cell epitopes: promiscuous binding to human MHC class II and promiscuous recognition by T cells," European Journal of Immunology 19, No. 12 (1989): 2237-2242.
Vitiello et al., "Analysis of the HLA-restricted Influenza-specific Cytotoxic T Lymphocyte Response in Transgenic Mice Carrying a Chimeric Human-Mouse Class I Major Histocompatibility Complex," The Journal of Experimental Medicine, vol. 173, No. 4, pp. 1007-1015, 1991.
Yachi et al., "Altered Peptide Ligands Induce Delayed CD8-T Cell Receptor Interaction—a Role for CD8 in Distinguishing Antigen Quality," Immunity vol. 25, No. 2, pp. 203-211, 2006.
Pushko et al., "Replicon-Helper Systems from Attenuated Venezuelan Equine Encephalitis Virus: Expression of Heterologous Genes in Vitro and Immunization against Heterologous Pathogens in Vivo," Virology vol. 239, No. 2, pp. 389-401, 1997.
Strauss et al., "The Alphaviruses: Gene Expression, Replication, and Evolution," Microbiological Reviews, vol. 58, No. 3, pp. 491-562, 1994.
Rhême et al., "Alphaviral cytotoxicity and its implication in vector development," Experimental Physiology vol. 90, No. 1, pp. 45-52, 2005.
Riley et al., "Recent advances in nanomaterials for gene delivery—a review," Nanomaterials, vol. 7, No. 5, p. 94, 2017.
Frolov et al., "Cis-acting RNA elements at the 5' end of Sindbis virus genome RNA regulate minus- and plus-strand RNA synthesis," RNA vol. 7, No. 11, pp. 1638-1651, 2001.
Jose et al., "A structural and functional perspective of alphavirus replication and assembly," Future Microbiology, vol. 4, No. 7, pp. 837-856, 2009.
Li et al., "RSEM: accurate transcript quantification from RNA-Seq data with or without a reference genome." BMC bioinformatics 12, No. 1 (2011): 323, 16 pages.
Pearson et al., "MHC class I-associated peptides derive from selective regions of the human genome," The Journal of Clinical Investigation, vol. 126, No. 12, pp. 4690-4701, Dec. 1, 2016.

(56) References Cited

OTHER PUBLICATIONS

Mommen et al., "Sampling from the Proteome to the Human Leukocyte Antigen-DR (HLA-DR) Ligandome ProceedsVia High Specificity," Molecular & Cellular Proteomics, vol. 15, No. 4, pp. 1412-1423, Apr. 1, 2016.
Kreiter et al., "Mutant MHC class II epitopes drive therapeutic immune responses to cancer," Nature, vol. 520, No. 7549, pp. 692-696, Apr. 2015.
Andreatta et al., "Accurate pan-specific prediction of peptide-MHC class II binding affinity with improved binding core identification." Immunogenetics 67, No. 11-12 (Nov. 2015): 641-650.
Nielsen et al., "NN-align. An artificial neural network-based alignment algorithm for MHC class II peptide binding prediction," BMC Bioinformatics, vol. 10, No. 1, p. 296, 2009.
Nielsen et al., "Prediction of MHC class II binding affinity using SMM-align, a novel stabilization matrix alignment method," BMC Bioinformatics, vol. 8, No. 1, pp. 238, 2007.
Zhang, et al., "PEAKS DB: De Novo Sequencing Assisted Database Search for Sensitive and Accurate Peptide Identification," Molecular & Cellular Proteomics vol. 11, No. 4, 2012.
Jensen et al., "Improved methods for predicting peptide binding affinity to MHC class II molecules," Immunology vol. 154, Issue 3, pp. 394-406, 2018.
Carter et al., "Absolute quantification of somatic DNA alterations in human cancer," Nature Biotechnology vol. 30, No. 5, 413-421, 2012.
Qiu et al., "Reviving virus based cancer vaccines by using cytomegalovirus vectors expressing modified tumor antigens," Oncolmmunology vol. 5, No. 1, p. e1056974, Jan. 2, 2016.
Farina et al., "Replication-Defective Vector Based on a Chimpanzee Adenovirus," Journal of Virology vol. 75, No. 23, pp. 11603-11613, 2001.
Ljungberg et al., "Self-replicating alphavirus RNA vaccines," Expert Review of Vaccines vol. 14, No. 2, pp. 177-194, Feb. 1, 2015.
Lundstrom, "Alphavirus-Based Vaccines," Viruses vol. 6, No. 6, pp. 2392-2415, 2014.
Geall et al., "Nonviral delivery of self-amplifying RNA vaccines," Proceedings of the National Academy of Sciences, vol. 109, Issue 36, pp. 14604-14609, 2012.
Rodriguez et al., "DNA Immunization with Minigenes: Low Frequency of Memory Cytotoxic T Lymphocytes and Inefficient Antiviral Protection are Rectified by Ubiquitination," Journal of Virology vol. 72, No. 6, pp. 5174-5181, 1998.
Velders et al., "Defined Flanking Spacers and Enhanced Proteolysis is Essential for Eradication of Established Tumors by an Epitope String DNA Vaccine," The Journal of Immunology, vol. 166, No. 9, pp. 5366-5373, 2001.
Kreiter et al., "Increased Antigen Presentation Efficiency by Coupling Antigens to MHC Class I Trafficking Signals," The Journal of Immunology, vol. 180, No. 1, pp. 309-318, 2008.
Rodriguez et al., "DNA Immunization: Ubiquitination of a Viral Protein Enhances Cytotoxic T-Lymphocyte Induction and Antiviral Protection but Abrogates Antibody Induction," Journal of Virology vol. 71, No. 11, pp. 8497-8503, 1997.
James et al., "Tetramer-guided epitope mapping reveals broad, individualized repertoires of tetanus toxin-specific CD4+ T cells and suggests HLA-based differences in epitope recognition," International Immunology vol. 19, No. 11, pp. 1291-1301, 2007.
Jayaraman et al., "Maximizing the Potency of siRNA Lipid Nanoparticles for Hepatic Gene Silencing In Vivo," Angewandte Chemie vol. 51, pp. 8529-8533, 2012.
Démoulins et al., "Polyethylenimine-based polyplex delivery of self-replicating RNA vaccines," Nanomedicine: Nanotechnology, Biology and Medicine vol. 12, No. 3, pp. 711-722, Apr. 1, 2016.
Chahal et al., "Dendrimer-RNA nanoparticles generate protective immunity against lethal Ebola, H1N1 influenza, and Toxoplasma gondii challenges with a single dose," Proceedings of the National Academy of Sciences vol. 113, No. 29 E4133-E4142, Jul. 19, 2016.
Vajdy et al., "Mucosal adjuvants and delivery systems for protein-, DNA- and RNA-based vaccines," Immunology and Cell Biology, vol. 82, No. 6, pp. 617-627, 2004.
Fleeton et al., "Self-Replicative RNA Vaccines Elicit Protection against Influenza A Virus, Respiratory Syncytial Virus, and a Tickborne Encephalitis Virus," The Journal of Infectious Diseases vol. 183, No. 9, pp. 1395-1398, 2001.
Strejan et al., "Suppression of chronic-relapsing experimental allergic encephalomyelitis in strain-13 guinea pigs by administration of liposome-associated myelin basic protein." Journal of Neuroimmunology 7 (1984): 27-41.
Johanning et al., "A Sindbis virus mRNA polynucleotide vector achieves prolonged and high level heterologous gene expression in vivo," Nucleic Aids Research vol. 23, Issue 9, pp. 1495-1501, 1995.
Martinon et al., "Induction of virus-specific cytotoxic T lymphocytes in vivo by liposome-entrapped mRNA," European Journal of Immunology 23, No. 7 (1993): 1719-1722.
Leitner et al., "DNA and RNA-based vaccines: principles, progress and prospects," Vaccine vol. 18, No. 9-10, pp. 765-777, 1999.
Del Val et al., "Efficient Processing of an Antigenic Sequence for Presentation by MHC Class I Molecules Depends on Its Neighboring Residues in the Protein," Cell vol. 66, No. 6, pp. 1145-1153, 1991.
Holzhütter et al., "A Theoretical Approach Towards the Identification of Cleavage-Determining Amino Acid Motifs of the 20S Proteasome," Journal of Molecular Biology, vol. 286, Issue 4, pp. 1251-1265, 1999.
Nussbaum et al., "Cleavage motifs of the yeast 20S proteasome β subunits deduced from digests of enolase 1," Proceedings of the National Academy of Sciences, vol. 95, No. 21, pp. 12504-12509, 1998.
Eggers et al., "The Cleavage Preference of the Proteasome Governs the Yield of Antigenic Peptides," The Journal of Experimental Medicine vol. 182, No. 6, pp. 1865-1870, 1995.
Borthwick et al., "Vaccine-elicited human T cells recognizing conserved protein regions inhibit HIV-1." Molecular therapy 22, No. 2 (2014): 464-475.
Ager et al, "31st Annual Meeting and Associated Programs of the Society for Immunotherapy of Cancer (SITC 2016): part two," in Journal for ImmunoTherapy of Cancer, vol. 4, Supplement 1, p. 73, 2016.
Warimwe et al. "Immunogenicity and efficacy of a chimpanzee adenovirus-vectored Rift Valley fever vaccine in mice," Virology Journal vol. 10, No. 1, pp. 1-9, 2013.
Cappuccini et al. "Immunogenicity and efficacy of the novel cancer vaccine based on simian adenovirus and MVA vectors alone and in combination with PD-1 mAb in a mouse model of prostate cancer," Cancer Immunol. Immunother. vol. 65, No. 6, pp. 701-713, Apr. 6, 2016.
Aurisicchio et al., "Immunogenicity and Therapeutic Efficacy of a Dual-Component Genetic Cancer Vaccine Cotargeting Carcinoembryonic Antigen and HER2/neu in Preclinical Models," Human Gene Therapy, vol. 25, Issue 2, pp. 121-131, Feb. 2014.
Morris et al. "Simian adenoviruses as vaccine vectors." Future Virology, vol. 11, No. 9 pp. 649-659, Sep. 15, 2016.
Letourneau et al. "Design and Pre-Clinical Evaluation of a Universal HIV-1 Vaccine," PloS One, vol. 2, No. 10, p. e984, 2007.
Colloca et al., "Vaccine Vectors Derived from a Large Collection of Simian Adenoviruses Induce Potent Cellular Immunity Across Multiple Species," Science Translational Medicine, vol. 4, No. 115, 115ra2, 2012.
Levy et al. "A melanoma multiepitope polypeptide induces specific CD8+ T-cell response," Cellular Immunology, vol. 250, No. 1-2, pp. 24-30, 2007.
Tatsis et al. "Chimpanzee-origin adenovirus vectors as vaccine carriers," Gene Therapy vol. 13, No. 5, pp. 421-429, 2006.
Zappasodi et al., "Alphavirus-based vaccines in melanoma: rationale and potential improvements in immunotherapeutic combinations." Immunotherapy 7, No. 9 (Sep. 2015): 981-997.
Riabov et al., "Anti-tumor effect of the alphavirus-based virus-like particlevector expressing prostate-specific antigen in a HLA-DR transgenic mouse model of prostate cancer." Vaccine 33, No. 41 (Oct. 5, 2015): 5386-5395.

(56) References Cited

OTHER PUBLICATIONS

Fang et al., "Stable antibody expression at therapeutic levels using the 2A peptide." Nature biotechnology 23, No. 5 (2005): 584-590.
Wu et al., "Targeting genes: delivery and persistent expression of a foreign gene driven by mammalian regulatory elements in vivo." Journal of Biological Chemistry 264, No. 29 (1989): 16985-16987.
Fisher et al., "The transmembrane domain of diphtheria toxin improves molecular conjugate gene transfer." Biochemical Journal 321, No. 1 (1997): 49-58.
Szoka et al., "Comparative properties and methods of preparation of lipid vesicles (liposomes)." Annual review of biophysics and bioengineering 9, No. 1 (1980): 467-508.
Wolff et al., "Direct gene transfer into mouse muscle in vivo." Science 247, No. 4949 (1990): 1465-1468.
Felgner et al., "Lipofection: a highly efficient, lipid-mediated DNA-transfection procedure." Proceedings of the National Academy of Sciences 84, No. 21 (1987): 7413-7417.
Mannino et al., "Liposome mediated gene transfer." Biotechniques 6, No. 7 (1988): 682-690.
Konarska et al., "Recognition of cap structure in splicing in vitro of mRNA precursors." Cell 38, No. 3 (1984): 731-736.
Huang, "Sindbis virus vectors for expression in animal cells." Current Opinion in Biotechnology 7, No. 5 (1996): 531-535.
Wan et al., "High-sensitivity monitoring of ctDNA by patient-specific sequencing panels and integration of variant reads." bioRxiv (2019): 759399, pp. 1-37.
Wang et al., "Identification of T Cell Receptors Targeting KRAS-Mutated Human Tumors", Cancer Immunology Research 4(3) Mar. 2016, pp. 204-214.
Hacohen et al., "Getting personal with neoantigen-based therapeutic cancer vaccines." Cancer immunology research 1, No. 1 (2013): 11-15.
Karasaki et al., "Identification of individual cancer-specific somatic mutations for neoantigen-based immunotherapy of lung cancer." Journal of Thoracic Oncology 11, No. 3 (Mar. 2016): 324-333.
Abbas et al., "Structure of human IFIT1 with capped RNA reveals adaptable mRNA binding and mechanisms for sensing N1 and N2 ribose 2?-O methylations." Proceedings of the National Academy of Sciences 114, No. 11 (2017): E2106-E2115.
PCT/US2020/035591—International Search Report and Written Opinion, dated Sep. 9, 2020, 17 pages.
Ngo et al., "CNTO 859, a humanized anti-tissue factor monoclonal antibody, is a potent inhibitor of breast cancer metastasis and tumor growth in xenograft models," International Journal of Cancer, vol. 120, No. 6, pp. 1261-1267, 2007.
Hong et al, Immuno-PET of Tissue Factor in Pancreatic Cancer, J Nucl Med, vol. 53, No. 11, pp. 1748-1754, 2012.
Trail et al., "Antibody drug conjugates for treatment of breast cancer: Novel targets and diverse approaches in ADC design," Pharmacol. Ther., vol. 181, pp. 126-142, 2018.
De Graaf et al., Beta-Glucuronidase-Mediated Drug Release, Curr Pharm Des., vol. 8, pp. 1391-1403, 2002.
Chari et al., Immunoconjugates Containing Novel Maytansinoids: Promising Anticancer Drugs, Cancer Research, vol. 52, pp. 127-131, 1992.
Kovtun et al., "Antibody-Mytansinoid Conjugates Designed to Bypass Multidrug Resistance," Cancer Research vol. 70, No. 6, pp. 2528-2537, 2010.
Vitetta et al., "Redesigning Nature's Poisons to Create Anti-Tumor Reagents," Science vol. 238, No. 4830, pp. 1098-1104, 1987.
Junutula et al., "Rapid identification of reactive cysteine residues for site-specific labeling of antibody-Fabs," Journal of Immunological Methods 332, No. 1-2 (2008): 41-52.
Junutula et al., "Site-specific conjugation of a cytotoxic drug to an antibody improves the therapeutic index." Nature Biotechnology 26, No. 8 (2008): 925.
Hofer et al., "An engineered selenocysteine defines a unique class of antibody derivatives," Proc. Natl. Acad. Sci. USA, 2008, 105:12451-12456.
Hofer et al., Molecularly defined antibody conjugation through a selenocysteine interface, Biochemistry, vol. 48, No. 50, pp. 12047-12057, 2009.
Hjortoe et al., Tissue factor-factor VIIa-specific up-regulation of IL-8 expression in MDA-MB-231 cells is mediated by PAR-2 and results in increased cell migration, Blood, 2004, vol. 103, No. 8, pp. 3029-3037.
Sakurai et al., "Expression of Tissue Factor in Epithelial Ovarian Carcinoma is Involved in the Development of Venous Thromboembolism," International Journal of Gynecologic Cancer, vol. 27, No. 1, pp. 37-43, 2017.
Cocco et al., "Expression of Tissue factor in Adenocarcinoma and Squamous Cell Carcinoma of the Uterine Cervix: Implications for immunotherapy with hl-con1, a factor VII-IgGFc chimeric protein targeting tissue factor," BMC Cancer, vol. 11 p. 263, 2011.
Christensen et al., Urokinase-type plasminogen activator receptor (uPAR), tissue factor (TF) and epidermal growth factor receptor (EGFR): tumor expression patterns and prognostic value in oral cancer, BMC Cancer, vol. 17, p. 572, 2017.
Yao et al., Tissue Factor and VEGF Expression in Prostate Carcinoma A Tissue Microarray Study, Cancer Invest., vol. 27, pp. 430-434, 2009.
Abdulkadir et al., "Tissue factor expression and angiogenesisin human prostate carcinoma," Human Pathology 31, No. 4 (2000): 443-447.
Zhang et al., "Pathological expression of tissue factor confers promising antitumor response to a novel therapeutic antibody SC1 in triple negative breast cancer and pancreatic adenocarcinoma," Oncotarget vol. 8, No. 35, pp. 59086-59102, 2017.
Guan et al., "Tissue factor expression and angiogenesis in human glioma." Clinical Biochemistry 35, No. 4 (2002): 321-325.
Carneiro-Lobo et al., Ixolaris, a tissue factor inhibitor, blocks primary tumor growth and angiogenesis in a glioblastoma model, J Thromb Haemost, 2009, 7:1855-1864.
Yeh et al., "Upregulation of Tissue Factor by Activated Stat3 Contributes to Malignant Pleural Effusion Generation via Enhancing Tumor Metastasis and Vascular Permeability in Lung Adenocarcinoma," PLoS One, vol. 8, No. 9, p. e75287, 2013.
Regina et al., "Increased tissue factor expression is associated with reduced survival in non-small cell lung cancer and with mutations of TP53 and PTEN," Clinical Chemistry, vol. 55, No. 10, pp. 1834-1842, 2009.
Lo et al., "Tissue factor expression in the metaplasia-adenoma-carcinoma sequence of gastric cancer in a European population," British Journal of Cancer vol. 107, No. 7, pp. 1125-1130, 2012.
Chen et al., "Immunolocalisation of tissue factor in esophageal cancer is correlated with intratumoral angiogenesis and prognosis of the patient." Acta Histochemica 112, No. 3 (2010): 233-239.
Patry et al., "Tissue factor expression correlates with disease-specific survival in patients with node-negative muscle-invasive bladder cancer," International Journal of Cancer, vol. 122, No. 7, pp. 1592-1597, 2008.
Bromberg et al., Tissue factor promotes melanoma metastasis by a pathway independent of blood coagulation, Proc Natl Acad Sci U S A., 1995, 92:8205-8209.
Silva et al., "Increased Tissue Factor Expression is an Independent Predictor of Mortality in Clear Cell Carcinoma of the Kidney," Int Braz J Urol., 2014, 40:499-506.
Van Den Berg et al., "The relationship between tissue factor and cancer progression: insights from bench and bedside," Blood vol. 119, No. 4, pp. 924-932, 2012.
Tripisciano et al., "Different Potential of Extracellular Vesicles to Support Thrombin Generation: Contributions of Phosphatidylserine, Tissue Factor, and Cellular Origin," Scientific Reports vol. 7, No. 1, pp. 1-11, 2017.
Teplyakov et al., "Crystal structure of tissue factor in complex with antibody 10H10 reveals the signaling epitope," Cellular Signalling vol. 36, pp. 139-144, 2017.
Liepe et al., "A large fraction of HLA class I ligands are proteasome-generated spliced peptides," Science vol. 354, No. 6310, Oct. 21, 2016.
Smith et al., "Comparison of biosequences," Advances in Applied Mathematics vol. 2, No. 4, pp. 482-489, 1981.

(56) References Cited

OTHER PUBLICATIONS

Needleman et al., "A General Method Applicable to the Search for Similarities in the Amino Acid Sequence of Two Proteins," Journal of Molecular Biology, vol. 48, No. 3, pp. 443-453, 1970.
Pearson et al., "Improved tools for biological sequence comparison," Proceedings of the National Academy of Sciences, vol. 85, No. 8, pp. 2444-2448, 1988.
Altschul et al., "Basic Local Alignment Search Tool." Journal of Molecular Biology vol. 215, Issue 3 (1990): 403-410.
Kornher et al., "Mutation detection using nucleotide analogs that alter electrophoretic mobility," Nucleic Acids Research vol. 17, No. 19, pp. 7779-7784, 1989.
Sokolov, "Primer extension technique for the detection of single nucleotide in genomic DNA," Nucleic Acids Research, vol. 18, No. 12, p. 3671, 1990.
Syvänen et al., "A Primer-Guided Nucleotide Incorporation Assay in the Genotyping of Apolipoprotein E," Genomics 8, No. 4 (1990): 684-692.
Kuppuswamy et al., "Single nucleotide primer extension to detect genetic diseases: experimental application to hemophilia B (factor IX) and cystic fibrosis genes," Proceedings of the National Academy of Sciences vol. 88, No. 4, pp. 1143-1147, 1991.
Prezant et al., "Trapped-Oligonucleotide Nucleotide Incorporation (TONI) Assay, a Simple Method for Screening Point Mutations," Human Mutation 1, No. 2 (1992): 159-164.
Ugozzoli et al., "Detection of specific alleles by using allele-specific primer extension followed by capture on solid support," Genetic Analysis: Biomolecular Engineering 9, No. 4 (1992): 107-112.
Nyrén et al., "Solid phase DNA minisequencing by an enzymatic luminometric inorganic pyrophosphate detection assay." Analytical Biochemistry 208, No. 1 (1993): 171-175.
Syvänen et al., "Identification of Individuals by Analysis of Biallelic DNA Markers, Using PCR and Solid-Phase Minisequencing," American Journal of Human Genetics vol. 52, No. 1, p. 46 1993.
Merrifield, "Solid phase synthesis." Science 232 (1986): 341-348.
Dupuis et al., "Dendritic cells internalize vaccine adjuvant after intramuscular injection," Cellular Immunology 186, No. 1 (1998), 18-27.
Allison, "The mode of action of immunological adjuvants," Developments in Biological Standardization 92 (1998): 3-11.
Gabrilovich et al., "IL-12 and Mutant P53 Peptide-Pulsed Dendritic Cells for the Specific Immunotherapy of Cancer," Journal of Immunotherapy, vol. 19, No. 6 (1996): 414-418.
Tatsis et al., "Adenoviruses as vaccine vectors," Molecular Therapy vol. 10, No. 4, pp. 616-629, 2004.
Hu et al., "Immunization Delivered by Lentiviral Vectors for Cancer and Infectious Diseases," Immunological Reviews, vol. 239, Issue 1, pp. 45-61, 2011.
Lundstrom, Kenneth. "Alphavirus-based vaccines." Current opinion in molecular therapeutics 4, No. 1 (Feb. 2002): 28-34.
Alexander et al., "Linear PADRE T helper epitope and carbohydrate B cell epitope conjugates induce specific high titer IgG antibody responses." The Journal of Immunology 164, No. 3 (Feb. 2000): 1625-1633.
Kim et al., "Neopepsee: accurate genome-level prediction of neoantigens by harnessing sequence and amino acid immunogenicity information." Annals of Oncology 29, No. 4 (Apr. 2018): 1030-1036.
Ott et al., "An immunogenic personal neoantigen vaccine for patients with melanoma." Nature 547, No. 7662 (Jul. 2017): 217-221.
Fluet et al., "Effects of rapid antigen degradation and VEE glycoprotein specificity on immune responses induced by a VEE replicon vaccine." Virology 370, No. 1 (Jan. 2008): 22-32.
Ogawa et al., "An Attempt of Cytokine Gene Therapy Using Adenovirus Vectors," Partial Translation of: Biotherapy, 1998, vol. 12 No 5, p. 785-787.
Nielsen et al., "An in vitro-transcribed-mRNA polyepitope construct encoding 32 distinct HLA class I-restricted epitopes from CMV, EBV, and Influenza for use as a functional control in human immune monitoring studies." Journal of Immunological methods 360, No. 1-2 (2010): 149-156.
Bergmann et al., "Differential effects of flanking residues on presentation of epitopes from chimeric peptides." Journal of virology 68, No. 8 (1994): 5306-5310.
Carroll et al., "Alphavirus replicon-based adjuvants enhance the immunogenicity and effectiveness of Fluzone in rhesus macaques." Vaccine 29, No. 5 (2011): 931-940.
Thompson et al., "The contribution of type I interferon signaling to immunity induced by alphavirus replicon vaccines." Vaccine 26, No. 39 (2008): 4998-5003.
Ljungberg et al,. "Increased immunogenicity of a DNA-launched Venezuelan equine encephalitis virus-based replicon DNA vaccine." Journal of virology 81, No. 24 (2007): 13412-13423.
Channon et al., "Improved adenoviral vectors: cautious optimism for gene therapy." QJM: monthly journal of the Association of Physicians 90, No. 2 (1997): 105-109.
Gao et al., "Biology of adenovirus vectors with E1 and E4 deletions for liver-directed gene therapy." Journal of virology 70, No. 12 (1996): 8934-8943.
Andrews et al., "Generation and characterization of E1/E2a/E3/E4-deficient adenoviral vectors encoding human factor VIII." Molecular Therapy 3, No. 3 (2001): 329-336.
Farina et al., "Replication-defective vector based on a chimpanzee adenovirus." Journal of virology 75, No. 23 (2001): 11603-11613.

* cited by examiner

| # | HLA | Sequence | Origin |
| --- | --- | --- | --- |
| 1 | A*0201 | NLVPMVATV | HCMV pp65 (495– 503) |
| 2 | A*0201 | CLGGLLTMV | EBV LMP2A(426-434) |
| 3 | A*0201 | GLCTLVAML | EBV BMLF1 (280–288) |
| 4 | A*0201 | LLFGYPVYV | HTLV-1 Tax (11-19) |
| 5 | A*0201 | GILGFVFTL | Influenza A Matrix 1 (58– 66) |
| | MHC-II | AKFVAAWTLKAAA | PADRE (artificial seq) |
| | MHC-II | QYIKANSKFIGITE | Tetanus toxoid (830–844) |

| # | HLA | Sequence | Origin |
|---|---|---|---|
| 1 | A*02:01 | NLVPMVATV | HCMV pp65 495-504 |
| 2 | A*02:01 | CLGGLLTMV | EBV LMP-2 426-434 |
| 3 | A*02:01 | GLCTLVAML | EBV BMLF-1 259-267 |
| 4 | A*02:01 | LLFGYPVYV | HTLV1 Tax 11-19 |
| 5 | A*02:01 | GILGFVFTL | Influenza A MP 58-66 |
| 6 | A*02:01 | DLMGYIPAV | HCV core 132-140 |
| 7 | A*02:01 | FLPSDFFPSV | HBV core antigen 18-27 |
| 8 | A*02:01 | FLLTRILTI | HBV envelope 183-191 |
| 9 | A*02:01 | WLSLLVPFV | HBV surface antigen 172-181 |
| 10 | A*02:01 | FLLSLGIHL | HBV polymerase 573-581 |
| 11 | A*02:01 | ILKEPVHGV | HIV-1 RT 476-484 |
| 12 | A*02:01 | YMLDLQPETT | HPV 16 E7 11-20 |
| 13 | A*02:01 | CINGVCWTV | HCV NS3 1073-1081 |
| 14 | A*02:01 | YLLPRRGPRL | HCV core 35-44 |
| 15 | A*02:01 | FLYALALLL | EBV LMP-2 356-364 |
| 16 | A*02:01 | AAGIGILTV | MELAN-A/MART-1 (27-35) |
| 17 | A*02:01 | SLLMWITQV | NY-ESO-1(157-165) C9V |
| 18 | A*03:01 | KLGGALQAK | CVM-IE1 |
| 19 | A*03:01 | RLRAEAQVK | EBV-EBNA-3a |
| 20 | B*44:05 | EENLLDFVRF | EBV EBNASC (281-290) |
| 21 | B*44:05 | EEYLQAFTY | Self ABCD3 protein |

FIG 5B

NHP Epitopes

| | MHC | Sequence |
|---|---|---|
| 1 | Mamu*01 | CTPYDINQM |
| 4 | Mamu*01 | TTPESANL |
| 7 | Mamu*01 | CAPPGYALL |
| 10 | Mamu*01 | SGPKTNIIV |
| 14 | Mamu*01 | LSPRTLNAW |
| 18 | Mamu*01 | TVPWPNASL |

Human Epitopes

| | HLA | Sequence |
|---|---|---|
| 3 | A*02:01 | GILGFVFTL |
| 6 | A*02:01 | LLFGYPVYV |
| 9 | A*02:01 | GLCTLVAML |
| 12 | A*02:01 | NLVPMVATV |
| 16 | A*02:01 | CLGGLLTMV |

Murine MHC-I Epitopes

| | MHC | Sequence |
|---|---|---|
| 2 | H-2Kb | SIINFEKL |
| 5 | H-2Ld | SPSYAYHQF |
| 8 | H-2Db | EGPRNQDWL |
| 11 | H-2Kb | DWENVSPEL |
| 13 | H-2Kb | SIIVFNLL |
| 15 | H-2Db | ASMTNMELM |
| 17 | H-2Db | AQLANDVVL |
| 19 | H-2Kb | SVYDFFVWL |
| 20 | H-2Ld | MNKYAYHML |

Universal MHC-II Epitopes

| | HLA | Sequence |
|---|---|---|
| 1 | MHC-II | AKFVAAWTLKAAA |
| 2 | MHC-II | QYIKANSKFIGITEL |

FIG 6B

"TETo" Response Region

ChAdV68-TETo-GFP

293F TETr Line Clone 17

293F Parental Line

SEQUENCE LISTING

<160> NUMBER OF SEQ ID NOS: 56

<210> SEQ ID NO 1
<211> LENGTH: 36519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
ccatcwtcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480

```
atttaaacct gcgctctcca gtcaagaggc cactcttgag tgccagcgag aagagttttc    540
tcctccgcgc cgcgagtcag atctacactt tgaaagatga ggcacctgag agacctgccc    600
gatgagaaaa tcatcatcgc ttccgggaac gagattctgg aactggtggt aaatgccatg    660
atgggcgacg accctccgga gccccccacc ccatttgaga caccttcgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac    840
tcttcactgc atacccctag acccggcaga ggtgagaaaa agatccccga gcttaaaggg    900
gaagagatgg acttgcgctg ctatgaggaa tgcttgcccc cgagcgatga tgaggacgag    960
caggcgatcc agaacgcagc gagccaggga gtgcaagccg ccagcgagag ctttgcgctg   1020
gactgcccgc ctctgcccgg acacggctgt aagtcttgtg aatttcatcg catgaatact   1080
ggagataaag ctgtgttgtg tgcactttgc tatatgagag cttacaacca ttgtgtttac   1140
agtaagtgtg attaagttga actttagagg gaggcagaga gcagggtgac tgggcgatga   1200
ctggtttatt tatgtatata tgttctttat ataggtcccg tctctgacgc agatgatgag   1260
acccccacta caaagtccac ttcgtcaccc ccagaaattg gcacatctcc acctgagaat   1320
attgttagac cagttcctgt tagagccact gggaggagag cagctgtgga atgtttggat   1380
gacttgctac agggtggggt tgaacctttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tctttttgac gctcttaact   1800
tgggccatca gtctcacttt aaccagagga tttcgagagc ccttgatttt actactcctg   1860
gcagaaccac tgcagcagta gccttttttg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggcctggggt caggtcggtg tgaggggctg   2760
cagtttttca gccaactgga tgggggtcgt gggcaggacc aagagtatgc tgtccgtgaa   2820
```

gaaatgcttg tttgagaggt gccacctggg ggtgatgagc gagggcgaag ccagaatccg 2880
ccactgcgcc tctaccgaga cgggctgctt tgtgctgtgc aagggcaatg ctaagatcaa 2940
gcataaatatg atctgtggag cctcggacga gcgcggctac cagatgctga cctgcgccgg 3000
cgggaacagc catatgctgg ccaccgtaca tgtggcttcc catgctcgca agccctggcc 3060
cgagttcgag cacaatgtca tgaccaggtg caatatgcat ctggggtccc gccgaggcat 3120
gttcatgccc taccagtgca acctgaatta tgtgaaggtg ctgctggagc ccgatgccat 3180
gtccagagtg agcctgacgg gggtgtttga catgaatgtg gaggtgtgga agattctgag 3240
atatgatgaa tccaagacca ggtgccgagc ctgcgagtgc ggagggaagc atgccaggtt 3300
ccagcccgtg tgtgtggatg tgacggagga cctgcgaccc gatcatttgg tgttgccctg 3360
caccgggacg gagttcggtt ccagcgggga agaatctgac tagagtgagt agtgttctgg 3420
ggcgggggag gacctgcatg agggccagaa taactgaaat ctgtgctttt ctgtgtgttg 3480
cagcagcatg agcggaagcg gctcctttga gggaggggta ttcagccctt atctgacggg 3540
gcgtctcccc tcctgggcgg gagtgcgtca gaatgtgatg ggatccacgg tggacggccg 3600
gcccgtgcag cccgcgaact cttcaaccct gacctatgca accctgagct cttcgtcgtt 3660
ggacgcagct gccgccgcag ctgctgcatc tgccgccagc gccgtgcgcg gaatggccat 3720
gggcgccggc tactacggca ctctggtggc caactcgagt tccaccaata atcccgccag 3780
cctgaacgag gagaagctgt tgctgctgat ggcccagctc gaggccttga cccagcgcct 3840
gggcgagctg acccagcagg tggctcagct gcaggagcag acgcgggccg cggttgccac 3900
ggtgaaatcc aaataaaaaa tgaatcaata aataaacgga gacggttgtt gattttaaca 3960
cagagtctga atctttattt gatttttcgc gcgcggtagg ccctggacca ccggtctcga 4020
tcattgagca cccggtggat cttttccagg acccggtaga ggtgggcttg gatgttgagg 4080
tacatgggca tgagcccgtc ccgggggtgg aggtagctcc attgcagggc ctcgtgctcg 4140
ggggtggtgt tgtaaatcac ccagtcatag caggggcgca gggcatggtg ttgcacaata 4200
tctttgagga ggagactgat ggccacgggc agccctttgg tgtaggtgtt tacaaatctg 4260
ttgagctggg agggatgcat gcggggggag atgaggtgca tcttggcctg gatcttgaga 4320
ttggcgatgt taccgcccag atcccgcctg gggttcatgt tgtgcaggac caccagcacg 4380
gtgtatccgg tgcacttggg gaatttatca tgcaacttgg aagggaaggc gtgaaagaat 4440
ttggcgacgc ctttgtgccc gcccaggttt tccatgcact catccatgat gatggcgatg 4500
ggcccgtggg cggcggcctg ggcaaagacg tttcgggggt cggacacatc atagttgtgg 4560
tcctgggtga ggtcatcata ggccatttta atgaatttgg ggcggagggt gccggactgg 4620
gggacaaagg taccctcgat cccgggggcg tagttcccct cacagatctg catctcccag 4680
gctttgagct cggagggggg gatcatgtcc acctgcgggg cgataaagaa cacggtttcc 4740
ggggcggggg agatgagctg ggccgaaagc aagttccgga gcagctggga cttgccgcag 4800
ccggtggggc cgtagatgac cccgatgacc ggctgcaggt ggtagttgag ggagagacag 4860
ctgccgtcct cccggaggag gggggccacc tcgttcatca tctcgcgcac gtgcatgttc 4920
tcgcgcacca gttccgccag gaggcgctct ccccccaggg ataggagctc ctggagcgag 4980
gcgaagtttt tcagcggctt gagtccgtcg gccatgggca ttttggagag ggtttgttgc 5040
aagagttcca ggcggtccca gagctcggtg atgtgctcta cggcatctcg atccagcaga 5100
cctcctcgtt tcgcgggttg ggacggctgc gggagtaggg caccagacga tgggcgtcca 5160
gcgcagccag ggtccggtcc ttccagggtc gcagcgtccg cgtcagggtg gtctccgtca 5220

```
cggtgaaggg gtgcgcgccg ggctgggcgc ttgcgagggt gcgcttcagg ctcatccggc   5280
tggtcgaaaa ccgctcccga tcggcgccct gcgcgtcggc caggtagcaa ttgaccatga   5340
gttcgtagtt gagcgcctcg gccgcgtggc ctttggcgcg gagcttacct ttggaagtct   5400
gcccgcaggc gggacagagg agggacttga gggcgtagag cttgggggcg aggaagacgg   5460
actcggggc gtaggcgtcc gcgccgcagt gggcgcagac ggtctcgcac tccacgagcc   5520
aggtgaggtc gggctggtcg gggtcaaaaa ccagtttccc gccgttcttt ttgatgcgtt   5580
tcttaccttt ggtctccatg agctcgtgtc cccgctgggt gacaaagagg ctgtccgtgt   5640
ccccgtagac cgactttatg ggccggtcct cgagcggtgt gccgcggtcc tcctcgtaga   5700
ggaaccccgc ccactccgag acgaaagccc gggtccaggc cagcacgaag gaggccacgt   5760
gggacgggta gcggtcgttg tccaccagcg ggtccacctt ttccagggta tgcaaacaca   5820
tgtccccctc gtccacatcc aggaaggtga ttggcttgta agtgtaggcc acgtgaccgg   5880
gggtcccggc cggggggta taaaagggtg cgggtccctg ctcgtcctca ctgtcttccg   5940
gatcgctgtc caggagcgcc agctgttggg gtaggtattc cctctcgaag gcgggcatga   6000
cctcggcact caggttgtca gtttctagaa acgaggagga tttgatattg acggtgccgg   6060
cggagatgcc tttcaagagc ccctcgtcca tctggtcaga aaagacgatc tttttgttgt   6120
cgagcttggt ggcgaaggag ccgtagaggg cgttggagag gagcttggcg atggagcgca   6180
tggtctggtt tttttccttg tcggcgcgct ccttggcggc gatgttgagc tgcacgtact   6240
cgcgcgccac gcacttccat tcggggaaga cggtggtcag ctcgtcgggc acgattctga   6300
cctgccagcc ccgattatgc agggtgatga ggtccacact ggtggccacc tcgccgcgca   6360
ggggctcatt agtccagcag aggcgtccgc ccttgcgcga gcagaagggg ggcagggggt   6420
ccagcatgac ctcgtcgggg gggtcggcat cgatggtgaa gatgccgggc aggaggtcgg   6480
ggtcaaagta gctgatggaa gtggccagat cgtccagggc agcttgccat tcgcgcacgg   6540
ccagcgcgcg ctcgtaggga ctgaggggcg tgccccaggg catgggatgg gtaagcgcgg   6600
aggcgtacat gccgcagatg tcgtagacgt agaggggctc ctcgaggatg ccgatgtagg   6660
tggggtagca gcgccccccg cggatgctgg cgcgcacgta gtcatacagc tcgtgcgagg   6720
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agcccccctg ctcccagagc tggaagtccg   7260
tgcgcttctt gtaggcgggg ttgggcaaag cgaaagtaac atcgttgaag aggatcttgc   7320
ccgcgcgggg cataaagttg cgagtgatgc ggaaaggttg ggcacctcg gcccggttgt    7380
tgatgacctg ggcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
```

```
tggcgcggag gaaggaagtc cagagatcca cggccagggc ggtttgcaga cggtcccggt   7620
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgcccctgg ggtgtgacca   8400
ccgtccccg tttcttcttg ggcggctggg gcgacggggg cggtgcctct tccatggtta   8460
gaagcggcgg cgaggacgcg cgccgggcgg caggggcggc tcggggcccg gaggcagggg   8520
cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag gcgttcatgc ccgcctcgtt   8880
ccagacgcgg ctgtagacca cgacgccctc gggatcgcgg gcgcgcatga ccacctgggc   8940
gaggttgagc tccacgtggc gcgtgaagac cgcgtagttg cagaggcgct ggtagaggta   9000
gttgagcgtg gtggcgatgt gctcggtgac gaagaaatac atgatccagc ggcggagcgg   9060
catctcgctg acgtcgccca gcgcctccaa acgttccatg gcctcgtaaa agtccacggc   9120
gaagttgaaa aactgggagt tgcgcgccga gacggtcaac tcctcctcca gaagacggat   9180
gagctcggcg atggtggcgc gcacctcgcg ctcgaaggcc cccgggagtt cctccacttc   9240
ctcttcttcc tcctccacta acatctcttc tacttcctcc tcaggcggca gtggtggcgg   9300
gggagggggc ctgcgtcgcc ggcggcgcac gggcagacgg tcgatgaagc gctcgatggt   9360
ctcgccgcgc cggcgtcgca tggtctcggt gacggcgcgc ccgtcctcgc ggggccgcag   9420
cgtgaagacg ccgccgcgca tctccaggtg gccgggggggg tccccgttgg gcagggagag   9480
ggcgctgacg atgcatctta tcaattgccc cgtagggact ccgcgcaagg acctgagcgt   9540
ctcgagatcc acgggatctg aaaaccgctg aacgaaggct tcgagccagt cgcagtcgca   9600
aggtaggctg agcacggttt cttctggcgg gtcatgttgg ttgggagcgg ggcgggcgat   9660
gctgctggtg atgaagttga aataggcggt tctgagacgg cggatggtgg cgaggagcac   9720
caggtctttg ggcccggctt gctggatgcg cagacggtcg gccatgcccc aggcgtggtc   9780
ctgacacctg gccaggtcct tgtagtagtc ctgcatgagc cgctccacgg gcacctcctc   9840
ctcgcccgcg cggccgtgca tgcgcgtgag cccgaagccg cgctggggct ggacgagcgc   9900
caggtcggcg acgacgcgct cggcgaggat ggcttgctgg atctgggtga gggtggtctg   9960
```

```
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
ttgttttgtt tgtttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gagggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
```

```
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccggggcca ggaggactac accaacttca tcagcgccct gcgcctgatg  12540
gtgaccgagg tgccccagag cgaggtgtac cagtccgggc cggactactt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgcgccc tgggccagga cgacccgggc  12900
aacctggaag ccaccctgaa ctttttgctg accaaccggt cgcagaagat cccgccccag  12960
tacgcgctca gcaccgagga ggagcgcatc ctgcgttacg tgcagcagag cgtgggcctg  13020
ttcctgatgc aggagggggc cacccccagc gccgcgctcg acatgaccgc gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc agggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggagggt cctcctccct  13920
cgtacgagag cgtgatgcag caggcgatgg cggcggcggc gatgcagccc ccgctggagg  13980
ctccttacgt gcccccgcgg tacctggcgc ctacggaggg gcggaacagc attcgttact  14040
cggagctggc acccttgtac gataccaccc ggttgtacct ggtggacaac aagtcggcgg  14100
acatcgcctc gctgaactac cagaacgacc acagcaactt cctgaccacc gtggtgcaga  14160
acaatgactt cacccccacg gaggccagca cccagaccat caactttgac gagcgctcgc  14220
ggtggggcgg ccagctgaaa accatcatgc acaccaacat gcccaacgtg aacgagttca  14280
tgtacagcaa caagttcaag gcgcgggtga tggtctcccg caagaccccc aatggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
agttcgacac taggaacttc aggctgggct gggaccccgt gaccgagctg gtcatgcccg  14580
ggtgtacac caacgaggct ttccatcccg atattgtctt gctgcccggc tgcggggtgg  14640
acttcaccga gagccgcctc agcaacctgc tgggcattcg caagaggcag cccttccagg  14700
```

```
aaggcttcca gatcatgtac gaggatctgg aggggggcaa catccccgcg ctcctggatg  14760
tcgacgccta tgagaaaagc aaggaggatg cagcagctga agcaactgca gccgtagcta  14820
ccgcctctac cgaggtcagg ggcgataatt ttgcaagcgc cgcagcagtg gcagcggccg  14880
aggcggctga aaccgaaagt aagatagtca ttcagccggt ggagaaggat agcaagaaca  14940
ggagctacaa cgtactaccg gacaagataa acaccgccta ccgcagctgg tacctagcct  15000
acaactatgg cgaccccgag aagggcgtgc gctcctggac gctgctcacc acctcggacg  15060
tcacctgcgg cgtggagcaa gtctactggt cgctgcccga catgatgcaa gacccggtca  15120
ccttccgctc cacgcgtcaa gttagcaact acccggtggt gggcgccgag ctcctgcccg  15180
tctactccaa gagcttcttc aacgagcagg ccgtctactc gcagcagctg cgcgccttca  15240
cctcgcttac gcacgtcttc aaccgcttcc ccgagaacca gatcctcgtc cgcccgcccg  15300
cgcccaccat taccaccgtc agtgaaaacg ttcctgctct cacagatcac gggaccctgc  15360
cgctgcgcag cagtatccgg ggagtccagc gcgtgaccgt tactgacgcc agacgccgca  15420
cctgccccta cgtctacaag gccctgggca tagtcgcgcc gcgcgtcctc tcgagccgca  15480
ccttctaaat gtccattctc atctcgccca gtaataacac cggttggggc ctgcgcgcgc  15540
ccagcaagat gtacggaggc gctcgccaac gctccacgca acaccccgtg cgcgtgcgcg  15600
ggcacttccg cgctccctgg ggcgccctca agggccgcgt gcggtcgcgc accaccgtcg  15660
acgacgtgat cgaccaggtg gtggccgacg cgcgcaacta cacccccgcc gccgcgcccg  15720
tctccaccgt ggacgccgtc atcgacagcg tggtggccga cgcgcgccgg tacgcccgcg  15780
ccaagagccg gcggcggcgc atcgcccggc ggcaccggag cacccccgcc atgcgcgcgg  15840
cgcgagcctt gctgcgcagg gccaggcgca cgggacgcag ggccatgctc agggcggcca  15900
gacgcgcggc ttcaggcgcc agcgccggca ggacccggag acgcgcggcc acggcggcgg  15960
cagcggccat cgccagcatg tcccgcccgc ggcgagggaa cgtgtactgg gtgcgcgacg  16020
ccgccaccgg tgtgcgcgtg cccgtgcgca cccgcccccc tcgcacttga agatgttcac  16080
ttcgcgatgt tgatgtgtcc cagcggcgag gaggatgtcc aagcgcaaat tcaaggaaga  16140
gatgctccag gtcatcgcgc ctgagatcta cggccctgcg gtggtgaagg aggaaagaaa  16200
gccccgcaaa atcaagcggg tcaaaaagga caaaaaggaa gaagaaagtg atgtggacgg  16260
attggtggag tttgtgcgcg agttcgcccc ccggcggcgc gtgcagtggc gcgggcggaa  16320
ggtgcaaccg gtgctgagac ccggcaccac cgtggtcttc acgcccggcg agcgctccgg  16380
caccgcttcc aagcgctcct acgacgaggt gtacggggat gatgatattc tggagcaggc  16440
ggccgagcgc ctgggcgagt ttgcttacgg caagcgcagc cgttccgcac cgaaggaaga  16500
ggcggtgtcc atcccgctgg accacggcaa ccccacgccg agcctcaagc ccgtgacctt  16560
gcagcaggtg ctgccgaccg cggcgccgcg ccgggggttc aagcgcgagg gcgaggatct  16620
gtaccccacc atgcagctga tggtgcccaa gcgccagaag ctggaagacg tgctggagac  16680
catgaaggtg gacccggacg tgcagcccga ggtcaaggtg cggcccatca agcaggtggc  16740
cccgggcctg ggcgtgcaga ccgtggacat caagattccc acggagccca tggaaacgca  16800
gaccgagccc atgatcaagc ccagcaccag caccatggag gtgcagacgg atccctggat  16860
gccatcggct cctagtcgaa gaccccggcg caagtacggc gcggccagcc tgctgatgcc  16920
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
```

```
cgccgctgca accaccccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt ggggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg gacccggtgc cgcccgccgg  17820
ctccgtggag atgccgcagg tggaggagga gctgcctccc ctggacaagc ggggcgagaa  17880
gcgaccccgc cccgatgcgg aggagacgct gctgacgcac acggacgagc cgccccccgta  17940
cgaggaggcg gtgaaactgg gtctgcccac cacgcggccc atcgcgcccc tggccaccgg  18000
ggtgctgaaa cccgaaaagc ccgcgaccct ggacttgcct cctccccagc cttcccgccc  18060
ctctacagtg gctaagcccc tgccgccggt ggccgtggcc cgcgcgcgac ccgggggcac  18120
cgcccgccct catgcgaact ggcagagcac tctgaacagc atcgtgggtc tgggagtgca  18180
gagtgtgaag cgccgccgct gctattaaac ctaccgtagc gcttaacttg cttgtctgtg  18240
tgtgtatgta ttatgtcgcc gccgccgctg tccaccagaa ggaggagtga agaggcgcgt  18300
cgccgagttg caagatggcc accccatcga tgctgcccca gtgggcgtac atgcacatcg  18360
ccggacagga cgcttcggag tacctgagtc cgggtctggt gcagtttgcc cgcgccacag  18420
acacctactt cagtctgggg aacaagttta ggaaccccac ggtggcgccc acgcacgatg  18480
tgaccaccga ccgcagccag cggctgacgc tgcgcttcgt gcccgtggac cgcgaggaca  18540
acacctactc gtacaaagtg cgctacacgc tggccgtggg cgacaaccgc gtgctggaca  18600
tggccagcac ctactttgac atccgcggcg tgctggatcg ggccctagc ttcaaaccct  18660
actccggcac cgcctacaac agtctggccc ccaagggagc acccaacact tgtcagtgga  18720
catataaagc cgatggtgaa actgccacag aaaaaaccta tacatatgga aatgcacccg  18780
tgcagggcat taacatcaca aaagatggta ttcaacttgg aactgacacc gatgatcagc  18840
caatctacgc agataaaacc tatcagcctg aacctcaagt gggtgatgct gaatggcatg  18900
acatcactgg tactgatgaa aagtatggag gcagagctct taagcctgat accaaaatga  18960
agccttgtta tggttctttt gccaagccta ctaataaaga aggaggtcag gcaaatgtga  19020
aaacaggaac aggcactact aaagaatatg acatagacat ggctttcttt gacaacagaa  19080
gtgcggctgc tgctggccta gctccagaaa ttgttttgta tactgaaaat gtggatttgg  19140
aaactccaga tacccatatt gtatacaaag caggcacaga tgacagcagc tcttctatta  19200
atttgggtca gcaagccatg cccaacagac ctaactacat tggtttcaga gacaacttta  19260
tcgggctcat gtactacaac agcactggca atatgggggt gctggccggt caggcttctc  19320
agctgaatgc tgtggttgac ttgcaagaca gaaacaccga gctgtcctac cagctcttgc  19380
ttgactctct gggtgacaga acccggtatt tcagtatgtg gaatcaggcg gtggacagct  19440
```

```
atgatcctga tgtgcgcatt attgaaaatc atggtgtgga ggatgaactt cccaactatt  19500
gtttccctct ggatgctgtt ggcagaacag atacttatca gggaattaag gctaatggaa  19560
ctgatcaaac cacatggacc aaagatgaca gtgtcaatga tgctaatgag ataggcaagg  19620
gtaatccatt cgccatggaa atcaacatcc aagccaacct gtggaggaac ttcctctacg  19680
ccaacgtggc cctgtacctg cccgactctt acaagtacac gccggccaat gttaccctgc  19740
ccaccaacac caacacctac gattacatga acggccgggt ggtggcgccc tcgctggtgg  19800
actcctacat caacatcggg gcgcgctggt cgctggatcc catggacaac gtgaacccct  19860
tcaaccacca ccgcaatgcg gggctgcgct accgctccat gctcctgggc aacgggcgct  19920
acgtgccctt ccacatccag gtgccccaga atttttcgc catcaagagc ctcctgctcc  19980
tgcccgggtc ctacacctac gagtggaact tccgcaagga cgtcaacatg atcctgcaga  20040
gctccctcgg caacgacctg cgcacggacg gggcctccat ctccttcacc agcatcaacc  20100
tctacgccac cttcttcccc atggcgcaca acacggcctc cacgctcgag gccatgctgc  20160
gcaacgacac caacgaccag tccttcaacg actacctctc ggcggccaac atgctctacc  20220
ccatcccggc caacgccacc aacgtgccca tctccatccc ctcgcgcaac tgggccgcct  20280
tccgcggctg gtccttcacg cgtctcaaga ccaaggagac gccctcgctg ggctccgggt  20340
tcgaccccta cttcgtctac tcgggctcca tcccctacct cgacggcacc ttctacctca  20400
accacacctt caagaaggtc tccatcacct tcgactcctc cgtcagctgg cccggcaacg  20460
accggctcct gacgcccaac gagttcgaaa tcaagcgcac cgtcgacggc gagggctaca  20520
acgtggccca gtgcaacatg accaaggact ggttcctggt ccagatgctg gcccactaca  20580
acatcggcta ccagggcttc tacgtgcccg agggctacaa ggaccgcatg tactccttct  20640
tccgcaactt ccagcccatg agccgccagg tggtggacga ggtcaactac aaggactacc  20700
aggccgtcac cctggcctac cagcacaaca actcgggctt cgtcggctac ctcgcgccca  20760
ccatgcgcca gggccagccc taccccgcca actaccccta cccgctcatc ggcaagagcg  20820
ccgtcaccag cgtcacccag aaaaagttcc tctgcgacag ggtcatgtgg cgcatcccct  20880
tctccagcaa cttcatgtcc atgggcgcgc tcaccgacct cggccagaac atgctctatg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacccccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgacccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
gcactggccc gaccgcccca tggacaagaa ccccaccatg aacttgctga cgggggtgcc  21600
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
```

```
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggacccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaagggggtc atcttgcagg tctgccttcc  22200
catggtgggc acgcacccgg gcttgtggtt gcaatcgcag tgcaggggga tcagcatcat  22260
ctgggcctgg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgcccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccataccct tctcccaggc cgagacgatg ggcaggctca tagggttctt  22920
caccatcatc ttagcgctag cagccgcggc cagggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
cgagggggag cgcgagttct cgctcaccac tactatctct tcctcttctt ggtccgaggc  23220
cacgcggcgg taggtatgtc tcttcggggg cagaggcgga ggcgacgggc tctcgccgcc  23280
gcgacttggc ggatggctgg cagagcccct tccgcgttcg ggggtgcgct cccggcggcg  23340
ctctgactga cttcctccgc ggccggccat tgtgttctcc tagggaggaa caacaagcat  23400
ggagactcag ccatcgccaa cctcgccatc tgccccccacc gccgacgaga agcagcagca  23460
gcagaatgaa agcttaaccg ccccgccgcc cagccccgcc acctccgacg cggccgtccc  23520
agacatgcaa gagatggagg aatccatcga gattgacctg ggctatgtga cgcccgcgga  23580
gcacgaggag gagctggcag tgcgcttttc acaagaagag atacaccaag aacagccaga  23640
gcaggaagca gagaatgagc agagtcaggc tgggctcgag catgacggcg actacctcca  23700
cctgagcggg ggggaggacg cgctcatcaa gcatctggcc cggcaggcca ccatcgtcaa  23760
ggatgcgctg ctcgaccgca ccgaggtgcc cctcagcgtg gaggagctca gccgcgccta  23820
cgagttgaac ctcttctcgc cgcgcgtgcc ccccaagcgc cagcccaatg gcacctgcga  23880
gcccaacccg cgcctcaact tctacccggt cttcgcggtg cccgaggccc tggccaccta  23940
ccacatcttt ttcaagaacc aaaagatccc cgtctcctgc cgcgccaacc gcacccgcgc  24000
cgacgccctt ttcaacctgg gtcccggcgc ccgcctacct gatatcgcct ccttggaaga  24060
ggttcccaag atcttcgagg gtctgggcag cgacgagact cgggccgcga acgctctgca  24120
aggagaagga ggagagcatg agcaccacag cgccctggtc gagttggaag gcgacaacgc  24180
```

```
gcggctggcg gtgctcaaac gcacggtcga gctgacccat ttcgcctacc cggctctgaa  24240
cctgcccccc aaagtcatga gcgcggtcat ggaccaggtg ctcatcaagc gcgcgtcgcc  24300
catctccgag gacgagggca tgcaagactc cgaggagggc aagcccgtgg tcagcgacga  24360
gcagctggcc cggtggctgg gtcctaatgc tagtccccag agtttggaag agcggcgcaa  24420
actcatgatg gccgtggtcc tggtgaccgt ggagctggag tgcctgcgcc gcttcttcgc  24480
cgacgcggag accctgcgca aggtcgagga gaacctgcac tacctcttca ggcacgggtt  24540
cgtgcgccag gcctgcaaga tctccaacgt ggagctgacc aacctggtct cctacatggg  24600
catcttgcac gagaaccgcc tggggcagaa cgtgctgcac accaccctgc gcggggaggc  24660
ccggcgcgac tacatccgcg actgcgtcta cctctacctc tgccacacct ggcagacggg  24720
catgggcgtg tggcagcagt gtctggagga gcagaacctg aaagagctct gcaagctcct  24780
gcagaagaac ctcaagggtc tgtggaccgg gttcgacgag cgcaccaccg cctcggacct  24840
ggccgacctc attttccccg agcgcctcag gctgacgctg cgcaacggcc tgcccgactt  24900
tatgagccaa agcatgttgc aaaactttcg ctctttcatc ctcgaacgct ccggaatcct  24960
gcccgccacc tgctccgcgc tgccctcgga cttcgtgccg ctgaccttcc gcgagtgccc  25020
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca agggggggtct  25260
gaaactcacc ccggggctgt ggacctcggc ctacttgcgc aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttccccc aggatgcccc gaggaaacaa gaagctgaaa gtggagctgc  25560
cgccccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
```

```
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
```

```
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aattttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgtgggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag gggtctaagg gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
gcgcttctgc tgttagtgct cccccgtccc gtcgaccccc ggtcccccac ccagtccccc  31080
gaggaggtcc gcaaatgcaa attccaagaa ccctggaaat tcctcaaatg ctaccgccaa  31140
aaatcagaca tgcatcccag ctggatcatg atcattggga tcgtgaacat tctggcctgc  31200
accctcatct cctttgtgat ttacccctgc tttgactttg gttggaactc gccagaggcg  31260
```

```
ctctatctcc cgcctgaacc tgacacacca ccacagcaac ctcaggcaca cgcactacca  31320
ccactacagc ctaggccaca atacatgccc atattagact atgaggccga gccacagcga  31380
cccatgctcc ccgctattag ttacttcaat ctaaccggcg gagatgactg acccactggc  31440
caacaacaac gtcaacgacc ttctcctgga catggacggc cgcgcctcgg agcagcgact  31500
cgcccaactt cgcattcgcc agcagcagga gagagccgtc aaggagctgc aggatgcggt  31560
ggccatccac cagtgcaaga gaggcatctt ctgcctggtg aaacaggcca agatctccta  31620
cgaggtcact ccaaacgacc atcgcctctc ctacgagctc ctgcagcagc gccagaagtt  31680
cacctgcctg gtcggagtca accccatcgt catcacccag cagtctggcg ataccaaggg  31740
gtgcatccac tgctcctgcg actcccccga ctgcgtccac actctgatca agaccctctg  31800
cggcctccgc gacctcctcc ccatgaacta atcaccccct tatccagtga aataaagatc  31860
atattgatga tgattttaca gaaataaaaa ataatcattt gatttgaaat aaagatacaa  31920
tcatattgat gatttgagtt taacaaaaaa ataaagaatc acttacttga aatctgatac  31980
caggtctctg tccatgtttt ctgccaacac cacttcactc ccctcttccc agctctggta  32040
ctgcaggccc cggcgggctg caaacttcct ccacacgctg aaggggatgt caaattcctc  32100
ctgtccctca atcttcattt tatcttctat cagatgtcca aaaagcgcgt ccgggtggat  32160
gatgacttcg accccgtcta cccctacgat gcagacaacg caccgaccgt gcccttcatc  32220
aacccccccct tcgtctcttc agatggattc caagagaagc ccctgggggt gttgtccctg  32280
cgactggccg accccgtcac caccaagaac ggggaaatca ccctcaagct gggagagggg  32340
gtggacctcg attcctcggg aaaactcatc tccaacacgg ccaccaaggc cgccgcccct  32400
ctcagttttt ccaacaacac catttccctt aacatggatc accccttttta cactaaagat  32460
ggaaaattat ccttacaagt ttctccacca ttaaatatac tgagaacaag cattctaaac  32520
acactagctt taggttttgg atcaggttta ggactccgtg gctctgcctt ggcagtacag  32580
ttagtctctc cacttacatt tgatactgat ggaaacataa agcttacctt agacagaggt  32640
ttgcatgtta caacaggaga tgcaattgaa agcaacataa gctgggctaa aggtttaaaa  32700
tttgaagatg gagccatagc aaccaacatt ggaaatgggt tagagtttgg aagcagtagt  32760
acagaaacag gtgttgatga tgcttaccca atccaagtta aacttggatc tggccttagc  32820
tttgacagta caggagccat aatggctggt aacaaagaag acgataaact cactttgtgg  32880
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg gtgttctttt aacagaacat tctacactaa aaaaatactg gggtatagg  33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg gggctaactc ttataccttc tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
```

```
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcgggggtc aaaaccatat cccagggcac  34440
ggggaactct tgcaggacag cgaaccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
tgttacactc ctgcaccatc cccagataat tttcattttt ccagccttga atgattcgaa  35220
ctagttcctg aggtaaatcc aagccagcca tgataaagag ctcgcgcaga gcgccctcca  35280
ccggcattct taagcacacc ctcataattc caagatattc tgctcctggt tcacctgcag  35340
cagattgaca agcggaatat caaaatctct gccgcgatcc ctgagctcct ccctcagcaa  35400
taactgtaag tactctttca tatcctctcc gaaattttta gccataggac caccaggaat  35460
aagattaggg caagccacag tacagataaa ccgaagtcct ccccagtgag cattgccaaa  35520
tgcaagactg ctataagcat gctggctaga cccggtgata tcttccagat aactggacag  35580
aaaatcgccc aggcaatttt taagaaaatc aacaaaagaa aaatcctcca ggtggacgtt  35640
tagagcctcg ggaacaacga tgaagtaaat gcaagcggtg cgttccagca tggttagtta  35700
gctgatctgt agaaaaaaca aaaatgaaca ttaaaccatg ctagcctggc gaacaggtgg  35760
gtaaatcgtt ctctccagca ccaggcaggc cacggggtct ccggcgcgac cctcgtaaaa  35820
attgtcgcta tgattgaaaa ccatcacaga gagacgttcc cggtggccgg cgtgaatgat  35880
tcgacaagat gaatacaccc ccggaacatt ggcgtccgcg agtgaaaaaa agcgcccgag  35940
gaagcaataa ggcactacaa tgctcagtct caagtccagc aaagcgatgc catgcggatg  36000
```

aagcacaaaa ttctcaggtg cgtacaaaat gtaattactc ccctcctgca caggcagcaa 36060
agcccccgat ccctccaggt acacatacaa agcctcagcg tccatagctt accgagcagc 36120
agcacacaac aggcgcaaga gtcagagaaa ggctgagctc taacctgtcc acccgctctc 36180
tgctcaatat atagcccaga tctacactga cgtaaaggcc aaagtctaaa aatacccgcc 36240
aaataatcac acacgcccag cacacgccca gaaaccggtg acacactcaa aaaaatacgc 36300
gcacttcctc aaacgcccaa aactgccgtc atttccgggt tcccacgcta cgtcatcaaa 36360
acacgacttt caaattccgt cgaccgttaa aaacgtcacc cgccccgccc ctaacggtcg 36420
cccgtctctc agccaatcag cgccccgcat ccccaaattc aaacacctca tttgcatatt 36480
aacgcgcaca aaaagtttga ggtatattat tgatgatgg 36519

<210> SEQ ID NO 2
<211> LENGTH: 31604
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480
atttaaacct gcgctctcca gtcaagaggc cactcttgag tgccagcgag aagagttttc 540
tcctccgcgc cgcgagtcag atctacactt tgaaagtagg gataacaggg taatgacatt 600
gattattgac tagttgttaa tagtaatcaa ttacggggtc attagttcat agcccatata 660
tggagttccg cgttacataa cttacggtaa atggcccgcc tggctgaccg cccaacgacc 720
cccgcccatt gacgtcaata atgacgtatg ttcccatagt aacgccaata gggactttcc 780
attgacgtca atgggtggag tatttacggt aaactgccca cttggcagta catcaagtgt 840
atcatatgcc aagtccgccc cctattgacg tcaatgacgg taaatggccc gcctggcatt 900
atgcccagta catgacctta cgggactttc ctacttggca gtacatctac gtattagtca 960
tcgctattac catggtgatg cggttttggc agtacaccaa tgggcgtgga tagcggtttg 1020
actcacgggg atttccaagt ctccacccca ttgacgtcaa tgggagtttg ttttggcacc 1080
aaaatcaacg ggactttcca aaatgtcgta ataaccccgc cccgttgacg caaatgggcg 1140
gtaggcgtgt acggtgggag gtctatataa gcagagctcg tttagtgaac cgtcagatcg 1200
cctggaacgc catccacgct gttttgacct ccatagaaga cagcgatcgc gccaccatgg 1260
ccgggatgtt ccaggcactg tccgaaggct gcacacccta tgatattaac cagatgctga 1320
atgtcctggg agaccaccag gtctctggcc tggagcagct ggagagcatc atcaacttcg 1380
agaagctgac cgagtggaca agctccaatg tgatgcctat cctgtcccca ctgaccaagg 1440
gcatcctggg cttcgtgttt accctgacag tgccttctga gcggggcctg tcttgcatca 1500

```
gcgaggcaga cgcaaccaca ccagagtccg ccaatctggg cgaggagatc ctgtctcagc   1560
tgtacctgtg gccccgggtg acatatcact cccctctta cgcctatcac cagttcgagc   1620
ggagagccaa gtacaagaga cacttcccag gctttggcca gtctctgctg ttcggctacc   1680
ccgtgtacgt gttcggcgat tgcgtgcagg gcgactggga tgccatccgg tttagatact   1740
gcgcaccacc tggatatgca ctgctgaggt gtaacgacac caattattcc gccctgctgg   1800
cagtgggcgc cctggagggc cctcgcaatc aggattggct gggcgtgcca aggcagctgg   1860
tgacacgcat gcaggccatc cagaacgcag gcctgtgcac cctggtggca atgctggagg   1920
agacaatctt ctggctgcag gcctttctga tggccctgac cgacagcggc cccaagacaa   1980
acatcatcgt ggattcccag tacgtgatgg gcatctccaa gccttctttc caggagtttg   2040
tggactggga gaacgtgagc ccagagctga attccaccga tcagccattc tggcaggcag   2100
gaatcctggc aaggaacctg gtgcctatgg tggccacagt gcagggccag aatctgaagt   2160
accagggcca gagcctggtc atcagcgcct ccatcatcgt gtttaacctg ctggagctgg   2220
agggcgacta tcgggacgat ggcaacgtgt gggtgcacac ccactgagc cccagaacac   2280
tgaacgcctg ggtgaaggcc gtggaggaga agaagggcat cccagtgcac ctggagctgg   2340
cctccatgac caatatggag ctgatgtcta gcatcgtgca ccagcaggtg aggacatacg   2400
gacccgtgtt catgtgcctg ggaggcctgc tgaccatggt ggcaggagcc gtgtggctga   2460
cagtgcgggt gctggagctg ttcagagccg cccagctggc caacgatgtg gtgctgcaga   2520
tcatggagct gtgcggagca gcctttcgcc aggtgtgcca caccacagtg ccatggccca   2580
atgcctccct gacccccaag tggaacaatg agacaacaca gcctcagatc gccaactgta   2640
gcgtgtacga cttcttcgtg tggctgcact actatagcgt gagggatacc ctgtggcccc   2700
gcgtgacata ccacatgaat aagtacgcct atcacatgct ggagaggcgc gccaagtata   2760
agagaggccc tggcccaggc gcaaagtttg tggcagcatg gaccctgaag gccgccgccg   2820
gccccggccc cggccagtat atcaaggcta acagtaagtt cattggaatc acagagctgg   2880
gacccggacc tggataatga gtttaaactc ccatttaaat gtgagggtta atgcttcgag   2940
cagacatgat aagatacatt gatgagtttg gacaaaccac aactagaatg cagtgaaaaa   3000
aatgctttat ttgtgaaatt tgtgatgcta ttgctttatt tgtaaccatt ataagctgca   3060
ataaacaagt taacaacaac aattgcattc attttatgtt tcaggttcag ggggagatgt   3120
gggaggtttt ttaaagcaag taaaacctct acaaatgtgg taaaataact ataacggtcc   3180
taaggtagcg agtgagtagt gttctggggc gggggaggac ctgcatgagg gccagaataa   3240
ctgaaatctg tgcttttctg tgtgttgcag cagcatgagc ggaagcggct cctttgaggg   3300
aggggtattc agcccttatc tgacggggcg tctcccctcc tgggcgggag tgcgtcagaa   3360
tgtgatggga tccacggtgg acggccggcc cgtgcagccc gcgaactctt caaccctgac   3420
ctatgcaacc ctgagctctt cgtcgttgga cgcagctgcc gccgcagctg ctgcatctgc   3480
cgccagcgcc gtgcgcggaa tggccatggg cgccggctac tacggcactc tggtggccaa   3540
ctcgagttcc accaataatc ccgccagcct gaacgaggag aagctgttgc tgctgatggc   3600
ccagctcgag gccttgaccc agcgcctggg cgagctgacc cagcaggtgg ctcagctgca   3660
ggagcagacg cgggccgcgg ttgccacggt gaaatccaaa taaaaaatga atcaataaat   3720
aaacggagac ggttgttgat tttaacacag agtctgaatc tttatttgat ttttcgcgcg   3780
cggtaggccc tggaccaccg gtctcgatca ttgagcaccc ggtggatctt ttccaggacc   3840
cggtagaggt gggcttggat gttgaggtac atgggcatga gcccgtcccg gggtggagg    3900
```

```
tagctccatt gcagggcctc gtgctcgggg gtggtgttgt aaatcaccca gtcatagcag   3960
gggcgcaggg catggtgttg cacaatatct ttgaggagga gactgatggc cacgggcagc   4020
cctttggtgt aggtgtttac aaatctgttg agctgggagg gatgcatgcg gggggagatg   4080
aggtgcatct tggcctggat cttgagattg gcgatgttac cgcccagatc ccgcctgggg   4140
ttcatgttgt gcaggaccac cagcacggtg tatccggtgc acttggggaa tttatcatgc   4200
aacttggaag ggaaggcgtg aaagaatttg gcgacgcctt tgtgcccgcc caggttttcc   4260
atgcactcat ccatgatgat ggcgatgggc ccgtgggcgg cggcctgggc aaagacgttt   4320
cgggggtcgg acacatcata gttgtggtcc tgggtgaggt catcataggc cattttaatg   4380
aatttggggc ggagggtgcc ggactggggg acaaaggtac cctcgatccc gggggcgtag   4440
ttcccctcac agatctgcat ctcccaggct ttgagctcgg aggggggat catgtccacc   4500
tgcggggcga taaagaacac ggtttccggg gcgggggaga tgagctgggc cgaaagcaag   4560
ttccggagca gctgggactt gccgcagccg gtggggccgt agatgacccc gatgaccggc   4620
tgcaggtggt agttgaggga gagacagctg ccgtcctccc ggaggagggg ggccacctcg   4680
ttcatcatct cgcgcacgtg catgttctcg cgcaccagtt ccgccaggag gcgctctccc   4740
cccagggata ggagctcctg gagcgaggcg aagtttttca gcggcttgag tccgtcggcc   4800
atgggcattt tggagagggt ttgttgcaag agttccaggc ggtcccagag ctcggtgatg   4860
tgctctacgg catctcgatc cagcagacct cctcgtttcg cgggttggga cggctgcggg   4920
agtagggcac cagacgatgg gcgtccagcg cagccagggt ccggtccttc cagggtcgca   4980
gcgtccgcgt cagggtggtc tccgtcacgg tgaaggggtg cgcgccgggc tgggcgcttg   5040
cgagggtgcg cttcaggctc atccggctgg tcgaaaaccg ctcccgatcg gcgccctgcg   5100
cgtcggccag gtagcaattg accatgagtt cgtagttgag cgcctcggcc gcgtggcctt   5160
tggcgcggag cttacctttg gaagtctgcc cgcaggcggg acagaggagg gacttgaggg   5220
cgtagagctt gggggcgagg aagacggact cgggggcgta ggcgtccgcg ccgcagtggg   5280
cgcagacggt ctcgcactcc acgagccagg tgaggtcggg ctggtcgggg tcaaaaacca   5340
gtttcccgcc gttctttttg atgcgtttct tacctttggt ctccatgagc tcgtgtcccc   5400
gctgggtgac aaagaggctg tccgtgtccc cgtagaccga ctttatgggc cggtcctcga   5460
gcggtgtgcc gcggtcctcc tcgtagagga accccgccca ctccgagacg aaagcccggg   5520
tccaggccag cacgaaggag gccacgtggg acgggtagcg gtcgttgtcc accagcgggt   5580
ccaccttttc cagggtatgc aaacacatgt ccccctcgtc cacatccagg aaggtgattg   5640
gcttgtaagt gtaggccacg tgaccggggg tcccggccgg gggggtataa aagggtgcgg   5700
gtccctgctc gtcctcactg tcttccggat cgctgtccag gagcgccagc tgttggggta   5760
ggtattccct ctcgaaggcg ggcatgacct cggcactcag gttgtcagtt tctagaaacg   5820
aggaggattt gatattgacg gtgccggcgg agatgccttt caagagcccc tcgtccatct   5880
ggtcagaaaa gacgatcttt ttgttgtcga gcttggtggc gaaggagccg tagagggcgt   5940
tggagaggag cttggcgatg gagcgcatgg tctggttttt ttccttgtcg gcgcgctcct   6000
tggcggcgat gttgagctgc acgtactcgc gcgccacgca cttccattcg gggaagacgg   6060
tggtcagctc gtcgggcacg attctgacct gccagccccg attatgcagg gtgatgaggt   6120
ccacactggt ggccacctcg ccgcgcaggg gctcattagt ccagcagagg cgtccgccct   6180
tgcgcgagca gaagggggc agggggtcca gcatgacctc gtcgggggg tcggcatcga   6240
```

```
tggtgaagat gccgggcagg aggtcggggt caaagtagct gatggaagtg gccagatcgt   6300
ccagggcagc ttgccattcg cgcacggcca gcgcgcgctc gtagggactg aggggcgtgc   6360
cccagggcat gggatgggta agcgcggagg cgtacatgcc gcagatgtcg tagacgtaga   6420
ggggctcctc gaggatgccg atgtaggtgg ggtagcagcg ccccccgcgg atgctggcgc   6480
gcacgtagtc atacagctcg tgcgaggggg cgaggagccc cgggcccagg ttggtgcgac   6540
tgggcttttc ggcgcggtag acgatctggc ggaaaatggc atgcgagttg gaggagatgg   6600
tgggcctttg gaagatgttg aagtgggcgt ggggcagtcc gaccgagtcg cggatgaagt   6660
gggcgtagga gtcttgcagc ttggcgacga gctcggcggt gactaggacg tccagagcgc   6720
agtagtcgag ggtctcctgg atgatgtcat acttgagctg tcccttttgt ttccacagct   6780
cgcggttgag aaggaactct tcgcggtcct tccagtactc ttcgaggggg aacccgtcct   6840
gatctgcacg gtaagagcct agcatgtaga actggttgac ggccttgtag gcgcagcagc   6900
ccttctccac ggggagggcg taggcctggg cggccttgcg cagggaggtg tgcgtgaggg   6960
cgaaagtgtc cctgaccatg accttgagga actggtgctt gaagtcgata tcgtcgcagc   7020
ccccctgctc ccagagctgg aagtccgtgc gcttcttgta ggcggggttg ggcaaagcga   7080
aagtaacatc gttgaagagg atcttgcccg cgcggggcat aaagttgcga gtgatgcgga   7140
aaggttgggg cacctcggcc cggttgttga tgacctgggc ggcgagcacg atctcgtcga   7200
agccgttgat gttgtggccc acgatgtaga gttccacgaa tcgcggacgg cccttgacgt   7260
ggggcagttt cttgagctcc tcgtaggtga gctcgtcggg gtcgctgagc ccgtgctgct   7320
cgagcgccca gtcggcgaga tgggggttgg cgcggaggaa ggaagtccag agatccacgg   7380
ccagggcggt ttgcagacgg tcccggtact gacggaactg ctgcccgacg gccatttttt   7440
cgggggtgac gcagtagaag gtgcgggggt ccccgtgcca gcgatcccat ttgagctgga   7500
gggcgagatc gagggcgagc tcgacgagcc ggtcgtcccc ggagagtttc atgaccagca   7560
tgaaggggac gagctgcttg ccgaaggacc ccatccaggt gtaggtttcc acatcgtagg   7620
tgaggaagag cctttcggtg cgaggatgcg agccgatggg gaagaactgg atctcctgcc   7680
accaattgga ggaatggctg ttgatgtgat ggaagtagaa atgccgacgg cgcgccgaac   7740
actcgtgctt gtgtttatac aagcggccac agtgctcgca acgctgcacg ggatgcacgt   7800
gctgcacgag ctgtacctga gttcctttga cgaggaattt cagtgggaag tggagtcgtg   7860
gcgcctgcat ctcgtgctgt actacgtcgt ggtggtcggc ctggccctct tctgcctcga   7920
tggtggtcat gctgacgagc ccgcgcggga ggcaggtcca gacctcggcg cgagcgggtc   7980
ggagagcgag gacgagggcg cgcaggccgg agctgtccag ggtcctgaga cgctgcggag   8040
tcaggtcagt gggcagcggc ggcgcgcggt tgacttgcag gagtttttcc agggcgcgcg   8100
ggaggtccag atggtacttg atctccaccg cgccattggt ggcgacgtcg atggcttgca   8160
gggtcccgtg cccctggggt gtgaccaccg tcccccgttt cttcttgggc ggctggggcg   8220
acgggggcgg tgcctcttcc atggttagaa gcggcggcga ggacgcgcgc cgggcggcag   8280
gggcggctcg gggcccggag gcaggggcgg caggggcacg tcggcgccgc gcgcgggtag   8340
gttctggtac tgcgcccgga gaagactggc gtgagcgacg acgcgacggt tgacgtcctg   8400
gatctgacgc ctctgggtga aggccacggg acccgtgagt ttgaacctga aagagagttc   8460
gacagaatca atctcggtat cgttgacggc ggcctgccgc aggatctctt gcacgtcgcc   8520
cgagttgtcc tggtaggcga tctcggtcat gaactgctcg atctcctcct cttgaaggtc   8580
tccgcggccg gcgcgctcca cggtggccgc gaggtcgttg gagatgcggc ccatgagctg   8640
```

```
cgagaaggcg ttcatgcccg cctcgttcca gacgcggctg tagaccacga cgccctcggg   8700
atcgcgggcg cgcatgacca cctgggcgag gttgagctcc acgtggcgcg tgaagaccgc   8760
gtagttgcag aggcgctggt agaggtagtt gagcgtggtg gcgatgtgct cggtgacgaa   8820
gaaatacatg atccagcggc ggagcggcat ctcgctgacg tcgcccagcg cctccaaacg   8880
ttccatggcc tcgtaaaagt ccacggcgaa gttgaaaaac tgggagttgc gcgccgagac   8940
ggtcaactcc tcctccagaa gacggatgag ctcggcgatg gtggcgcgca cctcgcgctc   9000
gaaggccccc gggagttcct ccacttcctc ttcttcctcc tccactaaca tctcttctac   9060
ttcctcctca ggcggcagtg gtggcggggg agggggcctg cgtcgccggc ggcgcacggg   9120
cagacggtcg atgaagcgct cgatggtctc gccgcgccgg cgtcgcatgg tctcggtgac   9180
ggcgcgcccg tcctcgcggg gccgcagcgt gaagacgccg ccgcgcatct ccaggtggcc   9240
gggggggtcc ccgttgggca gggagagggc gctgacgatg catcttatca attgccccgt   9300
agggactccg cgcaaggacc tgagcgtctc gagatccacg ggatctgaaa accgctgaac   9360
gaaggcttcg agccagtcgc agtcgcaagg taggctgagc acggtttctt ctggcgggtc   9420
atgttggttg ggagcggggc gggcgatgct gctggtgatg aagttgaaat aggcggttct   9480
gagacggcgg atggtggcga ggagcaccag gtctttgggc ccggcttgct ggatgcgcag   9540
acggtcggcc atgccccagg cgtggtcctg acacctggcc aggtccttgt agtagtcctg   9600
catgagccgc tccacgggca cctcctcctc gcccgcgcgg ccgtgcatgc gcgtgagccc   9660
gaagccgcgc tggggctgga cgagcgccag gtcggcgacg acgcgctcgg cgaggatggc   9720
ttgctggatc tgggtgaggg tggtctggaa gtcatcaaag tcgacgaagc ggtggtaggc   9780
tccggtgttg atggtgtagg agcagttggc catgacggac cagttgacgg tctggtggcc   9840
cggacgcacg agctcgtggt acttgaggcg cgagtaggcg cgcgtgtcga agatgtagtc   9900
gttgcaggtg cgcaccaggt actggtagcc gatgaggaag tgcggcggcg gctggcggta   9960
gagcggccat cgctcggtgg cgggggcgcc gggcgcgagg tcctcgagca tggtgcggtg  10020
gtagccgtag atgtacctgg acatccaggt gatgccggcg gcggtggtgg aggcgcgcgg  10080
gaactcgcgg acgcggttcc agatgttgcg cagcggcagg aagtagttca tggtgggcac  10140
ggtctggccc gtgaggcgcg cgcagtcgtg gatgctctat acgggcaaaa acgaaagcgg  10200
tcagcggctc gactccgtgg cctggaggct aagcgaacgg gttgggctgc gcgtgtaccc  10260
cggttcgaat ctcgaatcag gctggagccg cagctaacgt ggtattggca ctcccgtctc  10320
gacccaagcc tgcaccaacc ctccaggata cggaggcggg tcgttttgca acttttttt   10380
ggaggccgga tgagactagt aagcgcggaa agcggccgac cgcgatggct cgctgccgta  10440
gtctggagaa gaatcgccag ggttgcgttg cggtgtgccc cggttcgagg ccggccggat  10500
tccgcggcta acgagggcgt ggctgccccg tcgtttccaa gaccccatag ccagccgact  10560
tctccagtta cggagcgagc ccctcttttg ttttgtttgt ttttgccaga tgcatcccgt  10620
actgcggcag atgcgccccc accaccctcc accgcaacaa cagccccctc cacagccggc  10680
gcttctgccc ccgccccagc agcaacttcc agccacgacc gccgcggccg ccgtgagcgg  10740
ggctggacag agttatgatc accagctggc cttggaagag ggcgaggggc tggcgcgcct  10800
gggggcgtcg tcgccggagc ggcacccgcg cgtgcagatg aaaagggacg ctcgcgaggc  10860
ctacgtgccc aagcagaacc tgttcagaga caggagcggc gaggagcccg aggagatgcg  10920
cgcggcccgg ttccacgcgg ggcgggagct gcggcgcggc ctggaccgaa agagggtgct  10980
```

```
gagggacgag gatttcgagg cggacgagct gacggggatc agccccgcgc gcgcgcacgt  11040
ggccgcggcc aacctggtca cggcgtacga gcagaccgtg aaggaggaga gcaacttcca  11100
aaaatccttc aacaaccacg tgcgcaccct gatcgcgcgc gaggaggtga ccctgggcct  11160
gatgcacctg tgggacctgc tggaggccat cgtgcagaac cccaccagca agccgctgac  11220
ggcgcagctg ttcctggtgg tgcagcatag tcgggacaac gaagcgttca gggaggcgct  11280
gctgaatatc accgagcccg agggccgctg gctcctggac ctggtgaaca ttctgcagag  11340
catcgtggtg caggagcgcg ggctgccgct gtccgagaag ctggcggcca tcaacttctc  11400
ggtgctgagt ttgggcaagt actacgctag gaagatctac aagaccccgt acgtgcccat  11460
agacaaggag gtgaagatcg acgggtttta catgcgcatg accctgaaag tgctgaccct  11520
gagcgacgat ctgggggtgt accgcaacga caggatgcac cgtgcggtga gcgccagcag  11580
gcggcgcgag ctgagcgacc aggagctgat gcatagtctg cagcgggccc tgaccggggc  11640
cgggaccgag ggggagagct actttgacat gggcgcggac ctgcactggc agcccagccg  11700
ccgggccttg gaggcggcgg caggacccta cgtagaagag gtggacgatg aggtggacga  11760
ggagggcgag tacctggaag actgatggcg cgaccgtatt tttgctagat gcaacaacaa  11820
cagccacctc ctgatcccgc gatgcgggcg gcgctgcaga gccagccgtc cggcattaac  11880
tcctcggacg attggaccca ggccatgcaa cgcatcatgg cgctgacgac ccgcaacccc  11940
gaagccttta gacagcagcc ccaggccaac cggctctcgg ccatcctgga ggccgtggtg  12000
ccctcgcgct ccaaccccac gcacgagaag gtcctggcca tcgtgaacgc gctggtggag  12060
aacaaggcca tccgcggcga cgaggccggc ctggtgtaca acgcgctgct ggagcgcgtg  12120
gcccgctaca acagcaccaa cgtgcagacc aacctggacc gcatggtgac cgacgtgcgc  12180
gaggccgtgg cccagcgcga gcggttccac cgcgagtcca acctgggatc catggtggcg  12240
ctgaacgcct tcctcagcac ccagcccgcc aacgtgcccc ggggccagga ggactacacc  12300
aacttcatca gcgccctgcg cctgatggtg accgaggtgc cccagagcga ggtgtaccag  12360
tccgggccgg actacttctt ccagaccagt cgccagggct tgcagaccgt gaacctgagc  12420
caggctttca agaacttgca gggcctgtgg ggcgtgcagg ccccggtcgg ggaccgcgcg  12480
acggtgtcga gcctgctgac gccgaactcg cgcctgctgc tgctgctggt ggccccottc  12540
acggacagcg gcagcatcaa ccgcaactcg tacctgggct acctgattaa cctgtaccgc  12600
gaggccatcg gccaggcgca cgtggacgag cagacctacc aggagatcac ccacgtgagc  12660
cgcgccctgg gccaggacga cccgggcaac ctggaagcca ccctgaactt tttgctgacc  12720
aaccggtcgc agaagatccc gccccagtac gcgctcagca ccgaggagga gcgcatcctg  12780
cgttacgtgc agcagagcgt gggcctgttc ctgatgcagg agggggccac ccccagcgcc  12840
gcgctcgaca tgaccgcgcg caacatggag cccagcatgt acgccagcaa ccgcccgttc  12900
atcaataaac tgatggacta cttgcatcgg gcggccgcca tgaactctga ctatttcacc  12960
aacgccatcc tgaatcccca ctggctcccg ccgccggggt tctacacggg cgagtacgac  13020
atgcccgacc ccaatgacgg gttcctgtgg gacgatgtgg acagcagcgt gttctccccc  13080
cgaccgggtg ctaacgagcg ccccttgtgg aagaaggaag gcagcgaccg acgcccgtcc  13140
tcggcgctgt ccggccgcga gggtgctgcc gcggcggtgc ccgaggccgc cagtcctttc  13200
ccgagcttgc ccttctcgct gaacagtatc cgcagcagcg agctgggcag gatcacgcgc  13260
ccgcgcttgc tgggcgaaga ggagtacttg aatgactcgc tgttgagacc cgagcgggag  13320
aagaacttcc ccaataacgg gatagaaagc ctggtggaca agatgagccg ctggaagacg  13380
```

```
tatgcgcagg agcacaggga cgatccccgg gcgtcgcagg gggccacgag ccggggcagc  13440
gccgcccgta aacgccggtg gcacgacagg cagcggggac agatgtggga cgatgaggac  13500
tccgccgacg acagcagcgt gttggacttg ggtgggagtg gtaacccgtt cgctcacctg  13560
cgcccccgta tcgggcgcat gatgtaagag aaaccgaaaa taaatgatac tcaccaaggc  13620
catggcgacc agcgtgcgtt cgtttcttct ctgttgttgt tgtatctagt atgatgaggc  13680
gtgcgtaccc ggagggtcct cctccctcgt acgagagcgt gatgcagcag gcgatggcgg  13740
cggcggcgat gcagcccccg ctggaggctc cttacgtgcc cccgcggtac ctggcgccta  13800
cggaggggcg gaacagcatt cgttactcgg agctggcacc cttgtacgat accacccggt  13860
tgtacctggt ggacaacaag tcggcggaca tcgcctcgct gaactaccag aacgaccaca  13920
gcaacttcct gaccaccgtg gtgcagaaca atgacttcac ccccacggag gccagcaccc  13980
agaccatcaa ctttgacgag cgctcgcggt ggggcggcca gctgaaaacc atcatgcaca  14040
ccaacatgcc caacgtgaac gagttcatgt acagcaacaa gttcaaggcg cgggtgatgg  14100
tctcccgcaa gacccccaat ggggtgacag tgacagagga ttatgatggt agtcaggatg  14160
agctgaagta tgaatgggtg gaatttgagc tgcccgaagg caacttctcg gtgaccatga  14220
ccatcgacct gatgaacaac gccatcatcg acaattactt ggcggtgggg cggcagaacg  14280
gggtgctgga gagcgacatc ggcgtgaagt tcgacactag gaacttcagg ctgggctggg  14340
accccgtgac cgagctggtc atgcccgggg tgtacaccaa cgaggctttc catcccgata  14400
ttgtcttgct gcccggctgc ggggtggact tcaccgagag ccgcctcagc aacctgctgg  14460
gcattcgcaa gaggcagccc ttccaggaag gcttccagat catgtacgag gatctggagg  14520
ggggcaacat ccccgcgctc ctggatgtcg acgcctatga gaaaagcaag gaggatgcag  14580
cagctgaagc aactgcagcc gtagctaccg cctctaccga ggtcaggggc gataattttg  14640
caagcgccgc agcagtggca gcggccgagg cggctgaaac cgaaagtaag atagtcattc  14700
agccggtgga gaaggatagc aagaacagga gctacaacgt actaccggac aagataaaca  14760
ccgcctaccg cagctggtac ctagcctaca actatggcga ccccgagaag ggcgtgcgct  14820
cctggacgct gctcaccacc tcggacgtca cctgcggcgt ggagcaagtc tactggtcgc  14880
tgcccgacat gatgcaagac ccggtcacct tccgctccac gcgtcaagtt agcaactacc  14940
cggtggtggg cgccgagctc ctgcccgtct actccaagag cttcttcaac gagcaggccg  15000
tctactcgca gcagctgcgc gccttcacct cgcttacgca cgtcttcaac cgcttccccg  15060
agaaccagat cctcgtccgc ccgcccgcgc ccaccattac caccgtcagt gaaaacgttc  15120
ctgctctcac agatcacggg accctgccgc tgcgcagcag tatccgggga gtccagcgcg  15180
tgaccgttac tgacgccaga cgccgcacct gcccctacgt ctacaaggcc ctgggcatag  15240
tcgcgccgcg cgtcctctcg agccgcacct tctaaatgtc cattctcatc tcgcccagta  15300
ataacaccgg ttggggcctg cgcgcgccca gcaagatgta cggaggcgct cgccaacgct  15360
ccacgcaaca ccccgtgcgc gtgcgcgggc acttccgcgc tccctggggc gccctcaagg  15420
gccgcgtgcg gtcgcgcacc accgtcgacg acgtgatcga ccaggtggtg gccgacgcgc  15480
gcaactacac ccccgccgcc gcgcccgtct ccaccgtgga cgccgtcatc gacagcgtgg  15540
tggccgacgc gcgccggtac gcccgcgcca agagccggcg gcggcgcatc gcccggcggc  15600
accggagcac ccccgccatg cgcgcggcgc gagccttgct gcgcagggcc aggcgcacgg  15660
gacgcagggc catgctcagg gcggccagac gcgcggcttc aggcgccagc gccggcagga  15720
```

```
cccggagacg cgcggccacg gcggcggcag cggccatcgc cagcatgtcc cgcccgcggc  15780
gagggaacgt gtactgggtg cgcgacgccg ccaccggtgt gcgcgtgccc gtgcgcaccc  15840
gcccccctcg cacttgaaga tgttcacttc gcgatgttga tgtgtcccag cggcgaggag  15900
gatgtccaag cgcaaattca aggaagagat gctccaggtc atcgcgcctg agatctacgg  15960
ccctgcggtg gtgaaggagg aaagaaagcc ccgcaaaatc aagcgggtca aaaaggacaa  16020
aaaggaagaa gaaagtgatg tggacggatt ggtggagttt gtgcgcgagt tcgccccccg  16080
gcggcgcgtg cagtggcgcg ggcggaaggt gcaaccggtg ctgagacccg gcaccaccgt  16140
ggtcttcacg cccggcgagc gctccggcac cgcttccaag cgctcctacg acgaggtgta  16200
cggggatgat gatattctgg agcaggcggc cgagcgcctg ggcgagtttg cttacggcaa  16260
gcgcagccgt tccgcaccga aggaagaggc ggtgtccatc ccgctggacc acggcaaccc  16320
cacgccgagc ctcaagcccg tgaccttgca gcaggtgctg ccgaccgcgg cgccgcgccg  16380
ggggttcaag cgcgagggcg aggatctgta ccccaccatg cagctgatgg tgcccaagcg  16440
ccagaagctg gaagacgtgc tggagaccat gaaggtggac ccggacgtgc agcccgaggt  16500
caaggtgcgg cccatcaagc aggtggcccc gggcctgggc gtgcagaccg tggacatcaa  16560
gattcccacg gagcccatgg aaacgcagac cgagcccatg atcaagccca gcaccagcac  16620
catggaggtg cagacggatc cctggatgcc atcggctcct agtcgaagac cccggcgcaa  16680
gtacggcgcg gccagcctgc tgatgcccaa ctacgcgctg catccttcca tcatccccac  16740
gccgggctac cgcggcacgc gcttctaccg cggtcatacc agcagccgcc gccgcaagac  16800
caccactcgc cgccgccgtc gccgcaccgc cgctgcaacc acccctgccg ccctggtgcg  16860
gagagtgtac cgccgcggcc gcgcacctct gaccctgccg cgcgcgcgct accacccgag  16920
catcgccatt taaactttcg cctgctttgc agatcaatgg ccctcacatg ccgccttcgc  16980
gttcccatta cgggctaccg aggaagaaaa ccgcgccgta gaaggctggc ggggaacggg  17040
atgcgtcgcc accaccaccg gcggcggcgc gccatcagca agcggttggg gggaggcttc  17100
ctgcccgcgc tgatccccat catcgccgcg gcgatcgggg cgatccccgg cattgcttcc  17160
gtggcggtgc aggcctctca gcgccactga gacacacttg gaaacatctt gtaataaacc  17220
aatggactct gacgctcctg gtcctgtgat gtgttttcgt agacagatgg aagacatcaa  17280
tttttcgtcc ctggctccgc gacacggcac gcggccgttc atgggcacct ggagcgacat  17340
cggcaccagc caactgaacg gggggcgcctt caattggagc agtctctgga gcgggcttaa  17400
gaatttcggg tccacgctta aaacctatgg cagcaaggcg tggaacagca ccacagggca  17460
ggcgctgagg gataagctga aagagcagaa cttccagcag aaggtggtcg atgggctcgc  17520
ctcgggcatc aacggggtgg tggacctggc caaccaggcc gtgcagcggc agatcaacag  17580
ccgcctggac ccggtgccgc ccgccggctc cgtggagatg ccgcaggtgg aggaggagct  17640
gcctcccctg gacaagcggg gcgagaagcg accccgcccc gatgcggagg agacgctgct  17700
gacgcacacg gacgagccgc ccccgtacga ggaggcggtg aaactgggtc tgcccaccac  17760
gcggcccatc gcgcccctgg ccaccggggt gctgaaaccc gaaaagcccg cgaccctgga  17820
cttgcctcct ccccagcctt cccgcccctc tacagtggct aagcccctgc cgccggtggc  17880
cgtggcccgc gcgcgacccg gggcaccgc ccgccctcat gcgaactggc agagcactct  17940
gaacagcatc gtgggtctgg gagtgcagag tgtgaagcgc cgccgctgct attaaaccta  18000
ccgtagcgct taacttgctt gtctgtgtgt gtatgtatta tgtcgccgcc gccgctgtcc  18060
accagaagga ggagtgaaga ggcgcgtcgc cgagttgcaa gatggccacc ccatcgatgc  18120
```

```
tgccccagtg ggcgtacatg cacatcgccg gacaggacgc ttcggagtac ctgagtccgg  18180
gtctggtgca gtttgcccgc gccacagaca cctacttcag tctggggaac aagtttagga  18240
accccacggt ggcgcccacg cacgatgtga ccaccgaccg cagccagcgg ctgacgctgc  18300
gcttcgtgcc cgtggaccgc gaggacaaca cctactcgta caaagtgcgc tacacgctgg  18360
ccgtgggcga caaccgcgtg ctggacatgg ccagcaccta ctttgacatc cgcggcgtgc  18420
tggatcgggg ccctagcttc aaaccctact ccggcaccgc ctacaacagt ctggccccca  18480
agggagcacc caacacttgt cagtggacat ataaagccga tggtgaaact gccacagaaa  18540
aaacctatac atatggaaat gcacccgtgc agggcattaa catcacaaaa gatggtattc  18600
aacttggaac tgacaccgat gatcagccaa tctacgcaga taaaacctat cagcctgaac  18660
ctcaagtggg tgatgctgaa tggcatgaca tcactggtac tgatgaaaag tatggaggca  18720
gagctcttaa gcctgatacc aaaatgaagc cttgttatgg ttcttttgcc aagcctacta  18780
ataaagaagg aggtcaggca aatgtgaaaa caggaacagg cactactaaa gaatatgaca  18840
tagacatggc tttctttgac aacagaagtg cggctgctgc tggcctagct ccagaaattg  18900
ttttgtatac tgaaaatgtg gatttggaaa ctccagatac ccatattgta tacaaagcag  18960
gcacagatga cagcagctct tctattaatt tgggtcagca agccatgccc aacagaccta  19020
actacattgg tttcagagac aactttatcg ggctcatgta ctacaacagc actggcaata  19080
tgggggtgct ggccggtcag gcttctcagc tgaatgctgt ggttgacttg caagacagaa  19140
acaccgagct gtcctaccag ctcttgcttg actctctggg tgacagaacc cggtatttca  19200
gtatgtggaa tcaggcggtg gacagctatg atcctgatgt gcgcattatt gaaaatcatg  19260
gtgtggagga tgaacttccc aactattgtt tccctctgga tgctgttggc agaacagata  19320
cttatcaggg aattaaggct aatggaactg atcaaaccac atggaccaaa gatgacagtg  19380
tcaatgatgc taatgagata ggcaagggta atccattcgc catggaaatc aacatccaag  19440
ccaacctgtg gaggaacttc ctctacgcca acgtggccct gtacctgccc gactcttaca  19500
agtacacgcc ggccaatgtt accctgccca ccaacaccaa cacctacgat tacatgaacg  19560
gccgggtggt ggcgccctcg ctggtggact cctacatcaa catcggggcg cgctggtcgc  19620
tggatcccat ggacaacgtg aaccccttca accaccaccg caatgcgggg ctgcgctacc  19680
gctccatgct cctgggcaac gggcgctacg tgcccttcca catccaggtg ccccagaaat  19740
tttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg acccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
gctacaagga ccgcatgtac tccttcttcc gcaacttcca gcccatgagc cgccaggtgg  20460
```

```
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc accccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc cccgcacaag ctggcctgcg ccatcgtcaa  21060
cacggccggc cgcgagaccg gggggcgagca ctggctggcc ttcgcctgga acccgcgctc  21120
gaacacctgc tacctcttcg acccccttcgg gttctcggac gagcgcctca agcagatcta  21180
ccagttcgag tacgagggcc tgctgcgccg cagcgccctg gccaccgagg accgctgcgt  21240
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
atcgcagtgc agggggatca gcatcatctg ggcctggtcg gcgttcatcc ccgggtacat  22080
ggccttcatg aaagcctcca attgcctgaa cgcctgctgg gccttggctc cctcggtgaa  22140
gaagaccccg caggacttgc tagagaactg gttggtggcg cacccggcgt cgtgcacgca  22200
gcagcgcgcg tcgttgttgg ccagctgcac cacgctgcgc ccccagcggt tctgggtgat  22260
cttggcccgg tcggggttct ccttcagcgc gcgctgcccg ttctcgctcg ccacatccat  22320
ctcgatcatg tgctccttct ggatcatggt ggtcccgtgc aggcaccgca gcttgccctc  22380
ggcctcggtg cacccgtgca gccacagcgc gcacccggtg cactcccagt tcttgtgggc  22440
gatctgggaa tgcgcgtgca cgaagccctg caggaagcgg cccatcatgg tggtcagggt  22500
cttgttgcta gtgaaggtca gcggaatgcc gcggtgctcc tcgttgatgt acaggtggca  22560
gatgcggcgg tacacctcgc cctgctcggg catcagctgg aagttggctt tcaggtcggt  22620
ctccacgcgg tagcggtcca tcagcatagt catgatttcc ataccttct cccaggccga  22680
gacgatgggc aggctcatag ggttcttcac catcatctta gcgctagcag ccgcggccag  22740
ggggtcgctc tcgtccaggg tctcaaagct ccgcttgccg tccttctcgg tgatccgcac  22800
cggggggtag ctgaagccca cggccgccag ctcctcctcg gcctgtcttt cgtcctcgct  22860
```

```
gtcctggctg acgtcctgca ggaccacatg cttggtcttg cggggtttct tcttgggcgg  22920
cagcggcggc ggagatgttg gagatggcga gggggagcgc gagttctcgc tcaccactac  22980
tatctcttcc tcttcttggt ccgaggccac gcggcggtag gtatgtctct tcgggggcag  23040
aggcggaggc gacgggctct cgccgccgcg acttggcgga tggctggcag agccccttcc  23100
gcgttcgggg gtgcgctccc ggcggcgctc tgactgactt cctccgcggc cggccattgt  23160
gttctcctag ggaggaacaa caagcatgga gactcagcca tcgccaacct cgccatctgc  23220
ccccaccgcc gacgagaagc agcagcagca gaatgaaagc ttaaccgccc cgccgcccag  23280
ccccgccacc tccgacgcgg ccgtcccaga catgcaagag atggaggaat ccatcgagat  23340
tgacctgggc tatgtgacgc ccgcggagca cgaggaggag ctggcagtgc gcttttcaca  23400
agaagagata caccaagaac agccagagca ggaagcagag aatgagcaga gtcaggctgg  23460
gctcgagcat gacggcgact acctccacct gagcgggggg gaggacgcgc tcatcaagca  23520
tctggcccgg caggccacca tcgtcaagga tgcgctgctc gaccgcaccg aggtgcccct  23580
cagcgtggag gagctcagcc gcgcctacga gttgaacctc ttctcgccgc gcgtgccccc  23640
caagcgccag cccaatggca cctgcgagcc caacccgcgc ctcaacttct acccggtctt  23700
cgcggtgccc gaggccctgg ccacctacca catctttttc aagaaccaaa agatccccgt  23760
ctcctgccgc gccaaccgca cccgcgccga cgcccttttc aacctgggtc ccggcgcccg  23820
cctacctgat atcgcctcct tggaagaggt tcccaagatc ttcgagggtc tgggcagcga  23880
cgagactcgg gccgcgaacg ctctgcaagg agaaggagga gagcatgagc accacagcgc  23940
cctggtcgag ttggaaggcg acaacgcgcg gctggcggtg ctcaaacgca cggtcgagct  24000
gacccatttc gcctacccgg ctctgaacct gccccccaaa gtcatgagcg cggtcatgga  24060
ccaggtgctc atcaagcgcg cgtcgcccat ctccgaggac gagggcatgc aagactccga  24120
ggagggcaag cccgtggtca gcgacgagca gctggcccgg tggctgggtc ctaatgctag  24180
tccccagagt ttggaagagc ggcgcaaact catgatggcc gtggtcctgg tgaccgtgga  24240
gctggagtgc ctgcgccgct tcttcgccga cgcggagacc ctgcgcaagg tcgaggagaa  24300
cctgcactac ctcttcaggc acgggttcgt gcgccaggcc tgcaagatct ccaacgtgga  24360
gctgaccaac ctggtctcct acatgggcat cttgcacgag aaccgcctgg ggcagaacgt  24420
gctgcacacc accctgcgcg gggaggcccg gcgcgactac atccgcgact gcgtctacct  24480
ctacctctgc cacacctggc agacgggcat gggcgtgtgg cagcagtgtc tggaggagca  24540
gaacctgaaa gagctctgca agctcctgca gaagaacctc aagggtctgt ggaccgggtt  24600
cgacgagcgc accaccgcct cggacctggc cgacctcatt ttccccgagc gcctcaggct  24660
gacgctgcgc aacggcctgc ccgactttat gagccaaagc atgttgcaaa actttcgctc  24720
tttcatcctc gaacgctccg gaatcctgcc cgccacctgc tccgcgctgc cctcggactt  24780
cgtgccgctg accttccgcg agtgcccccc gccgctgtgg agccactgct acctgctgcg  24840
cctggccaac tacctggcct accactcgga cgtgatcgag gacgtcagcg gcgagggcct  24900
gctcgagtgc cactgccgct gcaacctctg cacgccgcac cgctccctgg cctgcaaccc  24960
ccagctgctg agcgagaccc agatcatcgg caccttcgag ttgcaagggc ccagcgaagg  25020
cgagggttca gccgccaagg ggggtctgaa actcaccccg ggctgtgga cctcggccta  25080
cttgcgcaag ttcgtgcccg aggactacca tcccttcgag atcaggttct acgaggacca  25140
atcccatccg cccaaggccg agctgtcggc ctgcgtcatc acccaggggg cgatcctggc  25200
```

```
ccaattgcaa gccatccaga aatcccgcca agaattcttg ctgaaaaagg gccgcggggt  25260
ctacctcgac ccccagaccg gtgaggagct caaccccggc ttcccccagg atgccccgag  25320
gaaacaagaa gctgaaagtg gagctgccgc ccgtggagga tttggaggaa gactgggaga  25380
acagcagtca ggcagaggag gaggagatgg aggaagactg ggacagcact caggcagagg  25440
aggacagcct gcaagacagt ctggaggaag acgaggagga ggcagaggag gaggtggaag  25500
aagcagccgc cgccagaccg tcgtcctcgg cgggggagaa agcaagcagc acggatacca  25560
tctccgctcc gggtcggggt cccgctcgac cacacagtag atgggacgag accggacgat  25620
tcccgaaccc caccacccag accggtaaga aggagcggca gggatacaag tcctggcggg  25680
ggcacaaaaa cgccatcgtc tcctgcttgc aggcctgcgg gggcaacatc tccttcaccc  25740
ggcgctacct gctcttccac cgcggggtga actttccccg caacatcttg cattactacc  25800
gtcacctcca cagcccctac tacttccaag aagaggcagc agcagcagaa aaagaccagc  25860
agaaaaccag cagctagaaa atccacagcg gcggcagcag gtggactgag gatcgcggcg  25920
aacgagccgg cgcaaacccg ggagctgagg aaccggatct ttcccaccct ctatgccatc  25980
ttccagcaga gtcgggggca ggagcaggaa ctgaaagtca agaaccgttc tctgcgctcg  26040
ctcacccgca gttgtctgta tcacaagagc gaagaccaac ttcagcgcac tctcgaggac  26100
gccgaggctc tcttcaacaa gtactgcgcg ctcactctta aagagtagcc cgcgcccgcc  26160
cagtcgcaga aaaaggcggg aattacgtca cctgtgccct tcgccctagc cgcctccacc  26220
catcatcatg agcaaagaga ttcccacgcc ttacatgtgg agctaccagc cccagatggg  26280
cctggccgcc ggtgccgccc aggactactc cacccgcatg aattggctca gcgccgggcc  26340
cgcgatgatc tcacgggtga atgacatccg cgcccaccga aaccagatac tcctagaaca  26400
gtcagcgctc accgccacgc cccgcaatca cctcaatccg cgtaattggc ccgccgccct  26460
ggtgtaccag gaaattcccc agcccacgac cgtactactt ccgcgagacg cccaggccga  26520
agtccagctg actaactcag gtgtccagct ggcgggcggc gccaccctgt gtcgtcaccg  26580
ccccgctcag ggtataaagc ggctggtgat ccggggcaga ggcacacagc tcaacgacga  26640
ggtggtgagc tcttcgctgg gtctgcgacc tgacggagtc ttccaactcg ccggatcggg  26700
gagatcttcc ttcacgcctc gtcaggccgt cctgactttg gagagttcgt cctcgcagcc  26760
ccgctcgggt ggcatcggca ctctccagtt cgtggaggag ttcactccct cggtctactt  26820
caaccccttc tccggctccc ccggccacta cccggacgag ttcatcccga acttcgacgc  26880
catcagcgag tcggtggacg gctacgattg aaactaatca ccccccttatc cagtgaaata  26940
aagatcatat tgatgatgat tttacagaaa taaaaaataa tcatttgatt tgaaataaag  27000
atacaatcat attgatgatt tgagtttaac aaaaaaataa agaatcactt acttgaaatc  27060
tgataccagg tctctgtcca tgttttctgc caacaccact tcactcccct cttcccagct  27120
ctggtactgc aggccccggc gggctgcaaa cttcctccac acgctgaagg ggatgtcaaa  27180
ttcctcctgt ccctcaatct tcattttatc ttctatcaga tgtccaaaaa gcgcgtccgg  27240
gtggatgatg acttcgaccc cgtctacccc tacgatgcag acaacgcacc gaccgtgccc  27300
ttcatcaacc ccccttcgt ctcttcagat ggattccaag agaagcccct gggggtgttg  27360
tccctgcgac tggccgaccc cgtcaccacc aagaacgggg aaatcaccct caagctggga  27420
gagggggtgg acctcgattc ctcgggaaaa ctcatctcca acacggccac caaggccgcc  27480
gcccctctca gtttttccaa caacaccatt tcccttaaca tggatcaccc cttttacact  27540
aaagatggaa aattatcctt acaagtttct ccaccattaa atatactgag aacaagcatt  27600
```

```
ctaaacacac tagctttagg ttttggatca ggtttaggac tccgtggctc tgccttggca  27660
gtacagttag tctctccact tacatttgat actgatggaa acataaagct taccttagac  27720
agaggtttgc atgttacaac aggagatgca attgaaagca acataagctg ggctaaaggt  27780
ttaaaatttg aagatggagc catagcaacc aacattggaa atgggttaga gtttggaagc  27840
agtagtacag aaacaggtgt tgatgatgct tacccaatcc aagttaaact tggatctggc  27900
cttagctttg acagtacagg agccataatg gctggtaaca aagaagacga taaactcact  27960
ttgtggacaa cacctgatcc atcaccaaac tgtcaaatac tcgcagaaaa tgatgcaaaa  28020
ctaacacttt gcttgactaa atgtggtagt caaatactgg ccactgtgtc agtcttagtt  28080
gtaggaagtg gaaacctaaa ccccattact ggcaccgtaa gcagtgctca ggtgtttcta  28140
cgttttgatg caaacggtgt tcttttaaca gaacattcta cactaaaaaa atactggggg  28200
tataggcagg gagatagcat agatggcact ccatatacca atgctgtagg attcatgccc  28260
aatttaaaag cttatccaaa gtcacaaagt tctactacta aaaataatat agtagggcaa  28320
gtatacatga atggagatgt ttcaaaacct atgcttctca ctataaccct caatggtact  28380
gatgacagca acagtacata ttcaatgtca ttttcataca cctggactaa tggaagctat  28440
gttggagcaa catttggggc taactcttat accttctcat acatcgccca agaatgaaca  28500
ctgtatccca ccctgcatgc caacccttcc caccccactc tgtggaacaa actctgaaac  28560
acaaaataaa ataaagttca agtgttttat tgattcaaca gttttacagg attcgagcag  28620
ttatttttcc tccaccctcc caggacatgg aatacaccac cctctccccc cgcacagcct  28680
tgaacatctg aatgccattg gtgatggaca tgcttttggt ctccacgttc cacacagttt  28740
cagagcgagc cagtctcggg tcggtcaggg agatgaaacc ctccgggcac tcccgcatct  28800
gcacctcaca gctcaacagc tgaggattgt cctcggtggt cgggatcacg gttatctgga  28860
agaagcagaa gagcggcggt gggaatcata gtccgcgaac gggatcggcc ggtggtgtcg  28920
catcaggccc cgcagcagtc gctgccgccg ccgctccgtc aagctgctgc tcagggggtc  28980
cgggtccagg gactccctca gcatgatgcc cacggccctc agcatcagtc gtctggtgcg  29040
gcgggcgcag cagcgcatgc ggatctcgct caggtcgctg cagtacgtgc aacacagaac  29100
caccaggttg ttcaacagtc catagttcaa cacgctccag ccgaaactca tcgcgggaag  29160
gatgctaccc acgtggccgt cgtaccagat cctcaggtaa atcaagtggt gccccctcca  29220
gaacacgctg cccacgtaca tgatctcctt gggcatgtgg cggttcacca cctcccggta  29280
ccacatcacc ctctggttga acatgcagcc ccggatgatc ctgcggaacc acagggccag  29340
caccgccccg cccgccatgc agcgaagaga ccccgggtcc cggcaatggc aatggaggac  29400
ccaccgctcg tacccgtgga tcatctggga gctgaacaag tctatgttgg cacagcacag  29460
gcatatgctc atgcatctct tcagcactct caactcctcg ggggtcaaaa ccatatccca  29520
gggcacgggg aactcttgca ggacagcgaa ccccgcagaa cagggcaatc ctcgcacaga  29580
acttacattg tgcatggaca gggtatcgca atcaggcagc accgggtgat cctccaccag  29640
agaagcgcgg gtctcggtct cctcacagcg tggtaagggg gccggccgat acgggtgatg  29700
gcgggacgcg gctgatcgtg ttcgcgaccg tgtcatgatg cagttgcttt cggacatttt  29760
cgtacttgct gtagcagaac ctggtccggg cgctgcacac cgatcgccgg cggcggtctc  29820
ggcgcttgga acgctcggtg ttgaaattgt aaaacagcca ctctctcaga ccgtgcagca  29880
gatctagggc ctcaggagtg atgaagatcc catcatgcct gatggctctg atcacatcga  29940
```

ccaccgtgga atgggccaga cccagccaga tgatgcaatt ttgttgggtt tcggtgacgg 30000
cgggggaggg aagaacagga agaaccatga ttaactttta atccaaacgg tctcggagta 30060
cttcaaaatg aagatcgcgg agatggcacc tctcgccccc gctgtgttgg tggaaaataa 30120
cagccaggtc aaaggtgata cggttctcga gatgttccac ggtggcttcc agcaaagcct 30180
ccacgcgcac atccagaaac aagacaatag cgaaagcggg agggttctct aattcctcaa 30240
tcatcatgtt acactcctgc accatcccca gataattttc atttttccag ccttgaatga 30300
ttcgaactag ttcctgaggt aaatccaagc cagccatgat aaagagctcg cgcagagcgc 30360
cctccaccgg cattcttaag cacaccctca taattccaag atattctgct cctggttcac 30420
ctgcagcaga ttgacaagcg gaatatcaaa atctctgccg cgatccctga gctcctccct 30480
cagcaataac tgtaagtact ctttcatatc ctctccgaaa tttttagcca taggaccacc 30540
aggaataaga ttagggcaag ccacagtaca gataaaccga agtcctcccc agtgagcatt 30600
gccaaatgca agactgctat aagcatgctg gctagacccg gtgatatctt ccagataact 30660
ggacagaaaa tcgcccaggc aatttttaag aaaatcaaca aaagaaaaat cctccaggtg 30720
gacgtttaga gcctcgggaa caacgatgaa gtaaatgcaa gcggtgcgtt ccagcatggt 30780
tagttagctg atctgtagaa aaaacaaaaa tgaacattaa accatgctag cctggcgaac 30840
aggtgggtaa atcgttctct ccagcaccag gcaggccacg gggtctccgg cgcgaccctc 30900
gtaaaaattg tcgctatgat tgaaaaccat cacagagaga cgttcccggt ggccggcgtg 30960
aatgattcga caagatgaat acacccccgg aacattggcg tccgcgagtg aaaaaaagcg 31020
cccgaggaag caataaggca ctacaatgct cagtctcaag tccagcaaag cgatgccatg 31080
cggatgaagc acaaaattct caggtgcgta caaaatgtaa ttactcccct cctgcacagg 31140
cagcaaagcc cccgatccct ccaggtacac atacaaagcc tcagcgtcca tagcttaccg 31200
agcagcagca cacaacaggc gcaagagtca gagaaaggct gagctctaac ctgtccaccc 31260
gctctctgct caatatatag cccagatcta cactgacgta aaggccaaag tctaaaaata 31320
cccgccaaat aatcacacac gcccagcaca cgcccagaaa ccggtgacac actcaaaaaa 31380
atacgcgcac ttcctcaaac gcccaaaact gccgtcattt ccgggttccc acgctacgtc 31440
atcaaaacac gactttcaaa ttccgtcgac cgttaaaaac gtcacccgcc ccgcccctaa 31500
cggtcgcccg tctctcagcc aatcagcgcc ccgcatcccc aaattcaaac acctcatttg 31560
catattaacg cgcacaaaaa gtttgaggta tattattgat gatg 31604

<210> SEQ ID NO 3
<211> LENGTH: 11447
<212> TYPE: DNA
<213> ORGANISM: Venezuelan equine encephalitis virus

<400> SEQUENCE: 3
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480

```
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
```

ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220

```
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
```

-continued

```
gatgttcccg ttccagccaa tgtatccgat gcagccaatg ccctatcgca acccgttcgc   7620
ggccccgcgc aggccctggt tccccagaac cgaccctttt ctggcgatgc aggtgcagga   7680
attaacccgc tcgatggcta acctgacgtt caagcaacgc cgggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga agaccaacaa gaaaccaggc aagagacagc gcatggtcat   7920
gaaattggaa tctgacaaga cgttcccaat catgttggaa gggaagataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcgggccg atacattcaa atacacccat gagaaacccc aaggctatta   8160
cagctggcat catggagcag tccaatatga aaatgggcgt ttcacggtgc cgaaaggagt   8220
tggggccaag ggagacagcg gacgacccat tctggataac cagggacggg tggtcgctat   8280
tgtgctggga ggtgtgaatg aaggatctag gacagccctt tcagtcgtca tgtggaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
aaaaccagca gagactttgg ccatgctcag cgttaacgtt gacaacccgg gctacgatga   8520
gctgctggaa gcagctgtta agtgccccgg aaggaaaagg agatccaccg aggagctgtt   8580
taaggagtat aagctaacgc gcccttacat ggccagatgc atcagatgtg cagttgggag   8640
ctgccatagt ccaatagcaa tcgaggcagt aaagagcgac gggcacgacg gttatgttag   8700
acttcagact tcctcgcagt atggcctgga ttcctccggc aacttaaagg gcaggaccat   8760
gcggtatgac atgcacggga ccattaaaga gataccacta catcaagtgt cactccatac   8820
atctcgcccg tgtcacattg tggatgggca cggttatttc ctgcttgcca ggtgcccggc   8880
aggggactcc atcaccatgg aatttaagaa agattccgtc acacactcct gctcggtgcc   8940
gtatgaagtg aaatttaatc ctgtaggcag agaactctat actcatcccc cagaacacgg   9000
agtagagcaa gcgtgccaag tctacgcaca tgatgcacag aacagaggag cttatgtcga   9060
gatgcacctc ccgggctcag aagtggacag cagtttggtt tccttgagcg gcagttcagt   9120
caccgtgaca cctcctgttg ggactagcgc cctggtggaa tgcgagtgtg gcggcacaaa   9180
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aacctttggt ttcagatcag tgtcactgaa   9420
actgcaccct aagaatccca catatctaac cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggttttgg gcacaggaaa cagcacccgg   9600
aaatccacat gggctaccgc acgaggtgat aactcattat taccacagat accctatgtc   9660
caccatcctg ggtttgtcaa tttgtgccgc cattgcaacc gtttccgttg cagcgtctac   9720
ctggctgttt tgcagatcta gagttgcgtg cctaactcct taccggctaa cacctaacgc   9780
taggatacca ttttgtctgg ctgtgctttg ctgcgcccgc actgcccggg ccgagaccac   9840
ctgggagtcc ttggatcacc tatggaacaa taaccaacag atgttctgga ttcaattgct   9900
gatccctctg gccgccttga tcgtagtgac tcgcctgctc aggtgcgtgt gctgtgtcgt   9960
```

```
gcctttttta gtcatggccg gcgccgcagg cgccggcgcc tacgagcacg cgaccacgat  10020

gccgagccaa gcgggaatct cgtataacac tatagtcaac agagcaggct acgcaccact  10080

ccctatcagc ataacaccaa caaagatcaa gctgatacct acagtgaact tggagtacgt  10140

cacctgccac tacaaaacag gaatggattc accagccatc aaatgctgcg gatctcagga  10200

atgcactcca acttacaggc ctgatgaaca gtgcaaagtc ttcacagggg tttacccgtt  10260

catgtggggt ggtgcatatt gcttttgcga cactgagaac acccaagtca gcaaggccta  10320

cgtaatgaaa tctgacgact gccttgcgga tcatgctgaa gcatataaag cgcacacagc  10380

ctcagtgcag gcgttcctca acatcacagt gggagaacac tctattgtga ctaccgtgta  10440

tgtgaatgga gaaactcctg tgaatttcaa tggggtcaaa ttaactgcag gtccgctttc  10500

cacagcttgg acaccctttg atcgcaaaat cgtgcagtat gccggggaga tctataatta  10560

tgattttcct gagtatgggg caggacaacc aggagcattt ggagatatac aatccagaac  10620

agtctcaagc tcagatctgt atgccaatac caacctagtg ctgcagagac ccaaagcagg  10680

agcgatccac gtgccataca ctcaggcacc ttcgggtttt gagcaatgga agaaagataa  10740

agctccatca ttgaaattta ccgccccttt cggatgcgaa atatatacaa accccattcg  10800

cgccgaaaac tgtgctgtag ggtcaattcc attagccttt gacattcccg acgccttgtt  10860

caccagggtg tcagaaacac cgacactttc agcggccgaa tgcactctta acgagtgcgt  10920

gtattcttcc gactttggtg ggatcgccac ggtcaagtac tcggccagca agtcaggcaa  10980

gtgcgcagtc catgtgccat cagggactgc taccctaaaa gaagcagcag tcgagctaac  11040

cgagcaaggg tcggcgacta tccatttctc gaccgcaaat atccacccgg agttcaggct  11100

ccaaatatgc acatcatatg ttacgtgcaa aggtgattgt caccccccga aagaccatat  11160

tgtgacacac cctcagtatc acgcccaaac atttacagcc gcggtgtcaa aaaccgcgtg  11220

gacgtggtta acatccctgc tgggaggatc agccgtaatt attataattg gcttggtgct  11280

ggctactatt gtggccatgt acgtgctgac caaccagaaa cataattgaa tacagcagca  11340

attggcaagc tgcttacata gaactcgcgg cgattggcat gccgccttaa aatttttatt  11400

ttatttttc ttttcttttc cgaatcggat tttgttttta atatttc                11447
```

<210> SEQ ID NO 4
<211> LENGTH: 9577
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540
```

```
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
```

-continued

```
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggg tg tgcggagcgc  4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
```

```
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gactctagaa tagtctttaa   7560
ttaagccacc atggcaggca tgtttcaggc gctgagcgaa ggctgcaccc cgtatgatat   7620
```

```
taaccagatg ctgaacgtgc tgggcgatca tcaggtctca ggccttgagc agcttgagag   7680

tataatcaac tttgaaaaac tgactgaatg gaccagttct aatgttatgc ctatcctgtc   7740

tcctctgaca aagggcatcc tgggcttcgt gtttaccctg accgtgcctt ctgagagagg   7800

acttagctgc attagcgaag cggatgcgac caccccggaa agcgcgaacc tgggcgaaga   7860

aattctgagc cagctgtatc tttggccaag ggtgacctac cattccccta gttatgctta   7920

ccaccaattt gaaagacgag ccaaatataa aagacacttc cccggctttg gccagagcct   7980

gctgtttggc taccctgtgt acgtgttcgg cgattgcgtg cagggcgatt gggatgcgat   8040

tcgctttcgc tattgcgcgc cgccgggcta tgcgctgctg cgctgcaacg ataccaacta   8100

tagcgctctg ctggctgtgg gggccctaga aggacccagg aatcaggact ggcttggtgt   8160

cccaagacaa cttgtaactc ggatgcaggc tattcagaat gccggcctgt gtaccctggt   8220

ggccatgctg gaagagacaa tcttctggct gcaagcgttt ctgatggcgc tgaccgatag   8280

cggcccgaaa accaacatta ttgtggatag ccagtatgtg atgggcatta gcaaaccgag   8340

ctttcaggaa tttgtggatt gggaaaacgt gagcccggaa ctgaacagca ccgatcagcc   8400

gttttggcaa gccggaatcc tggccagaaa tctggtgcct atggtggcca cagtgcaggg   8460

ccagaacctg aagtaccagg gtcagtcact agtcatctct gcttctatca ttgtcttcaa   8520

cctgctggaa ctggaaggtg attatcgaga tgatggcaac gtgtgggtgc ataccccgct   8580

gagcccgcgc accctgaacg cgtgggtgaa agcggtggaa gaaaaaaaag gtattccagt   8640

tcacctagag ctggccagta tgaccaacat ggagctcatg agcagtattg tgcatcagca   8700

ggtcagaaca tacggccccg tgttcatgtg tctcggcgga ctgcttacaa tggtggctgg   8760

tgctgtgtgg ctgacagtgc gagtgctcga gctgttccgg gccgcgcagc tggccaacga   8820

cgtggtcctc cagatcatgg agctttgtgg tgcagcgttt cgccaggtgt gccataccac   8880

cgtgccgtgg ccgaacgcga gcctgacccc gaaatggaac aacgaaacca cccagcccca   8940

gatcgccaac tgcagcgtgt atgacttttt tgtgtggctc cattattatt ctgttcgaga   9000

cacactttgg ccaagggtga cctaccatat gaacaaatat gcgtatcata tgctggaaag   9060

acgagccaaa tataaaagag gaccaggacc tggcgctaaa tttgtggccg cctggacact   9120

gaaagccgct gctggtcctg gacctggcca gtacatcaag gccaacagca agttcatcgg   9180

catcaccgaa ctcggacccg gaccaggctg atgattcgaa cggccgtatc acgcccaaac   9240

atttacagcc gcggtgtcaa aaaccgcgtg gacgtggtta acatccctgc tgggaggatc   9300

agccgtaatt attataattg gcttggtgct ggctactatt gtggccatgt acgtgctgac   9360

caaccagaaa cataattgaa tacagcagca attggcaagc tgcttacata gaactcgcgg   9420

cgattggcat gccgccttaa aatttttatt ttattttttc ttttcttttc cgaatcggat   9480

tttgttttta atatttcaaa aaaaaaaaaa aaaaaaaaaa aaaaaaaaaa aaaaaaaaaa   9540

aaaaaaaaaa aaaaaaaaaa aaaaaaaaaa aaaaaaa                            9577
```

<210> SEQ ID NO 5
<211> LENGTH: 11447
<212> TYPE: DNA
<213> ORGANISM: Venezuelan equine encephalitis virus

<400> SEQUENCE: 5

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180
```

```
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc  2520
```

```
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
```

```
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
```

```
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgttcccg ttccagccaa tgtatccgat gcagccaatg ccctatcgca acccgttcgc   7620
ggccccgcgc aggccctggt tccccagaac cgaccctttt ctggcgatgc aggtgcagga   7680
attaacccgc tcgatggcta acctgacgtt caagcaacgc cgggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga agaccaacaa gaaaccaggc aagagacagc gcatggtcat   7920
gaaattggaa tctgacaaga cgttcccaat catgttggaa gggaagataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcgggccg atacattcaa atacacccat gagaaacccc aaggctatta   8160
cagctggcat catggagcag tccaatatga aaatgggcgt ttcacggtgc cgaaaggagt   8220
tggggccaag ggagacagcg gacgacccat tctggataac cagggacggg tggtcgctat   8280
tgtgctggga ggtgtgaatg aaggatctag gacagccctt tcagtcgtca tgtggaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
aaaaccagca gagactttgg ccatgctcag cgttaacgtt gacaacccgg gctacgatga   8520
gctgctggaa gcagctgtta agtgccccgg aaggaaaagg agatccaccg aggagctgtt   8580
taaggagtat aagctaacgc gcccttacat ggccagatgc atcagatgtg cagttgggag   8640
ctgccatagt ccaatagcaa tcgaggcagt aaagagcgac gggcacgacg gttatgttag   8700
acttcagact tcctcgcagt atggcctgga ttcctccggc aacttaaagg gcaggaccat   8760
gcggtatgac atgcacggga ccattaaaga gataccacta catcaagtgt cactccatac   8820
atctcgcccg tgtcacattg tggatgggca cggttatttc ctgcttgcca ggtgcccggc   8880
aggggactcc atcaccatgg aatttaagaa agattccgtc acacactcct gctcggtgcc   8940
gtatgaagtg aaatttaatc ctgtaggcag agaactctat actcatcccc cagaacacgg   9000
agtagagcaa gcgtgccaag tctacgcaca tgatgcacag aacagaggag cttatgtcga   9060
gatgcacctc ccgggctcag aagtggacag cagtttggtt tccttgagcg gcagttcagt   9120
caccgtgaca cctcctgttg ggactagcgc cctggtggaa tgcgagtgtg gcggcacaaa   9180
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aacctttggt ttcagatcag tgtcactgaa   9420
actgcaccct aagaatccca catatctaac cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggttttgg gcacaggaaa cagcacccgg   9600
aaatccacat gggctaccgc acgaggtgat aactcattat taccacagat accctatgtc   9660
```

```
caccatcctg ggtttgtcaa tttgtgccgc cattgcaacc gtttccgttg cagcgtctac   9720

ctggctgttt tgcagatcta gagttgcgtg cctaactcct taccggctaa cacctaacgc   9780

taggatacca ttttgtctgg ctgtgctttg ctgcgcccgc actgcccggg ccgagaccac   9840

ctgggagtcc ttggatcacc tatggaacaa taaccaacag atgttctgga ttcaattgct   9900

gatccctctg gccgccttga tcgtagtgac tcgcctgctc aggtgcgtgt gctgtgtcgt   9960

gccttttta gtcatggccg gcgccgcagg cgccggcgcc tacgagcacg cgaccacgat  10020

gccgagccaa gcgggaatct cgtataacac tatagtcaac agagcaggct acgcaccact  10080

ccctatcagc ataacaccaa caaagatcaa gctgatacct acagtgaact tggagtacgt  10140

cacctgccac tacaaaacag gaatggattc accagccatc aaatgctgcg gatctcagga  10200

atgcactcca acttacaggc ctgatgaaca gtgcaaagtc ttcacagggg tttacccgtt  10260

catgtggggt ggtgcatatt gcttttgcga cactgagaac acccaagtca gcaaggccta  10320

cgtaatgaaa tctgacgact gccttgcgga tcatgctgaa gcatataaag cgcacacagc  10380

ctcagtgcag gcgttcctca acatcacagt gggagaacac tctattgtga ctaccgtgta  10440

tgtgaatgga gaaactcctg tgaatttcaa tggggtcaaa ttaactgcag gtccgctttc  10500

cacagcttgg acaccctttg atcgcaaaat cgtgcagtat gccggggaga tctataatta  10560

tgattttcct gagtatgggg caggacaacc aggagcattt ggagatatac aatccagaac  10620

agtctcaagc tcagatctgt atgccaatac caacctagtg ctgcagagac ccaaagcagg  10680

agcgatccac gtgccataca ctcaggcacc ttcgggtttt gagcaatgga agaaagataa  10740

agctccatca ttgaaattta ccgccccttt cggatgcgaa atatatacaa accccattcg  10800

cgccgaaaac tgtgctgtag ggtcaattcc attagccttt gacattcccg acgccttgtt  10860

caccagggtg tcagaaacac cgacactttc agcggccgaa tgcactctta acgagtgcgt  10920

gtattcttcc gactttggtg ggatcgccac ggtcaagtac tcggccagca agtcaggcaa  10980

gtgcgcagtc catgtgccat cagggactgc taccctaaaa gaagcagcag tcgagctaac  11040

cgagcaaggg tcggcgacta tccatttctc gaccgcaaat atccacccgg agttcaggct  11100

ccaaatatgc acatcatatg ttacgtgcaa aggtgattgt caccccccga aagaccatat  11160

tgtgacacac cctcagtatc acgcccaaac atttacagcc gcggtgtcaa aaaccgcgtg  11220

gacgtggtta acatccctgc tgggaggatc agccgtaatt attataattg gcttggtgct  11280

ggctactatt gtggccatgt acgtgctgac caaccagaaa cataattgaa tacagcagca  11340

attggcaagc tgcttacata gaactcgcgg cgattggcat gccgccttaa aatttttatt  11400

ttattttttc ttttcttttc cgaatcggat tttgttttta atatttc                11447
```

<210> SEQ ID NO 6
<211> LENGTH: 7894
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240
```

```
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
```

```
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
```

```
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
```

```
aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gactatcacg cccaaacatt   7560

tacagccgcg gtgtcaaaaa ccgcgtggac gtggttaaca tccctgctgg gaggatcagc   7620

cgtaattatt ataattggct tggtgctggc tactattgtg gccatgtacg tgctgaccaa   7680

ccagaaacat aattgaatac agcagcaatt ggcaagctgc ttacatagaa ctcgcggcga   7740

ttggcatgcc gccttaaaat ttttattta tttttcttt tcttttccga atcggatttt   7800

gtttttaata tttcaaaaaa aaaaaaaaaa aaaaaaaaaa aaaaaaaaaa aaaaaaaaaa   7860

aaaaaaaaaa aaaaaaaaaa aaaaaaaaaa aaaa                               7894


<210> SEQ ID NO 7
<211> LENGTH: 7893
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440
```

```
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
```

-continued

```
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
```

```
ctgccagttt ttgccctgca aagctgcgca gctttccaaa gaaacactcc tatttggaac   6240

ccacaatacg atcggcagtg ccttcagcga tccagaacac gctccagaac gtcctggcag   6300

ctgccacaaa aagaaattgc aatgtcacgc aaatgagaga attgcccgta ttggattcgg   6360

cggcctttaa tgtggaatgc ttcaagaaat atgcgtgtaa taatgaatat tgggaaacgt   6420

ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga cccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

ggcccctat aactctctac ggctaacctg aatggactac gactatcacg cccaaacatt   7560

tacagccgcg gtgtcaaaaa ccgcgtggac gtggttaaca tccctgctgg gaggatcagc   7620

cgtaattatt ataattggct tggtgctggc tactattgtg gccatgtacg tgctgaccaa   7680

ccagaaacat aattgaatac agcagcaatt ggcaagctgc ttacatagaa ctcgcggcga   7740

ttggcatgcc gccttaaaat ttttattta tttttcttt cttttccgaa tcggattttg   7800

tttttaatat ttcaaaaaaa aaaaaaaaaa aaaaaaaaaa aaaaaaaaaa aaaaaaaaaa   7860

aaaaaaaaaa aaaaaaaaaa aaaaaaaaaa aaa                                7893
```

```
<210> SEQ ID NO 8
<211> LENGTH: 7927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

taatacgact cactatagga tgggcggcgc atgagagaag cccagaccaa ttacctaccc     60

aaaatggaga aagttcacgt tgacatcgag gaagacagcc cattcctcag agctttgcag    120

cggagcttcc cgcagtttga ggtagaagcc aagcaggtca ctgataatga ccatgctaat    180

gccagagcgt tttcgcatct ggcttcaaaa ctgatcgaaa cggaggtgga cccatccgac    240

acgatccttg acattggaag tgcgcccgcc cgcagaatgt attctaagca caagtatcat    300
```

```
tgtatctgtc cgatgagatg tgcggaagat ccggacagat tgtataagta tgcaactaag    360
ctgaagaaaa actgtaagga aataactgat aaggaattgg acaagaaaat gaaggagctc    420
gccgccgtca tgagcgaccc tgacctggaa actgagacta tgtgcctcca cgacgacgag    480
tcgtgtcgct acgaagggca agtcgctgtt taccaggatg tatacgcggt tgacggaccg    540
acaagtctct atcaccaagc caataaggga gttagagtcg cctactggat aggctttgac    600
accacccctt ttatgtttaa gaacttggct ggagcatatc catcatactc taccaactgg    660
gccgacgaaa ccgtgttaac ggctcgtaac ataggcctat gcagctctga cgttatggag    720
cggtcacgta gagggatgtc cattcttaga aagaagtatt tgaaaccatc caacaatgtt    780
ctattctctg ttggctcgac catctaccac gagaagaggg acttactgag gagctggcac    840
ctgccgtctg tatttcactt acgtggcaag caaaattaca catgtcggtg tgagactata    900
gttagttgcg acgggtacgt cgttaaaaga atagctatca gtccaggcct gtatgggaag    960
ccttcaggct atgctgctac gatgcaccgc gagggattct tgtgctgcaa agtgacagac   1020
acattgaacg gggagagggt ctcttttccc gtgtgcacgt atgtgccagc tacattgtgt   1080
gaccaaatga ctggcatact ggcaacagat gtcagtgcgg acgacgcgca aaaactgctg   1140
gttgggctca accagcgtat agtcgtcaac ggtcgcaccc agagaaacac caataccatg   1200
aaaaattacc ttttgcccgt agtggcccag gcatttgcta ggtgggcaaa ggaatataag   1260
gaagatcaag aagatgaaag gccactagga ctacgagata gacagttagt catggggtgt   1320
tgttgggctt ttagaaggca caagataaca tctatttata agcgcccgga tacccaaacc   1380
atcatcaaag tgaacagcga tttccactca ttcgtgctgc ccaggatagg cagtaacaca   1440
ttggagatcg ggctgagaac aagaatcagg aaaatgttag aggagcacaa ggagccgtca   1500
cctctcatta ccgccgagga cgtacaagaa gctaagtgcg cagccgatga ggctaaggag   1560
gtgcgtgaag ccgaggagtt gcgcgcagct ctaccacctt tggcagctga tgttgaggag   1620
cccactctgg aagccgatgt cgacttgatg ttacaagagg ctggggccgg ctcagtggag   1680
acacctcgtg gcttgataaa ggttaccagc tacgctggcg aggacaagat cggctcttac   1740
gctgtgcttt ctccgcaggc tgtactcaag agtgaaaaat tatcttgcat ccaccctctc   1800
gctgaacaag tcatagtgat aacacactct ggccgaaaag ggcgttatgc cgtggaacca   1860
taccatggta aagtagtggt gccagaggga catgcaatac ccgtccagga ctttcaagct   1920
ctgagtgaaa gtgccaccat tgtgtacaac gaacgtgagt tcgtaaacag gtacctgcac   1980
catattgcca cacatggagg agcgctgaac actgatgaag aatattacaa aactgtcaag   2040
cccagcgagc acgacggcga atacctgtac gacatcgaca ggaaacagtg cgtcaagaaa   2100
gaactagtca ctgggctagg gctcacaggc gagctggtgg atcctccctt ccatgaattc   2160
gcctacgaga gtctgagaac acgaccagcc gctccttacc aagtaccaac catagggggtg   2220
tatggcgtgc caggatcagg caagtctggc atcattaaaa gcgcagtcac caaaaaagat   2280
ctagtggtga gcgccaagaa agaaaactgt gcagaaatta taagggacgt caagaaaatg   2340
aaagggctgg acgtcaatgc cagaactgtg gactcagtgc tcttgaatgg atgcaaacac   2400
cccgtagaga ccctgtatat tgacgaagct tttgcttgtc atgcaggtac tctcagagcg   2460
ctcatagcca ttataagacc taaaaaggca gtgctctgcg gggatcccaa acagtgcggt   2520
ttttttaaca tgatgtgcct gaaagtgcat tttaaccacg agatttgcac acaagtcttc   2580
cacaaaagca tctctcgccg ttgcactaaa tctgtgactt cggtcgtctc aaccttgttt   2640
tacgacaaaa aaatgagaac gacgaatccg aaagagacta agattgtgat tgacactacc   2700
```

```
ggcagtacca aacctaagca ggacgatctc attctcactt gtttcagagg gtgggtgaag   2760
cagttgcaaa tagattacaa aggcaacgaa ataatgacgg cagctgcctc tcaagggctg   2820
acccgtaaag gtgtgtatgc cgttcggtac aaggtgaatg aaaatcctct gtacgcaccc   2880
acctcagaac atgtgaacgt cctactgacc cgcacggagg accgcatcgt gtggaaaaca   2940
ctagccggcg acccatggat aaaaacactg actgccaagt accctgggaa tttcactgcc   3000
acgatagagg agtggcaagc agagcatgat gccatcatga ggcacatctt ggagagaccg   3060
gaccctaccg acgtcttcca gaataaggca aacgtgtgtt gggccaaggc tttagtgccg   3120
gtgctgaaga ccgctggcat agacatgacc actgaacaat ggaacactgt ggattatttt   3180
gaaacggaca aagctcactc agcagagata gtattgaacc aactatgcgt gaggttcttt   3240
ggactcgatc tggactccgg tctattttct gcacccactg ttccgttatc cattaggaat   3300
aatcactggg ataactcccc gtcgcctaac atgtacgggc tgaataaaga agtggtccgt   3360
cagctctctc gcaggtaccc acaactgcct cgggcagttg ccactggaag agtctatgac   3420
atgaacactg gtacactgcg caattatgat ccgcgcataa acctagtacc tgtaaacaga   3480
agactgcctc atgctttagt cctccaccat aatgaacacc cacagagtga cttttcttca   3540
ttcgtcagca aattgaaggg cagaactgtc ctggtggtcg gggaaaagtt gtccgtccca   3600
ggcaaaatgg ttgactggtt gtcagaccgg cctgaggcta ccttcagagc tcggctggat   3660
ttaggcatcc caggtgatgt gcccaaatat gacataaatat ttgttaatgt gaggacccca   3720
tataaatacc atcactatca gcagtgtgaa gaccatgcca ttaagcttag catgttgacc   3780
aagaaagctt gtctgcatct gaatcccggc ggaacctgtg tcagcatagg ttatggttac   3840
gctgacaggg ccagcgaaag catcattggt gctatagcgc ggcagttcaa gttttcccgg   3900
gtatgcaaac cgaaatcctc acttgaagag acggaagttc tgtttgtatt cattgggtac   3960
gatcgcaagg cccgtacgca caatccttac aagctttcat caaccttgac caacatttat   4020
acaggttcca gactccacga agccggatgt gcaccctcat atcatgtggt gcgaggggat   4080
attgccacgg ccaccgaagg agtgattata aatgctgcta acagcaaagg acaacctggc   4140
ggaggggtgt gcggagcgct gtataagaaa ttcccggaaa gcttcgattt acagccgatc   4200
gaagtaggaa aagcgcgact ggtcaaaggt gcagctaaac atatcattca tgccgtagga   4260
ccaaacttca acaaagtttc ggaggttgaa ggtgacaaac agttggcaga ggcttatgag   4320
tccatcgcta agattgtcaa cgataacaat tacaagtcag tagcgattcc actgttgtcc   4380
accggcatct tttccgggaa caaagatcga ctaacccaat cattgaacca tttgctgaca   4440
gctttagaca ccactgatgc agatgtagcc atatactgca gggacaagaa atgggaaatg   4500
actctcaagg aagcagtggc taggagagaa gcagtggagg agatatgcat atccgacgac   4560
tcttcagtga cagaacctga tgcagagctg gtgagggtgc atccgaagag ttctttggct   4620
ggaaggaagg gctacagcac aagcgatggc aaaactttct catatttgga agggaccaag   4680
tttcaccagg cggccaagga tatagcagaa attaatgcca tgtggcccgt tgcaacggag   4740
gccaatgagc aggtatgcat gtatatcctc ggagaaagca tgagcagtat taggtcgaaa   4800
tgccccgtcg aagagtcgga agcctccaca ccacctagca cgctgccttg cttgtgcatc   4860
catgccatga ctccagaaag agtacagcgc ctaaaagcct cacgtccaga acaaattact   4920
gtgtgctcat cctttccatt gccgaagtat agaatcactg gtgtgcagaa gatccaatgc   4980
tcccagccta tattgttctc accgaaagtg cctgcgtata ttcatccaag gaagtatctc   5040
```

```
gtggaaacac caccggtaga cgagactccg gagccatcgg cagagaacca atccacagag   5100
gggacacctg aacaaccacc acttataacc gaggatgaga ccaggactag aacgcctgag   5160
ccgatcatca tcgaagagga agaagaggat agcataagtt tgctgtcaga tggcccgacc   5220
caccaggtgc tgcaagtcga ggcagacatt cacgggccgc cctctgtatc tagctcatcc   5280
tggtccattc ctcatgcatc cgactttgat gtggacagtt tatccatact tgacaccctg   5340
gagggagcta gcgtgaccag cggggcaacg tcagccgaga ctaactctta cttcgcaaag   5400
agtatggagt ttctggcgcg accggtgcct gcgcctcgaa cagtattcag gaaccctcca   5460
catcccgctc cgcgcacaag aacaccgtca cttgcaccca gcagggcctg ctcgagaacc   5520
agcctagttt ccaccccgcc aggcgtgaat agggtgatca ctagagagga gctcgaggcg   5580
cttaccccgt cacgcactcc tagcaggtcg gtctcgagaa ccagcctggt ctccaacccg   5640
ccaggcgtaa atagggtgat tacaagagag gagtttgagg cgttcgtagc acaacaacaa   5700
tgacggtttg atgcgggtgc atacatcttt tcctccgaca ccggtcaagg gcatttacaa   5760
caaaaatcag taaggcaaac ggtgctatcc gaagtggtgt tggagaggac cgaattggag   5820
atttcgtatg ccccgcgcct cgaccaagaa aaagaagaat tactacgcaa gaaattacag   5880
ttaaatccca cacctgctaa cagaagcaga taccagtcca ggaaggtgga gaacatgaaa   5940
gccataacag ctagacgtat tctgcaaggc ctagggcatt atttgaaggc agaaggaaaa   6000
gtggagtgct accgaaccct gcatcctgtt cctttgtatt catctagtgt gaaccgtgcc   6060
ttttcaagcc ccaaggtcgc agtggaagcc tgtaacgcca tgttgaaaga gaactttccg   6120
actgtggctt cttactgtat tattccagag tacgatgcct atttggacat ggttgacgga   6180
gcttcatgct gcttagacac tgccagtttt tgccctgcaa agctgcgcag ctttccaaag   6240
aaacactcct atttggaacc cacaatacga tcggcagtgc cttcagcgat ccagaacacg   6300
ctccagaacg tcctggcagc tgccacaaaa agaaattgca atgtcacgca aatgagagaa   6360
ttgcccgtat tggattcggc ggcctttaat gtggaatgct tcaagaaata tgcgtgtaat   6420
aatgaatatt gggaaacgtt taaagaaaac cccatcaggc ttactgaaga aaacgtggta   6480
aattacatta ccaaattaaa aggaccaaaa gctgctgctc tttttgcgaa gacacataat   6540
ttgaatatgt tgcaggacat accaatggac aggtttgtaa tggacttaaa gagagacgtg   6600
aaagtgactc caggaacaaa acatactgaa gaacggccca aggtacaggt gatccaggct   6660
gccgatccgc tagcaacagc gtatctgtgc ggaatccacc gagagctggt taggagatta   6720
aatgcggtcc tgcttccgaa cattcataca ctgtttgata tgtcggctga agactttgac   6780
gctattatag ccgagcactt ccagcctggg gattgtgttc tggaaactga catcgcgtcg   6840
tttgataaaa gtgaggacga cgccatggct ctgaccgcgt taatgattct ggaagactta   6900
ggtgtggacg cagagctgtt gacgctgatt gaggcggctt tcggcgaaat ttcatcaata   6960
catttgccca ctaaaactaa atttaaattc ggagccatga tgaaatctgg aatgttcctc   7020
acactgtttg tgaacacagt cattaacatt gtaatcgcaa gcagagtgtt gagagaacgg   7080
ctaaccggat caccatgtgc agcattcatt ggagatgaca atatcgtgaa aggagtcaaa   7140
tcggacaaat taatggcaga caggtgcgcc acctggttga atatggaagt caagattata   7200
gatgctgtgg tgggcgagaa agcgccttat ttctgtggag ggtttatttt gtgtgactcc   7260
gtgaccggca cagcgtgccg tgtggcagac cccctaaaaa ggctgtttaa gcttggcaaa   7320
cctctggcag cagacgatga acatgatgat gacaggagaa gggcattgca tgaagagtca   7380
acacgctgga accgagtggg tattctttca gagctgtgca aggcagtaga atcaaggtat   7440
```

```
gaaaccgtag gaacttccat catagttatg gccatgacta ctctagctag cagtgttaaa   7500

tcattcagct acctgagagg ggcccctata actctctacg gctaacctga atggactacg   7560

actatcacgc ccaaacattt acagccgcgg tgtcaaaaac cgcgtggacg tggttaacat   7620

ccctgctggg aggatcagcc gtaattatta taattggctt ggtgctggct actattgtgg   7680

ccatgtacgt gctgaccaac cagaaacata attgaataca gcagcaattg gcaagctgct   7740

tacatagaac tcgcggcgat tggcatgccg ccttaaaatt tttattttat tttttctttt   7800

cttttccgaa tcggattttg tttttaatat ttcaaaaaaa aaaaaaaaaa aaaaaaaaaa   7860

aaaaaaaaaa aaaaaaaaaa aaaaaaaaaa aaaaaaaaaa aaaaaaaaaa aaatacgtag   7920

tttaaac                                                             7927
```

```
<210> SEQ ID NO 9
<211> LENGTH: 7926
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

taatacgact cactatagga taggcggcgc atgagagaag cccagaccaa ttacctaccc     60

aaaatggaga aagttcacgt tgacatcgag gaagacagcc cattcctcag agctttgcag    120

cggagcttcc cgcagtttga ggtagaagcc aagcaggtca ctgataatga ccatgctaat    180

gccagagcgt tttcgcatct ggcttcaaaa ctgatcgaaa cggaggtgga cccatccgac    240

acgatccttg acattggaag tgcgcccgcc cgcagaatgt attctaagca caagtatcat    300

tgtatctgtc cgatgagatg tgcggaagat ccggacagat tgtataagta tgcaactaag    360

ctgaagaaaa actgtaagga aataactgat aaggaattgg acaagaaaat gaaggagctc    420

gccgccgtca tgagcgaccc tgacctggaa actgagacta tgtgcctcca cgacgacgag    480

tcgtgtcgct acgaagggca agtcgctgtt taccaggatg tatacgcggt tgacggaccg    540

acaagtctct atcaccaagc caataaggga gttagagtcg cctactggat aggctttgac    600

accacccctt ttatgtttaa gaacttggct ggagcatatc catcatactc taccaactgg    660

gccgacgaaa ccgtgttaac ggctcgtaac ataggcctat gcagctctga cgttatggag    720

cggtcacgta gagggatgtc cattcttaga aagaagtatt tgaaaccatc caacaatgtt    780

ctattctctg ttggctcgac catctaccac gagaagaggg acttactgag gagctggcac    840

ctgccgtctg tatttcactt acgtggcaag caaaattaca catgtcggtg tgagactata    900

gttagttgcg acgggtacgt cgttaaaaga atagctatca gtccaggcct gtatgggaag    960

ccttcaggct atgctgctac gatgcaccgc gagggattct tgtgctgcaa agtgacagac   1020

acattgaacg gggagagggt ctcttttccc gtgtgcacgt atgtgccagc tacattgtgt   1080

gaccaaatga ctggcatact ggcaacagat gtcagtgcgg acgacgcgca aaaactgctg   1140

gttgggctca accagcgtat agtcgtcaac ggtcgcaccc agagaaacac caataccatg   1200

aaaaattacc ttttgcccgt agtggcccag gcatttgcta ggtgggcaaa ggaatataag   1260

gaagatcaag aagatgaaag gccactagga ctacgagata gacagttagt catggggtgt   1320

tgttgggctt ttagaaggca caagataaca tctatttata agcgcccgga tacccaaacc   1380

atcatcaaag tgaacagcga tttccactca ttcgtgctgc ccaggatagg cagtaacaca   1440

ttggagatcg ggctgagaac aagaatcagg aaaatgttag aggagcacaa ggagccgtca   1500
```

```
cctctcatta ccgccgagga cgtacaagaa gctaagtgcg cagccgatga ggctaaggag   1560
gtgcgtgaag ccgaggagtt gcgcgcagct ctaccacctt tggcagctga tgttgaggag   1620
cccactctgg aagccgatgt cgacttgatg ttacaagagg ctggggccgg ctcagtggag   1680
acacctcgtg gcttgataaa ggttaccagc tacgatggcg aggacaagat cggctcttac   1740
gctgtgcttt ctccgcaggc tgtactcaag agtgaaaaat tatcttgcat ccaccctctc   1800
gctgaacaag tcatagtgat aacacactct ggccgaaaag ggcgttatgc cgtggaacca   1860
taccatggta aagtagtggt gccagaggga catgcaatac ccgtccagga ctttcaagct   1920
ctgagtgaaa gtgccaccat tgtgtacaac gaacgtgagt tcgtaaacag gtacctgcac   1980
catattgcca cacatggagg agcgctgaac actgatgaag aatattacaa aactgtcaag   2040
cccagcgagc acgacggcga atacctgtac gacatcgaca ggaaacagtg cgtcaagaaa   2100
gaactagtca ctgggctagg gctcacaggc gagctggtgg atcctccctt ccatgaattc   2160
gcctacgaga gtctgagaac acgaccagcc gctccttacc aagtaccaac catagggtg    2220
tatggcgtgc caggatcagg caagtctggc atcattaaaa gcgcagtcac caaaaaagat   2280
ctagtggtga gcgccaagaa agaaaactgt gcagaaatta taagggacgt caagaaaatg   2340
aaagggctgg acgtcaatgc cagaactgtg gactcagtgc tcttgaatgg atgcaaacac   2400
cccgtagaga ccctgtatat tgacgaagct tttgcttgtc atgcaggtac tctcagagcg   2460
ctcatagcca ttataagacc taaaaaggca gtgctctgcg gggatcccaa acagtgcggt   2520
tttttaaca tgatgtgcct gaaagtgcat tttaaccacg agatttgcac acaagtcttc    2580
cacaaaagca tctctcgccg ttgcactaaa tctgtgactt cggtcgtctc aaccttgttt   2640
tacgacaaaa aaatgagaac gacgaatccg aaagagacta agattgtgat tgacactacc   2700
ggcagtacca aacctaagca ggacgatctc attctcactt gtttcagagg gtgggtgaag   2760
cagttgcaaa tagattacaa aggcaacgaa ataatgacgg cagctgcctc tcaagggctg   2820
acccgtaaag gtgtgtatgc cgttcggtac aaggtgaatg aaaatcctct gtacgcaccc   2880
acctcagaac atgtgaacgt cctactgacc cgcacggagg accgcatcgt gtggaaaaca   2940
ctagccggcg acccatggat aaaaacactg actgccaagt accctgggaa tttcactgcc   3000
acgatagagg agtggcaagc agagcatgat gccatcatga ggcacatctt ggagagaccg   3060
gaccctaccg acgtcttcca gaataaggca aacgtgtgtt gggccaaggc tttagtgccg   3120
gtgctgaaga ccgctggcat agacatgacc actgaacaat ggaacactgt ggattatttt   3180
gaaacggaca aagctcactc agcagagata gtattgaacc aactatgcgt gaggttcttt   3240
ggactcgatc tggactccgg tctattttct gcacccactg ttccgttatc cattaggaat   3300
aatcactggg ataactcccc gtcgcctaac atgtacgggc tgaataaaga agtggtccgt   3360
cagctctctc gcaggtaccc acaactgcct cgggcagttg ccactggaag agtctatgac   3420
atgaacactg gtacactgcg caattatgat ccgcgcataa acctagtacc tgtaaacaga   3480
agactgcctc atgctttagt cctccaccat aatgaacacc cacagagtga cttttcttca   3540
ttcgtcagca aattgaaggg cagaactgtc ctggtggtcg gggaaaagtt gtccgtccca   3600
ggcaaaatgg ttgactggtt gtcagaccgg cctgaggcta ccttcagagc tcggctggat   3660
ttaggcatcc caggtgatgt gcccaaatat gacataatat ttgttaatgt gaggacccca   3720
tataaatacc atcactatca gcagtgtgaa gaccatgcca ttaagcttag catgttgacc   3780
aagaaagctt gtctgcatct gaatcccggc ggaacctgtg tcagcatagg ttatggttac   3840
```

```
gctgacaggg ccagcgaaag catcattggt gctatagcgc ggcagttcaa gttttcccgg   3900

gtatgcaaac cgaaatcctc acttgaagag acggaagttc tgtttgtatt cattgggtac   3960

gatcgcaagg cccgtacgca caatccttac aagctttcat caaccttgac caacatttat   4020

acaggttcca gactccacga agccggatgt gcaccctcat atcatgtggt gcgaggggat   4080

attgccacgg ccaccgaagg agtgattata aatgctgcta acagcaaagg acaacctggc   4140

ggaggggtgt gcggagcgct gtataagaaa ttcccggaaa gcttcgattt acagccgatc   4200

gaagtaggaa aagcgcgact ggtcaaaggt gcagctaaac atatcattca tgccgtagga   4260

ccaaacttca acaaagtttc ggaggttgaa ggtgacaaac agttggcaga ggcttatgag   4320

tccatcgcta agattgtcaa cgataacaat tacaagtcag tagcgattcc actgttgtcc   4380

accggcatct tttccgggaa caaagatcga ctaacccaat cattgaacca tttgctgaca   4440

gctttagaca ccactgatgc agatgtagcc atatactgca gggacaagaa atgggaaatg   4500

actctcaagg aagcagtggc taggagagaa gcagtggagg agatatgcat atccgacgac   4560

tcttcagtga cagaacctga tgcagagctg gtgagggtgc atccgaagag ttctttggct   4620

ggaaggaagg gctacagcac aagcgatggc aaaactttct catatttgga agggaccaag   4680

tttcaccagg cggccaagga tatagcagaa attaatgcca tgtggcccgt tgcaacggag   4740

gccaatgagc aggtatgcat gtatatcctc ggagaaagca tgagcagtat taggtcgaaa   4800

tgccccgtcg aagagtcgga agcctccaca ccacctagca cgctgccttg cttgtgcatc   4860

catgccatga ctccagaaag agtacagcgc ctaaaagcct cacgtccaga acaaattact   4920

gtgtgctcat cctttccatt gccgaagtat agaatcactg gtgtgcagaa gatccaatgc   4980

tcccagccta tattgttctc accgaaagtg cctgcgtata ttcatccaag gaagtatctc   5040

gtggaaacac caccggtaga cgagactccg gagccatcgg cagagaacca atccacagag   5100

gggacacctg aacaaccacc acttataacc gaggatgaga ccaggactag aacgcctgag   5160

ccgatcatca tcgaagagga agaagaggat agcataagtt tgctgtcaga tggcccgacc   5220

caccaggtgc tgcaagtcga ggcagacatt cacgggccgc cctctgtatc tagctcatcc   5280

tggtccattc ctcatgcatc cgactttgat gtggacagtt tatccatact tgacaccctg   5340

gagggagcta gcgtgaccag cggggcaacg tcagccgaga ctaactctta cttcgcaaag   5400

agtatggagt ttctggcgcg accggtgcct gcgcctcgaa cagtattcag gaaccctcca   5460

catcccgctc cgcgcacaag aacaccgtca cttgcaccca gcagggcctg ctcgagaacc   5520

agcctagttt ccaccccgcc aggcgtgaat agggtgatca ctagagagga gctcgaggcg   5580

cttaccccgt cacgcactcc tagcaggtcg gtctcgagaa ccagcctggt ctccaacccg   5640

ccaggcgtaa atagggtgat tacaagagag gagtttgagg cgttcgtagc acaacaacaa   5700

tgacggtttg atgcgggtgc atacatcttt tcctccgaca ccggtcaagg gcatttacaa   5760

caaaaatcag taaggcaaac ggtgctatcc gaagtggtgt tggagaggac cgaattggag   5820

atttcgtatg ccccgcgcct cgaccaagaa aaagaagaat tactacgcaa gaaattacag   5880

ttaaatccca cacctgctaa cagaagcaga taccagtcca ggaaggtgga gaacatgaaa   5940

gccataacag ctagacgtat tctgcaaggc ctagggcatt atttgaaggc agaaggaaaa   6000

gtggagtgct accgaaccct gcatcctgtt cctttgtatt catctagtgt gaaccgtgcc   6060

ttttcaagcc ccaaggtcgc agtggaagcc tgtaacgcca tgttgaaaga gaactttccg   6120

actgtggctt cttactgtat tattccagag tacgatgcct atttggacat ggttgacgga   6180

gcttcatgct gcttagacac tgccagtttt tgccctgcaa agctgcgcag ctttccaaag   6240
```

```
aaacactcct atttggaacc cacaatacga tcggcagtgc cttcagcgat ccagaacacg   6300
ctccagaacg tcctggcagc tgccacaaaa agaaattgca atgtcacgca aatgagagaa   6360
ttgcccgtat tggattcggc ggcctttaat gtggaatgct tcaagaaata tgcgtgtaat   6420
aatgaatatt gggaaacgtt taaagaaaac cccatcaggc ttactgaaga aaacgtggta   6480
aattacatta ccaaattaaa aggaccaaaa gctgctgctc tttttgcgaa gacacataat   6540
ttgaatatgt tgcaggacat accaatggac aggtttgtaa tggacttaaa gagagacgtg   6600
aaagtgactc caggaacaaa acatactgaa gaacggccca aggtacaggt gatccaggct   6660
gccgatccgc tagcaacagc gtatctgtgc ggaatccacc gagagctggt taggagatta   6720
aatgcggtcc tgcttccgaa cattcataca ctgtttgata tgtcggctga agactttgac   6780
gctattatag ccgagcactt ccagcctggg gattgtgttc tggaaactga catcgcgtcg   6840
tttgataaaa gtgaggacga cgccatggct ctgaccgcgt taatgattct ggaagactta   6900
ggtgtggacg cagagctgtt gacgctgatt gaggcggctt tcggcgaaat ttcatcaata   6960
catttgccca ctaaaactaa atttaaattc ggagccatga tgaaatctgg aatgttcctc   7020
acactgtttg tgaacacagt cattaacatt gtaatcgcaa gcagagtgtt gagagaacgg   7080
ctaaccggat caccatgtgc agcattcatt ggagatgaca atatcgtgaa aggagtcaaa   7140
tcggacaaat taatggcaga caggtgcgcc acctggttga atatggaagt caagattata   7200
gatgctgtgg tgggcgagaa agcgccttat ttctgtggag ggtttatttt gtgtgactcc   7260
gtgaccggca cagcgtgccg tgtggcagac cccctaaaaa ggctgtttaa gcttggcaaa   7320
cctctggcag cagacgatga acatgatgat gacaggagaa gggcattgca tgaagagtca   7380
acacgctgga accgagtggg tattctttca gagctgtgca aggcagtaga atcaaggtat   7440
gaaaccgtag gaacttccat catagttatg gccatgacta ctctagctag cagtgttaaa   7500
tcattcagct acctgagagg ggccccctata actctctacg gctaacctga atggactacg   7560
actatcacgc ccaaacattt acagccgcgg tgtcaaaaac cgcgtggacg tggttaacat   7620
ccctgctggg aggatcagcc gtaattatta taattggctt ggtgctggct actattgtgg   7680
ccatgtacgt gctgaccaac cagaaacata attgaataca gcagcaattg gcaagctgct   7740
tacatagaac tcgcggcgat tggcatgccg ccttaaaatt tttattttat ttttcttttc   7800
ttttccgaat cggattttgt ttttaatatt tcaaaaaaaa aaaaaaaaaa aaaaaaaaaa   7860
aaaaaaaaaa aaaaaaaaaa aaaaaaaaaa aaaaaaaaaa aaaaaaaaaa aatacgtagt   7920
ttaaac                                                               7926
```

<210> SEQ ID NO 10
<211> LENGTH: 36519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
ccatcttcaa taatatacct caaacttttt gtgcgcgtta atatgcaaat gaggcgtttg     60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaaacgg gccattttcg cgcgaaaact    300
```

```
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagatga ggcacctgag agacctgccc    600
gatgagaaaa tcatcatcgc ttccgggaac gagattctgg aactggtggt aaatgccatg    660
atgggcgacg accctccgga gcccccccacc ccatttgaga caccttcgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac    840
tcttcactgc ataccccctag acccggcaga ggtgagaaaa agatccccga gcttaaaggg    900
gaagagatgg acttgcgctg ctatgaggaa tgcttgcccc cgagcgatga tgaggacgag    960
caggcgatcc agaacgcagc gagccaggga gtgcaagccg ccagcgagag ctttgcgctg   1020
gactgcccgc ctctgcccgg acacggctgt aagtcttgtg aatttcatcg catgaatact   1080
ggagataaag ctgtgttgtg tgcactttgc tatatgagag cttacaacca ttgtgtttac   1140
agtaagtgtg attaagttga actttagagg gaggcagaga gcagggtgac tgggcgatga   1200
ctggtttatt tatgtatata tgttctttat ataggtcccg tctctgacgc agatgatgag   1260
acccccacta caaagtccac ttcgtcaccc ccagaaattg gcacatctcc acctgagaat   1320
attgttagac cagttcctgt tagagccact gggaggagag cagctgtgga atgtttggat   1380
gacttgctac agggtggggt tgaacctttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tctttttgac gctcttaact   1800
tgggccatca gtctcacttt aaccagagga tttcgagagc ccttgatttt actactcctg   1860
gcagaaccac tgcagcagta gcctttttttg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
```

```
agatgggtat aatggcacgg tctttatggc caataccaag ctgacagtcc atggctgctc   2700
cttctttggg tttaataaca cctgcatcga ggcctggggt caggtcggtg tgaggggctg   2760
cagtttttca gccaactgga tgggggtcgt gggcaggacc aagagtatgc tgtccgtgaa   2820
gaaatgcttg tttgagaggt gccacctggg ggtgatgagc gagggcgaag ccagaatccg   2880
ccactgcgcc tctaccgaga cgggctgctt tgtgctgtgc aagggcaatg ctaagatcaa   2940
gcataatatg atctgtggag cctcggacga gcgcggctac cagatgctga cctgcgccgg   3000
cgggaacagc catatgctgg ccaccgtaca tgtggcttcc catgctcgca agccctggcc   3060
cgagttcgag cacaatgtca tgaccaggtg caatatgcat ctggggtccc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggagggaagc atgccaggtt   3300
ccagcccgtg tgtgtggatg tgacggagga cctgcgaccc gatcatttgg tgttgccctg   3360
caccgggacg gagttcggtt ccagcgggga agaatctgac tagagtgagt agtgttctgg   3420
ggcgggggag gacctgcatg agggccagaa taactgaaat ctgtgctttt ctgtgtgttg   3480
cagcagcatg agcggaagcg gctcctttga gggaggggta ttcagccctt atctgacggg   3540
gcgtctcccc tcctgggcgg gagtgcgtca gaatgtgatg ggatccacgg tggacggccg   3600
gcccgtgcag cccgcgaact cttcaaccct gacctatgca accctgagct cttcgtcgtt   3660
ggacgcagct gccgccgcag ctgctgcatc tgccgccagc gccgtgcgcg gaatggccat   3720
gggcgccggc tactacggca ctctggtggc caactcgagt tccaccaata atcccgccag   3780
cctgaacgag gagaagctgt tgctgctgat ggcccagctc gaggccttga cccagcgcct   3840
gggcgagctg acccagcagg tggctcagct gcaggagcag acgcgggccg cggttgccac   3900
ggtgaaatcc aaataaaaaa tgaatcaata aataaacgga gacggttgtt gattttaaca   3960
cagagtctga atctttattt gatttttcgc gcgcggtagg ccctggacca ccggtctcga   4020
tcattgagca cccggtggat cttttccagg acccggtaga ggtgggcttg gatgttgagg   4080
tacatgggca tgagcccgtc ccgggggtgg aggtagctcc attgcagggc ctcgtgctcg   4140
ggggtggtgt tgtaaatcac ccagtcatag caggggcgca gggcatggtg ttgcacaata   4200
tctttgagga ggagactgat ggccacgggc agccctttgg tgtaggtgtt tacaaatctg   4260
ttgagctggg agggatgcat gcggggggag atgaggtgca tcttggcctg gatcttgaga   4320
ttggcgatgt taccgcccag atcccgcctg ggttcatgt tgtgcaggac caccagcacg   4380
gtgtatccgg tgcacttggg gaatttatca tgcaacttgg aagggaaggc gtgaaagaat   4440
ttggcgacgc ctttgtgccc gcccaggttt tccatgcact catccatgat gatggcgatg   4500
ggcccgtggg cggcggcctg ggcaaagacg tttcgggggt cggacacatc atagttgtgg   4560
tcctgggtga ggtcatcata ggccatttta atgaatttgg ggcggagggt gccggactgg   4620
gggacaaagg taccctcgat cccgggggcg tagttcccct cacagatctg catctcccag   4680
gctttgagct cggagggggg gatcatgtcc acctgcgggg cgataaagaa cacggtttcc   4740
ggggcggggg agatgagctg ggccgaaagc aagttccgga gcagctggga cttgccgcag   4800
ccggtggggc cgtagatgac cccgatgacc ggctgcaggt ggtagttgag ggagagacag   4860
ctgccgtcct cccggaggag gggggccacc tcgttcatca tctcgcgcac gtgcatgttc   4920
tcgcgcacca gttccgccag gaggcgctct ccccccaggg ataggagctc ctggagcgag   4980
gcgaagtttt tcagcggctt gagtccgtcg gccatgggca ttttggagag ggtttgttgc   5040
```

```
aagagttcca ggcggtccca gagctcggtg atgtgctcta cggcatctcg atccagcaga   5100
cctcctcgtt tcgcgggttg ggacggctgc gggagtaggg caccagacga tgggcgtcca   5160
gcgcagccag ggtccggtcc ttccagggtc gcagcgtccg cgtcagggtg gtctccgtca   5220
cggtgaaggg gtgcgcgccg ggctgggcgc ttgcgagggt gcgcttcagg ctcatccggc   5280
tggtcgaaaa ccgctcccga tcggcgccct gcgcgtcggc caggtagcaa ttgaccatga   5340
gttcgtagtt gagcgcctcg gccgcgtggc ctttggcgcg gagcttacct ttggaagtct   5400
gcccgcaggc gggacagagg agggacttga gggcgtagag cttgggggcg aggaagacgg   5460
actcgggggc gtaggcgtcc gcgccgcagt gggcgcagac ggtctcgcac tccacgagcc   5520
aggtgaggtc gggctggtcg ggtcaaaaa ccagtttccc gccgttcttt ttgatgcgtt   5580
tcttaccttt ggtctccatg agctcgtgtc cccgctgggt gacaaagagg ctgtccgtgt   5640
ccccgtagac cgactttatg ggccggtcct cgagcggtgt gccgcggtcc tcctcgtaga   5700
ggaaccccgc ccactccgag acgaaagccc gggtccaggc cagcacgaag gaggccacgt   5760
gggacgggta gcggtcgttg tccaccagcg ggtccacctt ttccagggta tgcaaacaca   5820
tgtccccctc gtccacatcc aggaaggtga ttggcttgta agtgtaggcc acgtgaccgg   5880
gggtcccggc cggggggta taaaagggtg cgggtccctg ctcgtcctca ctgtcttccg   5940
gatcgctgtc caggagcgcc agctgttggg gtaggtattc cctctcgaag gcgggcatga   6000
cctcggcact caggttgtca gtttctagaa acgaggagga tttgatattg acggtgccgg   6060
cggagatgcc tttcaagagc ccctcgtcca tctggtcaga aaagacgatc tttttgttgt   6120
cgagcttggt ggcgaaggag ccgtagaggg cgttggagag gagcttggcg atggagcgca   6180
tggtctggtt tttttccttg tcggcgcgct ccttggcggc gatgttgagc tgcacgtact   6240
cgcgcgccac gcacttccat tcggggaaga cggtggtcag ctcgtcgggc acgattctga   6300
cctgccagcc ccgattatgc agggtgatga ggtccacact ggtggccacc tcgccgcgca   6360
ggggctcatt agtccagcag aggcgtccgc ccttgcgcga gcagaagggg ggcagggggt   6420
ccagcatgac ctcgtcgggg gggtcggcat cgatggtgaa gatgccgggc aggaggtcgg   6480
ggtcaaagta gctgatggaa gtggccagat cgtccagggc agcttgccat tcgcgcacgg   6540
ccagcgcgcg ctcgtaggga ctgaggggcg tgccccaggg catgggatgg gtaagcgcgg   6600
aggcgtacat gccgcagatg tcgtagacgt agaggggctc ctcgaggatg ccgatgtagg   6660
tggggtagca gcgccccccg cggatgctgg cgcgcacgta gtcatacagc tcgtgcgagg   6720
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agccccccctg ctcccagagc tggaagtccg   7260
tgcgcttctt gtaggcgggg ttgggcaaag cgaaagtaac atcgttgaag aggatcttgc   7320
ccgcgcgggg cataaagttg cgagtgatgc ggaaaggttg ggcacctcg gcccggttgt   7380
```

```
tgatgacctg ggcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgcccctgg ggtgtgacca   8400
ccgtcccccg tttcttcttg ggcggctggg gcgacggggg cggtgcctct tccatggtta   8460
gaagcggcgg cgaggacgcg cgccgggcgg caggggcggc tcggggcccg gaggcagggg   8520
cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag gcgttcatgc ccgcctcgtt   8880
ccagacgcgg ctgtagacca cgacgccctc gggatcgcgg gcgcgcatga ccacctgggc   8940
gaggttgagc tccacgtggc gcgtgaagac cgcgtagttg cagaggcgct ggtagaggta   9000
gttgagcgtg gtggcgatgt gctcggtgac gaagaaatac atgatccagc ggcggagcgg   9060
catctcgctg acgtcgccca gcgcctccaa acgttccatg gcctcgtaaa agtccacggc   9120
gaagttgaaa aactgggagt tgcgcgccga gacggtcaac tcctcctcca gaagacggat   9180
gagctcggcg atggtggcgc gcacctcgcg ctcgaaggcc cccgggagtt cctccacttc   9240
ctcttcttcc tcctccacta acatctcttc tacttcctcc tcaggcggca gtggtggcgg   9300
gggagggggc ctgcgtcgcc ggcggcgcac gggcagacgg tcgatgaagc gctcgatggt   9360
ctcgccgcgc cggcgtcgca tggtctcggt gacggcgcgc ccgtcctcgc ggggccgcag   9420
cgtgaagacg ccgccgcgca tctccaggtg gccgggggggg tccccgttgg gcagggagag   9480
ggcgctgacg atgcatctta tcaattgccc cgtagggact ccgcgcaagg acctgagcgt   9540
ctcgagatcc acgggatctg aaaaccgctg aacgaaggct tcgagccagt cgcagtcgca   9600
aggtaggctg agcacggttt cttctggcgg gtcatgttgg ttgggagcgg ggcgggcgat   9660
gctgctggtg atgaagttga aataggcggt tctgagacgg cggatggtgg cgaggagcac   9720
caggtctttg ggcccggctt gctggatgcg cagacggtcg gccatgcccc aggcgtggtc   9780
```

```
ctgacacctg gccaggtcct tgtagtagtc ctgcatgagc cgctccacgg gcacctcctc   9840
ctcgcccgcg cggccgtgca tgcgcgtgag cccgaagccg cgctggggct ggacgagcgc   9900
caggtcggcg acgacgcgct cggcgaggat ggcttgctgg atctgggtga gggtggtctg   9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
ttgttttgtt tgtttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gagggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
```

```
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccggggcca ggaggactac accaacttca tcagcgccct gcgcctgatg  12540
gtgaccgagg tgccccagag cgaggtgtac cagtccgggc cggactactt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgcgccc tgggccagga cgacccgggc  12900
aacctggaag ccaccctgaa ctttttgctg accaaccggt cgcagaagat cccgccccag  12960
tacgcgctca gcaccgagga ggagcgcatc ctgcgttacg tgcagcagag cgtgggcctg  13020
ttcctgatgc aggagggggc caccccccagc gccgcgctcg acatgaccgc gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc agggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggagggt cctcctccct  13920
cgtacgagag cgtgatgcag caggcgatgg cggcggcggc gatgcagccc ccgctggagg  13980
ctccttacgt gcccccgcgg tacctggcgc ctacggaggg gcggaacagc attcgttact  14040
cggagctggc acccttgtac gataccaccc ggttgtacct ggtggacaac aagtcggcgg  14100
acatcgcctc gctgaactac cagaacgacc acagcaactt cctgaccacc gtggtgcaga  14160
acaatgactt cacccccacg gaggccagca cccagaccat caactttgac gagcgctcgc  14220
ggtggggcgg ccagctgaaa accatcatgc acaccaacat gcccaacgtg aacgagttca  14280
tgtacagcaa caagttcaag gcgcgggtga tggtctcccg caagaccccc aatggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
```

```
agttcgacac taggaacttc aggctgggct gggaccccgt gaccgagctg gtcatgcccg  14580
gggtgtacac caacgaggct ttccatcccg atattgtctt gctgcccggc tgcggggtgg  14640
acttcaccga gagccgcctc agcaacctgc tgggcattcg caagaggcag cccttccagg  14700
aaggcttcca gatcatgtac gaggatctgg agggggcaa catccccgcg ctcctggatg  14760
tcgacgccta tgagaaaagc aaggaggatg cagcagctga agcaactgca gccgtagcta  14820
ccgcctctac cgaggtcagg ggcgataatt ttgcaagcgc cgcagcagtg gcagcggccg  14880
aggcggctga aaccgaaagt aagatagtca ttcagccggt ggagaaggat agcaagaaca  14940
ggagctacaa cgtactaccg gacaagataa acaccgccta ccgcagctgg tacctagcct  15000
acaactatgg cgaccccgag aagggcgtgc gctcctggac gctgctcacc acctcggacg  15060
tcacctgcgg cgtggagcaa gtctactggt cgctgcccga catgatgcaa gacccggtca  15120
ccttccgctc cacgcgtcaa gttagcaact acccggtggt gggcgccgag ctcctgcccg  15180
tctactccaa gagcttcttc aacgagcagg ccgtctactc gcagcagctg cgcgccttca  15240
cctcgcttac gcacgtcttc aaccgcttcc ccgagaacca gatcctcgtc cgcccgcccg  15300
cgcccaccat taccaccgtc agtgaaaacg ttcctgctct cacagatcac gggaccctgc  15360
cgctgcgcag cagtatccgg ggagtccagc gcgtgaccgt tactgacgcc agacgccgca  15420
cctgccccta cgtctacaag gccctgggca tagtcgcgcc gcgcgtcctc tcgagccgca  15480
ccttctaaat gtccattctc atctcgccca gtaataacac cggttggggc ctgcgcgcgc  15540
ccagcaagat gtacggaggc gctcgccaac gctccacgca acaccccgtg cgcgtgcgcg  15600
ggcacttccg cgctccctgg ggcgccctca agggccgcgt gcggtcgcgc accaccgtcg  15660
acgacgtgat cgaccaggtg gtggccgacg cgcgcaacta cacccccgcc gccgcgcccg  15720
tctccaccgt ggacgccgtc atcgacagcg tggtggccga cgcgcgccgg tacgcccgcg  15780
ccaagagccg gcggcggcgc atcgcccggc ggcaccggag cacccccgcc atgcgcgcgg  15840
cgcgagcctt gctgcgcagg gccaggcgca cgggacgcag ggccatgctc agggcggcca  15900
gacgcgcggc ttcaggcgcc agcgccggca ggacccggag acgcgcggcc acggcggcgg  15960
cagcggccat cgccagcatg tcccgcccgc ggcgagggaa cgtgtactgg gtgcgcgacg  16020
ccgccaccgg tgtgcgcgtg cccgtgcgca cccgcccccc tcgcacttga agatgttcac  16080
ttcgcgatgt tgatgtgtcc cagcggcgag gaggatgtcc aagcgcaaat tcaaggaaga  16140
gatgctccag gtcatcgcgc ctgagatcta cggccctgcg gtggtgaagg aggaaagaaa  16200
gccccgcaaa atcaagcggg tcaaaaagga caaaaaggaa gaagaaagtg atgtggacgg  16260
attggtggag tttgtgcgcg agttcgcccc ccggcggcgc gtgcagtggc gcgggcggaa  16320
ggtgcaaccg gtgctgagac ccggcaccac cgtggtcttc acgcccggcg agcgctccgg  16380
caccgcttcc aagcgctcct acgacgaggt gtacggggat gatgatattc tggagcaggc  16440
ggccgagcgc ctgggcgagt ttgcttacgg caagcgcagc cgttccgcac cgaaggaaga  16500
ggcggtgtcc atcccgctgg accacggcaa ccccacgccg agcctcaagc ccgtgacctt  16560
gcagcaggtg ctgccgaccg cggcgccgcg ccgggggttc aagcgcgagg gcgaggatct  16620
gtaccccacc atgcagctga tggtgcccaa gcgccagaag ctggaagacg tgctggagac  16680
catgaaggtg gacccggacg tgcagcccga ggtcaaggtg cggcccatca agcaggtggc  16740
cccgggcctg ggcgtgcaga ccgtggacat caagattccc acggagccca tggaaacgca  16800
gaccgagccc atgatcaagc ccagcaccag caccatggag gtgcagacgg atccctggat  16860
```

```
gccatcggct cctagtcgaa gaccccggcg caagtacggc gcggccagcc tgctgatgcc  16920
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
cgccgctgca accaccccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt ggggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg gacccggtgc cgcccgccgg  17820
ctccgtggag atgccgcagg tggaggagga gctgcctccc ctggacaagc ggggcgagaa  17880
gcgaccccgc cccgatgcgg aggagacgct gctgacgcac acggacgagc cgcccccgta  17940
cgaggaggcg gtgaaactgg gtctgcccac cacgcggccc atcgcgcccc tggccaccgg  18000
ggtgctgaaa cccgaaaagc ccgcgaccct ggacttgcct cctccccagc cttcccgccc  18060
ctctacagtg gctaagcccc tgccgccggt ggccgtggcc cgcgcgcgac ccgggggcac  18120
cgcccgccct catgcgaact ggcagagcac tctgaacagc atcgtgggtc tgggagtgca  18180
gagtgtgaag cgccgccgct gctattaaac ctaccgtagc gcttaacttg cttgtctgtg  18240
tgtgtatgta ttatgtcgcc gccgccgctg tccaccagaa ggaggagtga agaggcgcgt  18300
cgccgagttg caagatggcc accccatcga tgctgcccca gtgggcgtac atgcacatcg  18360
ccggacagga cgcttcggag tacctgagtc cgggtctggt gcagtttgcc cgcgccacag  18420
acacctactt cagtctgggg aacaagttta ggaaccccac ggtggcgccc acgcacgatg  18480
tgaccaccga ccgcagccag cggctgacgc tgcgcttcgt gcccgtggac cgcgaggaca  18540
acacctactc gtacaaagtg cgctacacgc tggccgtggg cgacaaccgc gtgctggaca  18600
tggccagcac ctactttgac atccgcggcg tgctggatcg gggccctagc ttcaaaccct  18660
actccggcac cgcctacaac agtctggccc ccaagggagc acccaacact tgtcagtgga  18720
catataaagc cgatggtgaa actgccacag aaaaaaccta tacatatgga aatgcacccg  18780
tgcagggcat taacatcaca aaagatggta ttcaacttgg aactgacacc gatgatcagc  18840
caatctacgc agataaaacc tatcagcctg aacctcaagt gggtgatgct gaatggcatg  18900
acatcactgg tactgatgaa aagtatggag gcagagctct taagcctgat accaaaatga  18960
agccttgtta tggttctttt gccaagccta ctaataaaga aggaggtcag gcaaatgtga  19020
aaacaggaac aggcactact aaagaatatg acatagacat ggctttcttt gacaacagaa  19080
gtgcggctgc tgctggccta gctccagaaa ttgttttgta tactgaaaat gtggatttgg  19140
aaactccaga tacccatatt gtatacaaag caggcacaga tgacagcagc tcttctatta  19200
atttgggtca gcaagccatg cccaacagac ctaactacat tggtttcaga gacaacttta  19260
```

tcgggctcat gtactacaac agcactggca atatgggggt gctggccggt caggcttctc 19320
agctgaatgc tgtggttgac ttgcaagaca gaaacaccga gctgtcctac cagctcttgc 19380
ttgactctct gggtgacaga acccggtatt tcagtatgtg gaatcaggcg gtggacagct 19440
atgatcctga tgtgcgcatt attgaaaatc atggtgtgga ggatgaactt cccaactatt 19500
gtttccctct ggatgctgtt ggcagaacag atacttatca gggaattaag gctaatggaa 19560
ctgatcaaac cacatggacc aaagatgaca gtgtcaatga tgctaatgag ataggcaagg 19620
gtaatccatt cgccatggaa atcaacatcc aagccaacct gtggaggaac ttcctctacg 19680
ccaacgtggc cctgtacctg cccgactctt acaagtacac gccggccaat gttaccctgc 19740
ccaccaacac caacacctac gattacatga acggccgggt ggtggcgccc tcgctggtgg 19800
actcctacat caacatcggg gcgcgctggt cgctggatcc catggacaac gtgaacccct 19860
tcaaccacca ccgcaatgcg gggctgcgct accgctccat gctcctgggc aacgggcgct 19920
acgtgccctt ccacatccag gtgccccaga aatttttcgc catcaagagc ctcctgctcc 19980
tgcccgggtc ctacacctac gagtggaact tccgcaagga cgtcaacatg atcctgcaga 20040
gctccctcgg caacgacctg cgcacggacg gggcctccat ctccttcacc agcatcaacc 20100
tctacgccac cttcttcccc atggcgcaca acacggcctc cacgctcgag gccatgctgc 20160
gcaacgacac caacgaccag tccttcaacg actacctctc ggcggccaac atgctctacc 20220
ccatcccggc caacgccacc aacgtgccca tctccatccc ctcgcgcaac tgggccgcct 20280
tccgcggctg gtccttcacg cgtctcaaga ccaaggagac gccctcgctg ggctccgggt 20340
tcgaccccta cttcgtctac tcgggctcca tcccctacct cgacggcacc ttctacctca 20400
accacacctt caagaaggtc tccatcacct tcgactcctc cgtcagctgg cccggcaacg 20460
accggctcct gacgcccaac gagttcgaaa tcaagcgcac cgtcgacggc gagggctaca 20520
acgtggccca gtgcaacatg accaaggact ggttcctggt ccagatgctg gcccactaca 20580
acatcggcta ccagggcttc tacgtgcccg agggctacaa ggaccgcatg tactccttct 20640
tccgcaactt ccagcccatg agccgccagg tggtggacga ggtcaactac aaggactacc 20700
aggccgtcac cctggcctac cagcacaaca actcgggctt cgtcggctac ctcgcgccca 20760
ccatgcgcca gggccagccc taccccgcca actaccccta cccgctcatc ggcaagagcg 20820
ccgtcaccag cgtcacccag aaaaagttcc tctgcgacag ggtcatgtgg cgcatcccct 20880
tctccagcaa cttcatgtcc atgggcgcgc tcaccgacct cggccagaac atgctctatg 20940
ccaactccgc ccacgcgcta gacatgaatt tcgaagtcga ccccatggat gagtccaccc 21000
ttctctatgt tgtcttcgaa gtcttcgacg tcgtccgagt gcaccagccc caccgcggcg 21060
tcatcgaggc cgtctacctg cgcacccccct tctcggccgg taacgccacc acctaagctc 21120
ttgcttcttg caagccatgg ccgcgggctc cggcgagcag gagctcaggg ccatcatccg 21180
cgacctgggc tgcgggccct acttcctggg caccttcgat aagcgcttcc cgggattcat 21240
ggccccgcac aagctggcct gcgccatcgt caacacggcc ggccgcgaga ccgggggcga 21300
gcactggctg gccttcgcct ggaacccgcg ctcgaacacc tgctacctct tcgacccctt 21360
cgggttctcg gacgagcgcc tcaagcagat ctaccagttc gagtacgagg gcctgctgcg 21420
ccgcagcgcc ctggccaccg aggaccgctg cgtcaccctg gaaaagtcca cccagaccgt 21480
gcagggtccg cgctcggccg cctgcgggct cttctgctgc atgttcctgc acgccttcgt 21540
gcactggccc gaccgcccca tggacaagaa ccccaccatg aacttgctga cgggggtgcc 21600

```
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggacccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaagggggtc atcttgcagg tctgccttcc  22200
catggtgggc acgcacccgg gcttgtggtt gcaatcgcag tgcaggggga tcagcatcat  22260
ctgggcctgg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgcccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccataccct tctcccaggc cgagacgatg ggcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
cgagggggag cgcgagttct cgctcaccac tactatctct tcctcttctt ggtccgaggc  23220
cacgcggcgg taggtatgtc tcttcggggg cagaggcgga ggcgacgggc tctcgccgcc  23280
gcgacttggc ggatggctgg cagagcccct tccgcgttcg ggggtgcgct cccggcggcg  23340
ctctgactga cttcctccgc ggccggccat tgtgttctcc tagggaggaa caacaagcat  23400
ggagactcag ccatcgccaa cctcgccatc tgcccccacc gccgacgaga agcagcagca  23460
gcagaatgaa agcttaaccg ccccgccgcc cagccccgcc acctccgacg cggccgtccc  23520
agacatgcaa gagatggagg aatccatcga gattgacctg ggctatgtga cgcccgcgga  23580
gcacgaggag gagctggcag tgcgcttttc acaagaagag atacaccaag aacagccaga  23640
gcaggaagca gagaatgagc agagtcaggc tgggctcgag catgacggcg actacctcca  23700
cctgagcggg ggggaggacg cgctcatcaa gcatctggcc cggcaggcca ccatcgtcaa  23760
ggatgcgctg ctcgaccgca ccgaggtgcc cctcagcgtg gaggagctca gccgcgccta  23820
cgagttgaac ctcttctcgc cgcgcgtgcc ccccaagcgc cagcccaatg gcacctgcga  23880
gcccaacccg cgcctcaact tctacccggt cttcgcggtg cccgaggccc tggccaccta  23940
ccacatcttt ttcaagaacc aaaagatccc cgtctcctgc cgcgccaacc gcacccgcgc  24000
```

```
cgacgccctt ttcaacctgg gtcccggcgc ccgcctacct gatatcgcct ccttggaaga  24060
ggttcccaag atcttcgagg gtctgggcag cgacgagact cgggccgcga acgctctgca  24120
aggagaagga ggagagcatg agcaccacag cgccctggtc gagttggaag gcgacaacgc  24180
gcggctggcg gtgctcaaac gcacggtcga gctgacccat ttcgcctacc cggctctgaa  24240
cctgcccccc aaagtcatga gcgcggtcat ggaccaggtg ctcatcaagc gcgcgtcgcc  24300
catctccgag gacgagggca tgcaagactc cgaggagggc aagcccgtgg tcagcgacga  24360
gcagctggcc cggtggctgg gtcctaatgc tagtccccag agtttggaag agcggcgcaa  24420
actcatgatg gccgtggtcc tggtgaccgt ggagctggag tgcctgcgcc gcttcttcgc  24480
cgacgcggag accctgcgca aggtcgagga gaacctgcac tacctcttca ggcacgggtt  24540
cgtgcgccag gcctgcaaga tctccaacgt ggagctgacc aacctggtct cctacatggg  24600
catcttgcac gagaaccgcc tggggcagaa cgtgctgcac accaccctgc gcggggaggc  24660
ccggcgcgac tacatccgcg actgcgtcta cctctacctc tgccacacct ggcagacggg  24720
catgggcgtg tggcagcagt gtctggagga gcagaacctg aaagagctct gcaagctcct  24780
gcagaagaac ctcaagggtc tgtggaccgg gttcgacgag cgcaccaccg cctcggacct  24840
ggccgacctc attttccccg agcgcctcag gctgacgctg cgcaacggcc tgcccgactt  24900
tatgagccaa agcatgttgc aaaactttcg ctctttcatc ctcgaacgct ccggaatcct  24960
gcccgccacc tgctccgcgc tgccctcgga cttcgtgccg ctgaccttcc gcgagtgccc  25020
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca agggggggtct  25260
gaaactcacc ccggggctgt ggacctcggc ctacttgcgc aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
```

-continued

```
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc cctgggaggg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
```

```
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aattttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgttggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag ggggtctaag gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
gcgcttctgc tgttagtgct cccccgtccc gtcgaccccc ggtcccccac ccagtccccc  31080
```

```
gaggaggtcc gcaaatgcaa attccaagaa ccctggaaat tcctcaaatg ctaccgccaa  31140
aaatcagaca tgcatcccag ctggatcatg atcattggga tcgtgaacat tctggcctgc  31200
accctcatct cctttgtgat ttacccctgc tttgactttg gttggaactc gccagaggcg  31260
ctctatctcc cgcctgaacc tgacacacca ccacagcaac ctcaggcaca cgcactacca  31320
ccactacagc ctaggccaca atacatgccc atattagact atgaggccga gccacagcga  31380
cccatgctcc ccgctattag ttacttcaat ctaaccggcg gagatgactg acccactggc  31440
caacaacaac gtcaacgacc ttctcctgga catggacggc cgcgcctcgg agcagcgact  31500
cgcccaactt cgcattcgcc agcagcagga gagagccgtc aaggagctgc aggatgcggt  31560
ggccatccac cagtgcaaga gaggcatctt ctgcctggtg aaacaggcca agatctccta  31620
cgaggtcact ccaaacgacc atcgcctctc ctacgagctc ctgcagcagc gccagaagtt  31680
cacctgcctg gtcggagtca accccatcgt catcacccag cagtctggcg ataccaaggg  31740
gtgcatccac tgctcctgcg actcccccga ctgcgtccac actctgatca agaccctctg  31800
cggcctccgc gacctcctcc ccatgaacta atcacccct tatccagtga aataaagatc  31860
atattgatga tgattttaca gaaataaaaa ataatcattt gatttgaaat aaagatacaa  31920
tcatattgat gatttgagtt taacaaaaaa ataaagaatc acttacttga aatctgatac  31980
caggtctctg tccatgtttt ctgccaacac cacttcactc ccctcttccc agctctggta  32040
ctgcaggccc cggcgggctg caaacttcct ccacacgctg aaggggatgt caaattcctc  32100
ctgtccctca atcttcattt tatcttctat cagatgtcca aaaagcgcgt ccgggtggat  32160
gatgacttcg accccgtcta cccctacgat gcagacaacg caccgaccgt gcccttcatc  32220
aacccccccct tcgtctcttc agatggattc caagagaagc cctgggggt gttgtccctg  32280
cgactggccg accccgtcac caccaagaac ggggaaatca ccctcaagct gggagagggg  32340
gtggacctcg attcctcggg aaaactcatc tccaacacgg ccaccaaggc cgccgcccct  32400
ctcagttttt ccaacaacac catttccctt aacatggatc accccttta cactaaagat  32460
ggaaaattat ccttacaagt ttctccacca ttaaatatac tgagaacaag cattctaaac  32520
acactagctt taggttttgg atcaggttta ggactccgtg gctctgcctt ggcagtacag  32580
ttagtctctc cacttacatt tgatactgat ggaaacataa agcttacctt agacagaggt  32640
ttgcatgtta caacaggaga tgcaattgaa agcaacataa gctgggctaa aggtttaaaa  32700
tttgaagatg gagccatagc aaccaacatt ggaaatgggt tagagtttgg aagcagtagt  32760
acagaaacag gtgttgatga tgcttaccca atccaagtta aacttggatc tggccttagc  32820
tttgacagta caggagccat aatggctggt aacaaagaag acgataaact cactttgtgg  32880
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg gtgttctttt aacagaacat tctacactaa aaaaatactg gggtatagg  33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg ggctaactc ttataccttc tcatacatcg cccaagaatg aacactgtat  33420
cccaccctgc atgccaaccc ttcccacccc actctgtgga acaaactctg aaacacaaaa  33480
```

```
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcgggggtc aaaaccatat cccagggcac  34440
ggggaactct tgcaggacag cgaaccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
tgttacactc ctgcaccatc cccagataat tttcattttt ccagccttga atgattcgaa  35220
ctagttcctg aggtaaatcc aagccagcca tgataaagag ctcgcgcaga gcgccctcca  35280
ccggcattct taagcacacc ctcataattc caagatattc tgctcctggt tcacctgcag  35340
cagattgaca agcggaatat caaaatctct gccgcgatcc ctgagctcct ccctcagcaa  35400
taactgtaag tactctttca tatcctctcc gaaattttta gccataggac caccaggaat  35460
aagattaggg caagccacag tacagataaa ccgaagtcct ccccagtgag cattgccaaa  35520
tgcaagactg ctataagcat gctggctaga cccggtgata tcttccagat aactggacag  35580
aaaatcgccc aggcaatttt taagaaaatc aacaaaagaa aaatcctcca ggtggacgtt  35640
tagagcctcg ggaacaacga tgaagtaaat gcaagcggtg cgttccagca tggttagtta  35700
gctgatctgt agaaaaaaca aaaatgaaca ttaaaccatg ctagcctggc gaacaggtgg  35760
gtaaatcgtt ctctccagca ccaggcaggc cacggggtct ccggcgcgac cctcgtaaaa  35820
```

```
attgtcgcta tgattgaaaa ccatcacaga gagacgttcc cggtggccgg cgtgaatgat  35880

tcgacaagat gaatacaccc ccggaacatt ggcgtccgcg agtgaaaaaa agcgcccgag  35940

gaagcaataa ggcactacaa tgctcagtct caagtccagc aaagcgatgc catgcggatg  36000

aagcacaaaa ttctcaggtg cgtacaaaat gtaattactc ccctcctgca caggcagcaa  36060

agcccccgat ccctccaggt acacatacaa agcctcagcg tccatagctt accgagcagc  36120

agcacacaac aggcgcaaga gtcagagaaa ggctgagctc taacctgtcc acccgctctc  36180

tgctcaatat atagcccaga tctacactga cgtaaaggcc aaagtctaaa aatacccgcc  36240

aaataatcac acacgcccag cacacgccca gaaaccggtg acacactcaa aaaaatacgc  36300

gcacttcctc aaacgcccaa aactgccgtc atttccgggt tcccacgcta cgtcatcaaa  36360

acacgacttt caaattccgt cgaccgttaa aaacgtcacc cgccccgccc ctaacggtcg  36420

cccgtctctc agccaatcag cgccccgcat ccccaaattc aaacacctca tttgcatatt  36480

aacgcgcaca aaaagtttga ggtatattat tgatgatgg                          36519
```

<210> SEQ ID NO 11
<211> LENGTH: 31867
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
ccatcttcaa taatatacct caaacttttt gtgcgcgtta atatgcaaat gaggcgtttg     60

aatttgggga ggaagggcgg tgattggtcg agggatgagc gaccgttagg ggcggggcga    120

gtgacgtttt gatgacgtgg ttgcgaggag gagccagttt gcaagttctc gtgggaaaag    180

tgacgtcaaa cgaggtgtgg tttgaacacg gaaatactca attttcccgc gctctctgac    240

aggaaatgag gtgtttctgg gcggatgcaa gtgaaaacgg gccattttcg cgcgaaaact    300

gaatgaggaa gtgaaaatct gagtaatttc gcgtttatgg cagggaggag tatttgccga    360

gggccgagta gactttgacc gattacgtgg gggtttcgat taccgtgttt ttcacctaaa    420

tttccgcgta cggtgtcaaa gtccggtgtt tttacgtagg tgtcagctga tcgccagggt    480

atttaaacct gcgctctcca gtcaagaggc cactcttgag tgccagcgag aagagttttc    540

tcctccgcgc cgcgagtcag atctacactt tgaaagtagg gataacaggg taatgacatt    600

gattattgac tagttgttaa tagtaatcaa ttacggggtc attagttcat agcccatata    660

tggagttccg cgttacataa cttacggtaa atggcccgcc tggctgaccg cccaacgacc    720

cccgcccatt gacgtcaata atgacgtatg ttcccatagt aacgccaata gggactttcc    780

attgacgtca atgggtggag tatttacggt aaactgccca cttggcagta catcaagtgt    840

atcatatgcc aagtccgccc cctattgacg tcaatgacgg taaatggccc gcctggcatt    900

atgcccagta catgacctta cgggactttc ctacttggca gtacatctac gtattagtca    960

tcgctattac catggtgatg cggttttggc agtacaccaa tgggcgtgga tagcggtttg   1020

actcacgggg atttccaagt ctccacccca ttgacgtcaa tgggagtttg ttttggcacc   1080

aaaatcaacg ggactttcca aaatgtcgta ataaccccgc cccgttgacg caaatgggcg   1140

gtaggcgtgt acggtgggag gtctatataa gcagagctcg tttagtgaac cgtcagatcg   1200

cctggaacgc catccacgct gttttgacct ccatagaaga cagcgatcgc gccaccatgg   1260

tgagcaaggg cgaggagctg ttcaccgggg tggtgcccat cctggtcgag ctggacggcg   1320
```

-continued

```
acgtaaacgg ccacaagttc agcgtgtccg gcgagggcga gggcgatgcc acctacggca   1380
agctgaccct gaagttcatc tgcaccaccg gcaagctgcc cgtgccctgg cccaccctcg   1440
tgaccaccct gacctacggc gtgcagtgct tcagccgcta ccccgaccac atgaagcagc   1500
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg gggcacaagc   1680
tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacaccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgagggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg ggaggttttt taaagcaagt   2220
aaaacctcta caaatgtggt aaaataacta taacggtcct aaggtagcga gtgagtagtg   2280
ttctggggcg gggggaggacc tgcatgaggg ccagaataac tgaaatctgt gcttttctgt   2340
gtgttgcagc agcatgagcg gaagcggctc ctttgaggga ggggtattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg gttgttgatt   2820
ttaacacaga gtctgaatct ttatttgatt tttcgcgcgc ggtaggccct ggaccaccgg   2880
tctcgatcat tgagcacccg gtggatcttt tccaggaccc ggtagaggtg ggcttggatg   2940
ttgaggtaca tgggcatgag cccgtcccgg gggtggaggt agctccattg cagggcctcg   3000
tgctcggggg tggtgttgta aatcacccag tcatagcagg ggcgcagggc atggtgttgc   3060
acaatatctt tgaggaggag actgatggcc acgggcagcc ctttggtgta ggtgtttaca   3120
aatctgttga gctgggaggg atgcatgcgg ggggagatga ggtgcatctt ggcctggatc   3180
ttgagattgg cgatgttacc gcccagatcc cgcctggggt tcatgttgtg caggaccacc   3240
agcacggtgt atccggtgca cttggggaat ttatcatgca acttggaagg gaaggcgtga   3300
aagaatttgg cgacgccttt gtgcccgccc aggttttcca tgcactcatc catgatgatg   3360
gcgatgggcc cgtgggcggc ggcctgggca aagacgtttc gggggtcgga cacatcatag   3420
ttgtggtcct gggtgaggtc atcataggcc attttaatga atttggggcg gagggtgccg   3480
gactggggga caaaggtacc ctcgatcccg gggcgtagt tcccctcaca gatctgcatc   3540
tcccaggctt tgagctcgga ggggggggatc atgtccacct gcggggcgat aaagaacacg   3600
gtttccgggg cgggggagat gagctgggcc gaaagcaagt tccggagcag ctgggacttg   3660
ccgcagccgg tggggccgta gatgaccccg atgaccggct gcaggtggta gttgagggag   3720
```

```
agacagctgc cgtcctcccg gaggaggggg gccacctcgt tcatcatctc gcgcacgtgc   3780
atgttctcgc gcaccagttc cgccaggagg cgctctcccc ccagggatag gagctcctgg   3840
agcgaggcga agtttttcag cggcttgagt ccgtcggcca tgggcatttt ggagagggtt   3900
tgttgcaaga gttccaggcg gtcccagagc tcggtgatgt gctctacggc atctcgatcc   3960
agcagacctc ctcgtttcgc gggttgggac ggctgcggga gtagggcacc agacgatggg   4020
cgtccagcgc agccagggtc cggtccttcc agggtcgcag cgtccgcgtc agggtggtct   4080
ccgtcacggt gaaggggtgc gcgccgggct gggcgcttgc gagggtgcgc ttcaggctca   4140
tccggctggt cgaaaaccgc tcccgatcgg cgccctgcgc gtcggccagg tagcaattga   4200
ccatgagttc gtagttgagc gcctcggccg cgtggccttt ggcgcggagc ttacctttgg   4260
aagtctgccc gcaggcggga cagaggaggg acttgagggc gtagagcttg ggggcgagga   4320
agacggactc gggggcgtag gcgtccgcgc cgcagtgggc gcagacggtc tcgcactcca   4380
cgagccaggt gaggtcgggc tggtcggggt caaaaaccag tttcccgccg ttctttttga   4440
tgcgtttctt acctttggtc tccatgagct cgtgtccccg ctgggtgaca aagaggctgt   4500
ccgtgtcccc gtagaccgac tttatgggcc ggtcctcgag cggtgtgccg cggtcctcct   4560
cgtagaggaa ccccgcccac tccgagacga aagcccgggt ccaggccagc acgaaggagg   4620
ccacgtggga cgggtagcgg tcgttgtcca ccagcgggtc caccttttcc agggtatgca   4680
aacacatgtc cccctcgtcc acatccagga aggtgattgg cttgtaagtg taggccacgt   4740
gaccgggggt cccggccggg ggggtataaa agggtgcggg tccctgctcg tcctcactgt   4800
cttccggatc gctgtccagg agcgccagct gttggggtag gtattccctc tcgaaggcgg   4860
gcatgacctc ggcactcagg ttgtcagttt ctagaaacga ggaggatttg atattgacgg   4920
tgccggcgga gatgcctttc aagagcccct cgtccatctg gtcagaaaag acgatctttt   4980
tgttgtcgag cttggtggcg aaggagccgt agagggcgtt ggagaggagc ttggcgatgg   5040
agcgcatggt ctggtttttt tccttgtcgg cgcgctcctt ggcggcgatg ttgagctgca   5100
cgtactcgcg cgccacgcac ttccattcgg ggaagacggt ggtcagctcg tcgggcacga   5160
ttctgacctg ccagccccga ttatgcaggg tgatgaggtc cacactggtg gccacctcgc   5220
cgcgcagggg ctcattagtc cagcagaggc gtccgccctt gcgcgagcag aaggggggca   5280
gggggtccag catgacctcg tcgggggggt cggcatcgat ggtgaagatg ccgggcagga   5340
ggtcggggtc aaagtagctg atggaagtgg ccagatcgtc cagggcagct tgccattcgc   5400
gcacggccag cgcgctctcg tagggactga ggggcgtgcc ccagggcatg ggatgggtaa   5460
gcgcggaggc gtacatgccg cagatgtcgt agacgtagag gggctcctcg aggatgccga   5520
tgtaggtggg gtagcagcgc cccccgcgga tgctggcgcg cacgtagtca tacagctcgt   5580
gcgagggggc gaggagcccc gggcccaggt tggtgcgact gggcttttcg gcgcggtaga   5640
cgatctggcg gaaaatggca tgcgagttgg aggagatggt gggcctttgg aagatgttga   5700
agtgggcgtg gggcagtccg accgagtcgc ggatgaagtg ggcgtaggag tcttgcagct   5760
tggcgacgag ctcggcggtg actaggacgt ccagagcgca gtagtcgagg gtctcctgga   5820
tgatgtcata cttgagctgt ccctttttgtt tccacagctc gcggttgaga aggaactctt   5880
cgcggtcctt ccagtactct tcgaggggga acccgtcctg atctgcacgg taagagccta   5940
gcatgtagaa ctggttgacg gccttgtagg cgcagcagcc cttctccacg gggagggcgt   6000
aggcctgggc ggccttgcgc agggaggtgt gcgtgagggc gaaagtgtcc ctgaccatga   6060
```

```
ccttgaggaa ctggtgcttg aagtcgatat cgtcgcagcc cccctgctcc cagagctgga   6120
agtccgtgcg cttcttgtag gcggggttgg gcaaagcgaa agtaacatcg ttgaagagga   6180
tcttgcccgc gcggggcata aagttgcgag tgatgcggaa aggttggggc acctcggccc   6240
ggttgttgat gacctgggcg gcgagcacga tctcgtcgaa gccgttgatg ttgtggccca   6300
cgatgtagag ttccacgaat cgcggacggc ccttgacgtg gggcagtttc ttgagctcct   6360
cgtaggtgag ctcgtcgggg tcgctgagcc cgtgctgctc gagcgcccag tcggcgagat   6420
gggggttggc gcggaggaag gaagtccaga gatccacggc cagggcggtt tgcagacggt   6480
cccggtactg acggaactgc tgcccgacgg ccatttttc ggggggtgacg cagtagaagg   6540
tgcgggggtc cccgtgccag cgatcccatt tgagctggag ggcgagatcg agggcgagct   6600
cgacgagccg gtcgtccccg gagagtttca tgaccagcat gaaggggacg agctgcttgc   6660
cgaaggaccc catccaggtg taggtttcca catcgtaggt gaggaagagc ctttcggtgc   6720
gaggatgcga gccgatgggg aagaactgga tctcctgcca ccaattggag gaatggctgt   6780
tgatgtgatg gaagtagaaa tgccgacggc gcgccgaaca ctcgtgcttg tgtttataca   6840
agcggccaca gtgctcgcaa cgctgcacgg gatgcacgtg ctgcacgagc tgtacctgag   6900
ttcctttgac gaggaatttc agtgggaagt ggagtcgtgg cgcctgcatc tcgtgctgta   6960
ctacgtcgtg gtggtcggcc tggccctctt ctgcctcgat ggtggtcatg ctgacgagcc   7020
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cgggggcggt gcctcttcca   7320
tggttagaag cggcggcgag gacgcgcgcc gggcggcagg ggcggctcgg ggcccggagg   7380
caggggcggc aggggcacgt cggcgccgcg cgcgggtagg ttctggtact gcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggcccccg ggagttcctc   8100
cacttcctct tcttcctcct ccactaacat ctcttctact tcctcctcag gcggcagtgg   8160
tggcgggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc cgcgcatctc caggtggccg ggggggtccc cgttgggcag   8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
```

```
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggct ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagccg atgaggaagt gcggcggcgg ctggcggtag agcggccatc gctcggtggc   9060
gggggcgccg ggcgcgaggt cctcgagcat ggtgcggtgg tagccgtaga tgtacctgga   9120
catccaggtg atgccggcgg cggtggtgga ggcgcgcggg aactcgcgga cgcggttcca   9180
gatgttgcgc agcggcagga agtagttcat ggtgggcacg gtctggcccg tgaggcgcgc   9240
gcagtcgtgg atgctctata cggcaaaaa cgaaagcggt cagcggctcg actccgtggc   9300
ctggaggcta agcgaacggg ttgggctgcg cgtgtacccc ggttcgaatc tcgaatcagg   9360
ctggagccgc agctaacgtg gtattggcac tcccgtctcg acccaagcct gcaccaaccc   9420
tccaggatac ggaggcgggt cgttttgcaa cttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag accccatagc cagccgactt ctccagttac ggagcgagcc   9660
cctcttttgt tttgtttgtt tttgccagat gcatcccgta ctgcggcaga tgcgccccca   9720
ccaccctcca ccgcaacaac agccccctcc acagccggcg cttctgcccc cgcccagca   9780
gcaacttcca gccacgaccg ccgcggccgc cgtgagcggg gctggacaga gttatgatca   9840
ccagctggcc ttggaagagg gcgaggggct ggcgcgcctg gggcgtcgt cgccggagcg   9900
gcacccgcgc gtgcagatga aaagggacgc tcgcgaggcc tacgtgccca agcagaacct   9960
gttcagagac aggagcggcg aggagcccga ggagatgcgc gcggcccggt tccacgcggg  10020
gcgggagctg cggcgcggcc tggaccgaaa gagggtgctg agggacgagg atttcgaggc  10080
ggacgagctg acggggatca gccccgcgcg cgcgcacgtg gccgcggcca acctggtcac  10140
ggcgtacgag cagaccgtga aggaggagag caacttccaa aaatccttca acaaccacgt  10200
gcgcaccctg atcgcgcgcg aggaggtgac cctgggcctg atgcacctgt gggacctgct  10260
ggaggccatc gtgcagaacc ccaccagcaa gccgctgacg gcgcagctgt tcctggtggt  10320
gcagcatagt cgggacaacg aagcgttcag ggaggcgctg ctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggttttac atgcgcatga ccctgaaagt gctgaccctg agcgacgatc tgggggtgta  10620
ccgcaacgac aggatgcacc gtgcggtgag cgccagcagg cggcgcgagc tgagcgacca  10680
ggagctgatg catagtctgc agcgggccct gaccggggcc gggaccgagg gggagagcta  10740
ctttgacatg ggcgcggacc tgcactggca gcccagccgc cgggccttgg aggcggcggc  10800
```

```
aggaccctac gtagaagagg tggacgatga ggtggacgag gagggcgagt acctggaaga  10860
ctgatggcgc gaccgtattt ttgctagatg caacaacaac agccacctcc tgatcccgcg  10920
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gcccccttca cggacagcgg cagcatcaac  11640
cgcaactcgt acctgggcta cctgattaac ctgtaccgcg aggccatcgg ccaggcgcac  11700
gtggacgagc agacctacca ggagatcacc cacgtgagcc gcgccctggg ccaggacgac  11760
ccgggcaacc tggaagccac cctgaacttt ttgctgacca accggtcgca gaagatcccg  11820
ccccagtacg cgctcagcac cgaggaggag cgcatcctgc gttacgtgca gcagagcgtg  11880
ggcctgttcc tgatgcagga gggggccacc cccagcgccg cgctcgacat gaccgcgcgc  11940
aacatggagc ccagcatgta cgccagcaac cgcccgttca tcaataaact gatggactac  12000
ttgcatcggg cggccgccat gaactctgac tatttcacca acgccatcct gaatccccac  12060
tggctcccgc cgccggggtt ctacacgggc gagtacgaca tgcccgaccc caatgacggg  12120
ttcctgtggg acgatgtgga cagcagcgtg ttctcccccc gaccgggtgc taacgagcgc  12180
cccttgtgga agaaggaagg cagcgaccga cgcccgtcct cggcgctgtc cggccgcgag  12240
ggtgctgccg cggcggtgcc cgaggccgcc agtcctttcc cgagcttgcc cttctcgctg  12300
aacagtatcc gcagcagcga gctgggcagg atcacgcgcc cgcgcttgct gggcgaagag  12360
gagtacttga atgactcgct gttgagaccc gagcgggaga agaacttccc caataacggg  12420
atagaaagcc tggtggacaa gatgagccgc tggaagacgt atgcgcagga gcacagggac  12480
gatccccggg cgtcgcaggg ggccacgagc cggggcagcg ccgcccgtaa acgccggtgg  12540
cacgacaggc agcggggaca gatgtgggac gatgaggact ccgccgacga cagcagcgtg  12600
ttggacttgg gtgggagtgg taacccgttc gctcacctgc gcccccgtat cgggcgcatg  12660
atgtaagaga aaccgaaaat aaatgatact caccaaggcc atggcgacca gcgtgcgttc  12720
gtttcttctc tgttgttgtt gtatctagta tgatgaggcg tgcgtacccg gagggtcctc  12780
ctccctcgta cgagagcgtg atgcagcagg cgatggcggc ggcggcgatg cagcccccgc  12840
tggaggctcc ttacgtgccc ccgcggtacc tggcgcctac ggaggggcgg aacagcattc  12900
gttactcgga gctggcaccc ttgtacgata ccacccggtt gtacctggtg gacaacaagt  12960
cggcggacat cgcctcgctg aactaccaga acgaccacag caacttcctg accaccgtgg  13020
tgcagaacaa tgacttcacc cccacggagg ccagcaccca gaccatcaac tttgacgagc  13080
gctcgcggtg gggcggccag ctgaaaacca tcatgcacac caacatgccc aacgtgaacg  13140
agttcatgta cagcaacaag ttcaaggcgc gggtgatggt ctcccgcaag acccccaatg  13200
```

```
gggtgacagt gacagaggat tatgatggta gtcaggatga gctgaagtat gaatgggtgg  13260
aatttgagct gcccgaaggc aacttctcgg tgaccatgac catcgacctg atgaacaacg  13320
ccatcatcga caattacttg gcggtggggc ggcagaacgg ggtgctggag agcgacatcg  13380
gcgtgaagtt cgacactagg aacttcaggc tgggctggga ccccgtgacc gagctggtca  13440
tgcccggggt gtacaccaac gaggctttcc atcccgatat tgtcttgctg cccggctgcg  13500
gggtggactt caccgagagc cgcctcagca acctgctggg cattcgcaag aggcagccct  13560
tccaggaagg cttccagatc atgtacgagg atctggaggg gggcaacatc cccgcgctcc  13620
tggatgtcga cgcctatgag aaaagcaagg aggatgcagc agctgaagca actgcagccg  13680
tagctaccgc ctctaccgag gtcaggggcg ataattttgc aagcgccgca gcagtggcag  13740
cggccgaggc ggctgaaacc gaaagtaaga tagtcattca gccggtggag aaggatagca  13800
agaacaggag ctacaacgta ctaccggaca agataaacac cgcctaccgc agctggtacc  13860
tagcctacaa ctatggcgac cccgagaagg gcgtgcgctc ctggacgctg ctcaccacct  13920
cggacgtcac ctgcggcgtg gagcaagtct actggtcgct gcccgacatg atgcaagacc  13980
cggtcacctt ccgctccacg cgtcaagtta gcaactaccc ggtggtgggc gccgagctcc  14040
tgcccgtcta ctccaagagc ttcttcaacg agcaggccgt ctactcgcag cagctgcgcg  14100
ccttcacctc gcttacgcac gtcttcaacc gcttccccga gaaccagatc ctcgtccgcc  14160
cgcccgcgcc caccattacc accgtcagtg aaaacgttcc tgctctcaca gatcacggga  14220
ccctgccgct gcgcagcagt atccggggag tccagcgcgt gaccgttact gacgccagac  14280
gccgcacctg cccctacgtc tacaaggccc tgggcatagt cgcgccgcgc gtcctctcga  14340
gccgcacctt ctaaatgtcc attctcatct cgcccagtaa taacaccggt tggggcctgc  14400
gcgcgcccag caagatgtac ggaggcgctc gccaacgctc cacgcaacac cccgtgcgcg  14460
tgcgcgggca cttccgcgct ccctggggcg ccctcaaggg ccgcgtgcgg tcgcgcacca  14520
ccgtcgacga cgtgatcgac caggtggtgg ccgacgcgcg caactacacc cccgccgccg  14580
cgcccgtctc caccgtggac gccgtcatcg acagcgtggt ggccgacgcg cgccggtacg  14640
cccgcgccaa gagccggcgg cggcgcatcg cccggcggca ccggagcacc cccgccatgc  14700
gcgcggcgcg agccttgctg cgcagggcca ggcgcacggg acgcagggcc atgctcaggg  14760
cggccagacg cgcggcttca ggcgccagcg ccggcaggac ccggagacgc gcggccacgg  14820
cggcggcagc ggccatcgcc agcatgtccc gcccgcggcg agggaacgtg tactgggtgc  14880
gcgacgccgc caccggtgtg cgcgtgcccg tgcgcacccg cccccctcgc acttgaagat  14940
gttcacttcg cgatgttgat gtgtcccagc ggcgaggagg atgtccaagc gcaaattcaa  15000
ggaagagatg ctccaggtca tcgcgcctga gatctacggc cctgcggtgg tgaaggagga  15060
aagaaagccc cgcaaaatca agcgggtcaa aaaggacaaa aaggaagaag aaagtgatgt  15120
ggacggattg gtggagtttg tgcgcgagtt cgcccccccgg cggcgcgtgc agtggcgcgg  15180
gcggaaggtg caaccggtgc tgagacccgg caccaccgtg gtcttcacgc ccggcgagcg  15240
ctccggcacc gcttccaagc gctcctacga cgaggtgtac ggggatgatg atattctgga  15300
gcaggcggcc gagcgcctgg gcgagtttgc ttacggcaag cgcagccgtt ccgcaccgaa  15360
ggaagaggcg gtgtccatcc cgctggacca cggcaacccc acgccgagcc tcaagcccgt  15420
gaccttgcag caggtgctgc cgaccgcggc gccgcgccgg gggttcaagc gcgagggcga  15480
ggatctgtac cccaccatgc agctgatggt gcccaagcgc cagaagctgg aagacgtgct  15540
```

```
ggagaccatg aaggtggacc cggacgtgca gcccgaggtc aaggtgcggc ccatcaagca  15600
ggtggccccg ggcctgggcg tgcagaccgt ggacatcaag attcccacgg agcccatgga  15660
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat tttcgtcccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
aacctatggc agcaaggcgt ggaacagcac cacagggcag gcgctgaggg ataagctgaa  16560
agagcagaac ttccagcaga aggtggtcga tgggctcgcc tcgggcatca acggggtggt  16620
ggacctggcc aaccaggccg tgcagcggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
tctgtgtgtg tatgtattat gtcgccgccg ccgctgtcca ccagaaggag gagtgaagag  17160
gcgcgtcgcc gagttgcaag atggccaccc catcgatgct gccccagtgg gcgtacatgc  17220
acatcgccgg acaggacgct tcggagtacc tgagtccggg tctggtgcag tttgcccgcg  17280
ccacagacac ctacttcagt ctggggaaca agtttaggaa ccccacggtg gcgcccacgc  17340
acgatgtgac caccgaccgc agccagcggc tgacgctgcg cttcgtgccc gtggaccgcg  17400
aggacaacac ctactcgtac aaagtgcgct acacgctggc cgtgggcgac aaccgcgtgc  17460
tggacatggc cagcacctac tttgacatcc gcggcgtgct ggatcggggc cctagcttca  17520
aaccctactc cggcaccgcc tacaacagtc tggcccccaa gggagcaccc aacacttgtc  17580
agtggacata taaagccgat ggtgaaactg ccacagaaaa aacctataca tatggaaatg  17640
cacccgtgca gggcattaac atcacaaaag atggtattca acttggaact gacaccgatg  17700
atcagccaat ctacgcagat aaaacctatc agcctgaacc tcaagtgggt gatgctgaat  17760
ggcatgacat cactggtact gatgaaaagt atggaggcag agctcttaag cctgatacca  17820
aaatgaagcc ttgttatggt tcttttgcca agcctactaa taaagaagga ggtcaggcaa  17880
atgtgaaaac aggaacaggc actactaaag aatatgacat agacatggct tctttgaca  17940
```

```
acagaagtgc ggctgctgct ggcctagctc cagaaattgt tttgtatact gaaaatgtgg  18000
atttggaaac tccagatacc catattgtat acaaagcagg cacagatgac agcagctctt  18060
ctattaattt gggtcagcaa gccatgccca acagacctaa ctacattggt ttcagagaca  18120
actttatcgg gctcatgtac tacaacagca ctggcaatat gggggtgctg gccggtcagg  18180
cttctcagct gaatgctgtg gttgacttgc aagacagaaa caccgagctg tcctaccagc  18240
tcttgcttga ctctctgggt gacagaaccc ggtatttcag tatgtggaat caggcggtgg  18300
acagctatga tcctgatgtg cgcattattg aaaatcatgg tgtggaggat gaacttccca  18360
actattgttt ccctctggat gctgttggca gaacagatac ttatcaggga attaaggcta  18420
atggaactga tcaaaccaca tggaccaaag atgacagtgt caatgatgct aatgagatag  18480
gcaagggtaa tccattcgcc atggaaatca acatccaagc caacctgtgg aggaacttcc  18540
tctacgccaa cgtggccctg tacctgcccg actcttacaa gtacacgccg gccaatgtta  18600
ccctgcccac caacaccaac acctacgatt acatgaacgg ccgggtggtg gcgccctcgc  18660
tggtggactc ctacatcaac atcggggcgc gctggtcgct ggatcccatg gacaacgtga  18720
accccttcaa ccaccaccgc aatgcggggc tgcgctaccg ctccatgctc ctgggcaacg  18780
ggcgctacgt gcccttccac atccaggtgc cccagaaatt tttcgccatc aagagcctcc  18840
tgctcctgcc cgggtcctac acctacgagt ggaacttccg caaggacgtc aacatgatcc  18900
tgcagagctc cctcggcaac gacctgcgca cggacggggc ctccatctcc ttcaccagca  18960
tcaacctcta cgccaccttc ttccccatgg cgcacaacac ggcctccacg ctcgaggcca  19020
tgctgcgcaa cgacaccaac gaccagtcct tcaacgacta cctctcggcg gccaacatgc  19080
tctaccccat cccggccaac gccaccaacg tgcccatctc catcccctcg cgcaactggg  19140
ccgccttccg cggctggtcc ttcacgcgtc tcaagaccaa ggagacgccc tcgctgggct  19200
ccgggttcga cccctacttc gtctactcgg gctccatccc ctacctcgac ggcaccttct  19260
acctcaacca caccttcaag aaggtctcca tcaccttcga ctcctccgtc agctggcccg  19320
gcaacgaccg gctcctgacg cccaacgagt tcgaaatcaa gcgcaccgtc gacggcgagg  19380
gctacaacgt ggcccagtgc aacatgacca aggactggtt cctggtccag atgctggccc  19440
actacaacat cggctaccag ggcttctacg tgcccgaggg ctacaaggac cgcatgtact  19500
ccttcttccg caacttccag cccatgagcc gccaggtggt ggacgaggtc aactacaagg  19560
actaccaggc cgtcaccctg gcctaccagc acaacaactc gggcttcgtc ggctacctcg  19620
cgcccaccat gcgccagggc cagccctacc ccgccaacta cccctacccg ctcatcggca  19680
agagcgccgt caccagcgtc acccagaaaa agttcctctg cgacagggtc atgtggcgca  19740
tccccttctc cagcaacttc atgtccatgg gcgcgctcac cgacctcggc cagaacatgc  19800
tctatgccaa ctccgcccac gcgctagaca tgaatttcga agtcgacccc atggatgagt  19860
ccacccttct ctatgttgtc ttcgaagtct tcgacgtcgt ccgagtgcac cagccccacc  19920
gcggcgtcat cgaggccgtc tacctgcgca ccccttctc ggccggtaac gccaccacct  19980
aagctcttgc ttcttgcaag ccatggccgc gggctccggc gagcaggagc tcagggccat  20040
catccgcgac ctgggctgcg ggccctactt cctgggcacc ttcgataagc gcttcccggg  20100
attcatggcc ccgcacaagc tggcctgcgc catcgtcaac acggccggcc gcgagaccgg  20160
gggcgagcac tggctggcct tcgcctggaa cccgcgctcg aacacctgct acctcttcga  20220
ccccttcggg ttctcggacg agcgcctcaa gcagatctac cagttcgagt acgagggcct  20280
```

gctgcgccgc agcgccctgg ccaccgagga ccgctgcgtc accctggaaa agtccaccca 20340
gaccgtgcag ggtccgcgct cggccgcctg cgggctcttc tgctgcatgt tcctgcacgc 20400
cttcgtgcac tggcccgacc gccccatgga caagaacccc accatgaact tgctgacggg 20460
ggtgcccaac ggcatgctcc agtcgcccca ggtggaaccc accctgcgcc gcaaccagga 20520
ggcgctctac cgcttcctca actcccactc cgcctacttt cgctcccacc gcgcgcgcat 20580
cgagaaggcc accgccttcg accgcatgaa tcaagacatg taaaccgtgt gtgtatgtta 20640
aatgtcttta ataaacagca ctttcatgtt acacatgcat ctgagatgat ttatttagaa 20700
atcgaaaggg ttctgccggg tctcggcatg gcccgcgggc agggacacgt tgcggaactg 20760
gtacttggcc agccacttga actcggggat cagcagtttg ggcagcgggg tgtcggggaa 20820
ggagtcggtc cacagcttcc gcgtcagttg cagggcgccc agcaggtcgg gcgcggagat 20880
cttgaaatcg cagttgggac ccgcgttctg cgcgcgggag ttgcggtaca cggggttgca 20940
gcactggaac accatcaggg ccgggtgctt cacgctcgcc agcaccgtcg cgtcggtgat 21000
gctctccacg tcgaggtcct cggcgttggc catcccgaag gggtcatct tgcaggtctg 21060 ccttcccatg gtgggcacgc acccgggctt gtggttgcaa tcgcagtgca gggggatcag 21120
catcatctgg gcctggtcgg cgttcatccc cgggtacatg gccttcatga aagcctccaa 21180
ttgcctgaac gcctgctggg ccttggctcc ctcggtgaag aagaccccgc aggacttgct 21240
agagaactgg ttggtggcgc acccggcgtc gtgcacgcag cagcgcgcgt cgttgttggc 21300
cagctgcacc acgctgcgcc cccagcggtt ctgggtgatc ttggcccggt cggggttctc 21360
cttcagcgcg cgctgcccgt tctcgctcgc cacatccatc tcgatcatgt gctccttctg 21420
gatcatggtg gtcccgtgca ggcaccgcag cttgccctcg gcctcggtgc acccgtgcag 21480
ccacagcgcg cacccggtgc actcccagtt cttgtgggcg atctgggaat gcgcgtgcac 21540
gaagccctgc aggaagcggc ccatcatggt ggtcagggtc ttgttgctag tgaaggtcag 21600
cggaatgccg cggtgctcct cgttgatgta caggtggcag atgcggcggt acacctcgcc 21660
ctgctcgggc atcagctgga agttggcttt caggtcggtc tccacgcggt agcggtccat 21720
cagcatagtc atgatttcca tacccttctc ccaggccgag acgatgggca ggctcatagg 21780
gttcttcacc atcatcttag cgctagcagc cgcggccagg gggtcgctct cgtccagggt 21840
ctcaaagctc cgcttgccgt ccttctcggt gatccgcacc ggggggtagc tgaagcccac 21900
ggccgccagc tcctcctcgg cctgtctttc gtcctcgctg tcctggctga cgtcctgcag 21960
gaccacatgc ttggtcttgc ggggtttctt cttgggcggc agcggcggcg gagatgttgg 22020
agatggcgag gggagcgcgg agttctcgct caccactact atctcttcct cttcttggtc 22080
cgaggccacg cggcggtagg tatgtctctt cgggggcaga ggcggaggcg acgggctctc 22140
gccgccgcga cttggcggat ggctggcaga gccccttccg cgttcggggg tgcgctcccg 22200
gcggcgctct gactgacttc ctccgcggcc ggccattgtg ttctcctagg gaggaacaac 22260
aagcatggag actcagccat cgccaacctc gccatctgcc cccaccgccg acgagaagca 22320
gcagcagcag aatgaaagct taaccgcccc gccgcccagc cccgccacct ccgacgcggc 22380
cgtcccagac atgcaagaga tggaggaatc catcgagatt gacctgggct atgtgacgcc 22440
cgcggagcac gaggaggagc tggcagtgcg cttttcacaa gaagagatac accaagaaca 22500
gccagagcag gaagcagaga atgagcagag tcaggctggg ctcgagcatg acggcgacta 22560
cctccacctg agcgggggggg aggacgcgct catcaagcat ctggcccggc aggccaccat 22620
cgtcaaggat gcgctgctcg accgcaccga ggtgcccctc agcgtggagg agctcagccg 22680

```
cgcctacgag ttgaacctct tctcgccgcg cgtgcccccc aagcgccagc ccaatggcac  22740
ctgcgagccc aacccgcgcc tcaacttcta cccggtcttc gcggtgcccg aggccctggc  22800
cacctaccac atctttttca agaaccaaaa gatccccgtc tcctgccgcg ccaaccgcac  22860
ccgcgccgac gccctttca acctgggtcc cggcgcccgc ctacctgata tcgcctcctt  22920
ggaagaggtt cccaagatct tcgagggtct gggcagcgac gagactcggg ccgcgaacgc  22980
tctgcaagga gaaggaggag agcatgagca ccacagcgcc ctggtcgagt tggaaggcga  23040
caacgcgcgg ctggcggtgc tcaaacgcac ggtcgagctg acccatttcg cctacccggc  23100
tctgaacctg ccccccaaag tcatgagcgc ggtcatggac caggtgctca tcaagcgcgc  23160
gtcgcccatc tccgaggacg agggcatgca agactccgag gagggcaagc ccgtggtcag  23220
cgacgagcag ctggcccggt ggctgggtcc taatgctagt ccccagagtt tggaagagcg  23280
gcgcaaactc atgatggccg tggtcctggt gaccgtggag ctggagtgcc tgcgccgctt  23340
cttcgccgac gcggagaccc tgcgcaaggt cgaggagaac ctgcactacc tcttcaggca  23400
cgggttcgtg cgccaggcct gcaagatctc caacgtggag ctgaccaacc tggtctccta  23460
catgggcatc ttgcacgaga accgcctggg gcagaacgtg ctgcacacca ccctgcgcgg  23520
ggaggcccgg cgcgactaca tccgcgactg cgtctacctc tacctctgcc acacctggca  23580
gacgggcatg ggcgtgtggc agcagtgtct ggaggagcag aacctgaaag agctctgcaa  23640
gctcctgcag aagaacctca agggtctgtg gaccgggttc gacgagcgca ccaccgcctc  23700
ggacctggcc gacctcattt tccccgagcg cctcaggctg acgctgcgca acggcctgcc  23760
cgactttatg agccaaagca tgttgcaaaa ctttcgctct ttcatcctcg aacgctccgg  23820
aatcctgccc gccacctgct ccgcgctgcc ctcggacttc gtgccgctga ccttccgcga  23880
gtgccccccg ccgctgtgga gccactgcta cctgctgcgc ctggccaact acctggccta  23940
ccactcggac gtgatcgagg acgtcagcgg cgagggcctg ctcgagtgcc actgccgctg  24000
caacctctgc acgccgcacc gctccctggc ctgcaacccc cagctgctga gcgagaccca  24060
gatcatcggc accttcgagt tgcaagggcc cagcgaaggc gagggttcag ccgccaaggg  24120
gggtctgaaa ctcaccccgg ggctgtggac ctcggcctac ttgcgcaagt tcgtgcccga  24180
ggactaccat cccttcgaga tcaggttcta cgaggaccaa tcccatccgc ccaaggccga  24240
gctgtcggcc tgcgtcatca cccagggggc gatcctggcc caattgcaag ccatccagaa  24300
atcccgccaa gaattcttgc tgaaaaaggg ccgcggggtc tacctcgacc cccagaccgg  24360
tgaggagctc aaccccggct tcccccagga tgccccgagg aaacaagaag ctgaaagtgg  24420
agctgccgcc cgtggaggat ttggaggaag actgggagaa cagcagtcag gcagaggagg  24480
aggagatgga ggaagactgg gacagcactc aggcagagga ggacagcctg caagacagtc  24540
tggaggaaga cgaggaggag gcagaggagg aggtggaaga agcagccgcc gccagaccgt  24600
cgtcctcggc gggggagaaa gcaagcagca cggataccat ctccgctccg ggtcggggtc  24660
ccgctcgacc acacagtaga tgggacgaga ccggacgatt cccgaacccc accacccaga  24720
ccggtaagaa ggagcggcag ggatacaagt cctggcgggg gcacaaaaac gccatcgtct  24780
cctgcttgca ggcctgcggg ggcaacatct ccttcacccg gcgctacctg ctcttccacc  24840
gcggggtgaa ctttccccgc aacatcttgc attactaccg tcacctccac agcccctact  24900
acttccaaga agaggcagca gcagcagaaa aagaccagca gaaaaccagc agctagaaaa  24960
tccacagcgg cggcagcagg tggactgagg atcgcggcga acgagccggc gcaaacccgg  25020
```

gagctgagga accggatctt tcccaccctc tatgccatct tccagcagag tcgggggcag 25080
gagcaggaac tgaaagtcaa gaaccgttct ctgcgctcgc tcacccgcag ttgtctgtat 25140
cacaagagcg aagaccaact tcagcgcact ctcgaggacg ccgaggctct cttcaacaag 25200
tactgcgcgc tcactcttaa agagtagccc gcgcccgccc agtcgcagaa aaaggcggga 25260
attacgtcac ctgtgccctt cgccctagcc gcctccaccc atcatcatga gcaaagagat 25320
tcccacgcct tacatgtgga gctaccagcc ccagatgggc ctggccgccg gtgccgccca 25380
ggactactcc acccgcatga attggctcag cgccgggccc gcgatgatct cacgggtgaa 25440
tgacatccgc gcccaccgaa accagatact cctagaacag tcagcgctca ccgccacgcc 25500
ccgcaatcac ctcaatccgc gtaattggcc cgccgccctg gtgtaccagg aaattcccca 25560
gcccacgacc gtactacttc cgcgagacgc ccaggccgaa gtccagctga ctaactcagg 25620
tgtccagctg gcgggcggcg ccaccctgtg tcgtcaccgc cccgctcagg gtataaagcg 25680
gctggtgatc cggggcagag gcacacagct caacgacgag gtggtgagct cttcgctggg 25740
tctgcgacct gacggagtct tccaactcgc cggatcgggg agatcttcct tcacgcctcg 25800
tcaggccgtc ctgactttgg agagttcgtc ctcgcagccc cgctcgggtg gcatcggcac 25860
tctccagttc gtggaggagt tcactccctc ggtctacttc aacccettct ccggctcccc 25920 cggccactac ccggacgagt tcatcccgaa cttcgacgcc atcagcgagt cggtggacgg 25980
ctacgattga atgtcccatg gtggcgcagc tgacctagct cggcttcgac acctggacca 26040
ctgccgccgc ttccgctgct tcgctcggga tctcgccgag tttgcctact ttgagctgcc 26100
cgaggagcac cctcagggcc cggcccacgg agtgcggatc gtcgtcgaag gggcctcga 26160 ctcccacctg cttcggatct tcagccagcg tccgatcctg gtcgagcgcg agcaaggaca 26220
gacccttctg actctgtact gcatctgcaa ccaccccggc ctgcatgaaa gtctttgttg 26280
tctgctgtgt actgagtata ataaaagctg agatcagcga ctactccgga cttccgtgtg 26340
ttcctgaatc catcaaccag tctttgttct tcaccgggaa cgagaccgag ctccagctcc 26400
agtgtaagcc ccacaagaag tacctcacct ggctgttcca gggctccccg atcgccgttg 26460
tcaaccactg cgacaacgac ggagtcctgc tgagcggccc tgccaacctt actttttcca 26520
cccgcagaag caagctccag ctcttccaac ccttcctccc cgggacctat cagtgcgtct 26580
cgggaccctg ccatcacacc ttccacctga tcccgaatac cacagcgtcg ctccccgcta 26640
ctaacaacca aactaacctc caccaacgcc accgtcgcga cggccacaat acatgcccat 26700
attagactat gaggccgagc cacagcgacc catgctcccc gctattagtt acttcaatct 26760
aaccggcgga gatgactgac ccactggcca acaacaacgt caacgacctt ctcctggaca 26820
tggacggccg cgcctcggag cagcgactcg cccaacttcg cattcgccag cagcaggaga 26880
gagccgtcaa ggagctgcag gatgcggtgg ccatccacca gtgcaagaga ggcatcttct 26940
gcctggtgaa acaggccaag atctcctacg aggtcactcc aaacgaccat cgcctctcct 27000
acgagctcct gcagcagcgc cagaagttca cctgcctggt cggagtcaac cccatcgtca 27060
tcacccagca gtctggcgat accaaggggt gcatccactg ctcctgcgac tcccccgact 27120
gcgtccacac tctgatcaag accctctgcg gcctccgcga cctcctcccc atgaactaat 27180 cacccccctta tccagtgaaa taaagatcat attgatgatg attttacaga aataaaaaat 27240
aatcatttga tttgaaataa agatacaatc atattgatga tttgagttta acaaaaaaat 27300
aaagaatcac ttacttgaaa tctgatacca ggtctctgtc catgttttct gccaacacca 27360
cttcactccc ctcttcccag ctctggtact gcaggccccg gcgggctgca aacttcctcc 27420

```
acacgctgaa ggggatgtca aattcctcct gtccctcaat cttcatttta tcttctatca  27480
gatgtccaaa aagcgcgtcc gggtggatga tgacttcgac cccgtctacc cctacgatgc  27540
agacaacgca ccgaccgtgc ccttcatcaa cccccccttc gtctcttcag atggattcca  27600
agagaagccc ctgggggtgt tgtccctgcg actggccgac cccgtcacca ccaagaacgg  27660
ggaaatcacc ctcaagctgg gagagggggt ggacctcgat tcctcgggaa aactcatctc  27720
caacacggcc accaaggccg ccgcccctct cagtttttcc aacaacacca tttcccttaa  27780
catggatcac cccttttaca ctaaagatgg aaaattatcc ttacaagttt ctccaccatt  27840
aaatatactg agaacaagca ttctaaacac actagcttta ggttttggat caggtttagg  27900
actccgtggc tctgccttgg cagtacagtt agtctctcca cttacatttg atactgatgg  27960
aaacataaag cttaccttag acagaggttt gcatgttaca acaggagatg caattgaaag  28020
caacataagc tgggctaaag gtttaaaatt tgaagatgga gccatagcaa ccaacattgg  28080
aaatgggtta gagtttggaa gcagtagtac agaaacaggt gttgatgatg cttacccaat  28140
ccaagttaaa cttggatctg gccttagctt tgacagtaca ggagccataa tggctggtaa  28200
caaagaagac gataaactca ctttgtggac aacacctgat ccatcaccaa actgtcaaat  28260
actcgcagaa aatgatgcaa aactaacact ttgcttgact aaatgtggta gtcaaatact  28320
ggccactgtg tcagtcttag ttgtaggaag tggaaaccta aaccccatta ctggcaccgt  28380
aagcagtgct caggtgtttc tacgttttga tgcaaacggt gttcttttaa cagaacattc  28440
tacactaaaa aaatactggg ggtataggca gggagatagc atagatggca ctccatatac  28500
caatgctgta ggattcatgc ccaatttaaa agcttatcca aagtcacaaa gttctactac  28560
taaaaataat atagtagggc aagtatacat gaatggagat gtttcaaaac ctatgcttct  28620
cactataacc ctcaatggta ctgatgacag caacagtaca tattcaatgt cattttcata  28680
cacctggact aatggaagct atgttggagc aacatttggg gctaactctt ataccttctc  28740
atacatcgcc caagaatgaa cactgtatcc caccctgcat gccaaccctt cccaccccac  28800
tctgtggaac aaactctgaa acacaaaata aaataaagtt caagtgtttt attgattcaa  28860
cagttttaca ggattcgagc agttattttt cctccaccct cccaggacat ggaatacacc  28920
accctctccc cccgcacagc cttgaacatc tgaatgccat tggtgatgga catgcttttg  28980
gtctccacgt tccacacagt ttcagagcga gccagtctcg ggtcggtcag ggagatgaaa  29040
ccctccgggc actcccgcat ctgcacctca cagctcaaca gctgaggatt gtcctcggtg  29100
gtcgggatca cggttatctg gaagaagcag aagagcggcg gtgggaatca tagtccgcga  29160
acgggatcgg ccggtggtgt cgcatcaggc cccgcagcag tcgctgccgc cgccgctccg  29220
tcaagctgct gctcaggggg tccgggtcca gggactccct cagcatgatg cccacggccc  29280
tcagcatcag tcgtctggtg cggcgggcgc agcagcgcat gcggatctcg ctcaggtcgc  29340
tgcagtacgt gcaacacaga accaccaggt tgttcaacag tccatagttc aacacgctcc  29400
agccgaaact catcgcggga aggatgctac ccacgtggcc gtcgtaccag atcctcaggt  29460
aaatcaagtg gtgccccctc cagaacacgc tgcccacgta catgatctcc ttgggcatgt  29520
ggcggttcac cacctcccgg taccacatca ccctctggtt gaacatgcag ccccggatga  29580
tcctgcggaa ccacagggcc agcaccgccc cgcccgccat gcagcgaaga gaccccgggt  29640
cccggcaatg gcaatggagg acccaccgct cgtacccgtg gatcatctgg gagctgaaca  29700
agtctatgtt ggcacagcac aggcatatgc tcatgcatct cttcagcact ctcaactcct  29760
```

cggggtcaa aaccatatcc cagggcacgg ggaactcttg caggacagcg aaccccgcag 29820
aacagggcaa tcctcgcaca gaacttacat tgtgcatgga cagggtatcg caatcaggca 29880
gcaccgggtg atcctccacc agagaagcgc gggtctcggt ctcctcacag cgtggtaagg 29940
gggccggccg atacgggtga tggcgggacg cggctgatcg tgttcgcgac cgtgtcatga 30000
tgcagttgct ttcggacatt ttcgtacttg ctgtagcaga acctggtccg ggcgctgcac 30060
accgatcgcc ggcggcggtc tcggcgcttg gaacgctcgg tgttgaaatt gtaaaacagc 30120
cactctctca gaccgtgcag cagatctagg gcctcaggag tgatgaagat cccatcatgc 30180
ctgatggctc tgatcacatc gaccaccgtg gaatgggcca gacccagcca gatgatgcaa 30240
ttttgttggg tttcggtgac ggcgggggag ggaagaacag gaagaaccat gattaacttt 30300
taatccaaac ggtctcggag tacttcaaaa tgaagatcgc ggagatggca cctctcgccc 30360
ccgctgtgtt ggtggaaaat aacagccagg tcaaaggtga tacggttctc gagatgttcc 30420
acggtggctt ccagcaaagc ctccacgcgc acatccagaa acaagacaat agcgaaagcg 30480
ggagggttct ctaattcctc aatcatcatg ttacactcct gcaccatccc cagataattt 30540
tcatttttcc agccttgaat gattcgaact agttcgtgag gtaaatccaa gccagccatg 30600
ataaagagct cgcgcagagc gccctccacc ggcattctta agcacaccct cataattcca 30660
agatattctg ctcctggttc acctgcagca gattgacaag cggaatatca aaatctctgc 30720
cgcgatccct gagctcctcc ctcagcaata actgtaagta ctctttcata tcctctccga 30780
aatttttagc cataggacca ccaggaataa gattagggca agccacagta cagataaacc 30840
gaagtcctcc ccagtgagca ttgccaaatg caagactgct ataagcatgc tggctagacc 30900
cggtgatatc ttccagataa ctggacagaa aatcgcccag gcaattttta agaaaatcaa 30960
caaaagaaaa atcctccagg tggacgttta gagcctcggg aacaacgatg aagtaaatgc 31020
aagcggtgcg ttccagcatg gttagttagc tgatctgtag aaaaaacaaa aatgaacatt 31080
aaaccatgct agcctggcga acaggtgggt aaatcgttct ctccagcacc aggcaggcca 31140
cggggtctcc ggcgcgaccc tcgtaaaaat tgtcgctatg attgaaaacc atcacagaga 31200
gacgttcccg gtggccggcg tgaatgattc gacaagatga atacaccccc ggaacattgg 31260
cgtccgcgag tgaaaaaaag cgcccgagga agcaataagg cactacaatg ctcagtctca 31320
agtccagcaa agcgatgcca tgcggatgaa gcacaaaatt ctcaggtgcg tacaaaatgt 31380
aattactccc ctcctgcaca ggcagcaaag cccccgatcc ctccaggtac acatacaaag 31440
cctcagcgtc catagcttac cgagcagcag cacacaacag gcgcaagagt cagagaaagg 31500
ctgagctcta acctgtccac ccgctctctg ctcaatatat agcccagatc tacactgacg 31560
taaaggccaa agtctaaaaa tacccgccaa ataatcacac acgcccagca cacgcccaga 31620
aaccggtgac acactcaaaa aaatacgcgc acttcctcaa acgcccaaaa ctgccgtcat 31680
ttccgggttc ccacgctacg tcatcaaaac acgactttca aattccgtcg accgttaaaa 31740
acgtcacccg ccccgcccct aacggtcgcc cgtctctcag ccaatcagcg ccccgcatcc 31800
ccaaattcaa acacctcatt tgcatattaa cgcgcacaaa aagtttgagg tatattattg 31860
atgatgg 31867

<210> SEQ ID NO 12
<211> LENGTH: 32788
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480
atttaaacct gcgctctcca gtcaagaggc cactcttgag tgccagcgag aagagttttc 540
tcctccgcgc cgcgagtcag atctacactt tgaaagtagg gataacaggg taatgacatt 600
gattattgac tagttgttaa tagtaatcaa ttacggggtc attagttcat agcccatata 660
tggagttccg cgttacataa cttacggtaa atggcccgcc tggctgaccg cccaacgacc 720
cccgcccatt gacgtcaata atgacgtatg ttcccatagt aacgccaata gggactttcc 780
attgacgtca atgggtggag tatttacggt aaactgccca cttggcagta catcaagtgt 840
atcatatgcc aagtccgccc cctattgacg tcaatgacgg taaatggccc gcctggcatt 900
atgcccagta catgacctta cgggactttc ctacttggca gtacatctac gtattagtca 960
tcgctattac catggtgatg cggttttggc agtacaccaa tgggcgtgga tagcggtttg 1020
actcacgggg atttccaagt ctccacccca ttgacgtcaa tgggagtttg ttttggcacc 1080
aaaatcaacg ggactttcca aaatgtcgta ataaccccgc cccgttgacg caaatgggcg 1140
gtaggcgtgt acggtgggag gtctatataa gcagagctcg tttagtgaac cgtcagatcg 1200
cctggaacgc catccacgct gttttgacct ccatagaaga cagcgatcgc gccaccatgg 1260
ccgggatgtt ccaggcactg tccgaaggct gcacacccta tgatattaac cagatgctga 1320
atgtcctggg agaccaccag gtctctggcc tggagcagct ggagagcatc atcaacttcg 1380
agaagctgac cgagtggaca agctccaatg tgatgcctat cctgtcccca ctgaccaagg 1440
gcatcctggg cttcgtgttt accctgacag tgccttctga gcggggcctg tcttgcatca 1500
gcgaggcaga cgcaaccaca ccagagtccg ccaatctggg cgaggagatc ctgtctcagc 1560
tgtacctgtg gccccgggtg acatatcact ccccttctta cgcctatcac cagttcgagc 1620
ggagagccaa gtacaagaga cacttcccag gctttggcca gtctctgctg ttcggctacc 1680
ccgtgtacgt gttcggcgat tgcgtgcagg gcgactggga tgccatccgg tttagatact 1740
gcgcaccacc tggatatgca ctgctgaggt gtaacgacac caattattcc gccctgctgg 1800
cagtgggcgc cctggagggc cctcgcaatc aggattggct gggcgtgcca aggcagctgg 1860
tgacacgcat gcaggccatc cagaacgcag gcctgtgcac cctggtggca atgctggagg 1920
agacaatctt ctggctgcag gcctttctga tggccctgac cgacagcggc cccaagacaa 1980
acatcatcgt ggattcccag tacgtgatgg gcatctccaa gccttctttc caggagtttg 2040
tggactggga gaacgtgagc ccagagctga attccaccga tcagccattc tggcaggcag 2100
gaatcctggc aaggaacctg gtgcctatgg tggccacagt gcagggccag aatctgaagt 2160
accagggcca gagcctggtc atcagcgcct ccatcatcgt gtttaacctg ctggagctgg 2220
agggcgacta tcgggacgat ggcaacgtgt gggtgcacac cccactgagc cccagaacac 2280

```
tgaacgcctg ggtgaaggcc gtggaggaga agaagggcat cccagtgcac ctggagctgg   2340
cctccatgac caatatggag ctgatgtcta gcatcgtgca ccagcaggtg aggacatacg   2400
gacccgtgtt catgtgcctg ggaggcctgc tgaccatggt ggcaggagcc gtgtggctga   2460
cagtgcgggt gctggagctg ttcagagccg cccagctggc caacgatgtg gtgctgcaga   2520
tcatggagct gtgcggagca gcctttcgcc aggtgtgcca caccacagtg ccatggccca   2580
atgcctccct gacccccaag tggaacaatg agacaacaca gcctcagatc gccaactgta   2640
gcgtgtacga cttcttcgtg tggctgcact actatagcgt gagggatacc ctgtggcccc   2700
gcgtgacata ccacatgaat aagtacgcct atcacatgct ggagaggcgc gccaagtata   2760
agagaggccc tggcccaggc gcaaagtttg tggcagcatg gaccctgaag gccgccgccg   2820
gccccggccc cggccagtat atcaaggcta acagtaagtt cattggaatc acagagctgg   2880
gacccggacc tggataatga gtttaaactc ccatttaaat gtgagggtta atgcttcgag   2940
cagacatgat aagatacatt gatgagtttg gacaaaccac aactagaatg cagtgaaaaa   3000
aatgctttat ttgtgaaatt tgtgatgcta ttgctttatt tgtaaccatt ataagctgca   3060
ataaacaagt taacaacaac aattgcattc attttatgtt tcaggttcag ggggagatgt   3120
gggaggtttt ttaaagcaag taaaacctct acaaatgtgg taaaataact ataacggtcc   3180
taaggtagcg agtgagtagt gttctggggc gggggaggac ctgcatgagg gccagaataa   3240
ctgaaatctg tgcttttctg tgtgttgcag cagcatgagc ggaagcggct cctttgaggg   3300
aggggtattc agcccttatc tgacggggcg tctcccctcc tgggcgggag tgcgtcagaa   3360
tgtgatggga tccacggtgg acggccggcc cgtgcagccc gcgaactctt caaccctgac   3420
ctatgcaacc ctgagctctt cgtcgttgga cgcagctgcc gccgcagctg ctgcatctgc   3480
cgccagcgcc gtgcgcggaa tggccatggg cgccggctac tacggcactc tggtggccaa   3540
ctcgagttcc accaataatc ccgccagcct gaacgaggag aagctgttgc tgctgatggc   3600
ccagctcgag gccttgaccc agcgcctggg cgagctgacc cagcaggtgg ctcagctgca   3660
ggagcagacg cgggccgcgg ttgccacggt gaaatccaaa taaaaaatga atcaataaat   3720
aaacggagac ggttgttgat tttaacacag agtctgaatc tttatttgat ttttcgcgcg   3780
cggtaggccc tggaccaccg gtctcgatca ttgagcaccc ggtggatctt ttccaggacc   3840
cggtagaggt gggcttggat gttgaggtac atgggcatga gcccgtcccg ggggtggagg   3900
tagctccatt gcagggcctc gtgctcgggg gtggtgttgt aaatcaccca gtcatagcag   3960
gggcgcaggg catggtgttg cacaatatct ttgaggagga gactgatggc cacgggcagc   4020
cctttggtgt aggtgtttac aaatctgttg agctgggagg gatgcatgcg gggggagatg   4080
aggtgcatct tggcctggat cttgagattg gcgatgttac cgcccagatc ccgcctgggg   4140
ttcatgttgt gcaggaccac cagcacggtg tatccggtgc acttggggaa tttatcatgc   4200
aacttggaag ggaaggcgtg aaagaatttg gcgacgcctt tgtgcccgcc caggttttcc   4260
atgcactcat ccatgatgat ggcgatgggc ccgtgggcgg cggcctgggc aaagacgttt   4320
cgggggtcgg acacatcata gttgtggtcc tgggtgaggt catcataggc cattttaatg   4380
aatttggggc ggagggtgcc ggactggggg acaaaggtac cctcgatccc gggggcgtag   4440
ttcccctcac agatctgcat ctcccaggct ttgagctcgg agggggggat catgtccacc   4500
tgcggggcga taaagaacac ggtttccggg gcgggggaga tgagctgggc cgaaagcaag   4560
ttccggagca gctgggactt gccgcagccg gtggggccgt agatgacccc gatgaccggc   4620
```

```
tgcaggtggt agttgaggga gagacagctg ccgtcctccc ggaggagggg ggccacctcg   4680
ttcatcatct cgcgcacgtg catgttctcg cgcaccagtt ccgccaggag gcgctctccc   4740
cccagggata ggagctcctg gagcgaggcg aagtttttca gcggcttgag tccgtcggcc   4800
atgggcattt tggagagggt ttgttgcaag agttccaggc ggtcccagag ctcggtgatg   4860
tgctctacgg catctcgatc cagcagacct cctcgtttcg cgggttggga cggctgcggg   4920
agtagggcac cagacgatgg gcgtccagcg cagccagggt ccggtccttc cagggtcgca   4980
gcgtccgcgt cagggtggtc tccgtcacgg tgaaggggtg cgcgccgggc tgggcgcttg   5040
cgagggtgcg cttcaggctc atccggctgg tcgaaaaccg ctcccgatcg gcgccctgcg   5100
cgtcggccag gtagcaattg accatgagtt cgtagttgag cgcctcggcc gcgtggcctt   5160
tggcgcggag cttacctttg gaagtctgcc cgcaggcggg acagaggagg gacttgaggg   5220
cgtagagctt gggggcgagg aagacggact cgggggcgta ggcgtccgcg ccgcagtggg   5280
cgcagacggt ctcgcactcc acgagccagg tgaggtcggg ctggtcgggg tcaaaaacca   5340
gtttcccgcc gttctttttg atgcgtttct tacctttggt ctccatgagc tcgtgtcccc   5400
gctgggtgac aaagaggctg tccgtgtccc cgtagaccga ctttatgggc cggtcctcga   5460
gcggtgtgcc gcggtcctcc tcgtagagga accccgccca ctccgagacg aaagcccggg   5520
tccaggccag cacgaaggag gccacgtggg acgggtagcg gtcgttgtcc accagcgggt   5580
ccaccttttc cagggtatgc aaacacatgt ccccctcgtc cacatccagg aaggtgattg   5640
gcttgtaagt gtaggccacg tgaccggggg tcccggccgg gggggtataa aagggtgcgg   5700
gtccctgctc gtcctcactg tcttccggat cgctgtccag gagcgccagc tgttggggta   5760
ggtattccct ctcgaaggcg ggcatgacct cggcactcag gttgtcagtt tctagaaacg   5820
aggaggattt gatattgacg gtgccggcgg agatgccttt caagagcccc tcgtccatct   5880
ggtcagaaaa gacgatcttt ttgttgtcga gcttggtggc gaaggagccg tagagggcgt   5940
tggagaggag cttggcgatg gagcgcatgg tctggttttt ttccttgtcg gcgcgctcct   6000
tggcggcgat gttgagctgc acgtactcgc gcgccacgca cttccattcg gggaagacgg   6060
tggtcagctc gtcgggcacg attctgacct gccagccccg attatgcagg gtgatgaggt   6120
ccacactggt ggccacctcg ccgcgcaggg gctcattagt ccagcagagg cgtccgccct   6180
tgcgcgagca gaagggggc aggggggtcca gcatgacctc gtcgggggggg tcggcatcga   6240
tggtgaagat gccgggcagg aggtcggggt caaagtagct gatggaagtg gccagatcgt   6300
ccagggcagc ttgccattcg cgcacggcca gcgcgctctc gtagggactg aggggcgtgc   6360
cccagggcat gggatgggta agcgcggagg cgtacatgcc gcagatgtcg tagacgtaga   6420
ggggctcctc gaggatgccg atgtaggtgg ggtagcagcg ccccccgcgg atgctggcgc   6480
gcacgtagtc atacagctcg tgcgaggggg cgaggagccc cgggcccagg ttggtgcgac   6540
tgggcttttc ggcgcggtag acgatctggc ggaaaatggc atgcgagttg gaggagatgg   6600
tgggcctttg gaagatgttg aagtgggcgt ggggcagtcc gaccgagtcg cggatgaagt   6660
gggcgtagga gtcttgcagc ttggcgacga gctcggcggt gactaggacg tccagagcgc   6720
agtagtcgag ggtctcctgg atgatgtcat acttgagctg tcccttttgt ttccacagct   6780
cgcggttgag aaggaactct tcgcggtcct tccagtactc ttcgaggggg aacccgtcct   6840
gatctgcacg gtaagagcct agcatgtaga actggttgac ggccttgtag gcgcagcagc   6900
ccttctccac ggggagggcg taggcctggg cggccttgcg cagggaggtg tgcgtgaggg   6960
cgaaagtgtc cctgaccatg accttgagga actggtgctt gaagtcgata tcgtcgcagc   7020
```

```
cccccctgctc ccagagctgg aagtccgtgc gcttcttgta ggcggggttg ggcaaagcga   7080
aagtaacatc gttgaagagg atcttgcccg cgcggggcat aaagttgcga gtgatgcgga   7140
aaggttgggg cacctcggcc cggttgttga tgacctgggc ggcgagcacg atctcgtcga   7200
agccgttgat gttgtggccc acgatgtaga gttccacgaa tcgcggacgg cccttgacgt   7260
ggggcagttt cttgagctcc tcgtaggtga gctcgtcggg gtcgctgagc ccgtgctgct   7320
cgagcgccca gtcggcgaga tgggggttgg cgcggaggaa ggaagtccag agatccacgg   7380
ccagggcggt ttgcagacgg tcccggtact gacggaactg ctgcccgacg gccatttttt   7440
cgggggtgac gcagtagaag gtgcgggggt ccccgtgcca gcgatcccat ttgagctgga   7500
gggcgagatc gagggcgagc tcgacgagcc ggtcgtcccc ggagagtttc atgaccagca   7560
tgaaggggac gagctgcttg ccgaaggacc ccatccaggt gtaggtttcc acatcgtagg   7620
tgaggaagag cctttcggtg cgaggatgcg agccgatggg gaagaactgg atctcctgcc   7680
accaattgga ggaatggctg ttgatgtgat ggaagtagaa atgccgacgg cgcgccgaac   7740
actcgtgctt gtgtttatac aagcggccac agtgctcgca acgctgcacg ggatgcacgt   7800
gctgcacgag ctgtacctga gttcctttga cgaggaattt cagtgggaag tggagtcgtg   7860
gcgcctgcat ctcgtgctgt actacgtcgt ggtggtcggc ctggccctct tctgcctcga   7920
tggtggtcat gctgacgagc ccgcgcggga ggcaggtcca gacctcggcg cgagcgggtc   7980
ggagagcgag gacgagggcg cgcaggccgg agctgtccag ggtcctgaga cgctgcggag   8040
tcaggtcagt gggcagcggc ggcgcgcggt tgacttgcag gagtttttcc agggcgcgcg   8100
ggaggtccag atggtacttg atctccaccg cgccattggt ggcgacgtcg atggcttgca   8160
gggtcccgtg cccctggggt gtgaccaccg tcccccgttt cttcttgggc ggctggggcg   8220
acgggggcgg tgcctcttcc atggttagaa gcggcggcga ggacgcgcgc cgggcggcag   8280
gggcggctcg gggcccggag gcaggggcgg caggggcacg tcggcgccgc gcgcgggtag   8340
gttctggtac tgcgcccgga gaagactggc gtgagcgacg acgcgacggt tgacgtcctg   8400
gatctgacgc ctctgggtga aggccacggg acccgtgagt ttgaacctga aagagagttc   8460
gacagaatca atctcggtat cgttgacggc ggcctgccgc aggatctctt gcacgtcgcc   8520
cgagttgtcc tggtaggcga tctcggtcat gaactgctcg atctcctcct cttgaaggtc   8580
tccgcggccg gcgcgctcca cggtggccgc gaggtcgttg gagatgcggc ccatgagctg   8640
cgagaaggcg ttcatgcccg cctcgttcca gacgcggctg tagaccacga cgccctcggg   8700
atcgcgggcg cgcatgacca cctgggcgag gttgagctcc acgtggcgcg tgaagaccgc   8760
gtagttgcag aggcgctggt agaggtagtt gagcgtggtg gcgatgtgct cggtgacgaa   8820
gaaatacatg atccagcggc ggagcggcat ctcgctgacg tcgcccagcg cctccaaacg   8880
ttccatggcc tcgtaaaagt ccacggcgaa gttgaaaaac tgggagttgc gcgccgagac   8940
ggtcaactcc tcctccagaa gacggatgag ctcggcgatg gtggcgcgca cctcgcgctc   9000
gaaggccccc gggagttcct ccacttcctc ttcttcctcc tccactaaca tctcttctac   9060
ttcctcctca ggcggcagtg gtggcggggg agggggcctg cgtcgccggc ggcgcacggg   9120
cagacggtcg atgaagcgct cgatggtctc gccgcgccgg cgtcgcatgg tctcggtgac   9180
ggcgcgcccg tcctcgcggg gccgcagcgt gaagacgccg ccgcgcatct ccaggtggcc   9240
gggggggtcc ccgttgggca gggagagggc gctgacgatg catcttatca attgccccgt   9300
agggactccg cgcaaggacc tgagcgtctc gagatccacg ggatctgaaa accgctgaac   9360
```

```
gaaggcttcg agccagtcgc agtcgcaagg taggctgagc acggtttctt ctggcgggtc   9420
atgttggttg ggagcggggc gggcgatgct gctggtgatg aagttgaaat aggcggttct   9480
gagacggcgg atggtggcga ggagcaccag gtctttgggc ccggcttgct ggatgcgcag   9540
acggtcggcc atgccccagg cgtggtcctg acacctggcc aggtccttgt agtagtcctg   9600
catgagccgc tccacgggca cctcctcctc gcccgcgcgg ccgtgcatgc gcgtgagccc   9660
gaagccgcgc tggggctgga cgagcgccag gtcggcgacg acgcgctcgg cgaggatggc   9720
ttgctggatc tgggtgaggg tggtctggaa gtcatcaaag tcgacgaagc ggtggtaggc   9780
tccggtgttg atggtgtagg agcagttggc catgacggac cagttgacgg tctggtggcc   9840
cggacgcacg agctcgtggt acttgaggcg cgagtaggcg cgcgtgtcga agatgtagtc   9900
gttgcaggtg cgcaccaggt actggtagcc gatgaggaag tgcggcggcg gctggcggta   9960
gagcggccat cgctcggtgg cgggggcgcc gggcgcgagg tcctcgagca tggtgcggtg  10020
gtagccgtag atgtacctgg acatccaggt gatgccggcg gcggtggtgg aggcgcgcgg  10080
gaactcgcgg acgcggttcc agatgttgcg cagcggcagg aagtagttca tggtgggcac  10140
ggtctggccc gtgaggcgcg cgcagtcgtg gatgctctat acgggcaaaa acgaaagcgg  10200
tcagcggctc gactccgtgg cctggaggct aagcgaacgg gttgggctgc gcgtgtaccc  10260
cggttcgaat ctcgaatcag gctggagccg cagctaacgt ggtattggca ctcccgtctc  10320
gacccaagcc tgcaccaacc ctccaggata cggaggcggg tcgttttgca actttttttt  10380
ggaggccgga tgagactagt aagcgcggaa agcggccgac cgcgatggct cgctgccgta  10440
gtctggagaa gaatcgccag ggttgcgttg cggtgtgccc cggttcgagg ccggccggat  10500
tccgcggcta acgagggcgt ggctgccccg tcgtttccaa gaccccatag ccagccgact  10560
tctccagtta cggagcgagc cctcttttg ttttgtttgt ttttgccaga tgcatcccgt  10620
actgcggcag atgcgccccc accaccctcc accgcaacaa cagccccctc cacagccggc  10680
gcttctgccc ccgccccagc agcaacttcc agccacgacc gccgcggccg ccgtgagcgg  10740
ggctggacag agttatgatc accagctggc cttggaagag ggcgaggggc tggcgcgcct  10800
gggggcgtcg tcgccggagc ggcacccgcg cgtgcagatg aaaagggacg ctcgcgaggc  10860
ctacgtgccc aagcagaacc tgttcagaga caggagcggc gaggagcccg aggagatgcg  10920
cgcggcccgg ttccacgcgg ggcgggagct gcggcgcggc ctggaccgaa agagggtgct  10980
gagggacgag gatttcgagg cggacgagct gacggggatc agccccgcgc gcgcgcacgt  11040
ggccgcggcc aacctggtca cggcgtacga gcagaccgtg aaggaggaga gcaacttcca  11100
aaaatccttc aacaaccacg tgcgcaccct gatcgcgcgc gaggaggtga ccctgggcct  11160
gatgcacctg tgggacctgc tggaggccat cgtgcagaac cccaccagca agccgctgac  11220
ggcgcagctg ttcctggtgg tgcagcatag tcgggacaac gaagcgttca gggaggcgct  11280
gctgaatatc accgagcccg agggccgctg gctcctggac ctggtgaaca ttctgcagag  11340
catcgtggtg caggagcgcg ggctgccgct gtccgagaag ctggcggcca tcaacttctc  11400
ggtgctgagt ttgggcaagt actacgctag gaagatctac aagaccccgt acgtgcccat  11460
agacaaggag gtgaagatcg acgggtttta catgcgcatg accctgaaag tgctgaccct  11520
gagcgacgat ctgggggtgt accgcaacga caggatgcac cgtgcggtga gcgccagcag  11580
gcggcgcgag ctgagcgacc aggagctgat gcatagtctg cagcgggccc tgaccggggc  11640
cgggaccgag ggggagagct actttgacat gggcgcggac ctgcactggc agcccagccg  11700
ccgggccttg gaggcggcgg caggacccta cgtagaagag gtggacgatg aggtggacga  11760
```

```
ggagggcgag tacctggaag actgatggcg cgaccgtatt tttgctagat gcaacaacaa  11820
cagccacctc ctgatcccgc gatgcgggcg gcgctgcaga gccagccgtc cggcattaac  11880
tcctcggacg attggaccca ggccatgcaa cgcatcatgg cgctgacgac ccgcaacccc  11940
gaagccttta gacagcagcc ccaggccaac cggctctcgg ccatcctgga ggccgtggtg  12000
ccctcgcgct ccaaccccac gcacgagaag gtcctggcca tcgtgaacgc gctggtggag  12060
aacaaggcca tccgcggcga cgaggccggc ctggtgtaca acgcgctgct ggagcgcgtg  12120
gcccgctaca acagcaccaa cgtgcagacc aacctggacc gcatggtgac cgacgtgcgc  12180
gaggccgtgg cccagcgcga gcggttccac cgcgagtcca acctgggatc catggtggcg  12240
ctgaacgcct tcctcagcac ccagcccgcc aacgtgcccc ggggccagga ggactacacc  12300
aacttcatca gcgccctgcg cctgatggtg accgaggtgc cccagagcga ggtgtaccag  12360
tccgggccgg actacttctt ccagaccagt cgccagggct tgcagaccgt gaacctgagc  12420
caggctttca agaacttgca gggcctgtgg ggcgtgcagg ccccggtcgg ggaccgcgcg  12480
acggtgtcga gcctgctgac gccgaactcg cgcctgctgc tgctgctggt ggccccottc  12540
acggacagcg gcagcatcaa ccgcaactcg tacctgggct acctgattaa cctgtaccgc  12600
gaggccatcg gccaggcgca cgtggacgag cagacctacc aggagatcac ccacgtgagc  12660
cgcgccctgg gccaggacga cccgggcaac ctggaagcca ccctgaactt tttgctgacc  12720
aaccggtcgc agaagatccc gccccagtac gcgctcagca ccgaggagga gcgcatcctg  12780
cgttacgtgc agcagagcgt gggcctgttc ctgatgcagg agggggccac ccccagcgcc  12840
gcgctcgaca tgaccgcgcg caacatggag cccagcatgt acgccagcaa ccgcccgttc  12900
atcaataaac tgatggacta cttgcatcgg gcggccgcca tgaactctga ctatttcacc  12960
aacgccatcc tgaatcccca ctggctcccg ccgccggggt tctacacggg cgagtacgac  13020
atgcccgacc ccaatgacgg gttcctgtgg gacgatgtgg acagcagcgt gttctccccc  13080
cgaccgggtg ctaacgagcg ccccttgtgg aagaaggaag gcagcgaccg acgcccgtcc  13140
tcggcgctgt ccggccgcga gggtgctgcc gcggcggtgc ccgaggccgc cagtcctttc  13200
ccgagcttgc ccttctcgct gaacagtatc cgcagcagcg agctgggcag gatcacgcgc  13260
ccgcgcttgc tgggcgaaga ggagtacttg aatgactcgc tgttgagacc cgagcgggag  13320
aagaacttcc ccaataacgg gatagaaagc ctggtggaca agatgagccg ctggaagacg  13380
tatgcgcagg agcacaggga cgatccccgg gcgtcgcagg gggccacgag ccggggcagc  13440
gccgcccgta aacgccggtg gcacgacagg cagcggggac agatgtggga cgatgaggac  13500
tccgccgacg acagcagcgt gttggacttg ggtgggagtg gtaacccgtt cgctcacctg  13560
cgcccccgta tcgggcgcat gatgtaagag aaaccgaaaa taaatgatac tcaccaaggc  13620
catggcgacc agcgtgcgtt cgtttcttct ctgttgttgt tgtatctagt atgatgaggc  13680
gtgcgtaccc ggagggtcct cctccctcgt acgagagcgt gatgcagcag gcgatggcgg  13740
cggcggcgat gcagcccccg ctggaggctc cttacgtgcc cccgcggtac ctggcgccta  13800
cggaggggcg gaacagcatt cgttactcgg agctggcacc cttgtacgat accacccggt  13860
tgtacctggt ggacaacaag tcggcggaca tcgcctcgct gaactaccag aacgaccaca  13920
gcaacttcct gaccaccgtg gtgcagaaca atgacttcac ccccacggag gccagcaccc  13980
agaccatcaa ctttgacgag cgctcgcggt ggggcggcca gctgaaaacc atcatgcaca  14040
ccaacatgcc caacgtgaac gagttcatgt acagcaacaa gttcaaggcg cgggtgatgg  14100
```

```
tctcccgcaa gacccccaat ggggtgacag tgacagagga ttatgatggt agtcaggatg  14160
agctgaagta tgaatgggtg gaatttgagc tgcccgaagg caacttctcg gtgaccatga  14220
ccatcgacct gatgaacaac gccatcatcg acaattactt ggcggtgggg cggcagaacg  14280
gggtgctgga gagcgacatc ggcgtgaagt tcgacactag gaacttcagg ctgggctggg  14340
accccgtgac cgagctggtc atgcccgggg tgtacaccaa cgaggctttc catcccgata  14400
ttgtcttgct gcccggctgc ggggtggact tcaccgagag ccgcctcagc aacctgctgg  14460
gcattcgcaa gaggcagccc ttccaggaag gcttccagat catgtacgag gatctggagg  14520
ggggcaacat ccccgcgctc ctggatgtcg acgcctatga gaaaagcaag gaggatgcag  14580
cagctgaagc aactgcagcc gtagctaccg cctctaccga ggtcaggggc gataattttg  14640
caagcgccgc agcagtggca gcggccgagg cggctgaaac cgaaagtaag atagtcattc  14700
agccggtgga gaaggatagc aagaacagga gctacaacgt actaccggac aagataaaca  14760
ccgcctaccg cagctggtac ctagcctaca actatggcga ccccgagaag ggcgtgcgct  14820
cctggacgct gctcaccacc tcggacgtca cctgcggcgt ggagcaagtc tactggtcgc  14880
tgcccgacat gatgcaagac ccggtcacct tccgctccac gcgtcaagtt agcaactacc  14940
cggtggtggg cgccgagctc ctgcccgtct actccaagag cttcttcaac gagcaggccg  15000
tctactcgca gcagctgcgc gccttcacct cgcttacgca cgtcttcaac cgcttccccg  15060
agaaccagat cctcgtccgc ccgcccgcgc ccaccattac caccgtcagt gaaaacgttc  15120
ctgctctcac agatcacggg accctgccgc tgcgcagcag tatccgggga gtccagcgcg  15180
tgaccgttac tgacgccaga cgccgcacct gcccctacgt ctacaaggcc ctgggcatag  15240
tcgcgccgcg cgtcctctcg agccgcacct tctaaatgtc cattctcatc tcgcccagta  15300
ataacaccgg ttggggcctg cgcgcgccca gcaagatgta cggaggcgct cgccaacgct  15360
ccacgcaaca ccccgtgcgc gtgcgcgggc acttccgcgc tccctggggc gccctcaagg  15420
gccgcgtgcg gtcgcgcacc accgtcgacg acgtgatcga ccaggtggtg gccgacgcgc  15480
gcaactacac ccccgccgcc gcgcccgtct ccaccgtgga cgccgtcatc gacagcgtgg  15540
tggccgacgc gcgccggtac gcccgcgcca agagccggcg gcggcgcatc gcccggcggc  15600
accggagcac ccccgccatg cgcgcggcgc gagccttgct gcgcagggcc aggcgcacgg  15660
gacgcagggc catgctcagg gcggccagac gcgcggcttc aggcgccagc gccggcagga  15720
cccggagacg cgcggccacg gcggcggcag cggccatcgc cagcatgtcc cgcccgcggc  15780
gagggaacgt gtactgggtg cgcgacgccg ccaccggtgt gcgcgtgccc gtgcgcaccc  15840
gcccccctcg cacttgaaga tgttcacttc gcgatgttga tgtgtcccag cggcgaggag  15900
gatgtccaag cgcaaattca aggaagagat gctccaggtc atcgcgcctg agatctacgg  15960
ccctgcggtg gtgaaggagg aaagaaagcc ccgcaaaatc aagcgggtca aaaaggacaa  16020
aaaggaagaa gaaagtgatg tggacggatt ggtggagttt gtgcgcgagt tcgccccccg  16080
gcggcgcgtg cagtggcgcg ggcggaaggt gcaaccggtg ctgagacccg gcaccaccgt  16140
ggtcttcacg cccggcgagc gctccggcac cgcttccaag cgctcctacg acgaggtgta  16200
cggggatgat gatattctgg agcaggcggc cgagcgcctg ggcgagtttg cttacggcaa  16260
gcgcagccgt tccgcaccga aggaagaggc ggtgtccatc ccgctggacc acggcaaccc  16320
cacgccgagc ctcaagcccg tgaccttgca gcaggtgctg ccgaccgcgg cgccgcgccg  16380
ggggttcaag cgcgagggcg aggatctgta ccccaccatg cagctgatgg tgcccaagcg  16440
ccagaagctg gaagacgtgc tggagaccat gaaggtggac ccggacgtgc agcccgaggt  16500
```

```
caaggtgcgg cccatcaagc aggtggcccc gggcctgggc gtgcagaccg tggacatcaa  16560
gattcccacg gagcccatgg aaacgcagac cgagcccatg atcaagccca gcaccagcac  16620
catggaggtg cagacggatc cctggatgcc atcggctcct agtcgaagac cccggcgcaa  16680
gtacggcgcg gccagcctgc tgatgcccaa ctacgcgctg catccttcca tcatccccac  16740
gccgggctac cgcggcacgc gcttctaccg cggtcatacc agcagccgcc gccgcaagac  16800
caccactcgc cgccgccgtc gccgcaccgc cgctgcaacc acccctgccg ccctggtgcg  16860
gagagtgtac cgccgcggcc gcgcacctct gaccctgccg cgcgcgcgct accacccgag  16920
catcgccatt taaactttcg cctgctttgc agatcaatgg ccctcacatg ccgccttcgc  16980
gttcccatta cgggctaccg aggaagaaaa ccgcgccgta gaaggctggc ggggaacggg  17040
atgcgtcgcc accaccaccg gcggcggcgc gccatcagca agcggttggg gggaggcttc  17100
ctgcccgcgc tgatccccat catcgccgcg gcgatcgggg cgatccccgg cattgcttcc  17160
gtggcggtgc aggcctctca gcgccactga gacacacttg gaaacatctt gtaataaacc  17220
aatggactct gacgctcctg gtcctgtgat gtgttttcgt agacagatgg aagacatcaa  17280
tttttcgtcc ctggctccgc gacacggcac gcggccgttc atgggcacct ggagcgacat  17340
cggcaccagc caactgaacg gggcgccctt caattggagc agtctctgga gcgggcttaa  17400
gaatttcggg tccacgctta aacctatggg cagcaaggcg tggaacagca ccacagggca  17460
ggcgctgagg gataagctga aagagcagaa cttccagcag aaggtggtcg atgggctcgc  17520
ctcgggcatc aacggggtgg tggacctggc caaccaggcc gtgcagcggc agatcaacag  17580
ccgcctggac ccggtgccgc ccgccggctc cgtggagatg ccgcaggtgg aggaggagct  17640
gcctcccctg gacaagcggg gcgagaagcg accccgcccc gatgcggagg agacgctgct  17700
gacgcacacg gacgagccgc ccccgtacga ggaggcggtg aaactgggtc tgcccaccac  17760
gcggcccatc gcgcccctgg ccaccggggt gctgaaaccc gaaaagcccg cgaccctgga  17820
cttgcctcct ccccagcctt cccgcccctc tacagtggct aagcccctgc cgccggtggc  17880
cgtggcccgc gcgcgacccg gggggcaccgc ccgccctcat gcgaactggc agagcactct  17940
gaacagcatc gtgggtctgg gagtgcagag tgtgaagcgc cgccgctgct attaaaccta  18000
ccgtagcgct taacttgctt gtctgtgtgt gtatgtatta tgtcgccgcc gccgctgtcc  18060
accagaagga ggagtgaaga ggcgcgtcgc cgagttgcaa gatggccacc ccatcgatgc  18120
tgccccagtg ggcgtacatg cacatcgccg gacaggacgc ttcggagtac ctgagtccgg  18180
gtctggtgca gtttgcccgc gccacagaca cctacttcag tctggggaac aagtttagga  18240
accccacggt ggcgcccacg cacgatgtga ccaccgaccg cagccagcgg ctgacgctgc  18300
gcttcgtgcc cgtggaccgc gaggacaaca cctactcgta caaagtgcgc tacacgctgg  18360
ccgtgggcga caaccgcgtg ctggacatgg ccagcaccta ctttgacatc cgcggcgtgc  18420
tggatcgggg ccctagcttc aaaccctact ccggcaccgc ctacaacagt ctggccccca  18480
agggagcacc caacacttgt cagtggacat ataaagccga tggtgaaact gccacagaaa  18540
aaacctatac atatggaaat gcacccgtgc agggcattaa catcacaaaa gatggtattc  18600
aacttggaac tgacaccgat gatcagccaa tctacgcaga taaaacctat cagcctgaac  18660
ctcaagtggg tgatgctgaa tggcatgaca tcactggtac tgatgaaaag tatggaggca  18720
gagctcttaa gcctgatacc aaaatgaagc cttgttatgg ttcttttgcc aagcctacta  18780
ataaagaagg aggtcaggca aatgtgaaaa caggaacagg cactactaaa gaatatgaca  18840
```

-continued

```
tagacatggc tttctttgac aacagaagtg cggctgctgc tggcctagct ccagaaattg  18900
ttttgtatac tgaaaatgtg gatttggaaa ctccagatac ccatattgta tacaaagcag  18960
gcacagatga cagcagctct tctattaatt tgggtcagca agccatgccc aacagaccta  19020
actacattgg tttcagagac aactttatcg ggctcatgta ctacaacagc actggcaata  19080
tgggggtgct ggccggtcag gcttctcagc tgaatgctgt ggttgacttg caagacagaa  19140
acaccgagct gtcctaccag ctcttgcttg actctctggg tgacagaacc cggtatttca  19200
gtatgtggaa tcaggcggtg gacagctatg atcctgatgt gcgcattatt gaaaatcatg  19260
gtgtggagga tgaacttccc aactattgtt tccctctgga tgctgttggc agaacagata  19320
cttatcaggg aattaaggct aatggaactg atcaaaccac atggaccaaa gatgacagtg  19380
tcaatgatgc taatgagata ggcaagggta atccattcgc catggaaatc aacatccaag  19440
ccaacctgtg gaggaacttc ctctacgcca acgtggccct gtacctgccc gactcttaca  19500
agtacacgcc ggccaatgtt accctgccca ccaacaccaa cacctacgat tacatgaacg  19560
gccgggtggt ggcgccctcg ctggtggact cctacatcaa catcggggcg cgctggtcgc  19620
tggatcccat ggacaacgtg aaccccttca accaccaccg caatgcgggg ctgcgctacc  19680
gctccatgct cctgggcaac gggcgctacg tgcccttcca catccaggtg ccccagaaat  19740
tttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg accccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
gctacaagga ccgcatgtac tccttcttcc gcaacttcca gcccatgagc cgccaggtgg  20460
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc accccccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc cccgcacaag ctggcctgcg ccatcgtcaa  21060
cacggccggc cgcgagaccg ggggcgagca ctggctggcc ttcgcctgga acccgcgctc  21120
gaacacctgc tacctcttcg acccccttcgg gttctcggac gagcgcctca agcagatcta  21180
ccagttcgag tacgagggcc tgctgcgccg cagcgccctg gccaccgagg accgctgcgt  21240
```

```
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
atcgcagtgc agggggatca gcatcatctg ggcctggtcg gcgttcatcc ccgggtacat  22080
ggccttcatg aaagcctcca attgcctgaa cgcctgctgg gccttggctc cctcggtgaa  22140
gaagaccccg caggacttgc tagagaactg gttggtggcg cacccggcgt cgtgcacgca  22200
gcagcgcgcg tcgttgttgg ccagctgcac cacgctgcgc cccagcggt  tctgggtgat  22260
cttggcccgg tcggggttct ccttcagcgc gcgctgcccg ttctcgctcg ccacatccat  22320
ctcgatcatg tgctccttct ggatcatggt ggtcccgtgc aggcaccgca gcttgccctc  22380
ggcctcggtg cacccgtgca gccacagcgc gcacccggtg cactcccagt tcttgtgggc  22440
gatctgggaa tgcgcgtgca cgaagccctg caggaagcgg cccatcatgg tggtcagggt  22500
cttgttgcta gtgaaggtca gcggaatgcc gcggtgctcc tcgttgatgt acaggtggca  22560
gatgcggcgg tacacctcgc cctgctcggg catcagctgg aagttggctt tcaggtcggt  22620
ctccacgcgg tagcggtcca tcagcatagt catgatttcc atacccttct cccaggccga  22680
gacgatgggc aggctcatag ggttcttcac catcatctta gcgctagcag ccgcggccag  22740
ggggtcgctc tcgtccaggg tctcaaagct ccgcttgccg tccttctcgg tgatccgcac  22800
cggggggtag ctgaagccca cggccgccag ctcctcctcg gcctgtcttt cgtcctcgct  22860
gtcctggctg acgtcctgca ggaccacatg cttggtcttg cggggtttct tcttgggcgg  22920
cagcggcggc ggagatgttg gagatggcga gggggagcgc gagttctcgc tcaccactac  22980
tatctcttcc tcttcttggt ccgaggccac gcggcggtag gtatgtctct tcgggggcag  23040
aggcggaggc gacgggctct cgccgccgcg acttggcgga tggctggcag agccccttcc  23100
gcgttcgggg gtgcgctccc ggcggcgctc tgactgactt cctccgcggc cggccattgt  23160
gttctcctag ggaggaacaa caagcatgga gactcagcca tcgccaacct cgccatctgc  23220
ccccaccgcc gacgagaagc agcagcagca gaatgaaagc ttaaccgccc cgccgcccag  23280
ccccgccacc tccgacgcgg ccgtcccaga catgcaagag atggaggaat ccatcgagat  23340
tgacctgggc tatgtgacgc ccgcggagca cgaggaggag ctggcagtgc gcttttcaca  23400
agaagagata caccaagaac agccagagca ggaagcagag aatgagcaga gtcaggctgg  23460
gctcgagcat gacggcgact acctccacct gagcgggggg gaggacgcgc tcatcaagca  23520
tctggcccgg caggccacca tcgtcaagga tgcgctgctc gaccgcaccg aggtgcccct  23580
```

-continued

```
cagcgtggag gagctcagcc gcgcctacga gttgaacctc ttctcgccgc gcgtgccccc  23640
caagcgccag cccaatggca cctgcgagcc caacccgcgc ctcaacttct acccggtctt  23700
cgcggtgccc gaggccctgg ccacctacca catctttttc aagaaccaaa agatccccgt  23760
ctcctgccgc gccaaccgca cccgcgccga cgcccttttc aacctgggtc ccggcgcccg  23820
cctacctgat atcgcctcct tggaagaggt tcccaagatc ttcgagggtc tgggcagcga  23880
cgagactcgg gccgcgaacg ctctgcaagg agaaggagga gagcatgagc accacagcgc  23940
cctggtcgag ttggaaggcg acaacgcgcg gctggcggtg ctcaaacgca cggtcgagct  24000
gacccatttc gcctacccgg ctctgaacct gccccccaaa gtcatgagcg cggtcatgga  24060
ccaggtgctc atcaagcgcg cgtcgcccat ctccgaggac gagggcatgc aagactccga  24120
ggagggcaag cccgtggtca gcgacgagca gctggcccgg tggctgggtc ctaatgctag  24180
tccccagagt ttggaagagc ggcgcaaact catgatggcc gtggtcctgg tgaccgtgga  24240
gctggagtgc ctgcgccgct tcttcgccga cgcggagacc ctgcgcaagg tcgaggagaa  24300
cctgcactac ctcttcaggc acgggttcgt gcgccaggcc tgcaagatct ccaacgtgga  24360
gctgaccaac ctggtctcct acatgggcat cttgcacgag aaccgcctgg ggcagaacgt  24420
gctgcacacc accctgcgcg gggaggcccg gcgcgactac atccgcgact gcgtctacct  24480
ctacctctgc cacacctggc agacgggcat gggcgtgtgg cagcagtgtc tggaggagca  24540
gaacctgaaa gagctctgca agctcctgca gaagaacctc aagggtctgt ggaccgggtt  24600
cgacgagcgc accaccgcct cggacctggc cgacctcatt ttccccgagc gcctcaggct  24660
gacgctgcgc aacggcctgc ccgactttat gagccaaagc atgttgcaaa actttcgctc  24720
tttcatcctc gaacgctccg gaatcctgcc cgccacctgc tccgcgctgc cctcggactt  24780
cgtgccgctg accttccgcg agtgcccccc gccgctgtgg agccactgct acctgctgcg  24840
cctggccaac tacctggcct accactcgga cgtgatcgag gacgtcagcg gcgagggcct  24900
gctcgagtgc cactgccgct gcaacctctg cacgccgcac cgctccctgg cctgcaaccc  24960
ccagctgctg agcgagaccc agatcatcgg caccttcgag ttgcaagggc ccagcgaagg  25020
cgagggttca gccgccaagg ggggtctgaa actcaccccg ggctgtgga cctcggccta  25080
cttgcgcaag ttcgtgcccg aggactacca tcccttcgag atcaggttct acgaggacca  25140
atcccatccg cccaaggccg agctgtcggc ctgcgtcatc acccaggggg cgatcctggc  25200
ccaattgcaa gccatccaga aatcccgcca agaattcttg ctgaaaaagg gccgcggggt  25260
ctacctcgac ccccagaccg gtgaggagct caaccccggc ttcccccagg atgccccgag  25320
gaaacaagaa gctgaaagtg gagctgccgc ccgtggagga tttggaggaa gactgggaga  25380
acagcagtca ggcagaggag gaggagatgg aggaagactg ggacagcact caggcagagg  25440
aggacagcct gcaagacagt ctggaggaag acgaggagga ggcagaggag gaggtggaag  25500
aagcagccgc cgccagaccg tcgtcctcgg cgggggagaa agcaagcagc acggatacca  25560
tctccgctcc gggtcggggt cccgctcgac cacacagtag atgggacgag accggacgat  25620
tcccgaaccc caccacccag accggtaaga aggagcggca gggatacaag tcctggcggg  25680
ggcacaaaaa cgccatcgtc tcctgcttgc aggcctgcgg gggcaacatc tccttcaccc  25740
ggcgctacct gctcttccac cgcggggtga actttccccg caacatcttg cattactacc  25800
gtcacctcca cagcccctac tacttccaag aagaggcagc agcagcagaa aaagaccagc  25860
agaaaaccag cagctagaaa atccacagcg gcggcagcag gtggactgag gatcgcggcg  25920
aacgagccgg cgcaaacccg ggagctgagg aaccggatct ttcccaccct ctatgccatc  25980
```

```
ttccagcaga gtcgggggca ggagcaggaa ctgaaagtca agaaccgttc tctgcgctcg  26040
ctcacccgca gttgtctgta tcacaagagc gaagaccaac ttcagcgcac tctcgaggac  26100
gccgaggctc tcttcaacaa gtactgcgcg ctcactctta aagagtagcc cgcgcccgcc  26160
cagtcgcaga aaaaggcggg aattacgtca cctgtgccct tcgccctagc cgcctccacc  26220
catcatcatg agcaaagaga ttcccacgcc ttacatgtgg agctaccagc cccagatggg  26280
cctggccgcc ggtgccgccc aggactactc cacccgcatg aattggctca gcgccgggcc  26340
cgcgatgatc tcacgggtga atgacatccg cgcccaccga aaccagatac tcctagaaca  26400
gtcagcgctc accgccacgc cccgcaatca cctcaatccg cgtaattggc ccgccgccct  26460
ggtgtaccag gaaattcccc agcccacgac cgtactactt ccgcgagacg cccaggccga  26520
agtccagctg actaactcag gtgtccagct ggcgggcggc gccaccctgt gtcgtcaccg  26580
ccccgctcag ggtataaagc ggctggtgat ccggggcaga ggcacacagc tcaacgacga  26640
ggtggtgagc tcttcgctgg gtctgcgacc tgacggagtc ttccaactcg ccggatcggg  26700
gagatcttcc ttcacgcctc gtcaggccgt cctgactttg gagagttcgt cctcgcagcc  26760
ccgctcgggt ggcatcggca ctctccagtt cgtggaggag ttcactccct cggtctactt  26820
caacccottc tccggctccc ccggccacta cccggacgag ttcatcccga acttcgacgc  26880
catcagcgag tcggtggacg gctacgattg aatgtcccat ggtggcgcag ctgacctagc  26940
tcggcttcga cacctggacc actgccgccg cttccgctgc ttcgctcggg atctcgccga  27000
gtttgcctac tttgagctgc ccgaggagca ccctcagggc ccggcccacg gagtgcggat  27060
cgtcgtcgaa gggggcctcg actcccacct gcttcggatc ttcagccagc gtccgatcct  27120
ggtcgagcgc gagcaaggac agacccttct gactctgtac tgcatctgca accaccccgg  27180
cctgcatgaa agtctttgtt gtctgctgtg tactgagtat aataaaagct gagatcagcg  27240
actactccgg acttccgtgt gttcctgaat ccatcaacca gtctttgttc ttcaccggga  27300
acgagaccga gctccagctc cagtgtaagc cccacaagaa gtacctcacc tggctgttcc  27360
agggctcccc gatcgccgtt gtcaaccact gcgacaacga cggagtcctg ctgagcggcc  27420
ctgccaacct tactttttcc acccgcagaa gcaagctcca gctcttccaa cccttcctcc  27480
ccgggaccta tcagtgcgtc tcgggaccct gccatcacac cttccacctg atcccgaata  27540
ccacagcgtc gctccccgct actaacaacc aaactaacct ccaccaacgc caccgtcgcg  27600
acggccacaa tacatgccca tattagacta tgaggccgag ccacagcgac ccatgctccc  27660
cgctattagt tacttcaatc taaccggcgg agatgactga cccactggcc aacaacaacg  27720
tcaacgacct tctcctggac atggacggcc gcgcctcgga gcagcgactc gcccaacttc  27780
gcattcgcca gcagcaggag agagccgtca aggagctgca ggatgcggtg gccatccacc  27840
agtgcaagag aggcatcttc tgcctggtga aacaggccaa gatctcctac gaggtcactc  27900
caaacgacca tcgcctctcc tacgagctcc tgcagcagcg ccagaagttc acctgcctgg  27960
tcggagtcaa ccccatcgtc atcacccagc agtctggcga taccaagggg tgcatccact  28020
gctcctgcga ctcccccgac tgcgtccaca ctctgatcaa gaccctctgc ggcctccgcg  28080
acctcctccc catgaactaa tcaccccctt atccagtgaa ataaagatca tattgatgat  28140
gattttacag aaataaaaaa taatcatttg atttgaaata aagatacaat catattgatg  28200
atttgagttt aacaaaaaaa taaagaatca cttacttgaa atctgatacc aggtctctgt  28260
ccatgttttc tgccaacacc acttcactcc cctcttccca gctctggtac tgcaggcccc  28320
```

```
ggcgggctgc aaacttcctc cacacgctga aggggatgtc aaattcctcc tgtccctcaa  28380
tcttcatttt atcttctatc agatgtccaa aaagcgcgtc cgggtggatg atgacttcga  28440
ccccgtctac ccctacgatg cagacaacgc accgaccgtg cccttcatca acccccccctt  28500
cgtctcttca gatggattcc aagagaagcc cctgggggtg ttgtccctgc gactggccga  28560
ccccgtcacc accaagaacg gggaaatcac cctcaagctg ggagaggggg tggacctcga  28620
ttcctcggga aaactcatct ccaacacggc caccaaggcc gccgcccctc tcagtttttc  28680
caacaacacc atttccctta acatggatca ccccttttac actaaagatg gaaaattatc  28740
cttacaagtt tctccaccat taaatatact gagaacaagc attctaaaca cactagcttt  28800
aggttttgga tcaggtttag gactccgtgg ctctgccttg gcagtacagt tagtctctcc  28860
acttacattt gatactgatg gaaacataaa gcttacctta gacagaggtt tgcatgttac  28920
aacaggagat gcaattgaaa gcaacataag ctgggctaaa ggtttaaaat ttgaagatgg  28980
agccatagca accaacattg gaaatgggtt agagtttgga agcagtagta cagaaacagg  29040
tgttgatgat gcttacccaa tccaagttaa acttggatct ggccttagct ttgacagtac  29100
aggagccata atggctggta acaaagaaga cgataaactc actttgtgga caacacctga  29160
tccatcacca aactgtcaaa tactcgcaga aaatgatgca aaactaacac tttgcttgac  29220
taaatgtggt agtcaaatac tggccactgt gtcagtctta gttgtaggaa gtggaaacct  29280
aaaccccatt actggcaccg taagcagtgc tcaggtgttt ctacgttttg atgcaaacgg  29340
tgttctttta acagaacatt ctacactaaa aaaatactgg gggtataggc agggagatag  29400
catagatggc actccatata ccaatgctgt aggattcatg cccaatttaa aagcttatcc  29460
aaagtcacaa agttctacta ctaaaaataa tatagtaggg caagtataca tgaatggaga  29520
tgtttcaaaa cctatgcttc tcactataac cctcaatggt actgatgaca gcaacagtac  29580
atattcaatg tcattttcat acacctggac taatggaagc tatgttggag caacatttgg  29640
ggctaactct tataccttct catacatcgc ccaagaatga acactgtatc ccaccctgca  29700
tgccaaccct tcccacccca ctctgtggaa caaactctga aacacaaaat aaaataaagt  29760
tcaagtgttt tattgattca acagttttac aggattcgag cagttatttt tcctccaccc  29820
tcccaggaca tggaatacac caccctctcc ccccgcacag ccttgaacat ctgaatgcca  29880
ttggtgatgg acatgctttt ggtctccacg ttccacacag tttcagagcg agccagtctc  29940
gggtcggtca gggagatgaa accctccggg cactcccgca tctgcacctc acagctcaac  30000
agctgaggat tgtcctcggt ggtcgggatc acggttatct ggaagaagca gaagagcggc  30060
ggtgggaatc atagtccgcg aacgggatcg gccggtggtg tcgcatcagg ccccgcagca  30120
gtcgctgccg ccgccgctcc gtcaagctgc tgctcagggg gtccgggtcc agggactccc  30180
tcagcatgat gcccacggcc ctcagcatca gtcgtctggt gcggcgggcg cagcagcgca  30240
tgcggatctc gctcaggtcg ctgcagtacg tgcaacacag aaccaccagg ttgttcaaca  30300
gtccatagtt caacacgctc cagccgaaac tcatcgcggg aaggatgcta cccacgtggc  30360
cgtcgtacca gatcctcagg taaatcaagt ggtgcccct ccagaacacg ctgcccacgt  30420
acatgatctc cttgggcatg tggcggttca ccacctcccg gtaccacatc accctctggt  30480
tgaacatgca gccccggatg atcctgcgga accacagggc cagcaccgcc ccgcccgcca  30540
tgcagcgaag agaccccggg tcccggcaat ggcaatggag gacccaccgc tcgtacccgt  30600
ggatcatctg ggagctgaac aagtctatgt tggcacagca caggcatatg ctcatgcatc  30660
tcttcagcac tctcaactcc tcgggggtca aaaccatatc ccagggcacg gggaactctt  30720
```

```
gcaggacagc gaaccccgca gaacagggca atcctcgcac agaacttaca ttgtgcatgg  30780
acagggtatc gcaatcaggc agcaccgggt gatcctccac cagagaagcg cgggtctcgg  30840
tctcctcaca gcgtggtaag gggcgcggcc gatacgggtg atggcgggac gcggctgatc  30900
gtgttcgcga ccgtgtcatg atgcagttgc tttcggacat tttcgtactt gctgtagcag  30960
aacctggtcc gggcgctgca caccgatcgc cggcggcggt ctcggcgctt ggaacgctcg  31020
gtgttgaaat tgtaaaacag ccactctctc agaccgtgca gcagatctag ggcctcagga  31080
gtgatgaaga tcccatcatg cctgatggct ctgatcacat cgaccaccgt ggaatgggcc  31140
agacccagcc agatgatgca attttgttgg gtttcggtga cggcggggga gggaagaaca  31200
ggaagaacca tgattaactt ttaatccaaa cggtctcgga gtacttcaaa atgaagatcg  31260
cggagatggc acctctcgcc cccgctgtgt tggtggaaaa taacagccag gtcaaaggtg  31320
atacggttct cgagatgttc cacggtggct tccagcaaag cctccacgcg cacatccaga  31380
aacaagacaa tagcgaaagc gggagggttc tctaattcct caatcatcat gttacactcc  31440
tgcaccatcc ccagataatt ttcatttttc cagccttgaa tgattcgaac tagttcgtga  31500
ggtaaatcca agccagccat gataaagagc tcgcgcagag cgccctccac cggcattctt  31560
aagcacaccc tcataattcc aagatattct gctcctggtt cacctgcagc agattgacaa  31620
gcggaatatc aaaatctctg ccgcgatccc tgagctcctc cctcagcaat aactgtaagt  31680
actctttcat atcctctccg aaatttttag ccataggacc accaggaata agattagggc  31740
aagccacagt acagataaac cgaagtcctc cccagtgagc attgccaaat gcaagactgc  31800
tataagcatg ctggctagac ccggtgatat cttccagata actggacaga aaatcgccca  31860
ggcaattttt aagaaaatca acaaaagaaa aatcctccag gtggacgttt agagcctcgg  31920
gaacaacgat gaagtaaatg caagcggtgc gttccagcat ggttagttag ctgatctgta  31980
gaaaaaacaa aaatgaacat taaaccatgc tagcctggcg aacaggtggg taaatcgttc  32040
tctccagcac caggcaggcc acggggtctc cggcgcgacc ctcgtaaaaa ttgtcgctat  32100
gattgaaaac catcacagag agacgttccc ggtggccggc gtgaatgatt cgacaagatg  32160
aatacacccc cggaacattg gcgtccgcga gtgaaaaaaa gcgcccgagg aagcaataag  32220
gcactacaat gctcagtctc aagtccagca aagcgatgcc atgcggatga agcacaaaat  32280
tctcaggtgc gtacaaaatg taattactcc cctcctgcac aggcagcaaa gcccccgatc  32340
cctccaggta cacatacaaa gcctcagcgt ccatagctta ccgagcagca gcacacaaca  32400
ggcgcaagag tcagagaaag gctgagctct aacctgtcca cccgctctct gctcaatata  32460
tagcccagat ctacactgac gtaaaggcca aagtctaaaa atacccgcca aataatcaca  32520
cacgcccagc acacgcccag aaaccggtga cacactcaaa aaaatacgcg cacttcctca  32580
aacgcccaaa actgccgtca tttccgggtt cccacgctac gtcatcaaaa cacgactttc  32640
aaattccgtc gaccgttaaa aacgtcaccc gccccgcccc taacggtcgc ccgtctctca  32700
gccaatcagc gccccgcatc cccaaattca aacacctcat ttgcatatta acgcgcacaa  32760
aaagtttgag gtatattatt gatgatgg                                      32788
```

<210> SEQ ID NO 13
<211> LENGTH: 30684
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
ccatcttcaa taatatacct caaacttttt gtgcgcgtta atatgcaaat gaggcgtttg     60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagtagg gataacaggg taatgacatt    600
gattattgac tagttgttaa tagtaatcaa ttacggggtc attagttcat agcccatata    660
tggagttccg cgttacataa cttacggtaa atggcccgcc tggctgaccg cccaacgacc    720
cccgcccatt gacgtcaata atgacgtatg ttcccatagt aacgccaata gggactttcc    780
attgacgtca atgggtggag tatttacggt aaactgccca cttggcagta catcaagtgt    840
atcatatgcc aagtccgccc cctattgacg tcaatgacgg taaatggccc gcctggcatt    900
atgcccagta catgacctta cgggactttc ctacttggca gtacatctac gtattagtca    960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta ataaccccgc cccgttgacg caaatgggcg   1140
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
tgagcaaggg cgaggagctg ttcaccgggg tggtgcccat cctggtcgag ctggacggcg   1320
acgtaaacgg ccacaagttc agcgtgtccg gcgagggcga gggcgatgcc acctacggca   1380
agctgaccct gaagttcatc tgcaccaccg gcaagctgcc cgtgccctgg cccaccctcg   1440
tgaccaccct gacctacggc gtgcagtgct tcagccgcta ccccgaccac atgaagcagc   1500
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg gggcacaagc   1680
tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacaccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgagggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg ggaggttttt taaagcaagt   2220
aaaacctcta caaatgtggt aaaataacta taacggtcct aaggtagcga gtgagtagtg   2280
```

```
ttctggggcg ggggaggacc tgcatgaggg ccagaataac tgaaatctgt gcttttctgt   2340
gtgttgcagc agcatgagcg gaagcggctc ctttgaggga ggggtattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg gttgttgatt   2820
ttaacacaga gtctgaatct ttatttgatt tttcgcgcgc ggtaggccct ggaccaccgg   2880
tctcgatcat tgagcacccg gtggatcttt tccaggaccc ggtagaggtg ggcttggatg   2940
ttgaggtaca tgggcatgag cccgtcccgg gggtggaggt agctccattg cagggcctcg   3000
tgctcggggg tggtgttgta aatcacccag tcatagcagg ggcgcagggc atggtgttgc   3060
acaatatctt tgaggaggag actgatggcc acgggcagcc ctttggtgta ggtgtttaca   3120
aatctgttga gctgggaggg atgcatgcgg ggggagatga ggtgcatctt ggcctggatc   3180
ttgagattgg cgatgttacc gcccagatcc cgcctggggt tcatgttgtg caggaccacc   3240
agcacggtgt atccggtgca cttggggaat ttatcatgca acttggaagg gaaggcgtga   3300
aagaatttgg cgacgccttt gtgcccgccc aggttttcca tgcactcatc catgatgatg   3360
gcgatgggcc cgtgggcggc ggcctgggca aagacgtttc gggggtcgga cacatcatag   3420
ttgtggtcct gggtgaggtc atcataggcc attttaatga atttggggcg gagggtgccg   3480
gactggggga caaaggtacc ctcgatcccg gggggcgtagt tcccctcaca gatctgcatc   3540
tcccaggctt tgagctcgga ggggggggatc atgtccacct gcggggcgat aaagaacacg   3600
gtttccgggg cgggggagat gagctgggcc gaaagcaagt tccggagcag ctgggacttg   3660
ccgcagccgg tggggccgta gatgaccccg atgaccggct gcaggtggta gttgagggag   3720
agacagctgc cgtcctcccg gaggaggggg gccacctcgt tcatcatctc gcgcacgtgc   3780
atgttctcgc gcaccagttc cgccaggagg cgctctcccc ccagggatag gagctcctgg   3840
agcgaggcga agtttttcag cggcttgagt ccgtcggcca tgggcatttt ggagagggtt   3900
tgttgcaaga gttccaggcg gtcccagagc tcggtgatgt gctctacggc atctcgatcc   3960
agcagacctc ctcgtttcgc gggttgggac ggctgcggga gtagggcacc agacgatggg   4020
cgtccagcgc agccagggtc cggtccttcc agggtcgcag cgtccgcgtc agggtggtct   4080
ccgtcacggt gaaggggtgc gcgccgggct gggcgcttgc gagggtgcgc ttcaggctca   4140
tccggctggt cgaaaaccgc tcccgatcgg cgccctgcgc gtcggccagg tagcaattga   4200
ccatgagttc gtagttgagc gcctcggccg cgtggccttt ggcgcggagc ttacctttgg   4260
aagtctgccc gcaggcggga cagaggaggg acttgagggc gtagagcttg ggggcgagga   4320
agacggactc gggggcgtag gcgtccgcgc cgcagtgggc gcagacggtc tcgcactcca   4380
cgagccaggt gaggtcgggc tggtcggggt caaaaaccag tttcccgccg ttctttttga   4440
tgcgtttctt acctttggtc tccatgagct cgtgtccccg ctgggtgaca aagaggctgt   4500
ccgtgtcccc gtagaccgac tttatgggcc ggtcctcgag cggtgtgccg cggtcctcct   4560
cgtagaggaa ccccgcccac tccgagacga aagcccgggt ccaggccagc acgaaggagg   4620
ccacgtggga cgggtagcgg tcgttgtcca ccagcgggtc caccttttcc agggtatgca   4680
```

```
aacacatgtc cccctcgtcc acatccagga aggtgattgg cttgtaagtg taggccacgt   4740
gaccgggggt cccggccggg ggggtataaa agggtgcggg tccctgctcg tcctcactgt   4800
cttccggatc gctgtccagg agcgccagct gttggggtag gtattccctc tcgaaggcgg   4860
gcatgacctc ggcactcagg ttgtcagttt ctagaaacga ggaggatttg atattgacgg   4920
tgccggcgga gatgcctttc aagagcccct cgtccatctg gtcagaaaag acgatctttt   4980
tgttgtcgag cttggtggcg aaggagccgt agagggcgtt ggagaggagc ttggcgatgg   5040
agcgcatggt ctggtttttt tccttgtcgg cgcgctcctt ggcggcgatg ttgagctgca   5100
cgtactcgcg cgccacgcac ttccattcgg ggaagacggt ggtcagctcg tcgggcacga   5160
ttctgacctg ccagccccga ttatgcaggg tgatgaggtc cacactggtg gccacctcgc   5220
cgcgcagggg ctcattagtc cagcagaggc gtccgccctt gcgcgagcag aagggggca    5280
gggggtccag catgacctcg tcgggggggt cggcatcgat ggtgaagatg ccgggcagga   5340
ggtcggggtc aaagtagctg atggaagtgg ccagatcgtc cagggcagct tgccattcgc   5400
gcacggccag cgcgcgctcg tagggactga ggggcgtgcc ccagggcatg ggatgggtaa   5460
gcgcggaggc gtacatgccg cagatgtcgt agacgtagag gggctcctcg aggatgccga   5520
tgtaggtggg gtagcagcgc cccccgcgga tgctggcgcg cacgtagtca tacagctcgt   5580
gcgagggggc gaggagcccc gggcccaggt tggtgcgact gggcttttcg gcgcggtaga   5640
cgatctggcg gaaaatggca tgcgagttgg aggagatggt gggcctttgg aagatgttga   5700
agtgggcgtg gggcagtccg accgagtcgc ggatgaagtg ggcgtaggag tcttgcagct   5760
tggcgacgag ctcggcggtg actaggacgt ccagagcgca gtagtcgagg gtctcctgga   5820
tgatgtcata cttgagctgt cccttttgtt tccacagctc gcggttgaga aggaactctt   5880
cgcggtcctt ccagtactct tcgaggggga acccgtcctg atctgcacgg taagagccta   5940
gcatgtagaa ctggttgacg gccttgtagg cgcagcagcc cttctccacg gggagggcgt   6000
aggcctgggc ggccttgcgc agggaggtgt gcgtgagggc gaaagtgtcc ctgaccatga   6060
ccttgaggaa ctggtgcttg aagtcgatat cgtcgcagcc cccctgctcc cagagctgga   6120
agtccgtgcg cttcttgtag gcggggttgg gcaaagcgaa agtaacatcg ttgaagagga   6180
tcttgcccgc gcggggcata aagttgcgag tgatgcggaa aggttggggc acctcggccc   6240
ggttgttgat gacctgggcg gcgagcacga tctcgtcgaa gccgttgatg ttgtggccca   6300
cgatgtagag ttccacgaat cgcggacggc ccttgacgtg gggcagtttc ttgagctcct   6360
cgtaggtgag ctcgtcgggg tcgctgagcc cgtgctgctc gagcgcccag tcggcgagat   6420
gggggttggc gcggaggaag gaagtccaga gatccacggc cagggcggtt tgcagacggt   6480
cccggtactg acggaactgc tgcccgacgg ccatttttc gggggtgacg cagtagaagg    6540
tgcgggggtc cccgtgccag cgatcccatt tgagctggag ggcgagatcg agggcgagct   6600
cgacgagccg gtcgtccccg gagagtttca tgaccagcat gaaggggacg agctgcttgc   6660
cgaaggaccc catccaggtg taggtttcca catcgtaggt gaggaagagc ctttcggtgc   6720
gaggatgcga gccgatgggg aagaactgga tctcctgcca ccaattggag gaatggctgt   6780
tgatgtgatg gaagtagaaa tgccgacggc gcgccgaaca ctcgtgcttg tgtttataca   6840
agcggccaca gtgctcgcaa cgctgcacgg gatgcacgtg ctgcacgagc tgtacctgag   6900
ttcctttgac gaggaatttc agtgggaagt ggagtcgtgg cgcctgcatc tcgtgctgta   6960
ctacgtcgtg gtggtcggcc tggccctctt ctgcctcgat ggtggtcatg ctgacgagcc   7020
```

```
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cgggggcggt gcctcttcca   7320
tggttagaag cggcggcgag gacgcgcgcc gggcggcagg ggcggctcgg ggcccggagg   7380
caggggcggc aggggcacgt cggcgccgcg cgcgggtagg ttctggtact gcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggcccccg ggagttcctc   8100
cacttcctct tcttcctcct ccactaacat ctcttctact tcctcctcag gcggcagtgg   8160
tggcggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc cgcgcatctc caggtggccg ggggggtccc cgttgggcag   8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggct ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagccg atgaggaagt gcggcggcgg ctggcggtag agcggccatc gctcggtggc   9060
gggggcgccg ggcgcgaggt cctcgagcat ggtgcggtgg tagccgtaga tgtacctgga   9120
catccaggtg atgccggcgg cggtggtgga ggcgcgcggg aactcgcgga cgcggttcca   9180
gatgttgcgc agcggcagga agtagttcat ggtgggcacg gtctggcccg tgaggcgcgc   9240
gcagtcgtgg atgctctata cgggcaaaaa cgaaagcggt cagcggctcg actccgtggc   9300
ctggaggcta agcgaacggg ttgggctgcg cgtgtacccc ggttcgaatc tcgaatcagg   9360
ctggagccgc agctaacgtg gtattggcac tcccgtctcg acccaagcct gcaccaaccc   9420
```

```
tccaggatac ggaggcgggt cgttttgcaa cttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag accccatagc cagccgactt ctccagttac ggagcgagcc   9660
cctcttttgt tttgtttgtt tttgccagat gcatcccgta ctgcggcaga tgcgccccca   9720
ccaccctcca ccgcaacaac agccccctcc acagccggcg cttctgcccc cgccccagca   9780
gcaacttcca gccacgaccg ccgcggccgc cgtgagcggg gctggacaga gttatgatca   9840
ccagctggcc ttggaagagg gcgaggggct ggcgcgcctg gggcgtcgt cgccggagcg   9900
gcacccgcgc gtgcagatga aaagggacgc tcgcgaggcc tacgtgccca agcagaacct   9960
gttcagagac aggagcggcg aggagcccga ggagatgcgc gcggcccggt tccacgcggg  10020
gcgggagctg cggcgcggcc tggaccgaaa gagggtgctg agggacgagg atttcgaggc  10080
ggacgagctg acggggatca gccccgcgcg cgcgcacgtg gccgcggcca acctggtcac  10140
ggcgtacgag cagaccgtga aggaggagag caacttccaa aaatccttca acaaccacgt  10200
gcgcaccctg atcgcgcgcg aggaggtgac cctgggcctg atgcacctgt gggacctgct  10260
ggaggccatc gtgcagaacc ccaccagcaa gccgctgacg gcgcagctgt tcctggtggt  10320
gcagcatagt cgggacaacg aagcgttcag ggaggcgctg ctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggttttac atgcgcatga ccctgaaagt gctgaccctg agcgacgatc tgggggtgta  10620
ccgcaacgac aggatgcacc gtgcggtgag cgccagcagg cggcgcgagc tgagcgacca  10680
ggagctgatg catagtctgc agcgggccct gaccggggcc gggaccgagg gggagagcta  10740
ctttgacatg ggcgcggacc tgcactggca gcccagccgc cgggccttgg aggcggcggc  10800
aggaccctac gtagaagagg tggacgatga ggtggacgag gagggcgagt acctggaaga  10860
ctgatggcgc gaccgtattt ttgctagatg caacaacaac agccacctcc tgatcccgcg  10920
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gcccccttca cggacagcgg cagcatcaac  11640
cgcaactcgt acctgggcta cctgattaac ctgtaccgcg aggccatcgg ccaggcgcac  11700
gtggacgagc agacctacca ggagatcacc cacgtgagcc gcgccctggg ccaggacgac  11760
```

```
ccgggcaacc tggaagccac cctgaacttt ttgctgacca accggtcgca gaagatcccg  11820
ccccagtacg cgctcagcac cgaggaggag cgcatcctgc gttacgtgca gcagagcgtg  11880
ggcctgttcc tgatgcagga gggggccacc cccagcgccg cgctcgacat gaccgcgcgc  11940
aacatggagc ccagcatgta cgccagcaac cgcccgttca tcaataaact gatggactac  12000
ttgcatcggg cggccgccat gaactctgac tatttcacca acgccatcct gaatccccac  12060
tggctcccgc cgccggggtt ctacacgggc gagtacgaca tgcccgaccc caatgacggg  12120
ttcctgtggg acgatgtgga cagcagcgtg ttctccccc gaccgggtgc taacgagcgc  12180
cccttgtgga agaaggaagg cagcgaccga cgcccgtcct cggcgctgtc cggccgcgag  12240
ggtgctgccg cggcggtgcc cgaggccgcc agtcctttcc cgagcttgcc cttctcgctg  12300
aacagtatcc gcagcagcga gctgggcagg atcacgcgcc cgcgcttgct gggcgaagag  12360
gagtacttga atgactcgct gttgagaccc gagcgggaga agaacttccc caataacggg  12420
atagaaagcc tggtggacaa gatgagccgc tggaagacgt atgcgcagga gcacagggac  12480
gatccccggg cgtcgcaggg ggccacgagc cggggcagcg ccgcccgtaa acgccggtgg  12540
cacgacaggc agcggggaca gatgtgggac gatgaggact ccgccgacga cagcagcgtg  12600
ttggacttgg gtgggagtgg taacccgttc gctcacctgc gcccccgtat cgggcgcatg  12660
atgtaagaga aaccgaaaat aaatgatact caccaaggcc atggcgacca gcgtgcgttc  12720
gtttcttctc tgttgttgtt gtatctagta tgatgaggcg tgcgtacccg gagggtcctc  12780
ctccctcgta cgagagcgtg atgcagcagg cgatggcggc ggcggcgatg cagcccccgc  12840
tggaggctcc ttacgtgccc ccgcggtacc tggcgcctac ggaggggcgg aacagcattc  12900
gttactcgga gctggcaccc ttgtacgata ccacccggtt gtacctggtg gacaacaagt  12960
cggcggacat cgcctcgctg aactaccaga acgaccacag caacttcctg accaccgtgg  13020
tgcagaacaa tgacttcacc cccacggagg ccagcaccca gaccatcaac tttgacgagc  13080
gctcgcggtg gggcggccag ctgaaaacca tcatgcacac caacatgccc aacgtgaacg  13140
agttcatgta cagcaacaag ttcaaggcgc gggtgatggt ctcccgcaag acccccaatg  13200
gggtgacagt gacagaggat tatgatggta gtcaggatga gctgaagtat gaatgggtgg  13260
aatttgagct gcccgaaggc aacttctcgg tgaccatgac catcgacctg atgaacaacg  13320
ccatcatcga caattacttg gcggtggggc ggcagaacgg ggtgctggag agcgacatcg  13380
gcgtgaagtt cgacactagg aacttcaggc tgggctggga ccccgtgacc gagctggtca  13440
tgcccggggt gtacaccaac gaggctttcc atcccgatat tgtcttgctg cccggctgcg  13500
gggtggactt caccgagagc cgcctcagca acctgctggg cattcgcaag aggcagccct  13560
tccaggaagg cttccagatc atgtacgagg atctggaggg ggcaacatc cccgcgctcc  13620
tggatgtcga cgcctatgag aaaagcaagg aggatgcagc agctgaagca actgcagccg  13680
tagctaccgc ctctaccgag gtcaggggcg ataattttgc aagcgccgca gcagtggcag  13740
cggccgaggc ggctgaaacc gaaagtaaga tagtcattca gccggtggag aaggatagca  13800
agaacaggag ctacaacgta ctaccggaca agataaacac cgcctaccgc agctggtacc  13860
tagcctacaa ctatggcgac cccgagaagg gcgtgcgctc ctggacgctg ctcaccacct  13920
cggacgtcac ctgcggcgtg gagcaagtct actggtcgct gcccgacatg atgcaagacc  13980
cggtcacctt ccgctccacg cgtcaagtta gcaactaccc ggtggtgggc gccgagctcc  14040
tgcccgtcta ctccaagagc ttcttcaacg agcaggccgt ctactcgcag cagctgcgcg  14100
ccttcacctc gcttacgcac gtcttcaacc gcttccccga gaaccagatc ctcgtccgcc  14160
```

```
cgcccgcgcc caccattacc accgtcagtg aaaacgttcc tgctctcaca gatcacggga  14220
ccctgccgct gcgcagcagt atccggggag tccagcgcgt gaccgttact gacgccagac  14280
gccgcacctg cccctacgtc tacaaggccc tgggcatagt cgcgccgcgc gtcctctcga  14340
gccgcacctt ctaaatgtcc attctcatct cgcccagtaa taacaccggt tggggcctgc  14400
gcgcgcccag caagatgtac ggaggcgctc gccaacgctc cacgcaacac cccgtgcgcg  14460
tgcgcgggca cttccgcgct ccctggggcg ccctcaaggg ccgcgtgcgg tcgcgcacca  14520
ccgtcgacga cgtgatcgac caggtggtgg ccgacgcgcg caactacacc cccgccgccg  14580
cgcccgtctc caccgtggac gccgtcatcg acagcgtggt ggccgacgcg cgccggtacg  14640
cccgcgccaa gagccggcgg cggcgcatcg cccggcggca ccggagcacc cccgccatgc  14700
gcgcggcgcg agccttgctg cgcagggcca ggcgcacggg acgcagggcc atgctcaggg  14760
cggccagacg cgcggcttca ggcgccagcg ccggcaggac ccggagacgc gcggccacgg  14820
cggcggcagc ggccatcgcc agcatgtccc gcccgcggcg agggaacgtg tactgggtgc  14880
gcgacgccgc caccggtgtg cgcgtgcccg tgcgcacccg ccccccctcgc acttgaagat  14940
gttcacttcg cgatgttgat gtgtcccagc ggcgaggagg atgtccaagc gcaaattcaa  15000
ggaagagatg ctccaggtca tcgcgcctga gatctacggc cctgcggtgg tgaaggagga  15060
aagaaagccc cgcaaaatca agcgggtcaa aaaggacaaa aaggaagaag aaagtgatgt  15120
ggacggattg gtggagtttg tgcgcgagtt cgcccccccgg cggcgcgtgc agtggcgcgg  15180
gcggaaggtg caaccggtgc tgagacccgg caccaccgtg gtcttcacgc ccggcgagcg  15240
ctccggcacc gcttccaagc gctcctacga cgaggtgtac ggggatgatg atattctgga  15300
gcaggcggcc gagcgcctgg gcgagtttgc ttacggcaag cgcagccgtt ccgcaccgaa  15360
ggaagaggcg gtgtccatcc cgctggacca cggcaacccc acgccgagcc tcaagcccgt  15420
gaccttgcag caggtgctgc cgaccgcggc gccgcgccgg gggttcaagc gcgagggcga  15480
ggatctgtac cccaccatgc agctgatggt gcccaagcgc cagaagctgg aagacgtgct  15540
ggagaccatg aaggtggacc cggacgtgca gcccgaggtc aaggtgcggc ccatcaagca  15600
ggtggccccg ggcctgggcg tgcagaccgt ggacatcaag attcccacgg agcccatgga  15660
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat tttcgtcccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
```

-continued

```
aacctatggc agcaaggcgt ggaacagcac cacagggcag gcgctgaggg ataagctgaa  16560
agagcagaac ttccagcaga aggtggtcga tgggctcgcc tcgggcatca acggggtggt  16620
ggacctggcc aaccaggccg tgcagcggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
tctgtgtgtg tatgtattat gtcgccgccg ccgctgtcca ccagaaggag gagtgaagag  17160
gcgcgtcgcc gagttgcaag atggccaccc catcgatgct gccccagtgg gcgtacatgc  17220
acatcgccgg acaggacgct tcggagtacc tgagtccggg tctggtgcag tttgcccgcg  17280
ccacagacac ctacttcagt ctggggaaca agtttaggaa ccccacggtg gcgcccacgc  17340
acgatgtgac caccgaccgc agccagcggc tgacgctgcg cttcgtgccc gtggaccgcg  17400
aggacaacac ctactcgtac aaagtgcgct acacgctggc cgtgggcgac aaccgcgtgc  17460
tggacatggc cagcacctac tttgacatcc gcggcgtgct ggatcggggc cctagcttca  17520
aaccctactc cggcaccgcc tacaacagtc tggcccccaa gggagcaccc aacacttgtc  17580
agtggacata taaagccgat ggtgaaactg ccacagaaaa aacctataca tatggaaatg  17640
cacccgtgca gggcattaac atcacaaaag atggtattca acttggaact gacaccgatg  17700
atcagccaat ctacgcagat aaaacctatc agcctgaacc tcaagtgggt gatgctgaat  17760
ggcatgacat cactggtact gatgaaaagt atggaggcag agctcttaag cctgatacca  17820
aaatgaagcc ttgttatggt tcttttgcca agcctactaa taaagaagga ggtcaggcaa  17880
atgtgaaaac aggaacaggc actactaaag aatatgacat agacatggct ttctttgaca  17940
acagaagtgc ggctgctgct ggcctagctc cagaaattgt tttgtatact gaaaatgtgg  18000
atttggaaac tccagatacc catattgtat acaaagcagg cacagatgac agcagctctt  18060
ctattaattt gggtcagcaa gccatgccca acagacctaa ctacattggt ttcagagaca  18120
actttatcgg gctcatgtac tacaacagca ctggcaatat gggggtgctg gccggtcagg  18180
cttctcagct gaatgctgtg gttgacttgc aagacagaaa caccgagctg tcctaccagc  18240
tcttgcttga ctctctgggt gacagaaccc ggtatttcag tatgtggaat caggcggtgg  18300
acagctatga tcctgatgtg cgcattattg aaaatcatgg tgtggaggat gaacttccca  18360
actattgttt ccctctggat gctgttggca gaacagatac ttatcaggga attaaggcta  18420
atggaactga tcaaaccaca tggaccaaag atgacagtgt caatgatgct aatgagatag  18480
gcaagggtaa tccattcgcc atggaaatca acatccaagc caacctgtgg aggaacttcc  18540
tctacgccaa cgtggccctg tacctgcccg actcttacaa gtacacgccg gccaatgtta  18600
ccctgcccac caacaccaac acctacgatt acatgaacgg ccgggtggtg gcgccctcgc  18660
tggtggactc ctacatcaac atcggggcgc gctggtcgct ggatcccatg gacaacgtga  18720
accccttcaa ccaccaccgc aatgcggggc tgcgctaccg ctccatgctc ctgggcaacg  18780
ggcgctacgt gcccttccac atccaggtgc cccagaaatt tttcgccatc aagagcctcc  18840
tgctcctgcc cgggtcctac acctacgagt ggaacttccg caaggacgtc aacatgatcc  18900
```

tgcagagctc cctcggcaac gacctgcgca cggacggggc ctccatctcc ttcaccagca 18960
tcaacctcta cgccaccttc ttccccatgg cgcacaacac ggcctccacg ctcgaggcca 19020
tgctgcgcaa cgacaccaac gaccagtcct tcaacgacta cctctcggcg gccaacatgc 19080
tctaccccat cccggccaac gccaccaacg tgcccatctc catcccctcg cgcaactggg 19140
ccgccttccg cggctggtcc ttcacgcgtc tcaagaccaa ggagacgccc tcgctgggct 19200
ccgggttcga cccctacttc gtctactcgg gctccatccc ctacctcgac ggcaccttct 19260
acctcaacca caccttcaag aaggtctcca tcaccttcga ctcctccgtc agctggcccg 19320
gcaacgaccg gctcctgacg cccaacgagt tcgaaatcaa gcgcaccgtc gacggcgagg 19380
gctacaacgt ggcccagtgc aacatgacca aggactggtt cctggtccag atgctggccc 19440
actacaacat cggctaccag ggcttctacg tgcccgaggg ctacaaggac cgcatgtact 19500
ccttcttccg caacttccag cccatgagcc gccaggtggt ggacgaggtc aactacaagg 19560
actaccaggc cgtcaccctg gcctaccagc acaacaactc gggcttcgtc ggctacctcg 19620
cgcccaccat gcgccagggc cagccctacc ccgccaacta cccctacccg ctcatcggca 19680
agagcgccgt caccagcgtc acccagaaaa agttcctctg cgacagggtc atgtggcgca 19740
tccccttctc cagcaacttc atgtccatgg gcgcgctcac cgacctcggc cagaacatgc 19800
tctatgccaa ctccgcccac gcgctagaca tgaatttcga agtcgacccc atggatgagt 19860
ccacccttct ctatgttgtc ttcgaagtct tcgacgtcgt ccgagtgcac cagccccacc 19920
gcggcgtcat cgaggccgtc tacctgcgca ccccccttctc ggccggtaac gccaccacct 19980
aagctcttgc ttcttgcaag ccatggccgc gggctccggc gagcaggagc tcagggccat 20040
catccgcgac ctgggctgcg ggccctactt cctgggcacc ttcgataagc gcttcccggg 20100
attcatggcc ccgcacaagc tggcctgcgc catcgtcaac acggccggcc gcgagaccgg 20160
gggcgagcac tggctggcct tcgcctggaa cccgcgctcg aacacctgct acctcttcga 20220
ccccttcggg ttctcggacg agcgcctcaa gcagatctac cagttcgagt acgagggcct 20280
gctgcgccgc agcgccctgg ccaccgagga ccgctgcgtc accctggaaa agtccaccca 20340
gaccgtgcag ggtccgcgct cggccgcctg cgggctcttc tgctgcatgt tcctgcacgc 20400
cttcgtgcac tggcccgacc gccccatgga caagaacccc accatgaact tgctgacggg 20460
ggtgcccaac ggcatgctcc agtcgcccca ggtggaaccc accctgcgcc gcaaccagga 20520
ggcgctctac cgcttcctca actcccactc cgcctacttt cgctcccacc gcgcgcgcat 20580
cgagaaggcc accgccttcg accgcatgaa tcaagacatg taaaccgtgt gtgtatgtta 20640
aatgtcttta ataaacagca ctttcatgtt acacatgcat ctgagatgat ttatttagaa 20700
atcgaaaggg ttctgccggg tctcggcatg gcccgcgggc agggacacgt tgcggaactg 20760
gtacttggcc agccacttga actcggggat cagcagtttg ggcagcgggg tgtcggggaa 20820
ggagtcggtc cacagcttcc gcgtcagttg cagggcgccc agcaggtcgg gcgcggagat 20880
cttgaaatcg cagttgggac ccgcgttctg cgcgcgggag ttgcggtaca cggggttgca 20940
gcactggaac accatcaggg ccgggtgctt cacgctcgcc agcaccgtcg cgtcggtgat 21000
gctctccacg tcgaggtcct cggcgttggc catcccgaag gggtcatct tgcaggtctg 21060
ccttcccatg gtgggcacgc acccgggctt gtggttgcaa tcgcagtgca gggggatcag 21120
catcatctgg gcctggtcgg cgttcatccc cgggtacatg gccttcatga aagcctccaa 21180
ttgcctgaac gcctgctggg ccttggctcc ctcggtgaag aagaccccgc aggacttgct 21240

```
agagaactgg ttggtggcgc acccggcgtc gtgcacgcag cagcgcgcgt cgttgttggc  21300
cagctgcacc acgctgcgcc cccagcggtt ctgggtgatc ttggcccggt cggggttctc  21360
cttcagcgcg cgctgcccgt tctcgctcgc cacatccatc tcgatcatgt gctccttctg  21420
gatcatggtg gtcccgtgca ggcaccgcag cttgccctcg gcctcggtgc acccgtgcag  21480
ccacagcgcg cacccggtgc actcccagtt cttgtgggcg atctgggaat gcgcgtgcac  21540
gaagccctgc aggaagcggc ccatcatggt ggtcagggtc ttgttgctag tgaaggtcag  21600
cggaatgccg cggtgctcct cgttgatgta caggtggcag atgcggcggt acacctcgcc  21660
ctgctcgggc atcagctgga agttggcttt caggtcggtc tccacgcggt agcggtccat  21720
cagcatagtc atgatttcca tacccttctc ccaggccgag acgatgggca ggctcatagg  21780
gttcttcacc atcatcttag cgctagcagc cgcggccagg gggtcgctct cgtccagggt  21840
ctcaaagctc cgcttgccgt ccttctcggt gatccgcacc ggggggtagc tgaagcccac  21900
ggccgccagc tcctcctcgg cctgtctttc gtcctcgctg tcctggctga cgtcctgcag  21960
gaccacatgc ttggtcttgc ggggtttctt cttgggcggc agcggcggcg gagatgttgg  22020
agatggcgag gggagcgcg agttctcgct caccactact atctcttcct cttcttggtc  22080
cgaggccacg cggcggtagg tatgtctctt cgggggcaga ggcggaggcg acgggctctc  22140
gccgccgcga cttggcggat ggctggcaga gccccttccg cgttcggggg tgcgctcccg  22200
gcggcgctct gactgacttc ctccgcggcc ggccattgtg ttctcctagg gaggaacaac  22260
aagcatggag actcagccat cgccaacctc gccatctgcc cccaccgccg acgagaagca  22320
gcagcagcag aatgaaagct taaccgcccc gccgcccagc cccgccacct ccgacgcggc  22380
cgtcccagac atgcaagaga tggaggaatc catcgagatt gacctgggct atgtgacgcc  22440
cgcggagcac gaggaggagc tggcagtgcg cttttcacaa gaagagatac accaagaaca  22500
gccagagcag gaagcagaga atgagcagag tcaggctggg ctcgagcatg acggcgacta  22560
cctccacctg agcgggggggg aggacgcgct catcaagcat ctggcccggc aggccaccat  22620
cgtcaaggat gcgctgctcg accgcaccga ggtgcccctc agcgtggagg agctcagccg  22680
cgcctacgag ttgaacctct tctcgccgcg cgtgcccccc aagcgccagc ccaatggcac  22740
ctgcgagccc aacccgcgcc tcaacttcta cccggtcttc gcggtgcccg aggccctggc  22800
cacctaccac atctttttca agaaccaaaa gatccccgtc tcctgccgcg ccaaccgcac  22860
ccgcgccgac gcccttttca acctgggtcc cggcgcccgc ctacctgata tcgcctcctt  22920
ggaagaggtt cccaagatct tcgagggtct gggcagcgac gagactcggg ccgcgaacgc  22980
tctgcaagga gaaggaggag agcatgagca ccacagcgcc ctggtcgagt tggaaggcga  23040
caacgcgcgg ctggcggtgc tcaaacgcac ggtcgagctg acccatttcg cctacccggc  23100
tctgaacctg ccccccaaag tcatgagcgc ggtcatggac caggtgctca tcaagcgcgc  23160
gtcgcccatc tccgaggacg agggcatgca agactccgag gagggcaagc ccgtggtcag  23220
cgacgagcag ctggcccggt ggctgggtcc taatgctagt ccccagagtt tggaagagcg  23280
gcgcaaactc atgatggccg tggtcctggt gaccgtggag ctggagtgcc tgcgccgctt  23340
cttcgccgac gcggagaccc tgcgcaaggt cgaggagaac ctgcactacc tcttcaggca  23400
cgggttcgtg cgccaggcct gcaagatctc caacgtggag ctgaccaacc tggtctccta  23460
catgggcatc ttgcacgaga accgcctggg gcagaacgtg ctgcacacca ccctgcgcgg  23520
ggaggcccgg cgcgactaca tccgcgactg cgtctacctc tacctctgcc acacctggca  23580
gacgggcatg ggcgtgtggc agcagtgtct ggaggagcag aacctgaaag agctctgcaa  23640
```

```
gctcctgcag aagaacctca agggtctgtg gaccgggttc gacgagcgca ccaccgcctc  23700
ggacctggcc gacctcattt tccccgagcg cctcaggctg acgctgcgca acggcctgcc  23760
cgactttatg agccaaagca tgttgcaaaa ctttcgctct ttcatcctcg aacgctccgg  23820
aatcctgccc gccacctgct ccgcgctgcc ctcggacttc gtgccgctga ccttccgcga  23880
gtgccccccg ccgctgtgga gccactgcta cctgctgcgc ctggccaact acctggccta  23940
ccactcggac gtgatcgagg acgtcagcgg cgagggcctg ctcgagtgcc actgccgctg  24000
caacctctgc acgccgcacc gctccctggc ctgcaacccc cagctgctga gcgagaccca  24060
gatcatcggc accttcgagt tgcaagggcc cagcgaaggc gagggttcag ccgccaaggg  24120
gggtctgaaa ctcaccccgg ggctgtggac ctcggcctac ttgcgcaagt tcgtgcccga  24180
ggactaccat cccttcgaga tcaggttcta cgaggaccaa tcccatccgc ccaaggccga  24240
gctgtcggcc tgcgtcatca cccagggggc gatcctggcc caattgcaag ccatccagaa  24300
atcccgccaa gaattcttgc tgaaaaaggg ccgcggggtc tacctcgacc cccagaccgg  24360
tgaggagctc aaccccggct tcccccagga tgccccgagg aaacaagaag ctgaaagtgg  24420
agctgccgcc cgtggaggat ttggaggaag actgggagaa cagcagtcag gcagaggagg  24480
aggagatgga ggaagactgg gacagcactc aggcagagga ggacagcctg caagacagtc  24540
tggaggaaga cgaggaggag gcagaggagg aggtggaaga agcagccgcc gccagaccgt  24600
cgtcctcggc gggggagaaa gcaagcagca cggataccat ctccgctccg ggtcggggtc  24660
ccgctcgacc acacagtaga tgggacgaga ccggacgatt cccgaacccc accacccaga  24720
ccggtaagaa ggagcggcag ggatacaagt cctggcgggg gcacaaaaac gccatcgtct  24780
cctgcttgca ggcctgcggg ggcaacatct ccttcacccg gcgctacctg ctcttccacc  24840
gcggggtgaa ctttccccgc aacatcttgc attactaccg tcacctccac agcccctact  24900
acttccaaga agaggcagca gcagcagaaa aagaccagca gaaaaccagc agctagaaaa  24960
tccacagcgg cggcagcagg tggactgagg atcgcggcga acgagccggc gcaaacccgg  25020
gagctgagga accggatctt tcccaccctc tatgccatct tccagcagag tcgggggcag  25080
gagcaggaac tgaaagtcaa gaaccgttct ctgcgctcgc tcacccgcag ttgtctgtat  25140
cacaagagcg aagaccaact tcagcgcact ctcgaggacg ccgaggctct cttcaacaag  25200
tactgcgcgc tcactcttaa agagtagccc gcgcccgccc agtcgcagaa aaaggcggga  25260
attacgtcac ctgtgccctt cgccctagcc gcctccaccc atcatcatga gcaaagagat  25320
tcccacgcct tacatgtgga gctaccagcc ccagatgggc ctggccgccg gtgccgccca  25380
ggactactcc acccgcatga attggctcag cgccgggccc gcgatgatct cacgggtgaa  25440
tgacatccgc gcccaccgaa accagatact cctagaacag tcagcgctca ccgccacgcc  25500
ccgcaatcac ctcaatccgc gtaattggcc cgccgccctg gtgtaccagg aaattcccca  25560
gcccacgacc gtactacttc cgcgagacgc ccaggccgaa gtccagctga ctaactcagg  25620
tgtccagctg gcgggcggcg ccaccctgtg tcgtcaccgc cccgctcagg gtataaagcg  25680
gctggtgatc cggggcagag gcacacagct caacgacgag gtggtgagct cttcgctggg  25740
tctgcgacct gacggagtct tccaactcgc cggatcgggg agatcttcct tcacgcctcg  25800
tcaggccgtc ctgactttgg agagttcgtc ctcgcagccc cgctcgggtg gcatcggcac  25860
tctccagttc gtggaggagt tcactccctc ggtctacttc aacccctttct ccggctcccc  25920
cggccactac ccggacgagt tcatcccgaa cttcgacgcc atcagcgagt cggtggacgg  25980
```

```
ctacgattga aactaatcac ccccttatcc agtgaaataa agatcatatt gatgatgatt  26040
ttacagaaat aaaaaataat catttgattt gaaataaaga tacaatcata ttgatgattt  26100
gagtttaaca aaaaaataaa gaatcactta cttgaaatct gataccaggt ctctgtccat  26160
gttttctgcc aacaccactt cactcccctc ttcccagctc tggtactgca ggccccggcg  26220
ggctgcaaac ttcctccaca cgctgaaggg gatgtcaaat tcctcctgtc cctcaatctt  26280
cattttatct tctatcagat gtccaaaaag cgcgtccggg tggatgatga cttcgacccc  26340
gtctacccct acgatgcaga caacgcaccg accgtgccct tcatcaaccc ccccttcgtc  26400
tcttcagatg gattccaaga gaagcccctg gggtgttgt ccctgcgact ggccgacccc  26460
gtcaccacca agaacgggga aatcaccctc aagctgggag agggggtgga cctcgattcc  26520
tcgggaaaac tcatctccaa cacggccacc aaggccgccg cccctctcag tttttccaac  26580
aacaccattt cccttaacat ggatcacccc ttttacacta aagatggaaa attatcctta  26640
caagtttctc caccattaaa tatactgaga acaagcattc taaacacact agctttaggt  26700
tttggatcag gtttaggact ccgtggctct gccttggcag tacagttagt ctctccactt  26760
acatttgata ctgatggaaa cataaagctt accttagaca gaggtttgca tgttacaaca  26820
ggagatgcaa ttgaaagcaa cataagctgg gctaaaggtt taaaatttga agatggagcc  26880
atagcaacca acattggaaa tgggttagag tttggaagca gtagtacaga aacaggtgtt  26940
gatgatgctt acccaatcca agttaaactt ggatctggcc ttagctttga cagtacagga  27000
gccataatgg ctggtaacaa agaagacgat aaactcactt tgtggacaac acctgatcca  27060
tcaccaaact gtcaaatact cgcagaaaat gatgcaaaac taacactttg cttgactaaa  27120
tgtggtagtc aaatactggc cactgtgtca gtcttagttg taggaagtgg aaacctaaac  27180
cccattactg gcaccgtaag cagtgctcag gtgtttctac gttttgatgc aaacggtgtt  27240
cttttaacag aacattctac actaaaaaaa tactgggggt ataggcaggg agatagcata  27300
gatggcactc catataccaa tgctgtagga ttcatgccca atttaaaagc ttatccaaag  27360
tcacaaagtt ctactactaa aaataatata gtagggcaag tatacatgaa tggagatgtt  27420
tcaaaaccta tgcttctcac tataaccctc aatggtactg atgacagcaa cagtacatat  27480
tcaatgtcat tttcatacac ctggactaat ggaagctatg ttggagcaac atttggggct  27540
aactcttata ccttctcata catcgcccaa gaatgaacac tgtatcccac cctgcatgcc  27600
aacccttccc accccactct gtggaacaaa ctctgaaaca caaaataaaa taaagttcaa  27660
gtgttttatt gattcaacag ttttacagga ttcgagcagt tatttttcct ccaccctccc  27720
aggacatgga atacaccacc ctctcccccc gcacagcctt gaacatctga atgccattgg  27780
tgatggacat gcttttggtc tccacgttcc acacagtttc agagcgagcc agtctcgggt  27840
cggtcaggga gatgaaaccc tccgggcact cccgcatctg cacctcacag ctcaacagct  27900
gaggattgtc ctcggtggtc gggatcacgg ttatctggaa gaagcagaag agcggcggtg  27960
ggaatcatag tccgcgaacg ggatcggccg gtggtgtcgc atcaggcccc gcagcagtcg  28020
ctgccgccgc cgctccgtca agctgctgct caggggggtcc gggtccaggg actccctcag  28080
catgatgccc acggccctca gcatcagtcg tctggtgcgg cgggcgcagc agcgcatgcg  28140
gatctcgctc aggtcgctgc agtacgtgca acacagaacc accaggttgt tcaacagtcc  28200
atagttcaac acgctccagc cgaaactcat cgcgggaagg atgctaccca cgtggccgtc  28260
gtaccagatc ctcaggtaaa tcaagtggtg ccccctccag aacacgctgc ccacgtacat  28320
gatctccttg ggcatgtggc ggttcaccac ctcccggtac cacatcaccc tctggttgaa  28380
```

```
catgcagccc cggatgatcc tgcggaacca cagggccagc accgccccgc ccgccatgca  28440
gcgaagagac cccgggtccc ggcaatggca atggaggacc caccgctcgt acccgtggat  28500
catctgggag ctgaacaagt ctatgttggc acagcacagg catatgctca tgcatctctt  28560
cagcactctc aactcctcgg gggtcaaaac catatcccag ggcacgggga actcttgcag  28620
gacagcgaac cccgcagaac agggcaatcc tcgcacagaa cttacattgt gcatggacag  28680
ggtatcgcaa tcaggcagca ccgggtgatc ctccaccaga gaagcgcggg tctcggtctc  28740
ctcacagcgt ggtaaggggg ccggccgata cgggtgatgg cgggacgcgg ctgatcgtgt  28800
tcgcgaccgt gtcatgatgc agttgctttc ggacattttc gtacttgctg tagcagaacc  28860
tggtccgggc gctgcacacc gatcgccggc ggcggtctcg gcgcttggaa cgctcggtgt  28920
tgaaattgta aaacagccac tctctcagac cgtgcagcag atctagggcc tcaggagtga  28980
tgaagatccc atcatgcctg atggctctga tcacatcgac caccgtggaa tgggccagac  29040
ccagccagat gatgcaattt tgttgggttt cggtgacggc gggggaggga agaacaggaa  29100
gaaccatgat taacttttaa tccaaacggt ctcggagtac ttcaaaatga agatcgcgga  29160
gatggcacct ctcgccccgg ctgtgttggt ggaaaataac agccaggtca aaggtgatac  29220
ggttctcgag atgttccacg gtggcttcca gcaaagcctc cacgcgcaca tccagaaaca  29280
agacaatagc gaaagcggga gggttctcta attcctcaat catcatgtta cactcctgca  29340
ccatccccag ataattttca tttttccagc cttgaatgat tcgaactagt tcctgaggta  29400
aatccaagcc agccatgata aagagctcgc gcagagcgcc ctccaccggc attcttaagc  29460
acaccctcat aattccaaga tattctgctc ctggttcacc tgcagcagat tgacaagcgg  29520
aatatcaaaa tctctgccgc gatccctgag ctcctccctc agcaataact gtaagtactc  29580
tttcatatcc tctccgaaat ttttagccat aggaccacca ggaataagat tagggcaagc  29640
cacagtacag ataaaccgaa gtcctcccca gtgagcattg ccaaatgcaa gactgctata  29700
agcatgctgg ctagacccgg tgatatcttc cagataactg gacagaaaat cgcccaggca  29760
atttttaaga aaatcaacaa aagaaaaatc ctccaggtgg acgtttagag cctcgggaac  29820
aacgatgaag taaatgcaag cggtgcgttc cagcatggtt agttagctga tctgtagaaa  29880
aaacaaaaat gaacattaaa ccatgctagc ctggcgaaca ggtgggtaaa tcgttctctc  29940
cagcaccagg caggccacgg ggtctccggc gcgaccctcg taaaaattgt cgctatgatt  30000
gaaaaccatc acagagagac gttcccggtg gccggcgtga atgattcgac aagatgaata  30060
cacccccgga acattggcgt ccgcgagtga aaaaaagcgc ccgaggaagc aataaggcac  30120
tacaatgctc agtctcaagt ccagcaaagc gatgccatgc ggatgaagca caaaattctc  30180
aggtgcgtac aaaatgtaat tactcccctc ctgcacaggc agcaaagccc ccgatccctc  30240
caggtacaca tacaaagcct cagcgtccat agcttaccga gcagcagcac acaacaggcg  30300
caagagtcag agaaaggctg agctctaacc tgtccacccg ctctctgctc aatatatagc  30360
ccagatctac actgacgtaa aggccaaagt ctaaaaatac ccgccaaata atcacacacg  30420
cccagcacac gcccagaaac cggtgacaca ctcaaaaaaa tacgcgcact tcctcaaacg  30480
cccaaaactg ccgtcatttc cgggttccca cgctacgtca tcaaaacacg actttcaaat  30540
tccgtcgacc gttaaaaacg tcacccgccc cgcccctaac ggtcgcccgt ctctcagcca  30600
atcagcgccc cgcatcccca aattcaaaca cctcatttgc atattaacgc gcacaaaaag  30660
tttgaggtat attattgatg atgg                                         30684
```

<210> SEQ ID NO 14
<211> LENGTH: 8602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
```

```
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
```

```
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
```

```
tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga cccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gactctagaa tagtctttaa   7560

ttaaagtccg ccatatgagg ccaccatgca gatcttcgtg aagaccctga ccggcaagac   7620

catcacccta gaggtggagc ccagtgacac catcgagaac gtgaaggcca agatccagga   7680

taaagagggc atcccccctg accagcagag gctgatcttt gccggcaagc agctggaaga   7740

tggccgcacc ctctctgatt acaacatcca gaaggagtca accctgcacc tggtccttcg   7800

cctgagaggt ggcgctgctt acagtataat caactttgaa aaactggctg cttacggcat   7860

cctgggcttt gtgtttacac tggctgccta cctgctgttt ggctatcctg tgtacgtggc   7920

cgcttatgga ctgtgtaccc tggtggccat gctggctgct tacaatctgg tgcctatggt   7980

ggccacagtg gccgcctatt gtcttggcgg actgctgaca atggtggcag cctacagccc   8040

gagctatgcg tatcatcagt ttgcagccta cggcccagga ccaggcgcta aatttgtggc   8100

tgcctggaca ctgaaagccg ccgctggacc aggtcctgga cagtacatca aggccaacag   8160

caagttcatc ggcatcaccg aactcggccc aggaccaggc tatccctacg atgtgcctga   8220

ttacgcctga tagtgatgat tcgaacggcc gtatcacgcc caaacattta cagccgcggt   8280

gtcaaaaacc gcgtggacgt ggttaacatc cctgctggga ggatcagccg taattattat   8340

aattggcttg gtgctggcta ctattgtggc catgtacgtg ctgaccaacc agaaacataa   8400

ttgaatacag cagcaattgg caagctgctt acatagaact cgcggcgatt ggcatgccgc   8460

cttaaaattt ttattttatt ttttcttttc ttttccgaat cggattttgt ttttaatatt   8520

tcaaaaaaaa aaaaaaaaaa aaaaaaaaaa aaaaaaaaaa aaaaaaaaaa aaaaaaaaaa   8580

aaaaaaaaaa aaaaaaaaaa aa                                            8602
```

<210> SEQ ID NO 15
<211> LENGTH: 9595
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180
```

-continued

```
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
```

```
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
```

```
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
```

```
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gactctagaa tagtctttaa   7560
ttaaagtccg ccatatgaga tggaagatgc caaaaacatt aagaagggcc cagcgccatt   7620
ctacccactc gaagacggga ccgccggcga gcagctgcac aaagccatga agcgctacgc   7680
cctggtgccc ggcaccatcg cctttaccga cgcacatatc gaggtggaca ttacctacgc   7740
cgagtacttc gagatgagcg ttcggctggc agaagctatg aagcgctatg ggctgaatac   7800
aaaccatcgg atcgtggtgt gcagcgagaa tagcttgcag ttcttcatgc ccgtgttggg   7860
tgccctgttc atcggtgtgg ctgtggcccc agctaacgac atctacaacg agcgcgagct   7920
gctgaacagc atgggcatca gccagcccac cgtcgtattc gtgagcaaga aagggctgca   7980
aaagatcctc aacgtgcaaa agaagctacc gatcatacaa aagatcatca tcatggatag   8040
caagaccgac taccagggct tccaaagcat gtacaccttc gtgacttccc atttgccacc   8100
cggcttcaac gagtacgact tcgtgcccga gagcttcgac cgggacaaaa ccatcgccct   8160
gatcatgaac agtagtggca gtaccggatt gcccaagggc gtagccctac cgcaccgcac   8220
cgcttgtgtc cgattcagtc atgcccgcga ccccatcttc ggcaaccaga tcatccccga   8280
caccgctatc ctcagcgtgg tgccatttca ccacggcttc ggcatgttca ccacgctggg   8340
ctacttgatc tgcggctttc gggtcgtgct catgtaccgc ttcgaggagg agctattctt   8400
gcgcagcttg caagactata agattcaatc tgccctgctg gtgcccacac tatttagctt   8460
cttcgctaag agcactctca tcgacaagta cgacctaagc aacttgcacg agatcgccag   8520
cggcggggcg ccgctcagca aggaggtagg tgaggccgtg gccaaacgct tccacctacc   8580
aggcatccgc cagggctacg gcctgacaga aacaaccagc gccattctga tcacccccga   8640
aggggacgac aagcctggcg cagtaggcaa ggtggtgccc ttcttcgagg ctaaggtggt   8700
ggacttggac accggtaaga cactgggtgt gaaccagcgc ggcgagctgt gcgtccgtgg   8760
ccccatgatc atgagcggct acgttaacaa ccccgaggct acaaacgctc tcatcgacaa   8820
ggacggctgg ctgcacagcg gcgacatcgc ctactgggac gaggacgagc acttcttcat   8880
cgtggaccgg ctgaagagcc tgatcaaata caagggctac caggtagccc cagccgaact   8940
ggagagcatc ctgctgcaac accccaacat cttcgacgcc ggggtcgccg gcctgcccga   9000
cgacgatgcc ggcgagctgc ccgccgcagt cgtcgtgctg gaacacggta aaaccatgac   9060
cgagaaggag atcgtggact atgtggccag ccaggttaca accgccaaga agctgcgcgg   9120
tggtgttgtg ttcgtggacg aggtgcctaa aggactgacc ggcaagttgg acgcccgcaa   9180
gatccgcgag attctcatta aggccaagaa gggcggcaag atcgccgtgt aattcgaacg   9240
gccgtatcac gcccaaacat ttacagccgc ggtgtcaaaa accgcgtgga cgtggttaac   9300
atccctgctg ggaggatcag ccgtaattat tataattggc ttggtgctgg ctactattgt   9360
ggccatgtac gtgctgacca accagaaaca taattgaata cagcagcaat tggcaagctg   9420
cttacataga actcgcggcg attggcatgc cgccttaaaa tttttatttt atttttttctt   9480
ttcttttccg aatcggattt tgtttttaat atttcaaaaa aaaaaaaaaa aaaaaaaaaa   9540
aaaaaaaaaa aaaaaaaaaa aaaaaaaaaa aaaaaaaaaa aaaaaaaaaa aaaaa        9595
```

<210> SEQ ID NO 16

<211> LENGTH: 139
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
    50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135
```

<210> SEQ ID NO 17
<211> LENGTH: 167
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Thr Phe Ser Ser Tyr Gly Met His
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Ile Trp Tyr Asp Gly Ser Asn Lys Tyr Tyr Ala Asp Ser Val
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Pro Arg Gly Ala Thr Leu Tyr Tyr Tyr Tyr Tyr Gly Met Asp Val
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Gln Ser Ile Asn Ser Tyr Leu Asp
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ser Ser Leu Gln Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Gln Gln Tyr Tyr Ser Thr Pro Phe Thr
1               5
```

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120
```

<210> SEQ ID NO 26
<211> LENGTH: 5
<212> TYPE: PRT
<213> ORGANISM: Artificial Sequence
<220> FEATURE:

<223> OTHER INFORMATION: Description of Artificial Sequence: Synthetic peptide

<400> SEQUENCE: 26

Arg Tyr Trp Met Ser
1 5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Asn Ile Lys Gln Asp Gly Ser Glu Lys Tyr Tyr Val Asp Ser Val Lys
1 5 10 15

Gly

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Glu Gly Gly Trp Phe Gly Glu Leu Ala Phe Asp Tyr
1 5 10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Arg Ala Ser Gln Arg Val Ser Ser Ser Tyr Leu Ala
1 5 10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Asp Ala Ser Ser Arg Ala Thr
1 5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gln Gln Tyr Gly Ser Leu Pro Trp Thr
1 5

<210> SEQ ID NO 32
<211> LENGTH: 2019
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
gcccgggcat ttaaatgcga tcgcatcgat tacgactcta gaatagtcta gtccgcaggc     60
caccatgcag atcttcgtga agaccctgac cggcaagacc atcaccctag aggtggagcc    120
cagtgacacc atcgagaacg tgaaggccaa gatccaggat aaagagggca tcccccctga    180
ccagcagagg ctgatctttg ccggcaagca gctggaagat ggccgcaccc tctctgatta    240
caacatccag aaggagtcaa ccctgcacct ggtccttcgc ctgagaggtg ccatgtttca    300
ggcgctgagc gaaggctgca ccccgtatga tattaaccag atgctgaacg tgctgggcga    360
tcatcaggtc tcaggccttg agcagcttga gagtataatc aactttgaaa aactgactga    420
atggaccagt tctaatgtta tgcctatcct gtctcctctg acaaagggca tcctgggctt    480
cgtgtttacc ctgaccgtgc cttctgagag aggacttagc tgcattagcg aagcggatgc    540
gaccaccccg gaaagcgcga acctgggcga agaaattctg agccagctgt atctttggcc    600
aagggtgacc taccattccc ctagttatgc ttaccaccaa tttgaaagac gagccaaata    660
taaaagacac ttccccggct ttggccagag cctgctgttt ggctaccctg tgtacgtgtt    720
cggcgattgc gtgcagggcg attgggatgc gattcgcttt cgctattgcg cgccgccggg    780
ctatgcgctg ctgcgctgca acgataccaa ctatagcgct ctgctggctg tgggggccct    840
agaaggaccc aggaatcagg actggcttgg tgtcccaaga caacttgtaa ctcggatgca    900
ggctattcag aatgccggcc tgtgtaccct ggtggccatg ctggaagaga caatcttctg    960
gctgcaagcg tttctgatgg cgctgaccga tagcggcccg aaaaccaaca ttattgtgga   1020
tagccagtat gtgatgggca ttagcaaacc gagctttcag gaatttgtgg attgggaaaa   1080
cgtgagcccg gaactgaaca gcaccgatca gccgttttgg caagccggaa tcctggccag   1140
aaatctggtg cctatggtgg ccacagtgca gggccagaac ctgaagtacc agggtcagtc   1200
actagtcatc tctgcttcta tcattgtctt caacctgctg gaactggaag gtgattatcg   1260
agatgatggc aacgtgtggg tgcatacccc gctgagcccg cgcaccctga acgcgtgggt   1320
gaaagcggtg gaagaaaaaa aaggtattcc agttcaccta gagctggcca gtatgaccaa   1380
catggagctc atgagcagta ttgtgcatca gcaggtcaga acatacggcc ccgtgttcat   1440
gtgtctcggc ggactgctta caatggtggc tggtgctgtg tggctgacag tgcgagtgct   1500
cgagctgttc cgggccgcgc agctggccaa cgacgtggtc ctccagatca tggagctttg   1560
tggtgcagcg tttcgccagg tgtgccatac caccgtgccg tggccgaacg cgagcctgac   1620
cccgaaatgg aacaacgaaa ccacccagcc ccagatcgcc aactgcagcg tgtatgactt   1680
ttttgtgtgg ctccattatt attctgttcg agacacactt tggccaaggg tgacctacca   1740
tatgaacaaa tatgcgtatc atatgctgga aagacgagcc aaatataaaa gaggaccagg   1800
acctggcgct aaatttgtgg ccgcctggac actgaaagcc gctgctggtc ctggacctgg   1860
ccagtacatc aaggccaaca gcaagttcat cggcatcacc gaactcggac ccggaccagg   1920
ctgatgattt cgaaatttaa ataagcttgc ggccgctagg gataacaggg taattatcac   1980
gcccaaacat ttacagccgc ggtgtcaaaa accgcgtgg                          2019
```

<210> SEQ ID NO 33
<211> LENGTH: 619
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Met Phe Gln Ala
65                  70                  75                  80

Leu Ser Glu Gly Cys Thr Pro Tyr Asp Ile Asn Gln Met Leu Asn Val
                85                  90                  95

Leu Gly Asp His Gln Val Ser Gly Leu Glu Gln Leu Glu Ser Ile Ile
            100                 105                 110

Asn Phe Glu Lys Leu Thr Glu Trp Thr Ser Ser Asn Val Met Pro Ile
        115                 120                 125

Leu Ser Pro Leu Thr Lys Gly Ile Leu Gly Phe Val Phe Thr Leu Thr
    130                 135                 140

Val Pro Ser Glu Arg Gly Leu Ser Cys Ile Ser Glu Ala Asp Ala Thr
145                 150                 155                 160

Thr Pro Glu Ser Ala Asn Leu Gly Glu Glu Ile Leu Ser Gln Leu Tyr
                165                 170                 175

Leu Trp Pro Arg Val Thr Tyr His Ser Pro Ser Tyr Ala Tyr His Gln
            180                 185                 190

Phe Glu Arg Arg Ala Lys Tyr Lys Arg His Phe Pro Gly Phe Gly Gln
        195                 200                 205

Ser Leu Leu Phe Gly Tyr Pro Val Tyr Val Phe Gly Asp Cys Val Gln
    210                 215                 220

Gly Asp Trp Asp Ala Ile Arg Phe Arg Tyr Cys Ala Pro Pro Gly Tyr
225                 230                 235                 240

Ala Leu Leu Arg Cys Asn Asp Thr Asn Tyr Ser Ala Leu Leu Ala Val
                245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val

```
        355                 360                 365

Gln Gly Gln Asn Leu Lys Tyr Gln Gly Gln Ser Leu Val Ile Ser Ala
    370                 375                 380

Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510

Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540

Tyr Tyr Ser Val Arg Asp Thr Leu Trp Pro Arg Val Thr Tyr His Met
545                 550                 555                 560

Asn Lys Tyr Ala Tyr His Met Leu Glu Arg Arg Ala Lys Tyr Lys Arg
                565                 570                 575

Gly Pro Gly Pro Gly Ala Lys Phe Val Ala Ala Trp Thr Leu Lys Ala
            580                 585                 590

Ala Ala Gly Pro Gly Pro Gly Gln Tyr Ile Lys Ala Asn Ser Lys Phe
        595                 600                 605

Ile Gly Ile Thr Glu Leu Gly Pro Gly Pro Gly
    610                 615
```

<210> SEQ ID NO 34
<211> LENGTH: 1638
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atggccggga tgttccaggc actgtccgaa ggctgcacac cctatgatat taaccagatg      60

ctgaatgtcc tgggagacca ccaggtctct ggcctggagc agctggagag catcatcaac     120

ttcgagaagc tgaccgagtg gacaagctcc aatgtgatgc ctatcctgtc cccactgacc     180

aagggcatcc tgggcttcgt gtttaccctg acagtgcctt ctgagcgggg cctgtcttgc     240

atcagcgagg cagacgcaac cacaccagag tccgccaatc tgggcgagga gatcctgtct     300

cagctgtacc tgtggccccg ggtgacatat cactcccctt cttacgccta tcaccagttc     360

gagcggagag ccaagtacaa gagacacttc ccaggctttg gccagtctct gctgttcggc     420

taccccgtgt acgtgttcgg cgattgcgtg cagggcgact gggatgccat ccggtttaga     480

tactgcgcac cacctggata tgcactgctg aggtgtaacg acaccaatta ttccgccctg     540
```

```
ctggcagtgg gcgccctgga gggccctcgc aatcaggatt ggctgggcgt gccaaggcag    600

ctggtgacac gcatgcaggc catccagaac gcaggcctgt gcaccctggt ggcaatgctg    660

gaggagacaa tcttctggct gcaggccttt ctgatggccc tgaccgacag cggccccaag    720

acaaacatca tcgtggattc ccagtacgtg atgggcatct ccaagccttc tttccaggag    780

tttgtggact gggagaacgt gagcccagag ctgaattcca ccgatcagcc attctggcag    840

gcaggaatcc tggcaaggaa cctggtgcct atggtggcca cagtgcaggg ccagaatctg    900

aagtaccagg gccagagcct ggtcatcagc gcctccatca tcgtgtttaa cctgctggag    960

ctggagggcg actatcggga cgatggcaac gtgtgggtgc acacccccact gagccccaga   1020

acactgaacg cctgggtgaa ggccgtggag gagaagaagg gcatcccagt gcacctggag   1080

ctggcctcca tgaccaatat ggagctgatg tctagcatcg tgcaccagca ggtgaggaca   1140

tacggacccg tgttcatgtg cctgggaggc ctgctgacca tggtggcagg agccgtgtgg   1200

ctgacagtgc gggtgctgga gctgttcaga gccgcccagc tggccaacga tgtggtgctg   1260

cagatcatgg agctgtgcgg agcagccttt cgccaggtgt gccacaccac agtgccatgg   1320

cccaatgcct ccctgacccc caagtggaac aatgagacaa cacagcctca gatcgccaac   1380

tgtagcgtgt acgacttctt cgtgtggctg cactactata gcgtgaggga taccctgtgg   1440

ccccgcgtga cataccacat gaataagtac gcctatcaca tgctggagag gcgcgccaag   1500

tataagagag gccctggccc aggcgcaaag tttgtggcag catggaccct gaaggccgcc   1560

gccggccccg gccccggcca gtatatcaag gctaacagta agttcattgg aatcacagag   1620

ctgggacccg gacctgga                                                  1638
```

<210> SEQ ID NO 35
<211> LENGTH: 546
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Ala Gly Met Phe Gln Ala Leu Ser Glu Gly Cys Thr Pro Tyr Asp
1               5                   10                  15

Ile Asn Gln Met Leu Asn Val Leu Gly Asp His Gln Val Ser Gly Leu
            20                  25                  30

Glu Gln Leu Glu Ser Ile Ile Asn Phe Glu Lys Leu Thr Glu Trp Thr
        35                  40                  45

Ser Ser Asn Val Met Pro Ile Leu Ser Pro Leu Thr Lys Gly Ile Leu
    50                  55                  60

Gly Phe Val Phe Thr Leu Thr Val Pro Ser Glu Arg Gly Leu Ser Cys
65                  70                  75                  80

Ile Ser Glu Ala Asp Ala Thr Thr Pro Glu Ser Ala Asn Leu Gly Glu
                85                  90                  95

Glu Ile Leu Ser Gln Leu Tyr Leu Trp Pro Arg Val Thr Tyr His Ser
            100                 105                 110

Pro Ser Tyr Ala Tyr His Gln Phe Glu Arg Arg Ala Lys Tyr Lys Arg
        115                 120                 125

His Phe Pro Gly Phe Gly Gln Ser Leu Leu Phe Gly Tyr Pro Val Tyr
    130                 135                 140

Val Phe Gly Asp Cys Val Gln Gly Asp Trp Asp Ala Ile Arg Phe Arg
145                 150                 155                 160
```

```
Tyr Cys Ala Pro Pro Gly Tyr Ala Leu Leu Arg Cys Asn Asp Thr Asn
                165                 170                 175

Tyr Ser Ala Leu Leu Ala Val Gly Ala Leu Glu Gly Pro Arg Asn Gln
            180                 185                 190

Asp Trp Leu Gly Val Pro Arg Gln Leu Val Thr Arg Met Gln Ala Ile
        195                 200                 205

Gln Asn Ala Gly Leu Cys Thr Leu Val Ala Met Leu Glu Glu Thr Ile
    210                 215                 220

Phe Trp Leu Gln Ala Phe Leu Met Ala Leu Thr Asp Ser Gly Pro Lys
225                 230                 235                 240

Thr Asn Ile Ile Val Asp Ser Gln Tyr Val Met Gly Ile Ser Lys Pro
                245                 250                 255

Ser Phe Gln Glu Phe Val Asp Trp Glu Asn Val Ser Pro Glu Leu Asn
            260                 265                 270

Ser Thr Asp Gln Pro Phe Trp Gln Ala Gly Ile Leu Ala Arg Asn Leu
        275                 280                 285

Val Pro Met Val Ala Thr Val Gln Gly Gln Asn Leu Lys Tyr Gln Gly
    290                 295                 300

Gln Ser Leu Val Ile Ser Ala Ser Ile Ile Val Phe Asn Leu Leu Glu
305                 310                 315                 320

Leu Glu Gly Asp Tyr Arg Asp Asp Gly Asn Val Trp Val His Thr Pro
                325                 330                 335

Leu Ser Pro Arg Thr Leu Asn Ala Trp Val Lys Ala Val Glu Glu Lys
            340                 345                 350

Lys Gly Ile Pro Val His Leu Glu Leu Ala Ser Met Thr Asn Met Glu
        355                 360                 365

Leu Met Ser Ser Ile Val His Gln Gln Val Arg Thr Tyr Gly Pro Val
    370                 375                 380

Phe Met Cys Leu Gly Gly Leu Leu Thr Met Val Ala Gly Ala Val Trp
385                 390                 395                 400

Leu Thr Val Arg Val Leu Glu Leu Phe Arg Ala Ala Gln Leu Ala Asn
                405                 410                 415

Asp Val Val Leu Gln Ile Met Glu Leu Cys Gly Ala Ala Phe Arg Gln
            420                 425                 430

Val Cys His Thr Thr Val Pro Trp Pro Asn Ala Ser Leu Thr Pro Lys
        435                 440                 445

Trp Asn Asn Glu Thr Thr Gln Pro Gln Ile Ala Asn Cys Ser Val Tyr
    450                 455                 460

Asp Phe Phe Val Trp Leu His Tyr Tyr Ser Val Arg Asp Thr Leu Trp
465                 470                 475                 480

Pro Arg Val Thr Tyr His Met Asn Lys Tyr Ala Tyr His Met Leu Glu
                485                 490                 495

Arg Arg Ala Lys Tyr Lys Arg Gly Pro Gly Pro Gly Ala Lys Phe Val
            500                 505                 510

Ala Ala Trp Thr Leu Lys Ala Ala Ala Gly Pro Gly Pro Gly Gln Tyr
        515                 520                 525

Ile Lys Ala Asn Ser Lys Phe Ile Gly Ile Thr Glu Leu Gly Pro Gly
    530                 535                 540

Pro Gly
545
```

<210> SEQ ID NO 36
<211> LENGTH: 2019
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 36

gcccgggcat ttaaatgcga tcgcatcgat tacgactcta gaatagtcta gtccgcaggc     60

caccatgcag atcttcgtga agaccctgac cggcaagacc atcaccctag aggtggagcc    120

cagtgacacc atcgagaacg tgaaggccaa gatccaggat aaagagggca tcccccctga    180

ccagcagagg ctgatctttg ccggcaagca gctggaagat ggccgcaccc tctctgatta    240

caacatccag aaggagtcaa ccctgcacct ggtccttcgc ctgagaggtg ccatgtttca    300

ggcgctgagc gaaggctgca ccccgtatga tattaaccag atgctgaacg tgctgggcga    360

tcatcagttt aagcacatca aagcctttga ccggacattt gctaacaacc caggtcccat    420

ggttgtgttt gccacacctg ggcctatcct gtctcctctg acaaagggca tcctgggctt    480

cgtgtttacc ctgaccgtgc cttctgagag aggacttagc tgcattagcg aagcggatgc    540

gaccaccccg gaaagcgcga acctgggcga agaaattctg agccagctgt atctttggcc    600

aagggtgacc taccattccc ctagttatgc ttaccaccaa tttgaaagac gagccaaata    660

taaaagacac ttccccggct ttggccagag cctgctgttt ggctaccctg tgtacgtgtt    720

cggcgattgc gtgcagggcg attgggatgc gattcgcttt cgctattgcg cgccgccggg    780

ctatgcgctg ctgcgctgca acgataccaa ctatagcgct ctgctggctg tgggggccct    840

agaaggaccc aggaatcagg actggcttgg tgtcccaaga caacttgtaa ctcggatgca    900

ggctattcag aatgccggcc tgtgtaccct ggtggccatg ctggaagaga caatcttctg    960

gctgcaagcg tttctgatgg cgctgaccga tagcggcccg aaaaccaaca ttattgtgga   1020

tagccagtat gtgatgggca ttagcaaacc gagctttcag gaatttgtgg attgggaaaa   1080

cgtgagcccg gaactgaaca gcaccgatca gccgttttgg caagccggaa tcctggccag   1140

aaatctggtg cctatggtgg ccacagtgca gggccagaac ctgaagtacc agggtcagtc   1200

actagtcatc tctgcttcta tcattgtctt caacctgctg gaactggaag gtgattatcg   1260

agatgatggc aacgtgtggg tgcatacccc gctgagcccg cgcaccctga acgcgtgggt   1320

gaaagcggtg gaagaaaaaa aaggtattcc agttcaccta gagctggcca gtatgaccaa   1380

catggagctc atgagcagta ttgtgcatca gcaggtcaga acatacggcc ccgtgttcat   1440

gtgtctcggc ggactgctta caatggtggc tggtgctgtg tggctgacag tgcgagtgct   1500

cgagctgttc cgggccgcgc agctggccaa cgacgtggtc ctccagatca tggagctttg   1560

tggtgcagcg tttcgccagg tgtgccatac caccgtgccg tggccgaacg cgagcctgac   1620

cccgaaatgg aacaacgaaa ccacccagcc ccagatcgcc aactgcagcg tgtatgactt   1680

ttttgtgtgg ctccattatt attctgttcg agacacactt tggccaaggg tgacctacca   1740

tatgaacaaa tatgcgtatc atatgctgga aagacgagcc aaatataaaa gaggaccagg   1800

acctggcgct aaatttgtgg ccgcctggac actgaaagcc gctgctggtc ctggacctgg   1860

ccagtacatc aaggccaaca gcaagttcat cggcatcacc gaactcggac ccggaccagg   1920

ctgatgattt cgaaatttaa ataagcttgc ggccgctagg gataacaggg taattatcac   1980

gcccaaacat ttacagccgc ggtgtcaaaa accgcgtgg                           2019

<210> SEQ ID NO 37
<211> LENGTH: 619
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 37

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Met Phe Gln Ala
65                  70                  75                  80

Leu Ser Glu Gly Cys Thr Pro Tyr Asp Ile Asn Gln Met Leu Asn Val
                85                  90                  95

Leu Gly Asp His Gln Phe Lys His Ile Lys Ala Phe Asp Arg Thr Phe
            100                 105                 110

Ala Asn Asn Pro Gly Pro Met Val Val Phe Ala Thr Pro Gly Pro Ile
        115                 120                 125

Leu Ser Pro Leu Thr Lys Gly Ile Leu Gly Phe Val Phe Thr Leu Thr
    130                 135                 140

Val Pro Ser Glu Arg Gly Leu Ser Cys Ile Ser Glu Ala Asp Ala Thr
145                 150                 155                 160

Thr Pro Glu Ser Ala Asn Leu Gly Glu Glu Ile Leu Ser Gln Leu Tyr
                165                 170                 175

Leu Trp Pro Arg Val Thr Tyr His Ser Pro Ser Tyr Ala Tyr His Gln
            180                 185                 190

Phe Glu Arg Arg Ala Lys Tyr Lys Arg His Phe Pro Gly Phe Gly Gln
        195                 200                 205

Ser Leu Leu Phe Gly Tyr Pro Val Tyr Val Phe Gly Asp Cys Val Gln
    210                 215                 220

Gly Asp Trp Asp Ala Ile Arg Phe Arg Tyr Cys Ala Pro Pro Gly Tyr
225                 230                 235                 240

Ala Leu Leu Arg Cys Asn Asp Thr Asn Tyr Ser Ala Leu Leu Ala Val
                245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val
        355                 360                 365

Gln Gly Gln Asn Leu Lys Tyr Gln Gly Gln Ser Leu Val Ile Ser Ala
    370                 375                 380
```

```
Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510

Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540

Tyr Tyr Ser Val Arg Asp Thr Leu Trp Pro Arg Val Thr Tyr His Met
545                 550                 555                 560

Asn Lys Tyr Ala Tyr His Met Leu Glu Arg Arg Ala Lys Tyr Lys Arg
                565                 570                 575

Gly Pro Gly Pro Gly Ala Lys Phe Val Ala Ala Trp Thr Leu Lys Ala
            580                 585                 590

Ala Ala Gly Pro Gly Pro Gly Gln Tyr Ile Lys Ala Asn Ser Lys Phe
        595                 600                 605

Ile Gly Ile Thr Glu Leu Gly Pro Gly Pro Gly
    610                 615
```

<210> SEQ ID NO 38
<211> LENGTH: 228
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
atgcagatct tcgtgaagac cctgaccggc aagaccatca ccctagaggt ggagcccagt     60

gacaccatcg agaacgtgaa ggccaagatc caggataaag agggcatccc ccctgaccag    120

cagaggctga tctttgccgg caagcagctg gaagatggcc gcaccctctc tgattacaac    180

atccagaagg agtcaaccct gcacctggtc cttcgcctga gaggtggc                 228
```

<210> SEQ ID NO 39
<211> LENGTH: 228
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
atgcagatct tcgtgaagac cctgaccggc aagaccatca ccctagaggt ggagcccagt     60

gacaccatcg agaacgtgaa ggccaagatc caggataaag agggcatccc ccctgaccag    120
```

cagaggctga tctttgccgg caagcagctg gaagatggcc gcaccctctc tgattacaac 180
atccagaagg agtcaaccct gcacctggtc cttcgcctga gaggtgcc 228

<210> SEQ ID NO 40
<211> LENGTH: 78
<212> TYPE: DNA
<213> ORGANISM: Homo sapiens

<400> SEQUENCE: 40
atggccgtca tggcgccccg aaccctcgtc ctgctactct cgggggctct ggccctgacc 60
cagacctggg cgggctct 78

<210> SEQ ID NO 41
<211> LENGTH: 201
<212> TYPE: DNA
<213> ORGANISM: Homo sapiens

<400> SEQUENCE: 41
ccgtcttccc agcccaccat ccccatcgtg ggcatcattg ctggcctggt tctctttgga 60
gctgtgatca ctggagctgt ggtcgctgct gtgatgtgga ggaggaagag ctcagataga 120
aaaggaggga gctactctca ggctgcaagc agtgacagtg cccagggctc tgatgtgtct 180
ctcacagctt gtaaagtgtg a 201

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
atggagaccg atacactgct gctgtgggtg ctgctcctgt gggtgccagg aagcacaggc 60

<210> SEQ ID NO 43
<211> LENGTH: 3178
<212> TYPE: DNA
<213> ORGANISM: Homo sapiens

<400> SEQUENCE: 43
ggcaccgatt cggggcctgc ccggacttcg ccgcacgctg cagaacctcg cccagcgccc 60
accatgcccc ggcagctcag cgcggcggcc gcgctcttcg cgtccctggc cgtaattttg 120
cacgatggca gtcaaatgag agcaaaagca tttccagaaa ccagagatta ttctcaacct 180
actgcagcag caacagtaca ggacataaaa aaacctgtcc agcaaccagc taagcaagca 240
cctcaccaaa ctttagcagc aagattcatg gatggtcata tcacctttca aacagcggcc 300
acagtaaaaa ttccaacaac taccccagca actacaaaaa acactgcaac caccagccca 360
attacctaca ccctggtcac aacccaggcc acacccaaca actcacacac agctcctcca 420
gttactgaag ttacagtcgg ccctagctta gccccttatt cactgccacc caccatcacc 480
ccaccagctc atacagctgg aaccagttca tcaaccgtca gccacacaac tgggaacacc 540
actcaaccca gtaaccagac cacccttcca gcaactttat cgatagcact gcacaaaagc 600
acaaccggtc agaagcctga tcaacccacc catgccccag gaacaacggc agctgcccac 660
aataccaccc gcacagctgc acctgcctcc acggttcctg ggcccaccct tgcacctcag 720
ccatcgtcag tcaagactgg aatttatcag gttctaaacg gaagcagact ctgtataaaa 780

```
gcagagatgg ggatacagct gattgttcaa gacaaggagt cggtttttc acctcggaga    840
tacttcaaca tcgaccccaa cgcaacgcaa gcctctggga actgtggcac ccgaaaatcc    900
aaccttctgt tgaattttca gggcggattt gtgaatctca catttaccaa ggatgaagaa    960
tcatattata tcagtgaagt gggagcctat ttgaccgtct cagatccaga gacagtttac   1020
caaggaatca aacatgcggt ggtgatgttc cagacagcag tcgggcattc cttcaagtgc   1080
gtgagtgaac agagcctcca gttgtcagcc cacctgcagg tgaaaacaac cgatgtccaa   1140
cttcaagcct ttgattttga agatgaccac tttggaaatg tggatgagtg ctcgtctgac   1200
tacacaattg tgcttcctgt gattggggcc atcgtggttg gtctctgcct tatgggtatg   1260
ggtgtctata aaatccgcct aaggtgtcaa tcatctggat accagagaat ctaattgttg   1320
cccgggggga atgaaaataa tggaatttag agaactcttt catcccttcc aggatggatg   1380
ttgggaaatt ccctcagagt gtgggtcctt caaacaatgt aaaccaccat cttctattca   1440
aatgaagtga gtcatgtgtg atttaagttc aggcagcaca tcaatttcta aatacttttt   1500
gtttatttta tgaaagatat agtgagctgt ttattttcta gtttccttta gaatatttta   1560
gccactcaaa gtcaacattt gagatatgtt gaattaacat aatatatgta aagtagaata   1620
agccttcaaa ttataaacca agggtcaatt gtaactaata ctactgtgtg tgcattgaag   1680
attttatttt acccttgatc ttaacaaagc ctttgctttg ttatcaaatg gactttcagt   1740
gcttttacta tctgtgtttt atggtttcat gtaacataca tattcctggt gtagcactta   1800
actccttttc cactttaaat ttgtttttgt tttttgagac ggagtttcac tcttgtcacc   1860
caggctggag tacagtggca cgatctcggc ttatggcaac ctccgcctcc cgggttcaag   1920
tgattctcct gcttcagctt cccgagtagc tgggattaca ggcacacact accacgcctg   1980
gctaattttt gtatttttat tatagacggg tttcaccatg ttggccagac tggtcttgaa   2040
ctcttgacct caggtgatcc acccacctca gcctcccaaa gtgctgggat tacaggcatg   2100
agccattgcg cccggcctta aatgtttttt ttaatcatca aaaagaacaa catatctcag   2160
gttgtctaag tgtttttatg taaaaccaac aaaaagaaca aatcagctta tattttttat   2220
cttgatgact cctgctccag aattgctaga ctaagaatta ggtggctaca gatggtagaa   2280
ctaaacaata agcaagagac aataataatg gcccttaatt attaacaaag tgccagagtc   2340
taggctaagc actttatcta tatctcattt cattctcaca acttataagt gaatgagtaa   2400
actgagactt aagggaactg aatcacttaa atgtcacctg gctaactgat ggcagagcca   2460
gagcttgaat tcatgttggt ctgacatcaa ggtctttggt cttctcccta caccaagtta   2520
cctacaagaa caatgacacc acactctgcc tgaaggctca cacctcatac cagcatacgc   2580
tcaccttaca gggaaatggg tttatccagg atcatgagac attagggtag atgaaaggag   2640
agctttgcag ataacaaaat agcctatcct taataaatcc tccactctct ggaaggagac   2700
tgaggggctt tgtaaaacat tagtcagttg ctcattttta tgggattgct tagctgggct   2760
gtaaagatga aggcatcaaa taaactcaaa gtatttttaa attttttga taatagagaa   2820
acttcgctaa ccaactgttc tttcttgagt gtatagcccc atcttgtggt aacttgctgc   2880
ttctgcactt catatccata tttcctattg ttcactttat tctgtagagc agcctgccaa   2940
gaattttatt tctgctgttt tttttgctgc taaagaaagg aactaagtca ggatgttaac   3000
agaaaagtcc acataaccct agaattctta gtcaaggaat aattcaagtc agcctagaga   3060
ccatgttgac tttcctcatg tgtttcctta tgactcagta agttggcaag gtcctgactt   3120
tagtcttaat aaaacattga attgtagtaa aggtttttgc aataaaaact tactttgg     3178
```

<210> SEQ ID NO 44
<211> LENGTH: 1858
<212> TYPE: DNA
<213> ORGANISM: Mus sp.

<400> SEQUENCE: 44

```
attccggagg tgaaaaacaa tggcacaacg tgtataatgg ccagcttctc tgcctccttt     60
ctgaccacct acgagactgc gaatggttct cagatcgtga acatttccct gccagcctct    120
gcagaagtac tgaaaaatgg cagttcttgt ggtaaagaaa atgtttctga ccccagcctc    180
acaattactt ttggaagagg atatttactg acactcaact tcacaaaaaa tacaacacgt    240
tacagtgtcc agcatatgta ttttacatat aacttgtcag atacagaaca ttttcccaat    300
gccatcagca aagagatcta caccatggat tccacaactg acatcaaggc agacatcaac    360
aaagcatacc ggtgtgtcag tgatatccgg gtctacatga agaatgtgac cgttgtgctc    420
cgggatgcca ctatccaggc ctacctgtcg agtggcaact tcagcaagga agagacacac    480
tgcacacagg atggaccttc ccccaaccact gggccaccca gcccctcacc accacttgtg    540
cccacaaacc ccactgtatc caagtacaat gttactggta acaacggaac ctgcctgctg    600
gcctctatgg cactgcaact gaatatcacc tacctgaaaa aggacaacaa gacggtgacc    660
agagcgttca acatcagccc aaatgacaca tctagtggga gttgcggtat caacttggtg    720
accctgaaag tggagaacaa gaacagagcc ctggaattgc agtttgggat gaatgccagc    780
tctagcctgt tttcttgca aggagtgcgc ttgaatatga ctcttcctga tgccctagtg    840
cccacattca gcatctccaa ccattcactg aaagctcttc aggccactgt gggaaactca    900
tacaagtgca acactgagga acacatcttt gtcagcaaga tgctctccct caatgtcttc    960
agtgtgcagg tccaggcttt caaggtggac agtgacaggt ttgggtctgt ggaagagtgt   1020
gttcaggatg gtaacaacat gttgatcccc attgctgtgg gcggtgccct ggcagggctg   1080
atcctcatcg tcctcattgc ctacctcatt ggcaggaaga ggagtcacgc cggctatcag   1140
accatctagc ctggtgggca ggtgcaccag agatgcacag ggcctgttc tcacatcccc   1200
aagcttagat aggtgtggaa gggaggcaca ctttctggca aactgtttta aaatctgctt   1260
tatcaaatgt gaagttcatc ttgcaacatt tactatgcac aaaggaataa ctattgaaat   1320
gacggtgtta attttgctaa ctgggttaaa tattgatgag aaggctccac tgatttgact   1380
tttaagactt ggtgtttggt tcttcattct tttactcaga tttaagccta tcaaagggat   1440
actctggtcc agaccttggc ctggcaaggg tggctgatgg ttaggctgca cacacttaag   1500
aagcaacggg agcagggaag gcttgcacac aggcacgcac agggtcaacc tctggacact   1560
tggcttgggc tacctggcct tggggggct gaactctggc atctggctgg gtacacaccc   1620
ccccaatttc tgtgctctgc cacccgtgag ctgccacttt cctaaataga aaatggcatt   1680
atttttattt acttttttgt aaagtgattt ccagtcttgt gttggcgttc agggtggccc   1740
tgtctctgca ctgtgtacaa taatagattc acactgctga cgtgtcttgc agcgtaggtg   1800
ggttgtacac tgggcatcag ctcacgtaat gcattgcctg taacgatgct aataaaaa     1858
```

<210> SEQ ID NO 45
<211> LENGTH: 2339
<212> TYPE: DNA
<213> ORGANISM: Homo sapiens

<400> SEQUENCE: 45

-continued

```
ggcccaaccg ccgcccgcgc ccccgctctc cgcaccgtac ccggccgcct cgcgccatgg     60
cggcccccgg cagcgcccgg cgacccctgc tgctgctact gctgttgctg ctgctcggcc    120
tcatgcattg tgcgtcagca gcaatgttta tggtgaaaaa tggcaacggg accgcgtgca    180
taatggccaa cttctctgct gccttctcag tgaactacga caccaagagt ggccctaaga    240
acatgacctt tgacctgcca tcagatgcca cagtggtgct caaccgcagc tcctgtggaa    300
aagagaacac ttctgacccc agtctcgtga ttgcttttgg aagaggacat acactcactc    360
tcaatttcac gagaaatgca acacgttaca gcgtccagct catgagtttt gtttataact    420
tgtcagacac acaccttttc cccaatgcga gctccaaaga aatcaagact gtggaatcta    480
taactgacat cagggcagat atagataaaa aatacagatg tgttagtggc acccaggtcc    540
acatgaacaa cgtgaccgta acgctccatg atgccaccat ccaggcgtac ctttccaaca    600
gcagcttcag caggggagag acacgctgtg aacaagacag gccttcccca accacagcgc    660
cccctgcgcc acccagcccc tcgccctcac ccgtgcccaa gagcccctct gtggacaagt    720
acaacgtgag cggcaccaac gggacctgcc tgctggccag catggggctg cagctgaacc    780
tcacctatga gaggaaggac aacacgacgg tgacaaggct tctcaacatc aaccccaaca    840
agacctcggc cagcgggagc tgcggcgccc acctggtgac tctggagctg cacagcgagg    900
gcaccaccgt cctgctcttc cagttcggga tgaatgcaag ttctagccgg tttttcctac    960
aaggaatcca gttgaataca attcttcctg acgccagaga ccctgccttt aaagctgcca   1020
acggctccct gcgagcgctg caggccacag tcggcaattc ctacaagtgc aacgcggagg   1080
agcacgtccg tgtcacgaag gcgttttcag tcaatatatt caaagtgtgg gtccaggctt   1140
tcaaggtgga aggtggccag tttggctctg tggaggagtg tctgctggac gagaacagca   1200
tgctgatccc catcgctgtg ggtggtgccc tggcggggct ggtcctcatc gtcctcatcg   1260
cctacctcgt cggcaggaag aggagtcacg caggctacca gactatctag cctggtgcac   1320
gcaggcacag cagctgcagg ggcctctgtt cctttctctg ggcttagggt cctgtcgaag   1380
gggaggcaca ctttctggca aacgtttctc aaatctgctt catccaatgt gaagttcatc   1440
ttgcagcatt tactatgcac aacagagtaa ctatcgaaat gacggtgtta attttgctaa   1500
ctgggttaaa tattttgcta actggttaaa cattaatatt taccaaagta ggattttgag   1560
ggtgggggtg ctctctctga gggggtgggg gtgccgctgt ctctgagggg tgggggtgcc   1620
gctgtctctg aggggtgggg gtgccgctct ctctgagggg gtgggggtgc cgctttctct   1680
gagggggtgg gggtgccgct ctctctgagg gggtgggggt gctgctctct ccgaggggtg   1740
gaatgccgct gtctctgagg ggtgggggtg ccgctctaaa ttggctccat atcatttgag   1800
tttagggttc tggtgtttgg tttcttcatt ctttactgca ctcagattta agccttacaa   1860
agggaaagcc tctggccgtc acacgtagga cgcatgaagg tcactcgtgg tgaggctgac   1920
atgctcacac attacaacag tagagaggga aaatcctaag acagaggaac tccagagatg   1980
agtgtctgga gcgcttcagt tcagctttaa aggccaggac gggccacacg tggctggcgg   2040
cctcgttcca gtggcggcac gtccttgggc gtctctaatg tctgcagctc aagggctggc   2100
actttttaa atataaaaat gggtgttatt tttattttt tttgtaaagt gatttttggt     2160
cttctgttga cattcggggt gatcctgttc tgcgctgtgt acaatgtgag atcggtgcgt   2220
tctcctgatg ttttgccgtg gcttggggat tgtacacggg accagctcac gtaatgcatt   2280
gcctgtaaca atgtaataaa aagcctcttt cttttaaaaa aaaaaaaaaa aaaaaaaaa    2339
```

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
cagtacatca aggccaacag caagttcatc ggcatcaccg aactc 45

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Gln Tyr Ile Lys Ala Asn Ser Lys Phe Ile Gly Ile Thr Glu Leu
1 5 10 15

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gctaaatttg tggctgcctg gacactgaaa gccgccgct 39

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Ala Lys Phe Val Ala Ala Trp Thr Leu Lys Ala Ala Ala
1 5 10

<210> SEQ ID NO 50
<211> LENGTH: 593
<212> TYPE: DNA
<213> ORGANISM: Woodchuck hepatitis virus

<400> SEQUENCE: 50
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaagctga cgtcctttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tgt 593

<210> SEQ ID NO 51
<211> LENGTH: 589
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51
tctccccccc ccccctctcc ctcccccccc cctaacgtta ctggccgaag ccgcttggaa 60
taaggccggt gtgcgtttgt ctatatgtta ttttccacca tattgccgtc ttttggcaat 120
gtgagggccc ggaaacctgg ccctgtcttc ttgacgagca ttcctagggg tctttcccct 180
ctcgccaaag gaatgcaagg tctgttgaat gtcgtgaagg aagcagttcc tctggaagct 240
tcttgaagac aaacaacgtc tgtagcgacc ctttgcaggc agcggaaccc cccacctggc 300
gacaggtgcc tctgcggcca aaagccacgt gtataagata cacctgcaaa ggcggcacaa 360
ccccagtgcc acgttgtgag ttggatagtt gtggaaagag tcaaatggct ctcctcaagc 420
gtattcaaca aggggctgaa ggatgcccag aaggtacccc attgtatggg atctgatctg 480
gggcctcggt gcacatgctt tacatgtgtt tagtcgaggt taaaaaaacg tctaggcccc 540
ccgaaccacg gggacgtggt ttcctttga aaaacacgat gataatatg 589

<210> SEQ ID NO 52
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtag 720

<210> SEQ ID NO 53
<211> LENGTH: 1563
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
atgctgctgc tgctgctgct gctgggcctg aggctacagc tctccctggg catcatccca     60

gttgaggagg agaacccgga cttctggaac cgcgaggcag ccgaggccct gggtgccgcc    120

aagaagctgc agcctgcaca gacagccgcc aagaacctca tcatcttcct gggcgatggg    180

atgggggtgt ctacggtgac agctgccagg atcctaaaag ggcagaagaa ggacaaactg    240

gggcctgaga taccccctggc catggaccgc ttcccatatg tggctctgtc caagacatac    300

aatgtagaca aacatgtgcc agacagtgga gccacagcca cggcctacct gtgcggggtc    360

aagggcaact tccagaccat tggcttgagt gcagccgccc gctttaacca gtgcaacacg    420

acacgcggca acgaggtcat ctccgtgatg aatcgggcca agaaagcagg gaagtcagtg    480

ggagtggtaa ccaccacacg agtgcagcac gcctcgccag ccggcaccta cgcccacacg    540

gtgaaccgca actggtactc ggacgccgac gtgcctgcct cggcccgcca ggaggggtgc    600

caggacatcg ctacgcagct catctccaac atggacattg acgtgatcct aggtggaggc    660

cgaaagtaca tgtttcgcat gggaacccca gaccctgagt acccagatga ctacagccaa    720

ggtgggacca ggctggacgg gaagaatctg gtgcaggaat ggctggcgaa gcgccagggt    780

gcccggtatg tgtggaaccg cactgagctc atgcaggctt ccctggaccc gtctgtgacc    840

catctcatgg gtctctttga gcctggagac atgaaatacg agatccaccg agactccaca    900

ctggacccct ccctgatgga gatgacagag gctgccctgc gcctgctgag caggaacccc    960

cgcggcttct tcctcttcgt ggagggtggt cgcatcgacc atggtcatca tgaaagcagg   1020

gcttaccggg cactgactga gacgatcatg ttcgacgacg ccattgagag ggcgggccag   1080

ctcaccagcg aggaggacac gctgagcctc gtcactgccg accactccca cgtcttctcc   1140

ttcggaggct acccccctgcg agggagctcc atcttcgggc tggcccctgg caaggcccgg   1200

gacaggaagg cctacacggt cctcctatac ggaaacggtc caggctatgt gctcaaggac   1260

ggcgcccggc cggatgttac cgagagcgag agcgggagcc ccgagtatcg gcagcagtca   1320

gcagtgcccc tggacgaaga gacccacgca ggcgaggacg tggcggtgtt cgcgcgcggc   1380

ccgcaggcgc acctggttca cggcgtgcag gagcagacct tcatagcgca cgtcatggcc   1440

ttcgccgcct gcctggagcc ctacaccgcc tgcgacctgg cgccccccgc cggcaccacc   1500

gacgccgcgc acccgggtta ctctagagtc ggggcggccg gccgcttcga gcagacatga   1560

taa                                                                1563
```

<210> SEQ ID NO 54
<211> LENGTH: 1653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atggaagatg ccaaaaacat taagaagggc ccagcgccat tctacccact cgaagacggg     60

accgccggcg agcagctgca caaagccatg aagcgctacg ccctggtgcc cggcaccatc    120

gcctttaccg acgcacatat cgaggtggac attacctacg ccgagtactt cgagatgagc    180

gttcggctgg cagaagctat gaagcgctat gggctgaata caaaccatcg gatcgtggtg    240

tgcagcgaga atagcttgca gttcttcatg cccgtgttgg gtgccctgtt catcggtgtg    300

gctgtggccc cagctaacga catctacaac gagcgcgagc tgctgaacag catgggcatc    360

agccagccca ccgtcgtatt cgtgagcaag aaagggctgc aaaagatcct caacgtgcaa    420
```

```
aagaagctac cgatcataca aaagatcatc atcatggata gcaagaccga ctaccagggc    480

ttccaaagca tgtacacctt cgtgacttcc catttgccac ccggcttcaa cgagtacgac    540

ttcgtgcccg agagcttcga ccgggacaaa accatcgccc tgatcatgaa cagtagtggc    600

agtaccggat tgcccaaggg cgtagcccta ccgcaccgca ccgcttgtgt ccgattcagt    660

catgcccgcg accccatctt cggcaaccag atcatccccg acaccgctat cctcagcgtg    720

gtgccatttc accacggctt cggcatgttc accacgctgg gctacttgat ctgcggcttt    780

cgggtcgtgc tcatgtaccg cttcgaggag gagctattct tgcgcagctt gcaagactat    840

aagattcaat ctgccctgct ggtgcccaca ctatttagct tcttcgctaa gagcactctc    900

atcgacaagt acgacctaag caacttgcac gagatcgcca gcggcggggc gccgctcagc    960

aaggaggtag gtgaggccgt ggccaaacgc ttccacctac caggcatccg ccagggctac   1020

ggcctgacag aaacaaccag cgccattctg atcacccccg aaggggacga caagcctggc   1080

gcagtaggca aggtggtgcc cttcttcgag gctaaggtgg tggacttgga caccggtaag   1140

acactgggtg tgaaccagcg cggcgagctg tgcgtccgtg gccccatgat catgagcggc   1200

tacgttaaca accccgaggc tacaaacgct ctcatcgaca aggacggctg gctgcacagc   1260

ggcgacatcg cctactggga cgaggacgag cacttcttca tcgtggaccg gctgaagagc   1320

ctgatcaaat acaagggcta ccaggtagcc ccagccgaac tggagagcat cctgctgcaa   1380

caccccaaca tcttcgacgc cggggtcgcc ggcctgcccg acgacgatgc cggcgagctg   1440

cccgccgcag tcgtcgtgct ggaacacggt aaaaccatga ccgagaagga gatcgtggac   1500

tatgtggcca gccaggttac aaccgccaag aagctgcgcg gtggtgttgt gttcgtggac   1560

gaggtgccta aaggactgac cggcaagttg gacgcccgca agatccgcga gattctcatt   1620

aaggccaaga agggcggcaa gatcgccgtg taa                                1653
```

<210> SEQ ID NO 55
<211> LENGTH: 66
<212> TYPE: DNA
<213> ORGANISM: Foot-and-mouth disease virus

<400> SEQUENCE: 55

```
gtaaagcaaa cactgaactt tgaccttctc aagttggctg gagacgttga gtccaatcct     60

gggccc                                                                66
```

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

```
Gly Pro Gly Pro Gly
1               5
```

MODIFIED ADENOVIRUSES

CROSS REFERENCE TO RELATED APPLICATIONS

This application is a continuation of International Application No. PCT/US2020/035591 filed Jun. 1, 2020, which application claims the benefit of U.S. Provisional Application No. 62/854,865 filed May 30, 2019, each of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Sep. 13, 2022, is named GSO-033WOC1 SL.txt and is 820,385 bytes in size.

BACKGROUND

Therapeutic vaccines based on tumor-specific antigens hold great promise as a next-generation of personalized cancer immunotherapy. [1-3] For example, cancers with a high mutational burden, such as non-small cell lung cancer (NSCLC) and melanoma, are particularly attractive targets of such therapy given the relatively greater likelihood of neoantigen generation. [4,5] Early evidence shows that neoantigen-based vaccination can elicit T-cell responses[6] and that neoantigen targeted cell-therapy can cause tumor regression under certain circumstances in selected patients.[7]

One question for antigen vaccine design in both cancer and infectious disease settings is which of the many coding mutations present generate the “best” therapeutic antigens, e.g., antigens that can elicit immunity.

In addition to the challenges of current antigen prediction methods certain challenges also exist with the available vector systems that can be used for antigen delivery in humans, many of which are derived from humans. For example, many humans have pre-existing immunity to human viruses as a result of previous natural exposure, and this immunity can be a major obstacle to the use of recombinant human viruses for antigen delivery in vaccination strategies, such as in cancer treatment or vaccinations against infectious diseases. While some progress has been made in vaccinations strategies addressing the above problems, improvements are still needed, particularly for clinical applications, such as improved vaccine potency and efficacy.

SUMMARY

An adenovirus vector comprising: an adenoviral backbone comprising one or more genes or regulatory sequences of an adenovirus genome, and wherein the adenoviral backbone comprises a partially deleted E4 gene with reference to the adenovirus genome, wherein the partially deleted E4 gene comprises a deleted or partially-deleted E4orf2 region and a deleted or partially-deleted E4orf3 region, and optionally a deleted or partially-deleted E4orf4 region, and optionally, wherein the adenovirus vector further comprises a cassette, the cassette comprising: (1) at least one payload nucleic acid sequence, optionally wherein the at least one payload nucleic acid sequence encodes a polypeptide, optionally wherein the polypeptide comprises an antigen, optionally wherein the antigen comprises: a MHC class I epitope, a MHC class II epitope, an epitope capable of stimulating a B cell response, or a combination thereof, and optionally wherein the at least one payload nucleic acid sequence further comprises a 5' linker sequence and/or a 3' linker sequence, and optionally wherein; (2) at least one promoter sequence operably linked to the at least one payload nucleic acid sequence, (3) optionally, at least one universal MHC class II antigen-encoding nucleic acid sequence; (4) optionally, at least one GPGPG-encoding linker sequence (SEQ ID NO:56); and (5) optionally, at least one polyadenylation sequence.

Also disclosed herein is a chimpanzee adenovirus vector comprising a modified ChAdV68 sequence, wherein the modified ChAdV68 sequence comprises: (a) a partially deleted E4 gene of the E4 gene sequence shown in SEQ ID NO:1 and that lacks at least nucleotides 34,916 to 35,642 of the sequence shown in SEQ ID NO:1; and (b) one or more genes or regulatory sequences of the ChAdV68 sequence shown in SEQ ID NO: 1, optionally wherein the one or more genes or regulatory sequences comprise at least one of the chimpanzee adenovirus inverted terminal repeat (ITR), E1A, E1B, E2A, E2B, E3, E4, L1, L2, L3, L4, and L5 genes of the sequence shown in SEQ ID NO: 1; and optionally, wherein the chimpanzee adenovirus vector further comprises a cassette, wherein the cassette comprises at least one payload nucleic acid sequence, and wherein the cassette comprises at least one promoter sequence operably linked to the at least one payload nucleic acid sequence.

Also disclosed herein is a chimpanzee adenovirus vector comprising a modified ChAdV68 sequence, wherein the modified ChAdV68 sequence comprises: (a) a partially deleted E4 gene of the E4 gene sequence shown in SEQ ID NO:1 and that lacks at least nucleotides 34,916 to 35,642 of the sequence shown in SEQ ID NO:1; (b) nucleotides 2 to 34,916 of the sequence shown in SEQ ID NO:1, wherein the partially deleted E4 gene is 3' of the nucleotides 2 to 34,916, and optionally the nucleotides 2 to 34,916 additionally lack nucleotides 577 to 3403 of the sequence shown in SEQ ID NO:1 corresponding to an E1 deletion and/or lack nucleotides 27,125 to 31,825 of the sequence shown in SEQ ID NO:1 corresponding to an E3 deletion; and (c) nucleotides 35,643 to 36,518 of the sequence shown in SEQ ID NO:1, and wherein the partially deleted E4 gene is 5' of the nucleotides 35,643 to 36,518, and optionally, wherein the chimpanzee adenovirus vector further comprises a cassette, wherein the cassette comprises at least one payload nucleic acid sequence, and wherein the cassette comprises at least one promoter sequence operably linked to the at least one payload nucleic acid sequence.

Also disclosed herein is a chimpanzee adenovirus vector comprising: a. a modified ChAdV68 sequence, wherein the modified ChAdV68 sequence comprises: (i) a partially deleted E4 gene of the E4 gene sequence shown in SEQ ID NO:1 and that lacks at least nucleotides 34,916 to 35,642 of the sequence shown in SEQ ID NO:1; (ii) nucleotides 2 to 34,916 of the sequence shown in SEQ ID NO:1, wherein the partially deleted E4 gene is 3' of the nucleotides 2 to 34,916, and optionally the nucleotides 2 to 34,916 additionally lack nucleotides 577 to 3403 of the sequence shown in SEQ ID NO:1 corresponding to an E1 deletion and/or lack nucleotides 27,125 to 31,825 of the sequence shown in SEQ ID NO:1 corresponding to an E3 deletion; and (iii) and nucleotides 35,643 to 36,518 of the sequence shown in SEQ ID NO:1, and wherein the partially deleted E4 gene is 5' of the nucleotides 35,643 to 36,518, and; b. a CMV-derived promoter sequence; c. an SV40 polyadenylation signal nucleotide sequence; and d. a cassette, the cassette comprising at least one at least one payload nucleic acid sequence encoding: at least one MHC class I epitope, optionally wherein the at least one MHC class I epitope comprises at least 2 distinct MHC class I epitopes linearly linked to each other and each optionally comprising: (A) at least one alteration that makes the encoded peptide sequence distinct from the corresponding peptide sequence encoded by a wild-type nucleic acid sequence, wherein the distinct MHC I epitope is 7-15 amino acids in length, (B) an N-terminal linker comprising a native N-terminal amino acid sequence of the distinct MHC I epitope that is at least 3 amino acids in length, (C) an C-terminal linker comprising a native C-terminal acid sequence of the distinct MHC I epitope that is at least 3 amino acids in length, or (D) combinations thereof, at least one MHC class II epitope, optionally wherein the at least one MHC class II epitope comprises at least 2 distinct MHC class II epitopes, at least one an epitope capable of stimulating a B cell response, or combinations thereof, and wherein the cassette is inserted within a deleted region of ChAdV68 and the CMV-derived promoter sequence is operably linked to the cassette.

Also disclosed herein is a method for stimulating an immune response in a subject, the method comprising administering to the subject an adenovirus vector comprising: an adenoviral backbone comprising one or more genes or regulatory sequences of an adenovirus genome, and wherein the adenoviral backbone comprises a partially deleted E4 gene with reference to the adenovirus genome, wherein the partially deleted E4 gene comprises a deleted or partially-deleted E4orf2 region and a deleted or partially-deleted E4orf3 region, and optionally a deleted or partially-deleted E4orf4 region, and wherein the adenovirus vector further comprises a cassette, the cassette comprising: (1) at least one payload nucleic acid sequence, optionally wherein the at least one payload nucleic acid sequence encodes a polypeptide, optionally wherein the polypeptide comprises an antigen, optionally wherein the antigen comprises: a MHC class I epitope, a MHC class II epitope, an epitope capable of stimulating a B cell response, or a combination thereof, and optionally wherein the at least one payload nucleic acid sequence further comprises a 5' linker sequence and/or a 3' linker sequence, and optionally wherein; (2) at least one promoter sequence operably linked to the at least one payload nucleic acid sequence, (3) optionally, at least one universal MHC class II antigen-encoding nucleic acid sequence; (4) optionally, at least one GPGPG-encoding linker sequence (SEQ ID NO:56); and (5) optionally, at least one polyadenylation sequence.

Also disclosed herein is a method for treating a subject with a disease, optionally wherein the disease is cancer or an infection, the method comprising administering to the subject an adenovirus vector comprising: an adenoviral backbone comprising one or more genes or regulatory sequences of an adenovirus genome, and wherein the adenoviral backbone comprises a partially deleted E4 gene with reference to the adenovirus genome, wherein the partially deleted E4 gene comprises a deleted or partially-deleted E4orf2 region and a deleted or partially-deleted E4orf3 region, and optionally a deleted or partially-deleted E4orf4 region, and wherein the adenovirus vector further comprises a cassette, the cassette comprising: (1) at least one payload nucleic acid sequence, optionally wherein the at least one payload nucleic acid sequence encodes a polypeptide, optionally wherein the polypeptide comprises an antigen, optionally wherein the antigen comprises: a MHC class I epitope, a MHC class II epitope, an epitope capable of stimulating a B cell response, or a combination thereof, and optionally wherein the at least one payload nucleic acid sequence further comprises a 5' linker sequence and/or a 3' linker sequence, and optionally wherein; (2) at least one promoter sequence operably linked to the at least one payload nucleic acid sequence, (3) optionally, at least one universal MHC class II antigen-encoding nucleic acid sequence; (4) optionally, at least one GPGPG-encoding linker sequence (SEQ ID NO:56); and (5) optionally, at least one polyadenylation sequence.

Also disclosed herein is a method for stimulating an immune response in a subject, the method comprising administering to the subject an adenovirus vector comprising a modified ChAdV68 sequence, wherein the modified ChAdV68 sequence comprises: (a) a partially deleted E4 gene of the E4 gene sequence shown in SEQ ID NO:1 and that lacks at least nucleotides 34,916 to 35,642 of the sequence shown in SEQ ID NO:1; and (b) one or more genes or regulatory sequences of the ChAdV68 sequence shown in SEQ ID NO: 1, optionally wherein the one or more genes or regulatory sequences comprise at least one of the chimpanzee adenovirus inverted terminal repeat (ITR), E1A, E1B, E2A, E2B, E3, E4, L1, L2, L3, L4, and L5 genes of the sequence shown in SEQ ID NO: 1; and wherein the chimpanzee adenovirus vector further comprises a cassette, wherein the cassette comprises at least one payload nucleic acid sequence, and wherein the cassette comprises at least one promoter sequence operably linked to the at least one payload nucleic acid sequence.

Also disclosed herein is a method for treating a subject with a disease, optionally wherein the disease is cancer or an infection, the method comprising administering to the subject an adenovirus vector comprising a modified ChAdV68 sequence, wherein the modified ChAdV68 sequence comprises: (a) a partially deleted E4 gene of the E4 gene sequence shown in SEQ ID NO:1 and that lacks at least nucleotides 34,916 to 35,642 of the sequence shown in SEQ ID NO:1; and (b) one or more genes or regulatory sequences of the ChAdV68 sequence shown in SEQ ID NO: 1, optionally wherein the one or more genes or regulatory sequences comprise at least one of the chimpanzee adenovirus inverted terminal repeat (ITR), E1A, E1B, E2A, E2B, E3, E4, L1, L2, L3, L4, and L5 genes of the sequence shown in SEQ ID NO: 1; and wherein the chimpanzee adenovirus vector further comprises a cassette, wherein the cassette comprises at least one payload nucleic acid sequence, and wherein the cassette comprises at least one promoter sequence operably linked to the at least one payload nucleic acid sequence.

Also disclosed herein is a method of producing a virus, wherein the method comprises the steps of: a. providing a viral vector comprising a cassette, the cassette comprising: (i) at least one payload nucleic acid sequence, optionally wherein the at least one payload nucleic acid sequence encodes a polypeptide, optionally wherein the polypeptide comprises an antigen, optionally wherein the antigen comprises: a MHC class I epitope, a MHC class II epitope, an epitope capable of stimulating a B cell response, or a combination thereof, and optionally wherein the at least one payload nucleic acid sequence further comprises a 5' linker sequence and/or a 3' linker sequence, and optionally wherein; (ii) at least one promoter sequence operably linked to the at least one payload nucleic acid sequence, wherein the at least one promoter is a tetracycline (TET) repressor protein (TETr) controlled promoter, (iii) optionally, at least one MHC class II antigen-encoding nucleic acid sequence; (iv) optionally, at least one GPGPG-encoding linker sequence (SEQ ID NO:56); and (v) optionally, at least one polyadenylation sequence; b. providing a cell engineered to express the TETr protein; and c. contacting the viral vector with the cell under conditions sufficient for production of the virus.

In some aspects, the viral vector comprises a chimpanzee adenovirus vector, optionally wherein the chimpanzee adenovirus vector is a ChAdV68 vector. In some aspects, the production of the virus is increased using the vector comprising the TETr controlled promoter relative to production of a virus produced using a vector without the TETr controlled promoter. In some aspects, the increased production is increased at least 1.5-fold, at least 2-fold, at least 2.5-fold, at least 4-fold, at least 5-fold, at least 6-fold, at least 7-fold, at least 8-fold, at least 9-fold, or at least 10-fold relative to production using a vector without the TETr controlled promoter. In some aspects, the increased production is increased at least 15-fold, at least 20-fold, at least 25-fold, at least 30-fold, at least 35-fold, at least 40-fold, at least 50-fold, at least 60-fold, at least 70-fold, at least 80-fold, at least 90-fold, or at least 100-fold relative to production using a vector without the TETr controlled promoter. In some aspects, the production of the virus is increased using the vector comprising the TETr controlled promoter relative to production of a virus produced using a cell that is not engineered to express the TETr protein. In some aspects, the increased production is increased at least 1.5-fold, at least 2-fold, at least 2.5-fold, at least 4-fold, at least 5-fold, at least 6-fold, at least 7-fold, at least 8-fold, at least 9-fold, or at least 10-fold relative to production using a cell that is not engineered to express the TETr protein.

Also provided herein is a viral vector comprising a cassette, the cassette comprising: (i) at least one payload nucleic acid sequence, optionally wherein the at least one payload nucleic acid sequence encodes a polypeptide, optionally wherein the polypeptide comprises an antigen, optionally wherein the antigen comprises: a MHC class I epitope, a MHC class II epitope, an epitope capable of stimulating a B cell response, or a combination thereof, and optionally wherein the at least one payload nucleic acid sequence further comprises a 5' linker sequence and/or a 3' linker sequence, and optionally wherein; (ii) at least one promoter sequence operably linked to the at least one payload nucleic acid sequence, wherein the at least one promoter is a tetracycline (TET) repressor protein (TETr) controlled promoter, (iii) optionally, at least one MHC class II antigen-encoding nucleic acid sequence; (iv) optionally, at least one GPGPG-encoding linker sequence (SEQ ID NO:56); and (v) optionally, at least one polyadenylation sequence.

In some aspects, the TETr controlled promoter comprises one or more TET operator (TETo) nucleic acid sequences, optionally wherein the one or more TETo nucleic acid sequences comprises the nucleotide sequence shown in SEQ ID NO:60. In some aspects, the one or more TETo nucleic acid sequences comprises 2, 3, 4, 5, 6, 7, 8, 9, or 10 or more TETo nucleic acid sequences, optionally wherein each of TETo nucleic acid sequences comprises the nucleotide sequence shown in SEQ ID NO:60. In some aspects, the 2 or more TETo nucleic acid sequences are linked together. In some aspects, the 2 or more TETo nucleic acid sequences are directly linked together. In some aspects, the 2 or more TETo nucleic acid sequences are linked together with a linker sequence, wherein the linker comprises 1, 2, 3, 4, 5, 6, 7, 8, 9, 10, 11, 12, 13, 14, 15, 16, 17, 18, 19, or 20 or more nucleotides, and optionally wherein the linker sequence comprises the linker nucleotide sequence shown in SEQ ID NO:61. In some aspects, the one or more TETo nucleic acid sequences are 5' of a RNA polymerase binding sequence of the promoter sequence. In some aspects, the one or more TETo nucleic acid sequences are 3' of a RNA polymerase binding sequence of the promoter sequence. In some aspects, the at least one promoter sequence comprises a CMV, SV40, EF-1, RSV, PGK, HSA, MCK or EBV promoter sequence. In some aspects, the at least one promoter sequence is a CMV-derived promoter sequence, optionally wherein the CMV promoter sequence comprises the CMV promoter nucleotide sequence shown in SEQ ID NO:64. In some aspects, the CMV-derived promoter sequence is a minimal CMV promoter sequence, optionally wherein the minimal CMV promoter sequence comprises the minimal CMV promoter nucleotide sequence as shown in SEQ ID NO:61.

In some aspects, the TETr controlled promoter operably linked to the at least one payload nucleic acid sequence comprises an ordered sequence described in the formula, from 5' to 3', comprising: $(T\text{-}L_Y)_X$-P-N wherein, N comprises one of the at least one payload nucleic acid sequences, optionally wherein each N encodes a MHC class I epitope, a MHC class II epitope, an epitope capable of stimulating a B cell response, or a combination thereof, optionally with at least one alteration that makes the encoded epitope sequence distinct from the corresponding peptide sequence encoded by a wild-type nucleic acid sequence P a RNA polymerase binding sequence of the promoter sequence operably linked to at least one of the at least one payload nucleic acid sequences, T comprises a TETo nucleic acid sequences comprising the nucleotide sequence shown in SEQ ID NO:60, L comprises a linker sequence, where Y=0 or 1 for each X, and wherein X=1, 2, 3, 4, 5, 6, 7, 8, 9, 10, 11, 12, 13, 14, 15, 16, 17, 18, 19, or 20. In some aspects, the TETr controlled promoter operably linked to the at least one payload nucleic acid sequence comprises an ordered sequence described in the formula, from 5' to 3', comprising: P-$(T\text{-}L_Y)_X$-N wherein, N comprises one of the at least one payload nucleic acid sequences, optionally wherein each N encodes a MHC class I epitope, a MHC class II epitope, an epitope capable of stimulating a B cell response, or a combination thereof, optionally with at least one alteration that makes the encoded epitope sequence distinct from the corresponding peptide sequence encoded by a wild-type nucleic acid sequence P a RNA polymerase binding sequence of the promoter sequence operably linked to at least one of the at least one payload nucleic acid sequences, T comprises a TETo nucleic acid sequences comprising the nucleotide sequence shown in SEQ ID NO:60, L comprises a linker sequence, where Y=0 or 1 for each X, and wherein X=1, 2, 3, 4, 5, 6, 7, 8, 9, 10, 11, 12, 13, 14, 15, 16, 17, 18, 19, or 20.

In some aspects, the TETr controlled promoter comprises: (1) a minimal CMV promoter sequence; (2) 7 TETo nucleic acid sequences, wherein each of TETo nucleic acid sequences comprises the nucleotide sequence shown in SEQ ID NO:60, and wherein each of the TETo nucleic acid sequences are linked together with a linker sequence, the 7 TETo nucleic acid sequences are 5' of the minimal CMV promoter sequence, and optionally wherein the TETr controlled promoter comprises the nucleotide sequence as shown in SEQ ID NO:61. In some aspects, the TETr controlled promoter comprises: (1) a CMV promoter sequence; (2) 2 TETo nucleic acid sequences, wherein each of the TETo nucleic acid sequences comprises the nucleotide sequence shown in SEQ ID NO:60, and wherein each of the TETo nucleic acid sequences are directly linked together, the 2 TETo nucleic acid sequences are 3' of the CMV promoter sequence, and optionally wherein the TETr controlled promoter comprises the nucleotide sequence as shown in SEQ ID NO:64.

In some aspects, the viral vector comprises a vector backbone, wherein the vector backbone comprises a chimpanzee adenovirus vector, optionally wherein the chimpanzee adenovirus vector is a ChAdV68 vector.

In some aspects, the cassette comprises an ordered sequence described in the formula, from 5' to 3', comprising: $P_a$-$(L5_b$-$N_c$-$L3_d)_X$-$(G5_e$-$U_f)_Y$-$G3_g$-$A_h$ wherein, N comprises one of the at least one payload nucleic acid sequences, optionally wherein each N encodes a MHC class I epitope, a MHC class II epitope, an epitope capable of stimulating a B cell response, or a combination thereof, optionally with at least one alteration that makes the encoded epitope sequence distinct from the corresponding peptide sequence encoded by a wild-type nucleic acid sequence, where c=1, P comprises the at least one promoter sequence operably linked to at least one of the at least one payload nucleic acid sequences, where a=1, L5 comprises the 5' linker sequence, where b=0 or 1, L3 comprises the 3' linker sequence, where d=0 or 1, G5 comprises one of the at least one nucleic acid sequences encoding a GPGPG amino acid linker (SEQ ID NO: 56), where e=0 or 1, G3 comprises one of the at least one nucleic acid sequences encoding a GPGPG amino acid linker (SEQ ID NO: 56), where g=0 or 1, U comprises one of the at least one universal MHC class II antigen-encoding nucleic acid sequence, where f=1, A comprises the at least one polyadenylation sequence, where h=0 or 1, X=2 to 400, where for each X the corresponding $N_c$ is a payload nucleic acid sequence, optionally wherein for each X the corresponding $N_c$ is a distinct payload nucleic acid sequence, and Y=0-2, where for each Y the corresponding $U_f$ is a universal MHC class II antigen-encoding nucleic acid sequence, optionally wherein for each Y the corresponding $U_f$ is a distinct universal MHC class II antigen-encoding nucleic acid sequence.

In some aspects, the cassette further comprises at least one additional payload nucleic acid sequence not encoded in the ordered sequence. In some aspects, b=1, d=1, e=1, g=1, h=1, X=10, Y=2, P is a CMV-derived promoter sequence, each N encodes a MHC class I epitope, a MHC class II epitope, an epitope capable of stimulating a B cell response, or a combination thereof, L5 encodes a native N-terminal amino acid sequence of the epitope, and wherein the 5' linker sequence encodes a peptide that is at least 3 amino acids in length, L3 encodes a native C-terminal amino acid sequence of the epitope, and wherein the 3' linker sequence encodes a peptide that is at least 3 amino acids in length, U is each of a PADRE class II sequence and a Tetanus toxoid MHC class II sequence, and the vector comprises a modified ChAdV68 sequence, wherein the modified ChAdV68 sequence comprises: (a) a partially deleted E4 gene of the E4 gene sequence shown in SEQ ID NO:1 and that lacks at least nucleotides 34,916 to 35,642 of the sequence shown in SEQ ID NO:1; (b) nucleotides 2 to 34,916 of the sequence shown in SEQ ID NO:1, wherein the partially deleted E4 gene is 3' of the nucleotides 2 to 34,916, and optionally the nucleotides 2 to 34,916 additionally lack nucleotides 577 to 3403 of the sequence shown in SEQ ID NO:1 corresponding to an E1 deletion and/or lack nucleotides 27,125 to 31,825 of the sequence shown in SEQ ID NO:1 corresponding to an E3 deletion; and (c) nucleotides 35,643 to 36,518 of the sequence shown in SEQ ID NO:1, and wherein the partially deleted E4 gene is 5' of the nucleotides 35,643 to 36,518.

In some aspects, the vector is a chimpanzee adenovirus vector, optionally wherein the chimpanzee adenovirus vector is a ChAdV68 vector.

In some aspects, the partially deleted E4 gene comprises: A. the E4 gene sequence shown in SEQ ID NO:1 and that lacks at least nucleotides 34,916 to 35,642 of the sequence shown in SEQ ID NO:1, B. the E4 gene sequence shown in SEQ ID NO:1 and that lacks at least nucleotides 34,916 to 34,942, nucleotides 34,952 to 35,305 of the sequence shown in SEQ ID NO:1, nucleotides 35,302 to 35,642 of the sequence shown in SEQ ID NO:1, and wherein the vector comprises at least nucleotides 2 to 36,518 of the sequence shown in SEQ ID NO:1, C. the E4 gene sequence shown in SEQ ID NO:1 and that lacks at least nucleotides 34,980 to 36,516 of the sequence shown in SEQ ID NO:1, and wherein the vector comprises at least nucleotides 2 to 36,518 of the sequence shown in SEQ ID NO:1, D. the E4 gene sequence shown in SEQ ID NO:1 and that lacks at least nucleotides 34,979 to 35,642 of the sequence shown in SEQ ID NO:1, and wherein the vector comprises at least nucleotides 2 to 36,518 of the sequence shown in SEQ ID NO:1, E. an E4 deletion of at least a partial deletion of E4Orf2, a fully deleted E4Orf3, and at least a partial deletion of E4Orf4, F. an E4 deletion of at least a partial deletion of E4Orf2, at least a partial deletion of E4Orf3, and at least a partial deletion of E4Orf4, G. an E4 deletion of at least a partial deletion of E4Orf1, a fully deleted E4Orf2, and at least a partial deletion of E4Orf3, or H. an E4 deletion of at least a partial deletion of E4Orf2 and at least a partial deletion of E4Orf3.

In some aspects, the vector comprises one or more genes or regulatory sequences of the ChAdV68 sequence shown in SEQ ID NO: 1, optionally wherein the one or more genes or regulatory sequences are selected from the group consisting of the chimpanzee adenovirus inverted terminal repeat (ITR), E1A, E1B, E2A, E2B, E3, E4, L1, L2, L3, L4, and L5 genes of the sequence shown in SEQ ID NO: 1. In some aspects, the adenoviral backbone or modified ChAdV68 sequence further comprises a functional deletion in at least one gene selected from the group consisting of an adenovirus E1A, E1B, E2A, E2B, E3, L1, L2, L3, L4, and L5 gene with reference to the adenovirus genome or with reference to the sequence shown in SEQ ID NO: 1, optionally wherein the adenoviral backbone or modified ChAdV68 sequence is fully deleted or functionally deleted in: (1) E1A and E1B; or (2) E1A, E1B, and E3 with reference to the adenovirus genome or with reference to the sequence shown in SEQ ID NO: 1, optionally wherein the E1 gene is functionally deleted through an E1 deletion of at least nucleotides 577 to 3403 with reference to the sequence shown in SEQ ID NO: 1 and optionally wherein the E3 gene is functionally deleted through an E3 deletion of at least nucleotides 27,125 to 31,825 with reference to the sequence shown in SEQ ID NO: 1.

In some aspects, the cassette is present and is inserted in the vector at the E1 region, E3 region, and/or any deleted AdV region that allows incorporation of the cassette.

In some aspects, the vector is generated from one of a first generation, a second generation, or a helper-dependent adenoviral vector.

In some aspects, the modified ChAdV68 sequence comprises nucleotides 2 to 34,916 of the sequence shown in SEQ ID NO:1, wherein the partially deleted E4 gene is 3' of the nucleotides 2 to 34,916. In some aspects, the nucleotides 2 to 34,916 lack nucleotides 577 to 3403 of the sequence shown in SEQ ID NO:1 corresponding to an E1 deletion. In some aspects, the nucleotides 2 to 34,916 lack nucleotides 456-3014 with reference to the sequence shown in SEQ ID NO: 1. In some aspects, the nucleotides 2 to 34,916 lack nucleotides 27,125-31,825 with reference to the sequence shown in SEQ ID NO:1 corresponding to an E3 deletion. In some aspects, the nucleotides 2 to 34,916 lack nucleotides 27,816-31,333 with reference to the sequence shown in SEQ ID NO:1. In some aspects, the nucleotides 2 to 34,916 lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion. In some aspects, the nucleotides 2 to 34,916 further lack nucleotides 3957-10346, nucleotides 21787-23370, nucleotides 33486-36193, or a combination thereof with reference to the sequence shown in SEQ ID NO: 1.

In some aspects, at least one of the at least one payload nucleic acid sequences encodes an antigen, wherein the antigen comprises: a MHC class I epitope, a MHC class II epitope, an epitope capable of stimulating a B cell response, or a combination thereof. In some aspects, at least one of the at least one payload nucleic acid sequences encodes a polypeptide sequence capable of undergoing antigen processing into an epitope, optionally wherein the epitope is known or suspected to be presented by MHC class I on a surface of a cell, optionally wherein the surface of the cell is a tumor cell surface or an infected cell surface.

In some aspects, at least one of the at least one payload nucleic acid sequences encodes a polypeptide sequence or portion thereof that is presented by MHC class I and/or MHC class II on a surface of a cell, optionally wherein the surface of the cell is a tumor cell surface or an infected cell surface. In some aspects, the a tumor cell selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, T cell lymphocytic leukemia, non-small cell lung cancer, and small cell lung cancer, or the infected cell selected from the group consisting of: a pathogen infected cell, a virally infected cell, a bacterially infected cell, an fungally infected cell, and a parasitically infected cell, optionally wherein the virally infected cell is selected from the group consisting of: an HIV infected cell, a Severe acute respiratory syndrome-related coronavirus (SARS) infected cell, a severe acute respiratory syndrome coronavirus 2 (SARS-CoV-2) infected cell, a Ebola infected cell, a Hepatitis B virus (HBV) infected cell, an influenza infected cell, and a Hepatitis C virus (HCV) infected cell.

In some aspects, at least one of the at least one payload nucleic acid sequences encodes a polypeptide sequence or portion thereof comprising an epitope capable of stimulating a B cell response, optionally wherein the polypeptide sequence or portion thereof comprises a full-length protein, a protein domain, a protein subunit, or an antigenic fragment predicted or known to be capable of being bound by an antibody.

In some aspects, at least one of the at least one payload nucleic acid sequences encodes an infectious disease organism peptide selected from the group consisting of: a pathogen-derived peptide, a virus-derived peptide, a bacteria-derived peptide, a fungus-derived peptide, and a parasite-derived peptide. In some aspects, at least one of the at least one payload nucleic acid sequences encodes an epitope with at least one alteration that makes the encoded epitope sequence distinct from the corresponding peptide sequence encoded by a wild-type nucleic acid sequence. In some aspects, at least one of the at least one payload nucleic acid sequences encodes a MHC class I epitope or MHC class II epitope with at least one alteration that makes the encoded peptide sequence distinct from the corresponding peptide sequence encoded by a wild-type nucleic acid sequence, optionally wherein the encoded polypeptide sequence or portion thereof has increased binding affinity to, increased binding stability to, and/or an increased likelihood of presentation on its corresponding MHC allele relative to the translated, corresponding wild-type nucleic acid sequence. In some aspects, the at least one alteration comprises a point mutation, a frameshift mutation, a non-frameshift mutation, a deletion mutation, an insertion mutation, a splice variant, a genomic rearrangement, or a proteasome-generated spliced antigen.

In some aspects, at least one of the at least one payload nucleic acid sequences encodes a full-length protein, a protein domain, or a protein subunit. In some aspects, at least one of the at least one payload nucleic acid sequences encodes an antibody, a cytokine, a chimeric antigen receptor (CAR), a T-cell receptor, and a genome-editing system nuclease.

In some aspects, at least one of the at least one payload nucleic acid sequences comprises a non-coding nucleic acid sequence. In some aspects, the non-coding nucleic acid sequence comprises an RNA interference (RNAi) polynucleotide or genome-editing system polynucleotide.

In some aspects, each of the at least one payload nucleic acid sequences is linked directly to one another. In some aspects, at least one of the at least one payload nucleic acid sequences is linked to a distinct payload nucleic acid sequence with a nucleic acid sequence encoding a linker. In some aspects, the linker links two payload nucleic acid sequences encoding MHC class I epitopes or links a first payload nucleic acid sequence encoding an MHC class I epitope to a second payload nucleic acid sequence encoding an MHC class II epitope or encoding an epitope sequence capable of stimulating a B cell response. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two payload nucleic acid sequences encoding MHC class II epitopes or links a first payload nucleic acid sequence encoding an MHC class II epitope to a second payload nucleic acid sequence encoding an MHC class I epitope or encoding an epitope sequence capable of stimulating a B cell response. In some aspects, the linker comprises the sequence GPGPG (SEQ ID NO: 56).

In some aspects, at least one of the at least one payload nucleic acid sequences is linked, operably or directly, to a separate or contiguous sequence that enhances the expression, stability, cell trafficking, processing and presentation, and/or immunogenicity of the at least one payload nucleic acid sequence, and optionally the expression, stability, cell trafficking, processing and presentation, and/or immunogenicity of the polypeptide encoded by the at least one payload nucleic acid sequence. In some aspects, the separate or contiguous sequence comprises at least one of: a ubiquitin sequence, a ubiquitin sequence modified to increase proteasome targeting, optionally wherein the ubiquitin sequence contains a Gly to Ala substitution at position 76, an immunoglobulin signal sequence, optionally wherein the immunoglobulin signal sequence comprises IgK, a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, the expression of each of the at least one payload nucleic acid sequences is driven by the at least one promoter.

In some aspects, the at least one payload nucleic acid sequence comprises at least 2, 3, 4, 5, 6, 7, 8, 9, or 10 payload nucleic acid sequences. In some aspects, the at least one payload nucleic acid sequence comprises at least 11, 12, 13, 14, 15, 16, 17, 18, 19, 20 or up to 400 payload nucleic acid sequences. In some aspects, the at least one payload nucleic acid sequence comprises at least 2-400 payload nucleic acid sequences and wherein at least one of the at least one payload nucleic acid sequences encodes a MHC class I epitope, a MHC class II epitope, an epitope capable of stimulating a B cell response, or a combination thereof. In some aspects, the at least one payload nucleic acid sequence comprises at least 2-400 payload nucleic acid sequences and wherein, when administered to the subject and translated, at least one of the at least one payload nucleic acid sequences encodes an antigen presented on antigen presenting cells resulting in an immune response targeting the antigen. In some aspects, the at least one payload nucleic acid sequence comprises at least 2-400 MHC class I and/or class II antigen-encoding nucleic acid sequences, wherein, when administered to the subject and translated, at least one of the MHC class I or class II antigens are presented on antigen presenting cells resulting in an immune response targeting at least one of the antigens on a cell surface, and optionally wherein the expression of each of the at least 2-400 MHC class I or class II antigen-encoding nucleic acid sequences is driven by the at least one promoter.

In some aspects, each MHC class I epitope is independently between 8 and 35 amino acids in length, optionally 7-15, 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length. In some aspects, the at least one universal MHC class II antigen-encoding nucleic acid sequence is present. In some aspects, the at least one universal MHC class II antigen-encoding nucleic acid sequence is present and comprises at least one universal MHC class II antigen-encoding nucleic acid sequence that comprises at least one alteration that makes the encoded peptide sequence distinct from the corresponding peptide sequence encoded by a wild-type nucleic acid sequence. In some aspects, the at least one universal MHC class II antigen-encoding nucleic acid sequence is 12-20, 12, 13, 14, 15, 16, 17, 18, 19, 20, or 20-40 amino acids in length. In some aspects, the at least one universal MHC class II antigen-encoding nucleic acid sequence is present and wherein the at least one universal sequence comprises at least one of Tetanus toxoid and PADRE.

In some aspects, the at least one promoter sequence is a regulatable promoter, optionally wherein the regulatable promoter is a tetracycline (TET) repressor protein (TETr) controlled promoter, optionally wherein the regulatable promoter comprises multiple TET operator (TETo) sequences 5' or 3' of a RNA polymerase binding sequence of the promoter. multiple TET operator (TETo) sequences are 5' or 3' of a RNA the at least one promoter sequence is constitutive. multiple TET operator (TETo) sequences are 5' or 3' of a RNA the at least one promoter sequence is a CMV, SV40, EF-1, RSV, PGK, HSA, MCK or EBV promoter sequence.

In some aspects, the cassette further comprises at least one poly-adenylation (polyA) sequence operably linked to at least one of the at least one payload nucleic acid sequences, optionally wherein the polyA sequence is located 3' of the at least one payload nucleic acid sequence. In some aspects, the polyA sequence comprises an SV40 or Bovine Growth Hormone (BGH) polyA sequence.

In some aspects, the cassette further comprises at least one of: an intron sequence, a woodchuck hepatitis virus post-transcriptional regulatory element (WPRE) sequence, an internal ribosome entry sequence (IRES) sequence, a nucleotide sequence encoding a 2A self-cleaving peptide sequence, a nucleotide sequence encoding a Furin cleavage site, a nucleotide sequence encoding a TEV cleavage site, or a sequence in the 5' or 3' non-coding region known to enhance the nuclear export, stability, or translation efficiency of mRNA that is operably linked to at least one of the at least one payload nucleic acid sequences.

In some aspects, the cassette comprises a reporter gene, including but not limited to, green fluorescent protein (GFP), a GFP variant, secreted alkaline phosphatase, luciferase, or a luciferase variant.

In some aspects, the vector further comprises one or more payload nucleic acid sequences encoding at least one immune modulator, optionally wherein the at least one immune modulator inhibits an immune checkpoint molecule. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the antibody or antigen-binding fragment thereof is a Fab fragment, a Fab' fragment, a single chain Fv (scFv), a single domain antibody (sdAb) either as single specific or multiple specificities linked together (e.g., camelid antibody domains), or full-length single-chain antibody (e.g., full-length IgG with heavy and light chains linked by a flexible linker). In some aspects, the heavy and light chain sequences of the antibody are a contiguous sequence separated by either a self-cleaving sequence such as 2A, optionally wherein the self-cleaving sequence has a Furin cleavage site sequence 5' of the self-cleaving sequence, or an IRES sequence; or the heavy and light chain sequences of the antibody are linked by a flexible linker such as consecutive glycine residues. In some aspects, the immune modulator is a cytokine. In some aspects, the cytokine is at least one of IL-2, IL-7, IL-12, IL-15, or IL-21 or variants thereof of each.

In some aspects, at least one of the at least one payload nucleic acid sequences are selected by performing the steps of: (a) obtaining at least one of exome, transcriptome, or whole genome nucleotide sequencing data from a tumor cell, an infected cell, or an infectious disease organism, wherein the nucleotide sequencing data is used to obtain data representing peptide sequences of each of a set of antigens; (b) inputting the peptide sequence of each antigen into a presentation model to generate a set of numerical likelihoods that each of the antigens is presented by one or more of the MHC alleles on a cell surface, optionally a tumor cell surface or an infected cell surface, the set of numerical likelihoods having been identified at least based on received mass spectrometry data; and (c) selecting a subset of the set of antigens based on the set of numerical likelihoods to generate a set of selected antigens which are used to generate the at least one payload nucleic acid sequence.

In some aspects, each of the at least one payload nucleic acid sequences are selected by performing the steps of: (a) obtaining at least one of exome, transcriptome, or whole genome nucleotide sequencing data from a tumor cell, an infected cell, or an infectious disease organism, wherein the nucleotide sequencing data is used to obtain data representing peptide sequences of each of a set of antigens; (b) inputting the peptide sequence of each antigen into a presentation model to generate a set of numerical likelihoods that each of the antigens is presented by one or more of the MHC alleles on a cell surface, optionally a tumor cell surface or an infected cell surface, the set of numerical likelihoods having been identified at least based on received mass spectrometry data; and (c) selecting a subset of the set of antigens based on the set of numerical likelihoods to generate a set of selected antigens which are used to generate each of the at least one payload nucleic acid sequences. In some aspects, a number of the set of selected antigens is 2-20. In some aspects, the presentation model represents dependence between: (a) presence of a pair of a particular one of the MHC alleles and a particular amino acid at a particular position of a peptide sequence; and (b) likelihood of presentation on a cell surface, optionally a tumor cell surface or an infected cell surface, by the particular one of the MHC alleles of the pair, of such a peptide sequence comprising the particular amino acid at the particular position. In some aspects, selecting the set of selected antigens comprises selecting antigens that have an increased likelihood of being presented on the cell surface relative to unselected antigens based on the presentation model. In some aspects, selecting the set of selected antigens comprises selecting antigens that have an increased likelihood of being capable of inducing a cell-specific immune response in the subject relative to unselected antigens based on the presentation model. In some aspects, selecting the set of selected antigens comprises selecting antigens that have an increased likelihood of being capable of being presented to naïve T cells by professional antigen presenting cells (APCs) relative to unselected antigens based on the presentation model, optionally wherein the APC is a dendritic cell (DC). In some aspects, selecting the set of selected antigens comprises selecting antigens that have a decreased likelihood of being subject to inhibition via central or peripheral tolerance relative to unselected antigens based on the presentation model. In some aspects, selecting the set of selected antigens comprises selecting antigens that have a decreased likelihood of being capable of inducing an autoimmune response to normal tissue in the subject relative to unselected antigens based on the presentation model. In some aspects, exome or transcriptome nucleotide sequencing data is obtained by performing sequencing on a tumor cell or tissue, an infected cell, or an infectious disease organism. In some aspects, the sequencing is next generation sequencing (NGS) or any massively parallel sequencing approach.

In some aspects, the cassette comprises junctional epitope sequences formed by adjacent sequences in the cassette. In some aspects, at least one or each junctional epitope sequence has an affinity of greater than 500 nM for MHC. In some aspects, each junctional epitope sequence is non-self. In some aspects, the cassette does not encode a non-therapeutic MHC class I or class II epitope, wherein the non-therapeutic epitope is predicted to be displayed on an MHC allele of a subject. In some aspects, the non-therapeutic predicted MHC class I or class II epitope sequence is a junctional epitope sequence formed by adjacent sequences in the cassette. In some aspects, the prediction in based on presentation likelihoods generated by inputting sequences of the non-therapeutic epitopes into a presentation model. In some aspects, an order of the at least one payload nucleic acid sequences in the cassette is determined by a series of steps comprising: i. generating a set of candidate cassette sequences corresponding to different orders of the at least one payload nucleic acid sequences; ii. determining, for each candidate cassette sequence, a presentation score based on presentation of non-therapeutic epitopes in the candidate cassette sequence; and iii. selecting a candidate cassette sequence associated with a presentation score below a predetermined threshold as the cassette sequence.

In some aspects, each of the MHC class I and/or class II epitopes is predicted or validated to be capable of presentation by at least one HLA allele present in at least 5% of a human population. In some aspects, each of the MHC class I and/or class II epitopes is predicted or validated to be capable of presentation by at least one HLA allele, wherein each antigen/HLA pair has an antigen/HLA prevalence of at least 0.01% in a human population. In some aspects, each of the MHC class I and/or class II epitopes is predicted or validated to be capable of presentation by at least one HLA allele, wherein each antigen/HLA pair has an antigen/HLA prevalence of at least 0.1% in a human population. In some aspects, the at least one payload nucleic acid sequence encoding the polypeptide is codon optimized relative to a native nucleic acid sequence directly extracted from a subject tissue or sample.

Also disclosed herein is a pharmaceutical composition comprising any of the vectors described herein and a pharmaceutically acceptable carrier. In some aspects, the composition further comprises an adjuvant. In some aspects, the composition further comprises an immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

Also disclosed herein is an isolated nucleotide sequence comprising the cassette of any of the vectors described herein and a gene of the sequence of SEQ ID NO: 1, optionally wherein the gene is selected from the group consisting of the chimpanzee adenovirus ITR, E1A, E1B, E2A, E2B, E3, E4, L1, L2, L3, L4, and L5 genes of the sequence shown in SEQ ID NO: 1, and optionally wherein the nucleotide sequence is cDNA.

Also disclosed herein is an isolated cell comprising any of the isolated nucleotide sequences described herein, optionally wherein the cell is a CHO, HEK293 or variants thereof, 911, HeLa, A549, LP-293, PER.C6, or AE1-2a cell.

Also disclosed is vector comprising any of the isolated nucleotide sequences described herein.

Also disclosed herein is a kit comprising any of the vectors or compositions described herein and instructions for use.

Also disclosed herein is a method for stimulating an immune response in a subject, the method comprising administering to the subject any of the vectors or compositions described herein. In some aspects, the vector or composition is administered intramuscularly (IM), intradermally (ID), or subcutaneously (SC). In some aspects, the method further comprises administering to the subject an immune modulator, optionally wherein the immune modulator is administered before, concurrently with, or after administration of the vector or pharmaceutical composition. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the immune modulator is administered intravenously (IV), intramuscularly (IM), intradermally (ID), or subcutaneously (SC). In some aspects, the subcutaneous administration is near the site of the vector or composition administration or in close proximity to one or more vector or composition draining lymph nodes.

In some aspects, the method further comprises administering to the subject a second vaccine composition. In some aspects, the second vaccine composition is administered prior to the administration of any of the vectors or compositions described herein. In some aspects, the second vaccine composition is administered subsequent to the administration of any of the vectors or compositions described herein. In some aspects, the second vaccine composition is the same as any of the vectors or compositions described herein. In some aspects, the second vaccine composition is different from any of the vectors or compositions described herein. In some aspects, the second vaccine composition comprises a self-amplifying RNA (samRNA) vector encoding at least one payload nucleic acid sequence. In some aspects, the at least one payload nucleic acid sequence encoded by the samRNA vector is the same as at least one of the at least one payload nucleic acid sequence of any of the above vector claims.

Also disclosed herein is a method of manufacturing the vector of any of the above vector claims, the method comprising: obtaining a plasmid sequence comprising the adenovirus vector or chimpanzee adenovirus vector; transfecting the plasmid sequence into one or more host cells; and isolating the vector from the one or more host cells. In some aspects, the isolating comprises: lysing the one or more host cells to obtain a cell lysate comprising the vector; and purifying the vector from the cell lysate and optionally also from media used to culture the one or more host cells. In some aspects, the plasmid sequence is generated using one of the following; DNA recombination or bacterial recombination or full genome DNA synthesis or full genome DNA synthesis with amplification of synthesized DNA in bacterial cells. In some aspects, the one or more host cells are at least one of CHO, HEK293 or variants thereof, 911, HeLa, A549, LP-293, PER.C6, and AE1-2a cells. In some aspects, the purifying the vector from the cell lysate involves one or more of chromatographic separation, centrifugation, virus precipitation, and filtration.

Also provided herein is a method of producing a virus, wherein the virus is produced using any of the vectors described herein. In some aspects, the production of the virus is increased using the vector comprising the partially deleted E4 gene relative to production of a virus produced using a vector without the partially deleted E4 gene. In some aspects, the infectious unit titer of the virus is increased using the vector comprising the partially deleted E4 gene relative to the infectious unit titer of a virus produced using a vector without the partially deleted E4 gene. In some aspects, the increased production is increased at least 1.5-fold, at least 2-fold, at least 2.5-fold, at least 4-fold, at least 5-fold, at least 6-fold, at least 7-fold, at least 8-fold, or at least 9-fold relative to production using a vector without the partially deleted E4 gene. In some aspects, the increased production is increased at least 10-fold, at least 18-fold, at least 20-fold, at least 25-fold, or at least 27-fold, relative to production using a vector without the partially deleted E4 gene.

BRIEF DESCRIPTION OF THE SEVERAL VIEWS OF THE DRAWINGS

These and other features, aspects, and advantages of the present invention will become better understood with regard to the following description, and accompanying drawings, where:

Figure (FIG. 1 illustrates development of an in vitro T cell activation assay. Schematic of the assay in which the delivery of a vaccine cassette to antigen presenting cells, leads to expression, processing and MHC-restricted presentation of distinct peptide antigens. Reporter T cells engineered with T cell receptors that match the specific peptide-MHC combination become activated resulting in luciferase expression.

FIG. 2B discloses SEQ ID NOS 78-79, 82, 81, 80, 49 and 194, respectively, in order of appearance.

FIG. 5B illustrates in vivo evaluation of the impact of epitope position in long 21-mer cassettes and shows the sequence information on the T cell epitopes used. FIG. 5B discloses SEQ ID NOS 78-79, 82, 81, 80, 195-197, 83 and 198-209, respectively, in order of appearance.

FIG. 6B illustrates final cassette design for preclinical IND-enabling studies and shows the sequence information for the T cell epitopes used that are presented on class I MHC of non-human primate, mouse and human origin, as well as sequences of 2 universal MHC class II epitopes PADRE and Tetanus toxoid. FIG. 6B discloses SEQ ID NOS 112-117, 80-82, 78-79, 72-73, 142, 210, 146-148, 144-145, 49 and 47, respectively, in order of columns.

FIG. 24A discloses SEQ ID NO: 77.

DETAILED DESCRIPTION

I. Definitions

Figure 1:
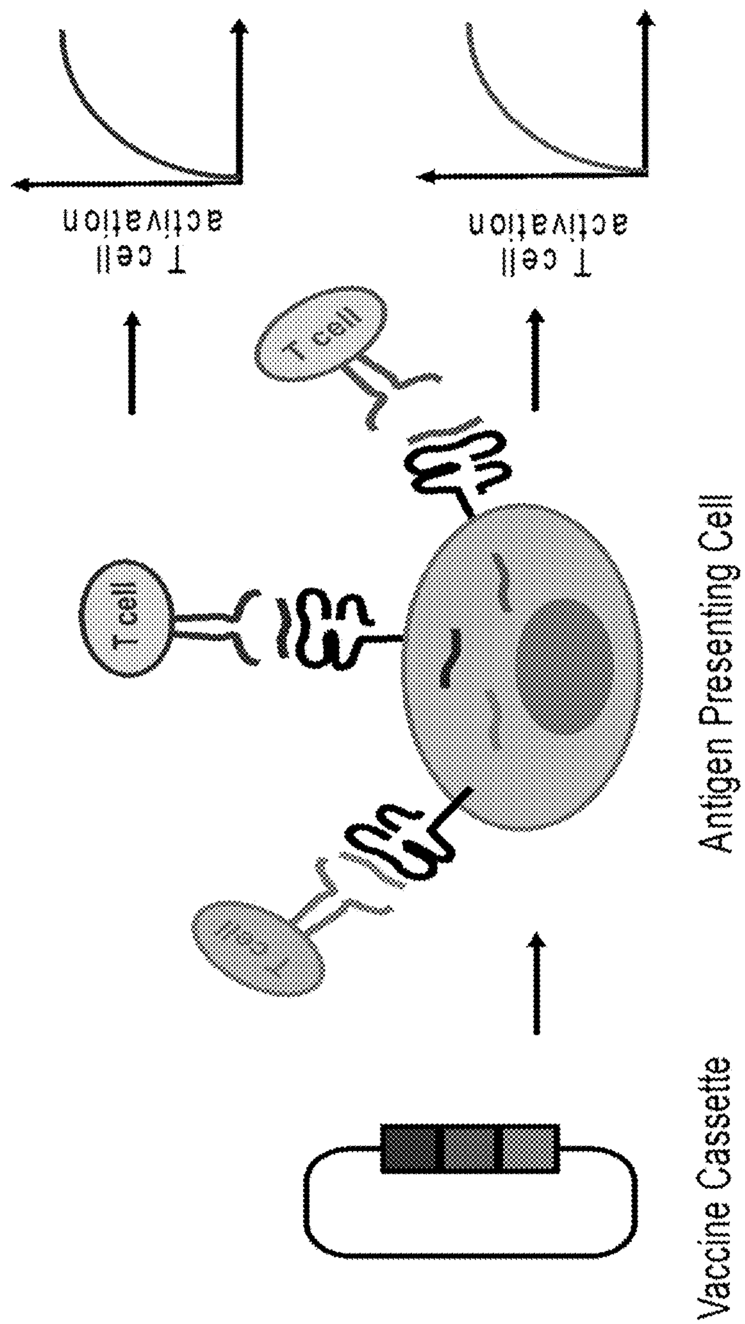

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that induces an immune response. An antigen can be a neoantigen. An antigen can be a "shared antigen" that is an antigen found among a specific population, e.g., a specific population of cancer patients or infected subjects. An antigen can be associated with or derived from an infectious disease organism.

As used herein the term "neoantigen" is an antigen that has at least one alteration that makes it distinct from the corresponding wild-type antigen, e.g., via mutation in a tumor cell or post-translational modification specific to a tumor cell. A neoantigen can include a polypeptide sequence or a nucleic acid sequence. A mutation can include a frameshift or nonframeshift indel, missense or nonsense substitution, splice site alteration, genomic rearrangement or gene fusion, or any genomic or expression alteration giving rise to a neoORF. A mutations can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354 (6310):354-358. The subject can be identified for administration through the use of various diagnostic methods, e.g., patient selection methods described further below.

As used herein the term "tumor antigen" is an antigen present in a subject's tumor cell or tissue but not in the subject's corresponding normal cell or tissue, or derived from a polypeptide known to or have been found to have altered expression in a tumor cell or cancerous tissue in comparison to a normal cell or tissue.

As used herein the term "antigen-based vaccine" is a vaccine composition based on one or more antigens, e.g., a plurality of antigens. The vaccines can be nucleotide-based (e.g., virally based, RNA based, or DNA based), protein-based (e.g., peptide based), or a combination thereof.

As used herein the term "candidate antigen" is a mutation or other aberration giving rise to a sequence that may represent an antigen.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon or causing removal of a canonical start codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al.).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T cell receptor.

As used herein the term "immunogenic" is the ability to elicit an immune response, e.g., via T cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "truncal mutation" is a mutation originating early in the development of a tumor and present in a substantial portion of the tumor's cells.

As used herein the term "subclonal mutation" is a mutation originating later in the development of a tumor and present in only a subset of the tumor's cells.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the tumor peptidome, meaning the union of the peptidomes of all cells that comprise the tumor).

As used herein the term "ELISPOT" means Enzyme-linked immunosorbent spot assay—which is a common method for monitoring immune responses in humans and animals.

As used herein the term "dextramers" is a dextran-based peptide-MHC multimers used for antigen-specific T-cell staining in flow cytometry.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or anergizing self-reactive T-cells that survive central tolerance or promoting these T cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include tumor type, tumor sub-type, and smoking history.

The term "derived" refers to sequences directly extracted from a subject tissue or sample (e.g., a tumor, cell, infected cell, or infectious disease organism), e.g. via RT-PCR; or sequence data obtained by sequencing the subject tissue or sample and then synthesizing the nucleic acid sequences using the sequencing data, e.g., via various synthetic or PCR-based methods known in the art. "Derived" can include nucleic acid sequence variants, such as codon-optimized nucleic acid sequence variants, that encode the same polypeptide sequence as a corresponding native nucleic acid sequence, such as a corresponding native infectious disease organism nucleic acid sequence. "Derived" can also include variants that encode a modified polypeptide sequence, such as an infectious disease organism polypeptide sequence, having one or more (e.g., 1, 2, 3, 4, or 5) mutations relative to a native polypeptide sequence, such as native infectious disease organism polypeptide sequence. For example, a modified polypeptide sequence can have one or more missense mutations (e.g., engineered mutations) relative to the native polypeptide sequence.

The term "alphavirus" refers to members of the family Togaviridae, and are positive-sense single-stranded RNA viruses. Alphaviruses are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis and its derivative strain TC-83. Alphaviruses are typically self-replicating RNA viruses.

The term "alphavirus backbone" refers to minimal sequence(s) of an alphavirus that allow for self-replication of the viral genome. Minimal sequences can include conserved sequences for nonstructural protein-mediated amplification, a nonstructural protein 1 (nsP1) gene, a nsP2 gene, a nsP3 gene, a nsP4 gene, and a polyA sequence, as well as sequences for expression of subgenomic viral RNA including a 26S promoter element.

The term "sequences for nonstructural protein-mediated amplification" includes alphavirus conserved sequence elements (CSE) well known to those in the art. CSEs include, but are not limited to, an alphavirus 5' UTR, a 51-nt CSE, a 24-nt CSE, or other 26S subgenomic promoter sequence, a 19-nt CSE, and an alphavirus 3' UTR.

The term "RNA polymerase" includes polymerases that catalyze the production of RNA polynucleotides from a DNA template. RNA polymerases include, but are not limited to, bacteriophage derived polymerases including T3, T7, and SP6.

The term "lipid" includes hydrophobic and/or amphiphilic molecules. Lipids can be cationic, anionic, or neutral. Lipids can be synthetic or naturally derived, and in some instances biodegradable. Lipids can include cholesterol, phospholipids, lipid conjugates including, but not limited to, polyethyleneglycol (PEG) conjugates (PEGylated lipids), waxes, oils, glycerides, fats, and fat-soluble vitamins. Lipids can also include dilinoleylmethyl-4-dimethylaminobutyrate (MC3) and MC3-like molecules.

The term "lipid nanoparticle" or "LNP" includes vesicle like structures formed using a lipid containing membrane surrounding an aqueous interior, also referred to as liposomes. Lipid nanoparticles includes lipid-based compositions with a solid lipid core stabilized by a surfactant. The core lipids can be fatty acids, acylglycerols, waxes, and mixtures of these surfactants. Biological membrane lipids such as phospholipids, sphingomyelins, bile salts (sodium taurocholate), and sterols (cholesterol) can be utilized as stabilizers. Lipid nanoparticles can be formed using defined ratios of different lipid molecules, including, but not limited to, defined ratios of one or more cationic, anionic, or neutral lipids. Lipid nanoparticles can encapsulate molecules within an outer-membrane shell and subsequently can be contacted with target cells to deliver the encapsulated molecules to the host cell cytosol. Lipid nanoparticles can be modified or functionalized with non-lipid molecules, including on their surface. Lipid nanoparticles can be single-layered (unilamellar) or multi-layered (multilamellar). Lipid nanoparticles can be complexed with nucleic acid. Unilamellar lipid nanoparticles can be complexed with nucleic acid, wherein the nucleic acid is in the aqueous interior. Multilamellar lipid nanoparticles can be complexed with nucleic acid, wherein the nucleic acid is in the aqueous interior, or to form or sandwiched between Abbreviations: MHC: major histocompatibility complex; HLA: human leukocyte antigen, or the human MHC gene locus; NGS: next-generation sequencing; PPV: positive predictive value; TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. Methods of Identifying Antigens

Methods for identifying antigens (e.g., antigens derived from a tumor or an infectious disease organism) include identifying antigens that are likely to be presented on a cell surface (e.g., presented by MHC on a tumor cell, an infected cell, or an immune cell, including professional antigen presenting cells such as dendritic cells), and/or are likely to be immunogenic. As an example, one such method may comprise the steps of: obtaining at least one of exome, transcriptome or whole genome nucleotide sequencing and/or expression data from a tumor, an infected cell, or an infectious disease organism, wherein the nucleotide sequencing data and/or expression data is used to obtain data representing peptide sequences of each of a set of antigens (e.g., antigens derived from the tumor or infectious disease organism); inputting the peptide sequence of each antigen into one or more presentation models to generate a set of numerical likelihoods that each of the antigens is presented by one or more MHC alleles on a cell surface, such as a tumor cell or an infected cell of the subject, the set of numerical likelihoods having been identified at least based on received mass spectrometry data; and selecting a subset of the set of antigens based on the set of numerical likelihoods to generate a set of selected antigens.

In one example directed to tumor vaccines, and which can be adapted to infectious disease vaccines, the presentation model can comprise a statistical regression or a machine learning (e.g., deep learning) model trained on a set of reference data (also referred to as a training data set) comprising a set of corresponding labels, wherein the set of reference data is obtained from each of a plurality of distinct subjects where optionally some subjects can have a tumor, and wherein the set of reference data comprises at least one of: data representing exome nucleic acid sequences from tumor tissue, data representing exome nucleic acid sequences from normal tissue, data representing transcriptome nucleic acid sequences from tumor tissue, data representing proteome sequences from tumor tissue, and data representing MHC peptidome sequences from tumor tissue, and data representing MHC peptidome sequences from normal tissue. The reference data can further comprise mass spectrometry data, sequencing data, RNA sequencing data, expression profiling data, and proteomics data for single-allele cell lines engineered to express a predetermined MHC allele that are subsequently exposed to synthetic protein, normal and tumor human cell lines, and fresh and frozen primary samples, and T cell assays (e.g., ELISPOT). In certain aspects, the set of reference data includes each form of reference data.

The presentation model can comprise a set of features derived at least in part from the set of reference data, and wherein the set of features comprises at least one of allele dependent-features and allele-independent features. In certain aspects each feature is included.

Methods for identifying antigens also include generating an output for constructing a personalized vaccine by identifying one or more antigens that are likely to be presented on a surface of subject's cells, such as a tumor cell or infected cell. As an example directed to tumor vaccines, and which can be adapted to infectious disease vaccines, one such method may comprise the steps of: obtaining at least one of exome, transcriptome, or whole genome nucleotide sequencing and/or expression data from the tumor cells and normal cells of the subject, wherein the nucleotide sequencing and/or expression data is used to obtain data representing peptide sequences of each of a set of antigens identified by comparing the nucleotide sequencing and/or expression data from the tumor cells and the nucleotide sequencing and/or expression data from the normal cells (e.g., in the case of neoantigens wherein the peptide sequence of each neoantigen comprises at least one alteration that makes it distinct from the corresponding wild-type peptide sequence or in cases of antigens without a mutation where peptides are derived from any polypeptide known to or have been found to have altered expression in a tumor cell or cancerous tissue in comparison to a normal cell or tissue), peptide sequence identified from the normal cells of the subject; encoding the peptide sequences of each of the antigens into a corresponding numerical vector, each numerical vector including information regarding a plurality of amino acids that make up the peptide sequence and a set of positions of the amino acids in the peptide sequence; inputting the numerical vectors, using a computer processor, into a deep learning presentation model to generate a set of presentation likelihoods for the set of antigens, each presentation likelihood in the set representing the likelihood that a corresponding antigen is presented by one or more class II MHC alleles on the surface of the tumor cells of the subject, the deep learning presentation model; selecting a subset of the set of antigens based on the set of presentation likelihoods to generate a set of selected antigens; and generating the output for constructing the personalized cancer vaccine based on the set of selected antigens.

Specific methods for identifying antigens, including neoantigens, are known to those skilled in the art, for example the methods described in more detail in international patent application publications WO/2017/106638, WO/2018/195357, and WO/2018/208856, each herein incorporated by reference, in their entirety, for all purposes.

A method of treating a subject having a tumor is disclosed herein, comprising performing the steps of any of the antigen identification methods described herein, and further comprising obtaining a tumor vaccine comprising the set of selected antigens, and administering the tumor vaccine to the subject.

A method disclosed herein can also include identifying one or more T cells that are antigen-specific for at least one of the antigens in the subset. In some embodiments, the identification comprises co-culturing the one or more T cells with one or more of the antigens in the subset under conditions that expand the one or more antigen-specific T cells. In further embodiments, the identification comprises contacting the one or more T cells with a tetramer comprising one or more of the antigens in the subset under conditions that allow binding between the T cell and the tetramer. In even further embodiments, the method disclosed herein can also include identifying one or more T cell receptors (TCR) of the one or more identified T cells. In certain embodiments, identifying the one or more T cell receptors comprises sequencing the T cell receptor sequences of the one or more identified T cells. The method disclosed herein can further comprise genetically engineering a plurality of T cells to express at least one of the one or more identified T cell receptors; culturing the plurality of T cells under conditions that expand the plurality of T cells; and infusing the expanded T cells into the subject. In some embodiments, genetically engineering the plurality of T cells to express at least one of the one or more identified T cell receptors comprises cloning the T cell receptor sequences of the one or more identified T cells into an expression vector; and transfecting each of the plurality of T cells with the expression vector. In some embodiments, the method disclosed herein further comprises culturing the one or more identified T cells under conditions that expand the one or more identified T cells; and infusing the expanded T cells into the subject.

Also disclosed herein is an isolated T cell that is antigen-specific for at least one selected antigen in the subset.

Also disclosed herein is a methods for manufacturing a tumor vaccine, comprising the steps of: obtaining at least one of exome, transcriptome or whole genome tumor nucleotide sequencing and/or expression data from the tumor cell of the subject, wherein the tumor nucleotide sequencing and/or expression data is used to obtain data representing peptide sequences of each of a set of antigens (e.g., in the case of neoantigens wherein the peptide sequence of each neoantigen comprises at least one alteration that makes it distinct from the corresponding wild-type peptide sequence or in cases of antigens without a mutation where peptides are derived from any polypeptide known to or have been found to have altered expression in a tumor cell or cancerous tissue in comparison to a normal cell or tissue); inputting the peptide sequence of each antigen into one or more presentation models to generate a set of numerical likelihoods that each of the antigens is presented by one or more MHC alleles on the tumor cell surface of the tumor cell of the subject, the set of numerical likelihoods having been identified at least based on received mass spectrometry data; and selecting a subset of the set of antigens based on the set of numerical likelihoods to generate a set of selected antigens; and producing or having produced a tumor vaccine comprising the set of selected antigens.

Also disclosed herein is a tumor vaccine including a set of selected antigens selected by performing the method comprising the steps of: obtaining at least one of exome, transcriptome or whole genome tumor nucleotide sequencing and/or expression data from the tumor cell of the subject, wherein the tumor nucleotide sequencing and/or expression data is used to obtain data representing peptide sequences of each of a set of antigens, and wherein the peptide sequence of each antigen (e.g., in the case of neoantigens wherein the peptide sequence of each neoantigen comprises at least one alteration that makes it distinct from the corresponding wild-type peptide sequence or in other cases of antigens without a mutation where peptides are derived from any polypeptide known to or have been found to have altered expression in a tumor cell or cancerous tissue in comparison to a normal cell or tissue); inputting the peptide sequence of each antigen into one or more presentation models to generate a set of numerical likelihoods that each of the antigens is presented by one or more MHC alleles on the tumor cell surface of the tumor cell of the subject, the set of numerical likelihoods having been identified at least based on received mass spectrometry data; and selecting a subset of the set of antigens based on the set of numerical likelihoods to generate a set of selected antigens; and producing or having produced a tumor vaccine comprising the set of selected antigens.

The tumor vaccine may include one or more of a nucleic acid sequence, a polypeptide sequence, RNA, DNA, a cell, a plasmid, or a vector.

The tumor vaccine may include one or more antigens presented on the tumor cell surface.

The tumor vaccine may include one or more antigens that is immunogenic in the subject.

The tumor vaccine may not include one or more antigens that induce an autoimmune response against normal tissue in the subject.

The tumor vaccine may include an adjuvant.

The tumor vaccine may include an excipient.

A method disclosed herein may also include selecting antigens that have an increased likelihood of being presented on the tumor cell surface relative to unselected antigens based on the presentation model.

A method disclosed herein may also include selecting antigens that have an increased likelihood of being capable of inducing a tumor-specific immune response in the subject relative to unselected antigens based on the presentation model.

A method disclosed herein may also include selecting antigens that have an increased likelihood of being capable of being presented to naïve T cells by professional antigen presenting cells (APCs) relative to unselected antigens based on the presentation model, optionally wherein the APC is a dendritic cell (DC).

A method disclosed herein may also include selecting antigens that have a decreased likelihood of being subject to inhibition via central or peripheral tolerance relative to unselected antigens based on the presentation model.

A method disclosed herein may also include selecting antigens that have a decreased likelihood of being capable of inducing an autoimmune response to normal tissue in the subject relative to unselected antigens based on the presentation model.

The exome or transcriptome nucleotide sequencing and/or expression data may be obtained by performing sequencing on the tumor tissue.

The sequencing may be next generation sequencing (NGS) or any massively parallel sequencing approach.

The set of numerical likelihoods may be further identified by at least MHC-allele interacting features comprising at least one of: the predicted affinity with which the MHC allele and the antigen encoded peptide bind; the predicted stability of the antigen encoded peptide-MHC complex; the sequence and length of the antigen encoded peptide; the probability of presentation of antigen encoded peptides with similar sequence in cells from other individuals expressing the particular MHC allele as assessed by mass-spectrometry proteomics or other means; the expression levels of the particular MHC allele in the subject in question (e.g. as measured by RNA-seq or mass spectrometry); the overall neoantigen encoded peptide-sequence-independent probability of presentation by the particular MHC allele in other distinct subjects who express the particular MHC allele; the overall neoantigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.

The set of numerical likelihoods are further identified by at least MHC-allele noninteracting features comprising at least one of: the C- and N-terminal sequences flanking the neoantigen encoded peptide within its source protein sequence; the presence of protease cleavage motifs in the neoantigen encoded peptide, optionally weighted according to the expression of corresponding proteases in the tumor cells (as measured by RNA-seq or mass spectrometry); the turnover rate of the source protein as measured in the appropriate cell type; the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data; the level of expression of the proteasome, immunoproteasome, thymoproteasome, or other proteases in the tumor cells (which may be measured by RNA-seq, proteome mass spectrometry, or immunohistochemistry); the expression of the source gene of the neoantigen encoded peptide (e.g., as measured by RNA-seq or mass spectrometry); the typical tissue-specific expression of the source gene of the neoantigen encoded peptide during various stages of the cell cycle; a comprehensive catalog of features of the source protein and/or its domains as can be found in e.g. uniProt or PDB www.rcsb.org/pdb/home/home.do; features describing the properties of the domain of the source protein containing the peptide, for example: secondary or tertiary structure (e.g., alpha helix vs beta sheet); alternative splicing; the probability of presentation of peptides from the source protein of the neoantigen encoded peptide in question in other distinct subjects; the probability that the peptide will not be detected or over-represented by mass spectrometry due to technical biases; the expression of various gene modules/pathways as measured by RNASeq (which need not contain the source protein of the peptide) that are informative about the state of the tumor cells, stroma, or tumor-infiltrating lymphocytes (TILs); the copy number of the source gene of the neoantigen encoded peptide in the tumor cells; the probability that the peptide binds to the TAP or the measured or predicted binding affinity of the peptide to the TAP; the expression level of TAP in the tumor cells (which may be measured by RNA-seq, proteome mass spectrometry, immunohistochemistry); presence or absence of tumor mutations, including, but not limited to: driver mutations in known cancer driver genes such as EGFR, KRAS, ALK, RET, ROS1, TP53, CDKN2A, CDKN2B, NTRK1, NTRK2, NTRK3, and in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation; presence or absence of functional germline polymorphisms, including, but not limited to: in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome); tumor type (e.g., NSCLC, melanoma); clinical tumor subtype (e.g., squamous lung cancer vs. non-squamous); smoking history; the typical expression of the source gene of the peptide in the relevant tumor type or clinical subtype, optionally stratified by driver mutation.

The at least one alteration may be a frameshift or non-frameshift indel, missense or nonsense substitution, splice site alteration, genomic rearrangement or gene fusion, or any genomic or expression alteration giving rise to a neoORF.

The tumor cell may be selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

A method disclosed herein may also include obtaining a tumor vaccine comprising the set of selected neoantigens or a subset thereof, optionally further comprising administering the tumor vaccine to the subject.

At least one of neoantigens in the set of selected neoantigens, when in polypeptide form, may include at least one of: a binding affinity with MHC with an IC50 value of less than 1000 nM, for MHC Class I polypeptides a length of 8-15, 8, 9, 10, 11, 12, 13, 14, or 15 amino acids, for MHC Class II polypeptides a length of 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the polypeptide in the parent protein sequence promoting proteasome cleavage, and presence of sequence motifs promoting TAP transport. For MHC Class II, presence of sequence motifs within or near the peptide promoting cleavage by extracellular or lysosomal proteases (e.g., cathepsins) or HLA-DM catalyzed HLA binding.

Disclosed herein is are methods for identifying one or more neoantigens that are likely to be presented on a tumor cell surface of a tumor cell, comprising executing the steps of: receiving mass spectrometry data comprising data associated with a plurality of isolated peptides eluted from major histocompatibility complex (MHC) derived from a plurality of fresh or frozen tumor samples; obtaining a training data set by at least identifying a set of training peptide sequences present in the tumor samples and presented on one or more MHC alleles associated with each training peptide sequence; obtaining a set of training protein sequences based on the training peptide sequences; and training a set of numerical parameters of a presentation model using the training protein sequences and the training peptide sequences, the presentation model providing a plurality of numerical likelihoods that peptide sequences from the tumor cell are presented by one or more MHC alleles on the tumor cell surface.

The presentation model may represent dependence between: presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include selecting a subset of neoantigens, wherein the subset of neoantigens is selected because each has an increased likelihood that it is presented on the cell surface of the tumor relative to one or more distinct tumor neoantigens.

A method disclosed herein can also include selecting a subset of neoantigens, wherein the subset of neoantigens is selected because each has an increased likelihood that it is capable of inducing a tumor-specific immune response in the subject relative to one or more distinct tumor neoantigens.

A method disclosed herein can also include selecting a subset of neoantigens, wherein the subset of neoantigens is selected because each has an increased likelihood that it is capable of being presented to naïve T cells by professional antigen presenting cells (APCs) relative to one or more distinct tumor neoantigens, optionally wherein the APC is a dendritic cell (DC).

A method disclosed herein can also include selecting a subset of neoantigens, wherein the subset of neoantigens is selected because each has a decreased likelihood that it is subject to inhibition via central or peripheral tolerance relative to one or more distinct tumor neoantigens.

A method disclosed herein can also include selecting a subset of neoantigens, wherein the subset of neoantigens is selected because each has a decreased likelihood that it is capable of inducing an autoimmune response to normal tissue in the subject relative to one or more distinct tumor neoantigens.

A method disclosed herein can also include selecting a subset of neoantigens, wherein the subset of neoantigens is selected because each has a decreased likelihood that it will be differentially post-translationally modified in tumor cells versus APCs, optionally wherein the APC is a dendritic cell (DC).

The practice of the methods herein will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); Remington's Pharmaceutical Sciences, 18th Edition (Easton, Pa.: Mack Publishing Company, 1990); Carey and Sundberg *Advanced Organic Chemistry 3^rd Ed.* (Plenum Press) Vols A and B (1992).

III. Identification of Tumor Specific Mutations in Neoantigens

Also disclosed herein are methods for the identification of certain mutations (e.g., the variants or alleles that are present in cancer cells). In particular, these mutations can be present in the genome, transcriptome, proteome, or exome of cancer cells of a subject having cancer but not in normal tissue from the subject. Specific methods for identifying neoantigens, including shared neoantigens, that are specific to tumors are known to those skilled in the art, for example the methods described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

Genetic mutations in tumors can be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence. Mutations can also include one or more of nonframeshift indel, missense or nonsense substitution, splice site alteration, genomic rearrangement or gene fusion, or any genomic or expression alteration giving rise to a neoORF.

Peptides with mutations or mutated polypeptides arising from for example, splice-site, frameshift, readthrough, or gene fusion mutations in tumor cells can be identified by sequencing DNA, RNA or protein in tumor versus normal cells.

Also mutations can include previously identified tumor specific mutations. Known tumor mutations can be found at the Catalogue of Somatic Mutations in Cancer (COSMIC) database.

A variety of methods are available for detecting the presence of a particular mutation or allele in an individual's DNA or RNA. Advancements in this field have provided accurate, easy, and inexpensive large-scale SNP genotyping. For example, several techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods utilize amplification of a target genetic region, typically by PCR. Still other methods, based on the generation of small signal molecules by invasive cleavage followed by mass spectrometry or immobilized padlock probes and rolling-circle amplification. Several of the methods known in the art for detecting specific mutations are summarized below.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. For example, a single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide(s) present in the polymorphic site of the target molecule is complementary to that of the nucleotide derivative used in the reaction. This method has the advantage that it does not require the determination of large amounts of extraneous sequence data.

A solution-based method can be used for determining the identity of a nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. can be a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA in that they utilize incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

A number of initiatives obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Any suitable sequencing-by-synthesis platform can be used to identify mutations. As described above, four major sequencing-by-synthesis platforms are currently available: the Genome Sequencers from Roche/454 Life Sciences, the 1G Analyzer from Illumina/Solexa, the SOLiD system from Applied BioSystems, and the Heliscope system from Helicos Biosciences. Sequencing-by-synthesis platforms have also been described by Pacific BioSciences and VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., US Patent Application No. 2006/0252077) can be linked to each fragment to be captured on a surface coated with a respective second member of that coupling pair.

Subsequent to the capture, the sequence can be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Sequencing can also include other massively parallel sequencing or next generation sequencing (NGS) techniques and platforms. Additional examples of massively parallel sequencing techniques and platforms are the Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies.

Any cell type or tissue can be utilized to obtain nucleic acid samples for use in methods described herein. For example, a DNA or RNA sample can be obtained from a tumor or a bodily fluid, e.g., blood, obtained by known techniques (e.g. venipuncture) or saliva. Alternatively, nucleic acid tests can be performed on dry samples (e.g. hair or skin). In addition, a sample can be obtained for sequencing from a tumor and another sample can be obtained from normal tissue for sequencing where the normal tissue is of the same tissue type as the tumor. A sample can be obtained for sequencing from a tumor and another sample can be obtained from normal tissue for sequencing where the normal tissue is of a distinct tissue type relative to the tumor.

Tumors can include one or more of lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

Alternatively, protein mass spectrometry can be used to identify or validate the presence of mutated peptides bound to MHC proteins on tumor cells. Peptides can be acid-eluted from tumor cells or from HLA molecules that are immunoprecipitated from tumor, and then identified using mass spectrometry.

IV. Antigens

Antigens can include nucleotides or polypeptides. For example, an antigen can be an RNA sequence that encodes for a polypeptide sequence. Antigens useful in vaccines can therefore include nucleic acid sequences or polypeptide sequences.

Disclosed herein are isolated peptides that comprise tumor specific mutations identified by the methods disclosed herein, peptides that comprise known tumor specific mutations, and mutant polypeptides or fragments thereof identified by methods disclosed herein. Neoantigen peptides can be described in the context of their coding sequence where a neoantigen includes the nucleic acid sequence (e.g., DNA or RNA) that codes for the related polypeptide sequence.

Also disclosed herein are peptides derived from any polypeptide known to or have been found to have altered expression in a tumor cell or cancerous tissue in comparison to a normal cell or tissue, for example any polypeptide known to or have been found to be aberrantly expressed in a tumor cell or cancerous tissue in comparison to a normal cell or tissue. Suitable polypeptides from which the antigenic peptides can be derived can be found for example in the COSMIC database. COSMIC curates comprehensive information on somatic mutations in human cancer. The peptide contains the tumor specific mutation.

The modified adenoviral vectors and other constructs described herein can be used to deliver antigens from any organism, including their toxins or other by-products, to prevent and/or treat infection or other adverse reactions associated with the organism or its by-product.

Antigens that can be incorporated into a vaccine (e.g., encoded in a cassette) include immunogens which are useful to immunize a human or non-human animal against viruses, such as pathogenic viruses which infect human and non-human vertebrates. Antigens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The Flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus (e.g., the glyco-(G) protein and the fusion (F) protein, for which sequences are available from GenBank). Influenza virus is classified within the family orthomyxovirus and can be suitable source of antigens (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. Nos. 5,891,994 and 6,193,981.] See, also, the HIV and SIV proteins described in D. H. Barouch et al, J. Virol., 75(5):2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (Human CMV), muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

Antigens that can be incorporated into a vaccine (e.g., encoded in a cassette) also include immunogens which are useful to immunize a human or non-human animal against pathogens including bacteria, fungi, parasitic microorganisms or multicellular parasites which infect human and non-human vertebrates. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus (*Haemophilus influenzae, Haemophilus somnus*); moraxella; *H. ducreyi* (which causes chancroid); brucella; *Franisella tularensis* (which causes tularemia); yersinia (pasteurella); *Streptobacillus moniliformis* and spirillum. Gram-positive bacilli include *Listeria monocytogenes; Erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Examples of specific bacterium species are, without limitation, *Streptococcus pneumoniae, Streptococcus pyogenes, Streptococcus agalactiae, Streptococcus faecalis, Moraxella catarrhalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium, Mycobacterium intracellulare* complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum*. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis (*Cryptococcus*), blastomycosis (*Blastomyces*), histoplasmosis (*Histoplasma*) and coccidioidomycosis (*Coccidiodes*); candidiasis (*Candida*), aspergillosis (*Aspergillis*), and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: *Mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis (e.g., caused by *Leishmania major*); trypanosomiasis; toxoplasmosis (e.g., caused by *Toxoplasma gondii*); *Pneumocystis carinii*; Trichans; *Toxoplasma gondii*; babesiosis; giardiasis (e.g., caused by Giardia); trichinosis (e.g., caused by *Trichomonas*); filariasis; schistosomiasis (e.g., caused by *Schistosoma*); nematodes; trematodes or flukes; and cestode (tapeworm) infections. Other parasitic infections may be caused by *Ascaris, Trichuris, Cryptosporidium*, and *Pneumocystis carinii*, among others.

Also disclosed herein are peptides derived from any polypeptide associated with an infectious disease organism, an infection in a subject, or an infected cell of a subject. Antigens can be derived from nucleic acid sequences or polypeptide sequences of an infectious disease organism. Polypeptide sequences of an infectious disease organism include, but are not limited to, a pathogen-derived peptide, a virus-derived peptide, a bacteria-derived peptide, a fungus-derived peptide, and/or a parasite-derived peptide. Infectious disease organism include, but are not limited to, Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), and tuberculosis.

Antigens can be selected that are predicted to be presented on the cell surface of a cell, such as a tumor cell, an infected cell, or an immune cell, including professional antigen presenting cells such as dendritic cells. Antigens can be selected that are predicted to be immunogenic.

One or more polypeptides encoded by an antigen nucleic acid sequence can comprise at least one of: a binding affinity with MHC with an IC50 value of less than 1000 nM, for MHC Class I peptides a length of 8-15, 8, 9, 10, 11, 12, 13, 14, or 15 amino acids, presence of sequence motifs within or near the peptide promoting proteasome cleavage, and presence or sequence motifs promoting TAP transport. For MHC Class II peptides a length 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the peptide promoting cleavage by extracellular or lysosomal proteases (e.g., cathepsins) or HLA-DM catalyzed HLA binding.

One or more antigens can be presented on the surface of a tumor. One or more antigens can be presented on the surface of an infected cell.

One or more antigens can be immunogenic in a subject having a tumor, e.g., capable of eliciting a T cell response or a B cell response in the subject. One or more antigens can be immunogenic in a subject having or suspected to have an infection, e.g., capable of eliciting a T cell response or a B cell response in the subject. One or more antigens can be immunogenic in a subject at risk of an infection, e.g., capable of eliciting a T cell response or a B cell response in the subject that provides immunological protection (i.e., immunity) against the infection, e.g., such as stimulating the production of memory T cells, memory B cells, or antibodies specific to the infection.

One or more antigens can be capable of eliciting a B cell response, such as the production of antibodies that recognize the one or more antigens. Antibodies can recognize linear polypeptide sequences or recognize secondary and tertiary structures. Accordingly, B cell antigens can include linear polypeptide sequences or polypeptides having secondary and tertiary structures, including, but not limited to, full-length proteins, protein subunits, protein domains, or any polypeptide sequence known or predicted to have secondary and tertiary structures.

One or more antigens that induce an autoimmune response in a subject can be excluded from consideration in the context of vaccine generation for a subject.

The size of at least one antigenic peptide molecule (e.g., an epitope sequence) can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the antigenic peptide molecules are equal to or less than 50 amino acids.

Antigenic peptides and polypeptides can be: for MHC Class I 15 residues or less in length and usually consist of between about 8 and about 11 residues, particularly 9 or 10 residues; for MHC Class II, 6-30 residues, inclusive.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific or infectious disease-specific amino acids—thus bypassing the need for computational or in vitro test-based selection of the strongest HLA-presented shorter peptide. In both cases, use of a longer peptide allows endogenous processing by patient cells and may lead to more effective antigen presentation and induction of T cell responses.

Antigenic peptides and polypeptides can be presented on an HLA protein. In some aspects antigenic peptides and polypeptides are presented on an HLA protein with greater affinity than a wild-type peptide. In some aspects, an antigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, antigenic peptides and polypeptides do not induce an autoimmune response and/or invoke immunological tolerance when administered to a subject.

Also provided are compositions comprising at least two or more antigenic peptides. In some embodiments the composition contains at least two distinct peptides. At least two distinct peptides can be derived from the same polypeptide. By distinct polypeptides is meant that the peptide vary by length, amino acid sequence, or both. The peptides can be derived from any polypeptide known to or have been found to contain a tumor specific mutation or peptides derived from any polypeptide known to or have been found to have altered expression in a tumor cell or cancerous tissue in comparison to a normal cell or tissue, for example any polypeptide known to or have been found to be aberrantly expressed in a tumor cell or cancerous tissue in comparison to a normal cell or tissue. Suitable polypeptides from which the antigenic peptides can be derived can be found for example in the COSMIC database or the AACR Genomics Evidence Neoplasia Information Exchange (GENIE) database. COSMIC curates comprehensive information on somatic mutations in human cancer. AACR GENIE aggregates and links clinical-grade cancer genomic data with clinical outcomes from tens of thousands of cancer patients. In some aspects the tumor specific mutation is a driver mutation for a particular cancer type. The peptides can be derived from any polypeptide known to or suspected to be associated with an infectious disease organism, or peptides derived from any polypeptide known to or have been found to have altered expression in an infected cell in comparison to a normal cell or tissue (e.g., an infectious disease polynucleotide or polypeptide, including infectious disease polynucleotides or polypeptides with expression restricted to a host cell).

Antigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T cell. For instance, antigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to induce CTL activity can be enhanced by linkage to a sequence which contains at least one epitope that is capable of inducing a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

An antigenic peptide can be linked to the T helper peptide either directly or via a spacer either at the amino or carboxy terminus of the peptide. The amino terminus of either the antigenic peptide or the T helper peptide can be acylated. Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect an antigen includes a nucleic acid (e.g. polynucleotide) that encodes an antigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothioate backbone, or combinations thereof and it may or may not contain introns. A still further aspect provides an expression vector capable of expressing a polypeptide or portion thereof. Expression vectors for different cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleic acid sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

V. Delivery Compositions

Also disclosed herein is an immunogenic composition, e.g., a vaccine composition, capable of raising a specific immune response, e.g., a tumor-specific immune response or an infectious disease organism-specific immune response. Vaccine compositions typically comprise one or a plurality of antigens, e.g., selected using a method described herein. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleic acid sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleic acid sequences, 6, 7, 8, 9, 10 11, 12, 13, or 14 different nucleic acid sequences, or 12, 13 or 14 different nucleic acid sequences. A vaccine can contain between 1 and 30 antigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different antigen sequences, 6, 7, 8, 9, 10 11, 12, 13, or 14 different antigen sequences, or 12, 13 or 14 different antigen sequences.

A vaccine can contain between 1 and 30 antigen-encoding nucleic acid sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different antigen-encoding nucleic acid sequences, 6, 7, 8, 9, 10 11, 12, 13, or 14 different antigen-encoding nucleic acid sequences, or 12, 13 or 14 different antigen-encoding nucleic acid sequences. Antigen-encoding nucleic acid sequences can refer to the antigen encoding portion of an antigen "cassette." Features of an cassette are described in greater detail below.

A vaccine can contain between 1 and 30 distinct epitope-encoding nucleic acid sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more distinct epitope-encoding nucleic acid sequences, 6, 7, 8, 9, 10 11, 12, 13, or 14 distinct epitope-encoding nucleic acid sequences, or 12, 13 or 14 distinct epitope-encoding nucleic acid sequences. Epitope-encoding nucleic acid sequences can refer to sequences for individual epitope sequences.

A vaccine can contain at least two repeats of an epitope-encoding nucleic acid sequence. A used herein, a "repeat" refers to two or more iterations of an identical nucleic acid epitope-encoding nucleic acid sequence (inclusive of the optional 5' linker sequence and/or the optional 3' linker sequences described herein) within an antigen-encoding nucleic acid sequence. In one example, the antigen-encoding nucleic acid sequence portion of a cassette encodes at least two repeats of an epitope-encoding nucleic acid sequence. In further non-limiting examples, the antigen-encoding nucleic acid sequence portion of a cassette encodes more than one distinct epitope, and at least one of the distinct epitopes is encoded by at least two repeats of the nucleic acid sequence encoding the distinct epitope (i.e., at least two distinct epitope-encoding nucleic acid sequences). In illustrative non-limiting examples, an antigen-encoding nucleic acid sequence encodes epitopes A, B, and C encoded by epitope-encoding nucleic acid sequences epitope-encoding sequence A (EA), epitope-encoding sequence B (EB), and epitope-encoding sequence C (Ec), and exemplary antigen-encoding nucleic acid sequences having repeats of at least one of the distinct epitopes are illustrated by, but is not limited to, the formulas below:

Repeat of one distinct epitope (repeat of epitope A):

$E_A$-$E_B$-$E_C$-$E_A$; or $E_A$-$E_A$-$E_B$-$E_C$

Repeat of multiple distinct epitopes (repeats of epitopes A, B, and C):

$E_A$-$E_B$-$E_C$-$E_A$-$E_B$-$E_C$; or $E_A$-$E_A$-$E_B$-$E_B$-$E_C$-$E_C$

Multiple repeats of multiple distinct epitopes (repeats of epitopes A, B, and C):

$E_A$-$E_B$-$E_C$-$E_A$-$E_B$-$E_C$-$E_A$-$E_B$-$E_C$; or $E_A$-$E_A$-$E_A$-$E_B$-$E_B$-$E_B$-$E_C$-$E_C$-$E_C$

The above examples are not limiting and the antigen-encoding nucleic acid sequences having repeats of at least one of the distinct epitopes can encode each of the distinct epitopes in any order or frequency. For example, the order and frequency can be a random arrangement of the distinct epitopes, e.g., in an example with epitopes A, B, and C, by the formula $E_A$-$E_B$-$E_C$-$E_C$-$E_A$-$E_B$-$E_A$-$E_C$-$E_A$-$E_C$-$E_C$-$E_B$.

Also provided for herein is an antigen-encoding cassette, the antigen-encoding cassette having at least one antigen-encoding nucleic acid sequence described, from 5' to 3', by the formula:

$$(E_x\text{-}(E^N{}_n)_y)_z$$

where E represents a nucleic acid sequence comprising at least one of the at least one distinct epitope-encoding nucleic acid sequences, n represents the number of separate distinct epitope-encoding nucleic acid sequences and is any integer including 0, $E^N$ represents a nucleic acid sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof.

Each E or $E^N$ can independently comprise any epitope-encoding nucleic acid sequence described herein. For example, Each E or $E^N$ can independently comprises a nucleic acid sequence described, from 5' to 3', by the formula ($L5_b$-$N_c$-$L3_d$), where N comprises the distinct epitope-encoding nucleic acid sequence associated with each E or $E^N$, where c=1, L5 comprises a 5' linker sequence, where b=0 or 1, and L3 comprises a 3' linker sequence, where d=0 or 1. Epitopes and linkers that can be used are further described herein, e.g., see "V.A. Cassettes" section.

Repeats of an epitope-encoding nucleic acid sequences (inclusive of optional 5' linker sequence and/or the optional 3' linker sequences) can be linearly linked directly to one another (e.g., $E_A$-$E_A$- . . . as illustrated above). Repeats of an epitope-encoding nucleic acid sequences can be separated by one or more additional nucleotides sequences. In general, repeats of an epitope-encoding nucleic acid sequences can be separated by any size nucleic acid sequence applicable for the compositions described herein. In one example, repeats of an epitope-encoding nucleic acid sequences can be separated by a separate distinct epitope-encoding nucleic acid sequence (e.g., $E_A$-$E_B$-$E_C$-$E_A$ . . . , as illustrated above). In examples where repeats are separated by a single separate distinct epitope-encoding nucleic acid sequence, and each epitope-encoding nucleic acid sequences (inclusive of optional 5' linker sequence and/or the optional 3' linker sequences) encodes a peptide 25 amino acids in length, the repeats can be separated by 75 nucleotides, such as in antigen-encoding nucleic acid represented by $E_A$-$E_B$-$E_A$ . . . , $E_A$ is separated by 75 nucleotides. In an illustrative example, an antigen-encoding nucleic acid having the sequence VTNTEMFVTAPDNLGYMYEVQWPGQT-QPQIANCSVYDFFVWLHYYSVRDTVTNTE MFVTAP-DNLGYMYEVQWPGQTQPQIANCSVYDFFVWLH-YYSVRDT (SEQ ID NO: 74) encoding repeats of 25mer antigens Trp1 (VTNTEMFVTAPDNLGYMYEVQWPGQ (SEQ ID NO: 75)) and Trp2 (TQPQIANCSVYDFFVW-LHYYSVRDT (SEQ ID NO: 76)), the repeats of Trp1 are separated by the 25mer Trp2 and thus the repeats of the Trp1 epitope-encoding nucleic acid sequences are separated the 75 nucleotide Trp2 epitope-encoding nucleic acid sequence. In examples where repeats are separated by 2, 3, 4, 5, 6, 7, 8, or 9 separate distinct epitope-encoding nucleic acid sequence, and each epitope-encoding nucleic acid sequences (inclusive of optional 5' linker sequence and/or the optional 3' linker sequences) encodes a peptide 25 amino acids in length, the repeats can be separated by 150, 225, 300, 375, 450, 525, 600, or 675 nucleotides, respectively.

In one embodiment, different peptides and/or polypeptides or nucleic acid sequences encoding them are selected so that the peptides and/or polypeptides capable of associating with different MHC molecules, such as different MHC class I molecules and/or different MHC class II molecules. In some aspects, one vaccine composition comprises coding sequence for peptides and/or polypeptides capable of associating with the most frequently occurring MHC class I molecules and/or different MHC class II molecules. Hence, vaccine compositions can comprise different fragments capable of associating with at least 2 preferred, at least 3 preferred, or at least 4 preferred MHC class I molecules and/or different MHC class II molecules.

The vaccine composition can be capable of raising a specific cytotoxic T-cells response and/or a specific helper T-cell response.

A vaccine composition can further comprise an adjuvant and/or a carrier. Examples of useful adjuvants and carriers are given herein below. A composition can be associated with a carrier such as e.g. a protein or an antigen-presenting cell such as e.g. a dendritic cell (DC) capable of presenting the peptide to a T-cell.

Adjuvants are any substance whose admixture into a vaccine composition increases or otherwise modifies the immune response to an antigen. Carriers can be scaffold structures, for example a polypeptide or a polysaccharide, to which an antigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diptheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleic acid sequences that encode one or more antigenic peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, Science. (2016) 352 (6291):1337-41, Lu et al., Efficient identification of mutated cancer antigens recognized by T cells associated with durable tumor regressions, *Clin Cancer Res.* (2014) 20(13): 3401-10). Upon introduction into a host, infected cells express the antigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

Also disclosed herein is an adenoviral vector delivery composition capable of delivering one or more payload nucleic acid sequences. A payload nucleic acid sequence can be any nucleic acid sequence desired to be delivered to a cell of interest. In general, the payload is a nucleic acid sequence linked to a promoter to drive expression of the nucleic acid sequence. The payload nucleic acid sequence can encode a polypeptide (i.e., a nucleic acid sequence capable of being transcribed and translated into a protein). In general, a payload nucleic acid sequence encoding a peptide can encode any protein desired to be expressed in a cell. Examples of proteins include, but are not limited to, an antigen (e.g., a MHC class I epitope, a MHC class II epitope, or an epitope capable of stimulating a B cell response), an antibody, a cytokine, a chimeric antigen receptor (CAR), a T-cell receptor, or a genome-editing system component (e.g., a nuclease used in a genome-editing system). Genome-editing systems include, but are not limited to, a CRISPR system, a zinc-finger system, a meganuclease system, or a TALEN system. The payload nucleic acid sequence can be non-coding (i.e., a nucleic acid sequence capable of being transcribed but is not translated into a protein). In general, a non-coding payload nucleic acid sequence can be any non-coding polynucleotide desired to be expressed in a cell. Examples of non-coding polynucleotides include, but are not limited to, RNA interference (RNAi) polynucleotides (e.g., antisense oligonucleotides, shRNAs, siRNAs, miRNAs etc.) or genome-editing system polynucleotide (e.g., a guide RNA [gRNA], a single-guide RNA [sgRNA], a trans-activating CRISPR [tracrRNA], and/or a CRISPR RNA [crRNA]). A payload nucleic acid sequence can encode two or more (e.g., 2, 3, 4, 5 or more) distinct polypeptides (e.g., two or more distinct epitope sequences linked together) or contain two or more distinct non-coding nucleic acid sequences (e.g., two or more distinct RNAi polynucleotides). A payload nucleic acid sequence can have a combination of polypeptide-encoding nucleic acid sequences and non-coding nucleic acid sequences.

V.A.1 Cassettes

The methods employed for the selection of one or more antigens, the cloning and construction of a "cassette" and its insertion into a viral vector are within the skill in the art given the teachings provided herein. A cassette can have one or more payload nucleic acid sequences, such as a cassette containing multiple payload nucleic acid sequences each independently operably linked to separate promoters and/or linked together using other multicistonic systems, such as 2A ribosome skipping sequence elements (e.g., E2A, P2A, F2A, or T2A sequences) or Internal Ribosome Entry Site (IRES) sequence elements. In a cassette containing more than one payload nucleic acid sequence, each payload nucleic acid sequence can contain one or more payloads, e.g., each payload nucleic acid sequence can encode two or more polypeptides or contain two or more non-coding nucleic acid sequences. A cassette can have a combination of polypeptide-encoding nucleic acid sequences and non-coding nucleic acid sequences.

A cassette can be an antigen cassette. By "antigen cassette" is meant the combination of a selected antigen or plurality of antigens and the other regulatory elements necessary to transcribe the antigen(s) and express the transcribed product. Antigen cassettes can include one or more antigens. The selected antigen or plurality of antigens can refer to distinct epitope sequences, e.g., an antigen-encoding nucleic acid sequence in the cassette can encode an epitope-encoding nucleic acid sequence (or plurality of epitope-encoding nucleic acid sequences) such that the epitopes are transcribed and expressed.

A payload nucleic acid sequence or plurality of payload nucleic acid sequences can be operatively linked to regulatory components in a manner which permits transcription. Such components include conventional regulatory elements that can drive expression of the antigen(s) in a cell transfected with the viral vector. Thus the cassette can also contain a selected promoter which is linked to the payload nucleic acid sequence(s) and located, with other, optional regulatory elements, within the selected viral sequences of the recombinant vector.

Useful promoters can be constitutive promoters or regulated (e.g., inducible) promoters, which will enable control of the amount of payload nucleic acid sequence(s), and in general the amount of a peptide (e.g., an antigen) in the case of coding payload nucleic acid sequences, to be expressed. For example, a desirable promoter is that of the cytomegalovirus immediate early promoter/enhancer [see, e.g., Boshart et al, Cell, 41:521-530 (1985)]. Another desirable promoter includes the Rous sarcoma virus LTR promoter/enhancer. Still another promoter/enhancer sequence is the chicken cytoplasmic beta-actin promoter [T. A. Kost et al, Nucl. Acids Res., 11(23):8287 (1983)]. Other suitable or desirable promoters can be selected by one of skill in the art, such as a CMV, SV40, EF-1, RSV, PGK, HSA, MCK or EBV promoter sequence.

The cassette can also include nucleic acid sequences heterologous to the viral vector sequences including sequences providing signals for efficient polyadenylation of the transcript (poly(A), poly-A or pA) and introns with functional splice donor and acceptor sites. A common poly-A sequence which is employed in the exemplary vectors of this invention is that derived from the papovavirus SV-40. The poly-A sequence generally can be inserted in the cassette following the payload nucleic acid sequences and before the viral vector sequences. A common intron sequence can also be derived from SV-40, and is referred to as the SV-40 T intron sequence. A cassette can also contain such an intron, located between the promoter/enhancer sequence and the payload nucleic acid sequence(s). Selection of these and other common vector elements are conventional [see, e.g., Sambrook et al, "Molecular Cloning. A Laboratory Manual.", 2d edit, Cold Spring Harbor Laboratory, New York (1989) and references cited therein] and many such sequences are available from commercial and industrial sources as well as from Genbank.

A cassette can have one or more payload nucleic acid sequences. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more payload nucleic acid sequences. Payload nucleic acid sequences can be linked directly to one another. Payload nucleic acid sequences can also be linked to one another with linkers.

A cassette can have one or more payload nucleic acid sequences encoding a polypeptide. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more payload nucleic acid sequences encoding a polypeptide. A cassette can have one or more payload nucleic acid sequences where each payload nucleic acid sequence encodes a distinct polypeptide. A cassette can have one or more payload nucleic acid sequences where each payload nucleic acid sequence encodes one or more polypeptides. A cassette can have one or more payload nucleic acid sequences where one or more payload nucleic acid sequences encode one or more polypeptides. Polypeptides encoded by a payload nucleic acid sequence can be in any orientation relative to one another including N to C or C to N.

An antigen cassette can have one or more antigens. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more antigens. Antigens can be linked directly to one another. Antigens can also be linked to one another with linkers. Antigens can be in any orientation relative to one another including N to C or C to N.

As above stated, the cassette can be located in the site of any selected deletion in the viral vector, such as the site of the E1 gene region deletion or E3 gene region deletion, among others which may be selected.

The cassette can be described using the following formula to describe the ordered sequence of each element, from 5' to 3':

$$(P_a\text{-}(L5_b\text{-}N_c\text{-}L3_d)_X)_Z\text{-}(P2_h\text{-}(G5_e\text{-}U_f)_Y)_W\text{-}G3_g$$

wherein P and P2 comprise promoter nucleic acid sequences, N comprises a distinct epitope-encoding nucleic acid sequence, L5 comprises a 5' linker sequence, L3 comprises a 3' linker sequence, G5 comprises a nucleic acid sequences encoding an amino acid linker, G3 comprises one of the at least one nucleic acid sequences encoding an amino acid linker, U comprises an MHC class II antigen-encoding nucleic acid sequence, where for each X the corresponding Nc is a epitope encoding nucleic acid sequence, where for each Y the corresponding Uf is an antigen-encoding nucleic acid sequence. The composition and ordered sequence can be further defined by selecting the number of elements present, for example where a=0 or 1, where b=0 or 1, where c=1, where d=0 or 1, where e=0 or 1, where f=1, where g=0 or 1, where h=0 or 1, X=1 to 400, Y=0, 1, 2, 3, 4 or 5, Z=1 to 400, and W=0, 1, 2, 3, 4 or 5.

In one example, elements present include where a=0, b=1, d=1, e=1, g=1, h=0, X=10, Y=2, Z=1, and W=1, describing where no additional promoter is present (i.e. only the promoter nucleic acid sequence provided by the RNA alphavirus backbone is present), 20 MHC class I epitope are present, a 5' linker is present for each N, a 3' linker is present for each N, 2 MHC class II epitopes are present, a linker is present linking the two MHC class II epitopes, a linker is present linking the 5' end of the two MHC class II epitopes to the 3' linker of the final MHC class I epitope, and a linker is present linking the 3' end of the two MHC class II epitopes to the to the RNA alphavirus backbone. Examples of linking the 3' end of the cassette to the RNA alphavirus backbone include linking directly to the 3' UTR elements provided by the RNA alphavirus backbone, such as a 3' 19-nt CSE. Examples of linking the 5' end of the cassette to the RNA alphavirus backbone include linking directly to a 26S promoter sequence, an alphavirus 5' UTR, a 51-nt CSE, or a 24-nt CSE.

Other examples include: where a=1 describing where a promoter other than the promoter nucleic acid sequence provided by the RNA alphavirus backbone is present; where a=1 and Z is greater than 1 where multiple promoters other than the promoter nucleic acid sequence provided by the RNA alphavirus backbone are present each driving expression of 1 or more distinct MHC class I epitope encoding nucleic acid sequences; where h=1 describing where a separate promoter is present to drive expression of the MHC class II antigen-encoding nucleic acid sequences; and where g=0 describing the MHC class II antigen-encoding nucleic acid sequence, if present, is directly linked to the RNA alphavirus backbone.

Other examples include where each MHC class I epitope that is present can have a 5' linker, a 3' linker, neither, or both. In examples where more than one MHC class I epitope is present in the same cassette, some MHC class I epitopes may have both a 5' linker and a 3' linker, while other MHC class I epitopes may have either a 5' linker, a 3' linker, or neither. In other examples where more than one MHC class I epitope is present in the same cassette, some MHC class I epitopes may have either a 5' linker or a 3' linker, while other MHC class I epitopes may have either a 5' linker, a 3' linker, or neither.

In examples where more than one MHC class II epitope is present in the same cassette, some MHC class II epitopes may have both a 5' linker and a 3' linker, while other MHC class II epitopes may have either a 5' linker, a 3' linker, or neither. In other examples where more than one MHC class II epitope is present in the same cassette, some MHC class II epitopes may have either a 5' linker or a 3' linker, while other MHC class II epitopes may have either a 5' linker, a 3' linker, or neither.

The promoter nucleic acid sequences P and/or P2 can be the same as a promoter nucleic acid sequence provided by the RNA alphavirus backbone. For example, the promoter sequence provided by the RNA alphavirus backbone, Pn and P2, can each comprise a 26S subgenomic promoter. The promoter nucleic acid sequences P and/or P2 can be different from the promoter nucleic acid sequence provided by the RNA alphavirus backbone, as well as can be different from each other.

The 5' linker L5 can be a native sequence or a non-natural sequence. Non-natural sequence include, but are not limited to, AAY, RR, and DPP. The 3' linker L3 can also be a native sequence or a non-natural sequence. Additionally, L5 and L3 can both be native sequences, both be non-natural sequences, or one can be native and the other non-natural. For each X, the amino acid linkers can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each X, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G5, for each Y, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each Y, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G3 can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. G3 can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

For each X, each N can encodes a MHC class I epitope 7-15 amino acids in length. For each X, each N can also encodes a MHC class I epitope 5, 6, 7, 8, 9, 10, 11, 12, 13, 14, 15, 16, 17, 18, 19, 20, 21, 22, 23, 24, 25, 26, 27, 28, 29, or 30 amino acids in length. For each X, each N can also encodes a MHC class I epitope at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The cassette encoding the payload nucleic acid sequence can be 700 nucleotides or less. The cassette encoding the payload nucleic acid sequence can be 700 nucleotides or less and encode 2 distinct epitope-encoding nucleic acid sequences. The cassette encoding the payload nucleic acid sequence can be 700 nucleotides or less and encode at least 2 distinct epitope-encoding nucleic acid sequences. The cassette encoding the payload nucleic acid sequence can be 700 nucleotides or less and encode 3 distinct epitope-encoding nucleic acid sequences. The cassette encoding the payload nucleic acid sequence can be 700 nucleotides or less and encode at least 3 distinct epitope-encoding nucleic acid sequences. The cassette encoding the payload nucleic acid sequence can be 700 nucleotides or less and include 1-10, 1-5, 1, 2, 3, 4, 5, 6, 7, 8, 9, 10, or more antigens.

The cassette encoding the payload nucleic acid sequence can be between 375-700 nucleotides in length. The cassette encoding the payload nucleic acid sequence can be between 375-700 nucleotides in length and encode 2 distinct epitope-encoding nucleic acid sequences. The cassette encoding the payload nucleic acid sequence can be between 375-700 nucleotides in length and encode at least 2 distinct epitope-encoding nucleic acid sequences. The cassette encoding the payload nucleic acid sequence can be between 375-700 nucleotides in length and encode 3 distinct epitope-encoding nucleic acid sequences. The cassette encoding the payload nucleic acid sequence be between 375-700 nucleotides in length and encode at least 3 distinct epitope-encoding nucleic acid sequences. The cassette encoding the payload nucleic acid sequence can be between 375-700 nucleotides in length and include 1-10, 1-5, 1, 2, 3, 4, 5, 6, 7, 8, 9, 10, or more antigens.

The cassette encoding the payload nucleic acid sequence can be 600, 500, 400, 300, 200, or 100 nucleotides in length or less. The cassette encoding the payload nucleic acid sequence can be 600, 500, 400, 300, 200, or 100 nucleotides in length or less and encode 2 distinct epitope-encoding nucleic acid sequences. The cassette encoding the payload nucleic acid sequence can be 600, 500, 400, 300, 200, or 100 nucleotides in length or less and encode at least 2 distinct epitope-encoding nucleic acid sequences. The cassette encoding the payload nucleic acid sequence can be 600, 500, 400, 300, 200, or 100 nucleotides in length or less and encode 3 distinct epitope-encoding nucleic acid sequences. The cassette encoding the payload nucleic acid sequence can be 600, 500, 400, 300, 200, or 100 nucleotides in length or less and encode at least 3 distinct epitope-encoding nucleic acid sequences. The cassette encoding the payload nucleic acid sequence can be 600, 500, 400, 300, 200, or 100 nucleotides in length or less and include 1-10, 1-5, 1, 2, 3, 4, 5, 6, 7, 8, 9, 10, or more antigens.

The cassette encoding the payload nucleic acid sequence can be between 375-600, between 375-500, or between 375-400 nucleotides in length. The cassette encoding the payload nucleic acid sequence can be between 375-600, between 375-500, or between 375-400 nucleotides in length and encode 2 distinct epitope-encoding nucleic acid sequences. The cassette encoding the payload nucleic acid sequence can be between 375-600, between 375-500, or between 375-400 nucleotides in length and encode at least 2 distinct epitope-encoding nucleic acid sequences. The cassette encoding the payload nucleic acid sequence can be between 375-600, between 375-500, or between 375-400 nucleotides in length and encode 3 distinct epitope-encoding nucleic acid sequences. The cassette encoding the payload nucleic acid sequence can be between 375-600, between 375-500, or between 375-400 nucleotides in length and encode at least 3 distinct epitope-encoding nucleic acid sequences. The cassette encoding the payload nucleic acid sequence can be between 375-600, between 375-500, or between 375-400 nucleotides in length and include 1-10, 1-5, 1, 2, 3, 4, 5, 6, 7, 8, 9, 10, or more antigens.

V.A.2 TET Promoter System

Also disclosed herein is a viral vector comprising a cassette with at least one payload sequence operably linked to a regulatable promoter that is a TET promoter system, such as a TET-On system or TET-Off system. Without wishing to be bound by theory, a TET promoter system can be used to minimize transcription of payload nucleic acids encoded in a cassette, such as antigens encoded in a vaccine cassette, during viral production. A TET promoter system can include a tetracycline (TET) repressor protein (TETr) controlled promoter. Accordingly, also disclosed herein is a viral vector comprising a cassette with at least one payload sequence operably linked to a tetracycline (TET) repressor protein (TETr) controlled promoter. TETr sequences (tTS) can include the amino acid sequence shown in a SEQ ID NO:63 and/or encoded by the nucleotide sequence shown in SEQ ID NO:62. A TETr controlled promoter can include the 19 bp TET operator (TETo) sequence TCCCTATCAGTGATAGAGA (SEQ ID NO:60). A TETr controlled promoter can include 2, 3, 4, 5, 6, 7, 8, 9, or 10 or more TETo nucleic acid sequences. In TETr controlled promoter have 2 or more TETo nucleic acid sequences, the TETo sequences can be linked together. In TETr controlled promoter have 2 or more TETo nucleic acid sequences, the TETo sequences can be directly linked together. In TETr controlled promoter have 2 or more TETo nucleic acid sequences, the TETo sequences can be linked together with a linker sequence, such as a linker sequence having 1, 2, 3, 4, 5, 6, 7, 8, 9, 10, 11, 12, 13, 14, 15, 16, 17, 18, 19, or 20 or more nucleotides. In one example, the linker sequence has the linker nucleotide sequence shown in SEQ ID NO:61. In general, a TETr controlled promoter can use any promoter sequence desired, such as a SV40, EF-1, RSV, PGK, HSA, MCK or EBV promoter sequence. A TETr controlled promoter can use a CMV promoter sequence. A TETr controlled promoter can use a minimal CMV promoter sequence. TETo sequences can be upstream (5') of a promoter sequence region where RNA polymerase binds. In an illustrative example, 7 TETo sequences are upstream (5') of a promoter sequence. A TETr controlled promoter operably linked to the at least one payload nucleic acid sequence with TETo sequence upstream of the promoter sequence region can have an ordered sequence described in the formula, from 5' to 3':

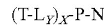

$$(T\text{-}L_Y)_X\text{-}P\text{-}N$$

where N is a payload nucleic acid sequence, P is a RNA polymerase binding sequence of the promoter sequence operably linked to payload nucleic acid sequence, T is a TETo nucleic acid sequences comprising the nucleotide sequence shown in SEQ ID NO:60, L is a linker sequence, where Y=0 or 1 for each X, and wherein X=1, 2, 3, 4, 5, 6, 7, 8, 9, 10, 11, 12, 13, 14, 15, 16, 17, 18, 19, or 20. In an illustrative example, X=7 and Y=1 for each X describes where 7 TETo sequences are upstream (5') of the promoter sequence and each TETo sequence is separated by a linker.

A TETo sequences can be downstream (3') of a promoter sequence region where RNA polymerase binds. In another illustrative example, 2 TETo sequences are downstream (3') of a promoter sequence. A TETr controlled promoter operably linked to the at least one payload nucleic acid sequence with TETo sequence downstream of the promoter sequence region can have an ordered sequence described in the formula, from 5' to 3':

$$P\text{-}(T\text{-}L_Y)_X\text{-}N$$

where N is a payload nucleic acid sequence, P is a RNA polymerase binding sequence of the promoter sequence operably linked to payload nucleic acid sequence, T is a TETo nucleic acid sequences comprising the nucleotide sequence shown in SEQ ID NO:60, L is a linker sequence, where Y=0 or 1 for each X, and wherein X=1, 2, 3, 4, 5, 6, 7, 8, 9, 10, 11, 12, 13, 14, 15, 16, 17, 18, 19, or 20. In an illustrative example, X=2 and Y=1 for each X describes where 2 TETo sequences are downstream (3') of the promoter sequence and each TETo sequence is separated by a linker.

Viral production of vectors with TETr controlled promoters can use any viral production cell line engineered to express a TETr sequence (tTS), such as a 293 cell line or its derivatives (e.g., a 293F cell line) engineered to express tTS. Viral production of vectors with TETr controlled promoters in tTS-expressing cell can improve viral production. Viral production of vectors with TETr controlled promoters in tTS-expressing cell can improve viral infectivity defined as viral particles (VP) per infectious unit (IU). Viral production of vectors with TETr controlled promoters in tTS-expressing cell can improve viral production and/or viral infectivity by at least 1.5, at least 2, at least 2.5, at least 3, at least 3.5, at least 4, at least 4.5, at least 5, at least 6, at least 7, at least 8, at least 9, or at least 10-fold relative to production in a non-tTS-expressing cell. Viral production of vectors with TETr controlled promoters in tTS-expressing cell can improve viral production and/or viral infectivity by at least 15, at least 20, at least 25, at least 30, at least 35, at least 40, at least 45, at least 50, at least 60, at least 70, at least 80, at least 90, or at least 100-fold relative to production in a non-tTS-expressing cell. Viral production of vectors with TETr controlled promoters in tTS-expressing cell can improve viral production and/or viral infectivity by at least 1.5, at least 2, at least 2.5, at least 3, at least 3.5, at least 4, at least 4.5, at least 5, at least 6, at least 7, at least 8, at least 9, or at least 10-fold relative to production of a vector not having a TETr controlled promoter. Viral production of vectors with TETr controlled promoters in tTS-expressing cell can improve viral production and/or viral infectivity by at least 15, at least 20, at least 25, at least 30, at least 35, at least 40, at least 45, at least 50, at least 60, at least 70, at least 80, at least 90, or at least 100-fold relative to production of a vector not having a TETr controlled promoter.

V.B. Immune Checkpoints

Vectors described herein, such as C68 vectors described herein or alphavirus vectors described herein, can comprise a nucleic acid which encodes at least one antigen and the same or a separate vector can comprise a nucleic acid which encodes at least one immune modulator (e.g., an antibody such as an scFv) which binds to and blocks the activity of an immune checkpoint molecule. Vectors can comprise a cassette and one or more nucleic acid molecules encoding a checkpoint inhibitor.

Illustrative immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, □□, and memory CD8+ (□□) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049. Illustrative immune checkpoint inhibitors include Tremelimumab (CTLA-4 blocking antibody), anti-OX40, PD-L1 monoclonal Antibody (Anti-B7-H1; MEDI4736), ipilimumab, MK-3475 (PD-1 blocker), Nivolumamb (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Antibody-encoding sequences can be engineered into vectors such as C68 using ordinary skill in the art. An exemplary method is described in Fang et al., Stable antibody expression at therapeutic levels using the 2A peptide. Nat Biotechnol. 2005 May; 23(5):584-90. Epub 2005 Apr. 17; herein incorporated by reference for all purposes.

V.C. Additional Considerations for Vaccine Design and Manufacture

V.C.1. Determination of a Set of Peptides that Cover All Tumor Subclones

Truncal peptides, meaning those presented by all or most tumor subclones, can be prioritized for inclusion into the vaccine.[53] Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of tumor subclones and choosing peptides so as to maximize the number of tumor subclones covered by the vaccine.'

V.C.2. Antigen Prioritization

After all of the above antigen filters are applied, more candidate antigens may still be available for vaccine inclusion than the vaccine technology can support. Additionally, uncertainty about various aspects of the antigen analysis may remain and tradeoffs may exist between different properties of candidate vaccine antigens. Thus, in place of predetermined filters at each step of the selection process, an integrated multi-dimensional model can be considered that places candidate antigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of antigens may lower the probability that a tumor will escape immune attack via downregulation or mutation of HLA molecules)
7. Coverage of HLA classes (covering both HLA-I and HLA-II may increase the probability of therapeutic response and decrease the probability of tumor escape)

Additionally, optionally, antigens can be deprioritized (e.g., excluded) from the vaccination if they are predicted to be presented by HLA alleles lost or inactivated in either all or part of the patient's tumor or infected cell. HLA allele loss can occur by either somatic mutation, loss of heterozygosity, or homozygous deletion of the locus. Methods for detection of HLA allele somatic mutation are well known in the art, e.g. (Shukla et al., 2015). Methods for detection of somatic LOH and homozygous deletion (including for HLA locus) are likewise well described. (Carter et al., 2012; McGranahan et al., 2017; Van Loo et al., 2010). Antigens can also be deprioritized if mass-spectrometry data indicates a predicted antigen is not presented by a predicted HLA allele.

V.D. Alphavirus

V.D.1. Alphavirus Biology

Alphaviruses are members of the family Togaviridae, and are positive-sense single stranded RNA viruses. Members are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis virus and its derivative strain TC-83 (Strauss Microbrial Review 1994). A natural alphavirus genome is typically around 12 kb in length, the first two-thirds of which contain genes encoding non-structural proteins (nsPs) that form RNA replication complexes for self-replication of the viral genome, and the last third of which contains a subgenomic expression cassette encoding structural proteins for virion production (Frolov RNA 2001).

A model lifecycle of an alphavirus involves several distinct steps (Strauss Microbrial Review 1994, Jose Future Microbiol 2009). Following virus attachment to a host cell, the virion fuses with membranes within endocytic compartments resulting in the eventual release of genomic RNA into the cytosol. The genomic RNA, which is in a plus-strand orientation and comprises a 5' methylguanylate cap and 3' polyA tail, is translated to produce non-structural proteins nsP1-4 that form the replication complex. Early in infection, the plus-strand is then replicated by the complex into a minus-stand template. In the current model, the replication complex is further processed as infection progresses, with the resulting processed complex switching to transcription of the minus-strand into both full-length positive-strand genomic RNA, as well as the 26S subgenomic positive-strand RNA containing the structural genes. Several conserved sequence elements (CSEs) of alphavirus have been identified to potentially play a role in the various RNA replication steps including; a complement of the 5' UTR in the replication of plus-strand RNAs from a minus-strand template, a 51-nt CSE in the replication of minus-strand synthesis from the genomic template, a 24-nt CSE in the junction region between the nsPs and the 26S RNA in the transcription of the subgenomic RNA from the minus-strand, and a 3' 19-nt CSE in minus-strand synthesis from the plus-strand template.

Following the replication of the various RNA species, virus particles are then typically assembled in the natural lifecycle of the virus. The 26S RNA is translated and the resulting proteins further processed to produce the structural proteins including capsid protein, glycoproteins E1 and E2, and two small polypeptides E3 and 6K (Strauss 1994). Encapsidation of viral RNA occurs, with capsid proteins normally specific for only genomic RNA being packaged, followed by virion assembly and budding at the membrane surface.

V.D.2. Alphavirus as a Delivery Vector

Alphaviruses (including alphavirus sequences, features, and other elements) can be used to generate alphavirus-based delivery vectors (also be referred to as alphavirus vectors, alphavirus viral vectors, alphavirus vaccine vectors, self-replicating RNA (srRNA) vectors, or self-amplifying RNA (samRNA) vectors). Alphaviruses have previously been engineered for use as expression vector systems (Pushko 1997, Rheme 2004). Alphaviruses offer several advantages, particularly in a vaccine setting where heterologous antigen expression can be desired. Due to its ability to self-replicate in the host cytosol, alphavirus vectors are generally able to produce high copy numbers of the expression cassette within a cell resulting in a high level of heterologous antigen production. Additionally, the vectors are generally transient, resulting in improved biosafety as well as reduced induction of immunological tolerance to the vector. The public, in general, also lacks pre-existing immunity to alphavirus vectors as compared to other standard viral vectors, such as human adenovirus. Alphavirus based vectors also generally result in cytotoxic responses to infected cells. Cytotoxicity, to a certain degree, can be important in a vaccine setting to properly illicit an immune response to the heterologous antigen expressed. However, the degree of desired cytotoxicity can be a balancing act, and thus several attenuated alphaviruses have been developed, including the TC-83 strain of VEE. Thus, an example of an antigen expression vector described herein can utilize an alphavirus backbone that allows for a high level of antigen expression, elicits a robust immune response to antigen, does not elicit an immune response to the vector itself, and can be used in a safe manner. Furthermore, the antigen expression cassette can be designed to elicit different levels of an immune response through optimization of which alphavirus sequences the vector uses, including, but not limited to, sequences derived from VEE or its attenuated derivative TC-83.

Several expression vector design strategies have been engineered using alphavirus sequences (Pushko 1997). In one strategy, a alphavirus vector design includes inserting a second copy of the 26S promoter sequence elements downstream of the structural protein genes, followed by a heterologous gene (Frolov 1993). Thus, in addition to the natural non-structural and structural proteins, an additional subgenomic RNA is produced that expresses the heterologous protein. In this system, all the elements for production of infectious virions are present and, therefore, repeated rounds of infection of the expression vector in non-infected cells can occur.

Another expression vector design makes use of helper virus systems (Pushko 1997). In this strategy, the structural proteins are replaced by a heterologous gene. Thus, following self-replication of viral RNA mediated by still intact non-structural genes, the 26S subgenomic RNA provides for expression of the heterologous protein. Traditionally, additional vectors that expresses the structural proteins are then supplied in trans, such as by co-transfection of a cell line, to produce infectious virus. A system is described in detail in U.S. Pat. No. 8,093,021, which is herein incorporated by reference in its entirety, for all purposes. The helper vector system provides the benefit of limiting the possibility of forming infectious particles and, therefore, improves biosafety. In addition, the helper vector system reduces the total vector length, potentially improving the replication and expression efficiency. Thus, an example of an antigen expression vector described herein can utilize an alphavirus backbone wherein the structural proteins are replaced by a cassette, the resulting vector both reducing biosafety concerns, while at the same time promoting efficient expression due to the reduction in overall expression vector size.

V.D.3. Alphavirus Production In Vitro

Alphavirus delivery vectors are generally positive-sense RNA polynucleotides. A convenient technique well-known in the art for RNA production is in vitro transcription IVT. In this technique, a DNA template of the desired vector is first produced by techniques well-known to those in the art, including standard molecular biology techniques such as cloning, restriction digestion, ligation, gene synthesis, and polymerase chain reaction (PCR). The DNA template contains a RNA polymerase promoter at the 5' end of the sequence desired to be transcribed into RNA. Promoters include, but are not limited to, bacteriophage polymerase promoters such as T3, T7, or SP6. The DNA template is then incubated with the appropriate RNA polymerase enzyme, buffer agents, and nucleotides (NTPs). The resulting RNA polynucleotide can optionally be further modified including, but limited to, addition of a 5' cap structure such as 7-methylguanosine or a related structure, and optionally modifying the 3' end to include a polyadenylate (polyA) tail. The RNA can then be purified using techniques well-known in the field, such as phenol-chloroform extraction.

V.D.4. Delivery Via Lipid Nanoparticle

An important aspect to consider in vaccine vector design is immunity against the vector itself (Riley 2017). This may be in the form of preexisting immunity to the vector itself, such as with certain human adenovirus systems, or in the form of developing immunity to the vector following administration of the vaccine. The latter is an important consideration if multiple administrations of the same vaccine are performed, such as separate priming and boosting doses, or if the same vaccine vector system is to be used to deliver different cassettes.

In the case of alphavirus vectors, the standard delivery method is the previously discussed helper virus system that provides capsid, E1, and E2 proteins in trans to produce infectious viral particles. However, it is important to note that the E1 and E2 proteins are often major targets of neutralizing antibodies (Strauss 1994). Thus, the efficacy of using alphavirus vectors to deliver antigens of interest to target cells may be reduced if infectious particles are targeted by neutralizing antibodies.

An alternative to viral particle mediated gene delivery is the use of nanomaterials to deliver expression vectors (Riley 2017). Nanomaterial vehicles, importantly, can be made of non-immunogenic materials and generally avoid eliciting immunity to the delivery vector itself. These materials can include, but are not limited to, lipids, inorganic nanomaterials, and other polymeric materials. Lipids can be cationic, anionic, or neutral. The materials can be synthetic or naturally derived, and in some instances biodegradable. Lipids can include fats, cholesterol, phospholipids, lipid conjugates including, but not limited to, polyethyleneglycol (PEG) conjugates (PEGylated lipids), waxes, oils, glycerides, and fat soulable vitamins.

Lipid nanoparticles (LNPs) are an attractive delivery system due to the amphiphilic nature of lipids enabling formation of membranes and vesicle like structures (Riley 2017). In general, these vesicles deliver the expression vector by absorbing into the membrane of target cells and releasing nucleic acid into the cytosol. In addition, LNPs can be further modified or functionalized to facilitate targeting of specific cell types. Another consideration in LNP design is the balance between targeting efficiency and cytotoxicity. Lipid compositions generally include defined mixtures of cationic, neutral, anionic, and amphipathic lipids. In some instances, specific lipids are included to prevent LNP aggregation, prevent lipid oxidation, or provide functional chemical groups that facilitate attachment of additional moieties. Lipid composition can influence overall LNP size and stability. In an example, the lipid composition comprises dilinoleylmethyl-4-dimethylaminobutyrate (MC3) or MC3-like molecules. MC3 and MC3-like lipid compositions can be formulated to include one or more other lipids, such as a PEG or PEG-conjugated lipid, a sterol, or neutral lipids.

Nucleic-acid vectors, such as expression vectors, exposed directly to serum can have several undesirable consequences, including degradation of the nucleic acid by serum nucleases or off-target stimulation of the immune system by the free nucleic acids. Therefore, encapsulation of the alphavirus vector can be used to avoid degradation, while also avoiding potential off-target affects. In certain examples, an alphavirus vector is fully encapsulated within the delivery vehicle, such as within the aqueous interior of an LNP. Encapsulation of the alphavirus vector within an LNP can be carried out by techniques well-known to those skilled in the art, such as microfluidic mixing and droplet generation carried out on a microfluidic droplet generating device. Such devices include, but are not limited to, standard T-junction devices or flow-focusing devices. In an example, the desired lipid formulation, such as MC3 or MC3-like containing compositions, is provided to the droplet generating device in parallel with the alphavirus delivery vector and other desired agents, such that the delivery vector and desired agents are fully encapsulated within the interior of the MC3 or MC3-like based LNP. In an example, the droplet generating device can control the size range and size distribution of the LNPs produced. For example, the LNP can have a size ranging from 1 to 1000 nanometers in diameter, e.g., 1, 10, 50, 100, 500, or 1000 nanometers. Following droplet generation, the delivery vehicles encapsulating the expression vectors can be further treated or modified to prepare them for administration.

V.E. Chimpanzee Adenovirus (ChAd)

V.E.1. Viral Delivery with Chimpanzee Adenovirus

Vaccine compositions for delivery of one or more antigens (e.g., via a cassette encoding one or more antigens or neoantigens) can be created by providing adenovirus nucleic acid sequences of chimpanzee origin, a variety of novel vectors, and cell lines expressing chimpanzee adenovirus genes. A nucleic acid sequence of a chimpanzee C68 adenovirus (also referred to herein as ChAdV68) can be used in a vaccine composition for antigen delivery (See SEQ ID NO: 1). Use of C68 adenovirus derived vectors is described in further detail in U.S. Pat. No. 6,083,716, which is herein incorporated by reference in its entirety, for all purposes.

In a further aspect, provided herein is a recombinant adenovirus comprising the DNA sequence of a chimpanzee adenovirus such as C68 and a cassette operatively linked to regulatory sequences directing its expression. The recombinant virus is capable of infecting a mammalian, preferably a human, cell and capable of expressing the cassette payload in the cell. In this vector, the native chimpanzee E1 gene, and/or E3 gene, and/or E4 gene can be deleted. A cassette can be inserted into any of these sites of gene deletion. The cassette can include an antigen against which a primed immune response is desired.

In another aspect, provided herein is a mammalian cell infected with a chimpanzee adenovirus such as C68.

In still a further aspect, a novel mammalian cell line is provided which expresses a chimpanzee adenovirus gene (e.g., from C68) or functional fragment thereof.

In still a further aspect, provided herein is a method for delivering a cassette into a mammalian cell comprising the step of introducing into the cell an effective amount of a chimpanzee adenovirus, such as C68, that has been engineered to express the cassette.

Still another aspect provides a method for eliciting an immune response in a mammalian host to treat cancer. The method can comprise the step of administering to the host an effective amount of a recombinant chimpanzee adenovirus, such as C68, comprising a cassette that encodes one or more antigens from the tumor against which the immune response is targeted.

Still another aspect provides a method for eliciting an immune response in a mammalian host to treat or prevent a disease in a subject, such as an infectious disease. The method can comprise the step of administering to the host an effective amount of a recombinant chimpanzee adenovirus, such as C68, comprising an antigen cassette that encodes one or more antigens, such as from the infectious disease against which the immune response is targeted.

Also disclosed is a non-simian mammalian cell that expresses a chimpanzee adenovirus gene obtained from the sequence of SEQ ID NO: 1. The gene can be selected from the group consisting of the adenovirus E1A, E1B, E2A, E2B, E3, E4, L1, L2, L3, L4 and L5 of SEQ ID NO: 1.

Also disclosed is a nucleic acid molecule comprising a chimpanzee adenovirus DNA sequence comprising a gene obtained from the sequence of SEQ ID NO: 1. The gene can be selected from the group consisting of said chimpanzee adenovirus E1A, E1B, E2A, E2B, E3, E4, L1, L2, L3, L4 and L5 genes of SEQ ID NO: 1. In some aspects the nucleic acid molecule comprises SEQ ID NO: 1. In some aspects the nucleic acid molecule comprises the sequence of SEQ ID NO: 1, lacking at least one gene selected from the group consisting of E1A, E1B, E2A, E2B, E3, E4, L1, L2, L3, L4 and L5 genes of SEQ ID NO: 1.

Also disclosed is a vector comprising a chimpanzee adenovirus DNA sequence obtained from SEQ ID NO: 1 and a cassette operatively linked to one or more regulatory sequences which direct expression of the cassette in a heterologous host cell, optionally wherein the chimpanzee adenovirus DNA sequence comprises at least the cis-elements necessary for replication and virion encapsidation, the cis-elements flanking the cassette and regulatory sequences. In some aspects, the chimpanzee adenovirus DNA sequence comprises a gene selected from the group consisting of E1A, E1B, E2A, E2B, E3, E4, L1, L2, L3, L4 and L5 gene sequences of SEQ ID NO: 1. In some aspects the vector can lack the E1A and/or E1B gene.

Also disclosed herein is a host cell transfected with a vector disclosed herein such as a C68 vector engineered to expression a cassette. Also disclosed herein is a human cell that expresses a selected gene introduced therein through introduction of a vector disclosed herein into the cell.

Also disclosed herein is a adenovirus vector comprising: a partially deleted E4 gene comprising a deleted or partially-deleted E4orf2 region and a deleted or partially-deleted E4orf3 region, and optionally a deleted or partially-deleted E4orf4 region. The partially deleted E4 can comprise an E4 deletion of at least nucleotides 34,916 to 35,642 of the sequence shown in SEQ ID NO:1, and wherein the vector comprises at least nucleotides 2 to 36,518 of the sequence set forth in SEQ ID NO:1. The partially deleted E4 can comprise an E4 deletion of at least a partial deletion of nucleotides 34,916 to 34,942 of the sequence shown in SEQ ID NO:1, at least a partial deletion of nucleotides 34,952 to 35,305 of the sequence shown in SEQ ID NO:1, and at least a partial deletion of nucleotides 35,302 to 35,642 of the sequence shown in SEQ ID NO:1, and wherein the vector comprises at least nucleotides 2 to 36,518 of the sequence set forth in SEQ ID NO:1 The partially deleted E4 can comprise an E4 deletion of at least nucleotides 34,980 to 36,516 of the sequence shown in SEQ ID NO:1, and wherein the vector comprises at least nucleotides 2 to 36,518 of the sequence set forth in SEQ ID NO:1. The partially deleted E4 can comprise an E4 deletion of at least nucleotides 34,979 to 35,642 of the sequence shown in SEQ ID NO:1, and wherein the vector comprises at least nucleotides 2 to 36,518 of the sequence set forth in SEQ ID NO:1. The partially deleted E4 can comprise an E4 deletion of at least a partial deletion of E4Orf2, a fully deleted E4Orf3, and at least a partial deletion of E4Orf4. The partially deleted E4 can comprise an E4 deletion of at least a partial deletion of E4Orf2, at least a partial deletion of E4Orf3, and at least a partial deletion of E4Orf4. The partially deleted E4 can comprise an E4 deletion of at least a partial deletion of E4Orf1, a fully deleted E4Orf2, and at least a partial deletion of E4Orf3. The partially deleted E4 can comprise an E4 deletion of at least a partial deletion of E4Orf2 and at least a partial deletion of E4Orf3. The partially deleted E4 can comprise an E4 deletion between the start site of E4Orf1 to the start site of E4Orf5. The partially deleted E4 can be an E4 deletion adjacent to the start site of E4Orf1. The partially deleted E4 can be an E4 deletion adjacent to the start site of E4Orf2. The partially deleted E4 can be an E4 deletion adjacent to the start site of E4Orf3. The partially deleted E4 can be an E4 deletion adjacent to the start site of E4Orf4. The E4 deletion can be at least 50, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, or at least 2000 nucleotides. The E4 deletion can be at least 700 nucleotides. The E4 deletion can be at least 1500 nucleotides. The E4 deletion can be 50 or less, 100 or less, 200 or less, 300 or less, 400 or less, 500 or less, 600 or less, 700 or less, 800 or less, 900 or less, 1000 or less, 1100 or less, 1200 or less, 1300 or less, 1400 or less, 1500 or less, 1600 or less, 1700 or less, 1800 or less, 1900 or less, or 2000 or less nucleotides. The E4 deletion can be 750 nucleotides or less. The E4 deletion can be at least 1550 nucleotides or less.

The partially deleted E4 gene can be the E4 gene sequence shown in SEQ ID NO:1 that lacks at least nucleotides 34,916 to 35,642 of the sequence shown in SEQ ID NO:1. The partially deleted E4 gene can be the E4 gene sequence shown in SEQ ID NO:1 that lacks the E4 gene sequence shown in SEQ ID NO:1 and that lacks at least nucleotides 34,916 to 34,942, nucleotides 34,952 to 35,305 of the sequence shown in SEQ ID NO:1, and nucleotides 35,302 to 35,642 of the sequence shown in SEQ ID NO:1. The partially deleted E4 gene can be the E4 gene sequence shown in SEQ ID NO:1 and that lacks at least nucleotides 34,980 to 36,516 of the sequence shown in SEQ ID NO:1. The partially deleted E4 gene can be the E4 gene sequence shown in SEQ ID NO:1 and that lacks at least nucleotides 34,979 to 35,642 of the sequence shown in SEQ ID NO:1. The adenovirus vector having the partially deleted E4 gene can have a cassette, wherein the cassette comprises at least one payload nucleic acid sequence, and wherein the cassette comprises at least one promoter sequence operably linked to the at least one payload nucleic acid sequence. The adenovirus vector having the partially deleted E4 gene can have one or more genes or regulatory sequences of the ChAdV68 sequence shown in SEQ ID NO: 1, optionally wherein the one or more genes or regulatory sequences comprise at least one of the chimpanzee adenovirus inverted terminal repeat (ITR), E1A, E1B, E2A, E2B, E3, E4, L1, L2, L3, L4, and L5 genes of the sequence shown in SEQ ID NO: 1. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, and optionally the nucleotides 2 to 34,916 additionally lack nucleotides 577 to 3403 of the sequence shown in SEQ ID NO:1 corresponding to an E1 deletion and/or lack nucleotides 27,125 to 31,825 of the sequence shown in SEQ ID NO:1 corresponding to an E3 deletion. The adenovirus vector having the partially deleted E4 gene can have nucleotides 35,643 to 36,518 of the sequence shown in SEQ ID NO:1, and wherein the partially deleted E4 gene is 5' of the nucleotides 35,643 to 36,518. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion, and have nucleotides 35,643 to 36,518 of the sequence shown in SEQ ID NO:1, and wherein the partially deleted E4 gene is 5' of the nucleotides 35,643 to 36,518.

The partially deleted E4 gene can be the E4 gene sequence shown in SEQ ID NO:1 that lacks at least nucleotides 34,916 to 35,642 of the sequence shown in SEQ ID NO:1, nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion, and have nucleotides 35,643 to 36,518 of the sequence shown in SEQ ID NO:1, and wherein the partially deleted E4 gene is 5' of the nucleotides 35,643 to 36,518.

The adenovirus vector having the partially deleted E4 gene can have

Also disclosed herein is a method for delivering a cassette to a mammalian cell comprising introducing into said cell an effective amount of a vector disclosed herein such as a C68 vector engineered to expression the cassette.

Also disclosed herein is a method for producing a comprising introducing a vector disclosed herein into a mammalian cell, culturing the cell under suitable conditions and producing the antigen.

V.E.2. E1-Expressing Complementation Cell Lines

To generate recombinant chimpanzee adenoviruses (Ad) deleted in any of the genes described herein, the function of the deleted gene region, if essential to the replication and infectivity of the virus, can be supplied to the recombinant virus by a helper virus or cell line, i.e., a complementation or packaging cell line. For example, to generate a replication-defective chimpanzee adenovirus vector, a cell line can be used which expresses the E1 gene products of the human or chimpanzee adenovirus; such a cell line can include HEK293 or variants thereof. The protocol for the generation of the cell lines expressing the chimpanzee E1 gene products (Examples 3 and 4 of U.S. Pat. No. 6,083,716) can be followed to generate a cell line which expresses any selected chimpanzee adenovirus gene.

An AAV augmentation assay can be used to identify a chimpanzee adenovirus E1-expressing cell line. This assay is useful to identify E1 function in cell lines made by using the E1 genes of other uncharacterized adenoviruses, e.g., from other species. That assay is described in Example 4B of U.S. Pat. No. 6,083,716.

A selected chimpanzee adenovirus gene, e.g., E1, can be under the transcriptional control of a promoter for expression in a selected parent cell line. Inducible or constitutive promoters can be employed for this purpose. Among inducible promoters are included the sheep metallothionine promoter, inducible by zinc, or the mouse mammary tumor virus (MMTV) promoter, inducible by a glucocorticoid, particularly, dexamethasone. Other inducible promoters, such as those identified in International patent application WO95/13392, incorporated by reference herein can also be used in the production of packaging cell lines. Constitutive promoters in control of the expression of the chimpanzee adenovirus gene can be employed also.

A parent cell can be selected for the generation of a novel cell line expressing any desired C68 gene. Without limitation, such a parent cell line can be HeLa [ATCC Accession No. CCL 2], A549 [ATCC Accession No. CCL 185], KB [CCL 17], Detroit [e.g., Detroit 510, CCL 72] and WI-38 [CCL 75] cells. Other suitable parent cell lines can be obtained from other sources. Parent cell lines can include CHO, HEK293 or variants thereof, 911, HeLa, A549, LP-293, PER.C6, or AE1-2a.

An E1-expressing cell line can be useful in the generation of recombinant chimpanzee adenovirus E1 deleted vectors. Cell lines constructed using essentially the same procedures that express one or more other chimpanzee adenoviral gene products are useful in the generation of recombinant chimpanzee adenovirus vectors deleted in the genes that encode those products. Further, cell lines which express other human Ad E1 gene products are also useful in generating chimpanzee recombinant Ads.

V.E.3. Recombinant Viral Particles as Vectors

The compositions disclosed herein can comprise viral vectors, that deliver at least one antigen to cells. Such vectors comprise a chimpanzee adenovirus DNA sequence such as C68 and a cassette operatively linked to regulatory sequences which direct expression of the cassette. The C68 vector is capable of expressing the cassette in an infected mammalian cell. The C68 vector can be functionally deleted in one or more viral genes. A cassette comprises at least one antigen under the control of one or more regulatory sequences such as a promoter. Optional helper viruses and/or packaging cell lines can supply to the chimpanzee viral vector any necessary products of deleted adenoviral genes.

The term "functionally deleted" means that a sufficient amount of the gene region is removed or otherwise altered, e.g., by mutation or modification, so that the gene region is no longer capable of producing one or more functional products of gene expression. Mutations or modifications that can result in functional deletions include, but are not limited to, nonsense mutations such as introduction of premature stop codons and removal of canonical and non-canonical start codons, mutations that alter mRNA splicing or other transcriptional processing, or combinations thereof. If desired, the entire gene region can be removed.

Modifications of the nucleic acid sequences forming the vectors disclosed herein, including sequence deletions, insertions, and other mutations may be generated using standard molecular biological techniques and are within the scope of this invention.

V.E.4. Construction of the Viral Plasmid Vector

The chimpanzee adenovirus C68 vectors useful in this invention include recombinant, defective adenoviruses, that is, chimpanzee adenovirus sequences functionally deleted in the E1a or E1b genes, and optionally bearing other mutations, e.g., temperature-sensitive mutations or deletions in other genes. It is anticipated that these chimpanzee sequences are also useful in forming hybrid vectors from other adenovirus and/or adeno-associated virus sequences. Homologous adenovirus vectors prepared from human adenoviruses are described in the published literature [see, for example, Kozarsky I and II, cited above, and references cited therein, U.S. Pat. No. 5,240,846].

In the construction of useful chimpanzee adenovirus C68 vectors for delivery of a cassette to a human (or other mammalian) cell, a range of adenovirus nucleic acid sequences can be employed in the vectors. A vector comprising minimal chimpanzee C68 adenovirus sequences can be used in conjunction with a helper virus to produce an infectious recombinant virus particle. The helper virus provides essential gene products required for viral infectivity and propagation of the minimal chimpanzee adenoviral vector. When only one or more selected deletions of chimpanzee adenovirus genes are made in an otherwise functional viral vector, the deleted gene products can be supplied in the viral vector production process by propagating the virus in a selected packaging cell line that provides the deleted gene functions in trans.

V.E.5. Recombinant Minimal Adenovirus

A minimal chimpanzee Ad C68 virus is a viral particle containing just the adenovirus cis-elements necessary for replication and virion encapsidation. That is, the vector contains the cis-acting 5' and 3' inverted terminal repeat (ITR) sequences of the adenoviruses (which function as origins of replication) and the native 5' packaging/enhancer domains (that contain sequences necessary for packaging linear Ad genomes and enhancer elements for the E1 promoter). See, for example, the techniques described for preparation of a "minimal" human Ad vector in International Patent Application WO96/13597 and incorporated herein by reference.

V.E.6. Other Defective Adenoviruses

Recombinant, replication-deficient adenoviruses can also contain more than the minimal chimpanzee adenovirus sequences. These other Ad vectors can be characterized by deletions of various portions of gene regions of the virus, and infectious virus particles formed by the optional use of helper viruses and/or packaging cell lines.

As one example, suitable vectors may be formed by deleting all or a sufficient portion of the C68 adenoviral immediate early gene Ela and delayed early gene E1b, so as to eliminate their normal biological functions. Replication-defective E1-deleted viruses are capable of replicating and producing infectious virus when grown on a chimpanzee adenovirus-transformed, complementation cell line containing functional adenovirus Ela and E1b genes which provide the corresponding gene products in trans. Based on the homologies to known adenovirus sequences, it is anticipated that, as is true for the human recombinant E1-deleted adenoviruses of the art, the resulting recombinant chimpanzee adenovirus is capable of infecting many cell types and can express antigen(s), but cannot replicate in most cells that do not carry the chimpanzee E1 region DNA unless the cell is infected at a very high multiplicity of infection.

As another example, all or a portion of the C68 adenovirus delayed early gene E3 can be eliminated from the chimpanzee adenovirus sequence which forms a part of the recombinant virus.

Chimpanzee adenovirus C68 vectors can also be constructed having a deletion of the E4 gene. Still another vector can contain a deletion in the delayed early gene E2a.

Deletions can also be made in any of the late genes L1 through L5 of the chimpanzee C68 adenovirus genome. Similarly, deletions in the intermediate genes IX and IVa2 can be useful for some purposes. Other deletions may be made in the other structural or non-structural adenovirus genes.

The above discussed deletions can be used individually, i.e., an adenovirus sequence can contain deletions of E1 only. Alternatively, deletions of entire genes or portions thereof effective to destroy or reduce their biological activity can be used in any combination. For example, in one exemplary vector, the adenovirus C68 sequence can have deletions of the E1 genes and the E4 gene, or of the E1, E2a and E3 genes, or of the E1 and E3 genes, or of E1, E2a and E4 genes, with or without deletion of E3, and so on. As discussed above, such deletions can be used in combination with other mutations, such as temperature-sensitive mutations, to achieve a desired result.

The cassette comprising antigen(s) be inserted optionally into any deleted region of the chimpanzee C68 Ad virus. Alternatively, the cassette can be inserted into an existing gene region to disrupt the function of that region, if desired.

V.E.7. Helper Viruses

Depending upon the chimpanzee adenovirus gene content of the viral vectors employed to carry the cassette, a helper adenovirus or non-replicating virus fragment can be used to provide sufficient chimpanzee adenovirus gene sequences to produce an infective recombinant viral particle containing the cassette.

Useful helper viruses contain selected adenovirus gene sequences not present in the adenovirus vector construct and/or not expressed by the packaging cell line in which the vector is transfected. A helper virus can be replication-defective and contain a variety of adenovirus genes in addition to the sequences described above. The helper virus can be used in combination with the E1-expressing cell lines described herein.

For C68, the "helper" virus can be a fragment formed by clipping the C terminal end of the C68 genome with SspI, which removes about 1300 bp from the left end of the virus. This clipped virus is then co-transfected into an E1-expressing cell line with the plasmid DNA, thereby forming the recombinant virus by homologous recombination with the C68 sequences in the plasmid.

Helper viruses can also be formed into poly-cation conjugates as described in Wu et al, J. Biol. Chem., 264:16985-16987 (1989); K. J. Fisher and J. M. Wilson, Biochem. J., 299:49 (Apr. 1, 1994). Helper virus can optionally contain a reporter gene. A number of such reporter genes are known to the art. The presence of a reporter gene on the helper virus which is different from the cassette on the adenovirus vector allows both the Ad vector and the helper virus to be independently monitored. This second reporter is used to enable separation between the resulting recombinant virus and the helper virus upon purification.

V.E.8. Assembly of Viral Particle and Infection of a Cell Line

Assembly of the selected DNA sequences of the adenovirus, the cassette, and other vector elements into various intermediate plasmids and shuttle vectors, and the use of the plasmids and vectors to produce a recombinant viral particle can all be achieved using conventional techniques. Such techniques include conventional cloning techniques of cDNA, in vitro recombination techniques (e.g., Gibson assembly), use of overlapping oligonucleotide sequences of the adenovirus genomes, polymerase chain reaction, and any suitable method which provides the desired nucleic acid sequence. Standard transfection and co-transfection techniques are employed, e.g., CaPO4 precipitation techniques or liposome-mediated transfection methods such as lipofectamine. Other conventional methods employed include homologous recombination of the viral genomes, plaquing of viruses in agar overlay, methods of measuring signal generation, and the like.

For example, following the construction and assembly of the desired cassette-containing viral vector, the vector can be transfected in vitro in the presence of a helper virus into the packaging cell line. Homologous recombination occurs between the helper and the vector sequences, which permits the adenovirus-antigen sequences in the vector to be replicated and packaged into virion capsids, resulting in the recombinant viral vector particles.

The resulting recombinant chimpanzee C68 adenoviruses are useful in transferring a cassette to a selected cell. In in vivo experiments with the recombinant virus grown in the packaging cell lines, the E1-deleted recombinant chimpanzee adenovirus demonstrates utility in transferring a cassette to a non-chimpanzee, preferably a human, cell.

V.E.9. Use of the Recombinant Virus Vectors

The resulting recombinant chimpanzee C68 adenovirus containing the cassette (produced by cooperation of the adenovirus vector and helper virus or adenoviral vector and packaging cell line, as described above) thus provides an efficient gene transfer vehicle which can deliver antigen(s) to a subject in vivo or ex vivo.

The above-described recombinant vectors are administered to humans according to published methods for gene therapy. A chimpanzee viral vector bearing a cassette can be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The chimpanzee adenoviral vectors are administered in sufficient amounts to transduce the human cells and to provide sufficient levels of antigen transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. The dosage will be adjusted to balance the therapeutic benefit against any side effects and such dosages may vary depending upon the therapeutic application for which the recombinant vector is employed. The levels of expression of antigen(s) can be monitored to determine the frequency of dosage administration.

Recombinant, replication defective adenoviruses can be administered in a "pharmaceutically effective amount", that is, an amount of recombinant adenovirus that is effective in a route of administration to transfect the desired cells and provide sufficient levels of expression of the selected gene to provide a vaccinal benefit, i.e., some measurable level of protective immunity. C68 vectors comprising a cassette can be co-administered with adjuvant. Adjuvant can be separate from the vector (e.g., alum) or encoded within the vector, in particular if the adjuvant is a protein. Adjuvants are well known in the art.

Conventional and pharmaceutically acceptable routes of administration include, but are not limited to, intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

The levels of immunity to antigen(s) can be monitored to determine the need, if any, for boosters. Following an assessment of antibody titers in the serum, for example, optional booster immunizations may be desired

VI. Therapeutic and Manufacturing Methods

Also provided is a method of inducing a tumor specific immune response in a subject, vaccinating against a tumor, treating and/or alleviating a symptom of cancer in a subject by administering to the subject one or more antigens such as a plurality of antigens identified using methods disclosed herein.

Also provided is a method of inducing an infectious disease organism-specific immune response in a subject, vaccinating against an infectious disease organism, treating and/or alleviating a symptom of an infection associated with an infectious disease organism in a subject by administering to the subject one or more antigens such as a plurality of antigens identified using methods disclosed herein.

In some aspects, a subject has been diagnosed with cancer or is at risk of developing cancer. A subject can be a human, dog, cat, horse or any animal in which a tumor specific immune response is desired. A tumor can be any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

In some aspects, a subject has been diagnosed with an infection or is at risk of an infection (e.g., age, geographical/travel, and/or work-related increased risk of or predisposition to an infection, or at risk to a seasonal and/or novel disease infection).

An antigen can be administered in an amount sufficient to induce a CTL response. An antigen can be administered in an amount sufficient to induce a T cell response. An antigen can be administered in an amount sufficient to induce a B cell response.

An antigen can be administered alone or in combination with other therapeutic agents. The therapeutic agent is for example, a chemotherapeutic agent, radiation, or immunotherapy. Any suitable therapeutic treatment for a particular cancer can be administered. Therapeutic agents can include those that target an infectious disease organism, such as an anti-viral or antibiotic agent.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each antigen to be included in a vaccine composition and the optimum dosing regimen can be determined. For example, an antigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of antigens present in the composition is/are tissue, cancer, infectious disease, and/or patient-specific. For instance, the exact selection of peptides can be guided by expression patterns of the parent proteins in a given tissue or guided by mutation or disease status of a patient. The selection can be dependent on the specific type of cancer, the specific infectious disease, the status of the disease, the goal of the vaccination (e.g., preventative or targeting an ongoing disease), earlier treatment regimens, the immune status of the patient, and, of course, the HLA-haplotype of the patient. Furthermore, a vaccine can contain individualized components, according to personal needs of the particular patient. Examples include varying the selection of antigens according to the expression of the antigen in the particular patient or adjustments for secondary treatments following a first round or scheme of treatment.

A patient can be identified for administration of an antigen vaccine through the use of various diagnostic methods, e.g., patient selection methods described further below. Patient selection can involve identifying mutations in, or expression patterns of, one or more genes. Patient selection can involve identifying the infectious disease of an ongoing infection. Patient selection can involve identifying risk of an infection by an infectious disease. In some cases, patient selection involves identifying the haplotype of the patient. The various patient selection methods can be performed in parallel, e.g., a sequencing diagnostic can identify both the mutations and the haplotype of a patient. The various patient selection methods can be performed sequentially, e.g., one diagnostic test identifies the mutations and separate diagnostic test identifies the haplotype of a patient, and where each test can be the same (e.g., both high-throughput sequencing) or different (e.g., one high-throughput sequencing and the other Sanger sequencing) diagnostic methods.

For a composition to be used as a vaccine for cancer or an infectious disease, antigens with similar normal self-peptides that are expressed in high amounts in normal tissues can be avoided or be present in low amounts in a composition described herein. On the other hand, if it is known that the tumor or infected cell of a patient expresses high amounts of a certain antigen, the respective pharmaceutical composition for treatment of this cancer or infection can be present in high amounts and/or more than one antigen specific for this particularly antigen or pathway of this antigen can be included.

Compositions comprising an antigen can be administered to an individual already suffering from cancer or an infection. In therapeutic applications, compositions are administered to a patient in an amount sufficient to elicit an effective CTL response to the tumor antigen or infectious disease organism antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when the cancer has metastasized. In such cases, in view of the minimization of extraneous substances and the relative nontoxic nature of an antigen, it is possible and can be felt desirable by the treating physician to administer substantial excesses of these compositions.

For therapeutic use, administration can begin at the detection or surgical removal of tumors or begin at the detection or treatment of an infection. This can be followed by boosting doses until at least symptoms are substantially abated and for a period thereafter.

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly. The compositions can be administered at the site of surgical excision to induce a local immune response to the tumor. The compositions can be administered to target specific infected tissues and/or cells (e.g., antigen presenting cells) of a subject. Disclosed herein are compositions for parenteral administration which comprise a solution of the antigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Antigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the antigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired antigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); U.S. Pat. No. 5,279,833 Rose U.S. Pat. Nos. 5,279,833; 9,106,309WOAWO 91/06309; and Feigner et al., Proc. Natl. Acad. Sci. USA 84: 7413-7414 (1987).

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleic acid sequences that encode one or more antigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, Science. (2016) 352 (6291):1337-41, Lu et al., Efficient identification of mutated cancer antigens recognized by T cells associated with durable tumor regressions, *Clin Cancer Res.* (2014) 20(13): 3401-10). Upon introduction into a host, infected cells express the antigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing a vaccine, comprising performing the steps of a method disclosed herein; and producing a vaccine comprising a plurality of antigens or a subset of the plurality of antigens. Also disclosed is a method of manufacturing adenoviral vector, comprising performing the steps of a method disclosed herein; and producing an adenoviral vector comprising a cassette. For example, disclosed is a method of manufacturing adenoviral vector using a TET promoter system, such as the TETr controlled promoter system described herein. Viral production using the TETr controlled promoter system can include a. providing a viral vector comprising a cassette, the cassette comprising: (i) at least one payload nucleic acid sequence, and (ii) at least one promoter sequence operably linked to the at least one payload nucleic acid sequence, wherein the at least one promoter is a tetracycline (TET) repressor protein (TETr) controlled promoter, b. providing a cell engineered to express the TETr protein; and c. contacting the viral vector with the cell under conditions sufficient for production of the virus.

Antigens disclosed herein can be manufactured using methods known in the art. For example, a method of producing an antigen or a vector (e.g., a vector including at least one sequence encoding one or more antigens) disclosed herein can include culturing a host cell under conditions suitable for expressing the antigen or vector wherein the host cell comprises at least one polynucleotide encoding the antigen or vector, and purifying the antigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NSO cell, yeast, or a HEK293 cell. Host cells can be transformed with one or more polynucleotides comprising at least one nucleic acid sequence that encodes an antigen or vector disclosed herein, optionally wherein the isolated polynucleotide further comprises a promoter sequence operably linked to the at least one nucleic acid sequence that encodes the antigen or vector. In certain embodiments the isolated polynucleotide can be cDNA.

VII. Antigen Use and Administration

A vaccination protocol can be used to dose a subject with one or more antigens. A priming vaccine and a boosting vaccine can be used to dose the subject. The priming vaccine can be based on C68 (e.g., the sequences shown in SEQ ID NO:1 or 2) or srRNA (e.g., the sequences shown in SEQ ID NO:3 or 4) and the boosting vaccine can be based on C68 (e.g., the sequences shown in SEQ ID NO:1 or 2) or srRNA (e.g., the sequences shown in SEQ ID NO:3 or 4). Each vector typically includes a cassette that includes antigens. Cassettes can include about 20 antigens, separated by spacers such as the natural sequence that normally surrounds each antigen or other non-natural spacer sequences such as AAY. Cassettes can also include MHCII antigens such a tetanus toxoid antigen and PADRE antigen, which can be considered universal class II antigens. Cassettes can also include a targeting sequence such as a ubiquitin targeting sequence. In addition, each vaccine dose can be administered to the subject in conjunction with (e.g., concurrently, before, or after) a checkpoint inhibitor (CPI). CPI's can include those that inhibit CTLA4, PD1, and/or PDL1 such as antibodies or antigen-binding portions thereof. Such antibodies can include tremelimumab or durvalumab.

A priming vaccine can be injected (e.g., intramuscularly) in a subject. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

A vaccine boost (boosting vaccine) can be injected (e.g., intramuscularly) after prime vaccination. A boosting vaccine can be administered about every 1, 2, 3, 4, 5, 6, 7, 8, 9, or 10 weeks, e.g., every 4 weeks and/or 8 weeks after the prime. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

Anti-CTLA-4 (e.g., tremelimumab) can also be administered to the subject. For example, anti-CTLA4 can be administered subcutaneously near the site of the intramuscular vaccine injection (ChAdV68 prime or srRNA low doses) to ensure drainage into the same lymph node. Tremelimumab is a selective human IgG2 mAb inhibitor of CTLA-4. Target Anti-CTLA-4 (tremelimumab) subcutaneous dose is typically 70-75 mg (in particular 75 mg) with a dose range of, e.g., 1-100 mg or 5-420 mg.

In certain instances an anti-PD-L1 antibody can be used such as durvalumab (MEDI 4736). Durvalumab is a selective, high affinity human IgG1 mAb that blocks PD-L1 binding to PD-1 and CD80. Durvalumab is generally administered at 20 mg/kg i.v. every 4 weeks.

Immune monitoring can be performed before, during, and/or after vaccine administration. Such monitoring can inform safety and efficacy, among other parameters.

To perform immune monitoring, PBMCs are commonly used. PBMCs can be isolated before prime vaccination, and after prime vaccination (e.g. 4 weeks and 8 weeks). PBMCs can be harvested just prior to boost vaccinations and after each boost vaccination (e.g. 4 weeks and 8 weeks).

T cell responses can be assessed as part of an immune monitoring protocol. For example, the ability of a vaccine composition described herein to stimulate an immune response can be monitored and/or assessed. As used herein, "stimulate an immune response" refers to any increase in an immune response, such as initiating an immune response (e.g., a priming vaccine stimulating the initiation of an immune response in a naïve subject) or enhancement of an immune response (e.g., a boosting vaccine stimulating the enhancement of an immune response in a subject having a pre-existing immune response to an antigen, such as a pre-existing immune response initiated by a priming vaccine). T cell responses can be measured using one or more methods known in the art such as ELISpot, intracellular cytokine staining, cytokine secretion and cell surface capture, T cell proliferation, MHC multimer staining, or by cytotoxicity assay. T cell responses to epitopes encoded in vaccines can be monitored from PBMCs by measuring induction of cytokines, such as IFN-gamma, using an ELISpot assay. Specific CD4 or CD8 T cell responses to epitopes encoded in vaccines can be monitored from PBMCs by measuring induction of cytokines captured intracellularly or extracellularly, such as IFN-gamma, using flow cytometry. Specific CD4 or CD8 T cell responses to epitopes encoded in the vaccines can be monitored from PBMCs by measuring T cell populations expressing T cell receptors specific for epitope/MHC class I complexes using MHC multimer staining. Specific CD4 or CD8 T cell responses to epitopes encoded in the vaccines can be monitored from PBMCs by measuring the ex vivo expansion of T cell populations following 3H-thymidine, bromodeoxyuridine and carboxyfluoresceine-diacetate-succinimidylester (CFSE) incorporation. The antigen recognition capacity and lytic activity of PBMC-derived T cells that are specific for epitopes encoded in vaccines can be assessed functionally by chromium release assay or alternative colorimetric cytotoxicity assays.

B cell responses can be measured using one or more methods known in the art such as assays used to determine B cell differentiation (e.g., differentiation into plasma cells), B cell or plasma cell proliferation, B cell or plasma cell activation (e.g., upregulation of costimulatory markers such as CD80 or CD86), antibody class switching, and/or antibody production (e.g., an ELISA).

VIII. Antigen Identification

VIII.A. Antigen Candidate Identification

Research methods for NGS analysis of tumor and normal exome and transcriptomes have been described and applied in the antigen identification space. [6,14,15] Certain optimizations for greater sensitivity and specificity for antigen identification in the clinical setting can be considered. These optimizations can be grouped into two areas, those related to laboratory processes and those related to the NGS data analysis. The research methods described can also be applied to identification of antigens in other settings, such as identification of identifying antigens from an infectious disease organism, an infection in a subject, or an infected cell of a subject. Examples of optimizations are known to those skilled in the art, for example the methods described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

VIII.B. Isolation and Detection of HLA Peptides

Isolation of HLA-peptide molecules was performed using classic immunoprecipitation (IP) methods after lysis and solubilization of the tissue sample (55-58). A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP. (59, 60) Immunoprecipitations can also be performed with antibodies that are not covalently attached to beads. Typically this is done using sepharose or magnetic beads coated with Protein A and/or Protein G to hold the antibody to the column. Some antibodies that can be used to selectively enrich MHC/peptide complex are listed below.

| Antibody Name | Specificity |
|---|---|
| W6/32 | Class I HLA-A, B, C |
| L243 | Class II-HLA-DR |
| Tu36 | Class II-HLA-DR |
| LN3 | Class II-HLA-DR |
| Tu39 | Class II-HLA-DR, DP, DQ |

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by SpeedVac evaporation and in some instances are stored at −20C prior to MS analysis.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector.

MS2 spectra from each analysis are searched against a protein database using Comet (61, 62) and the peptide identification are scored using Percolator (63-65). Additional sequencing is performed using PEAKS studio (Bioinformatics Solutions Inc.) and other search engines or sequencing methods can be used including spectral matching and de novo sequencing (97).

VIII.B.1. MS Limit of Detection Studies in Support of Comprehensive HLA Peptide Sequencing.

Figure 24A:
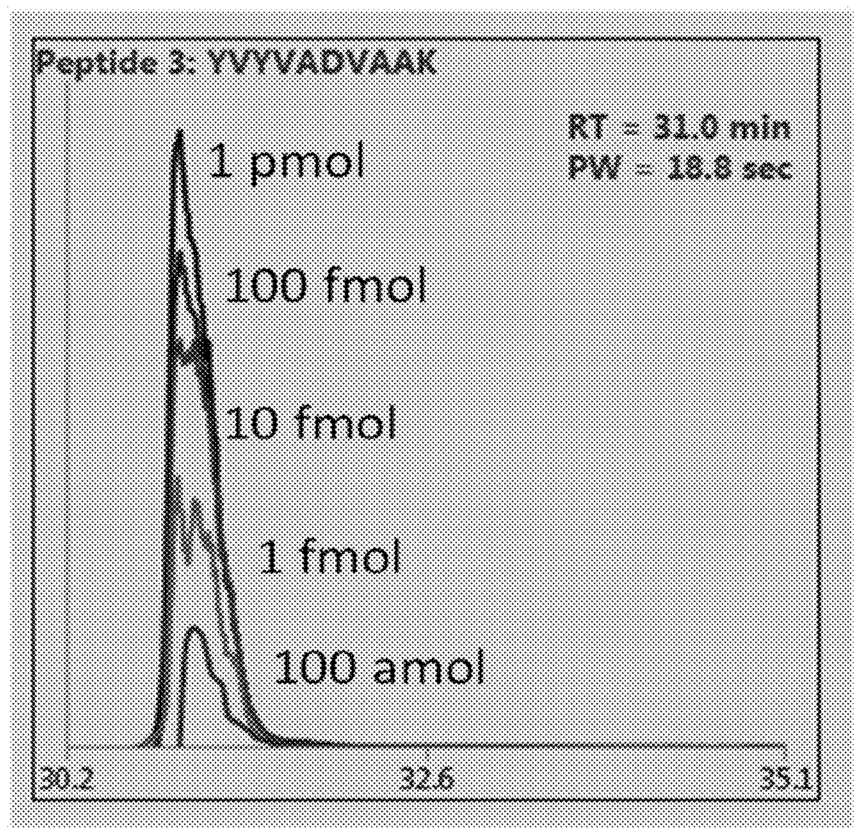
FIG. 24A shows an example peptide spectrum generated from Promega's dynamic range standard.
Figure 24B:
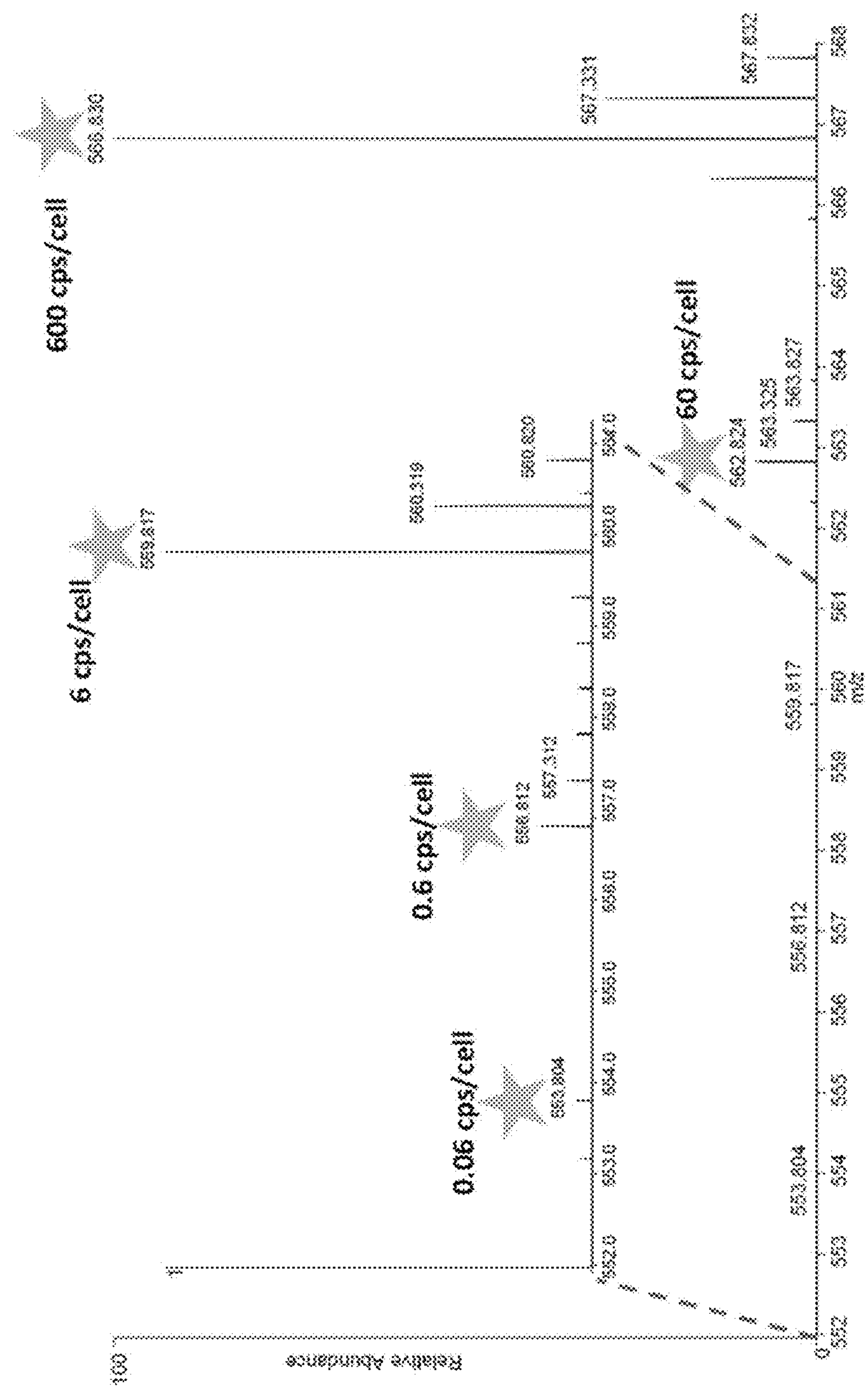
FIG. 24B shows an example peptide spectrum generated from Promega's dynamic range standard.

Using the peptide YVYVADVAAK (SEQ ID NO: 77) it was determined what the limits of detection are using different amounts of peptide loaded onto the LC column. The amounts of peptide tested were 1 pmol, 100 fmol, 10 fmol, 1 fmol, and 100 amol. (Table 1) The results are shown in FIGS. 24A and 24B. These results indicate that the lowest limit of detection (LoD) is in the attomol range ($10^{18}$), that the dynamic range spans five orders of magnitude, and that the signal to noise appears sufficient for sequencing at low femtomol ranges ($10^{-15}$).

TABLE 1

| Peptide m/z | Loaded on Column | Copies/Cell in 1e9cells |
|---|---|---|
| 566.830 | 1 pmol | 600 |
| 562.823 | 100 fmol | 60 |
| 559.816 | 10 fmol | 6 |
| 556.810 | 1 fmol | 0.6 |
| 553.802 | 100 amol | 0.06 |

IX. Presentation Model

Presentation models can be used to identify likelihoods of peptide presentation in patients. Various presentation models are known to those skilled in the art, for example the presentation models described in more detail in U.S. Pat. No. 10,055,540, US Application Pub. No. US20200010849A1 and US20110293637, and international patent application publications WO/2018/195357, WO/2018/208856, and WO2016187508, each herein incorporated by reference, in their entirety, for all purposes.

X. Training Module

Training modules can be used to construct one or more presentation models based on training data sets that generate likelihoods of whether peptide sequences will be presented by MHC alleles associated with the peptide sequences. Various training modules are known to those skilled in the art, for example the presentation models described in more detail in U.S. Pat. No. 10,055,540, US Application Pub. No. US20200010849A1, and international patent application publications WO/2018/195357, and WO/2018/208856, each herein incorporated by reference, in their entirety, for all purposes. A training module can construct a presentation model to predict presentation likelihoods of peptides on a per-allele basis. A training module can also construct a presentation model to predict presentation likelihoods of peptides in a multiple-allele setting where two or more MHC alleles are present.

XI. Prediction Module

A prediction module can be used to receive sequence data and select candidate antigens in the sequence data using a presentation model. Specifically, the sequence data may be DNA sequences, RNA sequences, and/or protein sequences extracted from tumor tissue cells of patients, infected cells patients, or infectious disease organisms themselves. A prediction module may identify candidate neoantigens that are mutated peptide sequences by comparing sequence data extracted from normal tissue cells of a patient with the sequence data extracted from tumor tissue cells of the patient to identify portions containing one or more mutations. A prediction module may identify candidate antigens that are pathogen-derived peptides, virally-derived peptides, bacterially-derived peptides, fungally-derived peptides, and parasitically-derived peptides, such as by comparing sequence data extracted from normal tissue cells of a patient with the sequence data extracted from infected cells of the patient to identify portions containing one or more infectious disease organism associated antigens. A prediction module may identify candidate antigens that have altered expression in a tumor cell or cancerous tissue in comparison to a normal cell or tissue by comparing sequence data extracted from normal tissue cells of a patient with the sequence data extracted from tumor tissue cells of the patient to identify improperly expressed candidate antigens. A prediction module may identify candidate antigens that are expressed in an infected cell or infected tissue in comparison to a normal cell or tissue by comparing sequence data extracted from normal tissue cells of a patient with the sequence data extracted from infected tissue cells of the patient to identify expressed candidate antigens (e.g., identifying expressed polynucleotides and/or polypeptides specific to an infectious disease).

A presentation module can apply one or more presentation model to processed peptide sequences to estimate presentation likelihoods of the peptide sequences. Specifically, the prediction module may select one or more candidate antigen peptide sequences that are likely to be presented on tumor HLA molecules or infected cell HLA molecules by applying presentation models to the candidate antigens. In one implementation, the presentation module selects candidate antigen sequences that have estimated presentation likelihoods above a predetermined threshold. In another implementation, the presentation model selects the N candidate antigen sequences that have the highest estimated presentation likelihoods (where N is generally the maximum number of epitopes that can be delivered in a vaccine). A vaccine including the selected candidate antigens for a given patient can be injected into the patient to induce immune responses.

XI.B. Cassette Design Module

XI.B.1 Overview

A cassette design module can be used to generate a vaccine cassette sequence based on selected candidate peptides for injection into a patient. Various cassette design modules are known to those skilled in the art, for example the cassette design modules described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

A set of therapeutic epitopes may be generated based on the selected peptides determined by a prediction module associated with presentation likelihoods above a predetermined threshold, where the presentation likelihoods are determined by the presentation models. However it is appreciated that in other embodiments, the set of therapeutic epitopes may be generated based on any one or more of a number of methods (alone or in combination), for example, based on binding affinity or predicted binding affinity to HLA class I or class II alleles of the patient, binding stability or predicted binding stability to HLA class I or class II alleles of the patient, random sampling, and the like.

Therapeutic epitopes may correspond to selected peptides themselves.

Therapeutic epitopes may also include C- and/or N-terminal flanking sequences in addition to the selected peptides. N- and C-terminal flanking sequences can be the native N- and C-terminal flanking sequences of the therapeutic vaccine epitope in the context of its source protein. Therapeutic epitopes can represent a fixed-length epitope Therapeutic epitopes can represent a variable-length epitope, in which the length of the epitope can be varied depending on, for example, the length of the C- or N-flanking sequence. For example, the C-terminal flanking sequence and the N-terminal flanking sequence can each have varying lengths of 2-5 residues, resulting in 16 possible choices for the epitope.

A cassette design module can also generate cassette sequences by taking into account presentation of junction epitopes that span the junction between a pair of therapeutic epitopes in the cassette. Junction epitopes are novel non-self but irrelevant epitope sequences that arise in the cassette due to the process of concatenating therapeutic epitopes and linker sequences in the cassette. The novel sequences of junction epitopes are different from the therapeutic epitopes of the cassette themselves.

A cassette design module can generate a cassette sequence that reduces the likelihood that junction epitopes are presented in the patient. Specifically, when the cassette is injected into the patient, junction epitopes have the potential to be presented by HLA class I or HLA class II alleles of the patient, and stimulate a CD8 or CD4 T-cell response, respectively. Such reactions are often times undesirable because T-cells reactive to the junction epitopes have no therapeutic benefit, and may diminish the immune response to the selected therapeutic epitopes in the cassette by antigenic competition.[76]

A cassette design module can iterate through one or more candidate cassettes, and determine a cassette sequence for which a presentation score of junction epitopes associated with that cassette sequence is below a numerical threshold. The junction epitope presentation score is a quantity associated with presentation likelihoods of the junction epitopes in the cassette, and a higher value of the junction epitope presentation score indicates a higher likelihood that junction epitopes of the cassette will be presented by HLA class I or HLA class II or both.

In one embodiment, a cassette design module may determine a cassette sequence associated with the lowest junction epitope presentation score among the candidate cassette sequences.

A cassette design module may iterate through one or more candidate cassette sequences, determine the junction epitope presentation score for the candidate cassettes, and identify an optimal cassette sequence associated with a junction epitope presentation score below the threshold.

A cassette design module may further check the one or more candidate cassette sequences to identify if any of the junction epitopes in the candidate cassette sequences are self-epitopes for a given patient for whom the vaccine is being designed. To accomplish this, the cassette design module checks the junction epitopes against a known database such as BLAST. In one embodiment, the cassette design module may be configured to design cassettes that avoid junction self-epitopes.

A cassette design module can perform a brute force approach and iterate through all or most possible candidate cassette sequences to select the sequence with the smallest junction epitope presentation score. However, the number of such candidate cassettes can be prohibitively large as the capacity of the vaccine increases. For example, for a vaccine capacity of 20 epitopes, the cassette design module has to iterate through $10^{18}$ possible candidate cassettes to determine the cassette with the lowest junction epitope presentation score. This determination may be computationally burdensome (in terms of computational processing resources required), and sometimes intractable, for the cassette design module to complete within a reasonable amount of time to generate the vaccine for the patient. Moreover, accounting for the possible junction epitopes for each candidate cassette can be even more burdensome. Thus, a cassette design module may select a cassette sequence based on ways of iterating through a number of candidate cassette sequences that are significantly smaller than the number of candidate cassette sequences for the brute force approach.

A cassette design module can generate a subset of randomly or at least pseudo-randomly generated candidate cassettes, and selects the candidate cassette associated with a junction epitope presentation score below a predetermined threshold as the cassette sequence. Additionally, the cassette design module may select the candidate cassette from the subset with the lowest junction epitope presentation score as the cassette sequence. For example, the cassette design module may generate a subset of ~1 million candidate cassettes for a set of 20 selected epitopes, and select the candidate cassette with the smallest junction epitope presentation score. Although generating a subset of random cassette sequences and selecting a cassette sequence with a low junction epitope presentation score out of the subset may be sub-optimal relative to the brute force approach, it requires significantly less computational resources thereby making its implementation technically feasible. Further, performing the brute force method as opposed to this more efficient technique may only result in a minor or even negligible improvement in junction epitope presentation score, thus making it not worthwhile from a resource allocation perspective. A cassette design module can determine an improved cassette configuration by formulating the epitope sequence for the cassette as an asymmetric traveling salesman problem (TSP). Given a list of nodes and distances between each pair of nodes, the TSP determines a sequence of nodes associated with the shortest total distance to visit each node exactly once and return to the original node. For example, given cities A, B, and C with known distances between each other, the solution of the TSP generates a closed sequence of cities, for which the total distance traveled to visit each city exactly once is the smallest among possible routes. The asymmetric version of the TSP determines the optimal sequence of nodes when the distance between a pair of nodes are asymmetric. For example, the “distance” for traveling from node A to node B may be different from the “distance” for traveling from node B to node A. By solving for an improved optimal cassette using an asymmetric TSP, the cassette design module can find a cassette sequence that results in a reduced presentation score across the junctions between epitopes of the cassette. The solution of the asymmetric TSP indicates a sequence of therapeutic epitopes that correspond to the order in which the epitopes should be concatenated in a cassette to minimize the junction epitope presentation score across the junctions of the cassette. A cassette sequence determined through this approach can result in a sequence with significantly less presentation of junction epitopes while potentially requiring significantly less computational resources than the random sampling approach, especially when the number of generated candidate cassette sequences is large. Illustrative examples of different computational approaches and comparisons for optimizing cassette design are described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

XI.B.2 Shared Antigen Vaccine Sequence Selection

Shared antigen sequences for inclusion in a shared antigen vaccine and appropriate patients for treatment with such vaccine can be chosen by one of skill in the art using the detailed disclosure provided herein. In certain instances a particular mutation and HLA allele combination can be preferred (e.g., based on sequencing data available from a given subject indicating that each are present in the subject) and subsequently used in combination together to identify a shared neoantigen sequence.

XIII. Example Computer

A computer can be used for any of the computational methods described herein. One skilled in the art will recognize a computer can have different architectures. Examples of computers are known to those skilled in the art, for example the computers described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

XIV. Antigen Delivery Vector Example

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3$^{rd}$ *Ed.* (Plenum Press) Vols A and B (1992).

XIV.A. Neoantigen Cassette Design

Through vaccination, multiple class I MHC restricted tumor-specific neoantigens (TSNAs) that stimulate the corresponding cellular immune response(s) can be delivered. In one example, a vaccine cassette was engineered to encode multiple epitopes as a single gene product where the epitopes were either embedded within their natural, surrounding peptide sequence or spaced by non-natural linker sequences. Several design parameters were identified that could potentially impact antigen processing and presentation and therefore the magnitude and breadth of the TSNA specific CD8 T cell responses. In the present example, several model cassettes were designed and constructed to evaluate: (1) whether robust T cell responses could be generated to multiple epitopes incorporated in a single expression cassette; (2) what makes an optimal linker placed between the TSNAs within the expression cassette—that leads to optimal processing and presentation of all epitopes; (3) if the relative position of the epitopes within the cassette impact T cell responses; (4) whether the number of epitopes within a cassette influences the magnitude or quality of the T cell responses to individual epitopes; (5) if the addition of cellular targeting sequences improves T cell responses.

Two readouts were developed to evaluate antigen presentation and T cell responses specific for marker epitopes within the model cassettes: (1) an in vitro cell-based screen which allowed assessment of antigen presentation as gauged by the activation of specially engineered reporter T cells (Aarnoudse et al., 2002; Nagai et al., 2012); and (2) an in vivo assay that used HLA-A2 transgenic mice (Vitiello et al., 1991) to assess post-vaccination immunogenicity of cassette-derived epitopes of human origin by their corresponding epitope-specific T cell responses (Cornet et al., 2006; Depla et al., 2008; Ishioka et al., 1999).

XIV.B. Antigen Cassette Design Evaluation

XIV.B.1. Methods and Materials

TCR and Cassette Design and Cloning

The selected TCRs recognize peptides NLVPMVATV (SEQ ID NO: 78) (PDB #5D2N), CLGGLLTMV (SEQ ID NO: 79) (PDB #3REV), GILGFVFTL (SEQ ID NO: 80) (PDB #1OGA) LLFGYPVYV (SEQ ID NO: 81) (PDB #1A07) when presented by A*0201. Transfer vectors were constructed that contain 2A peptide-linked TCR subunits (beta followed by alpha), the EMCV IRES, and 2A-linked CD8 subunits (beta followed by alpha and by the puromycin resistance gene). Open reading frame sequences were codon-optimized and synthesized by GeneArt.

Cell Line Generation for In Vitro Epitope Processing and Presentation Studies

Peptides were purchased from ProImmune or Genscript diluted to 10 mg/mL with 10 mM tris(2-carboxyethyl) phosphine (TCEP) in water/DMSO (2:8, v/v). Cell culture medium and supplements, unless otherwise noted, were from Gibco. Heat inactivated fetal bovine serum (FBShi) was from Seradigm. QUANTI-Luc Substrate, Zeocin, and Puromycin were from InvivoGen. Jurkat-Lucia NFAT Cells (InvivoGen) were maintained in RPMI 1640 supplemented with 10% FBShi, Sodium Pyruvate, and 100 μg/mL Zeocin. Once transduced, these cells additionally received 0.3 μg/mL Puromycin. T2 cells (ATCC CRL-1992) were cultured in Iscove's Medium (IMDM) plus 20% FBShi. U-87 MG (ATCC HTB-14) cells were maintained in MEM Eagles Medium supplemented with 10% FBShi.

Jurkat-Lucia NFAT cells contain an NFAT-inducible Lucia reporter construct. The Lucia gene, when activated by the engagement of the T cell receptor (TCR), causes secretion of a coelenterazine-utilizing luciferase into the culture medium. This luciferase can be measured using the QUANTI-Luc luciferase detection reagent. Jurkat-Lucia cells were transduced with lentivirus to express antigen-specific TCRs. The HIV-derived lentivirus transfer vector was obtained from GeneCopoeia, and lentivirus support plasmids expressing VSV-G (pCMV-VsvG), Rev (pRSV-Rev) and Gag-pol (pCgpV) were obtained from Cell Design Labs.

Lentivirus was prepared by transfection of 50-80% confluent T75 flasks of HEK293 cells with Lipofectamine 2000 (Thermo Fisher), using 40 μl of lipofectamine and 20 μg of the DNA mixture (4:2:1:1 by weight of the transfer plasmid: pCgpV:pRSV-Rev:pCMV-VsvG). 8-10 mL of the virus-containing media were concentrated using the Lenti-X system (Clontech), and the virus resuspended in 100-200 μl of fresh medium. This volume was used to overlay an equal volume of Jurkat-Lucia cells (5×10E4-1×10E6 cells were used in different experiments). Following culture in 0.3 μg/ml puromycin-containing medium, cells were sorted to obtain clonality. These Jurkat-Lucia TCR clones were tested for activity and selectivity using peptide loaded T2 cells.

In Vitro Epitope Processing and Presentation Assay

T2 cells are routinely used to examine antigen recognition by TCRs. T2 cells lack a peptide transporter for antigen processing (TAP deficient) and cannot load endogenous peptides in the endoplasmic reticulum for presentation on the MHC. However, the T2 cells can easily be loaded with exogenous peptides. The five marker peptides (NLVPMVATV (SEQ ID NO: 78), CLGGLLTMV (SEQ ID NO: 79), GLCTLVAML (SEQ ID NO: 82), LLFGYPVYV (SEQ ID NO: 81), GILGFVFTL (SEQ ID NO: 80)) and two irrelevant peptides (WLSLLVPFV (SEQ ID NO: 83), FLLTRICT (SEQ ID NO: 84)) were loaded onto T2 cells. Briefly, T2 cells were counted and diluted to 1×106 cells/mL with IMDM plus 1% FBShi. Peptides were added to result in 10 μg peptide/1×106 cells. Cells were then incubated at 37° C. for 90 minutes. Cells were washed twice with IMDM plus 20% FBShi, diluted to 5×10E5 cells/mL and 100 μL plated into a 96-well Costar tissue culture plate. Jurkat-Lucia TCR clones were counted and diluted to 5×10E5 cells/mL in RPMI 1640 plus 10% FBShi and 100 μL added to the T2 cells. Plates were incubated overnight at 37° C., 5% CO2. Plates were then centrifuged at 400 g for 3 minutes and 20 μL supernatant removed to a white flat bottom Greiner plate. QUANTI-Luc substrate was prepared according to instructions and 50 μL/well added. Luciferase expression was read on a Molecular Devices SpectraMax iE3x.

To test marker epitope presentation by the adenoviral cassettes, U-87 MG cells were used as surrogate antigen presenting cells (APCs) and were transduced with the adenoviral vectors. U-87 MG cells were harvested and plated in culture media as 5×10E5 cells/100 μl in a 96-well Costar tissue culture plate. Plates were incubated for approximately 2 hours at 37° C. Adenoviral cassettes were diluted with MEM plus 10% FBShi to an MOI of 100, 50, 10, 5, 1 and 0 and added to the U-87 MG cells as 5 μl/well. Plates were again incubated for approximately 2 hours at 37° C. Jurkat-Lucia TCR clones were counted and diluted to 5×10E5 cells/mL in RPMI plus 10% FBShi and added to the U-87 MG cells as 100 μL/well. Plates were then incubated for approximately 24 hours at 37° C., 5% CO2. Plates were centrifuged at 400 g for 3 minutes and 20 μL supernatant removed to a white flat bottom Greiner plate. QUANTI-Luc substrate was prepared according to instructions and 50 μL/well added. Luciferase expression was read on a Molecular Devices SpectraMax iE3x.

Mouse Strains for Immunogenicity Studies

Transgenic HLA-A2.1 (HLA-A2 Tg) mice were obtained from Taconic Labs, Inc. These mice carry a transgene consisting of a chimeric class I molecule comprised of the human HLA-A2.1 leader, α1, and α2 domains and the murine H2-Kb α3, transmembrane, and cytoplasmic domains (Vitiello et al., 1991). Mice used for these studies were the first generation offspring (F1) of wild type BALB/cAnNTac females and homozygous HLA-A2.1 Tg males on the C57Bl/6 background.

Adenovirus Vector (Ad5v) Immunizations

HLA-A2 Tg mice were immunized with $1\times10^{10}$ to $1\times10^{6}$ viral particles of adenoviral vectors via bilateral intramuscular injection into the tibialis anterior. Immune responses were measured at 12 days post-immunization.

Lymphocyte Isolation

Lymphocytes were isolated from freshly harvested spleens and lymph nodes of immunized mice. Tissues were dissociated in RPMI containing 10% fetal bovine serum with penicillin and streptomycin (complete RPMI) using the GentleMACS tissue dissociator according to the manufacturer's instructions.

Ex Vivo Enzyme-Linked Immunospot (ELISPOT) Analysis

ELISPOT analysis was performed according to ELISPOT harmonization guidelines (Janetzki et al., 2015) with the mouse IFNg ELISpotPLUS kit (MABTECH). $1\times10^{5}$ splenocytes were incubated with 10 uM of the indicated peptides for 16 hours in 96-well IFNg antibody coated plates. Spots were developed using alkaline phosphatase. The reaction was timed for 10 minutes and was quenched by running the plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Ex Vivo Intracellular Cytokine Staining (ICS) and Flow Cytometry Analysis

Freshly isolated lymphocytes at a density of $2\text{-}5\times10^{6}$ cells/mL were incubated with 10 uM of the indicated peptides for 2 hours. After two hours, brefeldin A was added to a concentration of 5 ug/ml and cells were incubated with stimulant for an additional 4 hours. Following stimulation, viable cells were labeled with fixable viability dye eFluor780 according to manufacturer's protocol and stained with anti-CD8 APC (clone 53-6.7, BioLegend) at 1:400 dilution. Anti-IFNg PE (clone XMG1.2, BioLegend) was used at 1:100 for intracellular staining. Samples were collected on an Attune N×T Flow Cytometer (Thermo Scientific). Flow cytometry data was plotted and analyzed using FlowJo. To assess degree of antigen-specific response, both the percent IFNg+ of CD8+ cells and the total IFNg+ cell number/1×10$^6$ live cells were calculated in response to each peptide stimulant.

XIV.B.2. In Vitro Evaluation of Antigen Cassette Designs

As an example of antigen cassette design evaluation, an in vitro cell-based assay was developed to assess whether selected human epitopes within model vaccine cassettes were being expressed, processed, and presented by antigen-presenting cells (FIG. 1). Upon recognition, Jurkat-Lucia reporter T cells that were engineered to express one of five TCRs specific for well-characterized peptide-HLA combinations become activated and translocate the nuclear factor of activated T cells (NFAT) into the nucleus which leads to transcriptional activation of a luciferase reporter gene. Antigenic stimulation of the individual reporter CD8 T cell lines was quantified by bioluminescence.

Individual Jurkat-Lucia reporter lines were modified by lentiviral transduction with an expression construct that includes an antigen-specific TCR beta and TCR alpha chain separated by a P2A ribosomal skip sequence to ensure equimolar amounts of translated product (Banu et al., 2014). The addition of a second CD8 beta-P2A-CD8 alpha element to the lentiviral construct provided expression of the CD8 co-receptor, which the parent reporter cell line lacks, as CD8 on the cell surface is crucial for the binding affinity to target pMHC molecules and enhances signaling through engagement of its cytoplasmic tail (Lyons et al., 2006; Yachi et al., 2006).

After lentiviral transduction, the Jurkat-Lucia reporters were expanded under puromycin selection, subjected to single cell fluorescence assisted cell sorting (FACS), and the monoclonal populations tested for luciferase expression. This yielded stably transduced reporter cell lines for specific peptide antigens 1, 2, 4, and 5 with functional cell responses. (Table 2).

TABLE 2

Development of an in vitro T cell activation assay. Peptide-specific T cell recognition as measured by induction of luciferase indicates effective processing and presentation of the vaccine cassette antigens.

| Epitope | Short Cassette Design AAY |
|---|---|
| 1 | 24.5 ± 0.5 |
| 2 | 11.3 ± 0.4 |
| 3* | n/a |
| 4 | 26.1 ± 3.1 |
| 5 | 46.3 ± 1.9 |

*Reporter T cell for epitope 3 not yet generated

In another example, a series of short cassettes, all marker epitopes were incorporated in the same position (FIG. 2A) and only the linkers separating the HLA-A*0201 restricted epitopes (FIG. 2B) were varied. Reporter T cells were individually mixed with U-87 antigen-presenting cells (APCs) that were infected with adenoviral constructs expressing these short cassettes, and luciferase expression was measured relative to uninfected controls. All four antigens in the model cassettes were recognized by matching reporter T cells, demonstrating efficient processing and presentation of multiple antigens. The magnitude of T cell responses follow largely similar trends for the natural and AAY-linkers. The antigens released from the RR-linker based cassette show lower luciferase inductions (Table 3). The DPP-linker, designed to disrupt antigen processing, produced a vaccine cassette that led to low epitope presentation (Table 3).

TABLE 3

Evaluation of linker sequences in short cassettes. Luciferase induction in the in vitro T cell activation assay indicated that, apart from the DPP-based cassette, all linkers facilitated efficient release of the cassette antigens. T cell epitope only (no linker) = 9AA, natural linker one side = 17AA, natural linker both sides = 25AA, non-natural linkers = AAY, RR, DPP

| | Short Cassette Designs | | | | | |
|---|---|---|---|---|---|---|
| Epitope | 9AA | 17AA | 25AA | AAY | RR | DPP |
| 1 | 33.6 ± 0.9 | 42.8 ± 2.1 | 42.3 ± 2.3 | 24.5 ± 0.5 | 21.7 ± 0.9 | 0.9 ± 0.1 |
| 2 | 12.0 ± 0.9 | 10.3 ± 0.6 | 14.6 ± 04 | 11.3 ± 0.4 | 8.5 ± 0.3 | 1.1 ± 0.2 |
| 3* | n/a | n/a | n/a | n/a | n/a | n/a |
| 4 | 26.6 ± 2.5 | 16.1 ± 0.6 | 16.6 ± 0.8 | 26.1 ± 3.1 | 12.5 ± 0.8 | 1.3 ± 0.2 |
| 5 | 29.7 ± 0.6 | 21.2 ± 0.7 | 24.3 ± 1.4 | 46.3 ± 1.9 | 19.7 ± 0.4 | 1.3 ± 0.1 |

*Reporter T cell for epitope 3 not yet generated

Figure 3:
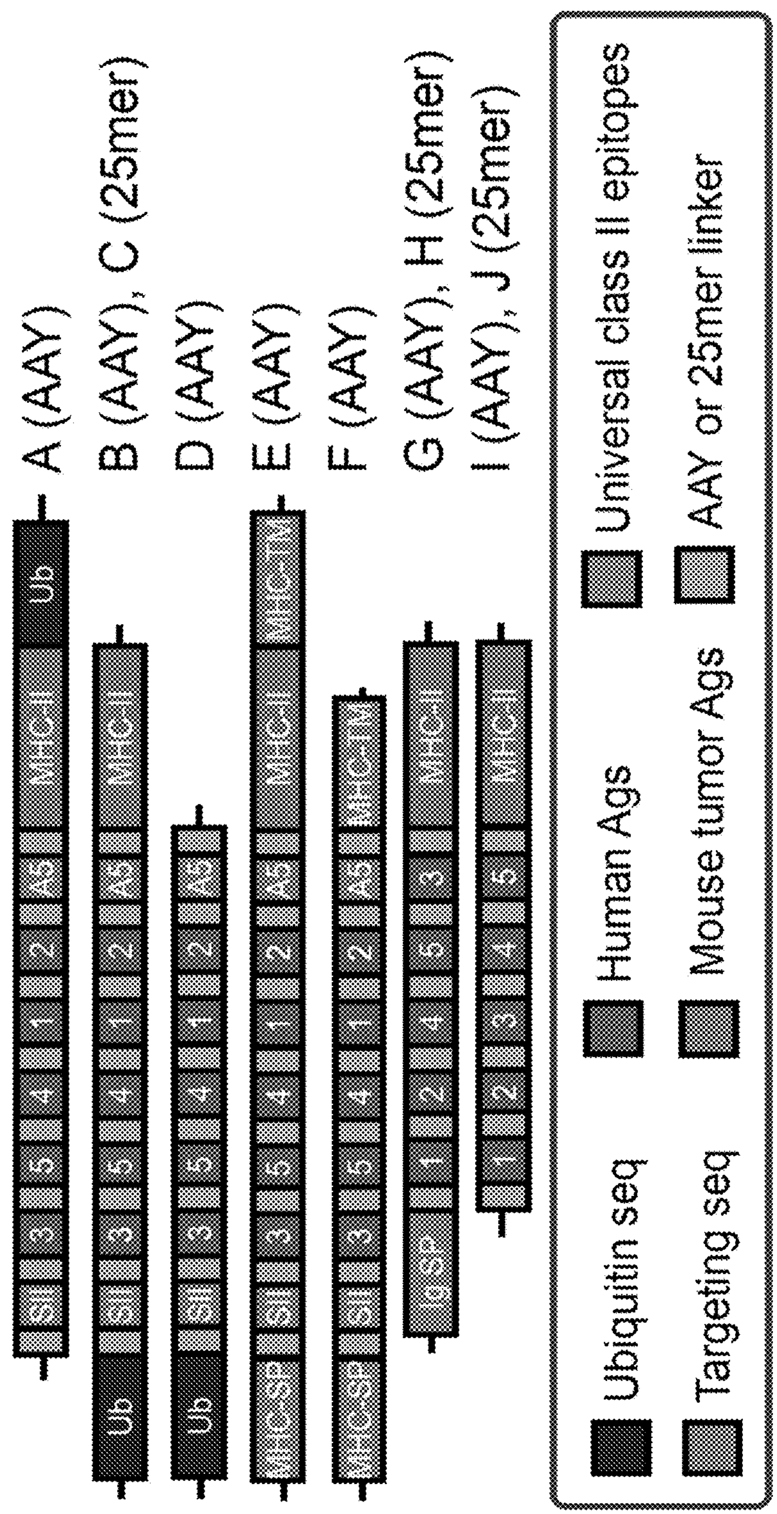
FIG. 3 illustrates evaluation of cellular targeting sequences added to model vaccine cassettes. The targeting cassettes extend the short cassette designs with ubiquitin (Ub), signal peptides (SP) and/or transmembrane (TM) domains, feature next to the five marker human T cell epitopes (epitopes 1 through 5) also two mouse T cell epitopes SIINFEKL (SII) (SEQ ID NO: 72) and SPSYAYHQF (A5) (SEQ ID NO: 73), and use either the non-natural linker AAY- or natural linkers flanking the T cell epitopes on both sides (25mer).

In another example, an additional series of short cassettes were constructed that, besides human and mouse epitopes, contained targeting sequences such as ubiquitin (Ub), MHC and Ig-kappa signal peptides (SP), and/or MHC transmembrane (TM) motifs positioned on either the N- or C-terminus of the cassette. (FIG. 3). When delivered to U-87 APCs by adenoviral vector, the reporter T cells again demonstrated efficient processing and presentation of multiple cassette-derived antigens. However, the magnitude of T cell responses were not substantially impacted by the various targeting features (Table 4).

TABLE 4

Evaluation of cellular targeting sequences added to model vaccine cassettes. Employing the in vitro T cell activation assay demonstrated that the four HLA-A*0201 restricted marker epitopes are liberated efficiently from the model cassettes and targeting sequences did not substantially improve T cell recognition and activation.

| | Short Cassette Designs | | | | | | | | | |
|---|---|---|---|---|---|---|---|---|---|---|
| Epitope | A | B | C | D | E | F | G | H | I | J |
| 1 | 32.5 ± 1.5 | 31.8 ± 0.8 | 29.1 ± 1.2 | 29.1 ± 1.1 | 28.4 ± 0.7 | 20.4 ± 0.5 | 35.0 ± 1.3 | 30.3 ± 2.0 | 22.5 ± 0.9 | 38.1 ± 1.6 |
| 2 | 6.1 ± 0.2 | 6.3 ± 0.2 | 7.6 ± 0.4 | 7.0 ± 0.5 | 5.9 ± 0.2 | 3.7 ± 0.2 | 7.6 ± 0.4 | 5.4 ± 0.3 | 6.2 ± 0.4 | 6.4 ± 0.3 |
| 3* | n/a | n/a | n/a | n/a | n/a | n/a | n/a | n/a | n/a | n/a |
| 4 | 12.3 ± 1.1 | 14.1 ± 0.7 | 12.2 ± 0.8 | 13.7 ± 1.0 | 11.7 ± 0.8 | 10.6 ± 0.4 | 11.0 ± 0.6 | 7.6 ± 0.6 | 16.1 ± 0.5 | 8.7 ± 0.5 |
| 5 | 44.4 ± 2.8 | 53.6 ± 1.6 | 49.9 ± 3.3 | 50.5 ± 2.8 | 41.7 ± 2.8 | 36.1 ± 1.1 | 46.5 ± 2.1 | 31.4 ± 0.6 | 75.4 ± 1.6 | 35.7 ± 2.2 |

*Reporter T cell for epitope 3 not yet generated

XIV.B.3. In Vivo Evaluation of Antigen Cassette Designs

Figures 2A, 2B:
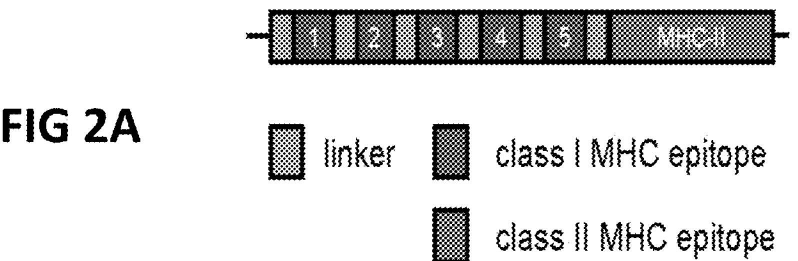
FIG. 2A illustrates evaluation of linker sequences in short cassettes and shows five class I MHC restricted epitopes (epitopes 1 through 5) concatenated in the same position relative to each other followed by two universal class II MHC epitopes (MHC-II). Various iterations were generated using different linkers. In some cases the T cell epitopes are directly linked to each other. In others, the T cell epitopes are flanked on one or both sides by its natural sequence. In other iterations, the T cell epitopes are linked by the non-natural sequences AAY, RR, and DPP.
FIG. 2B illustrates evaluation of linker sequences in short cassettes and shows sequence information on the T cell epitopes embedded in the short cassettes.
Figure 4:
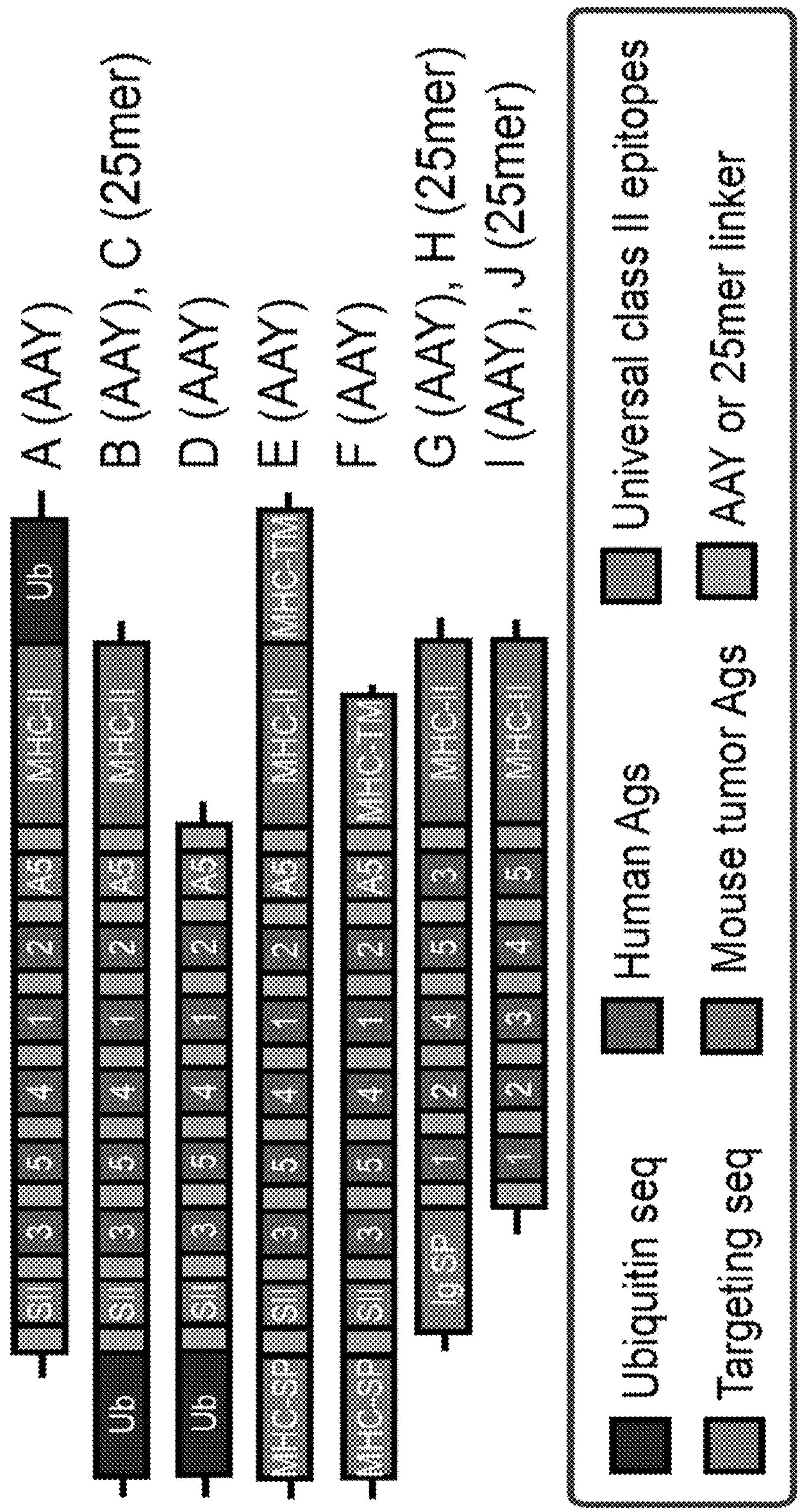
FIG. 4 illustrates in vivo evaluation of linker sequences in short cassettes. A) Experimental design of the in vivo evaluation of vaccine cassettes using HLA-A2 transgenic mice.
Figure 5A:
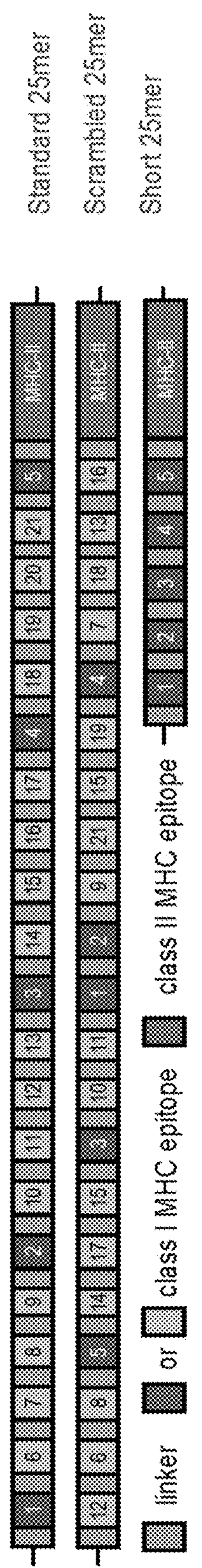
FIG. 5A illustrates in vivo evaluation of the impact of epitope position in long 21-mer cassettes and shows the design of long cassettes entails five marker class I epitopes (epitopes 1 through 5) contained in their 25-mer natural sequence (linker=natural flanking sequences), spaced with additional well-known T cell class I epitopes (epitopes 6 through 21) contained in their 25-mer natural sequence, and two universal class II epitopes (MHC-II0, with only the relative position of the class I epitopes varied.

As another example of antigen cassette design evaluation, vaccine cassettes were designed to contain 5 well-characterized human class I MHC epitopes known to stimulate CD8 T cells in an HLA-A*02:01 restricted fashion (FIG. 2A, 3, 5A). For the evaluation of their in vivo immunogenicity, vaccine cassettes containing these marker epitopes were incorporated in adenoviral vectors and used to infect HLA-A2 transgenic mice (FIG. 4). This mouse model carries a transgene consisting partly of human HLA-A*0201 and mouse H2-Kb thus encoding a chimeric class I MHC molecule consisting of the human HLA-A2.1 leader, $\alpha$1 and $\alpha$2 domains ligated to the murine $\alpha$3, transmembrane and cytoplasmic H2-Kb domain (Vitiello et al., 1991). The chimeric molecule allows HLA-A*02:01-restricted antigen presentation whilst maintaining the species-matched interaction of the CD8 co-receptor with the $\alpha$3 domain on the MHC.

For the short cassettes, all marker epitopes generated a T cell response, as determined by IFN-gamma ELISPOT, that was approximately 10-50× stronger of what has been commonly reported (Cornet et al., 2006; Depla et al., 2008; Ishioka et al., 1999). Of all the linkers evaluated, the concatamer of 25mer sequences, each containing a minimal epitope flanked by their natural amino acids sequences, generated the largest and broadest T cell response (Table 5). Intracellular cytokine staining (ICS) and flow cytometry analysis revealed that the antigen-specific T cell responses are derived from CD8 T cells.

TABLE 5

In vivo evaluation of linker sequences in short cassettes. ELISPOT data indicated that HLA-A2 transgenic mice, 17 days post-infection with 1e11 adenovirus viral particles, generated a T cell response to all class I MHC restricted epitopes in the cassette.

| | Short Cassette Designs | | | | | |
|---|---|---|---|---|---|---|
| Epitope | 9AA | 17AA | 25AA | AAY | RR | DPP |
| 1 | 2020 +/− 583 | 2505 +/− 1281 | 6844 +/− 956 | 1489 +/− 762 | 1675 +/− 690 | 1781 +/− 774 |
| 2 | 4472 +/− 755 | 3792 +/− 1319 | 7629 +/− 996 | 3851 +/− 1748 | 4726 +/− 1715 | 5868 +/− 1427 |
| 3 | 5830 +/− 315 | 3629 +/− 862 | 7253 +/− 491 | 4813 +/− 1761 | 6779 +/− 1033 | 7328 +/− 1700 |
| 4 | 5536 +/− 375 | 2446 +/− 955 | 2961 +/− 1487 | 4230 +/− 1759 | 6518 +/− 909 | 7222 +/− 1824 |
| 5 | 8800 +/− 0 | 7943 +/− 821 | 8423 +/− 442 | 8312 +/− 696 | 8800 +/− 0 | 1836 +/− 328 |

In another example, a series of long vaccine cassettes was constructed and incorporated in adenoviral vectors that, next to the original 5 marker epitopes, contained an additional 16 HLA-A*02:01, A*03:01 and B*44:05 epitopes with known CD8 T cell reactivity (FIG. 5A, 5B). The size of these long cassettes closely mimicked the final clinical cassette design, and only the position of the epitopes relative to each other was varied. The CD8 T cell responses were comparable in magnitude and breadth for both long and short vaccine cassettes, demonstrating that (a) the addition of more epitopes did not substantially impact the magnitude of immune response to the original set of epitopes, and (b) the position of an epitope in a cassette did not substantially influence the ensuing T cell response to it (Table 6).

TABLE 6

In vivo evaluation of the impact of epitope position in long cassettes. ELISPOT data indicated that HLA-A2 transgenic mice, 17 days post-infection with 5e10 adenovirus viral particles, generated a T cell response comparable in magnitude for both long and short vaccine cassettes.

| | Long Cassette Designs | | |
|---|---|---|---|
| Epitope | Standard | Scrambled | Short |
| 1 | 863 +/− 1080 | 804 +/ −1113 | 1871 +/− 2859 |
| 2 | 6425 +/− 1594 | 28 +/ −62 | 5390 +/− 1357 |
| 3* | 23 +/− 30 | 36 +/ −18 | 0 +/− 48 |
| 4 | 2224 +/− 1074 | 2727 +/ −644 | 2637 +/− 1673 |
| 5 | 7952 +/− 297 | 8100 +/ −0 | 8100 +/− 0 |

*Suspected technical error caused an absence of a T cell response.

XIV.B.4. Antigen Cassette Design for Immunogenicity and Toxicology Studies

In summary, the findings of the model cassette evaluations (FIG. 2-5, Tables 2-6) demonstrated that, for model vaccine cassettes, robust immunogenicity was achieved when a "string of beads" approach was employed that encodes around 20 epitopes in the context of an adenovirus-based vector. The epitopes were assembled by concatenating 25mer sequences, each embedding a minimal CD8 T cell epitope (e.g. 9 amino acid residues) that were flanked on both sides by its natural, surrounding peptide sequence (e.g. 8 amino acid residues on each side). As used herein, a "natural" or "native" flanking sequence refers to the N- and/or C-terminal flanking sequence of a given epitope in the naturally occurring context of that epitope within its source protein. For example, the HCMV pp65 MHC I epitope NLVPMVATV (SEQ ID NO: 78) is flanked on its 5' end by the native 5' sequence WQAGILAR (SEQ ID NO: 85) and on its 3' end by the native 3' sequence QGQNLKYQ (SEQ ID NO: 86), thus generating the WQAGILARNLVPMVATVQGQNLKYQ (SEQ ID NO: 87) 25mer peptide found within the HCMV pp65 source protein. The natural or native sequence can also refer to a nucleic acid sequence that encodes an epitope flanked by native flanking sequence(s). Each 25mer sequence is directly connected to the following 25mer sequence. In instances where the minimal CD8 T cell epitope is greater than or less than 9 amino acids, the flanking peptide length can be adjusted such that the total length is still a 25mer peptide sequence. For example, a 10 amino acid CD8 T cell epitope can be flanked by an 8 amino acid sequence and a 7 amino acid. The concatamer was followed by two universal class II MHC epitopes that were included to stimulate CD4 T helper cells and improve overall in vivo immunogenicity of the vaccine cassette antigens. (Alexander et al., 1994; Panina-Bordignon et al., 1989) The class II epitopes were linked to the final class I epitope by a GPGPG amino acid linker (SEQ ID NO:56). The two class II epitopes were also linked to each other by a GPGPG amino acid linker (SEQ ID NO: 56), as a well as flanked on the C-terminus by a GPGPG amino acid linker (SEQ ID NO: 56). Neither the position nor the number of epitopes appeared to substantially impact T cell recognition or response. Targeting sequences also did not appear to substantially impact the immunogenicity of cassette-derived antigens.

Figure 6A:
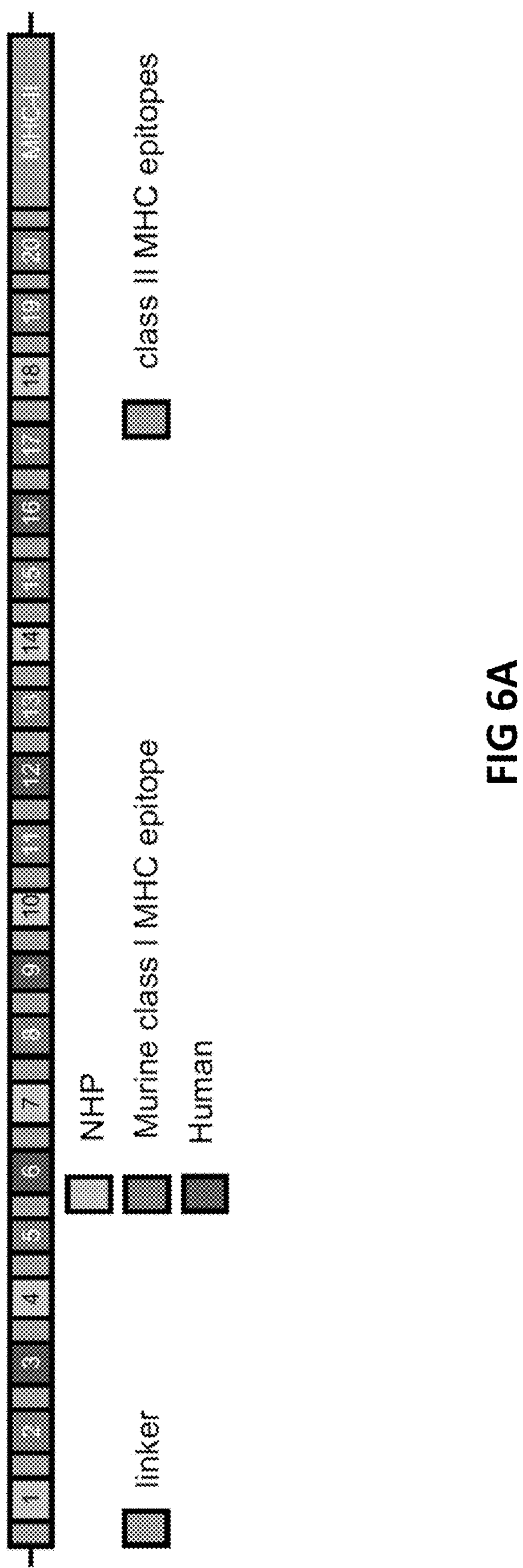
FIG. 6A illustrates final cassette design for preclinical IND-enabling studies and shows the design of the final cassettes comprises 20 MHC I epitopes contained in their 25-mer natural sequence (linker=natural flanking sequences), composed of 6 non-human primate (NHP) epitopes, 5 human epitopes, 9 murine epitopes, as well as 2 universal MHC class II epitopes.

As a further example, based on the in vitro and in vivo data obtained with model cassettes (FIG. 2-5, Tables 2-6), a cassette design was generated that alternates well-characterized T cell epitopes known to be immunogenic in non-human primates (NHPs), mice and humans. The 20 epitopes, all embedded in their natural 25mer sequences, are followed by the two universal class II MHC epitopes that were present in all model cassettes evaluated (FIG. 6). This cassette design was used to study immunogenicity as well as pharmacology and toxicology studies in multiple species.

XIV.B.5. Antigen Cassette Design and Evaluation for 30, 40, and 50 Antigens

Figure 29:
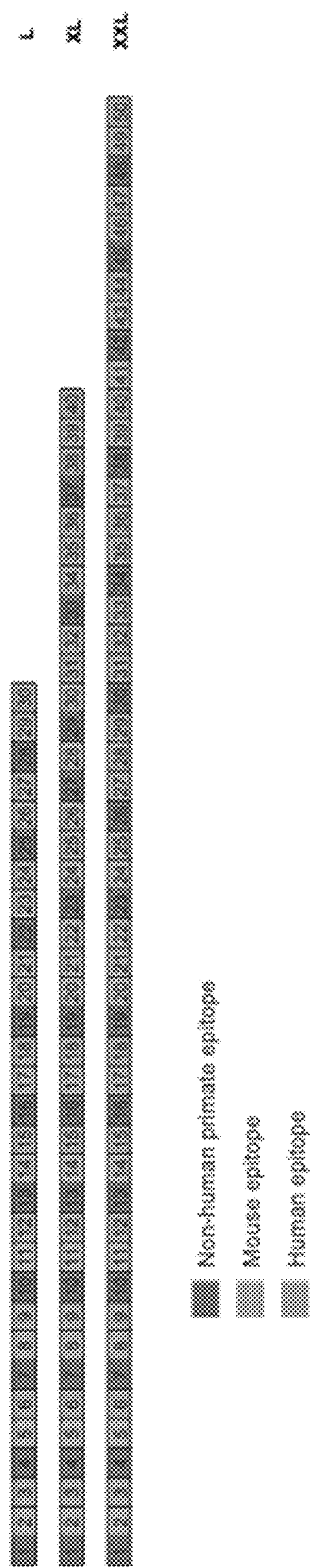
FIG. 29 illustrates the general organization of the model epitopes from the various species for large antigen cassettes that had either 30 (L), 40 (XL) or 50 (XXL) epitopes.

Large antigen cassettes were designed that had either 30 (L), 40 (XL) or 50 (XXL) epitopes, each 25 amino acids in length. The epitopes were a mix of human, NHP and mouse epitopes to model disease antigens including tumor antigens. FIG. 29 illustrates the general organization of the epitopes from the various species. The model antigens used are described in Tables 32, 33 and 34 for human, primate, and mouse model epitopes, respectively. Each of Tables 32, 33 and 34 described the epitope position, name, minimal epitope description, and MHC class.

Figure 30:
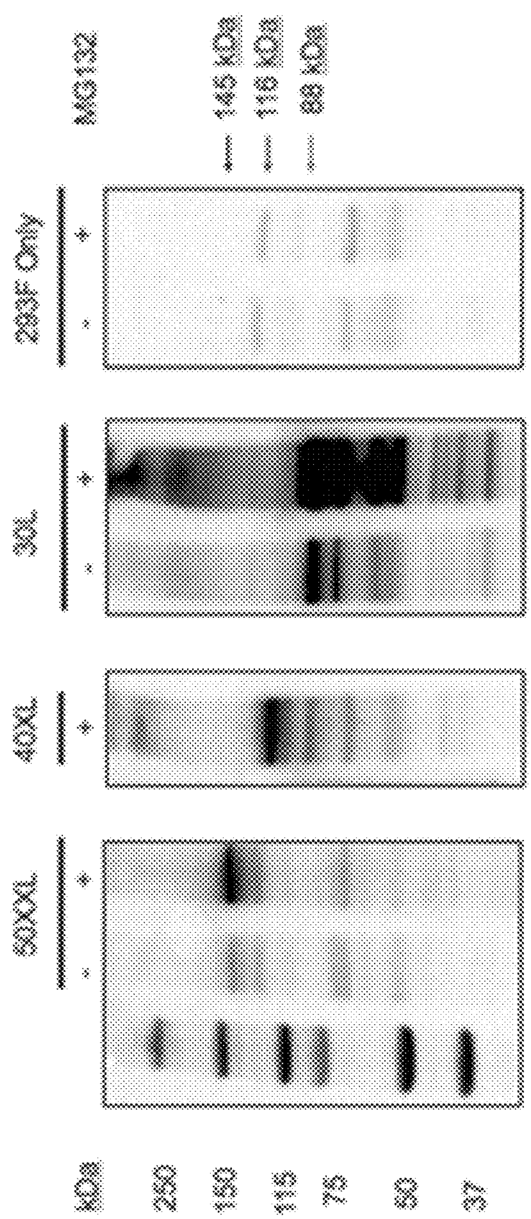
FIG. 30 shows ChAd vectors express long cassettes as indicated by the above Western blot using an anti-class II (PADRE) antibody that recognizes a sequence common to all cassettes. HEK293 cells were infected with ChAdV68 vectors expressing large cassettes (ChAdV68-50XXL, ChAdV68-40XL & ChAdV68-30L) of variable size. Infections were set up at a MOI of 0.2. Twenty-four hours post infection MG132 a proteasome inhibitor was added to a set of the infected wells (indicated by the plus sign). Another set of virus treated wells were not treated with MG132 (indicated by minus sign). Uninfected HEK293 cells (293F) were used as a negative control. Forty-eight hours post infection cell pellets were harvested and analyzed by SDS/PAGE electrophoresis, and immunoblotting using a rabbit anti-Class II PADRE antibody. A HRP anti-rabbit antibody and ECL chemiluminescent substrate was used for detection.

These cassettes were cloned into the ChAdV68 and alphavirus vaccine vectors as described to evaluate the efficacy of longer multiple-epitope cassettes. FIG. 30 shows that each of the large antigen cassettes were expressed from a ChAdV vector as indicated by at least one major band of the expected size by Western blot.

Figure 31:
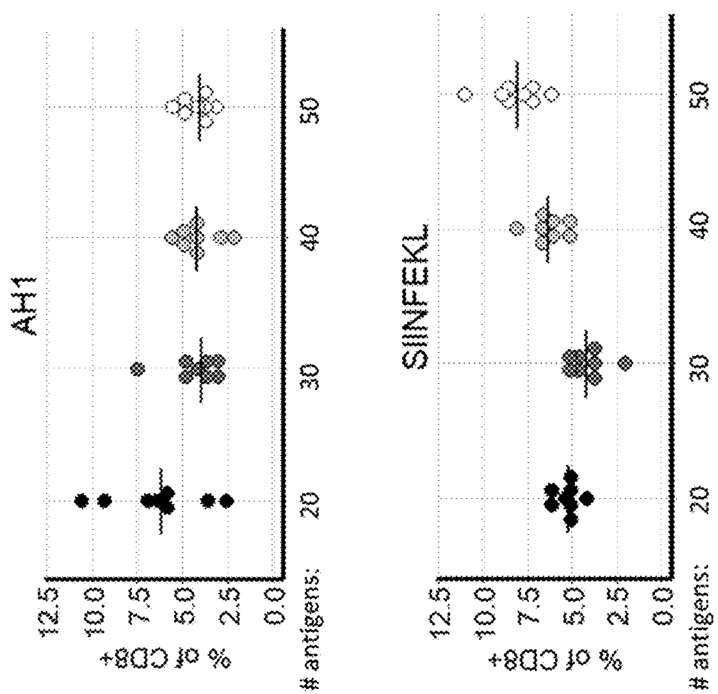
FIG. 31 shows CD8+ immune responses in ChAdV68 large cassette immunized mice, detected against AH1 (top) and SIINFEKL (SEQ ID NO: 72) (bottom) by ICS. Data is presented as IFNg+ cells against the model epitope as % of total CD8 cells
Figure 32:
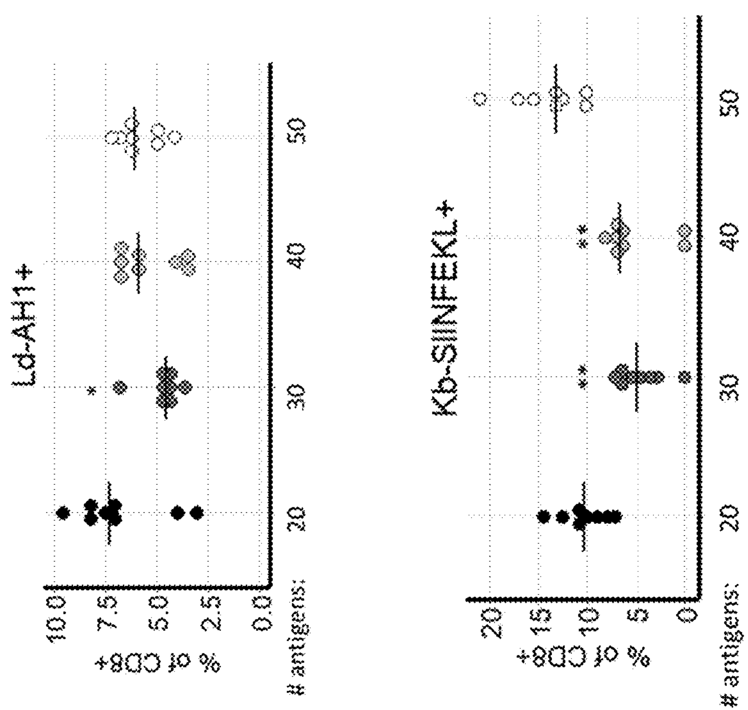
FIG. 32 shows CD8+ responses to LD-AH1+ (top) and Kb-SIINFEKL+ (bottom) ("SIINFEKL" disclosed as SEQ ID NO: 72) Tetramers post ChAdV68 large cassette vaccination. Data is presented as % of total CD8 cells reactive against the model Tetramer peptide complex. *$p<0.05$, **$p<0.01$ by ANOVA with Tukey's test. All p-values compared to MAG 20-antigen cassette.
Figure 33:
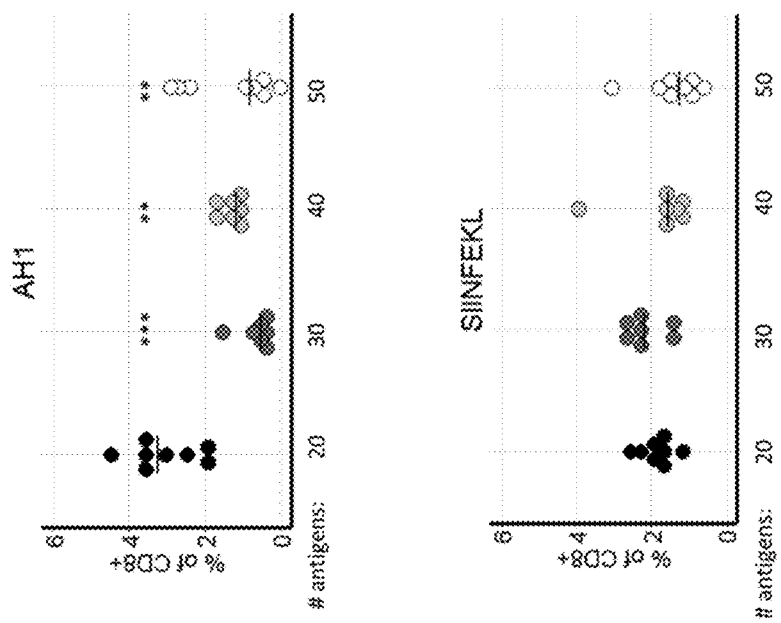
FIG. 33 shows CD8+ immune responses in alphavirus large cassette treated mice, detected against AH1 (top) and SIINFEKL (SEQ ID NO: 72) (bottom) by ICS. Data is presented as IFNg+ cells against the model epitope as % of total CD8 cells. *$p<0.05$, $p<0.01$, *$p<0.001$ by ANOVA with Tukey's test. All p-values compared to MAG 20-antigen cassette.

Mice were immunized as described to evaluate the efficacy of the large cassettes. T cell responses were analyzed by ICS and tetramer staining following immunization with a ChAdV68 vector (FIG. 31/Table 35 and FIG. 32/Table 36, respectively) and by ICS following immunization with a srRNA vector (FIG. 33/Table 37) for epitopes AH1 (top panels) and SIINFEKL (SEQ ID NO: 72) (bottom panels). Immunizations using ChAdV68 and srRNA vaccine vectors expressing either 30 (L), 40 (XL) or 50 (XXL) epitopes induced CD8+ immune responses to model disease epitopes.

TABLE 32

Human epitopes in large cassettes (TABLE 32 discloses SEQ ID NOS 80-82, 78-79, 88-100, 87 and 101-111, respectively, in order of columns)

| Epitope position in each cassette L | XL | XXL | Name | Minimal epitope | 25 mer | MHC | Restriction | Strain | Species |
|---|---|---|---|---|---|---|---|---|---|
| 3 | 3 | 3 | 5.influenza M | GILGFVFTL | PILSPLTKGILGFVFTLTVPSERGL | Class I | A*02:01 | Human | Human |
| 6 | 6 | 6 | 4.HTLV-1 Tax | LLFGYPVYV | HFPGFGQSLLFGYPVYVFGDCVQGD | Class I | A*02:01 | Human | Human |
| 9 | 9 | 9 | 3.EBV BMLF1 | GLCTLVAML | RMQAIQNAGLCTLVAMLEETIFWLQ | Class I | A*02:01 | Human | Human |
| 12 | 12 | 12 | 1.HCMV pp65 | NLVPMVATV | WQAGILARNLVPMVATVQGQNLKYQ | Class I | A*02:01 | Human | Human |
| 15 | 15 | 15 | 2.EBV LMP2A | CLGGLLTMV | RTYGPVFMCLGGLLTMVAGAVWLTV | Class I | A*02:01 | Human | Human |
| 18 | 18 | 18 | CT83 | NTDNNLAVY | SSSGLINSNTDNNLAVYDLSRDILN | Class I | A*01:01 | Human | Human |
| | 21 | 21 | MAGEA6 | EVDPIGHVY | LVEGIELMEVDPIGHVYIFATCLGL | Class I | B*35:01 | Human | Human |
| 21 | 25 | 25 | CT83 | LLASSILCA | MNFYLLLASSILCALIVFWKYRRFQ | Class I | A*02:01 | Human | Human |
| 24 | 31 | 28 | FOXE1 | AIFPGAVPAA | AAAAAAAAIFPGAVPAARPPYPGAV | Class I | A*02:01 | Human | Human |
| 27 | 35 | 32 | CT83 | VYDLSRDIL | SNTDNNLAVYDLSRDILNNFPHSIA | Class I | A*24:02 | Human | Human |
| | 38 | 36 | MAGE3/6 | ASSLPTTMNY | DPPQSPQGASSLPTTMNYPLWSQSY | Class I | A*01:01 | Human | Human |
| 30 | 40 | 40 | Influenza HA | PKYVKQNTLKLAT | ITYGACPKYVKQNTLKLATGMRNVP | Class II | DRB1*0101 | Human | Human |
| | | 44 | CMV pp65 | LPLKMLNIPSINVH | SIYVYALPLKMLNIPSINVHHYPSA | Class II | DRB1*0101 | Human | Human |

TABLE 32 -continued

Human epitopes in large cassettes (TABLE 32 discloses SEQ ID NOS 80-82, 78-79, 88-100, 87 and 101-111, respectively, in order of columns)

| Epitope position in each cassette | | | | | | | | |
|---|---|---|---|---|---|---|---|---|
| L | XL | XXL | Name | Minimal epitope25 mer | MHC | Restriction | Strain | Species |
| | | 47 | EBV EBNA3A | PEQWMFQGAPPSQGTEGPWVPEQWMFQGAPPSQGTDVVQH | Class II | DRB1*0102 | Human | Human |
| | | 50 | CMV pp65 | EHPTFTSQYRIQGKLRGPQYSEHPTFTSQYRIQGKLEYRH | Class II | DRB1*1101 | Human | Human |

TABLE 33

NHP epitopes in large cassettes (TABLE 33 discloses SEQ ID NOS 112-141, respectively, in order of columns)

| Epitope position in each cassette | | | | epitope | | | | | |
|---|---|---|---|---|---|---|---|---|---|
| L | XL | XXL | Name | Minimal | 25 mer | MHC | Restriction | Strain | Species |
| 1 | 1 | 1 | Gag CM9 | CTPYDINQM | MFQALSEGCTPYD INQMLNVLGDHQ | Class I | Mamu-A*01 | Rhesus | NHP |
| 4 | 4 | 4 | Tat TL8 | TTPESANL | SCISEADATTPES ANLGEEILSQLY | Class I | Mamu-A*01 | Rhesus | NHP |
| 7 | 7 | 7 | Env CL9 | CAPPGYALL | WDAIRFRYCAPPG YALLRCNDTNYS | Class I | Mamu-A*01 | Rhesus | NHP |
| 10 | 10 | 10 | Pol SV9 | SGPKTNIIV | AFLMALTDSGPKT NIIVDSQYVMGI | Class I | Mamu-A*01 | Rhesus | NHP |
| 13 | 13 | 13 | Gag LW9 | LSPRTLNAW | GNVWVHTPLSPRT LNAWVKAVEEKK | Class I | Mamu-A*01 | Rhesus | NHP |
| | | 16 | Env_TL9 | TVPWPNASL | AFRQVCHTTVPWP NASLTPKWNNET | Class I | Mamu-A*01 | Rhesus | NHP |
| 16 | 16 | 19 | Ag856 | PNGTHSWEYWGAQLN | VFNFPPNGTHSWE YWGAQLNAMKGD | Class II | Mamu-DR*W | Rhesus | NHP |
| 19 | 19 | 23 | HIV-1 Env | YKYKVVKIEPLGV | NWRSELYKYKVVK IEPLGVAPTKAK | Class II | Mamu-DR*W | Rhesus | NHP |
| | | 26 | Gag TE15 | TEEAKQIVQRHLV VE | EKVKHTEEAKQIV QRHLVVETGTTE | Class II | Mamu-DRB* | Rhesus | NHP |
| | 23 | 30 | CFP-10 36-48 | AGSLQGQWRGAAG | DQVESTAGSLQGQ WRGAAGTAAQAA | Class II | Mafa-DRB1* | Cyno | NHP |
| | 27 | 34 | CFP-10 71-86 | EISTNIRQAGVQY SRA | QELDEISTNIRQA GVQYSRADEEQQ | Class II | Mafa-DRB1* | Cyno | NHP |
| 22 | 29 | 38 | Env 338-346 | RPKQAWCWF | FHSQPINERPKQA WCWEGGSWKEAI | Class I | Mafa-A1*063 | Cyno | NHP |
| 25 | 33 | 42 | Nef 103-111 | RPKVPLRTM | DDIDEEDDDLVGV SVRPKVPLRTMS | Class I | Mafa-A1*063 | Cyno | NHP |
| 28 | 37 | 45 | Gag 386-394 | GPRKPIKCW | PFAAAQQRGPRKP IKCWNCGKEGHS | Class I | Mafa-A1*063 | Cyno | NHP |
| | | 48 | Nef LT9 | LNMADKKET | RRLTARGLLNMAD KKETRTPKKAKA | Class I | Mafa-B*1043 | Cyno | NHP |

TABLE 34

Epitope position in each cassette (TABLE 34 discloses SEQ ID NOS 72, 142-144, 73, 145-161, 75-76 and 162-177, respectively, in order of columns)

| Epitopes in large cassettes | | | | Minimal | | | | | |
|---|---|---|---|---|---|---|---|---|---|
| L | XL | XXL | Name | epitope | 25 mer | MHC | Restriction | Strain | Species |
| 2 | 2 | 2 | OVA257 | SIINFEKL | VSGLEQLESIINF EKLTEWTSSNVM | Class I | H2-Kb | B6 | Mouse |
| | | 5 | B16-EGP | EGPRNQDWL | ALLAVGALEGPRN QDWLGVPRQLVT | Class I | H2-Db | B6 | Mouse |
| | | 8 | B16-TRP1 455-463 | TAPDNLGYM | VTNTEMFVTAPDN LGYMYEVQWPGQ | Class I | H2-Db | B6 | Mouse |
| | | 11 | Trp2180-188 | SVYDFFVWL | TQPQIANCSVYDF FVWLHYYSVRDT | Class I | H2-Kb | B6 | Mouse |
| 5 | 5 | 14 | CT26 AH1-A5 | SPSYAYHQF | LWPRVTYHSPSYA YHQFERRAKYKR | Class I | H2-Ld | Balb/C | Mouse |
| | 8 | 17 | CT26 AH1-39 | MNKYAYHML | LWPRVTYHMNKYA YHMLERRAKYKR | Class I | H2-Ld | Balb/C | Mouse |
| | 11 | 20 | MC38 Dpagt1 | SIIVFNLL | GQSLVISASIIVF NLLELEGDYRDD | Class I | H2-Kb | B6 | Mouse |
| | 14 | 22 | MC38 Adpgk | ASMTNMELM | GIPVHLELASMTN MELMSSIVHQQV | Class I | H2-Db | B6 | Mouse |
| | 17 | 24 | MC38 Reps1 | AQLANDVVL | RVLELFRAAQLAN DVVLQIMELCGA | Class I | H2-Db | B6 | Mouse |
| 8 | 20 | 27 | P815 P1A 35-44 | LPYLGWLVF | HRYSLEEILPYLG WLVFAVVTTSFL | Class I | H2-Ld | DBA/2 | Mouse |
| 11 | 22 | 29 | P815 P1E | GYCGLRGTGV | YLSKNPDGYCGLR GTGVSCPMAIKK | Class I | H2-Kd | DBA/2 | Mouse |
| 14 | 24 | 31 | Panc02 Mesothelin | LSIFKHKL | NEIPFTYEQLSIF KHKLDKTYPQGY | Class I | H2-Kb | B6 | Mouse |
| 17 | 26 | 33 | Panc02 Mesothelin | LIWIPALL | SRASLLGPGFVLI WIPALLPALRLS | Class I | H2-Kb | B6 | Mouse |
| 20 | 28 | 35 | ID8 FRa 161-169 | SSGHNECPV | NWHKGWNWSSGHN ECPVGASCHPFT | Class I | H2-Kb | B6 | Mouse |
| 23 | 30 | 37 | ID8 Mesothelin 400 | GQKMNAQAI | KTLLKVSKGQKMN AQAIALVACYLR | Class I | H2-Db | B6 | Mouse |
| 26 | 32 | 39 | OVA-II | ISQAVHAAH AEINEAGR | ESLKISQAVHAAH AEINEAGREVVG | Class II | I-Ab, I-Ad | B6 | Mouse |
| 29 | 34 | 41 | ESAT-6 | MTEQQWNFAG IEAAASAIQ | MTEQQWNFAGIEA AASAIQGNVTSI | Class II | I-Ab | B6 | Mouse |
| | 36 | 43 | TT p30 | FNNFTVSFWL RVPKVSASHL | DMFNNFTVSFWLR VPKVSASHLEQY | Class II | I-Ad | Balb/C | Mouse |
| | 39 | 46 | HEL | DGSTDYGIL INSRW | QTNRNTDGSTDYGI LQINSRWWCNDG | Class II | I-Ak | CBA | Mouse |
| | | 49 | MOG | MEVGWYRSPF SRVVHLYRN | TGMEVGWYRSPFS RVVHLYRNGKDQ | Class II | I-Ab | B6 | Mouse |

TABLE 35

Average IFNg+ cells in response to AH1 and SIINFEKL peptides in ChAd large cassette treated mice. Data is presented as % of total CD8 cells. Shown is average and standard deviation per group and p-value by ANOVA with Tukey's test. All p-values compared to MAG 20-antigen cassette.

| # antigens | Antigen | Average | Standard deviation | p-value | N |
|---|---|---|---|---|---|
| 20 | SIINFEKL | 5.308 | 0.660 | n/a | 8 |
| 30 | SIINFEKL | 4.119 | 1.019 | 0.978 | 8 |
| 40 | SIINFEKL | 6.324 | 0.954 | 0.986 | 8 |
| 50 | SIINFEKL | 8.169 | 1.469 | 0.751 | 8 |
| 20 | AH1 | 6.405 | 2.664 | n/a | 8 |
| 30 | AH1 | 4.373 | 1.442 | 0.093 | 8 |
| 40 | AH1 | 4.126 | 1.135 | 0.050 | 8 |
| 50 | AH1 | 4.216 | 0.808 | 0.063 | 8 |

TABLE 36

Average tetramer+ cells for AH1 and SIINFEKL antigens in ChAd large cassette treated mice. Data is presented as % of total CD8 cells. Shown is average and standard deviation per group and p-value by ANOVA with Tukey's test. All p-values compared to MAG 20-antigen cassette.

| # antigens | Antigen | Average | Standard deviation | p-value | N |
|---|---|---|---|---|---|
| 20 | SIINFEKL | 10.314 | 2.384 | n/a | 8 |
| 30 | SIINFEKL | 4.551 | 2.370 | 0.003 | 8 |
| 40 | SIINFEKL | 5.186 | 3.254 | 0.009 | 8 |
| 50 | SIINFEKL | 14.113 | 3.660 | 0.072 | 8 |
| 20 | AH1 | 6.864 | 2.207 | n/a | 8 |
| 30 | AH1 | 4.713 | 0.922 | 0.036 | 8 |
| 40 | AH1 | 5.393 | 1.452 | 0.223 | 8 |
| 50 | AH1 | 5.860 | 1.041 | 0.543 | 8 |

TABLE 37

Average IFNg+ cells in response to AH1 and SIINFEKL peptides in SAM large cassette treated mice. Data is presented as % of total CD8 cells. Shown is average and standard deviation per group and p-value by ANOVA with Tukey's test. All p-values compared to MAG 20-antigen cassette.

| # antigens | Antigen | Average | Standard deviation | p-value | N |
|---|---|---|---|---|---|
| 20 | SIINFEKL | 1.843 | 0.422 | n/a | 8 |
| 30 | SIINFEKL | 2.112 | 0.522 | 0.879 | 7 |
| 40 | SIINFEKL | 1.754 | 0.978 | 0.995 | 7 |
| 50 | SIINFEKL | 1.409 | 0.766 | 0.606 | 8 |
| 20 | AH1 | 3.050 | 0.909 | n/a | 8 |
| 30 | AH1 | 0.618 | 0.427 | 1.91E−05 | 7 |
| 40 | AH1 | 1.286 | 0.284 | 0.001 | 7 |
| 50 | AH1 | 1.309 | 1.149 | 0.001 | 8 |

XV. ChAd Antigen Cassette Delivery Vector

XV.A. ChAd Antigen Cassette Delivery Vector Construction

In one example, Chimpanzee adenovirus (ChAd) was engineered to be a delivery vector for antigen cassettes. In a further example, a full-length ChAdV68 vector was synthesized based on AC_000011.1 (sequence 2 from U.S. Pat. No. 6,083,716) with E1 (nt 457 to 3014) and E3 (nt 27,816-31,332) sequences deleted. Reporter genes under the control of the CMV promoter/enhancer were inserted in place of the deleted E1 sequences. Transfection of this clone into HEK293 cells did not yield infectious virus. To confirm the sequence of the wild-type C68 virus, isolate VR-594 was obtained from the ATCC, passaged, and then independently sequenced (SEQ ID NO:10). When comparing the AC_000011.1 sequence to the ATCC VR-594 sequence (SEQ ID NO:10) of wild-type ChAdV68 virus, 6 nucleotide differences were identified. In one example, a modified ChAdV68 vector was generated based on AC_000011.1, with the corresponding ATCC VR-594 nucleotides substituted at five positions (ChAdV68.5WTnt SEQ ID NO:1).

In another example, a modified ChAdV68 vector was generated based on AC_000011.1 with E1 (nt 577 to 3403) and E3 (nt 27,816-31,332) sequences deleted and the corresponding ATCC VR-594 nucleotides substituted at four positions. A GFP reporter (ChAdV68.4WTnt.GFP; SEQ ID NO:11) or model neoantigen cassette (ChAdV68.4WTnt.MAG25mer; SEQ ID NO:12) under the control of the CMV promoter/enhancer was inserted in place of deleted E1 sequences.

In another example, a modified ChAdV68 vector was generated based on AC_000011.1 with E1 (nt 577 to 3403) and E3 (nt 27,125-31,825) sequences deleted and the corresponding ATCC VR-594 nucleotides substituted at five positions. A GFP reporter (ChAdV68.5WTnt.GFP; SEQ ID NO:13) or model neoantigen cassette (ChAdV68.5WTnt.MAG25mer; SEQ ID NO:2) under the control of the CMV promoter/enhancer was inserted in place of deleted E1 sequences.

Relevant vectors are described below:

Full-Length ChAdVC68 sequence "ChAdV68.5WTnt" (SEQ ID NO:1); AC_000011.1 sequence with corresponding ATCC VR-594 nucleotides substituted at five positions.

ATCC VR-594 C68 (SR) ID NO:10); independently sequenced; Full-Length C68

ChAdV68.4WTnt.GFP (SEC) ID NO:11); AC_000011.1 with E1 (nt 577 to 3403) and E3 (nt 27,816-31,332) sequences deleted; corresponding ATCC VR-594 nucleotides substituted at four positions; GFP reporter under the control of the CMV promoter/enhancer inserted in place of deleted E1

ChAdV68.4WTnt.MAG25mer (SEQ ID NO:12); AC_000011.1 with E1 (nt 577 to 3403) and E3 (nt 27,816-31,332) sequences deleted; corresponding ATCC VR-594 nucleotides substituted at four positions: model neoantigen cassette under the control of the CMV promoter/enhancer inserted in place of deleted E1

ChAdV68.5WTnt.GFP (SEQ ID NO:13); AC_000011.1 with E1 (nt 577 to 3403) and E3 (nt 27,125-31,825) sequences deleted; corresponding ATCC VR-594 nucleotides substituted at five positions; GFP reporter under the control of the CMV promoter/enhancer inserted in place of deleted E1

XV.B. ChAd Antigen Cassette Delivery Vector Testing

XV.B.1. ChAd Vector Evaluation Methods and Materials

Transfection of HEK293A cells using lipofectamine

DNA for the ChAdV68 constructs (ChAdV68.4WTnt.GFP, ChAdV68.5WTnt.GFP, ChAdV68.4WTnt.MAG25mer and ChAdV68.5WTnt.MAG25mer) was prepared and transfected into HEK293A cells using the following protocol.

10 ug of plasmid DNA was digested with PacI to liberate the viral genome. DNA was then purified using GeneJet DNA cleanup Micro columns (Thermo Fisher) according to manufacturer's instructions for long DNA fragments, and eluted in 20 ul of pre-heated water; columns were left at 37 degrees for 0.5-1 hours before the elution step.

HEK293A cells were introduced into 6-well plates at a cell density of $10^6$ cells/well 14-18 hours prior to transfection. Cells were overlaid with 1 ml of fresh medium (DMEM-10% hiFBS with pen/strep and glutamate) per well. 1-2 ug of purified DNA was used per well in a transfection with twice the ul volume (2-4 ul) of Lipofectamine2000, according to the manufacturer's protocol. 0.5 ml of OPTI-MEM medium containing the transfection mix was added to the 1 ml of normal growth medium in each well, and left on cells overnight.

Transfected cell cultures were incubated at 37° C. for at least 5-7 days. If viral plaques were not visible by day 7 post-transfection, cells were split 1:4 or 1:6, and incubated at 37° C. to monitor for plaque development. Alternatively, transfected cells were harvested and subjected to 3 cycles of freezing and thawing and the cell lysates were used to infect HEK293A cells and the cells were incubated until virus plaques were observed.

Transfection of ChAdV68 Vectors into HEK293A Cells Using Calcium Phosphate and Generation of the Tertiary Viral Stock DNA for the ChAdV68 constructs (ChAdV68.4WTnt.GFP, ChAdV68.5WTnt.GFP, ChAdV68.4WTnt.MAG25mer, ChAdV68.5WTnt.MAG25-mer) was prepared and transfected into HEK293A cells using the following protocol.

HEK293A cells were seeded one day prior to the transfection at $10^6$ cells/well of a 6 well plate in 5% BS/DMEM/1XP/S, 1XGlutamax. Two wells are needed per transfection. Two to four hours prior to transfection the media was changed to fresh media. The ChAdV68.4WTnt.GFP plasmid was linearized with PacI. The linearized DNA was then phenol chloroform extracted and precipitated using one tenth volume of 3M Sodium acetate pH 5.3 and two volumes of 100% ethanol. The precipitated DNA was pelleted by centrifugation at 12,000×g for 5 min before washing 1× with 70% ethanol. The pellet was air dried and re-suspended in 50 μL of sterile water. The DNA concentration was determined using a NanoDrop™ (ThermoFisher) and the volume adjusted to 5 μg of DNA/50 μL.

169 μL of sterile water was added to a microfuge tube. 54 of 2M $CaCl_2$ was then added to the water and mixed gently by pipetting. 504 of DNA was added dropwise to the $CaCl_2$ water solution. Twenty six μL of 2M $CaCl_2$ was then added and mixed gently by pipetting twice with a micro-pipettor. This final solution should consist of 5 μg of DNA in 250 μL of 0.25M $CaCl_2$. A second tube was then prepared containing 250 μL of 2×HBS (Hepes buffered solution). Using a 2 mL sterile pipette attached to a Pipet-Aid air was slowly bubbled through the 2×HBS solution. At the same time the DNA solution in the 0.25M $CaCl_2$ solution was added in a dropwise fashion. Bubbling was continued for approximately 5 seconds after addition of the final DNA droplet. The solution was then incubated at room temperature for up to 20 minutes before adding to 293A cells. 250 μL of the DNA/Calcium phosphate solution was added dropwise to a monolayer of 293A cells that had been seeded one day prior at $10^6$ cells per well of a 6 well plate. The cells were returned to the incubator and incubated overnight. The media was changed 24 h later. After 72 h the cells were split 1:6 into a 6 well plate. The monolayers were monitored daily by light microscopy for evidence of cytopathic effect (CPE). 7-10 days post transfection viral plaques were observed and the monolayer harvested by pipetting the media in the wells to lift the cells. The harvested cells and media were transferred to a 50 mL centrifuge tube followed by three rounds of freeze thawing (at −80° C. and 37° C.). The subsequent lysate, called the primary virus stock was clarified by centrifugation at full speed on a bench top centrifuge (4300×g) and a proportion of the lysate 10-50%) used to infect 293A cells in a T25 flask. The infected cells were incubated for 48 h before harvesting cells and media at complete CPE. The cells were once again harvested, freeze thawed and clarified before using this secondary viral stock to infect a T150 flask seeded at $1.5\times10^7$ cells per flask. Once complete CPE was achieved at 72 h the media and cells were harvested and treated as with earlier viral stocks to generate a tertiary stock.

Production in 293F Cells

ChAdV68 virus production was performed in 293F cells grown in 293 FreeStyle™ (ThermoFisher) media in an incubator at 8% CO2. On the day of infection cells were diluted to $10^6$ cells per mL, with 98% viability and 400 mL were used per production run in 1 L Shake flasks (Corning). 4 mL of the tertiary viral stock with a target MOI of >3.3 was used per infection. The cells were incubated for 48-72 h until the viability was <70% as measured by Trypan blue. The infected cells were then harvested by centrifugation, full speed bench top centrifuge and washed in 1×PBS, re-centrifuged and then re-suspended in 20 mL of 10 mM Tris pH7.4. The cell pellet was lysed by freeze thawing 3× and clarified by centrifugation at 4,300×g for 5 minutes.

Purification by CsCl Centrifugation

Viral DNA was purified by CsCl centrifugation. Two discontinuous gradient runs were performed. The first to purify virus from cellular components and the second to further refine separation from cellular components and separate defective from infectious particles.

10 mL of 1.2 (26.8 g CsCl dissolved in 92 mL of 10 mM Tris pH 8.0) CsCl was added to polyallomer tubes. Then 8 mL of 1.4 CsCl (53 g CsCl dissolved in 87 mL of 10 mM Tris pH 8.0) was carefully added using a pipette delivering to the bottom of the tube. The clarified virus was carefully layered on top of the 1.2 layer. If needed more 10 mM Tris was added to balance the tubes. The tubes were then placed in a SW-32Ti rotor and centrifuged for 2 h 30 min at 10° C. The tube was then removed to a laminar flow cabinet and the virus band pulled using an 18 gauge needle and a 10 mL syringe. Care was taken not to remove contaminating host cell DNA and protein. The band was then diluted at least 2× with 10 mM Tris pH 8.0 and layered as before on a discontinuous gradient as described above. The run was performed as described before except that this time the run was performed overnight. The next day the band was pulled with care to avoid pulling any of the defective particle band. The virus was then dialyzed using a Slide-a-Lyzer™ Cassette (Pierce) against ARM buffer (20 mM Tris pH 8.0, 25 mM NaCl, 2.5% Glycerol). This was performed 3×, 1 h per buffer exchange. The virus was then aliquoted for storage at −80° C.

Viral Assays

VP concentration was performed by using an OD 260 assay based on the extinction coefficient of $1.1\times10^{12}$ viral particles (VP) is equivalent to an Absorbance value of 1 at OD260 nm. Two dilutions (1:5 and 1:10) of adenovirus were made in a viral lysis buffer (0.1% SDS, 10 mM Tris pH 7.4, 1 mM EDTA). OD was measured in duplicate at both dilutions and the VP concentration/mL was measured by multiplying the OD260 value X dilution factor X $1.1\times10^{12}$VP.

An infectious unit (IU) titer was calculated by a limiting dilution assay of the viral stock. The virus was initially diluted 100× in DMEM/5% NS/1×PS and then subsequently diluted using 10-fold dilutions down to $1\times10^{-7}$. 100 μL of these dilutions were then added to 293A cells that were seeded at least an hour before at 3e5 cells/well of a 24 well plate. This was performed in duplicate. Plates were incubated for 48 h in a CO2 (5%) incubator at 37° C. The cells were then washed with 1×PBS and were then fixed with 100% cold methanol (−20° C.). The plates were then incubated at −20° C. for a minimum of 20 minutes. The wells were washed with 1×PBS then blocked in 1×PBS/0.1% BSA for 1 h at room temperature. A rabbit anti-Ad antibody (Abcam, Cambridge, Mass.) was added at 1:8,000 dilution in blocking buffer (0.25 ml per well) and incubated for 1 h at room temperature. The wells were washed 4× with 0.5 mL PBS per well. A HRP conjugated Goat anti-Rabbit antibody (Bethyl Labs, Montgomery Tex.) diluted 1000× was added per well and incubated for 1 h prior to a final round of washing. 5 PBS washes were performed and the plates were developed using DAB (Diaminobenzidine tetrahydrochloride) substrate in Tris buffered saline (0.67 mg/mL DAB in 50 mM Tris pH 7.5, 150 mM NaCl) with 0.01% $H_2O_2$. Wells were developed for 5 min prior to counting. Cells were counted under a 10× objective using a dilution that gave between 4-40 stained cells per field of view. The field of view that was used was a 0.32 $mm^2$ grid of which there are equivalent to 625 per field of view on a 24 well plate. The number of infectious viruses/mL can be determined by the number of stained cells per grid multiplied by the number of grids per field of view multiplied by a dilution factor 10. Similarly, when working with GFP expressing cells florescent can be used rather than capsid staining to determine the number of GFP expressing virions per mL.

Immunizations

C57BL/6J female mice and Balb/c female mice were injected with $1\times10^8$ viral particles (VP) of ChAdV68.5WTnt.MAG25mer in 100 uL volume, bilateral intramuscular injection (50 uL per leg).

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune N×T flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XV.B.2. Production of ChAdV68 Viral Delivery Particles after DNA Transfection

Figure 7C:
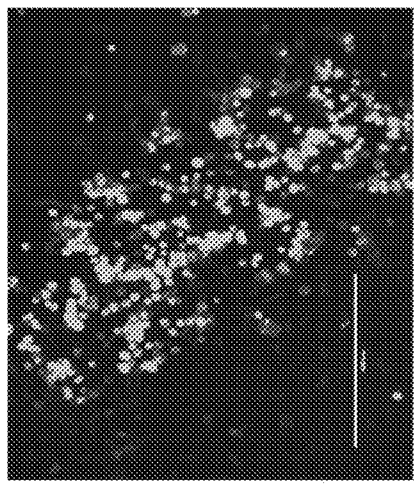
FIG. 7C illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 100× magnification.
Figure 7B:
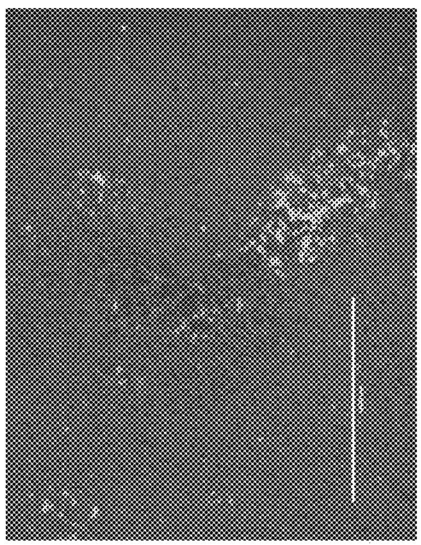
FIG. 7B illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 40× magnification.
Figure 7A:
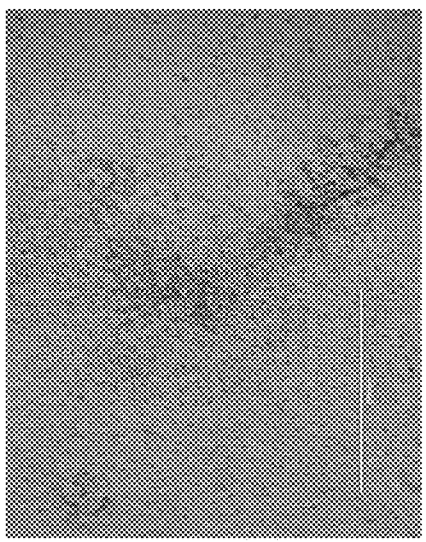
FIG. 7A illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using light microscopy (40× magnification).
Figure 8C:
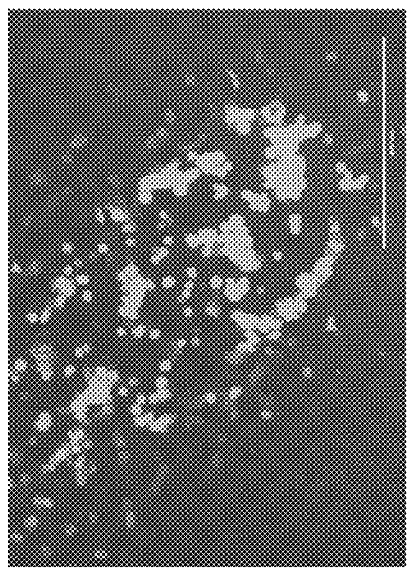
FIG. 8C illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 100× magnification.
Figure 8B:
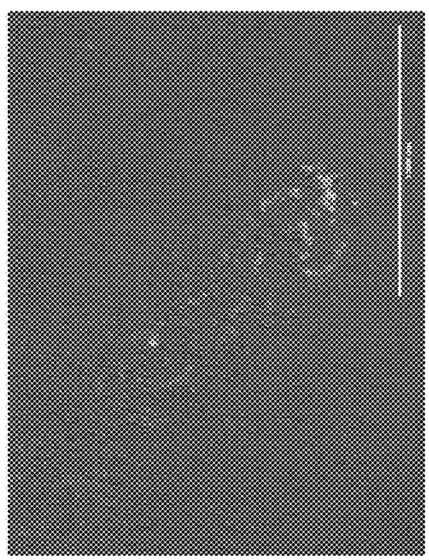
FIG. 8B illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 40× magnification.
Figure 8A:
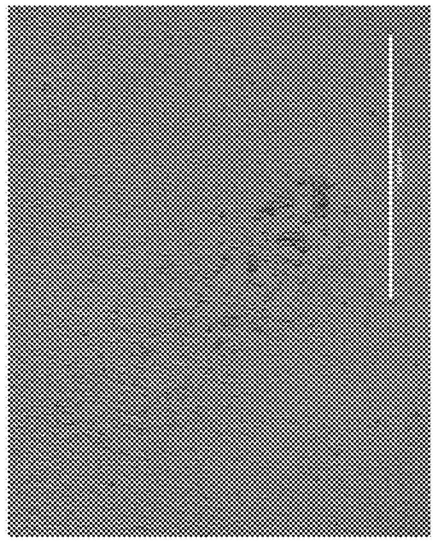
FIG. 8A illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using light microscopy (40× magnification)

In one example, ChAdV68.4WTnt.GFP (FIG. 7) and ChAdV68.5WTnt.GFP (FIG. 8) DNA was transfected into HEK293A cells and virus replication (viral plaques) was observed 7-10 days after transfection. ChAdV68 viral plaques were visualized using light (FIGS. 7A and 8A) and fluorescent microscopy (FIGS. 7B-C and FIGS. 8B-C). GFP denotes productive ChAdV68 viral delivery particle production.

XV.B.3. ChAdV68 Viral Delivery Particles Expansion

Figure 9:
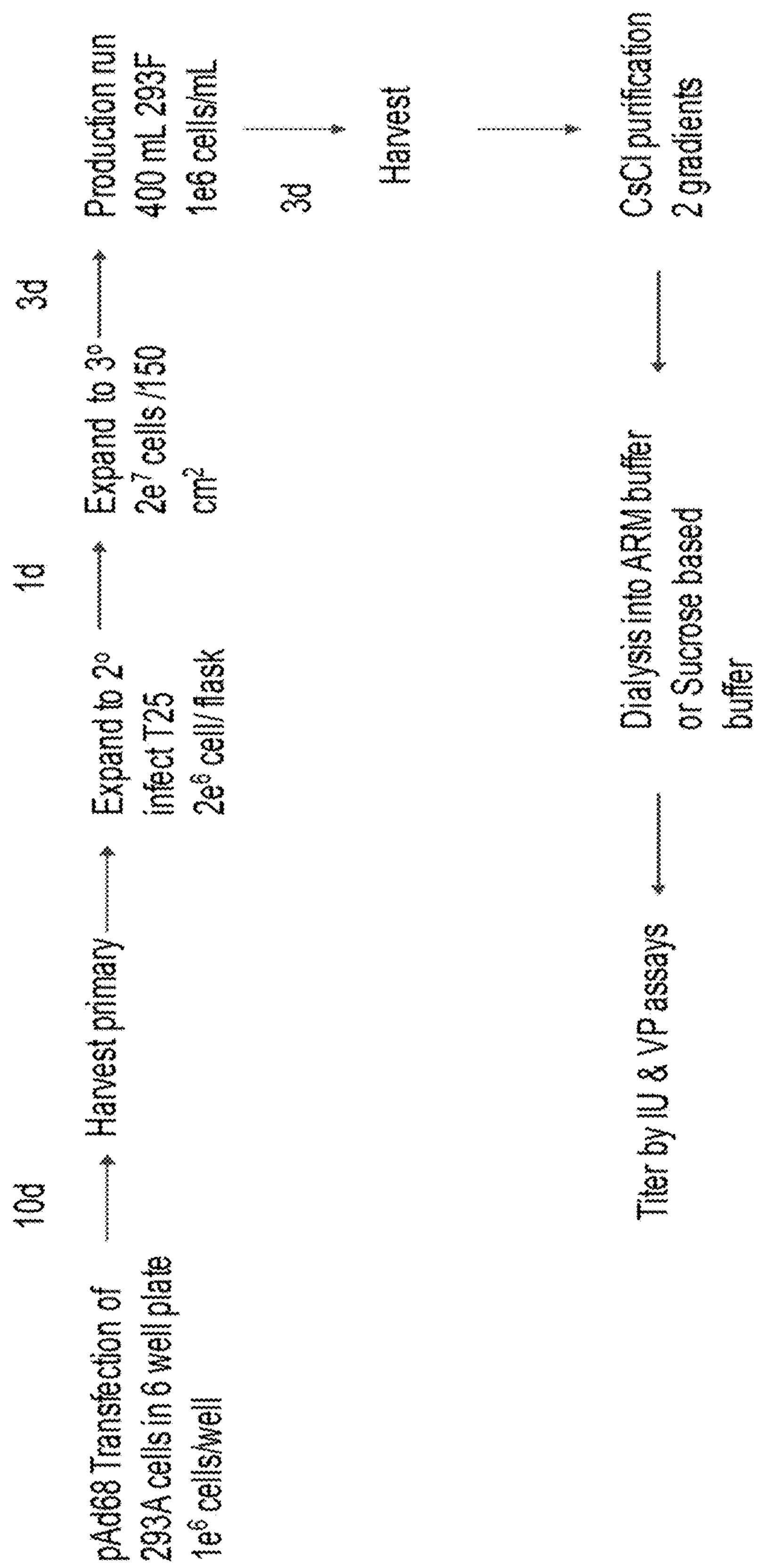
FIG. 9 illustrates the viral particle production scheme.

In one example, ChAdV68.4WTnt.GFP, ChAdV68.5WTnt.GFP, and ChAdV68.5WTnt.MAG25mer viruses were expanded in HEK293F cells and a purified virus stock produced 18 days after transfection (FIG. 9). Viral particles were quantified in the purified ChAdV68 virus stocks and compared to adenovirus type 5 (Ad5) and ChAdVY25 (a closely related ChAdV; Dicks, 2012, PloS ONE 7, e40385) viral stocks produced using the same protocol. ChAdV68 viral titers were comparable to Ad5 and ChAdVY25 (Table 7).

TABLE 7

Adenoviral vector production in 293F suspension cells

| Construct | Average VP/cell +/− SD |
|---|---|
| Ad5-Vectors (Multiple vectors) | 2.96e4 +/− 2.26e4 |
| Ad5-GFP | 3.89e4 |
| chAdY25-GFP | 1.75e3 +/− 6.03e1 |
| ChAdV68.4WTnt.GFP | 1.2e4 +/− 6.5e3 |
| ChAdV68.5WTnt.GFP | 1.8e3 |
| ChAdV68.5WTnt.MAG25mer | 1.39e3 +/− 1.1e3 |

*SD is only reported where multiple Production runs have been performed

XV.B.4. Evaluation of Immunogenicity in Tumor Models

Figure 15:
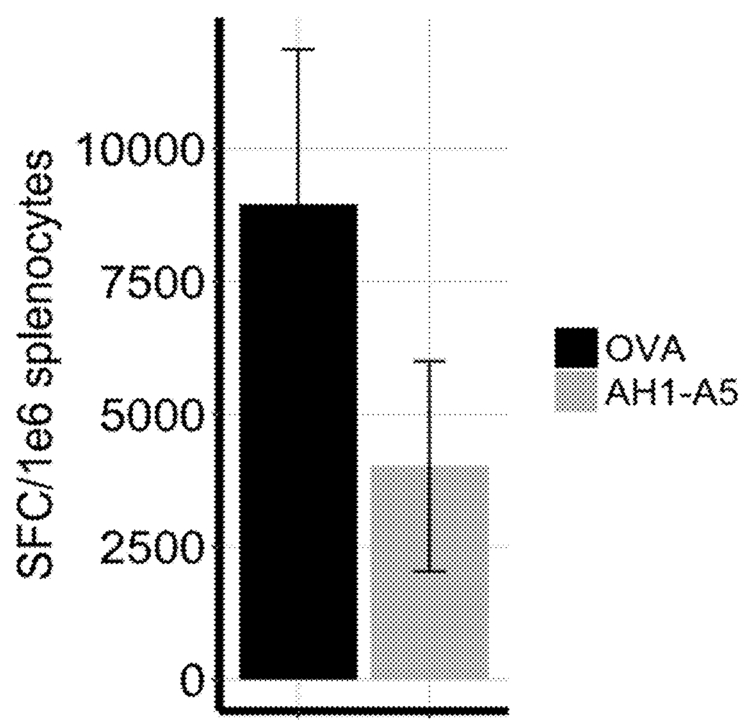
FIG. 15 illustrates ChAdV68 eliciting T-Cell responses to mouse tumor antigens in mice. Mice were immunized with ChAdV68.5WTnt.MAG25mer, and T-cell responses to the MHC class I epitope SIINFEKL (SEQ ID NO: 72) (OVA) were measured in C57BL/6J female mice and the MHC class I epitope AH1-A5 measured in Balb/c mice. Mean spot forming cells (SFCs) per $10^6$ splenocytes measured in ELISpot assays presented. Error bars represent standard deviation.

C68 vector expressing mouse tumor antigens were evaluated in mouse immunogenicity studies to demonstrate the C68 vector elicits T-cell responses. T-cell responses to the MHC class I epitope SIINFEKL (SEQ ID NO: 72) were measured in C57BL/6J female mice and the MHC class I epitope AH1-A5 (Slansky et al., 2000, Immunity 13:529-538) measured in Balb/c mice. As shown in FIG. 15, strong T-cell responses relative to control were measured after immunization of mice with ChAdV68.5WTnt.MAG25mer. Mean cellular immune responses of 8957 or 4019 spot forming cells (SFCs) per $10^6$ splenocytes were observed in ELISpot assays when C57BL/6J or Balb/c mice were immunized with ChAdV68.5WTnt.MAG25mer, respectively, 10 days after immunization.

Tumor infiltrating lymphocytes were also evaluated in CT26 tumor model evaluating ChAdV and co-administration of a an anti-CTLA4 antibody. Mice were implanted with CT26 tumors cells and 7 days after implantation, were immunized with ChAdV vaccine and treated with anti-CTLA4 antibody (clone 9D9) or IgG as a control. Tumor infiltrating lymphocytes were analyzed 12 days after immunization. Tumors from each mouse were dissociated using the gentleMACS Dissociator (Miltenyi Biotec) and mouse tumor dissociation kit (Miltenyi Biotec). Dissociated cells were filtered through a 30 micron filter and resuspended in complete RPMI. Cells were counted on the Attune N×T flow cytometer (Thermo Fisher) using propidium iodide staining to exclude dead and apoptotic cells. Cell were then adjusted to the appropriate concentration of live cells for subsequent analysis. Antigen specific cells were identified by MHC-tetramer complexes and co-stained with anti-CD8 and a viability marker. Tumors were harvested 12 days after prime immunization.

Figure 41:
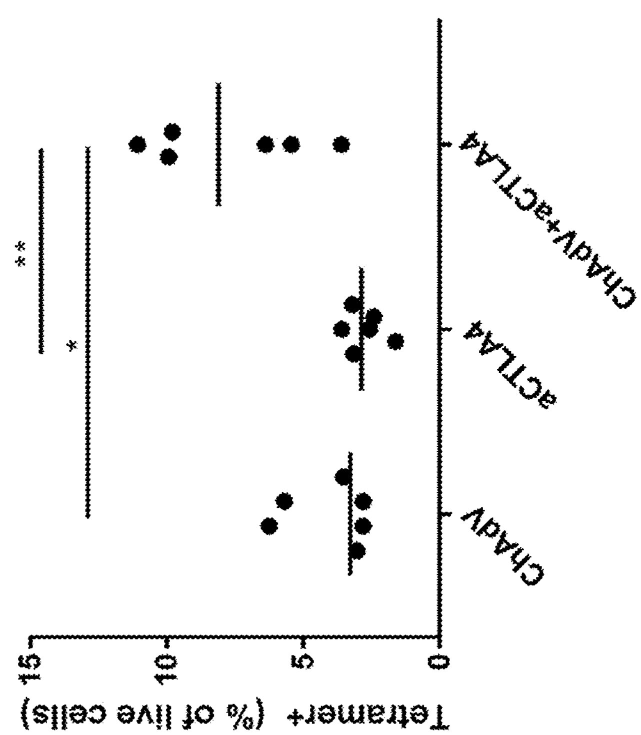
FIG. 41 shows frequency of CD8+ T cells recognizing the CT26 tumor antigen AH1 in CT26 tumor-bearing mice. P values determined using the one-way ANOVA with Tukey's multiple comparisons test; **P<0.001, *P<0.05. ChAdV=ChAdV68.5WTnt.MAG25mer; aCTLA4=anti-CTLA4 antibody, clone 9D9.

Antigen-specific CD8+ T cells within the tumor comprised a median of 3.3%, 2.2%, or 8.1% of the total live cell population in ChAdV, anti-CTLA4, and ChAdV+anti-CTLA4 treated groups, respectively (FIG. 41 and Table 40). Treatment with anti-CTLA in combination with active ChAdV immunization resulted in a statistically significant increase in the antigen-specific CD8+ T cell frequency over both ChAdV alone and anti-CTLA4 alone demonstrating anti-CTLA4, when co-administered with the ChAdV68 vaccine, increased the number of infiltrating T cells within a tumor.

TABLE 40

Tetramer+ infiltrating CD8 T cell frequencies in CT26 tumors

| Treatment | Median % tetramer+ |
|---|---|
| ChAdV68.5WTnt.MAG25mer (ChAdV) | 3.3 |
| Anti-CTLA4 | 2.2 |
| ChAdV68.5WTnt.MAG25mer (ChAdV) + anti-CTLA4 | 8.1 |

XVI. Alphavirus Antigen Cassette Delivery Vector

XVI.A. Alphavirus Delivery Vector Evaluation Materials and Methods In Vitro Transcription to Generate RNA For in vitro testing: plasmid DNA was linearized by restriction digest with PmeI, column purified following manufacturer's protocol (GeneJet DNA cleanup kit, Thermo) and used as template. In vitro transcription was performed using the RiboMAX Large Scale RNA production System (Promega) with the $m^7G$ cap analog (Promega) according to manufacturer's protocol. mRNA was purified using the RNeasy kit (Qiagen) according to manufacturer's protocol.

For in vivo studies: RNA was generated and purified by TriLink Biotechnologies and capped with Enzymatic Capt.

Transfection of RNA

HEK293A cells were seeded at 6e4 cells/well for 96 wells and 2e5 cells/well for 24 wells, ~16 hours prior to transfection. Cells were transfected with mRNA using MessengerMAX lipofectamine (Invitrogen) and following manufacturer's protocol. For 96-wells, 0.15 uL of lipofectamine and 10 ng of mRNA was used per well, and for 24-wells, 0.75 uL of lipofectamine and 150 ng of mRNA was used per well. A GFP expressing mRNA (TriLink Biotechnologies) was used as a transfection control.

Luciferase Assay

Luciferase reporter assay was performed in white-walled 96-well plates with each condition in triplicate using the ONE-Glo luciferase assay (Promega) following manufacturer's protocol. Luminescence was measured using the SpectraMax. qRT-PCR Transfected cells were rinsed and replaced with fresh media 2 hours post transfection to remove any untransfected mRNA. Cells were then harvested at various timepoints in RLT plus lysis buffer (Qiagen), homogenized using a QiaShredder (Qiagen) and RNA was extracted using the RNeasy kit (Qiagen), all according to manufacturer's protocol. Total RNA was quantified using a Nanodrop (Thermo Scientific). qRT-PCR was performed using the Quantitect Probe One-Step RT-PCR kit (Qiagen) on the qTower[3] (Analytik Jena) according to manufacturer's protocol, using 20 ng of total RNA per reaction. Each sample was run in triplicate for each probe. Actin or GusB were used as reference genes. Custom primer/probes were generated by IDT (Table 8).

TABLE 8 qPCR primers/probes

| Target | | | SEQ ID NO: |
|---|---|---|---|
| Luci | Primer1 | GTGGTGTGCAGCGAGAATAG | 178 |
| | Primer2 | CGCTCGTTGTAGATGTCGTTAG | 179 |
| | Probe | /56-FAM/TTGCAGTTC/ZEN/TTCATGCCCGTGTTG/3IABkFQ/ | 180 |
| GusB | Primer1 | GTTTTTGATCCAGACCCAGATG | 181 |
| | Primer2 | GCCCATTATTCAGAGCGAGTA | 182 |
| | Probe | /56-FAM/TGCAGGGTT/ZEN/TCACCAGGATCCAC/3IABkFQ/ | 183 |
| ActB | Primer1 | CCTTGCACATGCCGGAG | 184 |
| | Primer2 | ACAGAGCCTCGCCTTTG | 185 |
| | Probe | /56-FAM/TCATCCATG/ZEN/GTGAGCTGGCGG/3IABkFQ/ | 186 |
| MAG-25 mer Set1 | Primer1 | CTGAAAGCTCGGTTTGCTAATG | 187 |
| | Primer2 | CCATGCTGGAAGAGACAATCT | 188 |
| | Probe | /56-FAM/CGTTTCTGA/ZEN/TGGCGCTGACCGATA/3IABkFQ/ | 189 |
| MAG-25mer Set2 | Primer1 | TATGCCTATCCTGTCTCCTCTG | 190 |
| | Primer2 | GCTAATGCAGCTAAGTCCTCTC | 191 |
| | Probe | /56-FAM/TGTTTACCC/ZEN/TGACCGTGCCTTCTG/3IABkFQ/ | 192 |

B16-OVA Tumor Model

C57BL/6J mice were injected in the lower left abdominal flank with $10^5$ B16-OVA cells/animal. Tumors were allowed to grow for 3 days prior to immunization.

CT26 Tumor Model

Balb/c mice were injected in the lower left abdominal flank with $10^6$ CT26 cells/animal. Tumors were allowed to grow for 7 days prior to immunization.

Immunizations

For srRNA vaccine, mice were injected with 10 ug of RNA in 100 uL volume, bilateral intramuscular injection (50 uL per leg). For Ad5 vaccine, mice were injected with $5\times10^{10}$ viral particles (VP) in 100 uL volume, bilateral intramuscular injection (50 uL per leg). Animals were injected with anti-CTLA-4 (clone 9D9, BioXcell), anti-PD-1 (clone RMP1-14, BioXcell) or anti-IgG (clone MPC-11, BioXcell), 250 ug dose, 2 times per week, via intraperitoneal injection.

In Vivo Bioluminescent Imaging

At each timepoint mice were injected with 150 mg/kg luciferin substrate via intraperitoneal injection and bioluminescence was measured using the IVIS In vivo imaging system (PerkinElmer) 10-15 minutes after injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune N×T flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XVI.B. Alphavirus Vector

XVI.B.1. Alphavirus Vector In Vitro Evaluation

Figure 10:
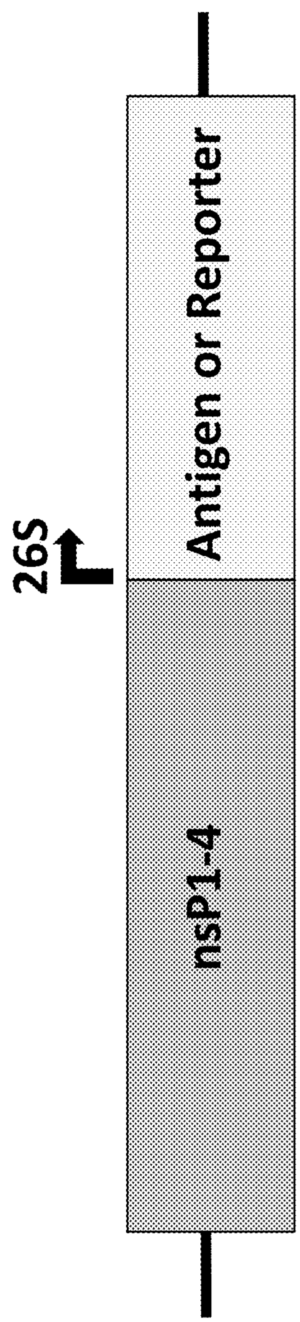
FIG. 10 illustrates the alphavirus derived VEE self-replicating RNA (srRNA) vector.

In one implementation of the present invention, a RNA alphavirus backbone for the antigen expression system was generated from a Venezuelan Equine Encephalitis (VEE) (Kinney, 1986, Virology 152: 400-413) based self-replicating RNA (srRNA) vector. In one example, the sequences encoding the structural proteins of VEE located 3' of the 26S sub-genomic promoter were deleted (VEE sequences 7544 to 11,175 deleted; numbering based on Kinney et al 1986; SEQ ID NO:6) and replaced by antigen sequences (SEQ ID NO:14 and SEQ ID NO:4) or a luciferase reporter (e.g., VEE-Luciferase, SEQ ID NO:15) (FIG. 10). RNA was transcribed from the srRNA DNA vector in vitro, transfected into HEK293A cells and luciferase reporter expression was measured. In addition, an (non-replicating) mRNA encoding luciferase was transfected for comparison. An 30,000-fold increase in srRNA reporter signal was observed for VEE-Luciferase srRNA when comparing the 23 hour measurement vs the 2 hour measurement (Table 9). In contrast, the mRNA reporter exhibited a less than 10-fold increase in signal over the same time period (Table 9).

TABLE 9

Expression of luciferase from VEE self-replicating vector increases over time. HEK293A cells transfected with 10 ng of VEE-Luciferase srRNA or 10 ng of non-replicating luciferase mRNA (TriLink L-6307) per well in 96 wells. Luminescence was measured at various times post transfection. Luciferase expression is reported as relative luminescence units (RLU). Each data point is the mean +/− SD of 3 transfected wells.

| Construct | Timepoint (hr) | Mean RLU | Standard Dev triplicate wells) |
|---|---|---|---|
| mRNA | 2 | 878.6666667 | 120.7904522 |
| mRNA | 5 | 1847.333333 | 978.515372 |
| mRNA | 9 | 4847 | 868.3271273 |
| mRNA | 23 | 8639.333333 | 751.6816702 |
| SRRNA | 2 | 27 | 15 |
| SRRNA | 5 | 4884.333333 | 2955.158935 |
| SRRNA | 9 | 182065.5 | 16030.81784 |
| SRRNA | 23 | 783658.3333 | 68985.05538 |

In another example, replication of the srRNA was confirmed directly by measuring RNA levels after transfection of either the luciferase encoding srRNA (VEE-Luciferase) or an srRNA encoding a multi-epitope cassette (VEE-MAG25mer) using quantitative reverse transcription polymerase chain reaction (qRT-PCR). An —150-fold increase in RNA was observed for the VEE-luciferase srRNA (Table 10), while a 30-50-fold increase in RNA was observed for the VEE-MAG25mer srRNA (Table 11). These data confirm that the VEE srRNA vectors replicate when transfected into cells.

TABLE 10

Direct measurement of RNA replication in VEE-Luciferase srRNA transfected cells. HEK293A cells transfected with VEE-Luciferase srRNA (150 ng per well, 24-well) and RNA levels quantified by qRT-PCR at various times after transfection. Each measurement was normalized based on the Actin reference gene and fold-change relative to the 2 hour timepoint is presented.

| Timepoint (hr) | Luciferase Ct | Actin Ct | dCt | Ref dCt | ddCt | Relative Fold change |
|---|---|---|---|---|---|---|
| 2 | 20.51 | 18.14 | 2.38 | 2.38 | 0.00 | 1.00 |
| 4 | 20.09 | 18.39 | 1.70 | 2.38 | −0.67 | 1.59 |
| 6 | 15.50 | 18.19 | −2.69 | 2.38 | −5.07 | 33.51 |
| 8 | 13.51 | 18.36 | −4.85 | 2.38 | −7.22 | 149.43 |

TABLE 11

Direct measurement of RNA replication in VEE-MAG25mer srRNA transfected cells. HEK293 cells transfected with VEE-MAG25mer srRNA (150 ng per well, 24-well) and RNA levels quantified by qRT-PCR at various times after transfection. Each measurement was normalized based on the GusB reference gene and fold-change relative to the 2 hour timepoint is presented. Different lines on the graph represent 2 different qPCR primer/probe sets, both of which detect the enitone cassette region of the srRNA.

| Primer/ probe | Timepoint (hr) | Ct | GusB Ct | dCt | Ref dCt | ddCt | Relative Fold-Change |
|---|---|---|---|---|---|---|---|
| Set1 | 2 | 18.96 | 22.41 | −3.45 | −3.45 | 0.00 | 1.00 |
| Set1 | 4 | 17.46 | 22.27 | −4.81 | −3.45 | −1.37 | 2.58 |
| Set1 | 6 | 14.87 | 22.04 | −7.17 | −3.45 | −3.72 | 13.21 |
| Set1 | 8 | 14.16 | 22.19 | −8.02 | −3.45 | −4.58 | 23.86 |
| Set1 | 24 | 13.16 | 22.01 | −8.86 | −3.45 | −5.41 | 42.52 |
| Set1 | 36 | 13.53 | 22.63 | −9.10 | −3.45 | −5.66 | 50.45 |
| Set2 | 2 | 17.75 | 22.41 | −4.66 | −4.66 | 0.00 | 1.00 |
| Set2 | 4 | 16.66 | 22.27 | −5.61 | −4.66 | −0.94 | 1.92 |
| Set2 | 6 | 14.22 | 22.04 | −7.82 | −4.66 | −3.15 | 8.90 |
| Set2 | 8 | 13.18 | 22.19 | −9.01 | −4.66 | −4.35 | 20.35 |
| Set2 | 24 | 12.22 | 22.01 | −9.80 | −4.66 | −5.13 | 35.10 |
| Set2 | 36 | 13.08 | 22.63 | −9.55 | −4.66 | −4.89 | 29.58 |

XVI.B.2. Alphavirus Vector in vivo Evaluation

Figure 11:
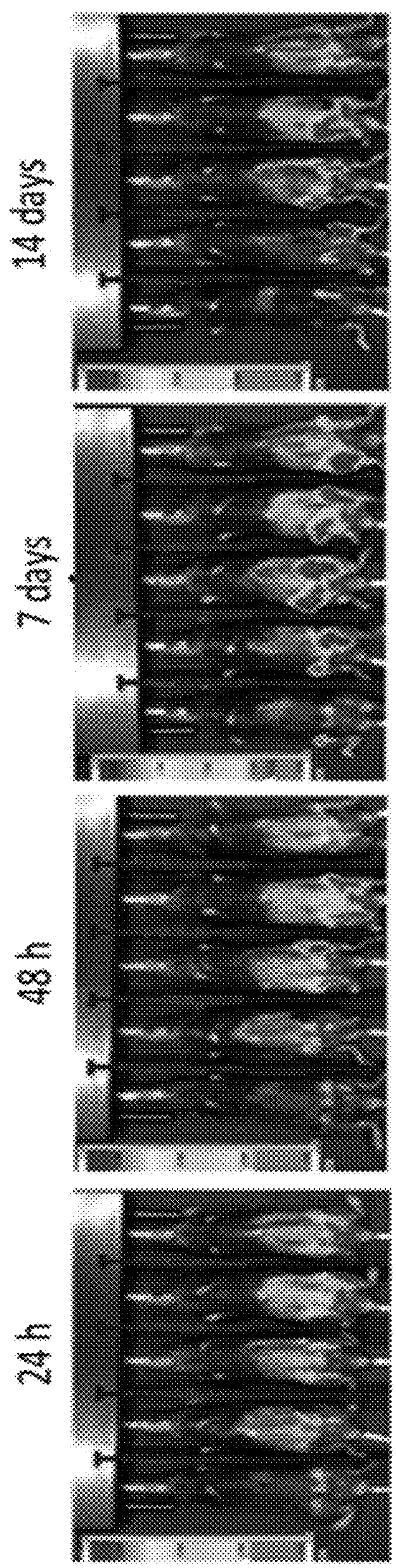
FIG. 11 illustrates in vivo reporter expression after inoculation of C57BL/6J mice with VEE-Luciferase srRNA. Shown are representative images of luciferase signal following immunization of C57BL/6J mice with VEE-Luciferase srRNA (10 ug per mouse, bilateral intramuscular injection, MC3 encapsulated) at various timepoints.

In another example, VEE-Luciferase reporter expression was evaluated in vivo. Mice were injected with 10 ug of VEE-Luciferase srRNA encapsulated in lipid nanoparticle (MC3) and imaged at 24 and 48 hours, and 7 and 14 days post injection to determine bioluminescent signal. Luciferase signal was detected at 24 hours post injection and increased over time and appeared to peak at 7 days after srRNA injection (FIG. 11).

XVI.B.3. Alphavirus Vector Tumor Model Evaluation

In one implementation, to determine if the VEE srRNA vector directs antigen-specific immune responses in vivo, a VEE srRNA vector was generated (VEE-UbAAY, SEQ ID NO:14) that expresses 2 different MHC class I mouse tumor epitopes, SIINFEKL (SEQ ID NO: 72) and AH1-A5 (Slansky et al., 2000, Immunity 13:529-538). The SFL (SIIN- FEKL (SEQ ID NO: 72)) epitope is expressed by the B16-OVA melanoma cell line, and the AH1-A5 (SPSYAYHQF (SEQ ID NO: 73); Slansky et al., 2000, Immunity) epitope induces T cells targeting a related epitope (AH1/SPSYVYHQF (SEQ ID NO: 193); Huang et al., 1996, Proc Natl Acad Sci USA 93:9730-9735) that is expressed by the CT26 colon carcinoma cell line. In one example, for in vivo studies, VEE-UbAAY srRNA was generated by in vitro transcription using T7 polymerase (TriLink Biotechnologies) and encapsulated in a lipid nanoparticle (MC3).

Figure 12A:
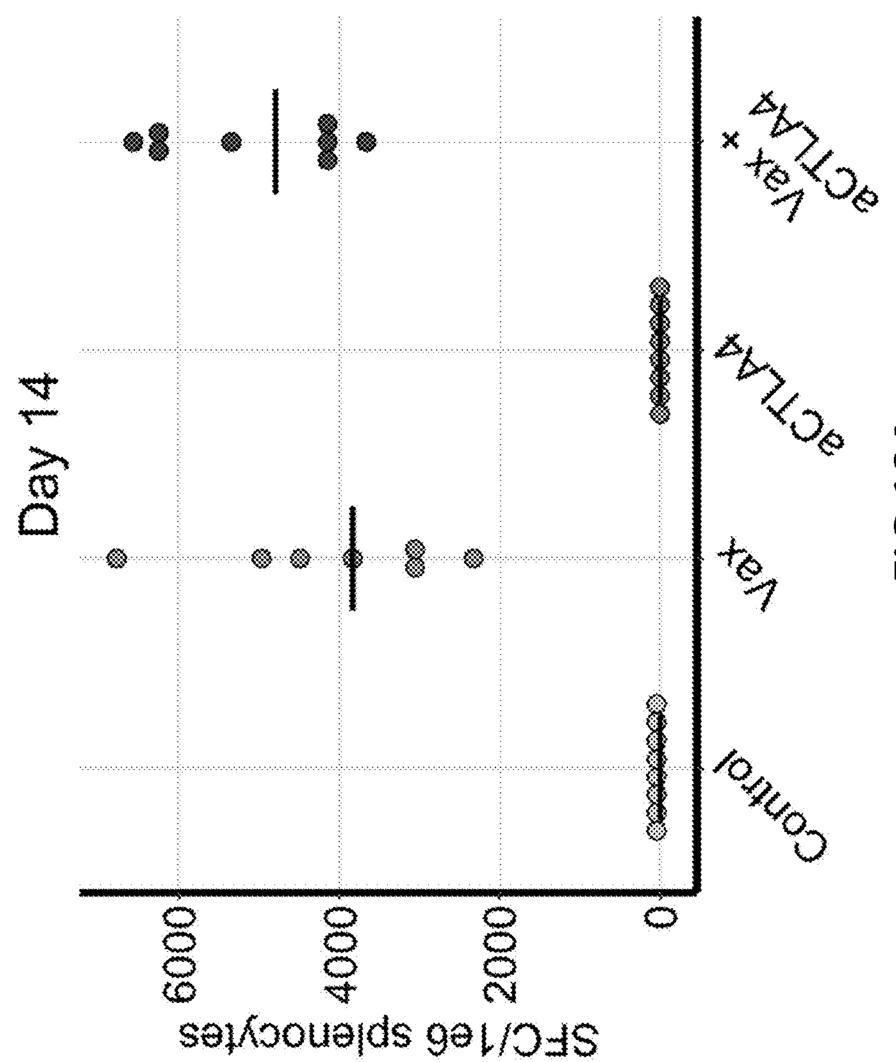
FIG. 12A illustrates T-cell responses measured 14 days after immunization with VEE srRNA formulated with MC3 LNP in B16-OVA tumor bearing mice. B16-OVA tumor bearing C57BL/6J mice were injected with 10 ug of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL-specific T-cell ("SIINFEKL" disclosed as SEQ ID NO: 72) responses were assessed by IFN-gamma ELISPOT and are reported as spot-forming cells (SFC) per 106 splenocytes. Lines represent medians.
Figure 12B:
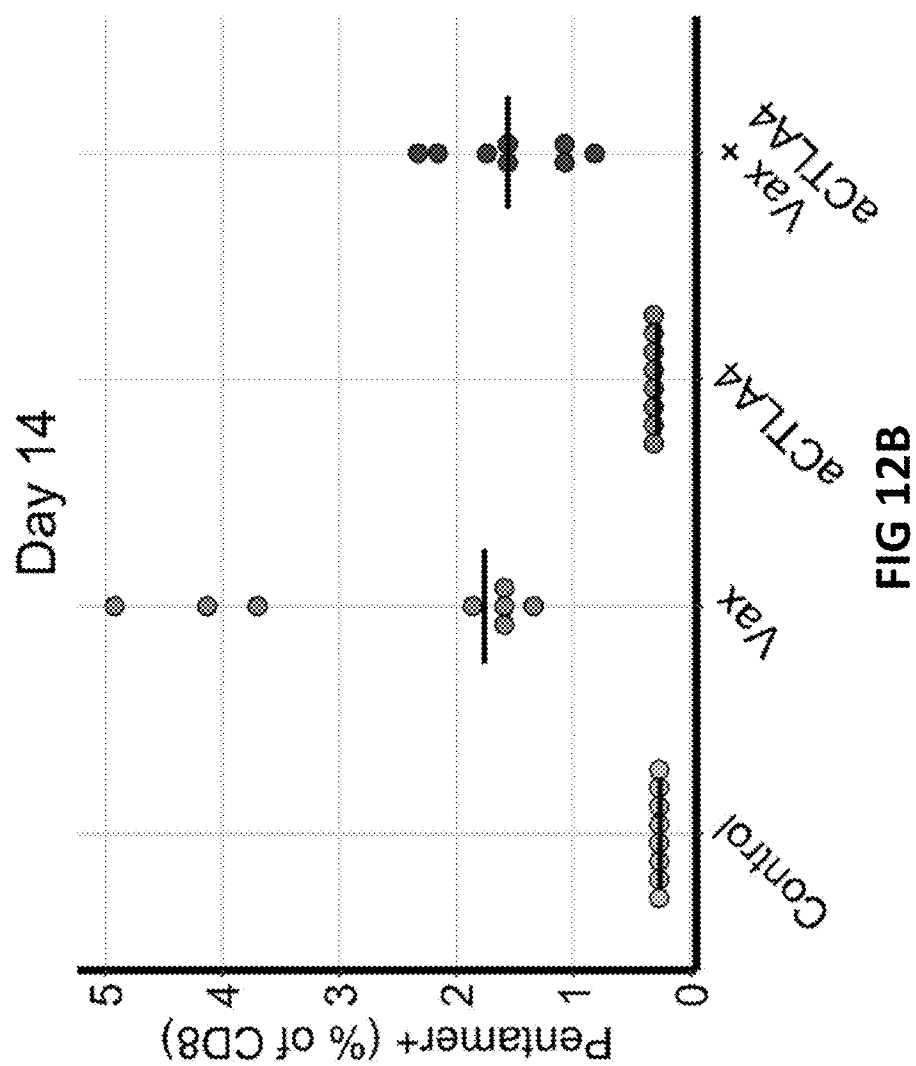
FIG. 12B illustrates T-cell responses measured 14 days after immunization with VEE srRNA formulated with MC3 LNP in B16-OVA tumor bearing mice. B16-OVA tumor bearing C57BL/6J mice were injected with 10 ug of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL-specific T-cell ("SIINFEKL" disclosed as SEQ ID NO: 72) responses were assessed by MHCI-pentamer staining, reported as pentamer positive cells as a percent of CD8 positive cells. Lines represent medians.

A strong antigen-specific T-cell response targeting SFL, relative to control, was observed two weeks after immunization of B16-0VA tumor bearing mice with MC3 formulated VEE-UbAAY srRNA. In one example, a median of 3835 spot forming cells (SFC) per $10^6$ splenocytes was measured after stimulation with the SFL peptide in ELISpot assays (FIG. 12A, Table 12) and 1.8% (median) of CD8 T-cells were SFL antigen-specific as measured by pentamer staining (FIG. 12B, Table 12). In another example, co-administration of an anti-CTLA-4 monoclonal antibody (mAb) with the VEE srRNA vaccine resulted in a moderate increase in overall T-cell responses with a median of 4794.5 SFCs per $10^6$ splenocytes measured in the ELISpot assay (FIG. 12A, Table 12).

TABLE 12

Results of ELISPOT and MHCI-pentamer staining assays 14 days post VEE srRNA immunization in B16-OVA tumor bearing C57BL/6J mice.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Control | 1 | 47 | 0.22 | Vax | 1 | 6774 | 4.92 |
| | 2 | 80 | 0.32 | | 2 | 2323 | 1.34 |
| | 3 | 0 | 0.27 | | 3 | 2997 | 1.52 |
| | 4 | 0 | 0.29 | | 4 | 4492 | 1.86 |
| | 5 | 0 | 0.27 | | 5 | 4970 | 3.7 |
| | 6 | 0 | 0.25 | | 6 | | 4.13 |
| | 7 | 0 | 0.23 | | 7 | 3835 | 1.66 |
| | 8 | 87 | 0.25 | | 8 | 3119 | 1.64 |
| aCTLA4 | 1 | 0 | 0.24 | Vax + aCTLA4 | 1 | 6232 | 2.16 |
| | 2 | 0 | 0.26 | | 2 | 4242 | 0.82 |
| | 3 | 0 | 0.39 | | 3 | 5347 | 1.57 |
| | 4 | 0 | 0.28 | | 4 | 6568 | 2.33 |
| | 5 | 0 | 0.28 | | 5 | 6269 | 1.55 |
| | 6 | 0 | 0.28 | | 6 | 4056 | 1.74 |
| | 7 | 0 | 0.31 | | 7 | 4163 | 1.14 |
| | 8 | 6 | 0.26 | | 8 | 3667 | 1.01 |

* Note that results from mouse #6 in the Vax group were excluded from analysis due to high variability between triplicate wells.

Figure 13A:
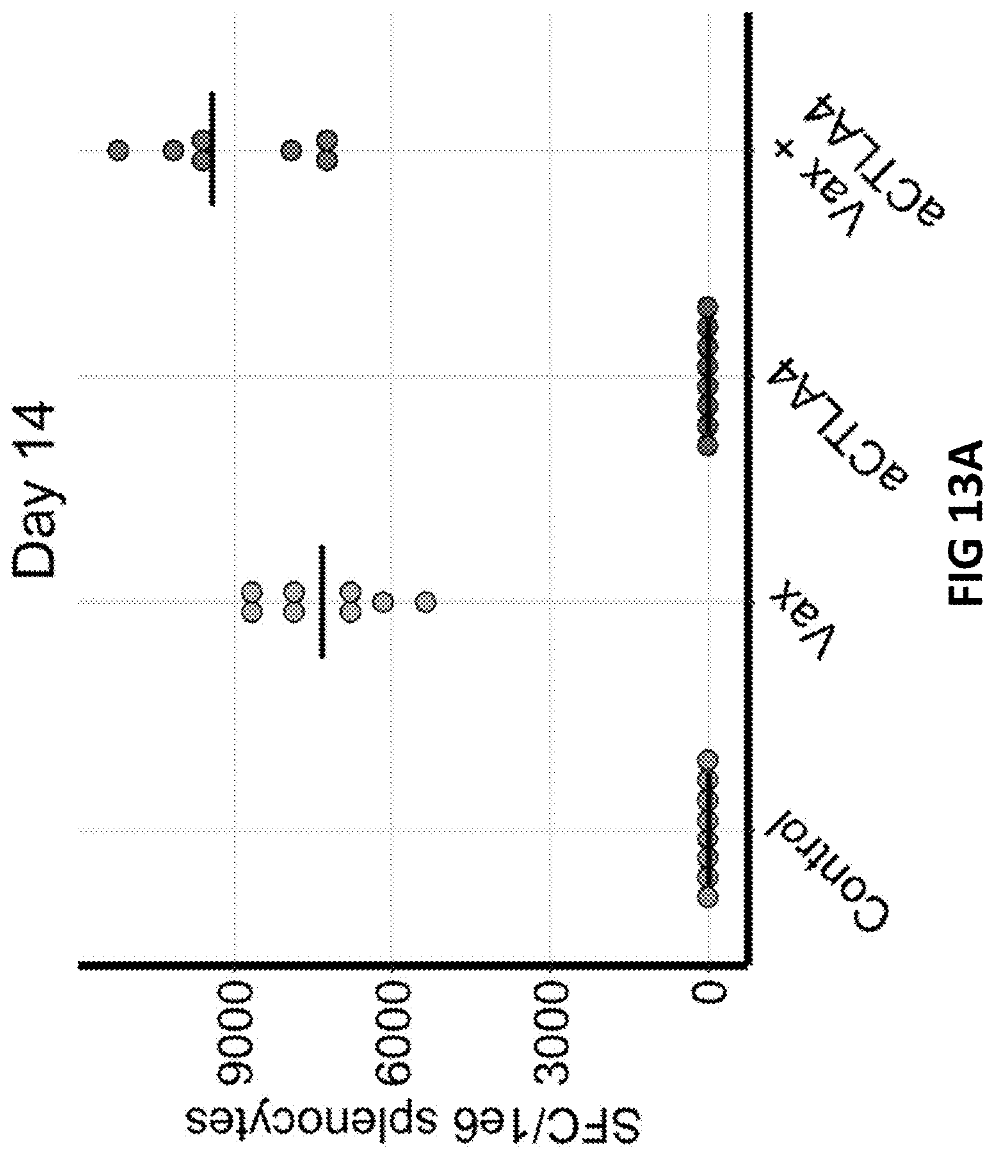
FIG. 13A illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus.
Figure 13B:
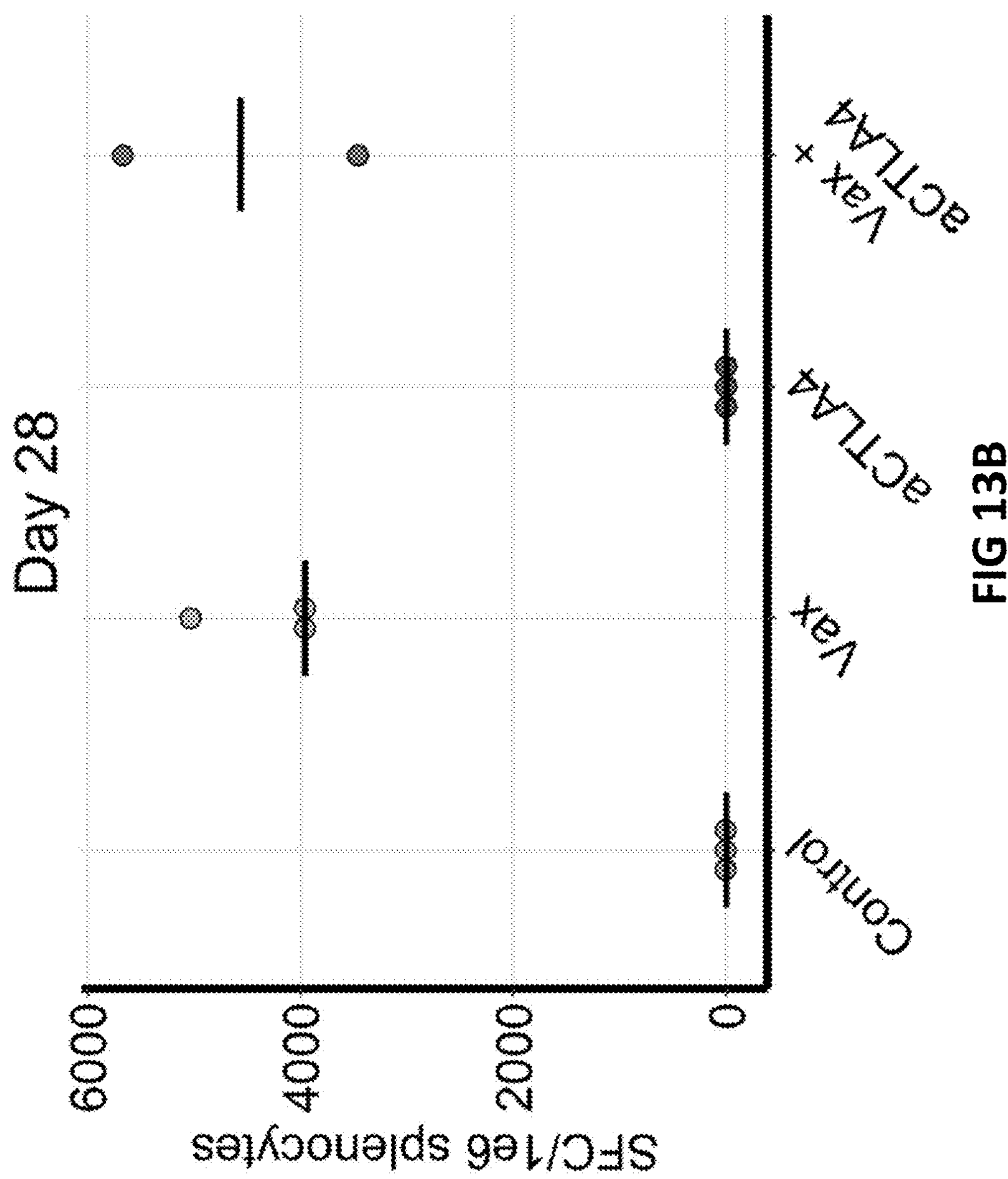
FIG. 13B illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus and 14 days post boost with srRNA (day 28 after prime).
Figure 13C:
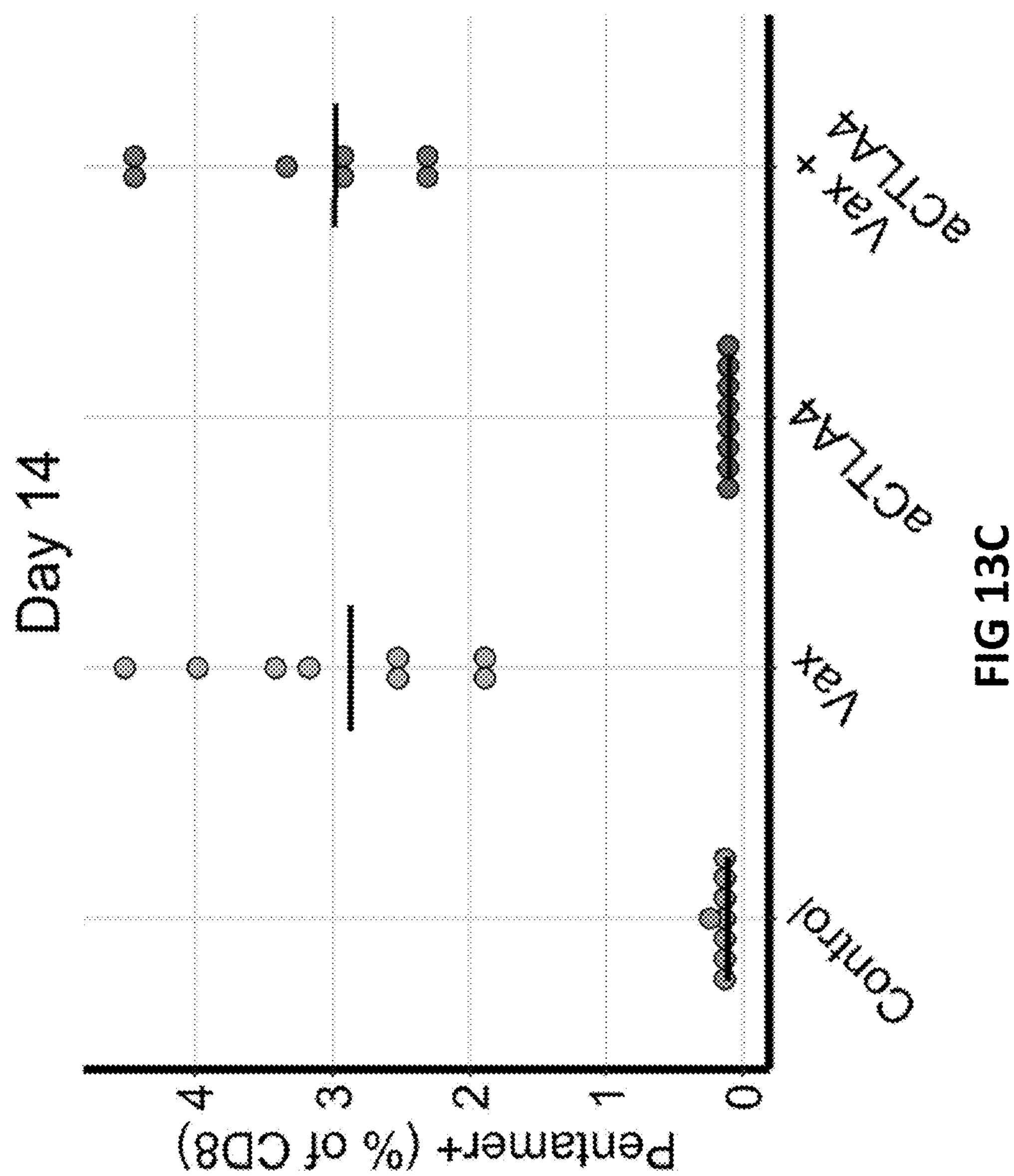
FIG. 13C illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus.
Figure 13D:
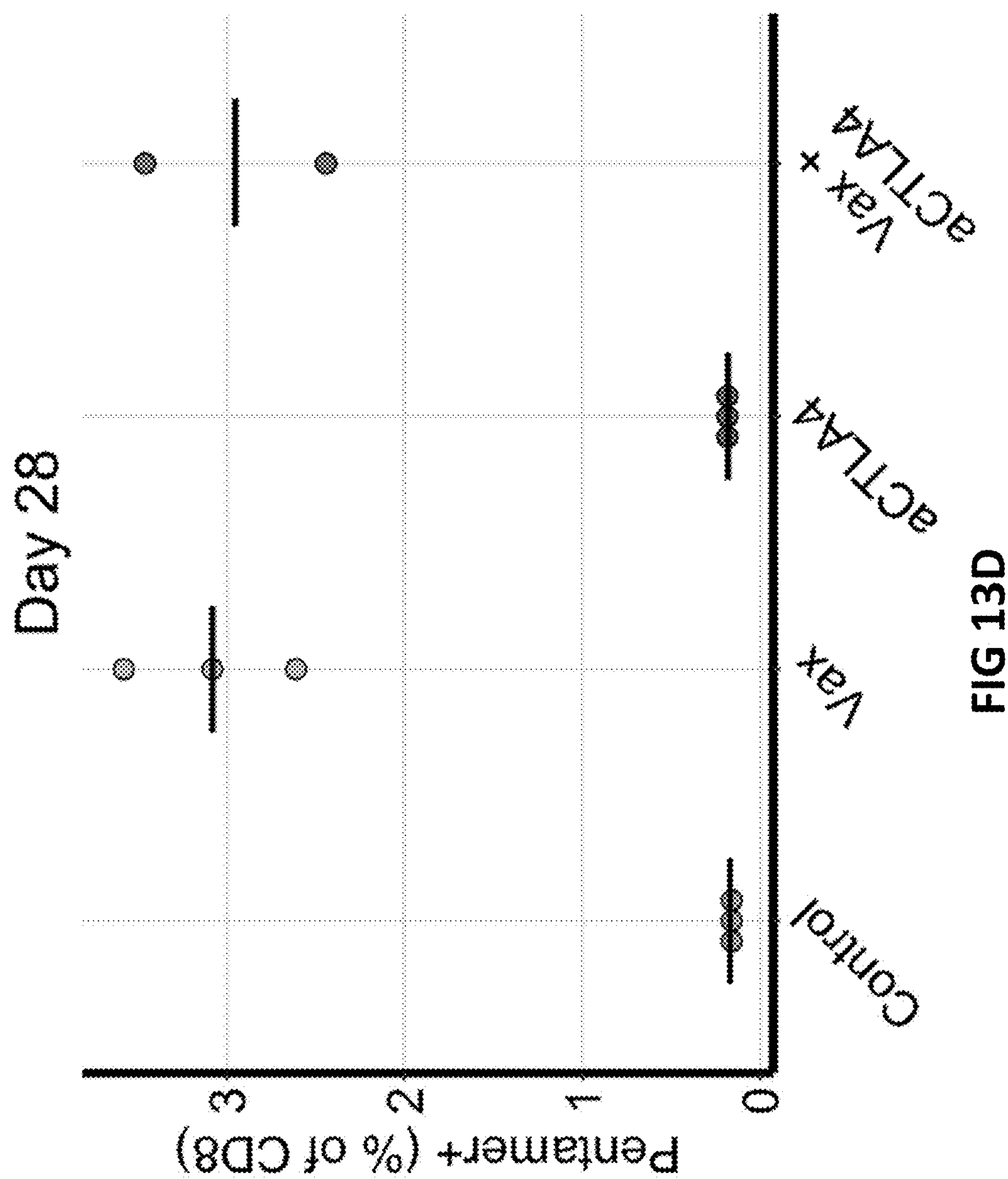
FIG. 13D illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus and 14 days post boost with srRNA (day 28 after prime).

In another implementation, to minor a clinical approach, a heterologous prime/boost in the B16-OVA and CT26 mouse tumor models was performed, where tumor bearing mice were immunized first with adenoviral vector expressing the same antigen cassette (Ad5-UbAAY), followed by a boost immunization with the VEE-UbAAY srRNA vaccine 14 days after the Ad5-UbAAY prime. In one example, an antigen-specific immune response was induced by the Ad5-UbAAY vaccine resulting in 7330 (median) SFCs per $10^6$ splenocytes measured in the ELISpot assay (FIG. 13A, Table 13) and 2.9% (median) of CD8 T-cells targeting the SFL antigen as measured by pentamer staining (FIG. 13C, Table 13). In another example, the T-cell response was maintained 2 weeks after the VEE-UbAAY srRNA boost in the B16-OVA model with 3960 (median) SFL-specific SFCs per $10^6$ splenocytes measured in the ELISpot assay (FIG. 13B, Table 13) and 3.1% (median) of CD8 T-cells targeting the SFL antigen as measured by pentamer staining (FIG. 13D, Table 13).

TABLE 13

Immune monitoring of B16-OVA mice following heterologous prime/boost with Ad5 vaccine prime and srRNA boost.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Day 14 | | | | | | | |
| Control | 1 | 0 | 0.10 | Vax | 1 | 8514 | 1.87 |
| | 2 | 0 | 0.09 | | 2 | 7779 | 1.91 |
| | 3 | 0 | 0.11 | | 3 | 6177 | 3.17 |
| | 4 | 46 | 0.18 | | 4 | 7945 | 3.41 |

TABLE 13-continued

Immune monitoring of B16-OVA mice following heterologous prime/boost with Ad5 vaccine prime and srRNA boost.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| | 5 | 0 | 0.11 | | 5 | 8821 | 4.51 |
| | 6 | 16 | 0.11 | | 6 | 6881 | 2.48 |
| | 7 | 0 | 0.24 | | 7 | 5365 | 2.57 |
| | 8 | 37 | 0.10 | | 8 | 6705 | 3.98 |
| aCTLA4 | 1 | 0 | 0.08 | Vax + | 1 | 9416 | 2.35 |
| | 2 | 29 | 0.10 | aCTLA4 | 2 | 7918 | 3.33 |
| | 3 | 0 | 0.09 | | 3 | 10153 | 4.50 |
| | 4 | 29 | 0.09 | | 4 | 7212 | 2.98 |
| | 5 | 0 | 0.10 | | 5 | 11203 | 4.38 |
| | 6 | 49 | 0.10 | | 6 | 9784 | 2.27 |
| | 7 | 0 | 0.10 | | 8 | 7267 | 2.87 |
| | 8 | 31 | 0.14 | | | | |
| Day 28 | | | | | | | |
| Control | 2 | 0 | 0.17 | Vax | 1 | 5033 | 2.61 |
| | 4 | 0 | 0.15 | | 2 | 3958 | 3.08 |
| | 6 | 20 | 0.17 | | 4 | 3960 | 3.58 |
| aCTLA4 | 1 | 7 | 0.23 | Vax + | 4 | 3460 | 2.44 |
| | 2 | 0 | 0.18 | aCTLA4 | 5 | 5670 | 3.46 |
| | 3 | 0 | 0.14 | | | | |

Figure 14A:
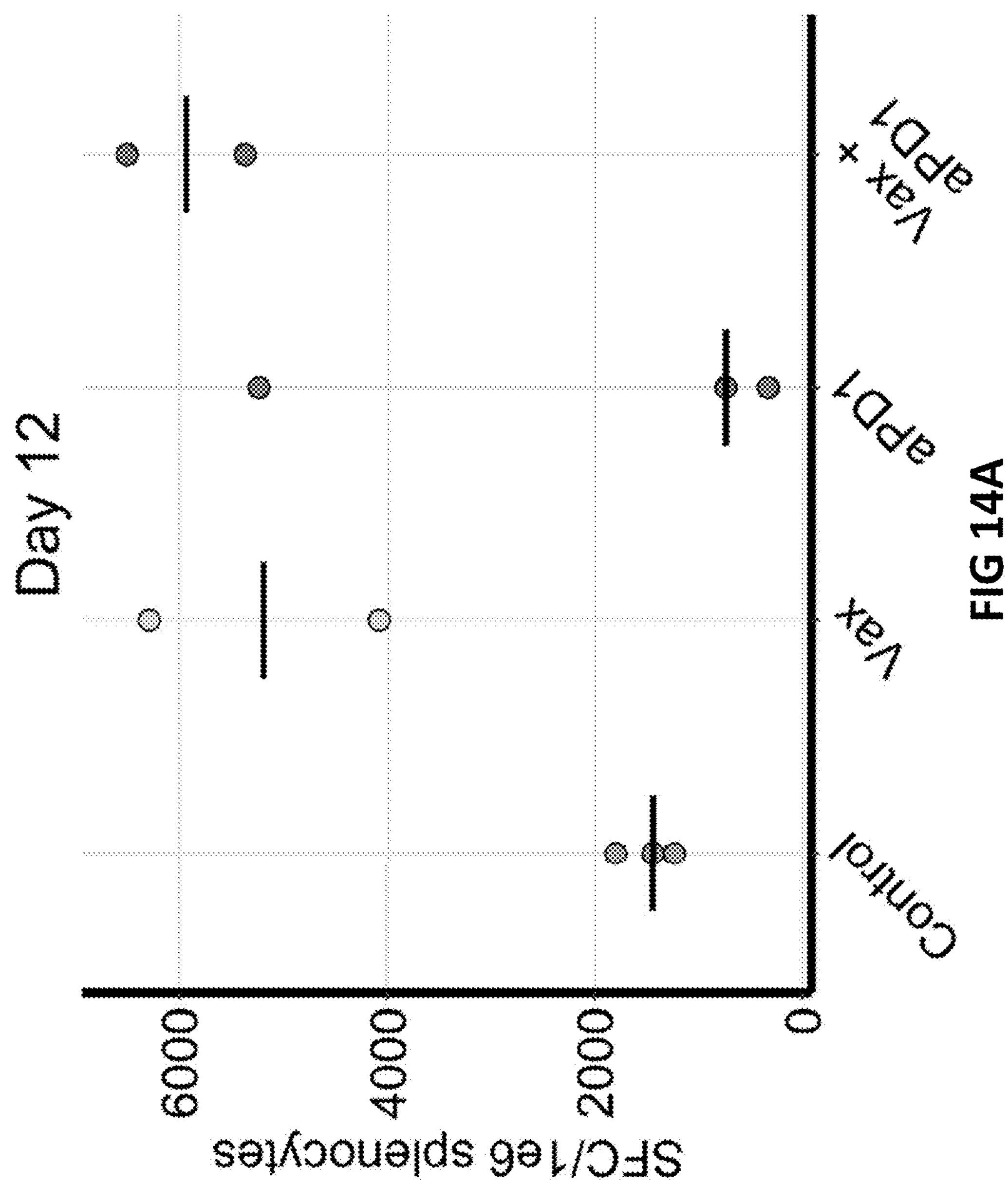
FIG. 14A illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFP/VEE-Luciferase srRNA prime/boost in combination with anti-PD-1 (aPD1), while a fourth group received the Ad5-UbAAYNEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus.
Figure 14B:
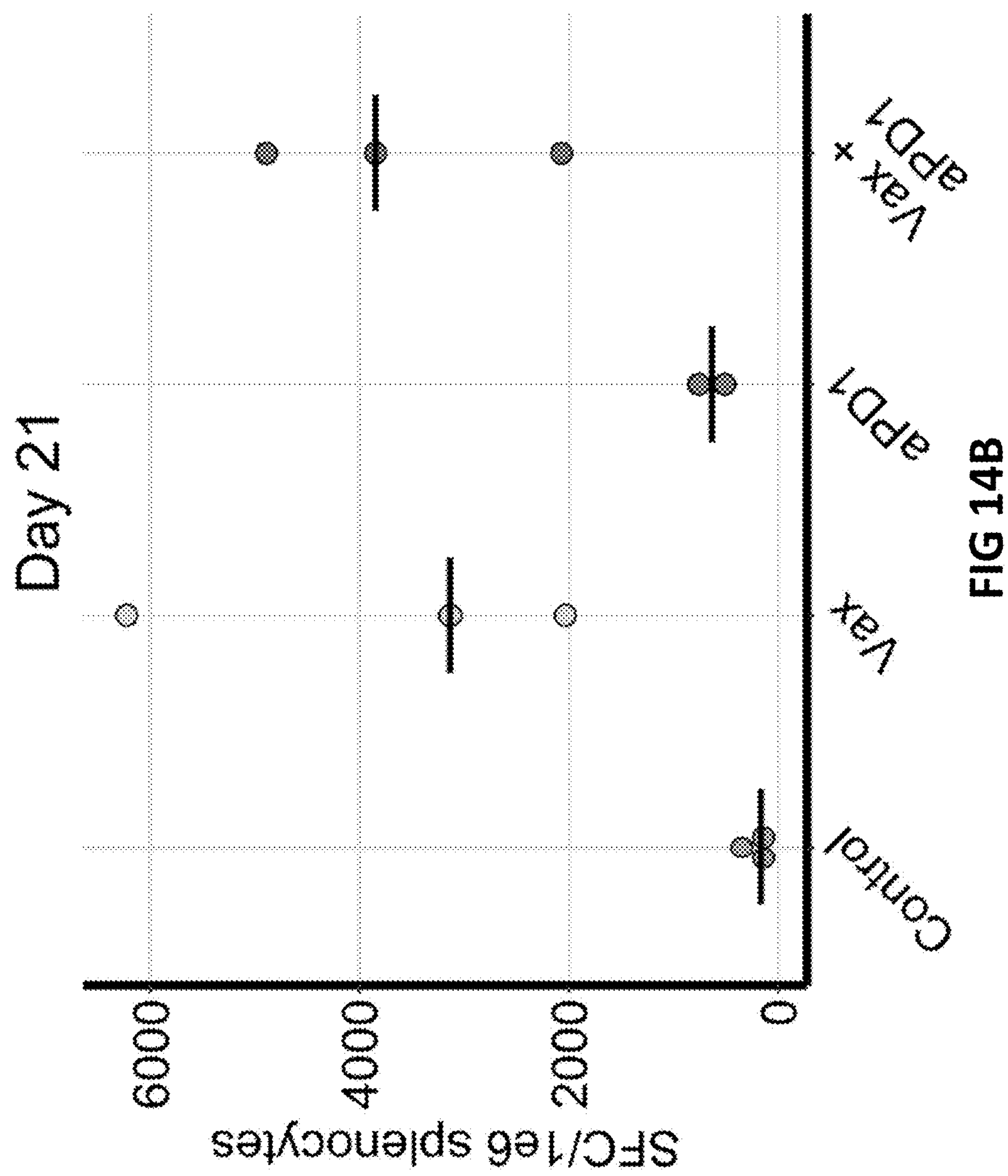
FIG. 14B illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFP/VEE-Luciferase srRNA prime/boost in combination with anti-PD-1 (aPD1), while a fourth group received the Ad5-UbAAYNEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus and 6 days post boost with srRNA (day 21 after prime).

In another implementation, similar results were observed after an Ad5-UbAAY prime and VEE-UbAAY srRNA boost in the CT26 mouse model. In one example, an AH1 antigen-specific response was observed after the Ad5-UbAAY prime (day 14) with a mean of 5187 SFCs per $10^6$ splenocytes measured in the ELISpot assay (FIG. 14A, Table 14) and 3799 SFCs per $10^6$ splenocytes measured in the ELISpot assay after the VEE-UbAAY srRNA boost (day 28) (FIG. 14B, Table 14).

TABLE 14

Immune monitoring after heterologous prime/boost in CT26 tumor mouse model.

| Day 12 | | | Day 21 | | |
|---|---|---|---|---|---|
| Group | Mouse | SFC/1e6 splenocytes | Group | Mouse | SFC/1e6 splenocytes |
| Control | 1 | 1799 | Control | 9 | 167 |
| | 2 | 1442 | | 10 | 115 |
| | 3 | 1235 | | 11 | 347 |
| aPD1 | 1 | 737 | aPD1 | 8 | 511 |
| | 2 | 5230 | | 11 | 758 |
| | 3 | 332 | Vax | 9 | 3133 |
| Vax | 1 | 6287 | | 10 | 2036 |
| | 2 | 4086 | | 11 | 6227 |

TABLE 14-continued

Immune monitoring after heterologous prime/boost in CT26 tumor mouse model.

| Day 12 | | | Day 21 | | |
|---|---|---|---|---|---|
| Group | Mouse | SFC/1e6 splenocytes | Group | Mouse | SFC/1e6 splenocytes |
| Vax + | 1 | 5363 | Vax+ | 8 | 3844 |
| aPD1 | 2 | 6500 | aPD1 | 9 | 2071 |
| | | | | 11 | 4888 |

XVII. ChAdV/srRNA Combination Tumor Model Evaluation

Various dosing protocols using ChAdV68 and self-replicating RNA (srRNA) were evaluated in murine CT26 tumor models.

XVII.A ChAdV/srRNA Combination Tumor Model Evaluation Methods and Materials

Tumor Injection

Balb/c mice were injected with the CT26 tumor cell line. 7 days after tumor cell injection, mice were randomized to the different study arms (28-40 mice per group) and treatment initiated. Balb/c mice were injected in the lower left abdominal flank with $10^6$ CT26 cells/animal. Tumors were allowed to grow for 7 days prior to immunization. The study arms are described in detail in Table 15.

TABLE 15

ChAdV/srRNA Combination Tumor Model Evaluation Study Arms

| Group | N | Treatment | Dose | Volume | Schedule | Route |
|---|---|---|---|---|---|---|
| 1 | 40 | ChAdV68 control | 1e11 vp | 2x 50 uL | day 0 | IM |
| | | srRNA control | 10 ug | 50 uL | day 14, 28, 42 | IM |
| | | Anti-PD1 | 250 ug | 100 uL | 2x/week (start day 0) | IP |
| 2 | 40 | ChAdV68 control | 1e11 vp | 2x 50 uL | day 0 | IM |
| | | srRNA control | 10 ug | 50 uL | day 14, 28, 42 | IM |
| | | Anti-IgG | 250 ug | 100 uL | 2x/week (start day 0) | IP |
| 3 | 28 | ChAdV68 vaccine | 1e11 vp | 2x 50 uL | day 0 | IM |
| | | srRNA vaccine | 10 ug | 50 uL | day 14, 28, 42 | IM |
| | | Anti-PD1 | 250 ug | 100 uL | 2x/week (start day 0) | IP |

TABLE 15-continued

| ChAdV/srRNA Combination Tumor Model Evaluation Study Arms | | | | | | |
|---|---|---|---|---|---|---|
| Group | N | Treatment | Dose | Volume | Schedule | Route |
| 4 | 28 | ChAdV68 vaccine | 1e11 vp | 2x 50 uL | day 0 | IM |
| | | srRNA vaccine | 10 ug | 50 uL | day 14, 28, 42 | IM |
| | | Anti-IgG | 250 ug | 100 uL | 2x/week (start day 0) | IP |
| 5 | 28 | srRNA vaccine | 10 ug | 50 uL | day 0, 28, 42 | IM |
| | | ChAdV68 vaccine | 1e11 vp | 2x 50 uL | day 14 | IM |
| | | Anti-PD1 | 250 ug | 100 uL | 2x/week (start day 0) | IP |
| 6 | 28 | srRNA vaccine | 10 ug | 50 uL | day 0, 28, 42 | IM |
| | | ChAdV68 vaccine | 1e11 vp | 2x 50 uL | day 14 | IM |
| | | Anti-IgG | 250 ug | 100 uL | 2x/week (start day 0) | IP |
| 7 | 40 | srRNA vaccine | 10 ug | 50 uL | day 0, 14, 28, 42 | IM |
| | | Anti-PD1 | 250 ug | 100 uL | 2x/week (start day 0) | IP |
| 8 | 40 | srRNA vaccine | 10 ug | 50 uL | day 0, 14, 28, 42 | IM |
| | | Anti-IgG | 250 ug | 100 uL | 2x/week (start day 0) | IP |

Immunizations

For srRNA vaccine, mice were injected with 10 ug of VEE-MAG25mer srRNA in 100 uL volume, bilateral intramuscular injection (50 uL per leg). For C68 vaccine, mice were injected with $1\times10^{11}$ viral particles (VP) of ChAdV68.5WTnt.MAG25mer in 100 uL volume, bilateral intramuscular injection (50 uL per leg). Animals were injected with anti-PD-1 (clone RMP1-14, BioXcell) or anti-IgG (clone MPC-11, BioXcell), 250 ug dose, 2 times per week, via intraperitoneal injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune N×T flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XVII.B ChAdV/srRNA Combination Evaluation in a CT26 Tumor Model

The immunogenicity and efficacy of the ChAdV68.5WTnt.MAG25mer/VEE-MAG25mer srRNA heterologous prime/boost or VEE-MAG25mer srRNA homologous prime/boost vaccines were evaluated in the CT26 mouse tumor model. Balb/c mice were injected with the CT26 tumor cell line. 7 days after tumor cell injection, mice were randomized to the different study arms and treatment initiated. The study arms are described in detail in Table 15 and more generally in Table 16.

TABLE 16

| Prime/Boost Study Arms | | |
|---|---|---|
| Group | Prime | Boost |
| 1 | Control | Control |
| 2 | Control + anti-PD-1 | Control + anti-PD-1 |
| 3 | ChAdV68.5WTnt.MAG25mer | VEE-MAG25mer srRNA |
| 4 | ChAdV68.5WTnt.MAG25mer + anti-PD-1 | VEE-MAG25mer srRNA + anti-PD-1 |
| 5 | VEE-MAG25mer srRNA | ChAdV68.5WTnt.MAG25mer |
| 6 | VEE-MAG25mer srRNA + anti-PD-1 | ChAdV68.5WTnt.MAG25mer + anti-PD-1 |
| 7 | VEE-MAG25mer srRNA | VEE-MAG25mer srRNA |
| 8 | VEE-MAG25mer srRNA + anti-PD-1 | VEE-MAG25mer srRNA + anti-PD-1 |

Spleens were harvested 14 days after the prime vaccination for immune monitoring. Tumor and body weight measurements were taken twice a week and survival was monitored. Strong immune responses relative to control were observed in all active vaccine groups.

Figure 16:
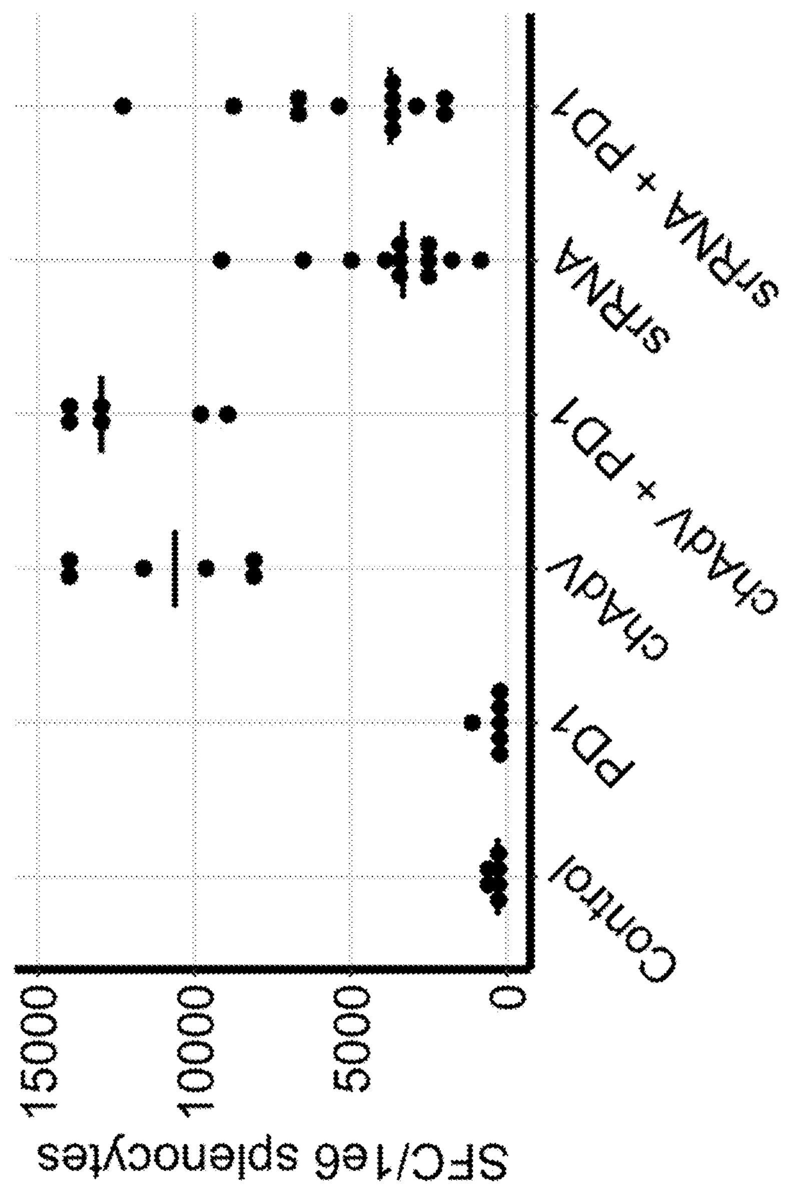
FIG. 16 illustrates cellular immune responses in a CT26 tumor model following a single immunization with either ChAdV6, ChAdV+anti-PD-1, srRNA, srRNA+anti-PD-1, or anti-PD-1 alone. Antigen-specific IFN-gamma production was measured in splenocytes for 6 mice from each group using ELISpot. Results are presented as spot forming cells (SFC) per $10^6$ splenocytes. Median for each group indicated by horizontal line. P values determined using the Dunnett's multiple comparison test; * P<0.0001, P<0.001, *P<0.05. ChAdV=ChAdV68.5WTnt.MAG25mer; srRNA=VEE-MAG25mer srRNA.

Median cellular immune responses of 10,630, 12,976, 3319, or 3745 spot forming cells (SFCs) per $10^6$ splenocytes were observed in ELISpot assays in mice immunized with ChAdV68.5WTnt.MAG25mer (ChAdV/group 3), ChAdV68.5WTnt.MAG25mer+anti-PD-1 (ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 16 and Table 17). In contrast, the vaccine control (group 1) or vaccine control with anti-PD-1 (group 2) exhibited median cellular immune responses of 296 or 285 SFC per $10^6$ splenocytes, respectively.

TABLE 17

| Cellular immune responses in a CT26 tumor model | |
|---|---|
| Treatment | Median SFC/$10^6$ Splenocytes |
| Control | 296 |
| PD1 | 285 |

TABLE 17-continued

| Cellular immune responses in a CT26 tumor model | |
|---|---|
| Treatment | Median SFC/$10^6$ Splenocytes |
| ChAdV68.5WTnt.MAG25mer (ChAdV) | 10630 |
| ChAdV68.5WTnt.MAG25mer + PD1 (ChAdV + PD-1) | 12976 |
| VEE-MAG25mer srRNA (srRNA) | 3319 |
| VEE-MAG25mer srRNA + PD-1 (srRNA + PD1) | 3745 |

Figure 17:
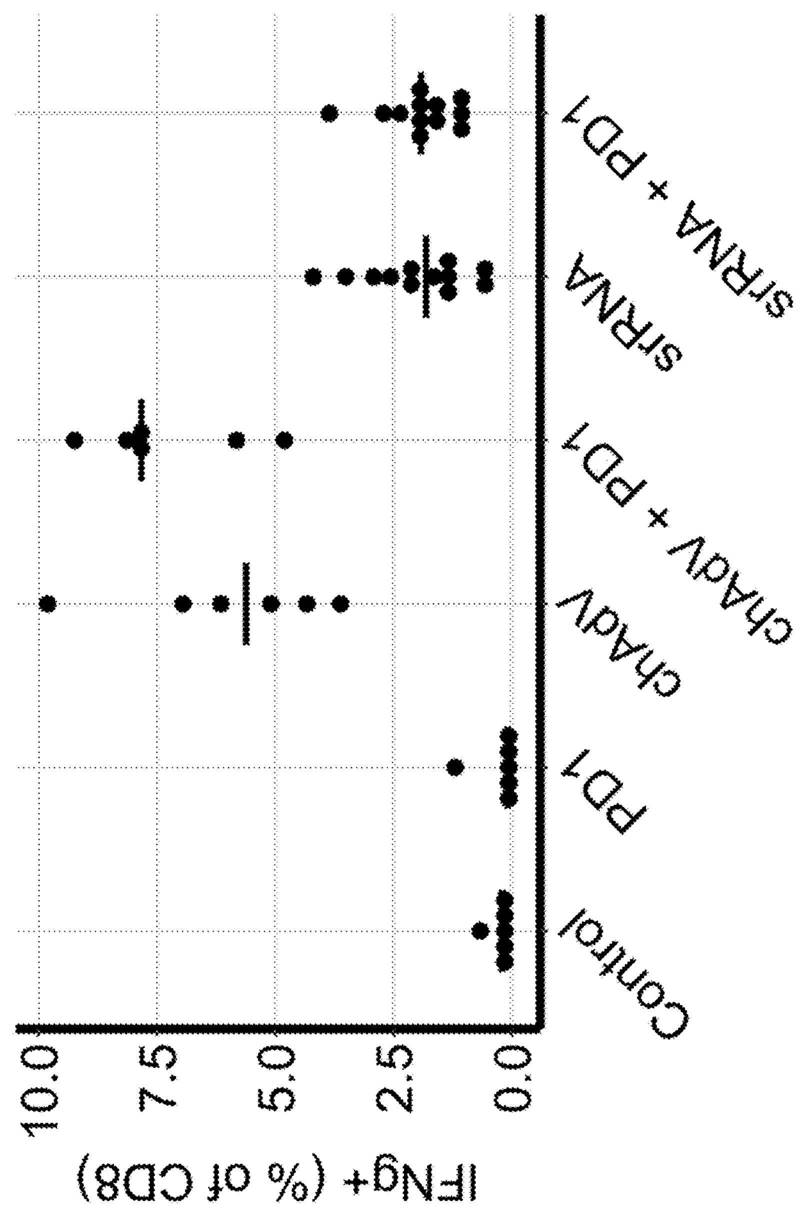
FIG. 17 illustrates CD8 T-Cell responses in a CT26 tumor model following a single immunization with either ChAdV6, ChAdV+anti-PD-1, srRNA, srRNA+anti-PD-1, or anti-PD-1 alone. Antigen-specific IFN-gamma production in CD8 T cells measured using ICS and results presented as antigen-specific CD8 T cells as a percentage of total CD8 T cells. Median for each group indicated by horizontal line. P values determined using the Dunnett's multiple comparison test; * P<0.0001, P<0.001, *P<0.05. ChAdV=ChAdV68.5WTnt.MAG25mer; srRNA=VEE-MAG25mer srRNA.

Consistent with the ELISpot data, 5.6, 7.8, 1.8 or 1.9% of CD8 T cells (median) exhibited antigen-specific responses in intracellular cytokine staining (ICS) analyses for mice immunized with ChAdV68.5WTnt.MAG25mer (ChAdV/group 3), ChAdV68.5WTnt.MAG25mer+anti-PD-1 (ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 17 and Table 18). Mice immunized with the vaccine control or vaccine control combined with anti-PD-1 showed antigen-specific CD8 responses of 0.2 and 0.1%, respectively.

TABLE 18

| CD8 T-Cell responses in a CT26 tumor model | |
|---|---|
| Treatment | Median % CD8 IFN-gamma Positive |
| Control | 0.21 |
| PD1 | 0.1 |
| ChAdV68.5WTnt.MAG25mer (ChAdV) | 5.6 |
| ChAdV68.5WTnt.MAG25mer + PD1 (ChAdV + PD-1) | 7.8 |
| VEE-MAG25mer srRNA (srRNA) | 1.8 |
| VEE-MAG25mer srRNA + PD-1 (srRNA + PD1) | 1.9 |

Figure 18:
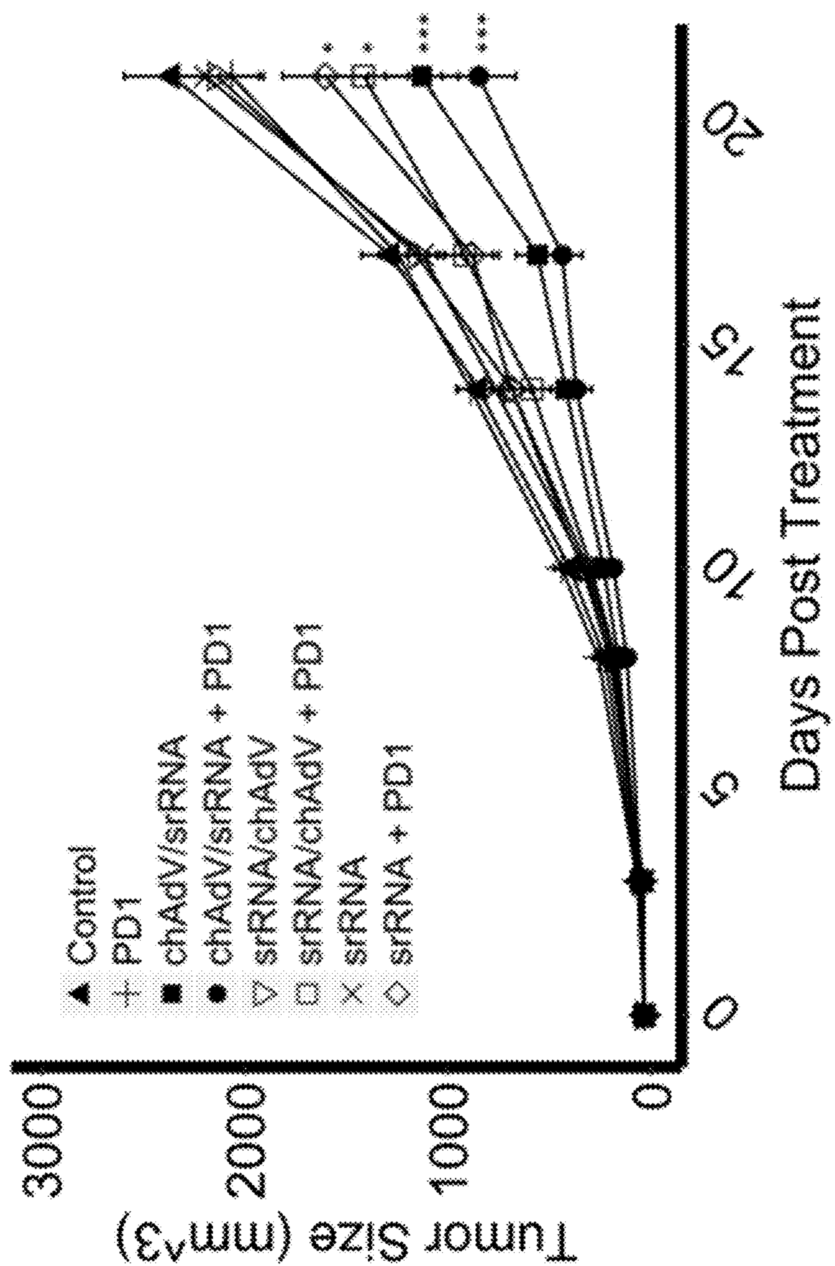
FIG. 18 illustrates tumor growth in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. Tumor volumes measured twice per week and mean tumor volumes presented for the first 21 days of the study. 22-28 mice per group at study initiation. Error bars represent standard error of the mean (SEM). P values determined using the Dunnett's test; * P<0.0001, P<0.001, *P<0.05. ChAdV=ChAdV68.5WTnt.MAG25mer; srRNA=VEE-MAG25mer srRNA.

Tumor growth was measured in the CT26 colon tumor model for all groups, and tumor growth up to 21 days after treatment initiation (28 days after injection of CT-26 tumor cells) is presented. Mice were sacrificed 21 days after treatment initiation based on large tumor sizes (>2500 $mm^3$); therefore, only the first 21 days are presented to avoid analytical bias. Mean tumor volumes at 21 days were 1129, 848, 2142, 1418, 2198 and 1606 $mm^3$ for ChAdV68.5WTnt.MAG25mer prime/VEE-MAG25mer srRNA boost (group 3), ChAdV68.5WTnt.MAG25mer prime/VEE-MAG25mer srRNA boost+anti-PD-1 (group 4), VEE-MAG25mer srRNA prime/ChAdV68.5WTnt.MAG25mer boost (group 5), VEE-MAG25mer srRNA prime/ChAdV68.5WTnt.MAG25mer boost+anti-PD-1 (group 6), VEE-MAG25mer srRNA prime/VEE-MAG25mer srRNA boost (group 7) and VEE-MAG25mer srRNA prime/VEE-MAG25mer srRNA boost+anti-PD-1 (group 8), respectively (FIG. 18 and Table 19). The mean tumor volumes in the vaccine control or vaccine control combined with anti-PD-1 were 2361 or 2067 $mm^3$, respectively. Based on these data, vaccine treatment with ChAdV68.5WTnt.MAG25mer/VEE-MAG25mer srRNA (group 3), ChAdV68.5WTnt.MAG25mer/VEE-MAG25mer srRNA+anti-PD-1 (group 4), VEE-MAG25mer srRNA/ChAdV68.5WTnt.MAG25mer+anti-PD-1 (group 6) and VEE-MAG25mer srRNA/VEE-MAG25mer srRNA+anti-PD-1 (group 8) resulted in a reduction of tumor growth at 21 days that was significantly different from the control (group 1).

TABLE 19

| Tumor size at day 21 measured in the CT26 model | | |
|---|---|---|
| Treatment | Tumor Size ($mm^3$) | SEM |
| Control | 2361 | 235 |
| PD1 | 2067 | 137 |
| chAdV/srRNA | 1129 | 181 |
| chAdV/srRNA + PD1 | 848 | 182 |
| srRNA/chAdV | 2142 | 233 |
| srRNA/chAdV + PD1 | 1418 | 220 |
| srRNA | 2198 | 134 |
| srRNA + PD1 | 1606 | 210 |

Figure 19:
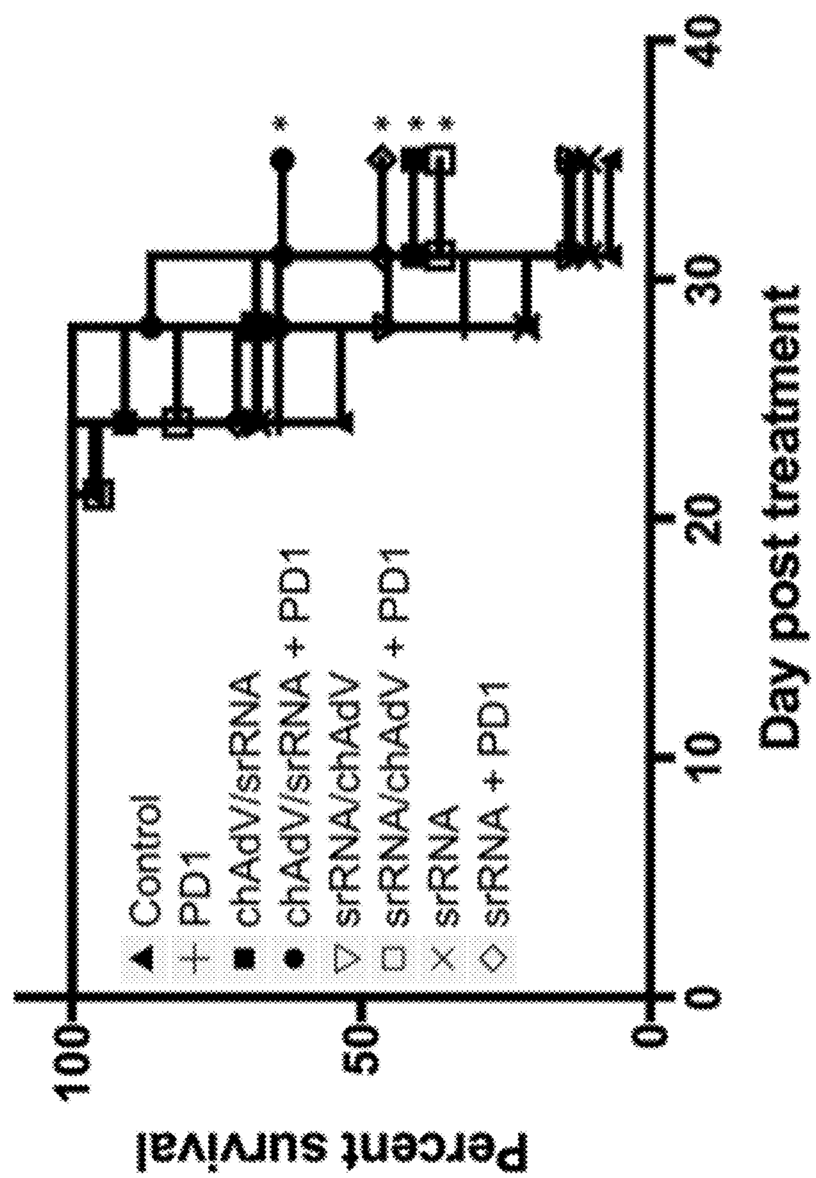
FIG. 19 illustrates survival in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. P values determined using the log-rank test; * P<0.0001, P<0.001, *P<0.01. ChAdV=ChAdV68.5WTnt.MAG25-mer; srRNA=VEE-MAG25mer srRNA.

Survival was monitored for 35 days after treatment initiation in the CT-26 tumor model (42 days after injection of CT-26 tumor cells). Improved survival was observed after vaccination of mice with 4 of the combinations tested. After vaccination, 64%, 46%, 41% and 36% of mice survived with ChAdV68.5WTnt.MAG25mer prime/VEE-MAG25mer srRNA boost in combination with anti-PD-1 (group 4; P<0.0001 relative to control group 1), VEE-MAG25mer srRNA prime/VEE-MAG25mer srRNA boost in combination with anti-PD-1 (group 8; P=0.0006 relative to control group 1), ChAdV68.5WTnt.MAG25mer prime/VEE-MAG25mer srRNA boost (group 3; P=0.0003 relative to control group 1) and VEE-MAG25mer srRNA prime/ChAdV68.5WTnt.MAG25mer boost in combination with anti-PD-1 (group 6; P=0.0016 relative to control group 1), respectively (FIG. 19 and Table 20). Survival was not significantly different from the control group 1 (<14%) for the remaining treatment groups [VEE-MAG25mer srRNA prime/ChAdV68.5WTnt.MAG25mer boost (group 5), VEE-MAG25mer srRNA prime/VEE-MAG25mer srRNA boost (group 7) and anti-PD-1 alone (group 2)].

TABLE 20

| Survival in the CT26 model | | | | | | | | |
|---|---|---|---|---|---|---|---|---|
| Timepoint | Control | PD1 | chAdV/ srRNA | chAdV/ srRNA + PD1 | srRNA/ chAdV | srRNA/ chAdV + PD1 | srRNA | srRNA + PD1 |
| 0 | 100 | 100 | 100 | 100.00 | 100.00 | 100 | 100 | 100 |
| 21 | 96 | 100 | 100 | 100 | 100 | 95 | 100 | 100 |
| 24 | 54 | 64 | 91 | 100 | 68 | 82 | 68 | 71 |
| 28 | 21 | 32 | 68 | 86 | 45 | 68 | 21 | 64 |
| 31 | 7 | 14 | 41 | 64 | 14 | 36 | 11 | 46 |
| 35 | 7 | 14 | 41 | 64 | 14 | 36 | 11 | 46 |

In conclusion, ChAdV68.5WTnt.MAG25mer and VEE-MAG25mer srRNA elicited strong T-cell responses to mouse tumor antigens encoded by the vaccines, relative to control. Administration of a ChAdV68.5WTnt.MAG25mer prime and VEE-MAG25mer srRNA boost with or without co-administration of anti-PD-1, VEE-MAG25mer srRNA prime and ChAdV68.5WTnt.MAG25mer boost in combination with anti-PD-1 or administration of VEE-MAG25mer srRNA as a homologous prime boost immunization in combination with anti-PD-1 to tumor bearing mice resulted in improved survival.

XVIII. Non-Human Primate Studies

Various dosing protocols using ChAdV68 and self-replicating RNA (srRNA) were evaluated in non-human primates (NHP).

Materials and Methods

A priming vaccine was injected intramuscularly (IM) in each NHP to initiate the study (vaccine prime). One or more boosting vaccines (vaccine boost) were also injected intramuscularly in each NHP. Bilateral injections per dose were administered according to groups outlined in tables and summarized below.

Immunizations

Mamu-A*01 Indian rhesus macaques were immunized bilaterally with $1\times10^{12}$ viral particles ($5\times10^{11}$ viral particles per injection) of ChAdV68.5WTnt.MAG25mer, 30 ug of VEE-MAG25MER srRNA, 100 ug of VEE-MAG25mer srRNA or 300 ug of VEE-MAG25mer srRNA formulated in LNP-1 or LNP-2. Vaccine boosts of 30 ug, 100 ug or 300 ug VEE-MAG25mer srRNA were administered intramuscularly at the indicated time after prime vaccination.

Immune Monitoring

PBMCs were isolated at indicated times after prime vaccination using Lymphocyte Separation Medium (LSM, MP Biomedicals) and LeucoSep separation tubes (Greiner Bio-One) and resuspended in RPMI containing 10% FBS and penicillin/streptomycin. Cells were counted on the Attune N×T flow cytometer (Thermo Fisher) using propidium iodide staining to exclude dead and apoptotic cells. Cell were then adjusted to the appropriate concentration of live cells for subsequent analysis. For each monkey in the studies, T cell responses were measured using ELISpot or flow cytometry methods. T cell responses to 6 different rhesus macaque Mamu-A*01 class I epitopes encoded in the vaccines were monitored from PBMCs by measuring induction of cytokines, such as IFN-gamma, using ex vivo enzyme-linked immunospot (ELISpot) analysis. ELISpot analysis was performed according to ELISPOT harmonization guidelines {DOI: 10.1038/nprot.2015.068} with the monkey IFNg ELISpotPLUS kit (MABTECH). 200,000 PBMCs were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Specific CD4 and CD8 T cell responses to 6 different rhesus macaque Mamu-A*01 class I epitopes encoded in the vaccines were monitored from PBMCs by measuring induction of intracellular cytokines, such as IFN-gamma, using flow cytometry. The results from both methods indicate that cytokines were induced in an antigen-specific manner to epitopes.

Immunogenicity in Rhesus Macaques

This study was designed to (a) evaluate the immunogenicity and preliminary safety of VEE-MAG25mer srRNA 30 pg and 100 pg doses as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2; (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5WTnt.MAG25mer or VEE-MAG25mer srRNA vector encoding model antigens that includes multiple Mamu-A*01 restricted epitopes. The study arms were as described below.

TABLE 21

Non-GLP immunogenicity study in Indian Rhesus Macaques

| Group | Prime | Boost 1 | Boost 2 |
|---|---|---|---|
| 1 | VEE-MAG25mer srRNA-LNP1(30 μg) | VEE-MAG25mer srRNA-LNP1 (30 μg) | VEE-MAG25mer srRNA-LNP1 (30 μg) |
| 2 | VEE-MAG25mer srRNA-LNP1 (100 μg) | VEE-MAG25mer srRNA-LNP1 (100 μg) | VEE-MAG25mer srRNA-LNP1 (100 μg) |
| 3 | VEE-MAG25mer srRNA-LNP2 (100 μg) | VEE-MAG25mer srRNA-LNP2 (100 μg) | VEE-MAG25mer srRNA-LNP2 (100 μg) |
| 4 | ChAdV68.5WTnt.MAG25mer | VEE-MAG25mer srRNA-LNP1 (100 μg) | VEE-MAG25mer srRNA-LNP1 (100 μg) |

PBMCs were collected prior to immunization and on weeks 1, 2, 3, 4, 5, 6, 8, 9, and 10 after the initial immunization for immune monitoring.

Results

Antigen-specific cellular immune responses in peripheral blood mononuclear cells (PBMCs) were measured to six different Mamu-A*01 restricted epitopes prior to immunization and 1, 2, 3, 4, 5, 6, 8, 9, and 10 weeks after the initial immunization. Animals received a boost immunization with VEE-MAG25mer srRNA on weeks 4 and 8 with either 30 μg or 100 μg doses, and either formulated with LNP1 or LNP2, as described in Table 21. Combined immune responses to all six epitopes were plotted for each immune monitoring timepoint (FIGS. 20A-D and Tables 22-25).

Figure 20A:
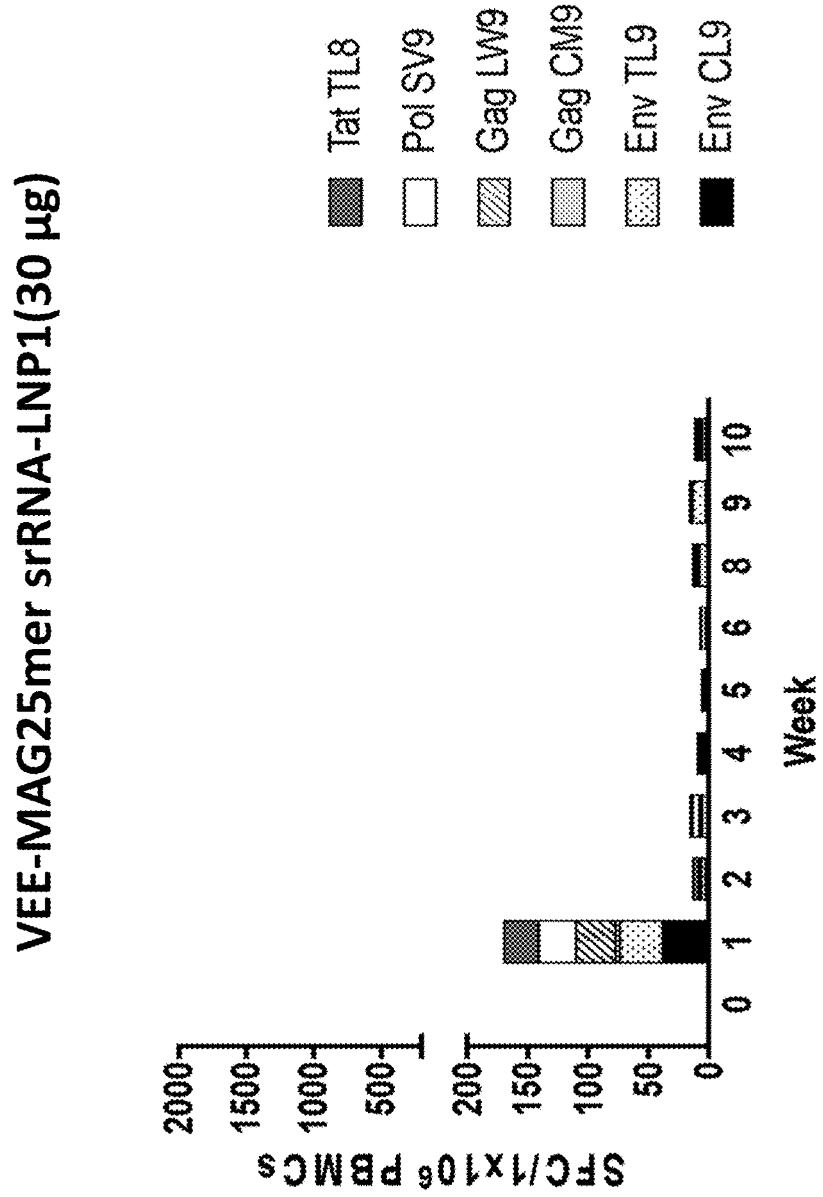
FIG. 20A illustrates antigen-specific cellular immune responses measured using ELISpot. Antigen-specific IFN-gamma production to six different mamu A01 restricted epitopes was measured in PBMCs for the VEE-MAG25mer srRNA-LNP1 (30 μg) using ELISpot 1, 2, 3, 4, 5, 6, 8, 9, or 10 weeks after the initial immunization (6 rhesus macaques per group). Results are presented as mean spot forming cells (SFC) per $10^6$ PBMCs for each epitope in a stacked bar graph format. Values for each animal were normalized to the levels at pre-bleed (week 0).
Figure 20B:
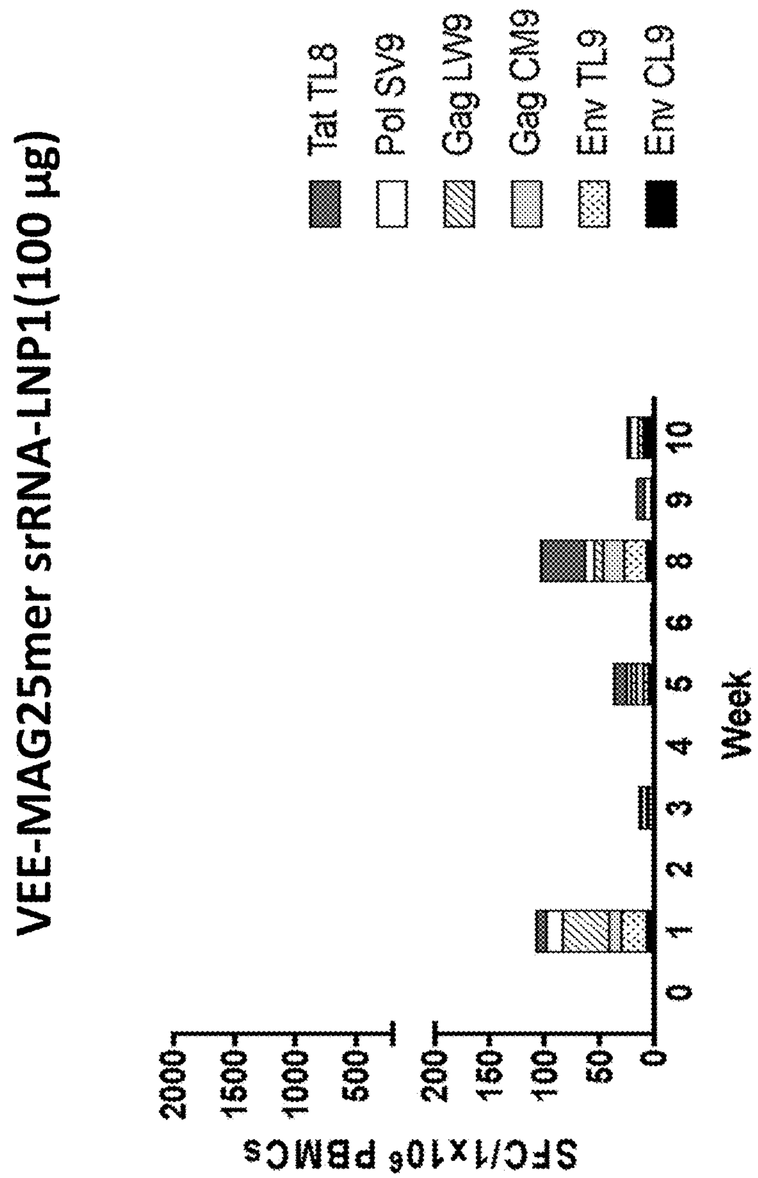
FIG. 20B illustrates antigen-specific cellular immune responses measured using ELISpot. Antigen-specific IFN-gamma production to six different mamu A01 restricted epitopes was measured in PBMCs for the VEE-MAG25mer srRNA-LNP1 (100 μg) using ELISpot 1, 2, 3, 4, 5, 6, 8, 9, or 10 weeks after the initial immunization (6 rhesus macaques per group). Results are presented as mean spot forming cells (SFC) per $10^6$ PBMCs for each epitope in a stacked bar graph format. Values for each animal were normalized to the levels at pre-bleed (week 0)
Figure 20C:
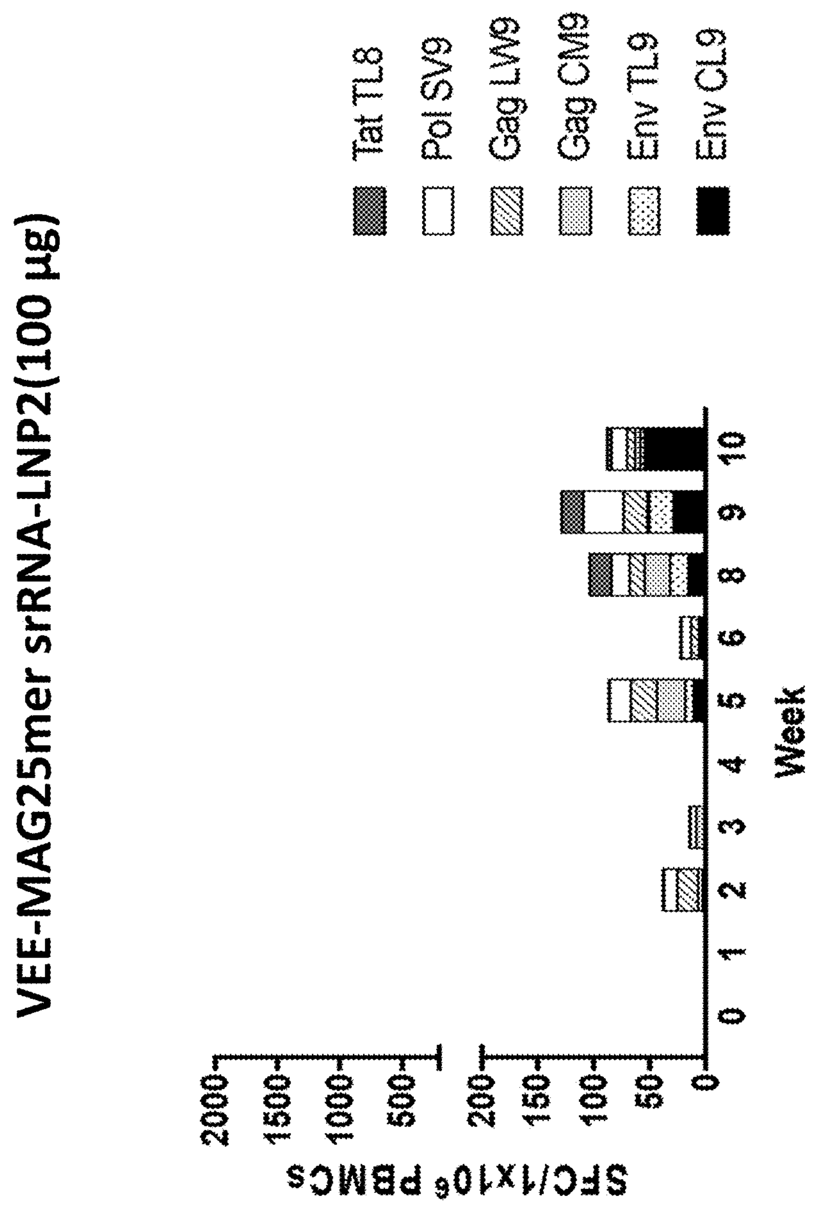
FIG. 20C illustrates antigen-specific cellular immune responses measured using ELISpot. Antigen-specific IFN-gamma production to six different mamu A01 restricted epitopes was measured in PBMCs for the VEE-MAG25mer srRNA-LNP2 (100 μg) homologous prime/boost using ELISpot 1, 2, 3, 4, 5, 6, 8, 9, or 10 weeks after the initial immunization (6 rhesus macaques per group). Results are presented as mean spot forming cells (SFC) per $10^6$ PBMCs for each epitope in a stacked bar graph format. Values for each animal were normalized to the levels at pre-bleed (week 0).

Combined antigen-specific immune responses were observed at all measurements with 170, 14, 15, 11, 7, 8, 14, 17, 12 SFCs per $10^6$ PBMCs (six epitopes combined) 1, 2, 3, 4, 5, 6, 8, 9, or 10 weeks after an initial VEE-MAG25mer srRNA-LNP1 (30 μg) prime immunization, respectively (FIG. 20A). Combined antigen-specific immune responses were observed at all measurements with 108, −3, 14, 1, 37, 4, 105, 17, 25 SFCs per $10^6$ PBMCs (six epitopes combined) 1, 2, 3, 4, 5, 6, 8, 9, or 10 weeks after an initial VEE-MAG25mer srRNA-LNP1 (100 μg) prime immunization, respectively (FIG. 20B). Combined antigen-specific immune responses were observed at all measurements with −17, 38, 14, −2, 87, 21, 104, 129, 89 SFCs per $10^6$ PBMCs (six epitopes combined) 1, 2, 3, 4, 5, 6, 8, 9, or 10 weeks after an initial VEE-MAG25mer srRNA-LNP2 (100 μg) prime immunization, respectively (FIG. 20C). Negative values are a result of normalization to pre-bleed values for each epitope/animal.

Figure 20D:
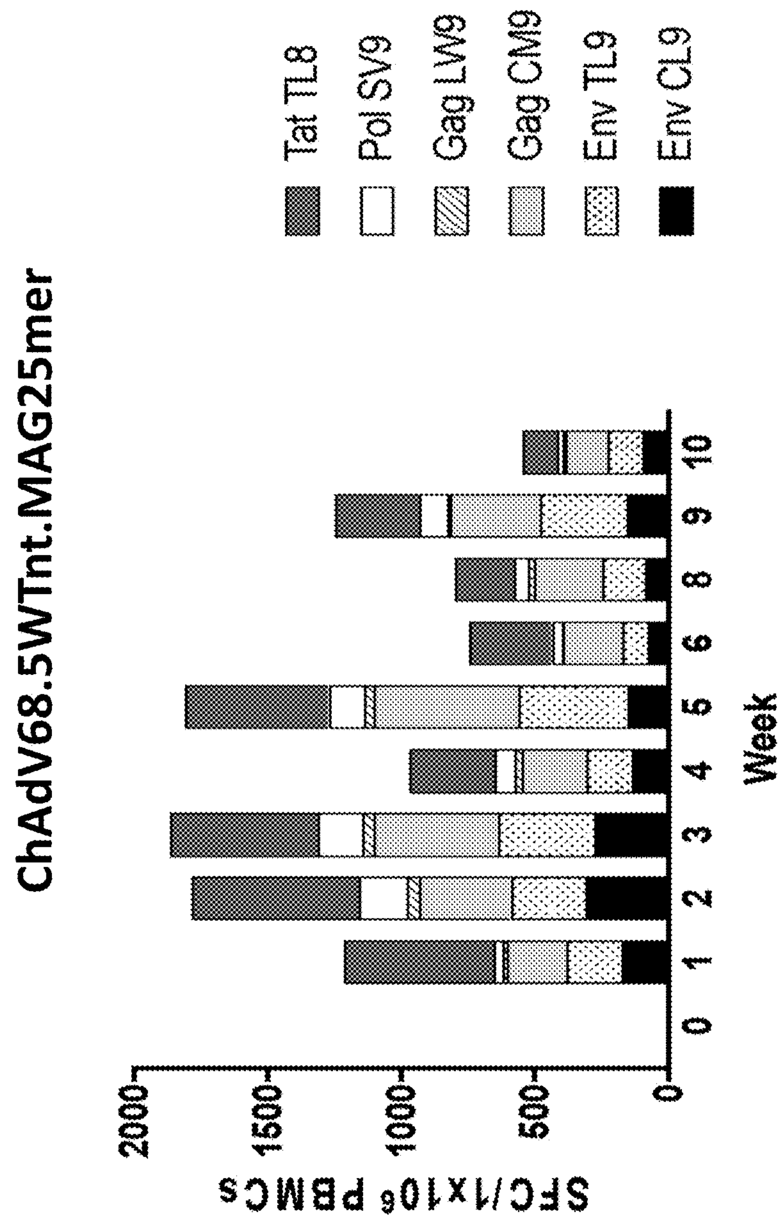
FIG. 20D illustrates antigen-specific cellular immune responses measured using ELISpot. Antigen-specific IFN-gamma production to six different mamu A01 restricted epitopes was measured in PBMCs for the ChAdV68.5WTnt.MAG25mer/VEE-MAG25mer srRNA heterologous prime/boost group using ELISpot 1, 2, 3, 4, 5, 6, 8, 9, or 10 weeks after the initial immunization (6 rhesus macaques per group). Results are presented as mean spot forming cells (SFC) per $10^6$ PBMCs for each epitope in a stacked bar graph format. Values for each animal were normalized to the levels at pre-bleed (week 0).

Combined antigen-specific immune responses were observed at all measurements with 1218, 1784, 1866, 973, 1813, 747, 797, 1249, and 547 SFCs per $10^6$ PBMCs (six epitopes combined) 1, 2, 3, 4, 5, 6, 8, 9, or 10 weeks after an initial ChAdV68.5WTnt.MAG25mer prime immunization, respectively (FIG. 20D). The immune response showed the expected profile with peak immune responses measured ~2-3 weeks after the prime immunization followed by a contraction in the immune response after 4 weeks. Combined antigen-specific cellular immune responses of 1813 SFCs per $10^6$ PBMCs (six epitopes combined) were measured 5 weeks after the initial immunization with ChAdV68.5WTnt.MAG25mer (i.e., 1 week after the first boost with VEE-MAG25mer srRNA). The immune response measured 1 week after the first boost with VEE-MAG25mer srRNA (week 5) was comparable to the peak immune response measured for the ChAdV68.5WTnt.MAG25mer prime immunization (week 3) (FIG. 20D). Combined antigen-specific cellular immune responses of 1249 SFCs per $10^6$ PBMCs (six epitopes combined) was measured 9 weeks after the initial immunization with ChAdV68.5WTnt.MAG25mer, respectively (i.e., 1 week after the second boost with VEE-MAG25mer srRNA). The immune responses measured 1 week after the second boost with VEE-MAG25mer srRNA (week 9) was ~2-fold higher than that measured just before the boost immunization (FIG. 20D).

TABLE 22

Mean spot forming cells (SFC) per $10^6$ PBMCs for each epitope ± SEM for VEE-MAG25mer srRNA-LNPl(30 μg) (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 39.7 ± 22.7 | 35.4 ± 25.1 | 3.2 ± 3.6 | 33 ± 28.1 | 30.9 ± 20.3 | 28.3 ± 17.5 |
| 3 | 2 ± 2.4 | 0.2 ± 1.8 | 1.8 ± 2.4 | 3.7 ± 1.9 | 1.7 ± 2.8 | 4.9 ± 2.3 |
| 4 | 1 ± 1.8 | 0.3 ± 1.2 | 5.5 ± 3.6 | 2.3 ± 2.2 | 5.7 ± 2.7 | 0.8 ± 0.8 |
| 5 | 0.5 ± 0.9 | 1.4 ± 3.8 | 3.1 ± 1.6 | 2.3 ± 2.7 | 1.9 ± 2 | 1.4 ± 1.2 |
| 6 | 1.9 ± 1.8 | −0.3 ± 3 | 1.7 ± 1.2 | 1.4 ± 1.4 | 0.8 ± 1.1 | 1.1 ± 1 |
| 8 | −0.4 ± 0.8 | −0.9 ± 2.9 | 0.5 ± 1.3 | 3 ± 1.1 | 2.2 ± 2.1 | 3.7 ± 2 |
| 9 | 1 ± 1.7 | 1.2 ± 4.2 | 7.2 ± 3.9 | 0.5 ± 0.7 | 1.6 ± 3 | 3 ± 1 |
| 10 | 3.8 ± 1.8 | 11 ± 5 | −1.1 ± 1.1 | 1.9 ± 0.9 | 1.3 ± 1.6 | 0.2 ± 0.5 |

TABLE 23

Mean spot forming cells (SFC) per $10^6$ PBMCs for each epitope ± SEM for VEE-MAG25mer srRNA-LNPl(100 μg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 7.9 ± 17.2 | 23.2 ± 17.4 | 11.4 ± 4.9 | 41.7 ± 16.5 | 15 ± 13.5 | 8.9 ± 6.2 |
| 3 | −3.1 ± 4.6 | −7.2 ± 6.5 | 2.3 ± 2.3 | −0.3 ± 2.7 | 2.7 ± 5.1 | 2.2 ± 1.4 |
| 4 | 1.9 ± 3.8 | −6.2 ± 7.6 | 10.5 ± 4.1 | 1.2 ± 2.9 | 5.6 ± 4.9 | 1.1 ± 0.8 |
| 5 | −2.6 ± 7 | −8 ± 5.9 | 1.5 ± 1.7 | 6.4 ± 2.3 | 0.7 ± 4.3 | 3.3 ± 1.3 |
| 6 | 6.3 ± 6.3 | 4.4 ± 8.3 | 6.6 ± 4.4 | 5.2 ± 5.2 | 3.9 ± 5 | 10.8 ± 6.9 |
| 8 | −3.6 ± 7.2 | −6.8 ± 7.3 | −0.8 ± 1.2 | 3.4 ± 4.2 | 6.4 ± 7.5 | 5.7 ± 2.7 |
| 9 | 8.1 ± 2.4 | 20.6 ± 23.4 | 18.9 ± 5.7 | 8.1 ± 8.9 | 9 ± 11.2 | 40 ± 17.6 |
| 10 | 3.1 ± 8 | −3.9 ± 8.5 | 3.3 ± 1.8 | 0.6 ± 2.9 | 7.4 ± 6.4 | 6.1 ± 2.5 |

TABLE 24

Mean spot forming cells (SFC) per $10^6$ PBMCs for each epitope ± SEM for VEE-MAG25mer srRNA-LNP2(100 μg) (Group 3)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | −5.9 ± 3.8 | −0.3 ± 0.5 | −0.5 ± 1.5 | −5.7 ± 6.1 | −1 ± 1.3 | −3.2 ± 5.5 |

TABLE 24-continued

| Mean spot forming cells (SFC) per $10^6$ PBMCs for each epitope ± SEM for VEE-MAG25mer srRNA-LNP2(100 µg) (Group 3) | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 3 | 0.7 ± 5.2 | 3.4 ± 2.4 | 4.2 ± 4.6 | 18.3 ± 15.5 | 11.9 ± 5.1 | −0.4 ± 8.2 |
| 4 | −3.8 ± 5.5 | 2.3 ± 1.8 | 11.3 ± 6.1 | −3.1 ± 5.6 | 8.5 ± 4 | −1.5 ± 6.1 |
| 5 | −3.7 ± 5.7 | −0.1 ± 0.7 | −0.2 ± 1.6 | 3.4 ± 8.5 | 3 ± 3.1 | −4.6 ± 5 |
| 6 | 12.3 ± 15 | 7.8 ± 4.9 | 24.7 ± 19.8 | 23.2 ± 22.5 | 18.7 ± 15.8 | 0.5 ± 6.2 |
| 8 | 5.9 ± 12.3 | −0.1 ± 0.7 | −0.5 ± 1.3 | 8.8 ± 14.4 | 8.7 ± 8 | −1.3 ± 4 |
| 9 | 16.1 ± 13.4 | 16.5 ± 4 | 22.9 ± 4.2 | 13 ± 13.2 | 16.4 ± 7.8 | 19.6 ± 9.2 |
| 10 | 29.9 ± 21.8 | 22 ± 19.5 | 0.5 ± 2.6 | 22.2 ± 22.6 | 35.3 ± 15.8 | 19.4 ± 17.3 |

TABLE 25

| Mean spot forming cells (SFC) per $10^6$ PBMCs for each epitope ± SEM for ChAdV68.5WTnt.MAG25mer prime | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 1 | 178 ± 68.7 | 206.5 ± 94.8 | 221.2 ± 120 | 15.4 ± 16.7 | 33.3 ± 25.9 | 563.5 ± 174.4 |
| 2 | 311.2 ± 165.5 | 278.8 ± 100.9 | 344.6 ± 110.8 | 46.3 ± 13.5 | 181.6 ± 76.8 | 621.4 ± 220.9 |
| 3 | 277.3 ± 101.1 | 359.6 ± 90.5 | 468.2 ± 106.6 | 41.7 ± 11.1 | 169.8 ± 57.8 | 549.4 ± 115.7 |
| 4 | 140 ± 46.5 | 169.6 ± 46.8 | 239.4 ± 37 | 26.5 ± 11.4 | 75 ± 31.6 | 322.2 ± 50.7 |
| 5 | 155.6 ± 62.1 | 406.7 ± 96.4 | 542.7 ± 143.3 | 35.1 ± 16.6 | 134.2 ± 53.7 | 538.5 ± 91.9 |
| 6 | 78.9 ± 42.5 | 95.5 ± 29.4 | 220.9 ± 75.3 | −1.4 ± 5.3 | 43.4 ± 19.6 | 308.1 ± 42.6 |
| 8 | 88.4 ± 30.4 | 162.1 ± 30.3 | 253.4 ± 78.6 | 21.4 ± 11.2 | 53.7 ± 22.3 | 217.8 ± 45.2 |
| 9 | 158.5 ± 69 | 322.3 ± 87.2 | 338.2 ± 137.1 | 5.6 ± 12.4 | 109.2 ± 17.9 | 314.8 ± 43.4 |
| 10 | 97.3 ± 32.5 | 133.2 ± 27 | 154.9 ± 59.2 | 10 ± 6 | 26 ± 16.7 | 125.5 ± 27.7 |

Results

Figure 21:
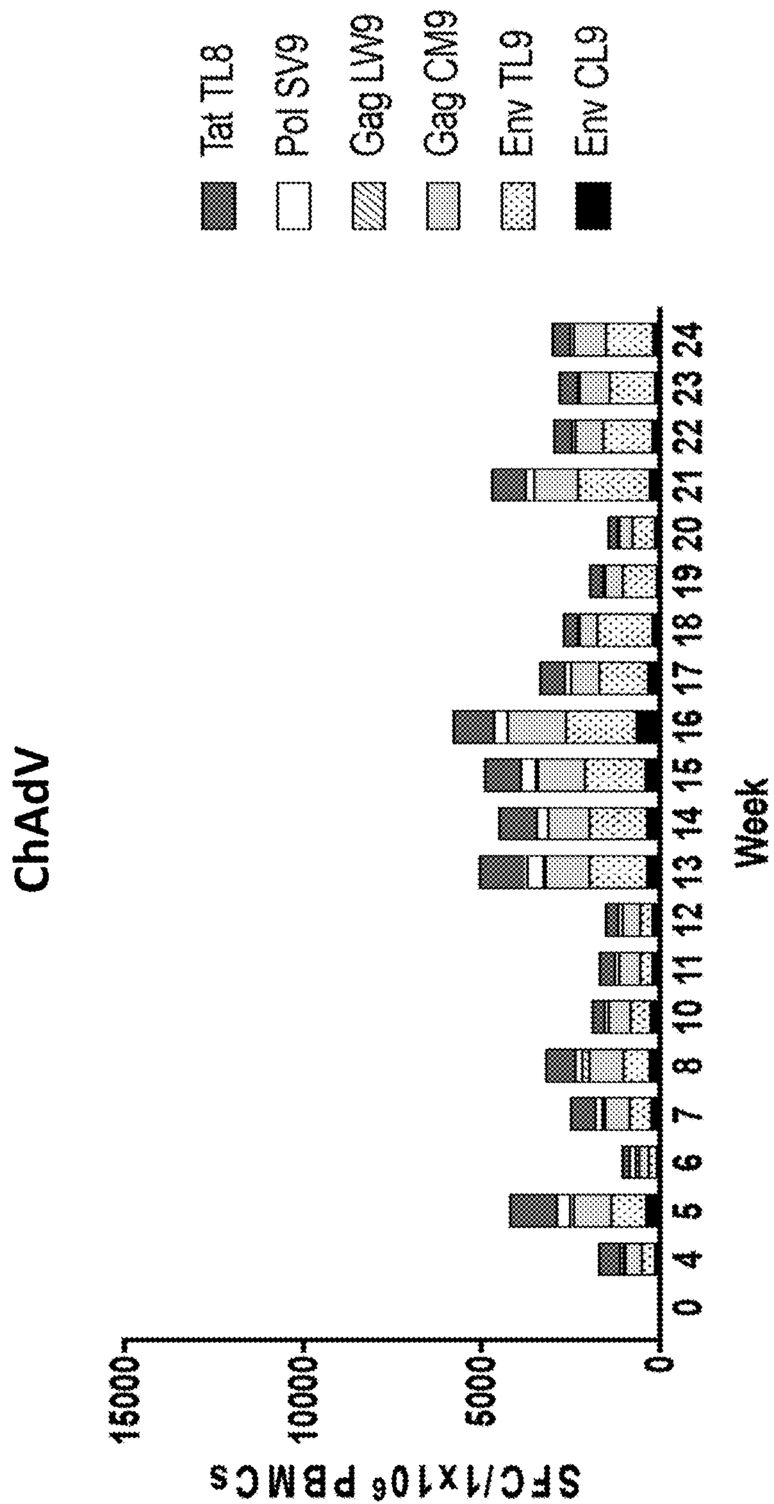
FIG. 21 shows antigen-specific cellular immune response measured using ELISpot. Antigen-specific IFN-gamma production to six different mamu A01 restricted epitopes was measured in PBMCs after immunization with the ChAdV68.5WTnt.MAG25mer/VEE-MAG25mer srRNA heterologous prime/boost regimen using ELISpot prior to immunization and 4, 5, 6, 7, 8, 10, 11, 12, 13, 14, 15, 16, 17, 18, 19, 20, 21, 22, 23 or 24 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were immunized with ChAdV68.5-WTnt.MAG25mer. Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, 15, 16, 17, 18, 19, 20, 21, 22, 23 or 24 weeks after the initial immunization (FIG. 21 and Table 27). Animals received boost immunizations with VEE-MAG25mer srRNA using the LNP2 formulation on weeks 4, 12, and 20. Combined antigen-specific immune responses of 1750, 4225, 1100, 2529, 3218, 1915, 1708, 1561, 5077, 4543, 4920, 5820, 3395, 2728, 1996, 1465, 4730, 2984, 2828, or 3043 SFCs per $10^6$ PBMCs (six epitopes combined) were measured 4, 5, 6, 7, 8, 10, 11, 12, 13, 14, 15, 16, 17, 18, 19, 20, 21, 22, 23 or 24 weeks after the initial immunization with ChAdV68.5WTnt.MAG25mer (FIG. 21). Immune responses measured 1 week after the second boost immunization (week 13) with VEE-MAG25mer srRNA were ~3-fold higher than that measured just before the boost immunization (week 12). Immune responses measured 1 week after the third boost immunization (week 21) with VEE-MAG25mer srRNA, were ~3-fold higher than that measured just before the boost immunization (week 20), similar to the response observed for the second boost.

Figure 22:
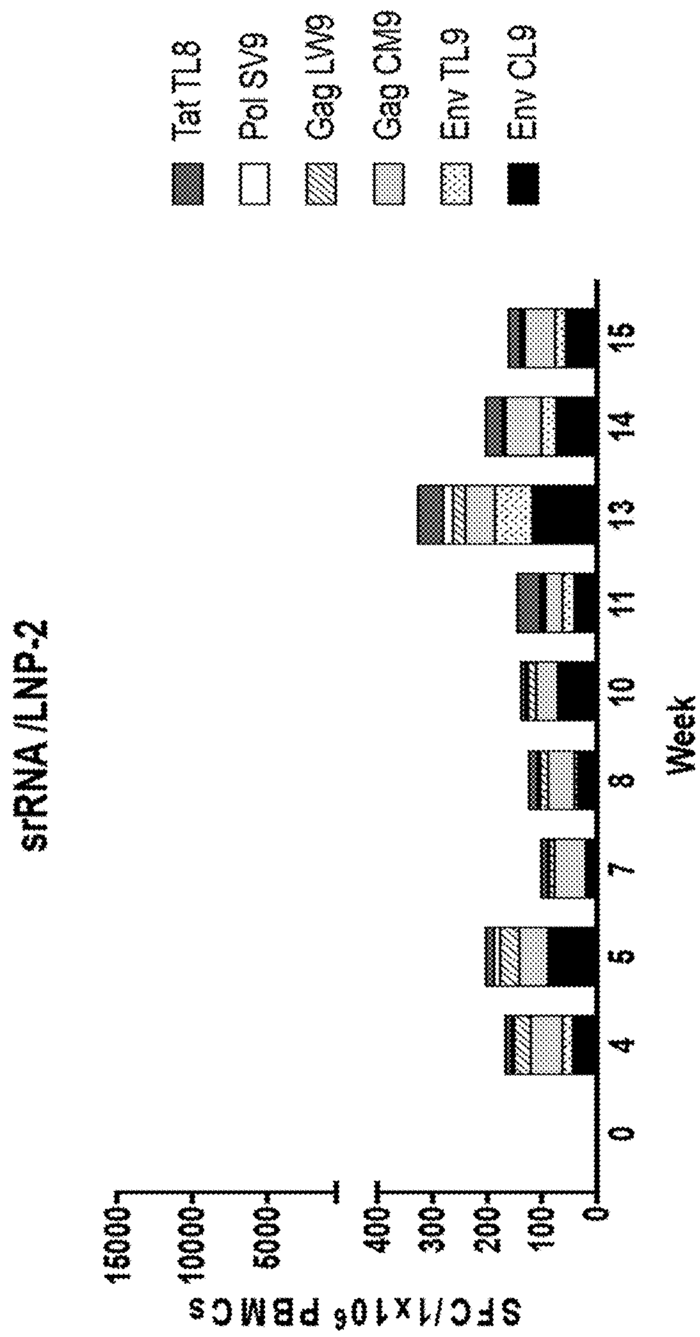
FIG. 22 shows antigen-specific cellular immune response measured using ELISpot. Antigen-specific IFN-gamma production to six different mamu A01 restricted epitopes was measured in PBMCs after immunization with the VEE-MAG25mer srRNA LNP2 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.
Figure 23:
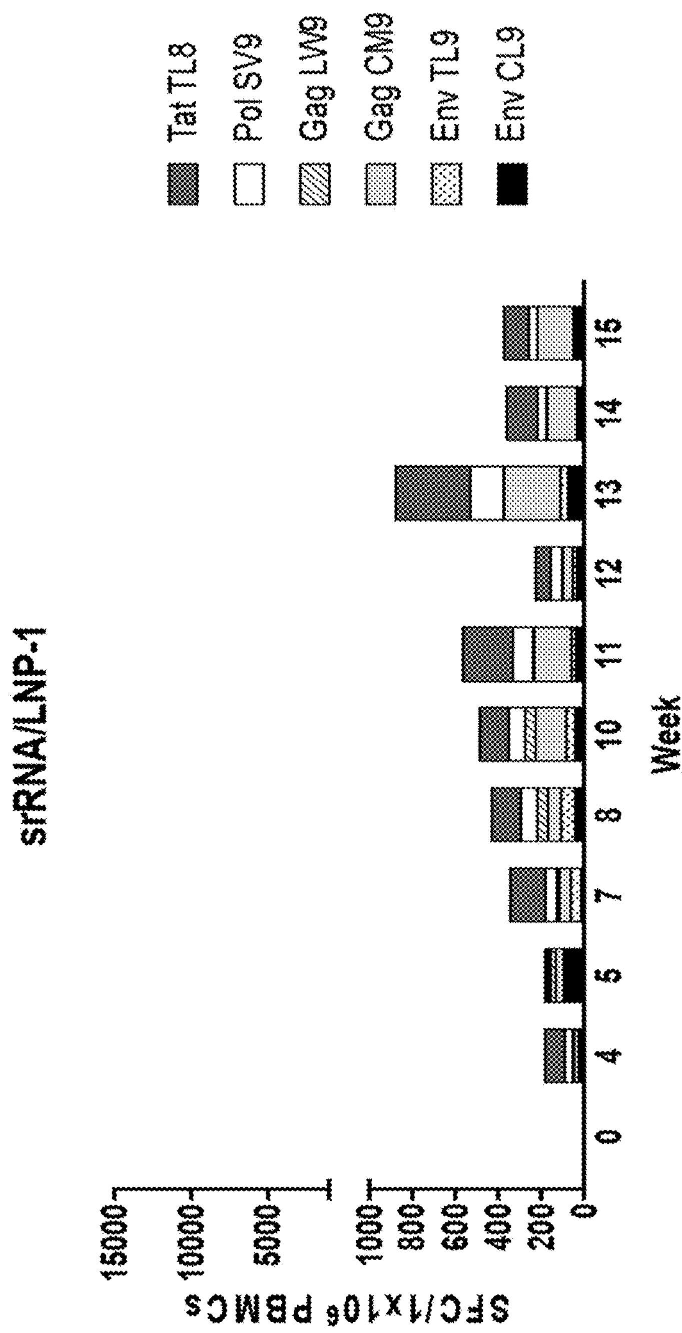
FIG. 23 shows antigen-specific cellular immune response measured using ELISpot. Antigen-specific IFN-gamma production to six different mamu A01 restricted epitopes was measured in PBMCs after immunization with the VEE-MAG25mer srRNA LNP1 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were also immunized with VEE-MAG25mer srRNA using two different LNP formulations (LNP1 and LNP2). Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, or 15 weeks after the initial immunization (FIGS. 22 and 23, Tables 28 and 29). Animals received boost immunizations with VEE-MAG25mer srRNA using the respective LNP1 or LNP2 formulation on weeks 4 and 12. Combined antigen-specific immune responses of 168, 204, 103, 126, 140, 145, 330, 203, and 162 SFCs per 106 PBMCs (six epitopes combined) were measured 4, 5, 7, 8, 10, 11, 13, 14, 15 weeks after the immunization with VEE-MAG25mer srRNA-LNP2 (FIG. 22). Combined antigen-specific immune responses of 189, 185, 349, 437, 492, 570, 233, 886, 369, and 381 SFCs per $10^6$ PBMCs (six epitopes combined) were measured 4, 5, 7, 8, 10, 11, 12, 13, 14, 15 weeks after the immunization with VEE-MAG25mer srRNA-LNP1 (FIG. 23).

TABLE 27

| Mean spot forming cells (SFC) per $10^6$ PBMCs for each epitope ± SEM for priming vaccination with ChAdV68.5WTnt.MAG25mer (Group 1) | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |

TABLE 27-continued

Mean spot forming cells (SFC) per $10^6$ PBMCs for each epitope ± SEM for priming vaccination with ChAdV68.5WTnt.MAG25mer (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 118.2 ± 68.1 | 473.3 ± 249.3 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |

TABLE 28

Mean spot forming cells (SFC) per $10^6$ PBMCs for each epitope ± SEM for priming vaccination with VEE-MAG25mer srRNA-LNP2 (300 μg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 4 | 46 ± 27.1 | 18.4 ± 6.8 | 58.3 ± 45.8 | 29.9 ± 20.8 | 4.9 ± 2.3 | 10.7 ± 4 |
| 5 | 85.4 ± 54 | 5.2 ± 5.8 | 52.4 ± 51.2 | 34.5 ± 35 | 11.8 ± 12.2 | 14.4 ± 7.9 |
| 7 | 18.6 ± 32.5 | 1.9 ± 1.7 | 59.4 ± 55.7 | 9.3 ± 10.7 | 3.3 ± 3 | 10.7 ± 6.1 |
| 8 | 36.6 ± 39.4 | 6.3 ± 3.9 | 48.7 ± 39.9 | 13.5 ± 8.8 | 3.8 ± 3.6 | 17.2 ± 9.7 |
| 10 | 69.1 ± 59.1 | 4.4 ± 1.9 | 39.3 ± 38 | 14.7 ± 10.8 | 4.4 ± 5.3 | 8.5 ± 5.3 |
| 11 | 43 ± 38.8 | 22.6 ± 21.1 | 30.2 ± 26.2 | 3.3 ± 2.2 | 5.8 ± 3.5 | 40.3 ± 25.5 |
| 13 | 120.4 ± 78.3 | 68.2 ± 43.9 | 54.2 ± 36.8 | 21.8 ± 7.4 | 17.7 ± 6.1 | 47.4 ± 27.3 |
| 14 | 76 ± 44.8 | 28 ± 19.5 | 65.9 ± 64.3 | −0.3 ± 1.3 | 2.5 ± 2 | 31.1 ± 26.5 |
| 15 | 58.9 ± 41.4 | 19.5 ± 15.1 | 55.4 ± 51 | 2.5 ± 2 | 5.5 ± 3.6 | 20.1 ± 15.7 |

TABLE 29

Mean spot forming cells (SFC) per $10^6$ PBMCs for each epitope ± SEM for priming vaccination with VEE-MAG25mer srRNA-LNP1 (300 μg) (Group 3)

| | Antigen | | | | | |
|---|---|---|---|---|---|---|
| Wk | Env CL9 | Env TL9 | Gag CM9 | Gag LW9 | Pol SV9 | Tat TL8 |
| 4 | 19.5 ± 8.7 | 13.3 ± 13.1 | 16.5 ± 15.3 | 10.5 ± 7.3 | 35.9 ± 24.8 | 92.9 ± 91.6 |
| 5 | 87.9 ± 43.9 | 12.7 ± 11.7 | 37.2 ± 31.9 | 21.1 ± 23.8 | 13.2 ± 13.7 | 12.6 ± 13.7 |
| 7 | 21.1 ± 13.3 | 48.8 ± 48.4 | 51.7 ± 39.5 | 9.1 ± 10.5 | 58.6 ± 55.8 | 159.4 ± 159 |
| 8 | 47.7 ± 21.7 | 66.4 ± 52.2 | 59.8 ± 57.4 | 49.4 ± 28 | 79.4 ± 63 | 133.8 ± 132.1 |
| 10 | 49 ± 30.2 | 42.2 ± 41.1 | 139.3 ± 139.3 | 51.6 ± 51.2 | 78.2 ± 75.8 | 131.7 ± 131.6 |
| 11 | 42 ± 26.8 | 20.9 ± 21.4 | 177.1 ± 162 | −6.3 ± 4.3 | 104.3 ± 104.1 | 231.5 ± 230.1 |
| 12 | 40.2 ± 19 | 20.3 ± 11.9 | 42.2 ± 46.7 | 3.7 ± 6.7 | 57 ± 44.7 | 70 ± 69.2 |
| 13 | 81.2 ± 48.9 | 38.2 ± 37.6 | 259.4 ± 222.2 | −4 ± 4.1 | 164.1 ± 159.3 | 347.3 ± 343.5 |
| 14 | 34.5 ± 31.8 | 5.3 ± 11.6 | 138.6 ± 137.3 | −4.7 ± 5.2 | 52.3 ± 52.9 | 142.6 ± 142.6 |
| 15 | 49 ± 24 | 6.7 ± 9.8 | 167.1 ± 163.8 | −6.4 ± 4.2 | 47.8 ± 42.3 | 116.6 ± 114.5 |

srRNA Dose Ranging Study

In one implementation of the present invention, an srRNA dose ranging study can be conducted in Mamu A01 Indian rhesus macaques to identify which srRNA dose to progress to NHP immunogenicity studies. In one example, Mamu A01 Indian rhesus macaques can be administered with an srRNA vector encoding model antigens that includes multiple Mamu A01 restricted epitopes by IM injection. In another example, an anti-CTLA-4 monoclonal antibody can be administered SC proximal to the site of IM vaccine injection to target the vaccine draining lymph node in one group of animals. PBMCs can be collected every 2 weeks after the initial vaccination for immune monitoring. The study arms are described in below (Table 30).

TABLE 30

| Non-GLP RNA dose ranging study in Indian Rhesus Macaques | | | |
|---|---|---|---|
| Group | Prime | Boost 1 | Boost 2 |
| 1 | srRNA-LNP (Low Dose) | srRNA-LNP (Low Dose) | srRNA-LNP (Low Dose) |
| 2 | srRNA-LNP (Mid Dose) | srRNA-LNP (Mid Dose) | srRNA-LNP (Mid Dose) |
| 3 | srRNA-LNP (High Dose) | srRNA-LNP (High Dose) | srRNA-LNP (High Dose) |
| 4 | srRNA-LNP (High Dose) + anti-CTLA-4 | srRNA-LNP (High Dose) + anti-CTLA-4 | srRNA-LNP (High Dose) + anti-CTLA-4 |

* Dose range of srRNA to be determined with the high dose ≤300 □g.

Immunogenicity Study in Indian Rhesus Macaques

Figure 34:
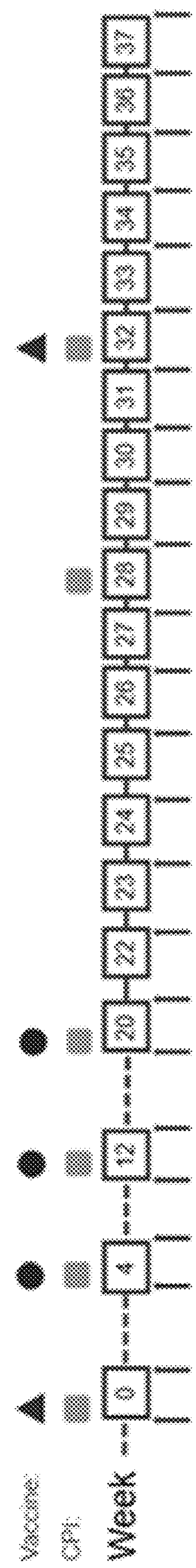
FIG. 34 illustrates the vaccination strategy used to evaluate immunogenicity of the antigen-cassette containing vectors in rhesus macaques. Triangles indicate ChAdV68 vaccination (1e12 vp/animal) at weeks 0 & 32. Circles represent alphavirus vaccination at weeks 0, 4, 12, 20, 28 & 32. Squares represent administration of an anti-CTLA4 antibody.

Vaccine studies were conducted in Mamu A01 Indian rhesus macaques (NHPs) to demonstrate immunogenicity using the antigen vectors. FIG. 34 illustrates the vaccination strategy. Three groups of NHPs were immunized with ChAdV68.5-WTnt.MAG25mer and either with the checkpoint inhibitor anti-CTLA-4 antibody Ipilimumab (Groups 5 & 6) or without the checkpoint inhibitor (Group 4). The antibody was administered either intra-venously (group 5) or subcutaneously (group 6). Triangles indicate ChAdV68 vaccination (1e12 vp/animal) at weeks 0 & 32. Circles represent alphavirus vaccination at weeks 0, 4, 12, 20, 28 and 32.

Figure 35:
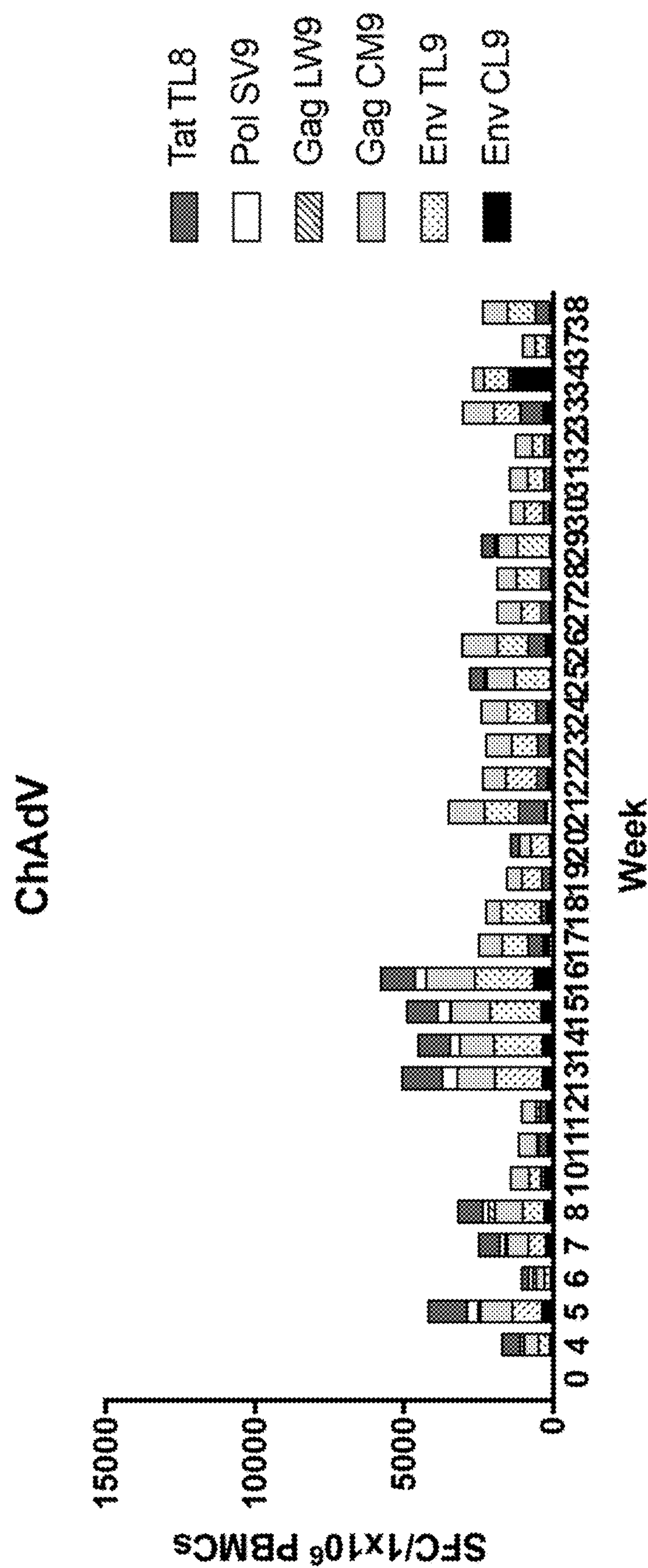
FIG. 35 shows a time course of CD8+ anti-epitope responses in Rhesus Macaques dosed with chAd-MAG alone (Group 4). Mean SFC/1e6 splenocytes is shown.
Figure 36:
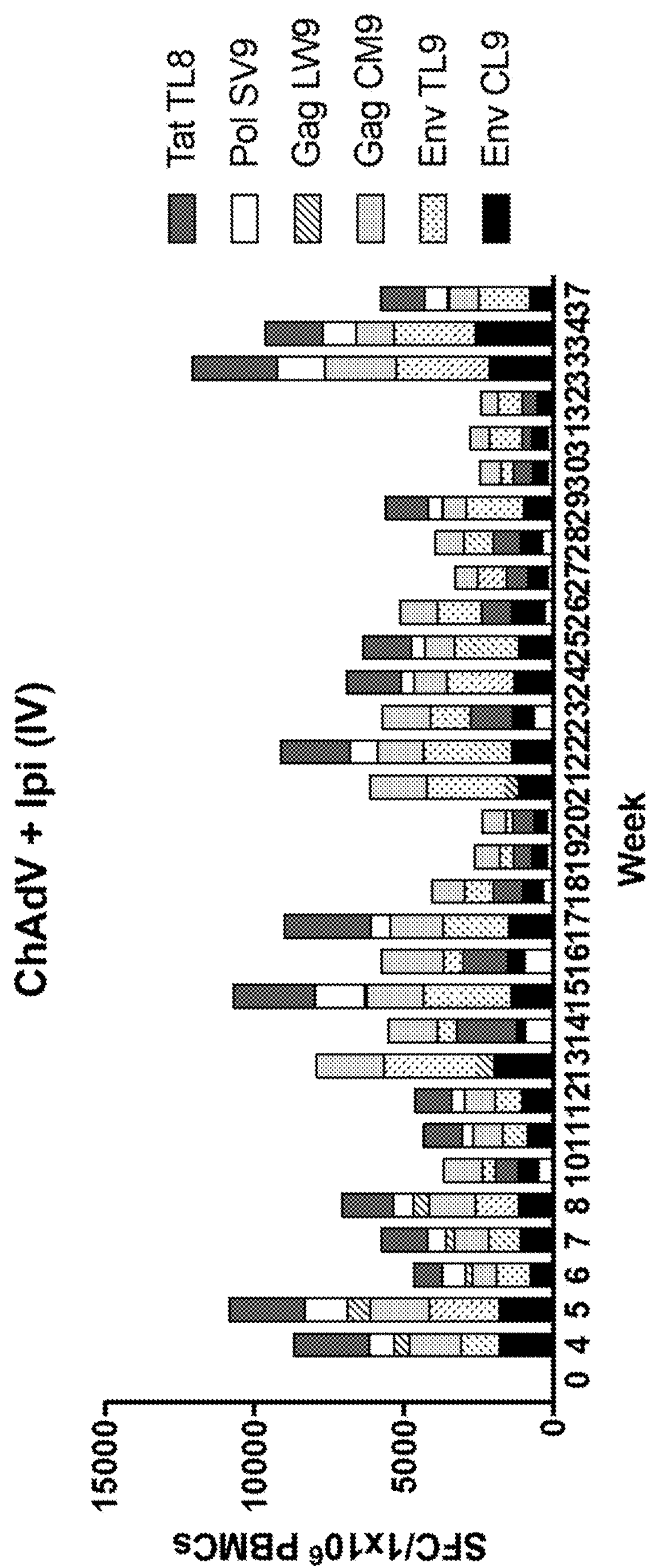
FIG. 36 shows a time course of CD8+ anti-epitope responses in Rhesus Macaques dosed with chAd-MAG plus anti-CTLA4 antibody (Ipilimumab) delivered IV (Group 5). Mean SFC/1e6 splenocytes is shown.
Figure 37:
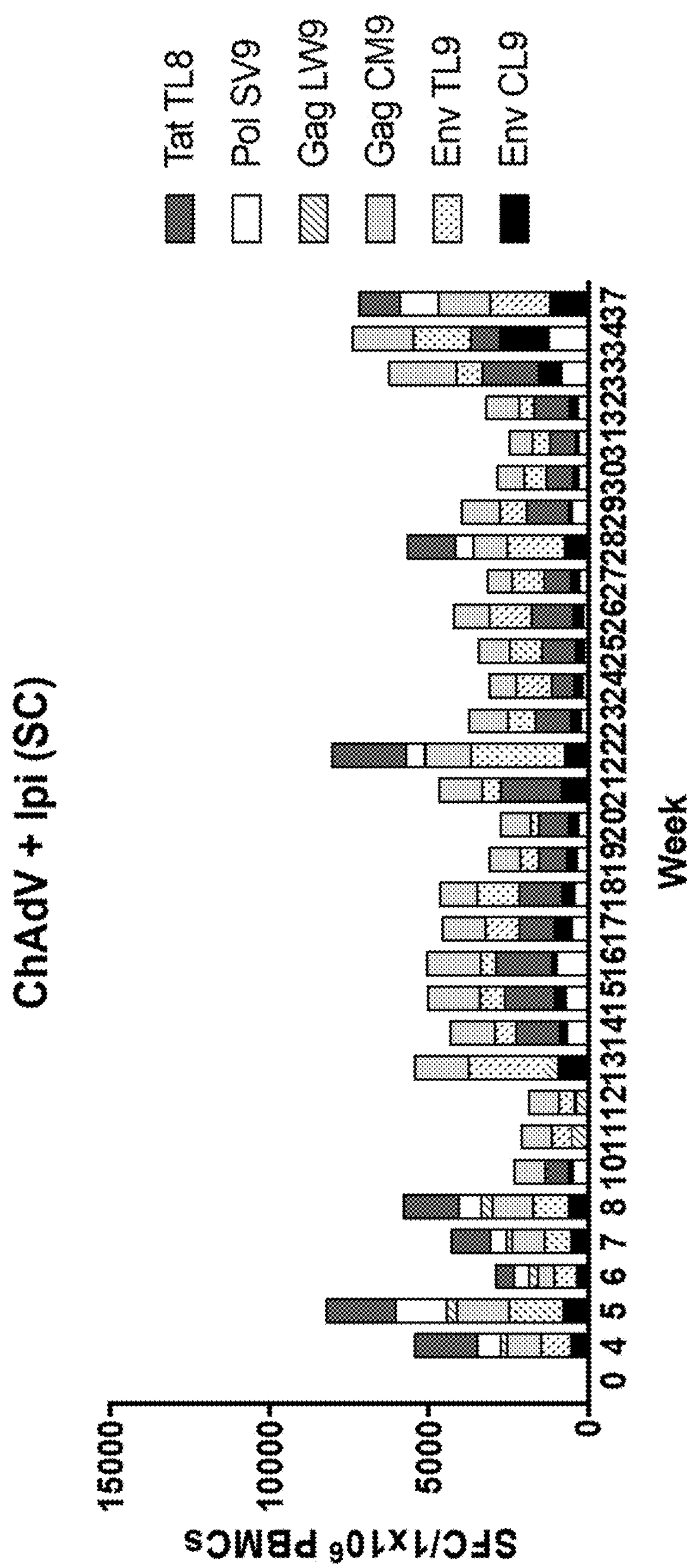
FIG. 37 shows a time course of CD8+ anti-epitope responses in Rhesus Macaques dosed with chAd-MAG plus anti-CTLA4 antibody (Ipilimumab) delivered SC (Group 6). Mean SFC/1e6 splenocytes is shown.

The time course of CD8+anti-epitope responses in the immunized NHPs are presented for ChAdV-MAG immunization alone (FIG. 35 and Table 31A), ChAdV-MAG immunization with the checkpoint inhibitor delivered IV (FIG. 36 and Table 31B), and ChAdV-MAG immunization with the checkpoint inhibitor delivered SC (FIG. 37 and Table 31C). The results demonstrate ChAdV68 vectors efficiently primed CD8+ responses in primates, alphavirus vectors efficiently boosted the ChAdV68 vaccine priming response, checkpoint inhibitor whether delivered IV or SC amplified both priming and boosting responses, and ChAdV vectors readministered post vaccination to effectively boosted the immune responses.

TABLE 31A

CD8+ anti-epitope responses in Rhesus Macaques dosed with chAd-MAG (Group 4). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 118.2 ± 68.1 | 473.3 ± 249.3 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |
| 25 | 136.4 ± 52.6 | 1207.1 ± 501.6 | 924 ± 358.5 | 6.2 ± 10.5 | 74.1 ± 34.4 | 484.6 ± 116.7 |
| 26 | 278.2 ± 114.4 | 1645 ± 661.7 | 1170.2 ± 469.9 | −2.9 ± 5.7 | 80.6 ± 55.8 | 784.4 ± 214.1 |
| 27 | 159 ± 56.8 | 961.7 ± 547.1 | 783.6 ± 366.4 | −5 ± 4.3 | 63.6 ± 27.5 | 402.9 ± 123.4 |
| 28 | 189.6 ± 75.7 | 1073.1 ± 508.8 | 668.3 ± 312.5 | −5.7 ± 4.1 | 80.3 ± 38.3 | 386.4 ± 122 |
| 29 | 155.3 ± 69.1 | 1102.9 ± 606.1 | 632.9 ± 235 | 34.5 ± 24.2 | 80 ± 35.5 | 422.5 ± 122.9 |
| 30 | 160.2 ± 59.9 | 859 ± 440.9 | 455 ± 209.1 | −3 ± 5.3 | 60.5 ± 28.4 | 302.7 ± 123.2 |
| 31 | 122.2 ± 49.7 | 771.1 ± 392.7 | 582.2 ± 233.5 | −5.7 ± 4.1 | 55.1 ± 27.3 | 295.2 ± 68.3 |
| 32 | 119.3 ± 28.3 | 619.4 ± 189.7 | 566 ± 222.1 | −3.7 ± 5.1 | 21.9 ± 4.5 | 320.5 ± 76.4 |
| 33 | 380.5 ± 122 | 1636.1 ± 391.4 | 1056.2 ± 205.7 | −5.7 ± 4.1 | 154.5 ± 38.5 | 988.4 ± 287.7 |
| 34 | 1410.8 ± 505.4 | 972.4 ± 301.5 | 319.6 ± 89.6 | −4.8 ± 4.2 | 141.1 ± 49.8 | 1375.5 ± 296.7 |
| 37 | 130.8 ± 29.2 | 500 ± 156.9 | 424.9 ± 148.9 | −3.5 ± 4.7 | 77.7 ± 24.6 | 207.1 ± 42.4 |
| 38 | 167.7 ± 54.8 | 1390.8 ± 504.7 | 830.4 ± 329.1 | −5.5 ± 4.1 | 111.8 ± 43.2 | 516 ± 121.7 |

TABLE 31B

CD8+ anti-epitope responses in Rhesus Macaques dosed with ChAdV-MAG plus anti-CTLA4 antibody (Ipilimumab) delivered IV (Group 5). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 4 | 1848.1 ± 432.2 | 1295.7 ± 479.7 | 1709.8 ± 416.9 | 513.7 ± 219.8 | 838.5 ± 221.1 | 2514.6 ± 246.5 |
| 5 | 1844.1 ± 410.2 | 2367.5 ± 334.4 | 1983.1 ± 370.7 | 732.1 ± 249.4 | 1429.7 ± 275.3 | 2517.7 ± 286.5 |
| 6 | 822.4 ± 216.7 | 1131.2 ± 194.7 | 796.8 ± 185.8 | 226.8 ± 70 | 802.2 ± 101.4 | 913.5 ± 222.7 |
| 7 | 1147.2 ± 332.9 | 1066 ± 311.2 | 1149.8 ± 467.3 | 267.4 ± 162.6 | 621.5 ± 283.2 | 1552.2 ± 395.1 |
| 8 | 1192.7 ± 188.8 | 1461.5 ± 237.7 | 1566.9 ± 310.5 | 522.5 ± 118.6 | 662.3 ± 142.4 | 1706 ± 216.7 |
| 10 | 1249 ± 220.3 | 1170.6 ± 227.7 | 1297.3 ± 264.7 | −0.3 ± 4.4 | 551.8 ± 90.5 | 1425.3 ± 142.6 |
| 11 | 934.2 ± 221.7 | 808 ± 191.3 | 1003.1 ± 293.4 | 1.9 ± 4.3 | 364.2 ± 76.6 | 1270.8 ± 191.6 |
| 12 | 1106.2 ± 216.6 | 896.7 ± 190.7 | 1020.1 ± 243.3 | 1.3 ± 3.9 | 436.6 ± 90 | 1222 ± 155.4 |
| 13 | 2023.8 ± 556.3 | 3696.7 ± 1.7 | 2248.5 ± 436.4 | −4.5 ± 3.5 | 2614 ± 406.1 | 3700 ± 0 |
| 14 | 1278.7 ± 240 | 2639.5 ± 387 | 1654.6 ± 381.1 | −6 ± 2.1 | 988.8 ± 197.9 | 2288.3 ± 298.7 |
| 15 | 1458.9 ± 281.8 | 2932.5 ± 488.7 | 1893.4 ± 499 | 74.6 ± 15.6 | 1657.8 ± 508.9 | 2709.1 ± 428.7 |
| 16 | 1556.8 ± 243 | 2143.8 ± 295.2 | 2082.8 ± 234.2 | −5.8 ± 2.5 | 1014.6 ± 161.4 | 2063.7 ± 86.7 |
| 17 | 1527 ± 495.1 | 2213 ± 677.1 | 1767.7 ± 391.8 | 15.1 ± 5.9 | 633.8 ± 133.9 | 2890.8 ± 433.9 |
| 18 | 1068.2 ± 279.9 | 1940.9 ± 204.1 | 1114.1 ± 216.1 | −5.8 ± 2.5 | 396.6 ± 77.6 | 1659.4 ± 171.7 |
| 19 | 760.7 ± 362.2 | 1099.5 ± 438.4 | 802.7 ± 192.5 | −2.4 ± 3.3 | 262.2 ± 62.2 | 1118.6 ± 224.2 |
| 20 | 696.3 ± 138.2 | 954.9 ± 198 | 765.1 ± 248.4 | −1.4 ± 4.4 | 279.6 ± 89.3 | 1139 ± 204.5 |
| 21 | 1201.4 ± 327.9 | 3096 ± 1.9 | 1901 ± 412.1 | −5.8 ± 2.5 | 1676.3 ± 311.5 | 2809.3 ± 195.8 |
| 22 | 1442.5 ± 508.3 | 2944.7 ± 438.6 | 1528.4 ± 349.6 | 2.8 ± 5.1 | 940.7 ± 160.5 | 2306.3 ± 218.6 |
| 23 | 1400.4 ± 502.2 | 2757.1 ± 452.9 | 1604.2 ± 450.1 | −5.1 ± 2.3 | 708.1 ± 162.6 | 2100.4 ± 362.9 |
| 24 | 1351 ± 585.1 | 2264.5 ± 496 | 1080.6 ± 253.8 | 0.3 ± 6.5 | 444.2 ± 126.4 | 1823.7 ± 306.5 |
| 25 | 1211.5 ± 505.2 | 2160.4 ± 581.8 | 970.8 ± 235.9 | 2.5 ± 3.8 | 450.4 ± 126.9 | 1626.2 ± 261.3 |
| 26 | 1443 ± 492.5 | 2485 ± 588 | 1252.5 ± 326.4 | −0.2 ± 6 | 360.2 ± 92.3 | 2081.9 ± 331.1 |
| 27 | 896.2 ± 413.3 | 1686 ± 559.5 | 751 ± 192.1 | −3.7 ± 2.5 | 247.4 ± 82.8 | 1364.1 ± 232 |
| 28 | 1147.8 ± 456.9 | 1912.1 ± 417.1 | 930.3 ± 211.4 | −5.8 ± 2.5 | 423.9 ± 79.6 | 1649.3 ± 315 |
| 29 | 1038.5 ± 431.9 | 1915.2 ± 626.1 | 786.8 ± 205.9 | 23.5 ± 8.3 | 462.8 ± 64 | 1441.5 ± 249.7 |
| 30 | 730.5 ± 259.3 | 1078.6 ± 211.5 | 699.1 ± 156.2 | −4.4 ± 2.7 | 234.4 ± 43.9 | 1160.6 ± 112.6 |
| 31 | 750.4 ± 328.3 | 1431 ± 549.9 | 650.6 ± 141.1 | −5.2 ± 3 | 243.4 ± 56.4 | 868.9 ± 142.8 |
| 32 | 581.4 ± 227.7 | 1326.6 ± 505.2 | 573.3 ± 138 | −3.2 ± 4.2 | 160.8 ± 49.2 | 936.4 ± 110.4 |
| 33 | 2198.4 ± 403.8 | 3093.4 ± 123.3 | 2391.8 ± 378.4 | 7.1 ± 8.5 | 1598.1 ± 343.1 | 2827.5 ± 289.5 |
| 34 | 2654.3 ± 337 | 2709.9 ± 204.3 | 1297.5 ± 291.4 | 0.4 ± 4.2 | 1091.8 ± 242.9 | 1924 ± 245.7 |
| 37 | 846.8 ± 301.7 | 1706.9 ± 196 | 973.6 ± 149.3 | 50.5 ± 45.2 | 777.3 ± 140.2 | 1478.8 ± 94.3 |

TABLE 31C

CD8+ anti-epitope responses in Rhesus Macaques dosed with chAd-MAG plus anti-CTLA4 antibody (Ipilimumab) delivered SC (Group 6). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 4 | 598.3 ± 157.4 | 923.7 ± 306.8 | 1075.6 ± 171.8 | 180.5 ± 74.1 | 752.3 ± 245.8 | 1955.3 ± 444.4 |
| 5 | 842.2 ± 188.5 | 1703.7 ± 514.2 | 1595.8 ± 348.4 | 352.7 ± 92.3 | 1598.9 ± 416.8 | 2163.7 ± 522.1 |
| 6 | 396.4 ± 45.3 | 728.3 ± 232.7 | 503.8 ± 151.9 | 282 ± 69 | 463.1 ± 135.7 | 555.2 ± 191.5 |
| 7 | 584.2 ± 177 | 838.3 ± 254.9 | 1013.9 ± 349.4 | 173.6 ± 64.3 | 507.4 ± 165.7 | 1222.8 ± 368 |
| 8 | 642.9 ± 134 | 1128.6 ± 240.6 | 1259.1 ± 163.8 | 366.1 ± 72.8 | 726.7 ± 220.9 | 1695.6 ± 359.4 |
| 10 | 660.4 ± 211.4 | 746.9 ± 222.7 | 944.8 ± 210.2 | −1.2 ± 1.9 | 523.4 ± 230.7 | 787.3 ± 308.3 |
| 11 | 571.2 ± 162 | 609.4 ± 194.3 | 937.9 ± 186.5 | −8.9 ± 2.3 | 511.6 ± 229.6 | 1033.3 ± 315.7 |
| 12 | 485.3 ± 123.7 | 489.4 ± 142.7 | 919.3 ± 214.1 | −8.9 ± 2.3 | 341.6 ± 139.4 | 1394.7 ± 432.1 |
| 13 | 986.9 ± 154.5 | 2811.9 ± 411.3 | 1687.7 ± 344.3 | −4.1 ± 5.1 | 1368.5 ± 294.2 | 2751 ± 501.9 |
| 14 | 945.9 ± 251.4 | 2027.7 ± 492.8 | 1386.7 ± 326.7 | −5.7 ± 2.8 | 708.9 ± 277.1 | 1588.2 ± 440.1 |
| 15 | 1075.2 ± 322.4 | 2386 ± 580.7 | 1606.3 ± 368.1 | −5.4 ± 3.2 | 763.3 ± 248.8 | 1896.5 ± 507.8 |
| 16 | 1171.8 ± 341.6 | 2255.1 ± 439.6 | 1672.2 ± 342.3 | −7.8 ± 2.4 | 1031.6 ± 228.8 | 1896.4 ± 419.9 |
| 17 | 1118.2 ± 415.4 | 2156.3 ± 476 | 1345.3 ± 377.7 | −1.1 ± 6.7 | 573.7 ± 118.8 | 1614.4 ± 382.3 |
| 18 | 861.3 ± 313.8 | 2668.2 ± 366.8 | 1157.2 ± 259.6 | −8.9 ± 2.3 | 481.2 ± 164 | 1725.8 ± 511.4 |
| 19 | 719.2 ± 294.2 | 1447.2 ± 285 | 968 ± 294.5 | −2.2 ± 4.6 | 395.6 ± 106.1 | 1199.6 ± 289.2 |
| 20 | 651.6 ± 184 | 1189.8 ± 242.8 | 947.4 ± 249.8 | −8.9 ± 2.3 | 355 ± 106.3 | 1234.7 ± 361.7 |
| 21 | 810.3 ± 301.9 | 2576.2 ± 283.7 | 1334 ± 363.1 | −8.9 ± 2.3 | 892.2 ± 305 | 1904.4 ± 448.1 |
| 22 | 775 ± 196.4 | 2949 ± 409.7 | 1421.8 ± 309.7 | 38 ± 27.8 | 577 ± 144.2 | 2330.6 ± 572.3 |
| 23 | 584.9 ± 240.2 | 1977.9 ± 361.4 | 1209.8 ± 405.1 | −7.3 ± 3.2 | 273.7 ± 93.3 | 1430.6 ± 363.9 |
| 24 | 485.4 ± 194.4 | 1819.8 ± 325.5 | 837.2 ± 261.4 | −3.4 ± 4.1 | 234.4 ± 71.1 | 943.9 ± 243.3 |
| 25 | 452.3 ± 175 | 2072 ± 405.7 | 957.1 ± 293.1 | −8.9 ± 2.3 | 163 ± 43.2 | 1341.2 ± 394.7 |
| 26 | 517.9 ± 179.1 | 2616 ± 567.5 | 1126.6 ± 289 | −8.3 ± 2.3 | 199.9 ± 89.2 | 1615.7 ± 385.6 |
| 27 | 592.8 ± 171.7 | 1838.3 ± 372.4 | 749.3 ± 170.4 | −7.3 ± 2.5 | 325.5 ± 98.7 | 1110.7 ± 308.8 |
| 28 | 793 ± 228.5 | 1795.4 ± 332.3 | 1068.7 ± 210.3 | 2.5 ± 4.1 | 553.1 ± 144.3 | 1480.8 ± 357.1 |
| 29 | 661.8 ± 199.9 | 2140.6 ± 599.3 | 1202.7 ± 292.2 | −8.7 ± 2.8 | 558.9 ± 279.2 | 1424.2 ± 408.6 |
| 30 | 529.1 ± 163.3 | 1528.2 ± 249.8 | 840.5 ± 218.3 | −8.9 ± 2.3 | 357.7 ± 149.4 | 1029.3 ± 335 |
| 31 | 464.8 ± 152.9 | 1332.2 ± 322.7 | 726.3 ± 194.3 | −8.9 ± 2.3 | 354.3 ± 158.6 | 884.4 ± 282 |
| 32 | 612.9 ± 175.3 | 1584.2 ± 390.2 | 1058.3 ± 219.8 | −8.7 ± 2.8 | 364.6 ± 149.8 | 1388.8 ± 467.3 |

TABLE 31C-continued

CD8+ anti-epitope responses in Rhesus Macaques dosed with chAd-MAG plus anti-CTLA4 antibody (Ipilimumab) delivered SC (Group 6). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 33 | 1600.2 ± 416.7 | 2597.4 ± 367.9 | 2086.4 ± 414.8 | −6.3 ± 3.3 | 893.8 ± 266 | 2490.6 ± 416.4 |
| 34 | 2814.6 ± 376.2 | 2713.6 ± 380.8 | 1888.8 ± 499.4 | −7.5 ± 3.1 | 1288.9 ± 438.9 | 2428.1 ± 458.9 |
| 37 | 1245.9 ± 471.7 | 1877.7 ± 291.2 | 1606.6 ± 441.9 | 14.2 ± 13 | 1227.5 ± 348.1 | 1260.7 ± 342 |

Memory Phenotyping in Indian Rhesus Macaques

Figure 38:
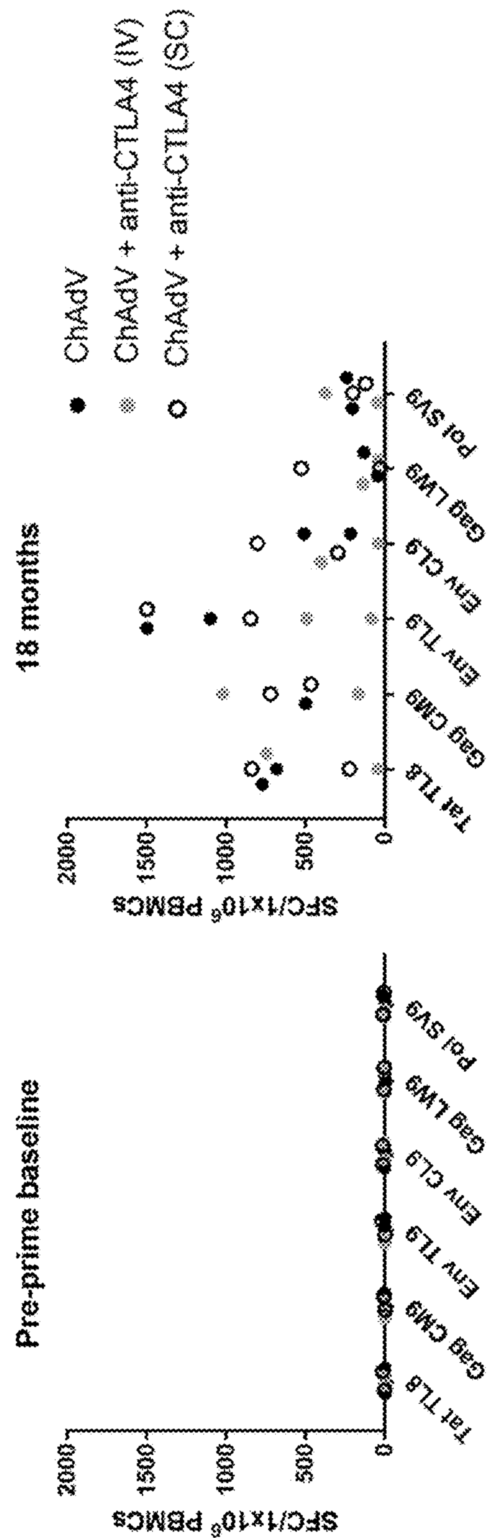
FIG. 38 shows antigen-specific memory responses generated by ChAdV68/samRNA vaccine protocol measured by ELISpot. Results are presented as individual dot plots, with each dot representing a single animal. Pre-immunization baseline (left panel) and memory response at 18 months post-prime (right panel) are shown.

Rhesus macaque were immunized with ChAdV68.5WTnt.MAG25mer/VEE-MAG25mer srRNA heterologous prime/boost regimen with or without anti-CTLA4, and boosted again with ChAdV68.5WTnt.MAG25mer. Groups were assessed 11 months after the final ChAdV68 administration (study month 18). by ELISpot was performed as described. FIG. 38 and Table 38 shows cellular responses to six different Mamu-A*01 restricted epitopes as measured by ELISpot both pre-immunization (left panel) and after 18 months (right panel). The detection of responses to the restricted epitopes demonstrates antigen-specific memory responses were generated by ChAdV68/samRNA vaccine protocol.

Figure 39:
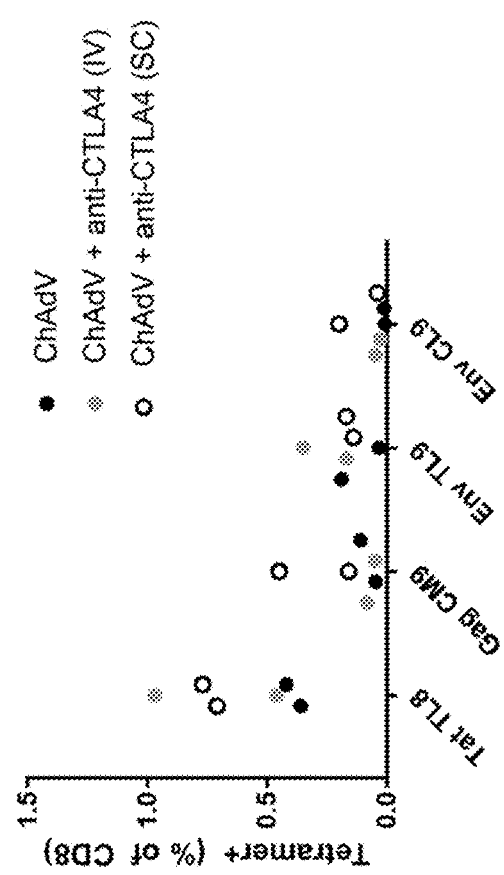
FIG. 39 shows memory cell phenotyping of antigen-specific CD8+ T-cells by flow cytometry using combinatorial tetramer staining and CD45RA/CCR7 co-staining.
Figure 40:
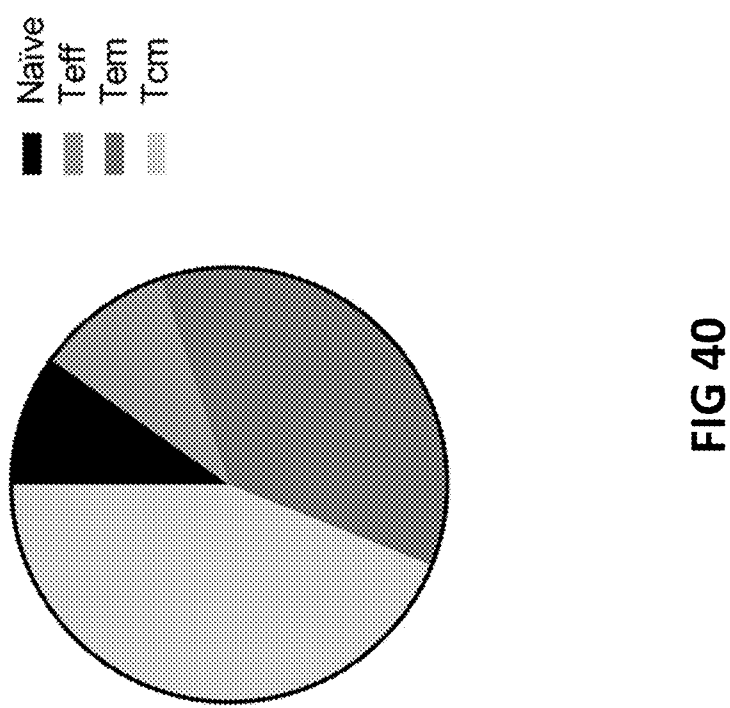
FIG. 40 shows the distribution of memory cell types within the sum of the four Mamu-A*01 tetramer+ CD8+ T-cell populations at study month 18. Memory cells were characterized as follows: CD45RA+CCR7+=naïve, CD45RA+CCR7-=effector (Teff), CD45RA-CCR7+=central memory (Tcm), CD45RA−CCR7−=effector memory (Tem).

To assess memory, CD8+ T-cells recognizing 4 different rhesus macaque Mamu-A*01 class I epitopes encoded in the vaccines were monitored using dual-color Mamu-A*01 tetramer labeling, with each antigen being represented by a unique double positive combination, and allowed the identification of all 4 antigen-specific populations within a single sample. Memory cell phenotyping was performed by co-staining with the cell surface markers CD45RA and CCR7. FIG. 39 and Table 39 shows the results of the combinatorial tetramer staining and CD45RA/CCR7 co-staining for memory T-cells recognizing four different Mamu-A*01 restricted epitopes. The T cell phenotypes were also assessed by flow cytometry. FIG. 40 shows the distribution of memory cell types within the sum of the four Mamu-A*01 tetramer+ CD8+ T-cell populations at study month 18. Memory cells were characterized as follows: CD45RA+ CCR7+=naïve, CD45RA+CCR7-=effector (Teff), CD45RA-CCR7+=central memory (Tcm), CD45RA-CCR7-=effector memory (Tem). Collectively, the results demonstrate that memory responses were detected at least one year following the last boost indicating long lasting immunity, including effector, central memory, and effector memory populations.

TABLE 38

Mean spot forming cells (SFC) per $10^6$ PBMCs for each animal at both pre-prime and memory assessment time points (18 months).

| | Pre-prime baseline | | | | | | 18 months | | | | | |
|---|---|---|---|---|---|---|---|---|---|---|---|---|
| Animal | Tat TL8 | Gag CM9 | Env TL9 | Env CL9 | Gag LW9 | Pol SV9 | Tat TL8 | Gag CM9 | Env TL9 | Env CL9 | Gag LW9 | Pol SV9 |
| 1 | 1.7 | 0.0 | 0.0 | 5.0 | 0.0 | 13.7 | 683.0 | 499.2 | 1100.3 | 217.5 | 47.7 | 205.3 |
| 2 | 0.0 | 0.0 | 0.0 | 0.2 | 0.1 | 0.0 | 773.4 | ND | 1500.0 | 509.3 | 134.5 | 242.5 |
| 3 | 0.0 | 0.0 | 6.7 | 6.8 | 10.2 | 3.3 | 746.3 | 167.5 | 494.1 | 402.8 | 140.6 | 376.0 |
| 4 | 0.0 | 0.0 | 0.0 | 0.0 | 0.0 | 0.0 | 47.6 | 1023.9 | 85.1 | 44.2 | 44.2 | 47.6 |
| 5 | 15.3 | 6.7 | 18.6 | 15.6 | 5.2 | 12.1 | 842.4 | 467.7 | 1500.0 | 805.9 | 527.8 | 201.8 |
| 6 | 3.1 | 0.0 | 0.0 | 15.5 | 6.9 | 5.3 | 224.3 | 720.3 | 849.0 | 296.9 | 32.4 | 121.9 |

ND = not determined due to technical exclusion

TABLE 39

Percent Mamu-A*01 tetramer positive out of live CD8+ cells

| Animal | Tat 118 | Gag CM9 | Env 119 | Env CL9 |
|---|---|---|---|---|
| 1 | 0.42 | 0.11 | 0.19 | 0.013 |
| 2 | 0.36 | 0.048 | 0.033 | 0.00834 |
| 3 | 0.97 | 0.051 | 0.35 | 0.048 |
| 4 | 0.46 | 0.083 | 0.17 | 0.028 |
| 5 | 0.77 | 0.45 | 0.14 | 0.2 |
| 6 | 0.71 | 0.16 | 0.17 | 0.04 |

Non-GLP RNA Dose Ranging Study (Higher Doses) in Indian Rhesus Macaques

This study was designed to (a) evaluate the immunogenicity of VEE-MAG25mer srRNA at a dose of 300 μg as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2 at the 300 μg dose; and (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Vaccine immunogenicity in nonhuman primate species, such as Rhesus, is the best predictor of vaccine potency in humans. Furthermore, select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5-WTnt.MAG25mer or VEE-MAG25mer srRNA encoding model antigens that includes multiple Mamu-A*01 restricted antigens. The study arms were as described below.

PBMCs were collected prior to immunization and 4, 5, 6, 7, 8, 10, 11, 12, 13, 14, 15, 16, 17, 18, 19, 20, 21, 22, 23 or 24 weeks after the initial immunization for immune monitoring for group 1 (heterologous prime/boost). PBMCs were collected prior to immunization and 4, 5, 7, 8, 10, 11, 12, 13, 14, or 15 weeks after the initial immunization for immune monitoring for groups 2 and 3 (homologous prime/boost).

TABLE 26

Non-GLP immunogenicity study in Indian Rhesus Macaques

| Group | Prime | Boost 1 | Boost 2 | Boost 3 |
|---|---|---|---|---|
| 1 | ChAdV68.5WTnt .MAG25mer | VEE-MAG25mer srRNA-LNP2 (300 μg) | VEE-MAG25mer srRNA-LNP2 (300 μg) | VEE-MAG25mer srRNA-LNP2 (300 μg) |
| 2 | VEE-MAG25mer srRNA-LNP2 (300 μg) | VEE-MAG25mer srRNA-LNP2 (300 μg) | VEE-MAG25mer srRNA-LNP2 (300 μg) | |
| 3 | VEE-MAG25mer srRNA-LNP1 (300 μg) | VEE-MAG25mer srRNA-LNP1 (300 μg) | VEE-MAG25mer srRNA-LNP1 (300 μg) | |

XIX. Identification of MHC/Peptide Target-Reactive T Cells and TCRs

Target reactive T cells and TCRs are identified for one or more of the antigen/HLA peptides pairs, including any antigens described herein, such as tumor-associated antigens or infectious disease associated antigens.

T cells can be isolated from blood, lymph nodes, or tumors of patients. T cells can be enriched for antigen-specific T cells, e.g., by sorting antigen-MHC tetramer binding cells or by sorting activated cells stimulated in an in vitro co-culture of T cells and antigen-pulsed antigen presenting cells. Various reagents are known in the art for antigen-specific T cell identification including antigen-loaded tetramers and other MHC-based reagents.

Antigen-relevant alpha-beta (or gamma-delta) TCR dimers can be identified by single cell sequencing of TCRs of antigen-specific T cells. Alternatively, bulk TCR sequencing of antigen-specific T cells can be performed and alpha-beta pairs with a high probability of matching can be determined using a TCR pairing method known in the art.

Alternatively or in addition, antigen-specific T cells can be obtained through in vitro priming of naïve T cells from healthy donors. T cells obtained from PBMCs, lymph nodes, or cord blood can be repeatedly stimulated by antigen-pulsed antigen presenting cells to prime differentiation of antigen-experienced T cells. TCRs can then be identified similarly as described above for antigen-specific T cells from patients.

XX. E4 Deletion in ChAdV68 Vectors Demonstrates Improved Productivity

Clones of a ChAdV68 adenoviral vector was selected for improved virus productivity. Fast growing/fit ChAdV68 viruses that express the model TSNA cassette MAG were selected for during plaque isolation and analyzed as described below.

Materials and Methods

ChAdV68 Plaque Isolation

Serial dilutions (from 10' to $10^{-9}$) of ChAdV68-MAG viruses were made and 100 uL plated on HEK293A (ThermoFisher cat. no. R70507) cells seeded at 1e6 cells/60 mM plate. 24 h post infection the media was removed and the infected cells were overlaid with DMEM/1.25% agarose and plaques were allowed to grow for 10-15 days. During this time, 72 viral plaques were picked. The virus was eluted overnight in 0.5 mL of DMEM/5% FBS media and half of the elution (0.25 mL) was used to re-infect 293A cells seeded at 1e5 cells/well of a 24 well plate. The viruses were amplified and infected onto 293A cells. Rapidly growing clones were selected for virus production in 400 mL 293F (ThermoFisher cat. No. A14528) suspension cultures. The virus was purified by 2× CsCl gradient purification and formulated into ARM buffer (25 mM NaCl, 20 mm Tris pH 8.0, 2.5% Glycerol) by 3 rounds of dialysis. Viral particle titers were determined by Absorbance at 260 nm measurement post 0.1% SDS lysis at 56 C. Infectious titers were determined using an anti-capsid immunostaining assay.

Next Generation Sequencing

DNA was purified from the purified virus using the QiAmp viral DNA kit (Qiagen) and subjected to NGS using the Illumina platform.

MOI Evaluation of Clone Productivity

Controlled infections were set up using the purified virus at an MOI of 0.1 IU and incubated for 96 h. Infectious units were measured in cell lysates. Production was compared to a non-plaque selected virus (pool).

Immunizations

Balb/c female mice were injected with $1\times10^9$ or $1\times10^{10}$ viral particles (VP) of ChAdV68.5WTnt.MAG25mer (SEQ ID NO:2) or ChAdV68-MAG-E4deleted (SEQ ID NO: 57; "MAG E4 Delta" and "ChAdV68-MAG-E4") in 100 uL volume, bilateral intramuscular injection (50 uL per leg).

Mamu-A*01 Indian rhesus macaques were immunized as bilateral intramuscular injections into the quadriceps muscle with $1\times10^{12}$ viral particles ($5\times10^{11}$ viral particles per injection) of ChAdV68.5WTnt.MAG25mer ("ChAdV68-CMV-MAG"; SEQ ID NO:2; no E4 deletion or TET response element) or ChAdV68-E4d-CMT-MAG (SEQ ID NO:71; E4 deletion and CMT TET response element [see below]). Macaques were also administered 50 mg of an anti-CTLA4 antibody (Ipilimumab) SC on the day of injection.

```
ChAdV68-E4d-CMT-MAG;
                                                        SEQ ID NO: 71
CATCATCAATAATATACCTCAAACTTTTTGTGCGCGTTAATATGCAAATGAGGCGTTTGAATTTGGGGAGGA

AGGGCGGTGATTGGTCGAGGGATGAGCGACCGTTAGGGGCGGGGCGAGTGACGTTTTGATGACGTGGTTG

CGAGGAGGAGCCAGTTTGCAAGTTCTCGTGGGAAAAGTGACGTCAAACGAGGTGTGGTTTGAACACGGAA

ATACTCAATTTTCCCGCGCTCTCTGACAGGAAATGAGGTGTTTCTGGGCGGATGCAAGTGAAAACGGGCCA

TTTTCGCGCGAAAACTGAATGAGGAAGTGAAAATCTGAGTAATTTCGCGTTTATGGCAGGGAGGAGTATTT

GCCGAGGGCCGAGTAGACTTTGACCGATTACGTGGGGGTTTCGATTACCGTGTTTTTCACCTAAATTTCCGC

GTACGGTGTCAAAGTCCGGTGTTTTTACGTAGGTGTCAGCTGATCGCCAGGGTATTTAAACCTGCGCTCTCC
```

-continued

AGTCAAGAGGCCACTCTTGAGTGCCAGCGAGAAGAGTTTTCTCCTCCGCGCCGCGAGTCAGATCTACACTT

TGAAAGTAGGGATAACAGGGTAATGACATTGATTATTGACTAGTTGTTAATAGTAATCAATTACGGGGTCA

TTAGTTCATAGCCCATATATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAATAGGGACTTTCCATTG

ACGTCAATGGGTGGAGTATTTACGGTAAACTGCCCACTTGGCAGTACATCAAGTGTATCATATGCCAAGTC

CGCCCCCTATTGACGTCAATGACGGTAAATGGCCCGCCTGGCATTATGCCCAGTACATGACCTTACGGGAC

TTTCCTACTTGGCAGTACATCTACGTATTAGTCATCGCTATTACCATGGTGATGCGGTTTTGGCAGTACACC

AATGGGCGTGGATAGCGGTTTGACTCACGGGGATTTCCAAGTCTCCACCCCATTGACGTCAATGGGAGTTT

GTTTTGGCACCAAAATCAACGGGACTTTCCAAAATGTCGTAATAACCCCGCCCCGTTGACGCAAATGGGCG

GTAGGCGTGTACGGTGGGAGGTCTATATAAGCAGAGCTCTCCCTATCAGTGATAGAGATCTCCCTATCAGT

GATAGAGATCGTCGACGAGCTCGTTTAGTGAACCGTCAGATCGCCTGGAACGCCATCCACGCTGTTTTGAC

CTCCATAGAAGACAGCGATCGCGCCACCATGGCCGGGATGTTCCAGGCACTGTCCGAAGGCTGCACACCCT

ATGATATTAACCAGATGCTGAATGTCCTGGGAGACCACCAGGTCTCTGGCCTGGAGCAGCTGGAGAGCATC

ATCAACTTCGAGAAGCTGACCGAGTGGACAAGCTCCAATGTGATGCCTATCCTGTCCCCACTGACCAAGGG

CATCCTGGGCTTCGTGTTTACCCTGACAGTGCCTTCTGAGCGGGGCCTGTCTTGCATCAGCGAGGCAGACGC

AACCACACCAGAGTCCGCCAATCTGGGCGAGGAGATCCTGTCTCAGCTGTACCTGTGGCCCCGGGTGACAT

ATCACTCCCCTTCTTACGCCTATCACCAGTTCGAGCGGAGAGCCAAGTACAAGAGACACTTCCCAGGCTTT

GGCCAGTCTCTGCTGTTCGGCTACCCCGTGTACGTGTTCGGCGATTGCGTGCAGGGCGACTGGGATGCCATC

CGGTTTAGATACTGCGCACCACCTGGATATGCACTGCTGAGGTGTAACGACACCAATTATTCCGCCCTGCTG

GCAGTGGGCGCCCTGGAGGGCCCTCGCAATCAGGATTGGCTGGGCGTGCCAAGGCAGCTGGTGACACGCA

TGCAGGCCATCCAGAACGCAGGCCTGTGCACCCTGGTGGCAATGCTGGAGGAGACAATCTTCTGGCTGCAG

GCCTTTCTGATGGCCCTGACCGACAGCGGCCCCAAGACAAACATCATCGTGGATTCCCAGTACGTGATGGG

CATCTCCAAGCCTTCTTTCCAGGAGTTTGTGGACTGGGAGAACGTGAGCCCAGAGCTGAATTCCACCGATC

AGCCATTCTGGCAGGCAGGAATCCTGGCAAGGAACCTGGTGCCTATGGTGGCCACAGTGCAGGGCCAGAA

TCTGAAGTACCAGGGCCAGAGCCTGGTCATCAGCGCCTCCATCATCGTGTTTAACCTGCTGGAGCTGGAGG

GCGACTATCGGGACGATGGCAACGTGTGGGTGCACACCCCACTGAGCCCCAGAACACTGAACGCCTGGGT

GAAGGCCGTGGAGGAGAAGAAGGGCATCCCAGTGCACCTGGAGCTGGCCTCCATGACCAATATGGAGCTG

ATGTCTAGCATCGTGCACCAGCAGGTGAGGACATACGGACCCGTGTTCATGTGCCTGGGAGGCCTGCTGAC

CATGGTGGCAGGAGCCGTGTGGCTGACAGTGCGGGTGCTGGAGCTGTTCAGAGCCGCCCAGCTGGCCAAC

GATGTGGTGCTGCAGATCATGGAGCTGTGCGGAGCAGCCTTTCGCCAGGTGTGCCACACCACAGTGCCATG

GCCCAATGCCTCCCTGACCCCCAAGTGGAACAATGAGACAACACAGCCTCAGATCGCCAACTGTAGCGTGT

ACGACTTCTTCGTGTGGCTGCACTACTATAGCGTGAGGGATACCCTGTGGCCCCGCGTGACATACCACATG

AATAAGTACGCCTATCACATGCTGGAGAGGCGCGCCAAGTATAAGAGAGGCCCTGGCCCAGGCGCAAAGT

TTGTGGCAGCATGGACCCTGAAGGCCGCCGCCGGCCCCGGCCCCGGCCAGTATATCAAGGCTAACAGTAAG

TTCATTGGAATCACAGAGCTGGGACCCGGACCTGGATAATGAGTTTAAACTCCCATTTAAATGTGAGGGTT

AATGCTTCGAGCAGACATGATAAGATACATTGATGAGTTTGGACAAACCACAACTAGAATGCAGTGAAAA

AAATGCTTTATTTGTGAAATTTGTGATGCTATTGCTTTATTTGTAACCATTATAAGCTGCAATAAACAAGTT

AACAACAACAATTGCATTCATTTTATGTTTCAGGTTCAGGGGGAGATGTGGGAGGTTTTTTAAAGCAAGTA

AAACCTCTACAAATGTGGTAAAATAACTATAACGGTCCTAAGGTAGCGAGTGAGTAGTGTTCTGGGGCGGG

GGAGGACCTGCATGAGGGCCAGAATAACTGAAATCTGTGCTTTTCTGTGTGTTGCAGCAGCATGAGCGGAA

-continued

GCGGCTCCTTTGAGGGAGGGGTATTCAGCCCTTATCTGACGGGGCGTCTCCCCTCCTGGGCGGGAGTGCGT

CAGAATGTGATGGGATCCACGGTGGACGGCCGGCCCGTGCAGCCCGCGAACTCTTCAACCCTGACCTATGC

AACCCTGAGCTCTTCGTCGTTGGACGCAGCTGCCGCCGCAGCTGCTGCATCTGCCGCCAGCGCCGTGCGCG

GAATGGCCATGGGCGCCGGCTACTACGGCACTCTGGTGGCCAACTCGAGTTCCACCAATAATCCCGCCAGC

CTGAACGAGGAGAAGCTGTTGCTGCTGATGGCCCAGCTCGAGGCCTTGACCCAGCGCCTGGGCGAGCTGAC

CCAGCAGGTGGCTCAGCTGCAGGAGCAGACGCGGGCCGCGGTTGCCACGGTGAAATCCAAATAAAAAATG

AATCAATAAATAAACGGAGACGGTTGTTGATTTTAACACAGAGTCTGAATCTTTATTTGATTTTTCGCGCGC

GGTAGGCCCTGGACCACCGGTCTCGATCATTGAGCACCCGGTGGATCTTTTCCAGGACCCGGTAGAGGTGG

GCTTGGATGTTGAGGTACATGGGCATGAGCCCGTCCCGGGGGTGGAGGTAGCTCCATTGCAGGGCCTCGTG

CTCGGGGGTGGTGTTGTAAATCACCCAGTCATAGCAGGGGCGCAGGGCATGGTGTTGCACAATATCTTTGA

GGAGGAGACTGATGGCCACGGGCAGCCCTTTGGTGTAGGTGTTTACAAATCTGTTGAGCTGGGAGGGATGC

ATGCGGGGGGAGATGAGGTGCATCTTGGCCTGGATCTTGAGATTGGCGATGTTACCGCCCAGATCCCGCCT

GGGGTTCATGTTGTGCAGGACCACCAGCACGGTGTATCCGGTGCACTTGGGGAATTTATCATGCAACTTGG

AAGGGAAGGCGTGAAAGAATTTGGCGACGCCTTTGTGCCCGCCCAGGTTTTCCATGCACTCATCCATGATG

ATGGCGATGGGCCCGTGGGCGGCGGCCTGGGCAAAGACGTTTCGGGGGTCGGACACATCATAGTTGTGGTC

CTGGGTGAGGTCATCATAGGCCATTTTAATGAATTTGGGGCGGAGGGTGCCGGACTGGGGGACAAAGGTTC

CCTCGATCCCGGGGGCGTAGTTCCCCTCACAGATCTGCATCTCCCAGGCTTTGAGCTCGGAGGGGGGGATC

ATGTCCACCTGCGGGGCGATAAAGAACACGGTTTCCGGGGCGGGGGAGATGAGCTGGGCCGAAAGCAAGT

TCCGGAGCAGCTGGGACTTGCCGCAGCCGGTGGGGCCGTAGATGACCCCGATGACCGGCTGCAGGTGGTA

GTTGAGGGAGAGACAGCTGCCGTCCTCCCGGAGGAGGGGGGCCACCTCGTTCATCATCTCGCGCACGTGCA

TGTTCTCGCGCACCAGTTCCGCCAGGAGGCGCTCTCCCCCCAGGGATAGGAGCTCCTGGAGCGAGGCGAAG

TTTTTCAGCGGCTTGAGTCCGTCGGCCATGGGCATTTTGGAGAGGGTTTGTTGCAAGAGTTCCAGGCGGTCC

CAGAGCTCGGTGATGTGCTCTACGGCATCTCGATCCAGCAGACCTCCTCGTTTCGCGGGTTGGGACGGCTG

CGGGAGTAGGGCACCAGACGATGGGCGTCCAGCGCAGCCAGGGTCCGGTCCTTCCAGGGTCGCAGCGTCC

GCGTCAGGGTGGTCTCCGTCACGGTGAAGGGGTGCGCGCCGGGCTGGGCGCTTGCGAGGGTGCGCTTCAGG

CTCATCCGGCTGGTCGAAAACCGCTCCCGATCGGCGCCCTGCGCGTCGGCCAGGTAGCAATTGACCATGAG

TTCGTAGTTGAGCGCCTCGGCCGCGTGGCCTTTGGCGCGGAGCTTACCTTTGGAAGTCTGCCCGCAGGCGG

GACAGAGGAGGGACTTGAGGGCGTAGAGCTTGGGGGCGAGGAAGACGGACTCGGGGGCGTAGGCGTCCG

CGCCGCAGTGGGCGCAGACGGTCTCGCACTCCACGAGCCAGGTGAGGTCGGGCTGGTCGGGGTCAAAAAC

CAGTTTCCCGCCGTTCTTTTTGATGCGTTTCTTACCTTTGGTCTCCATGAGCTCGTGTCCCCGCTGGGTGACA

AAGAGGCTGTCCGTGTCCCCGTAGACCGACTTTATGGGCCGGTCCTCGAGCGGTGTGCCGCGGTCCTCCTC

GTAGAGGAACCCCGCCCACTCCGAGACGAAAGCCCGGGTCCAGGCCAGCACGAAGGAGGCCACGTGGGAC

GGGTAGCGGTCGTTGTCCACCAGCGGGTCCACCTTTTCCAGGGTATGCAAACACATGTCCCCCTCGTCCACA

TCCAGGAAGGTGATTGGCTTGTAAGTGTAGGCCACGTGACCGGGGGTCCCGGCCGGGGGGGTATAAAAGG

GTGCGGGTCCCTGCTCGTCCTCACTGTCTTCCGGATCGCTGTCCAGGAGCGCCAGCTGTTGGGGTAGGTATT

CCCTCTCGAAGGCGGGCATGACCTCGGCACTCAGGTTGTCAGTTTCTAGAAACGAGGAGGATTTGATATTG

ACGGTGCCGGCGGAGATGCCTTTCAAGAGCCCCTCGTCCATCTGGTCAGAAAAGACGATCTTTTTGTTGTCG

AGCTTGGTGGCGAAGGAGCCGTAGAGGGCGTTGGAGAGGAGCTTGGCGATGGAGCGCATGGTCTGGTTTTT

TTCCTTGTCGGCGCGCTCCTTGGCGGCGATGTTGAGCTGCACGTACTCGCGCGCCACGCACTTCCATTCGGG

GAAGACGGTGGTCAGCTCGTCGGGCACGATTCTGACCTGCCAGCCCCGATTATGCAGGGTGATGAGGTCCA

CACTGGTGGCCACCTCGCCGCGCAGGGGCTCATTAGTCCAGCAGAGGCGTCCGCCCTTGCGCGAGCAGAAG

-continued

GGGGGCAGGGGGTCCAGCATGACCTCGTCGGGGGGGTCGGCATCGATGGTGAAGATGCCGGGCAGGAGGT

CGGGGTCAAAGTAGCTGATGGAAGTGGCCAGATCGTCCAGGGCAGCTTGCCATTCGCGCACGGCCAGCGC

GCGCTCGTAGGGACTGAGGGGCGTGCCCCAGGGCATGGGATGGGTAAGCGCGGAGGCGTACATGCCGCAG

ATGTCGTAGACGTAGAGGGGCTCCTCGAGGATGCCGATGTAGGTGGGGTAGCAGCGCCCCCCGCGGATGCT

GGCGCGCACGTAGTCATACAGCTCGTGCGAGGGGGCGAGGAGCCCCGGGCCCAGGTTGGTGCGACTGGGC

TTTTCGGCGCGGTAGACGATCTGGCGGAAAATGGCATGCGAGTTGGAGGAGATGGTGGGCCTTTGGAAGAT

GTTGAAGTGGGCGTGGGGCAGTCCGACCGAGTCGCGGATGAAGTGGGCGTAGGAGTCTTGCAGCTTGGCG

ACGAGCTCGGCGGTGACTAGGACGTCCAGAGCGCAGTAGTCGAGGGTCTCCTGGATGATGTCATACTTGAG

CTGTCCCTTTTGTTTCCACAGCTCGCGGTTGAGAAGGAACTCTTCGCGGTCCTTCCAGTACTCTTCGAGGGG

GAACCCGTCCTGATCTGCACGGTAAGAGCCTAGCATGTAGAACTGGTTGACGGCCTTGTAGGCGCAGCAGC

CCTTCTCCACGGGGAGGGCGTAGGCCTGGGCGGCCTTGCGCAGGGAGGTGTGCGTGAGGGCGAAAGTGTC

CCTGACCATGACCTTGAGGAACTGGTGCTTGAAGTCGATATCGTCGCAGCCCCCCTGCTCCCAGAGCTGGA

AGTCCGTGCGCTTCTTGTAGGCGGGGTTGGGCAAAGCGAAAGTAACATCGTTGAAGAGGATCTTGCCCGCG

CGGGGCATAAAGTTGCGAGTGATGCGGAAAGGTTGGGGCACCTCGGCCCGGTTGTTGATGACCTGGGCGGC

GAGCACGATCTCGTCGAAGCCGTTGATGTTGTGGCCCACGATGTAGAGTTCCACGAATCGCGGACGGCCCT

TGACGTGGGGCAGTTTCTTGAGCTCCTCGTAGGTGAGCTCGTCGGGGTCGCTGAGCCCGTGCTGCTCGAGC

GCCCAGTCGGCGAGATGGGGGTTGGCGCGGAGGAAGGAAGTCCAGAGATCCACGGCCAGGGCGGTTTGCA

GACGGTCCCGGTACTGACGGAACTGCTGCCCGACGGCCATTTTTTCGGGGGTGACGCAGTAGAAGGTGCGG

GGGTCCCCGTGCCAGCGATCCCATTTGAGCTGGAGGGCGAGATCGAGGGCGAGCTCGACGAGCCGGTCGT

CCCCGGAGAGTTTCATGACCAGCATGAAGGGGACGAGCTGCTTGCCGAAGGACCCCATCCAGGTGTAGGTT

TCCACATCGTAGGTGAGGAAGAGCCTTTCGGTGCGAGGATGCGAGCCGATGGGGAAGAACTGGATCTCCTG

CCACCAATTGGAGGAATGGCTGTTGATGTGATGGAAGTAGAAATGCCGACGGCGCGCCGAACACTCGTGCT

TGTGTTTATACAAGCGGCCACAGTGCTCGCAACGCTGCACGGGATGCACGTGCTGCACGAGCTGTACCTGA

GTTCCTTTGACGAGGAATTTCAGTGGGAAGTGGAGTCGTGGCGCCTGCATCTCGTGCTGTACTACGTCGTGG

TGGTCGGCCTGGCCCTCTTCTGCCTCGATGGTGGTCATGCTGACGAGCCCGCGCGGGAGGCAGGTCCAGAC

CTCGGCGCGAGCGGGTCGGAGAGCGAGGACGAGGGCGCGCAGGCCGGAGCTGTCCAGGGTCCTGAGACGC

TGCGGAGTCAGGTCAGTGGGCAGCGGCGGCGCGCGGTTGACTTGCAGGAGTTTTTCCAGGGCGCGCGGGA

GGTCCAGATGGTACTTGATCTCCACCGCGCCATTGGTGGCGACGTCGATGGCTTGCAGGGTCCCGTGCCCCT

GGGGTGTGACCACCGTCCCCCGTTTCTTCTTGGGCGGCTGGGGCGACGGGGGCGGTGCCTCTTCCATGGTTA

GAAGCGGCGGCGAGGACGCGCGCCGGGCGGCAGGGGCGGCTCGGGGCCCGGAGGCAGGGGCGGCAGGGG

CACGTCGGCGCCGCGCGCGGGTAGGTTCTGGTACTGCGCCCGGAGAAGACTGGCGTGAGCGACGACGCGA

CGGTTGACGTCCTGGATCTGACGCCTCTGGGTGAAGGCCACGGGACCCGTGAGTTTGAACCTGAAAGAGAG

TTCGACAGAATCAATCTCGGTATCGTTGACGGCGGCCTGCCGCAGGATCTCTTGCACGTCGCCCGAGTTGTC

CTGGTAGGCGATCTCGGTCATGAACTGCTCGATCTCCTCCTCTTGAAGGTCTCCGCGGCCGGCGCGCTCCAC

GGTGGCCGCGAGGTCGTTGGAGATGCGGCCCATGAGCTGCGAGAAGGCGTTCATGCCCGCCTCGTTCCAGA

CGCGGCTGTAGACCACGACGCCCTCGGGATCGCGGGCGCGCATGACCACCTGGGCGAGGTTGAGCTCCAC

GTGGCGCGTGAAGACCGCGTAGTTGCAGAGGCGCTGGTAGAGGTAGTTGAGCGTGGTGGCGATGTGCTCG

GTGACGAAGAAATACATGATCCAGCGGCGGAGCGGCATCTCGCTGACGTCGCCCAGCGCCTCCAAACGTTC

CATGGCCTCGTAAAAGTCCACGGCGAAGTTGAAAAACTGGGAGTTGCGCGCCGAGACGGTCAACTCCTCCT

CCAGAAGACGGATGAGCTCGGCGATGGTGGCGCGCACCTCGCGCTCGAAGGCCCCCGGGAGTTCCTCCACT

-continued

TCCTCTTCTTCCTCCTCCACTAACATCTCTTCTACTTCCTCCTCAGGCGGCAGTGGTGGCGGGGGAGGGGGC

CTGCGTCGCCGGCGGCGCACGGGCAGACGGTCGATGAAGCGCTCGATGGTCTCGCCGCGCCGGCGTCGCAT

GGTCTCGGTGACGGCGCGCCCGTCCTCGCGGGGCCGCAGCGTGAAGACGCCGCCGCGCATCTCCAGGTGGC

CGGGGGGGTCCCCGTTGGGCAGGGAGAGGGCGCTGACGATGCATCTTATCAATTGCCCCGTAGGGACTCCG

CGCAAGGACCTGAGCGTCTCGAGATCCACGGGATCTGAAAACCGCTGAACGAAGGCTTCGAGCCAGTCGC

AGTCGCAAGGTAGGCTGAGCACGGTTTCTTCTGGCGGGTCATGTTGGTTGGGAGCGGGGCGGGCGATGCTG

CTGGTGATGAAGTTGAAATAGGCGGTTCTGAGACGGCGGATGGTGGCGAGGAGCACCAGGTCTTTGGGCCC

GGCTTGCTGGATGCGCAGACGGTCGGCCATGCCCCAGGCGTGGTCCTGACACCTGGCCAGGTCCTTGTAGT

AGTCCTGCATGAGCCGCTCCACGGGCACCTCCTCCTCGCCCGCGCGGCCGTGCATGCGCGTGAGCCCGAAG

CCGCGCTGGGGCTGGACGAGCGCCAGGTCGGCGACGACGCGCTCGGCGAGGATGGCTTGCTGGATCTGGG

TGAGGGTGGTCTGGAAGTCATCAAAGTCGACGAAGCGGTGGTAGGCTCCGGTGTTGATGGTGTAGGAGCA

GTTGGCCATGACGGACCAGTTGACGGTCTGGTGGCCCGGACGCACGAGCTCGTGGTACTTGAGGCGCGAGT

AGGCGCGCGTGTCGAAGATGTAGTCGTTGCAGGTGCGCACCAGGTACTGGTAGCCGATGAGGAAGTGCGG

CGGCGGCTGGCGGTAGAGCGGCCATCGCTCGGTGGCGGGGGCGCCGGGCGCGAGGTCCTCGAGCATGGTG

CGGTGGTAGCCGTAGATGTACCTGGACATCCAGGTGATGCCGGCGGCGGTGGTGGAGGCGCGCGGGAACT

CGCGGACGCGGTTCCAGATGTTGCGCAGCGGCAGGAAGTAGTTCATGGTGGGCACGGTCTGGCCCGTGAGG

CGCGCGCAGTCGTGGATGCTCTATACGGGCAAAAACGAAAGCGGTCAGCGGCTCGACTCCGTGGCCTGGA

GGCTAAGCGAACGGGTTGGGCTGCGCGTGTACCCCGGTTCGAATCTCGAATCAGGCTGGAGCCGCAGCTAA

CGTGGTATTGGCACTCCCGTCTCGACCCAAGCCTGCACCAACCCTCCAGGATACGGAGGCGGGTCGTTTTG

CAACTTTTTTTTGGAGGCCGGATGAGACTAGTAAGCGCGGAAAGCGGCCGACCGCGATGGCTCGCTGCCGT

AGTCTGGAGAAGAATCGCCAGGGTTGCGTTGCGGTGTGCCCCGGTTCGAGGCCGGCCGGATTCCGCGGCTA

ACGAGGGCGTGGCTGCCCCGTCGTTTCCAAGACCCCATAGCCAGCCGACTTCTCCAGTTACGGAGCGAGCC

CCTCTTTTGTTTTGTTTGTTTTTGCCAGATGCATCCCGTACTGCGGCAGATGCGCCCCCACCACCCTCCACCG

CAACAACAGCCCCCTCCACAGCCGGCGCTTCTGCCCCCGCCCCAGCAGCAACTTCCAGCCACGACCGCCGC

GGCCGCCGTGAGCGGGGCTGGACAGAGTTATGATCACCAGCTGGCCTTGGAAGAGGGCGAGGGGCTGGCG

CGCCTGGGGGCGTCGTCGCCGGAGCGGCACCCGCGCGTGCAGATGAAAAGGGACGCTCGCGAGGCCTACG

TGCCCAAGCAGAACCTGTTCAGAGACAGGAGCGGCGAGGAGCCCGAGGAGATGCGCGCGGCCCGGTTCCA

CGCGGGGCGGGAGCTGCGGCGCGGCCTGGACCGAAAGAGGGTGCTGAGGGACGAGGATTTCGAGGCGGA

CGAGCTGACGGGGATCAGCCCCGCGCGCGCGCACGTGGCCGCGGCCAACCTGGTCACGGCGTACGAGCAG

ACCGTGAAGGAGGAGAGCAACTTCCAAAAATCCTTCAACAACCACGTGCGCACCCTGATCGCGCGCGAGG

AGGTGACCCTGGGCCTGATGCACCTGTGGGACCTGCTGGAGGCCATCGTGCAGAACCCCACCAGCAAGCCG

CTGACGGCGCAGCTGTTCCTGGTGGTGCAGCATAGTCGGGACAACGAAGCGTTCAGGGAGGCGCTGCTGAA

TATCACCGAGCCCGAGGGCCGCTGGCTCCTGGACCTGGTGAACATTCTGCAGAGCATCGTGGTGCAGGAGC

GCGGGCTGCCGCTGTCCGAGAAGCTGGCGGCCATCAACTTCTCGGTGCTGAGTTTGGGCAAGTACTACGCT

AGGAAGATCTACAAGACCCCGTACGTGCCCATAGACAAGGAGGTGAAGATCGACGGGTTTTACATGCGCA

TGACCCTGAAAGTGCTGACCCTGAGCGACGATCTGGGGGTGTACCGCAACGACAGGATGCACCGTGCGGT

GAGCGCCAGCAGGCGGCGCGAGCTGAGCGACCAGGAGCTGATGCATAGTCTGCAGCGGGCCCTGACCGGG

GCCGGGACCGAGGGGGAGAGCTACTTTGACATGGGCGCGGACCTGCACTGGCAGCCCAGCCGCCGGGCCT

TGGAGGCGGCGGCAGGACCCTACGTAGAAGAGGTGGACGATGAGGTGGACGAGGAGGGCGAGTACCTGG

AAGACTGATGGCGCGACCGTATTTTTGCTAGATGCAACAACAACAGCCACCTCCTGATCCCGCGATGCGGG

CGGCGCTGCAGAGCCAGCCGTCCGGCATTAACTCCTCGGACGATTGGACCCAGGCCATGCAACGCATCATG

-continued

GCGCTGACGACCCGCAACCCCGAAGCCTTTAGACAGCAGCCCCAGGCCAACCGGCTCTCGGCCATCCTGGA

GGCCGTGGTGCCCTCGCGCTCCAACCCCACGCACGAGAAGGTCCTGGCCATCGTGAACGCGCTGGTGGAGA

ACAAGGCCATCCGCGGCGACGAGGCCGGCCTGGTGTACAACGCGCTGCTGGAGCGCGTGGCCCGCTACAA

CAGCACCAACGTGCAGACCAACCTGGACCGCATGGTGACCGACGTGCGCGAGGCCGTGGCCCAGCGCGAG

CGGTTCCACCGCGAGTCCAACCTGGGATCCATGGTGGCGCTGAACGCCTTCCTCAGCACCCAGCCCGCCAA

CGTGCCCCGGGGCCAGGAGGACTACACCAACTTCATCAGCGCCCTGCGCCTGATGGTGACCGAGGTGCCCC

AGAGCGAGGTGTACCAGTCCGGGCCGGACTACTTCTTCCAGACCAGTCGCCAGGGCTTGCAGACCGTGAAC

CTGAGCCAGGCTTTCAAGAACTTGCAGGGCCTGTGGGGCGTGCAGGCCCCGGTCGGGGACCGCGCGACGG

TGTCGAGCCTGCTGACGCCGAACTCGCGCCTGCTGCTGCTGCTGGTGGCCCCCTTCACGGACAGCGGCAGC

ATCAACCGCAACTCGTACCTGGGCTACCTGATTAACCTGTACCGCGAGGCCATCGGCCAGGCGCACGTGGA

CGAGCAGACCTACCAGGAGATCACCCACGTGAGCCGCGCCCTGGGCCAGGACGACCCGGGCAACCTGGAA

GCCACCCTGAACTTTTTGCTGACCAACCGGTCGCAGAAGATCCCGCCCCAGTACGCGCTCAGCACCGAGGA

GGAGCGCATCCTGCGTTACGTGCAGCAGAGCGTGGGCCTGTTCCTGATGCAGGAGGGGGCCACCCCCAGCG

CCGCGCTCGACATGACCGCGCGCAACATGGAGCCCAGCATGTACGCCAGCAACCGCCCGTTCATCAATAAA

CTGATGGACTACTTGCATCGGGCGGCCGCCATGAACTCTGACTATTTCACCAACGCCATCCTGAATCCCCAC

TGGCTCCCGCCGCCGGGGTTCTACACGGGCGAGTACGACATGCCCGACCCCAATGACGGGTTCCTGTGGGA

CGATGTGGACAGCAGCGTGTTCTCCCCCCGACCGGGTGCTAACGAGCGCCCCTTGTGGAAGAAGGAAGGC

AGCGACCGACGCCCGTCCTCGGCGCTGTCCGGCCGCGAGGGTGCTGCCGCGGCGGTGCCCGAGGCCGCCA

GTCCTTTCCCGAGCTTGCCCTTCTCGCTGAACAGTATCCGCAGCAGCGAGCTGGGCAGGATCACGCGCCCG

CGCTTGCTGGGCGAAGAGGAGTACTTGAATGACTCGCTGTTGAGACCCGAGCGGGAGAAGAACTTCCCCAA

TAACGGGATAGAAAGCCTGGTGGACAAGATGAGCCGCTGGAAGACGTATGCGCAGGAGCACAGGGACGAT

CCCCGGGCGTCGCAGGGGGCCACGAGCCGGGGCAGCGCCGCCCGTAAACGCCGGTGGCACGACAGGCAGC

GGGGACAGATGTGGGACGATGAGGACTCCGCCGACGACAGCAGCGTGTTGGACTTGGGTGGGAGTGGTAA

CCCGTTCGCTCACCTGCGCCCCCGTATCGGGCGCATGATGTAAGAGAAACCGAAAATAAATGATACTCACC

AAGGCCATGGCGACCAGCGTGCGTTCGTTTCTTCTCTGTTGTTGTTGTATCTAGTATGATGAGGCGTGCGTA

CCCGGAGGGTCCTCCTCCCTCGTACGAGAGCGTGATGCAGCAGGCGATGGCGGCGGCGGCGATGCAGCCC

CCGCTGGAGGCTCCTTACGTGCCCCCGCGGTACCTGGCGCCTACGGAGGGGCGGAACAGCATTCGTTACTC

GGAGCTGGCACCCTTGTACGATACCACCCGGTTGTACCTGGTGGACAACAAGTCGGCGGACATCGCCTCGC

TGAACTACCAGAACGACCACAGCAACTTCCTGACCACCGTGGTGCAGAACAATGACTTCACCCCCACGGAG

GCCAGCACCCAGACCATCAACTTTGACGAGCGCTCGCGGTGGGGCGGCCAGCTGAAAACCATCATGCACA

CCAACATGCCCAACGTGAACGAGTTCATGTACAGCAACAAGTTCAAGGCGCGGGTGATGGTCTCCCGCAAG

ACCCCCAATGGGGTGACAGTGACAGAGGATTATGATGGTAGTCAGGATGAGCTGAAGTATGAATGGGTGG

AATTTGAGCTGCCCGAAGGCAACTTCTCGGTGACCATGACCATCGACCTGATGAACAACGCCATCATCGAC

AATTACTTGGCGGTGGGGCGGCAGAACGGGGTGCTGGAGAGCGACATCGGCGTGAAGTTCGACACTAGGA

ACTTCAGGCTGGGCTGGGACCCCGTGACCGAGCTGGTCATGCCCGGGGTGTACACCAACGAGGCTTTCCAT

CCCGATATTGTCTTGCTGCCCGGCTGCGGGGTGGACTTCACCGAGAGCCGCCTCAGCAACCTGCTGGGCAT

TCGCAAGAGGCAGCCCTTCCAGGAAGGCTTCCAGATCATGTACGAGGATCTGGAGGGGGGCAACATCCCC

GCGCTCCTGGATGTCGACGCCTATGAGAAAAGCAAGGAGGATGCAGCAGCTGAAGCAACTGCAGCCGTAG

CTACCGCCTCTACCGAGGTCAGGGGCGATAATTTTGCAAGCGCCGCAGCAGTGGCAGCGGCCGAGGCGGCT

GAAACCGAAAGTAAGATAGTCATTCAGCCGGTGGAGAAGGATAGCAAGAACAGGAGCTACAACGTACTAC

-continued

```
CGGACAAGATAAACACCGCCTACCGCAGCTGGTACCTAGCCTACAACTATGGCGACCCCGAGAAGGGCGT

GCGCTCCTGGACGCTGCTCACCACCTCGGACGTCACCTGCGGCGTGGAGCAAGTCTACTGGTCGCTGCCCG

ACATGATGCAAGACCCGGTCACCTTCCGCTCCACGCGTCAAGTTAGCAACTACCCGGTGGTGGGCGCCGAG

CTCCTGCCCGTCTACTCCAAGAGCTTCTTCAACGAGCAGGCCGTCTACTCGCAGCAGCTGCGCGCCTTCACC

TCGCTTACGCACGTCTTCAACCGCTTCCCCGAGAACCAGATCCTCGTCCGCCCGCCCGCGCCCACCATTACC

ACCGTCAGTGAAAACGTTCCTGCTCTCACAGATCACGGGACCCTGCCGCTGCGCAGCAGTATCCGGGGAGT

CCAGCGCGTGACCGTTACTGACGCCAGACGCCGCACCTGCCCCTACGTCTACAAGGCCCTGGGCATAGTCG

CGCCGCGCGTCCTCTCGAGCCGCACCTTCTAAATGTCCATTCTCATCTCGCCCAGTAATAACACCGGTTGGG

GCCTGCGCGCGCCCAGCAAGATGTACGGAGGCGCTCGCCAACGCTCCACGCAACACCCCGTGCGCGTGCGC

GGGCACTTCCGCGCTCCCTGGGGCGCCCTCAAGGGCCGCGTGCGGTCGCGCACCACCGTCGACGACGTGAT

CGACCAGGTGGTGGCCGACGCGCGCAACTACACCCCCGCCGCCGCGCCCGTCTCCACCGTGGACGCCGTCA

TCGACAGCGTGGTGGCCGACGCGCGCCGGTACGCCCGCGCCAAGAGCCGGCGGCGGCGCATCGCCCGGCG

GCACCGGAGCACCCCCGCCATGCGCGCGGCGCGAGCCTTGCTGCGCAGGGCCAGGCGCACGGGACGCAGG

GCCATGCTCAGGGCGGCCAGACGCGCGGCTTCAGGCGCCAGCGCCGGCAGGACCCGGAGACGCGCGGCCA

CGGCGGCGGCAGCGGCCATCGCCAGCATGTCCCGCCCGCGGCGAGGGAACGTGTACTGGGTGCGCGACGC

CGCCACCGGTGTGCGCGTGCCCGTGCGCACCCGCCCCCCTCGCACTTGAAGATGTTCACTTCGCGATGTTGA

TGTGTCCCAGCGGCGAGGAGGATGTCCAAGCGCAAATTCAAGGAAGAGATGCTCCAGGTCATCGCGCCTG

AGATCTACGGCCCTGCGGTGGTGAAGGAGGAAAGAAAGCCCCGCAAAATCAAGCGGGTCAAAAAGGACA

AAAAGGAAGAAGAAAGTGATGTGGACGGATTGGTGGAGTTTGTGCGCGAGTTCGCCCCCCGGCGGCGCGT

GCAGTGGCGCGGGCGGAAGGTGCAACCGGTGCTGAGACCCGGCACCACCGTGGTCTTCACGCCCGGCGAG

CGCTCCGGCACCGCTTCCAAGCGCTCCTACGACGAGGTGTACGGGGATGATGATATTCTGGAGCAGGCGGC

CGAGCGCCTGGGCGAGTTTGCTTACGGCAAGCGCAGCCGTTCCGCACCGAAGGAAGAGGCGGTGTCCATCC

CGCTGGACCACGGCAACCCCACGCCGAGCCTCAAGCCCGTGACCTTGCAGCAGGTGCTGCCGACCGCGGCG

CCGCGCCGGGGGTTCAAGCGCGAGGGCGAGGATCTGTACCCCACCATGCAGCTGATGGTGCCCAAGCGCC

AGAAGCTGGAAGACGTGCTGGAGACCATGAAGGTGGACCCGGACGTGCAGCCCGAGGTCAAGGTGCGGCC

CATCAAGCAGGTGGCCCCGGGCCTGGGCGTGCAGACCGTGGACATCAAGATTCCCACGGAGCCCATGGAA

ACGCAGACCGAGCCCATGATCAAGCCCAGCACCAGCACCATGGAGGTGCAGACGGATCCCTGGATGCCAT

CGGCTCCTAGTCGAAGACCCCGGCGCAAGTACGGCGCGGCCAGCCTGCTGATGCCCAACTACGCGCTGCAT

CCTTCCATCATCCCCACGCCGGGCTACCGCGGCACGCGCTTCTACCGCGGTCATACCAGCAGCCGCCGCCG

CAAGACCACCACTCGCCGCCGCCGTCGCCGCACCGCCGCTGCAACCACCCCTGCCGCCCTGGTGCGGAGAG

TGTACCGCCGCGGCCGCGCACCTCTGACCCTGCCGCGCGCGCGCTACCACCCGAGCATCGCCATTTAAACT

TTCGCCTGCTTTGCAGATCAATGGCCCTCACATGCCGCCTTCGCGTTCCCATTACGGGCTACCGAGGAAGAA

AACCGCGCCGTAGAAGGCTGGCGGGGAACGGGATGCGTCGCCACCACCACCGGCGGCGGCGCGCCATCAG

CAAGCGGTTGGGGGGAGGCTTCCTGCCCGCGCTGATCCCCATCATCGCCGCGGCGATCGGGGCGATCCCCG

GCATTGCTTCCGTGGCGGTGCAGGCCTCTCAGCGCCACTGAGACACACTTGGAAACATCTTGTAATAAACC

AATGGACTCTGACGCTCCTGGTCCTGTGATGTGTTTTCGTAGACAGATGGAAGACATCAATTTTTCGTCCCT

GGCTCCGCGACACGGCACGCGGCCGTTCATGGGCACCTGGAGCGACATCGGCACCAGCCAACTGAACGGG

GGCGCCTTCAATTGGAGCAGTCTCTGGAGCGGGCTTAAGAATTTCGGGTCCACGCTTAAAACCTATGGCAG

CAAGGCGTGGAACAGCACCACAGGGCAGGCGCTGAGGGATAAGCTGAAAGAGCAGAACTTCCAGCAGAA

GGTGGTCGATGGGCTCGCCTCGGGCATCAACGGGGTGGTGGACCTGGCCAACCAGGCCGTGCAGCGGCAG

ATCAACAGCCGCCTGGACCCGGTGCCGCCCGCCGGCTCCGTGGAGATGCCGCAGGTGGAGGAGGAGCTGC
```

-continued

CTCCCCTGGACAAGCGGGGCGAGAAGCGACCCCGCCCCGATGCGGAGGAGACGCTGCTGACGCACACGGA

CGAGCCGCCCCCGTACGAGGAGGCGGTGAAACTGGGTCTGCCCACCACGCGGCCCATCGCGCCCCTGGCCA

CCGGGGTGCTGAAACCCGAAAAGCCCGCGACCCTGGACTTGCCTCCTCCCCAGCCTTCCCGCCCCTCTACA

GTGGCTAAGCCCCTGCCGCCGGTGGCCGTGGCCCGCGCGCGACCCGGGGGCACCGCCCGCCCTCATGCGAA

CTGGCAGAGCACTCTGAACAGCATCGTGGGTCTGGGAGTGCAGAGTGTGAAGCGCCGCCGCTGCTATTAAA

CCTACCGTAGCGCTTAACTTGCTTGTCTGTGTGTGTATGTATTATGTCGCCGCCGCCGCTGTCCACCAGAAG

GAGGAGTGAAGAGGCGCGTCGCCGAGTTGCAAGATGGCCACCCCATCGATGCTGCCCCAGTGGGCGTACA

TGCACATCGCCGGACAGGACGCTTCGGAGTACCTGAGTCCGGGTCTGGTGCAGTTTGCCCGCGCCACAGAC

ACCTACTTCAGTCTGGGGAACAAGTTTAGGAACCCCACGGTGGCGCCCACGCACGATGTGACCACCGACCG

CAGCCAGCGGCTGACGCTGCGCTTCGTGCCCGTGGACCGCGAGGACAACACCTACTCGTACAAAGTGCGCT

ACACGCTGGCCGTGGGCGACAACCGCGTGCTGGACATGGCCAGCACCTACTTTGACATCCGCGGCGTGCTG

GATCGGGGCCCTAGCTTCAAACCCTACTCCGGCACCGCCTACAACAGTCTGGCCCCCAAGGGAGCACCCAA

CACTTGTCAGTGGACATATAAAGCCGATGGTGAAACTGCCACAGAAAAAACCTATACATATGGAAATGCAC

CCGTGCAGGGCATTAACATCACAAAAGATGGTATTCAACTTGGAACTGACACCGATGATCAGCCAATCTAC

GCAGATAAAACCTATCAGCCTGAACCTCAAGTGGGTGATGCTGAATGGCATGACATCACTGGTACTGATGA

AAAGTATGGAGGCAGAGCTCTTAAGCCTGATACCAAAATGAAGCCTTGTTATGGTTCTTTTGCCAAGCCTA

CTAATAAAGAAGGAGGTCAGGCAAATGTGAAAACAGGAACAGGCACTACTAAAGAATATGACATAGACAT

GGCTTTCTTTGACAACAGAAGTGCGGCTGCTGCTGGCCTAGCTCCAGAAATTGTTTTGTATACTGAAAATGT

GGATTTGGAAACTCCAGATACCCATATTGTATACAAAGCAGGCACAGATGACAGCAGCTCTTCTATTAATT

TGGGTCAGCAAGCCATGCCCAACAGACCTAACTACATTGGTTTCAGAGACAACTTTATCGGGCTCATGTAC

TACAACAGCACTGGCAATATGGGGGTGCTGGCCGGTCAGGCTTCTCAGCTGAATGCTGTGGTTGACTTGCA

AGACAGAAACACCGAGCTGTCCTACCAGCTCTTGCTTGACTCTCTGGGTGACAGAACCCGGTATTTCAGTAT

GTGGAATCAGGCGGTGGACAGCTATGATCCTGATGTGCGCATTATTGAAAATCATGGTGTGGAGGATGAAC

TTCCCAACTATTGTTTCCCTCTGGATGCTGTTGGCAGAACAGATACTTATCAGGGAATTAAGGCTAATGGAA

CTGATCAAACCACATGGACCAAAGATGACAGTGTCAATGATGCTAATGAGATAGGCAAGGGTAATCCATTC

GCCATGGAAATCAACATCCAAGCCAACCTGTGGAGGAACTTCCTCTACGCCAACGTGGCCCTGTACCTGCC

CGACTCTTACAAGTACACGCCGGCCAATGTTACCCTGCCCACCAACACCAACACCTACGATTACATGAACG

GCCGGGTGGTGGCGCCCTCGCTGGTGGACTCCTACATCAACATCGGGGCGCGCTGGTCGCTGGATCCCATG

GACAACGTGAACCCCTTCAACCACCACCGCAATGCGGGGCTGCGCTACCGCTCCATGCTCCTGGGCAACGG

GCGCTACGTGCCCTTCCACATCCAGGTGCCCCAGAAATTTTTCGCCATCAAGAGCCTCCTGCTCCTGCCCGG

GTCCTACACCTACGAGTGGAACTTCCGCAAGGACGTCAACATGATCCTGCAGAGCTCCCTCGGCAACGACC

TGCGCACGGACGGGGCCTCCATCTCCTTCACCAGCATCAACCTCTACGCCACCTTCTTCCCCATGGCGCACA

ACACGGCCTCCACGCTCGAGGCCATGCTGCGCAACGACACCAACGACCAGTCCTTCAACGACTACCTCTCG

GCGGCCAACATGCTCTACCCCATCCCGGCCAACGCCACCAACGTGCCCATCTCCATCCCCTCGCGCAACTG

GGCCGCCTTCCGCGGCTGGTCCTTCACGCGTCTCAAGACCAAGGAGACGCCCTCGCTGGGCTCCGGGTTCG

ACCCCTACTTCGTCTACTCGGGCTCCATCCCCTACCTCGACGGCACCTTCTACCTCAACCACACCTTCAAGA

AGGTCTCCATCACCTTCGACTCCTCCGTCAGCTGGCCCGGCAACGACCGGCTCCTGACGCCCAACGAGTTC

GAAATCAAGCGCACCGTCGACGGCGAGGGCTACAACGTGGCCCAGTGCAACATGACCAAGGACTGGTTCC

TGGTCCAGATGCTGGCCCACTACAACATCGGCTACCAGGGCTTCTACGTGCCCGAGGGCTACAAGGACCGC

ATGTACTCCTTCTTCCGCAACTTCCAGCCCATGAGCCGCCAGGTGGTGGACGAGGTCAACTACAAGGACTA

-continued

CCAGGCCGTCACCCTGGCCTACCAGCACAACAACTCGGGCTTCGTCGGCTACCTCGCGCCCACCATGCGCC

AGGGCCAGCCCTACCCCGCCAACTACCCCTACCCGCTCATCGGCAAGAGCGCCGTCACCAGCGTCACCCAG

AAAAAGTTCCTCTGCGACAGGGTCATGTGGCGCATCCCCTTCTCCAGCAACTTCATGTCCATGGGCGCGCTC

ACCGACCTCGGCCAGAACATGCTCTATGCCAACTCCGCCCACGCGCTAGACATGAATTTCGAAGTCGACCC

CATGGATGAGTCCACCCTTCTCTATGTTGTCTTCGAAGTCTTCGACGTCGTCCGAGTGCACCAGCCCCACCG

CGGCGTCATCGAGGCCGTCTACCTGCGCACCCCCTTCTCGGCCGGTAACGCCACCACCTAAGCTCTTGCTTC

TTGCAAGCCATGGCCGCGGGCTCCGGCGAGCAGGAGCTCAGGGCCATCATCCGCGACCTGGGCTGCGGGC

CCTACTTCCTGGGCACCTTCGATAAGCGCTTCCCGGGATTCATGGCCCCGCACAAGCTGGCCTGCGCCATCG

TCAACACGGCCGGCCGCGAGACCGGGGGCGAGCACTGGCTGGCCTTCGCCTGGAACCCGCGCTCGAACAC

CTGCTACCTCTTCGACCCCTTCGGGTTCTCGGACGAGCGCCTCAAGCAGATCTACCAGTTCGAGTACGAGG

GCCTGCTGCGCCGCAGCGCCCTGGCCACCGAGGACCGCTGCGTCACCCTGGAAAAGTCCACCCAGACCGTG

CAGGGTCCGCGCTCGGCCGCCTGCGGGCTCTTCTGCTGCATGTTCCTGCACGCCTTCGTGCACTGGCCCGAC

CGCCCCATGGACAAGAACCCCACCATGAACTTGCTGACGGGGGTGCCCAACGGCATGCTCCAGTCGCCCCA

GGTGGAACCCACCCTGCGCCGCAACCAGGAGGCGCTCTACCGCTTCCTCAACTCCCACTCCGCCTACTTTCG

CTCCCACCGCGCGCGCATCGAGAAGGCCACCGCCTTCGACCGCATGAATCAAGACATGTAAACCGTGTGTG

TATGTTAAATGTCTTTAATAAACAGCACTTTCATGTTACACATGCATCTGAGATGATTTATTTAGAAATCGA

AAGGGTTCTGCCGGGTCTCGGCATGGCCCGCGGGCAGGGACACGTTGCGGAACTGGTACTTGGCCAGCCAC

TTGAACTCGGGGATCAGCAGTTTGGGCAGCGGGGTGTCGGGGAAGGAGTCGGTCCACAGCTTCCGCGTCAG

TTGCAGGGCGCCCAGCAGGTCGGGCGCGGAGATCTTGAAATCGCAGTTGGGACCCGCGTTCTGCGCGCGGG

AGTTGCGGTACACGGGGTTGCAGCACTGGAACACCATCAGGGCCGGGTGCTTCACGCTCGCCAGCACCGTC

GCGTCGGTGATGCTCTCCACGTCGAGGTCCTCGGCGTTGGCCATCCCGAAGGGGGTCATCTTGCAGGTCTG

CCTTCCCATGGTGGGCACGCACCCGGGCTTGTGGTTGCAATCGCAGTGCAGGGGGATCAGCATCATCTGGG

CCTGGTCGGCGTTCATCCCCGGGTACATGGCCTTCATGAAAGCCTCCAATTGCCTGAACGCCTGCTGGGCCT

TGGCTCCCTCGGTGAAGAAGACCCCGCAGGACTTGCTAGAGAACTGGTTGGTGGCGCACCCGGCGTCGTGC

ACGCAGCAGCGCGCGTCGTTGTTGGCCAGCTGCACCACGCTGCGCCCCCAGCGGTTCTGGGTGATCTTGGC

CCGGTCGGGGTTCTCCTTCAGCGCGCGCTGCCCGTTCTCGCTCGCCACATCCATCTCGATCATGTGCTCCTTC

TGGATCATGGTGGTCCCGTGCAGGCACCGCAGCTTGCCCTCGGCCTCGGTGCACCCGTGCAGCCACAGCGC

GCACCCGGTGCACTCCCAGTTCTTGTGGGCGATCTGGGAATGCGCGTGCACGAAGCCCTGCAGGAAGCGGC

CCATCATGGTGGTCAGGGTCTTGTTGCTAGTGAAGGTCAGCGGAATGCCGCGGTGCTCCTCGTTGATGTACA

GGTGGCAGATGCGGCGGTACACCTCGCCCTGCTCGGGCATCAGCTGGAAGTTGGCTTTCAGGTCGGTCTCC

ACGCGGTAGCGGTCCATCAGCATAGTCATGATTTCCATACCCTTCTCCCAGGCCGAGACGATGGGCAGGCT

CATAGGGTTCTTCACCATCATCTTAGCGCTAGCAGCCGCGGCCAGGGGGTCGCTCTCGTCCAGGGTCTCAA

AGCTCCGCTTGCCGTCCTTCTCGGTGATCCGCACCGGGGGGTAGCTGAAGCCCACGGCCGCCAGCTCCTCCT

CGGCCTGTCTTTCGTCCTCGCTGTCCTGGCTGACGTCCTGCAGGACCACATGCTTGGTCTTGCGGGGTTTCTT

CTTGGGCGGCAGCGGCGGCGGAGATGTTGGAGATGGCGAGGGGGAGCGCGAGTTCTCGCTCACCACTACT

ATCTCTTCCTCTTCTTGGTCCGAGGCCACGCGGCGGTAGGTATGTCTCTTCGGGGGCAGAGGCGGAGGCGA

CGGGCTCTCGCCGCCGCGACTTGGCGGATGGCTGGCAGAGCCCCTTCCGCGTTCGGGGGTGCGCTCCCGGC

GGCGCTCTGACTGACTTCCTCCGCGGCCGGCCATTGTGTTCTCCTAGGGAGGAACAACAAGCATGGAGACT

CAGCCATCGCCAACCTCGCCATCTGCCCCCACCGCCGACGAGAAGCAGCAGCAGCAGAATGAAAGCTTAA

CCGCCCCGCCGCCCAGCCCCGCCACCTCCGACGCGGCCGTCCCAGACATGCAAGAGATGGAGGAATCCATC

GAGATTGACCTGGGCTATGTGACGCCCGCGGAGCACGAGGAGGAGCTGGCAGTGCGCTTTTCACAAGAAG

-continued

AGATACACCAAGAACAGCCAGAGCAGGAAGCAGAGAATGAGCAGAGTCAGGCTGGGCTCGAGCATGACG

GCGACTACCTCCACCTGAGCGGGGGGGAGGACGCGCTCATCAAGCATCTGGCCCGGCAGGCCACCATCGTC

AAGGATGCGCTGCTCGACCGCACCGAGGTGCCCCTCAGCGTGGAGGAGCTCAGCCGCGCCTACGAGTTGA

ACCTCTTCTCGCCGCGCGTGCCCCCCAAGCGCCAGCCCAATGGCACCTGCGAGCCCAACCCGCGCCTCAAC

TTCTACCCGGTCTTCGCGGTGCCCGAGGCCCTGGCCACCTACCACATCTTTTTCAAGAACCAAAAGATCCCC

GTCTCCTGCCGCGCCAACCGCACCCGCGCCGACGCCCTTTTCAACCTGGGTCCCGGCGCCCGCCTACCTGAT

ATCGCCTCCTTGGAAGAGGTTCCCAAGATCTTCGAGGGTCTGGGCAGCGACGAGACTCGGGCCGCGAACGC

TCTGCAAGGAGAAGGAGGAGAGCATGAGCACCACAGCGCCCTGGTCGAGTTGGAAGGCGACAACGCGCGG

CTGGCGGTGCTCAAACGCACGGTCGAGCTGACCCATTTCGCCTACCCGGCTCTGAACCTGCCCCCCAAAGT

CATGAGCGCGGTCATGGACCAGGTGCTCATCAAGCGCGCGTCGCCCATCTCCGAGGACGAGGGCATGCAA

GACTCCGAGGAGGGCAAGCCCGTGGTCAGCGACGAGCAGCTGGCCCGGTGGCTGGGTCCTAATGCTAGTC

CCCAGAGTTTGGAAGAGCGGCGCAAACTCATGATGGCCGTGGTCCTGGTGACCGTGGAGCTGGAGTGCCTG

CGCCGCTTCTTCGCCGACGCGGAGACCCTGCGCAAGGTCGAGGAGAACCTGCACTACCTCTTCAGGCACGG

GTTCGTGCGCCAGGCCTGCAAGATCTCCAACGTGGAGCTGACCAACCTGGTCTCCTACATGGGCATCTTGC

ACGAGAACCGCCTGGGGCAGAACGTGCTGCACACCACCCTGCGCGGGGAGGCCCGGCGCGACTACATCCG

CGACTGCGTCTACCTCTACCTCTGCCACACCTGGCAGACGGGCATGGGCGTGTGGCAGCAGTGTCTGGAGG

AGCAGAACCTGAAAGAGCTCTGCAAGCTCCTGCAGAAGAACCTCAAGGGTCTGTGGACCGGGTTCGACGA

GCGCACCACCGCCTCGGACCTGGCCGACCTCATTTTCCCCGAGCGCCTCAGGCTGACGCTGCGCAACGGCC

TGCCCGACTTTATGAGCCAAAGCATGTTGCAAAACTTTCGCTCTTTCATCCTCGAACGCTCCGGAATCCTGC

CCGCCACCTGCTCCGCGCTGCCCTCGGACTTCGTGCCGCTGACCTTCCGCGAGTGCCCCCCGCCGCTGTGGA

GCCACTGCTACCTGCTGCGCCTGGCCAACTACCTGGCCTACCACTCGGACGTGATCGAGGACGTCAGCGGC

GAGGGCCTGCTCGAGTGCCACTGCCGCTGCAACCTCTGCACGCCGCACCGCTCCCTGGCCTGCAACCCCCA

GCTGCTGAGCGAGACCCAGATCATCGGCACCTTCGAGTTGCAAGGGCCCAGCGAAGGCGAGGGTTCAGCC

GCCAAGGGGGGTCTGAAACTCACCCCGGGGCTGTGGACCTCGGCCTACTTGCGCAAGTTCGTGCCCGAGGA

CTACCATCCCTTCGAGATCAGGTTCTACGAGGACCAATCCCATCCGCCCAAGGCCGAGCTGTCGGCCTGCG

TCATCACCCAGGGGGCGATCCTGGCCCAATTGCAAGCCATCCAGAAATCCCGCCAAGAATTCTTGCTGAAA

AAGGGCCGCGGGGTCTACCTCGACCCCCAGACCGGTGAGGAGCTCAACCCCGGCTTCCCCCAGGATGCCCC

GAGGAAACAAGAAGCTGAAAGTGGAGCTGCCGCCCGTGGAGGATTTGGAGGAAGACTGGGAGAACAGCA

GTCAGGCAGAGGAGGAGGAGATGGAGGAAGACTGGGACAGCACTCAGGCAGAGGAGGACAGCCTGCAAG

ACAGTCTGGAGGAAGACGAGGAGGAGGCAGAGGAGGAGGTGGAAGAAGCAGCCGCCGCCAGACCGTCGT

CCTCGGCGGGGGAGAAAGCAAGCAGCACGGATACCATCTCCGCTCCGGGTCGGGGTCCCGCTCGACCACA

CAGTAGATGGGACGAGACCGGACGATTCCCGAACCCCACCACCCAGACCGGTAAGAAGGAGCGGCAGGGA

TACAAGTCCTGGCGGGGGCACAAAAACGCCATCGTCTCCTGCTTGCAGGCCTGCGGGGGCAACATCTCCTT

CACCCGGCGCTACCTGCTCTTCCACCGCGGGGTGAACTTTCCCCGCAACATCTTGCATTACTACCGTCACCT

CCACAGCCCCTACTACTTCCAAGAAGAGGCAGCAGCAGCAGAAAAAGACCAGCAGAAAACCAGCAGCTAG

AAAATCCACAGCGGCGGCAGCAGGTGGACTGAGGATCGCGGCGAACGAGCCGGCGCAAACCCGGGAGCT

GAGGAACCGGATCTTTCCCACCCTCTATGCCATCTTCCAGCAGAGTCGGGGGCAGGAGCAGGAACTGAAAG

TCAAGAACCGTTCTCTGCGCTCGCTCACCCGCAGTTGTCTGTATCACAAGAGCGAAGACCAACTTCAGCGC

ACTCTCGAGGACGCCGAGGCTCTCTTCAACAAGTACTGCGCGCTCACTCTTAAAGAGTAGCCCGCGCCCGC

CCAGTCGCAGAAAAAGGCGGGAATTACGTCACCTGTGCCCTTCGCCCTAGCCGCCTCCACCCATCATCATG

-continued

```
AGCAAAGAGATTCCCACGCCTTACATGTGGAGCTACCAGCCCCAGATGGGCCTGGCCGCCGGTGCCGCCCA

GGACTACTCCACCCGCATGAATTGGCTCAGCGCCGGGCCCGCGATGATCTCACGGGTGAATGACATCCGCG

CCCACCGAAACCAGATACTCCTAGAACAGTCAGCGCTCACCGCCACGCCCCGCAATCACCTCAATCCGCGT

AATTGGCCCGCCGCCCTGGTGTACCAGGAAATTCCCCAGCCCACGACCGTACTACTTCCGCGAGACGCCCA

GGCCGAAGTCCAGCTGACTAACTCAGGTGTCCAGCTGGCGGGCGGCGCCACCCTGTGTCGTCACCGCCCCG

CTCAGGGTATAAAGCGGCTGGTGATCCGGGGCAGAGGCACACAGCTCAACGACGAGGTGGTGAGCTCTTC

GCTGGGTCTGCGACCTGACGGAGTCTTCCAACTCGCCGGATCGGGGAGATCTTCCTTCACGCCTCGTCAGG

CCGTCCTGACTTTGGAGAGTTCGTCCTCGCAGCCCCGCTCGGGTGGCATCGGCACTCTCCAGTTCGTGGAGG

AGTTCACTCCCTCGGTCTACTTCAACCCCTTCTCCGGCTCCCCCGGCCACTACCCGGACGAGTTCATCCCGA

ACTTCGACGCCATCAGCGAGTCGGTGGACGGCTACGATTGAAACTAATCACCCCCTTATCCAGTGAAATAA

AGATCATATTGATGATGATTTTACAGAAATAAAAAATAATCATTTGATTTGAAATAAAGATACAATCATAT

TGATGATTTGAGTTTAACAAAAAAATAAAGAATCACTTACTTGAAATCTGATACCAGGTCTCTGTCCATGTT

TTCTGCCAACACCACTTCACTCCCCTCTTCCCAGCTCTGGTACTGCAGGCCCCGGCGGGCTGCAAACTTCCT

CCACACGCTGAAGGGGATGTCAAATTCCTCCTGTCCCTCAATCTTCATTTTATCTTCTATCAGATGTCCAAA

AAGCGCGTCCGGGTGGATGATGACTTCGACCCCGTCTACCCCTACGATGCAGACAACGCACCGACCGTGCC

CTTCATCAACCCCCCCTTCGTCTCTTCAGATGGATTCCAAGAGAAGCCCCTGGGGGTGTTGTCCCTGCGACT

GGCCGACCCCGTCACCACCAAGAACGGGGAAATCACCCTCAAGCTGGGAGAGGGGGTGGACCTCGATTCC

TCGGGAAAACTCATCTCCAACACGGCCACCAAGGCCGCCGCCCCTCTCAGTTTTTCCAACAACACCATTTCC

CTTAACATGGATCACCCCTTTTACACTAAAGATGGAAAATTATCCTTACAAGTTTCTCCACCATTAAATATA

CTGAGAACAAGCATTCTAAACACACTAGCTTTAGGTTTTGGATCAGGTTTAGGACTCCGTGGCTCTGCCTTG

GCAGTACAGTTAGTCTCTCCACTTACATTTGATACTGATGGAAACATAAAGCTTACCTTAGACAGAGGTTTG

CATGTTACAACAGGAGATGCAATTGAAAGCAACATAAGCTGGGCTAAAGGTTTAAAATTTGAAGATGGAG

CCATAGCAACCAACATTGGAAATGGGTTAGAGTTTGGAAGCAGTAGTACAGAAACAGGTGTTGATGATGCT

TACCCAATCCAAGTTAAACTTGGATCTGGCCTTAGCTTTGACAGTACAGGAGCCATAATGGCTGGTAACAA

AGAAGACGATAAACTCACTTTGTGGACAACACCTGATCCATCACCAAACTGTCAAATACTCGCAGAAAATG

ATGCAAAACTAACACTTTGCTTGACTAAATGTGGTAGTCAAATACTGGCCACTGTGTCAGTCTTAGTTGTAG

GAAGTGGAAACCTAAACCCCATTACTGGCACCGTAAGCAGTGCTCAGGTGTTTCTACGTTTTGATGCAAAC

GGTGTTCTTTTAACAGAACATTCTACACTAAAAAAATACTGGGGGTATAGGCAGGGAGATAGCATAGATGG

CACTCCATATACCAATGCTGTAGGATTCATGCCCAATTTAAAAGCTTATCCAAAGTCACAAAGTTCTACTAC

TAAAAATAATATAGTAGGGCAAGTATACATGAATGGAGATGTTTCAAAACCTATGCTTCTCACTATAACCC

TCAATGGTACTGATGACAGCAACAGTACATATTCAATGTCATTTTCATACACCTGGACTAATGGAAGCTATG

TTGGAGCAACATTTGGGGCTAACTCTTATACCTTCTCATACATCGCCCAAGAATGAACACTGTATCCCACCC

TGCATGCCAACCCTTCCCACCCCACTCTGTGGAACAAACTCTGAAACACAAAATAAAATAAAGTTCAAGTG

TTTTATTGATTCAACAGTTTTACAGGATTCGAGCAGTTATTTTTCCTCCACCCTCCCAGGACATGGAATACA

CCACCCTCTCCCCCCGCACAGCCTTGAACATCTGAATGCCATTGGTGATGGACATGCTTTTGGTCTCCACGT

TCCACACAGTTTCAGAGCGAGCCAGTCTCGGGTCGGTCAGGGAGATGAAACCCTCCGGGCACTCCCGCATC

TGCACCTCACAGCTCAACAGCTGAGGATTGTCCTCGGTGGTCGGGATCACGGTTATCTGGAAGAAGCAGAA

GAGCGGCGGTGGGAATCATAGTCCGCGAACGGGATCGGCCGGTGGTGTCGCATCAGGCCCCGCAGCAGTC

GCTGCCGCCGCCGCTCCGTCAAGCTGCTGCTCAGGGGGTCCGGGTCCAGGGACTCCCTCAGCATGATGCCC

ACGGCCCTCAGCATCAGTCGTCTGGTGCGGCGGGCGCAGCAGCGCATGCGGATCTCGCTCAGGTCGCTGCA

GTACGTGCAACACAGAACCACCAGGTTGTTCAACAGTCCATAGTTCAACACGCTCCAGCCGAAACTCATCG
```

-continued

```
CGGGAAGGATGCTACCCACGTGGCCGTCGTACCAGATCCTCAGGTAAATCAAGTGGTGCCCCCTCCAGAAC

ACGCTGCCCACGTACATGATCTCCTTGGGCATGTGGCGGTTCACCACCTCCCGGTACCACATCACCCTCTGG

TTGAACATGCAGCCCCGGATGATCCTGCGGAACCACAGGGCCAGCACCGCCCCGCCCGCCATGCAGCGAA

GAGACCCCGGGTCCCGGCAATGGCAATGGAGGACCCACCGCTCGTACCCGTGGATCATCTGGGAGCTGAA

CAAGTCTATGTTGGCACAGCACAGGCATATGCTCATGCATCTCTTCAGCACTCTCAACTCCTCGGGGGTCAA

AACCATATCCCAGGGCACGGGGAACTCTTGCAGGACAGCGAACCCCGCAGAACAGGGCAATCCTCGCACA

GAACTTACATTGTGCATGGACAGGGTATCGCAATCAGGCAGCACCGGGTGATCCTCCACCAGAGAAGCGC

GGGTCTCGGTCTCCTCACAGCGTGGTAAGGGGGCCGGCCGATACGGGTGATGGCGGGACGCGGCTGATCGT

GTTCGCGACCGTGTCATGATGCAGTTGCTTTCGGACATTTTCGTACTTGCTGTAGCAGAACCTGGTCCGGGC

GCTGCACACCGATCGCCGGCGGCGGTCTCGGCGCTTGGAACGCTCGGTGTTGAAATTGTAAAACAGCCACT

CTCTCAGACCGTGCAGCAGATCTAGGGCCTCAGGAGTGATGAAGATCCCATCATGCCTGATGGCTCTGATC

ACATCGACCACCGTGGAATGGGCCAGACCCAGCCAGATGATGCAATTTTGTTGGGTTTCGGTGACGGCGAG

CCTCGGGAACAACGATGAAGTAAATGCAAGCGGTGCGTTCCAGCATGGTTAGTTAGCTGATCTGTAGAAAA

AACAAAAATGAACATTAAACCATGCTAGCCTGGCGAACAGGTGGGTAAATCGTTCTCTCCAGCACCAGGCA

GGCCACGGGGTCTCCGGCGCGACCCTCGTAAAAATTGTCGCTATGATTGAAAACCATCACAGAGAGACGTT

CCCGGTGGCCGGCGTGAATGATTCGACAAGATGAATACACCCCCGGAACATTGGCGTCCGCGAGTGAAAA

AAAGCGCCCGAGGAAGCAATAAGGCACTACAATGCTCAGTCTCAAGTCCAGCAAAGCGATGCCATGCGGA

TGAAGCACAAAATTCTCAGGTGCGTACAAAATGTAATTACTCCCCTCCTGCACAGGCAGCAAAGCCCCCGA

TCCCTCCAGGTACACATACAAAGCCTCAGCGTCCATAGCTTACCGAGCAGCAGCACACAACAGGCGCAAG

AGTCAGAGAAAGGCTGAGCTCTAACCTGTCCACCCGCTCTCTGCTCAATATATAGCCCAGATCTACACTGA

CGTAAAGGCCAAAGTCTAAAAATACCCGCCAAATAATCACACACGCCCAGCACACGCCCAGAAACCGGTG

ACACACTCAAAAAAATACGCGCACTTCCTCAAACGCCCAAAACTGCCGTCATTTCCGGGTTCCCACGCTAC

GTCATCAAAACACGACTTTCAAATTCCGTCGACCGTTAAAAACGTCACCCGCCCCGCCCCTAACGGTCGCC

CGTCTCTCAGCCAATCAGCGCCCCGCATCCCCAAATTCAAACACCTCATTTGCATATTAACGCGCACAAAA

AGTTTGAGGTATATTATTGATGATG
```

Immune Monitoring Mice

Lymphocytes were isolated from freshly harvested spleens and lymph nodes of immunized mice. Tissues were dissociated in RPMI containing 10% fetal bovine serum with penicillin and streptomycin (complete RPMI) using the GentleMACS tissue dissociator according to the manufacturer's instructions. Freshly isolated lymphocytes at a density of 2-5×$10^6$ cells/mL were incubated with 10 uM of the indicated peptides for 2 hours. After two hours, brefeldin A was added to a concentration of 5 ug/ml and cells were incubated with stimulant for an additional 4 hours. Following stimulation, viable cells were labeled with fixable viability dye eFluor780 according to manufacturer's protocol and stained with anti-CD8 APC (clone 53-6.7, BioLegend) at 1:400 dilution. Anti-IFNg PE (clone XMG1.2, BioLegend) was used at 1:100 for intracellular staining. Samples were collected on an Attune N×T Flow Cytometer (Thermo Scientific). Flow cytometry data was plotted and analyzed using FlowJo. To assess degree of antigen-specific response, both the percent IFNg+ of CD8+ cells and the total IFNg+ cell number/1×$10^6$ live cells were calculated in response to each peptide stimulant.

Immune Monitoring NHPs

PBMCs were isolated at indicated times after prime vaccination using Lymphocyte Separation Medium (LSM, MP Biomedicals) and LeucoSep separation tubes (Greiner Bio-One) and resuspended in RPMI containing 10% FBS and penicillin/streptomycin. Cells were counted on the Attune N×T flow cytometer (Thermo Fisher) using propidium iodide staining to exclude dead and apoptotic cells. Cell were then adjusted to the appropriate concentration of live cells for subsequent analysis. For each monkey in the studies, T cell responses were measured using ELISpot or flow cytometry methods. T cell responses to 6 different rhesus macaque Mamu-A*01 class I epitopes encoded in the vaccines were monitored from PBMCs by measuring induction of cytokines, such as IFN-gamma, using ex vivo enzyme-linked immunospot (ELISpot) analysis. ELISpot analysis was performed according to ELISPOT harmonization guidelines {DOI: 10.1038/nprot.2015.068} with the monkey IFNg ELISpotPLUS kit (MABTECH). 200,000 PBMCs were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Results

Figure 25:
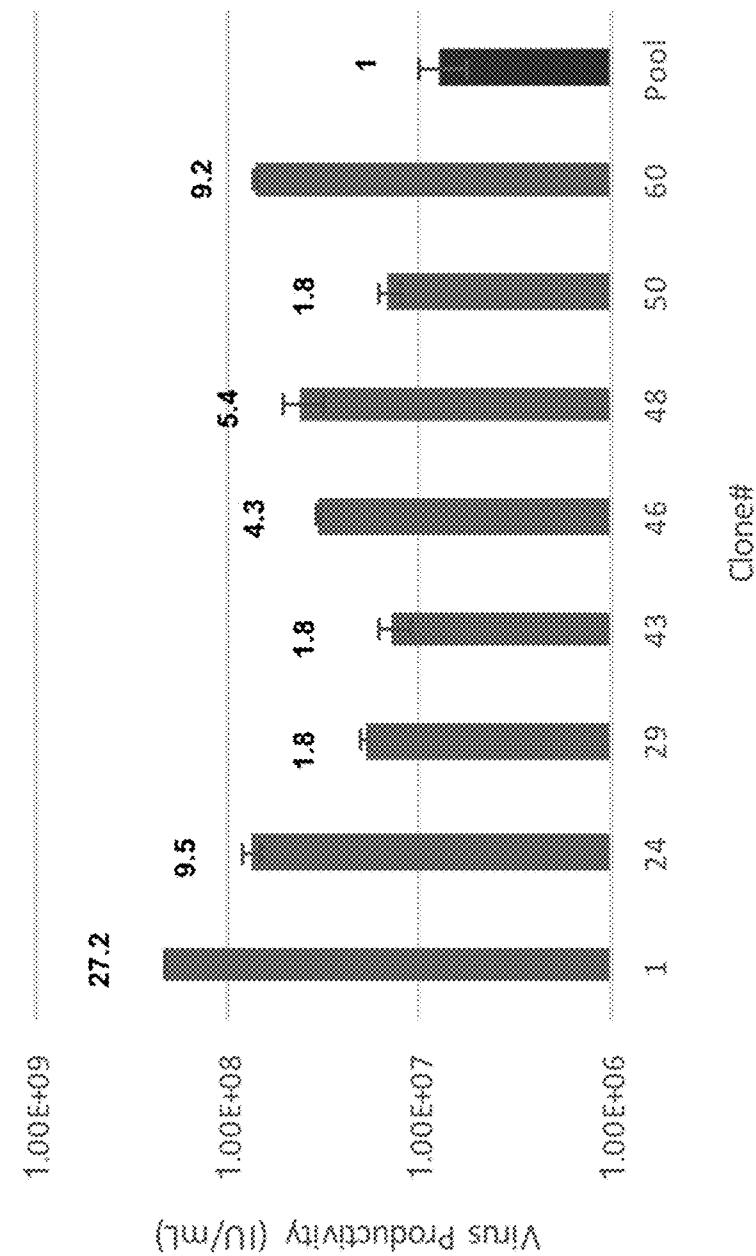
FIG. 25 shows productivity, as assessed by IU titers, of the eight selected ChAdV68-MAG rapidly growing plaques compared to the non-purified pooled virus. Numbers above the columns on the graph indicate fold improvement over the pooled virus in a controlled infection at an MOI of 0.1.

Fast growing/fit ChAdV68 viruses that express the model TSNA cassette MAG (ChAdV68.5WTnt.MAG25mer; SEQ ID NO:2) were selected for during plaque isolation, as described. Of the original 75 plaques, 33 produced virus, as indicated by some signs of CPE (Cytopathic effect) and of those 8 grew more rapidly than the rest as indicated by significant plaque numbers or the size of plaques after 7 days of incubation. Rapidly growing clones were selected for virus production in 400 mL 293F (ThermoFisher cat. No. A14528) suspension cultures. Infectious units (IU) titers were determined for the 8 clones. As shown in FIG. 25, all selected clones demonstrated IU titers at or above the unpurified pooled virus reference. Clones 1, 24, and 60 demonstrated at least a 9-fold increase in IU titers relative to the unpurified pooled virus reference.

Figure 26:
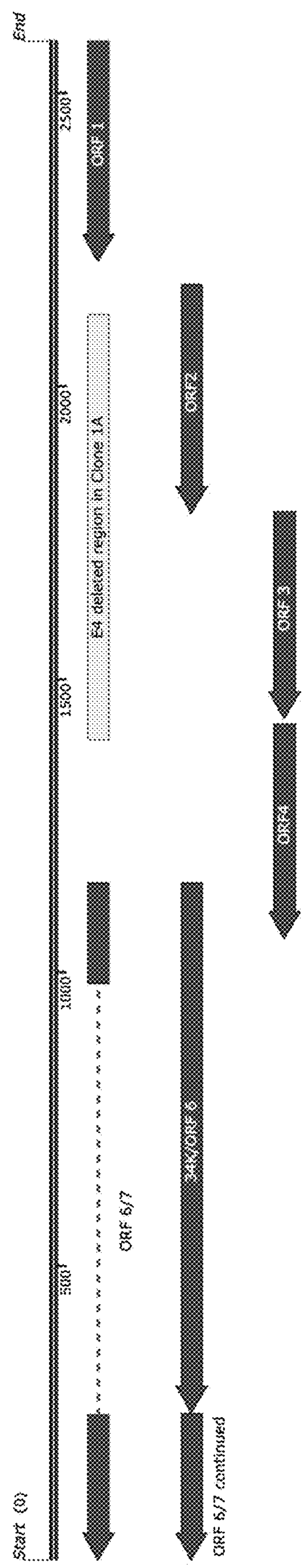
FIG. 26 shows a schematic of the E4 locus and the 727 bp deletion between E4orf2-E4orf4 identified in Clone 1A.

Clones 1, 24, and 60 (the 3 most productive clones) were further analyzed by NGS and indicated each contained deletions in the E4 region. Two of the clones (Clone 1A & clone 24) shared an identical 727 bp mutation between E4orf2-E4orf4 (FIG. 26), specifically between 34,916 to 35,642 bp of the wild-type ChAdV68 virus (SEQ ID NO: 1). Clone 60 was deleted in the E4orf1-E4orf3 region (34,980-36,516), but the deletion was larger (1539 bp). Based on these deletions Orf 2 & 3 deletions (34,979-35,642) are common to both clone sets suggesting the Orf 2 & 3 deletions contribute to the productivity improvement.

Figure 27:
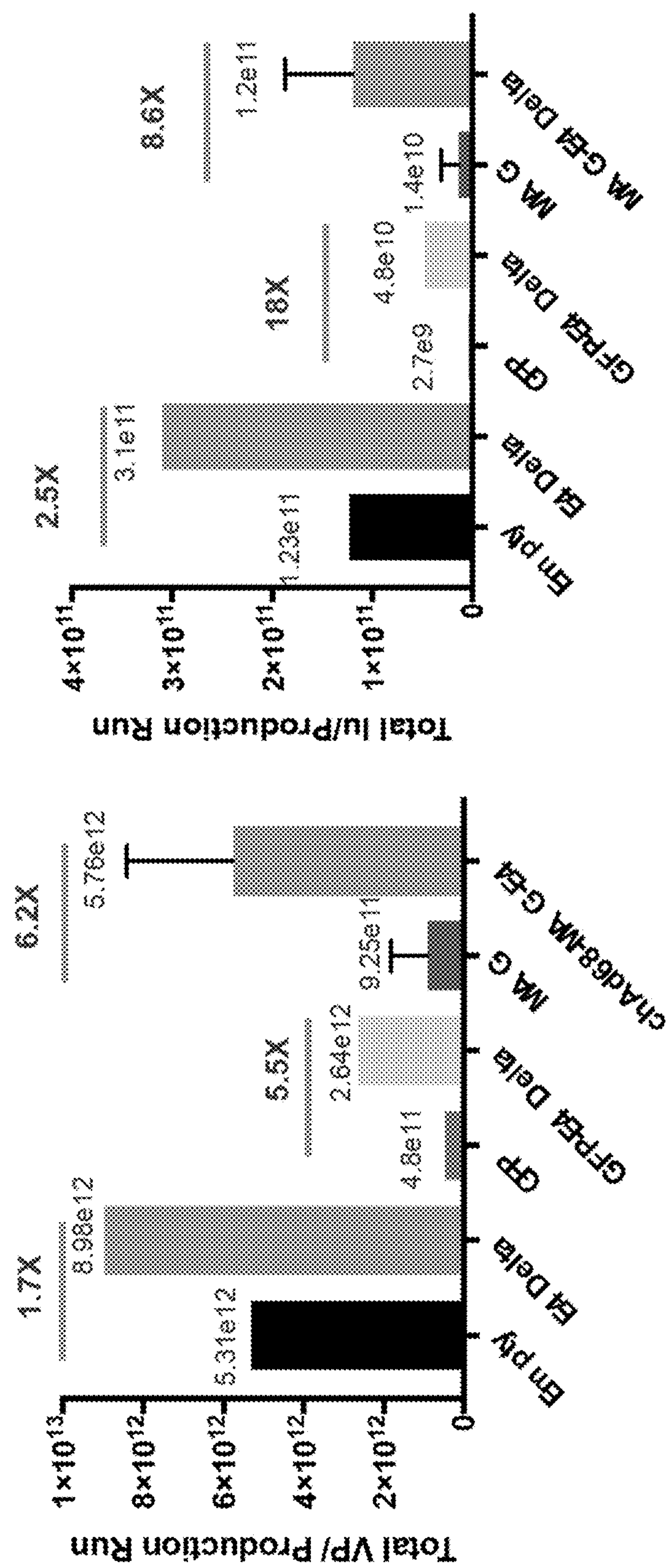
FIG. 27 shows virus productivity with viruses plus and minus the E4 deletion. Numbers above the bar indicate fold improvement over non-E4 deleted virus. The ChAdV68-MAG comparison to ChAdV68-MAG-E4 virus was performed on 3 separate occasions. In each case a 400 mL production run with both viruses was performed at an MOI of 1.0. Shown are viral particle (VP) titers (left panel) and infectious unit (IU) titers (right panel).

Three E4 deleted viral vectors were generated deleting the E4 region portion deleted in Clones 1A and 24 and compared with their original non-E4 deleted vectors. The vectors chosen were 1) ChAdV-Empty ("Empty") with no cassette or regulatory regions (promoter or poly-A) 2) ChAdV68.5WTnt.GFP (SEQ ID NO: 13; "GFP"), and 3) ChAdV68.5WTnt.MAG25mer (SEQ ID NO:2; "MAG"). They are all based on sequence AC_000011.1 with E1 (nt577 to 3403) and E3 deleted (nt 27,125-31,825) [SEQ ID NO: 1]. These were compared to the same vectors but deleted in the E4 region that we identified (34,916 to 35,642 of SEQ ID NO:1); ChAdV68-Empty-E4deleted (SEQ ID NO: 59; "E4 Delta"), ChAdV68-GFP-E4deleted (SEQ ID NO: 58; "GFP E4 Delta"), and ChAdV68-MAG-E4deleted (SEQ ID NO: 57; "MAG E4 Delta" and "ChAdV68-MAG-E4"), respectively. These six vectors were made and viral particle (VP) and infectious unit (IU) titers determined. Productivity was evaluated at the 400 mL production scale. As shown in FIG. 27, in each comparison the E4 deleted version demonstrated increased viral particle titers (left panel) and infectious unit titers (right panel).

Figure 28:
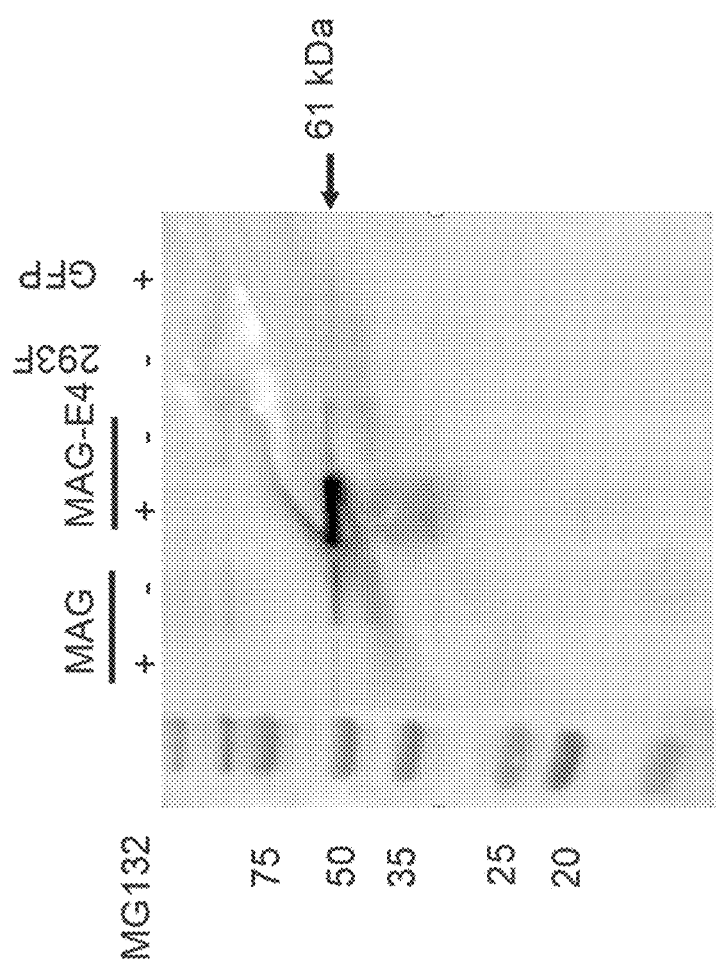
FIG. 28 shows a Western blot analysis of MAG expression using rabbit anti-class II epitope antibody expression in cells infected with ChAdV68.5WTnt.MAG25mer ("MAG") and ChAdV68-MAG-E4deleted ("MAG-E4") viruses. Samples were treated with and without the proteasome inhibitor, MG-132, as indicated by plus and minus signs.

Expression of the MAG cassette was compared between E4 deleted and non-deleted vectors. As shown in FIG. 28, Western analysis on HEK293F cell lysates infected with ChAdV68.5WTnt.MAG25mer ("MAG") and ChAdV68-MAG-E4deleted ("MAG-E4") viruses indicated that the E4 deleted virus had higher levels of the MAG cassette expressed compared to the non E4-deleted viruses.

Figure 42A:
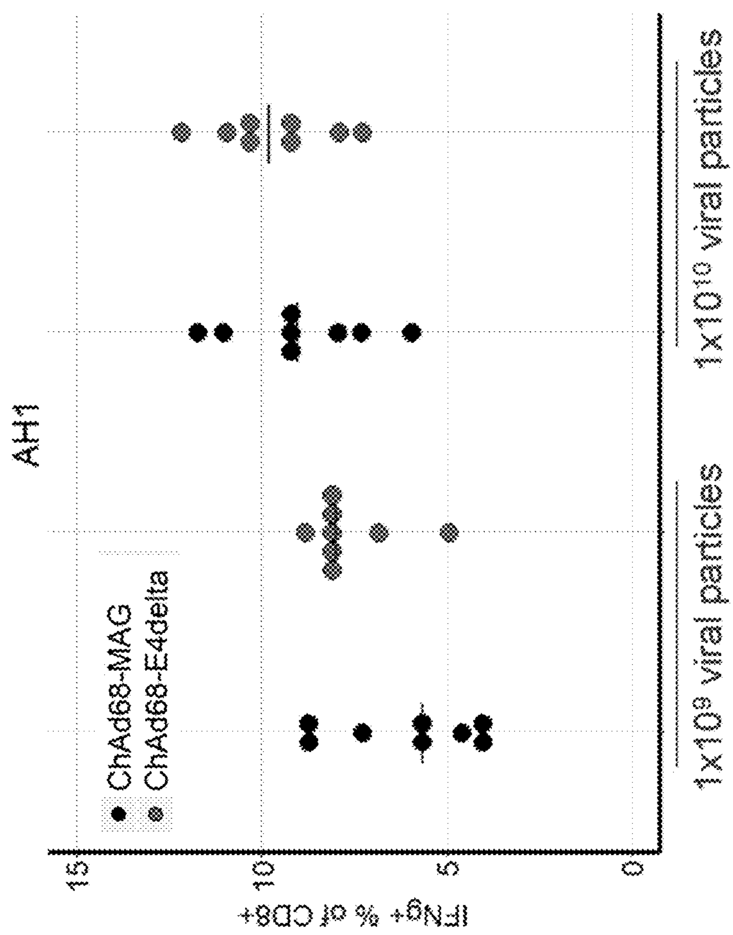
FIG. 42A shows the CD8+ immune responses by assessing IFN-gamma production by ICS following stimulation with an AH1 (a dominant epitope from Murine leukemia virus envelope protein gp70) in ChAdV68-MAG and ChAdV68-E4delta-MAG vector treated Balb/c mice. Balb/c mice were immunized by bilateral injection of 50 uL of virus into the Quadriceps (100 uL in total, 50 uL/leg).

Mice were then immunized comparing the ChAdV68.5WTnt.MAG25mer ("ChAdV68-MAG") and its E4-deleted counterpart ChAdV68-MAG-E4deleted ("ChAdV68-E4delta"). T cell responses were analyzed for IFN-gamma production by ICS following stimulation with an AH1 peptide. As shown in FIG. 42A and Table 41A, immunization with the E4-deleted vector demonstrated at least equivalent immune responses at both doses tested ($1\times10^9$ left panel, $1\times10^{10}$ right panel), with a positive trend towards an increased response in E4-deleted vectors.

TABLE 41A

IFN-gamma production by E4 deleted ChAdV68 (ICS)

| Treatment | Dose | Average IFNg + as % of CD8 | Standard deviation | N |
|---|---|---|---|---|
| ChAdV68-MAG | 1.00E+10 | 1.040875 | 0.211938 | 8 |
| ChAdV68-E4delta | 1.00E+10 | 1.084125 | 0.213109 | 8 |
| ChAdV68-MAG | 1.00E+09 | 0.61575 | 0.202046 | 8 |
| ChAdV68-E4delta | 1.00E+09 | 0.800125 | 0.189558 | 8 |

Figure 42B:
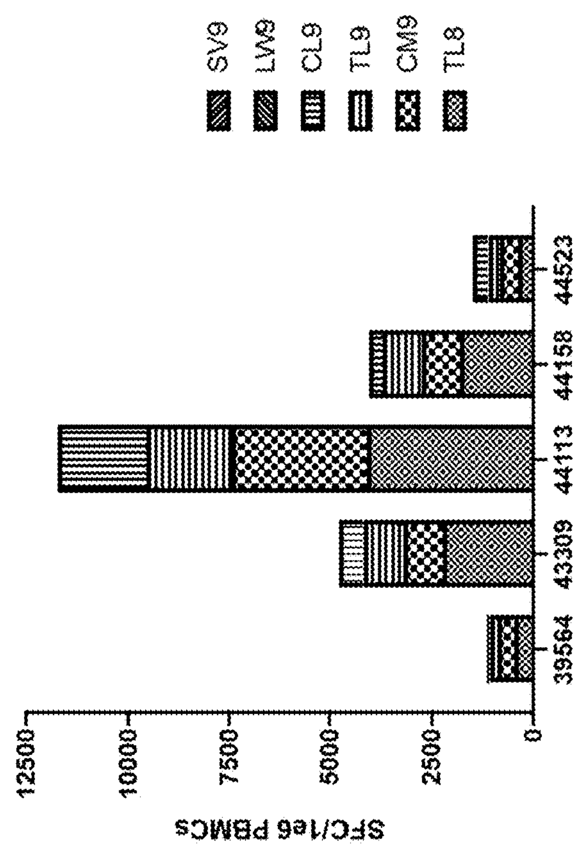
FIG. 42B shows T cell responses by assessing IFN-gamma production by ELISpot following stimulation with 6 different rhesus macaque Mamu-A*01 class I epitopes at week 2 in Rhesus macaques were immunized with ChAdV68-CMV-MAG (left panel) and ChAdV68-E4d-CMT-MAG (right panel), and both conditions administered an anti-CTLA4 antibody (Ipilimumab).
Figure 42B:
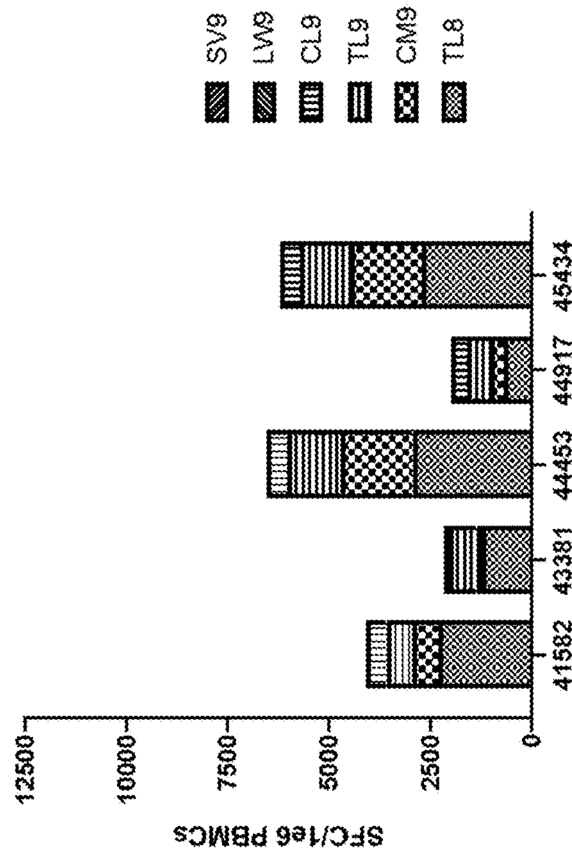
Figure 42C:
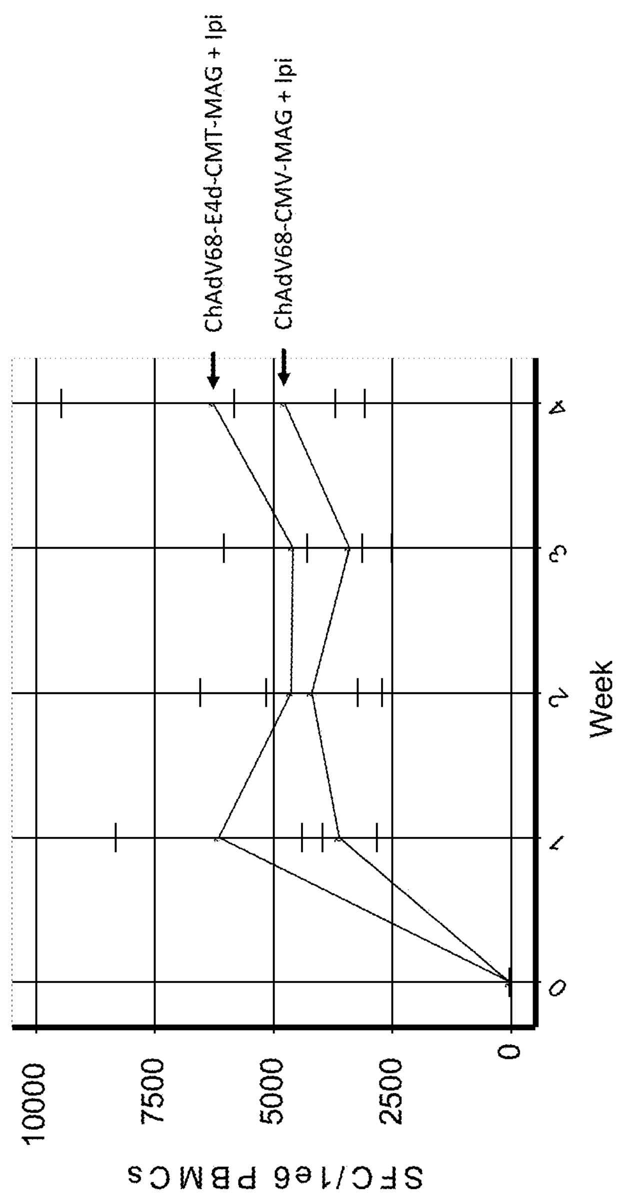
FIG. 42C shows T cell responses by assessing IFN-gamma production by ELISpot following stimulation with 6 different rhesus macaque Mamu-A*01 class I epitopes over a time course in Rhesus macaques were immunized with ChAdV68-CMV-MAG (left panel) and ChAdV68-E4d-CMT-MAG (right panel), and both conditions administered an anti-CTLA4 antibody (Ipilimumab).

Rhesus macaques were then immunized with ChAdV68.5WTnt.MAG25mer ("ChAdV68-CMV-MAG"; SEQ ID NO:2) or ChAdV68-E4d-CMT-MAG (SEQ ID NO:71), with each group also administered an anti-CTLA4 antibody (Ipilimumab). T cell responses were analyzed for IFN-gamma production by ELISpot following stimulation with 6 different rhesus macaque Mamu-A*01 class I epitopes. As shown in FIG. 42B and FIG. 42C, and quantified in Table 41B (ChAdV68-CMV-MAG) and Table 41C (ChAdV68-E4d-CMT-MAG), immunization with the E4-deleted vector demonstrated at least equivalent immune responses, with a positive trend towards an increased response in E4-deleted vectors.

TABLE 41B

Mean spot forming cells (SFC) per $10^6$ PBMCs for each epitope ± SEM for ChAdV68-CMV-MAG

| | Antigen | | | | | |
|---|---|---|---|---|---|---|
| Wk | Env CL9 | Env TL9 | Gag CM9 | Gag LW9 | Pol SV9 | Tat TL8 |
| 1 | 531 +/− 131 | 950 +/− 215 | 654 +/− 216 | 14 +/− 6 | 12 +/− 0 | 1460 +/− 272 |
| 2 | 399 +/− 74 | 887 +/− 159 | 924 +/− 351 | 0 +/− 0 | 0 +/− 0 | 1986 +/− 434 |
| 3 | 312 +/− 101 | 616 +/− 155 | 675 +/− 212 | 0 +/− 0 | 0 +/− 0 | 1795 +/− 481 |
| 4 | 533 +/− 151 | 851 +/− 129 | 1011 +/− 207 | 10 +/− 7 | 73 +/− 12 | 2290 +/− 729 |

TABLE 41C

| Mean spot forming cells (SFC) per $10^6$ PBMCs for each epitope ± SEM for ChAdV68-E4d-CMT-MAG | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 1 | 1037 +/− 285 | 966 +/− 287 | 1341 +/− 470 | 20 +/− 13 | 10 +/− 9 | 2777 +/− 1180 |
| 2 | 707 +/− 376 | 905 +/− 343 | 1217 +/− 543 | 0 +/− 0 | 0 +/− 0 | 1805 +/− 681 |
| 3 | 612 +/− 302 | 1038 +/− 361 | 1040 +/− 474 | 0 +/− 0 | 0 +/− 0 | 1906 +/− 462 |
| 4 | 1237 +/− 722 | 1282 +/− 665 | 1487 +/− 760 | 3 +/− 2 | 183 +/− 122 | 2084 +/− 943 |

XXI. Construction of a TETr-Regulated Cassette Expression System

Figure 43:
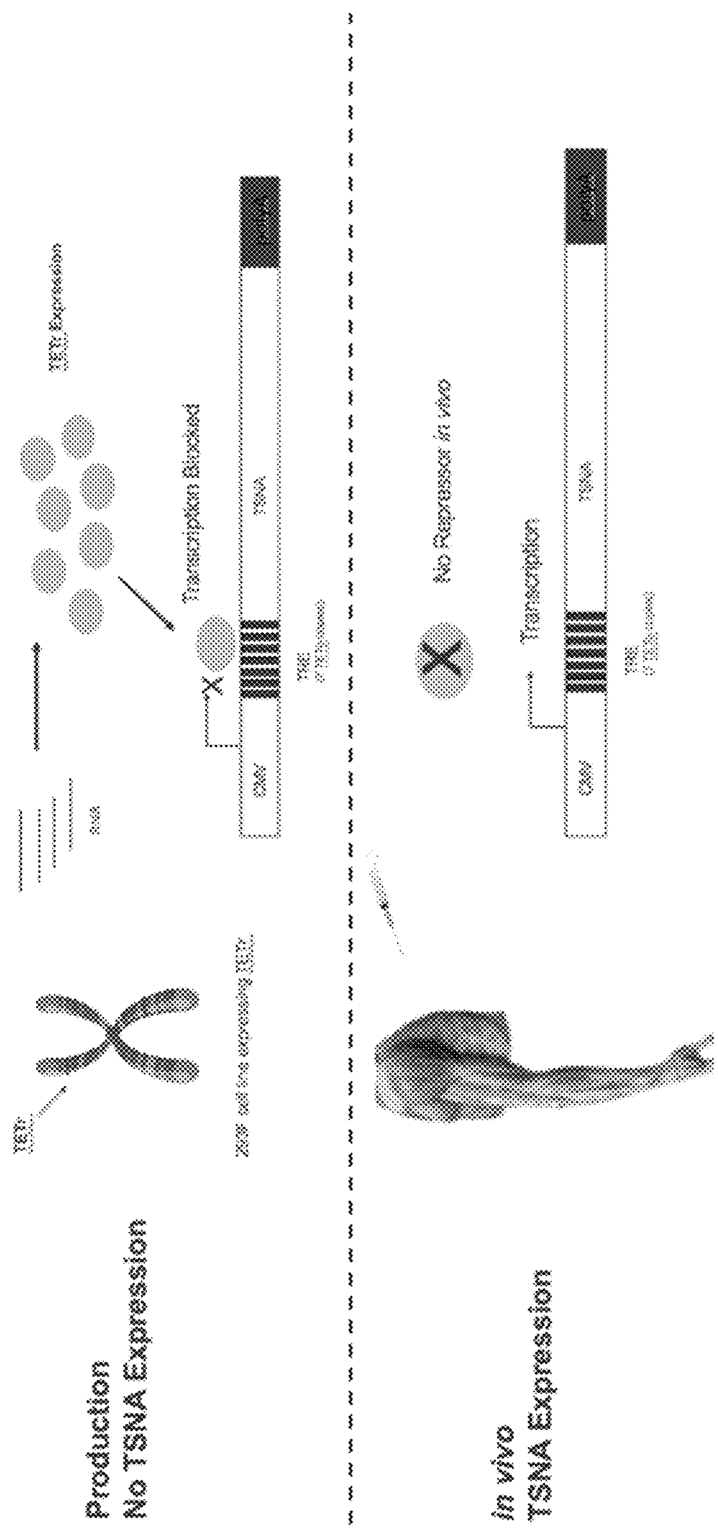
FIG. 43 illustrates the general strategy for a tetracycline-controlled viral production system using the example of antigen encoding vaccine.
Figure 44A:
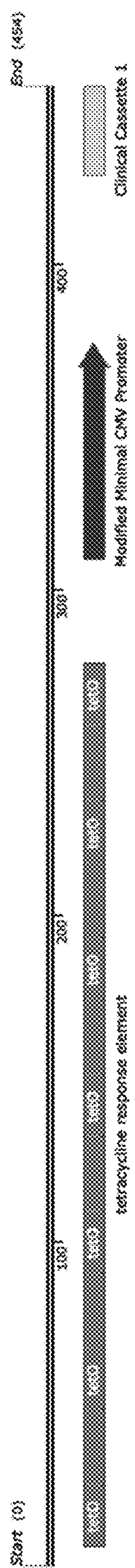
FIG. 44A presents a schematic showing arrangement of a "TETo" response region in reference to the promoter and cassette to be expressed.

A TETr-regulated viral expression system was established to minimize transcription of nucleic acids encoded in a cassette, such as an antigen encoding cassette in a vaccine, during viral production. FIG. 43 illustrates the general strategy for one example of a tetracycline-controlled viral production system using the example of antigen encoding vaccine, namely:

- 293F cells expressing a TET repressor protein (TETr) repress expression of the vaccine cassette by binding to the TET operator sequence upstream of a minimal CMV promoter
- Transcription of the cassette sequence facilitates Adenovirus production without the influence of cassette expression
- Once administered in vivo, no repressor is present, and transcription of the cassette can proceed unimpeded FIG. 44A presents a schematic showing arrangement of one example of a TET response region, referred to as a "TETo" response region, in reference to the promoter and cassette to be expressed. The TET response region consists of seven repeats of the 19 bp TET operator (TETo) sequence (TCCCTATCAGTGATAGAGA; SEQ ID NO:60) linked with spacers (aaagtgaaagtcgagtttaccac; SEQ ID NO:70) between each TETo. The TET response region is upstream (5') of the minimal CMV promoter (67 bp; see SEQ ID NO:61) and the start of the cassette location. The arrangement of the TETo response region and promoter sequences are shown and described in SEQ ID NO:61.

Figure 44B:
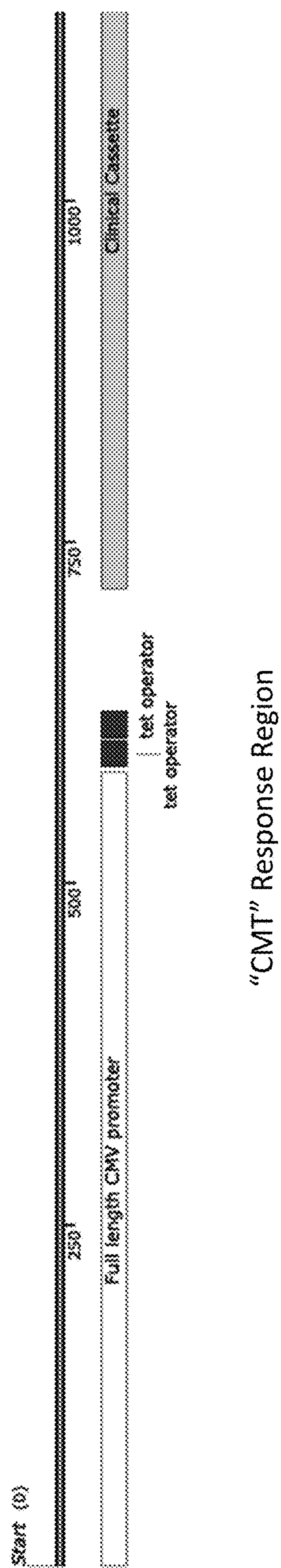
FIG. 44B presents a schematic showing arrangement of a "CMT" response region in reference to the promoter and cassette to be expressed.

FIG. 44B presents a schematic showing arrangement of another example of a TET response region, referred to as a "CMT" response region, in reference to the promoter and cassette to be expressed. The TET response region includes two repeats of the 19 bp TET operator (TETo) sequence (TCCCTATCAGTGATAGAGA; SEQ ID NO:60) linked together with a two nucleotide spacer. The TET response region is downstream (3') of a full-length CMV promoter (605 bp; see SEQ ID NO: 64) and upstream (5') of the start of the cassette location. The arrangement of the CMT response region and promoter sequences are shown and described in SEQ ID NO:64.

Figure 45A:
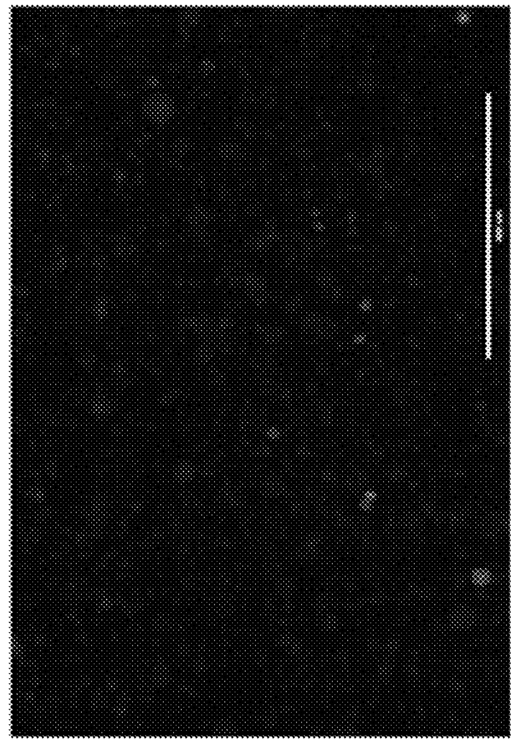
FIG. 45A shows TETr mediated regulation of GFP expressed from a ChAdV68 vector with a TETo sequence. GFP is significantly reduced in 293F cells expressing the TETr (Clone 17, right panel) relative to the parental 293F cell line (left panel). Cells were infected at an MOI of 1 with ChAdV68-TETo-GFP and 24 h later GFP was evaluated by florescent microscopy under a 10× objective.
Figure 45A:
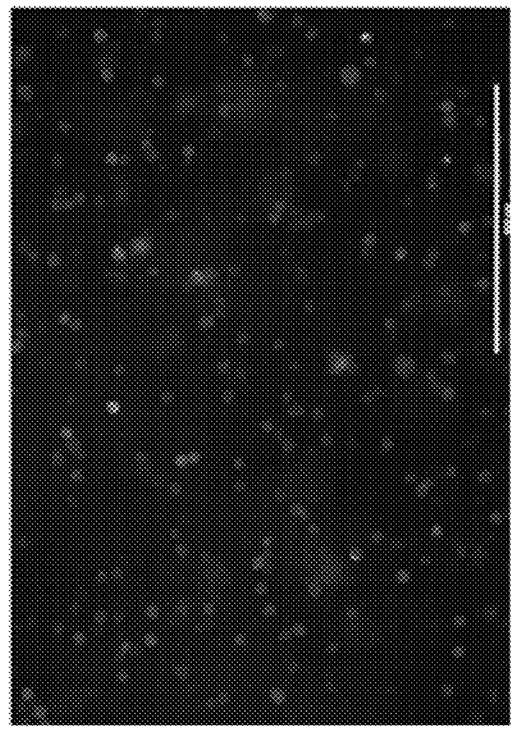

The TETo response region was inserted between the I-SceI and AsisI sites of ChAdV68.5WTnt.GFP (SEQ ID NO: 13) to generate ChAdV68-TETo-GFP. A TETr sequence (tTS; SEQ ID NO: 62) was cloned into a Lentivirus pLX vector to generate pLXCMV-tTS-iPuro and used to transduce 293F cells. Sequences used in constructing the system are presented below. A clonal 293F TETr line was generated after Puromycin selection. GFP transgene expression was evaluated to assess expression regulation by the TETr line in vitro. As shown in FIG. 45A, following infection with ChAdV68-TETo-GFP virus, GFP was significantly reduced in 293F cells expressing the TETr (Clone 17, right panel) relative to the parental 293F cell line (left panel).

Figure 45B:
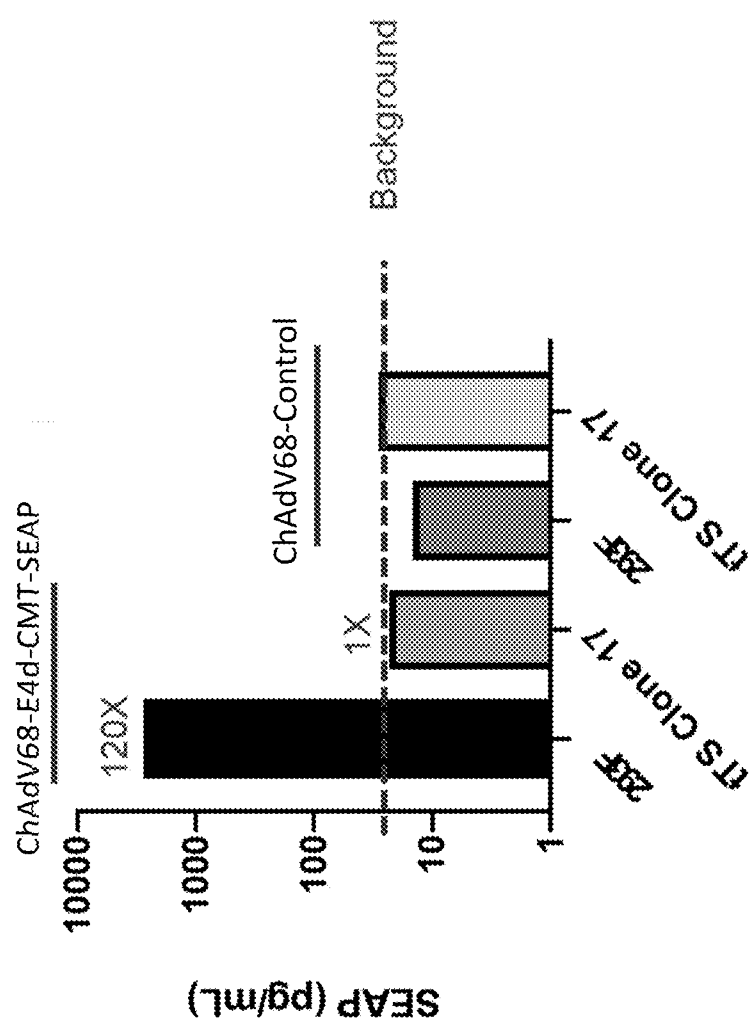
FIG. 45B shows TETr mediated regulation of SEAP expressed from a ChAdV68 vector with a CMT sequence. SEAP is significantly reduced in 293F cells expressing the TETr (Clone 17, second column from left) relative to the parental 293F cell line (left column). Background signal was established using a ChAdV68 vector expressing a control expression cassette (right two columns). 293F cells were infected at an MOI of 0.3 and 24 h later media was harvested for the SEAP assay (Phospha-Light™ System (Applied Biosystems) using a chemiluminescent substrate for the detection of secreted alkaline phosphatase) that was followed according to the manufacturers description.

A secreted embryonic alkaline phosphatase SEAP reporter construct was generated using the CMT response region inserted between the I-SceI and AsisI sites of ChAdV68-Empty-E4deleted (SEQ ID NO:59) and with SEAP inserted in place of the deleted E1 ("ChAdV68-E4d-CMT-SEAP"). 293F cells were infected at an MOI of 0.3 and 24 h later media was harvested for the SEAP assay (Phospha-Light™ System (Applied Biosystems) using a chemiluminescent substrate for the detection of secreted alkaline phosphatase) that was followed according to the manufacturers description. As shown in FIG. 45B, following infection with ChAdV68-E4d-CMT-SEAP virus, SEAP secretion was reduced 120-fold to background level in 293F cells expressing the TETr ("tTS Clone 17"), with background set using a ChAdV68 vector expressing a control expression cassette, relative to the parental 293F cell line ("293F"). Thus, adenoviral cassettes expressed from a TETr-controlled promoter demonstrate reduced cassette expression when used in TETr-expressing cell lines in vitro.

TETo response region between I-SceI and AsisI sites of ChAdV68 vector backbone. One of seven repeats of the 19 bp TETo sequences is bold italicized. The minimal CMV promoter is bold (SEQ ID NO: 61)

ccatgttgacattgattattgactagttattaaagtact*tccctatcagtgatagaga*aaagtgaaagtcgagtttaccactccctatcagtgatag agaaaagtgaaagtcgagtttaccactccctatcagtgatagagaaaagtgaaagtcgagtttaccactccctatcagtgatagagaaaagtgaaagtcg atattaccactccctatcagtgatagagaaaagtgaaagtcgagtttaccactccctatcagtgatagagaaaagtgaaagtcgaccactccctatcagt gatagagaaaagtgaaagtcgagacggtacccggctcgaggtaggcgtgtacggtgggaggcctatataagcagagctcgtttagtgaaccgtcagatcg cctggag

-continued

TETr sequence (tTS) nucleic acid sequence (SEQ ID NO: 62)

ATGAGCAGACTGGACAAGAGCAAAGTGATCAACAGCGCCCTGGAACTGCTGAACGAAGTGGGCATCGAGG

GCCTGACAACCAGAAAGCTGGCCCAGAAGCTGGGCGTTGAGCAGCCTACACTGTATTGGCACGTGCGGAA

CAAGCAGACCCTGATGAATATGCTGAGCGAGGCCATCCTGGCCAAGCACCATACAAGATCTGCCCCTCTGC

CAACCGAGAGCTGGCAGCAGTTTCTGCAAGAGAACGCCCTGAGCTTCAGAAAGGCCCTGCTGGTGCATAG

AGATGGCGCCAGACTGCACATCGGCACATCTCCCACACCTCCACAGTTTGAGCAGGCTGAGGCACAGCTGA

GATGTCTGTGTGATGCCGGCTTTAGCGTGGAAGAGGCCCTGTTCATCCTGCAGTCCATCAGCCACTTTACAC

TGGGCGCCGTGCTGGAAGAACAGGCCACCAACCAGATCGAGAACAACCACGTGATCGACGCTGCCCCTCC

ACTGCTGCAAGAGGCCTTCAATATCCAAGCCAGAACCAGCGCCGAGATGGCCTTCCACTTTGGCCTGAAGT

CCCTGATCTTTGGCTTCAGCGCCCAGCTGGACGAGAAGAAGCACACACCTATCGAGGACGGCAACAAGCCC

AAGAAGAAGCGGAAGCTGGCCGTCAGCGTGACCTTTGAAGATGTGGCCGTGCTGTTCACCCGGGACGAGT

GGAAGAAACTGGACCTGAGCCAGCGGAGCCTGTACCGGGAAGTGATGCTGGAAAACTACAGCAACCTGGC

CTCCATGGCCGGCTTTCTGTTCACCAAGCCTAAAGTGATCTCCCTGCTTCAGCAGGGCGAAGATCCTTGGTA

A

TETr sequence (tTs) amino acid sequetic (SEQ ID NO: 63)

MSRLDKSKVINSALELLNEVGIEGLTTRKLAQKLGVEQPTLYWHVRNKQTLMNMLSEAILAKHHTR

SAPLPTESWQQFLQENALSFRKALLVHRDGARLHIGTSPTPPQFEQAEAQLRCLCDAGFSVEEALFIL

QSISHFTLGAVLEEQATNQIENNHVIDAAPPLLQEAFNIQARTSAEMAFHFGLKSLIFGFSAQLDEKK

HTPIEDGNKPKKKRKLAVSVTEDVAVLFTRDEWKKLDLSQRSLYREVMLENYSNLASMAGFLFTK

PKVISLLQQGEDPW

CMT response region between I-SceI and AsisI sites of ChAdV68 vector backbone. The two repeats of the 19 bp TETo sequences are bolded. The full-length CMV promoter is italicized. (SEQ ID NO: 64)

GACATTGATTATTGACTAGTTGTTAATAGTAATCAATTACGGGGTCATTAGTTCATAGCCCATAT

ATGGAGTTCCG*CGTTACATAACTTACGCTTAAATGGCCCGCCTGGCTGACCGCCCAACGACCCCCGCC*

*CATTGACGTCAATAATGACGTATGTTCCCATAGTAACGCCAATAGGGACTTTCCATTGACGTCAATGGG*

*TGGAGTATTTACGGTAAACTGCCCACTTGGCAGTACATCAAGTGTATCATATGCCAAGTCCGCCCCCTA*

*TTGACGTCAAGTACGGTAAATGGCCCGCCTGGCATTATGCCCAGTACATGACCTTACGGGACTTTCCT*

*ACTTGGCACTTACATCTACGTATTAGTCATCGCTAATTACCATCTGTGTGCGGTTTTGGCAGTACACCAAT*

*GGGCGTGGATAGCGGTTTGACTCACGGGGATTTCCAAGTCTCCACCCCATTGACGTCAATGGGAGTTT*

*GTTTTGGCACCAAAATCAACGGGACTTTCCAAAATGTCGTAATAACCCCGCCCCGTTGACGCAAATGG*

*GCGGTAGGCGTGTACGGTGGGAGGTCTATATAAGCAGAGCTC*TCCCTATCAGTGATAGAGATCTC

CCTATCAGTGATAGAGATC

XXII. Viral Production in the TETr-Regulated Cassette Expression System

Figure 46:
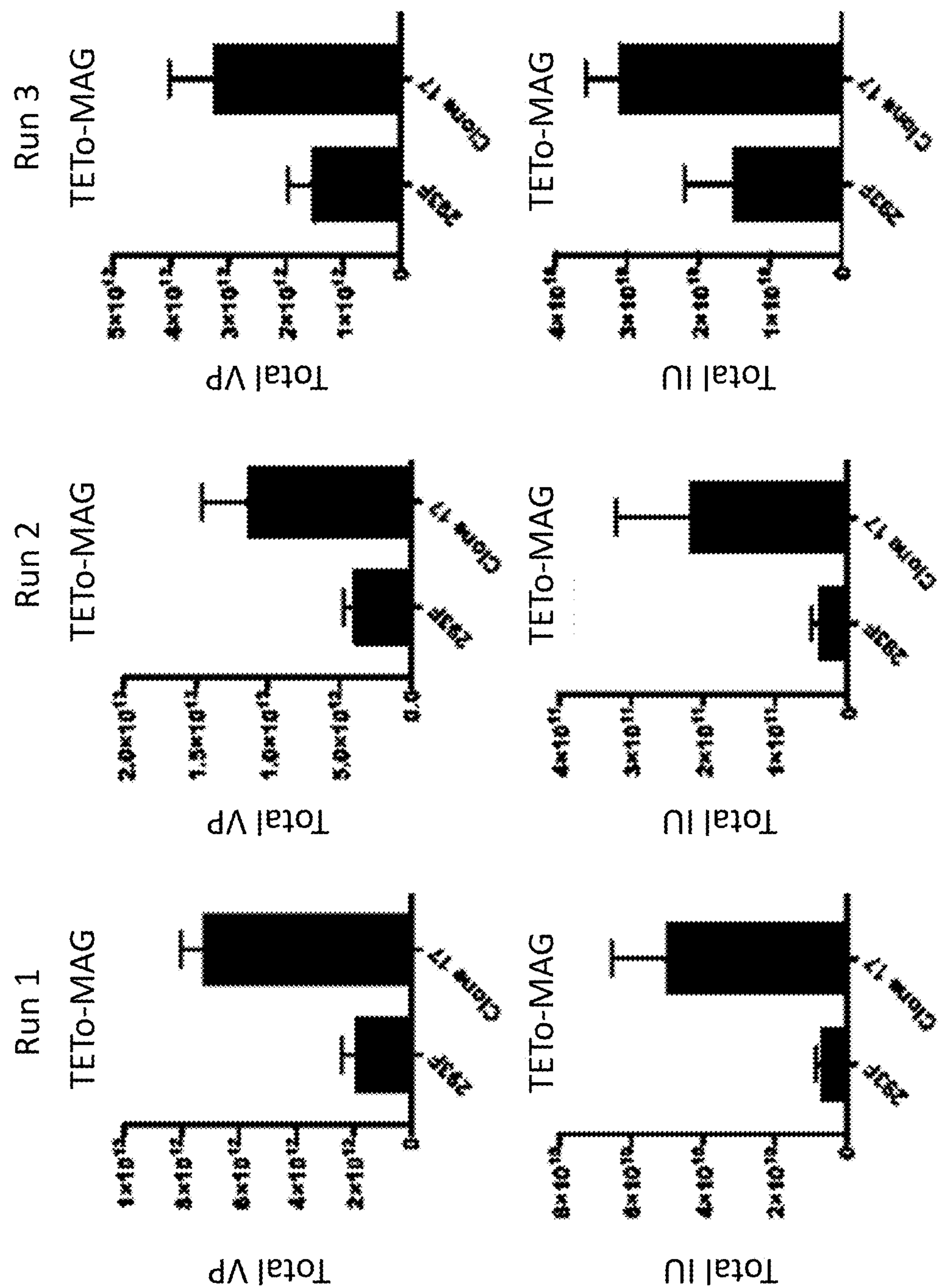
FIG. 46 shows viral production for a ChAdV68-Teto-MAG vector in a 293F TETr repressor line (Clone 17) relative to production in the parental 293F line. The experiment was performed in triplicate (run 1-3). In each experiment 400 mL of 293F cells were infected at an MOI of approximately 3 and incubated for 48-72 h before harvesting. Virus was purified by two discontinuous CsCl ultracentrifugation steps and dialyzed into storage buffer. Viral particles were measured by Absorbance at 260 nm. Shown are viral particle (VP; top panels) and infectious unit (IU; bottom panels) titers.

The TETo response region was inserted between the I-SceI and AsisI sites of ChAdV68.5WTnt.MAG25mer ("ChAdV68-CMV-MAG"; SEQ ID NO:2) to generate a ChAdV68-TETo-MAG virus (SEQ ID NO:65) expressing a model antigen cassette under control of a TET regulated promoter. Viral production was compared between cell lines expressing TETr (Clone 17) and the parental cell line that did not express TETr (293F). As shown in FIG. 46, viral production was improved as assessed by viral particle (VP; top panels) and infectious unit (IU; bottom panels) titers across three independent replicates.

Figure 47A:
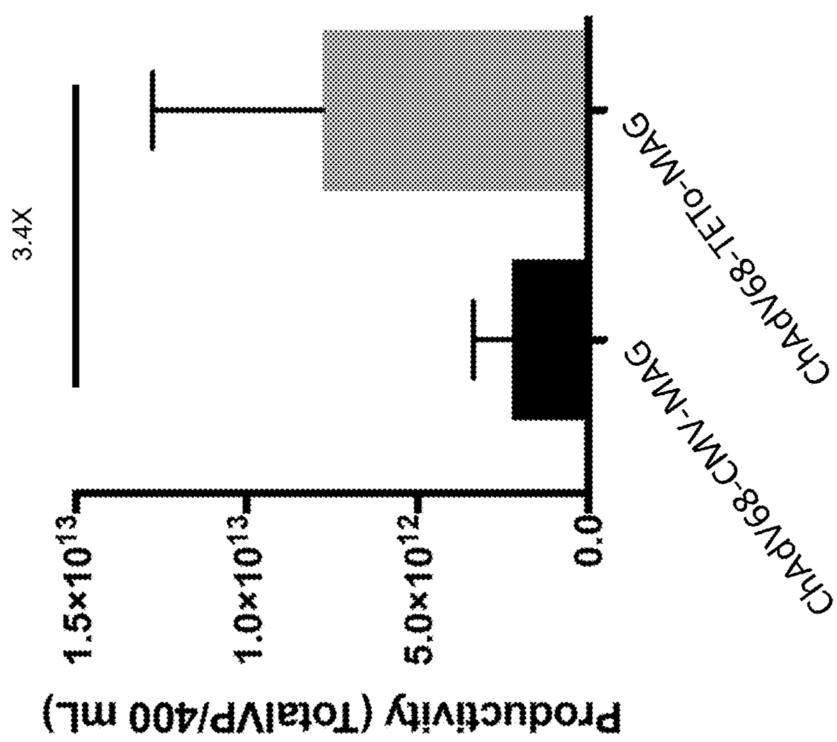
FIG. 47A shows overall productivity of a Tet regulated virus ("TETo-MAG") in a 293F TETr line (Clone 17) relative to a non-regulated virus ("MAG") with the same cassette in a normal 293F cell line. Shown are date from multiple 400 mL production runs followed by centrifugation. Fold improvement with Tet regulated virus is indicated by the number above the graph.

Viral production of a ChAdV68-TETo-MAG virus produced in a cell line expressing TETr (Clone 17) was also compared to a virus lacking the TETo sequences ("ChAdV68-CMV-MAG"). As shown in FIG. 47A, viral production was improved by 3.4-fold for the ChAdV68-TETo-MAG virus relative to ChAdV68-CMV-MAG. These results indicate reduction in in vitro expression of the delivered cassette transgenes translated into more consistent and improved virus productivity.

Viral production produced in a cell line expressing TETr (tTS Clone 17) was further compared for a series of viral constructs, including constructs featuring E4 deletions and TET response elements. The constructs all expressed the same, control tumor-specific neoantigen (TSNA) cassette. The general backbone featuring E1/E3 deletions and 5 nucleotide substitutions was the same as ChAdV68.5WTnt.MAG25mer (SEQ ID NO:2), with TETo and CMT response regions inserted between the I-SceI and AsisI sites, as indicated, and the MAG25mer cassette substituted for the TSNA cassette. The deleted E4 region was that identified above (deletion 34,916 to 35,642 of SEQ ID NO:1). The various constructs examined are described below:

- ChAdV68-CMV-TSNA; E1/E3 deleted, full-length CMV promoter
- ChAdV68-CT-TSNA; E1/E3 deleted, full-length CMV promoter, TSNA cassette codon optimized using an alternate codon optimization (SEQ ID NO:66)
- ChAdV68-TETo-TSNA; E1/E3 deleted, 7 repeats of TETo linked with spacers upstream (5') of minimal CMV promoter ("TETo" response region) (SEQ ID NO:67)
- ChAdV68-CMT-TSNA; E1/E3 deleted, 2 repeats of TETo directly linked together downstream (3') of full-length CMV promoter ("CMT" response region) (SEQ ID NO:68)
- ChAdV68-E4d-CMT-TSNA; E1/E3/E4 deleted, 2 repeats of TETo directly linked together downstream (3') of full-length CMV promoter (SEQ ID NO:69)

Figure 47B:
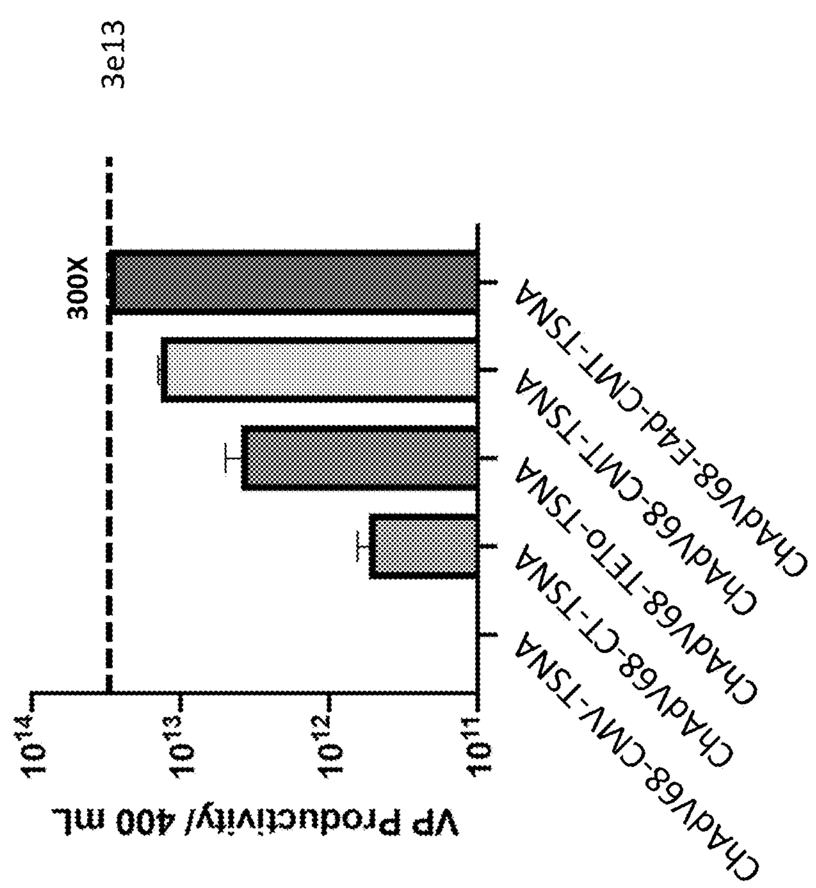
FIG. 47B shows viral production for the ChAdV68-CT-TSNA, ChAdV68-TETo-TSNA, ChAdV68-CMT-TSNA, and ChAdV68-E4d-CMT-TSNA viruses relative to ChAdV68-CMV-TSNA.

As shown in FIG. 47B, viral production for the ChAdV68-CT-TSNA, ChAdV68-TETo-TSNA, ChAdV68-CMT-TSNA, and ChAdV68-E4d-CMT-TSNA viruses was improved by about 6-fold, 39-fold, 137-fold, or 300-fold relative to ChAdV68-CMV-TSNA. respectively. The ratio of viral particles to infectious units was also assessed to measure the virus's infectious capability and is calculated by dividing the virus particle (VP) titer/mL by the infectious unit (IU) titer/mL, where a lower ratio represents a higher infectivity per particle (a ratio of 1:1 represents a perfect ratio of every particle being infectious). As shown in Table 42A, TET-controlled vectors ChAdV68-TETo-TSNA, ChAdV68-CMT-TSNA, and ChAdV68-E4d-CMT-TSNA all demonstrated improved infectious capability relative to ChAdV68-CMV-TSNA, with CMT vectors demonstrating the best infectious capability.

Figure 47C:
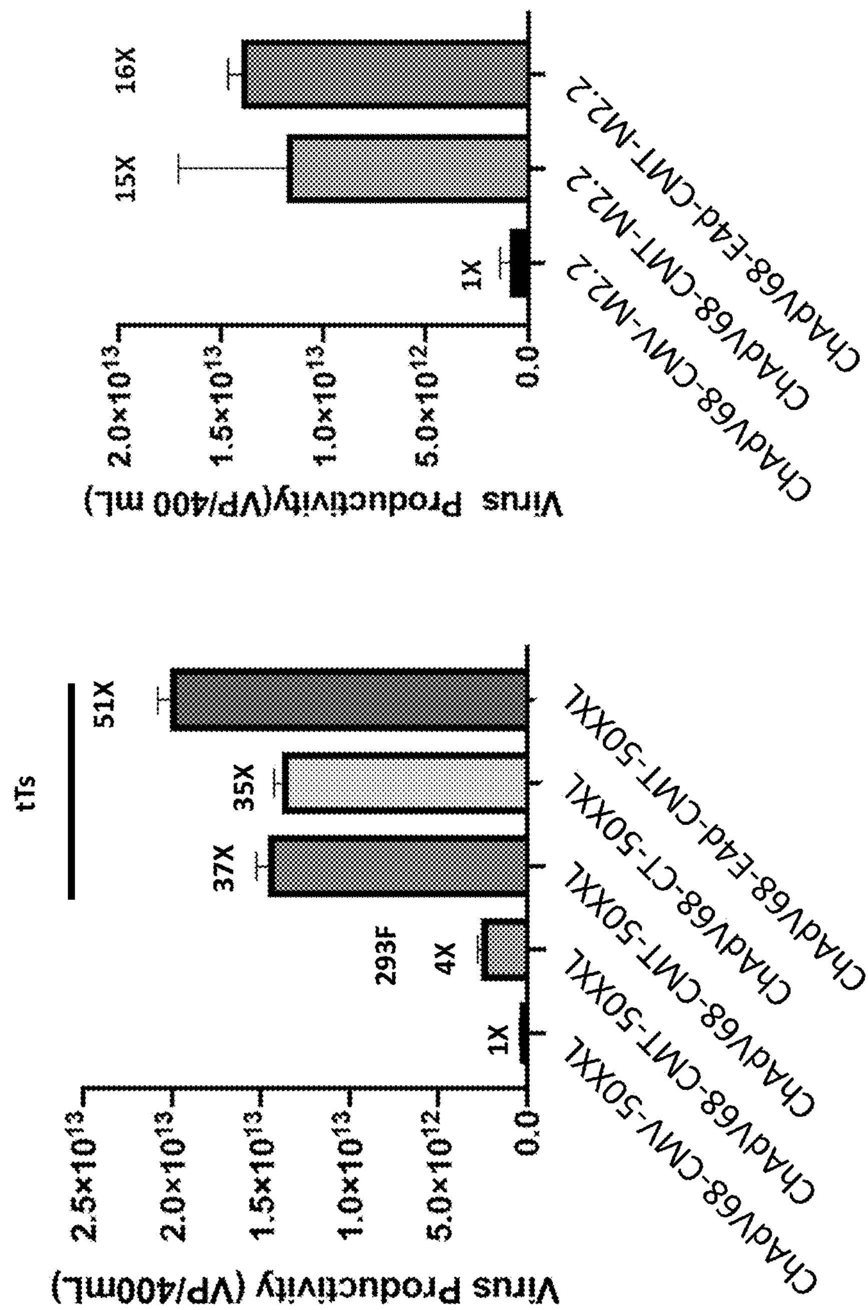
FIG. 47C shows viral production for model antigen cassettes 50XXL and M2.2 using adenoviral vectors having a CMT response region in a tTS expressing cell line.

Viral production of another series of viral constructs, including constructs featuring E4 deletions and TET response elements, was assessed for constructs featuring either a large model antigen cassette (50XXL; see FIG. 29 and Tables 32-34) or M2.2 model antigen cassette. The general backbone featuring E1/E3 deletions and 5 nucleotide substitutions was the same as ChAdV68.5WTnt.MAG25mer (SEQ ID NO:2), with TETo and CMT response regions inserted between the I-SceI and AsisI sites, as indicated, and the MAG25mer cassette substituted for the indicated cassettes. The deleted E4 region was that identified above (deletion 34,916 to 35,642 of SEQ ID NO:1). The various constructs examined are described below:

- ChAdV68-CMV-50 XXL; E1/E3 deleted, full length CMV promoter, 50XXL cassette codon optimized using Genscript codon optimization tool
- ChAdV68-CMT-50XXL; E1/E3 deleted, 2 repeats of TETo directly linked together downstream (3') of full-length CMV promoter, 50XXL cassette codon optimized using Genscript codon optimization tool
- ChAdV68-CT-50XXL; E1/E3 deleted, full length CMV promoter, 50XXL cassette codon optimized using an alternate codon optimization tool
- ChAdV68-E4d-CMT-50XXL; E1/E3/E4 deleted, 2 repeats of TETo directly linked together downstream (3') of full-length CMV promoter; 50XXL cassette codon optimized using Genscript codon optimization tool
- ChAdV68-CMV-M2.2; E1/E3 deleted, full length CMV promoter, M2.2 cassette codon optimized using Genscript codon optimization tool
- ChAdV68-CMT-M2.2; E1/E3 deleted, 2 repeats of TETo directly linked together downstream (3') of full-length CMV promoter, M2.2 cassette codon optimized using Genscript codon optimization tool
- ChAdV68-E4d-CMT-M2.2; E1/E3/E4 deleted, 2 repeats of TETo directly linked together downstream (3') of full-length CMV promoter, M2.2 cassette codon optimized using Genscript codon optimization tool As shown in FIG. 47C, viral production for model antigen cassettes 50XXL and M2.2 was improved by the use adenoviral vectors having a CMT response region in a tTS expressing cell line. For example, viral production was almost 10-fold greater for ChAdV68-CMT-50XXL in the tTS expressing cell line (left panel; middle column) relative to a parental 293F cell line (left panel; second column from left), and 15-fold greater for ChAdV68-CMT-M2.2 (right panel; middle column) relative to a vector lacking the CMT response region in a parental 293F cell line (right panel; left column). In the case of 50XXL constructs, further improvements in viral production were achieved by combining a CMT response region with an E4 deletion (left panel middle column vs left panel right column). Improvements were also achieved under certain circumstances by alternative codon optimization (as shown for ChAdV68-CT-50XXL). The ratio of viral particles to infectious units was also assessed. As shown in Table 42C, TET-controlled vectors in a E4 deleted background all demonstrated improved infectious capability relative to vectors without an E4 deletion and TET response element.

TABLE 42A

Viral particle to infectious unit ratio TSNA constructs

| Construct | VP:IU Ratio |
|---|---|
| ChAdV68-CMV-TSNA | 591:1 |
| ChAdV68-CT-TSNA | 63:1 |
| ChAdV68-TETo-TSNA | 135:1 |
| ChAdV68-CMT-TSNA | 22:1 |
| ChAdV68-E4d-CMT-TSNA | 34:1 |

TABLE 42B

Viral particle to infectious unit ratio 50XXL constructs

| Construct | VP:IU Ratio |
|---|---|
| ChAdV68-CMV-50XXL | 260:1 |
| ChAdV68-E4d-CMT-50XXL | 32:1 |
| ChAdV68-CMV-M2.2 | 662:1 |
| ChAdV68-E4d-CMT-M2.2 | 50:1 |

ChAdV68-TETo-MAG (SEQ ID NO: 65)

CATCATCAATAATATACCTCAAACTTTTTGTGCGCGTTAATATGCAAATGAGGCGTTTGAATTTGGGGAGGA

AGGGCGGTGATTGGTCGAGGGATGAGCGACCGTTAGGGGCGGGGCGAGTGACGTTTTGATGACGTGGTTG

CGAGGAGGAGCCAGTTTGCAAGTTCTCGTGGGAAAAGTGACGTCAAACGAGGTGTGGTTTGAACACGGAA

ATACTCAATTTTCCCGCGCTCTCTGACAGGAAATGAGGTGTTTCTGGGCGGATGCAAGTGAAAACGGGCCA

TTTTCGCGCGAAAACTGAATGAGGAAGTGAAAATCTGAGTAATTTCGCGTTTATGGCAGGGAGGAGTATTT

GCCGAGGGCCGAGTAGACTTTGACCGATTACGTGGGGGTTTCGATTACCGTGTTTTTCACCTAAATTTCCGC

GTACGGTGTCAAAGTCCGGTGTTTTTACGTAGGTGTCAGCTGATCGCCAGGGTATTTAAACCTGCGCTCTCC

AGTCAAGAGGCCACTCTTGAGTGCCAGCGAGAAGAGTTTTCTCCTCCGCGCCGCGAGTCAGATCTACACTT

TGAAAGTAGGGATAACAGGGTAATCCATGTTGACATTGATTATTGACTAGTTATTAAAGTACTTCCCTATCA

GTGATAGAGAAAAGTGAAAGTCGAGTTTACCACTCCCTATCAGTGATAGAGAAAAGTGAAAGTCGAGTTTA

CCACTCCCTATCAGTGATAGAGAAAAGTGAAAGTCGAGTTTACCACTCCCTATCAGTGATAGAGAAAAGTG

AAAGTCGAGTTTACCACTCCCTATCAGTGATAGAGAAAAGTGAAAGTCCGAGTTTACCACTCCCTATCAGTG

ATAGAGAAAAGTGAAAGTCGAGTTTACCACTCCCTATCAGTGATAGAGAAAAGTGAAAGTCGAGCTCGGT

ACCCGGGTCGAGGTAGGCGTGTACGGTGGGAGGCCTATATAAGCAGAGCTCGTTTAGTGAACCGTCAGATC

GCCTGGAGACGCCATCCACGCTGTTTTGACCTCCATAGAAGACAGCGATCGCGCCACCATGGCCGGGATGT

TCCAGGCACTGTCCGAAGGCTGCACACCCTATGATATTAACCAGATGCTGAATGTCCTGGGAGACCACCAG

GTCTCTGGCCTGGAGCAGCTGGAGAGCATCATCAACTTCGAGAAGCTGACCGAGTGGACAAGCTCCAATGT

GATGCCTATCCTGTCCCCACTGACCAAGGGCATCCTGGGCTTCGTGTTTACCCTGACAGTGCCTTCTGAGCG

GGGCCTGTCTTGCATCAGCGAGGCAGACGCAACCACACCAGAGTCCGCCAATCTGGGCGAGGAGATCCTGT

CTCAGCTGTACCTGTGGCCCCGGGTGACATATCACTCCCCTTCTTACGCCTATCACCAGTTCGAGCGGAGAG

CCAAGTACAAGAGACACTTCCCAGGCTTTGGCCAGTCTCTGCTGTTCGGCTACCCCGTGTACGTGTTCGGCG

ATTGCGTGCAGGGCGACTGGGATGCCATCCGGTTTAGATACTGCGCACCACCTGGATATGCACTGCTGAGG

TGTAACGACACCAATTATTCCGCCCTGCTGGCAGTGGGCGCCCTGGAGGGCCCTCGCAATCAGGATTGGCT

GGGCGTGCCAAGGCAGCTGGTGACACGCATGCAGGCCATCCAGAACGCAGGCCTGTGCACCCTGGTGGCA

ATGCTGGAGGAGACAATCTTCTGGCTGCAGGCCTTTCTGATGGCCCTGACCGACAGCGGCCCCAAGACAAA

CATCATCGTGGATTCCCAGTACGTGATGGGCATCTCCAAGCCTTCTTTCCAGGAGTTTGTGGACTGGGAGAA

CGTGAGCCCAGAGCTGAATTCCACCGATCAGCCATTCTGGCAGGCAGGAATCCTGGCAAGGAACCTGGTGC

CTATGGTGGCCACAGTGCAGGGCCAGAATCTGAAGTACCAGGGCCAGAGCCTGGTCATCAGCGCCTCCATC

ATCGTGTTTAACCTGCTGGAGCTGGAGGGCGACTATCGGGACGATGGCAACGTGTGGGTGCACACCCCACT

GAGCCCCAGAACACTGAACGCCTGGGTGAAGGCCGTGGAGGAGAAGAAGGGCATCCCAGTGCACCTGGAG

CTGGCCTCCATGACCAATATGGAGCTGATGTCTAGCATCGTGCACCAGCAGGTGAGGACATACGGACCCGT

GTTCATGTGCCTGGGAGGCCTGCTGACCATGGTGGCAGGAGCCGTGTGGCTGACAGTGCGGGTGCTGGAGC

TGTTCAGAGCCGCCCAGCTGGCCAACGATGTGGTGCTGCAGATCATGGAGCTGTGCGGAGCAGCCTTTCGC

CAGGTGTGCCACACCACAGTGCCATGGCCCAATGCCTCCCTGACCCCCAAGTGGAACAATGAGACAACACA

GCCTCAGATCGCCAACTGTAGCGTGTACGACTTCTTCGTGTGGCTGCACTACTATAGCGTGAGGGATACCCT

GTGGCCCCGCGTGACATACCACATGAATAAGTACGCCTATCACATGCTGGAGAGGCGCGCCAAGTATAAG

AGAGGCCCTGGCCCAGGCGCAAAGTTTGTGGCAGCATGGACCCTGAAGGCCGCCGCCGGCCCCGGCCCCG

GCCAGTATATCAAGGCTAACAGTAAGTTCATTGGAATCACAGAGCTGGGACCCGGACCTGGATAATGAGTT

TAAACTCCCATTTAAATGTGAGGGTTAATGCTTCGAGCAGACATGATAAGATACATTGATGAGTTTGGACA

AACCACAACTAGAATGCAGTGAAAAAAATGCTTTATTTGTGAAATTTGTGATGCTATTGCTTTATTTGTAAC

-continued

CATTATAAGCTGCAATAAACAAGTTAACAACAACAATTGCATTCATTTTATGTTTCAGGTTCAGGGGGAGA

TGTGGGAGGTTTTTTAAAGCAAGTAAAACCTCTACAAATGTGGTAAAATAACTATAACGGTCCTAAGGTAG

CGAGTGAGTAGTGTTCTGGGGCGGGGGAGGACCTGCATGAGGGCCAGAATAACTGAAATCTGTGCTTTTCT

GTGTGTTGCAGCAGCATGAGCGGAAGCGGCTCCTTTGAGGGAGGGGTATTCAGCCCTTATCTGACGGGGCG

TCTCCCCTCCTGGGCGGGAGTGCGTCAGAATGTGATGGGATCCACGGTGGACGGCCGGCCCGTGCAGCCCG

CGAACTCTTCAACCCTGACCTATGCAACCCTGAGCTCTTCGTCGTTGGACGCAGCTGCCGCCGCAGCTGCTG

CATCTGCCGCCAGCGCCGTGCGCGGAATGGCCATGGGCGCCGGCTACTACGGCACTCTGGTGGCCAACTCG

AGTTCCACCAATAATCCCGCCAGCCTGAACGAGGAGAAGCTGTTGCTGCTGATGGCCCAGCTCGAGGCCTT

GACCCAGCGCCTGGGCGAGCTGACCCAGCAGGTGGCTCAGCTGCAGGAGCAGACGCGGGCCGCGGTTGCC

ACGGTGAAATCCAAATAAAAAATGAATCAATAAATAAACGGAGACGGTTGTTGATTTTAACACAGAGTCTG

AATCTTTATTTGATTTTTCGCGCGCGGTAGGCCCTGGACCACCGGTCTCGATCATTGAGCACCCGGTGGATC

TTTTCCAGGACCCGGTAGAGGTGGGCTTGGATGTTGAGGTACATGGGCATGAGCCCGTCCCGGGGGTGGAG

GTAGCTCCATTGCAGGGCCTCGTGCTCGGGGGTGGTGTTGTAAATCACCCAGTCATAGCAGGGGCGCAGGG

CATGGTGTTGCACAATATCTTTGAGGAGGAGACTGATGGCCACGGGCAGCCCTTTGGTGTAGGTGTTTACA

AATCTGTTGAGCTGGGAGGGATGCATGCGGGGGGAGATGAGGTGCATCTTGGCCTGGATCTTGAGATTGGC

GATGTTACCGCCCAGATCCCGCCTGGGGTTCATGTTGTGCAGGACCACCAGCACGGTGTATCCGGTGCACT

TGGGGAATTTATCATGCAACTTGGAAGGGAAGGCGTGAAAGAATTTGGCGACGCCTTTGTGCCCGCCCAGG

TTTTCCATGCACTCATCCATGATGATGGCGATGGGCCCGTGGGCGGCGGCCTGGGCAAAGACGTTTCGGGG

GTCGGACACATCATAGTTGTGGTCCTGGGTGAGGTCATCATAGGCCATTTTAATGAATTTGGGGCGGAGGG

TGCCGGACTGGGGGACAAAGGTACCCTCGATCCCGGGGGCGTAGTTCCCCTCACAGATCTGCATCTCCCAG

GCTTTGAGCTCGGAGGGGGGGATCATGTCCACCTGCGGGGCGATAAAGAACACGGTTTCCGGGGCGGGGG

AGATGAGCTGGGCCGAAAGCAAGTTCCGGAGCAGCTGGGACTTGCCGCAGCCGGTGGGGCCGTAGATGAC

CCCGATGACCGGCTGCAGGTGGTAGTTGAGGGAGAGACAGCTGCCGTCCTCCCGGAGGAGGGGGGCCACC

TCGTTCATCATCTCGCGCACGTGCATGTTCTCGCGCACCAGTTCCGCCAGGAGGCGCTCTCCCCCCAGGGAT

AGGAGCTCCTGGAGCGAGGCGAAGTTTTTCAGCGGCTTGAGTCCGTCGGCCATGGGCATTTTGGAGAGGGT

TTGTTGCAAGAGTTCCAGGCGGTCCCAGAGCTCGGTGATGTGCTCTACGGCATCTCGATCCAGCAGACCTC

CTCGTTTCGCGGGTTGGGACGGCTGCGGGAGTAGGGCACCAGACGATGGGCGTCCAGCGCAGCCAGGGTC

CGGTCCTTCCAGGGTCGCAGCGTCCGCGTCAGGGTGGTCTCCGTCACGGTGAAGGGGTGCGCGCCGGGCTG

GGCGCTTGCGAGGGTGCGCTTCAGGCTCATCCGGCTGGTCGAAAACCGCTCCCGATCGGCGCCCTGCGCGT

CGGCCAGGTAGCAATTGACCATGAGTTCGTAGTTGAGCGCCTCGGCCGCGTGGCCTTTGGCGCGGAGCTTA

CCTTTGGAAGTCTGCCCGCAGGCGGGACAGAGGAGGGACTTGAGGGCGTAGAGCTTGGGGGCGAGGAAGA

CGGACTCGGGGGCGTAGGCGTCCGCGCCGCAGTGGGCGCAGACGGTCTCGCACTCCACGAGCCAGGTGAG

GTCGGGCTGGTCGGGGTCAAAAACCAGTTTCCCGCCGTTCTTTTTGATGCGTTTCTTACCTTTGGTCTCCATG

AGCTCGTGTCCCCGCTGGGTGACAAAGAGGCTGTCCGTGTCCCCGTAGACCGACTTTATGGGCCGGTCCTC

GAGCGGTGTGCCGCGGTCCTCCTCGTAGAGGAACCCCGCCCACTCCGAGACGAAAGCCCGGGTCCAGGCC

AGCACGAAGGAGGCCACGTGGGACGGGTAGCGGTCGTTGTCCACCAGCGGGTCCACCTTTTCCAGGGTATG

CAAACACATGTCCCCCTCGTCCACATCCAGGAAGGTGATTGGCTTGTAAGTGTAGGCCACGTGACCGGGGG

TCCCGGCCGGGGGGGTATAAAAGGGTGCGGGTCCCTGCTCGTCCTCACTGTCTTCCGGATCGCTGTCCAGG

AGCGCCAGCTGTTGGGGTAGGTATTCCCTCTCGAAGGCGGGCATGACCTCGGCACTCAGGTTGTCAGTTTCT

AGAAACGAGGAGGATTTGATATTGACGGTGCCGGCGGAGATGCCTTTCAAGAGCCCCTCGTCCATCTGGTC

-continued

AGAAAAGACGATCTTTTTGTTGTCGAGCTTGGTGGCGAAGGAGCCGTAGAGGGCGTTGGAGAGGAGCTTGG

CGATGGAGCGCATGGTCTGGTTTTTTTCCTTGTCGGCGCGCTCCTTGGCGFCGATGTTGAGCTGCACGTACT

CGCGCGCCACGCACTTCCATTCGGGGAAGACGGTGGTCAGCTCGTCGGGCACGATTCTGACCTGCCAGCCC

CGATTATGCAGGGTGATGAGGTCCACACTGGTGGCCACCTCGCCGCGCAGGGGCTCATTAGTCCAGCAGAG

GCGTCCGCCCTTGCGCGAGCAGAAGGGGGGCAGGGGGTCCAGCATGACCTCGTCGGGGGGGTCGGCATCG

ATGGTGAAGATGCCGGGCAGGAGGTCGGGGTCAAAGTAGCTGATGGAAGTGGCCAGATCGTCCAGGGCAG

CTTGCCATTCGCGCACGGCCAGCGCGCGCTCGTAGGGACTGAGGGGCGTGCCCCAGGGCATGGGATGGGT

AAGCGCGGAGGCGTACATGCCGCAGATGTCGTAGACGTAGAGGGGCTCCTCGAGGATGCCGATGTAGGTG

GGGTAGCAGCGCCCCCCGCGGATGCTGGCGCGCACGTAGTCATACAGCTCGTGCGAGGGGGCGAGGAGCC

CCGGGCCCAGGTTGGTGCGACTGGGCTTTTCGGCGCGGTAGACGATCTGGCGGAAAATGGCATGCGAGTTG

GAGGAGATGGTGGGCCTTTGGAAGATGTTGAAGTGGGCGTGGGGCAGTCCGACCGAGTCGCGGATGAAGT

GGGCGTAGGAGTCTTGCAGCTTGGCGACGAGCTCGGCGGTGACTAGGACGTCCAGAGCGCAGTAGTCGAG

GGTCTCCTGGATGATGTCATACTTGAGCTGTCCCTTTTGTTTCCACAGCTCGCGGTTGAGAAGGAACTCTTC

GCGGTCCTTCCAGTACTCTTCGAGGGGGAACCCGTCCTGATCTGCACGGTAAGAGCCTAGCATGTAGAACT

GGTTGACGGCCTTGTAGGCGCAGCAGCCCTTCTCCACCGGGAGGGCGTAGGCCTGGGCGGCCTTGCGCAGG

GAGGTGTGCGTGAGGGCGAAAGTGTCCCTGACCATGACCTTGAGGAACTGGTGCTTGAAGTCGATATCGTC

GCAGCCCCCCTGCTCCCAGAGCTGGAAGTCCGTGCGCTTCTTGTAGGCGGGGTTGGGCAAAGCGAAAGTAA

CATCGTTGAAGAGGATCTTGCCCGCGCGGGGCATAAAGTTGCGAGTGATGCGGAAAGGTTGGGGCACCTCG

GCCCGGTTGTTGATGACCTGGGCGGCGAGCACGATCTCGTCGAAGCCGTTGATGTTGTGGCCCACGATGTA

GAGTTCCACGAATCGCGGACGGCCCTTGACGTGGGGCAGTTTCTTGAGCTCCTCGTAGGTGAGCTCGTCGG

GGTCGCTGAGCCCGTGCTGCTCGAGCGCCCAGTCGGCGAGATGGGGGTTGGCGCGGAGGAAGGAAGTCCA

GAGATCCACGGCCAGGGCGGTTTGCAGACGGTCCCGGTACTGACGGAACTGCTGCCCGACGGCCATTTTTT

CGGGGGTGACGCAGTAGAAGGTGCGGGGGTCCCCGTGCCAGCGATCCCATTTGAGCTGGAGGGCGAGATC

GAGGGCGAGCTCGACGAGCCGGTCGTCCCCGGAGAGTTTCATGACCAGCATGAAGGGGACGAGCTGCTTG

CCGAAGGACCCCATCCAGGTGTAGGTTTCCACATCGTAGGTGAGGAAGAGCCTTTCGGTGCGAGGATGCGA

GCCGATGGGGAAGAACTGGATCTCCTGCCACCAATTGGAGGAATGGCTGTTGATGTGATGGAAGTAGAAAT

GCCGACGGCGCGCCGAACACTCGTGCTTGTGTTTATACAAGCGGCCACAGTGCTCGCAACGCTGCACGGGA

TGCACGTGCTGCACGAGCTGTACCTGAGTTCCTTTGACGAGGAATTTCAGTGGGAAGTGGAGTCGTGGCGC

CTGCATCTCGTGCTGTACTACGTCGTGGTGGTCGGCCTGGCCCTCTTCTGCCTCGATGGTGGTCATGCTGAC

GAGCCCGCGCGGGAGGCAGGTCCAGACCTCGGCGCGAGCGGGTCGGAGAGCGAGGACGAGGGCGCGCAG

GCCGGAGCTGTCCAGGGTCCTGAGACGCTGCGGAGTCAGGTCAGTGGGCAGCGGCGGCGCGCGGTTGACT

TGCAGGAGTTTTTCCAGGGCGCGCGGGAGGTCCAGATGGTACTTGATCTCCACCGCGCCATTGGTGGCGAC

GTCGATGGCTTGCAGGGTCCCGTGCCCCTGGGGTGTGACCACCGTCCCCCGTTTCTTCTTGGGCGGCTGGGG

CGACGGGGGCGGTGCCTCTTCCATGGTTAGAAGCGGCGGCGAGGACGCGCGCCGGGCGGCAGGGGCGGCT

CGGGGCCCGGAGGCAGGGGCGGCAGGGGCACGTCGGCGCCGCGCGCGGGTAGGTTCTGGTACTGCGCCCG

GAGAAGACTGGCGTGAGCGACGACGCGACGGTTGACGTCCTGGATCTGACGCCTCTGGGTGAAGGCCACG

GGACCCGTGAGTTTGAACCTGAAAGAGAGTTCGACAGAATCAATCTCGGTATCGTTGACGGCGGCCTGCCG

CAGGTACTCTTGCACGTCGCCCGAGTTGTCCTGGTAGGCGATCTCGGTCATGAACTGCTCGATCTCCTCCTC

TTGAAGGTCTCCGCGGCCGGCGCGCTCCACGGTGGCCGCGAGGTCGTTGGAGATGCGGCCCATGAGCTGCG

AGAAGGCGTTCATGCCCGCCTCGTTCCAGACGCGGCTGTAGACCACGACGCCCTCGGGATCGCGGGCGCGC

ATGACCACCTGGGCGAGGTTGAGCTCCACGTGGCGCGTGAAGACCGCGTAGTTGCAGAGGCGCTGGTAGA

-continued

GGTAGTTGAGCGTGGTGGCGATGTGCTCGGTGACGAAGAAATACATGATCCAGCGGCGGAGCGGCATCTC

GCTGACGTCGCCCAGCGCCTCCAAACGTTCCATGGCCTCGTAAAAGTCCACGGCGAAGTTGAAAAACTGGG

AGTTGCGCGCCGAGACGGTCAACTCCTCCTCCAGAAGACGGATGAGCTCGGCGATGGTGGCGCGCACCTCG

CGCTCGAAGGCCCCCGGAGTTCCTCCACTTCCTCTTCTTCCTCCTCCACTAACATCTCTTCTACTTCCTCCT

CAGGCGGCAGTGGTGGCGGGGGAGGGGGCCTGCGTCGCCGGCGGCGCACGGGCAGACGGTCGATGAAGC

GCTCGATGGTCTCGCCGCGCCGGCGTCGCATGGTCTCGGTGACGGCGCGCCCGTCCTCGCGGGGCCGCAGC

GTGAAGACGCCGCCGCGCATCTCCAGGTGGCCGGGGGGGTCCCCGTTGGGCAGGGAGAGGGCGCTGACGA

TGCATCTTATCAATTGCCCCGTAGGGACTCCGCGCAAGGACCTGAGCGTCTCGAGATCCACGGGATCTGAA

AACCGCTGAACGAAGGCTTCGAGCCAGTCGCAGTCGCAAGGTAGGCTGAGCACGGTTTCTTCTGGCGGGTC

ATGTTGGTTGGGAGCGGGGCGGGCGATGCTGCTGGTGATGAAGTTGAAATAGGCGGTTCTGAGACGGCGG

ATGGTGGCGAGGAGCACCAGGTCTTTGGGCCCGGCTTGCTGGATGCGCAGACGGTCGGCCATGCCCCAGGC

GTGGTCCTGACACCTGGCCAGGTCCTTGTAGTAGTCCTGCATGAGCCGCTCCACGGGCACCTCCTCCTCGCC

CGCGCGGCCGTGCATGCGCGTGAGCCCGAAGCCGCGCTGGGGCTGGACGAGCGCCAGGTCGGCGACGACG

CGCTCGGCGAGGATGGCTTGCTGGATCTGGGTGAGGGTGGTCTGGAAGTCATCAAAGTCGACGAAGCGGTG

GTAGGCTCCGGTGTTGATGGTGTAGGAGCAGTTGGCCATGACGGACCAGTTGACGGTCTGGTGGCCCGGAC

GCACGAGCTCGTGGTACTTGAGGCGCGAGTAGGCGCGCGTGTCGAAGATGTAGTCGTTGCAGGTGCGCACC

AGGTACTGGTAGCCGATGAGGAAGTGCGGCGGCGGCTGGCGGTAGAGCGGCCATCGCTCGGTGGCGGGGG

CGCCGGGCGCGAGGTCCTCGAGCATGGTGCGGTGGTAGCCGTAGATGTACCTGGACATCCAGGTGATGCCG

GCGGCGGTGGTGGAGGCGCGCGGGAACTCGCGGACGCGGTTCCAGATGTTGCGCAGCGGCAGGAAGTAGT

TCATGGTGGGCACGGTCTGGCCCGTGAGGCGCGCGCAGTCGTGGATGCTCTATACGGGCAAAAACGAAAG

CGGTCAGCGGCTCGACTCCGTGGCCTGGAGGCTAAGCGAACGGGTTGGGCTGCGCGTGTACCCCGGTTCGA

ATCTCGAATCAGGCTGGAGCCGCAGCTAACGTGGTATTGGCACTCCCGTCTCGACCCAAGCCTGCACCAAC

CCTCCAGGATACGGAGGCGGGTCGTTTTGCAACTTTTTTTTGGAGGCCGGATGAGACTAGTAAGCGCGGAA

AGCGGCCGACCGCGATGGCTCGCTGCCGTAGTCTGGAGAAGAATCGCCAGGGTTGCGTTGCGGTGTGCCC

GGTTCGAGGCCGGCCGGATTCCGCGGCTAACGAGGGCGTGGCTGCCCCGTCGTTTCCAAGACCCCATAGCC

AGCCGACTTCTCCAGTTACGGAGCGAGCCCCTCTTTTGTTTTGTTTGTTTTTGCCAGATGCATCCCGTACTGC

GGCAGATGCGCCCCCACCACCCTCCACCGCAACAACAGCCCCCTCCACAGCCGGCGCTTCTGCCCCCGCCC

CAGCAGCAACTTCCAGCCACGACCGCCGCGGCCGCCGTGAGCGGGGCTGGACAGAGTTATGATCACCAGC

TGGCCTTGGAAGAGGGCGAGGGGCTGGCGCGCCTGGGGGCGTCGTCGCCGGAGCGGCACCCGCGCGTGCA

GATGAAAAGGGACGCTCGCGAGGCCTACGTGCCCAAGCAGAACCTGTTCAGAGACAGGAGCGGCGAGGAG

CCCGAGGAGATGCGCGCGGCCCGGTTCCACGCGGGGCGGGAGCTGCGGCGCGGCCTGGACCGAAAGAGGG

TGCTGAGGGACGAGGATTTCGAGGCGGACGAGCTGACGGGGATCAGCCCCGCGCGCGCGCACGTGGCCGC

GGCCAACCTGGTCACGGCGTACGAGCAGACCGTGAAGGAGGAGAGCAACTTCCAAAAATCCTTCAACAAC

CACGTGCGCACCCTGATCGCGCGCGAGGAGGTGACCCTGGGCCTGATGCACCTGTGGGACCTGCTGGAGGC

CATCGTGCAGAACCCCACCAGCAAGCCGCTGACGGCGCAGCTGTTCCTGGTGGTGCAGCATAGTCGGGACA

ACGAAGCGTTCAGGGAGGCGCTGCTGAATATCACCGAGCCCGAGGGCCGCTGGCTCCTGGACCTGGTGAA

CATTCTGCAGAGCATCGTGGTGCAGGAGCGCGGGCTGCCGCTGTCCGAGAAGCTGGCGGCCATCAACTTCT

CGGTGCTGAGTTTGGGCAAGTACTACGCTAGGAAGATCTACAAGACCCCGTACGTGCCCATAGACAAGGAG

GTGAAGATCGACGGGTTTTACATGCGCATGACCCTGAAAGTGCTGACCCTGAGCGACGATCTGGGGGTGTA

CCGCAACGACAGGATGCACCGTGCGGTGAGCGCCAGCAGGCGGCGCGAGCTGAGCGACCAGGAGCTGATG

-continued

CATAGTCTGCAGCGGGCCCTGACCGGGGCCGGGACCGAGGGGGAGAGCTACTTTGACATGGGCGCGGACC

TGCACTGGCAGCCCAGCCGCCGGGCCTTGGAGGCGGCGGCAGGACCCTACGTAGAAGAGGTGGACGATGA

GGTGGACGAGGAGGGCGAGTACCTGGAAGACTGATGGCGCGACCGTATTTTTGCTAGATGCAACAACAAC

AGCCACCTCCTGATCCCGCGATGCGGGCGGCGCTGCAGAGCCAGCCGTCCGGCATTAACTCCTCGGACGAT

TGGACCCAGGCCATGCAACGCATCATGGCGCTGACGACCCGCAACCCCGAAGCCTTTAGACAGCAGCCCCA

GGCCAACCGGCTCTCGGCCATCCTGGAGGCCGTGGTGCCCTCGCGCTCCAACCCCACGCACGAGAAGGTCC

TGGCCATCGTGAACGCGCTGGTGGAGAACAAGGCCATCCGCGGCGACGAGGCCGGCCTGGTGTACAACGC

GCTGCTGGAGCGCGTGGCCCGCTACAACAGCACCAACGTGCAGACCAACCTGGACCGCATGGTGACCGAC

GTGCGCGAGGCCGTGGCCCAGCGCGAGCGGTTCCACCGCGAGTCCAACCTGGGATCCATGGTGGCGCTGA

ACGCCTTCCTCAGCACCCAGCCCGCCAACGTGCCCCGGGGCCAGGAGGACTACACCAACTTCATCAGCGCC

CTGCGCCTGATGGTGACCGAGGTGCCCCAGAGCGAGGTGTACCAGTCCGGGCCGGACTACTTCTTCCAGAC

CAGTCGCCAGGGCTTGCAGACCGTGAACCTGAGCCAGGCTTTCAAGAACTTGCAGGGCCTGTGGGGCGTGC

AGGCCCCGGTCGGGGACCGCGCGACGGTGTCGAGCCTGCTGACGCCGAACTCGCGCCTGCTGCTGCTGCTG

GTGGCCCCCTTCACGGACAGCGGCAGCATCAACCGCAACTCGTACCTGGGCTACCTGATTAACCTGTACCG

CGAGGCCATCGGCCAGGCGCACGTGGACGAGCAGACCTACCAGGAGATCACCCACGTGAGCCGCGCCCTG

GGCCAGGACGACCCGGGCAACCTGGAAGCCACCCTGAACTTTTTGCTGACCAACCGGTCGCAGAAGATCCC

GCCCCAGTACGCGCTCAGCACCGAGGAGGAGCGCATCCTGCGTTACGTGCAGCAGAGCGTGGGCCTGTTCC

TGATGCAGGAGGGGGCCACCCCCAGCGCCGCGCTCGACATGACCGCGCGCAACATGGAGCCCAGCATGTA

CGCCAGCAACCGCCCGTTCATCAATAAACTGATGGACTACTTGCATCGGGCGGCCGCCATGAACTCTGACT

ATTTCACCAACGCCATCCTGAATCCCCACTGGCTCCCGCCGCCGGGGTTCTACACGGGCGAGTACGACATG

CCCGACCCCAATGACGGGTTCCTGTGGGACGATGTGGACAGCAGCGTGTTCTCCCCCCGACCGGGTGCTAA

CGAGCGCCCCTTGTGGAAGAAGGAAGGCAGCGACCGACGCCCGTCCTCGGCGCTGTCCGGCCGCGAGGGT

GCTGCCGCGGCGGTGCCGAGGCCGCCAGTCCTTTCCCGAGCTTGCCCTTCTCGCTGAACAGTATCCGCAGC

AGCGAGCTGGGCAGGATCACGCGCCCGCGCTTGCTGGGCGAAGAGGAGTACTTGAATGACTCGCTGTTGAG

ACCCGAGCGGGAGAAGAACTTCCCCAATAACGGGATAGAAAGCCTGGTGGACAAGATGAGCCGCTGGAAG

ACGTATGCGCAGGAGCACAGGGACGATCCCCGGGCGTCGCAGGGGGCCACGAGCCGGGGCAGCGCCGCCC

GTAAACGCCGGTGGCACGACAGGCAGCGGGGACAGATGTGGGACGATGAGGACTCCGCCGACGACAGCA

GCGTGTTGGACTTGGGTGGGAGTGGTAACCCGTTCGCTCACCTGCGCCCCCGTATCGGGCGCATGATGTAA

GAGAAACCGAAAATAAATGATACTCACCAAGGCCATGGCGACCAGCGTGCGTTCGTTTCTTCTCTGTTGTT

GTTGTATCTAGTATGATGAGGCGTGCGTACCCGGAGGGTCCTCCTCCCTCGTACGAGAGCGTGATGCAGCA

GGCGATGGCGGCGGCGGCGATGCAGCCCCCGCTGGAGGCTCCTTACGTGCCCCCGCGGTACCTGGCGCCTA

CGGAGGGGCGGAACAGCATTCGTTACTCGGAGCTGGCACCCTTGTACGATACCACCCGGTTGTACCTGGTG

GACAACAAGTCGGCGGACATCGCCTCGCTGAACTACCAGAACGACCACAGCAACTTCCTGACCACCGTGGT

GCAGAACAATGACTTCACCCCCACGGAGGCCAGCACCCAGACCATCAACTTTGACGAGCGCTCGCGGTGG

GGCGGCCAGCTGAAAACCATCATGCACACCAACATGCCCAACGTGAACGAGTTCATGTACAGCAACAAGT

TCAAGGCGCGGGTGATGGTCTCCCGCAAGACCCCCAATGGGGTGACAGTGACAGAGGATTATGATGGTAGT

CAGGATGAGCTGAAGTATGAATGGGTGGAATTTGAGCTGCCCGAAGGCAACTTCTCGGTGACCATGACCAT

CGACCTGATGAACAACGCCATCATCGACAATTACTTGGCGGTGGGGCGGCAGAACGGGGTGCTGGAGAGC

GACATCGGCGTGAAGTTCGACACTAGGAACTTCAGGCTGGGCTGGGACCCCGTGACCGAGCTGGTCATGCC

CGGGGTGTACACCAACGAGGCTTTCCATCCCGATATTGTCTTGCTGCCCGGCTGCGGGGTGGACTTCACCG

AGAGCCGCCTCAGCAACCTGCTGGGCATTCGCAAGAGGCAGCCCTTCCAGGAAGGCTTCCAGATCATGTAC

-continued

GAGGATCTGGAGGGGGGCAACATCCCCGCGCTCCTGGATGTCGACGCCTATGAGAAAAGCAAGGAGGATG

CAGCAGCTGAAGCAACTGCAGCCGTAGCTACCGCCTCTACCGAGGTCAGGGGCGATAATTTTGCAAGCGCC

GCAGCAGTGGCAGCGGCCGAGGCGGCTGAAACCGAAAGTAAGATAGTCATTCAGCCGGTGGAGAAGGATA

GCAAGAACAGGAGCTACAACGTACTACCGGACAAGATAAACACCGCCTACCGCAGCTGGTACCTAGCCTA

CAACTATGGCGACCCCGAGAAGGGCGTGCGCTCCTGGACGCTGCTCACCACCTCGGACGTCACCTGCGGCG

TGGAGCAAGTCTACTGGTCGCTGCCCGACATGATGCAAGACCCGGTCACCTTCCGCTCCACGCGTCAAGTT

AGCAACTACCCGGTGGTGGGCGCCGAGCTCCTGCCCGTCTACTCCAAGAGCTTCTTCAACGAGCAGGCCGT

CTACTCGCAGCAGCTGCGCGCCTTCACCTCGCTTACGCACGTCTTCAACCGCTTCCCCGAGAACCAGATCCT

CGTCCGCCCGCCCGCGCCCACCATTACCACCGTCAGTGAAAACGTTCCTGCTCTCACAGATCACGGGACCC

TGCCGCTGCGCAGCAGTATCCGGGGAGTCCAGCGCGTGACCGTTACTGACGCCAGACGCCGCACCTGCCCC

TACGTCTACAAGGCCCTGGGCATAGTCGCGCCGCGCGTCCTCTCGAGCCGCACCTTCTAAATGTCCATTCTC

ATCTCGCCCAGTAATAACACCGGTTGGGGCCTGCGCGCGCCCAGCAAGATGTACGGAGGCGCTCGCCAACG

CTCCACGCAACACCCCGTGCGCGTGCGCGGGCACTTCCGCGCTCCCTGGGGCGCCCTCAAGGGCCGCGTGC

GGTCGCGCACCACCGTCGACGACGTGATCGACCAGGTGGTGGCCGACGCGCGCAACTACACCCCCGCCGCC

GCGCCCGTCTCCACCGTGGACGCCGTCATCGACAGCGTGGTGGCCGACGCGCGCCGGTACGCCCGCGCCAA

GAGCCGGCGGCGGCGCATCGCCCGGCGGCACCGGAGCACCCCCGCCATGCGCGCGGCGCGAGCCTTGCTG

CGCAGGGCCAGGCGCACGGGACGCAGGGCCATGCTCAGGGCGGCCAGACGCGCGGCTTCAGGCGCCAGCG

CCGGCAGGACCCGGAGACGCGCGGCCACGGCGGCGGCAGCGGCCATCGCCAGCATGTCCCGCCCGCGGCG

AGGGAACGTGTACTGGGTGCGCGACGCCGCCACCGGTGTGCGCGTGCCCGTGCGCACCCGCCCCCCTCGCA

CTTGAAGATGTTCACTTCGCGATGTTGATGTGTCCCAGCGGCGAGGAGGATGTCCAAGCGCAAATTCAAGG

AAGAGATGCTCCAGGTCATCGCGCCTGAGATCTACGGCCCTGCGGTGGTGAAGGAGGAAAGAAAGCCCCG

CAAAATCAAGCGGGTCAAAAAGGACAAAAAGGAAGAAGAAAGTGATGTGGACGGATTGGTGGAGTTTGTG

CGCGAGTTCGCCCCCCGGCGGCGCGTGCAGTGGCGCGGGCGGAAGGTGCAACCGGTGCTGAGACCCGGCA

CCACCGTGGTCTTCACGCCCGGCGAGCGCTCCGGCACCGCTTCCAAGCGCTCCTACGACGAGGTGTACGGG

GATGATGATATTCTGGAGCAGGCGGCCGAGCGCCTGGGCGAGTTTGCTTACGGCAAGCGCAGCCGTTCCGC

ACCGAAGGAAGAGGCGGTGTCCATCCCGCTGGACCACGGCAACCCCACGCCGAGCCTCAAGCCCGTGACC

TTGCAGCAGGTGCTGCCGACCGCGGCGCCGCGCCGGGGGTTCAAGCGCGAGGGCGAGGATCTGTACCCCA

CCATGCAGCTGATGGTGCCCAAGCGCCAGAAGCTGGAAGACGTGCTGGAGACCATGAAGGTGGACCCGGA

CGTGCAGCCCGAGGTCAAGGTGCGGCCCATCAAGCAGGTGGCCCCGGGCCTGGGCGTGCAGACCGTGGAC

ATCAAGATTCCCACGGAGCCCATGGAAACGCAGACCGAGCCCATGATCAAGCCCAGCACCAGCACCATGG

AGGTGCAGACGGATCCCTGGATGCCATCGGCTCCTAGTCGAAGACCCCGGCGCAAGTACGGCGCGGCCAG

CCTGCTGATGCCCAACTACGCGCTGCATCCTTCCATCATCCCCACGCCGGGCTACCGCGGCACGCGCTTCTA

CCGCGGTCATACCAGCAGCCGCCGCCGCAAGACCACCACTCGCCGCCGCCGTCGCCGCACCGCCGCTGCAA

CCACCCCTGCCGCCCTGGTGCGGAGAGTGTACCGCCGCGGCCGCGCACCTCTGACCCTGCCGCGCGCGCGC

TACCACCCGAGCATCGCCATTTAAACTTTCGCCTGCTTTGCAGATCAATGGCCCTCACATGCCGCCTTCGCG

TTCCCATTACGGGCTACCGAGGAAGAAAACCGCGCCGTAGAAGGCTGGCGGGGAACGGGATGCGTCGCCA

CCACCACCGGCGGCGGCGCGCCATCAGCAAGCGGTTGGGGGGAGGCTTCCTGCCCGCGCTGATCCCCATCA

TCGCCGCGGCGATCGGGGCGATCCCCGGCATTGCTTCCGTGGCGGTGCAGGCCTCTCAGCGCCACTGAGAC

ACACTTGGAAACATCTTGTAATAAACCAATGGACTCTGACGCTCCTGGTCCTGTGATGTGTTTTCGTAGACA

GATGGAAGACATCAATTTTTCGTCCCTGGCTCCGCGACACGGCACGCGGCCGTTCATGGGCACCTGGAGCG

-continued

ACATCGGCACCAGCCAACTGAACGGGGGCGCCTTCAATTGGAGCAGTCTCTGGAGCGGGCTTAAGAATTTC

GGGTCCACGCTTAAAACCTATGGCAGCAAGGCGTGGAACAGCACCACAGGGCAGGCGCTGAGGGATAAGC

TGAAAGAGCAGAACTTCCAGCAGAAGGTGGTCGATGGGCTCGCCTCGGGCATCAACGGGGTGGTGGACCT

GGCCAACCAGGCCGTGCAGCGGCAGATCAACAGCCGCCTGGACCCGGTGCCGCCCGCCGGCTCCGTGGAG

ATGCCGCAGGTGGAGGAGGAGCTGCCTCCCCTGGACAAGCGGGGCGAGAAGCGACCCCGCCCCGATGCGG

AGCAGACGCTGCTGACGCACACGGACGAGCCGCCCCCGTACGAGGAGGCGGTGAAACTGGGTCTGCCCAC

CACGCGGCCCATCGCGCCCCTGGCCACCGGGGTGCTGAAACCCGAAAAGCCCGCGACCCTGGACTTGCCTC

CTCCCCAGCCTTCCCGCCCCTCTACAGTGGCTAAGCCCCTGCCGCCGGTGGCCGTGGCCCGCGCGCGACCC

GGGGGCACCGCCCGCCCTCATGCGAACTGGCAGAGCACTCTGAACAGCATCGTGGGTCTGGGAGTGCAGA

GTGTGAAGCGCCGCCGCTGCTATTAAACCTACCGTAGCGCTTAACTTGCTTGTCTGTGTGTGTATGTATTAT

GTCGCCGCCGCCGCTGTCCACCAGAAGGAGGAGTGAAGAGGCGCGTCGCCGAGTTGCAAGATGGCCACCC

CATCGATGCTGCCCCAGTGGGCGTACATGCACATCGCCGGACAGGACGCTTCGGAGTACCTGAGTCCGGGT

CTGGTGCAGTTTGCCCGCGCCACAGACACCTACTTCAGTCTGGGGAACAAGTTTAGGAACCCCACGGTGGC

GCCCACGCACGATGTGACCACCGACCGCAGCCAGCGGCTGACGCTGCGCTTCGTGCCCGTGGACCGCGAGG

ACAACACCTACTCGTACAAAGTGCGCTACACGCTGGCCGTGGGCGACAACCGCGTGCTGGACATGGCCAGC

ACCTACTTTGACATCCGCGGCGTGCTGGATCGGGGCCCTAGCTTCAAACCCTACTCCGGCACCGCCTACAA

CAGTCTGGCCCCCAAGGGAGCACCCAACACTTGTCAGTGGACATATAAAGCCGATGGTGAAACTGCCACA

GAAAAAACCTATACATATGGAAATGCACCCGTGCAGGGCATTAACATCACAAAAGATGGTATTCAACTTGG

AACTGACACCGATGATCAGCCAATCTACGCAGATAAAACCTATCAGCCTGAACCTCAAGTGGGTGATGCTG

AATGGCATGACATCACTGGTACTGATGAAAAGTATGGAGGCAGAGCTCTTAAGCCTGATACCAAAATGAA

GCCTTGTTATGGTTCTTTTGCCAAGCCTACTAATAAAGAAGGAGGTCAGGCAAATGTGAAAACAGGAACAG

GCACTACTAAAGAATATGACATAGACATGGCTTTCTTTGACAACAGAAGTGCGGCTGCTGCTGGCCTAGCT

CCAGAAATTGTTTTGTATACTGAAAATGTGGATTTGGAAACTCCAGATACCCATATTGTATACAAAGCAGG

CACAGATGACAGCAGCTCTTCTATTAATTTGGGTCAGCAAGCCATGCCCAACAGACCTAACTACATTGGTTT

CAGAGACAACTTTATCGGGCTCATGTACTACAACAGCACTGGCAATATGGGGGTGCTGGCCGGTCAGGCTT

CTCAGCTGAATGCTGTGGTTGACTTGCAAGACAGAAACACCGAGCTGTCCTACCAGCTCTTGCTTGACTCTC

TGGGTGACAGAACCCGGTATTTCAGTATGTGGAATCAGGCGGTGGACAGCTATGATCCTGATGTGCGCATT

ATTGAAAATCATGGTGTGGAGGATGAACTTCCCAACTATTGTTTCCCTCTGGATGCTGTTGGCAGAACAGAT

ACTTATCAGGGAATTAAGGCTAATGGAACTGATCAAACCACATGGACCAAAGATGACAGTGTCAATGATGC

TAATGAGATAGGCAAGGGTAATCCATTCGCCATGGAAATCAACATCCAAGCCAACCTGTGGAGGAACTTCC

TCTACGCCAACGTGGCCCTGTACCTGCCCGACTCTTACAAGTACACGCCGGCCAATGTTACCCTGCCCACCA

ACACCAACACCTACGATTACATGAACGGCCGGGTGGTGGCGCCCTCGCTGGTGGACTCCTACATCAACATC

GGGGCGCGCTGGTCGCTGGATCCCATGGACAACGTGAACCCCTTCAACCACCACCGCAATGCGGGGCTGCG

CTACCGCTCCATGCTCCTGGGCAACGGGCGCTACGTGCCCTTCCACATCCAGGTGCCCCAGAAATTTTCGC

CATCAAGAGCCTCCTGCTCCTGCCCGGGTCCTACACCTACGAGTGGAACTTCCGCAAGGACGTCAACATGA

TCCTGCAGAGCTCCCTCGGCAACGACCTGCGCACGGACGGGGCCTCCATCTCCTTCACCAGCATCAACCTCT

ACGCCACCTTCTTCCCCATGGCGCACAACACGGCCTCCACGCTCGAGGCCATGCTGCGCAACGACACCAAC

GACCAGTCCTTCAACGACTACCTCTCGGCGGCCAACATGCTCTACCCCATCCCGGCCAACGCCACCAACGT

GCCCATCTCCATCCCCTCGCGCAACTGGGCCGCCTTCCGCGGCTGGTCCTTCACGCGTCTCAAGACCAAGGA

GACGCCCTCGCTGGGCTCCGGGTTCGACCCCTACTTCGTCTACTCGGGCTCCATCCCCTACCTCGACGGCAC

CTTCTACCTCAACCACACCTTCAAGAAGGTCTCCATCACCTTCGACTCCTCCGTCAGCTGGCCCGGCAACGA

-continued

CCGGCTCCTGACGCCCAACGAGTTCGAAATCAAGCGCACCGTCGACGGCGAGGGCTACAACGTGGCCCAG

TGCAACATGACCAAGGACTGGTTCCTGGTCCAGATGCTGGCCCACTACAACATCGGCTACCAGGGCTTCTA

CGTGCCCGAGGGCTACAAGGACCGCATGTACTCCTTCTTCCGCAACTTCCAGCCCATGAGCCGCCAGGTGG

TGGACGAGGTCAACTACAAGGACTACCAGGCCGTCACCCTGGCCTACCAGCACAACAACTCGGGCTTCGTC

GGCTACCTCGCGCCCACCATGCGCCAGGGCCAGCCCTACCCCGCCAACTACCCCTACCCGCTCATCGGCAA

GAGCGCCGTCACCAGCGTCACCCAGAAAAAGTTCCTCTGCGACAGGGTCATGTGGCGCATCCCCTTCTCCA

GCAACTTCATGTCCATGGGCGCGCTCACCGACCTCGGCCAGAACATGCTCTATGCCAACTCCGCCCACGCG

CTAGACATGAATTTCGAAGTCGACCCCATGGATGAGTCCACCCTTCTCTATGTTGTCTTCGAAGTCTTCGAC

GTCGTCCGAGTGCACCAGCCCCACCGCGGCGTCATCGAGGCCGTCTACCTGCGCACCCCCTTCTCGGCCGG

TAACGCCACCACCTAAGCTCTTGCTTCTTGCAAGCCATGGCCGCGGGCTCCGGCGAGCAGGAGCTCAGGGC

CATCATCCGCGACCTGGGCTGCGGGCCTACTTCCTGGGCACCTTCGATAAGCGCTTCCCGGGATTCATGGC

CCCGCACAAGCTGGCCTGCGCCATCGTCAACACGGCCGGCCGCGAGACCGGGGGCGAGCACTGGCTGGCC

TTCGCCTGGAACCCGCGCTCGAACACCTGCTACCTCTTCGACCCCTTCGGGTTCTCGGACGAGCGCCTCAAG

CAGATCTACCAGTTCGAGTACGAGGGCCTGCTGCGCCGCAGCGCCCTGGCCACCGAGGACCGCTGCGTCAC

CCTGGAAAAGTCCACCCAGACCGTGCAGGGTCCGCGCTCGGCCGCCTGCGGGCTCTTCTGCTGCATGTTCCT

GCACGCCTTCGTGCACTGGCCCGACCGCCCCATGGACAAGAACCCCACCATGAACTTGCTGACGGGGGTGC

CCAACGGCATGCTCCAGTCGCCCCAGGTGGAACCCACCCTGCGCCGCAACCAGGAGGCGCTCTACCGCTTC

CTCAACTCCCACTCCGCCTACTTTCGCTCCCACCGCGCGCGCATCGAGAAGGCCACCGCCTTCGACCGCATG

AATCAAGACATGTAAACCGTGTGTGTATGTTAAATGTCTTTAATAAACAGCACTTTCATGTTACACATGCAT

CTGAGATGATTTATTTAGAAATCGAAAGGGTTCTGCCGGGTCTCGGCATGGCCCGCGGGCAGGGACACGTT

GCGGAACTGGTACTTGGCCAGCCACTTGAACTCGGGGATCAGCAGTTTGGGCAGCGGGGTGTCGGGGAAG

GAGTCGGTCCACAGCTTCCGCGTCAGTTGCAGGGCGCCCAGCAGGTCGGGCGCGGAGATCTTGAAATCGCA

GTTGGGACCCGCGTTCTGCGCGCGGGAGTTGCGGTACACGGGGTTGCAGCACTGGAACACCATCAGGGCCG

GGTGCTTCACGCTCGCCAGCACCGTCGCGTCGGTGATGCTCTCCACGTCGAGGTCCTCGGCGTTGGCCATCC

CGAAGGGGGTCATCTTGCAGGTCTGCCTTCCCATGGTGGGCACGCACCCGGGCTTGTGGTTGCAATCGCAG

TGCAGGGGGATCAGCATCATCTGGGCCTGGTCGGCGTTCATCCCCGGGTACATGGCCTTCATGAAAGCCTC

CAATTGCCTGAACGCCTGCTGGGCCTTGGCTCCCTCGGTGAAGAAGACCCCGCAGGACTTGCTAGAGAACT

GGTTGGTGGCGCACCCGGCGTCGTGCACGCAGCAGCGCGCGTCGTTGTTGGCCAGCTGCACCACGCTGCGC

CCCCAGCGGTTCTGGGTGATCTTGGCCCGGTCGGGGTTCTCCTTCAGCGCGCGCTGCCCGTTCTCGCTCGCC

ACATCCATCTCGATCATGTGCTCCTTCTGGATCATGGTGGTCCCGTGCAGGCACCGCAGCTTGCCCTCGGCC

TCGGTGCACCCGTGCAGCCACAGCGCGCACCCGGTGCACTCCCAGTTCTTGTGGGCGATCTGGGAATGCGC

GTGCACGAAGCCCTGCAGGAAGCGGCCCATCATGGTGGTCAGGGTCTTGTTGCTAGTGAAGGTCAGCGGAA

TGCCGCGGTGCTCCTCGTTGATGTACAGGTGGCAGATGCGGCGGTACACCTCGCCCTGCTCGGGCATCAGC

TGGAAGTTGGCTTTCAGGTCGGTCTCCACGCGGTAGCGGTCCATCAGCATAGTCATGATTTCCATACCCTTC

TCCCAGGCCGAGACGATGGGCAGGCTCATAGGGTTCTTCACCATCATCTTAGCGCTAGCAGCCGCGGCCAG

GGGGTCGCTCTCGTCCAGGGTCTCAAAGCTCCGCTTGCCGTCCTTCTCGGTGATCCGCACCGGGGGGTAGCT

GAAGCCCACGGCCGCCAGCTCCTCCTCGGCCTGTCTTTCGTCCTCGCTGTCCTGGCTGACGTCCTGCAGGAC

CACATGCTTGGTCTTGCGGGGTTTCTTCTTGGGCGGCAGCGGCGGCGGAGATGTTGGAGATGGCGAGGGGG

AGCGCGAGTTCTCGCTCACCACTACTATCTCTTCCTCTTCTTGGTCCGAGGCCACGCGGCGGTAGGTATGTC

TCTTCGGGGGCAGAGGCGGAGGCGACGGGCTCTCGCCGCCGCGACTTGGCGGATGGCTGGCAGAGCCCCTT

-continued

CCGCGTTCGGGGGTGCGCTCCCGGCGGCGCTCTGACTGACTTCCTCCGCGGCCGGCCATTGTGTTCTCCTAG

GGAGGAACAACAAGCATGGAGACTCAGCCATCGCCAACCTCGCCATCTGCCCCCACCGCCGACGAGAAGC

AGCAGCAGCAGAATGAAAGCTTAACCGCCCCGCCGCCCAGCCCCGCCACCTCCGACGCGGCCGTCCCAGA

CATGCAAGAGATGGAGGAATCCATCGAGATTGACCTGGGCTATGTGACGCCCGCGGAGCACGAGGAGGAG

CTGGCAGTGCGCTTTTCACAAGAAGAGATACACCAAGAACAGCCAGAGCAGGAAGCAGAGAATGAGCAGA

GTCAGGCTGGGCTCGAGCATGACGGCGACTACCTCCACCTGAGCGGGGGGGAGGACGCGCTCATCAAGCA

TCTGGCCCGGCAGGCCACCATCGTCAAGGATGCGCTGCTCGACCGCACCGAGGTGCCCCTCAGCGTGGAGG

AGCTCAGCCGCGCCTACGAGTTGAACCTCTTCTCGCCGCGCGTGCCCCCCAAGCGCCAGCCCAATGGCACC

TGCGAGCCCAACCCGCGCCTCAACTTCTACCCGGTCTTCGCGGTGCCCGAGGCCCTGGCCACCTACCACATC

TTTTTCAAGAACCAAAAGATCCCCGTCTCCTGCCGCGCCAACCGCACCCGCGCCGACGCCCTTTTCAACCTG

GGTCCCGGCGCCCGCCTACCTGATATCGCCTCCTTGGAAGAGGTTCCCAAGATCTTCGAGGGTCTGGGCAG

CGACGAGACTCGGGCCGCGAACGCTCTGCAAGGAGAAGGAGGAGAGCATGAGCACCACAGCGCCCTGGTC

GAGTTGGAAGGCGACAACGCGCGGCTGGCGGTGCTCAAACGCACGGTCGAGCTGACCCATTCGCCTACCC

GGCTCTGAACCTGCCCCCCAAAGTCATGAGCGCGGTCATGGACCAGGTGCTCATCAAGCGCGCGTCGCCCA

TCTCCGAGGACGAGGGCATGCAAGACTCCGAGGAGGGCAAGCCCGTGGTCAGCGACGAGCAGCTGGCCCG

GTGGCTGGGTCCTAATGCTAGTCCCCAGAGTTTGGAAGAGCGGCGCAAACTCATGATGGCCGTGGTCCTGG

TGACCGTGGAGCTGGAGTGCCTGCGCCGCTTCTTCGCCGACGCGGAGACCCTGCGCAAGGTCGAGGAGAAC

CTGCACTACCTCTTCAGGCACGGGTTCGTGCGCCAGGCCTGCAAGATCTCCAACGTGGAGCTGACCAACCT

GGTCTCCTACATGGGCATCTTGCACGAGAACCGCCTGGGGCAGAACGTGCTGCACACCACCCTGCGCGGGG

AGGCCCGGCGCGACTACATCCGCGACTGCGTCTACCTCTACCTCTGCCACACCTGGCAGACGGGCATGGGC

GTGTGGCAGCAGTGTCTGGAGGAGCAGAACCTGAAAGAGCTCTGCAAGCTCCTGCAGAAGAACCTCAAGG

GTCTGTGGACCGGGTTCGACGAGCGCACCACCGCCTCGGACCTGGCCGACCTCATTTTCCCCGAGCGCCTC

AGGCTGACGCTGCGCAACGGCCTGCCCGACTTTATGAGCCAAAGCATGTTGCAAAACTTTCGCTCTTTCATC

CTCGAACGCTCCGGAATCCTGCCCGCCACCTGCTCCGCGCTGCCCTCGGACTTCGTGCCGCTGACCTTCCGC

GAGTGCCCCCCGCCGCTGTGGAGCCACTGCTACCTGCTGCGCCTGGCCAACTACCTGGCCTACCACTCGGA

CGTGATCGAGGACGTCAGCGGCGAGGGCCTGCTCGAGTGCCACTGCCGCTGCAACCTCTGCACGCCGCACC

GCTCCCTGGCCTGCAACCCCCAGCTGCTGAGCGAGACCCAGATCATCGGCACCTTCGAGTTGCAAGGGCCC

AGCGAAGGCGAGGGTTCAGCCGCCAAGGGGGGTCTGAAACTCACCCCGGGGCTGTGGACCTCGGCCTACT

TGCGCAAGTTCGTGCCCGAGGACTACCATCCCTTCGAGATCAGGTTCTACGAGGACCAATCCCATCCGCCC

AAGGCCGAGCTGTCGGCCTGCGTCATCACCCAGGGGGCGATCCTGGCCCAATTGCAAGCCATCCAGAAATC

CCGCCAAGAATTCTTGCTGAAAAAGGGCCGCGGGGTCTACCTCGACCCCCAGACCGGTGAGGAGCTCAACC

CCGGCTTCCCCCAGGATGCCCCGAGGAAACAAGAAGCTGAAAGTGGAGCTGCCGCCCGTGGAGGATTTGG

AGGAAGACTGGGAGAACAGCAGTCAGGCAGAGGAGGAGGAGATGGAGGAAGACTGGGACAGCACTCAGG

CAGAGGAGGACAGCCTGCAAGACAGTCTGGAGGAAGACGAGGAGGAGGCAGAGGAGGAGGTGGAAGAAG

CAGCCGCCGCCAGACCGTCGTCCTCGGCGGGGGAGAAAGCAAGCAGCACGGATACCATCTCCGCTCCGGG

TCGGGGTCCCGCTCGACCACACAGTAGATGGGACGAGACCGGACGATTCCCGAACCCCACCACCCAGACC

GGTAAGAAGGAGCGGCAGGGATACAAGTCCTGGCGGGGGCACAAAAACGCCATCGTCTCCTGCTTGCAGG

CCTGCGGGGGCAACATCTCCTTCACCCGGCGCTACCTGCTCTTCCACCGCGGGGTGAACTTTCCCCGCAACA

TCTTGCATTACTACCGTCACCTCCACAGCCCCTACTACTTCCAAGAAGAGGCAGCAGCAGCAGAAAAAGAC

CAGCAGAAAACCAGCAGCTAGAAAATCCACAGCGGCGGCAGCAGGTGGACTGAGGATCGCGGCGAACGA

GCCGGCGCAAACCCGGGAGCTGAGGAACCGGATCTTTCCCACCCTCTATGCCATCTTCCAGCAGAGTCGGG

-continued

GGCAGGAGCAGGAACTGAAAGTCAAGAACCGTTCTCTGCGCTCGCTCACCCGCAGTTGTCTGTATCACAAG

AGCGAAGACCAACTTCAGCGCACTCTCGAGGACGCCGAGGCTCTCTTCAACAAGTACTGCGCGCTCACTCT

TAAAGAGTAGCCCGCGCCCGCCCAGTCGCAGAAAAAGGCGGGAATTACGTCACCTGTGCCCTTCGCCCTAG

CCGCCTCCACCCATCATCATGAGCAAAGAGATTCCCACGCCTTACATGTGGAGCTACCAGCCCCAGATGGG

CCTGGCCGCCGGTGCCGCCCAGGACTACTCCACCCGCATGAATTGGCTCAGCGCCGGGCCCGCGATGATCT

CACGGGTGAATGACATCCGCGCCCACCGAAACCAGATACTCCTAGAACAGTCAGCGCTCACCGCCACGCCC

CGCAATCACCTCAATCCGCGTAATTGGCCCGCCGCCCTGGTGTACCAGGAAATTCCCCAGCCCACGACCGT

ACTACTTCCGCGAGACGCCCAGGCCGAAGTCCAGCTGACTAACTCAGGTGTCCAGCTGGCGGGCGGCGCCA

CCCTGTGTCGTCACCGCCCCGCTCAGGGTATAAAGCGGCTGGTGATCCGGGGCAGAGGCACACAGCTCAAC

GACGAGGTGGTGAGCTCTTCGCTGGGTCTGCGACCTGACGGAGTCTTCCAACTCGCCGGATCGGGGAGATC

TTCCTTCACGCCTCGTCAGGCCGTCCTGACTTTGGAGAGTTCGTCCTCGCAGCCCCGCTCGGGTGGCATCGG

CACTCTCCAGTTCGTGGAGGAGTTCACTCCCTCGGTCTACTTCAACCCCTTCTCCGGCTCCCCCGGCCACTA

CCCGGACGAGTTCATCCCGAACTTCGACGCCATCAGCGAGTCGGTGGACGGCTACGATTGAAACTAATCAC

CCCCTTATCCAGTGAAATAAAGATCATATTGATGATGATTTTACAGAAATAAAAAATAATCATTTGATTTGA

AATAAAGATACAATCATATTGATGATTTGAGTTTAACAAAAAAATAAAGAATCACTTACTTGAAATCTGAT

ACCAGGTCTCTGTCCATGTTTTCTGCCAACACCACTTCACTCCCCTCTTCCCAGCTCTGGTACTGCAGGCCCC

GGCGGGCTGCAAACTTCCTCCACACGCTGAAGGGGATGTCAAATTCCTCCTGTCCCTCAATCTTCATTTTAT

CTTCTATCAGATGTCCAAAAAGCGCGTCCGGGTGGATGATGACTTCGACCCCGTCTACCCCTACGATGCAG

ACAACGCACCGACCGTGCCCTTCATCAACCCCCCCTTCGTCTCTTCAGATGGATTCCAAGAGAAGCCCCTGG

GGGTGTTGTCCCTGCGACTGGCCGACCCCGTCACCACCAAGAACGGGGAAATCACCCTCAAGCTGGGAGA

GGGGGTGGACCTCGATTCCTCGGGAAAACTCATCTCCAACACGGCCACCAAGGCCGCCGCCCCTCTCAGTT

TTTCCAACAACACCATTTCCCTTAACATGGATCACCCCTTTTACACTAAAGATGGAAAATTATCCTTACAAG

TTTCTCCACCATTAAATATACTGAGAACAAGCATTCTAAACACACTAGCTTTAGGTTTTGGATCAGGTTTAG

GACTCCGTGGCTCTGCCTTGGCAGTACAGTTAGTCTCTCCACTTACATTTGATACTGATGGAAACATAAAGC

TTACCTTAGACAGAGGTTTGCATGTTACAACAGGAGATGCAATTGAAAGCAACATAAGCTGGGCTAAAGGT

TTAAAATTTGAAGATGGAGCCATAGCAACCAACATTGGAAATGGGTTAGAGTTTGGAAGCAGTAGTACAG

AAACAGGTGTTGATGATGCTTACCCAATCCAAGTTAAACTTGGATCTGGCCTTAGCTTTGACAGTACAGGA

GCCATAATGGCTGGTAACAAAGAAGACGATAAACTCACTTTGTGGACAACACCTGATCCATCACCAAACTG

TCAAATACTCGCAGAAAATGATGCAAAACTAACACTTTGCTTGACTAAATGTGGTAGTCAAATACTGGCCA

CTGTGTCAGTCTTAGTTGTAGGAAGTGGAAACCTAAACCCCATTACTGGCACCGTAAGCAGTGCTCAGGTG

TTTCTACGTTTTGATGCAAACGGTGTTCTTTTAACAGAACATTCTACACTAAAAAAATACTGGGGGTATAGG

CAGGGAGATAGCATAGATGGCACTCCATATACCAATGCTGTAGGATTCATGCCCAATTTAAAAGCTTATCC

AAAGTCACAAAGTTCTACTACTAAAAATAATATAGTAGGGCAAGTATACATGAATGGAGATGTTTCAAAAC

CTATGCTTCTCACTATAACCCTCAATGGTACTGATGACAGCAACAGTACATATTCAATGTCATTTTCATACA

CCTGGACTAATGGAAGCTATGTTGGAGCAACATTTGGGGCTAACTCTTATACCTTCTCATACATCGCCCAAG

AATGAACACTGTATCCCACCCTGCATGCCAACCCTTCCCACCCCACTCTGTGGAACAAACTCTGAAACACA

AAATAAAATAAAGTTCAAGTGTTTTATTGATTCAACAGTTTTACAGGATTCGAGCAGTTATTTTTCCTCCAC

CCTCCCAGGACATGGAATACACCACCCTCTCCCCCCGCACAGCCTTGAACATCTGAATGCCATTGGTGATG

GACATGCTTTTGGTCTCCACGTTCCACACAGTTTCAGAGCGAGCCAGTCTCGGGTCGGTCAGGGAGATGAA

ACCCTCCGGGCACTCCCGCATCTGCACCTCACAGCTCAACAGCTGAGGATTGTCCTCGGTGGTCGGGATCA

CGGTTATCTGGAAGAAGCAGAAGAGCGGCGGTGGGAATCATAGTCCGCGAACGGGATCGGCCGGTGGTGT

CGCATCAGGCCCCGCAGCAGTCGCTGCCGCCGCCGCTCCGTCAAGCTGCTGCTCAGGGGGTCCGGGTCCAG

GGACTCCCTCAGCATGATGCCCACGGCCCTCAGCATCAGTCGTCTGGTGCGGCGGGCGCAGCAGCGCATGC

GGATCTCGCTCAGGTCGCTGCAGTACGTGCAACACAGAACCACCAGGTTGTTCAACAGTCCATAGTTCAAC

ACGCTCCAGCCGAAACTCATCGCGGGAAGGATGCTACCCACGTGGCCGTCGTACCAGATCCTCAGGTAAAT

CAAGTGGTGCCCCCTCCAGAACACGCTGCCCACGTACATGATCTCCTTGGGCATGTGGCGGTTCACCACCTC

CCGGTACCACATCACCCTCTGGTTGAACATGCAGCCCCGGATGATCCTGCGGAACCACAGGGCCAGCACCG

CCCCGCCCGCCATGCAGCGAAGAGACCCCGGGTCCCGGCAATGGCAATGGAGGACCCACCGCTCGTACCC

GTGGATCATCTGGGAGCTGAACAAGTCTATGTTGGCACAGCACAGGCATATGCTCATGCATCTCTTCAGCA

CTCTCAACTCCTCGGGGGTCAAAACCATATCCCAGGGCACGGGGAACTCTTGCAGGACAGCGAACCCCGCA

GAACAGGGCAATCCTCGCACAGAACTTACATTGTGCATGGACAGGGTATCGCAATCAGGCAGCACCGGGT

GATCCTCCACCAGAGAAGCGCGGGTCTCGGTCTCCTCACAGCGTGGTAAGGGGGGCCGGCCGATACGGGTG

ATGGCGGGACGCGGCTGATCGTGTTCGCGACCGTGTCATGATGCAGTTGCTTTCGGACATTTTCGTACTTGC

TGTAGCAGAACCTGGTCCGGGCGCTGCACACCGATCGCCGGCGGCGGTCTCGGCGCTTGGAACGCTCGGTG

TTGAAATTGTAAAACAGCCACTCTCTCAGACCGTGCAGCAGATCTAGGGCCTCAGGAGTGATGAAGATCCC

ATCATGCCTGATGGCTCTGATCACATCGACCACCGTGGAATGGGCCAGACCCAGCCAGATGATGCAATTTT

GTTGGGTTTCGGTGACGGCGGGGGAGGGAAGAACAGGAAGAACCATGATTAACTTTTAATCCAAACGGTCT

CGGAGTACTTCAAAATGAAGATCGCGGAGATGGCACCTCTCGCCCCCGCTGTGTTGGTGGAAAATAACAGC

CAGGTCAAAGGTGATACGGTTCTCGAGATGTTCCACGGTGGCTTCCAGCAAAGCCTCCACGCGCACATCCA

GAAACAAGACAATAGCGAAAGCGGGAGGGTTCTCTAATTCCTCAATCATCATGTTACACTCCTGCACCATC

CCCAGATAATTTTCATTTTTCCAGCCTTGAATGATTCGAACTAGTTCCTGAGGTAAATCCAAGCCAGCCATG

ATAAAGAGCTCGCGCAGAGCGCCCTCCACCGGCATTCTTAAGCACACCCTCATAATTCCAAGATATTCTGC

TCCTGGTTCACCTGCAGCAGATTGACAAGCGGAATATCAAAATCTCTGCCGCGATCCCTGAGCTCCTCCCTC

AGCAATAACTGTAAGTACTCTTTCATATCCTCTCCGAAATTTTTAGCCATAGGACCACCAGGAATAAGATTA

GGGCAAGCCACAGTACAGATAAACCGAAGTCCTCCCCAGTGAGCATTGCCAAATGCAAGACTGCTATAAG

CATGCTGGCTAGACCCGGTGATATCTTCCAGATAACTGGACAGAAAATCGCCCAGGCAATTTTTAAGAAAA

TCAACAAAAGAAAAATCCTCCAGGTGGACGTTTAGAGCCTCGGGAACAACGATGAAGTAAATGCAAGCGG

TGCGTTCCAGCATGGTTAGTTAGCTGATCTGTAGAAAAAACAAAAATGAACATTAAACCATGCTAGCCTGG

CGAACAGGTGGGTAAATCGTTCTCTCCAGCACCAGGCAGGCCACGGGGTCTCCGGCGCGACCCTCGTAAAA

ATTGTCGCTATGATTGAAAACCATCACAGAGAGACGTTCCCGGTGGCCGGCGTGAATGATTCGACAAGATG

AATACACCCCCGGAACATTGGCGTCCGCGAGTGAAAAAAAGCGCCCGAGGAAGCAATAAGGCACTACAAT

GCTCAGTCTCAAGTCCAGCAAAGCGATGCCATGCGGATGAAGCACAAAATTCTCAGGTGCGTACAAAATGT

AATTACTCCCCTCCTGCACAGGCAGCAAAGCCCCCGATCCCTCCAGGTACACATACAAAGCCTCAGCGTCC

ATAGCTTACCGAGCAGCAGCACACAACAGGCGCAAGAGTCAGAGAAAGGCTGAGCTCTAACCTGTCCACC

CGCTCTCTGCTCAATATATAGCCCAGATCTACACTGACGTAAAGGCCAAAGTCTAAAAATACCCGCCAAAT

AATCACACACGCCCAGCACACGCCCAGAAACCGGTGACACACTCAAAAAAATACGCGCACTTCCTCAAAC

GCCCAAAACTGCCGTCATTTCCGGGTTCCCACGCTACGTCATCAAAACACGACTTTCAAATTCCGTCGACCG

TTAAAAACGTCACCCGCCCCGCCCCTAACGGTCGCCCGTCTCTCAGCCAATCAGCGCCCCGCATCCCCAAA

TTCAAACACCTCATTTGCATATTAACGCGCACAAAAAGTTTGAGGTATATTATTGATGATGG

-continued

ChAdV68-CT-TSNA (SEQ ID NO: 66)

CATCATCAATAATATACCTCAAACTTTTTGTGCGCGTTAATATGCAAATGAGGCGTTTGAATTTGGGGAGGA

AGGGCGGTGATTGGTCGAGGGATGAGCGACCGTTAGGGGCGGGGCGAGTGACGTTTTGATGACGTGGTTG

CGAGGAGGAGCCAGTTTGCAAGTTCTCGTGGGAAAAGTGACGTCAAACGAGGTGTGGTTTGAACACGGAA

ATACTCAATTTTCCCGCGCTCTCTGACAGGAAATGAGGTGTTTCTGGGCGGATGCAAGTGAAAACGGGCCA

TTTTCGCGCGAAAACTGAATGAGGAAGTGAAAATCTGAGTAATTTCGCGTTTATGGCAGGGAGGAGTATTT

GCCGAGGGCCGAGTAGACTTTGACCGATTACGTGGGGGTTTCGATTACCGTGTTTTTCACCTAAATTTCCGC

GTACGGTGTCAAAGTCCGGTGTTTTTACGTAGGTGTCAGCTGATCGCCAGGGTATTTAAACCTGCGCTCTCC

AGTCAAGAGGCCACTCTTGAGTGCCAGCGAGAAGAGTTTTCTCCTCCGCGCCGCGAGTCAGATCTACACTT

TGAAAGTAGGGATAACAGGGTAATGACATTGATTATTGACTAGTTGTTAATAGTAATCAATTACGGGGTCA

TTAGTTCATAGCCCATATATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAATAGGGACTTTCCATTG

ACGTCAATGGGTGGAGTATTTACGGTAAACTGCCCACTTGGCAGTACATCAAGTGTATCATATGCCAAGTC

CGCCCCCTATTGACGTCAATGACGGTAAATGGCCCGCCTGGCATTATGCCCAGTACATGACCTTACGGGAC

TTTCCTACTTGGCAGTACATCTACGTATTAGTCATCGCTATTACCATGGTGATGCGGTTTTGGCAGTACACC

AATGGGCGTGGATAGCGGTTTGACTCACGGGGATTTCCAAGTCTCCACCCCATTGACGTCAATGGGAGTTT

GTTTTGGCACCAAAATCAACGGGACTTTCCAAAATGTCGTAATAACCCCGCCCCGTTGACGCAAATGGGCG

GTAGGCGTGTACGGTGGGAGGTCTATATAAGCAGAGCTCGTTTAGTGAACCGTCAGATCGCCTGGAACGCC

ATCCACGCTGTTTTGACCTCCATAGAAGACAGCGATCGCGCCACCATGGCTGGCATGACCGAGTACAAGCT

GGTGGTAGTGGGAGCAGGGGATGTTGGAAAATCAGCCTTGACTATTCAGCTCATCCAGGGCACAGATCTGG

ATCACCAGGAGAAATGTCTCTCGCGACTGTACGACCACATGCCTGAGGGTCTGACCCCCCTTATGGGAGTG

TCGTCCTCTTCTGCGCTGGCCCGTCTCGGATTACCCATGGATAAACTCAATAAAATCACCGCCCCGGCGAGC

CAGAAGTTAAGACAACTGCAAAAGATGGAAACTCCTGAACTACTGCCCTGTGGGTATCTTGTAGAAGAAAA

TACCACGATCTCTGTGACAGTGAAGGGCCTGGAGGCTCAGAATAAGATCAAAGGGTGCACTGGGTCGGTG

AACATGACTTTACAGAGAGCCAGCGCAGCTCCTAAGACTGGTGGCGGGGGTGAAGCCGCTGCATACAACA

ACACTCTTGTGGCACGGCACGTGCCCCAGATACCAAAGCCCGATTCCTTGGTGGGGCTTAGTGATGAGTTG

GGGAAGCGGGACACTTTTGCAGAGTCTCTGATTCGTAGGATGGCATCCGCGGGCTACCTGTTCCTGGACAT

CATCACATACGTGGTCTTTGCTGTAACCTTCGTGCTTGGTGTTTTAGGAGGGCTGAACACAGAAACCAATGA

GAAGGCTTTAGAAGCTGTGTTTGGCAAGTATGGAAGAATAGTGGAGGTGCTGGGGGGCCGGTCATGCGAG

GAGCTGACGGCGGTACTTCCTCCACCTCAGCTTTTGGGCAGGAGATTTAACTTCTTCTCATACTCCTATGTG

GCCGCAGGAAGTTCCGGGAATAACTATGACCTCATGGCCCAACCCATCACGCCCGGGCCCGACACAACCCC

GTTACCAGTGACCGATACTAGTTCCGTGAGTACAGGCCACGCCACCAGCCTGCCTGTGACTGACGCTGGAC

TCAGGGTTACAGAGAGTAAGGGGCACAGCGATTCATGGCACCTGTCTTTGGATACGGCCATCAGGGTCAAC

ACCCCTAAACTGGTGTCCGAGGTTGAGGAACTCAACAAAAGCATTACAGCGCTACGAGAAAAGCTACTGC

AGATGGTGGAGGCCGACAGACCCGGAAACCTCTTCATTGGGGGCTTAAATACAGAGACTAATGAAGACAG

CCCGGTCAAGGATGAAGTAGTGGTGAATGATCAGTGGGGACAGAACTGCAGCTGCCACCACGGCGGTTAC

GAGTTTCCGGACCTGCACCGCACCATCGTGTCTGAGTGTGACGTGTACCTCACCTACATGCTGCGCCAGGCC

GCCCTTCAGCTGTTCTTTGATCTCTACCACTCCATTCCGTCAAGCTTCAGCCCCTTAGTCCTCAGCTGTTTAG

TGCAGCCCTTGGAAGATGTGGAGGTCATGGAGAAGGACGGCACCACATTCTCCTGTGAAGTTTCTCATGAC

GAGGTTCCTCGGACATATGGACCCGTGTTTATGTGTCTGGGAGGACTGCTGACCATGGTGGCTGGAGCTGTT

-continued

TGGCTGACAGTTGGACCCGGACCAGGCGCCAAATTTGTTGCTGCTTGGACACTGAAAGCTGCTGCTGGGCC

CGGACCAGGCCAGTACATCAAGGCCAACTCTAAGTTTATCGGCATCACCGAATTGGGACCTGGACCCGGCT

AGTAGTGAGTTTAAACTCCCATTTAAATGTGAGGGTTAATGCTTCGAGCAGACATGATAAGATACATTGAT

GAGTTTGGACAAACCACAACTAGAATGCAGTGAAAAAAATGCTTTATTTGTGAAATTTGTGATGCTATTGC

TTTATTTGTAACCATTATAAGCTGCAATAAACAAGTTAACAACAACAATTGCATTCATTTTATGTTTCAGGT

TCAGGGGGAGATGTGGGAGGTTTTTTAAAGCAAGTAAAACCTCTACAAATGTGGTAAAATAACTATAACGG

TCCTAAGGTAGCGAGTGAGTAGTGTTCTGGGGCGGGGGAGGACCTGCATGAGGGCCAGAATAACTGAAAT

CTGTGCTTTTCTGTGTGTTGCAGCAGCATGAGCGGAAGCGGCTCCTTTGAGGGAGGGGTATTCAGCCCTTAT

CTGACGGGGCGTCTCCCCTCCTGGGCGGGAGTGCGTCAGAATGTGATGGGATCCACGGTGGACGGCCGGCC

CGTGCAGCCCGCGAACTCTTCAACCCTGACCTATGCAACCCTGAGCTCTTCGTCGTTGGACGCAGCTGCCGC

CGCAGCTGCTGCATCTGCCGCCAGCGCCGTGCGCGGAATGGCCATGGGCGCCGGCTACTACGGCACTCTGG

TGGCCAACTCGAGTTCCACCAATAATCCCGCCAGCCTGAACGAGGAGAAGCTGTTGCTGCTGATGGCCCAG

CTCGAGGCCTTGACCCAGCGCCTGGGCGAGCTGACCCAGCAGGTGGCTCAGCTGCAGGAGCAGACGCGGG

CCGCGGTTGCCACGGTGAAATCCAAATAAAAAATGAATCAATAAATAAACGGAGACGGTTGTTGATTTTAA

CACAGAGTCTGAATCTTTATTTGATTTTTCGCGCGCGGTAGGCCCTGGACCACCGGTCTCGATCATTGAGCA

CCCGGTGGATCTTTTCCAGGACCCGGTAGAGGTGGGCTTGGATGTTGAGGTACATGGGCATGAGCCCGTCC

CGGGGGTGGAGGTAGCTCCATTGCAGGGCCTCGTGCTCGGGGGTGGTGTTGTAAATCACCCAGTCATAGCA

GGGGCGCAGGGCATGGTGTTGCACAATATCTTTGAGGAGGAGACTGATGGCCACGGGCAGCCCTTTGGTGT

AGGTGTTTACAAATCTGTTGAGCTGGGAGGGATGCATGCGGGGGGAGATGAGGTGCATCTTGGCCTGGATC

TTGAGATTGGCGATGTTACCGCCCAGATCCCGCCTGGGGTTCATGTTGTGCAGGACCACCAGCACGGTGTA

TCCGGTGCACTTGGGGAATTTATCATGCAACTTGGAAGGGAAGGCGTGAAAGAATTTGGCGACGCCTTTGT

GCCCGCCCAGGTTTTCCATGCACTCATCCATGATGATGGCGATGGGCCCGTGGGCGGCGGCCTGGGCAAAG

ACGTTTCGGGGGTCGGACACATCATAGTTGTGGTCCTGGGTGAGGTCATCATAGGCCATTTTAATGAATTTG

GGGCGGAGGGTGCCGGACTGGGGGACAAAGGTACCCTCGATCCCGGGGGCGTAGTTCCCCTCACAGATCT

GCATCTCCCAGGCTTTGAGCTCGGAGGGGGGGATCATGTCCACCTGCGGGGCGATAAAGAACACGGTTTCC

GGGGCGGGGGAGATGAGCTGGGCCGAAAGCAAGTTCCGGAGCAGCTGGGACTTGCCGCAGCCGGTGGGGC

CGTAGATGACCCCGATGACCGGCTGCAGGTGGTAGTTGAGGGAGAGACAGCTGCCGTCCTCCCGGAGGAG

GGGGGCCACCTCGTTCATCATCTCGCGCACGTGCATGTTCTCGCGCACCAGTTCCGCCAGGAGGCGCTCTCC

CCCCAGGGATAGGAGCTCCTGGAGCGAGGCGAAGTTTTTCAGCGGCTTGAGTCCGTCGGCCATGGGCATTT

TGGAGAGGGTTTGTTGCAAGAGTTCCAGGCGGTCCCAGAGCTCGGTGATGTGCTCTACGGCATCTCGATCC

AGCAGACCTCCTCGTTTCGCGGGTTGGGACGGCTGCGGGAGTAGGGCACCAGACGATGGGCGTCCAGCGC

AGCCAGGGTCCGGTCCTTCCAGGGTCGCAGCGTCCGCGTCAGGGTGGTCTCCGTCACGGTGAAGGGGTGCG

CGCCGGGCTGGGCGCTTGCGAGGGTGCGCTTCAGGCTCATCCGGCTGGTCGAAAACCGCTCCCGATCGGCG

CCCTGCGCGTCGGCCAGGTAGCAATTGACCATGAGTTCGTAGTTGAGCGCCTCGGCCGCGTGGCCTTTGGC

GCGGAGCTTACCTTTGGAAGTCTGCCCGCAGGCGGGACAGAGGAGGGACTTGAGGGCGTAGAGCTTGGGG

GCGAGGAAGACGGACTCGGGGGCGTAGGCGTCCGCGCCGCAGTGGGCGCAGACGGTCTCGCACTCCACGA

GCCAGGTGAGGTCGGGCTGGTCGGGGTCAAAAACCAGTTTCCCGCCGTTCTTTTTGATGCGTTTCTTACCTT

TGGTCTCCATGAGCTCGTGTCCCCGCTGGGTGACAAAGAGGCTGTCCGTGTCCCCGTAGACCGACTTTATGG

GCCGGTCCTCGAGCGGTGTGCCGCGGTCCTCCTCGTAGAGGAACCCCGCCCACTCCGAGACGAAAGCCCGG

GTCCAGGCCAGCACGAAGGAGGCCACGTGGGACGGGTAGCGGTCGTTGTCCACCAGCGGGTCCACCTTTTC

CAGGGTATGCAAACACATGTCCCCCTCGTCCACATCCAGGAAGGTGATTGGCTTGTAAGTGTAGGCCACGT

-continued

GACCGGGGGTCCCGGCCGGGGGGGTATAAAAGGGTGCGGGTCCCTGCTCGTCCTCACTGTCTTCCGGATCG

CTGTCCAGGAGCGCCAGCTGTTGGGGTAGGTATTCCCTCTCGAAGGCGGGCATGACCTCGGCACTCAGGTT

GTCAGTTTCTAGAAACGAGGAGGATTTGATATTGACGGTGCCGGCGGAGATGCCTTTCAAGAGCCCCTCGT

CCATCTGGTCAGAAAAGACGATCTTTTTGTTGTCGAGCTTGGTGGCGAAGGAGCCGTAGAGGGCGTTGGAG

AGGAGCTTGGCGATGGAGCGCATGGTCTGGTTTTTTTCCTTGTCGGCGCGCTCCTTGGCGGCGATGTTGAGC

TGCACGTACTCGCGCGCCACGCACTTCCATTCGGGGAAGACGGTGGTCAGCTCGTCGGGCACGATTCTGAC

CTGCCAGCCCCGATTATGCAGGGTGATGAGGTCCACACTGGTGGCCACCTCGCCGCGCAGGGGCTCATTAG

TCCAGCAGAGGCGTCCGCCCTTGCGCGAGCAGAAGGGGGGCAGGGGGTCCAGCATGACCTCGTCGGGGGG

GTCGGCATCGATGGTGAAGATGCCGGGCAGGAGGTCGGGGTCAAAGTAGCTGATGGAAGTGGCCAGATCG

TCCAGGGCAGCTTGCCATTCGCGCACGGCCAGCGCGCGCTCGTAGGGACTGAGGGGCGTGCCCCAGGGCAT

GGGATGGGTAAGCGCGGAGGCGTACATGCCGCAGATGTCGTAGACGTAGAGGGGCTCCTCGAGGATGCCG

ATGTAGGTGGGGTAGCAGCGCCCCCCGCGGATGCTGGCGCGCACGTAGTCATACAGCTCGTGCGAGGGGG

CGAGGAGCCCCGGGCCCAGGTTGGTGCGACTGGGCTTTTCGGCGCGGTAGACGATCTGGCGGAAAATGGC

ATGCGAGTTGGAGGAGATGGTGGGCCTTTGGAAGATGTTGAAGTGGGCGTGGGGCAGTCCGACCGAGTCG

CGGATGAAGTGGCGTAGGAGTCTTGCAGCTTGGCGACGAGCTCGGCGGTGACTAGGACGTCCAGAGCGC

AGTAGTCGAGGGTCTCCTGGATGATGTCATACTTGAGCTGTCCCTTTTGTTTCCACAGCTCGCGGTTGAGAA

GGAACTCTTCGCGGTCCTTCCAGTACTCTTCGAGGGGGAACCCGTCCTGATCTGCACGGTAAGAGCCTAGC

ATGTAGAACTGGTTGACGGCCTTGTAGGCGCAGCAGCCCTTCTCCACGGGGAGGGCGTAGGCCTGGGCGGC

CTTGCGCAGGGAGGTGTGCGTGAGGGCGAAAGTGTCCCTGACCATGACCTTGAGGAACTGGTGCTTGAAGT

CGATATCGTCGCAGCCCCCCTGCTCCCAGAGCTGGAAGTCCGTGCGCTTCTTGTAGGCGGGGTTGGGCAAA

GCGAAAGTAACATCGTTGAAGAGGATCTTGCCCGCGCGGGGCATAAAGTTGCGAGTGATGCGGAAAGGTT

GGGGCACCTCGGCCCGGTTGTTGATGACCTGGGCGGCGAGCACGATCTCGTCGAAGCCGTTGATGTTGTGG

CCCACGATGTAGAGTTCCACGAATCGCGGACGGCCCTTGACGTGGGGCAGTTTCTTGAGCTCCTCGTAGGT

GAGCTCGTCGGGGTCGCTGAGCCCGTGCTGCTCGAGCGCCCAGTCGGCGAGATGGGGGTTGGCGCGGACG

AAGGAAGTCCAGAGATCCACGGCCAGGGCGGTTTGCAGACGGTCCCGGTACTGACGGAACTGCTGCCCGA

CGGCCATTTTTTCGGGGGTGACGCAGTAGAAGGTGCGGGGGTCCCCGTGCCAGCGATCCCATTTGAGCTGG

AGGGCGAGATCGAGGGCGAGCTCGACGAGCCGGTCGTCCCCGGAGAGTTTCATGACCAGCATGAAGGGGA

CGAGCTGCTTGCCGAAGGACCCCATCCAGGTGTAGGTTTCCACATCGTAGGTGAGGAAGAGCCTTTCGGTG

CGAGGATGCGAGCCGATGGGGAAGAACTGGATCTCCTGCCACCAATTGGAGGAATGGCTGTTGATGTGATG

GAAGTAGAAATGCCGACGGCGCGCCGAACACTCGTGCTTGTGTTTATACAAGCGGCCACAGTGCTCGCAAC

GCTGCACGGGATGCACGTGCTGCACGAGCTGTACCTGAGTTCCTTTGACGAGGAATTTCAGTGGGAAGTGG

AGTCGTGGCGCCTGCATCTCGTGCTGTACTACGTCGTGGTGGTCGGCCTGGCCCTCTTCTGCCTCGATGGTG

GTCATGCTGACGAGCCCGCGCGGGAGGCAGGTCCAGACCTCGGCGCGAGCGGGTCGGAGAGCGAGGACGA

GGGCGCGCAGGCCGGAGCTGTCCAGGGTCCTGAGACGCTGCGGAGTCAGGTCAGTGGGCAGCGGCGGCGC

GCGGTTGACTTGCAGGAGTTTTTCCAGGGCGCGCGGGAGGTCCAGATGGTACTTGATCTCCACCGCGCCAT

TGGTGGCGACGTCGATGGCTTGCAGGGTCCCGTGCCCCTGGGGTGTGACCACCGTCCCCCGTTTCTTCTTGG

GCGGCTGGGGCGACGGGGGCGGTGCCTCTTCCATGGTTAGAAGCGGCGGCGAGGACGCGCGCCGGGCGGC

AGGGGCGGCTCGGGGCCCGGAGGCAGGGGCGGCAGGGGCACGTCGGCGCCGCGCGCGGGTAGGTTCTGGT

ACTGCGCCCGGAGAAGACTGGCGTGAGCGACGACGCGACGGTTGACGTCCTGGATCTGACGCCTCTGGGTG

AAGGCCACGGGACCCGTGAGTTTGAACCTGAAAGAGAGTTCGACAGAATCAATCTCGGTATCGTTGACGGC

-continued

GGCCTGCCGCAGGATCTCTTGCACGTCGCCCGAGTTGTCCTGGTAGGCGATCTCGGTCATGAACTGCTCGAT

CTCCTCCTCTTGAAGGTCTCCGCGGCCGGCGCGCTCCACGGTGGCCGCGAGGTCGTTGGAGATGCGGCCCA

TGAGCTGCGAGAAGGCGTTCATGCCCGCCTCGTTCCAGACGCGGCTGTAGACCACGACGCCCTCGGGATCG

CGGGCGCGCATGACCACCTGGGCGAGGTTGAGCTCCACGTGGCGCGTGAAGACCGCGTAGTTGCAGAGGC

GCTGGTAGAGGTAGTTGAGCGTGGTGGCGATGTGCTCGGTGACGAAGAAATACATGATCCAGCGGCGGAG

CGGCATCTCGCTGACGTCGCCCAGCGCCTCCAAACGTTCCATGGCCTCGTAAAAGTCCACGGCGAAGTTGA

AAAACTGGGAGTTGCGCGCCGAGACGGTCAACTCCTCCTCCAGAAGACGGATGAGCTCGGCGATGGTGGC

GCGCACCTCGCGCTCGAAGGCCCCCGGGAGTTCCTCCACTTCCTCTTCTTCCTCCTCCACTAACATCTCTTCT

ACTTCCTCCTCAGGCGGCAGTGGTGGCGGGGGAGGGGGCCTGCGTCGCCGGCGGCGCACGGGCAGACGGT

CGATGAAGCGCTCGATGGTCTCGCCGCGCCGGCGTCGCATGGTCTCGGTGACGGCGCGCCCGTCCTCGCGG

GGCCGCAGCGTGAAGACGCCGCCGCGCATCTCCAGGTGGCCGGGGGGGTCCCCGTTGGGCAGGGAGAGGG

CGCTGACGATGCATCTTATCAATTGCCCCGTAGGGACTCCGCGCAAGGACCTGAGCGTCTCGAGATCCACG

GGATCTGAAAACCGCTGAACGAAGGCTTCGAGCCAGTCGCAGTCGCAAGGTAGGCTGAGCACGGTTTCTTC

TGGCGGGTCATGTTGGTTGGGAGCGGGGCGGGCGATGCTGCTGGTGATGAAGTTGAAATAGGCGGTTCTGA

GACGGCGGATGGTGGCGAGGAGCACCAGGTCTTTGGGCCCGGCTTGCTGGATGCGCAGACGGTCGGCCAT

GCCCCAGGCGTGGTCCTGACACCTGGCCAGGTCCTTGTAGTAGTCCTGCATGAGCCGCTCCACGGGCACCT

CCTCCTCGCCCGCGCGGCCGTGCATGCGCGTGAGCCCGAAGCCGCGCTGGGGCTGGACGAGCGCCAGGTCG

GCGACGACGCGCTCGGCGAGGATGGCTTGCTGGATCTGGGTGAGGGTGGTCTGGAAGTCATCAAAGTCGAC

GAAGCGGTGGTAGGCTCCGGTGTTGATGGTGTAGGAGCAGTTGGCCATGACGGACCAGTTGACGGTCTGGT

GGCCCGGACGCACGAGCTCGTGGTACTTGAGGCGCGAGTAGGCGCGCGTGTCGAAGATGTAGTCGTTGCAG

GTGCGCACCAGGTACTGGTAGCCGATGAGGAAGTGCGGCGGCGGCTGGCGGTAGAGCGGCCATCGCTCGG

TGGCGGGGGCGCCGGGCGCGAGGTCCTCGAGCATGGTGCGGTGGTAGCCGTAGATGTACCTGGACATCCA

GGTGATGCCGGCGGCGGTGGTGGAGGCGCGCGGGAACTCGCGGACGCGGTTCCAGATGTTGCGCAGCGGC

AGGAAGTAGTTCATGGTGGGCACGGTCTGGCCCGTGAGGCGCGCGCAGTCGTGGATGCTCTATACGGGCAA

AAACGAAAGCGGTCAGCGGCTCGACTCCGTGGCCTGGAGGCTAAGCGAACGGGTTGGGCTGCGCGTGTAC

CCCGGTTCGAATCTCGAATCAGGCTGGAGCCGCAGCTAACGTGGTATTGGCACTCCCGTCTCGACCCAAGC

CTGCACCAACCCTCCAGGATACGGAGGCGGGTCGTTTTGCAACTTTTTTTTGGAGGCCGGATGAGACTAGT

AAGCGCGGAAAGCGGCCGACCGCGATGGCTCGCTGCCGTAGTCTGGAGAAGAATCGCCAGGGTTGCGTTG

CGGTGTGCCCCGGTTCGAGGCCGGCCGGATTCCGCGGCTAACGAGGGCGTGGCTGCCCCGTCGTTTCCAAG

ACCCCATAGCCAGCCGACTTCTCCAGTTACGGAGCGAGCCCCTCTTTTGTTTTGTTTGTTTTTGCCAGATGCA

TCCCGTACTGCGGCAGATGCGCCCCCACCACCCTCCACCGCAACAACAGCCCCCTCCACAGCCGGCGCTTC

TGCCCCCGCCCCAGCAGCAACTTCCAGCCACGACCGCCGCGGCCGCCGTGAGCGGGGCTGGACAGAGTTAT

GATCACCAGCTGGCCTTGGAAGAGGGCGAGGGGCTGGCGCGCCTGGGGGCGTCGTCGCCGGAGCGGCACC

CGCGCGTGCAGATGAAAAGGGACGCTCGCGAGGCCTACGTGCCCAAGCAGAACCTGTTCAGAGACAGGAG

CGGCGAGGAGCCCGAGGAGATGCGCGCGGCCCGGTTCCACGCGGGGCGGGAGCTGCGGCGCGGCCTGGAC

CGAAAGAGGGTGCTGAGGGACGAGGATTTCGAGGCGGACGAGCTGACGGGGATCAGCCCCGCGCGCGCGC

ACGTGGCCGCGGCCAACCTGGTCACGGCGTACGAGCAGACCGTGAAGGAGGAGAGCAACTTCCAAAAATC

CTTCAACAACCACGTGCGCACCCTGATCGCGCGCGAGGAGGTGACCCTGGGCCTGATGCACCTGTGGGACC

TGCTGGAGGCCATCGTGCAGAACCCCACCAGCAAGCCGCTGACGGCGCAGCTGTTCCTGGTGGTGCAGCAT

AGTCGGGACAACGAAGCGTTCAGGGAGGCGCTGCTGAATATCACCGAGCCCGAGGGCCGCTGGCTCCTGG

ACCTGGTGAACATTCTGCAGAGCATCGTGGTGCAGGAGCGCGGGCTGCCGCTGTCCGAGAAGCTGGCGGCC

-continued

ATCAACTTCTCGGTGCTGAGTTTGGGCAAGTACTACGCTAGGAAGATCTACAAGACCCCGTACGTGCCCAT
AGACAAGGAGGTGAAGATCGACGGGTTTTACATGCGCATGACCCTGAAAGTGCTGACCCTGAGCGACGAT
CTGGGGGTGTACCGCAACGACAGGATGCACCGTGCGGTGAGCGCCAGCAGGCGGCGCGAGCTGAGCGACC
AGGAGCTGATGCATAGTCTGCAGCGGGCCCTGACCGGGGCCGGGACCGAGGGGGAGAGCTACTTTGACAT
GGGCGCGGACCTGCACTGGCAGCCCAGCCGCCGGGCCTTGGAGGCGGCGGCAGGACCCTACGTAGAAGAG
GTGGACGATGAGGTGGACGAGGAGGGCGAGTACCTGGAAGACTGATGGCGCGACCGTATTTTTGCTAGAT
GCAACAACAACAGCCACCTCCTGATCCCGCGATGCGGGCGGCGCTGCAGAGCCAGCCGTCCGGCATTAACT
CCTCGGACGATTGGACCCAGGCCATGCAACGCATCATGGCGCTGACGACCCGCAACCCCGAAGCCTTTAGA
CAGCAGCCCCAGGCCAACCGGCTCTCGGCCATCCTGGAGGCCGTGGTGCCCTCGCGCTCCAACCCCACGCA
CGAGAAGGTCCTGGCCATCGTGAACGCGCTGGTGGAGAACAAGGCCATCCGCGGCGACGAGGCCGGCCTG
GTGTACAACGCGCTGCTGGAGCGCGTGGCCCGCTACAACAGCACCAACGTGCAGACCAACCTGGACCGCA
TGGTGACCGACGTGCGCGAGGCCGTGGCCCAGCGCGAGCGGTTCCACCGCGAGTCCAACCTGGGATCCATG
GTGGCGCTGAACGCCTTCCTCAGCACCCAGCCCGCCAACGTGCCCCGGGGCCAGGAGGACTACACCAACTT
CATCAGCGCCCTGCGCCTGATGGTGACCGAGGTGCCCCAGAGCGAGGTGTACCAGTCCGGGCCGGACTACT
TCTTCCAGACCAGTCGCCAGGGCTTGCAGACCGTGAACCTGAGCCAGGCTTTCAAGAACTTGCAGGGCCTG
TGGGGCGTGCAGGCCCCGGTCGGGGACCGCGCGACGGTGTCGAGCCTGCTGACGCCGAACTCGCGCCTGCT
GCTGCTGCTGGTGGCCCCCTTCACGGACAGCGGCAGCATCAACCGCAACTCGTACCTGGGCTACCTGATTA
ACCTGTACCGCGAGGCCATCGGCCAGGCGCACGTGGACGAGCAGACCTACCAGGAGATCACCCACGTGAG
CCGCGCCCTGGGCCAGGACGACCCGGGCAACCTGGAAGCCACCCTGAACTTTTTGCTGACCAACCGGTCGC
AGAAGATCCCGCCCCAGTACGCGCTCAGCACCGAGGAGGAGCGCATCCTGCGTTACGTGCAGCAGAGCGT
GGGCCTGTTCCTGATGCAGGAGGGGGCCACCCCCAGCGCCGCGCTCGACATGACCGCGCGCAACATGGAG
CCCAGCATGTACGCCAGCAACCGCCCGTTCATCAATAAACTGATGGACTACTTGCATCGGGCGGCCGCCAT
GAACTCTGACTATTTCACCAACGCCATCCTGAATCCCCACTGGCTCCCGCCGCCGGGGTTCTACACGGGCG
AGTACGACATGCCCGACCCCAATGACGGGTTCCTGTGGGACGATGTGGACAGCAGCGTGTTCTCCCCCCGA
CCGGGTGCTAACGAGCGCCCCTTGTGGAAGAAGGAAGGCAGCGACCGACGCCCGTCCTCGGCGCTGTCCG
GCCGCGAGGGTGCTGCCGCGGCGGTGCCCGAGGCCGCCAGTCCTTTCCCGAGCTTGCCCTTCTCGCTGAAC
AGTATCCGCAGCAGCGAGCTGGGCAGGATCACGCGCCCGCGCTTGCTGGGCGAAGAGGAGTACTTGAATG
ACTCGCTGTTGAGACCCGAGCGGGAGAAGAACTTCCCCAATAACGGGATAGAAAGCCTGGTGGACAAGAT
GAGCCGCTGGAAGACGTATGCGCAGGAGCACAGGGACGATCCCCGGGCGTCGCAGGGGGCCACGAGCCGG
GGCAGCGCCGCCCGTAAACGCCGGTGGCACGACAGGCAGCGGGGACAGATGTGGGACGATGAGGACTCCG
CCGACGACAGCAGCGTGTTGGACTTGGGTGGGAGTGGTAACCCGTTCGCTCACCTGCGCCCCCGTATCGGG
CGCATGATGTAAGAGAAACCGAAAATAAATGATACTCACCAAGGCCATGGCGACCAGCGTGCGTTCGTTTC
TTCTCTGTTGTTGTTGTATCTAGTATGATGAGGCGTGCGTACCCGGAGGGTCCTCCTCCCTCGTACGAGAGC
GTGATGCAGCAGGCGATGGCGGCGGCGGCGATGCAGCCCCCGCTGGAGGCTCCTTACGTGCCCCCGCGGTA
CCTGGCGCCTACGGAGGGGCGGAACAGCATTCGTTACTCGGAGCTGGCACCCTTGTACGATACCACCCGGT
TGTACCTGGTGGACAACAAGTCGGCGGACATCGCCTCGCTGAACTACCAGAACGACCACAGCAACTTCCTG
ACCACCGTGGTGCAGAACAATGACTTCACCCCCACGGAGGCCAGCACCCAGACCATCAACTTTGACGAGCG
CTCGCGGTGGGGCGGCCAGCTGAAAACCATCATGCACACCAACATGCCCAACGTGAACGAGTTCATGTACA
GCAACAAGTTCAAGGCGCGGGTGATGGTCTCCCGCAAGACCCCCAATGGGGTGACAGTGACAGAGGATTA
TGATGGTAGTCAGGATGAGCTGAAGTATGAATGGGTGGAATTTGAGCTGCCCGAAGGCAACTTCTCGGTGA

-continued

CCATGACCATCGACCTGATGAACAACGCCATCATCGACAATTACTTGGCGGTGGGGCGGCAGAACGGGGT

GCTGGAGAGCGACATCGGCGTGAAGTTCGACACTAGGAACTTCAGGCTGGGCTGGGACCCCGTGACCGAG

CTGGTCATGCCCGGGGTGTACACCAACGAGGCTTTCCATCCCGATATTGTCTTGCTGCCCGGCTGCGGGGTG

GACTTCACCGAGAGCCGCCTCAGCAACCTGCTGGGCATTCGCAAGAGGCAGCCCTTCCAGGAAGGCTTCCA

GATCATGTACGAGGATCTGGAGGGGGGCAACATCCCCGCGCTCCTGGATGTCGACGCCTATGAGAAAAGC

AAGGAGGATGCAGCAGCTGAAGCAACTGCAGCCGTAGCTACCGCCTCTACCGAGGTCAGGGGCGATAATT

TTGCAAGCGCCGCAGCAGTGGCAGCGGCCGAGGCGGCTGAAACCGAAAGTAAGATAGTCATTCAGCCGGT

GGAGAAGGATAGCAAGAACAGGAGCTACAACGTACTACCGGACAAGATAAACACCGCCTACCGCAGCTGG

TACCTAGCCTACAACTATGGCGACCCCGAGAAGGGCGTGCGCTCCTGGACGCTGCTCACCACCTCGGACGT

CACCTGCGGCGTGGAGCAAGTCTACTGGTCGCTGCCCGACATGATGCAAGACCCGGTCACCTTCCGCTCCA

CGCGTCAAGTTAGCAACTACCCGGTGGTGGGCGCCGAGCTCCTGCCCGTCTACTCCAAGAGCTTCTTCAAC

GAGCAGGCCGTCTACTCGCAGCAGCTGCGCGCCTTCACCTCGCTTACGCACGTCTTCAACCGCTTCCCCGAG

AACCAGATCCTCGTCCGCCCGCCCGCGCCCACCATTACCACCGTCAGTGAAAACGTTCCTGCTCTCACAGAT

CACGGGACCCTGCCGCTGCGCAGCAGTATCCGGGGAGTCCAGCGCGTGACCGTTACTGACGCCAGACGCCG

CACCTGCCCCTACGTCTACAAGGCCCTGGGCATAGTCGCGCCGCGCGTCCTCTCGAGCCGCACCTTCTAAAT

GTCCATTCTCATCTCGCCCAGTAATAACACCGGTTGGGGCCTGCGCGCGCCCAGCAAGATGTACGGAGGCG

CTCGCCAACGCTCCACGCAACACCCCGTGCGCGTGCGCGGGCACTTCCGCGCTCCCTGGGGCGCCCTCAAG

GGCCGCGTGCGGTCGCGCACCACCGTCGACGACGTGATCGACCAGGTGGTGGCCGACGCGCGCAACTACA

CCCCCGCCGCCGCGCCCGTCTCCACCGTGGACGCCGTCATCGACAGCGTGGTGGCCGACGCGCGCCGGTAC

GCCCGCGCCAAGAGCCGGCGGCGGCGCATCGCCCGGCGGCACCGGAGCACCCCCGCCATGCGCGCGGCGC

GAGCCTTGCTGCGCAGGGCCAGGCGCACGGGACGCAGGGCCATGCTCAGGGCGGCCAGACGCGCGGCTTC

AGGCGCCAGCGCCGGCAGGACCCGGAGACGCGCGGCCACGGCGGCGGCAGCGGCCATCGCCAGCATGTCC

CGCCCGCGGCGAGGGAACGTGTACTGGGTGCGCGACGCCGCCACCGGTGTGCGCGTGCCCGTGCGCACCC

GCCCCCCTCGCACTTGAAGATGTTCACTTCGCGATGTTGATGTGTCCCAGCGGCGAGGAGGATGTCCAAGC

GCAAATTCAAGGAAGAGATGCTCCAGGTCATCGCGCCTGAGATCTACGGCCCTGCGGTGGTGAAGGAGGA

AAGAAAGCCCCGCAAAATCAAGCGGGTCAAAAAGGACAAAAAGGAAGAAGAAAGTGATGTGGACGGATT

GGTGGAGTTTGTGCGCGAGTTCGCCCCCCGGCGGCGCGTGCAGTGGCGCGGGCGGAAGGTGCAACCGGTG

CTGAGACCCGGCACCACCGTGGTCTTCACGCCCGGCGAGCGCTCCGGCACCGCTTCCAAGCGCTCCTACGA

CGAGGTGTACGGGGATGATGATATTCTGGAGCAGGCGGCCGAGCGCCTGGGCGAGTTTGCTTACGGCAAGC

GCAGCCGTTCCGCACCGAAGGAAGAGGCGGTGTCCATCCCGCTGGACCACGGCAACCCCACGCCGAGCCT

CAAGCCCGTGACCTTGCAGCAGGTGCTGCCGACCGCGGCGCCGCGCCGGGGGTTCAAGCGCGAGGGCGAG

GATCTGTACCCCACCATGCAGCTGATGGTGCCCAAGCGCCAGAAGCTGGAAGACGTGCTGGAGACCATGA

AGGTGGACCCGGACGTGCAGCCCGAGGTCAAGGTGCGGCCCATCAAGCAGGTGGCCCCGGGCCTGGGCGT

GCAGACCGTGGACATCAAGATTCCCACGGAGCCCATGGAAACGCAGACCGAGCCCATGATCAAGCCCAGC

ACCAGCACCATGGAGGTGCAGACGGATCCCTGGATGCCATCGGCTCCTAGTCGAAGACCCCGGCGCAAGT

ACGGCGCGGCCAGCCTGCTGATGCCCAACTACGCGCTGCATCCTTCCATCATCCCCACGCCGGGCTACCGC

GGCACGCGCTTCTACCGCGGTCATACCAGCAGCCGCCGCCGCAAGACCACCACTCGCCGCCGCCGTCGCCG

CACCGCCGCTGCAACCACCCCTGCCGCCCTGGTGCGGAGAGTGTACCGCCGCGGCCGCGCACCTCTGACCC

TGCCGCGCGCGCGCTACCACCCGAGCATCGCCATTTAAACTTTCGCCTGCTTTGCAGATCAATGGCCCTCAC

ATGCCGCCTTCGCGTTCCCATTACGGGCTACCGAGGAAGAAAACCGCGCCGTAGAAGGCTGGCGGGGAAC

GGGATGCGTCGCCACCACCACCGGCGGCGGCGCGCCATCAGCAAGCGGTTGGGGGGAGGCTTCCTGCCCG

-continued

CGCTGATCCCCATCATCGCCGCGGCGATCGGGGCGATCCCCGGCATTGCTTCCGTGGCGGTGCAGGCCTCT

CAGCGCCACTGAGACACACTTGGAAACATCTTGTAATAAACCAATGGACTCTGACGCTCCTGGTCCTGTGA

TGTGTTTTCGTAGACAGATGGAAGACATCAATTTTTCGTCCCTGGCTCCGCGACACGGCACGCGGCCGTTCA

TGGGCACCTGGAGCGACATCGGCACCAGCCAACTGAACGGGGGCGCCTTCAATTGGAGCAGTCTCTGGAG

CGGGCTTAAGAATTTCGGGTCCACGCTTAAAACCTATGGCAGCAAGGCGTGGAACAGCACCACAGGGCAG

GCGCTGAGGGATAAGCTGAAAGAGCAGAACTTCCAGCAGAAGGTGGTCGATGGGCTCGCCTCGGGCATCA

ACGGGGTGGTGGACCTGGCCAACCAGGCCGTGCAGCGGCAGATCAACAGCCGCCTGGACCCGGTGCCGCC

CGCCGGCTCCGTGGAGATGCCGCAGGTGGAGGAGGAGCTGCCTCCCCTGGACAAGCGGGGCGAGAAGCGA

CCCCGCCCCGATGCGGAGGAGACGCTGCTGACGCACACGGACGAGCCGCCCCCGTACGAGGAGGCGGTGA

AACTGGGTCTGCCCACCACGCGGCCCATCGCGCCCCTGGCCACCGGGGTGCTGAAACCCGAAAAGCCCGCG

ACCCTGGACTTGCCTCCTCCCCAGCCTTCCCGCCCCTCTACAGTGGCTAAGCCCCTGCCGCCGGTGGCCGTG

GCCCGCGCGCGACCCGGGGGCACCGCCCGCCCTCATGCGAACTGGCAGAGCACTCTGAACAGCATCGTGG

GTCTGGGAGTGCAGAGTGTGAAGCGCCGCCGCTGCTATTAAACCTACCGTAGCGCTTAACTTGCTTGTCTGT

GTGTGTATGTATTATGTCGCCGCCGCCGCTGTCCACCAGAAGGAGGAGTGAAGAGGCGCGTCGCCGAGTTG

CAAGATGGCCACCCCATCGATGCTGCCCCAGTGGGCGTACATGCACATCGCCGGACAGGACGCTTCGGAGT

ACCTGAGTCCGGGTCTGGTGCAGTTTGCCCGCGCCACAGACACCTACTTCAGTCTGGGGAACAAGTTTAGG

AACCCCACGGTGGCGCCCACGCACGATGTGACCACCGACCGCAGCCAGCGGCTGACGCTGCGCTTCGTGCC

CGTGGACCGCGAGGACAACACCTACTCGTACAAAGTGCGCTACACGCTGGCCGTGGGCGACAACCGCGTG

CTGGACATGGCCAGCACCTACTTTGACATCCGCGGCGTGCTGGATCGGGGCCCTAGCTTCAAACCCTACTC

CGGCACCGCCTACAACAGTCTGGCCCCCAAGGGAGCACCCAACACTTGTCAGTGGACATATAAAGCCGATG

GTGAAACTGCCACAGAAAAAACCTATACATATGGAAATGCACCCGTGCAGGGCATTAACATCACAAAAGA

TGGTATTCAACTTGGAACTGACACCGATGATCAGCCAATCTACGCAGATAAAACCTATCAGCCTGAACCTC

AAGTGGGTGATGCTGAATGGCATGACATCACTGGTACTGATGAAAAGTATGGAGGCAGAGCTCTTAAGC CT

GATACCAAAATGAAGCCTTGTTATGGTTCTTTTGCCAAGCCTACTAATAAAGAAGGAGGTCAGGCAAATGT

GAAAACAGGAACAGGCACTACTAAAGAATATGACATAGACATGGCTTTCTTTGACAACAGAAGTGCGGCT

GCTGCTGGCCTAGCTCCAGAAATTGTTTTGTATACTGAAAATGTGGATTTGGAAACTCCAGATACCCATATT

GTATACAAAGCAGGCACAGATGACAGCAGCTCTTCTATTAATTTGGGTCAGCAAGCCATGCCCAACAGACC

TAACTACATTGGTTTCAGAGACAACTTTATCGGGCTCATGTACTACAACAGCACTGGCAATATGGGGGTGC

TGGCCGGTCAGGCTTCTCAGCTGAATGCTGTGGTTGACTTGCAAGACAGAAACACCGAGCTGTCCTACCAG

CTCTTGCTTGACTCTCTGGGTGACAGAACCCGGTATTTCAGTATGTGGAATCAGGCGGTGGACAGCTATGAT

CCTGATGTGCGCATTATTGAAAATCATGGTGTGGAGGATGAACTTCCCAACTATTGTTTCCCTCTGGATGCT

GTTGGCAGAACAGATACTTATCAGGGAATTAAGGCTAATGGAACTGATCAAACCACATGGACCAAAGATG

ACAGTGTCAATGATGCTAATGAGATAGGCAAGGGTAATCCATTCGCCATGGAAATCAACATCCAAGCCAAC

CTGTGGAGGAACTTCCTCTACGCCAACGTGGCCCTGTACCTGCCCGACTCTTACAAGTACACGCCGGCCAA

TGTTACCCTGCCCACAACACCAACACCTACGATTACATGAACGGCCGGGTGGTGGCGCCCTCGCTGGTGG

ACTCCTACATCAACATCGGGGCGCGCTGGTCGCTGGATCCCATGGACAACGTGAACCCCTTCAACCACCAC

CGCAATGCGGGGCTGCGCTACCGCTCCATGCTCCTGGGCAACGGGCGCTACGTGCCCTTCCACATCCAGGT

GCCCCAGAAATTTTTCGCCATCAAGAGCCTCCTGCTCCTGCCCGGGTCCTACACCTACGAGTGGAACTTCCG

CAAGGACGTCAACATGATCCTGCAGAGCTCCCTCGGCAACGACCTGCGCACGGACGGGGCCTCCATCTCCT

TCACCAGCATCAACCTCTACGCCACCTTCTTCCCCATGGCGCACAACACGGCCTCCACGCTCGAGGCCATGC

-continued

TGCGCAACGACACCAACGACCAGTCCTTCAACGACTACCTCTCGGCGGCCAACATGCTCTACCCCATCCCG

GCCAACGCCACCAACGTGCCCATCTCCATCCCCTCGCGCAACTGGGCCGCCTTCCGCGGCTGGTCCTTCACG

CGTCTCAAGACCAAGGAGACGCCCTCGCTGGGCTCCGGGTTCGACCCCTACTTCGTCTACTCGGGCTCCATC

CCCTACCTCGACGGCACCTTCTACCTCAACCACACCTTCAAGAAGGTCTCCATCACCTTCGACTCCTCCGTC

AGCTGGCCCGGCAACGACCGGCTCCTGACGCCCAACGAGTTCGAAATCAAGCGCACCGTCGACGGCGAGG

GCTACAACGTGGCCCAGTGCAACATGACCAAGGACTGGTTCCTGGTCCAGATGCTGGCCCACTACAACATC

GGCTACCAGGGCTTCTACGTGCCCGAGGGCTACAAGGACCGCATGTACTCCTTCTTCCGCAACTTCCAGCCC

ATGAGCCGCCAGGTGGTGGACGAGGTCAACTACAAGGACTACCAGGCCGTCACCCTGGCCTACCAGCACA

ACAACTCGGGCTTCGTCGGCTACCTCGCGCCCACCATGCGCCAGGGCCAGCCCTACCCCGCCAACTACCCC

TACCCGCTCATCGGCAAGAGCGCCGTCACCAGCGTCACCCAGAAAAAGTTCCTCTGCGACAGGGTCATGTG

GCGCATCCCCTTCTCCAGCAACTTCATGTCCATGGGCGCGCTCACCGACCTCGGCCAGAACATGCTCTATGC

CAACTCCGCCCACGCGCTAGACATGAATTTCGAAGTCGACCCCATGGATGAGTCCACCCTTCTCTATGTTGT

CTTCGAAGTCTTCGACGTCGTCCGAGTGCACCAGCCCCACCGCGGCGTCATCGAGGCCGTCTACCTGCGCA

CCCCCTTCTCGGCCGGTAACGCCACCACCTAAGCTCTTGCTTCTTGCAAGCCATGGCCGCGGGCTCCGGCGA

GCAGGAGCTCAGGGCCATCATCCGCGACCTGGGCTGCGGGCCCTACTTCCTGGGCACCTTCGATAAGCGCT

TCCCGGGATTCATGGCCCCGCACAAGCTGGCCTGCGCCATCGTCAACACGGCCGGCCGCGAGACCGGGGGC

GAGCACTGGCTGGCCTTCGCCTGGAACCCGCGCTCGAACACCTGCTACCTCTTCGACCCCTTCGGGTTCTCG

GACGAGCGCCTCAAGCAGATCTACCAGTTCGAGTACGAGGGCCTGCTGCGCCGCAGCGCCCTGGCCACCGA

GGACCGCTGCGTCACCCTGGAAAAGTCCACCCAGACCGTGCAGGGTCCGCGCTCGGCCGCCTGCGGGCTCT

TCTGCTGCATGTTCCTGCACGCCTTCGTGCACTGGCCCGACCGCCCCATGGACAAGAACCCCACCATGAACT

TGCTGACGGGGGTGCCCAACGGCATGCTCCAGTCGCCCCAGGTGGAACCCACCCTGCGCCGCAACCAGGA

GGCGCTCTACCGCTTCCTCAACTCCCACTCCGCCTACTTCGCTCCCACCGCGCGCGCATCGAGAAGGCCAC

CGCCTTCGACCGCATGAATCAAGACATGTAAACCGTGTGTGTATGTTAAATGTCTTTAATAAACAGCACTTT

CATGTTACACATGCATCTGAGATGATTTATTTAGAAATCGAAAGGGTTCTGCCGGGTCTCGGCATGGCCCGC

GGGCAGGGACACGTTGCGGAACTGGTACTTGGCCAGCCACTTGAACTCGGGGATCAGCAGTTTGGGCAGCG

GGGTGTCGGGGAAGGAGTCGGTCCACAGCTTCCGCGTCAGTTGCAGGGCGCCCAGCAGGTCGGGCGCGGA

GATCTTGAAATCGCAGTTGGGACCCGCGTTCTGCGCGCGGGAGTTGCGGTACACGGGGTTGCAGCACTGGA

ACACCATCAGGGCCGGGTGCTTCACGCTCGCCAGCACCGTCGCGTCGGTGATGCTCTCCACGTCGAGGTCC

TCGGCGTTGGCCATCCCGAAGGGGGTCATCTTGCAGGTCTGCCTTCCCATGGTGGGCACGCACCCGGGCTT

GTGGTTGCAATCGCAGTGCAGGGGGATCAGCATCATCTGGGCCTGGTCGGCGTTCATCCCCGGGTACATGG

CCTTCATGAAAGCCTCCAATTGCCTGAACGCCTGCTGGGCCTTGGCTCCCTCGGTGAAGAAGACCCCGCAG

GACTTGCTAGAGAACTGGTTGGTGGCGCACCCGGCGTCGTGCACGCAGCAGCGCGCGTCGTTGTTGGCCAG

CTGCACCACGCTGCGCCCCCAGCGGTTCTGGGTGATCTTGGCCCGGTCGGGGTTCTCCTTCAGCGCGCGCTG

CCCGTTCTCGCTCGCCACATCCATCTCGATCATGTGCTCCTTCTGGATCATGGTGGTCCCGTGCAGGCACCG

CAGCTTGCCCTCGGCCTCGGTGCACCCGTGCAGCCACAGCGCGCACCCGGTGCACTCCCAGTTCTTGTGGG

CGATCTGGGAATGCGCGTGCACGAAGCCCTGCAGGAAGCGCTCCCATCATGGTGGTCAGGGTCTTGTTGCTA

GTGAAGGTCAGCGGAATGCCGCGGTGCTCCTCGTTGATGTACAGGTGGCAGATGCGGCGGTACACCTCGCC

CTGCTCGGGCATCAGCTGGAAGTTGGCTTTCAGGTCGGTCTCCACGCGGTAGCGGTCCATCAGCATAGTCAT

GATTTCCATACCCTTCTCCCAGGCCGAGACGATGGGCAGGCTCATAGGGTTCTTCACCATCATCTTAGCGCT

AGCAGCCGCGGCCAGGGGGTCGCTCTCGTCCAGGGTCTCAAAGCTCCGCTTGCCGTCCTTCTCGGTGATCC

GCACCGGGGGGTAGCTGAAGCCCACGGCCGCCAGCTCCTCCTCGGCCTGTCTTTCGTCCTCGCTGTCCTGGC

-continued

TGACGTCCTGCAGGACCACATGCTTGGTCTTGCGGGGTTTCTTCTTGGGCGGCAGCGGCGGCGGAGATGTT

GGAGATGGCGAGGGGGAGCGCGAGTTCTCGCTCACCACTACTATCTCTTCCTCTTCTTGGTCCGAGGCCAC

GCGGCGGTAGGTATGTCTCTTCGGGGGCAGAGGCGGAGGCGACGGGCTCTCGCCGCCGCGACTTGGCGGA

TGGCTGGCAGAGCCCCTTCCGCGTTCGGGGGTGCGCTCCCGGCGGCGCTCTGACTGACTTCCTCCGCGGCC

GGCCATTGTGTTCTCCTAGGGAGGAACAACAAGCATGGAGACTCAGCCATCGCCAACCTCGCCATCTGCCC

CCACCGCCGACGAGAAGCAGCAGCAGCAGAATGAAAGCTTAACCGCCCCGCCGCCCAGCCCCGCCACCTC

CGACGCGGCCGTCCCAGACATGCAAGAGATGGAGGAATCCATCGAGATTGACCTGGGCTATGTGACGCCC

GCGGAGCACGAGGAGGAGCTGGCAGTGCGCTTTTCACAAGAAGAGATACACCAAGAACAGCCAGAGCAG

GAAGCAGAGAATGAGCAGAGTCAGGCTGGGCTCGAGCATGACGGCGACTACCTCCACCTGAGCGGGGGG

AGGACGCGCTCATCAAGCATCTGGCCCGGCAGGCCACCATCGTCAAGGATGCGCTGCTCGACCGCACCGAG

GTGCCCCTCAGCGTGGAGGAGCTCAGCCGCGCCTACGAGTTGAACCTCTTCTCGCCGCGCGTGCCCCCCAA

GCGCCAGCCCAATGGCACCTGCGAGCCCAACCCGCGCCTCAACTTCTACCCGGTCTTCGCGGTGCCCGAGG

CCCTGGCCACCTACCACATCTTTTTCAAGAACCAAAAGATCCCCGTCTCCTGCCGCGCCAACCGCACCCGCG

CCGACGCCCTTTTCAACCTGGGTCCCGGCGCCCGCCTACCTGATATCGCCTCCTTGGAAGAGGTTCCCAAGA

TCTTCGAGGGTCTGGGCAGCGACGAGACTCGGGCCGCGAACGCTCTGCAAGGAGAAGGAGGAGAGCATGA

GCACCACAGCGCCCTGGTCGAGTTGGAAGGCGACAACGCGCGGCTGGCGGTGCTCAAACGCACGGTCGAG

CTGACCCATTTCGCCTACCCGGCTCTGAACCTGCCCCCCAAAGTCATGAGCGCGGTCATGGACCAGGTGCT

CATCAAGCGCGCGTCGCCCATCTCCGAGGACGAGGGCATGCAAGACTCCGAGGAGGGCAAGCCCGTGGTC

AGCGACGAGCAGCTGGCCCGGTGGCTGGGTCCTAATGCTAGTCCCCAGAGTTTGGAAGAGCGGCGCAAAC

TCATGATGGCCGTGGTCCTGGTGACCGTGGAGCTGGAGTGCCTGCGCCGCTTCTTCGCCGACGCGGAGACC

CTGCGCAAGGTCGAGGAGAACCTGCACTACCTCTTCAGGCACGGGTTCGTGCGCCAGGCCTGCAAGATCTC

CAACGTGGAGGTGACCAACCTGGTCTCCTACATGGGCATCTTGCACGAGAACCGCCTGGGGCAGAACGTGC

TGCACACCACCCTGCGCGGGGAGGCCCGGCGCGACTACATCCGCGACTGCGTCTACCTCTACCTCTGCCAC

ACCTGGCAGACGGGCATGGGCGTGTGGCAGCAGTGTCTGGAGGAGCAGAACCTGAAAGAGCTCTGCAAGC

TCCTGCAGAAGAACCTCAAGGGTCTGTGGACCGGGTTCGACGAGCGCACCACCGCCTCGGACCTGGCCGAC

CTCATTTTCCCCGAGCGCCTCAGGCTGACGCTGCGCAACGGCCTGCCCGACTTTATGAGCCAAAGCATGTTG

CAAAACTTTCGCTCTTTCATCCTCGAACGCTCCGGAATCCTGCCCGCCACCTGCTCCGCGCTGCCCTCGGAC

TTCGTGCCGCTGACCTTCCGCGAGTGCCCCCCGCCGCTGTGGAGCCACTGCTACCTGCTGCGCCTGGCCAAC

TACCTGGCCTACCACTCGGACGTGATCGAGGACGTCAGCGGCGAGGGCCTGCTCGAGTGCCACTGCCGCTG

CAACCTCTGCACGCCGCACCGCTCCCTGGCCTGCAACCCCCAGCTGCTGAGCGAGACCCAGATCATCGGCA

CCTTCGAGTTGCAAGGGCCCAGCGAAGGCGAGGGTTCAGCCGCCAAGGGGGGTCTGAAACTCACCCCGGG

GCTGTGGACCTCGGCCTACTTGCGCAAGTTCGTGCCCGAGGACTACCATCCCTTCGAGATCAGGTTCTACGA

GGACCAATCCCATCCGCCCAAGGCCGAGCTGTCGGCCTGCGTCATCACCCAGGGGGCGATCCTGGCCCAAT

TGCAAGCCATCCAGAAATCCCGCCAAGAATTCTTGCTGAAAAAGGGCCGCGGGGTCTACCTCGACCCCCAG

ACCGGTGAGGAGCTCAACCCCGGCTTCCCCCAGGATGCCCCGAGGAAACAAGAAGCTGAAAGTGGAGCTG

CCGCCCGTGGAGGATTTGGAGGAAGACTGGGAGAACAGCAGTCAGGCAGAGGAGGAGGAGATGGAGGAA

GACTGGGACAGCACTCAGGCAGAGGAGGACAGCCTGCAAGACAGTCTGGAGGAAGACGACGAGGAGGCA

GAGGAGGAGGTGGAAGAAGCAGCCGCCGCCAGACCGTCGTCCTCGGCGGGGGAGAAAGCAAGCAGCACG

GATACCATCTCCGCTCCGGGTCGGGGTCCCGCTCGACCACACAGTAGATGGGACGAGACCGGACGATTCCC

GAACCCCACCACCCAGACCGGTAAGAAGGAGCGGCAGGGATACAAGTCCTGGCGGGGGCACAAAAACGC

-continued

CATCGTCTCCTGCTTGCAGGCCTGCGGGGGCAACATCTCCTTCACCCGGCGCTACCTGCTCTTCCACCGCGG

GGTGAACTTTCCCCGCAACATCTTGCATTACTACCGTCACCTCCACAGCCCCTACTACTTCCAAGAAGAGGC

AGCAGCAGCAGAAAAAGACCAGCAGAAAACCAGCAGCTAGAAAATCCACAGCGGCGGCAGCAGGTGGAC

TGAGGATCGCGGCGAACGAGCCGGCGCAAACCCGGGAGCTGAGGAACCGGATCTTTCCCACCCTCTATGCC

ATCTTCCAGCAGAGTCGGGGGCAGGAGCAGGAACTGAAAGTCAAGAACCGTTCTCTGCGCTCGCTCACCCG

CAGTTGTCTGTATCACAAGAGCGAAGACCAACTTCAGCGCACTCTCGAGGACGCCGAGGCTCTCTTCAACA

AGTACTGCGCGCTCACTCTTAAAGAGTAGCCCGCGCCCGCCCAGTCGCAGAAAAAGGCGGGAATTACGTCA

CCTGTGCCCTTCGCCCTACCGCCTCCACCCATCATCATGAGCAAAGAGATTCCCACGCCTTACATGTGGAG

CTACCAGCCCCAGATGGGCCTGGCCGCCGOTGCCGCCCACGACTACTCCACCCGCATGAATTGGCTCAGCG

CCGGGCCCGCGATGATCTCACGGGTGAATGACATCCGCGCCCACCGAAACCAGATACTCCTAGAACAGTCA

GCGCTCACCGCCACGCCCCGCAATCACCTCAATCCGCGTAATTGGCCCGCCGCCCTGGTGTACCAGGAAAT

TCCCCAGCCCACGACCGTACTACTTCCGCGAGACGCCCAGGCCGAAGTCCAGCTGACTAACTCAGGTGTCC

AGCTGGCGGGCGGCGCCACCCTGTGTCGTCACCGCCCCGCTCAGGGTATAAAGCGGCTGGTGATCCGGGGC

AGAGGCACACAGCTCAACGACGAGGTGGTGAGCTCTTCGCTGGGTCTGCGACCTGACGGAGTCTTCCAACT

CGCCGGATCGGGGAGATCTTCCTTCACGCCTCGTCAGGCCGTCCTGACTTTGGAGAGTTCGTCCTCGCAGCC

CCGCTCGGGTGGCATCGGCACTCTCCAGTTCGTGGAGGAGTTCACTCCCTCGGTCTACTTCAACCCCTTCTC

CGGCTCCCCCGGCCACTACCCGGACGAGTTCATCCCGAACTTCGACGCCATCAGCGAGTCGGTGGACGGCT

ACGATTGAAACTAATCACCCCCTTATCCAGTGAAATAAAGATCATATTGATGATGATTTTACAGAAATAAA

AAATAATCATTTGATTTGAAATAAAGATACAATCATATTGATGATTTGAGTTTAACAAAAAAATAAAGAAT

CACTTACTTGAAATCTGATACCAGGTCTCTGTCCATGTTTTCTGCCAACACCACTTCACTCCCCTCTTCCCAG

CTCTGGTACTGCAGGCCCCGGCGGGCTGCAAACTTCCTCCACACGCTGAAGGGGATGTCAAATTCCTCCTG

TCCCTCAATCTTCATTTTATCTTCTATCAGATGTCCAAAAAGCGCGTCCGGGTGGATGATGACTTCGACCCC

GTCTACCCCTACGATGCAGACAACGCACCGACCGTGCCCTTCATCAACCCCCCCTTCGTCTCTTCAGATGGA

TTCCAAGAGAAGCCCCTGGGGGTGTTGTCCCTGCGACTGGCCGACCCCGTCACCACCAAGAACGGGGAAAT

CACCCTCAAGCTGGGAGAGGGGGTGGACCTCGATTCCTCGGGAAAACTCATCTCCAACACGGCCACCAAG

GCCGCCGCCCCTCTCAGTTTTTCCAACAACACCATTTCCCTTAACATGGATCACCCCTTTTACACTAAAGAT

GGAAAATTATCCTTACAAGTTTCTCCACCATTAAATATACTGAGAACAAGCATTCTAAACACACTAGCTTTA

GGTTTTGGATCAGGTTTAGGACTCCGTGGCTCTGCCTTGGCAGTACAGTTAGTCTCTCCACTTACATTTGAT

ACTGATGGAAACATAAAGCTTACCTTAGACAGAGGTTTGCATGTTACAACAGGAGATGCAATTGAAAGCAA

CATAAGCTGGGCTAAAGGTTTAAAATTTGAAGATGGAGCCATAGCAACCAACATTGGAAATGGGTTAGAGT

TTGGAAGCAGTAGTACAGAAACAGGTGTTGATGATGCTTACCCAATCCAAGTTAAACTTGGATCTGGCCTT

AGCTTTGACAGTACAGGAGCCATAATGGCTGGTAACAAAGAAGACGATAAACTCACTTTGTGGACAACACC

TGATCCATCACCAAACTGTCAAATACTCGCAGAAAATGATGCAAAACTAACACTTTGCTTGACTAAATGTG

GTAGTCAAATACTGGCCACTGTGTCAGTCTTAGTTGTAGGAAGTGGAAACCTAAACCCCATTACTGGCACC

GTAAGCAGTGCTCAGGTGTTTCTACGTTTTGATGCAAACGGTGTTCTTTTAACAGAACATTCTACACTAAAA

AAATACTGGGGGTATAGGCAGGGAGATAGCATAGATGGCACTCCATATACCAATGCTGTAGGATTCATGCC

CAATTTAAAAGCTTATCCAAAGTCACAAAGTTCTACTACTAAAAATAATATAGTAGGGCAAGTATACATGA

ATGGAGATGTTTCAAAACCTATGCTTCTCACTATAACCCTCAATGGTACTGATGACAGCAACAGTACATATT

CAATGTCATTTTCATACACCTGGACTAATGGAAGCTATGTTGGAGCAACATTTGGGGCTAACTCTTATACCT

TCTCATACATCGCCCAAGAATGAACACTGTATCCCACCCTGCATGCCAACCCTTCCCACCCCACTCTGTGGA

ACAAACTCTGAAACACAAAATAAAATAAAGTTCAAGTGTTTTATTGATTCAAACAGTTTTACAGGATTCGAG

-continued

CAGTTATTTTTCCTCCACCCTCCCAGGACATGGAATACACCACCCTCTCCCCCCGCACAGCCTTGAACATCT

GAATGCCATTGGTGATGGACATGCTTTTGGTCTCCACGTTCCACACAGTTTCAGAGCGAGCCAGTCTCGGGT

CGGTCAGGGAGATGAAACCCTCCGGGCACTCCCGCATCTGCACCTCACAGCTCAACAGCTGAGGATTGTCC

TCGGTGGTCGGGATCACGGTTATCTGGAAGAAGCAGAAGAGCGGCGGTGGGAATCATAGTCCGCGAACGG

GATCGGCCGGTGGTGTCGCATCAGGCCCCGCAGCAGTCGCTGCCGCCGCCGCTCCGTCAAGCTGCTGCTCA

GGGGGTCCGGGTCCAGGGACTCCCTCAGCATGATGCCCACGGCCCTCAGCATCAGTCGTCTGGTGCGGCGG

GCGCAGCAGCGCATGCGGATCTCGCTCAGGTCGCTGCAGTACGTGCAACACAGAACCACCAGGTTGTTCAA

CAGTCCATAGTTCAACACGCTCCAGCCGAAACTCATCGCGGGAAGGATGCTACCCACCGTGGCCGTCGTACC

AGATCCTCAGGTAAATCAAGTGGTGCCCCCTCCAGAACACGCTGCCCACGTACATGATCTCCTTGGGCATG

TGGCGGTTCACCACCTCCCGGTACCACATCACCCTCTGGTTGAACATGCAGCCCCGATGATCCTGCGGAA

CCACAGGGCCAGCACCGCCCCGCCCGCCATGCAGCGAAGAGACCCCGGGTCCCGGCAATGGCAATGGAGG

ACCCACCGCTCGTACCCGTGGATCATCTGGGAGCTGAACAAGTCTATGTTGGCACAGCACAGGCATATGCT

CATGCATCTCTTCAGCACTCTCAACTCCTCGGGGGTCAAAACCATATCCCAGGGCACGGGGAACTCTTGCA

GGACAGCGAACCCCGCAGAACAGGGCAATCCTCGCACAGAACTTACATTGTGCATGGACAGGGTATCGCA

ATCAGGCAGCACCGGGTGATCCTCCACCAGAGAAGCGCGGGTCTCGGTCTCCTCACAGCGTGGTAAGGGG

GCCGGCCGATACGGGTGATGGCGGGACGCGGCTGATCGTGTTCGCGACCGTGTCATGATGCAGTTGCTTTC

GGACATTTTCGTACTTGCTGTAGCAGAACCTGGTCCGGGCGCTGCACACCGATCGCCGGCGGCGGTCTCGG

CGCTTGGAACGCTCGGTGTTGAAATTGTAAAACAGCCACTCTCTCAGACCGTGCAGCAGATCTAGGGCCTC

AGGAGTGATGAAGATCCCATCATGCCTGATGGCTCTGATCACATCGACCACCGTGGAATGGGCCAGACCAC

GCCAGATGATGCAATTTTGTTGGGTTTCGGTGACGGCGGGGGAGGGAAGAACAGGAAGAACCATGATTAA

CTTTTAATCCAAACGGTCTCGGAGTACTTCAAAATGAAGATCGCGGAGATGGCACCTCTCGCCCCCGCTGT

GTTGGTGGAAAATAACAGCCAGGTCAAAGGTGATACGGTTCTCGAGATGTTCCACGGTGGCTTCCAGCAAA

GCCTCCACGCGCACATCCAGAAACAAGACAATAGCGAAAGCGGGAGGGTTCTCTAATTCCTCAATCATCAT

GTTACACTCCTGCACCATCCCCAGATAATTTTCATTTTTCCAGCCTTGAATGATTCGAACTAGTTCCTGAGGT

AAATCCAAGCCAGCCATGATAAAGAGCTCGCGCAGAGCGCCCTCCACCGGCATTCTTAAGCACACCCTCAT

AATTCCAAGATATTCTGCTCCTGGTTCACCTGCAGCAGATTGACAAGCGGAATATCAAAATCTCTGCCGCG

ATCCCTGAGCTCCTCCCTCAGCAATAACTGTAAGTACTCTTTCATATCCTCTCCGAAATTTTTAGCCATAGG

ACCACCAGGAATAAGATTAGGGCAAGCCACAGTACAGATAAACCGAAGTCCTCCCCAGTGAGCATTGCCA

AATGCAAGACTGCTATAAGCATGCTGGCTAGACCCGGTGATATCTTCCAGATAACTGGACAGAAAATCGCC

CAGGCAATTTTTAAGAAAATCAACAAAAGAAAAATCCTCCAGGTGGACGTTTAGAGCCTCGGGAACAACG

ATGAAGTAAATGCAAGCGGTGCGTTCCAGCATGGTTAGTTAGCTGATCTGTAGAAAAAACAAAAATGAAC

ATTAAACCATGCTAGCCTGGCGAACAGGTGGGTAAATCGTTCTCTCCAGCACCAGGCAGGCCACGGGGTCT

CCGGCGCGACCCTCGTAAAAATTGTCGCTATGATTGAAAACCATCACAGAGAGACGTTCCCGGTGGCCGGC

GTGAATGATTCCACAAGATGAATACACCCCCGGAACATTGGCGTCCGCGAGTGAAAAAAAGCGCCCGAGG

AAGCAATAAGGCACTACAATGCTCAGTCTCAAGTCCAGCAAAGCGATGCCATGCGGATGAAGCACAAAAT

TCTCAGGTGCGTACAAAATGTAATTACTCCCCTCCTGCACAGGCAGCAAAGCCCCCGATCCCTCCAGGTAC

ACATACAAAGCCTCAGCGTCCATAGCTTACCGAGCAGCAGCACACAACAGGCGCAAGAGTCAGAGAAAGG

CTGAGCTCTAACCTGTCCACCCGCTCTCTGCTCAATATATAGCCCAGATCTACACTGACGTAAAGGCCAAA

GTCTAAAAATACCCGCCAAATAATCACACACGCCCAGCACACGCCCAGAAACCGGTGACACACTCAAAAA

AATACGCGCACTTCCTCAAACGCCCAAAACTGCCGTCATTTCCGGGTTCCCACGCTACGTCATCAAAACAC

-continued

GACTTTCAAATTCCGTCGACCGTTAAAAACGTCACCCGCCCCGCCCCTAACGGTCGCCCGTCTCTCAGCCAA

TCAGCGCCCCGCATCCCCAAATTCAAACACCTCATTTGCATATTAACGCGCACAAAAAGTTTGAGGTATATT

ATTGATGATG

ChAdV68-TETo-TSNA (SEQ ID NO: 67)

CCATCTTCAATAATATACCTCAAACTTTTTGTGCGCGTTAATATGCAAATGAGGCGTTTGAATTTGGGGAGG

AAGGGCGGTGATTGGTCGAGGGATGAGCGACCGTTAGGGGCGGGGCGAGTGACGTTTTGATGACGTGGTT

GCGAGGAGGAGCCAGTTTGCAAGTTCTCGTGGGAAAAGTGACGTCAAACGAGGTGTGGTTTGAACACGGA

AATACTCAATTTTCCCGCGCTCTCTGACAGGAAATGAGGTGTTTCTGGGCGGATGCAAGTGAAAACGGGCC

ATTTTCGCGCGAAAACTGAATGAGGAAGTGAAAATCTGAGTAATTTCGCGTTTATGGCAGGGAGGAGTATT

TGCCGAGGGCCGAGTAGACTTTGACCGATTACGTGGGGGTTTCGATTACCGTGTTTTTCACCTAAATTTCCG

CGTACGGTGTCAAAGTCCGGTGTTTTTACGTAGGTGTCAGCTGATCGCCAGGGTATTTAAACCTGCGCTCTC

CAGTCAAGAGGCCACTCTTGAGTGCCAGCGAGAAGAGTTTTCTCCTCCGCGCCGCGAGTCAGATCTACACT

TTGAAAGTAGGGATAACAGGGTAATCCATGTTGACATTGATTATTGACTAGTTATTAAAGTACTTCCCTATC

AGTGATAGAGAAAAGTGAAAGTCGAGTTTACCACTCCCTATCAGTGATAGAGAAAAGTGAAAGTCGAGTTT

ACCACTCCCTATCAGTGATAGAGAAAAGTGAAAGTCGAGTTTACCACTCCCTATCAGTGATAGAGAAAAGT

GAAAGTCGAGTTTACCACTCCCTATCAGTGATAGAGAAAAGTGAAAGTCGAGTTTACCACTCCCTATCAGT

GATAGAGAAAAGTGAAAGTCGAGTTTACCACTCCCTATCAGTGATAGAGAAAAGTGAAAGTCGAGCTCGG

TACCCGGGTCGAGGTAGGCGTGTACGGTGGGAGGCCTATATAAGCAGAGCTCGTTTAGTGAACCGTCAGAT

CGCCTGGAGACGCCATCCACGCTGTTTTGACCTCCATAGAAGACAGCGATCGCGCCACCATGGCTGGCATG

ACCGAGTACAAGCTAGTCGTTGTGGGAGCTGGAGATGTGGGCAAATCTGCTCTGACCATTCAGCTGATTCA

GGGCACAGATCTGGATCACCAGGAGAAGTGTCTGAGCAGGCTGTACGACCACATGCCAGAAGGATTAACC

CCTCTTATGGGAGTGAGCTCTTCTTCTGCTCTGGCCAGACTGGGACTGCCTATGGATAAGCTGAACAAGATC

ACAGCTCCTGCCTCTCAGAAACTGAGACAGCTGCAGAAGATGGAGACCCCTGAACTGCTGCCTTGTGGATA

TCTGGTGGAGGAGAATACCACAATCAGCGTGACCGTGAAAGGCCTGGAAGCCCAGAACAAGATCAAAGGC

TGTACCGGCTCTGTGAATATGACACTGCAGAGAGCTTCTGCCGCCCCTAAGACAGGAGGAGGAGGAGAAG

CTGCTGCCTACAATAATACATTAGTGGCCAGACATGTGCCCCAGATCCCTAAGCCTGACAGCCTGGTTGGC

CTGAGCGATGAATTAGGAAAAAGAGACACATTTGCCGAGAGCCTGATCCGGAGAATGGCCTCTGCCGGCT

ACCTGTTCCTGGATATCATCACATATGTTGTGTTTGCCGTGACCTTCGTGCTGGGAGTTCTGGGCGGCCTGA

ATACCGAGACCAATGAAAAAGCTCTTGAAGCCGTGTTTGGCAAGTACGGCAGAATCGTGGAGGTGCTGGG

CGGCAGATCTTGTGAAGAATTAACAGCTGTGTTACCACCTCCTCAGCTGCTTGGCAGACGGTTCAACTTCTT

CAGCTACAGCTACGTTGCTGCTGGCTCTTCTGGCAACAACTACGACCTGATGGCCCAGCCTATTACACCTGG

ACCTGATACAACACCTCTGCCTGTGACCGATACATCTTCTGTGTCTACCGGACACGCCACATCTCTGCCAGT

GACAGATGCTGGACTGAGAGTGACAGAGTCTAAAGGACACAGCGATTCTTGGCACCTGAGCCTGGATACA

GCCATCAGGGTGAATACCCCTAAGCTGGTTTCTGAAGTGGAAGAGCTGAACAAGAGCATCACCGCCCTGAG

GGAGAAGTTACTGCAGATGGTGGAAGCCGATAGACCTGGAAACCTGTTTATTGGAGGCCTGAACACCGAG

ACCAATGAGGACTCTCCCGTGAAGGATGAAGTGGTGGTGAACGATCAATGGGGCCAGAATTGTAGCTGCC

ATCATGGAGGCTACGAGTTCCCTGATCTGCACAGGACAATCGTGTCTGAGTGCGATGTGTATCTGACCTAC

ATGCTGAGACAGGCTGCTCTGCAGCTGTTCTTCGACCTGTATCACAGCATCCCTAGCAGCTTTTCTCCTCTG

GTTCTGAGCTGTCTGGTGCAGCCTCTGGAAGATGTGGAAGTGATGGAGAAGGATGGCACAACCTTTAGCTG

TGAGGTGAGCCACGATGAGGTGCCTCGGACATATGGACCCGTGTTTATGTGTCTGGGAGGACTGCTGACCA

TGGTGGCTGGAGCTGTTTGGCTGACAGTTGGACCCGGACCAGGCGCCAAATTTGTTGCTGCTTGGACACTG

-continued

AAAGCTGCTGCTGGGCCCGGACCAGGCCAGTACATCAAGGCCAACTCTAAGTTTATCGGCATCACCGAATT

GGGACCTGGACCCGGCTAGTAGTGAGTTTAAACTCCCATTTAAATGTGAGGGTTAATGCTTCGAGCAGACA

TGATAAGATACATTGATGAGTTTGGACAAACCACAACTAGAATGCAGTGAAAAAAATGCTTTATTTGTGAA

ATTTGTGATGCTATTGCTTTATTTGTAACCATTATAAGCTGCAATAAACAAGTTAACAACAACAATTGCATT

CATTTTATGTTTCAGGTTCAGGGGGAGATGTGGGAGGTTTTTTAAAGCAAGTAAAACCTCTACAAATGTGGT

AAAATAACTATAACGGTCCTAAGGTAGCGAGTGAGTAGTGTTCTGGGGCGGGGGAGGACCTGCATGAGGG

CCAGAATAACTGAAATCTGTGCTTTTCTGTGTGTTGCAGCAGCATGAGCGGAAGCGGCTCCTTTGAGGGAG

GGGTATTCAGCCCTTATCTGACGGGGCGTCTCCCCTCCTGGGCGGGAGTGCGTCAGAATGTGATGGGATCC

ACGGTGGACGGCCGGCCCGTGCAGCCCGCGAACTCTTCAACCCTGACCTATGCAACCCTGAGCTCTTCGTC

GTTGGACGCAGCTGCCGCCGCAGCTGCTGCATCTGCCGCCAGCGCCGTGCGCGGAATGGCCATGGGCGCCG

GCTACTACGGCACTCTGGTGGCCAACTCGAGTTCCACCAATAATCCCGCCAGCCTGAACGAGGAGAAGCTG

TTGCTGCTGATGGCCCAGCTCGAGGCCTTGACCCAGCGCCTGGGCGAGCTGACCCAGCAGGTGGCTCAGCT

GCAGGAGCAGACGCGGGCCGCGGTTGCCACGGTGAAATCCAAATAAAAAATGAATCAATAAATAAACGGA

GACGGTTGTTGATTTTAACACAGAGTCTGAATCTTTATTTGATTTTTCGCGCGCGGTAGGCCCTGGACCACC

GGTCTCGATCATTGAGCACCCGGTGGATCTTTTCCAGGACCCGGTAGAGGTGGGCTTGGATGTTGAGGTAC

ATGGGCATGAGAGCCCGTCCCGGGGGTGGAGGTAGCTCCATTGCAGGGCCTCGTGCTCGGGGGTGGTGTTGTA

AATCACCCAGTCATAGCAGGGGCGCAGGGCATGGTGTTGCACAATATCTTTGAGGAGGAGACTGATGGCCA

CGGGCAGCCCTTTGGTGTAGGTGTTTACAAATCTGTTGAGCTGGGAGGGATGCATGCGGGGGGAGATGAGG

TGCATCTTGGCCTGGATCTTGAGATTGGCGATGTTACCGCCCAGATCCCGCCTGGGGTTCATGTTGTGCAGG

ACCACCAGCACGGTGTATCCGGTGCACTTGGGGAATTTATCATGCAACTTGGAAGGGAAGGCGTGAAAGA

ATTTGGCGACGCCTTTGTGCCCGCCCAGGTTTTCCATGCACTCATCCATGATGATGGCGATGGGCCCGTGGG

CGGCGGCCTGGGCAAAGACGTTTCGGGGGTCGGACACATCATAGTTGTGGTCCTGGGTGAGGTCATCATAG

GCCATTTTAATGAATTTGGGGCGGAGGGTGCCGGACTGGGGGACAAAGGTACCCTCGATCCCGGGGGCGTA

GTTCCCCTCACAGATCTGCATCTCCCAGGCTTTGAGCTCGGAGGGGGGGATCATGTCCACCTGCGGGGCGA

TAAAGAACACGGTTTCCGGGGCGGGGGAGATGAGCTGGGCCGAAAGCAAGTTCCGGAGCAGCTGGGACTT

GCCGCAGCCGGTGGGGCCGTAGATGACCCCGATGACCGGCTGCAGGTGGTAGTTGAGGGAGAGACAGCTG

CCGTCCTCCCGGAGGAGGGGGGCCACCTCGTTCATCATCTCGCGCACGTGCATGTTCTCGCGCACCAGTTCC

GCCAGGAGGCGCTCTCCCCCCAGGGATAGGAGCTCCTGGAGCGAGGCGAAGTTTTTCAGCGGCTTGAGTCC

GTCGGCCATGGGCATTTTGGAGAGGGTTTGTTGCAAGAGTTCCAGGCGGTCCCAGAGCTCGGTGATGTGCT

CTACGGCATCTCGATCCAGCAGACCTCCTCGTTTCGCGGGTTGGGACGGCTGCGGGAGTAGGGCACCAGAC

GATGGGCGTCCAGCGCAGCCAGGGTCCGGTCCTTCCAGGGTCGCAGCGTCCGCGTCAGGGTGGTCTCCGTC

ACGGTGAAGGGGTGCGCGCCGGGCTGGGCGCTTGCGAGGGTGCGCTTCAGGCTCATCCGGCTGGTCGAAA

ACCGCTCCCGATCGGCGCCCTGCGCGTCGGCCAGGTAGCAATTGACCATGAGTTCGTAGTTGAGCGCCTCG

GCCGCGTGGCCTTTGGCGCGGAGCTTACCTTTGGAAGTCTGCCCGCAGGCGGGACAGAGGAGGGACTTGAG

GGCGTAGAGCTTGGGGGCGAGGAAGACGGACTCGGGGGCGTAGGCGTCCGCGCCGCAGTGGGCGCAGACG

GTCTCGCACTCCACGAGCCAGGTGAGGTCGGGCTGGTCGGGGTCAAAAACCAGTTTCCCGCCGTTCTTTTTG

ATGCGTTTCTTACCTTTGGTCTCCATGAGCTCGTGTCCCCGCTGGGTGACAAAGAGGCTGTCCGTGTCCCCG

TAGACCGACTTTATGGGCCGGTCCTCGAGCGGTGTGCCGCGGTCCTCCTCGTAGAGGAACCCCGCCCACTC

CGAGACGAAAGCCCGGGTCCAGGCCAGCACGAAGGAGGCCACGTGGGACGGGTAGCGGTCGTTGTCCACC

AGCGGGTCCACCTTTTCCAGGGTATGCAAACACATGTCCCCCTCGTCCACATCCAGGAAGGTGATTGGCTT

-continued

GTAAGTGTAGGCCACGTGACCGGGGGTCCCGGCCGGGGGGGTATAAAAGGGTGCGGGTCCCTGCTCGTCCT

CACTGTCTTCCGGATCGCTGTCCAGGAGCGCCAGCTGTTGGGGTAGGTATTCCCTCTCGAAGGCGGGCATG

ACCTCGGCACTCAGGTTGTCAGTTTCTAGAAACGAGGAGGATTTGATATTGACGGTGCCGGCGGAGATGCC

TTTCAAGAGCCCCTCGTCCATCTGGTCAGAAAAGACGATCTTTTTGTTGTCGAGCTTGGTGGCGAAGGAGCC

GTAGAGGGCGTTGGAGAGGAGCTTGGCGATGGAGCGCATGGTCTGGTTTTTTTCCTTGTCGGCGCGCTCCTT

GGCGGCGATGTTGAGCTGCACGTACTCGCGCGCCACGCACTTCCATTCGGGGAAGACGGTGGTCAGCTCGT

CGGGCACGATTCTGACCTGCCAGCCCCGATTATGCAGGGTGATGAGGTCCACACTGGTGGCCACCTCGCCG

CGCAGGGGCTCATTAGTCCAGCAGAGGCGTCCGCCCTTGCGCGAGCAGAAGGGGGGCAGGGGGTCCAGCA

TGACCTCGTCGGGGGGGTCGGCATCGATGGTGAAGATGCCGGGCAGGAGGTCGGGGTCAAAGTAGCTGAT

GGAAGTGGCCAGATCGTCCAGGGCAGCTTGCCATTCGCGCACGGCCAGCGCGCGCTCGTAGGGACTGAGG

GGCGTGCCCCAGGGCATGGGATGGGTAAGCGCGGAGGCGTACATGCCGCAGATGTCGTAGACGTAGAGGG

GCTCCTCGAGGATGCCGATGTAGGTGGGGTAGCAGCGCCCCCCGCGGATGCTGGCGCGCACGTAGTCATAC

AGCTCGTGCGAGGGGGCGAGGAGCCCCGGGCCCAGGTTGGTGCGACTGGGCTTTTCGGCGCGGTAGACGA

TCTGGCGGAAAATGGCATGCGAGTTGGAGGAGATGGTGGGCCTTTGGAAGATGTTGAAGTGGGCGTGGGG

CAGTCCGACCGAGTCGCGGATGAAGTGGGCGTAGGAGTCTTGCAGCTTGGCGACGAGCTCGGCGGTGACTA

GGACGTCCAGAGCGCAGTAGTCGAGGGTCTCCTGGATGATGTCATACTTGAGCTGTCCCTTTTGTTTCCACA

GCTCGCGGTTGAGAAGGAACTCTTCGCGGTCCTTCCAGTACTCTTCGAGGGGGAACCCGTCCTGATCTGCA

CGGTAAGAGCCTAGCATGTAGAACTGGTTGACGGCCTTGTAGGCGCAGCAGCCCTTCTCCACGGGGAGGGC

GTAGGCCTGGGCGGCCTTGCGCAGGGAGGTGTGCGTGAGGGCGAAAGTGTCCCTGACCATGACCTTGAGG

AACTGGTGCTTGAAGTCGATATCGTCGCAGCCCCCCTGCTCCCAGAGCTGGAAGTCCGTGCGCTTCTTGTAG

GCGGGGTTGGGCAAAGCGAAAGTAACATCGTTGAAGAGGATCTTGCCCGCGCGGGGCATAAAGTTGCGAG

TGATGCGGAAAGGTTGGGGCACCTCGGCCCGGTTGTTGATGACCTGGGCGGCGAGCACGATCTCGTCGAAG

CCGTTGATGTTGTGGCCCACGATGTAGAGTTCCACGAATCGCGGACGGCCCTTGACGTGGGGCAGTTTCTTG

AGCTCCTCGTAGGTGAGCTCGTCGGGGTCGCTGAGCCCGTGCTGCTCGAGCGCCCAGTCGGCGAGATGGGG

GTTGGCGCGGAGGAAGGAAGTCCAGAGATCCACGGCCAGGGCGGTTTGCAGACGGTCCCGGTACTGACGG

AACTGCTGCCCGACGGCCATTTTTTCGGGGGTGACGCAGTAGAAGGTGCGGGGGTCCCCGTGCCAGCGATC

CCATTTGAGCTGGAGGGCGAGATCGAGGGCGAGCTCGACGAGCCGGTCGTCCCCGGAGAGTTTCATGACC

AGCATGAAGGGGACGAGCTGCTTGCCGAAGGACCCCATCCAGGTGTAGGTTTCCACATCGTAGGTGAGGA

AGAGCCTTTCGGTGCGAGGATGCGAGCCGATGGGGAAGAACTGGATCTCCTGCCACCAATTGGAGGAATG

GCTGTTGATGTGATGGAAGTAGAAATGCCGACGGCGCGCCGAACACTCGTGCTTGTGTTTATACAAGCGGC

CACAGTGCTCGCAACGCTGCACGGGATGCACGTGCTGCACGAGCTGTACCTGAGTTCCTTTGACGAGGAAT

TTCAGTGGGAAGTGGAGTCGTGGCGCCTGCATCTCGTGCTGTACTACGTCGTGGTGGTCGGCCTGGCCCTCT

TCTGCCTCGATGGTGGTCATGCTGACGAGCCCGCGCGGGAGGCAGGTCCAGACCTCGGCGCGAGCGGGTCG

GAGAGCGAGGACGAGGGCGCGCAGGCCGGAGCTGTCCAGGGTCCTGAGACGCTGCGGAGTCAGGTCAGTG

GGCAGCGGCGGCGCGCGGTTGACTTGCAGGAGTTTTTCCAGGGCGCGCGGGAGGTCCAGATGGTACTTGAT

CTCCACCGCGCCATTGGTGGCGACGTCGATGGCTTGCAGGGTCCGTGCCCCTGGGGTGTGACCACCGTCC

CCCGTTTCTTCTTGGGCGGCTGGGGCGACGGGGGCGGTGCCTCTTCCATGGTTAGAAGCGGCGGCGAGGAC

GCGCGCCGGGCGGCAGGGGCGGCTCGGGGCCCGGAGGCAGGGGCGGCAGGGGCACGTCGGCGCCGCGCG

CGGGTAGGTTCTGGTACTGCGCCCGGAGAAGACTGGCGTGAGCGACGACGCGACGGTTGACGTCCTGGATC

TGACGCCTCTGGGTGAAGGCCACGGGACCCGTGAGTTTGAACCTGAAAGAGAGTTCGACAGAATCAATCTC

GGTATCGTTGACGGCGGCCTGCCGCAGGATCTCTTGCACGTCGCCCGAGTTGTCCTGGTAGGCGATCTCGGT

-continued

CATGAACTGCTCGATCTCCTCCTCTTGAAGGTCTCCGCGGCCGGCGCGCTCCACGGTGGCCGCGAGGTCGTT

GGAGATGCGGCCCATGAGGTGCGAGAAGGCGTTCATGCCCGCCTCGTTCCAGACGCGGCTGTAGACCACGA

CGCCCTCGGGATCGCGGGCGCGCATGACCACCTGGGCGAGGTTGAGCTCCACGTGGCGCGTGAAGACCGC

GTAGTTGCAGAGGCGCTGGTAGAGGTAGTTGAGCGTGGTGGCGATGTGCTCGGTGACGAAGAAATACATG

ATCCAGCGGCGGAGCGGCATCTCGCTGACGTCGCCCAGCGCCTCCAAACGTTCCATGGCCTCGTAAAAGTC

CACGGCGAAGTTGAAAAACTGGGAGTTGCGCGCCGAGACGGTCAACTCCTCCTCCAGAAGACGGATGAGC

TCGGCGATGGTGGCGCGCACCTCGCGCTCGAAGGCCCCCGGGAGTTCCTCCACTTCCTCTTCTTCCTCCTCC

ACTAACATCTCTTCTACTTCCTCCTCAGGCGGCAGTGGTGGCGGGGGAGGGGGCCTGCGTCGCCGGCGGCG

CACGGGCAGACGGTCGATGAAGCGCTCGATGGTCTCGCCGCGCCGGCGTCGCATGGTCTCGGTGACGGCGC

GCCCGTCCTCGCGGGGCCGCAGCGTGAAGACGCCGCCGCGCATCTCCAGGTGGCCGGGGGGGTCCCCGTTG

GGCAGGGAGAGGGCGCTGACGATGCATCTTATCAATTGCCCCGTAGGGACTCCGCGCAAGGACCTGAGCG

TCTCGAGATCCACGGGATCTGAAAACCGCTGAACGAAGGCTTCGAGCCAGTCGCAGTCGCAAGGTAGGCT

GAGCACGGTTTCTTCTGGCGGGTCATGTTGGTTGGGAGCGGGGCGGGCGATGCTGCTGGTGATGAAGTTGA

AATAGGCGGTTCTGAGACGGCGGATGGTGGCGAGGAGCACCAGGTCTTTGGGCCCGGCTTGCTGGATGCGC

AGACGGTCGGCCATGCCCCAGGCGTGGTCCTGACACCTGGCCAGGTCCTTGTAGTAGTCCTGCATGAGCCG

CTCCACGGGCACCTCCTCCTCGCCCGCGCGGCCGTGCATGCGCGTGAGCCCGAAGCCGCGCTGGGGCTGGA

CGAGCGCCAGGTCGGCGACGACGCGCTCGGCGAGGATGGCTTGCTGGATCTGGGTGAGGGTGGTCTGGAA

GTCATCAAAGTCGACGAAGCGGTGGTAGGCTCCGGTGTTGATGGTGTAGGAGCAGTTGGCCATGACGGACC

AGTTGACGGTCTGGTGGCCCGGGACGCACGAGCTCGTGGTACTTGAGGCGCGAGTAGGCGCGCGTGTCGAAG

ATGTAGTCGTTGCAGGTGCGCACCAGGTACTGGTAGCCGATGAGGAAGTGCGGCGGCGGCTGGCGGTAGA

GCGGCCATCGCTCGGTGGCGGGGGCGCCGGGCGCGAGGTCCTCGAGCATGGTGCGGTGGTAGCCGTAGAT

GTACCTGGACATCCAGGTGATGCCGGCGGCGGTGGTGGAGGCGCGCGGGAACTCGCGGACGCGGTTCCAG

ATGTTGCGCAGCGGCAGGAAGTAGTTCATGGTGGGCACGGTCTGGCCCGTGAGGCGCGCGCAGTCGTGGAT

GCTCTATACGGGCAAAAACGAAAGCGGTCAGCGGCTCGACTCCGTGGCCTGGAGGCTAAGCGAACGGGTT

GGGCTGCGCGTGTACCCCGGTTCGAATCTCGAATCAGGCTGGAGCCGCAGCTAACGTGGTATTGGCACTCC

CGTCTCGACCCAAGCCTGCACCAACCCTCCAGGATACGGAGGCGGGTCGTTTTGCAACTTTTTTTTGGAGGC

CGGATGAGACTAGTAAGCGCGGAAAGCGGCCGACCGCGATGGCTCGCTGCCGTAGTCTGGAGAAGAATCG

CCAGGGTTGCGTTGCGGTGTGCCCCGGTTCGAGGCCGGCCGGATTCCGCGGCTAACGAGGGCGTGGCTGCC

CCGTCGTTTCCAAGACCCCATAGCCAGCCGACTTCTCCAGTTACGGAGCGAGCCCCTCTTTTGTTTTGTTTGT

TTTTGCCAGATGCATCCCGTACTGCGGCAGATGCGCCCCCACCACCCTCCACCGCAACAACAGCCCCCTCC

ACAGCCGGCGCTTCTGCCCCCGCCCCAGCAGCAACTTCCAGCCACGACCGCCGCGGCCGCCGTGAGCGGGG

CTGGACAGAGTTATGATCACCAGCTGGCCTTGGAAGAGGGCGAGGGGCTGGCGCGCCTGGGGGCGTCGTC

GCCGGAGCGGCACCCGCGCGTGCAGATGAAAAGGGACGCTCGCGAGGCCTACGTGCCCAAGCAGAACCTG

TTCAGAGACAGGAGCGGCGAGGAGCCCGAGGAGATGCGCGCGGCCCGGTTCCACGCGGGGCGGGAGCTGC

GGCGCGGCCTGGACCGAAAGAGGGTGCTGAGGGACGAGGATTTCGAGGCGGACGAGCTGACGGGGATCAG

CCCCGCGCGCGCGCACGTGGCCGCGGCCAACCTGGTCACGGCGTACGAGCAGACCGTGAAGGAGGAGAGC

AACTTCCAAAAATCCTTCAACAACCACGTGCGCACCCTGATCGCGCGCGAGGAGGTGACCCTGGGCCTGAT

GCACCTGTGGGACCTGCTGGAGGCCATCGTGCAGAACCCCACCAGCAAGCCGCTGACGGCGCAGCTGTTCC

TGGTGGTGCAGCATAGTCGGGACAACGAAGCGTTCAGGGAGGCGCTGCTGAATATCACCGAGCCCGAGGG

CCGCTGGCTCCTGGACCTGGTGAACATTCTGCAGAGCATCGTGGTGCAGGAGCGCGGGCTGCCGCTGTCCG

-continued

AGAAGCTGGCGGCCATCAACTTCTCGGTGCTGAGTTTGGGCAAGTACTACGCTAGGAAGATCTACAAGACC

CCGTACGTGCCCATAGACAAGGAGGTGAAGATCGACGGGTTTTACATGCGCATGACCCTGAAAGTGCTGAC

CCTGAGCGACGATCTGGGGGTGTACCGCAACGACAGGATGCACCGTGCGGTGAGCGCCAGCAGGCGGCGC

GAGCTGAGCGACCAGGAGCTGATGCATAGTCTGCAGCGGGCCCTGACCGGGGCCGGGACCGAGGGGGAGA

GCTACTTTGACATGGGCGCGGACCTGCACTGGCAGCCCAGCCGCCGGGCCTTGGAGGCGGCGGCAGGACC

CTACGTAGAAGAGGTGGACGATGAGGTGGACGAGGAGGGCGAGTACCTGGAAGACTGATGGCGCGACCGT

ATTTTTGCTAGATGCAACAACAACAGCCACCTCCTGATCCCGCGATGCGGGCGGCGCTGCAGAGCCAGCCG

TCCGGCATTAACTCCTCGGACGATTGGACCCAGGCCATGCAACGCATCATGGCGCTGACGACCCGCAACCC

CGAAGCCTTTAGACAGCAGCCCCAGGCCAACCGGCTCTCGGCCATCCTGGAGGCCGTGGTGCCCTCGCGCT

CCAACCCCACGCACGAGAAGGTCCTGGCCATCGTGAACGCGCTGGTGGAGAACAAGGCCATCCGCGGCGA

CGAGGCCGGCCTGGTGTACAACGCGCTGCTGGAGCGCGTGGCCCGCTACAACAGCACCAACGTGCAGACC

AACCTGGACCGCATGGTGACCGACGTGCGCGAGGCCGTGGCCCAGCGCGAGCGGTTCCACCGCGAGTCCA

ACCTGGGATCCATGGTGGCGCTGAACGCCTTCCTCAGCACCCAGCCCGCCAACGTGCCCCGGGGCCAGGAG

GACTACACCAACTTCATCAGCGCCCTGCGCCTGATGGTGACCGAGGTGCCCCAGAGCGAGGTGTACCAGTC

CGGGCCGGACTACTTCTTCCAGACCAGTCGCCAGGGCTTGCAGACCGTGAACCTGAGCCAGGCTTTCAAGA

ACTTGCAGGGCCTGTGGGGCGTGCAGGCCCCGGTCGGGGACCGCGCGACGGTGTCGAGCCTGCTGACGCC

GAACTCGCGCCTGCTGCTGCTGCTGGTGGCCCCCTTCACGGACAGCGGCAGCATCAACCGCAACTCGTACC

TGGGCTACCTGATTAACCTGTACCGCGAGGCCATCGGCCAGGCGCACGTGGACGAGCAGACCTACCAGGA

GATCACCCACGTGAGCCGCGCCCTGGGCCAGGACGACCCGGGCAACCTGGAAGCCACCCTGAACTTTTTGC

TGACCAACCGGTCGCAGAAGATCCCGCCCCAGTACGCGCTCAGCACCGAGGAGGAGCGCATCCTGCGTTAC

GTGCAGCAGAGCGTGGGCCTGTTCCTGATGCAGGAGGGGGCCACCCCCAGCGCCGCGCTCGACATGACCG

CGCGCAACATGGAGCCCAGCATGTACGCCAGCAACCGCCCGTTCATCAATAAACTGATGGACTACTTGCAT

CGGGCGGCCGCCATGAACTCTGACTATTTCACCAACGCCATCCTGAATCCCACTGGCTCCCGCCGCCGGG

GTTCTACACGGGCGAGTACGACATGCCCGACCCCAATGACGGGTTCCTGTGGGACGATGTGGACAGCAGCG

TGTTCTCCCCCCGACCGGGTGCTAACGAGCGCCCCTTGTGGAAGAAGGAAGGCAGCGACCGACGCCCGTCC

TCGGCGCTGTCCGGCCGCGAGGGTGCTGCCGCGGCGGTGCCCGAGGCCGCCAGTCCTTTCCCGAGCTTGCC

CTTCTCGCTGAACAGTATCCGCAGCAGCGAGCTGGGCAGGATCACGCGCCCGCGCTTGCTGGGCGAAGAGG

AGTACTTGAATGACTCGCTGTTGAGACCCGAGCGGGAGAAGAACTTCCCCAATAACGGGATAGAAAGCCT

GGTGGACAAGATGAGCCGCTGGAAGACGTATGCGCAGGAGCACAGGGACGATCCCCGGGCGTCGCAGGGG

GCCACGAGCCGGGGCAGCGCCGCCCGTAAACGCCGGTGGCACGACAGGCAGCGGGGACAGATGTGGGAC

GATGAGGACTCCGCCGACGACAGCAGCGTGTTGGACTTGGGTGGGAGTGGTAACCCGTTCGCTCACCTGCG

CCCCCGTATCGGGCGCATGATGTAAGAGAAACCGAAAATAAATGATACTCACCAAGGCCATGGCGACCAG

CGTGCGTTCGTTTCTTCTCTGTTGTTGTTGTATCTAGTATGATGAGGCGTGCGTACCCGGAGGGTCCTCCTCC

CTCGTACGAGAGCGTGATGCAGCAGGCGATGGCGGCGGCGGCGATGCAGCCCCCGCTGGAGGCTCCTTAC

GTGCCCCCGCGGTACCTGGCGCCTACGGAGGGGCGGAACAGCATTCGTTACTCGGAGCTGGCACCCTTGTA

CGATACCACCCGGTTGTACCTGGTGGACAACAAGTCGGCGGACATCGCCTCGCTGAACTACCAGAACGACC

ACAGCAACTTCCTGACCACCGTGGTGCAGAACAATGACTTCACCCCCACGGAGGCCAGCACCCAGACCATC

AACTTTGACGAGCGCTCGCGGTGGGGCGGCCAGCTGAAAACCATCATGCACACCAACATGCCCAACGTGA

ACGAGTTCATGTACAGCAACAAGTTCAAGGCGCGGGTGATGGTCTCCCGCAAGACCCCCAATGGGGTGAC

AGTGACAGAGGATTATGATGGTAGTCAGGATGAGCTGAAGTATGAATGGGTGGAATTTGAGCTGCCCGAA

GGCAACTTCTCGGTGACCATGACCATCGACCTGATGAACAACGCCATCATCGACAATTACTTGGCGGTGGG

-continued

GCGGCAGAACGGGGTGCTGGAGAGCGACATCGGCGTGAAGTTCGACACTAGGAACTTCAGGCTGGGCTGG

GACCCCGTGACCGAGCTGGTCATGCCCGGGGTGTACACCAACGAGGCTTTCCATCCCGATATTGTCTTGCTG

CCCGGCTGCGGGGTGGACTTCACCGAGAGCCGCCTCAGCAACCTGCTGGGCATTCGCAAGAGGCAGCCCTT

CCAGGAAGGCTTCCAGATCATGTACGAGGATCTGGAGGGGGGCAACATCCCCGCGCTCCTGGATGTCGACG

CCTATGAGAAAAGCAAGGAGGATGCAGCAGCTGAAGCAACTGCAGCCGTAGCTACCGCCTCTACCGAGGT

CAGGGGCGATAATTTTGCAAGCGCCGCAGCAGTGGCAGCGGCCGAGGCGGCTGAAACCGAAAGTAAGATA

GTCATTCAGCCGGTGGAGAAGGATAGCAAGAACAGGAGCTACAACGTACTACCGGACAAGATAAACACCG

CCTACCGCAGCTGGTACCTAGCCTACAACTATGGCGACCCCGAGAAGGGCGTGCGCTCCTGGACGCTGCTC

ACCACCTCGGACGTCACCTGCGGCGTGGAGCAAGTCTACTGGTCGCTGCCCGACATGATGCAAGACCCGGT

CACCTTCCGCTCCACGCGTCAAGTTAGCAACTACCCGGTGGTGGGCGCCGAGCTCCTGCCCGTCTACTCCAA

GAGCTTCTTCAACGAGCAGGCCGTCTACTCGCAGCAGCTGCGCGCCTTCACCTCGCTTACGCACGTCTTCAA

CCGCTTCCCCGAGAACCAGATCCTCGTCCGCCCGCCCGCGCCCACCATTACCACCGTCAGTGAAAACGTTC

CTGCTCTCACAGATCACGGGACCCTGCCGCTGCGCAGCAGTATCCGGGGAGTCCAGCGCGTGACCGTTACT

GACGCCAGACGCCGCACCTGCCCCTACGTCTACAAGGCCCTGGGCATAGTCGCGCCGCGCGTCCTCTCGAG

CCGCACCTTCTAAATGTCCATTCTCATCTCGCCCAGTAATAACACCGGTTGGGGCCTGCGCGCGCCCAGCAA

GATGTACGGAGGCGCTCGCCAACGCTCCACGCAACACCCCGTGCGCGTGCGCGGGCACTTCCGCGCTCCCT

GGGGCGCCCTCAAGGGCCGCGTGCGGTCGCGCACCACCGTCGACGACGTGATCGACCAGGTGGTGGCCGA

CGCGCGCAACTACACCCCCGCCGCCGCGCCCGTCTCCACCGTGGACGCCGTCATCGACAGCGTGGTGGCCG

ACGCGCGCCGGTACGCCCGCGCCAAGAGCCGGCGGCGGCGCATCGCCCGGCGGCACCGGAGCACCCCCGC

CATGCGCGCGGCGCGAGCCTTGCTGCGCAGGGCCAGGCGCACGGGACGCAGGGCCATGCTCAGGGCGGCC

AGACGCGCGGCTTCAGGCGCCAGCGCCGGCAGGACCCGGAGACGCGCGGCCACGGCGGCGGCAGCGGCCA

TCGCCAGCATGTCCCGCCCGCGGCGAGGGAACGTGTACTGGGTGCGCGACGCCGCCACCGGTGTGCGCGTG

CCCGTGCGCACCCGCCCCCCTCGCACTTGAAGATGTTCACTTCGCGATGTTGATGTGTCCCAGCGGCGAGG

AGGATGTCCAAGCGCAAATTCAAGGAAGAGATGCTCCAGGTCATCGCGCCTGAGATCTACGGCCCTGCGGT

GGTGAAGGAGGAAAGAAAGCCCCGCAAAATCAAGCGGGTCAAAAAGGACAAAAAGGAAGAAGAAAGTGA

TGTGGACGGATTGGTGGAGTTTGTGCGCGAGTTCGCCCCCCGGCGGCGCGTGCAGTGGCGCGGGCGGAAGG

TGCAACCGGTGCTGAGACCCGGCACCACCGTGGTCTTCACGCCCGGCGAGCGCTCCGGCACCGCTTCCAAG

CGCTCCTACGACGAGGTGTACGGGGGATGATGATATTCTGGAGCAGGCGGCCGAGCGCCTGGGCGAGTTTGC

TTACGGCAAGCGCAGCCGTTCCGCACCGAAGGAAGAGGCGGTGTCCATCCCGCTGGACCACGGCAACCCC

ACGCCGAGCCTCAAGCCCGTGACCTTGCAGCAGGTGCTGCCGACCGCGGCGCCGCGCCGGGGGTTCAAGC

GCGAGGGCGAGGATCTGTACCCCACCATGCAGCTGATGGTGCCCAAGCGCCAGAAGCTGGAAGACGTGCT

GGAGACCATGAAGGTGGACCCGGACGTGCAGCCCGAGGTCAAGGTGCGGCCCATCAAGCAGGTGGCCCCG

GGCCTGGGCGTGCAGACCGTGGACATCAAGATTCCCACGGAGCCCATGGAAACGCAGACCGAGCCCATGA

TCAAGCCCAGCACCAGCACCATGGAGGTGCAGACGGATCCCTGGATGCCATCGGCTCCTAGTCGAAGACCC

CGGCGCAAGTACGGCGCGGCCAGCCTGCTGATGCCCAACTACGCGCTGCATCCTTCCATCATCCCCACGCC

GGGCTACCGCGGCACGCGCTTCTACCGCGGTCATACCAGCAGCCGCCGCCGCAAGACCACCACTCGCCGCC

GCCGTCGCCGCACCGCCGCTGCAACCACCCCTGCCGCCCTGGTGCGGAGAGTGTACCGCCGCGGCCGCGCA

CCTCTGACCCTGCCGCGCGCGCGCTACCACCCGAGCATCGCCATTTAAACTTTCGCCTGCTTTGCAGATCAA

TGGCCCTCACATGCCGCCTTCGCGTTCCCATTACGGGCTACCGAGGAAGAAAACCGCGCCGTAGAAGGCTG

GCGGGGAACGGGATGCGTCGCCACCACCACCGGCGGCGGCGCGCCATCAGCAAGCGGTTGGGGGGAGGCT

-continued

TCCTGCCCGCGCTGATCCCCATCATCGCCGCGGCGATCGGGGCGATCCCCGGCATTGCTTCCGTGGCGGTGC

AGGCCTCTCAGCGCCACTGAGACACACTTGGAAACATCTTGTAATAAACCAAATGGACTCTGACGCTCCTGG

TCCTGTGATGTGTTTTCGTAGACAGATGGAAGACATCAATTTTTCGTCCCTGGCTCCGCGACACGGCACGCG

GCCGTTCATGGGCACCTGGAGCGACATCGGCACCAGCCAACTGAACGGGGGCGCCTTCAATTGGAGCAGTC

TCTGGAGCGGGCTTAAGAATTTCGGGTCCACGCTTAAAACCTATGGCAGCAAGGCGTGGAACAGCACCACA

GGGCAGGCGCTGAGGGATAAGCTGAAAGAGCAGAACTTCCAGCAGAAGGTGGTCGATGGGCTCGCCTCGG

GCATCAACGGGGTGGTGGACCTGGCCAACCAGGCCGTGCAGCGGCAGATCAACAGCCGCCTGGACCCGGT

GCCGCCCGCCGGCTCCGTGGAGATGCCGCAGGTGGAGGAGGAGCTGCCTCCCCTGGACAAGCGGGGCGAG

AAGCGACCCCGCCCCGATGCGGAGGAGACGCTGCTGACGCACACGGACGAGCCGCCCCCGTACGAGGAGG

CGGTGAAACTGGGTCTGCCCACCACGCGGCCCATCGCGCCCCTGGCCACCGGGGTGCTGAAACCCGAAAA

GCCCGCGACCCTGGACTTGCCTCCTCCCCAGCCTTCCCGCCCCTCTACAGTGGCTAAGCCCCTGCCGCCGGT

GGCCGTGGCCCGCGCGCGACCCGGGGGCACCGCCCGCCCTCATGCGAACTGGCAGAGCACTCTGAACAGC

ATCGTGGGTCTGGGAGTGCAGAGTGTGAAGCGCCGCCGCTGCTATTAAACCTACCGTAGCGCTTAACTTGC

TTGTCTGTGTGTGTATGTATTATGTCGCCGCCGCCGCTGTCCACCAGAAGGAGGAGTGAAGAGGCGCGTCG

CCGAGTTGCAAGATGGCCACCCCATCGATGCTGCCCCAGTGGGCGTACATGCACATCGCCGGACAGGACGC

TTCGGAGTACTGAGTCCGGGTCTGGTGCAGTTTGCCCGCGCCACAGACACCTACTTCAGTCTGGGGAACA

AGTTTAGGAACCCCACGGTGGCGCCCACGCACGATGTGACCACCGACCGCAGCCAGCGGCTGACGCTGCG

CTTCGTGCCCGTGGACCGCGAGGACAACACCTACTCGTACAAAGTGCGCTACACGCTGGCCGTGGGCGACA

ACCGCGTGCTGGACATGGCCAGCACCTACTTTGACATCCGCGGCGTGCTGGATCGGGGCCCTAGCTTCAAA

CCCTACTCCGGCACCGCCTACAACAGTCTGGCCCCCAAGGGAGCACCCAACACTTGTCAGTGGACATATAA

AGCCGATGGTGAAACTGCCACAGAAAAAACCTATACATATGGAAATGCACCCGTGCAGGGCATTAACATC

ACAAAAGATGGTATTCAACTTGGAACTGACACCGATGATCAGCCAATCTACGCAGATAAAACCTATCAGCC

TGAACCTCAAGTGGGTGATGCTGAATGGCATGACATCACTGGTACTGATGAAAAGTATGGAGGCAGAGCTC

TTAAGCCTGATACCAAAATGAAGCCTTGTTATGGTTCTTTTGCCAAGCCTACTAATAAAGAAGGAGGTCAG

GCAAATGTGAAAACAGGAACAGGCACTACTAAAGAATATGACATAGACATGGCTTTCTTTGACAACAGAA

GTGCGGCTGCTGCTGGCCTAGCTCCAGAAATTGTTTGTATACTGAAAATGTGGATTTGGAAACTCCAGATA

CCCATATTGTATACAAAGCAGGCACAGATGACAGCAGCTTCTTCTATTAATTTGGGTCAGCAAGCCATGCCC

AACAGACCTAACTACATTGGTTTCAGAGACAACTTTATCGGGCTCATGTACTACAACAGCACTGGCAATAT

GGGGGTGCTGGCCGGTCAGGCTTCTCAGCTGAATGCTGTGGTTGACTTGCAAGACAGAAACACCGAGCTGT

CCTACCAGCTCTTGCTTGACTCTCTGGGTGACAGAACCCGGTATTTCAGTATGTGGAATCAGGCGGTGGACA

GCTATGATCCTGATGTGCGCATTATTGAAAATCATGGTGTGGAGGATGAACTTCCCAACTATTGTTTCCCTC

TGGATGCTGTTGGCAGAACAGATACTTATCAGGGAATTAAGGCTAATGGAACTGATCAAACCACATGGACC

AAAGATGACAGTGTCAATGATGCTAATGAGATAGGCAAGGGTAATCCATTCGCCATGGAAATCAACATCCA

AGCCAACCTGTGGAGGAACTTCCTCTACGCCAACGTGGCCCTGTACCTGCCCGACTCTTACAAGTACACOC

CGGCCAATGTTACCCTGCCCACCAACACCAACACCTACGATTACATGAACGGCCGGGTGGTGGCGCCCTCG

CTGGTGGACTCCTACATCAACATCGGGGCGCGCTGGTCGCTGGATCCCATGGACAACGTGAACCCCTTCAA

CCACCACCGCAATGCGGGGCTGCGCTACCGCTCCATGCTCCTGGGCAACGGGCGCTACGTGCCCTTCCACA

TCCAGGTGCCCCAGAAATTTTTCGCCATCAAGAGCCTCCTGCTCCTGCCCGGGTCCTACACCTACGAGTGGA

ACTTCCGCAAGGACGTCAACATGATCCTGCAGAGCTCCCTCGGCAACGACCTGCGCACGGACGGGGCCTCC

ATCTCCTTCACCAGCATCAACCTCTACGCCACCTTCTTCCCCATGGCGCACAACACGGCCTCCACGCTCGAG

GCCATGCTGCGCAACGACACCAACGACCAGTCCTTCAACGACTACCTCTCGGCGGCCAACATGCTCTACCC

-continued

CATCCCGGCCAACGCCACCAACGTGCCCATCTCCATCCCCTCGCGCAACTGGGCCGCCTTCCGCGGCTGGTC

CTTCACGCGTCTCAAGACCAAGGAGACGCCCTCGCTGGGCTCCGGGTTCGACCCCTACTTCGTCTACTCGGG

CTCCATCCCCTACCTCGACGGCACCTTCTACCTCAACCACACCTTCAAGAAGGTCTCCATCACCTTCGACTC

CTCCGTCAGCTGGCCCGGCAACGACCGGCTCCTGACGCCCAACGAGTTCGAAATCAAGCGCACCGTCGACG

GCGAGGGCTACAACGTGGCCCAGTGCAACATGACCAAGGACTGGTTCCTGGTCCAGATGCTGGCCCACTAC

AACATCGGCTACCAGGGCTTCTACGTGCCCGAGGGCTACAAGGACCGCATGTACTCCTTCTTCCGCAACTTC

CAGCCCATGAGCCGCCAGGTGGTGGACGAGGTCAACTACAAGGACTACCAGGCCGTCACCCTGGCCTACC

AGCACAACAACTCGGGCTTCGTCGGCTACCTCGCGCCCACCATGCGCCAGGGCCAGCCCTACCCCGCCAAC

TACCCCTACCCGCTCATCGGCAAGAGCGCCGTCACCAGCGTCACCCAGAAAAAGTTCCTCTGCGACAGGGT

CATGTGGCGCATCCCCTTCTCCAGCAACTTCATGTCCATGGGCGCGCTCACCGACCTCGGCCAGAACATGCT

CTATGCCAACTCCGCCCACGCGCTAGACATGAATTTCGAAGTCGACCCCATGGATGAGTCCACCCTTCTCTA

TGTTGTCTTCGAAGTCTTCGACGTCGTCCGAGTGCACCAGCCCCACCGCGGCGTCATCGAGGCCGTCTACCT

GCGCACCCCCTTCTCGGCCGGTAACGCCACCACCTAAGCTCTTGCTTCTTGCAAGCCATGGCCGCGGGCTCC

GGCGAGCAGGAGCTCAGGGCCATCATCCGCGACCTGGGCTGCGGGCCCTACTTCCTGGGCACCTTCGATAA

GCGCTTCCCGGGATTCATGGCCCCGCACAAGCTGGCCTGCGCCATCGTCAACACGGCCGGCCGCGAGACCG

GGGGCGAGCACTGGCTGGCCTTCGCCTGGAACCCGCGCTCGAACACCTGCTACCTCTTCGACCCCTTCGGG

TTCTCGGACGAGCGCCTCAAGCAGATCTACCAGTTCGAGTACGAGGGCCTGCTGCGCCGCAGCGCCCTGGC

CACCGAGGACCGCTGCGTCACCCTGGAAAAGTCCACCCAGACCGTGCAGGGTCCGCGCTCGGCCGCCTGCG

GGCTCTTCTGCTGCATGTTCCTGCACGCCTTCGTGCACTGGCCCGACCGCCCCATGGACAAGAACCCCACCA

TGAACTTGCTGACGGGGGTGCCCAACGGCATGCTCCAGTCGCCCCAGGTGGAACCCACCCTGCGCCGCAAC

CAGGAGGCGCTCTACCGCTTCCTCAACTCCCACTCCGCCTACTTTCGCTCCCACCGCGCGCGCATCGAGAAG

GCCACCGCCTTCGACCGCATGAATCAAGACATGTAAACCGTGTGTGTATGTTAAATGTCTTTAATAAACAG

CACTTTCATGTTACACATGCATCTGAGATGATTTATTTAGAAATCGAAAGGGTTCTGCCGGGTCTCGGCATG

GCCCGCGGGCAGGGACACGTTGCGGAACTGGTACTTGGCCAGCCACTTGAACTCGGGGATCAGCAGTTTGG

GCAGCGGGGTGTCGGGGAAGGAGTCGGTCCACAGCTTCCGCGTCAGTTGCAGGGCGCCCAGCAGGTCGGG

CGCGGAGATCTTGAAATCGCAGTTGGGACCCGCGTTCTGCGCGCGGGAGTTGCGGTACACGGGGTTGCAGC

ACTGGAACACCATCAGGGCCGGGTGCTTCACGCTCGCCAGCACCGTCGCGTCGGTGATGCTCTCCACGTCG

AGGTCCTCGGCGTTGGCCATCCCGAAGGGGGTCATCTTGCAGGTCTGCCTTCCCATGGTGGGCACGCACCC

GGGCTTGTGGTTGCAATCGCAGTGCAGGGGGATCAGCATCATCTGGGCCTGGTCGGCGTTCATCCCCGGGT

ACATGGCCTTCATGAAAGCCTCCAATTGCCTGAACGCCTGCTGGGCCTTGGCTCCCTCGGTGAAGAAGACC

CCGCAGGACTTGCTAGAGAACTGGTTGGTGGCGCACCCGGCGTCGTGCACGCAGCAGCGCGCGTCGTTGTT

GGCCAGCTGCACCACGCTGCGCCCCCAGCGGTTCTGGGTGATCTTGGCCCGGTCGGGGTTCTCCTTCAGCGC

GCGCTGCCCGTTCTCGCTCGCCACATCCATCTCGATCATGTGCTCCTTCTGGATCATGGTGGTCCCGTGCAG

GCACCGCAGCTTGCCCTCGGCCTCGGTGCACCCGTGCAGCCACAGCGCGCACCCGGTGCACTCCCAGTTCT

TGTGGGCGATCTGGGAATGCGCGTGCACGAAAGCCCTGCAGGAAGCGGCCCATCATGGTGGTCAGGGTCTTG

TTGCTAGTGAAGGTCAGCGGAATGCCGCGGTGCTCCTCGTTGATGTACAGGTGGCAGATGCGGCGGTACAC

CTCGCCCTGCTCGGGCATCAGCTGGAAGTTGGCTTTCAGGTCGGTCTCCACGCGGTAGCGGTCCATCAGCAT

AGTCATGATTTCCATACCCTTCTCCCAGGCCGAGACGATGGGCAGGCTCATAGGGTTCTTCACCATCATCTT

AGCGCTAGCAGCCGCGGCCAGGGGGTCGCTCTCGTCCAGGGTCTCAAAGCTCCGCTTGCCGTCCTTCTCGG

TGATCCGCACCGGGGGGTAGCTGAAGCCCACGGCCGCCAGCTCCTCCTCGGCCTGTCTTTCGTCCTCGCTGT

-continued

CCTGGCTGACGTCCTGCAGGACCACATGCTTGGTCTTGCGGGGTTTCTTCTTGGGCGGCAGCGGCGGCGGA

GATGTTGGAGATGGCGAGGGGGAGCGCGAGTTCTCGCTCACCACTACTATCTCTTCCTCTTCTTGGTCCGAG

GCCACGCGGCGGTAGGTATGTCTCTTCGGGGGCAGAGGCGGAGGCGACGGGCTCTCGCCGCCGCGACTTG

GCGGATGGCTGGCAGAGCCCCTTCCGCGTTCGGGGGTGCGCTCCCGGCGGCGCTCTGACTGACTTCCTCCG

CGGCCGGCCATTGTGTTCTCCTAGGGAGGAACAACAAGCATGGAGACTCAGCCATCGCCAACCTCGCCATC

TGCCCCCACCGCCGACGAGAAGCAGCAGCAGCAGAATGAAAGCTTAACCGCCCCGCCGCCCAGCCCCGCC

ACCTCCGACGCGGCCGTCCCAGACATGCAAGAGATGGAGGAATCCATCGAGATTGACCTGGGCTATGTGAC

GCCCGCGGAGCACGAGGAGGAGCTGGCAGTGCGCTTTTCACAAGAAGAGATACACCAAGAACAGCCAGAG

CAGGAAGCAGAGAATGAGCAGAGTCAGGCTGGGCTCGAGCATGACGGCGACTACCTCCACCTGAGCGGGG

GGGAGGACGCGCTCATCAAGCATCTGGCCCGGCAGGCCACCATCGTCAAGGATGCGCTGCTCGACCGCACC

GAGGTGCCCCTCAGCGTGGAGGAGCTCAGCCGCGCCTACGAGTTGAACCTCTTCTCGCCGCGCGTGCCCCC

CAAGCGCCAGCCCAATGGCACCTGCGAGCCCAACCCGCGCCTCAACTTCTACCCGGTCTTCGCGGTGCCCG

AGGCCCTGGCCACCTACCACATCTTTTTCAAGAACCAAAAGATCCCCGTCTCCTGCCGCGCCAACCGCACC

CGCGCCGACGCCCTTTTCAACCTGGGTCCCGGCGCCCGCCTACCTGATATCGCCTCCTTGGAAGAGGTTCCC

AAGATCTTCGAGGGTCTGGGCAGCGACGAGACTCGGGCCGCGAACGCTCTGCAAGGAGAAGGAGGAGAGC

ATGAGCACCACAGCGCCCTGGTCGAGTTGGAAGGCGACAACGCGCGGCTGGCGGTGCTCAAACGCACGGT

CGAGCTGACCCATTTCGCCTACCCGGCTCTGAACCTGCCCCCCAAAGTCATGAGCGCGGTCATGGACCAGG

TGCTCATCAAGCGCGCGTCGCCCATCTCCGAGGACGAGGGCATGCAAGACTCCGAGGAGGGCAAGCCCGT

GGTCAGCGACGAGCAGCTGGCCCGGTGGCTGGGTCCTAATGCTAGTCCCCAGAGTTTGGAAGAGCGGCGC

AAACTCATGATGGCCGTGGTCCTGGTGACCGTGGAGCTGGAGTGCCTGCGCCGCTTCTTCGCCGACGCGGA

GACCCTGCGCAAGGTCGAGGAGAACCTGCACTACCTCTTCAGGCACGGGTTCGTGCGCCAGGCCTGCAAGA

TCTCCAACGTGGAGCTGACCAACCTGGTCTCCTACATGGGCATCTTGCACGAGAACCGCCTGGGGCAGAAC

GTGCTGCACACCACCCTGCGCGGGGAGGCCCGGCGCGACTACATCCGCGACTGCGTCTACCTCTACCTCTG

CCACACCTGGCAGACGGGCATGGGCGTGTGGCAGCAGTGTCTGGAGGAGCAGAACCTGAAAGAGCTCTGC

AAGCTCCTGCAGAAGAACCTCAAGGGTCTGTGGACCGGGTTCGACGAGCGCACCACCGCCTCGGACCTGGC

CGACCTCATTTTCCCCGAGCGCCTCAGGCTGACGCTGCGCAACGGCCTGCCCGACTTTATGAGCCAAAGCA

TGTTGCAAAACTTTCGCTCTTTCATCCTCGAACGCTCCGGAATCCTGCCCGCCACCTGCTCCGCGCTGCCCT

CGGACTTCGTGCCGCTGACCTTCCGCGAGTGCCCCCCGCCGCTGTGGAGCCACTGCTACCTGCTGCGCCTGG

CCAACTACCTGGCCTACCACTCGGACGTGATCGAGGACGTCAGCGGCGAGGGCCTGCTCGAGTGCCACTGC

CGCTGCAACCTCTGCACGCCGCACCGCTCCCTGGCCTGCAACCCCCAGCTGCTGAGCGAGACCCAGATCAT

CGGCACCTTCGAGTTGCAAGGGCCCAGCGAAGGCGAGGGTTCAGCCGCCAAGGGGGGTCTGAAACTCACC

CCGGGGCTGTGGACCTCGGCCTACTTGCGCAAGTTCGTGCCCGAGGACTACCATCCCTTCGAGATCAGGTT

CTACGAGGACCAATCCCATCCGCCCAAGGCCGAGCTGTCGGCCTGCGTCATCACCCAGGGGGCGATCCTGG

CCCAATTGCAAGCCATCCAGAAATCCCGCCAAGAATTCTTGCTGAAAAAGGGCCGCGGGGTCTACCTCGAC

CCCCAGACCGGTGAGGAGCTCAACCCCGGCTTCCCCCAGGATGCCCCGAGGAAACAAGAAGCTGAAAGTG

GAGCTGCCGCCCGTGGAGGATTTGGAGGAAGACTGGGAGAACAGCAGTCAGGCAGAGGAGGAGGAGATG

GAGGAAGACTGGGACAGCACTCAGGCAGAGGAGGACAGCCTGCAAGACAGTCTGGAGGAAGACGAGGAG

GAGGCAGAGGAGGAGGTGGAAGAAGCAGCCGCCGCCAGACCGTCGTCCTCGGCGGGGGAGAAAGCAAGC

AGCACGGATACCATCTCCGCTCCGGGTCGGGGTCCCGCTCGACCACACAGTAGATGGGACGAGACCGGAC

GATTCCCGAACCCCACCACCCAGACCGGTAAGAAGGAGCGGCAGGGATACAAGTCCTGGCGGGGGCACAA

AAACGCCATCGTCTCCTGCTTGCAGGCCTGCGGGGGCAACATCTCCTTCACCCGGCGCTACCTGCTCTTCCA

-continued

CCGCGGGGTGAACTTTCCCCGCAACATCTTGCATTACTACCGTCACCTCCACAGCCCCTACTACTTCCAAGA

AGAGGCAGCAGCAGCAGAAAAAGACCAGCAGAAAACCAGCAGCTAGAAAATCCACAGCGGCGGCAGCAG

GTGGACTGAGGATCGCGGCGAACGAGCCGGCGCAAACCCGGGAGCTGAGGAACCGGATCTTTCCCACCCT

CTATGCCATCTTCCAGCAGAGTCGGGGGCAGGAGCAGGAACTGAAAGTCAAGAACCGTTCTCTGCGCTCGC

TCACCCGCAGTTGTCTGTATCACAAGAGCGAAGACCAACTTCAGCGCACTCTCGAGGACGCCGAGGCTCTC

TTCAACAAGTACTGCGCGCTCACTCTTAAAGAGTAGCCCGCGCCCGCCCAGTCGCAGAAAAAGGCGGGAAT

TACGTCACCTGTGCCCTTCGCCCTAGCCGCCTCCACCCATCATCATGAGCAAAGAGATTCCCACGCCTTACA

TGTGGAGCTACCAGCCCCAGATGGGCCTGGCCGCCGGTGCCGCCCAGGACTACTCCACCCGCATGAATTGG

CTCAGCGCCGGGCCCGCGATGATCTCACGGGTGAATGACATCCGCGCCCACCGAAACCAGATACTCCTAGA

ACAGTCAGCGCTCACCGCCACGCCCCGCAATCACCTCAATCCGCGTAATTGGCCCGCCGCCCTGGTGTACC

AGGAAATTCCCCAGCCCACGACCGTACTACTTCCGCGAGACGCCCAGGCCGAAGTCCAGCTGACTAACTCA

GGTGTCCAGCTGGCGGGCGGCGCCACCCTGTGTCGTCACCGCCCCGCTCAGGGTATAAAGCGGCTGGTGAT

CCGGGGCAGAGGCACACAGCTCAACGACGAGGTGGTGAGCTCTTCGCTGGGTCTGCGACCTGACGGAGTCT

TCCAACTCGCCGGATCGGGGAGATCTTCCTTCACGCCTCGTCAGGCCGTCCTGACTTTGGAGAGTTCGTCCT

CGCAGCCCCGCTCGGGTGGCATCGGCACTCTCCAGTTCGTGGAGGAGTTCACTCCCTCGGTCTACTTCAACC

CCTTCTCCGGCTCCCCGGCCACTACCCGGACGAGTTCATCCCGAACTTCGACGCCATCAGCGAGTCGGTG

GACGGCTACGATTGAAACTAATCACCCCCTTATCCAGTGAAATAAAGATCATATTGATGATGATTTTACAG

AAATAAAAAATAATCATTTGATTTGAAATAAAGATACAATCATATTGATGATTTGAGTTTAACAAAAAAAT

AAAGAATCACTTACTTGAAATCTGATACCAGGTCTCTGTCCATGTTTTCTGCCAACACCACTTCACTCCCCT

CTTCCCAGCTCTGGTACTGCAGGCCCCGGCGGGCTGCAAACTTCCTCCACACGCTGAAGGGGATGTCAAAT

TCCTCCTGTCCCTCAATCTTCATTTTATCTTCTATCAGATCCAAAAAGCGCGTCCGGGTGGATGATGACTT

CGACCCCGTCTACCCCTACGATGCAGACAACGCACCGACCGTGCCCTTCATCAACCCCCCCTTCGTCTCTTC

AGATGGATTCCAAGAGAAGCCCCTGGGGGTGTTGTCCCTGCGACTGGCCGACCCCGTCACCACCAAGAACG

GGGAAATCACCCTCAAGCTGGGAGAGGGGGTGGACCTCGATTCCTCGGGAAAACTCATCTCCAACACGGC

CACCAAGGCCGCCGCCCCTCTCAGTTTTTCCAACAACACCATTTCCCTTAACATGGATCACCCCTTTTACAC

TAAAGATGGAAAATTATCCTTACAAGTTTCTCCACCATTAAATATACTGAGAACAAGCATTCTAAACACAC

TAGCTTTAGGTTTTGGATCAGGTTTAGGACTCCGTGGCTCTGCCTTGGCAGTACAGTTAGTCTCTCCACTTAC

ATTTGATACTGATGGAAACATAAAGCTTACCTTAGACAGAGGTTTGCATGTTACAACAGGAGATGCAATTG

AAAGCAACATAAGCTGGGCTAAAGGTTTAAAATTTGAAGATGGAGCCATAGCAACCAACATTGGAAATGG

GTTAGAGTTTGGAAGCAGTAGTACAGAAACAGGTGTTGATGATGCTTACCCAATCCAAGTTAAACTTGGAT

CTGGCCTTAGCTTTGACAGTACAGGAGCCATAATGGCTGGTAACAAAGAAGACGATAAACTCACTTTGTGG

ACAACACCTGATCCATCACCAAACTGTCAAATACTCGCAGAAAATGATGCAAAACTAACACTTTGCTTGAC

TAAATGTGGTAGTCAAATACTGGCCACTGTGTCAGTCTTAGTTGTAGGAAGTGGAAACCTAAACCCCATTA

CTGGCACCGTAAGCAGTGCTCAGGTGTTTCTACGTTTTGATGCAAACGGTGTTCTTTTAACAGAACATTCTA

CACTAAAAAAATACTGGGGGTATAGGCAGGGAGATAGCATAGATGGCACTCCATATACCAATGCTGTAGG

ATTCATGCCCAATTTAAAAGCTTATCCAAAGTCACAAAGTTCTACTACTAAAAATAATATAGTAGGGCAAG

TATACATGAATGGAGATGTTTCAAAACCTATGCTTCTCACTATAACCCTCAATGGTACTGATGACAGCAACA

GTACATATTCAATGTCATTTTCATACACCTGGACTAATGGAAGCTATGTTGGAGCAACATTTGGGGCTAACT

CTTATACCTTCTCATACATCGCCCAAGAATGAACACTGTATCCCACCCTGCATGCCAACCCTTCCCACCCCA

CTCTGTGGAACAAACTCTGAAACACAAAATAAAATAAAGTTCAAGTGTTTTATTGATTCAACAGTTTTACA

-continued

GGATTCGAGCAGTTATTTTTCCTCCACCCTCCCAGGACATGGAATACACCACCCTCTCCCCCCGCACAGCCT

TGAACATCTGAATGCCATTGGTGATGGACATGCTTTTGGTCTCCACGTTCCACACAGTTTCAGAGCGAGCCA

GTCTCGGGTCGGTCAGGGAGATGAAACCCTCCGGGCACTCCCGCATCTGCACCTCACAGCTCAACAGCTGA

GGATTGTCCTCGGTGGTCGGGATCACGGTTATCTGGAAGAAGCAGAAGAGCGGCGGTGGGAATCATAGTCC

GCGAACGGGATCGGCCGGTGGTGTCGCATCAGGCCCCGCAGCAGTCGCTGCCGCCGCCGCTCCGTCAAGCT

GCTGCTCAGGGGGTCCGGGTCCAGGGACTCCCTCAGCATGATGCCCACGGCCCTCAGCATCAGTCGTCTGG

TGCGGCGGGCGCAGCAGCGCATGCGGATCTCGCTCAGGTCGCTGCAGTACGTGCAACACAGAACCACCAG

GTTGTTCAACAGTCCATAGTTCAACACGCTCCAGCCGAAACTCATCGCGGGAAGGATGCTACCCACGTGGC

CGTCGTACCAGATCCTCAGGTAAATCAAGTGGTGCCCCCTCCAGAACACGCTGCCCACGTACATGATCTCC

TTGGGCATGTGGCGGTTCACCACCTCCCGGTACCACATCACCCTCTGGTTGAACATGCAGCCCCGGATGATC

CTGCGGAACCACAGGGCCAGCACCGCCCCGCCCGCCATGCAGCGAAGAGACCCCGGGTCCCGGCAATGGC

AATGGAGGACCCACCGCTCGTACCCGTGGATCATCTGGGAGCTGAACAAGTCTATGTTGGCACAGCACAGG

CATATGCTCATGCATCTCTTCAGCACTCTCAACTCCTCGGGGGTCAAAACCATATCCCAGGGCACGGGGAA

CTCTTGCAGGACAGCGAACCCCGCAGAACAGGGCAATCCTCGCACAGAACTTACATTGTGCATGGACAGG

GTATCGCAATCAGGCAGCACCGGGTGATCCTCCACCAGAGAAGCGCGGGTCTCGGTCTCCTCACAGCGTGG

TAAGGGGGCCGGCCGATACGGGTGATGGCGGGACGCGGCTGATCGTGTTCGCGACCGTGTCATGATGCAGT

TGCTTTCGGACATTTTCGTACTTGCTGTAGCAGAACCTGGTCCGGGCGCTGCACACCGATCGCCGGCGGCG

GTCTCGGCGCTTGGAACGCTCGGTGTTGAAATTGTAAAACAGCCACTCTCTCAGACCGTGCAGCAGATCTA

GGGCCTCAGGAGTGATGAAGATCCCATCATGCCTGATGGCTCTGATCACATCGACCACCGTGGAATGGGCC

AGACCCAGCCAGATGATGCAATTTTGTTGGGTTTCGGTGACGGCGGGGGAGGGAAGAACAGGAAGAACCA

TGATTAACTTTTAATCCAAACGGTCTCGGAGTACTTCAAAATGAAGATCGCGGAGATGGCACCTCTCGCCC

CCGCTGTGTTGGTGGAAAATAACAGCCAGGTCAAAGGTGATACGGTTCTCGAGATGTTCCACGGTGGCTTC

CAGCAAAGCCTCCACGCGCACATCCAGAAACAAGACAATAGCGAAAGCGGGAGGGTTCTCTAATTCCTCA

ATCATCATGTTACACTCCTGCACCATCCCCAGATAATTTTCATTTTTCCAGCCTTGAATGATTCGAACTAGTT

CCTGAGGTAAATCCAAGCCAGCCATGATAAAGAGCTCGCGCAGAGCGCCCTCCACCGGCATTCTTAAGCAC

ACCCTCATAATTCCAAGATATTCTGCTCCTGGTTCACCTGCAGCAGATTGACAAGCGGAATATCAAAATCTC

TGCCGCGATCCCTGAGCTCCTCCCTCAGCAATAACTGTAAGTACTCTTTCATATCCTCTCCGAAATTTTAGC

CATAGGACCACCAGGAATAAGATTAGGGCAAGCCACAGTACAGATAAACCGAAGTCCTCCCCAGTGAGCA

TTGCCAAATGCAAGACTGCTATAAGCATGCTGGCTAGACCCGGTGATATCTTCCAGATAACTGGACAGAAA

ATCGCCCAGGCAATTTTTAAGAAAATCAACAAAAGAAAAATCCTCCAGGTGGACGTTTAGAGCCTCGGGAA

CAACGATGAAGTAAATGCAAGCGGTGCGTTCCAGCATGGTTAGTTAGCTGATCTGTAGAAAAAACAAAAAT

GAACATTAAACCATGCTAGCCTGGCGAACAGGTGGGTAAATCGTTCTCTCCAGCACCAGGCAGGCCACGGG

GTCTCCGGCGCGACCCTCGTAAAAATTGTCGCTATGATTGAAAACCATCACAGAGAGACGTTCCCGGTGGC

CGGCGTGAATGATTCGACAAGATGAATACACCCCCGGAACATTGGCGTCCGCGAGTGAAAAAAAGCGCCC

GAGGAAGCAATAAGGCACTACAATGCTCAGTCTCAAGTCCAGCAAAGCGATGCCATGCGGATGAAGCACA

AAATTCTCAGGTGCGTACAAAATGTAATTACTCCCCTCCTGCACAGGCAGCAAAGCCCCCGATCCCTCCAG

GTACACATACAAAGCCTCAGCGTCCATAGCTTACCGAGCAGCAGCACACAACAGGCGCAAGAGTCAGAGA

AAGGCTGAGCTCTAACCTGTCCACCCGCTCTCTGCTCAATATATAGCCCAGATCTACACTGACGTAAAGGC

CAAAGTCTAAAAATACCCGCCAAATAATCACACACGCCCAGCACACGCCCAGAAACCGGTGACACACTCA

AAAAAATACGCGCACTTCCTCAAACGCCCAAAACTGCCGTCATTTCCGGGTTCCCACGCTACGTCATCAAA

ACACGACTTTCAAATTCCGTCGACCGTTAAAAACGTCACCCGCCCCGCCCCTAACGGTCGCCCGTCTCTCAG

-continued

CCAATCAGCGCCCCGCATCCCCAAATTCAAACACCTCATTTGCATATTAACGCGCACAAAAAGTTTGAGGT

ATATTATTGATGATGG

ChAdV68-CMT-TSNA (SEQ ID NO: 68)

CATCATCAATAATATACCTCAAACTTTTTGTGCGCGTTAATATGCAAATGAGGCGTTTGAATTTGGGGAGGA

AGGGCGGTGATTGGTCGAGGGATGAGCGACCGTTAGGGGCGGGGCGAGTGACGTTTTGATGACGTGGTTG

CGAGGAGGAGCCAGTTTGCAAGTTCTCGTGGGAAAAGTGACGTCAAACGAGGTGTGGTTTGAACACGGAA

ATACTCAATTTTCCCGCGCTCTCTGACAGGAAATGAGGTGTTTCTGGGCGGATGCAAGTGAAAACGGGCCA

TTTTCGCGCGAAAACTGAATGAGGAAGTGAAAATCTGAGTAATTTCGCGTTTATGGCAGGGAGGAGTATTT

GCCGAGGGCCGAGTAGACTTTGACCGATTACGTGGGGGTTTCGATTACCGTGTTTTTCACCTAAATTTCCGC

GTACGGTGTCAAAGTCCGGTGTTTTTACGTAGGTGTCAGCTGATCGCCAGGGTATTTAAACCTGCGCTCTCC

AGTCAAGAGGCCACTCTTGAGTGCCAGCGAGAAGAGTTTTCTCCTCCGCGCCGCGAGTCAGATCTACACTT

TGAAAGTAGGGATAACAGGGTAATGACATTGATTATTGACTAGTTGTTAATAGTAATCAATTACGGGGTCA

TTAGTTCATAGCCCATATATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAATAGGGACTTTCCATTG

ACGTCAATGGGTGGAGTATTTACGGTAAACTGCCCACTTGGCAGTACATCAAGTGTATCATATGCCAAGTC

CGCCCCCTATTGACGTCAATGACGGTAAATGGCCCGCCTGGCATTATGCCCAGTACATGACCTTACGGGAC

TTTCCTACTTGGCAGTACATCTACGTATTAGTCATCGCTATTACCATGGTGATGCGGTTTTGGCAGTACACC

AATGGGCGTGGATAGCGGTTTGACTCACGGGGATTTCCAAGTCTCCACCCCATTGACGTCAATGGGAGTTT

GTTTTGGCACCAAAATCAACGGGACTTTCCAAAATGTCGTAATAACCCCGCCCCGTTGACGCAAATGGGCG

GTAGGCGTGTACGGTGGGAGGTCTATATAAGCAGAGCTCTCCCTATCAGTGATAGAGATCTCCCTATCAGT

GATAGAGATCGTCGACGAGCTCGTTTAGTGAACCGTCAGATCGCCTGGAACGCCATCCACGCTGTTTTGAC

CTCCATAGAAGACAGCGATCGCGCCACCATGGCTGGCATGACCGAGTACAAGCTAGTCGTTGTGGGAGCTG

GAGATGTGGGCAAATCTGCTCTGACCATTCAGCTGATTCAGGGCACAGATCTGGATCACCAGGAGAAGTGT

CTGAGCAGGCTGTACGACCACATGCCAGAAGGATTAACCCCTCTTATGGGAGTGAGCTCTTCTTCTGCTCTG

GCCAGACTGGGACTGCCTATGGATAAGCTGAACAAGATCACAGCTCCTGCCTCTCAGAAACTGAGACAGT

GCAGAAGATGGAGACCCCTGAACTGCTGCCTTGTGGATATCTGGTGGAGGAGAATACCACAATCAGCGTGA

CCGTGAAAGGCCTGGAAGCCCAGAACAAGATCAAAGGCTGTACCGGCTCTGTGAATATGACACTGCAGAG

AGCTTCTGCCGCCCCTAAGACAGGAGGAGGAGGAGAAGCTGCTGCCTACAATAATACATTAGTGGCCAGA

CATGTGCCCCAGATCCCTAAGCCTGACAGCCTGGTTGGCCTGAGCGATGAATTAGGAAAAAGAGACACATT

TGCCGAGAGCCTGATCCGGAGAATGGCCTCTGCCGGCTACCTGTTCCTGGATATCATCACATATGTTGTGTT

TGCCGTGACCTTCGTGCTGGGAGTTCTGGGCGGCCTGAATACCGAGACCAATGAAAAAGCTCTTGAAGCCG

TGTTTGGCAAGTACGGCAGAATCGTGGAGGTGCTGGGCGGCAGATCTTGTGAAGAATTAACAGCTGTGTTA

CCACCTCCTCAGCTGCTTGGCAGACGGTTCAACTTCTTCAGCTACAGCTACGTTGCTGCTGGCTCTTCTGGC

AACAACTACGACCTGATGGCCCAGCCTATTACACCTGGACCTGATACAACACCTCTGCCTGTGACCGATAC

ATCTTCTGTGTCTACCGGACACGCCACATCTCTGCCAGTGACAGATGCTGGACTGAGAGTGACAGAGTCTA

AAGGACACAGCGATTCTTGGCACCTGAGCCTGGATACAGCCATCAGGGTGAATACCCCTAAGCTGGTTTCT

GAAGTGGAAGAGCTGAACAAGAGCATCACCGCCCTGAGGGAGAAGTTACTGCAGATGGTGGAAGCCGATA

GACCTGGAAACCTGTTTATTGGAGGCCTGAACACCGAGACCAATGAGGACTCTCCCGTGAAGGATGAAGTG

GTGGTGAACGATCAATGGGGCCAGAATTGTAGCTGCCATCATGGAGGCTACGAGTTCCCTGATCTGCACAG

GACAATCGTGTCTGAGTGCGATGTGTATCTGACCTACATGCTGAGACAGGCTGCTCTGCAGCTGTTCTTCGA

-continued

CCTGTATCACAGCATCCCTAGCAGCTTTTCTCCTCTGGTTCTGAGCTGTCTGGTGCAGCCTCTGGAAGATGT

GGAAGTGATGGAGAAGGATGGCACAACCTTTAGCTGTGAGGTGAGCCACGATGAGGTGCCTCGGACATAT

GGACCCGTGTTTATGTGTCTGGGAGGACTGCTGACCATGGTGGCTGGAGCTGTTTGGCTGACAGTTGGACC

CGGACCAGGCGCCAAATTTGTTGCTGCTTGGACACTGAAAGCTGCTGCTGGGCCCGGACCAGGCCAGTACA

TCAAGGCCAACTCTAAGTTTATCGGCATCACCGAATTGGGACCTGGACCCGGCTAGTAGTGAGTTTAAACT

CCCATTTAAATGTGAGGGTTAATGCTTCGAGCAGACATGATAAGATACATTGATGAGTTTGGACAAACCAC

AACTAGAATGCAGTGAAAAAAATGCTTTATTTGTGAAATTTGTGATGCTATTGCTTTATTTGTAACCATTAT

AAGCTGCAATAAACAAGTTAACAACAACAATTGCATTCATTTTATGTTTCAGGTTCAGGGGGAGATGTGGG

AGGTTTTTTAAAGCAAGTAAAACCTCTACAAATGTGGTAAAATAACTATAACGGTCCTAAGGTAGCGAGTG

AGTAGTGTTCTGGGGCGGGGGAGGACCTGCATGAGGGCCAGAATAACTGAAATCTGTGCTTTTCTGTGTGT

TGCAGCAGCATGAGCGGAAGCGGCTCCTTTGAGGGAGGGGTATTCAGCCCTTATCTGACGGGGCGTCTCCC

CTCCTGGGCGGGAGTGCGTCAGAATGTGATGGGATCCACGGTGGACGGCCGGCCCGTGCAGCCCGCGAAC

TCTTCAACCCTGACCTATGCAACCCTGAGCTCTTCGTCGTTGGACGCAGCTGCCGCCGCAGCTGCTGCATCT

GCCGCCAGCGCCGTGCGCGGAATGGCCATGGGCGCCGGCTACTACGGCACTCTGGTGGCCAACTCGAGTTC

CACCAATAATCCCGCCAGCCTGAACGAGGAGAAGCTGTTGCTGCTGATGGCCCAGCTCGAGGCCTTGACCC

AGCGCCTGGGCGAGCTGACCCAGCAGGTGGCTCAGCTGCAGGAGCAGACGCGGGCCGCGGTTGCCACGGT

GAAATCCAAATAAAAAATGAATCAATAAATAAACGGAGACGGTTGTTGATTTTAACACAGAGTCTGAATCT

TTATTTGATTTTTCGCGCGCGGTAGGCCCTGGACCACCGGTCTCGATCATTGAGCACCCGGTGGATCTTTTC

CAGGACCCGGTAGAGGTGGGCTTGGATGTTGAGGTACATGGGCATGAGCCCGTCCCGGGGGTGGAGGTAG

CTCCATTGCAGGGCCTCGTGCTCGGGGTGGTGTTGTAAATCACCCAGTCATAGCAGGGGCGCAGGGCATG

GTGTTGCACAATATCTTTGAGGAGGAGACTGATGGCCACGGGCAGCCCTTTGGTGTAGGTGTTTACAAATC

TGTTGAGCTGGGAGGGATGCATGCGGGGGGAGATGAGGTGCATCTTGGCCTGGATCTTGAGATTGGCGATG

TTACCGCCCAGATCCCGCCTGGGGTTCATGTTGTGCAGGACCACCAGCACGGTGTATCCGGTGCACTTGGG

GAATTTATCATGCAACTTGGAAGGGAAGGCGTGAAAGAATTTGGCGACGCCTTTGTGCCCGCCCAGGTTTT

CCATGCACTCATCCATGATGATGGCGATGGGCCCGTGGGCGGCGGCCTGGGCAAAGACGTTTCGGGGGTCG

GACACATCATAGTTGTGGTCCTGGGTGAGGTCATCATAGGCCATTTTAATGAATTTGGGGCGGAGGGTGCC

GGACTGGGGGACAAAGGTTCCCTCGATCCCGGGGGCGTAGTTCCCCTCACAGATCTGCATCTCCCAGGCTT

TGAGCTCGGAGGGGGGGATCATGTCCACCTGCGGGGCGATAAAGAACACGGTTTCCGGGGCGGGGGAGAT

GAGCTGGGCCGAAAGCAAGTTCCGGAGCAGCTGGGACTTGCCGCAGCCGGTGGGGCCGTAGATGACCCCG

ATGACCGGCTGCAGGTGGTAGTTGAGGGAGAGACAGCTGCCGTCCTCCCGGAGGAGGGGGGCCACCTCGT

TCATCATCTCGCGCACGTGCATGTCTCGCGCACCAGTTCCGCCAGGAGGCGCTCTCCCCCCAGGGATAGG

AGCTCCTGGAGCGAGGCGAAGTTTTTCAGCGGCTTGAGTCCGTCGGCCATGGGCATTTTGGAGAGGGTTTG

TTGCAAGAGTTCCAGGCGGTCCCAGAGCTCGGTGATGTGCTCTACGGCATCTCGATCCAGCAGACCTCCTC

GTTTCGCGGGTTGGGACGGCTGCGGGAGTAGGGCACCAGACGATGGGCGTCCAGCGCAGCCAGGGTCCGG

TCCTTCCAGGGTCGCAGCGTCCGCGTCAGGGTGGTCTCCGTCACGGTGAAGGGGTGCGCGCCGGGCTGGGC

GCTTGCGAGGGTGCGCTTCAGGCTCATCCGGCTGGTCGAAAACCGCTCCCGATCGGCGCCCTGCGCGTCGG

CCAGGTAGCAATTGACCATGAGTTCGTAGTTGAGCGCCTCGGCCGCGTGGCCTTTGGCGCGGAGCTTACCTT

TGGAAGTCTGCCCGCAGGCGGGACAGAGGAGGGACTTGAGGGCGTAGAGCTTGGGGGCGAGGAAGACGG

ACTCGGGGGCGTAGGCGTCCGCGCCGCAGTGGGCGCAGACGGTCTCGCACTCCACGAGCCAGGTGAGGTC

GGGCTGGTCGGGGTCAAAAACCAGTTTCCCGCCGTTCTTTTTGATGCGTTTCTTACCTTTGGTCTCCATGAGC

TCGTGTCCCCGCTGGGTGACAAAGAGGCTGTCCGTGTCCCCGTAGACCGACTTTATGGGCCGGTCCTCGAG

-continued

CGGTGTGCCGCGGTCCTCCTCGTAGAGGAACCCCGCCCACTCCGAGACGAAAGCCCGGGTCCAGGCCAGCA

CGAAGGAGGCCACGTGGGACGGGTAGCGGTCGTTGTCCACCAGCGGGTCCACCTTTTCCAGGGTATGCAAA

CACATGTCCCCCTCGTCCACATCCAGGAAGGTGATTGGCTTGTAAGTGTAGGCCACGTGACCGGGGGTCCC

GGCCGGGGGGGTATAAAAGGGTGCGGGTCCCTGCTCGTCCTCACTGTCTTCCGGATCGCTGTCCAGGAGCG

CCAGCTGTTGGGGTAGGTATTCCCTCTCGAAGGCGGGCATGACCTCGGCACTCAGGTTGTCAGTTTCTAGAA

ACGAGGAGGATTTGATATTGACGGTGCCGGCGGAGATGCCTTTCAAGAGCCCCTCGTCCATCTGGTCAGAA

AAGACGATCTTTTTGTTGTCGAGCTTGGTGGCGAAGGAGCCGTAGAGGGCGTTGGAGAGGAGCTTGGCGAT

GGAGCGCATGGTCTGGTTTTTTTCCTTGTCGGCGCGCTCCTTGGCGGCGATGTTGAGCTGCACGTACTCGCG

CGCCACGCACTTCCATTCGGGGAAGACGGTGGTCAGCTCGTCGGGCACGATTCTGACCTGCCAGCCCCGAT

TATGCAGGGTGATGAGGTCCACACTGGTGGCCACCTCGCCGCGCAGGGGCTCATTAGTCCAGCAGAGGCGT

CCGCCCTTGCGCGAGCAGAAGGGGGGCAGGGGGTCCAGCATGACCTCGTCGGGGGGGTCGGCATCGATGG

TGAAGATGCCGGGCAGGAGGTCGGGGTCAAAGTAGCTGATGGAAGTGGCCAGATCGTCCAGGGCAGCTTG

CCATTCGCGCACGGCCAGCGCGCGCTCGTAGGGACTGAGGGGCGTGCCCCAGGGCATGGGATGGGTAAGC

GCGGAGGCGTACATGCCGCAGATGTCGTAGACGTAGAGGGGCTCCTCGAGGATGCCGATGTAGGTGGGGT

AGCAGCGCCCCCCGCGGATGCTGGCGCGCACGTAGTCATACAGCTCGTGCGAGGGGGCGAGGAGCCCCGG

GCCCAGGTTGGTGCGACTGGGCTTTTCGGCGCGGTAGACGATCTGGCGGAAAATGGCATGCGAGTTGGAGG

AGATGGTGGGCCTTTGGAAGATGTTGAAGTGGGCGTGGGGCAGTCCGACCGAGTCGCGGATGAAGTGGGC

GTAGGAGTCTTGCAGCTTGGCGACGAGCTCGGCGGTGACTAGGACGTCCAGAGCGCAGTAGTCGAGGGTCT

CCTGGATGATGTCATACTTGAGCTGTCCCTTTTGTTTCCACAGCTCGCGGTTGAGAAGGAACTCTTCGCGGT

CCTTCCAGTACTCTTCGAGGGGGAACCCGTCCTGATCTGCACGGTAAGAGCCTAGCATGTAGAACTGGTTG

ACGGCCTTGTAGGCGCAGCAGCCCTTCTCCACGGGGAGGGCGTAGGCCTGGGCGGCCTTGCGCAGGGAGG

TGTGCGTGAGGGCGAAAGTGTCCCTGACCATGACCTTGAGGAACTGGTGCTTGAAGTCGATATCGTCGCAG

CCCCCCTGCTCCCAGAGCTGGAAGTCCGTGCGCTTCTTGTAGGCGGGGTTGGGCAAAGCGAAGTAACATC

GTTGAAGAGGATCTTGCCCGCGCGGGGCATAAAGTTGCGAGTGATTGCGGAAAGGTTGGGGCACCTCGGCC

CGGTTGTTGATGACCTGGGCGGCGAGCACGATCTCGTCGAAGCCGTTGATGTTGTGGCCCACGATGTAGAG

TTCCACGAATCGCGGACGGCCCTTGACGTGGGGCAGTTTCTTGAGCTCCTCGTAGGTGAGCTCGTCGGGGTC

GCTGAGCCCGTGCTGCTCGAGCGCCCAGTCGGCGAGATGGGGGTTGGCGCGGAGGAAGGAAGTCCAGAGA

TCCACGGCCAGGGCGGTTTGCAGACGGTCCCGGTACTGACGGAACTGCTGCCCGACGGCCATTTTTTCGGG

GGTGACGCAGTAGAAGGTGCGGGGGTCCCCGTGCCAGCGATCCCATTTGAGCTGGAGGGCGAGATCGAGG

GCGAGCTCGACGAGCCGGTCGTCCCCGGAGAGTTTCATGACCAGCATGAAGGGGACGAGCTGCTTGCCGA

AGGACCCCATCCAGGTGTAGGTTTCCACATCGTAGGTGAGGAAGAGCCTTTCGGTGCGAGGATGCGAGCCG

ATGGGGAAGAACTGGATCTCCTGCCACCAATTGGAGGAATGGCTGTTGATGTGATGGAAGTAGAAATGCCG

ACGGCGCGCCGAACACTCGTGCTTGTGTTTATACAAGCGGCCACAGTGCTCGCAACGCTGCACGGGATGCA

CGTGCTGCACGAGCTGTACCTGAGTTCCTTTGACGAGGAATTTCAGTGGGAAGTGGAGTCGTGGCGCCTGC

ATCTCGTGCTGTACTACGTCGTGGTGGTCGGCCTGGCCCTCTTCTGCCTCGATGGTGGTCATGCTGACGAGC

CCGCGCGGGAGGCAGGTCCAGACCTCGGCGCGAGCGGGTCGGAGAGCGAGGACGAGGGCGCGCAGGCCG

GAGCTGTCCAGGGTCCTGAGACGCTGCGGAGTCAGGTCAGTGGGCAGCGGCGGCGCGCGGTTGACTTGCA

GGAGTTTTTCCAGGGCGCGCGGGAGGTCCAGATGGTACTTGATCTCCACCGCGCCATTGGTGGCGACGTCG

ATGGCTTGCAGGGTCCCGTGCCCCTGGGGTGTGACCACCGTCCCCCGTTTCTTCTTGGGCGGCTGGGGCGAC

GGGGGCGGTGCCTCTTCCATGGTTAGAAGCGGCGGCGAGGACGCGCGCCGGGCGGCAGGGGCGGCTCGGG

-continued

GCCCGGAGGCAGGGGCGGCAGGGGCACGTCGGCGCCGCGCGGGTAGGTTCTGGTACTGCGCCCGGAGA

AGACTGGCGTGAGCGACGACGCGACGGTTGACGTCCTGGATCTGACGCCTCTGGGTGAAGGCCACGGGAC

CCGTGAGTTTGAACCTGAAAGAGAGTTCGACAGAATCAATCTCGGTATCGTTGACGGCGGCCTGCCGCAGG

ATCTCTTGCACGTCGCCCGAGTTGTCCTGGTAGGCGATCTCGGTCATGAACTGCTCGATCTCCTCCTCTTGA

AGGTCTCCGCGGCCGGCGCGCTCCACGGTGGCCGCGAGGTCGTTGGAGATGCGGCCCATGAGCTGCGAGA

AGGCGTTCATGCCCGCCTCGTTCCAGACGCGGCTGTAGACCACGACGCCCTCGGGATCGCGGGCGCGCATG

ACCACCTGGGCGAGGTTGAGCTCCACGTGGCGCGTGAAGACCGCGTAGTTGCAGAGGCGCTGGTAGAGGT

AGTTGAGCGTGGTGGCGATGTGCTCGGTGACGAAGAAATACATGATCCAGCGGCGGAGCGGCATCTCGCTG

ACGTCGCCCAGCGCCTCCAAACGTTCCATGGCCTCGTAAAAGTCCACGGCGAAGTTGAAAAACTGGGAGTT

GCGCGCCGAGACGGTCAACTCCTCCTCCAGAAGACGGATGAGCTCGGCGATGGTGGCGCGCACCTCGCGCT

CGAAGGCCCCCGGGAGTTCCTCCACTTCCTCTTCTTCCTCCTCCACTAACATCTCTTCTACTTCCTCCTCAGG

CGGCAGTGGTGGCGGGGGAGGGGGCCTGCGTCGCCGGCGGCGCACOGGCAGACGGTCGATGAAGCGCTCG

ATGGTCTCGCCGCGCCGGCGTCGCATGGTCTCGGTGACGGCGCGCCCGTCCTCGCGGGGCCGCAGCGTGAA

GACGCCGCCGCGCATCTCCAGGTGGCCGGGGGGGTCCCCGTTGGGCAGGGAGAGGGCGCTGACGATGCAT

CTTATCAATTGCCCCGTAGGGACTCCGCGCAAGGACCTGAGCGTCTCGAGATCCACGGGATCTGAAAACCG

CTGAACGAAGGCTTCGAGCCAGTCGCAGTCGCAAGGTAGGCTGAGCACGGTTTCTTCTGGCGGGTCATGTT

GGTTGGGAGCGGGGCGGGCGATGCTGCTGGTGATGAAGTTGAAATAGGCGGTTCTGAGACGGCGGATGGT

GGCGAGGAGCACCAGGTCTTTGGGCCCGGCTTGCTGGATGCGCAGACGGTCGGCCATGCCCCAGGCGTGGT

CCTGACACCTGGCCAGGTCCTTGTAGTAGTCCTGCATGAGCCGCTCCACGGGCACCTCCTCCTCGCCCGCGC

GGCCGTGCATGCGCGTGAGCCCGAAGCCGCGCTGGGGCTGGACGAGCGCCAGGTCGGCGACGACGCGCTC

GGCGAGGATGGCTTGCTGGATCTGGGTGAGGGTGGTCTGGAAGTCATCAAAGTCGACGAAGCGGTGGTAG

GCTCCGGTGTTGATGGTGTAGGAGCAGTTGGCCATGACGGACCAGTTGACGGTCTGGTGGCCCGGACGCAC

GAGCTCGTGGTACTTGAGGCGCGAGTAGGCGCGCGTGTCGAAGATGTAGTCGTTGCAGGTGCGCACCAGGT

ACTGGTAGCCGATGAGGAAGTGCGGCGGCGGCTGGCGGTAGAGCGGCCATCGCTCGGTGGCGGGGGCGCC

GGGCGCGAGGTCCTCGAGCATGGTGCGGTGGTAGCCGTAGATGTACCTGGACATCCAGGTGATGCCGGCGG

CGGTGGTGGAGGCGCGCGGGAACTCGCGGACGCGGTTCCAGATGTTGCGCAGCGGCAGGAAGTAGTTCAT

GGTGGGCACGGTCTGGCCCGTGAGGCGCGCGCAGTCGTGGATGCTCTATACGGGCAAAAACGAAAGCGGT

CAGCGGCTCGACTCGTGGCCTGGAGGCTAAGCGAACGGGTTGGGCTGCGCGTGTACCCCGGTTCGAATCT

CGAATCAGGCTGGAGCCGCAGCTAACGTGGTATTGGCACTCCCGTCTCGACCCAAGCCTGCACCAACCCTC

CAGGATACGGAGGCGGGTCGTTTTGCAACTTTTTTTTGGAGGCCGGATGAGACTAGTAAGCGCGGAAAGCG

GCCGACCGCGATGGCTCGCTGCCGTAGTCTGGAGAAGAATCGCCAGGGTTGCGTTGCGGTGTGCCCCGGTT

CGAGGCCGGCCGGATTCCGCGGCTAACGAGGGCGTGGCTGCCCCGTCGTTTCCAAGACCCCATAGCCAGCC

GACTTCTCCAGTTACGGAGCGAGCCCCTCTTTTGTTTTGTTTGTTTTTGCCAGATGCATCCCGTACTGCGGCA

GATGCGCCCCCACCACCCTCCACCGCAACAACAGCCCCCTCCACAGCCGGCGCTTCTGCCCCCGCCCCAGC

AGCAACTTCCAGCCACGACCGCCGCGGCCGCCGTGAGCGGGGCTGGACAGAGTTATGATCACCAGCTGGC

CTTGGAAGAGGGCGAGGGGCTGGCGCGCCTGGGGGCGTCGTCGCCGGAGCGGCACCCGCGCGTGCAGATG

AAAAGGGACGCTCGCGAGGCCTACGTGCCCAAGCAGAACCTGTTCAGAGACAGGAGCGGCGAGGAGCCCG

AGGAGATGCGCGCGGCCCGGTTCCACGCGGGGCGGGAGCTGCGGCGCGGCCTGGACCGAAAGAGGGTGCT

GAGGGACGAGGATTTCGAGGCGGACGAGCTGACGGGGATCAGCCCCGCGCGCGCGCACGTGGCCGCGGCC

AACCTGGTCACGGCGTACGAGCAGACCGTGAAGGAGGAGAGCAACTTCCAAAAATCCTTCAACAACCACG

TGCGCACCCTGATCGCGCGCGAGGAGGTGACCCTGGGCCTGATGCACCTGTGGGACCTGCTGGAGGCCATC

-continued

GTGCAGAACCCCACCAGCAAGCCGCTGACGGCGCAGCTGTTCCTGGTGGTGCAGCATAGTCGGGACAACG

AAGCGTTCAGGGAGGCGCTGCTGAATATCACCGAGCCCGAGGGCCGCTGGCTCCTGGACCTGGTGAACATT

CTGCAGAGCATCGTGGTGCAGGAGCGCGGGCTGCCGCTGTCCGAGAAGCTGGCGGCCATCAACTTCTCGGT

GCTGAGTTTGGGCAAGTACTACGCTAGGAAGATCTACAAGACCCCGTACGTGCCCATAGACAAGGAGGTG

AAGATCGACGGGTTTTACATGCGCATGACCCTGAAAGTGCTGACCCTGAGCGACGATCTGGGGGTGTACCG

CAACGACAGGATGCACCGTGCGGTGAGCGCCAGCAGGCGGCGCGAGCTGAGCGACCAGGAGCTGATGCAT

AGTCTGCAGCGGGCCCTGACCGGGGCCGGGACCGAGGGGGAGAGCTACTTTGACATGGGCGCGGACCTGC

ACTGGCAGCCCAGCCGCCGGGCCTTGGAGGCGGCGGCAGGACCCTACGTAGAAGAGGTGGACGATGAGGT

GGACGAGGAGGGCGAGTACCTGGAAGACTGATGGCGCGACCGTATTTTTGCTAGATGCAACAACAACAGC

CACCTCCTGATCCCGCGATGCGGGCGGCGCTGCAGAGCCAGCCGTCCGGCATTAACTCCTCGGACGATTGG

ACCCAGGCCATGCAACGCATCATGGCGCTGACGACCCGCAACCCCGAAGCCTTTAGACAGCAGCCCCAGG

CCAACCGGCTCTCGGCCATCCTGGAGGCCGTGGTGCCCTCGCGCTCCAACCCCACGCACGAGAAGGTCCTG

GCCATCGTGAACGCGCTGGTGGAGAACAAGGCCATCCGCGGCGACGAGGCCGGCCTGGTGTACAACGCGC

TGCTGGAGCGCGTGGCCCGCTACAACAGCACCAACGTGCAGACCAACCTGGACCGCATGGTGACCGACGT

GCGCGAGGCCGTGGCCCAGCGCGAGCGGTTCCACCGCGAGTCCAACCTGGGATCCATGGTGGCGCTGAAC

GCCTTCCTCAGCACCCAGCCCGCCAACGTGCCCCGGGGCCAGGAGGACTACACCAACTTCATCAGCGCCCT

GCGCCTGATGGTGACCGAGGTGCCCCAGAGCGAGGTGTACCAGTCCGGGCCGGACTACTTCTTCCAGACCA

GTCGCCAGGGCATTGCAGACCGTGAACCTGAGCCAGGCTTTCAAGAACTTGCAGGGCCTGTGGGGCGTGCAG

GCCCCGGTCGGGGACCGCGCGACGGTGTCGAGCCTGCTGACGCCGAACTCGCGCCTGCTGCTGCTGCTGGT

GGCCCCCTTCACGGACAGCGGCAGCATCAACCGCAACTCGTACCTGGGCTACCTGATTAACCTGTACCGCG

AGGCCATCGGCCAGGCGCACGTGGACGAGCAGACCTACCAGGAGATCACCCACGTGAGCCGCGCGCCCTGGG

CCAGGACGACCCGGGCAACCTGGAAGCCACCCTGAACTTTTTGCTGACCAACCGGTCGCAGAAGATCCCGC

CCCAGTACGCGCTCAGCACCGAGGAGGAGCGCATCCTGCGTTACGTGCAGCAGAGCGTGGGCCTGTTCCTG

ATGCAGGAGGGGGCCACCCCCAGCGCCGCGCTCGACATGACCGCGCGCAACATGGAGCCCAGCATGTACG

CCAGCAACCGCCCGTTCATCAATAAACTGATGGACTACTTGCATCGGGCGGCCGCCATGAACTCTGACTAT

TTCACCAACGCCATCCTGAATCCCCACTGGCTCCCGCCGCCGGGGTTCTACACGGGCGAGTACGACATGCC

CGACCCCAATGACGGGTTCCTGTGGGACGATGTGGACAGCAGCGTGTTCTCCCCCCGACCGGGTGCTAACG

AGCGCCCCTTGTGGAAGAAGGAAGGCAGCGACCGACGCCCGTCCTCGGCGCTGTCCGGCCGCGAGGGTGC

TGCCGCGGCGGTGCCCGAGGCCGCCAGTCCTTTCCCGAGCTTGCCCTTCTCGCTGAACAGTATCCGCAGCA

GCGAGCTGGGCAGGATCACGCGCCCGCGCTTGCTGGGCGAAGAGGAGTACTTGAATGACTCGCTGTTGAGA

CCCGAGCGGGAGAAGAACTTCCCCAATAACGGGATAGAAAGCCTGGTGGACAAGATGAGCCGCTGGAAGA

CGTATGCGCAGGAOCACAGGGACGATCCCCGGGCGTCGCAGGGGGCCACGAGCCGGGGCAGCGCCGCCCG

TAAACGCCGGTGGCACGACAGGCAGCGGGGACAGATGTGGGACGATGAGGACTCCGCCGACGACAGCAGC

GTGTTGGACTTGGGTGGGAGTGGTAACCCGTTCGCTCACCTGCGCCCCCGTATCGGGCGCATGATGTAAGA

GAAACCGAAAATAAATGATACTCACCAAGGCCATGGCGACCAGCGTGCGTTCGTTTCTTCTCTGTTGTTGTT

GTATCTAGTATGATGAGGCGTGCGTACCCGGAGGGTCCTCCTCCCTCGTACGAGAGCGTGATGCAGCAGGC

GATGGCGGCGGCGGCGATGCAGCCCCCGCTGGAGGCTCCTTACGTGCCCCCGCGGTACCTGGCGCCTACGG

AGGGGCGGAACAGCATTCGTTACTCGGAGCTGGCACCCTTGTACGATACCACCCGGTTGTACCTGGTGGAC

AACAAGTCGGCGGACATCGCCTCGCTGAACTACCAGAACGACCACAGCAACTTCCTGACCACCGTGGTGCA

GAACAATGACTTCACCCCCACGGAGGCCAGCACCCAGACCATCAACTTTGACGAGCGCTCGCGGTGGGGC

-continued

GGCCAGCTGAAAACCATCATGCACACCAACATGCCCAACGTGAACGAGTTCATGTACAGCAACAAGTTCA

AGGCGCGGGTGATGGTCTCCCGCAAGACCCCCAATGGGGTGACAGTGACAGAGGATTATGATGGTAGTCA

GGATGAGCTGAAGTATGAATGGGTGGAATTTGAGCTGCCCGAAGGCAACTTCTCGGTGACCATGACCATCG

ACCTGATGAACAACGCCATCATCGACAATTACTTGGCGGTGGGGCGGCAGAACGGGGTGCTGGAGAGCGA

CATCGGCGTGAAGTTCGACACTAGGAACTTCAGGCTGGCTGGGACCCCGTGACCGAGCTGGTCATGCCCG

GGGTGTACACCAACGAGGCTTTCCATCCCGATATTGTCTTGCTGCCCGGCTGCGGGGTGGACTTCACCGAG

AGCCGCCTCAGCAACCTGCTGGGCATTCGCAAGAGGCAGCCCTTCCAGGAAGGCTTCCAGATCATGTACGA

GGATCTGGAGGGGGGCAACATCCCCGCGCTCCTGGATGTCGACGCCTATGAGAAAAGCAAGGAGGATGCA

GCAGCTGAAGCAACTGCAGCCGTAGCTACCGCCTCTACCGAGGTCAGGGGCGATAATTTTGCAAGCGCCGC

AGCAGTGGCAGCGGCCGAGGCGGCTGAAACCGAAAGTAAGATAGTCATTCAGCCGGTGGAGAAGGATAGC

AAGAACAGGAGCTACAACGTACTACCGGACAAGATAAACACCGCCTACCGCAGCTGGTACCTAGCCTACA

ACTATGGCGACCCCGAGAAGGGCGTGCGCTCCTGGACGCTGCTCACCACCTCGGACGTCACCTGCGGCGTG

GAGCAAGTCTACTGGTCGCTGCCCGACATGATGCAAGACCCGGTCACCTTCCGCTCCACGCGTCAAGTTAG

CAACTACCCGGTGGTGGGCGCCGAGCTCCTGCCCGTCTACTCCAAGAGCTTCTTCAACGAGCAGGCCGTCT

ACTCGCAGCAGCTGCGCGCCTTCACCTCGCTTACGCACGTCTTCAACCGCTTCCCCGAGAACCAGATCCTCG

TCCGCCCGCCCGCGCCCACCATTACCACCGTCAGTGAAAACGTTCCTGCTCTCACAGATCACGGGACCCTG

CCGCTGCGCAGCAGTATCCGGGGAGTCCAGCGCGTGACCGTTACTGACGCCAGACGCCGCACCTGCCCCTA

CGTCTACAAGGCCCTGGGCATAGTCGCGCCGCGCGTCCTCTCGAGCCGCACCTTCTAAATGTCCATTCTCAT

CTCGCCCAGTAATAACACCGGTTGGGGCCTGCGCGCGCCCAGCAAGATGTACGGAGGCGCTCGCCAACGCT

CCACGCAACACCCCGTGCGCGTGCGCGGGCACTTCCGCGCTCCCTGGGGCGCCCTCAAGGGCCGCGTGCGG

TCGCGCACCACCGTCGACGACGTGATCGACCAGGTGGTGGCCGACGCGCGCAACTACACCCCCGCCGCCGC

GCCCGTCTCCACCGTGGACGCCGTCATCGACAGCGTGGTGGCCGACGCGCGCCGGTACGCCCGCGCCAAGA

GCCGGCGGCGGCGCATCGCCCGGCGGCACCGGAGCACCCCCGCCATGCGCGCGGCGCGAGCCTTGCTGCG

CAGGGCCAGGCGCACGGGACGCAGGGCCATGCTCAGGGCGGCCAGACGCGCGGCTTCAGGCGCCAGCGCC

GGCAGGACCCGGAGACGCGCGGCCACGGCGGCGGCAGCGGCCATCGCCAGCATGTCCCGCCCGCGGCGAG

GGAACGTGTACTGGGTGCGCGACGCCGCCACCGGTGTGCGCGTGCCCGTGCGCACCCGCCCCCCTCGCACT

TGAAGATGTTCACTTCGCGATGTTGATGTGTCCCAGCGGCGAGGAGGATGTCCAAGCGCAAATTCAAGGAA

GAGATGCTCCAGGTCATCGCGCCTGAGATCTACGGCCCTGCGGTGGTGAAGGAGGAAAGAAAGCCCCGCA

AAATCAAGCGGGTCAAAAAGGACAAAAAGGAAGAAGAAAGTGATGTGGACGGATTGGTGGAGTTTGTGCG

CGAGTTCGCCCCCCGGCGGCGCGTGCAGTGGCGCGGGCGGAAGGTGCAACCGGTGCTGAGACCCGGCACC

ACCGTGGTCTTCACGCCCGGCGAGCGCTCCGGCACCGCTTCCAAGCGCTCCTACGACGAGGTGTACGGGGA

TGATGATATTCTGGAGCAGGCGGCCGAGCGCCTGGGCGAGTTTGCTTACGGCAAGCGCAGCCGTTCCGCAC

CGAAGGAAGAGGCGGTGTCCATCCCGCTGGACCACGGCAACCCCACGCCGAGCCTCAAGCCCGTGACCTT

GCAGCAGGTGCTGCCGACCGCGGCGCCGCGCCGGGGGTTCAAGCGCGAGGGCGAGGATCTGTACCCCACC

ATGCAGCTGATGGTGCCCAAGCGCCAGAAGCTGGAAGACGTGCTGGAGACCATGAAGGTGGACCCGGACG

TGCAGCCCGAGGTCAAGGTGCGGCCCATCAAGCAGGTGGCCCCGGGCCTGGGCGTGCAGACCGTGGACAT

CAAGATTCCCACGGAGCCCATGGAAACGCAGACCGAGCCCATGATCAAGCCCAGCACCAGCACCATGGAG

GTGCAGACGGATCCCTGGATGCCATCGGCTCCTAGTCGAAGACCCCGGCGCAAGTACGGCGCGGCCAGCCT

GCTGATGCCCAACTACGCGCTGCATCCTTCCATCATCCCCACGCCGGGCTACCGCGGCACGCGCTTCTACCG

CGGTCATACCAGCAGCCGCCGCCGCAAGACCACCACTCGCCGCCGCCGTCGCCGCACCGCCGCTGCAACCA

CCCCTGCCGCCCTGGTGCGGAGAGTGTACCGCCGCGGCCGCGCACCTCTGACCCTGCCGCGCGCGCGCTAC

CACCCGAGCATCGCCATTTAAACTTTCGCCTGCTTTGCAGATCAATGGCCCTCACATGCCGCCTTCGCGTTC

CCATTACGGGCTACCGAGGAAGAAAACCGCGCCGTAGAAGGCTGGCGGGGAACGGGATGCGTCGCCACCA

CCACCGGCGGCGGCGCGCCATCAGCAAGCGGTTGGGGGGAGGCTTCCTGCCCGCGCTGATCCCCATCATCG

CCGCGGCGATCGGGGCGATCCCCGGCATTGCTTCCGTGGCGGTGCAGGCCTCTCAGCGCCACTGAGACACA

CTTGGAAACATCTTGTAATAAACCAATGGACTCTGACGCTCCTGGTCCTGTGATGTGTTTTCGTAGACAGAT

GGAAGACATCAATTTTTCGTCCCTGGCTCCGCGACACGGCACGCGGCCGTTCATGGGCACCTGGAGCGACA

TCGGCACCAGCCAACTGAACGGGGGCGCCTTCAATTGGAGCAGTCTCTGGAGCGGGCTTAAGAATTTCGGG

TCCACGCTTAAAACCTATGGCAGCAAGGCGTGGAACAGCACCACAGGGCAGGCGCTGAGGGATAAGCTGA

AAGAGCAGAACTTCCAGCAGAAGGTGGTCGATGGGCTCGCCTCGGGCATCAACGGGGTGGTGGACCTGGC

CAACCAGGCCGTGCAGCGGCAGATCAACAGCCGCCTGGACCCGGTGCCGCCCGCCGGCTCCGTGGAGATG

CCGCAGGTOGAGGAGGAGCTGCCTCCCCTGGACAAGCGOGGCGAGAAGCGACCCCGCCCCGATGCGGAGG

AGACGCTGCTGACGCACACGGACGAGCCGCCCCCGTACGAGGAGGCGGTGAAACTGGGTCTGCCCACCAC

GCGGCCCATCGCGCCCCTGGCCACCGGGGTGCTGAAACCCGAAAAGCCCGCGACCCTGGACTTGCCTCCTC

CCCAGCCTTCCCGCCCCTCTACAGTGGCTAAGCCCCTGCCGCCGGTGGCCGTGGCCCGCGCGCGACCCGGG

GGCACCGCCCGCCCTCATGCGAACTGGCAGAGCACTCTGAACAGCATCGTGGGTCTGGGAGTGCAGAGTGT

GAAGCGCCGCCGCTGCTATTAAACCTACCGTAGCGCTTAACTTGCTTGTCTGTGTGTGTATGTATTATGTCG

CCGCCGCCGCTGTCCACCAGAAGGAGGAGTGAAGAGGCGCGTCGCCGAGTTGCAAGATGGCCACCCCATC

GATGCTGCCCCAGTGGGCGTACATGCACATCGCCGGACAGGACGCTTCGGAGTACCTGAGTCCGGGTCTGG

TGCAGTTTGCCCGCGCCACAGACACCTACTTCAGTCTGGGGAACAAGTTTAGGAACCCCACGGTGGCGCCC

ACGCACGATGTGACCACCGACCGCAGCCAGCGGCTGACGCTGCGCTTCGTGCCCGTGGACCGCGAGGACA

ACACCTACTCGTACAAAGTGCGCTACACGCTGGCCGTGGGCGACAACCGCGTGCTGGACATGGCCAGCACC

TACTTTGACATCCGCGGCGTGCTGGATCGGGGCCCTAGCTTCAAACCCTACTCCGGCACCGCCTACAACAG

TCTGGCCCCCAAGGGAGCACCCAACACTTGTCAGTGGACATATAAAGCCGATGGTGAAACTGCCACAGAA

AAAACCTATACATATGGAAATGCACCCGTGCAGGGCATTAACATCACAAAAGATGGTATTCAACTTGGAAC

TGACACCGATGATCAGCCAATCTACGCAGATAAAACCTATCAGCCTGAACCTCAAGTGGGTGATGCTGAAT

GGCATGACATCACTGGTACTGATGAAAAGTATGGAGGCAGAGCTCTTAAGCCTGATACCAAAATGAAGCCT

TGTTATGGTTCTTTTGCCAAGCCTACTAATAAAGAAGGAGGTCAGGCAAATGTGAAAACAGGAACAGGCAC

TACTAAAGAATATGACATAGACATGGCTTTCTTTGACAACAGAAGTGCGGCTGCTGCTGGCCTAGCTCCAG

AAATTGTTTTGTATACTGAAAATGTGGATTTGGAAACTCCAGATACCCATATTGTATACAAAGCAGGCACA

GATGACAGCAGCTCTTCTATTAATTTGGGTCAGCAAGCCATGCCCAACAGACCTAACTACATTGGTTTCAGA

GACAACTTTATCGGGCTCATGTACTACAACAGCACTGGCAATATGGGGGTGCTGGCCGGTCAGGCTTCTCA

GCTGAATGCTGTGGTTGACTTGCAAGACAGAAACACCGAGCTGTCCTACCAGCTCTTGCTTGACTCTCTGGG

TGACAGAACCCGGTATTTCAGTATGTGGAATCAGGCGGTGGACAGCTATGATCCTGATGTGCGCATTATTG

AAAATCATGGTGTGGAGGATGAACTTCCCAACTATTGTTTCCCTCTGGATGCTGTTGGCAGAACAGATACTT

ATCAGGGAATTAAGGCTAATGGAACTGATCAAACCACATGGACCAAAGATGACAGTGTCAATGATGCTAA

TGAGATAGGCAAGGGTAATCCATTCGCCATGGAAATCAACATCCAAGCCAACCTGTGGAGGAACTTCCTCT

ACGCCAACGTGGCCCTGTACCTGCCCGACTCTTACAAGTACACGCCGGCCAATGTTACCCTGCCCACCAAC

ACCAACACCTACGATTACATGAACGGCCGGGTGGTGGCGCCCTCGCTGGTGGACTCCTACATCAACATCGG

GGCGCGCTGGTCGCTGGATCCCATGGACAACGTGAACCCCTTCAACCACCACCGCAATGCGGGGCTGCGCGT

ACCGCTCCATGCTCCTGGGCAACGGGCGCTACGTGCCCTTCCACATCCAGGTGCCCCAGAAATTTTTCGCCA

-continued

TCAAGAGCCTCCTGCTCCTGCCCGGGTCCTACACCTACGAGTGGAACTTCCGCAAGGACGTCAACATGATC

CTGCAGAGCTCCCTCGGCAACGACCTGCGCACGGACGGGGCCTCCATCTCCTTCACCAGCATCAACCTCTA

CGCCACCTTCTTCCCCATGGCGCACAACACGGCCTCCACGCTCGAGGCCATGCTGCGCAACGACACCAACG

ACCAGTCCTTCAACGACTACCTCTCGGCGGCCAACATGCTCTACCCCATCCCGGCCAACGCCACCAACGTG

CCCATCTCCATCCCCTCGCGCAACTGGGCCGCCTTCCGCGGCTGGTCCTTCACGCGTCTCAAGACCAAGGAG

ACGCCCTCGCTGGGCTCCGGGTTCGACCCCTACTTCGTCTACTCGGGCTCCATCCCCTACCTCGACGGCACC

TTCTACCTCAACCACACCTTCAAGAAGGTCTCCATCACCTTCGACTCCTCCGTCAGCTGGCCCGGCAACGAC

CGGCTCCTGACGCCCAACGAGTTCGAAATCAAGCGCACCGTCGACGGCGAGGGCTACAACGTGGCCCAGT

GCAACATGACCAAGGACTGGTTCCTGGTCCAGATGCTGGCCCACTACAACATCGGCTACCAGGGCTTCTAC

GTGCCCGAGGGTACAAGGACCGCATGTACTCCTTCTTCCGCAACTTCCAGCCCATGAGCCGCCAGGTGGT

GGACGAGGTCAACTACAAGGACTACCAGGCCGTCACCCTGGCCTACCAGCACAACAACTCGGGCTTCGTCG

GCTACCTCGCGCCCACCATGCGCCAGGGCCAGCCCTACCCCGCCAACTACCCCTACCCGCTCATCGGCAAG

AGCGCCGTCACCAGCGTCACCCAGAAAAAGTTCCTCTGCGACAGGGTCATGTGGCGCATCCCCTTCTCCAG

CAACTTCATGTCCATGGGCGCGCTCACCGACCTCGGCCAGAACATGCTCTATGCCAACTCCGCCCACGCGC

TAGACATGAATTTCGAAGTCGACCCCATGGATGAGTCCACCCTTCTCTATGTTGTCTTCGAAGTCTTCGACG

TCGTCCGAGTGCACCAGCCCCACCGCGGCGTCATCGAGGCCGTCTACCTGCGCACCCCCTTCTCGGCCGGT

AACGCCACCACCTAAGCTCTTGCTTCTTGCAAGCCATGGCCGCGGGCTCCGGCGAGCAGGAGCTCAGGGCC

ATCATCCGCGACCTGGGCTGCGGGCCCTACTTCCTGGGCACCTTCGATAAGCGCTTCCCGGGATTCATGGCC

CCGCACAAGCTGGCCTGCGCCATCGTCAACACGGCCGGCCGCGAGACCGGGGGCGAGCACTGGCTGGCCT

TCGCCTGGAACCCGCGCTCGAACACCTGCTACCTCTTCGACCCCTTCGGGTTCTCGGACGAGCGCCTCAAGC

AGATCTACCAGTTCGAGTACGAGGGCCTGCTGCGCCGCAGCGCCCTGGCCACCGAGGACCGCTGCGTCACC

CTGGAAAAGTCCACCCAGACCGTGCAGGGTCCGCGCTCGGCCGCCTGCGGGCTCTTCTGCTGCATGTTCCT

GCACGCCTTCGTGCACTGGCCCGCCGCCCCATGGACAAGAACCCCACCATGAACTTGCTGACGGGGGTGC

CCAACGGCATGCTCCAGTCGCCCCAGGTGGAACCCACCCTGCGCCGCAACCAGGAGGCGCTCTACCGCTTC

CTCAACTCCCACTCCGCCTACTTTCGCTCCCACCGCGCGCGCATCGAGAAGGCCACCGCCTTCGACCGCATG

AATCAAGACATGTAAACCGTGTGTGTATGTTAAATGTCTTTAATAAACAGCACTTTCATGTTACACATGCAT

CTGAGATGATTTATTTAGAAATCGAAAGGGTTCTGCCGGGTCTCGGCATGGCCCGCGGGCAGGGACACGTT

GCGGAACTGGTACTTGGCCAGCCACTTGAACTCGGGGATCAGCAGTTTGGGCAGCGGGGTGTCGGGGAAG

GAGTCGGTCCACAGCTTCCGCGTCAGTTGCAGGGCGCCCAGCAGGTCGGGCGCGGAGATCTTGAAATCGCA

GTTGGGACCCGCGTTCTGCGCGCGGGAGTTGCGGTACACGGGGTTGCAGCACTGGAACACCATCAGGGCCG

GGTGCTTCACGCTCGCCAGCACCGTCGCGTCGGTGATGCTCTCCACGTCGAGGTCCTCGGCGTTGGCCATCC

CGAAGGGGGTCATCTTGCAGGTCTGCCTTCCCATGGTGGGCACGCACCCGGGCTTGTGGTTGCAATCGCAG

TGCAGGGGGATCAGCATCATCTGGGCCTGGTCGGCGTTCATCCCCGGGTACATGGCCTTCATGAAAGCCTC

CAATTGCCTGAACGCCTGCTGGGCCTTGGCTCCCTCGGTGAAGAAGACCCCGCAGGACTTGCTAGAGAACT

GGTTGGTGGCGCACCCGGCGTCGTGCACGCAGCAGCGCGCGTCGTTGTTGGCCAGCTGCACCACGCTGCGC

CCCCAGCGGTTCTGGGTGATCTTGGCCCGGTCGGGGTTCTCCTTCAGCGCGCGCTGCCCGTTCTCGCTCGCC

ACATCCATCTCGATCATGTGCTCCTTCTGGATCATGGTGGTCCCGTGCAGGCACCGCAGCTTGCCCTCGGCC

TCGGTGCACCCGTGCAGCCACAGCGCGCACCCGGTGCACTCCCAGTTCTTGTGGGCGATCTGGGAATGCGC

GTGCACGAAGCCCTGCAGGAAGCGGCCCATCATGGTGGTCAGGGTCTTGTTGCTAGTGAAGGTCAGCGGAA

TGCCGCGGTGCTCCTCGTTGATGTACAGGTGGCAGATGCGGCGGTACACCTCGCCCTGCTCGGGCATCAGC

TGGAAGTTGGCTTTCAGGTCGGTCTCCACGCGGTAGCGGTCCATCAGCATAGTCATGATTTCCATACCCTTC

-continued

TCCCAGGCCGAGACGATGGGCAGGCTCATAGGGTTCTTCACCATCATCTTAGCGCTAGCAGCCGCGGCCAG

GGGGTCGCTCTCGTCCAGGGTCTCAAAGCTCCGCTTGCCGTCCTTCTCGGTGATCCGCACCGGGGGGTAGCT

GAAGCCCACGGCCGCCAGCTCCTCCTCGGCCTGTCTTTCGTCCTCGCTGTCCTGGCTGACGTCCTGCAGGAC

CACATGCTTGGTCTTGCGGGGTTTCTTCTTGGGCGGCAGCGGCGGCGGAGATGTTGGAGATGGCGAGGGGG

AGCGCGAGTTCTCGCTCACCACTACTATCTCTTCCTCTTCTTGGTCCGAGGCCACGCGGCGGTAGGTATGTC

TCTTCGGGGGCAGAGGCGGAGGCGACGGGCTCTCGCCGCCGCGACTTGGCGGATGGCTGGCAGAGCCCCTT

CCGCGTTCGGGGGTGCGCTCCCGGCGGCGCTCTGACTGACTTCCTCCGCGGCCGGCCATTGTGTTCTCCTAG

GGAGGAACAACAAGCATGGAGACTCAGCCATCGCCAACCTCGCCATCTGCCCCCACCGCCGACGAGAAGC

AGCAGCAGCAGAATGAAAGCTTAACCGCCCCGCCGCCCAGCCCCGCCACCTCCGACGCGGCCGTCCCAGA

CATGCAAGAGATGGAGGAATCCATCGAGATTGACCTGGGCATATGTGACGCCCGCGGAGCACGAGGAGGAG

CTGGCAGTGCGCTTTTCACAAGAAGAGATACACCAAGAACAGCCAGAGCAGGAAGCAGAGAATGAGCAGA

GTCAGGCTGGGCTCGAGCATGACGGCGACTACCTCCACCTGAGCGGGGGGGAGGACGCGCTCATCAAGCA

TCTGGCCCGGCAGGCCACCATCGTCAAGGATGCGCTGCTCGACCGCACCGAGGTGCCCCTCAGCGTGGAGG

AGCTCAGCCGCGCCTACGAGTTGAACCTCTTCTCGCCGCGCGTGCCCCCCAAGCGCCAGCCCAATGGCACC

TGCGAGCCCAACCCGCGCCTCAACTTCTACCCGGTCTTCGCGGTGCCCGAGGCCCTGGCCACCTACCACATC

TTTTTCAAGAACCAAAAGATCCCCGTCTCCTGCCGCGCCAACCGCACCCGCGCCGACGCCCTTTTCAACCTG

GGTCCCGGCGCCCGCCTACCTGATATCGCCTCCTTGGAAGAGGTTCCCAAGATCTTCGAGGGTCTGGGCAG

CGACGAGACTCGGGCCGCGAACGCTCTGCAAGGAGAAGGAGGAGAGCATGAGCACCACACGCGCCCTGGTC

GAGTTGGAAGGCGACAACGCGCGGCTGGCGGTGCTCAAACGCACGGTCGAGCTGACCCATTTCGCCTACCC

GGCTCTGAACCTGCCCCCCAAAGTCATGAGCGCGGTCATGGACCAGGTGCTCATCAAGCGCGCGTCGCCCA

TCTCCGAGGACGAGGGCATGCAAGACTCCGAGGAGGGCAAGCCCGTGGTCAGCGACGAGCAGCTGGCCCG

GTGGCTGGGTCCTAATGCTAGTCCCCAGAGTTTGGAAGAGCGGCGCAAACTCATGATGGCCGTGGTCCTGG

TGACCGTGGAGCTGGAGTGCCTGCGCCGCTTCTTCGCCGACGCGGAGACCCTGCGCAAGGTCGAGGAGAAC

CTGCACTACCTCTTCAGGCACGGGTTCGTGCGCCAGGCCTGCAAGATCTCCAACGTGGAGCTGACCAACCT

GGTCTCCTACATGGGCATCTTGCACGAGAACCGCCTGGGGCAGAACGTGCTGCACACCACCCTGCGCGGGG

AGGCCCGGCGCGACTACATCCGCGACTGCGTCTACCTCTACCTCTGCCACACCTGGCAGACGGGCATGGC

GTGTGGCAGCAGTGTCTGGAGGAGCAGAACCTGAAAGAGCTCTGCAAGCTCCTGCAGAAGAACCTCAAGG

GTCTGTGGACCGGGTTCGACGAGCGCACCACCGCCTCGGACCTGGCCGACCTCATTTTCCCCGAGCGCCTC

AGGCTGACGCTGCGCAACGGCCTGCCCGACTTTATGAGCCAAAGCATGTTGCAAAACTTTCGCTCTTTCATC

CTCGAACGCTCCGGAATCCTGCCCGCCACCTGCTCCGCGCTGCCCTCGGACTTCGTGCCGCTGACCTTCCGC

GAGTGCCCCCCGCCGCTGTGGAGCCACTGCTACCTGCTGCGCCTGGCCAACTACCTGGCCTACCACTCGGA

CGTGATCGAGGACGTCAGCGGCGAGGGCCTGCTCGAGTGCCACTGCCGCTGCAACCTCTGCACGCCGCACC

GCTCCCTGGCCTGCAACCCCCAGCTGCTGAGCGAGACCCAGATCATCGGCACCTTCGAGTTGCAAGGGCCC

AGCGAAGGCGAGGGTTCAGCCGCCAAGGGGGGTCTGAAACTCACCCCGGGGCTGTGGACCTCGGCCTACT

TGCGCAAGTTCGTGCCCGAGGACTACCATCCCTTCGAGATCAGGTTCTACGAGGACCAATCCCATCCGCCC

AAGGCCGAGCTGTCGGCCTGCGTCATCACCCAGGGGGCGATCCTGGCCCAATTGCAAGCCATCCAGAAATC

CCGCCAAGAATTCTTGCTGAAAAAGGGCCGCGGGGTCTACCTCGACCCCCAGACCGGTGAGGAGCTCAACC

CCGGCTTCCCCCAGGATGCCCCGAGGAAACAAGAAGCTGAAAGTGGAGCTGCCGCCCGTGGAGGATTTGG

AGGAAGACTGGGAGAACAGCAGTCAGGCAGAGGAGGAGGAGATGGAGGAAGACTGGGACAGCACTCAGG

CAGAGGAGGACAGCCTGCAAGACAGTCTGGAGGAAGACGAGGAGGAGGCAGAGGAGGAGGTGGAAGAAG

-continued

CAGCCGCCGCCAGACCGTCGTCCTCGGCGGGGGAGAAAGCAAGCAGCACGGATACCATCTCCGCTCCGGG

TCGGGGTCCCGCTCGACCACACAGTAGATGGGACGAGACCGGACGATTCCCGAACCCCACCACCCAGACC

GGTAAGAAGGAGCGGCAGGGATACAAGTCCTGGCGGGGGCACAAAAACGCCATCGTCTCCTGCTTGCAGG

CCTGCGGGGGCAACATCTCCTTCACCCGGCGCTACCTGCTCTTCCACCGCGGGGTGAACTTTCCCCGCAACA

TCTTGCATTACTACCGTCACCTCCACAGCCCCTACTACTTCCAAGAAGAGGCAGCAGCAGCAGAAAAAGAC

CAGCAGAAAACCAGCAGCTAGAAAATCCACAGCGGCGGCAGCAGGTGGACTGAGGATCGCGGCGAACGA

GCCGGCGCAAACCCGGGAGCTGAGGAACCGGATCTTTCCCACCCTCTATGCCATCTTCCAGCAGAGTCGGG

GGCAGGAGCAGGAACTGAAAGTCAAGAACCGTTCTCTGCGCTCGCTCACCCGCAGTTGTCTGTATCACAAG

AGCGAAGACCAACTTCAGCGCACTCTCGAGGACGCCGAGGCTCTCTTCAACAAGTACTGCGCGCTCACTCT

TAAAGAGTAGCCCGCGCCCGCCAGTCGCAGAAAAAGGCGGGAATTACGTCACCTGTGCCCTTCGCCCTAG

CCGCCTCCACCCATCATCATGAGCAAAGAGATTCCCACGCCTTACATGTGGAGCTACCAGCCCCAGATGGG

CCTGGCCGCCGGTGCCGCCCAGGACTACTCCACCCGCATGAATTGGCTCAGCGCCGGGCCCGCGATGATCT

CACGGGTGAATGACATCCGCGCCCACCGAAACCAGATACTCCTAGAACAGTCAGCGCTCACCGCCACGCCC

CGCAATCACCTCAATCCGCGTAATTGGCCCGCCGCCCTGGTGTACCAGGAAATTCCCCAGCCCACGACCGT

ACTACTTCCGCGAGACGCCCAGGCCGAAGTCCAGCTGACTAACTCAGGTGTCCAGCTGGCGGGCGGCGCCA

CCCTGTGTCGTCACCGCCCCGCTCAGGGTATAAAGCGGCTGGTGATCCGGGGCAGAGGCACACAGCTCAAC

GACGAGGTGGTGAGCTCTTCGCTGGGTCTGCGACCTGACGGAGTCTTCCAACTCGCCGGATCGGGGAGATC

TTCCTTCACGCCTCGTCAGGCCGTCCTGACTTTGGAGAGTTCGTCCTCGCAGCCCCGCTCGGGTGGCATCGG

CACTCTCCAGTTCGTGGAGGAGTTCACTCCCTCGGTCTACTTCAACCCCTTCTCCGGCTCCCCCGGCCACTA

CCCGGACGAGTTCATCCCGAACTTCGACGCCATCAGCGAGTCGGTGGACGGCTACGATTGAAACTAATCAC

CCCCTTATCCAGTGAAATAAAGATCATATTGATGATGATTTTACAGAAATAAAAAATAATCATTTGATTTGA

AATAAAGATACAATCATATTGATGATTTGAGTTTAACAAAAAAATAAAGAATCACTTACTTGAAATCTGAT

ACCAGGTCTCTGTCCATGTTTTCTGCCAACACCACTTCACTCCCCTCTTCCCAGCTCTGGTACTGCAGGCCCC

GGCGGGCTGCAAACTTCCTCCACACGCTGAAGGGGATGTCAAATTCCTCCTGTCCCTCAATCTTCATTTTAT

CTTCTATCAGATGTCCAAAAAGCGCGTCCGGGTGGATGATGACTTCGACCCCGTCTACCCCTACGATGCAG

ACAACGCACCGACCGTGCCCTTCATCAACCCCCCCTTCGTCTCTTCAGATGGATTCCAAGAGAAGCCCCTGG

GGGTGTTGTCCCTGCGACTGGCCGACCCCGTCACCACCAAGAACGGGGAAATCACCCTCAAGCTGGGAGA

GGGGGTGGACCTCGATTCCTCGGGAAAACTCATCTCCAACACGGCCACCAAGGCCGCCGCCCCTCTCAGTT

TTTCCAACAACACCATTTCCCTTAACATGGATCACCCCTTTTACACTAAAGATGGAAAATTATCCTTACAAG

TTTCTCCACCATTAAATATACTGAGAACAAGCATTCTAAACACACTAGCTTTAGGTTTTGGATCAGGTTTAG

GACTCCGTGGCTCTGCCTTGGCAGTACAGTTAGTCTCTCCACTTACATTTGATACTGATGGAAACATAAAGC

TTACCTTAGACAGAGGTTTGCATGTTACAACAGGAGATGCAATTGAAAGCAACATAAGCTGGGCTAAAGGT

TTAAAATTTGAAGATGGAGCCATAGCAACCAACATTGGAAATGGGTTAGAGTTTGGAAGCAGTAGTACAG

AAACAGGTGTTGATGATGCTTACCCAATCCAAGTTAAACTTGGATCTGGCCTTAGCTTTGACAGTACAGGA

GCCATAATGGCTGGTAACAAAGAAGACGATAAACTCACTTTGTGGACAACACCTGATCCATCACCAAACTG

TCAAATACTCGCAGAAAATGATGCAAAACTAACACTTTGCTTGACTAAATGTGGTAGTCAAATACTGGCCA

CTGTGTCAGTCTTAGTTGTAGGAAGTGGAAACCTAAACCCCATTACTGGCACCGTAAGCAGTGCTCAGGTG

TTTCTACGTTTTGATGCAAACGGTGTTCTTTTAACAGAACATTCTACACTAAAAAAATACTGGGGGTATAGG

CAGGGAGATAGCATAGATGGCACTCCATATACCAATGCTGTAGGATTCATGCCCAATTTAAAAGCTTATCC

AAAGTCACAAAGTTCTACTACTAAAAATAATATAGTAGGGCAAGTATACATGAATGGAGATGTTTCAAAAC

CTATGCTTCTCACTATAACCCTCAATGGTACTGATGACAGCAACAGTACATATTCAATGTCATTTTCATACA

-continued

CCTGGACTAATGGAAGCTATGTTGGAGCAACATTTGGGGCTAACTCTTATACCTTCTCATACATCGCCCAAG

AATGAACACTGTATCCCACCCTGCATGCCAACCCTTCCCACCCCACTCTGTGGAACAAACTCTGAAACACA

AAATAAAATAAAGTTCAAGTGTTTATTGATTCAACAGTTTTACAGGATTCGAGCAGTTATTTTTCCTCCAC

CCTCCCAGGACATGGAATACACCACCCTCTCCCCCCGCACAGCCTTGAACATCTGAATGCCATTGGTGATG

GACATGCTTTTGGTCTCCACGTTCCACACAGTTTCAGAGCGAGCCAGTCTCGGGTCGGTCAGGGAGATGAA

ACCCTCCGGGCACTCCCGCATCTGCACCTCACAGCTCAACAGCTGAGGATTGTCCTCGGTGGTCGGGATCA

CGGTTATCTGGAAGAAGCAGAAGAGCGGCGGTGGGAATCATAGTCCGCGAACGGGATCGGCCGGTGGTGT

CGCATCAGGCCCCGCAGCAGTCGCTGCCGCCGCCGCTCCGTCAAGCTGCTGCTCAGGGGGTCCGGGTCCAG

GGACTCCCTCAGCATGATGCCCACGGCCCTCAGCATCAGTCGTCTGGTGCGGCGGGCGCAGCAGCGCATGC

GGATCTCGCTCAGGTCGCTGCAGTACGTGCAACACAGAACCACCAGGTTGTTCAACAGTCCATAGTTCAAC

ACGCTCCAGCCGAAACTCATCGCGGGAAGGATGCTACCCACGTGGCCGTCGTACCAGATCCTCAGGTAAT

CAAGTGGTGCCCCCTCCAGAACACGCTGCCCACGTACATGATCTCCTTGGGCATGTGGCGGTTCACCACCTC

CCGGTACCACATCACCCTCTGGTTGAACATGCAGCCCCGGATGATCCTGCGGAACCACAGGGCCAGCACCG

CCCCGCCCGCCATGCAGCGAAGAGACCCCGGGTCCCGGCAATGGCAATGGAGGACCCACCGCTCGTACCC

GTGGATCATCTGGGAGCTGAACAAGTCTATGTTGGCACAGCACAGGCATATGCTCATGCATCTCTTCAGCA

CTCTCAACTCCTCGGGGGTCAAAACCATATCCCAGGGCACGGGGAACTCTTGCAGGACAGCGAACCCCGCA

GAACAGGGCAATCCTCGCACAGAACTTACATTGTGCATGGACAGGGTATCGCAATCAGGCAGCACCGGGT

GATCCTCCACCAGAGAAGCGCGGGTCTCGGTCTCCTCACAGCGTGGTAAGGGGGCCGGCCGATACGGGTG

ATGGCGGGACGCGGCTGATCGTGTTCGCGACCGTGTCATGATGCAGTTGCTTTCGGACATTTTCGTACTTGC

TGTAGCAGAACCTGGTCCGGGCGCTGCACACCGATCGCCGGCGGCGGTCTCGGCGCTTGGAACGCTCGGTG

TTGAAATTGTAAAACAGCCACTCTCTCAGACCGTGCAGCAGATCTAGGGCCTCAGGAGTGATGAAGATCCC

ATCATGCCTGATGGCTCTGATCACATCGACCACCGTGGAATGGGCCAGACCCAGCCAGATGATGCAATTTT

GTTGGGTTTCGGTGACGGCGGGGGAGGGAAGAACAGGAAGAACCATGATTAACTTTTAATCCAAACGGTCT

CGGAGTACTTCAAAATGAAGATCGCGGAGATGGCACCTCTCGCCCCCGCTGTGTTGGTGGAAAATAACAGC

CAGGTCAAAGGTGATACGGTTCTCGAGATGTTCCACGGTGGCTTCCAGCAAAGCCTCCACGCGCACATCCA

GAAACAAGACAATAGCGAAAGCGGGAGGGTTCTCTAATTCCTCAATCATCATGTTACACTCCTGCACCATC

CCCAGATAATTTTCATTTTTCCAGCCTTGAATGATTCGAACTAGTTCCTGAGGTAAATCCAAGCCAGCCATG

ATAAAGAGCTCGCGCAGAGCGCCCTCCACCGGCATTCTTAAGCACACCCTCATAATTCCAAGATATTCTGC

TCCTGGTTCACCTGCAGCAGATTGACAGCGGAATATCAAAATCTCTGCCGCGATCCCTGAGCTCCTCCCTC

AGCAATAACTGTAAGTACTCTTTCATATCCTCTCCGAAATTTTTAGCCATAGGACCACCAGGAATAAGATTA

GGGCAAGCCACAGTACAGATAAACCGAAGTCCTCCCCAGTGAGCATTGCCAAATGCAAGACTGCTATAAG

CATGCTGGCTAGACCCGGTGATATCTTCCAGATAACTGGACAGAAAATCGCCCAGGCAATTTTTAAGAAAA

TCAACAAAAGAAAAATCCTCCAGGTGGACGTTTAGAGCCTCGGGAACAACGATGAAGTAAATGCAAGCGG

TGCGTTCCAGCATGGTTAGTTAGCTGATCTGTAGAAAAAACAAAAATGAACATTAAACCATGCTAGCCTGG

CGAACAGGTGGGTAAATCGTTCTCTCCAGCACCAGGCAGGCCACGGGGTCTCCGGCGCGACCCTCGTAAAA

ATTGTCGCTATGATTGAAAACCATCACAGAGAGACGTTCCCGGTGGCCGGCGTGAATGATTCGACAAGATG

AATACACCCCCGGAACATTGGCGTCCGCGAGTGAAAAAAAGCGCCCGAGGAAGCAATAAGGCACTACAAT

GCTCAGTCTCAAGTCCAGCAAAGCGATGCCATGCGGATGAAGCACAAAATTCTCAGGTGCGTACAAAATGT

AATTACTCCCCTCCTGCACAGGCAGCAAAGCCCCCGATCCCTCCAGGTACACATACAAAGCCTCAGCGTCC

ATAGCTTACCGAGCAGCAGCACACAACAGGCGCAAGAGTCAGAGAAAGGCTGAGCTCTAACCTGTCCACC

-continued

CGCTCTCTGCTCAATATATAGCCCAGATCTACACTGACGTAAAGGCCAAAGTCTAAAAATACCCGCCAAAT

AATCACACACGCCCAGCACACGCCCAGAAACCGGTGACACACTCAAAAAAATACGCGCACTTCCTCAAAC

GCCCAAAACTGCCGTCATTTCCGGGTTCCCACGCTACGTCATCAAAACACGACTTTCAAATTCCGTCGACCG

TTAAAAACGTCACCCGCCCCGCCCCTAACGGTCGCCCGTCTCTCAGCCAATCAGCGCCCCGCATCCCCAAA

TTCAAACACCTCATTTGCATATTAACGCGCACAAAAAGTTTGAGGTATATTATTGATGATG

ChAdV68-E4d-CMT-TSNA (SEQ ID NO: 69)

CATCATCAATAATATACCTCAAACTTTTTGTGCGCGTTAATATGCAAATGAGGCGTTTGAATTTGGGGAGGA

AGGGCGGTGATTGGTCGAGGGATGAGCGACCGTTAGGGGCGGGGCGAGTGACGTTTTGATGACGTGGTTG

CGAGGAGGAGCCAGTTTGCAAGTTCTCGTGGGAAAAGTGACGTCAAACGAGGTGTGGTTTGAACACGGAA

ATACTCAATTTTCCCGCGCTCTCTGACAGGAAATGAGGTGTTTCTGGGCGGATGCAAGTGAAAACGGGCCA

TTTTCGCGCGAAAACTGAATGAGGAAGTGAAAATCTGAGTAATTTCGCGTTTATGGCAGGGAGGAGTATTT

GCCGAGGGCCGAGTAGACTTTGACCGATTACGTGGGGGTTTCGATTACCGTGTTTTTCACCTAAATTTCCGC

GTACGGTGTCAAAGTCCGGTGTTTTTACGTAGGTGTCAGCTGATCGCCAGGGTATTTAAACCTGCGCTCTCC

AGTCAAGAGGCCACTCTTGAGTGCCAGCGAGAAGAGTTTTCTCCTCCGCGCCGCGAGTCAGATCTACACTT

TGAAAGTAGGGATAACAGGGTAATGACATTGATTATTGACTAGTTGTTAATAGTAATCAATTACGGGGTCA

TTAGTTCATAGCCCATATATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAATAGGGACTTTCCATTG

ACGTCAATGGGTGGAGTATTTACGGTAAACTGCCCACTTGGCAGTACATCAAGTGTATCATATGCCAAGTC

CGCCCCCTATTGACGTCAATGACGGTAAATGGCCCGCCTGGCATTATGCCCAGTACATGACCTTACGGGAC

TTTCCTACTTGGCAGTACATCTACGTATTAGTCATCGCTATTACCATGGTGATGCGGTTTTGGCAGTACACC

AATGGGCGTGGATAGCGGTTTGACTCACGGGGATTTCCAAGTCTCCACCCCATTGACGTCAATGGGAGTTT

GTTTTGGCACCAAAATCAACGGGACTTTCCAAAATGTCGTAATAACCCCGCCCCGTTGACGCAAATGGGCG

GTAGGCGTGTACGGTGGGAGGTCTATATAAGCAGAGCTCTCCCTATCAGTGATAGAGATCTCCCTATCAGT

GATAGAGATCGTCGACGAGCTCGTTTAGTGAACCGTCAGATCGCCTGGAACGCCATCCACGCTGTTTTGAC

CTCCATAGAAGACAGCGATCGCGCCACCATGGCTGGCATGACCGAGTACAAGCTAGTCGTTGTGGGAGCTG

GAGATGTGGGCAAATCTGCTCTGACCATTCAGCTGATTCAGGGCACAGATCTGGATCACCAGGAGAAGTGT

CTGAGCAGGCTGTACGACCACATGCCAGAAGGATTAACCCCTCTTATGGGAGTGAGCTCTTCTTCTGCTCTG

GCCAGACTGGGACTGCCTATGGATAAGCTGAACAAGATCACAGCTCCTGCCTCTCAGAAACTGAGACAGCT

GCAGAAGATGGAGACCCCTGAACTGCTGCCTTGTGGATATCTGGTGGAGGAGAATACCACAATCAGCGTGA

CCGTGAAAGGCCTGGAAGCCCAGAAACAAGATCAAAGGCTGTACCGGCTCTGTGAATATGACACTGCAGAG

AGCTTCTGCCGCCCCTAAGACAGGAGGAGGAGGAGAAGCTGCTGCCTACAATAATACATTAGTGGCCAGA

CATGTGCCCCAGATCCCTAAGCCTGACAGCCTGGTTGGCCTGAGCGATGAATTAGGAAAAAGAGACACATT

TGCCGAGAGCCTGATCCGGAGAATGGCCTCTGCCGGCTACCTGTTCCTGGATATCATCACATATGTTGTGTT

TGCCGTGACCTTCGTGCTGGGAGTTCTGGGCGGCCTGAATACCGAGACCAATGAAAAAGCTCTTGAAGCCG

TGTTTGGCAAGTACGGCAGAATCGTGGAGGTGCTGGGCGGCAGATCTTGTGAAGAATTAACAGCTGTGTTA

CCACCTCCTCAGCTGCTTGGCAGACGGTTCAACTTCTTCAGCTACAGCTACGTTGCTGCTGGCTCTTCTGGC

AACAACTACGACCTGATGGCCCAGCCTATTACACCTGGACCTGATACAACACCTCTGCCTGTGACCGATAC

ATCTTCTGTGTCTACCGGACACGCCACATCTCTGCCAGTGACAGATGCTGGACTGAGAGTGACAGAGTCTA

AAGGACACAGCGATTCTTGGCACCTGAGCCTGGATACAGCCATCAGGGTGAATACCCCTAAGCTGGTTTCT

GAAGTGGAAGAGCTGAACAAGAGCATCACCGCCCTGAGGGAGAAGTTACTGCAGATGGTGGAAGCCGATA

GACCTGGAAACCTGTTTATTGGAGGCCTGAACACCGAGACCAATGAGGACTCTCCCGTGAAGGATGAAGTG

-continued

GTGGTGAACGATCAATGOGGCCAGAATTGTAGCTGCCATCATGGAGGCTACGAGTTCCCTGATCTGCACAG

GACAATCGTGTCTGAGTGCGATGTGTATCTGACCTACATGCTGAGACAGGCTGCTCTGCAGCTGTTCTTCGA

CCTGTATCACAGCATCCCTAGCAGCTTTTCTCCTCTGGTTCTGAGCTGTCTGGTGCAGCCTCTGGAAGATGT

GGAAGTGATGGAGAAGGATGGCACAACCTTTAGCTGTGAGGTGAGCCACGATGAGGTGCCTCGGACATAT

GGACCCGTGTTTATGTGTCTGGGAGGACTGCTGACCATGGTGGCTGGAGCTGTTTGGCTGACAGTTGGACC

CGGACCAGGCGCCAAATTTGTTGCTGCTTGGACACTGAAAGCTGCTGCTGGGCCCGGACCAGGCCAGTACA

TCAAGGCCAACTCTAAGTTTATCGGCATCACCGAATTGGGACCTGGACCCGGCTAGTAGTGAGTTTAAACT

CCCATTTAAATGTGAGGGTTAATGCTTCGAGCAGACATGATAAGATACATTGATGAGTTTGGACAAACCAC

AACTAGAATGCAGTGAAAAAAATGCTTTATTTGTGAAATTTGTGATGCTATTGCTTTATTTGTAACCATTAT

AAGCTGCAATAAACAAGTTAACAACAACAATTGCATTCATTTTATGTTTCAGGTTCAGGGGGAGATGTGGG

AGGTTTTTTAAAGCAAGTAAAACCTCTACAAATGTGGTAAAATAACTATAACGGTCCTAAGGTAGCGAGTG

AGTAGTGTTCTGGGGCGGGGGAGGACCTGCATGAGGGCCAGAATAACTGAAATCTGTGCTTTTCTGTGTGT

TGCAGCAGCATGAGCGGAAGCGGCTCCTTTGAGGGAGGGGTATTCAGCCCTTATCTGACGGGGCGTCTCCC

CTCCTGGGCGGGAGTGCGTCAGAATGTGATGGGATCCACGGTGGACGGCCGGCCCGTGCAGCCCGCGAAC

TCTTCAACCCTGACCTATGCAACCCTGAGCTCTTCGTCGTTGGACGCAGCTGCCGCCGCAGCTGCTGCATCT

GCCGCAGCGCCGTGCGCGGAATGGCCATGGGCGCCGGCTACTACGGCACTCTGGTGGCCAACTCGAGTTC

CACCAATAATCCCGCCAGCCTGAACGAGGAGAAGCTGTTGCTGCTGATGGCCCAGCTCGAGGCCTTGACCC

AGCGCCTGGGCGAGCTGACCCAGCAGGTGGCTCAGCTGCAGGAGCAGACGCGGGCCGCGGTTGCCACGGT

GAAATCCAAATAAAAAATGAATCAATAAATAAACGGAGACGGTTGTTGATTTTAACACAGAGTCTGAATCT

TTATTTGATTTTTCGCGCGCGGTAGGCCCTGGACCACCGGTCTCGATCATTGAGCACCCGGTGGATCTTTTC

CAGGACCCGGTAGAGGTGGGCTTGGATGTGAGGTACATGGGCATGAGCCCGTCCCGGGGGTGGAGGTAG

CTCCATTGCAGGGCCTCGTGCTCGGGGGTGGTGTTGTAAATCACCCAGTCATAGCAGGGGCAGGGCATG

GTGTTGCACAATATCTTTGAGGAGGAGACTGATGGCCACGGGCAGCCCTTTGGTGTAGGTGTTTACAAATC

TGTTGAGCTGGGAGGGATGCATGCGGGGGGAGATGAGGTGCATCTTGGCCTGGATCTTGAGATTGGCGATG

TTACCGCCCAGATCCCGCCTGGGGTTCATGTTGTGCAGGACCACCAGCACGGTGTATCCGGTGCACTTGGG

GAATTTATCATGCAACTTGGAAGGGAAGGCGTGAAAGAATTTGGCGACGCCTTTGTGCCCGCCCAGGTTTT

CCATGCACTCATCCATGATGATGGCGATGGGCCCGTGGGCGGCGGCCTGGGCAAAGACGTTTCGGGGGTCG

GACACATCATAGTTGTGGTCCTGGGTGAGGTCATCATAGGCCATTTTAATGAATTTGGGGCGGAGGGTGCC

GGACTGGGGGACAAGGTTCCCTCGATCCCGGGGGCGTAGTTCCCCTCACAGATCTGCATCTCCCAGGCTT

TGAGCTCGGAGGGGGGGATCATGTCCACCTGCGGGGCGATAAAGAACACGGTTTCCGGGGCGGGGGAGAT

GAGCTGGGCCGAAAGCAAGTTCCGGAGCAGCTGGGACTTGCCGCAGCCGGTGGGGCCGTAGATGACCCCG

ATGACCGGCTGCAGGTGGTAGTTGAGGGAGAGACAGCTGCCGTCCTCCCGGAGGAGGGGGGCCACCTCGT

TCATCATCTCGCGCACGTGCATGTTCTCGCGCACCAGTTCCGCCAGGAGGCGCTCTCCCCCCAGGGATAGG

AGCTCCTGGAGCGAGGCGAAGTTTTTCAGCGGCTTGAGTCCGTCGGCCATGGGCATTTTGGAGAGGGTTTG

TTGCAAGAGTTCCAGGCGGTCCCAGAGCTCGGTGATGTGCTCTACGGCATCTCGATCCAGCAGACCTCCTC

GTTTCGCGGGTTGGGACGGCTGCGGGAGTAGGGCACCAGACGATGGGCGTCCAGCGCAGCCAGGGTCCGG

TCCTTCCAGGGTCGCAGCGTCCGCGTCAGGGTGGTCTCCGTCACGGTGAAGGGGTGCGCGCCGGGCTGGGC

GCTTGCGAGGGTGCGCTTCAGGCTCATCCGGCTGGTCGAAAACCGCTCCCGATCGGCGCCCTGCGCGTCGG

CCAGGTAGCAATTGACCATGAGTTCGTAGTTGAGCGCCTCGGCCGCGTGGCCTTTGGCGCGGAGCTTACCTT

TGGAAGTCTGCCCGCAGGCGGGACAGAGGAGGGACTTGAGGGCGTAGAGCTTGGGGGCGAGGAAGACGG

-continued

ACTCGGGGGCGTAGGCGTCCGCGCCGCAGTGGGCGCAGACGGTCTCGCACTCCACGAGCCAGGTGAGGTC

GGGCTGGTCGGGGTCAAAAACCAGTTTCCCGCCGTTCTTTTTGATGCGTTTCTTACCTTTGGTCTCCATGAGC

TCGTGTCCCCGCTGGGTGACAAAGAGGCTGTCCGTGCCCCGTAGACCGACTTTATGGGCCGGTCCTCGAG

CGGTGTGCCGCGGTCCTCCTCGTAGAGGAACCCCGCCCACTCCGAGACGAAAGCCCGGGTCCAGGCCAGCA

CGAAGGAGGCCACGTGGGACGGGTAGCGGTCGTTGTCCACCAGCGGGTCCACCTTTTCCAGGGTATGCAAA

CACATGTCCCCCTCGTCCACATCCAGGAAGGTGATTGGCTTGTAAGTGTAGGCCACGTGACCGGGGGTCCC

GGCCGGGGGGGTATAAAAGGGTGCGGGTCCCTGCTCGTCCTCACTGTCTTCCGGATCGCTGTCCAGGAGCG

CCAGCTGTTGGGGTAGGTATTCCCTCTCGAAGGCGGGCATGACCTCGGCACTCAGGTTGTCAGTTTCTAGAA

ACGAGGAGGATTTGATATTGACGGTGCCGGCGGAGATGCCTTTCAAGAGCCCCTCGTCCATCTGGTCAGAA

AAGACGATCTTTTTGTTGTCGAGCTTGGTGGCGAAGGAGCCGTAGAGGGCGTTGGAGAGGAGCTTGGCGAT

GGAGCGCATGGTCTGGTTTTTTTCCTTGTCGGCGCGCTCCTTGGCGGCGATGTTGAGCTGCACGTACTCGCG

CGCCACGCACTTCCATTCGGGGAAGACGGTGGTCAGCTCGTCGGGCACGATTCTGACCTGCCAGCCCCGAT

TATGCAGGGTGATGAGGTCCACACTGGTGGCCACCTCGCCGCGCAGGGGCTCATTAGTCCAGCAGAGGCGT

CCGCCCTTGCGCGAGCAGAAGGGGGGCAGGGGGTCCAGCATGACCTCGTCGGGGGGGTCGGCATCGATGG

TGAAGATGCCGGGCAGGAGGTCGGGGTCAAAGTAGCTGATGGAAGTGGCCAGATCGTCCAGGGCAGCTTG

CCATTCGCGCACGGCCAGCGCGCGCTCGTAGGGACTGAGGGGCGTGCCCCAGGGCATGGGATGGGTAAGC

GCGGAGGCGTACATGCCGCAGATGTCGTAGACGTAGAGGGGCTCCTCGAGGATGCCGATGTAGGTGGGGT

AGCAGCGCCCCCCGCGGATGCTGGCGCGCACGTAGTCATACAGCTCGTGCGAGGGGGCGAGGAGCCCCGG

GCCCAGGTTGGTGCGACTGGGCTTTTCGGCGCGGTAGACGATCTGGCGGAAAATGGCATGCGAGTTGGAGG

AGATGGTGGGCCTTTGGAAGATGTTGAAGTGGGCGTGGGGCAGTCCGACCGAGTCGCGGATGAAGTGGGC

GTAGGAGTCTTGCAGCTTGGCGACGAGCTCGGCGGTGACTAGGACGTCCAGAGCGCAGTAGTCGAGGGTCT

CCTGGATGATGTCATACTTGAGCTGTCCCTTTTGTTTCCACAGCTCGCGGTTGAGAAGGAACTCTTCGCGGT

CCTTCCAGTACTCTTCGAGGGGGAACCCGTCCTGATCTGCACGGTAAGAGCCTAGCATGTAGAACTGGTTG

ACGGCCTTGTAGGCGCAGCAGCCCTTCTCCACGGGAGGGCGTAGGCCTGGGCGGCCTTGCGCAGGGAGG

TGTGCGTGAGGGCGAAAGTGTCCCTGACCATGACCTTGAGGAACTGGTGCTTGAAGTCGATATCGTCGCAG

CCCCCCTGCTCCCAGAGCTGGAAGTCCGTGCGCTTCTTGTAGGCGGGGTTGGGCAAAGCGAAAGTAACATC

GTTGAAGAGGATCTTGCCCGCGCGGGGCATAAAGTTGCGAGTGATGCGGAAAGGTTGGGGCACCTCGGCC

CGGTTGTTGATGACCTGGGCGGCGAGCACGATCTCGTCGAAGCCGTTGATGTTGTGGCCCACGATGTAGAG

TTCCACGAATCGCGGACGGCCCTTGACGTGGGGCAGTTTCTTGAGCTCCTCGTAGGTGAGCTCGTCGGGGTC

GCTGAGCCCGTGCTGCTCGAGCGCCCAGTCGGCGAGATGGGGGTTGGCGCGGAGGAAGGAAGTCCAGAGA

TCCACGGCCAGGGCGGTTTGCAGACGGTCCCGGTACTGACGGAACTGCTGCCCGACGGCCATTTTTTCGGG

GGTGACGCAGTAGAAGGTGCGGGGGTCCCCGTGCCAGCGATCCCATTTGAGCTGGAGGGCGAGATCGAGG

GCGAGCTCGACGAGCCGGTCGTCCCCGGAGAGTTTCATGACCAGCATGAAGGGGACGAGCTGCTTGCCGA

AGGACCCCATCCAGGTGTAGGTTTCCACATCGTAGGTGAGGAAGAGCCTTTCGGTGCGAGGATGCGAGCCG

ATGGGGAAGAACTGGATCTCCTGCCACCAATTGGAGGAATGGCTGTTGATGTGATGGAAGTAGAAATGCCG

ACGGCGCGCCGAACACTCGTGCTTGTGTTTATACAAGCGGCCACAGTGCTCGCAACGCTGCACGGGATGCA

CGTGCTGCACGAGCTGTACCTGAGTTCCTTTGACGAGGAATTTCAGTGGGAAGTGGAGTCGTGGCGCCTGC

ATCTCGTGCTGTACTACGTCGTGGTGGTCGGCCTGGCCCTCTTCTGCCTCGATGGTGGTCATGCTGACGAGC

CCGCGCGGGAGGCAGGTCCAGACCTCGGCGCGAGCGGGTCGGAGAGCGAGGACGAGGGCGCGCAGGCCG

GAGCTGTCCAGGGTCCTGAGACGCTGCGGAGTCAGGTCAGTGGGCAGCGGCGGCGCGCGGTTGACTTGCA

GGAGTTTTTCCAGGGCGCGCGGGAGGTCCAGATGGTACTTGATCTCCACCGCGCCATTGGTGGCGACGTCG

-continued

ATGGCTTGCAGGGTCCCGTGCCCCTGGGGTGTGACCACCGTCCCCCGTTTCTTCTTGGGCGGCTGGGGCGAC

GGGGGCGGTGCCTCTTCCATGGTTAGAAGCGGCGGCGAGGACGCGCGCCGGGCGGCAGGGGCGGCTCGGG

GCCCGGAGGCAGGGGCGGCAGGGGCACGTCGGCGCCGCGCGCGGGTAGGTTCTGGTACTGCGCCCGGAGA

AGACTGGCGTGAGCGACGACGCGACGGTTGACGTCCTGGATCTGACGCCTCTGGGTGAAGGCCACGGGAC

CCGTGAGTTTGAACCTGAAAGAGAGTTCGACAGAATCAATCTCGGTATCGTTGACGGCGGCCTGCCGCAGG

ATCTCTTGCACGTCGCCCGAGTTGTCCTGGTAGGCGATCTCGGTCATGAACTGCTCGATCTCCTCCTCTTGA

AGGTCTCCGCGGCCGGCGCGCTCCACGGTGGCCGCGAGGTCGTTGGAGATGCGGCCCATGAGCTGCGAGA

AGGCGTTCATGCCCGCCTCGTTCCAGACGCGGCTGTAGACCACGACGCCCTCGGGATCGCGGGCGCGCATG

ACCACCTGGGCGAGGTTGAGCTCCACGTGGCGCGTGAAGACCGCGTAGTTGCAGAGGCGCTGGTAGAGGT

AGTTGAGCGTGGTGGCGATGTGCTCGGTGACGAAGAAATACATGATCCAGCGGCGGAGCGGCATCTCGCTG

ACGTCGCCCAGCGCCTCCAAACGTTCCATGGCCTCGTAAAAGTCCACGGCGAAGTTGAAAAACTGGGAGTT

GCGCGCCGAGACGGTCAACTCCTCCTCCAGAAGACGGATGAGCTCGGCGATGGTGGCGCGCACCTCGCGCT

CGAAGGCCCCCGGGAGTTCCTCCACTTCCTCTTCTTCCTCCTCCACTAACATCTCTTCTACTTCCTCCTCAGG

CGGCAGTGGTGGCGGGGGAGGGGGCCTGCGTCGCCGGCGGCGCACGGGCAGACGGTCGATGAAGCGCTCG

ATGGTCTCGCCGCGCCGGCGTCGCATGGTCTCGGTGACGGCGCGCCCGTCCTCGCGGGGCCGCAGCGTGAA

GACGCCGCCGCGCATCTCCAGGTGGCCGGGGGGGTCCCCGTTGGGCAGGGAGAGGGCGCTGACGATGCAT

CTTATCAATTGCCCCGTAGGGACTCCGCGCAAGGACCTGAGCGTCTCGAGATCCACGGGATCTGAAAACCG

CTGAACGAAGGCTTCGAGCCAGTCGCAGTCGCAAGGTAGGCTGAGCACGGTTTCTTCTGGCGGGTCATGTT

GGTTGGGAGCGGGGCGGGCGATGCTGCTGGTGATGAAGTTGAAATAGGCGGTTCTGAGACGGCGGATGGT

GGCGAGGAGCACCAGGTCTTTGGGCCCGGCTTGCTGGATGCGCAGACGGTCGGCCATGCCCCAGGCGTGGT

CCTGACACCTGGCCAGGTCCTTGTAGTAGTCCTGCATGAGCCGCTCCACGGGCACCTCCTCCTCGCCCGCGC

GGCCGTGCATGCGCGTGAGCCCGAAGCCGCGCTGGGGCTGGACGAGCGCCAGGTCGGCGACGACGCGCTC

GGCGAGGATGGCTTGCTGGATCTGGGTGAGGGTGGTCTGGAAGTCATCAAAGTCGACGAAGCGGTGGTAG

GCTCCGGTGTTGATGGTGTAGGAGCAGTTGGCCATGACGGACCAGTTGACGGTCTGGTGGCCCGGACGCAC

GAGCTCGTGGTACTTGAGGCGCGAGTAGGCGCGCGTGTCGAAGATGTAGTCGTTGCAGGTGCGCACCAGGT

ACTGGTAGCCGATGAGGAAGTGCGGCGGCGGCTGGCGGTAGAGCGGCCATCGCTCGGTGGCGGGGGCGCC

GGGCGCGAGGTCCTCGAGCATGGTGCGGTGGTAGCCGTAGATGTACCTGGACATCCAGGTGATGCCGGCGG

CGGTGGTGGAGGCGCGCGGGAACTCGCGGACGCGGTTCCAGATGTTGCGCAGCGGCAGGAAGTAGTTCAT

GGTGGGCACGGTCTGGCCCGTGAGGCGCGCGCAGTCGTGGATGCTCTATACGGGCAAAAACGAAGCGGT

CAGCGGCTCGACTCCGTGGCCTGGAGGCTAAGCGAACGGGTTGGGCTGCGCGTGTACCCCGGTTCGAATCT

CGAATCAGGCTGGAGCCGCAGCTAACGTGGTATTGGCACTCCCGTCTCGACCCAAGCCTGCACCAACCCTC

CAGGATACGGAGGCGGGTCGTTTTGCAACTTTTTTTTGGAGGCCGGATGAGACTAGTAAGCGCGGAAAGCG

GCCGACCGCGATGGCTCGCTGCCGTAGTCTGGAGAAGAATCGCCAGGGTTGCGTTGCGGTGTGCCCCGGTT

CGAGGCCGGCCGGATTCCGCGGCTAACGAGGGCGTGGCTGCCCCGTCGTTTCCAAGACCCCATAGCCAGCC

GACTTCTCCAGTTACGGAGCGAGCCCCTCTTTTGTTTGTTTGTTTTTGCCAGATGCATCCCGTACTGCGGCA

GATGCGCCCCCACCACCCTCCACCGCAACAACAGCCCCCTCCACAGCCGGCGCTTCTGCCCCCGCCCCAGC

AGCAACTTCCAGCCACGACCGCCGCGGCCGCCGTGAGCGGGGCTGGACAGAGTTATGATCACCAGCTGGC

CTTGGAAGAGGGCGAGGGGCTGGCGCGCCTGGGGGCGTCGTCGCCGGAGCGGCACCCGCGCGTGCAGATG

AAAAGGGACGCTCGCGAGGCCTACGTGCCCAAGCAGAACCTGTTCAGAGACAGGAGCGGCGAGGAGCCCG

AGGAGATGCGCGCGGCCCGGTTCCACGCGGGGCGGGAGCTGCGGCGCGGCCTGGACCGAAAGAGGGTGCT

-continued

GAGGGACGAGGATTTCGAGGCGGACGAGCTGACGGGGATCAGCCCCGCGCGCGCACGTGGCCGCGGCC

AACCTGGTCACGGCGTACGAGCAGACCGTGAAGGAGGAGAGCAACTTCCAAAATCCTTCAACAACCACG

TGCGCACCCTGATCGCGCGCGAGGAGGTGACCCTGGGCCTGATGCACCTGTGGGACCTGCTGGAGGCCATC

GTGCAGAACCCCACCAGCAAGCCGCTGACGGCGCAGCTGTTCCTGGTGGTGCAGCATAGTCGGGACAACG

AAGCGTTCAGGGAGGCGCTGCTGAATATCACCGAGCCCGAGGGCCGCTGGCTCCTGGACCTGGTGAACATT

CTGCAGAGCATCGTGGTGCAGGAGCGCGGGCTGCCGCTGTCCGAGAAGCTGGCGGCCATCAACTTCTCGGT

GCTGAGTTTGGGCAAGTACTACGCTAGGAAGATCTACAAGACCCCGTACGTGCCCATAGACAAGGAGGTG

AAGATCGACGGGTTTTACATGCGCATGACCCTGAAAGTGCTGACCCTGAGCGACGATCTGGGGGTGTACCG

CAACGACAGGATGCACCGTGCGGTGAGCGCCAGCAGGCGGCGCGAGCTGAGCGACCAGGAGCTGATGCAT

AGTCTGCAGCGGGCCCTGACCGGGGCCGGGACCGAGGGGGAGAGCTACTTTGACATGGGCGCGGACCTGC

ACTGGCAGCCCAGCCGCCGGGCCTTGGAGGCGGCGGCAGGACCCTACGTGAAGAGGTGGACGATGAGGT

GGACGAGGAGGGCGAGTACCTGGAAGACTGATGGCGCGACCGTATTTTGCTAGATGCAACAACAACAGC

CACCTCCTGATCCCGCGATGCGGGCGGCGCTGCAGAGCCAGCCGTCCGGCATTAACTCCTCGGACGATTGG

ACCCAGGCCATGCAACGCATCATGGCGCTGACGACCCGCAACCCCGAAGCCTTTAGACAGCAGCCCCAGG

CCAACCGGCTCTCGGCCATCCTGGAGGCCGTGGTGCCCTCGCGCTCCAACCCCACGCACGAGAAGGTCCTG

GCCATCGTGAACGCGCTGGTGGAGAACAAGGCCATCCGCGGCGACGAGGCCGGCCTGGTGTACAACGCGC

TGCTGGAGCGCGTGGCCCGCTACAACAGCACCAACGTGCAGACCAACCTGGACCGCATGGTGACCGACGT

GCGCGAGGCCGTGGCCCAGCGCGAGCGGTTCCACCGCGAGTCCAACCTGGGATCCATGGTGGCGCTGAAC

GCCTTCCTCAGCACCCAGCCCGCCAACGTGCCCCGGGGCCAGGAGGACTACACCAACTTCATCAGCGCCCT

GCGCCTGATGGTGACCGAGGTGCCCCAGAGCGAGGTGTACCAGTCCGGGCCGGACTACTTCTTCCAGACCA

GTCGCCAGGGCTTGCAGACCGTGAACCTGAGCCAGGCTTCAAGAACTTGCAGGGCCTGTGGGGCGTGCAG

GCCCCGGTCGGGGACCGCGCGACGGTGTCGAGCCTGCTGACGCCGAACTCGCGCCTGCTGCTGCTGCTGGT

GGCCCCCTTCACGGACAGCGGCAGCATCAACCGCAACTCGTACCTGGGCTACCTGATTAACCTGTACCGCG

AGGCCATCGGCCAGGCGCACGTGGACGAGCAGACCTACCAGGAGATCACCCACGTGAGCCGCGCCCTGGG

CCAGGACGACCCGGGCAACCTGGAAGCCACCCTGAACTTTTTGCTGACCAACCGGTCGCAGAAGATCCCGA

CCCAGTACGCGCTCAGCACCGAGGAGGAGCGCATCCTGCGTTACGTGCAGCAGAGCGTGGGCCTGTTCCTG

ATGCAGGAGGGGGCCACCCCCAGCGCCGCGCTCGACATGACCGCGCGCAACATGGAGCCCAGCATGTACG

CCAGCAACCGCCCGTTCATCAATAACTGATGGACTACTTGCATCGGGCGGCCGCCATGAACTCTGACTAT

TTCACCAACGCCATCCTGAATCCCCACTGGCTCCCGCCGCCGGGGTTCTACACGGGCGAGTACGACATGCC

CGACCCCAATGACGGGTTCCTGTGGGACGATGTGGACAGCAGCGTGTTCTCCCCCCGACCGGGTGCTAACG

AGCGCCCCTTGTGGAAGAAGGAAGGCAGCGACCGACGCCCGTCCTCGGCGCTGTCCGGCCGCGAGGGTGC

TGCCGCGGCGGTGCCCGAGGCCGCCAGTCCTTTCCCGAGCTTGCCCTTCTCGCTGAACAGTATCCGCAGCA

GCGAGCTGGGCAGGATCACGCGCCCGCGCTTGCTGGGCGAAGAGGAGTACTTGAATGACTCGCTGTTGAGA

CCCGAGCGGGAGAAGAACTTCCCCAATAACGGGATAGAAAGCCTGGTGGACAAGATGAGCCGCTGGAAGA

CGTATGCGCAGGAGCACAGGGACGATCCCCGGGCGTCGCAGGGGGCCACGAGCCGGGGCAGCGCCGCCCG

TAAACGCCGGTGGCACGACAGGCAGCGGGGACAGATGTGGGACGATGAGGACTCCGCCGACGACAGCAGC

GTGTTGGACTTGGGTGGGAGTGGTAACCCGTTCGCTCACCTGCGCCCCCGTATCGGGCGCATGATGTAAGA

GAAACCGAAAATAAATGATACTCACCAAGGCCATGGCGACCAGCGTGCGTTCGTTTCTTCTCTGTTGTTGTT

GTATCTAGTATGATGAGGCGTGCGTACCCGGAGGGTCCTCCTCCCTCGTACGAGAGCGTGATGCAGCAGGC

GATGGCGGCGGCGGCGATGCAGCCCCCGCTGGAGGCTCCTTACGTGCCCCCGCGGTACCTGGCGCCTACGG

AGGGGCGGAACAGCATTCGTTACTCGGAGCTGGCACCCTTGTACGATACCACCCGGTTGTACCTGGTGGAC

-continued

AACAAGTCGGCGGACATCGCCTCGCTGAACTACCAGAACGACCACAGCAACTTCCTGACCACCGTGGTGCA

GAACAATGACTTCACCCCCACGGAGGCCAGCACCCAGACCATCAACTTTGACGAGCGCTCGCGGTGGGGC

GGCCAGCTGAAAACCATCATGCACACCAACATGCCCAACGTGAACGAGTTCATGTACAGCAACAAGTTCA

AGGCGCGGGTGATGGTCTCCCGCAAGACCCCCAATGGGGTGACAGTGACAGAGGATTATGATGGTAGTCA

GGATGAGCTGAAGTATGAATGGGTGGAATTTGAGCTGCCCGAAGGCAACTTCTCGGTGACCATGACCATCG

ACCTGATGAACAACGCCATCATCGACAATTACTTGGCGGTGGGGCGGCAGAACGGGGTGCTGGAGAGCGA

CATCGGCGTGAAGTTCGACACTAGGAACTTCAGGCTGGGCTGGGACCCCGTGACCGAGCTGGTCATGCCCG

GGGTGTACACCAACGAGGCTTTCCATCCCGATATTGTCTTGCTGCCCGGCTGCGGGGTGGACTTCACCGAG

AGCCGCCTCAGCAACCTGCTGGGCATTCGCAAGAGGCAGCCCTTCCAGGAAGGCTTCCAGATCATGTACGA

GGATCTGGAGGGGGGCAACATCCCCGCGCTCCTGGATGTCGACGCCTATGAGAAAAGCAAGGAGGATGCA

GCAGCTGAAGCAACTGCAGCCGTAGCTACCGCCTCTACCGAGGTCAGGGGCGATAATTTTGCAAGCGCCGC

AGCAGTGGCAGCGGCCGAGGCGGCTGAAACCGAAAGTAAGATAGTCATTCAGCCGGTGGAGAAGGATAGC

AAGAACAGGAGCTACAACGTACTACCGGACAAGATAAACACCGCCTACCGCAGCTGGTACCTAGCCTACA

ACTATGGCGACCCCGAGAAGGGCGTGCGCTCCTGGACGCTGCTCACCACCTCGGACGTCACCTGCGGCGTG

GAGCAAGTCTACTGGTCGCTGCCCGACATGATGCAAGACCCGGTCACCTTCCGCTCCACGCGTCAAGTTAG

CAACTACCCGGTGGTGGGCGCCGAGCTCCTGCCCGTCTACTCCAAGAGCTTCTTCAACGAGCAGGCCGTCT

ACTCGCAGCAGCTGCGCGCCTTCACCTCGCTTACGCACGTCTTCAACCGCTTCCCCGAGAACCAGATCCTCG

TCCGCCCGCCCGCGCCCACCATTACCACCGTCAGTGAAAACGTTCCTGCTCTCACAGATCACGGGACCCTG

CCGCTGCGCGCAGTATCCGGGGAGTCCAGCGCGTGACCGTTACTGCGCCAGACGCCGCACCTGCCCCTA

CGTCTACAAGGCCCTGGGCATAGTCGCGCCGCGCGTCCTCTCGAGCCGCACCTTCTAAATGTCCATTCTCAT

CTCGCCCAGTAATAACACCGGTTGGGGCCTGCGCGCGCCCAGCAAGATGTACGGAGGCGCTCGCCAACGCT

CCACGCAACACCCCGTGCGCGTGCGCGGGCACTTCCGCGCTCCCTGGGGCGCCCTCAAGGGCCGCGTGCGG

TCGCGCACCACCGTCGACGACGTGATCGACCAGGTGGTGGCCGACGCGCGCAACTACACCCCCGCCGCCGC

GCCCGTCTCCACCGTGGACGCCGTCATCGACAGCGTGGTGGCCGACGCGCGCCGGTACGCCCGCGCCAAGA

GCCGGCGGCGGCGCATCGCCCGGCGGCACCGGAGCACCCCCGCCATGCGCGCGGCGCGAGCCTTGCTGCG

CAGGGCCAGGCGCACGGGACGCAGGGCCATGCTCAGGGCGGCCAGACGCGCGGCTTCAGGCGCCAGCGCC

GGCAGGACCCGGAGACGCGCGGCCACGGCGGCGGCAGCGGCCATCGCCAGCATGTCCCGCCCGCGGCGAG

GGAACGTGTACTGGGTGCGCGACGCCGCCACCGGTGTGCGCGTGCCCGTGCGCACCCGCCCCCCTCGCACT

TGAAGATGTTCACTTCGCGATGTTGATGTGTCCCAGCGGCGAGGAGGATGTCCAAGCGCAAATTCAAGGAA

GAGATGCTCCAGGTCATCGCGCCTGAGATCTACGGCCCTGCGGTGGTGAAGGAGGAAAGAAAGCCCCGCA

AAATCAAGCGGGTCAAAAAGGACAAAAAGGAAGAAGAAAGTGATGTGGACGGATTGGTGGAGTTTGTGCG

CGAGTTCGCCCCCCGGCGGCGCGTGCAGTGGCGCGGGCGGAAGGTGCAACCGGTGCTGAGACCCGGCACC

ACCGTGGTCTTCACGCCCGGCGAGCGCTCCGGCACCGCTTCCAAGCGCTCCTACGACGAGGTGTACGGGGA

TGATGATATTCTGGAGCAGGCGGCCGAGCGCCTGGGCGAGTTTGCTTACGGCAAGCGCAGCCGTTCCGCAC

CGAAGGAAGAGGCGGTGTCCATCCCGCTGGACCACGGCAACCCCACGCCGAGCCTCAAGCCCGTGACCTT

GCAGCAGGTGCTGCCGACCGCGGCGCCGCGCCGGGGGTTCAAGCGCGAGGGCGAGCATCTGTACCCCACC

ATGCAGCTGATGGTGCCCAAGCGCCAGAAGCTGGAAGACGTGCTGGAGACCATGAAGGTGGACCCGGACG

TGCAGCCCGAGGTCAAGGTGCGGCCCATCAAGCAGGTGGCCCCGGGCCTGGGCGTGCAGACCGTGGACAT

CAAGATTCCCACGGAGCCCATGGAAACGCAGACCGAGCCCATGATCAAGCCCAGCACCAGCACCATGGAG

GTGCAGACGGATCCCTGGATGCCATCGGCTCCTAGTCGAAGACCCCGGCGCAAGTACGGCGCGGCCAGCCT

-continued

GCTGATGCCCAACTACGCGCTGCATCCTTCCATCATCCCCACGCCGGGCTACCGCGGCACGCGCTTCTACCG
CGGTCATACCAGCAGCCGCCGCCGCAAGACCACCACTCGCCGCCGCCGTCGCCGCACCGCCGCTGCAACCA
CCCCTGCCGCCCTGGTGCGGAGAGTGTACCGCCGCGGCCGCGCACCTCTGACCCTGCCGCGCGCGCGCTAC
CACCCGAGCATCGCCATTTAAACTTTCGCCTGCTTTGCAGATCAATGGCCCTCACATGCCGCCTTCGCGTTC
CCATTACGGGCTACCGAGGAAGAAAACCGCGCCGTAGAAGGCTGGCGGGGAACGGGATGCGTCGCCACCA
CCACCGGCGGCGGCGCGCCATCAGCAAGCGGTTGGGGGAGGCTTCCTGCCCGCGCTGATCCCCATCATCG
CCGCGGCGATCGGGGCGATCCCCGGCATTGCTTCCGTGGCGGTGCAGGCCTCTCAGCGCCACTGAGACACA
CTTGGAAACATCTTGTAATAAACCAATGGACTCTGACGCTCCTGGTCCTGTGATGTGTTTTCGTAGACAGAT
GGAAGACATCAATTTTTCGTCCCTGGCTCCGCGACACGGCACGCGGCCGTTCATGGGCACCTGGAGCGACA
TCGGCACCAGCCAACTGAACGGGGGCGCCTTCAATTGGAGCAGTCTCTGGAGCGGGCTTAAGAATTTCGGG
TCCACGCTTAAAACCTATGGCAGCAAGGCGTGGAACAGCACCACAGGGCAGGCGCTGAGGGATAAGCTGA
AAGAGCAGAACTTCCAGCAGAAGGTGGTCGATGGGCTCGCCTCGGGCATCAACGGGGTGGTGGACCTGGC
CAACCAGGCCGTGCAGCGGCAGATCAACAGCCGCCTGGACCCGGTGCCGCCCGCCGGCTCCGTGGAGATG
CCGCAGGTGGAGGAGGAGCTGCCTCCCCTGGACAAGCGGGGCGAGAAGCGACCCCGCCCCGATGCGGAGG
AGACGCTGCTGACGCACACGGACGAGCCGCCCCCGTACGAGGAGGCGGTGAAACTGGGTCTGCCCACCAC
GCGGCCCATCGCGCCCCTGGCCACCGGGGTGCTGAAACCCGAAAAGCCCGCGACCCTGGACTTGCCTCCTC
CCCAGCCTTCCCGCCCCTCTACAGTGGCTAAGCCCCTGCCGCCGGTGGCCGTGGCCCGCGCGCGACCCGGG
GGCACCGCCCGCCCTCATGCGAACTGGCAGAGCACTCTGAACAGCATCGTGGGTCTGGGAGTGCAGAGTGT
GAAGCGCCGCCGCTGCTATTAAACCTACCGTAGCGCTTAACTTGCTTGTCTGTGTGTGTATGTATTATGTCG
CCGCCGCCGCTGTCCACCAGAAGGAGGAGTGAAGAGGCGCGTCGCCGAGTTGCAAGATGGCCACCCCATC
GATGCTGCCCCAGTGGGCGTACATGCACATCGCCGGACAGGACGCTTCGGAGTACCTGAGTCCGGGTCTGG
TGCAGTTTGCCCGCGCCACAGACACCTACTTCAGTCTGGGGAACAAGTTTAGGAACCCCACGGTGGCGCCC
ACGCACGATGTGACCACCGACCGCAGCCAGCGGCTGACGCTGCGCTTCGTGCCCGTGGACCGCGAGGACA
ACACCTACTCGTACAAAGTGCGCTACACGCTGGCCGTGGGCGACAACCGCGTGCTGGACATGGCCAGCACC
TACTTTGACATCCGCGGCGTGCTGGATCGGGGCCCTAGCTTCAAACCCTACTCCGGCACCGCCTACAACAG
TCTGGCCCCCAAGGGAGCACCCAACACTTGTCAGTGGACATATAAAGCCGATGGTGAAACTGCCACAGAA
AAAACCTATACATATGGAAATGCACCCGTGCAGGGCATTAACATCACAAAAGATGGTATTCAACTTGGAAC
TGACACCGATGATCAGCCAATCTACGCAGATAAAACCTATCAGCCTGAACCTCAAGTGGGTGATGCTGAAT
GGCATGACATCACTGGTACTGATGAAAAGTATGGAGGCAGAGCTCTTAAGCCTGATACCAAAATGAAGCCT
TGTTATGGTTCTTTTGCCAAGCCTACTAATAAAGAAGGAGGTCAGGCAAATGTGAAAACAGGAACAGGCAC
TACTAAAGAATATGACATAGACATGGCTTTCTTTGACAACAGAAGTGCGGCTGCTGCTGGCCTAGCTCCAG
AAATTGTTTTGTATACTGAAAATGTGGATTTGGAAACTCCAGATACCCATATTGTATACAAAGCAGGCACA
GATGACAGCAGCTCTTCTATTAATTTGGGTCAGCAAGCCATGCCCAACAGACCTAACTACATTGGTTTCAGA
GACAACTTTATCGGGCTCATGTACTACAACAGCACTGGCAATATGGGGGTGCTGGCCGGTCAGGCTTCTA
GCTGAATGCTGTGGTTGACTTGCAAGACAGAAACACCGAGCTGTCCTACCAGCTCTTGCTTGACTCTCTGGG
TGACAGAACCCGGTATTTCAGTATGTGGAATCAGGCGGTGGACAGCTATGATCCTGATGTGCGCATTATTG
AAAATCATGGTGTGGAGGATGAACTTCCCAACTATTGTTTCCCTCTGGATGCTGTTGGCAGAACAGATACTT
ATCAGGGAATTAAGGCTAATGGAACTGATCAAACCACATGGACCAAAGATGACAGTGTCAATGATGCTAA
TGAGATAGGCAAGGGTAATCCATTCGCCATGGAAATCAACATCCAAGCCAACCTGTGGAGGAACTTCCTCT
ACGCCAACGTGGCCCTGTACCTGCCCGACTCTTACAAGTACACGCCGGCCAATGTTACCCTGCCCACCAAC
ACCAACACCTACGATTACATGAACGGCCGGGTGGTGGCGCCCTCGCTGGTGGACTCCTACATCAACATCGG

-continued

GGCGCGCTGGTCGCTGGATCCCATGGACAACGTGAACCCTTCAACCACCACCGCAATGCGGGGCTGCGCT

ACCGCTCCATGCTCCTGGGCAACGGGCGCTACGTGCCCTTCCACATCCAGGTGCCCCAGAAATTTTTCGCCA

TCAAGAGCCTCCTGCTCCTGCCCGGGTCCTACACCTACGAGTGGAACTTCCGCAAGGACGTCAACATGATC

CTGCAGAGCTCCCTCGGCAACGACCTGCGCACGGACGGGGCCTCCATCTCCTTCACCAGCATCAACCTCTA

CGCCACCTTCTTCCCCATGGCGCACAACACGGCCTCCACGCTCGAGGCCATGCTGCGCAACGACACCAACG

ACCAGTCCTTCAACGACTACCTCTCGGCGGCCAACATGCTCTACCCCATCCCGGCCAACGCCACCAACGTG

CCCATCTCCATCCCCTCGCGCAACTGGGCCGCCTTCCGCGGCTGGTCCTTCACGCGTCTCAAGACCAAGGAG

ACGCCCTCGCTGGGCTCCGGGTTCGACCCCTACTTCGTCTACTCGGGCTCCATCCCTACCTCGACGGCACC

TTCTACCTCAACCACACCTTCAAGAAGGTCTCCATCACCTTCGACTCCTCCGTCAGCTGGCCCGGCAACGAC

CGGCTCCTGACGCCCAACGAGTTCGAAATCAAGCGCACCGTCGACGGCGAGGGCTACAACGTGGCCCAGT

GCAACATGACCAAGGACTGGTTCCTGGTCCAGATGCTGGCCCACTACAACATCGGCTACCAGGGCTTCTAC

GTGCCCGAGGGCTACAAGGACCGCATGTACTCCTTCTTCCGCAACTTCCAGCCCATGAGCCGCCAGGTGGT

GGACGAGGTCAACTACAAGGACTACCAGGCCGTCACCCTGGCCTACCAGCACAACAACTCGGGCTTCGTCG

GCTACCTCGCGCCCACCATGCGCCAGGGCCAGCCCTACCCCGCCAACTACCCCTACCCGCTCATCGGCAAG

AGCGCCGTCACCAGCGTCACCCAGAAAAAGTTCCTCTGCGACAGGTCATGTGGCGCATCCCCTTCTCCAG

CAACTTCATGTCCATGGGCGCGCTCACCGACCTCGGCCAGAACATGCTCTATGCCAACTCCGCCCACGCGC

TAGACATGAATTTCGAAGTCGACCCCATGGATGAGTCCACCCTTCTCTATGTTGTCTTCGAAGTCTTCGACG

TCGTCCGAGTGCACCAGCCCCACCGCGGCGTCATCGAGGCCGTCTACCTGCGCACCCCCTTCTCGGCCGGT

AACGCCACCACCTAAGCTCTTGCTTCTTGCAAGCCATGGCCGCGGGCTCCGGCGAGCAGGAGCTCAGGGCC

ATCATCCGCGACCTGGGCTGCGGGCCCTACTTCCTGGGCACCTTCGATAAGCGCTTCCCGGGATTCATGGCC

CCGCACAAGCTGGCCTGCGCCATCGTCAACACGGCCGGCCGCGAGACCGGGGGCGAGCACTGGCTGGCCT

TCGCCTGGAACCCGCGCTCGAACACCTGCTACCTCTTCGACCCTTCGGGTTCTCGGACGAGCGCCTCAAGC

AGATCTACCAGTTCGAGTACGAGGGCCTGCTGCGCCGCAGCGCCCTGGCCACCGAGGACCGCTGCGTCACC

CTGGAAAAGTCCACCCAGACCGTGCAGGGTCCGCGCTCGGCCGCCTGCGGGCTCTTCTGCTGCATGTTCCT

GCACGCCTTCGTGCACTGGCCCGACCGCCCCATGGACAAGAACCCCACCATGAACTTGCTGACGGGGGTGC

CCAACGGCATGCTCCAGTCGCCCCAGGTGGAACCCACCCTGCGCCGCAACCAGGAGGCGCTCTACCGCTTC

CTCAACTCCCACTCCGCCTACTTTCGCTCCCACCGCGCGCGCATCGAGAAGGCCACCGCCTTCGACCGCATG

AATCAAGACATGTAAACCGTGTGTGTATGTTAAATGTCTTTAATAAACAGCACTTTCATGTTACACATGCAT

CTGAGATGATTTATTTAGAAATCGAAAGGGTTCTGCCGGGTCTCGGCATGGCCCGCGGGCAGGGACACGTT

GCGGAACTGGTACTTGGCCAGCCACTTGAACTCGGGGATCAGCAGTTTGGGCAGCGGGGTGTCGGGGAAG

GAGTCGGTCCACAGCTTCCGCGTCAGTTGCAGGGCGCCCAGCAGGTCGGGCGCGGAGATCTTGAAATCGCA

GTTGGGACCCGCGTTCTGCGCGCGGGAGTTGCGGTACACGGGGTTGCAGCACTGGAACACCATCAGGGCCG

GGTGCTTCACGCTCGCCAGCACCGTCGCGTCGGTGATGCTCTCCACGTCGAGGTCCTCGGCGTTGGCCATCC

CGAAGGGGGTCATCTTGCAGGTCTGCCTTCCCATGGTGGGCACGCACCCGGGCTTGTGGTTGCAATCGCAG

TGCAGGGGGATCAGCATCATCTGGGCCTGGTCGGCGTTCATCCCCGGGTACATGGCCTTCATGAAAGCCTC

CAATTGCCTGAACGCCTGCTGGGCCTTGGCTCCCTCGGTGAAGAAGACCCCGCAGGACTTGCTAGAGAACT

GGTTGGTGGCGCACCCGGCGTCGTGCACGCAGCAGCGCGCGTCGTTGTTGGCCAGCTGCACCACGCTGCGC

CCCCAGCGGTTCTGGGTGATCTTGGCCCGGTCGGGGTTCTCCTTCAGCGCGCGCTGCCCGTTCTCGCTCGCC

ACATCCATCTCGATCATGTGCTCCTTCTGGATCATGGTGGTCCCGTGCAGGCACCGCAGCTTGCCCTCGGCC

TCGGTGCACCCGTGCAGCCACAGCGCGCACCCGGTGCACTCCCAGTTCTTGTGGGCGATCTGGGAAATGCGC

-continued

GTGCACGAAGCCCTGCAGGAAGCGGCCCATCATGGTGGTCAGGGTCTTGTTGCTAGTGAAGGTCAGCGGAA

TGCCGCGGTGCTCCTCGTTGATGTACAGGTGGCAGATGCGGCGGTACACCTCGCCCTGCTCGGGCATCAGC

TGGAAGTTGGCTTTCAGGTCGGTCTCCACGCGGTAGCGGTCCATCAGCATAGTCATGATTTCCATACCCTTC

TCCCAGGCCGAGACGATGGGCAGGCTCATAGGGTTCTTCACCATCATCTTAGCGCTAGCAGCCGCGGCCAG

GGGGTCGCTCTCGTCCAGGGTCTCAAAGCTCCGCTTGCCGTCCTTCTCGGTGATCCGCACCGGGGGGTAGCT

GAAGCCCACGGCCGCCAGCTCCTCCTCGGCCTGTCTTTCGTCCTCGCTGTCCTGGCTGACGTCCTGCAGGAC

CACATGCTTGGTCTTGCGGGGTTTCTTCTTGGGCGGCAGCGGCGGCGGAGATGTTGGAGATGGCGAGGGGG

AGCGCGAGTTCTCGCTCACCACTACTATCTCTTCCTCTTCTTGGTCCGAGGCCACGCGGCGGTAGGTATGTC

TCTTCGGGGGCAGAGGCGGAGGCGACGGGCTCTCGCCGCCGCGACTTGGCGGATGGCTGGCAGAGCCCCTT

CCGCGTTCGGGGGTGCGCTCCCGGCGGCGCTCTGACTGACTTCCTCCGCGGCCGGCCATTGTGTTCTCCTAG

GGAGGAACAACAAGCATGGAGACTCAGCCATCGCCAACCTCGCCATCTGCCCCCACCGCCGACGAGAAGC

AGCAGCAGCAGAATGAAAGCTTAACCGCCCCGCCGCCCAGCCCCGCCACCTCCGACGCGGCCGTCCCAGA

CATGCAAGAGATGGAGGAATCCATCGAGATTGACCTGGGCTATGTGACGCCCGCGGAGCACGAGGAGGAG

CTGGCAGTGCGCTTTTCACAAGAAGAGATACACCAAGAACAGCCAGAGCAGGAAGCAGAGAATGAGCAGA

GTCAGGCTGGGCTCGAGCATGACGGCGACTACCTCCACCTGAGCGGGGGGGAGGACGCGCTCATCAAGCA

TCTGGCCCGGCAGGCCACCATCGTCAAGGATGCGCTGCTCGACCGCACCGAGGTGCCCCTCAGCGTGGAGG

AGCTCAGCCGCGCCTACGAGTTGAACCTCTTCTCGCCGCGCGTGCCCCCCAAGCGCCAGCCCAATGGCACC

TGCGAGCCCAACCCGCGCCTCAACTTCTACCCGGTCTTCGCGGTGCCCGAGGCCCTGGCCACCTACCACATC

TTTTTCAAGAACCAAAAGATCCCCGTCTCCTGCCGCGCCAACCGCACCCGCGCCGACGCCCTTTTCAACCTG

GGTCCCGGCGCCCGCCTACCTGATATCGCCTCCTTGGAAGAGGTTCCCAAGATCTTCGAGGGTCTGGGCAG

CGACGAGACTCGGGCCGCGAACGCTCTGCAAGGAGAAGGAGGAGAGCATGAGCACCACAGCGCCCTGGTC

GAGTTGGAAGGCGACAACGCGCGGCTGGCGGTGCTCAAACGCACGGTCGAGCTGACCCATTTCGCCTACCC

GGCTCTGAACCTGCCCCCCAAAGTCATGAGCGCGGTCATGGACCAGGTGCTCATCAAGCGCGCGTCGCCCA

TCTCCGAGGACGAGGGCATGCAAGACTCCGAGGAGGGCAAGCCCGTGGTCAGCGACGAGCAGCTGGCCCG

GTGGCTGGGTCCTAATGCTAGTCCCCAGAGTTTGGAAGAGCGGCGCAAACTCATGATGGCCGTGGTCCTGG

TGACCGTGGAGCTGGAGTGCCTGCGCCGCTTCTTCGCCGACGCGGAGACCCTGCGCAAGGTCGAGGAGAAC

CTGCACTACCTCTTCAGGCACGGGTTCGTGCGCCAGGCCTGCAAGATCTCCAACGTGGAGCTGACCAACCT

GGTCTCCTACATGGGCATCTTGCACGAGAACCGCCTGGGGCAGAACGTGCTGCACACCACCTGCGCGGGG

AGGCCCGGCGCGACTACATCCGCGACTGCGTCTACCTCTACCTCTGCCACACCTGGCAGACGGGCATGGGC

GTGTGGCAGCAGTGTCTGGAGGAGCAGAACCTGAAAGAGCTCTGCAAGCTCCTGCAGAAGAACCTCAAGG

GTCTGTGGACCGGGTTCGACGAGCGCACCACCGCCTCGGACCTGGCCGACCTCATTTTCCCCGAGCGCCTC

AGGCTGACGCTGCGCAACGGCCTGCCCGACTTTATGAGCCAAAGCATGTTGCAAAACTTTCGCTCTTTCATC

CTCGAACGCTCCGGAATCCTGCCCGCCACCTGCTCCGCGCTGCCCTCGGACTTCGTGCCGCTGACCTTCCGC

GAGTGCCCCCCGCCGCTGTGGAGCCACTGCTACCTGCTGCGCCTGGCCAACTACCTGGCCTACCACTCGGA

CGTGATCGAGGACGTCAGCGGCGAGGGCCTGCTCGAGTGCCACTGCCGCTGCAACCTCTGCACGCCGCACC

GCTCCCTGGCCTGCAACCCCCAGCTGCTGAGCGAGACCCAGATCATCGGCACCTTCGAGTTGCAAGGGCCC

AGCGAAGGCGAGGGTTCAGCCGCCAAGGGGGGTCTGAAACTCACCCCGGGGCTGTGGACCTCGGCCTACT

TGCGCAAGTTCGTGCCCGAGGACTACCATCCCTTCGAGATCAGGTTCTACGAGGACCAATCCCATCCGCCC

AAGGCCGAGCTGTCGGCCTGCGTCATCACCCAGGGGGCGATCCTGGCCCAATTGCAAGCCATCCAGAAATC

CCGCCAAGAATTCTTGCTGAAAAAGGGCCGCGGGGTCTACCTCGACCCCCAGACCGGTGAGGAGCTCAACC

CCGGCTTCCCCCAGGATGCCCCGAGGAAACAAGAAGCTGAAAGTGGAGCTGCCGCCCGTGGAGGATTTGG

-continued

AGGAAGACTGGGAGAACAGCAGTCAGGCAGAGGAGGAGGAGATGGAGGAAGACTGGGACAGCACTCAGG

CAGAGGAGGACAGCCTGCAAGACAGTCTGGAGGAAGACGAGGAGGAGGCAGAGGAGGAGGTGGAAGAAG

CAGCCGCCGCCAGACCGTCGTCCTCGGCGGGGGAGAAAGCAAGCAGCACGGATACCATCTCCGCTCCGGG

TCGGGGTCCCGCTCGACCACACAGTAGATGGGACGAGACCGGACGATTCCCGAACCCCACCACCCAGACC

GGTAAGAAGGAGCGGCAGGGATACAAGTCCTGGCGGGGGCACAAAAACGCCATCGTCTCCTGCTTGCAGG

CCTGCGGGGGCAACATCTCCTTCACCCGGCGCTACCTGCTCTTCCACCGCGGGGTGAACTTTCCCCGCAACA

TCTTGCATTACTACCGTCACCTCCACAGCCCCTACTACTTCCAAGAAGAGGCAGCAGCAGCAGAAAAAGAC

CAGCAGAAAACCAGCAGCTAGAAAATCCACAGCGGCGGCAGCAGGTGGACTGAGGATCGCGGCGAACGA

GCCGGCGCAAACCCGGGAGCTGAGGAACCGGATCTTTCCCACCCTCTATGCCATCTTCCAGCAGAGTCGGG

GGCAGGAGCAGGAACTGAAAGTCAAGAACCGTTCTCTGCGCTCGCTCACCCGCAGTTGTCTGTATCACAAG

AGCGAAGACCAACTTCAGCGCACTCTCGAGGACGCCCGAGGCTCTCTTCAACAAGTACTGCGCGCTCACTCT

TAAAGAGTAGCCCGCGCCCGCCCAGTCGCAGAAAAAGGCGGGAATTACGTCACCTGTGCCCTTCGCCCTAG

CCGCCTCCACCCATCATCATGAGCAAAGAGATTCCCACGCCTTACATGTGGAGCTACCAGCCCCAGATGGG

CCTGGCCGCCGGTGCCGCCCAGGACTACTCCACCCGCATGAATTGGCTCAGCGCCGGGCCCGCGATGATCT

CACGGGTGAATGACATCCGCGCCCACCGAAACCAGATACTCCTAGAACAGTCAGCGCTCACCGCCACGCCC

CGCAATCACCTCAATCCGCGTAATTGGCCCGCCGCCCTGGTGTACCAGGAAATTCCCCAGCCCACGACCGT

ACTACTTCCGCGAGACGCCCAGGCCGAAGTCCAGCTGACTAACTCAGGTGTCCAGCTGGCGGGCGGCGCCA

CCCTGTGTCGTCACCGCCCCGCTCAGGGTATAAAGCGGCTGGTGATCCGGGGCAGAGGCACACAGCTCAAC

GACGAGGTGGTGAGCTCTTCGCTGGGTCTGCGACCTGACGGAGTCTTCCAACTCGCCGGATCGGGGAGATC

TTCCTTCACGCCTCGTCAGGCCGTCCTGACTTTGGAGAGTTCGTCCTCGCAGCCCCGCTCGGGTGGCATCGG

CACTCTCCAGTTCGTGGAGGAGTTCACTCCCTCGGTCTACTTCAACCCCTTCTCCGGCTCCCCCGGCCACTA

CCCGGACGAGTTCATCCCGAACTTCGACGCCATCAGCGAGTCGGTGGACGGCTACGATTGAAACTAATCAC

CCCCTTATCCAGTGAAATAAAGATCATATTGATGATGATTTTACAGAAATAAAAAATAATCATTTGATTTGA

AATAAAGATACAATCATATTGATGATTTGAGTTTAACAAAAAAATAAAGAATCACTTACTTGAAATCTGAT

ACCAGGTCTCTGTCCATGTTTTCTGCCAACACCACTTCACTCCCCTCTTCCCAGCTCTGGTACTGCAGGCCCC

GGCGGGCTGCAAACTTCCTCCACACGCTGAAGGGGATGTCAAATTCCTCCTGTCCCTCAATCTTCATTTTAT

CTTCTATCAGATGTCCAAAAAGCGCGTCCGGGTGGATGATGACTTCGACCCCGTCTACCCCTACGATGCAG

ACAACGCACCGACCGTGCCCTTCATCAACCCCCCCTTCGTCTCTTCAGATGGATTCCAAGAGAAGCCCCTGG

GGGTGTTGTCCCTGCGACTGGCCGACCCCGTCACCACCAAGAACGGGGAAATCACCCTCAAGCTGGGAGA

GGGGGTGGACCTCGATTCCTCGGGAAAACTCATCTCCAACACGGCCACCAAGGCCGCCGCCCCTCTCAGTT

TTTCCAACAACACCATTTCCCTTAACATGGATCACCCCTTTTACACTAAAGATGGAAAATTATCCTTACAAG

TTTCTCCACCATTAAATATACTGAGAACAAGCATTCTAAACACACTAGCTTTAGGTTTTGGATCAGGTTTAG

GACTCCGTGGCTCTGCCTTGGCAGTACAGTTAGTCTCTCCACTTACATTTGATACTGATGGAAACATAAAGC

TTACCTTAGACAGAGGTTTGCATGTTACAACAGGAGATGCAATTGAAAGCAACATAAGCTGGGCTAAAGGT

TTAAAATTTGAAGATGGAGCCATAGCAACCAACATTGGAAATGGGTTAGAGTTTGGAAGCAGTAGTACAG

AAACAGGTGTTGATGATGCTTACCCAATCCAAGTTAAACTTGGATCTGGCCTTAGCTTTGACAGTACAGGA

GCCATAATGGCTGGTAACAAAGAAGACGATAAACTCACTTTGTGGACAACACCTGATCCATCACCAAACTG

TCAAATACTCGCAGAAAATGATGCAAAACTAACACTTTGCTTGACTAAATGTGGTAGTCAAATACTGGCCA

CTGTGTCAGTCTTAGTTGTAGGAAGTGGAAACCTAAACCCCATTACTGGCACCGTAAGCAGTGCTCAGGTG

TTTCTACGTTTTGATGCAAACGGTGTTCTTTTAACAGAACATTCTACACTAAAAAAATACTGGGGGTATAGG

-continued

CAGGGAGATAGCATAGATGGCACTCCATATACCAATGCTGTAGGATTCATGCCCAATTTAAAAGCTTATCC

AAAGTCACAAAGTTCTACTACTAAAAATAATATAGTAGGGCAAGTATACATGAATGGAGATGTTTCAAAAC

CTATGCTTCTCACTATAACCCTCAATGGTACTGATGACAGCAACAGTACATATTCAATGTCATTTTCATACA

CCTGGACTAATGGAAGCTATGTTGGAGCAACATTTGGGGCTAACTCTTATACCTTCTCATACATCGCCCAAG

AATGAACACTGTATCCCACCCTGCATGCCAACCCTTCCCACCCCACTCTGTGGAACAAACTCTGAAACACA

AAATAAAATAAAGTTCAAGTGTTTTATTGATTCAACAGTTTTACAGGATTCGAGCAGTTATTTTTCCTCCAC

CCTCCCAGGACATGGAATACACCACCCTCTCCCCCCGCACAGCCTTGAACATCTGAATGCCATTGGTGATG

GACATGCTTTTGGTCTCCACGTTCCACACAGTTTCAGAGCGAGCCAGTCTCGGGTCGGTCAGGGAGATGAA

ACCCTCCGGGCACTCCCGCATCTGCACCTCACAGCTCAACAGCTGAGGATTGTCCTCGGTGGTCGGGATCA

CGGTTATCTGGAAGAAGCAGAAGAGCGGCGGTGGGAATCATAGTCCGCGAACGGGATCGGCCGGTGGTGT

CGCATCAGGCCCCGCAGCAGTCGCTGCCGCCGCCGCTCCGTCAAGCTGCTGCTCAGGGGGTCCGGGTCCAG

GGACTCCCTCAGCATGATGCCCACGGCCCTCAGCATCAGTCGTCTGGTGCGGCGGGCGCAGCAGCGCATGC

GGATCTCGCTCAGGTCGCTGCAGTACGTGCAACACAGAACCACCAGGTTGTTCAACAGTCCATAGTTCAAC

ACGCTCCAGCCGAAACTCATCGCGGGAAGGATGCTACCCACGTGGCCGTCGTACCAGATCCTCAGGTAAG

CAAGTGGTGCCCCCTCCAGAACACGCTGCCCACGTACATGATCTCCTTGGGCATGTGGCGGTTCACCACCTC

CCGGTACCACATCACCCTCTGGTTGAACATGCAGCCCCGGATGATCCTGCGGAACCACAGGGCCAGCACCG

CCCCGCCCGCCATGCAGCGAAGAGACCCCGGGTCCCGGCAATGGCAATGGAGGACCCACCGCTCGTACCC

GTGGATCATCTGGGAGCTGAACAAGTCTATGTTGGCACAGCACAGGCATATGCTCATGCATCTCTTCAGCA

CTCTCAACTCCTCGGGGGTCAAAACCATATCCCAGGGCACGGGGAACTCTTGCAGGACAGCGAACCCCGCA

GAACAGGGCAATCCTCGCACAGAACTTACATTGTGCATGGACAGGGTATCGCAATCAGGCAGCACCGGGT

GATCCTCCACCAGAGAAGCGCGGGTCTCGGTCTCCTCACAGCGTGGTAAGGGGGGCCGGCCGATACGGTG

ATGGCGGGACGCGGCTGATCGTGTTCGCGACCGTGTCATGATGCAGTTGCTTTCGGACATTTTCGTACTTGC

TGTAGCAGAACCTGGTCCGGGCGCTGCACACCGATXGCCGGCGGCGGTCTCGGCGCTTGGAACGCTCGGTG

TTGAAATTGTAAAACAGCCACTCTCTCAGACCGTGCAGCAGATCTAGGGCCTCAGGAGTGATGAAGATCCC

ATCATGCCTGATGGCTCTGATCACATCGACCACCGTGGAATGGGCCAGACCCAGCCAGATGATGCAATTTT

GTTGGGTTTCGGTGACGGCGAGCCTCGGGAACAACGATGAAGTAAATGCAAGCGGTGCGTTCCAGCATGGT

TAGTTAGCTGATCTGTAGAAAAAACAAAAATGAACATTAAACCATGCTAGCCTGGCGAACAGGTGGGTAA

ATCGTTCTCTCCAGCACCAGGCAGGCCACGGGGTCTCCGGCGCGACCCTCGTAAAAATTGTCGCTATGATT

GAAAACCATCACAGAGAGACGTTCCCGGTGGCCGGCGTGAATGATTCGACAAGATGAATACACCCCCGGA

ACATTGGCGTCCGCGAGTGAAAAAAAGCGCCCGAGGAAGCAATAAGGCACTACAATGCTCAGTCTCAAGT

CCAGCAAAGCGATGCCATGCGGATGAAGCACAAAATTCTCAGGTGCGTACAAAATGTAATTACTCCCCTCC

TGCACAGGCAGCAAAGCCCCCGATCCCTCCAGGTACACATACAAAGCCTCAGCGTCCATAGCTTACCGAGC

AGCAGCACACAACAGGCGCAAGAGTCAGAGAAAGGCTGAGCTCTAACCTGTCCACCCGCTCTCTGCTCAAT

ATATAGCCCAGATCTACACTGACGTAAAGGCCAAAGTCTAAAAATACCCGCCAAATAATCACACACGCCCA

GCACACGCCCAGAAACCGGTGACACACTCAAAAAAATACGCGCACTTCCTCAAACGCCCAAAACTGCCGT

CATTTCCGGGTTCCCACGCTACGTCATCAAAACACGACTTTCAAATTCCGTCGACCGTTAAAAACGTCACCC

GCCCCGCCCCTAACGGTCGCCCGTCTCTCAGCCAATCAGCGCCCCGCATCCCCAAATTCAAACACCTCATTT

GCATATTAACGCGCACAAAAAGTTTGAGGTATATTATTGATGATG

XXIII. Immunogenicity in the TETr-regulated Cassette Expression System

Figure 48:
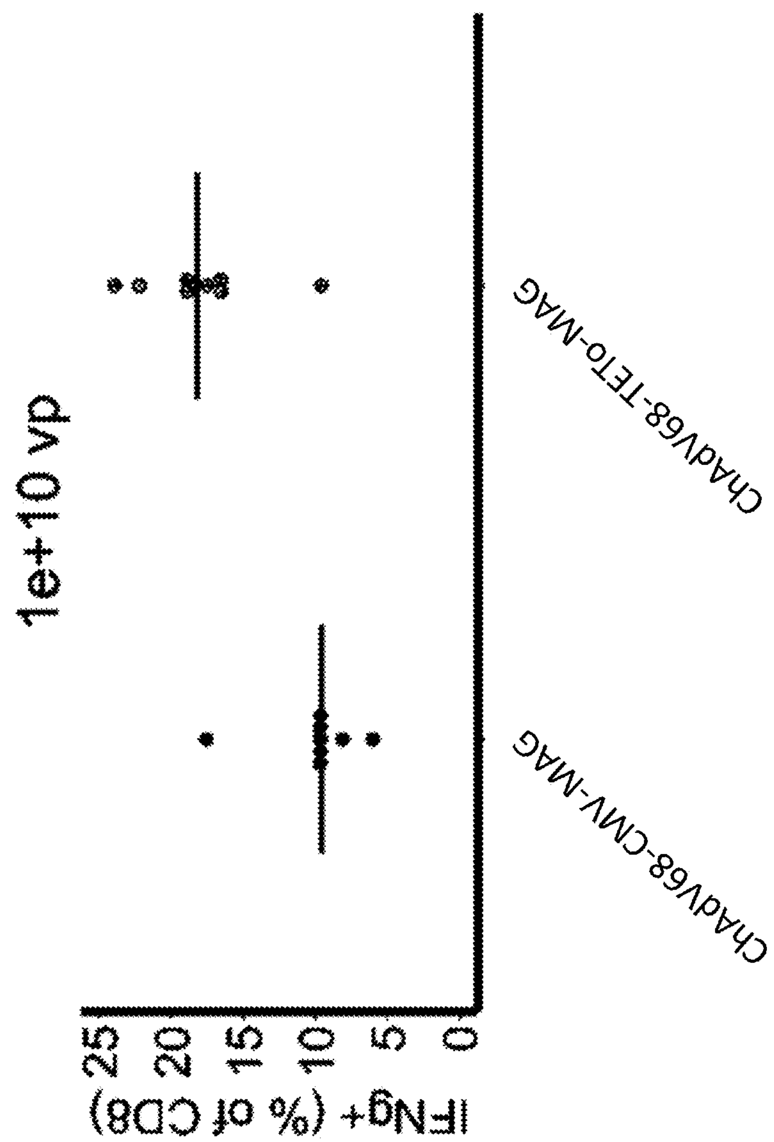
FIG. 48 shows antigen specific T-Cell responses following vaccination with regulated versus no-regulated vectors. Antigen-specific IFN-gamma production in CD8 T cells measured using ICS and results presented as antigen-specific CD8 T cells as a percentage of total CD8 T cells. Median for each group indicated by horizontal line. Balb/c mice were immunized with $1\times10^{10}$ VP of ChAdV68 vaccines expressing a model antigen cassette either under control of normal CMV promoter (ChAdV-MAG) or a TETo regulated promoter (TET-ChAdV-MAG). 12 d post vaccination spleens were harvested and single cell suspensions made.

Balb/c mice were immunized with $1\times10^{10}$ VP of ChAdV68 vaccines expressing a model antigen cassette either under control of normal CMV promoter (ChAdV-MAG) or a TETo regulated promoter (TET-ChAdV-MAG). 12 d post vaccination spleens were harvested and single cell suspensions made. Antigen-specific IFN-gamma production in CD8 T cells was measured using ICS. As shown in FIG. 48 and Table 43, in vivo efficacy was the same or better when mice were immunized with the antigen cassette expressed from the TETo regulated promoter. Thus, the regulated ChAd vector was equally potent, and potentially more so, at inducing CD8+ immune responses to the vaccine targets in vivo.

As described in greater detail above, Rhesus macaques were also immunized with ChAdV68.5WTnt.MAG25mer ("ChAdV68-CMV-MAG"; SEQ ID NO:2) or ChAdV68-E4d-CMT-MAG (SEQ ID NO:71), with each group also administered an anti-CTLA4 antibody (Ipilimumab). T cell responses were analyzed for IFN-gamma production by ELISpot following stimulation with 6 different rhesus macaque Mamu-A*01 class I epitopes. As shown in FIG. 42B and FIG. 42C, and quantified in Table 41B (ChAdV68-CMV-MAG) and Table 41C (ChAdV68-E4d-CMT-MAG), immunization with a construct featuring a "CMT" response region in E4-deleted vector background demonstrated at least equivalent immune responses, with a positive trend towards an increased response in CMT-E4-deleted vectors.

TABLE 43

% CD8+ response in ChAdV68-MAG and ChAdV68-Teto-MAG immunized mice

| ChAdV68-MAG1e10 VP | Mouse # | % CD8+ | ChAdV68-TETo-MAG 1e10 VP | Mouse # | % CD8+ |
|---|---|---|---|---|---|
| | 1 | 9.35 | | 1 | 17.58 |
| | 2 | 9.31 | | 2 | 16.88 |
| | 3 | 17.60 | | 3 | 18.93 |
| | 4 | 10.08 | | 4 | 9.59 |
| | 5 | 6.06 | | 5 | 24 |
| | 6 | 8.15 | | 6 | 16.28 |
| | 7 | 10.08 | | 7 | 18.92 |
| | 8 | 9.87 | | 8 | 22.24 |
| Median | | 9.61 | Median | | 18.25 |

XXIV. Selection of Patient Populations

One or more antigens are used to formulate a vaccine composition using a modified adenovirus, such as the E4 modified adenovirus, described herein. The vaccine is administered to a patient, e.g., to treat cancer. In certain instances the patient is selected, e.g., using a companion diagnostic or a commonly use cancer gene panel NGS assay such as FoundationOne, FoundationOne CDx, Guardant 360, Guardant OMNI, or MSK IMPACT. Exemplary patient selection criteria are described below.

Patient Selection

Patient selection for shared neoantigen vaccination is performed by consideration of tumor gene expression, somatic mutation status, and patient HLA type. Specifically, a patient is considered eligible for the vaccine therapy if:

(a) the patient carries an HLA allele predicted or known to present an epitope included in a vaccine and the patient tumor expresses a gene with the epitope sequence, or (b) the patient carries an HLA allele predicted or known to present an epitope included in a vaccine, and the patient tumor carries the mutation giving rise to the epitope sequence, or (c) Same as (b), but also requiring that the patient tumor expresses the gene with the mutation above a certain threshold (e.g., 1 TPM or 10 TPM), or (d) Same as (b), but also requiring that the patient tumor expresses the mutation above a certain threshold (e.g., at least 1 mutated read observed at the level of RNA)

(e) Same as (b), but also requiring both additional criteria in (c) and (d)

(f) Any of the above, but also optionally requiring that loss of the presenting HLA allele is not detected in the tumor Gene expression is measured at the RNA or protein level by any of the established methods including RNASeq, microarray, PCR, Nanostring, ISH, Mass spectrometry, or IHC. Thresholds for positivity of gene expression is established by several methods, including: (1) predicted probability of presentation of the epitope by the HLA allele at various gene expression levels, (2) correlation of gene expression and HLA epitope presentation as measured by mass spectrometry, and/or (3) clinical benefits of vaccination attained for patients expressing the genes at various levels. Patient selection is further extended to require positivity for greater than 1 epitope, for examples, at least 2, 3, 4 or 5 epitopes included in the vaccine.

Somatic mutational status is assessed by any of the established methods, including exome sequencing (NGS DNASeq), targeted exome sequencing (panel of genes), transcriptome sequencing (RNASeq), Sanger sequencing, PCR-based genotyping assays (e.g., Taqman or droplet digital PCR), Mass-spectrometry based methods (e.g., by Sequenom), or any other method known to those skilled in the art.

Additional new shared neoantigens are identified using any of the methods described, e.g., by mass spectrometry. These newly identified shared neoantigens are incorporated into the vaccine cassettes described herein.

Previously validated neoantigens are additionally validated as being presented by additional HLA alleles and informs neoantigen selection for the vaccine cassette and/or expands the potential treatable population.

Inclusions of a new neoantigen enables the broadening of addressable tumor type (e.g., EGFR mutated NSCLC) or inclusion of patients with a new tumor type.

Certain Sequences

Vectors, cassettes, and antibodies referred to herein are described below and referred to by SEQ ID NO.

```
Full-Length ChAdVC68 sequence "ChAdV68.5WTnt"(SEQ ID NO: 1); AC_000011.1
sequence with corresponding ATCC VR-594 nucleotides substituted at five
positions; W at position 6 = A or T
CCATCWTCAATAATATACCTCAAACTTTTTGTGCGCGTTAATATGCAAATGAGGCGTTTGAATTTGGGGAGGA

AGGGCGGTGATTGGTCGAGGGATGAGCGACCGTTAGGGGCGGGGCGAGTGACGTTTTGATGACGTGGTTGCG
```

-continued

AGGAGGAGCCAGTTTGCAAGTTCTCGTGGGAAAAGTGACGTCAAACGAGGTGTGGTTTGAACACGGAAATAC

TCAATTTTCCCGCGCTCTCTGACAGGAAATGAGGTGTTTCTGGGCGGATGCAAGTGAAAACGGGCCATTTTCG

CGCGAAAACTGAATGAGGAAGTGAAAATCTGAGTAATTTCGCGTTTATGGCAGGGAGGAGTATTTGCCGAGG

GCCGAGTAGACTTTGACCGATTACGTGGGGGTTTCGATTACCGTGTTTTTCACCTAAATTTCCGCGTACGGTGT

CAAAGTCCGGTGTTTTTACGTAGGTGTCAGCTGATCGCCAGGGTATTTAAACCTGCGCTCTCCAGTCAAGAGG

CCACTCTTGAGTGCCAGCGAGAAGAGTTTTCTCCTCCGCGCCGCGAGTCAGATCTACACTTTGAAAGATGAGG

CACCTGAGAGACCTGCCCGATGAGAAAATCATCATCGCTTCCGGGAACGAGATTCTGGAACTGGTGGTAAAT

GCCATGATGGGCGACGACCCTCCGGAGCCCCCCACCCCATTTGAGACACCTTCGCTGCACGATTTGTATGATC

TGGAGGTGGATGTGCCCGAGGACGATCCCAATGAGGAGGCGGTAAATGATTTTTTTAGCGATGCCGCGCTGC

TAGCTGCCGAGGAGGCTTCGAGCTCTAGCTCAGACAGCGACTCTTCACTGCATACCCCTAGACCCGGCAGAG

GTGAGAAAAAGATCCCCGAGCTTAAAGGGGAAGAGATGGACTTGCGCTGCTATGAGGAATGCTTGCCCCCGA

GCGATGATGAGGACGAGCAGGCGATCCAGAACGCAGCGAGCCAGGGAGTGCAAGCCGCCAGCGAGAGCTTT

GCGCTGGACTGCCCGCCTCTGCCCGGACACGGCTGTAAGTCTTGTGAATTTCATCGCATGAATACTGGAGATA

AAGCTGTGTTGTGTGCACTTTGCTATATGAGAGCTTACAACCATTGTGTTTACAGTAAGTGTGATTAAGTTGA

ACTTTAGAGGGAGGCAGAGAGCAGGGTGACTGGGCGATGACTGGTTTATTTATGTATATATGTTCTTTATATA

GGTCCCGTCTCTGACGCAGATGATGAGACCCCCACTACAAAGTCCACTTCGTCACCCCCAGAAATTGGCACAT

CTCCACCTGAGAATATTGTTAGACCAGTTCCTGTTAGAGCCACTGGGAGGAGAGCAGCTGTGGAATGTTTGGA

TGACTTGCTACAGGGTGGGGTTGAACCTTTGGACTTGTGTACCCGGAAACGCCCCAGGCACTAAGTGCCACAC

ATGTGTGTTTACTTGAGGTGATGTCAGTATTTATAGGGTGTGGAGTGCAATAAAAAATGTGTTGACTTTAAGT

GCGTGGTTTATGACTCAGOGGTGGGGACTGTGAGTATATAAGCAGGTGCAGACCTGTGTGGTTAGCTCAGAG

CGGCATGGAGATTTGGACGGTCTTGGAAGACTTTCACAAGACTAGACAGCTGCTAGAGAACGCCTCGAACGG

AGTCTCTTACCTGTGGAGATTCTGCTTCGGTGGCGACCTAGCTAGGCTAGTCTACAGGGCCAAACAGGATTAT

AGTGAACAATTTGAGGTTATTTTGAGAGAGTGTTCTGGTCTTTTTTGACGCTCTTAACTTGGGCCATCAGTCTCA

CTTTAACCAGAGGATTTCGAGAGCCCTGATTTTACTACTCCTGGCAGAACCACTGCAGCAGTAGCCTTTTTTG

CTTTTATTCTTGACAAATGGAGTCAAGAAACCCATTTCAGCAGGGATTACCAGCTGGATTTCTTAGCAGTAGC

CTGAGGATCCTGAATCTCCAGGAGAGTCCCAGGGCACGCCAACGTCGCCAGCAGCAGCAGCAGGAGGAGGA

TCAAGAAGAGAACCCGAGAGCCGGCCTGGACCCTCCGGCGGAGGAGGAGGAGTAGCTGACCTGTTTCCTGAA

CTGCGCCGGGTGCTGACTAGGTCTTCGAGTGGTCGGGAGAGGGGGATTAAGCGGGAGAGGCATGATGAGACT

AATCACAGAACTGAACTGACTGTGGGTCTGATGAGTCGCAAGCGCCCAGAAACAGTGTGGTGGCATGAGGTG

CAGTCGACTGGCACAGATGAGGTGTCGGTGATGCATGAGAGGTTTTCTCTAGAACAAGTCAAGACTTGTTGGT

TAGAGCCTGAGGATGATTGGGAGGTAGCCATCAGGAATTATGCCAAGCTGGCTCTGAGGCCAGACAAGAAGT

ACAAGATTACTAAGCTGATAAATATCAGAAATGCCTGCTACATCTCAGGGAATGGGGCTGAAGTGGAGATCT

GTCTCCAGGAAAGGGTGGCTTTCAGATGCTGCATGATGAATATGTACCCGGGAGTGGTGGGCATGGATGGGG

TTACCTTTATGAACATGAGGTTCAGGGGAGATGGGTATAATGGCACGGTCTTTATGGCCAATACCAAGCTGAC

AGTCCATGGCTGCTCCTTCTTTGGGTTTAATAACACCTGCATCGAGGCCTGGGGTCAGGTCGGTGTGAGGGGC

TGCAGTTTTTTCAGCCAACTGGATGGGGGTCGTGGGCAGGACCAAGAGTATGCTGTCCGTGAAGAAATGCTTG

TTTGAGAGGTGCCACCTGGGGGTGATGAGCGAGGGCGAAGCCAGAATCCGCCACATGCGCCTCTACCGAGACG

GGCTGCTTTGTGCTGTGCAAGGGCAATGCTAAGATCAAGCATAATATGATCTGTGGAGCCTCGGACGAGCGC

GGCTACCAGATGCTGACCTGCGCCGGCGGGAACAGCCATATGCTGGCCACCGTACATGTGGCTTCCCATGCTC

GCAAGCCCTGGCCCGAGTTCGAGCACAATGTCATGACCAGGTGCAATATGCATCTGGGGTCCCGCCGAGGCA

-continued

TGTTCATGCCCTACCAGTGCAACCTGAATTATGTGAAGGTGCTGCTGGAGCCCGATGCCATGTCCAGAGTGAG

CCTGACGGGGGTGTTTGACATGAATGTGGAGGTGTGGAAGATTCTGAGATATGATGAATCCAAGACCAGGTG

CCGAGCCTGCGAGTGCGGAGGGAAGCATGCCAGTTCCAGCCCGTGTGTGTGGATGTGACGGAGGACCTGCG

ACCCGATCATTTGGTGTTGCCCTGCACCGGGACGGAGTTCGGTTCCAGCGGGGAAGAATCTGACTAGAGTGA

GTAGTGTTCTGGGGCGGGGGAGGACCTGCATGAGGGCCAGAATAACTGAAATCTGTGCTTTTCTGTGTGTTGC

AGCAGCATGAGCGGAAGCGGCTCCTTTGAGGGAGGGGTATTCAGCCCTTATCTGACGGGGCGTCTCCCCTCCT

GGGCGGGAGTGCGTCAGAATGTGATGGGATCCACGGTGGACGGCCGGCCCGTGCAGCCCGCGAACTCTTCAA

CCCTGACCTATGCAACCCTGAGCTCTTCGTCGTTGGACGCAGCTGCCGCCGCAGCTGCTGCATCTGCCGCCAG

CGCCGTGCGCGGAATGGCCATGGGCGCCGGCTACTACGGCACTCTGGTGGCCAACTCGAGTTCCACCAATAA

TCCCGCCAGCCTGAACGAGGAGAAGCTGTTGCTGCTGATGGCCCAGCTCGAGGCCTTGACCCAGCGCCTGGG

CGAGCTGACCCAGCAGGTGGCTCAGCTGCAGGAGCAGACGCGGGCCGCGGTTGCCACGGTGAAATCCAAATA

AAAAATGAATCAATAAATAAACGGAGACGGTTGTTATTTTAACACAGAGTCTGAATCTTTATTTGATTTTTC

GCGCGCGGTAGGCCCTGGACCACCGGTCTCGATCATTGAGCACCCGGTGGATCTTTTCCAGGACCCGGTAGA

GGTGGGCTTGGATGTTGAGGTACATGGGCATGAGCCCGTCCCGGGGGTGGAGGTAGCTCCATTGCAGGGCCT

CGTGCTCGGGGGTGGTGTTGTAAATCACCCAGTCATAGCAGGGGCGCAGGGCATGGTGTTGCACAATATCTTT

GAGGAGGAGACTGATGGCCACGGGCAGCCCTTTGGTGTAGGTGTTTACAAATCTGTTGAGCTGGGAGGGATG

CATGCGGGGGGAGATGAGGTGCATCTTGGCCTGGATCTTGAGATTGGCGATGTTACCGCCCAGATCCCGCCTG

GGGTTCATGTTGTGCAGGACCACCAGCACGGTGTATCCGGTGCACTTGGGGAATTTATCATGCAACTTGGAAG

GGAAGGCGTGAAAGAATTTGGCGACGCCTTTGTGCCCGCCCAGGTTTTCCATGCACTCATCCATGATGATGGC

GATGGGCCCGTGGGCGGCGGCCTGGGCAAAGACGTTTCGGGGGTCGGAACATCATAGTTGTGGTCCTGGGT

GAGGTCATCATAGGCCATTTTAATGAATTTGGGGCGGAGGGTGCCGGACTGGGGGACAAAGGTACCCTCGAT

CCCGGGGGCGTAGTTCCCCTCACAGATCTGCATCTCCCAGGCTTTGAGCTCGGAGGGGGGGATCATGTCCACC

TGCGGGGCGATAAAGAACACGGTTTCCGGGGCGGGGGAGATGAGCTGGGCCGAAAGCAAGTTCCGGAGCAG

CTGGGACTTGCCGCAGCCGGTGGGGCCGTAGATGACCCCGATGACCGGCTGCAGGTGGTAGTTGAGGGAGAG

ACAGCTGCCGTCCTCCCGGAGGAGGGGGGCCACCTCGTTCATCATCTCGCGCACGTGCATGTTCTCGCGCACC

AGTTCCGCCAGGAGGCGCTCTCCCCCCAGGGATAGGAGCTCCTGGAGCGAGGCGAAGTTTTTCAGCGGCTTG

AGTCCGTCGGCCATGGGCATTTTGGAGAGGGTTTGTTGCAAGAGTTCCAGGCGGTCCCAGAGCTCGGTGATGT

GCTCTACGGCATCTCGATCCAGCAGACCTCCTCGTTTCGCGGGTTGGGACGGCTGCGGGAGTAGGGCACCAG

ACGATGGGCGTCCAGCGCAGCCAGGGTCCGGTCCTTCCAGGGTCGCAGCGTCCGCGTCAGGGTGGTCTCCGT

CACGGTGAAGGGGTGCGCGCCGGGCTGGGCGCTTGCGAGGGTGCGCTTCAGGCTCATCCGGCTGGTCGAAAA

CCGCTCCCGATCGGCGCCCTGCGCGTCGGCCAGGTAGCAATTGACCATGAGTTCGTAGTTGAGCGCCTCGGCC

GCGTGGCCTTTGGCGCGGAGCTTACCTTTGGAAGTCTGCCCGCAGGCGGGACAGAGGAGGGACTTGAGGGCG

TAGAGCTTGGGGGCGAGGAAGACGGACTCGGGGGCGTAGGCGTCCGCGCCGCAGTGGGCGCAGACGGTCTC

GCACTCCACGAGCCAGGTGAGGTCGGGCTGGTCGGGGTCAAAAACCAGTTTCCCGCCGTTCTTTTTGATGCGT

TTCTTACCTTTGGTCTCCATGAGCTCGTGTCCCCGCTGGGTGACAAAGAGGCTGTCCGTGTCCCCGTAGACCG

ACTTTATGGGCCGGTCCTCGAGCGGTGTGCCGCGGTCCTCCTCGTAGAGGAACCCCGCCCACTCCGAGACGAA

AGCCCGGGTCCAGGCCAGCACGAAGGAGGCCACGTGGGACGGGTAGCGGTCGTTGTCCACCAGCGGGTCCAC

CTTTTCCAGGGTATGCAAACACATGTCCCCCTCGTCCACATCCAGGAAGGTGATTGGCTTGTAAGTGTAGGCC

ACGTGACCGGGGGTCCCGGCCGGGGGGGTATAAAAGGGTGCGGGTCCCTGCTCGTCCTCACTGTCTTCCGGA

TCGCTGTCCAGGAGCGCCAGCTGTTGGGGTAGGTATTCCCTCTCGAAGGCGGGCATGACCTCGGCACTCAGGT

TGTCAGTTTCTAGAAACGAGGAGGATTTGATATTGACGGTGCCGGCGGAGATGCCTTTCAAGAGCCCCTCGTC

-continued

CATCTGGTCAGAAAAGACGATCTTTTTGTTGTCGAGCTTGGTGGCGAAGGAGCCGTAGAGGGCGTTGGAGAG

GAGCTTGGCGATGGAGCGCATGGTCTGGTTTTTTTCCTTGTCGGCGCGCTCCTTGGCGGCGATGTTGAGCTGC

ACGTACTCGCGCGCCACGCACTTCCATTCGGGGAAGACGGTGGTCAGCTCGTCGGGCACGATTCTGACCTGCC

AGCCCCGATTATGCAGGGTGATGAGGTCCACACTGGTGGCCACCTCGCCGCGCAGGGGCTCATTAGTCCAGC

AGAGGCGTCCGCCCTTGCGCGAGCAGAAGGGGGGCAGGGGGTCCAGCATGACCTCGTCGGGGGGGTCGGCA

TCGATGGTGAAGATGCCGGGCAGGAGGTCGGGGTCAAAGTAGCTGATGGAAGTGGCCAGATCGTCCAGGGC

AGCTTGCCATTCGCGCACGGCCAGCGCGCGCTCGTAGGGACTGAGGGGCGTGCCCCAGGGCATGGGATGGGT

AAGCGCGGAGGCGTACATGCCGCAGATGTCGTAGACGTAGAGGGGCTCCTCGAGGATGCCGATGTAGGTGGG

GTAGCAGCGCCCCCCGCGGATGCTGGCGCGCACGTAGTCATACAGCTCGTGCGAGGGGGCGAGGAGCCCCGG

GCCCAGGTTGGTGCGACTGGGCTTTTCGGCGCGGTAGACGATCTGGCGGAAAATGGCATGCGAGTTGGAGGA

GATGGTGGGCCTTTGGAAGATGTTGAAGTGGGCGTGGGGCAGTCCGACCGAGTCGCGGATGAAGTGGGCGTA

GGAGTCTTGCAGCTTGGCGACGAGCTCGGCGGTGACTAGGACGTCCAGAGCGCAGTAGTCGAGGGTCTCCTG

GATGATGTCATACTTGAGCTGTCCCTTTTGTTTCCACAGCTCGCGGTTGAGAAGGAACTCTTCGCGGTCCTTCC

AGTACTCTTCGAGGGGGAACCCGTCCTGATCTGCACGGTAAGAGCCTAGCATGTAGAACTGGTTGACGGCCTT

GTAGGCGCAGCAGCCCTTCTCCACGGGGAGGGCGTAGGCCTGGGCGGCCTTGCGCAGGGAGGTGTGCGTGAG

GGCGAAAGTGTCCCTGACCATGACCTTGAGGAACTGGTGCTTGAAGTCGATATCGTCGCAGCCCCCCTGCTCC

CAGAGCTGGAAGTCCGTGCGCTTCTTGTAGGCGGGGTTGGGCAAAGCGAAAGTAACATCGTTGAAGAGGATC

TTGCCCGCGCGGGGCATAAAGTTGCGAGTGATGCGGAAAGGTTGGGGCACCTCGGCCCGGTTGTTGATGACC

TGGGCGGCGAGCACGATCTCGTCGAAGCCGTTGATGTTGTGGCCCACGATGTAGAGTTCCACGAATCGCGGA

CGGCCCTTGACGTGGGGCAGTTTCTTGAGCTCCTCGTAGGTGAGCTCGTCGGGGTCGCTGAGCCCGTGCTGCT

CGAGCGCCCAGTCGGCGAGATGGGGGTTGGCGCGGAGGAAGGAAGTCCAGAGATCCACGGCCAGGGCGGTT

TGCAGACGGTCCCGGTACTGACGGAACTGCTGCCCGACGGCCATTTTTTCGGGGGTGACGCAGTAGAAGGTG

CGGGGGGTCCCCGTGCCAGCGATCCCATTTGAGCTGGAGGGCGAGATCGAGGGCGAGCTCGACGAGCCGGTCG

TCCCCGGAGAGTTTCATGACCAGCATGAAGGGGACGAGCTGCTTGCCGAAGGACCCCATCCAGGTGTAGGTT

TCCACATCGTAGGTGAGGAAGAGCCTTTCGGTGCGAGGATGCGAGCCGATGGGGAAGAACTGGATCTCCTGC

CACCAATTGGAGGAATGGCTGTTGATGTGATGGAAGTAGAAATGCCGACGGCGCGCCGAACACTCGTGCTTG

TGTTTATACAAGCGGCCACAGTGCTCGCAACGCTGCACGGGATGCACGTGCTGCACGAGCTGTACCTGAGTTC

CTTTGACGAGGAATTTCAGTGGGAAGTGGAGTCGTGGCGCCTGCATCTCGTGCTGTACTACGTCGTGGTGGTC

GGCCTGGCCCTCTTCTGCCTCGATGGTGGTCATGCTGACGAGCCCGCGCGGGAGGCAGGTCCAGACCTCGGC

GCGAGCGGGTCGGAGAGCGAGGACGAGGGCGCGCAGGCCGGAGCTGTCCAGGGTCCTGAGACGCTGCGGAG

TCAGGTCAGTGGGCAGCGGCGGCGCGCGGTTGACTTGCAGGAGTTTTTCCAGGGCGCGCGGGAGGTCCAGAT

GGTACTTGATCTCCACCGCGCCATTGGTGGCGACGTCGATGGCTTGCAGGGTCCCGTGCCCCTGGGGTGTGAC

CACCGTCCCCCGTTTCTTCTTGGGCGGCTGGGGCGACGGGGGCGGTGCCTCTTCCATGGTTAGAAGCGGCGGC

GAGGACGCGCGCCGGGCGGCAGGGGCGGCTCGGGGCCCGGAGGCAGGGGCGGCAGGGGCACGTCGGCGCCG

CGCGCGGGTAGGTTCTGGTACTGCGCCCGGAGAAGACTGGCGTGAGCGACGACGCGACGGTTGACGTCCTGG

ATCTGACGCCTTCTGGGTGAAGGCCACGGGACCCGTGAGTTTGAACCTGAAAGAGAGTTCGACAGAATCAATC

TCGGTATCGTTGACGGCGGCCTGCCGCAGGATCTCTTGCACGTCGCCCGAGTTGTCCTGGTAGGCGATCTCGG

TCATGAACTGCTCGATCTCCTCCTCTTGAAGGTCTCCGCGGCCGGCGCGCTCCACGGTGGCCGCGAGGTCGTT

GGAGATGCGGCCCATGAGCTGCGAGAAGGCGTTCATGCCCGCCTCGTTCCAGACGCGGCTGTAGACCACGAC

GCCCTCGGGATCGCgGGCGCGCATGACCACCTGGGCGAGGTTGAGCTCCACGTGGCGCGTGAAGACCGCGTA

-continued

GTTGCAGAGGCGCTGGTAGAGGTAGTTGAGCGTGGTGGCGATGTGCTCGGTGACGAAGAAATACATGATCCA

GCGGCGGAGCGGCATCTCGCTGACGTCGCCCAGCGCCTCCAAACGTTCCATGGCCTCGTAAAAGTCCACGGC

GAAGTTGAAAAACTGGGAGTTGCGCGCCGAGACGGTCAACTCCTCCTCCAGAAGACGGATGAGCTCGGCGAT

GGTGGCGCGCACCTCGCGCTCGAAGGCCCCCGGGAGTTCCTCCACTTCCTCTTCTTCCTCCTCCACTAACATCT

CTTCTACTICCTCCTCAGGCGGCAGTGGTGGCGGGGGAGGGGGCCTGCGTCGCCGGCGGCGCACGGGCAGAC

GGTCGATGAAGCGCTCGATGGTCTCGCCGCGCCGGCGTCGCATGGTCTCGGTGACGGCGCGCCCGTCCTCGCG

GGGCCCCAGCGTGAAGACGCCGCCGCGCATCTCCAGGTGGCCGGGGGGGTCCCCGTTGGGCAGGGAGAGGG

CGCTGACGATGCATCTTATCAATTGCCCCGTAGGGACTCCGCGCAAGGACCTGAGCGTCTCGAGATCCACGC

GATCTGAAAACCGCTGAACGAAGGCTTCGAGCCAGTCGCAGTCGCAAGGTAGGCTGAGCACGGTTTCTTCTG

GCGGGTCATGTTGGTTGGGAGCGGGGCGGGCGATGCTGCTGGTGATGAAGTTGAAATAGGCGGTTCTGAGAC

GGCGGATGGTGGCGAGGAGCACCAGGTCTTTGGGCCCGGCTTGCTGGATGCGCAGACGGTCGGCCATGCCCC

AGGCGTGGTCCTGACACCTGGCCAGGTCCTTGTAGTAGTCCTGCATGAGCCGCTCCACGGGCACCTCCTCCTC

GCCCGCGCGGCCGTGCATGCGCGTGAGCCCGAAGCCGCGCTGGGGCTGGACGAGCGCCAGGTCGGCGACGA

CGCGCTCGGCGAGGATGGCTTGCTGGATCTGGGTGAGGGTGGTCTGGAAGTCATTCAAAGTCGACGAAGCGGT

GGTAGGCTCCGGTGTTGATGGTGTAGGAGCAGTTGGCCATGACGGACCAGTTGACGGTCTGGTGGCCCGGAC

GCACGAGCTCGTGGTACTTGAGGCGCGAGTAGGCGCGCGTGTCGAAGATGTAGTCGTTGCAGGTGCGCACCA

GGTACTGGTAGCCGATGAGGAAGTGCGGCGGCGGCTGGCGGTAGAGCGGCCATCGCTCGGTGGCGGGGGCG

CCGGGCGCGAGGTCCTCGAGCATGGTGCGGTGGTAGCCGTAGATGTACCTGGACATCCAGGTGATGCCGGCG

GCGGTGGTGGAGGCGCGCGGGAACTCGCGGACGCGGTTCCAGATGTTGCGCAGCGGCAGGAAGTAGTTCATG

GTGGGCACGGTCTGGCCCGTGAGGCGCGCGCAGTCGTGGATGCTCTATACGGGCAAAAACGAAAGCGGTCAG

CGGCTCGACTCCGTTGGCCTGGAGGCTAAGCGAACGGGTTGGCCTGCGCGTGTACCCCGGTTCGAATCTCGAA

TCAGGCTGGAGCCGCAGCTAACGTGGTATTGGCACTCCCGTCTCGACCCAAGCCTGCACCAACCCTCCAGGAT

ACGGAGGCGGGTCGTTTTGCAACTTTTTTTTGGAGGCCGGATGAGACTAGTAAGCGCGGAAAGCGGCCGACC

GCGATGGCTCGCTGCCGTAGTCTGGAGAAGAATCGCCAGGGTTGCGTTGCGGTGTGCCCCGGTTCGAGGCCG

GCCGGATTCCGCGGCTAACGAGGGCGTGGCTGCCCCGTCGTTTCCAAGACCCCATAGCCAGCCGACTTCTCCA

GTTACGGAGCGAGCCCCTCTTTTGTTTTGTTTGTTTTTGCCAGATGCATCCCGTACTGCGGCAGATGCGCCCCC

ACCACCCTCCACCGCAACAACAGCCCCCTCCACAGCCGGCGCTTCTGCCCCCGCCCCAGCAGCAACTTCCAGC

CACGACCGCCGCGGCCGCCGTGAGCGGGGCTGGACAGAGTTATGATCACCAGCTGGCCTTGGAAGAGGGCGA

GGGGCTGGCGCGCCTGGGGGCGTCGTCGCCGGAGCGOCACCCGCGCGTGCAGATGAAAAGGGACGCTCGCG

AGGCCTACGTGCCCAAGCAGAACCTGTTCAGAGACAGGAGCGGCGAGGAGCCCGAGGAGATGCGCGCGGCC

CGGTTCCACGCGGGGCGGGAGCTGCGGCGCGGCCTGGACCGAAAGAGGGTGCTGAGGGACGAGGATTTCGA

GGCGGACGAGCTGACGGGGATCAGCCCCGCGCGCGCGCACGTGGCCGCGGCCAACCTGGTCACGGCGTACG

AGCAGACCGTGAAGGAGGAGAGCAACTTCCAAAAATCCTTCAACAACCACGTGCGCACCCTGATCGCGCGCG

AGGAGGTGACCCTGGGCCTGATGCACCTGTGGGACCTGCTGGAGGCCATCGTGCAGAACCCCACCAGCAAGC

CGCTGACGGCGCAGCTGTTCCTGGTGGTGCAGCATAGTCGGGACAACGAAGCGTTCAGGGAGGCGCTGCTGA

ATATCACCGAGCCCGAGGGCCGCTGGCTCCTGGACCTGGTGAACATTCTGCAGAGCATCGTGGTGCAGGAGC

GCGGGCTGCCGCTGTCCGAGAAGCTGGCGGCCATCAACTTCTCGGTGCTGAGTTTGGGCAAGTACTACGCTAG

GAAGATCTACAAGACCCCGTACGTGCCCATAGACAAGGAGGTGAAGATCGACGGGTTTTACATGCGCATGAC

CCTGAAAGTGCTGACCCTGAGCGACGATCTGGGGGTGTACCGCAACGACAGGATGCACCGTGCGGTGAGCGC

CAGCAGGCGGCGCGAGCTGAGCGACCAGGAGCTGATGCATAGTCTGCAGCGGGCCCTGACCGGGGCCGGGA

CCGAGGGGGAGAGCTACTTTGACATGGGCGCGGACCTGCACTGGCAGCCCAGCCGCCGGGCCTTGGAGGCGG

-continued

CGGCAGGACCCTACGTAGAAGAGGTGGACGATGAGGTGGACGAGGAGGGCGAGTACCTGGAAGACTGATGG

CGCGACCGTATTTTTGCTAGATGCAACAACAACAGCCACCTCCTGATCCCGCGATGCGGGCGGCGCTGCAGA

GCCAGCCGTCCGGCATTAACTCCTCGGACGATTGGACCCAGGCCATGCAACGCATCATGGCGCTGACGACCC

GCAACCCCGAAGCCTTTAGACAGCAGCCCCAGGCCAACCGGCTCTCGGCCATCCTGGAGGCCGTGGTGCCCT

CGCGCTCCAACCCCACGCACGAGAAGGTCCTGGCCATCGTGAACGCGCTGGTGGAGAACAAGGCCATCCGCG

GCGACGAGGCCGGCCTGGTGTACAACGCGCTGCTGGAGCGCGTGGCCCGCTACAACAGCACCAACGTGCAGA

CCAACCTGGACCGCATGGTGACCGACGTGCGCGAGGCCGTGGCCCAGCGCGAGCGGTTCCACCGCGAGTCCA

ACCTGGGATCCATGGTGGCGCTGAACGCCTTCCTCAGCACCCAGCCCGCCAACGTGCCCCGGGGCCAGGAGG

ACTACACCAACTTCATCAGCGCCCTGCGCCTGATGGTGACCGAGGTGCCCCAGAGCGAGGTGTACCAGTCCG

GGCCGGACTACTTCTTCCAGACCAGTCGCCAGGGCTTGCAGACCGTGAACCTGAGCCAGGCTTTCAAGAACTT

GCAGGGCCTGTGGGGCGTGCAGGCCCCGGTCGGGGACCGCGCGACGGTGTCGAGCCTGCTGACGCCGAACTC

GCGCCTGCTGCTGCTGCTGGTGGCCCCCTTCACGGACAGCGGCAGCATCAACCGCAACTCGTACCTGGGCTAC

CTGATTAACCTGTACCGCGAGGCCATCGGCCAGGCGCACGTGGACGAGCAGACCTACCAGGAGATCACCCAC

GTGAGCCGCGCCCTGGGCCAGGACGACCCGGGCAACCTGGAAGCCACCCTGAACTTITTGCTGACCAACCGG

TCGCAGAAGATCCCGCCCCAGTACGCGCTCAGCACCGAGGAGGAGCGCATCCTGCGTTACGTGCAGCAGAGC

GTGGGCCTGTTCCTGATGCAGGAGGGGGCCACCCCCAGCGCCGCGCTCGACATGACCGCGCGCAACATGGAG

CCCAGCATGTACGCCAGCAACCGCCCGTTCATCAATAAACTGATGGACTACTTGCATCGGGCGGCCGCCATG

AACTCTGACTATTTCACCAACGCCATCCTGAATCCCCACTGGCTCCCGCCGCCGGGGTTCTACACGGGCGAGT

ACGACATGCCCGACCCCAATGACGGGTTCCTGTGGGACGATGTGGACAGCAGCGTGTTCTCCCCCCGACCGG

GTGCTAACGAGCGCCCCTTGTGGAAGAAGGAAGGCAGCGACCGACGCCCGTCCTCGGCGCTGTCCGGCCGCG

AGGGTGCTGCCGCGGCGGTGCCCGAGGCCGCCAGTCCTTTCCCGAGCTTGCCCTTCTCGCTGAACAGTATCCG

CAGCAGCGAGCTGGGCAGGATCACGCGCCCGCGCTTGCTGGGCGAAGAGGAGTACTTGAATGACTCGCTGTT

GAGACCCGAGCGGGAGAAGAACTTCCCCAATAACGGGATAGAAAGCCTGGTGGACAAGATGAGCCGCTGGA

AGACGTATGCGCAGGAGCACAGGGACGATCCCCGGGCGTCGCAGGGGGCCACGAGCCGGGGCAGCGCCGCC

CGTAAACGCCGGTGGCACGACAGGCAGCGGGGACAGATGTGGGACGATGAGGACTCCGCCGACGACAGCAG

CGTGTTGGACTTGGGTGGGAGTGGTAACCCGTTCGCACCTGCGCCCCCGTATCGGGCGCATGATGTAAGAG

AAACCGAAAATAAATGATACTCACCAAGGCCATGGCGACCAGCGTGCGTTCGTTTCTTCTCTGTTGTTGTTGT

ATCTAGTATGATGAGGCGTGCGTACCCGGAGGGTCCTCCTCCCTCGTACGAGAGCGTGATGCAGCAGGCGAT

GGCGGCGGCGGCGATGCAGCCCCCGCTGGAGGCTCCTTACGTGCCCCCGCGGTACCTGGCGCCTACGGAGGG

GCGGAACAGCATTCGTTACTCGGAGCTGGCACCCTTGTACGATACCACCCGGTTGTACCTGGTGGACAACAA

GTCGGCGGACATCGCCGCTGAACTACCAGAACGACCACAGCAACTTCCTGACCACCGTGGTGCAGAACAA

TGACTTCACCCCCACGGAGGCCAGCACCCACACCATCAACTTTTGACGAGCGCTCGCGGTGGGGCGGCCAGCT

GAAAACCATCATGCACACCAACATGCCCAACGTGAACGAGTTCATOTACAGCAACAAGTTCAAGGCGCGGGT

GATGGTCTCCCGCAAGACCCCCAATGGGGTGACAGTGACAGAGGATTATGATGGTAGTCAGGATGAGCTGAA

GTATGAATGGGTGGAATTTGAGCTGECCCGAAGGCAACTTCTCGGTGACCATGACCATCGACCTGATGAACAA

CGCCATCATCGACAATTACTTGGCGGTGGGGCGGCAGAACGGGGTGCTGGAGAGCGACATCGGCGTGAAGTT

CGACACTAGGAACTTCAGGCTGGGCTGGGACCCCGTGACCGAGCTGGTCATGCCCGGGGTGTACACCAACGA

GGCTTTCCATCCCGATATTGTCTTGCTGCCCGGCTGCGGGGTGGACTTCACCGAGAGCCGCCTCAGCAACCTG

CTGGGCATTCGCAAGAGGCAGCCCTTCCAGGAAGGCTTCCAGATCATGTACGAGGATCTGGAGGGGGGCAAC

ATCCCCGCGCTCCTGGATGTCGACGCCTATGAGAAAAGCAAGGAGGATGCAGCAGCTGAAGCAACTGCAGCC

-continued

GTAGCTACCGCCTCTACCGAGGTCAGGGGCGATAATTTTGCAAGCGCCGCAGCAGTGGCAGCGGCCGAGGCG

GCTGAAACCGAAAGTAAGATAGTCATTCAGCCGGTGGAGAAGGATAGCAAGAACAGGAGCTACAACGTACT

ACCGGACAAGATAAACACCGCCTACCGCAGCTGGTACCTAGCCTACAACTATGGCGACCCCGAGAAGGGCGT

GCGCTCCTGGACGCTGCTCACCACCTCGGACGTCACCTGCGGCGTGGAGCAAGTCTACTGGTCGCTGCCCGAC

ATGATGCAAGACCCGGTCACCTTCCGCTCCACGCGTCAAGTTAGCAACTACCCGGTGGTGGGCGCCGAGCTCC

TGCCCGTCTACTCCAAGAGCTTCTTCAACGAGCAGGCCGTCTACTCGCAGCAGCTGCGCGCCTTCACCTCGCT

TACGCACGTCTTCAACCGCTTCCCCGAGAACCAGATCCTCGTCCGCCCGCCCGCGCCCACCATTACCACCGTC

AGTGAAAACGTTCCTGCTCTCACAGATCACGGGACCCTGCCGCTGCGCAGCAGTATCCGGGGAGTCCAGCGC

GTGACCGTTACTGACGCCAGACGCCGCACCTGCCCCTACGTCTACAAGGCCCTGGGCATAGTCGCGCCGCGC

GTCCTCTCGAGCCGCACCTTCTAAATGTCCATTCTCATCTCGCCCAGTAATAACACCGGTTGGGGCCTGCGCG

CGCCCAGCAAGATGTACGGAGGCGCTCGCCAACGCTCCACGCAACACCCCGTGCGCGTGCGCGGGCACTTCC

GCGCTCCCTGGGGCGCCCTCAAGGGCCGCGTGCGGTCGCGCACCACCGTCGACGACGTGATCGACCAGGTGG

TGGCCGACGCGCGCAACTACACCCCCGCCGCCGCGCCCGTCTCCACCGTGGACGCCOTCATCGACAGCGTGG

TGGCcGACGCGCGCCGGTACGCCCGCGCCAAGAGCCGGCGGCGGCGCATCGCCCGGCGGCACCGGAGCACCC

CCGCCATGCGCGCGGCGCGAGCCTTGCTGCGCAGGGCCAGGCGCACGGGACGCAGGGCCATGCTCAGGGCG

GCCAGACGCGCGGCTTCAGGCGCCAGCGCCGGCAGGACCCGGAGACGCGCGGCCACGGCGGCGGCAGCGGC

CATCGCCAGCATGTCCCGCCCGCGGCGAGGGAACGTGTACTGGGTGCGCGACGCCGCCACCGGTGTGCGCGT

GCCCGTGCGCACCCGCCCCCCTCGCACTTGAAGATGTTCACTTCGCGATGTTGATGTGTCCCAGCGGCGAGGA

GGATGTCCAAGCGCAAATTCAAGGAAGAGATGCTCCAGGTCATCGCGCCTGAGATCTACGGCCCTGCGGTGG

TGAAGGAGGAAAGAAAGCCCCGCAAAATCAAGCGGGTCAAAAAGGACAAAAAGGAAGAAGAAAGTGATGT

GGACGGATTGGTGGAGTTTGTGCGCGAGTTCGCCCCCCGGCGGCGCGTGCAGTGGCGCGGGCGGAAGGTGCA

ACCGGTGCTGAGACCCGGCACCACCGTGGTCTTCACGCCCGGCGAGCGCTCCGGCACCGCTTCCAAGCGCTCC

TACGACGAGGTGTACGGGGATGATGATATTCTGGAGCAGGCGGCCGAGCGCCTGGGCGAGTTTGCTTACGGC

AAGCGCAGCCGTTCCGCACCGAAGGAAGAGGCGGTGTCCATCCCGCTGGACCACGGCAACCCCACGCCGAGC

CTCAAGCCCGTGACCTTGCAGCAGGTGCTGCCGACCGCGGCGCCGCGCCGGGGGTTCAAGCGCGAGGGCGAG

GATCTGTACCCCACCATGCAGCTGATGGTGCCCAAGCGCCAGAAGCTGGAAGACGTGCTGGAGACCATGAAG

GTGGACCCGGACGTGCAGCCCGAGGTCAAGGTGCGGCCCATCAAGCAGGTGGCCCCGGGCCTGGGCGTGCAG

ACCGTOGACATCAAGATTCCCACGGAGCCCATGOAAACGCAGACCGAGCCCATGATCAAGCCCAGCACCAGC

ACCATGGAGGTGCAGACGGATCCCTGGATGCCATCGGCTCCTAGTCGAAGACCCCGGCGCAAGTACGGCGCG

GCCAGCCTGCTGATGCCCAACTACGCGCTGCATCCTTCCATCATCCCCACGCCGGGCTACCGCGGCACGCGCT

TCTACCGCGGTCATACCAGCAGCCGCCGCCGCAAGACCACCACTCGCCGCCGCCGTCGCCGCACCGCCGCTG

CAACCACCCCTGCCGCCCTGGTGCGGAGAGTGTACCGCCGCGGCCGCGCACCTCTGACCCTGCCGCGCGCGC

GCTACCACCCGAGCATCGCCATTTAAACTTTCGCCtGCTTTGCAGATCAATGGCCCTCACATGCCGCCTTCGCG

TTCCCATTACGGGCTACCGAGGAAGAAAACCGCGCCGTAGAAGGCTGGCGGGGAACGGGATGCGTCGCCACC

ACCACCGGCGGCGGCGCGCCATCAGCAAGCGGTTGGGGGGAGGCTTCCTGCCCGCGCTGATCCCCATCATCG

CCGCGGCGATCGGGGCGATCCCCGGCATTGCTTCCGTGGCGGTGCAGGCCTCTCAGCGCCACTGAGACACAC

TTGGAAACATCTTGTAATAAACCaATGGACTCTGACGCTCCTGGTCCTGTGATGTGTTTTCGTAGACAGATGGA

AGACATCAATTTTTCGTCCCTGGCTCCGCGACACGGCACGCGGCCGTTCATGGGCACCTGGAGCGACATCGGC

ACCAGCCAACTGAACGGGGGCGCCTTCAATTGGAGCAGTCTCTGGAGCGGGCTTAAGAATTTCGGGTCCACG

CTTAAAACCTATGGCAGCAAGGCGTGGAACAGCACCACAGGGCAGGCGCTGAGGGATAAGCTGAAAGAGCA

GAACTTCCAGCAGAAGGTGGTCGATGGGCTCGCCTCGGGCATCAACGGGGTGGTGGACCTGGCCAACCAGGC

-continued

CGTGCAGCGGCAGATCAACAGCCGCCTGGACCCGGTGCCGCCCGCCGGCTCCGTGGAGATGCCGCAGGTGGA

GGAGGAGCTGCCTCCCCTGGACAAGCGGGGCGAGAAGCGACCCCGCCCCGATGCGGAGGAGACGCTGCTGA

CGCACACGGACGAGCCGCCCCCGTACGAGGAGGCGGTGAAACTGGGTCTGCCCACCACGCGGCCCATCGCGC

CCCTGGCCACCGGGGTGCTGAAACCCGAAAAGCCCGCGA.CCCTGGACTTGCCTCCTCCCCAGCCTTCCCGCCC

CTCTACAGTGGCTAAGCCCCTGCCGCCGGTGGCCGTGGCCCGCGCGCGACCCGGGGGCACCGCCCGCCCTCA

TGCGAACTGGCAGAGCACTCTGAACAGCATCGTGGGTCTGGGAGTGCAGAGTGTGAAGCGCCGCCGCTGCTA

TTAAACCTACCGTAGCGCTTAACTTGCTTGTCTGTGTGTGTATGTATTATGTCGCCGCCGCCGCTGTCCACCAG

AAGGAGGAGTGAAGAGOCGCGTCOCCGAGTTGCAAGATGGCCACCCCATCGATGCTGCCCCAGTGGGCGTAC

ATGCACATCGCCGGACAGGACGCTTCGGAGTACCTGAGTCCGGGTCTGGTGCAGTTTGCCCGCGCCACAGAC

ACCTACTTCAGTCTGGGGAACAAGTTTAGGAACCCCACGGTGGCGCCCACGCACGATGTGACCACCGACCGC

AGCCAGCGGCTGACGCTGCTTCGTGCCCGTGGACCGCGAGGACAACACCTACTCGTACAAAGTGCGCTAC

ACGCTGGCCGTGGGCGACAACCGCGTGCTGGACATGGCCAGCACCTACTTTGACATCCGCGGCGTGCTGGAT

CGGGGCCCTAGCTTCAAACCCTACTCCGGCACCGCCTACAACAGTCTGGCCCCCAAGGGAGCACCCAACACT

TGTCAGTGGACATATAAAGCCGATGGTGAAACTGCCACAGAAAAAACCTATACATATGGAAATGCACCCGTG

CAGGGCATTAACATCACAAAAGATGGTATTCAACTTGGAACTGACACCGATGATCAGCCAATCTACGCAGAT

AAAACCTATCAGCCTGAACCTCAAGTGGGTGATGCTGAATGGCATGACATCACTGGTACTGATGAAAAGTAT

GGAGGCAGAGCTCTTAAGCCTGATACCAAAATGAAGCCTTGTTATGGTTCTTTTGCCAAGCCTACTAATAAAG

AAGGAGGTCAGGCAAATGTGAAAACAGGAACAGGCACTACTAAAGAATATGACATAGACATGGCTTTCTTTG

ACAACAGAAGTGCGGCTGCTGCTGGCCTAGCTCCAGAAATTGTTTTGTATACTGAAAATGTGGATTTGGAAAC

TCCAGATACCCATATTGTATACAAAGCAGGCACAGATGACAGCAGCTCTTCTATTAATTTGGGTCAGCAAGCC

ATGCCCAACAGACCTAACTACATTGGTTTCAGAGACAACTTTATCGGGCTCATGTACTACAACAGCACTGGCA

ATATGGGGGTGCTGGCCGGTCAGGCTTCTCAGCTGAATGCTGTGGTTGACTTGCAAGACAGAAACACCGAGC

TGTCCTACCAGCTCTTGCTTGACTCTCTGGGTGACAGAACCCGGTATTTCAGTATGTGGAATCAGGCGGTGGA

CAGCTATGATCCTGATGTGCGCATTATTGAAAATCATGGTGTTGGAGGATGAACTTCCCAACTATTGTTTCCCT

CTGGATGCTGTGGCAGAACAGATACTTATCAGGGAATTAAGGCTAATGGAACTGATCAAACCACATGGACC

AAAGATGACAGTGTCAATGATGCTAATGAGATAGGCAAGGGTAATCCATTCGCCATGGAAATCAACATCCAA

GCCAACCTGTGGAGGAACTTCCTCTACGCCAACGTGGCCCTGTACCTGCCCGACTCTTACAAGTACACGCCGG

CCAATGTTACCCTGCCCACCAACACCAACACCTACGATTACATGAACGGCCGGGTGGTGGCGCCCTCGCTGGT

GGACTCCTACATCAACATCGGGGCGCGCTGGICGCTGGATCCCATGGACAACGTGAACCCCTTCAACCACCA

CCGCAATGCGGGGCTGCGCTACCGCTCCATGCTCCTGGGCAACGGGCGCTACGTGCCCTTCCACATCCAGGTG

CCCCAGAAATTTTTCGCCATCAAGAGCCTCCTGCTCCTGCCCGGGTCCTACACCTACGAGTGGAACTTCCGCA

AGGACGTCAACATGATCCTGCAGAGCTCCCTCGGCAACGACCTGCGCACGGGGCCTCCATCTCCTTCAC

CAGCATCAACCTCTACGCCACCTTCTTCCCCATGGCGCACAACACGGCCTCCACGCTCGAGGCCATGCTGCGC

AACGACACCAACGACCAGTCCTTCAACGACTACCTCTCGGCGGCCAACATGCTCTACCCCATCCCGGCCAACG

CCACCAACGTGCCCATCTCCATCCCCTCGCGCAACTGGGCCGCCTTCCGCGGCTGGTCCTTCACGCGTCTCAA

GACCAAGGAGACGCCCTCGCTGGGCTCCGGGTTCGACCCCTACTTCGTCTACTCGGGCTCCATCCCCTACCTC

GACGGCACCTTCTACCTCAACCACACCTTCAAGAAGGTCTCCATCACCTICGACTCCTCCGTCAGCTGGCCCG

GCAACGACCGGCTCCTGACGCCCAACGAGTTCGAAATCAAGCGCACCGTCGACGGCGAGGGCTACAACGTGG

CCCAGTGCAACATGACCAAGGACTGGTTCCTGGTCCAGATGCTGGCCCACTACAACATCGGCTACCAGGCTT

CTACGTGCCCGAGGGCTACAAGGACCGCATGTACTCCTTCTTCCGCAACTTCCAGCCCATGAGCCGCCAGGTG

-continued

```
GTGGACGAGGTCAACTACAAGGACTACCAGGCCGTCACCCTGGCCTACCAGCACAACAACTCGGGCTTCGTC

GGCTACCTCGCGCCCACCATGCGCCAGGGCCAGCCCTACCCCGCCAACTACCCCTACCCGCTCATCGGCAAGA

GCGCCGTCACCAGCGTCACCCAGAAAAAGTTCCTCTGCGACAGGGTCATGTGGCGCATCCCCTTCTCCAGCAA

CTTCATGTCCATGGGCGCGCTCACCGACCTCGGCCAGAACATGCTCTATGCCAACTCCGCCCACGCGCTAGAC

ATGAATTTCGAAGTCGACCCCATGGATGAGTCCACCCTTCTCTATGTTGTCTTCGAAGTCTTCGACGTCGTCCG

AGTGCACCAGCCCCACCGCGGCGTCATCGAGGCCGTCTACCTGCGCACCCCCTTCTCGCCGGTAACGCCACC

ACCTAAGCTCTTGCTTCTTGCAAGCCATGGCCGCGGGCTCCGGCGAGCAGGAGCTCAGGGCCATCATCCGCG

ACCTGGGCTGCGGGCCCTACTTCCTGGGCACCTTCGATAAGCGCTTCCCGGGATTCATGGCCCCGCACAAGCT

GGCCTGCGCCATCGTCAACACGGCCGGCCGCGAGACCGGGGGCGAGCACTGGCTGGCCTTCGCCTGGAACCC

GCGCTCGAACACCTGCTACCTCTTCGACCCCTTCGGGTTCTCGGACGAGCGCCTCAAGCAGATCTACCAGTTC

GAGTACGAGGGCCTGCTGCGCCGCAGCGCCCTGGCCACCGAGGACCGCTGCGTCACCCTGGAAAAGTCCACC

CAGACCGTGCAGGGTCCGCGCTCGGCCGCCTGCGGGCTCTTCTGCTGCATGTTCCTGCACGCCTTCGTGCACT

GGCCCGACCGCCCCATGGACAAGAACCCCACCATGAACTTGCTGACGGGGGTGCCCAACGGCATGCTCCAGT

CGCCCCAGGTGGAACCCACCCTGCGCCGCAACCAGGAGGCGCTCTACCGCTTCCTCAACTCCCACTCCGCCTA

CTTTCGCTCCCACCGCGCGCGCATCGAGAAGGCCACCGCCTTCGACCGCATGAATCAAGACATGTAAACCGT

GTGTGTATGTTAAATGTCTTTAATAAACAGCACTTTCATGTTACACATGCATCTGAGATGATTTATTTAGAAAT

CGAAAGGGTTCTGCCGGGTCTCGGCATGGCCCGCGGGCAGGGACACGTTGCGGAACTGGTACTTGGCCAGCC

ACTTGAACTCGGGGATCAGCAGTTTGGGCAGCGGGGTGTCGGGGAAGGAGTCGGTCCACAGCTTCCGCGTCA

GTTGCAGGGCGCCCAGCAGGTCGGGCGCGGAGATCTTGAAATCGCAGTTGGGACCCGCGTTCTGCGCGCGGG

AGTTGCGGTACACGGGGTTGCAGCACTGGAACACCATCAGGGCCGGGTGCTTCACGCTCGCCACCACCGTCG

CGTCGGTGATGCTCTCCACGTCGAGGTCCTCGGCGTTGGCCATCCCGAAGGGGGTCATCTTGCAGGTCTGCCT

TCCCATGGTGGGCACGCACCCGGGCTTGTGGTTGCAATCGCAGTGCAGGGGGATCAGCATCATCTGGGCCTG

GTCGGCGTTCATCCCCGGGTACATGGCCTTCATGAAAGCCTCCAATTGCCTGAACGCCTGCTGGGCCTTGGCT

CCCTCGGTGAAGAAGACCCCGCAGGACTTGCTAGAGAACTGGTTGGTGGCGCACCCGGCGTCGTGCACGCAG

CAGCGCGCGTCGTTGTTGGCCAGCTGCACCACGCTGCGCCCCCAGCGGTTCTGGGTGATCTTGGCCCGGTCGG

GGTTCTCCTTCAGCGCGCGCTGCCCGTTCTCGCTCGCCACATCCATCTCGATCATGTGCTCCTTCTGGATCATG

GTGGTCCCGTGCAGGCACCGCAGCTTGCCCTCGGCCTCGGTGCACCCGTGCAGCCACAGCGCGCACCCGGTG

CACTCCCAGTTCTTGTGGGCGATCTGGGAATGCGCGTGCACGAAGCCCTGCAGGAAGCGGCCCATCATGGTG

GTCAGGGTCTTGTTGCTAGTGAAGGTCAGCGGAATGCCGCGGTGCTCCTCGTTGATGTACAGGTGGCAGATGC

GGCGGTACACCTCGCCCTGCTCGGGCATCAGCTGGAAGTTGGCTTTCAGGTCGGTCTCCACGCGGTAGCGGTC

CATCAGCATAGTCATGATITCCATACCCTTCTCCCAGGCCGAGACGATGGGCAGGCTCATAGGGTTCTTCACC

ATCATCTTAGCGCTAGCAGCCGCGGCCAGGGGGTCGCTCTCGTCCAGGGTCTCAAAGCTCCGCTTGCCGTCCT

TCTCGGTGATCCGCACCGGGGGGTAGCTGAAGCCCACGGCCGCCAGCTCCTCCTCGGCCTGTCTTTCGTCCTC

GCTGTCCTGGCTGACGTCCTGCAGGACCACATGCTTGGTCTTGCGGGGTTTCTTCTTGGGCGGCAGCGGCGGC

GGAGATGTTGGAGATGGCGAGGGGGAGCGCGAGTTCTCGCTCACCACTACTATCTCTTCCTCTTCTTGGTCCG

AGGCCACGCGGCGGTAGGTATGTCTCTTCGGGGGCAGAGGCGGAGGCGACGGGTCTCGCCGCCGCGACTTG

GCGGATGGCTGGCAGAGCCCCTTCCGCGTTCGGGGGTGCGCTCCCGGCGGCGCTCTGACTGACTTCCTCCGCG

GCCGGCCATTGTGTTCTCCTAGGGAGGAACAACAAGCATGGAGACTCAGCCATCGCCAACCTCGCCATCTGC

CCCCACCGCCGACGAGAAGCAGCAGCAGCAGAATGAAAGCTTAACCGCCCCGCCGCCCAGCCCCGCCACCTC

CGACGCGGCCGTCCCAGACATGCAAGAGATGGAGGAATCCATCGAGATTGACCTGGGCTATGTGACGCCCGC

GGAGCACGAGGAGGAGCTGGCAGTGCGCTTTTCACAAGAAGAGATACACCAAGAACAGCCAGAGCAGGAAG
```

-continued

CAGAGAATGAGCAGAGTCAGGCTGGGCTCGAGCATGACGGCGACTACCTCCACCTGAGCGGGGGGGAGGAC

GCGCTCATCAAGCATCTTGGCCCGGCAGGCCACCATCGTCAAGGATGCGCTGCTCGACCGCACCGAGGTGCCC

CTCAGCGTGGAGGAGCTCAGCCGCGCCTACGAGTTGAACCTCTTCTCGCCGCGCGTGCCCCCCAAGCGCCAGC

CCAATGGCACCTGCGAGCCCAACCCGCGCCTCAACTTCTACCCGGTCTTCGCGGTGCCCGAGGCCCTGGCCAC

CTACCACATCTTTTTCAAGAACCAAAAGATCCCCGTCTCCTGCCGCGCCAACCGCACCCGCGCCGACGCCCTT

TTCAACCTGGGTCCCGGCGCCCGCCTACCTGATATCGCCTCCTTGGAAGAGGTTCCCAAGATCTTCGAGGGTC

TGGGCAGCGACGAGACTCGGGCCGCGAACGCTCTGCAAGGAGAAGGAGGAGAGCATGAGCACCACAGCGCC

CTGGTCGAGTTGGAAGGCGACAACGCGCGGCTGGCGGTGCTCAAACGCACGGTCGAGCTGACCCATTTCGCC

TACCCGGCTCTGAACCTGCCCCCCAAAGTCATGAGCGCGGTTCATGGACCAGGTGCTCATCAAGCGCGCGTCG

CCCATCTCCGAGGACGAGGGCATGCAAGACTCCGAGGAGGGCAAGCCCGTGGTCAGCGACGAGCAGCTGGC

CCGGTGGCTGGGTCCTAATGCTAGTCCCCAGAGTTTGGAAGAGCGGCGCAAACTCATGATGGCCGTGGTCCT

GGTGACCGTGGAGCTGGAGTGCCTGCGCCGCTTCTTCGCCGACGCGGAGACCCTGCGCAAGGTCGAGGAGAA

CCTGCACTACCTCTTCAGGCACGGGTTCGTGCGCCAGGCCTGCAAGATCTCCAACGTGGAGCTGACCAACCTG

GTCTCCTACATGGGCATCTTGCACGAGAACCGCCTGGGGCAGAACGTGCTGCACACCACCCTGCGCGGGGAG

GCCCGGCGCGACTACATCCGCGACTGCGTCTACCTCTACCTCTGCCACACCTGGCAGACGGGCATGGGCGTGT

GGCAGCAGTGTCTGGAGGAGCAGAACCTGAAAGAGCTTCTGCAAGCTTCCTGCAGAAGAACTCAAGGGTCTGT

GGACCGGGITCGACGAGCGCACCACCGCCTCGGACCTGGCCGACCTCATTTTCCCCGAGCGCCTCAGGCTGAC

GCTGCGCAACGGCCTGCCCGACTTTATGAGCCAAAGCATGTTGCAAAACTTTCGCTCTTTCATCCTCGAACGC

TCCGGAATCCTGCCCGCCACCTGCTCCGCGCTGCCCTCGGACTTCGTGCCGCTGACCTTCCGCGAGTGCCCCC

CGCCGCTGTGGAGCCACTGCTACCTGCTGCGCCTGGCCAACTACCTGGCCTACCACTCGGACGTGATCGAGGA

CGTCAGCGGCGAGGGCCTGCTCGAGTGCCACTGCCGCTGCAACCTCTGCACGCCGCACCGCTCCCTGGCCTGC

AACCCCCAGCTGCTGAGCGAGACCCAGATCATCGGCACCTTCGAGTTGCAAGGGCCCAGCGAAGGCGAGGGT

TCAGCCGCCAAGGGGGGTCTGAAACTCACCCCGGGGCTGTGGACCTCGGCCTACTTGCGCAACUTCGTGCCC

GAGGACTACCATCCCTTCGAGATCAGGTTCTACGAGGACCAATCCCATCCGCCCAAGGCCGAGCTGTCGGCCT

GCGTCATCACCCAGGGGGCGATCCTGGCCCAATTGCAAGCCATCCAGAAATCCCGCCAAGAATTCTTGCTGA

AAAAGGGCCGCGGGGTCTACCTCGACCCCCAGACCGGTGAGGAGCTCAACCCCGGCTTCCCCCAGGATGCCC

CGAGGAAACAAGAAGCTGAAAGTGGAGCTGCCGCCCGTGGAGGATTTGGAGGAAGACTGGGAGAACAGCAG

TCAGGCAGAGGAGGAGGAGATGGAGGAAGACTGGGACAGCACTCAGGCAGAGGAGGACAGCCTGCAAGAC

AGTCTGGAGGAAGACGAGGAGGAGGCAGAGGAGGAGGTGGAAGAAGCAGCCGCCGCCAGACCGTCGTCCTC

GGCGGGGGAGAAAGCAAGCAGCACGGATACCATCTCCGCTCCGGGTCGGGGTCCCGCTCGACCACACAGTAG

ATGGGACGAGACCGGACGATTCCCGAACCCCACCACCCAGACCGGTAAGAAGGAGCGGCAGGGATACAAGT

CCTGGCGGGGGCACAAAAACGCCATCGTCTCCTGCTTGCAGGCCTGCGGGGGCAACATCTCCTTCACCCGGC

GCTACCTGCTCTTCCACCGCGGGGTGAACTTTCCCCGCAACATCTTGCATTACTACCGTCACCTCCACAGCCCC

TACTACTTCCAAGAAGAGGCAGCAGCAGCAGAAAAAGACCAGCAGAAAACCAGCAGCTAGAAAATCCACAG

CGGCGGCAGCAGGTGGACTGAGGATCGCGGCGAACGAGCCGGCGCAAACCCGGGAGCTGAGGAACCGGATC

TTTCCCACCCTCTATGCCATCTTCCAGCAGAGTCGGGGGCAGGAGCAGGAACTGAAAGTCAAGAACCGTTCTC

TGCGCTCGCTCACCCGCAGTTGTCTGTATCACAAGAGCGAAGACCAACTTCAGCGCACTCTCGAGGACGCCG

AGGCTTCTCTTCAACAAGTACTGCGCGCTCACTCTTAAAGAGTAGCCCGCGCCCGCCCAGTCGCAGAAAAAGG

CGGGAATTACGTCACCTGTGCCCTTCGCCCTAGCCGCCTCCACCCATCATCATGAGCAAAGAGATTCCCACGC

CTTACATGTGGAGCTACCAGCCCCAGATGGGCCTGGCCGCCGGTGCCGCCCAGGACTACTCCACCCGCATGA

-continued

ATTGGCTCAGCGCCGGGCCCGCGATGATCTCACGGGTGAATGACATCCGCGCCCACCGAAACCAGATACTCC

TAGAACAGTCAGCGCTCACCGCCACGCCCCGCAATCACCTCAATCCGCGTAATTGGCCCGCCGCCCTGGTGTA

CCAGGAAATTCCCCAGCCCACGACCGTACTACTTCCGCGAGACGCCCAGGCCGAAGTCCAGCTGACTAACTC

AGGTGTCCAGCTGGCGGGCGGCGCCACCCTGTGTCGTCACCGCCCCGCTCAGGGTATAAAGCGGCTGGTGAT

CCGGGGCAGAGGCACACAGCTTCAACGACGAGGTGGTGAGCTCTTCGCTGGGTCTGCGACCTGACGGAGTCTT

CCAACTCGCCGGATCGGGGAGATCTTCCTTCACGCCTCGTCAGGCCGTCCTGACTTTGGAGAGTTCGTCCTCG

CAGCCCCGCTCGGGTGGCATCGGCACTCTCCAGTTCGTGGAGGAGTTCACTCCCTCGGTCTACTTCAACCCCT

TCTCCGGCTCCCCCGGCCACTACCCGGACGAGTTCATCCCGAACTTCGACGCCATCAGCGAGTCGGTGGACGG

CTACGATTGAATGTCCCATGGTGGCGCAGCTGACCTAGCTCGGCTTCGACACCTGGACCACTGCCGCCGCTTC

CGCTGCTTCGCTCGGGATCTCGCCGAGTTTGCCTACTTTGAGCTGCCCGAGGAGCACCCTCAGGGCCCGGCCC

ACGGAGTGCGATCGTCGTCGAAGGGGGCCTCGACTCCCACCTGCTTCGGATCTTCAGCCAGCGTCCGATCCT

GGTCGAGCGCGAGCAAGGACAGACCCTTCTGACTCTGTACTGCATCTGCAACCACCCCGGCCTGCATGAAAG

TCTTTGTTGTCTGCTGTGTACTGAGTATAATAAAAGCTGAGATCAGCGACTACTCCGGACTTCCGTGTGTTCCT

GAATCCATCAACCAGTCTTTGTTCTTCACCGGGAACGAGACCGAGCTCCAGCTCCAGTGTAAGCCCCACAAGA

AGTACCTCACCTGGCTGTTCCAGGGCTCCCCGATCGCCGTTGTCAACCACTGCGACAACGACGGAGTCCTGCT

GAGCGGCCCTGCCAACCTTACTITTTCCACCCGCAGAAGCAAGCTCCAGCTCTTCCAACCCTTCCTCCCCGGG

ACCTATCAGTGCGTCTCGGGACCCTGCCATCACACCTTCCACCTGATCCCGAATACCACAGCGTCGCTCCCCG

CTACTAACAACCAAACTAACCTCCACCAACGCCACCGTCGCGACCTTTCTGAATCTAATACTACCACCCACAC

CGGAGGTGAGCTTCCGAGGTCAACCAACCTCTGGGATTTACTACGGCCCCTGGGAGGTGGTTGGGTTAATAGC

GCTAGGCCTAGTTGCGGGTGGGCTTTTGGTTCTCTGCTACCTATACCTCCCTTGCTGTTCGTACTTAGTGGTGC

TGTGTTGCTGGTTTAAGAAATGGGGAAGATCACCCTAGTGAGCTGCGGTGCGCTGGFGGCGGTGTTGCTTTCG

ATTGTGGGACTGGGCGGTGCGGCTGTAGTGAAGGAGAAGGCCGATCCCTGCTTGCATTTCAATCCCAACAAA

TGCCAGCTGAGTTTTCAGCCCGATGGCAATCGGTGCGCGGTACTGATCAAGTGCGGATGGGAATGCGAGAAC

GTGAGAATCGAGTACAATAACAAGACTCGGAACAATACTCTCGCGTCCGTGTGGCAGCCCGGGGACCCCGAG

TGGTACACCGTCTCTGTCCCCGGTGCTGACGGCTCCCCGCGCACCGTGAATAATACTTTCATTTTTGCGCACAT

GTGCGACACGGTCATGTGGATGAGCAAGCAGTACGATATGTGGCCCCCCACGAAGGAGAACATCGTGGTCTT

CTCCATCGCTTACAGCCTGTGCACGGCGCTAATCACCGCTATCGTGTGCCTGAGCATTCACATGCTCATCGCT

ATTCGCCCCAGAAATAATGCCGAAAAAGAAAAACAGCCATAACGTTTTTTTTCACACCTTTTTCAGACCATGG

CCTCTGTTAAATTTTTGCTTTTATTTGCCAGTCTCATTGCCGTCATTCATGGAATGAGTAATGAGAAAATTACT

ATTTACACTGGCACTAATCACACATTGAAAGGTCCAGAAAAAGCCACAGAAGTTTCATGGTATTGTTATTTTA

ATGAATCAGATGTATCTACTGAACTCTGTGGAAACAATAACAAAAAAAATGAGAGCATTACTCTCATCAAGT

TTCAATGTGGATCTGACTTAACCCTAATTAACATCACTAGAGACTATGTAGGTATGTATTATGGAACTACAGC

AGGCATTTCGGACATGGAATTTTATCAAGTTTCTGTGTCTGAACCCACCACGCCTAGAATGACCACAACCACA

AAAACTACACCTGTTACCACTATGCAGCTCACTACCAATAACATTTTTGCCATGCGTCAAATGGTCAACAATA

GCACTCAACCCACCCCACCCAGTGAGGAAATTCCCAAATCCATGATTGGCATTATTGTTGCTGTAGTTGGTGTG

CATGTTGATCATCGCCTTGTGCATGGTGTACTATGCCTTCTGCTACAGAAAGCACAGACTGAACGACAAGCTG

GAACACTTACTAAGTGTTGAATTTTAATTTTTTAGAACCATGAAGATCCTAGGCCTTTTAATTTTTTCTATCAT

TACCTCTGCTCTATGCAATTCTGACAATGAGGACGTTACTGTCGTTGTCGGATCAAATTATACACTGAAAGGT

CCAGCGAAGGGTATGCTTTCGTGGTATTGCTATTTTGGATCTGACACTACAGAAACTGAATTATGCAATCTTA

AGAATGGCAAAATTCAAAATTCTAAAATTAACAATTATATATGCAATGGTACTGATCTGATACTCCTCAATAT

CACGAAATCATATGCTGGCAGTTACACCTGCCCTGGAGATGATGCTGACAGTATGATTTTTTACAAAGTAACT

-continued

GTTGTTGATCCCACTACTCCACCTCCACCCACCACAACTACTCACACCACACACACAGATCAAACCGCAGCAG

AGGAGGCAGCAAAGTTAGCCTTGCAGGTCCAAGACAGTTCATTTGTTGGCATTACCCCTACACCTGATCAGCG

GTGTCCGGGGCTGCTAGTCAGCGGCATTGTCGGTGTGCTTTCGGGATTAGCAGTCATAATCATCTGCATGTTC

ATTTTTGCTTGCTGCTATAGAAGGCTTTACCGACAAAAATCAGACCCACTGCTGAACCTCTATGTTTAATTTTT

TCCAGAGTCATGAAGGCAGTTAGCGCTCTAGTTTTTTGTTCTTTGATTGGCATTGTTTTTTGCAATCCTATTCCT

AAAGTTAGCTTTATTAAAGATGTGAATGTTACTGAGGGGGGCAATGTGACACTGGTAGGTGTAGAGGGTGCT

GAAAACACCACCTGGACAAAATACCACCTCAATGGGTGGAAAGATATTTGCAATTGGAGTGTATTAGTTTAT

ACATGTGAGGGAGTTAATCTTACCATTGTCAATGCCACCTCAGCTCAAAATGGTAGAATTCAAGGACAAAGT

GTCAGTGTATCTAATGGGTATTTTACCCAACATACTTTTATCTATGACGTTAAAGTCATACCACTGCCTACGCC

TAGCCCACCTAGCACTACCACACAGACAACCCACACTACACAGACAACCACATACAGTACATTAAATCAGCC

TACCACCACTACAGCAGCAGAGGTTGCCAGCTCGTCTGGGGTCCGAGTGGCATTTTTGATGTGGGCCCCATCT

AGCAGTCCCACTGCTAGTACCAATGAGCAGACTACTGAATTTTTGTCCACTGTCGAGAGCCACACCACAGCTA

CCTCCAGTGCCTTCTCTAGCACCGCCAATCTCTCCTCGCTTTCCTCTACACCAATCAGTCCCGCTACTACTCCT

AGCCCCGCTCCTCTTCCCACTCCCCTGAAGCAAACAGACGGCGGCATGCAATGGCAGATCACCCTGCTCATTG

TGATCGGGTTGGTCATCCTGGCCGTGTTGCTCTACTACATCTTCTGCCGCCGCATTCCCAACGCGCACCGCAA

GCCGGTCTACAAGCCCATCATTGTCGGGCAGCCGGAGCCGCTTCAGGTGGAAGGGGGTCTAAGGAATCTTCT

CTTCTCTTTTACAGTATGGTGATTGAACTATGATTCCTAGACAATTCTTGATCACTATTCTTATCTGCCTCCTCC

AAGTCTGTGCCACCCTCGCTCTGGTGGCCAACGCCAGTCCAGACTGTATTGGGCCCTTCGCCTCCTACGTGCT

CTTTGCCTTCACCACCTGCATCTGCTGCTGTAGCATAGTCTGCCTGCTTATCACCTTCTTCCAGTTCATTGACTG

GATCTTTGIGCGCATCGCCTACCTGCGCCACCACCCCCAGTACCGCGACCAGCGAGTGGCGCGGCTGCTCAGG

CTCCTCTGATAAGCATGCGGGCTCTGCTACTTCTCGCGCTTCTGCTGTTAGTGCTCCCCCGTCCCGTCGACCCC

CGGTCCCCCACCCAGTCCCCCGAGGAGGTCCGCAAATGCAAATTCCAAGAACCCTGGAAATTCCTCAAATGC

TACCGCCAAAAATCAGACATGCATCCCAGCTGGATCATGATCATTGGGATCGTGAACATTCTGGCCTGCACCC

TCATCTCCTTTGTGATTTACCCCTGCTTTGACTTTGGTTGGAACTCGCCAGAGGCGCTCTATCTCCCGCCTGAA

CCTGACACACCACCACAGCAACCTCAGGCACACGCACTACCACCACTACAGCCTAGGCCACAATACATGCCC

ATATTAGACTATGAGGCCGAGCCACAGCGACCCATGCTCCCCGCTATTAGTTACTTCAATCTAACCGGCGGAG

ATGACTGACCCACTGGCCAACAACAACGTCAACGACCTTCTCCTGGACATGGACGGCCGCGCCTCGGAGCAG

CGACTCGCCCAACTTCGCATTCGCCAGCAGCAGGAGAGAGCCGTCAAGGAGCTGCAGGATGCGGTGGCCATC

CACCAGTGCAAGAGAGGCATCTTCTGCCTGGTGAAACAGGCCAAGATCTCCTACGAGGTCACTCCAAACGAC

CATCGCCTCTCCTACGAGCTCCTGCAGCAGCGCCAGAAGTTCACCTGCCTGGTCGGAGTCAACCCCATCGTCA

TCACCCAGCAGTCTGGCGATACCAAGGGGTGCATCCACTGCTCCTGCGACTCCCCCGACTGCGTCCACACTCT

GATCAAGACCCTCTGCGGCCTCCGCGACCTCCTCCCCATGAACTAATCACCCCCTTATCCAGTGAAATAAAGA

TCATATTGATGATGATTTTACAGAAATAAAAAATAATCATTTGATTTGAAATAAAGATACAATCATATTGATG

ATTTGAGTTTAACAAAAAAATAAAGAATCACTTACTTGAAATCTGATACCAGGTCTCTGTCCATGTTTTCTGC

CAACACCACTTCACTCCCCTCTTCCCAGCTCTGGTACTGCAGGCCCCGGCGGGCTGCAAACTTCCTCCACACG

CTGAAGGGGGATGTCAAATTCCTCCTGTCCCTCAATCTTCATTTTATCTTCTATCAGATGTCCAAAAAGCGCGTC

CGGGTGGATGATGACTTCGACCCCGTCTACCCCTACGATGCAGACAACGCACCGACCGTCCCTTCATCAACC

CCCCCTTCGTCTCTTCAGATGGATTCCAAGAGAAGCCCCTGGGGGTGTTGTCCCTGCGACTGGCCGACCCCGT

CACCACCAAGAACGGGGAAATCACCCTCAAGCTGGGAGAGGGGGTGGACCTCGATTCCTCGGGAAAACTCAT

CTCCAACACGGCCACCAAGGCCGCCGCCCCTCTCAGTTTTTCCAACAACACCATTTCCCTTAACATGGATCAC

-continued

CCCTTTTACACTAAAGATGGAAAATTATCCTTACAAGTTTCTCCACCATTAAATATACTGAGAACAAGCATTC

TAAACACACTAGCTTTAGGTTTTGGATCAGGTTTAGGACTCCGTGGCTCTGCCTTGGCAGTACAGTTAGTCTCT

CCACTTACATTTGATACTGATGGAAACATAAAGCTTACCTTAGACAGAGGTTTGCATGTTACAACAGGAGATG

CAATTGAAAGCAACATAAGCTGGGCTAAAGGTTTAAAATTTGAAGATGGAGCCATAGCAACCAACATTGGAA

ATGGGTTAGAGTTTGGAAGCAGTAGTACAGAAACAGGTGTTGATGATGCTTACCCAATCCAAGTTAAACTTG

GATCTGGCCTTAGCTTTGACAGTACAGGAGCCATAATGGCTGGTAACAAAGAAGACGATAAACTCACTTTGT

GGACAACACCTGATCCATCACCAAACTGTCAAATACTCGCAGAAAATGATGCAAAACTAACACTTTGCTTTGA

CTAAATGTGGTAGTCAAATACTGGCCACTGTGTCAGTCTTAGTTGTAGGAAGTGGAAACCTAAACCCCATTAC

TGGCACCGTAAGCAGTGCTCAGGTGTTTCTACGTTTTGATGCAAACGGTGTTCTTTTAACAGAACATTCTACA

CTAAAAAAATACTGGGGGTATAGGCAGGGAGATAGCATAGATGGCACTCCATATACCAATGCTGTAGGATTC

ATGCCCAATTTAAAAGCTTATCCAAAGTCACAAAGTTCTACTACTAAAAATAATATAGTAGGGCAAGTATAC

ATGAATGGAGATGTTTCAAAACCTATGCTTCTCACTATAACCCTCAATGGTACTGATGACAGCAACAGTACAT

ATTCAATGTCATTTTCATACACCTGGACTAATGGAAGCTATGTTGGAGCAACATTTGGGGCTAACTCTTATAC

CTTCTCATACATCGCCCAAGAATGAACACTTGTATCCCACCCTGCATGCCAACCCTTCCCACCCCACTCTGTGG

AACAAACTCTGAAACACAAAATAAAATAAAGTTCAAGTGTTTTATTGATTCAACAGTTTTACAGGATTCGAGC

AGTTATTTTTCCTCCACCCTCCCAGGACATGGAATACACCACCCTCTCCCCCCGCACAGCCTTGAACATCTGA

ATGCCATTGGTGATGGACATGCTTTTGGTCTCCACGTTCCACACAGTTTCAGAGCGAGCCAGTCTCGGGTCGG

TCAGGGAGATGAAACCCTCCGGGCACTCCCGCATCTGCACCTCACAGCTCAACAGCTGAGGATTGTCCTCGGT

GGTCGGGATCACGGTTATCTGGAAGAAGCAGAAGAGCGGCGGTGGGAATCATAGTCCGCGAACGGGATCGG

CCGGTGGTGTCGCATCAGGCCCCGCAGCAGTCGCTGCCGCCGCCGCTCCGTTCAAGCTGCTTGCTCAGGGGGTCC

GGGTCCAGGGACTCCCTCAGCATGATGCCCACGGCCCTCAGCATCAGTCGTCTGGTGCGGCGGGCGCAGCAG

CGCATGCGGATCTCGCTCAGGTCGCTGCAGTACGTGCAACACAGAACCACCAGGTTGTTCAACAGTCCATAGT

TCAACACGCTCCAGCCGAAACTCATCGCGGGAAGGATGCTACCCACGTGGCCGTCGTACCAGATCCTCAGGT

AAATCAAGTGGTGCCCCCTCCAGAACACGCTGCCCACGTACATGATCTCCTTGGGCATGTGGCGGTTCACCAC

CTCCCGGTACCACATCACCCTCTGGTTGAACATGCAGCCCCGGATGATCCTGCGGAACCACAGGGCCAGCAC

CGCCCCGCCCGCCATGCAGCGAAGAGACCCCGGGTCCCGGCAATGGCAATGGAGGACCCACCGCTCGTACCC

GTGGATCATCTGGGAGCTGAACAAGTCTATGTTGGCACAGCACAGGCATATGCTCATGCATCTCTTCAGCACT

CTCAACTCCTCGGGGGTCAAAACCATATCCCAGGGCACGGGGAACTCTTGCAGGACAGCGAACCCCGCAGAA

CAGGGCAATCCTCGCACAGAACTTACATTGTGCATGGACAGGGTATCGCAATCAGGCAGCACCGGGTGATCC

TCCACCAGAGAAGCGCGGGTCTCGGTCTCCTCACAGCGTGGTAAGGGGGCCGGCCGATACGGGTGATGGCGG

GACGCGGCTGATCGTGTTCGCGACCGTGTCATGATGCAGTTGCTTTCGGACATTTTCGTACTTGCTGTAGCAG

AACCTGGTCCGGGCGCTGCACACCGATCGCCGGCGGCGGTCTCGGCGCTTGGAACGCTCGGTGTTGAAATTGT

AAAACAGCCACTCTCTCAGACCGTGCAGCAGATCTAGGGCCTCAGGAGTGATGAAGATCCCACATGCCTGA

TGGCTCTGATCACATCGACCACCGTGGAATGGGCCAGACCCAGCCAGATGATGCAATTTTGTTGGGTTTCGGT

GACGGCGGGGGAGGGAAGAACAGGAAGAACCATGATTAACTTTTAATCCAAACGGTCTCGGAGTACTTCAAA

ATGAAGATCGCGGAGATGGCACCTCTCGCCCCCGCTGTGTTGGTGGAAAATAACAGCCAGGTCAAAGGTGAT

ACGGTTCTCGAGATGTTCCACGGTGGCTTCCAGCAAAGCCTCCACGCGCACATCCAGAAACAAGACAATAGC

GAAAGCGGGAGGGTICTCTAATTCCTCAATCATCATGTTACACTCCTGCACCATCCCCAGATAATTTTCATTTT

TCCAGCCTTGAATGATTCGAACTAGTTCcTGAGGTAAATCCAAGCCAGCCATGATAAAGAGCTCGCGCAGAGC

GCCCTCCACCGGCATTCTTAAGCACACCCTCATAATTCCAAGATATTCTGCTCCTGGTTCACCTGCAGCAGATT

GACAAGCGGAATATCAAAATCTCTGCCGCGATCCCTGAGCTCCTCCCTCAGCAATAACTGTAAGTACTCTTTC

ATATCCTCTCCGAAATTTTTAGCCATAGGACCACCAGGAATAAGATTAGGGCAAGCCACAGTACAGATAAAC

CGAAGTCCTCCCCAGTGAGCATTGCCAAATGCAAGACTGCTATAAGCATGCTGGCTAGACCCGGTGATATCTT

CCAGATAACTGGACAGAAAATCGCCCAGGCAATTTTTAAGAAAATCAACAAAAGAAAAATCCTCCAGGTGGA

CGTTTAGAGCCTCGGGAACAACGATGAAGTAAATGCAAGCGGTGCGTTCCAGCATGGTTAGTTAGCTGATCT

GTAGAAAAAACAAAAATGAACATTAAACCATGCTAGCCTGGCGAACAGGTGGGTAAATCGTTCTCTCCAGCA

CCAGGCAGGCCACGGGCUCTCCGGCGCGACCCTCGTAAAAATTGTCGCTATGATTGAAAACCATCACAGAGA

GACGTTCCCGGTGGCCGGCGTGAATGATTCGACAAGATGAATACACCCCCGGAACATTGGCGTCCGCGAGTG

AAAAAAAGCGCCCGAGGAAGCAATAAGGCACTACAATGCTCAGTCCAAGTCCAGCAAAGCGATGCCATGC

GGATGAAGCACAAAATTCTCAGGTGCGTACAAAATGTAATTACTCCCCTCCTGCACAGGCAGCAAAGCCCCC

GATCCCTCCAGGTACACATACAAAGCCTCAGCGTCCATAGCTTACCGAGCAGCAGCACACAACAGGCGCAAG

AGTCAGAGAAAGGCTGAGCTCTAACCTGTCCACCCGCTCTCTGCTCAATATATAGCCCAGATCTACACTGACG

TAAAGGCCAAAGTCTAAAAATACCCGCCAAATAATCACACACGCCCAGCACACGCCCAGAAACCGGTGACAC

ACTCAAAAAAATACGCGCACTTCCTCAAACGCCCAAAACTGCCGTCATTTCCGGGTTCCCACGCTACGTCATC

AAAACACGACTTTCAAATTCCGTCGACCGTTAAAAACGTCACCCGCCCCGCCCCTAACGGTCGCCCGTCTCTC

AGCCAATCAGCGCCCCGCATCCCCAAATTCAAACACCTCATTTGCATATTAACGCGCACAAAAAGTTTGAGGT

ATATTATTGATGATGG

Tremelimumab VL (SEQ ID NO: 16)

Tremelimumab VH (SEQ ID NO: 17)

Tremelimumab VH CDR (SEQ ID NO: 18)

Tremelimumab VH CDR2 (SEQ ID NO: 19)

Tremelimumab VH CDR3 (SEQ ID NO: 20)

Tremelimumab VL CDR1 (SEQ ID NO: 21)

Tremelimumab VL CDR2 (SEQ ID NO: 22)

Tremelimumab VL CDR3 (SEQ ID NO: 23)

Durvalumab (MEDI4736) VL (SEQ ID NO: 24)

MEDI4736 VH (SEQ ID NO: 25)

MEDI4736 VH CDR1 (SEQ ID NO: 26)

MEDI4736 VH CDR2 (SEQ ID NO: 27)

MEDI4736 VH CDR3 (SEQ ID NO: 28)

MEDI4736 VL CDR1 (SEQ ID NO: 29)

MEDI4736 VL CDR2 (SEQ ID NO: 30)

MEDI4736 VL CDR3 (SEQ ID NO: 31)

UbA76-25merPDTT nucleotide (SEQ ID NO: 32)

UbA76-25merPDTT polypeptide (SEQ ID NO: 33)

MAG-25merPDTT nucleotide (SEQ ID NO: 34)

MAG-25merPDTT polypeptide (SEQ ID NO: 35)

Ub7625merPDTT_NoSFL nucleotide (SEQ ID NO: 36)

Ub7625merPDTT_NoSFL polypeptide (SEQ ID NO: 37)

-continued

ChAdV68.5WTnt.MAG25mer (SEQ ID NO: 2); AC_000011.1 with E1 (nt 577 to 3403) and E3 (nt 27, 125-31, 825) sequences deleted; corresponding ATCC VR-594 nucleotides substituted at five positions; model neoantigen cassette under the control of the CMV promoter/enhancer inserted in place of deleted E1; SV40 polyA 3' of cassette Venezuelan equine encephalitis virus [VEE] (SEQ ID NO: 3) GenBank: L01442.2

VEE-MAG25mer (SEQ ID NO: 4); contains MAG-25merPDTT nucleotide (bases 30-1755)

Venezuelan equine encephalitis virus strain TC-83 [TC-83] (SEQ ID NO: 5) GenBank: L01443.1

VEE Delivery Vector (SEQ ID NO: 6); VEE genome with nucleotides 7544-11175 deleted [alphavirus structural proteins removed]

TC-83 Delivery Vector(SEQ ID NO: 7); TC-83 genome with nucleotides 7544-11175 deleted [alphavirus structural proteins removed]

VEE Production Vector (SEQ ID NO: 8); VEE genome with nucleotides 7544-11175 deleted, plus 5' T7-promoter, plus 3' restriction sites TC-83 Production Vector(SEQ ID NO: 9); TC-83 genome with nucleotides 7544-11175 deleted, plus 5' T7-promoter, plus 3' restriction sites VEE-UbAAY (SEQ ID NO: 14); VEE delivery vector with MHC class I mouse tumor epitopes SIINFEKL and AH1-A5 inserted VEE-Luciferase (SEQ ID NO: 15); VEE delivery vector with luciferase gene inserted at 7545 ubiquitin (SEQ ID NO: 38) > UbG76 0-228

Ubiquitin A76 (SEQ ID NO: 39) > UbA76 0-228

HLA-A2 (MHC class I) signal peptide (SEQ ID NO 40) > MHC SignalPep 0-78

HLA-A2 (MHC class I) Trans Membrane domain (SEQ ID NO: 41) > HLA A2 TM Domain 0-201

IgK Leader Seq (SEQ ID NO: 42) > IgK Leader Seq 0-60

Human DC-Lamp (SEQ ID NO: 43) > HumanDCLAMP 0-3178

Mouse LAMP1 (SEQ ID NO: 44) > MouseLamp1 0-1858

Human Lamp1 cDNA (SEQ ID NO: 45) > Human Lamp1 0-2339

Tetanus toxoid nulceic acid sequence (SEQ ID NO: 46)

Tetanus toxoid amino acid sequence (SEQ ID NO: 47)

PADRE nulceotide sequence (SEQ ID NO: 48)

PADRE amino acid sequence (SEQ ID NO: 49)

WPRE (SEQ ID NO: 50) > WPRE 0-593

IRES (SEQ ID N0: 51) > eGFP_IRES_SEAP_Insert 1746-2335

GFP (SEQ ID NO: 52)

SEAP (SEQ ID NO: 53)

Firefly Luciferase (SEQ ID NO: 54)

FMDV 2A (SEQ ID NO: 55)

ChAdV68-MAG-E4deleted (SEQ ID NO: 57)

CATCaTCAATAATATACCTCAAACTTTTTGTGCGCGTTAATATGCAAATGAGGCGTTTGAATTTGGGGAGGAA

GGGCGGTGATTGGTCGAGGGATGAGCGACCGTTAGGGGCGGGGCGAGTGACGTTTTGATGACGTGGTTGCGA

GGAGGAGCCAGTTTGCAAGTTCTCGTGGGAAAAGTGACGTCAAACGAGGTGTGGTTTGAACACGGAAATACT

CAATTTTCCCGCGCTCTCTGACAGGAAATGAGGTGTTTCTGGGCGGATGCAAGTGAAAACGGGCCATTTTCGC

GCGAAAACTGAATGAGGAAGTGAAAATCTGAGTAATTTCGCGTTTATGGCAGGGAGGAGTATTTGCCGAGGG

-continued

CCGAGTAGACTTTGACCGATTACGTGGGGGTTTCGATTACCGTGTTTTTCACCTAAATTTCCGCGTACGGTGTC

AAAGTCCGGTGTTTTTACGTAGGTGTCAGCTGATCGCCAGGGTATTTAAACCTGCGCTCTCCAGTCAAGAGGC

CACTCTTGAGTGCCAGCGAGAAGAGTTTTCTCCTCCGCGCCGCGAGTCAGATCTACACTTTGAAAGTAGGGAT

AACAGGGTAATgacattgattattgactagttGttaaTAGTAATCAATTACGGGGTCATTAGTTCATAGCCCATATAT

GGAGTTCCGCGTTACATAACTTACGGTAAATGGCCCGCCTGGCTGACCGCCCAACGACCCCCGCCCATTGACGTCAATA

ATGACGTATGTTCCCATAGTAACGCCAATAGGGACTTTCCATTGACGTCAATGGGTGGAGTATTTACGGTAAA

CTGCCCACTTGGCAGTACATCAAGTGTATCATATGCCAAGTCCGCCCCCTATTGACGTCAATGACGGTAAATG

GCCCGCCTGGCATTATGCCCAGTACATGACCTTACGGGACTTTCCTACTTGGCAGTACATCTACGTATTAGTC

ATCGCTATTACCATGgTGATGCGGTTTTGGCAGTACACCAATGGGCGTGGATAGCGGTTTGACTCACGGGGAT

TTCCAAGTCTCCACCCCATTGACGTCAATGGGAGTTTGTTTTGGCACCAAAATCAACGGGACTTTCCAAAATG

TCGTAATAACCCCGCCCCGTTGACGCAAATGGGCGGTAGGCGTGTACGGTGGGAGGTCTATATAAGCAGAgcT

CGTTTAGTGAACCGTCAGATCGCCTGGAACGCCATCCACGCTGTTTTGACCTCCATAGAAGACAGCGATCGCG ccaccATGGCCGGGATGTTCCAGGCACTGTCCGAAGGCTGCACACCCTATGATATTAACCAGATGCTGAATGTC

CTGGGAGACCACCAGGTCTCTGGCCTGGAGCAGCTGGAGAGCATCATCAACTTCGAGAAGCTGACCGAGTGG

ACAAGCTCCAATGTGATGCCTATCCTGTCCCCACTGACCAAGGGCATCCTGGGCTTCGTGTTTACCCTGACAG

TGCCTTCTGAGCGGGGCCTGTCTTGCATCAGCGAGGCAGACGCAACCACACCAGAGTCCGCCAATCTGGGCG

AGGAGATCCTGTCTCAGCTGTACCTGTGGCCCCGGGTGACATATCACTCCCCTTCTTACGCCTATCACCAGTTC

GAGCGGAGAGCCAAGTACAAGAGACACTTCCCAGGCTTTGGCCAGTCTCTGCTGTTCGGCTACCCCGTGTACG

TGTTCGGCGATTGCGTGCAGGGCGACTGGGATGCCATCCGGTTTAGATACTGCGCACCACCTGGATATGCACT

GCTGAGGTGTAACGACACCAATTATTCCGCCCTGCTGGCAGTGGGCGCCCTGGAGGGCCCTCGCAATCAGGA

TTGGCTGGGCGTGCCAAGGCAGCTGGTGACACGCATGCAGGCCATCCAGAACGCAGGCCTGTGCACCCTGGT

GGCAATGCTGGAGGAGACAATCTTCTGGCTGCAGGCCTTTCTGATGGCCCTGACCGACAGCGGCCCCAAGAC

AAACATCATCGTGGATTCCCAGTACGTGATGGGCATCTCCAAGCCTTCTTTCCAGGAGTTTGTGGACTGGGAG

AACGTGAGCCCAGAGCTGAATTCCACCGATCAGCCATTCTGGCAGGCAGGAATCCTGGCAAGGAACCTGGTG

CCTATGGTGGCCACAGTGCAGGGCCAGAATCTGAAGTACCAGGGCCAGAGCCTGGTCATCAGCGCCTCCATC

ATCGTGTTTAACCTGCTGGAGCTGGAGGGCGACTATCGGGACGATGGCAACGTGTGGGTGCACACCCCACTG

AGCCCCAGAACACTGAACGCCTGGGTGAAGGCCGTGGAGGAGAAGAAGGGCATCCCAGTGCACCTGGAGCT

GGCCTCCATGACCAATATGGAGCTGATGTCTAGCATCGTGCACCAGCAGGTGAGGACATACGGACCCGTGTT

CATGTGCCTGGGAGGCCTGCTGACCATGGTGGCAGGAGCCGTGTGGCTGACAGTGCGGGTGCTGGAGCTGTT

CAGAGCCGCCCAGCTGGCCAACGATGTGGTGCTGCAGATCATGGAGCTGTGCGGAGCAGCCTTTCGCCAGGT

GTGCCACACCACAGTGCCATGGCCCAATGCCTCCCTGACCCCCAAGTGGAACAATGAGACAACACAGCCTCA

GATCGCCAACTGTAGCGTGTACGACTTCTTCGTGTGGCTGCACTACTATAGCGTGAGGGATACCCTGTGGCCC

CGCGTGACATACCACATGAATAAGTACGCCTATCACATGCTGGAGAGGCGCGCCAAGTATAAGAGAGGCCCT

GGCCCAGGCGCAAAGTTTGTGGCAGCATGGACCCTGAAGGCCGCCGCCGGCCCCGGCCCCGGCCAGTATATC

AAGGCTAACAGTAAGTTCATTGGAATCACAGAGCTGGGACCCGGACCTGGATAATGAGTTTAAACTCCCATT

TAAATGTGAGGGTTAATGCTTCGAGCAGACATGATAAGATACATTGATGAGTTTGGACAAACCACAACTAGA

ATGCAGTGAAAAAAATGCTTTATTTGTGAAATTTGTGATGCTATTGCTTTATTTGTAACCATTATAAGCTGCAA

TAAACAAGTTAACAACAACAATTGCATTCATTTTATGTTTCAGGTTCAGGGGGAGATGTGGGAGGTTTTTTAA

AGCAAGTAAAACCTCTACAAATGTGGTAAAATAACTATAACGGTCCTAAGGTAGCGAGTGAGTAGTGTTCTG

GGGCGGGGGAGGACCTGCATGAGGGCCAGAATAACTGAAATCTGTGCTTTTCTGTGTGTTGCAGCAGCATGA

GCGGAAGCGGCTCCTTTGAGGGAGGGGTATTCAGCCCTTATCTGACGGGGCGTCTCCCCTCCTGGGCGGGAGT

-continued

GCGTCAGAATGTGATGGGATCCACGGTGGACGGCCGGCCCGTGCAGCCCGCGAACTCTTCAACCCTGACCTA

TGCAACCCTGAGCTCTTCGTCGTTGGACGCAGCTGCCGCCGCAGCTGCTGCATCTGCCGCCAGCGCCGTGCGC

GGAATGGCCATGGGCGCCGGCTACTACGGCACTCTGGTGGCCAACTCGAGTTCCACCAATAATCCCGCCAGC

CTGAACGAGGAGAAGCTGTTGCTGCTGATGGCCCAGCTCGAGGCCTTGACCCAGCGCCTGGGCGAGCTGACC

CAGCAGGTGGCTCAGCTGCAGGAGCAGACGCGGGCCGCGGTTGCCACGGTGAAATCCAAATAAAAAATGAA

TCAATAAATAAACGGAGACGGTTGTTGATTTTAACACAGAGTCTGAATCTTTATTTGATTTTTCGCGCGCGGT

AGGCCCTGGACCACCGGTCTCGATCATTGAGCACCCGGTGGATCTTTTCCAGGACCCGGTAGAGGTGGGCTTG

GATGTTGAGGTACATGGGCATGAGCCCGTCCCGGGGGTGGAGGTAGCTCCATTGCAGGGCCTCGTGCTCGGG

GGTGGTGTTGTAAATCACCCAGTCATAGCAGGGGCGCAGGGCATGGTGTTGCACAATATCTTTGAGGAGGAG

ACTGATGGCCACGGGCAGCCCTTTGGTGTAGGTGTTTACAAATCTGTTGAGCTGGGAGGGATGCATGCGGGG

GGAGATGAGGTGCATCTTGGCCTGGATCTTGAGATTGGCGATGTTACCGCCCAGATCCCGCCTGGGGTTCATG

TTGTGCAGGACCACCAGCACGGTGTATCCGGTGCACTTGGGGAATTTATCATGCAACTTGGAAGGGAAGGCG

TGAAAGAATTTGGCGACGCCTTTGTGCCCGCCCAGGTTTTCCATGCACTCATCCATGATGATGGCGATGGGCC

CGTGGGCGGCGGCCTGGGCAAAGACGTTTCGGGGGTCGGACACATCATAGTTGTGGTCCTGGGTGAGGTCAT

CATAGGCCATTTTAATGAATTTGGGGCGGAGGGTGCCGGACTGGGGGACAAAGGTtCCCTCGATCCCGGGGGC

GTAGTTCCCCTCACAGATCTGCATCTCCCAGGCTTTGAGCTCGGAGGGGGGGATCATGTCCACCTGCGGGGCG

ATAAAGAACACGGTTTCCGGGGCGGGGGAGATGAGCTGGGCCGAAAGCAAGTTCCGGAGCAGCTGGGACTT

GCCGCAGCCGGTGGGGCCGTAGATGACCCCGATGACCGGCTGCAGGTGGTAGTTGAGGGAGAGACAGCTGCC

GTCCTCCCGGAGGAGGGGGGCCACCTCGTTCATCATCTCGCGCACGTGCATGTTCTCGCGCACCAGTTCCGCC

AGGAGGCGCTCTCCCCCCAGGGATAGGAGCTCCTGGAGCGAGGCGAAGTTTTTCAGCGGCTTGAGTCCGTCG

GCCATGGGCATTTTGGAGAGGGTTTGTTGCAAGAGTTCCAGGCGGTCCCAGAGCTCGGTGATGTGCTCTACGG

CATCTCGATCCAGCAGACCTCCTCGTTTCGCGGGTTGGGACGGCTGCGGGAGTAGGGCACCAGACGATGGGC

GTCCAGCGCAGCCAGGGTCCGGTCCTTCCAGGGTCGCAGCGTCCGCGTCAGGGTGGTCTCCGTCACGGTGAA

GGGGTGCGCGCCGGGCTGGGCGCTTGCGAGGGTGCGCTTCAGGCTCATCCGGCTGGTCGAAAACCGCTCCCG

ATCGGCGCCCTGCGCGTCGGCCAGGTAGCAATTGACCATGAGTTCGTAGTTGAGCGCCTCGGCCGCGTGGCCT

TTGGCGCGGAGCTTACCTTTGGAAGTCTGCCCGCAGGCGGGACAGAGGAGGGACTTGAGGGCGTAGAGCTTG

GGGGCGAGGAAGACGGACTCGGGGGCGTAGGCGTCCGCGCCGCAGTGGGCGCAGACGGTCTCGCACTCCAC

GAGCCAGGTGAGGTCGGGCTGGTCGGGGTCAAAAACCAGTTTCCCGCCGTTCTTTTTGATGCGTTTCTTACCT

TTGGTCTCCATGAGCTCGTGTCCCCGCTGGGTGACAAAGAGGCTGTCCGTGTCCCCGTAGACCGACTTTATGG

GCCGGTCCTCGAGCGGTGTGCCGCGGTCCTCCTCGTAGAGGAACCCCGCCCACTCCGAGACGAAAGCCCGGG

TCCAGGCCAGCACGAAGGAGGCCACGTGGGACGGGTAGCGGTCGTTGTCCACCAGCGGGTCCACCTTTTCCA

GGGTATGCAAACACATGTCCCCCTCGTCCACATCCAGGAAGGTGATTGGCTTGTAAGTGTAGGCCACGTGACC

GGGGGTCCCGGCCGGGGGGGTATAAAAGGGTGCGGGTCCCTGCTCGTCCTCACTGTCTTCCGGATCGCTGTCC

AGGAGCGCCAGCTGTTGGGGTAGGTATTCCCTCTCGAAGGCGGGCATGACCTCGGCACTCAGGTTGTCAGTTT

CTAGAAACGAGGAGGATTTGATATTGACGGTGCCGGCGGAGATGCCTTTCAAGAGCCCCTCGTCCATCTGGTC

AGAAAAGACGATCTTTTTGTTGTCGAGCTTGGTGGCGAAGGAGCCGTAGAGGGCGTTGGAGAGGAGCTTGGC

GATGGAGCGCATGGTCTGGTTTTTTTCCTTGTCGGCGCGCTCCTTGGCGGCGATGTTGAGCTGCACGTACTCGC

GCGCCACGCACTTCCATTCGGGGAAGACGGTGGTCAGCTCGTCGGGCACGATTCTGACCTGCCAGCCCCGATT

ATGCAGGGTGATGAGGTCCACACTGGTGGCCACCTCGCCGCGCAGGGGCTCATTAGTCCAGCAGAGGCGTCC

GCCCTTGCGCGAGCAGAAGGGGGGCAGGGGGTCCAGCATGACCTCGTCGGGGGGGTCGGCATCGATGGTGA

-continued

AGATGCCGGGCAGGAGGTCGGGGTCAAAGTAGCTGATGGAAGTGGCCAGATCGTCCAGGGCAGCTTGCCATT

CGCGCACGGCCAGCGCGCGCTCGTAGGGACTGAGGGGCGTGCCCCAGGGCATGGGATGGGTAAGCGCGGAG

GCGTACATGCCGCAGATGTCGTAGACGTAGAGGGGCTCCTCGAGGATGCCGATGTAGGTGGGGTAGCAGCGC

CCCCCGCGGATGCTGGCGCGCACGTAGTCATACAGCTCGTGCGAGGGGGCGAGGAGCCCCGGGCCCAGGTTG

GTGCGACTGGGCTTTTCGGCGCGGTAGACGATCTGGCGGAAAATGGCATGCGAGTTGGAGGAGATGGTGGGC

CTTTGGAAGATGTTGAAGTGGGCGTGGGGCAGTCCGACCGAGTCGCGGATGAAGTGGGCGTAGGAGTCTTGC

AGCTTGGCGACGAGCTCGGCGGTGACTAGGACGTCCAGAGCGCAGTAGTCGAGGGTCTCCTGGATGATGTCA

TACTTGAGCTGTCCCTTTTGTTTCCACAGCTCGCGGTTGAGAAGGAACTCTTCGCGGTCCTTCCAGTACTCTTC

GAGGGGGAACCCGTCCTGATCTGCACGGTAAGAGCCTAGCATGTAGAACTGGTTGACGGCCTTGTAGGCGCA

GCAGCCCTTCTCCACGGGGAGGGCGTAGGCCTGGGCGGCCTTGCGCAGGGAGGTGTGCGTGAGGGCGAAAGT

GTCCCTGACCATGACCTTGAGGAACTGGTGCTTGAAGTCGATATCGTCGCAGCCCCCCTGCTCCCAGAGCTGG

AAGTCCGTGCGCTTCTTGTAGGCGGGGTTGGGCAAAGCGAAAGTAACATCGTTGAAGAGGATCTTGCCCGCG

CGGGGCATAAAGTTGCGAGTGATGCGGAAAGGTTGGGGCACCTCGGCCCGGTTGTTGATGACCTGGGCGGCG

AGCACGATCTCGTCGAAGCCGTTGATGTTGTGGCCCACGATGTAGAGTTCCACGAATCGCGGACGGCCCTTGA

CGTGGGGCAGTTTCTTGAGCTCCTCGTAGGTGAGCTCGTCGGGGTCGCTGAGCCCGTGCTGCTCGAGCGCCCA

GTCGGCGAGATGGGGGTTGGCGCGGAGGAAGGAAGTCCAGAGATCCACGGCCAGGGCGGTTTGCAGACGGT

CCCGGTACTGACGGAACTGCTGCCCGACGGCCATTTTTTCGGGGGTGACGCAGTAGAAGGTGCGGGGGTCCC

CGTGCCAGCGATCCCATTTGAGCTGGAGGGCGAGATCGAGGGCGAGCTCGACGAGCCGGTCGTCCCCGGAGA

GTTTCATGACCAGCATGAAGGGGACGAGCTGCTTGCCGAAGGACCCCATCCAGGTGTAGGTTTCCACATCGT

AGGTGAGGAAGAGCCTTTCGGTGCGAGGATGCGAGCCGATGGGGAAGAACTGGATCTCCTGCCACCAATTGG

AGGAATGGCTGTTGATGTGATGGAAGTAGAAATGCCGACGGCGCGCCGAACACTCGTGCTTGTGTTTATACA

AGCGGCCACAGTGCTCGCAACGCTGCACGGGATGCACGTGCTGCACGAGCTGTACCTGAGTTCCTTTGACGA

GGAATTTCAGTGGGAAGTGGAGTCGTGGCGCCTGCATCTCGTGCTGTACTACGTCGTGGTGGTCGGCCTGGCC

CTCTTCTGCCTCGATGGTGGTCATGCTGACGAGCCCGCGCGGGAGGCAGGTCCAGACCTCGGCGCGAGCGGG

TCGGAGAGCGAGGACGAGGGCGCGCAGGCCGGAGCTGTCCAGGGTCCTGAGACGCTGCGGAGTCAGGTCAG

TGGGCAGCGGCGGCGCGCGGTTGACTTGCAGGAGTTTTTCCAGGGCGCGCGGGAGGTCCAGATGGTACTTGA

TCTCCACCGCGCCATTGGTGGCGACGTCGATGGCTTGCAGGGTCCCGTGCCCCTGGGGTGTGACCACCGTCCC

CCGTTTCTTCTTGGGCGGCTGGGGCGACGGGGGCGGTGCCTCTTCCATGGTTAGAAGCGGCGGCGAGGACGC

GCGCCGGGCGGCAGGGGCGGCTCGGGGCCCGGAGGCAGGGGCGGCAGGGGCACGTCGGCGCCGCGCGCGGG

TAGGTTCTGGTACTGCGCCCGGAGAAGACTGGCGTGAGCGACGACGCGACGGTTGACGTCCTGGATCTGACG

CCTCTGGGTGAAGGCCACGGGACCCGTGAGTTTGAACCTGAAAGAGAGTTCGACAGAATCAATCTCGGTATC

GTTGACGGCGGCCTGCCGCAGGATCTCTTGCACGTCGCCCGAGTTGTCCTGGTAGGCGATCTCGGTCATGAAC

TGCTCGATCTCCTCCTCTTGAAGGTCTCCGCGGCCGGCGCGCTCCACGGTGGCCGCGAGGTCGTTGGAGATGC

GGCCCATGAGCTGCGAGAAGGCGTTCATGCCCGCCTCGTTCCAGACGCGGCTGTAGACCACGACGCCCTCGG

GATCGCgGGCGCGCATGACCACCTGGGCGAGGTTGAGCTCCACGTGGCGCGTGAAGACCGCGTAGTTGCAGA

GGCGCTGGTAGAGGTAGTTGAGCGTGGTGGCGATGTGCTCGGTGACGAAGAAATACATGATCCAGCGGCGGA

GCGGCATCTCGCTGACGTCGCCCAGCGCCTCCAAACGTTCCATGGCCTCGTAAAAGTCCACGGCGAAGTTGA

AAAACTGGGAGTTGCGCGCCGAGACGGTCAACTCCTCCTCCAGAAGACGGATGAGCTCGGCGATGGTGGCGC

GCACCTCGCGCTCGAAGGCCCCCGGGAGTTCCTCCACTTCCTCTTCTTCCTCCTCCACTAACATCTCTTCTACT

TCCTCCTCAGGCGGCAGTGGTGGCGGGGGAGGGGGCCTGCGTCGCCGGCGGCGCACGGGCAGACGGTCGATG

AAGCGCTCGATGGTCTCGCCGCGCCGGCGTCGCATGGTCTCGGTGACGGCGCGCCCGTCCTCGCGGGGCCGC

-continued

AGCGTGAAGACGCCGCCGCGCATCTCCAGGTGGCCGGGGGGGTCCCCGTTGGGCAGGGAGAGGGCGCTGAC

GATGCATCTTATCAATTGCCCCGTAGGGACTCCGCGCAAGGACCTGAGCGTCTCGAGATCCACGGGATCTGA

AAACCGCTGAACGAAGGCTTCGAGCCAGTCGCAGTCGCAAGGTAGGCTGAGCACGGTTTCTTCTGGCGGGTC

ATGTTGGTTGGGAGCGGGGCGGGCGATGCTGCTGGTGATGAAGTTGAAATAGGCGGTTCTGAGACGGCGGAT

GGTGGCGAGGAGCACCAGGTCTTTGGGCCCGGCTTGCTGGATGCGCAGACGGTCGGCCATGCCCCAGGCGTG

GTCCTGACACCTGGCCAGGTCCTTGTAGTAGTCCTGCATGAGCCGCTCCACGGGCACCTCCTCCTCGCCCGCG

CGGCCGTGCATGCGCGTGAGCCCGAAGCCGCGCTGGGGCTGGACGAGCGCCAGGTCGGCGACGACGCGCTCG

GCGAGGATGGCTTGCTGGATCTGGGTGAGGGTGGTCTGGAAGTCATCAAAGTCGACGAAGCGGTGGTAGGCT

CCGGTGTTGATGGTGTAGGAGCAGTTGGCCATGACGGACCAGTTGACGGTCTGGTGGCCCGGACGCACGAGC

TCGTGGTACTTGAGGCGCGAGTAGGCGCGCGTGTCGAAGATGTAGTCGTTGCAGGTGCGCACCAGGTACTGG

TAGCCGATGAGGAAGTGCGGCGGCGGCTGGCGGTAGAGCGGCCATCGCTCGGTGGCGGGGGCGCCGGGCGC

GAGGTCCTCGAGCATGGTGCGGTGGTAGCCGTAGATGTACCTGGACATCCAGGTGATGCCGGCGGCGGTGGT

GGAGGCGCGCGGGAACTCGCGGACGCGGTTCCAGATGTTGCGCAGCGGCAGGAAGTAGTTCATGGTGGGCAC

GGTCTGGCCCGTGAGGCGCGCGCAGTCGTGGATGCTCTATACGGGCAAAAACGAAAGCGGTCAGCGGCTCGA

CTCCGTGGCCTGGAGGCTAAGCGAACGGGTTGGGCTGCGCGTGTACCCCGGTTCGAATCTCGAATCAGGCTG

GAGCCGCAGCTAACGTGGTATTGGCACTCCCGTCTCGACCCAAGCCTGCACCAACCCTCCAGGATACGGAGG

CGGGTCGTTTTGCAACTTTTTTTTGGAGGCCGGATGAGACTAGTAAGCGCGGAAAGCGGCCGACCGCGATGG

CTCGCTGCCGTAGTCTGGAGAAGAATCGCCAGGGTTGCGTTGCGGTGTGCCCCGGTTCGAGGCCGGCCGGATT

CCGCGGCTAACGAGGGCGTGGCTGCCCCGTCGTTTCCAAGACCCCATAGCCAGCCGACTTCTCCAGTTACGGA

GCGAGCCCCTCTTTTGTTTTGTTTGTTTTTGCCAGATGCATCCCGTACTGCGGCAGATGCGCCCCCACCACCCT

CCACCGCAACAACAGCCCCCTCCACAGCCGGCGCTTCTGCCCCCGCCCCAGCAGCAACTTCCAGCCACGACC

GCCGCGGCCGCCGTGAGCGGGGCTGGACAGAGTTATGATCACCAGCTGGCCTTGGAAGAGGGCGAGGGGCT

GGCGCGCCTGGGGGCGTCGTCGCCGGAGCGGCACCCGCGCGTGCAGATGAAAAGGGACGCTCGCGAGGCCT

ACGTGCCCAAGCAGAACCTGTTCAGAGACAGGAGCGGCGAGGAGCCCGAGGAGATGCGCGCGGCCCGGTTC

CACGCGGGGCGGGAGCTGCGGCGCGGCCTGGACCGAAAGAGGGTGCTGAGGGACGAGGATTTCGAGGCGGA

CGAGCTGACGGGGATCAGCCCCGCGCGCGCGCACGTGGCCGCGGCCAACCTGGTCACGGCGTACGAGCAGAC

CGTGAAGGAGGAGAGCAACTTCCAAAAATCCTTCAACAACCACGTGCGCACCCTGATCGCGCGCGAGGAGGT

GACCCTGGGCCTGATGCACCTGTGGGACCTGCTGGAGGCCATCGTGCAGAACCCCACCAGCAAGCCGCTGAC

GGCGCAGCTGTTCCTGGTGGTGCAGCATAGTCGGGACAACGAAGCGTTCAGGGAGGCGCTGCTGAATATCAC

CGAGCCCGAGGGCCGCTGGCTCCTGGACCTGGTGAACATTCTGCAGAGCATCGTGGTGCAGGAGCGCGGGCT

GCCGCTGTCCGAGAAGCTGGCGGCCATCAACTTCTCGGTGCTGAGTTTGGGCAAGTACTACGCTAGGAAGAT

CTACAAGACCCCGTACGTGCCCATAGACAAGGAGGTGAAGATCGACGGGTTTTACATGCGCATGACCCTGAA

AGTGCTGACCCTGAGCGACGATCTGGGGGTGTACCGCAACGACAGGATGCACCGTGCGGTGAGCGCCAGCAG

GCGGCGCGAGCTGAGCGACCAGGAGCTGATGCATAGTCTGCAGCGGGCCCTGACCGGGGCCGGGACCGAGG

GGGAGAGCTACTTTGACATGGGCGCGGACCTGCACTGGCAGCCCAGCCGCCGGGCCTTGGAGGCGGCGGCAG

GACCCTACGTAGAAGAGGTGGACGATGAGGTGGACGAGGAGGGCGAGTACCTGGAAGACTGATGGCGCGAC

CGTATTTTTGCTAGATGCAACAACAACAGCCACCTCCTGATCCCGCGATGCGGGCGGCGCTGCAGAGCCAGC

CGTCCGGCATTAACTCCTCGGACGATTGGACCCAGGCCATGCAACGCATCATGGCGCTGACGACCCGCAACC

CCGAAGCCTTTAGACAGCAGCCCCAGGCCAACCGGCTCTCGGCCATCCTGGAGGCCGTGGTGCCCTCGCGCTC

CAACCCCACGCACGAGAAGGTCCTGGCCATCGTGAACGCGCTGGTGGAGAACAAGGCCATCCGCGGCGACG

-continued

AGGCCGGCCTGGTGTACAACGCGCTGCTGGAGCGCGTGGCCCGCTACAACAGCACCAACGTGCAGACCAACC

TGGACCGCATGGTGACCGACGTGCGCGAGGCCGTGGCCCAGCGCGAGCGGTTCCACCGCGAGTCCAACCTGG

GATCCATGGTGGCGCTGAACGCCTTCCTCAGCACCCAGCCCGCCAACGTGCCCCGGGGCCAGGAGGACTACA

CCAACTTCATCAGCGCCCTGCGCCTGATGGTGACCGAGGTGCCCCAGAGCGAGGTGTACCAGTCCGGGCCGG

ACTACTTCTTCCAGACCAGTCGCCAGGGCTTGCAGACCGTGAACCTGAGCCAGGCTTTCAAGAACTTGCAGGG

CCTGTGGGGCGTGCAGGCCCCGGTCGGGGACCGCGCGACGGTGTCGAGCCTGCTGACGCCGAACTCGCGCCT

GCTGCTGCTGCTGGTGGCCCCCTTCACGGACAGCGGCAGCATCAACCGCAACTCGTACCTGGGCTACCTGATT

AACCTGTACCGCGAGGCCATCGGCCAGGCGCACGTGGACGAGCAGACCTACCAGGAGATCACCCACGTGAGC

CGCGCCCTGGGCCAGGACGACCCGGGCAACCTGGAAGCCACCCTGAACTTTTTGCTGACCAACCGGTCGCAG

AAGATCCCGCCCCAGTACGCGCTCAGCACCGAGGAGGAGCGCATCCTGCGTTACGTGCAGCAGAGCGTGGGC

CTGTTCCTGATGCAGGAGGGGGCCACCCCCAGCGCCGCGCTCGACATGACCGCGCGCAACATGGAGCCCAGC

ATGTACGCCAGCAACCGCCCGTTCATCAATAAACTGATGGACTACTTGCATCGGGCGGCCGCCATGAACTCTG

ACTATTTCACCAACGCCATCCTGAATCCCCACTGGCTCCCGCCGCCGGGGTTCTACACGGGCGAGTACGACAT

GCCCGACCCCAATGACGGGTTCCTGTGGGACGATGTGGACAGCAGCGTGTTCTCCCCCCGACCGGGTGCTAA

CGAGCGCCCCTTGTGGAAGAAGGAAGGCAGCGACCGACGCCCGTCCTCGGCGCTGTCCGGCCGCGAGGGTGC

TGCCGCGGCGGTGCCCGAGGCCGCCAGTCCTTTCCCGAGCTTGCCCTTCTCGCTGAACAGTATCCGCAGCAGC

GAGCTGGGCAGGATCACGCGCCCGCGCTTGCTGGGCGAAGAGGAGTACTTGAATGACTCGCTGTTGAGACCC

GAGCGGGAGAAGAACTTCCCCAATAACGGGATAGAAAGCCTGGTGGACAAGATGAGCCGCTGGAAGACGTA

TGCGCAGGAGCACAGGGACGATCCCCGGGCGTCGCAGGGGGCCACGAGCCGGGGCAGCGCCCGCCCGTAAAC

GCCGGTGGCACGACAGGCAGCGGGGACAGATGTGGGACGATGAGGACTCCGCCGACGACAGCAGCGTGTTG

GACTTGGGTGGGAGTGGTAACCCGTTCGCTCACCTGCGCCCCCGTATCGGGCGCATGATGTAAGAGAAACCG

AAAATAAATGATACTCACCAAGGCCATGGCGACCAGCGTGCGTTCGTTTCTTCTCTGTTGTTGTTGTATCTAGT

ATGATGAGGCGTGCGTACCCGGAGGGTCCTCCTCCCTCGTACGAGAGCGTGATGCAGCAGGCGATGGCGGCG

GCGGCGATGCAGCCCCCGCTGGAGGCTCCTTACGTGCCCCCGCGGTACCTGGCGCCTACGGAGGGGCGGAAC

AGCATTCGTTACTCGGAGCTGGCACCCTTGTACGATACCACCCGGTTGTACCTGGTGGACAACAAGTCGGCGG

ACATCGCCTCGCTGAACTACCAGAACGACCACAGCAACTTCCTGACCACCGTGGTGCAGAACAATGACTTCA

CCCCCACGGAGGCCAGCACCCAGACCATCAACTTTGACGAGCGCTCGCGGTGGGGCGGCCAGCTGAAAACCA

TCATGCACACCAACATGCCCAACGTGAACGAGTTCATGTACAGCAACAAGTTCAAGGCGCGGGTGATGGTCT

CCCGCAAGACCCCCAATGGGGTGACAGTGACAGAGGATTATGATGGTAGTCAGGATGAGCTGAAGTATGAAT

GGGTGGAATTTGAGCTGCCCGAAGGCAACTTCTCGGTGACCATGACCATCGACCTGATGAACAACGCCATCA

TCGACAATTACTTGGCGGTGGGGCGGCAGAACGGGGTGCTGGAGAGCGACATCGGCGTGAAGTTCGACACTA

GGAACTTCAGGCTGGGCTGGGACCCCGTGACCGAGCTGGTCATGCCCGGGGTGTACACCAACGAGGCTTTCC

ATCCCGATATTGTCTTGCTGCCCGGCTGCGGGGTGGACTTCACCGAGAGCCGCCTCAGCAACCTGCTGGGCAT

TCGCAAGAGGCAGCCCTTCCAGGAAGGCTTCCAGATCATGTACGAGGATCTGGAGGGGGGCAACATCCCCGC

GCTCCTGGATGTCGACGCCTATGAGAAAAGCAAGGAGGATGCAGCAGCTGAAGCAACTGCAGCCGTAGCTAC

CGCCTCTACCGAGGTCAGGGGCGATAATTTTGCAAGCGCCGCAGCAGTGGCAGCGGCCGAGGCGGCTGAAAC

CGAAAGTAAGATAGTCATTCAGCCGGTGGAGAAGGATAGCAAGAACAGGAGCTACAACGTACTACCGGACA

AGATAAACACCGCCTACCGCAGCTGGTACCTAGCCTACAACTATGGCGACCCCGAGAAGGGCGTGCGCTCCT

GGACGCTGCTCACCACCTCGGACGTCACCTGCGGCGTGGAGCAAGTCTACTGGTCGCTGCCCGACATGATGC

AAGACCCGGTCACCTTCCGCTCCACGCGTCAAGTTAGCAACTACCCGGTGGTGGGCGCCGAGCTCCTGCCCGT

CTACTCCAAGAGCTTCTTCAACGAGCAGGCCGTCTACTCGCAGCAGCTGCGCGCCTTCACCTCGCTTACGCAC

-continued

GTCTTCAACCGCTTCCCCGAGAACCAGATCCTCGTCCGCCCGCCCGCGCCCACCATTACCACCGTCAGTGAAA

ACGTTCCTGCTCTCACAGATCACGGGACCCTGCCGCTGCGCAGCAGTATCCGGGGAGTCCAGCGCGTGACCGT

TACTGACGCCAGACGCCGCACCTGCCCCTACGTCTACAAGGCCCTGGGCATAGTCGCGCCGCGCGTCCTCTCG

AGCCGCACCTTCTAAATGTCCATTCTCATCTCGCCCAGTAATAACACCGGTTGGGGCCTGCGCGCGCCCAGCA

AGATGTACGGAGGCGCTCGCCAACGCTCCACGCAACACCCCGTGCGCGTGCGCGGGCACTTCCGCGCTCCCT

GGGGCGCCCTCAAGGGCCGCGTGCGGTCGCGCACCACCGTCGACGACGTGATCGACCAGGTGGTGGCCGACG

CGCGCAACTACACCCCCGCCGCCGCGCCCGTCTCCACCGTGGACGCCGTCATCGACAGCGTGGTGGCcGACGC

GCGCCGGTACGCCCGCGCCAAGAGCCGGCGGCGGCGCATCGCCCGGCGGCACCGGAGCACCCCCGCCATGCG

CGCGGCGCGAGCCTTGCTGCGCAGGGCCAGGCGCACGGGACGCAGGGCCATGCTCAGGGCGGCCAGACGCG

CGGCTTCAGGCGCCAGCGCCGGCAGGACCCGGAGACGCGCGGCCACGGCGGCGGCAGCGGCCATCGCCAGC

ATGTCCCGCCCGCGGCGAGGGAACGTGTACTGGGTGCGCGACGCCGCCACCGGTGTGCGCGTGCCCGTGCGC

ACCCGCCCCCCTCGCACTTGAAGATGTTCACTTCGCGATGTTGATGTGTCCCAGCGGCGAGGAGGATGTCCAA

GCGCAAATTCAAGGAAGAGATGCTCCAGGTCATCGCGCCTGAGATCTACGGCCCTGCGGTGGTGAAGGAGGA

AAGAAAGCCCCGCAAAATCAAGCGGGTCAAAAAGGACAAAAAGGAAGAAGAAAGTGATGTGGACGGATTG

GTGGAGTTTGTGCGCGAGTTCGCCCCCCGGCGGCGCGTGCAGTGGCGCGGGCGGAAGGTGCAACCGGTGCTG

AGACCCGGCACCACCGTGGTCTTCACGCCCGGCGAGCGCTCCGGCACCGCTTCCAAGCGCTCCTACGACGAG

GTGTACGGGGATGATGATATTCTGGAGCAGGCGGCCGAGCGCCTGGGCGAGTTTGCTTACGGCAAGCGCAGC

CGTTCCGCACCGAAGGAAGAGGCGGTGTCCATCCCGCTGGACCACGGCAACCCCACGCCGAGCCTCAAGCCC

GTGACCTTGCAGCAGGTGCTGCCGACCGCGGCGCCGCGCCGGGGGTTCAAGCGCGAGGGCGAGGATCTGTAC

CCCACCATGCAGCTGATGGTGCCCAAGCGCCAGAAGCTGGAAGACGTGCTGGAGACCATGAAGGTGGACCCG

GACGTGCAGCCCGAGGTCAAGGTGCGGCCCATCAAGCAGGTGGCCCCGGGCCTGGGCGTGCAGACCGTGGAC

ATCAAGATTCCCACGGAGCCCATGGAAACGCAGACCGAGCCCATGATCAAGCCCAGCACCAGCACCATGGAG

GTGCAGACGGATCCCTGGATGCCATCGGCTCCTAGTCGAAGACCCCGGCGCAAGTACGGCGCGGCCAGCCTG

CTGATGCCCAACTACGCGCTGCATCCTTCCATCATCCCCACGCCGGGCTACCGCGGCACGCGCTTCTACCGCG

GTCATACCAGCAGCCGCCGCCGCAAGACCACCACTCGCCGCCGCCGTCGCCGCACCGCCGCTGCAACCACCC

CTGCCGCCCTGGTGCGGAGAGTGTACCGCCGCGGCCGCGCACCTCTGACCCTGCCGCGCGCGCGCTACCACCC

GAGCATCGCCATTTAAACTTTCGCCtGCTTTGCAGATCAATGGCCCTCACATGCCGCCTTCGCGTTCCCATTAC

GGGCTACCGAGGAAGAAAACCGCGCCGTAGAAGGCTGGCGGGGAACGGGATGCGTCGCCACCACCACCGGC

GGCGGCGCGCCATCAGCAAGCGGTTGGGGGGAGGCTTCCTGCCCGCGCTGATCCCCATCATCGCCGCGGCGA

TCGGGGCGATCCCCGGCATTGCTTCCGTGGCGGTGCAGGCCTCTCAGCGCCACTGAGACACACTTGGAAACAT

CTTGTAATAAACCaATGGACTCTGACGCTCCTGGTCCTGTGATGTGTTTTCGTAGACAGATGGAAGACATCAA

TTTTTCGTCCCTGGCTCCGCGACACGGCACGCGGCCGTTCATGGGCACCTGGAGCGACATCGGCACCAGCCAA

CTGAACGGGGGCGCCTTCAATTGGAGCAGTCTCTGGAGCGGGCTTAAGAATTTCGGGTCCACGCTTAAAACCT

ATGGCAGCAAGGCGTGGAACAGCACCACAGGGCAGGCGCTGAGGGATAAGCTGAAAGAGCAGAACTTCCAG

CAGAAGGTGGTCGATGGGCTCGCCTCGGGCATCAACGGGGTGGTGGACCTGGCCAACCAGGCCGTGCAGCGG

CAGATCAACAGCCGCCTGGACCCGGTGCCGCCCGCCGGCTCCGTGGAGATGCCGCAGGTGGAGGAGGAGCTG

CCTCCCCTGGACAAGCGGGGCGAGAAGCGACCCCGCCCCGATGCGGAGGAGACGCTGCTGACGCACACGGA

CGAGCCGCCCCCGTACGAGGAGGCGGTGAAACTGGGTCTGCCCACCACGCGGCCCATCGCGCCCCTGGCCAC

CGGGGTGCTGAAACCCGAAAAGCCCGCGACCCTGGACTTGCCTCCTCCCCAGCCTTCCCGCCCCTCTACAGTG

GCTAAGCCCCTGCCGCCGGTGGCCGTGGCCCGCGCGCGACCCGGGGGCACCGCCCGCCCTCATGCGAACTGG

-continued

CAGAGCACTCTGAACAGCATCGTGGGTCTGGGAGTGCAGAGTGTGAAGCGCCGCCGCTGCTATTAAACCTAC

CGTAGCGCTTAACTTGCTTGTCTGTGTGTGTATGTATTATGTCGCCGCCGCCGCTGTCCACCAGAAGGAGGAG

TGAAGAGGCGCGTCGCCGAGTTGCAAGATGGCCACCCCATCGATGCTGCCCCAGTGGGCGTACATGCACATC

GCCGGACAGGACGCTTCGGAGTACCTGAGTCCGGGTCTGGTGCAGTTTGCCCGCGCCACAGACACCTACTTCA

GTCTGGGGAACAAGTTTAGGAACCCCACGGTGGCGCCCACGCACGATGTGACCACCGACCGCAGCCAGCGGC

TGACGCTGCGCTTCGTGCCCGTGGACCGCGAGGACAACACCTACTCGTACAAAGTGCGCTACACGCTGGCCG

TGGGCGACAACCGCGTGCTGGACATGGCCAGCACCTACTTTGACATCCGCGGCGTGCTGGATCGGGGCCCTA

GCTTCAAACCCTACTCCGGCACCGCCTACAACAGTCTGGCCCCCAAGGGAGCACCCAACACTTGTCAGTGGA

CATATAAAGCCGATGGTGAAACTGCCACAGAAAAAACCTATACATATGGAAATGCACCCGTGCAGGGCATTA

ACATCACAAAAGATGGTATTCAACTTGGAACTGACACCGATGATCAGCCAATCTACGCAGATAAAACCTATC

AGCCTGAACCTCAAGTGGGTGATGCTGAATGGCATGACATCACTGGTACTGATGAAAAGTATGGAGGCAGAG

CTCTTAAGCCTGATACCAAAATGAAGCCTTGTTATGGTTCTTTTGCCAAGCCTACTAATAAAGAAGGAGGTCA

GGCAAATGTGAAAACAGGAACAGGCACTACTAAAGAATATGACATAGACATGGCTTTCTTTGACAACAGAAG

TGCGGCTGCTGCTGGCCTAGCTCCAGAAATTGTTTTGTATACTGAAAATGTGGATTTGGAAACTCCAGATACC

CATATTGTATACAAAGCAGGCACAGATGACAGCAGCTCTTCTATTAATTTGGGTCAGCAAGCCATGCCCAACA

GACCTAACTACATTGGTTTCAGAGACAACTTTATCGGGCTCATGTACTACAACAGCACTGGCAATATGGGGGT

GCTGGCCGGTCAGGCTTCTCAGCTGAATGCTGTGGTTGACTTGCAAGACAGAAACACCGAGCTGTCCTACCAG

CTCTTGCTTGACTCTCTGGGTGACAGAACCCGGTATTTCAGTATGTGGAATCAGGCGGTGGACAGCTATGATC

CTGATGTGCGCATTATTGAAAATCATGGTGTGGAGGATGAACTTCCCAACTATTGTTTCCCTCTGGATGCTGTT

GGCAGAACAGATACTTATCAGGGAATTAAGGCTAATGGAACTGATCAAACCACATGGACCAAAGATGACAGT

GTCAATGATGCTAATGAGATAGGCAAGGGTAATCCATTCGCCATGGAAATCAACATCCAAGCCAACCTGTGG

AGGAACTTCCTCTACGCCAACGTGGCCCTGTACCTGCCCGACTCTTACAAGTACACGCCGGCCAATGTTACCC

TGCCCACCAACACCAACACCTACGATTACATGAACGGCCGGGTGGTGGCGCCCTCGCTGGTGGACTCCTACAT

CAACATCGGGGCGCGCTGGTCGCTGGATCCCATGGACAACGTGAACCCCTTCAACCACCACCGCAATGCGGG

GCTGCGCTACCGCTCCATGCTCCTGGGCAACGGGCGCTACGTGCCCTTCCACATCCAGGTGCCCCAGAAATTT

TTCGCCATCAAGAGCCTCCTGCTCCTGCCCGGGTCCTACACCTACGAGTGGAACTTCCGCAAGGACGTCAACA

TGATCCTGCAGAGCTCCCTCGGCAACGACCTGCGCACGGACGGGGCCTCCATCTCCTTCACCAGCATCAACCT

CTACGCCACCTTCTTCCCCATGGCGCACAACACGGCCTCCACGCTCGAGGCCATGCTGCGCAACGACACCAAC

GACCAGTCCTTCAACGACTACCTCTCGGCGGCCAACATGCTCTACCCCATCCCGGCCAACGCCACCAACGTGC

CCATCTCCATCCCCTCGCGCAACTGGGCCGCCTTCCGCGGCTGGTCCTTCACGCGTCTCAAGACCAAGGAGAC

GCCCTCGCTGGGCTCCGGGTTCGACCCCTACTTCGTCTACTCGGGCTCCATCCCCTACCTCGACGGCACCTTCT

ACCTCAACCACACCTTCAAGAAGGTCTCCATCACCTTCGACTCCTCCGTCAGCTGGCCCGGCAACGACCGGCT

CCTGACGCCCAACGAGTTCGAAATCAAGCGCACCGTCGACGGCGAGGGCTACAACGTGGCCCAGTGCAACAT

GACCAAGGACTGGTTCCTGGTCCAGATGCTGGCCCACTACAACATCGGCTACCAGGGCTTCTACGTGCCCGAG

GGCTACAAGGACCGCATGTACTCCTTCTTCCGCAACTTCCAGCCCATGAGCCGCCAGGTGGTGGACGAGGTCA

ACTACAAGGACTACCAGGCCGTCACCCTGGCCTACCAGCACAACAACTCGGGCTTCGTCGGCTACCTCGCGCC

CACCATGCGCCAGGGCCAGCCCTACCCCGCCAACTACCCCTACCCGCTCATCGGCAAGAGCGCCGTCACCAG

CGTCACCCAGAAAAAGTTCCTCTGCGACAGGGTCATGTGGCGCATCCCCTTCTCCAGCAACTTCATGTCCATG

GGCGCGCTCACCGACCTCGGCCAGAACATGCTCTATGCCAACTCCGCCCACGCGCTAGACATGAATTTCGAA

GTCGACCCCATGGATGAGTCCACCCTTCTCTATGTTGTCTTCGAAGTCTTCGACGTCGTCCGAGTGCACCAGCC

CCACCGCGGCGTCATCGAGGCCGTCTACCTGCGCACCCCCTTCTCGGCCGGTAACGCCACCACCTAAGCTCTT

-continued

GCTTCTTGCAAGCCATGGCCGCGGGCTCCGGCGAGCAGGAGCTCAGGGCCATCATCCGCGACCTGGGCTGCG
GGCCCTACTTCCTGGGCACCTTCGATAAGCGCTTCCCGGGATTCATGGCCCCGCACAAGCTGGCCTGCGCCAT
CGTCAACACGGCCGGCCGCGAGACCGGGGGCGAGCACTGGCTGGCCTTCGCCTGGAACCCGCGCTCGAACAC
CTGCTACCTCTTCGACCCCTTCGGGTTCTCGGACGAGCGCCTCAAGCAGATCTACCAGTTCGAGTACGAGGGC
CTGCTGCGCCGCAGCGCCCTGGCCACCGAGGACCGCTGCGTCACCCTGGAAAAGTCCACCCAGACCGTGCAG
GGTCCGCGCTCGGCCGCCTGCGGGCTCTTCTGCTGCATGTTCCTGCACGCCTTCGTGCACTGGCCCGACCGCC
CCATGGACAAGAACCCCACCATGAACTTGCTGACGGGGGTGCCCAACGGCATGCTCCAGTCGCCCCAGGTGG
AACCCACCCTGCGCCGCAACCAGGAGGCGCTCTACCGCTTCCTCAACTCCCACTCCGCCTACTTTCGCTCCCA
CCGCGCGCGCATCGAGAAGGCCACCGCCTTCGACCGCATGAATCAAGACATGTAAACCGTGTGTGTATGTTA
AATGTCTTTAATAAACAGCACTTTCATGTTACACATGCATCTGAGATGATTTATTTAGAAATCGAAAGGGTTC
TGCCGGGTCTCGGCATGGCCCGCGGGCAGGGACACGTTGCGGAACTGGTACTTGGCCAGCCACTTGAACTCG
GGGATCAGCAGTTTGGGCAGCGGGGTGTCGGGGAAGGAGTCGGTCCACAGCTTCCGCGTCAGTTGCAGGGCG
CCCAGCAGGTCGGGCGCGGAGATCTTGAAATCGCAGTTGGGACCCGCGTTCTGCGCGCGGGAGTTGCGGTAC
ACGGGGTTGCAGCACTGGAACACCATCAGGGCCGGGTGCTTCACGCTCGCCAGCACCGTCGCGTCGGTGATG
CTCTCCACGTCGAGGTCCTCGGCGTTGGCCATCCCGAAGGGGGTCATCTTGCAGGTCTGCCTTCCCATGGTGG
GCACGCACCCGGGCTTGTGGTTGCAATCGCAGTGCAGGGGGATCAGCATCATCTGGGCCTGGTCGGCGTTCAT
CCCCGGGTACATGGCCTTCATGAAAGCCTCCAATTGCCTGAACGCCTGCTGGGCCTTGGCTCCCTCGGTGAAG
AAGACCCCGCAGGACTTGCTAGAGAACTGGTTGGTGGCGCACCCGGCGTCGTGCACGCAGCAGCGCGCGTCG
TTGTTGGCCAGCTGCACCACGCTGCGCCCCCAGCGGTTCTGGGTGATCTTGGCCCGGTCGGGGTTCTCCTTCA
GCGCGCGCTGCCCGTTCTCGCTCGCCACATCCATCTCGATCATGTGCTCCTTCTGGATCATGGTGGTCCCGTGC
AGGCACCGCAGCTTGCCCTCGGCCTCGGTGCACCCGTGCAGCCACAGCGCGCACCCGGTGCACTCCCAGTTCT
TGTGGGCGATCTGGGAATGCGCGTGCACGAAGCCCTGCAGGAAGCGGCCCATCATGGTGGTCAGGGTCTTGT
TGCTAGTGAAGGTCAGCGGAATGCCGCGGTGCTCCTCGTTGATGTACAGGTGGCAGATGCGGCGGTACACCT
CGCCCTGCTCGGGCATCAGCTGGAAGTTGGCTTTCAGGTCGGTCTCCACGCGGTAGCGGTCCATCAGCATAGT
CATGATTTCCATACCCTTCTCCCAGGCCGAGACGATGGGCAGGCTCATAGGGTTCTTCACCATCATCTTAGCG
CTAGCAGCCGCGGCCAGGGGGTCGCTCTCGTCCAGGGTCTCAAAGCTCCGCTTGCCGTCCTTCTCGGTGATCC
GCACCGGGGGGTAGCTGAAGCCCACGGCCGCCAGCTCCTCCTCGGCCTGTCTTTCGTCCTCGCTGTCCTGGCT
GACGTCCTGCAGGACCACATGCTTGGTCTTGCGGGGTTTCTTCTTGGGCGGCAGCGGCGGCGGAGATGTTGGA
GATGGCGAGGGGGAGCGCGAGTTCTCGCTCACCACTACTATCTCTTCCTCTTCTTGGTCCGAGGCCACGCGGC
GGTAGGTATGTCTCTTCGGGGGCAGAGGCGGAGGCGACGGGCTCTCGCCGCCGCGACTTGGCGGATGGCTGG
CAGAGCCCCTTCCGCGTTCGGGGGTGCGCTCCCGGCGGCGCTCTGACTGACTTCCTCCGCGGCCGGCCATTGT
GTTCTCCTAGGGAGGAACAACAAGCATGGAGACTCAGCCATCGCCAACCTCGCCATCTGCCCCCACCGCCGA
CGAGAAGCAGCAGCAGCAGAATGAAAGCTTAACCGCCCCGCCGCCCAGCCCCGCCACCTCCGACGCGGCCGT
CCCAGACATGCAAGAGATGGAGGAATCCATCGAGATTGACCTGGGCTATGTGACGCCCGCGGAGCACGAGG
AGGAGCTGGCAGTGCGCTTTTCACAAGAAGAGATACACCAAGAACAGCCAGAGCAGGAAGCAGAGAATGAG
CAGAGTCAGGCTGGGCTCGAGCATGACGGCGACTACCTCCACCTGAGCGGGGGGGAGGACGCGCTCATCAAG
CATCTGGCCCGGCAGGCCACCATCGTCAAGGATGCGCTGCTCGACCGCACCGAGGTGCCCCTCAGCGTGGAG
GAGCTCAGCCGCGCCTACGAGTTGAACCTCTTCTCGCCGCGCGTGCCCCCCAAGCGCCAGCCCAATGGCACCT
GCGAGCCCAACCCGCGCCTCAACTTCTACCCGGTCTTCGCGGTGCCCGAGGCCCTGGCCACCTACCACATCTT
TTTCAAGAACCAAAAGATCCCCGTCTCCTGCCGCGCCAACCGCACCCGCGCCGACGCCCTTTTCAACCTGGGT

-continued

CCCGGCGCCCGCCTACCTGATATCGCCTCCTTGGAAGAGGTTCCCAAGATCTTCGAGGGTCTGGGCAGCGACG

AGACTCGGGCCGCGAACGCTCTGCAAGGAGAAGGAGGAGAGCATGAGCACCACAGCGCCCTGGTCGAGTTG

GAAGGCGACAACGCGCGGCTGGCGGTGCTCAAACGCACGGTCGAGCTGACCCATTTCGCCTACCCGGCTCTG

AACCTGCCCCCCAAAGTCATGAGCGCGGTCATGGACCAGGTGCTCATCAAGCGCGCGTCGCCCATCTCCGAG

GACGAGGGCATGCAAGACTCCGAGGAGGGCAAGCCCGTGGTCAGCGACGAGCAGCTGGCCCGGTGGCTGGG

TCCTAATGCTAGTCCCCAGAGTTTGGAAGAGCGGCGCAAACTCATGATGGCCGTGGTCCTGGTGACCGTGGA

GCTGGAGTGCCTGCGCCGCTTCTTCGCCGACGCGGAGACCCTGCGCAAGGTCGAGGAGAACCTGCACTACCT

CTTCAGGCACGGGTTCGTGCGCCAGGCCTGCAAGATCTCCAACGTGGAGCTGACCAACCTGGTCTCCTACATG

GGCATCTTGCACGAGAACCGCCTGGGGCAGAACGTGCTGCACACCACCCTGCGCGGGGAGGCCCGGCGCGAC

TACATCCGCGACTGCGTCTACCTCTACCTCTGCCACACCTGGCAGACGGGCATGGGCGTGTGGCAGCAGTGTC

TGGAGGAGCAGAACCTGAAAGAGCTCTGCAAGCTCCTGCAGAAGAACCTCAAGGGTCTGTGGACCGGGTTCG

ACGAGCGCACCACCGCCTCGGACCTGGCCGACCTCATTTTCCCCGAGCGCCTCAGGCTGACGCTGCGCAACG

GCCTGCCCGACTTTATGAGCCAAAGCATGTTGCAAAACTTTCGCTCTTTCATCCTCGAACGCTCCGGAATCCT

GCCCGCCACCTGCTCCGCGCTGCCCTCGGACTTCGTGCCGCTGACCTTCCGCGAGTGCCCCCCGCCGCTGTGG

AGCCACTGCTACCTGCTGCGCCTGGCCAACTACCTGGCCTACCACTCGGACGTGATCGAGGACGTCAGCGGC

GAGGGCCTGCTCGAGTGCCACTGCCGCTGCAACCTCTGCACGCCGCACCGCTCCCTGGCCTGCAACCCCCAGC

TGCTGAGCGAGACCCAGATCATCGGCACCTTCGAGTTGCAAGGGCCCAGCGAAGGCGAGGGTTCAGCCGCCA

AGGGGGGTCTGAAACTCACCCCGGGGCTGTGGACCTCGGCCTACTTGCGCAAGTTCGTGCCCGAGGACTACC

ATCCCTTCGAGATCAGGTTCTACGAGGACCAATCCCATCCGCCCAAGGCCGAGCTGTCGGCCTGCGTCATCAC

CCAGGGGGCGATCCTGGCCCAATTGCAAGCCATCCAGAAATCCCGCCAAGAATTCTTGCTGAAAAAGGGCCG

CGGGGTCTACCTCGACCCCCAGACCGGTGAGGAGCTCAACCCCGGCTTCCCCCAGGATGCCCCGAGGAAACA

AGAAGCTGAAAGTGGAGCTGCCGCCCGTGGAGGATTTGGAGGAAGACTGGGAGAACAGCAGTCAGGCAGAG

GAGGAGGAGATGGAGGAAGACTGGGACAGCACTCAGGCAGAGGAGGACAGCCTGCAAGACAGTCTGGAGG

AAGACGAGGAGGAGGCAGAGGAGGAGGTGGAAGAAGCAGCCGCCGCCAGACCGTCGTCCTCGGCGGGGGA

GAAAGCAAGCAGCACGGATACCATCTCCGCTCCGGGTCGGGGTCCCGCTCGACCACACAGTAGATGGGACGA

GACCGGACGATTCCCGAACCCCACCACCCAGACCGGTAAGAAGGAGCGGCAGGGATACAAGTCCTGGCGGG

GGCACAAAAACGCCATCGTCTCCTGCTTGCAGGCCTGCGGGGGCAACATCTCCTTCACCCGGCGCTACCTGCT

CTTCCACCGCGGGGTGAACTTTCCCCGCAACATCTTGCATTACTACCGTCACCTCCACAGCCCCTACTACTTCC

AAGAAGAGGCAGCAGCAGCAGAAAAAGACCAGCAGAAAACCAGCAGCTAGAAAATCCACAGCGGCGGCAG

CAGGTGGACTGAGGATCGCGGCGAACGAGCCGGCGCAAACCCGGGAGCTGAGGAACCGGATCTTTCCCACCC

TCTATGCCATCTTCCAGCAGAGTCGGGGGCAGGAGCAGGAACTGAAAGTCAAGAACCGTTCTCTGCGCTCGC

TCACCCGCAGTTGTCTGTATCACAAGAGCGAAGACCAACTTCAGCGCACTCTCGAGGACGCCGAGGCTCTCTT

CAACAAGTACTGCGCGCTCACTCTTAAAGAGTAGCCCGCGCCCGCCCAGTCGCAGAAAAAGGCGGGAATTAC

GTCACCTGTGCCCTTCGCCCTAGCCGCCTCCACCCATCATCATGAGCAAAGAGATTCCCACGCCTTACATGTG

GAGCTACCAGCCCCAGATGGGCCTGGCCGCCGGTGCCGCCCAGGACTACTCCACCCGCATGAATTGGCTCAG

CGCCGGGCCCGCGATGATCTCACGGGTGAATGACATCCGCGCCCACCGAAACCAGATACTCCTAGAACAGTC

AGCGCTCACCGCCACGCCCCGCAATCACCTCAATCCGCGTAATTGGCCCGCCGCCCTGGTGTACCAGGAAATT

CCCCAGCCCACGACCGTACTACTTCCGCGAGACGCCCAGGCCGAAGTCCAGCTGACTAACTCAGGTGTCCAG

CTGGCGGGCGGCGCCACCCTGTGTCGTCACCGCCCCGCTCAGGGTATAAAGCGGCTGGTGATCCGGGGCAGA

GGCACACAGCTCAACGACGAGGTGGTGAGCTCTTCGCTGGGTCTGCGACCTGACGGAGTCTTCCAACTCGCC

GGATCGGGGAGATCTTCCTTCACGCCTCGTCAGGCCGTCCTGACTTTGGAGAGTTCGTCCTCGCAGCCCCGCT

-continued

CGGGTGGCATCGGCACTCTCCAGTTCGTGGAGGAGTTCACTCCCTCGGTCTACTTCAACCCCTTCTCCGGCTCC

CCCGGCCACTACCCGGACGAGTTCATCCCGAACTTCGACGCCATCAGCGAGTCGGTGGACGGCTACGATTGA

AACTAATCACCCCCTTATCCAGTGAAATAAAGATCATATTGATGATGATTTTACAGAAATAAAAAATAATCAT

TTGATTTGAAATAAAGATACAATCATATTGATGATTTGAGTTTAACAAAAAAATAAAGAATCACTTACTTGAA

ATCTGATACCAGGTCTCTGTCCATGTTTTCTGCCAACACCACTTCACTCCCCTCTTCCCAGCTCTGGTACTGCA

GGCCCCGGCGGGCTGCAAACTTCCTCCACACGCTGAAGGGGATGTCAAATTCCTCCTGTCCCTCAATCTTCAT

TTTATCTTCTATCAGATGTCCAAAAAGCGCGTCCGGGTGGATGATGACTTCGACCCCGTCTACCCCTACGATG

CAGACAACGCACCGACCGTGCCCTTCATCAACCCCCCCTTCGTCTCTTCAGATGGATTCCAAGAGAAGCCCCT

GGGGGTGTTGTCCCTGCGACTGGCCGACCCCGTCACCACCAAGAACGGGGAAATCACCCTCAAGCTGGGAGA

GGGGGTGGACCTCGATTCCTCGGGAAAACTCATCTCCAACACGGCCACCAAGGCCGCCGCCCCTCTCAGTTTT

TCCAACAACACCATTTCCCTTAACATGGATCACCCCTTTTACACTAAAGATGGAAAATTATCCTTACAAGTTTC

TCCACCATTAAATATACTGAGAACAAGCATTCTAAACACACTAGCTTTAGGTTTTGGATCAGGTTTAGGACTC

CGTGGCTCTGCCTTGGCAGTACAGTTAGTCTCTCCACTTACATTTGATACTGATGGAAACATAAAGCTTACCTT

AGACAGAGGTTTGCATGTTACAACAGGAGATGCAATTGAAAGCAACATAAGCTGGGCTAAAGGTTTAAAATT

TGAAGATGGAGCCATAGCAACCAACATTGGAAATGGGTTAGAGTTTGGAAGCAGTAGTACAGAAACAGGTGT

TGATGATGCTTACCCAATCCAAGTTAAACTTGGATCTGGCCTTAGCTTTGACAGTACAGGAGCCATAATGGCT

GGTAACAAAGAAGACGATAAACTCACTTTGTGGACAACACCTGATCCATCACCAAACTGTCAAATACTCGCA

GAAAATGATGCAAAACTAACACTTTGCTTGACTAAATGTGGTAGTCAAATACTGGCCACTGTGTCAGTCTTAG

TTGTAGGAAGTGGAAACCTAAACCCCATTACTGGCACCGTAAGCAGTGCTCAGGTGTTTCTACGTTTTGATGC

AAACGGTGTTCTTTTAACAGAACATTCTACACTAAAAAAATACTGGGGGTATAGGCAGGGAGATAGCATAGA

TGGCACTCCATATACCAATGCTGTAGGATTCATGCCCAATTTAAAAGCTTATCCAAAGTCACAAAGTTCTACT

ACTAAAAATAATATAGTAGGGCAAGTATACATGAATGGAGATGTTTCAAAACCTATGCTTCTCACTATAACCC

TCAATGGTACTGATGACAGCAACAGTACATATTCAATGTCATTTTCATACACCTGGACTAATGGAAGCTATGT

TGGAGCAACATTTGGGGCTAACTCTTATACCTTCTCATACATCGCCCAAGAATGAACACTGTATCCCACCCTG

CATGCCAACCCTTCCCACCCCACTCTGTGGAACAAACTCTGAAACACAAAATAAAATAAAGTTCAAGTGTTTT

ATTGATTCAACAGTTTTACAGGATTCGAGCAGTTATTTTTCCTCCACCCTCCCAGGACATGGAATACACCACC

CTCTCCCCCCGCACAGCCTTGAACATCTGAATGCCATTGGTGATGGACATGCTTTTGGTCTCCACGTTCCACAC

AGTTTCAGAGCGAGCCAGTCTCGGGTCGGTCAGGGAGATGAAACCCTCCGGGCACTCCCGCATCTGCACCTC

ACAGCTCAACAGCTGAGGATTGTCCTCGGTGGTCGGGATCACGGTTATCTGGAAGAAGCAGAAGAGCGGCGG

TGGGAATCATAGTCCGCGAACGGGATCGGCCGGTGGTGTCGCATCAGGCCCCGCAGCAGTCGCTGCCGCCGC

CGCTCCGTCAAGCTGCTGCTCAGGGGGTCCGGGTCCAGGGACTCCCTCAGCATGATGCCCACGGCCCTCAGCA

TCAGTCGTCTGGTGCGGCGGGCGCAGCAGCGCATGCGGATCTCGCTCAGGTCGCTGCAGTACGTGCAACACA

GAACCACCAGGTTGTTCAACAGTCCATAGTTCAACACGCTCCAGCCGAAACTCATCGCGGGAAGGATGCTAC

CCACGTGGCCGTCGTACCAGATCCTCAGGTAAATCAAGTGGTGCCCCCTCCAGAACACGCTGCCCACGTACAT

GATCTCCTTGGGCATGTGGCGGTTCACCACCTCCCGGTACCACATCACCCTCTGGTTGAACATGCAGCCCCGG

ATGATCCTGCGGAACCACAGGGCCAGCACCGCCCCGCCCGCCATGCAGCGAAGAGACCCCGGGTCCCGGCAA

TGGCAATGGAGGACCCACCGCTCGTACCCGTGGATCATCTGGGAGCTGAACAAGTCTATGTTGGCACAGCAC

AGGCATATGCTCATGCATCTCTTCAGCACTCTCAACTCCTCGGGGGTCAAAACCATATCCCAGGGCACGGGGA

ACTCTTGCAGGACAGCGAACCCCGCAGAACAGGGCAATCCTCGCACAGAACTTACATTGTGCATGGACAGGG

TATCGCAATCAGGCAGCACCGGGTGATCCTCCACCAGAGAAGCGCGGGTCTCGGTCTCCTCACAGCGTGGTA

-continued

AGGGGGCCGGCCGATACGGGTGATGGCGGGACGCGGCTGATCGTGTTCGCGACCGTGTCATGATGCAGTTGC

TTTCGGACATTTTCGTACTTGCTGTAGCAGAACCTGGTCCGGGCGCTGCACACCGATCGCCGGCGGCGGTCTC

GGCGCTTGGAACGCTCGGTGTTGAAATTGTAAAACAGCCACTCTCTCAGACCGTGCAGCAGATCTAGGGCCTC

AGGAGTGATGAAGATCCCATCATGCCTGATGGCTCTGATCACATCGACCACCGTGGAATGGGCCAGACCCAG

CCAGATGATGCAATTTTGTTGGGTTTCGGTGACGGCGAGCCTCGGGAACAACGATGAAGTAAATGCAAGCGG

TGCGTTCCAGCATGGTTAGTTAGCTGATCTGTAGAAAAAACAAAAATGAACATTAAACCATGCTAGCCTGGC

GAACAGGTGGGTAAATCGTTCTCTCCAGCACCAGGCAGGCCACGGGGTCTCCGGCGCGACCCTCGTAAAAAT

TGTCGCTATGATTGAAAACCATCACAGAGAGACGTTCCCGGTGGCCGGCGTGAATGATTCGACAAGATGAAT

ACACCCCCGGAACATTGGCGTCCGCGAGTGAAAAAAAGCGCCCGAGGAAGCAATAAGGCACTACAATGCTC

AGTCTCAAGTCCAGCAAAGCGATGCCATGCGGATGAAGCACAAAATTCTCAGGTGCGTACAAAATGTAATTA

CTCCCCTCCTGCACAGGCAGCAAAGCCCCCGATCCCTCCAGGTACACATACAAAGCCTCAGCGTCCATAGCTT

ACCGAGCAGCAGCACACAACAGGCGCAAGAGTCAGAGAAAGGCTGAGCTCTAACCTGTCCACCCGCTCTCTG

CTCAATATATAGCCCAGATCTACACTGACGTAAAGGCCAAAGTCTAAAAATACCCGCCAAATAATCACACAC

GCCCAGCACACGCCCAGAAACCGGTGACACACTCAAAAAAATACGCGCACTTCCTCAAACGCCCAAAACTGC

CGTCATTTCCGGGTTCCCACGCTACGTCATCAAAACACGACTTTCAAATTCCGTCGACCGTTAAAAACGTCAC

CCGCCCCGCCCCTAACGGTCGCCCGTCTCTCAGCCAATCAGCGCCCCGCATCCCCAAATTCAAACACCTCATT

TGCATATTAACGCGCACAAAAAGTTTGAGGTATATTATTGATGATG

ChAdV68-GFP-E4deleted (SEQ ID NO: 58); Bold italicized = GFP transgene

CATCaTCAATAATATACCTCAAACTTTTTGTGCGCGTTAATATGCAAATGAGGCGTTTGAATTTGGGGAGGAA

GGGCGGTGATTGGTCGAGGGATGAGCGACCGTTAGGGGCGGGGCGAGTGACGTTTTGATGACGTGGTTGCGA

GGAGGAGCCAGTTTGCAAGTTCTCGTGGGAAAAGTGACGTCAAACGAGGTGTGGTTTGAACACGGAAATACT

CAATTTTCCCGCGCTCTCTGACAGGAAATGAGGTGTTTCTGGGCGGATGCAAGTGAAAACGGGCCATTTTCGC

GCGAAAACTGAATGAGGAAGTGAAAATCTGAGTAATTTCGCGTTTATGGCAGGGAGGAGTATTTGCCGAGGG

CCGAGTAGACTTTGACCGATTACGTGGGGGTTTCGATTACCGTGTTTTTCACCTAAATTTCCGCGTACGGTGTC

AAAGTCCGGTGTTTTTACGTAGGTGTCAGCTGATCGCCAGGGTATTTAAACCTGCGCTCTCCAGTCAAGAGGC

CACTCTTGAGTGCCAGCGAGAAGAGTTTTCTCCTCCGCGCCGCGAGTCAGATCTACACTTTGAAAGTAGGGAT

AACAGGGTAATgacattgattattgactagttGttaaTAGTAATCAATTACGGGGTCATTAGTTCATAGCCCATATAT

GGAGTTCCGCGTTACATAACTTACGGTAAATGGCCCGCCTGGCTGACCGCCCAACGACCCCCGCCCATTGACGTCAATA

ATGACGTATGTTCCCATAGTAACGCCAATAGGGACTTTCCATTGACGTCAATGGGTGGAGTATTTACGGTAAA

CTGCCCACTTGGCAGTACATCAAGTGTATCATATGCCAAGTCCGCCCCCTATTGACGTCAATGACGGTAAATG

GCCCGCCTGGCATTATGCCCAGTACATGACCTTACGGGACTTTCCTACTTGGCAGTACATCTACGTATTAGTC

ATCGCTATTACCATGgTGATGCGGTTTTGGCAGTACACCAATGGGCGTGGATAGCGGTTTGACTCACGGGGAT

TTCCAAGTCTCCACCCCATTGACGTCAATGGGAGTTTGTTTTGGCACCAAAATCAACGGGACTTTCCAAAATG

TCGTAATAACCCCGCCCCGTTGACGCAAATGGGCGGTAGGCGTGTACGGTGGGAGGTCTATATAAGCAGAgcT

CGTTTAGTGAACCGTCAGATCGCCTGGAACGCCATCCACGCTGTTTTGACCTCCATAGAAGACAGCGATCGCG ccacc

*ATGGTGAGCAAGGGCGAGGAGCTGTTCACCGGGGTGGTGCCCATCCTGGTCGAGCTGGACGGCGACGTAAACG*

*GCCACAAGTTCAGCGTGTCCGGCGAGGGCGAGGGCGATGCCACCTACGGCAAGCTGACCCTGAAGTTCATCTG*

*CACCACCGGCAAGCTGCCCGTGCCCTGGCCCACCCTCGTGACCACCCTGACCTACGGCGTGCAGTGCTTCAGCC*

*GCTACCCCGACCACATGAAGCAGCACGACTTCTTCAAGTCCGCCATGCCCGAAGGCTACGTCCAGGAGCGCACC*

*ATCTTCTTCAAGGACGACGGCAACTACAAGACCCGCGCCGAGGTGAAGTTCGAGGGCGACACCCTGGTGAACC*

-continued

*GCATCGAGCTGAAGGGCATCGACTTCAAGGAGGACGGCAACATCCTGGGGCACAAGCTGGAGTACAACTACAA*

*CAGCCACAACGTCTATATCATGGCCGACAAGCAGAAGAACGGCATCAAGGTGAACTTCAAGATCCGCCACAACA*

*TCGAGGACGGCAGCGTGCAGCTCGCCGACCACTACCAGCAGAACACCCCCATCGGCGACGGCCCCGTGCTGCT*

*GCCCGACAACCACTACCTGAGCACCCAGTCCGCCCTGAGCAAAGACCCCAACGAGAAGCGCGATCACATGGTCC*

*TGCTGGAGTTCGTGACCGCCGCCGGGATCACTCTCGGCATGGACGAGCTtTACAAGTAG* tgaGTTTAAACTCCCATTTAAATGTGAGGGTTAATGCTTCGAGCAGACATGATAAGATACATTGATGAGTTTGG

ACAAACCACAACTAGAATGCAGTGAAAAAAATGCTTTATTTGTGAAATTTGTGATGCTATTGCTTTATTTGTA

ACCATTATAAGCTGCAATAAACAAGTTAACAACAACAATTGCATTCATTTTATGTTTCAGGTTCAGGGGGAGA

TGTGGGAGGTTTTTTAAAGCAAGTAAAACCTCTACAAATGTGGTAAAATAACTATAACGGTCCTAAGGTAGC

GAGTGAGTAGTGTTCTGGGGCGGGGGAGGACCTGCATGAGGGCCAGAATAACTGAAATCTGTGCTTTTCTGT

GTGTTGCAGCAGCATGAGCGGAAGCGGCTCCTTTGAGGGAGGGGTATTCAGCCCTTATCTGACGGGGCGTCT

CCCCTCCTGGGCGGGAGTGCGTCAGAATGTGATGGGATCCACGGTGGACGGCCGGCCCGTGCAGCCCGCGAA

CTCTTCAACCCTGACCTATGCAACCCTGAGCTCTTCGTCGTTGGACGCAGCTGCCGCCGCAGCTGCTGCATCT

GCCGCCAGCGCCGTGCGCGGAATGGCCATGGGCGCCGGCTACTACGGCACTCTGGTGGCCAACTCGAGTTCC

ACCAATAATCCCGCCAGCCTGAACGAGGAGAAGCTGTTGCTGCTGATGGCCCAGCTCGAGGCCTTGACCCAG

CGCCTGGGCGAGCTGACCCAGCAGGTGGCTCAGCTGCAGGAGCAGACGCGGGCCGCGGTTGCCACGGTGAA

ATCCAAATAAAAAATGAATCAATAAATAAACGGAGACGGTTGTTGATTTTAACACAGAGTCTGAATCTTTATT

TGATTTTTCGCGCGCGGTAGGCCCTGGACCACCGGTCTCGATCATTGAGCACCCGGTGGATCTTTTCCAGGAC

CCGGTAGAGGTGGGCTTGGATGTTGAGGTACATGGGCATGAGCCCGTCCCGGGGGTGGAGGTAGCTCCATTG

CAGGGCCTCGTGCTCGGGGGTGGTGTTGTAAATCACCCAGTCATAGCAGGGGCGCAGGGCATGGTGTTGCAC

AATATCTTTGAGGAGGAGACTGATGGCCACGGGCAGCCCTTTGGTGTAGGTGTTTACAAATCTGTTGAGCTGG

GAGGGATGCATGCGGGGGGAGATGAGGTGCATCTTGGCCTGGATCTTGAGATTGGCGATGTTACCGCCCAGA

TCCCGCCTGGGGTTCATGTTGTGCAGGACCACCAGCACGGTGTATCCGGTGCACTTGGGGAATTTATCATGCA

ACTTGGAAGGGAAGGCGTGAAAGAATTTGGCGACGCCTTTGTGCCCGCCCAGGTTTTCCATGCACTCATCCAT

GATGATGGCGATGGGCCCGTGGGCGGCGGCCTGGGCAAAGACGTTTCGGGGGTCGGACACATCATAGTTGTG

GTCCTGGGTGAGGTCATCATAGGCCATTTTAATGAATTTGGGGCGGAGGGTGCCGGACTGGGGGACAAAGGTt

CCCTCGATCCCGGGGGCGTAGTTCCCCTCACAGATCTGCATCTCCCAGGCTTTGAGCTCGGAGGGGGGGATCA

TGTCCACCTGCGGGGCGATAAAGAACACGGTTTCCGGGGCGGGGGAGATGAGCTGGGCCGAAAGCAAGTTCC

GGAGCAGCTGGGACTTGCCGCAGCCGGTGGGGCCGTAGATGACCCCGATGACCGGCTGCAGGTGGTAGTTGA

GGGAGAGACAGCTGCCGTCCTCCCGGAGGAGGGGGGCCACCTCGTTCATCATCTCGCGCACGTGCATGTTCTC

GCGCACCAGTTCCGCCAGGAGGCGCTCTCCCCCCAGGGATAGGAGCTCCTGGAGCGAGGCGAAGTTTTTCAG

CGGCTTGAGTCCGTCGGCCATGGGCATTTTGGAGAGGGTTTGTTGCAAGAGTTCCAGGCGGTCCCAGAGCTCG

GTGATGTGCTCTACGGCATCTCGATCCAGCAGACCTCCTCGTTTCGCGGGTTGGGACGGCTGCGGGAGTAGGG

CACCAGACGATGGGCGTCCAGCGCAGCCAGGGTCCGGTCCTTCCAGGGTCGCAGCGTCCGCGTCAGGGTGGT

CTCCGTCACGGTGAAGGGGTGCGCGCCGGGCTGGGCGCTTGCGAGGGTGCGCTTCAGGCTCATCCGGCTGGT

CGAAAACCGCTCCCGATCGGCGCCCTGCGCGTCGGCCAGGTAGCAATTGACCATGAGTTCGTAGTTGAGCGC

CTCGGCCGCGTGGCCTTTGGCGCGGAGCTTACCTTTGGAAGTCTGCCCGCAGGCGGGACAGAGGAGGGACTT

GAGGGCGTAGAGCTTGGGGGCGAGGAAGACGGACTCGGGGGCGTAGGCGTCCGCGCCGCAGTGGGCGCAGA

CGGTCTCGCACTCCACGAGCCAGGTGAGGTCGGGCTGGTCGGGGTCAAAAACCAGTTTCCCGCCGTTCTTTTT

GATGCGTTTCTTACCTTTGGTCTCCATGAGCTCGTGTCCCCGCTGGGTGACAAAGAGGCTGTCCGTGTCCCCGT

AGACCGACTTTATGGGCCGGTCCTCGAGCGGTGTGCCGCGGTCCTCCTCGTAGAGGAACCCCGCCCACTCCGA

-continued

GACGAAAGCCCGGGTCCAGGCCAGCACGAAGGAGGCCACGTGGGACGGGTAGCGGTCGTTGTCCACCAGCG

GGTCCACCTTTTCCAGGGTATGCAAACACATGTCCCCCTCGTCCACATCCAGGAAGGTGATTGGCTTGTAAGT

GTAGGCCACGTGACCGGGGGTCCCGGCCGGGGGGGTATAAAAGGGTGCGGGTCCCTGCTCGTCCTCACTGTC

TTCCGGATCGCTGTCCAGGAGCGCCAGCTGTTGGGGTAGGTATTCCCTCTCGAAGGCGGGCATGACCTCGGCA

CTCAGGTTGTCAGTTTCTAGAAACGAGGAGGATTTGATATTGACGGTGCCGGCGGAGATGCCTTTCAAGAGCC

CCTCGTCCATCTGGTCAGAAAAGACGATCTTTTTGTTGTCGAGCTTGGTGGCGAAGGAGCCGTAGAGGGCGTT

GGAGAGGAGCTTGGCGATGGAGCGCATGGTCTGGTTTTTTTCCTTGTCGGCGCGCTCCTTGGCGGCGATGTTG

AGCTGCACGTACTCGCGCGCCACGCACTTCCATTCGGGGAAGACGGTGGTCAGCTCGTCGGGCACGATTCTG

ACCTGCCAGCCCCGATTATGCAGGGTGATGAGGTCCACACTGGTGGCCACCTCGCCGCGCAGGGGCTCATTA

GTCCAGCAGAGGCGTCCGCCCTTGCGCGAGCAGAAGGGGGGCAGGGGGTCCAGCATGACCTCGTCGGGGGG

GTCGGCATCGATGGTGAAGATGCCGGGCAGGAGGTCGGGGTCAAAGTAGCTGATGGAAGTGGCCAGATCGTC

CAGGGCAGCTTGCCATTCGCGCACGGCCAGCGCGCGCTCGTAGGGACTGAGGGGCGTGCCCCAGGGCATGGG

ATGGGTAAGCGCGGAGGCGTACATGCCGCAGATGTCGTAGACGTAGAGGGGCTCCTCGAGGATGCCGATGTA

GGTGGGGTAGCAGCGCCCCCCGCGGATGCTGGCGCGCACGTAGTCATACAGCTCGTGCGAGGGGGCGAGGA

GCCCCGGGCCCAGGTTGGTGCGACTGGGCTTTTCGGCGCGGTAGACGATCTGGCGGAAAATGGCATGCGAGT

TGGAGGAGATGGTGGGCCTTTGGAAGATGTTGAAGTGGGCGTGGGGCAGTCCGACCGAGTCGCGGATGAAGT

GGGCGTAGGAGTCTTGCAGCTTGGCGACGAGCTCGGCGGTGACTAGGACGTCCAGAGCGCAGTAGTCGAGGG

TCTCCTGGATGATGTCATACTTGAGCTGTCCCTTTTGTTTCCACAGCTCGCGGTTGAGAAGGAACTCTTCGCGG

TCCTTCCAGTACTCTTCGAGGGGGAACCCGTCCTGATCTGCACGGTAAGAGCCTAGCATGTAGAACTGGTTGA

CGGCCTTGTAGGCGCAGCAGCCCTTCTCCACGGGGAGGGCGTAGGCCTGGGCGGCCTTGCGCAGGGAGGTGT

GCGTGAGGGCGAAAGTGTCCCTGACCATGACCTTGAGGAACTGGTGCTTGAAGTCGATATCGTCGCAGCCCC

CCTGCTCCCAGAGCTGGAAGTCCGTGCGCTTCTTGTAGGCGGGGTTGGGCAAAGCGAAAGTAACATCGTTGA

AGAGGATCTTGCCCGCGCGGGGCATAAAGTTGCGAGTGATGCGGAAAGGTTGGGGCACCTCGGCCCGGTTGT

TGATGACCTGGGCGGCGAGCACGATCTCGTCGAAGCCGTTGATGTTGTGGCCCACGATGTAGAGTTCCACGA

ATCGCGGACGGCCCTTGACGTGGGGCAGTTTCTTGAGCTCCTCGTAGGTGAGCTCGTCGGGGTCGCTGAGCCC

GTGCTGCTCGAGCGCCCAGTCGGCGAGATGGGGGTTGGCGCGGAGGAAGGAAGTCCAGAGATCCACGGCCA

GGGCGGTTTGCAGACGGTCCCGGTACTGACGGAACTGCTGCCCGACGGCCATTTTTTCGGGGGTGACGCAGT

AGAAGGTGCGGGGGTCCCCGTGCCAGCGATCCCATTTGAGCTGGAGGGCGAGATCGAGGGCGAGCTCGACG

AGCCGGTCGTCCCCGGAGAGTTTCATGACCAGCATGAAGGGGACGAGCTGCTTGCCGAAGGACCCCATCCAG

GTGTAGGTTTCCACATCGTAGGTGAGGAAGAGCCTTTCGGTGCGAGGATGCGAGCCGATGGGGAAGAACTGG

ATCTCCTGCCACCAATTGGAGGAATGGCTGTTGATGTGATGGAAGTAGAAATGCCGACGGCGCGCCGAACAC

TCGTGCTTGTGTTTATACAAGCGGCCACAGTGCTCGCAACGCTGCACGGGATGCACGTGCTGCACGAGCTGTA

CCTGAGTTCCTTTGACGAGGAATTTCAGTGGGAAGTGGAGTCGTGGCGCCTGCATCTCGTGCTGTACTACGTC

GTGGTGGTCGGCCTGGCCCTCTTCTGCCTCGATGGTGGTCATGCTGACGAGCCCGCGCGGGAGGCAGGTCCAG

ACCTCGGCGCGAGCGGGTCGGAGAGCGAGGACGAGGGCGCGCAGGCCGGAGCTGTCCAGGGTCCTGAGACG

CTGCGGAGTCAGGTCAGTGGGCAGCGGCGGCGCGCGGTTGACTTGCAGGAGTTTTTCCAGGGCGCGCGGGAG

GTCCAGATGGTACTTGATCTCCACCGCGCCATTGGTGGCGACGTCGATGGCTTGCAGGGTCCCGTGCCCCTGG

GGTGTGACCACCGTCCCCCGTTTCTTCTTGGGCGGCTGGGGCGACGGGGGCGGTGCCTCTTCCATGGTTAGAA

GCGGCGGCGAGGACGCGCGCCGGGCGGCAGGGGCGGCTCGGGGCCCGGAGGCAGGGGCGGCAGGGGCACG

TCGGCGCCGCGCGCGGGTAGGTTCTGGTACTGCGCCCGGAGAAGACTGGCGTGAGCGACGACGCGACGGTTG

-continued

ACGTCCTGGATCTGACGCCTCTGGGTGAAGGCCACGGGACCCGTGAGTTTGAACCTGAAAGAGAGTTCGACA

GAATCAATCTCGGTATCGTTGACGGCGGCCTGCCGCAGGATCTCTTGCACGTCGCCCGAGTTGTCCTGGTAGG

CGATCTCGGTCATGAACTGCTCGATCTCCTCCTCTTGAAGGTCTCCGCGGCCGGCGCGCTCCACGGTGGCCGC

GAGGTCGTTGGAGATGCGGCCCATGAGCTGCGAGAAGGCGTTCATGCCCGCCTCGTTCCAGACGCGGCTGTA

GACCACGACGCCCTCGGGATCGCgGGCGCGCATGACCACCTGGGCGAGGTTGAGCTCCACGTGGCGCGTGAA

GACCGCGTAGTTGCAGAGGCGCTGGTAGAGGTAGTTGAGCGTGGTGGCGATGTGCTCGGTGACGAAGAAATA

CATGATCCAGCGGCGGAGCGGCATCTCGCTGACGTCGCCCAGCGCCTCCAAACGTTCCATGGCCTCGTAAAA

GTCCACGGCGAAGTTGAAAAACTGGGAGTTGCGCGCCGAGACGGTCAACTCCTCCTCCAGAAGACGGATGAG

CTCGGCGATGGTGGCGCGCACCTCGCGCTCGAAGGCCCCCGGGAGTTCCTCCACTTCCTCTTCTTCCTCCTCCA

CTAACATCTCTTCTACTTCCTCCTCAGGCGGCAGTGGTGGCGGGGGAGGGGGCCTGCGTCGCCGGCGGCGCAC

GGGCAGACGGTCGATGAAGCGCTCGATGGTCTCGCCGCGCCGGCGTCGCATGGTCTCGGTGACGGCGCGCCC

GTCCTCGCGGGGCCGCAGCGTGAAGACGCCGCCGCGCATCTCCAGGTGGCCGGGGGGGTCCCCGTTGGGCAG

GGAGAGGGCGCTGACGATGCATCTTATCAATTGCCCCGTAGGGACTCCGCGCAAGGACCTGAGCGTCTCGAG

ATCCACGGGATCTGAAAACCGCTGAACGAAGGCTTCGAGCCAGTCGCAGTCGCAAGGTAGGCTGAGCACGGT

TTCTTCTGGCGGGTCATGTTGGTTGGGAGCGGGGCGGCGATGCTGCTGGTGATGAAGTTGAAATAGGCGGTT

CTGAGACGGCGGATGGTGGCGAGGAGCACCAGGTCTTTGGGCCCGGCTTGCTGGATGCGCAGACGGTCGGCC

ATGCCCCAGGCGTGGTCCTGACACCTGGCCAGGTCCTTGTAGTAGTCCTGCATGAGCCGCTCCACGGGCACCT

CCTCCTCGCCCGCGCGGCCGTGCATGCGCGTGAGCCCGAAGCCGCGCTGGGGCTGGACGAGCGCCAGGTCGG

CGACGACGCGCTCGGCGAGGATGGCTTGCTGGATCTGGGTGAGGGTGGTCTGGAAGTCATCAAAGTCGACGA

AGCGGTGGTAGGCTCCGGTGTTGATGGTGTAGGAGCAGTTGGCCATGACGGACCAGTTGACGGTCTGGTGGC

CCGGACGCACGAGCTCGTGGTACTTGAGGCGCGAGTAGGCGCGCGTGTCGAAGATGTAGTCGTTGCAGGTGC

GCACCAGGTACTGGTAGCCGATGAGGAAGTGCGGCGGCGGCTGGCGGTAGAGCGGCCATCGCTCGGTGGCG

GGGGCGCCGGGCGCGAGGTCCTCGAGCATGGTGCGGTGGTAGCCGTAGATGTACCTGGACATCCAGGTGATG

CCGGCGGCGGTGGTGGAGGCGCGCGGGAACTCGCGGACGCGGTTCCAGATGTTGCGCAGCGGCAGGAAGTA

GTTCATGGTGGGCACGGTCTGGCCCGTGAGGCGCGCGCAGTCGTGGATGCTCTATACGGGCAAAAACGAAAG

CGGTCAGCGGCTCGACTCCGTGGCCTGGAGGCTAAGCGAACGGGTTGGGCTGCGCGTGTACCCCGGTTCGAA

TCTCGAATCAGGCTGGAGCCGCAGCTAACGTGGTATTGGCACTCCCGTCTCGACCCAAGCCTGCACCAACCCT

CCAGGATACGGAGGCGGGTCGTTTTGCAACTTTTTTTTGGAGGCCGGATGAGACTAGTAAGCGCGGAAAGCG

GCCGACCGCGATGGCTCGCTGCCGTAGTCTGGAGAAGAATCGCCAGGGTTGCGTTGCGGTGTGCCCCGGTTC

GAGGCCGGCCGGATTCCGCGGCTAACGAGGGCGTGGCTGCCCCGTCGTTTCCAAGACCCCATAGCCAGCCGA

CTTCTCCAGTTACGGAGCGAGCCCCTCTTTTGTTTTGTTTGTTTTTGCCAGATGCATCCCGTACTGCGGCAGAT

GCGCCCCCACCACCCTCCACCGCAACAACAGCCCCCTCCACAGCCGGCGCTTCTGCCCCCGCCCCAGCAGCAA

CTTCCAGCCACGACCGCCGCGGCCGCCGTGAGCGGGGCTGGACAGAGTTATGATCACCAGCTGGCCTTGGAA

GAGGGCGAGGGGCTGGCGCGCCTGGGGGCGTCGTCGCCGGAGCGGCACCCGCGCGTGCAGATGAAAAGGGA

CGCTCGCGAGGCCTACGTGCCCAAGCAGAACCTGTTCAGAGACAGGAGCGGCGAGGAGCCCGAGGAGATGC

GCGCGGCCCGGTTCCACGCGGGGCGGGAGCTGCGGCGCGGCCTGGACCGAAAGAGGGTGCTGAGGGACGAG

GATTTCGAGGCGGACGAGCTGACGGGGATCAGCCCCGCGCGCGCGCACGTGGCCGCGGCCAACCTGGTCACG

GCGTACGAGCAGACCGTGAAGGAGGAGAGCAACTTCCAAAAATCCTTCAACAACCACGTGCGCACCCTGATC

GCGCGCGAGGAGGTGACCCTGGGCCTGATGCACCTGTGGGACCTGCTGGAGGCCATCGTGCAGAACCCCACC

AGCAAGCCGCTGACGGCGCAGCTGTTCCTGGTGGTGCAGCATAGTCGGGACAACGAAGCGTTCAGGGAGGCG

CTGCTGAATATCACCGAGCCCGAGGGCCGCTGGCTCCTGGACCTGGTGAACATTCTGCAGAGCATCGTGGTGC

-continued

AGGAGCGCGGGCTGCCGCTGTCCGAGAAGCTGGCGGCCATCAACTTCTCGGTGCTGAGTTTGGGCAAGTACT

ACGCTAGGAAGATCTACAAGACCCCGTACGTGCCCATAGACAAGGAGGTGAAGATCGACGGGTTTTACATGC

GCATGACCCTGAAAGTGCTGACCCTGAGCGACGATCTGGGGGTGTACCGCAACGACAGGATGCACCGTGCGG

TGAGCGCCAGCAGGCGGCGCGAGCTGAGCGACCAGGAGCTGATGCATAGTCTGCAGCGGGCCCTGACCGGG

GCCGGGACCGAGGGGGAGAGCTACTTTGACATGGGCGCGGACCTGCACTGGCAGCCCAGCCGCCGGGCCTTG

GAGGCGGCGGCAGGACCCTACGTAGAAGAGGTGGACGATGAGGTGGACGAGGAGGGCGAGTACCTGGAAGA

CTGATGGCGCGACCGTATTTTTGCTAGATGCAACAACAACAGCCACCTCCTGATCCCGCGATGCGGGCGGCGC

TGCAGAGCCAGCCGTCCGGCATTAACTCCTCGGACGATTGGACCCAGGCCATGCAACGCATCATGGCGCTGA

CGACCCGCAACCCCGAAGCCTTTAGACAGCAGCCCCAGGCCAACCGGCTCTCGGCCATCCTGGAGGCCGTGG

TGCCCTCGCGCTCCAACCCCACGCACGAGAAGGTCCTGGCCATCGTGAACGCGCTGGTGGAGAACAAGGCCA

TCCGCGGCGACGAGGCCGGCCTGGTGTACAACGCGCTGCTGGAGCGCGTGGCCCGCTACAACAGCACCAACG

TGCAGACCAACCTGGACCGCATGGTGACCGACGTGCGCGAGGCCGTGGCCCAGCGCGAGCGGTTCCACCGCG

AGTCCAACCTGGGATCCATGGTGGCGCTGAACGCCTTCCTCAGCACCCAGCCCGCCAACGTGCCCCGGGGCC

AGGAGGACTACACCAACTTCATCAGCGCCCTGCGCCTGATGGTGACCGAGGTGCCCCAGAGCGAGGTGTACC

AGTCCGGGCCGGACTACTTCTTCCAGACCAGTCGCCAGGGCTTGCAGACCGTGAACCTGAGCCAGGCTTTCAA

GAACTTGCAGGGCCTGTGGGGCGTGCAGGCCCCGGTCGGGGACCGCGCGACGGTGTCGAGCCTGCTGACGCC

GAACTCGCGCCTGCTGCTGCTGCTGGTGGCCCCCTTCACGGACAGCGGCAGCATCAACCGCAACTCGTACCTG

GGCTACCTGATTAACCTGTACCGCGAGGCCATCGGCCAGGCGCACGTGGACGAGCAGACCTACCAGGAGATC

ACCCACGTGAGCCGCGCCCTGGGCCAGGACGACCCGGGCAACCTGGAAGCCACCCTGAACTTTTTGCTGACC

AACCGGTCGCAGAAGATCCCGCCCCAGTACGCGCTCAGCACCGAGGAGGAGCGCATCCTGCGTTACGTGCAG

CAGAGCGTGGGCCTGTTCCTGATGCAGGAGGGGGCCACCCCCAGCGCCGCGCTCGACATGACCGCGCGCAAC

ATGGAGCCCAGCATGTACGCCAGCAACCGCCCGTTCATCAATAAACTGATGGACTACTTGCATCGGGCGGCC

GCCATGAACTCTGACTATTTCACCAACGCCATCCTGAATCCCCACTGGCTCCCGCCGCCGGGGTTCTACACGG

GCGAGTACGACATGCCCGACCCCAATGACGGGTTCCTGTGGGACGATGTGGACAGCAGCGTGTTCTCCCCCC

GACCGGGTGCTAACGAGCGCCCCTTGTGGAAGAAGGAAGGCAGCGACCGACGCCCGTCCTCGGCGCTGTCCG

GCCGCGAGGGTGCTGCCGCGGCGGTGCCCGAGGCCGCCAGTCCTTTCCCGAGCTTGCCCTTCTCGCTGAACAG

TATCCGCAGCAGCGAGCTGGGCAGGATCACGCGCCCGCGCTTGCTGGGCGAAGAGGAGTACTTGAATGACTC

GCTGTTGAGACCCGAGCGGGAGAAGAACTTCCCCAATAACGGGATAGAAAGCCTGGTGGACAAGATGAGCC

GCTGGAAGACGTATGCGCAGGAGCACAGGGACGATCCCCGGGCGTCGCAGGGGGCCACGAGCCGGGGCAGC

GCCGCCCGTAAACGCCGGTGGCACGACAGGCAGCGGGGACAGATGTGGGACGATGAGGACTCCGCCGACGA

CAGCAGCGTGTTGGACTTGGGTGGGAGTGGTAACCCGTTCGCTCACCTGCGCCCCCGTATCGGGCGCATGATG

TAAGAGAAACCGAAAATAAATGATACTCACCAAGGCCATGGCGACCAGCGTGCGTTCGTTTCTTCTCTGTTGT

TGTTGTATCTAGTATGATGAGGCGTGCGTACCCGGAGGGTCCTCCTCCCTCGTACGAGAGCGTGATGCAGCAG

GCGATGGCGGCGGCGGCGATGCAGCCCCCGCTGGAGGCTCCTTACGTGCCCCCGCGGTACCTGGCGCCTACG

GAGGGGCGGAACAGCATTCGTTACTCGGAGCTGGCACCCTTGTACGATACCACCCGGTTGTACCTGGTGGAC

AACAAGTCGGCGGACATCGCCTCGCTGAACTACCAGAACGACCACAGCAACTTCCTGACCACCGTGGTGCAG

AACAATGACTTCACCCCCACGGAGGCCAGCACCCAGACCATCAACTTTGACGAGCGCTCGCGGTGGGGCGGC

CAGCTGAAAACCATCATGCACACCAACATGCCCAACGTGAACGAGTTCATGTACAGCAACAAGTTCAAGGCG

CGGGTGATGGTCTCCCGCAAGACCCCCAATGGGGTGACAGTGACAGAGGATTATGATGGTAGTCAGGATGAG

CTGAAGTATGAATGGGTGGAATTTGAGCTGCCCGAAGGCAACTTCTCGGTGACCATGACCATCGACCTGATG

AACAACGCCATCATCGACAATTACTTGGCGGTGGGGCGGCAGAACGGGGTGCTGGAGAGCGACATCGGCGTG

AAGTTCGACACTAGGAACTTCAGGCTGGGCTGGGACCCCGTGACCGAGCTGGTCATGCCCGGGGTGTACACC

AACGAGGCTTTCCATCCCGATATTGTCTTGCTGCCCGGCTGCGGGGTGGACTTCACCGAGAGCCGCCTCAGCA

ACCTGCTGGGCATTCGCAAGAGGCAGCCCTTCCAGGAAGGCTTCCAGATCATGTACGAGGATCTGGAGGGGG

GCAACATCCCCGCGCTCCTGGATGTCGACGCCTATGAGAAAAGCAAGGAGGATGCAGCAGCTGAAGCAACTG

CAGCCGTAGCTACCGCCTCTACCGAGGTCAGGGGCGATAATTTTGCAAGCGCCGCAGCAGTGGCAGCGGCCG

AGGCGGCTGAAACCGAAAGTAAGATAGTCATTCAGCCGGTGGAGAAGGATAGCAAGAACAGGAGCTACAAC

GTACTACCGGACAAGATAAACACCGCCTACCGCAGCTGGTACCTAGCCTACAACTATGGCGACCCCGAGAAG

GGCGTGCGCTCCTGGACGCTGCTCACCACCTCGGACGTCACCTGCGGCGTGGAGCAAGTCTACTGGTCGCTGC

CCGACATGATGCAAGACCCGGTCACCTTCCGCTCCACGCGTCAAGTTAGCAACTACCCGGTGGTGGGCGCCG

AGCTCCTGCCCGTCTACTCCAAGAGCTTCTTCAACGAGCAGGCCGTCTACTCGCAGCAGCTGCGCGCCTTCAC

CTCGCTTACGCACGTCTTCAACCGCTTCCCCGAGAACCAGATCCTCGTCCGCCCGCCCGCGCCCACCATTACC

ACCGTCAGTGAAAACGTTCCTGCTCTCACAGATCACGGGACCCTGCCGCTGCGCAGCAGTATCCGGGGAGTC

CAGCGCGTGACCGTTACTGACGCCAGACGCCGCACCTGCCCCTACGTCTACAAGGCCCTGGGCATAGTCGCG

CCGCGCGTCCTCTCGAGCCGCACCTTCTAAATGTCCATTCTCATCTCGCCCAGTAATAACACCGGTTGGGGCC

TGCGCGCGCCCAGCAAGATGTACGGAGGCGCTCGCCAACGCTCCACGCAACACCCCGTGCGCGTGCGCGGGC

ACTTCCGCGCTCCCTGGGGCGCCCTCAAGGGCCGCGTGCGGTCGCGCACCACCGTCGACGACGTGATCGACC

AGGTGGTGGCCGACGCGCGCAACTACACCCCCGCCGCCGCGCCCGTCTCCACCGTGGACGCCGTCATCGACA

GCGTGGTGGCcGACGCGCGCCGGTACGCCCGCGCCAAGAGCCGGCGGCGGCGCATCGCCCGGCGGCACCGGA

GCACCCCCGCCATGCGCGCGGCGCGAGCCTTGCTGCGCAGGGCCAGGCGCACGGGACGCAGGGCCATGCTCA

GGGCGGCCAGACGCGCGGCTTCAGGCGCCAGCGCCGGCAGGACCCGGAGACGCGCGGCCACGGCGGCGGCA

GCGGCCATCGCCAGCATGTCCCGCCCGCGGCGAGGGAACGTGTACTGGGTGCGCGACGCCGCCACCGGTGTG

CGCGTGCCCGTGCGCACCCGCCCCCCTCGCACTTGAAGATGTTCACTTCGCGATGTTGATGTGTCCCAGCGGC

GAGGAGGATGTCCAAGCGCAAATTCAAGGAAGAGATGCTCCAGGTCATCGCGCCTGAGATCTACGGCCCTGC

GGTGGTGAAGGAGGAAAGAAAGCCCCGCAAAATCAAGCGGGTCAAAAAGGACAAAAAGGAAGAAGAAAGT

GATGTGGACGGATTGGTGGAGTTTGTGCGCGAGTTCGCCCCCCGGCGGCGCGTGCAGTGGCGCGGGCGGAAG

GTGCAACCGGTGCTGAGACCCGGCACCACCGTGGTCTTCACGCCCGGCGAGCGCTCCGGCACCGCTTCCAAG

CGCTCCTACGACGAGGTGTACGGGGATGATGATATTCTGGAGCAGGCGGCCGAGCGCCTGGGCGAGTTTGCT

TACGGCAAGCGCAGCCGTTCCGCACCGAAGGAAGAGGCGGTGTCCATCCCGCTGGACCACGGCAACCCCACG

CCGAGCCTCAAGCCCGTGACCTTGCAGCAGGTGCTGCCGACCGCGGCGCCGCGCCGGGGGTTCAAGCGCGAG

GGCGAGGATCTGTACCCCACCATGCAGCTGATGGTGCCCAAGCGCCAGAAGCTGGAAGACGTGCTGGAGACC

ATGAAGGTGGACCCGGACGTGCAGCCCGAGGTCAAGGTGCGGCCCATCAAGCAGGTGGCCCCGGGCCTGGG

CGTGCAGACCGTGGACATCAAGATTCCCACGGAGCCCATGGAAACGCAGACCGAGCCCATGATCAAGCCCAG

CACCAGCACCATGGAGGTGCAGACGGATCCCTGGATGCCATCGGCTCCTAGTCGAAGACCCCGGCGCAAGTA

CGGCGCGGCCAGCCTGCTGATGCCCAACTACGCGCTGCATCCTTCCATCATCCCCACGCCGGGCTACCGCGGC

ACGCGCTTCTACCGCGGTCATACCAGCAGCCGCCGCCGCAAGACCACCACTCGCCGCCGCCGTCGCCGCACC

GCCGCTGCAACCACCCCTGCCGCCCTGGTGCGGAGAGTGTACCGCCGCGGCCGCGCACCTCTGACCCTGCCGC

GCGCGCGCTACCACCCGAGCATCGCCATTTAAACTTTCGCCtGCTTTGCAGATCAATGGCCCTCACATGCCGCC

TTCGCGTTCCCATTACGGGCTACCGAGGAAGAAAACCGCGCCGTAGAAGGCTGGCGGGGAACGGGATGCGTC

GCCACCACCACCGGCGGCGGCGCGCCATCAGCAAGCGGTTGGGGGGAGGCTTCCTGCCCGCGCTGATCCCCA

TCATCGCCGCGGCGATCGGGGCGATCCCCGGCATTGCTTCCGTGGCGGTGCAGGCCTCTCAGCGCCACTGAGA

-continued

CACACTTGGAAACATCTTGTAATAAACCaATGGACTCTGACGCTCCTGGTCCTGTGATGTGTTTTCGTAGACAG

ATGGAAGACATCAATTTTTCGTCCCTGGCTCCGCGACACGGCACGCGGCCGTTCATGGGCACCTGGAGCGAC

ATCGGCACCAGCCAACTGAACGGGGGCGCCTTCAATTGGAGCAGTCTCTGGAGCGGGCTTAAGAATTTCGGG

TCCACGCTTAAAACCTATGGCAGCAAGGCGTGGAACAGCACCACAGGGCAGGCGCTGAGGGATAAGCTGAA

AGAGCAGAACTTCCAGCAGAAGGTGGTCGATGGGCTCGCCTCGGGCATCAACGGGGTGGTGGACCTGGCCAA

CCAGGCCGTGCAGCGGCAGATCAACAGCCGCCTGGACCCGGTGCCGCCCGCCGGCTCCGTGGAGATGCCGCA

GGTGGAGGAGGAGCTGCCTCCCCTGGACAAGCGGGGCGAGAAGCGACCCCGCCCCGATGCGGAGGAGACGC

TGCTGACGCACACGGACGAGCCGCCCCCGTACGAGGAGGCGGTGAAACTGGGTCTGCCCACCACGCGGCCCA

TCGCGCCCCTGGCCACCGGGGTGCTGAAACCCGAAAAGCCCGCGACCCTGGACTTGCCTCCTCCCCAGCCTTC

CCGCCCCTCTACAGTGGCTAAGCCCCTGCCGCCGGTGGCCGTGGCCCGCGCGCGACCCGGGGGCACCGCCCG

CCCTCATGCGAACTGGCAGAGCACTCTGAACAGCATCGTGGGTCTGGGAGTGCAGAGTGTGAAGCGCCGCCG

CTGCTATTAAACCTACCGTAGCGCTTAACTTGCTTGTCTGTGTGTGTATGTATTATGTCGCCGCCGCCGCTGTC

CACCAGAAGGAGGAGTGAAGAGGCGCGTCGCCGAGTTGCAAGATGGCCACCCCATCGATGCTGCCCCAGTGG

GCGTACATGCACATCGCCGGACAGGACGCTTCGGAGTACCTGAGTCCGGGTCTGGTGCAGTTTGCCCGCGCC

ACAGACACCTACTTCAGTCTGGGGAACAAGTTTAGGAACCCCACGGTGGCGCCCACGCACGATGTGACCACC

GACCGCAGCCAGCGGCTGACGCTGCGCTTCGTGCCCGTGGACCGCGAGGACAACACCTACTCGTACAAAGTG

CGCTACACGCTGGCCGTGGGCGACAACCGCGTGCTGGACATGGCCAGCACCTACTTTGACATCCGCGGCGTG

CTGGATCGGGGCCCTAGCTTCAAACCCTACTCCGGCACCGCCTACAACAGTCTGGCCCCCAAGGGAGCACCC

AACACTTGTCAGTGGACATATAAAGCCGATGGTGAAACTGCCACAGAAAAAACCTATACATATGGAAATGCA

CCCGTGCAGGGCATTAACATCACAAAAGATGGTATTCAACTTGGAACTGACACCGATGATCAGCCAATCTAC

GCAGATAAAACCTATCAGCCTGAACCTCAAGTGGGTGATGCTGAATGGCATGACATCACTGGTACTGATGAA

AAGTATGGAGGCAGAGCTCTTAAGCCTGATACCAAAATGAAGCCTTGTTATGGTTCTTTTGCCAAGCCTACTA

ATAAAGAAGGAGGTCAGGCAAATGTGAAAACAGGAACAGGCACTACTAAAGAATATGACATAGACATGGCT

TTCTTTGACAACAGAAGTGCGGCTGCTGCTGGCCTAGCTCCAGAAATTGTTTTGTATACTGAAAATGTGGATT

TGGAAACTCCAGATACCCATATTGTATACAAAGCAGGCACAGATGACAGCAGCTCTTCTATTAATTTGGGTCA

GCAAGCCATGCCCAACAGACCTAACTACATTGGTTTCAGAGACAACTTTATCGGGCTCATGTACTACAACAGC

ACTGGCAATATGGGGGTGCTGGCCGGTCAGGCTTCTCAGCTGAATGCTGTGGTTGACTTGCAAGACAGAAAC

ACCGAGCTGTCCTACCAGCTCTTGCTTGACTCTCTGGGTGACAGAACCCGGTATTTCAGTATGTGGAATCAGG

CGGTGGACAGCTATGATCCTGATGTGCGCATTATTGAAAATCATGGTGTGGAGGATGAACTTCCCAACTATTG

TTTCCCTCTGGATGCTGTTGGCAGAACAGATACTTATCAGGGAATTAAGGCTAATGGAACTGATCAAACCACA

TGGACCAAAGATGACAGTGTCAATGATGCTAATGAGATAGGCAAGGGTAATCCATTCGCCATGGAAATCAAC

ATCCAAGCCAACCTGTGGAGGAACTTCCTCTACGCCAACGTGGCCCTGTACCTGCCCGACTCTTACAAGTACA

CGCCGGCCAATGTTACCCTGCCCACCAACACCAACACCTACGATTACATGAACGGCCGGGTGGTGGCGCCCT

CGCTGGTGGACTCCTACATCAACATCGGGGCGCGCTGGTCGCTGGATCCCATGGACAACGTGAACCCCTTCAA

CCACCACCGCAATGCGGGGCTGCGCTACCGCTCCATGCTCCTGGGCAACGGGCGCTACGTGCCCTTCCACATC

CAGGTGCCCCAGAAATTTTTCGCCATCAAGAGCCTCCTGCTCCTGCCCGGGTCCTACACCTACGAGTGGAACT

TCCGCAAGGACGTCAACATGATCCTGCAGAGCTCCCTCGGCAACGACCTGCGCACGGACGGGGCCTCCATCT

CCTTCACCAGCATCAACCTCTACGCCACCTTCTTCCCCATGGCGCACAACACGGCCTCCACGCTCGAGGCCAT

GCTGCGCAACGACACCAACGACCAGTCCTTCAACGACTACCTCTCGGCGGCCAACATGCTCTACCCCATCCCG

GCCAACGCCACCAACGTGCCCATCTCCATCCCCTCGCGCAACTGGGCCGCCTTCCGCGGCTGGTCCTTCACGC

-continued

GTCTCAAGACCAAGGAGACGCCCTCGCTGGGCTCCGGGTTCGACCCCTACTTCGTCTACTCGGGCTCCATCCC

CTACCTCGACGGCACCTTCTACCTCAACCACACCTTCAAGAAGGTCTCCATCACCTTCGACTCCTCCGTCAGCT

GGCCCGGCAACGACCGGCTCCTGACGCCCAACGAGTTCGAAATCAAGCGCACCGTCGACGGCGAGGGCTACA

ACGTGGCCCAGTGCAACATGACCAAGGACTGGTTCCTGGTCCAGATGCTGGCCCACTACAACATCGGCTACC

AGGGCTTCTACGTGCCCGAGGGCTACAAGGACCGCATGTACTCCTTCTTCCGCAACTTCCAGCCCATGAGCCG

CCAGGTGGTGGACGAGGTCAACTACAAGGACTACCAGGCCGTCACCCTGGCCTACCAGCACAACAACTCGGG

CTTCGTCGGCTACCTCGCGCCCACCATGCGCCAGGGCCAGCCCTACCCCGCCAACTACCCCTACCCGCTCATC

GGCAAGAGCGCCGTCACCAGCGTCACCCAGAAAAAGTTCCTCTGCGACAGGGTCATGTGGCGCATCCCCTTC

TCCAGCAACTTCATGTCCATGGGCGCGCTCACCGACCTCGGCCAGAACATGCTCTATGCCAACTCCGCCCACG

CGCTAGACATGAATTTCGAAGTCGACCCCATGGATGAGTCCACCCTTCTCTATGTTGTCTTCGAAGTCTTCGAC

GTCGTCCGAGTGCACCAGCCCCACCGCGGCGTCATCGAGGCCGTCTACCTGCGCACCCCCTTCTCGGCCGGTA

ACGCCACCACCTAAGCTCTTGCTTCTTGCAAGCCATGGCCGCGGGCTCCGGCGAGCAGGAGCTCAGGGCCAT

CATCCGCGACCTGGGCTGCGGGCCCTACTTCCTGGGCACCTTCGATAAGCGCTTCCCGGGATTCATGGCCCCG

CACAAGCTGGCCTGCGCCATCGTCAACACGGCCGGCCGCGAGACCGGGGGCGAGCACTGGCTGGCCTTCGCC

TGGAACCCGCGCTCGAACACCTGCTACCTCTTCGACCCCTTCGGGTTCTCGGACGAGCGCCTCAAGCAGATCT

ACCAGTTCGAGTACGAGGGCCTGCTGCGCCGCAGCGCCCTGGCCACCGAGGACCGCTGCGTCACCCTGGAAA

AGTCCACCCAGACCGTGCAGGGTCCGCGCTCGGCCGCCTGCGGGCTCTTCTGCTGCATGTTCCTGCACGCCTT

CGTGCACTGGCCCGACCGCCCCATGGACAAGAACCCCACCATGAACTTGCTGACGGGGGTGCCCAACGGCAT

GCTCCAGTCGCCCCAGGTGGAACCCACCCTGCGCCGCAACCAGGAGGCGCTCTACCGCTTCCTCAACTCCCAC

TCCGCCTACTTTCGCTCCCACCGCGCGCGCATCGAGAAGGCCACCGCCTTCGACCGCATGAATCAAGACATGT

AAACCGTGTGTGTATGTTAAATGTCTTTAATAAACAGCACTTTCATGTTACACATGCATCTGAGATGATTTATT

TAGAAATCGAAAGGGTTCTGCCGGGTCTCGGCATGGCCCGCGGGCAGGGACACGTTGCGGAACTGGTACTTG

GCCAGCCACTTGAACTCGGGGATCAGCAGTTTGGGCAGCGGGGTGTCGGGGAAGGAGTCGGTCCACAGCTTC

CGCGTCAGTTGCAGGGCGCCCAGCAGGTCGGGCGCGGAGATCTTGAAATCGCAGTTGGGACCCGCGTTCTGC

GCGCGGGAGTTGCGGTACACGGGGTTGCAGCACTGGAACACCATCAGGGCCGGGTGCTTCACGCTCGCCAGC

ACCGTCGCGTCGGTGATGCTCTCCACGTCGAGGTCCTCGGCGTTGGCCATCCCGAAGGGGGTCATCTTGCAGG

TCTGCCTTCCCATGGTGGGCACGCACCCGGGCTTGTGGTTGCAATCGCAGTGCAGGGGGATCAGCATCATCTG

GGCCTGGTCGGCGTTCATCCCCGGGTACATGGCCTTCATGAAAGCCTCCAATTGCCTGAACGCCTGCTGGGCC

TTGGCTCCCTCGGTGAAGAAGACCCCGCAGGACTTGCTAGAGAACTGGTTGGTGGCGCACCCGGCGTCGTGC

ACGCAGCAGCGCGCGTCGTTGTTGGCCAGCTGCACCACGCTGCGCCCCCAGCGGTTCTGGGTGATCTTGGCCC

GGTCGGGGTTCTCCTTCAGCGCGCGCTGCCCGTTCTCGCTCGCCACATCCATCTCGATCATGTGCTCCTTCTGG

ATCATGGTGGTCCCGTGCAGGCACCGCAGCTTGCCCTCGGCCTCGGTGCACCCGTGCAGCCACAGCGCGCACC

CGGTGCACTCCCAGTTCTTGTGGGCGATCTGGGAATGCGCGTGCACGAAGCCCTGCAGGAAGCGGCCCATCA

TGGTGGTCAGGGTCTTGTTGCTAGTGAAGGTCAGCGGAATGCCGCGGTGCTCCTCGTTGATGTACAGGTGGCA

GATGCGGCGGTACACCTCGCCCTGCTCGGGCATCAGCTGGAAGTTGGCTTTCAGGTCGGTCTCCACGCGGTAG

CGGTCCATCAGCATAGTCATGATTTCCATACCCTTCTCCCAGGCCGAGACGATGGGCAGGCTCATAGGGTTCT

TCACCATCATCTTAGCGCTAGCAGCCGCGGCCAGGGGGTCGCTCTCGTCCAGGGTCTCAAAGCTCCGCTTGCC

GTCCTTCTCGGTGATCCGCACCGGGGGGTAGCTGAAGCCCACGGCCGCCAGCTCCTCCTCGGCCTGTCTTTCG

TCCTCGCTGTCCTGGCTGACGTCCTGCAGGACCACATGCTTGGTCTTGCGGGGTTTCTTCTTGGGCGGCAGCG

GCGGCGGAGATGTTGGAGATGGCGAGGGGGAGCGCGAGTTCTCGCTCACCACTACTATCTCTTCCTCTTCTTG

GTCCGAGGCCACGCGGCGGTAGGTATGTCTCTTCGGGGGCAGAGGCGGAGGCGACGGGCTCTCGCCGCCGCG

-continued

ACTTGGCGGATGGCTGGCAGAGCCCCTTCCGCGTTCGGGGGTGCGCTCCCGGCGGCGCTCTGACTGACTTCCT

CCGCGGCCGGCCATTGTGTTCTCCTAGGGAGGAACAACAAGCATGGAGACTCAGCCATCGCCAACCTCGCCA

TCTGCCCCCACCGCCGACGAGAAGCAGCAGCAGCAGAATGAAAGCTTAACCGCCCCGCCGCCCAGCCCCGCC

ACCTCCGACGCGGCCGTCCCAGACATGCAAGAGATGGAGGAATCCATCGAGATTGACCTGGGCTATGTGACG

CCCGCGGAGCACGAGGAGGAGCTGGCAGTGCGCTTTTCACAAGAAGAGATACACCAAGAACAGCCAGAGCA

GGAAGCAGAGAATGAGCAGAGTCAGGCTGGGCTCGAGCATGACGGCGACTACCTCCACCTGAGCGGGGGG

AGGACGCGCTCATCAAGCATCTGGCCCGGCAGGCCACCATCGTCAAGGATGCGCTGCTCGACCGCACCGAGG

TGCCCCTCAGCGTGGAGGAGCTCAGCCGCGCCTACGAGTTGAACCTCTTCTCGCCGCGCGTGCCCCCCAAGCG

CCAGCCCAATGGCACCTGCGAGCCCAACCCGCGCCTCAACTTCTACCCGGTCTTCGCGGTGCCCGAGGCCCTG

GCCACCTACCACATCTTTTTCAAGAACCAAAAGATCCCCGTCTCCTGCCGCGCCAACCGCACCCGCGCCGACG

CCCTTTTCAACCTGGGTCCCGGCGCCCGCCTACCTGATATCGCCTCCTTGGAAGAGGTTCCCAAGATCTTCGA

GGGTCTGGGCAGCGACGAGACTCGGGCCGCGAACGCTCTGCAAGGAGAAGGAGGAGAGCATGAGCACCACA

GCGCCCTGGTCGAGTTGGAAGGCGACAACGCGCGGCTGGCGGTGCTCAAACGCACGGTCGAGCTGACCCATT

TCGCCTACCCGGCTCTGAACCTGCCCCCCAAAGTCATGAGCGCGGTCATGGACCAGGTGCTCATCAAGCGCGC

GTCGCCCATCTCCGAGGACGAGGGCATGCAAGACTCCGAGGAGGGCAAGCCCGTGGTCAGCGACGAGCAGC

TGGCCCGGTGGCTGGGTCCTAATGCTAGTCCCCAGAGTTTGGAAGAGCGGCGCAAACTCATGATGGCCGTGG

TCCTGGTGACCGTGGAGCTGGAGTGCCTGCGCCGCTTCTTCGCCGACGCGGAGACCCTGCGCAAGGTCGAGG

AGAACCTGCACTACCTCTTCAGGCACGGGTTCGTGCGCCAGGCCTGCAAGATCTCCAACGTGGAGCTGACCA

ACCTGGTCTCCTACATGGGCATCTTGCACGAGAACCGCCTGGGGCAGAACGTGCTGCACACCACCCTGCGCG

GGGAGGCCCGGCGCGACTACATCCGCGACTGCGTCTACCTCTACCTCTGCCACACCTGGCAGACGGGCATGG

GCGTGTGGCAGCAGTGTCTGGAGGAGCAGAACCTGAAAGAGCTCTGCAAGCTCCTGCAGAAGAACCTCAAGG

GTCTGTGGACCGGGTTCGACGAGCGCACCACCGCCTCGGACCTGGCCGACCTCATTTTCCCCGAGCGCCTCAG

GCTGACGCTGCGCAACGGCCTGCCCGACTTTATGAGCCAAAGCATGTTGCAAAACTTTCGCTCTTTCATCCTC

GAACGCTCCGGAATCCTGCCCGCCACCTGCTCCGCGCTGCCCTCGGACTTCGTGCCGCTGACCTTCCGCGAGT

GCCCCCCGCCGCTGTGGAGCCACTGCTACCTGCTGCGCCTGGCCAACTACCTGGCCTACCACTCGGACGTGAT

CGAGGACGTCAGCGGCGAGGGCCTGCTCGAGTGCCACTGCCGCTGCAACCTCTGCACGCCGCACCGCTCCCT

GGCCTGCAACCCCCAGCTGCTGAGCGAGACCCAGATCATCGGCACCTTCGAGTTGCAAGGGCCCAGCGAAGG

CGAGGGTTCAGCCGCCAAGGGGGGTCTGAAACTCACCCCGGGGCTGTGGACCTCGGCCTACTTGCGCAAGTT

CGTGCCCGAGGACTACCATCCCTTCGAGATCAGGTTCTACGAGGACCAATCCCATCCGCCCAAGGCCGAGCT

GTCGGCCTGCGTCATCACCCAGGGGGCGATCCTGGCCCAATTGCAAGCCATCCAGAAATCCCGCCAAGAATT

CTTGCTGAAAAAGGGCCGCGGGGTCTACCTCGACCCCCAGACCGGTGAGGAGCTCAACCCCGGCTTCCCCCA

GGATGCCCCGAGGAAACAAGAAGCTGAAAGTGGAGCTGCCGCCCGTGGAGGATTTGGAGGAAGACTGGGAG

AACAGCAGTCAGGCAGAGGAGGAGGAGATGGAGGAAGACTGGGACAGCACTCAGGCAGAGGAGGACAGCC

TGCAAGACAGTCTGGAGGAAGACGAGGAGGAGGCAGAGGAGGAGGTGGAAGAAGCAGCCGCCGCCAGACC

GTCGTCCTCGGCGGGGGAGAAAGCAAGCAGCACGGATACCATCTCCGCTCCGGGTCGGGGTCCCGCTCGACC

ACACAGTAGATGGGACGAGACCGGACGATTCCCGAACCCCACCACCCAGACCGGTAAGAAGGAGCGGCAGG

GATACAAGTCCTGGCGGGGGCACAAAAACGCCATCGTCTCCTGCTTGCAGGCCTGCGGGGGCAACATCTCCT

TCACCCGGCGCTACCTGCTCTTCCACCGCGGGGTGAACTTTCCCCGCAACATCTTGCATTACTACCGTCACCTC

CACAGCCCCTACTACTTCCAAGAAGAGGCAGCAGCAGCAGAAAAAGACCAGCAGAAAACCAGCAGCTAGAA

AATCCACAGCGGCGGCAGCAGGTGGACTGAGGATCGCGGCGAACGAGCCGGCGCAAACCCGGGAGCTGAGG

-continued

AACCGGATCTTTCCCACCCTCTATGCCATCTTCCAGCAGAGTCGGGGGCAGGAGCAGGAACTGAAAGTCAAG

AACCGTTCTCTGCGCTCGCTCACCCGCAGTTGTCTGTATCACAAGAGCGAAGACCAACTTCAGCGCACTCTCG

AGGACGCCGAGGCTCTCTTCAACAAGTACTGCGCGCTCACTCTTAAAGAGTAGCCCGCGCCCGCCCAGTCGC

AGAAAAAGGCGGGAATTACGTCACCTGTGCCCTTCGCCCTAGCCGCCTCCACCCATCATCATGAGCAAAGAG

ATTCCCACGCCTTACATGTGGAGCTACCAGCCCCAGATGGGCCTGGCCGCCGGTGCCGCCCAGGACTACTCCA

CCCGCATGAATTGGCTCAGCGCCGGGCCCGCGATGATCTCACGGGTGAATGACATCCGCGCCCACCGAAACC

AGATACTCCTAGAACAGTCAGCGCTCACCGCCACGCCCCGCAATCACCTCAATCCGCGTAATTGGCCCGCCGC

CCTGGTGTACCAGGAAATTCCCCAGCCCACGACCGTACTACTTCCGCGAGACGCCCAGGCCGAAGTCCAGCT

GACTAACTCAGGTGTCCAGCTGGCGGGCGGCGCCACCCTGTGTCGTCACCGCCCCGCTCAGGGTATAAAGCG

GCTGGTGATCCGGGGCAGAGGCACACAGCTCAACGACGAGGTGGTGAGCTCTTCGCTGGGTCTGCGACCTGA

CGGAGTCTTCCAACTCGCCGGATCGGGGAGATCTTCCTTCACGCCTCGTCAGGCCGTCCTGACTTTGGAGAGT

TCGTCCTCGCAGCCCCGCTCGGGTGGCATCGGCACTCTCCAGTTCGTGGAGGAGTTCACTCCCTCGGTCTACTT

CAACCCCTTCTCCGGCTCCCCCGGCCACTACCCGGACGAGTTCATCCCGAACTTCGACGCCATCAGCGAGTCG

GTGGACGGCTACGATTGAAACTAATCACCCCCTTATCCAGTGAAATAAAGATCATATTGATGATGATTTTACA

GAAATAAAAAATAATCATTTGATTTGAAATAAAGATACAATCATATTGATGATTTGAGTTTAACAAAAAAAT

AAAGAATCACTTACTTGAAATCTGATACCAGGTCTCTGTCCATGTTTTCTGCCAACACCACTTCACTCCCCTCT

TCCCAGCTCTGGTACTGCAGGCCCCGGCGGGCTGCAAACTTCCTCCACACGCTGAAGGGGATGTCAAATTCCT

CCTGTCCCTCAATCTTCATTTTATCTTCTATCAGATGTCCAAAAAGCGCGTCCGGGTGGATGATGACTTCGACC

CCGTCTACCCCTACGATGCAGACAACGCACCGACCGTGCCCTTCATCAACCCCCCCTTCGTCTCTTCAGATGG

ATTCCAAGAGAAGCCCCTGGGGGTGTTGTCCCTGCGACTGGCCGACCCCGTCACCACCAAGAACGGGGAAAT

CACCCTCAAGCTGGGAGAGGGGGTGGACCTCGATTCCTCGGGAAAACTCATCTCCAACACGGCCACCAAGGC

CGCCGCCCCTCTCAGTTTTTCCAACAACACCATTTCCCTTAACATGGATCACCCCTTTTACACTAAAGATGGAA

AATTATCCTTACAAGTTTCTCCACCATTAAATATACTGAGAACAAGCATTCTAAACACACTAGCTTTAGGTTTT

GGATCAGGTTTAGGACTCCGTGGCTCTGCCTTGGCAGTACAGTTAGTCTCTCCACTTACATTTGATACTGATGG

AAACATAAAGCTTACCTTAGACAGAGGTTTGCATGTTACAACAGGAGATGCAATTGAAAGCAACATAAGCTG

GGCTAAAGGTTTAAAATTTGAAGATGGAGCCATAGCAACCAACATTGGAAATGGGTTAGAGTTTGGAAGCAG

TAGTACAGAAACAGGTGTTGATGATGCTTACCCAATCCAAGTTAAACTTGGATCTGGCCTTAGCTTTGACAGT

ACAGGAGCCATAATGGCTGGTAACAAAGAAGACGATAAACTCACTTTGTGGACAACACCTGATCCATCACCA

AACTGTCAAATACTCGCAGAAAATGATGCAAAACTAACACTTTGCTTGACTAAATGTGGTAGTCAAATACTG

GCCACTGTGTCAGTCTTAGTTGTAGGAAGTGGAAACCTAAACCCCATTACTGGCACCGTAAGCAGTGCTCAGG

TGTTTCTACGTTTTGATGCAAACGGTGTTCTTTTAACAGAACATTCTACACTAAAAAAATACTGGGGGTATAG

GCAGGGAGATAGCATAGATGGCACTCCATATACCAATGCTGTAGGATTCATGCCCAATTTAAAAGCTTATCCA

AAGTCACAAAGTTCTACTACTAAAAATAATATAGTAGGGCAAGTATACATGAATGGAGATGTTTCAAAACCT

ATGCTTCTCACTATAACCCTCAATGGTACTGATGACAGCAACAGTACATATTCAATGTCATTTTCATACACCTG

GACTAATGGAAGCTATGTTGGAGCAACATTTGGGGCTAACTCTTATACCTTCTCATACATCGCCCAAGAATGA

ACACTGTATCCCACCCTGCATGCCAACCCTTCCCACCCCACTCTGTGGAACAAACTCTGAAACACAAAATAAA

ATAAAGTTCAAGTGTTTTATTGATTCAACAGTTTTACAGGATTCGAGCAGTTATTTTTCCTCCACCCTCCCAGG

ACATGGAATACACCACCCTCTCCCCCCGCACAGCCTTGAACATCTGAATGCCATTGGTGATGGACATGCTTTT

GGTCTCCACGTTCCACACAGTTTCAGAGCGAGCCAGTCTCGGGTCGGTCAGGGAGATGAAACCCTCCGGGCA

CTCCCGCATCTGCACCTCACAGCTCAACAGCTGAGGATTGTCCTCGGTGGTCGGGATCACGGTTATCTGGAAG

AAGCAGAAGAGCGGCGGTGGGAATCATAGTCCGCGAACGGGATCGGCCGGTGGTGTCGCATCAGGCCCCGC

-continued

AGCAGTCGCTGCCGCCGCCGCTCCGTCAAGCTGCTGCTCAGGGGGTCCGGGTCCAGGGACTCCCTCAGCATG

ATGCCCACGGCCCTCAGCATCAGTCGTCTGGTGCGGCGGGCGCAGCAGCGCATGCGGATCTCGCTCAGGTCG

CTGCAGTACGTGCAACACAGAACCACCAGGTTGTTCAACAGTCCATAGTTCAACACGCTCCAGCCGAAACTC

ATCGCGGGAAGGATGCTACCCACGTGGCCGTCGTACCAGATCCTCAGGTAAATCAAGTGGTGCCCCCTCCAG

AACACGCTGCCCACGTACATGATCTCCTTGGGCATGTGGCGGTTCACCACCTCCCGGTACCACATCACCCTCT

GGTTGAACATGCAGCCCCGGATGATCCTGCGGAACCACAGGGCCAGCACCGCCCCGCCCGCCATGCAGCGAA

GAGACCCCGGGTCCCGGCAATGGCAATGGAGGACCCACCGCTCGTACCCGTGGATCATCTGGGAGCTGAACA

AGTCTATGTTGGCACAGCACAGGCATATGCTCATGCATCTCTTCAGCACTCTCAACTCCTCGGGGGTCAAAAC

CATATCCCAGGGCACGGGGAACTCTTGCAGGACAGCGAACCCCGCAGAACAGGGCAATCCTCGCACAGAACT

TACATTGTGCATGGACAGGGTATCGCAATCAGGCAGCACCGGGTGATCCTCCACCAGAGAAGCGCGGGTCTC

GGTCTCCTCACAGCGTGGTAAGGGGGCCGGCCGATACGGGTGATGGCGGGACGCGGCTGATCGTGTTCGCGA

CCGTGTCATGATGCAGTTGCTTTCGGACATTTTCGTACTTGCTGTAGCAGAACCTGGTCCGGGCGCTGCACAC

CGATCGCCGGCGGCGGTCTCGGCGCTTGGAACGCTCGGTGTTGAAATTGTAAAACAGCCACTCTCTCAGACCG

TGCAGCAGATCTAGGGCCTCAGGAGTGATGAAGATCCCATCATGCCTGATGGCTCTGATCACATCGACCACC

GTGGAATGGGCCAGACCCAGCCAGATGATGCAATTTTGTTGGGTTTCGGTGACGGCGAGCCTCGGGAACAAC

GATGAAGTAAATGCAAGCGGTGCGTTCCAGCATGGTTAGTTAGCTGATCTGTAGAAAAAACAAAAATGAACA

TTAAACCATGCTAGCCTGGCGAACAGGTGGGTAAATCGTTCTCTCCAGCACCAGGCAGGCCACGGGGTCTCC

GGCGCGACCCTCGTAAAAATTGTCGCTATGATTGAAAACCATCACAGAGAGACGTTCCCGGTGGCCGGCGTG

AATGATTCGACAAGATGAATACACCCCCGGAACATTGGCGTCCGCGAGTGAAAAAAAGCGCCCGAGGAAGC

AATAAGGCACTACAATGCTCAGTCTCAAGTCCAGCAAAGCGATGCCATGCGGATGAAGCACAAAATTCTCAG

GTGCGTACAAAATGTAATTACTCCCCTCCTGCACAGGCAGCAAAGCCCCCGATCCCTCCAGGTACACATACAA

AGCCTCAGCGTCCATAGCTTACCGAGCAGCAGCACACAACAGGCGCAAGAGTCAGAGAAAGGCTGAGCTCTA

ACCTGTCCACCCGCTCTCTGCTCAATATATAGCCCAGATCTACACTGACGTAAAGGCCAAAGTCTAAAAATAC

CCGCCAAATAATCACACACGCCCAGCACACGCCCAGAAACCGGTGACACACTCAAAAAAATACGCGCACTTC

CTCAAACGCCCAAAACTGCCGTCATTTCCGGGTTCCCACGCTACGTCATCAAAACACGACTTTCAAATTCCGT

CGACCGTTAAAAACGTCACCCGCCCCGCCCCTAACGGTCGCCCGTCTCTCAGCCAATCAGCGCCCCGCATCCC

CAAATTCAAACACCTCATTTGCATATTAACGCGCACAAAAAGTTTGAGGTATATTATTGATGATG

ChAdV68-Empty-E4deleted (SEQ ID NO: 59)

CATCTTCAATAATATACCTCAAACTTTTTGTGCGCGTTAATATGCAAATGAGGCGTTTGAATTTGGGGAGGAA

GGGCGGTGATTGGTCGAGGGATGAGCGACCGTTAGGGGCGGGGCGAGTGACGTTTTGATGACGTGGTTGCGA

GGAGGAGCCAGTTTGCAAGTTCTCGTGGGAAAAGTGACGTCAAACGAGGTGTGGTTTGAACACGGAAATACT

CAATTTTCCCGCGCTCTCTGACAGGAAATGAGGTGTTTCTGGGCGGATGCAAGTGAAAACGGGCCATTTTCGC

GCGAAAACTGAATGAGGAAGTGAAAATCTGAGTAATTTCGCGTTTATGGCAGGGAGGAGTATTTGCCGAGGG

CCGAGTAGACTTTGACCGATTACGTGGGGGTTTCGATTACCGTGTTTTTCACCTAAATTTCCGCGTACGGTGTC

AAAGTCCGGTGTTTTTACGTAGGTGTCAGCTGATCGCCAGGGTATTTAAACCTGCGCTCTCCAGTCAAGAGGC

CACTCTTGAGTGCCAGCGAGAAGAGTTTTCTCCTCCGCGCCGCGAGTCAGATCTACACTTTGAAAGTAGGGata aGGTAGCGAGTGAGTAGTGTTCTGGGGCGGGGGAGGACCTGCATGAGGGCCAGAATAACTGAAATCTGTGCT

TTTCTGTGTGTTGCAGCAGCATGAGCGGAAGCGGCTCCTTTGAGGGAGGGGTATTCAGCCCTTATCTGACGGG

GCGTCTCCCCTCCTGGGCGGGAGTGCGTCAGAATGTGATGGGATCCACGGTGGACGGCCGGCCCGTGCAGCC

CGCGAACTCTTCAACCCTGACCTATGCAACCCTGAGCTCTTCGTCGTTGGACGCAGCTGCCGCCGCAGCTGCT

GCATCTGCCGCCAGCGCCGTGCGCGGAATGGCCATGGGCGCCGGCTACTACGGCACTCTGGTGGCCAACTCG

AGTTCCACCAATAATCCCGCCAGCCTGAACGAGGAGAAGCTGTTGCTGCTGATGGCCCAGCTCGAGGCCTTG

ACCCAGCGCCTGGGCGAGCTGACCCAGCAGGTGGCTCAGCTGCAGGAGCAGACGCGGGCCGCGGTTGCCACG

GTGAAATCCAAATAAAAAATGAATCAATAAATAAACGGAGACGGTTGTTGATTTTAACACAGAGTCTGAATC

TTTATTTGATTTTTCGCGCGCGGTAGGCCCTGGACCACCGGTCTCGATCATTGAGCACCCGGTGGATCTTTTCC

AGGACCCGGTAGAGGTGGGCTTGGATGTTGAGGTACATGGGCATGAGCCCGTCCCGGGGGTGGAGGTAGCTC

CATTGCAGGGCCTCGTGCTCGGGGGTGGTGTTGTAAATCACCCAGTCATAGCAGGGGCGCAGGGCATGGTGT

TGCACAATATCTTTGAGGAGGAGACTGATGGCCACGGGCAGCCCTTTGGTGTAGGTGTTTACAAATCTGTTGA

GCTGGGAGGGATGCATGCGGGGGGAGATGAGGTGCATCTTGGCCTGGATCTTGAGATTGGCGATGTTACCGC

CCAGATCCCGCCTGGGGTTCATGTTGTGCAGGACCACCAGCACGGTGTATCCGGTGCACTTGGGGAATTTATC

ATGCAACTTGGAAGGGAAGGCGTGAAAGAATTTGGCGACGCCTTTGTGCCCGCCCAGGTTTTCCATGCACTCA

TCCATGATGATGGCGATGGGCCCGTGGGCGGCGGCCTGGGCAAAGACGTTTCGGGGGTCGGACACATCATAG

TTGTGGTCCTGGGTGAGGTCATCATAGGCCATTTTAATGAATTTGGGGCGGAGGGTGCCGGACTGGGGGACA

AAGGTACCCTCGATCCCGGGGGCGTAGTTCCCCTCACAGATCTGCATCTCCCAGGCTTTGAGCTCGGAGGGGG

GGATCATGTCCACCTGCGGGGCGATAAAGAACACGGTTTCCGGGGCGGGGGAGATGAGCTGGGCCGAAAGC

AAGTTCCGGAGCAGCTGGGACTTGCCGCAGCCGGTGGGGCCGTAGATGACCCCGATGACCGGCTGCAGGTGG

TAGTTGAGGGAGAGACAGCTGCCGTCCTCCCGGAGGAGGGGGGCCACCTCGTTCATCATCTCGCGCACGTGC

ATGTTCTCGCGCACCAGTTCCGCCAGGAGGCGCTCTCCCCCCAGGGATAGGAGCTCCTGGAGCGAGGCGAAG

TTTTTCAGCGGCTTGAGTCCGTCGGCCATGGGCATTTTGGAGAGGGTTTGTTGCAAGAGTTCCAGGCGGTCCC

AGAGCTCGGTGATGTGCTCTACGGCATCTCGATCCAGCAGACCTCCTCGTTTCGCGGGTTGGGACGGCTGCGG

GAGTAGGGCACCAGACGATGGGCGTCCAGCGCAGCCAGGGTCCGGTCCTTCCAGGGTCGCAGCGTCCGCGTC

AGGGTGGTCTCCGTCACGGTGAAGGGGTGCGCGCCGGGCTGGGCGCTTGCGAGGGTGCGCTTCAGGCTCATC

CGGCTGGTCGAAAACCGCTCCCGATCGGCGCCCTGCGCGTCGGCCAGGTAGCAATTGACCATGAGTTCGTAG

TTGAGCGCCTCGGCCGCGTGGCCTTTGGCGCGGAGCTTACCTTTGGAAGTCTGCCCGCAGGCGGGACAGAGG

AGGGACTTGAGGGCGTAGAGCTTGGGGGCGAGGAAGACGGACTCGGGGGCGTAGGCGTCCGCGCCGCAGTG

GGCGCAGACGGTCTCGCACTCCACGAGCCAGGTGAGGTCGGGCTGGTCGGGGTCAAAAACCAGTTTCCCGCC

GTTCTTTTTGATGCGTTTCTTACCTTTGGTCTCCATGAGCTCGTGTCCCCGCTGGGTGACAAAGAGGCTGTCCG

TGTCCCCGTAGACCGACTTTATGGGCCGGTCCTCGAGCGGTGTGCCGCGGTCCTCCTCGTAGAGGAACCCCGC

CCACTCCGAGACGAAAGCCCGGGTCCAGGCCAGCACGAAGGAGGCCACGTGGGACGGGTAGCGGTCGTTGT

CCACCAGCGGGTCCACCTTTTCCAGGGTATGCAAACACATGTCCCCCTCGTCCACATCCAGGAAGGTGATTGG

CTTGTAAGTGTAGGCCACGTGACCGGGGGTCCCGGCCGGGGGGGTATAAAAGGGTGCGGGTCCCTGCTCGTC

CTCACTGTCTTCCGGATCGCTGTCCAGGAGCGCCAGCTGTTGGGGTAGGTATTCCCTCTCGAAGGCGGGCATG

ACCTCGGCACTCAGGTTGTCAGTTTCTAGAAACGAGGAGGATTTGATATTGACGGTGCCGGCGGAGATGCCTT

TCAAGAGCCCCTCGTCCATCTGGTCAGAAAAGACGATCTTTTTGTTGTCGAGCTTGGTGGCGAAGGAGCCGTA

GAGGGCGTTGGAGAGGAGCTTGGCGATGGAGCGCATGGTCTGGTTTTTTTCCTTGTCGGCGCGCTCCTTGGCG

GCGATGTTGAGCTGCACGTACTCGCGCGCCACGCACTTCCATTCGGGGAAGACGGTGGTCAGCTCGTCGGGC

ACGATTCTGACCTGCCAGCCCCGATTATGCAGGGTGATGAGGTCCACACTGGTGGCCACCTCGCCGCGCAGG

GGCTCATTAGTCCAGCAGAGGCGTCCGCCCTTGCGCGAGCAGAAGGGGGGCAGGGGGTCCAGCATGACCTCG

TCGGGGGGGTCGGCATCGATGGTGAAGATGCCGGGCAGGAGGTCGGGGTCAAAGTAGCTGATGGAAGTGGC

CAGATCGTCCAGGGCAGCTTGCCATTCGCGCACGGCCAGCGCGCGCTCGTAGGGACTGAGGGGCGTGCCCCA

GGGCATGGGATGGGTAAGCGCGGAGGCGTACATGCCGCAGATGTCGTAGACGTAGAGGGGCTCCTCGAGGA

TGCCGATGTAGGTGGGGTAGCAGCGCCCCCCGCGGATGCTGGCGCGCACGTAGTCATACAGCTCGTGCGAGG

GGGCGAGGAGCCCCGGGCCCAGGTTGGTGCGACTGGGCTTTTCGGCGCGGTAGACGATCTGGCGGAAAATGG

CATGCGAGTTGGAGGAGATGGTGGGCCTTTGGAAGATGTTGAAGTGGGCGTGGGGCAGTCCGACCGAGTCGC

GGATGAAGTGGGCGTAGGAGTCTTGCAGCTTGGCGACGAGCTCGGCGGTGACTAGGACGTCCAGAGCGCAGT

AGTCGAGGGTCTCCTGGATGATGTCATACTTGAGCTGTCCCTTTTGTTTCCACAGCTCGCGGTTGAGAAGGAA

CTCTTCGCGGTCCTTCCAGTACTCTTCGAGGGGGAACCCGTCCTGATCTGCACGGTAAGAGCCTAGCATGTAG

AACTGGTTGACGGCCTTGTAGGCGCAGCAGCCCTTCTCCACGGGGAGGGCGTAGGCCTGGGCGGCCTTGCGC

AGGGAGGTGTGCGTGAGGGCGAAAGTGTCCCTGACCATGACCTTGAGGAACTGGTGCTTGAAGTCGATATCG

TCGCAGCCCCCCTGCTCCCAGAGCTGGAAGTCCGTGCGCTTCTTGTAGGCGGGGTTGGGCAAAGCGAAAGTA

ACATCGTTGAAGAGGATCTTGCCCGCGCGGGGCATAAAGTTGCGAGTGATGCGGAAAGGTTGGGGCACCTCG

GCCCGGTTGTTGATGACCTGGGCGGCGAGCACGATCTCGTCGAAGCCGTTGATGTTGTGGCCCACGATGTAGA

GTTCCACGAATCGCGGACGGCCCTTGACGTGGGGCAGTTTCTTGAGCTCCTCGTAGGTGAGCTCGTCGGGGTC

GCTGAGCCCGTGCTGCTCGAGCGCCCAGTCGGCGAGATGGGGGTTGGCGCGGAGGAAGGAAGTCCAGAGAT

CCACGGCCAGGGCGGTTTGCAGACGGTCCCGGTACTGACGGAACTGCTGCCCGACGGCCATTTTTTCGGGGGT

GACGCAGTAGAAGGTGCGGGGGTCCCCGTGCCAGCGATCCCATTTGAGCTGGAGGGCGAGATCGAGGGCGA

GCTCGACGAGCCGGTCGTCCCCGGAGAGTTTCATGACCAGCATGAAGGGGACGAGCTGCTTGCCGAAGGACC

CCATCCAGGTGTAGGTTTCCACATCGTAGGTGAGGAAGAGCCTTTCGGTGCGAGGATGCGAGCCGATGGGGA

AGAACTGGATCTCCTGCCACCAATTGGAGGAATGGCTGTTGATGTGATGGAAGTAGAAATGCCGACGGCGCG

CCGAACACTCGTGCTTGTGTTTATACAAGCGGCCACAGTGCTCGCAACGCTGCACGGGATGCACGTGCTGCAC

GAGCTGTACCTGAGTTCCTTTGACGAGGAATTTCAGTGGGAAGTGGAGTCGTGGCGCCTGCATCTCGTGCTGT

ACTACGTCGTGGTGGTCGGCCTGGCCCTCTTCTGCCTCGATGGTGGTCATGCTGACGAGCCCGCGCGGGAGGC

AGGTCCAGACCTCGGCGCGAGCGGGTCGGAGAGCGAGGACGAGGGCGCGCAGGCCGGAGCTGTCCAGGGTC

CTGAGACGCTGCGGAGTCAGGTCAGTGGGCAGCGGCGGCGCGCGGTTGACTTGCAGGAGTTTTTCCAGGGCG

CGCGGGAGGTCCAGATGGTACTTGATCTCCACCGCGCCATTGGTGGCGACGTCGATGGCTTGCAGGGTCCCGT

GCCCCTGGGGTGTGACCACCGTCCCCCGTTTCTTCTTGGGCGGCTGGGGCGACGGGGGCGGTGCCTCTTCCAT

GGTTAGAAGCGGCGGCGAGGACGCGCGCCGGGCGGCAGGGGCGGCTCGGGGCCCGGAGGCAGGGGCGGCA

GGGGCACGTCGGCGCCGCGCGCGGGTAGGTTCTGGTACTGCGCCCGGAGAAGACTGGCGTGAGCGACGACGC

GACGGTTGACGTCCTGGATCTGACGCCTCTGGGTGAAGGCCACGGGACCCGTGAGTTTGAACCTGAAAGAGA

GTTCGACAGAATCAATCTCGGTATCGTTGACGGCGGCCTGCCGCAGGATCTCTTGCACGTCGCCCGAGTTGTC

CTGGTAGGCGATCTCGGTCATGAACTGCTCGATCTCCTCCTCTTGAAGGTCTCCGCGGCCGGCGCGCTCCACG

GTGGCCGCGAGGTCGTTGGAGATGCGGCCCATGAGCTGCGAGAAGGCGTTCATGCCCGCCTCGTTCCAGACG

CGGCTGTAGACCACGACGCCCTCGGGATCGCgGGCGCGCATGACCACCTGGGCGAGGTTGAGCTCCACGTGG

CGCGTGAAGACCGCGTAGTTGCAGAGGCGCTGGTAGAGGTAGTTGAGCGTGGTGGCGATGTGCTCGGTGACG

AAGAAATACATGATCCAGCGGCGGAGCGGCATCTCGCTGACGTCGCCCAGCGCCTCCAAACGTTCCATGGCC

TCGTAAAAGTCCACGGCGAAGTTGAAAAACTGGGAGTTGCGCGCCGAGACGGTCAACTCCTCCTCCAGAAGA

CGGATGAGCTCGGCGATGGTGGCGCGCACCTCGCGCTCGAAGGCCCCCGGGAGTTCCTCCACTTCCTCTTCTT

CCTCCTCCACTAACATCTCTTCTACTTCCTCCTCAGGCGGCAGTGGTGGCGGGGGAGGGGGCCTGCGTCGCCG

GCGGCGCACGGGCAGACGGTCGATGAAGCGCTCGATGGTCTCGCCGCGCCGGCGTCGCATGGTCTCGGTGAC

GGCGCGCCCGTCCTCGCGGGGCCGCAGCGTGAAGACGCCGCCGCGCATCTCCAGGTGGCCGGGGGGGTCCCC

GTTGGGCAGGGAGAGGGCGCTGACGATGCATCTTATCAATTGCCCCGTAGGGACTCCGCGCAAGGACCTGAG

-continued

CGTCTCGAGATCCACGGGATCTGAAAACCGCTGAACGAAGGCTTCGAGCCAGTCGCAGTCGCAAGGTAGGCT

GAGCACGGTTTCTTCTGGCGGGTCATGTTGGTTGGGAGCGGGGCGGGCGATGCTGCTGGTGATGAAGTTGAA

ATAGGCGGTTCTGAGACGGCGGATGGTGGCGAGGAGCACCAGGTCTTTGGGCCCGGCTTGCTGGATGCGCAG

ACGGTCGGCCATGCCCCAGGCGTGGTCCTGACACCTGGCCAGGTCCTTGTAGTAGTCCTGCATGAGCCGCTCC

ACGGGCACCTCCTCCTCGCCCGCGCGGCCGTGCATGCGCGTGAGCCCGAAGCCGCGCTGGGGCTGGACGAGC

GCCAGGTCGGCGACGACGCGCTCGGCGAGGATGGCTTGCTGGATCTGGGTGAGGGTGGTCTGGAAGTCATCA

AAGTCGACGAAGCGGTGGTAGGCTCCGGTGTTGATGGTGTAGGAGCAGTTGGCCATGACGGACCAGTTGACG

GTCTGGTGGCCCGGACGCACGAGCTCGTGGTACTTGAGGCGCGAGTAGGCGCGCGTGTCGAAGATGTAGTCG

TTGCAGGTGCGCACCAGGTACTGGTAGCCGATGAGGAAGTGCGGCGGCGGCTGGCGGTAGAGCGGCCATCGC

TCGGTGGCGGGGGCGCCGGGCGCGAGGTCCTCGAGCATGGTGCGGTGGTAGCCGTAGATGTACCTGGACATC

CAGGTGATGCCGGCGGCGGTGGTGGAGGCGCGCGGGAACTCGCGGACGCGGTTCCAGATGTTGCGCAGCGGC

AGGAAGTAGTTCATGGTGGGCACGGTCTGGCCCGTGAGGCGCGCGCAGTCGTGGATGCTCTATACGGGCAAA

AACGAAAGCGGTCAGCGGCTCGACTCCGTGGCCTGGAGGCTAAGCGAACGGGTTGGGCTGCGCGTGTACCCC

GGTTCGAATCTCGAATCAGGCTGGAGCCGCAGCTAACGTGGTATTGGCACTCCCGTCTCGACCCAAGCCTGCA

CCAACCCTCCAGGATACGGAGGCGGGTCGTTTTGCAACTTTTTTTTGGAGGCCGGATGAGACTAGTAAGCGCG

GAAAGCGGCCGACCGCGATGGCTCGCTGCCGTAGTCTGGAGAAGAATCGCCAGGGTTGCGTTGCGGTGTGCC

CCGGTTCGAGGCCGGCCGGATTCCGCGGCTAACGAGGGCGTGGCTGCCCCGTCGTTTCCAAGACCCCATAGC

CAGCCGACTTCTCCAGTTACGGAGCGAGCCCCTCTTTTGTTTTGTTTGTTTTTGCCAGATGCATCCCGTACTGC

GGCAGATGCGCCCCCACCACCCTCCACCGCAACAACAGCCCCCTCCACAGCCGGCGCTTCTGCCCCCGCCCCA

GCAGCAACTTCCAGCCACGACCGCCGCGGCCGCCGTGAGCGGGGCTGGACAGAGTTATGATCACCAGCTGGC

CTTGGAAGAGGGCGAGGGGCTGGCGCGCCTGGGGGCGTCGTCGCCGGAGCGGCACCCGCGCGTGCAGATGA

AAAGGGACGCTCGCGAGGCCTACGTGCCCAAGCAGAACCTGTTCAGAGACAGGAGCGGCGAGGAGCCCGAG

GAGATGCGCGCGGCCCGGTTCCACGCGGGGCGGGAGCTGCGGCGCGGCCTGGACCGAAAGAGGGTGCTGAG

GGACGAGGATTTCGAGGCGGACGAGCTGACGGGGATCAGCCCCGCGCGCGCGCACGTGGCCGCGGCCAACC

TGGTCACGGCGTACGAGCAGACCGTGAAGGAGGAGAGCAACTTCCAAAAATCCTTCAACAACCACGTGCGCA

CCCTGATCGCGCGCGAGGAGGTGACCCTGGGCCTGATGCACCTGTGGGACCTGCTGGAGGCCATCGTGCAGA

ACCCCACCAGCAAGCCGCTGACGGCGCAGCTGTTCCTGGTGGTGCAGCATAGTCGGGACAACGAAGCGTTCA

GGGAGGCGCTGCTGAATATCACCGAGCCCGAGGGCCGCTGGCTCCTGGACCTGGTGAACATTCTGCAGAGCA

TCGTGGTGCAGGAGCGCGGGCTGCCGCTGTCCGAGAAGCTGGCGGCCATCAACTTCTCGGTGCTGAGTTTGG

GCAAGTACTACGCTAGGAAGATCTACAAGACCCCGTACGTGCCCATAGACAAGGAGGTGAAGATCGACGGGT

TTTACATGCGCATGACCCTGAAAGTGCTGACCCTGAGCGACGATCTGGGGGTGTACCGCAACGACAGGATGC

ACCGTGCGGTGAGCGCCAGCAGGCGGCGCGAGCTGAGCGACCAGGAGCTGATGCATAGTCTGCAGCGGGCC

CTGACCGGGGCCGGGACCGAGGGGGAGAGCTACTTTGACATGGGCGCGGACCTGCACTGGCAGCCCAGCCGC

CGGGCCTTGGAGGCGGCGGCAGGACCCTACGTAGAAGAGGTGGACGATGAGGTGGACGAGGAGGGCGAGTA

CCTGGAAGACTGATGGCGCGACCGTATTTTTGCTAGATGCAACAACAACAGCCACCTCCTGATCCCGCGATGC

GGGCGGCGCTGCAGAGCCAGCCGTCCGGCATTAACTCCTCGGACGATTGGACCCAGGCCATGCAACGCATCA

TGGCGCTGACGACCCGCAACCCCGAAGCCTTTAGACAGCAGCCCCAGGCCAACCGGCTCTCGGCCATCCTGG

AGGCCGTGGTGCCCTCGCGCTCCAACCCCACGCACGAGAAGGTCCTGGCCATCGTGAACGCGCTGGTGGAGA

ACAAGGCCATCCGCGGCGACGAGGCCGGCCTGGTGTACAACGCGCTGCTGGAGCGCGTGGCCCGCTACAACA

GCACCAACGTGCAGACCAACCTGGACCGCATGGTGACCGACGTGCGCGAGGCCGTGGCCCAGCGCGAGCGGT

TCCACCGCGAGTCCAACCTGGGATCCATGGTGGCGCTGAACGCCTTCCTCAGCACCCAGCCCGCCAACGTGCC

-continued

CCGGGGCCAGGAGGACTACACCAACTTCATCAGCGCCCTGCGCCTGATGGTGACCGAGGTGCCCCAGAGCGA

GGTGTACCAGTCCGGGCCGGACTACTTCTTCCAGACCAGTCGCCAGGGCTTGCAGACCGTGAACCTGAGCCA

GGCTTTCAAGAACTTGCAGGGCCTGTGGGGCGTGCAGGCCCCGGTCGGGGACCGCGCGACGGTGTCGAGCCT

GCTGACGCCGAACTCGCGCCTGCTGCTGCTGCTGGTGGCCCCCTTCACGGACAGCGGCAGCATCAACCGCAA

CTCGTACCTGGGCTACCTGATTAACCTGTACCGCGAGGCCATCGGCCAGGCGCACGTGGACGAGCAGACCTA

CCAGGAGATCACCCACGTGAGCCGCGCCCTGGGCCAGGACGACCCGGGCAACCTGGAAGCCACCCTGAACTT

TTTGCTGACCAACCGGTCGCAGAAGATCCCGCCCCAGTACGCGCTCAGCACCGAGGAGGAGCGCATCCTGCG

TTACGTGCAGCAGAGCGTGGGCCTGTTCCTGATGCAGGAGGGGGCCACCCCCAGCGCCGCGCTCGACATGAC

CGCGCGCAACATGGAGCCCAGCATGTACGCCAGCAACCGCCCGTTCATCAATAAACTGATGGACTACTTGCA

TCGGGCGGCCGCCATGAACTCTGACTATTTCACCAACGCCATCCTGAATCCCCACTGGCTCCCGCCGCCGGGG

TTCTACACGGGCGAGTACGACATGCCCGACCCCAATGACGGGTTCCTGTGGGACGATGTGGACAGCAGCGTG

TTCTCCCCCCGACCGGGTGCTAACGAGCGCCCCTTGTGGAAGAAGGAAGGCAGCGACCGACGCCCGTCCTCG

GCGCTGTCCGGCCGCGAGGGTGCTGCCGCGGCGGTGCCCGAGGCCGCCAGTCCTTTCCCGAGCTTGCCCTTCT

CGCTGAACAGTATCCGCAGCAGCGAGCTGGGCAGGATCACGCGCCCGCGCTTGCTGGGCGAAGAGGAGTACT

TGAATGACTCGCTGTTGAGACCCGAGCGGGAGAAGAACTTCCCCAATAACGGGATAGAAAGCCTGGTGGACA

AGATGAGCCGCTGGAAGACGTATGCGCAGGAGCACAGGGACGATCCCCGGGCGTCGCAGGGGGCCACGAGC

CGGGGCAGCGCCGCCCGTAAACGCCGGTGGCACGACAGGCAGCGGGGACAGATGTGGGACGATGAGGACTC

CGCCGACGACAGCAGCGTGTTGGACTTGGGTGGGAGTGGTAACCCGTTCGCTCACCTGCGCCCCCGTATCGG

GCGCATGATGTAAGAGAAACCGAAAATAAATGATACTCACCAAGGCCATGGCGACCAGCGTGCGTTCGTTTC

TTCTCTGTTGTTGTTGTATCTAGTATGATGAGGCGTGCGTACCCGGAGGGTCCTCCTCCCTCGTACGAGAGCGT

GATGCAGCAGGCGATGGCGGCGGCGGCGATGCAGCCCCCGCTGGAGGCTCCTTACGTGCCCCCGCGGTACCT

GGCGCCTACGGAGGGGCGGAACAGCATTCGTTACTCGGAGCTGGCACCCTTGTACGATACCACCCGGTTGTA

CCTGGTGGACAACAAGTCGGCGGACATCGCCTCGCTGAACTACCAGAACGACCACAGCAACTTCCTGACCAC

CGTGGTGCAGAACAATGACTTCACCCCCACGGAGGCCAGCACCCAGACCATCAACTTTGACGAGCGCTCGCG

GTGGGGCGGCCAGCTGAAAACCATCATGCACACCAACATGCCCAACGTGAACGAGTTCATGTACAGCAACAA

GTTCAAGGCGCGGGTGATGGTCTCCCGCAAGACCCCCAATGGGGTGACAGTGACAGAGGATTATGATGGTAG

TCAGGATGAGCTGAAGTATGAATGGGTGGAATTTGAGCTGCCCGAAGGCAACTTCTCGGTGACCATGACCAT

CGACCTGATGAACAACGCCATCATCGACAATTACTTGGCGGTGGGGCGGCAGAACGGGGTGCTGGAGAGCGA

CATCGGCGTGAAGTTCGACACTAGGAACTTCAGGCTGGGCTGGGACCCCGTGACCGAGCTGGTCATGCCCGG

GGTGTACACCAACGAGGCTTTCCATCCCGATATTGTCTTGCTGCCCGGCTGCGGGGTGGACTTCACCGAGAGC

CGCCTCAGCAACCTGCTGGGCATTCGCAAGAGGCAGCCCTTCCAGGAAGGCTTCCAGATCATGTACGAGGAT

CTGGAGGGGGGCAACATCCCCGCGCTCCTGGATGTCGACGCCTATGAGAAAAGCAAGGAGGATGCAGCAGCT

GAAGCAACTGCAGCCGTAGCTACCGCCTCTACCGAGGTCAGGGGCGATAATTTTGCAAGCGCCGCAGCAGTG

GCAGCGGCCGAGGCGGCTGAAACCGAAAGTAAGATAGTCATTCAGCCGGTGGAGAAGGATAGCAAGAACAG

GAGCTACAACGTACTACCGGACAAGATAAACACCGCCTACCGCAGCTGGTACCTAGCCTACAACTATGGCGA

CCCCGAGAAGGGCGTGCGCTCCTGGACGCTGCTCACCACCTCGGACGTCACCTGCGGCGTGGAGCAAGTCTA

CTGGTCGCTGCCCGACATGATGCAAGACCCGGTCACCTTCCGCTCCACGCGTCAAGTTAGCAACTACCCGGTG

GTGGGCGCCGAGCTCCTGCCCGTCTACTCCAAGAGCTTCTTCAACGAGCAGGCCGTCTACTCGCAGCAGCTGC

GCGCCTTCACCTCGCTTACGCACGTCTTCAACCGCTTCCCCGAGAACCAGATCCTCGTCCGCCCGCCCGCGCC

CACCATTACCACCGTCAGTGAAAACGTTCCTGCTCTCACAGATCACGGGACCCTGCCGCTGCGCAGCAGTATC

-continued

CGGGGAGTCCAGCGCGTGACCGTTACTGACGCCAGACGCCGCACCTGCCCCTACGTCTACAAGGCCCTGGGC

ATAGTCGCGCCGCGCGTCCTCTCGAGCCGCACCTTCTAAATGTCCATTCTCATCTCGCCCAGTAATAACACCG

GTTGGGGCCTGCGCGCGCCCAGCAAGATGTACGGAGGCGCTCGCCAACGCTCCACGCAACACCCCGTGCGCG

TGCGCGGGCACTTCCGCGCTCCCTGGGGCGCCCTCAAGGGCCGCGTGCGGTCGCGCACCACCGTCGACGACG

TGATCGACCAGGTGGTGGCCGACGCGCGCAACTACACCCCCGCCGCCGCGCCCGTCTCCACCGTGGACGCCG

TCATCGACAGCGTGGTGGCcGACGCGCGCCGGTACGCCCGCGCCAAGAGCCGGCGGCGGCGCATCGCCCGGC

GGCACCGGAGCACCCCCGCCATGCGCGCGGCGCGAGCCTTGCTGCGCAGGGCCAGGCGCACGGGACGCAGG

GCCATGCTCAGGGCGGCCAGACGCGCGGCTTCAGGCGCCAGCGCCGGCAGGACCCGGAGACGCGCGGCCAC

GGCGGCGGCAGCGGCCATCGCCAGCATGTCCCGCCCGCGGCGAGGGAACGTGTACTGGGTGCGCGACGCCGC

CACCGGTGTGCGCGTGCCCGTGCGCACCCGCCCCCCTCGCACTTGAAGATGTTCACTTCGCGATGTTGATGTG

TCCCAGCGGCGAGGAGGATGTCCAAGCGCAAATTCAAGGAAGAGATGCTCCAGGTCATCGCGCCTGAGATCT

ACGGCCCTGCGGTGGTGAAGGAGGAAAGAAAGCCCCGCAAAATCAAGCGGGTCAAAAAGGACAAAAAGGA

AGAAGAAAGTGATGTGGACGGATTGGTGGAGTTTGTGCGCGAGTTCGCCCCCCGGCGGCGCGTGCAGTGGCG

CGGGCGGAAGGTGCAACCGGTGCTGAGACCCGGCACCACCGTGGTCTTCACGCCCGGCGAGCGCTCCGGCAC

CGCTTCCAAGCGCTCCTACGACGAGGTGTACGGGGATGATGATATTCTGGAGCAGGCGGCCGAGCGCCTGGG

CGAGTTTGCTTACGGCAAGCGCAGCCGTTCCGCACCGAAGGAAGAGGCGGTGTCCATCCCGCTGGACCACGG

CAACCCCACGCCGAGCCTCAAGCCCGTGACCTTGCAGCAGGTGCTGCCGACCGCGGCGCCGCGCCGGGGGTT

CAAGCGCGAGGGCGAGGATCTGTACCCCACCATGCAGCTGATGGTGCCCAAGCGCCAGAAGCTGGAAGACGT

GCTGGAGACCATGAAGGTGGACCCGGACGTGCAGCCCGAGGTCAAGGTGCGGCCCATCAAGCAGGTGGCCC

CGGGCCTGGGCGTGCAGACCGTGGACATCAAGATTCCCACGGAGCCCATGGAAACGCAGACCGAGCCCATGA

TCAAGCCCAGCACCAGCACCATGGAGGTGCAGACGGATCCCTGGATGCCATCGGCTCCTAGTCGAAGACCCC

GGCGCAAGTACGGCGCGGCCAGCCTGCTGATGCCCAACTACGCGCTGCATCCTTCCATCATCCCCACGCCGGG

CTACCGCGGCACGCGCTTCTACCGCGGTCATACCAGCAGCCGCCGCCGCAAGACCACCACTCGCCGCCGCCG

TCGCCGCACCGCCGCTGCAACCACCCCTGCCGCCCTGGTGCGGAGAGTGTACCGCCGCGGCCGCGCACCTCTG

ACCCTGCCGCGCGCGCGCTACCACCCGAGCATCGCCATTTAAACTTTCGCCtGCTTTGCAGATCAATGGCCCTC

ACATGCCGCCTTCGCGTTCCCATTACGGGCTACCGAGGAAGAAAACCGCGCCGTAGAAGGCTGGCGGGGAAC

GGGATGCGTCGCCACCACCACCGGCGGCGGCGCGCCATCAGCAAGCGGTTGGGGGGAGGCTTCCTGCCCGCG

CTGATCCCCATCATCGCCGCGGCGATCGGGGCGATCCCCGGCATTGCTTCCGTGGCGGTGCAGGCCTCTCAGC

GCCACTGAGACACACTTGGAAACATCTTGTAATAAACCaATGGACTCTGACGCTCCTGGTCCTGTGATGTGTTT

TCGTAGACAGATGGAAGACATCAATTTTTCGTCCCTGGCTCCGCGACACGGCACGCGGCCGTTCATGGGCACC

TGGAGCGACATCGGCACCAGCCAACTGAACGGGGGCGCCTTCAATTGGAGCAGTCTCTGGAGCGGGCTTAAG

AATTTCGGGTCCACGCTTAAAACCTATGGCAGCAAGGCGTGGAACAGCACCACAGGGCAGGCGCTGAGGGAT

AAGCTGAAAGAGCAGAACTTCCAGCAGAAGGTGGTCGATGGGCTCGCCTCGGGCATCAACGGGGTGGTGGA

CCTGGCCAACCAGGCCGTGCAGCGGCAGATCAACAGCCGCCTGGACCCGGTGCCGCCCGCCGGCTCCGTGGA

GATGCCGCAGGTGGAGGAGGAGCTGCCTCCCCTGGACAAGCGGGGCGAGAAGCGACCCCGCCCCGATGCGG

AGGAGACGCTGCTGACGCACACGGACGAGCCGCCCCCGTACGAGGAGGCGGTGAAACTGGGTCTGCCCACC

ACGCGGCCCATCGCGCCCCTGGCCACCGGGGTGCTGAAACCCGAAAAGCCCGCGACCCTGGACTTGCCTCCT

CCCCAGCCTTCCCGCCCCTCTACAGTGGCTAAGCCCCTGCCGCCGGTGGCCGTGGCCCGCGCGCGACCCGGGG

GCACCGCCCGCCCTCATGCGAACTGGCAGAGCACTCTGAACAGCATCGTGGGTCTGGGAGTGCAGAGTGTGA

AGCGCCGCCGCTGCTATTAAACCTACCGTAGCGCTTAACTTGCTTGTCTGTGTGTGTATGTATTATGTCGCCGC

CGCCGCTGTCCACCAGAAGGAGGAGTGAAGAGGCGCGTCGCCGAGTTGCAAGATGGCCACCCCATCGATGCT

-continued

GCCCCAGTGGGCGTACATGCACATCGCCGGACAGGACGCTTCGGAGTACCTGAGTCCGGGTCTGGTGCAGTT

TGCCCGCGCCACAGACACCTACTTCAGTCTGGGGAACAAGTTTAGGAACCCCACGGTGGCGCCCACGCACGA

TGTGACCACCGACCGCAGCCAGCGGCTGACGCTGCGCTTCGTGCCCGTGGACCGCGAGGACAACACCTACTC

GTACAAAGTGCGCTACACGCTGGCCGTGGGCGACAACCGCGTGCTGGACATGGCCAGCACCTACTTTGACAT

CCGCGGCGTGCTGGATCGGGGCCCTAGCTTCAAACCCTACTCCGGCACCGCCTACAACAGTCTGGCCCCCAAG

GGAGCACCCAACACTTGTCAGTGGACATATAAAGCCGATGGTGAAACTGCCACAGAAAAAACCTATACATAT

GGAAATGCACCCGTGCAGGGCATTAACATCACAAAAGATGGTATTCAACTTGGAACTGACACCGATGATCAG

CCAATCTACGCAGATAAAACCTATCAGCCTGAACCTCAAGTGGGTGATGCTGAATGGCATGACATCACTGGT

ACTGATGAAAAGTATGGAGGCAGAGCTCTTAAGCCTGATACCAAAATGAAGCCTTGTTATGGTTCTTTTGCCA

AGCCTACTAATAAAGAAGGAGGTCAGGCAAATGTGAAAACAGGAACAGGCACTACTAAAGAATATGACATA

GACATGGCTTTCTTTGACAACAGAAGTGCGGCTGCTGCTGGCCTAGCTCCAGAAATTGTTTTGTATACTGAAA

ATGTGGATTTGGAAACTCCAGATACCCATATTGTATACAAAGCAGGCACAGATGACAGCAGCTCTTCTATTAA

TTTGGGTCAGCAAGCCATGCCCAACAGACCTAACTACATTGGTTTCAGAGACAACTTTATCGGGCTCATGTAC

TACAACAGCACTGGCAATATGGGGGTGCTGGCCGGTCAGGCTTCTCAGCTGAATGCTGTGGTTGACTTGCAAG

ACAGAAACACCGAGCTGTCCTACCAGCTCTTGCTTGACTCTCTGGGTGACAGAACCCGGTATTTCAGTATGTG

GAATCAGGCGGTGGACAGCTATGATCCTGATGTGCGCATTATTGAAAATCATGGTGTGGAGGATGAACTTCC

CAACTATTGTTTCCCTCTGGATGCTGTTGGCAGAACAGATACTTATCAGGGAATTAAGGCTAATGGAACTGAT

CAAACCACATGGACCAAAGATGACAGTGTCAATGATGCTAATGAGATAGGCAAGGGTAATCCATTCGCCATG

GAAATCAACATCCAAGCCAACCTGTGGAGGAACTTCCTCTACGCCAACGTGGCCCTGTACCTGCCCGACTCTT

ACAAGTACACGCCGGCCAATGTTACCCTGCCCACCAACACCAACACCTACGATTACATGAACGGCCGGGTGG

TGGCGCCCTCGCTGGTGGACTCCTACATCAACATCGGGGCGCGCTGGTCGCTGGATCCCATGGACAACGTGA

ACCCCTTCAACCACCACCGCAATGCGGGGCTGCGCTACCGCTCCATGCTCCTGGGCAACGGGCGCTACGTGCC

CTTCCACATCCAGGTGCCCCAGAAATTTTTCGCCATCAAGAGCCTCCTGCTCCTGCCCGGGTCCTACACCTAC

GAGTGGAACTTCCGCAAGGACGTCAACATGATCCTGCAGAGCTCCCTCGGCAACGACCTGCGCACGGACGGG

GCCTCCATCTCCTTCACCAGCATCAACCTCTACGCCACCTTCTTCCCCATGGCGCACAACACGGCCTCCACGCT

CGAGGCCATGCTGCGCAACGACACCAACGACCAGTCCTTCAACGACTACCTCTCGGCGGCCAACATGCTCTA

CCCCATCCCGGCCAACGCCACCAACGTGCCCATCTCCATCCCCTCGCGCAACTGGGCCGCCTTCCGCGGCTGG

TCCTTCACGCGTCTCAAGACCAAGGAGACGCCCTCGCTGGGCTCCGGGTTCGACCCCTACTTCGTCTACTCGG

GCTCCATCCCCTACCTCGACGGCACCTTCTACCTCAACCACACCTTCAAGAAGGTCTCCATCACCTTCGACTCC

TCCGTCAGCTGGCCCGGCAACGACCGGCTCCTGACGCCCAACGAGTTCGAAATCAAGCGCACCGTCGACGGC

GAGGGCTACAACGTGGCCCAGTGCAACATGACCAAGGACTGGTTCCTGGTCCAGATGCTGGCCCACTACAAC

ATCGGCTACCAGGGCTTCTACGTGCCCGAGGGCTACAAGGACCGCATGTACTCCTTCTTCCGCAACTTCCAGC

CCATGAGCCGCCAGGTGGTGGACGAGGTCAACTACAAGGACTACCAGGCCGTCACCCTGGCCTACCAGCACA

ACAACTCGGGCTTCGTCGGCTACCTCGCGCCCACCATGCGCCAGGGCCAGCCCTACCCCGCCAACTACCCCTA

CCCGCTCATCGGCAAGAGCGCCGTCACCAGCGTCACCCAGAAAAAGTTCCTCTGCGACAGGGTCATGTGGCG

CATCCCCTTCTCCAGCAACTTCATGTCCATGGGCGCGCTCACCGACCTCGGCCAGAACATGCTCTATGCCAAC

TCCGCCCACGCGCTAGACATGAATTTCGAAGTCGACCCCATGGATGAGTCCACCCTTCTCTATGTTGTCTTCG

AAGTCTTCGACGTCGTCCGAGTGCACCAGCCCCACCGCGGCGTCATCGAGGCCGTCTACCTGCGCACCCCCTT

CTCGGCCGGTAACGCCACCACCTAAGCTCTTGCTTCTTGCAAGCCATGGCCGCGGGCTCCGGCGAGCAGGAG

CTCAGGGCCATCATCCGCGACCTGGGCTGCGGGCCCTACTTCCTGGGCACCTTCGATAAGCGCTTCCCGGGAT

-continued

TCATGGCCCCGCACAAGCTGGCCTGCGCCATCGTCAACACGGCCGGCCGCGAGACCGGGGGCGAGCACTGGC

TGGCCTTCGCCTGGAACCCGCGCTCGAACACCTGCTACCTCTTCGACCCCTTCGGGTTCTCGGACGAGCGCCT

CAAGCAGATCTACCAGTTCGAGTACGAGGGCCTGCTGCGCCGCAGCGCCCTGGCCACCGAGGACCGCTGCGT

CACCCTGGAAAAGTCCACCCAGACCGTGCAGGGTCCGCGCTCGGCCGCCTGCGGGCTCTTCTGCTGCATGTTC

CTGCACGCCTTCGTGCACTGGCCCGACCGCCCCATGGACAAGAACCCCACCATGAACTTGCTGACGGGGGTG

CCCAACGGCATGCTCCAGTCGCCCCAGGTGGAACCCACCCTGCGCCGCAACCAGGAGGCGCTCTACCGCTTC

CTCAACTCCCACTCCGCCTACTTTCGCTCCCACCGCGCGCGCATCGAGAAGGCCACCGCCTTCGACCGCATGA

ATCAAGACATGTAAACCGTGTGTGTATGTTAAATGTCTTTAATAAACAGCACTTTCATGTTACACATGCATCT

GAGATGATTTATTTAGAAATCGAAAGGGTTCTGCCGGGTCTCGGCATGGCCCGCGGGCAGGGACACGTTGCG

GAACTGGTACTTGGCCAGCCACTTGAACTCGGGGATCAGCAGTTTGGGCAGCGGGGTGTCGGGGAAGGAGTC

GGTCCACAGCTTCCGCGTCAGTTGCAGGGCGCCCAGCAGGTCGGGCGCGGAGATCTTGAAATCGCAGTTGGG

ACCCGCGTTCTGCGCGCGGGAGTTGCGGTACACGGGGTTGCAGCACTGGAACACCATCAGGGCCGGGTGCTT

CACGCTCGCCAGCACCGTCGCGTCGGTGATGCTCTCCACGTCGAGGTCCTCGGCGTTGGCCATCCCGAAGGGG

GTCATCTTGCAGGTCTGCCTTCCCATGGTGGGCACGCACCCGGGCTTGTGGTTGCAATCGCAGTGCAGGGGGA

TCAGCATCATCTGGGCCTGGTCGGCGTTCATCCCCGGGTACATGGCCTTCATGAAAGCCTCCAATTGCCTGAA

CGCCTGCTGGGCCTTGGCTCCCTCGGTGAAGAAGACCCCGCAGGACTTGCTAGAGAACTGGTTGGTGGCGCA

CCCGGCGTCGTGCACGCAGCAGCGCGCGTCGTTGTTGGCCAGCTGCACCACGCTGCGCCCCCAGCGGTTCTGG

GTGATCTTGGCCCGGTCGGGGTTCTCCTTCAGCGCGCGCTGCCCGTTCTCGCTCGCCACATCCATCTCGATCAT

GTGCTCCTTCTGGATCATGGTGGTCCCGTGCAGGCACCGCAGCTTGCCCTCGGCCTCGGTGCACCCGTGCAGC

CACAGCGCGCACCCGGTGCACTCCCAGTTCTTGTGGGCGATCTGGGAATGCGCGTGCACGAAGCCCTGCAGG

AAGCGGCCCATCATGGTGGTCAGGGTCTTGTTGCTAGTGAAGGTCAGCGGAATGCCGCGGTGCTCCTCGTTGA

TGTACAGGTGGCAGATGCGGCGGTACACCTCGCCCTGCTCGGGCATCAGCTGGAAGTTGGCTTTCAGGTCGGT

CTCCACGCGGTAGCGGTCCATCAGCATAGTCATGATTTCCATACCCTTCTCCCAGGCCGAGACGATGGGCAGG

CTCATAGGGTTCTTCACCATCATCTTAGCGCTAGCAGCCGCGGCCAGGGGGTCGCTCTCGTCCAGGGTCTCAA

AGCTCCGCTTGCCGTCCTTCTCGGTGATCCGCACCGGGGGGTAGCTGAAGCCCACGGCCGCCAGCTCCTCCTC

GGCCTGTCTTTCGTCCTCGCTGTCCTGGCTGACGTCCTGCAGGACCACATGCTTGGTCTTGCGGGGTTTCTTCT

TGGGCGGCAGCGGCGGCGGAGATGTTGGAGATGGCGAGGGGGAGCGCGAGTTCTCGCTCACCACTACTATCT

CTTCCTCTTCTTGGTCCGAGGCCACGCGGCGGTAGGTATGTCTCTTCGGGGGCAGAGGCGGAGGCGACGGGCT

CTCGCCGCCGCGACTTGGCGGATGGCTGGCAGAGCCCCTTCCGCGTTCGGGGGTGCGCTCCCGGCGGCGCTCT

GACTGACTTCCTCCGCGGCCGGCCATTGTGTTCTCCTAGGGAGGAACAACAAGCATGGAGACTCAGCCATCG

CCAACCTCGCCATCTGCCCCCACCGCCGACGAGAAGCAGCAGCAGCAGAATGAAAGCTTAACCGCCCCGCCG

CCCAGCCCCGCCACCTCCGACGCGGCCGTCCCAGACATGCAAGAGATGGAGGAATCCATCGAGATTGACCTG

GGCTATGTGACGCCCGCGGAGCACGAGGAGGAGCTGGCAGTGCGCTTTTCACAAGAAGAGATACACCAAGA

ACAGCCAGAGCAGGAAGCAGAGAATGAGCAGAGTCAGGCTGGGCTCGAGCATGACGGCGACTACCTCCACC

TGAGCGGGGGGGAGGACGCGCTCATCAAGCATCTGGCCCGGCAGGCCACCATCGTCAAGGATGCGCTGCTCG

ACCGCACCGAGGTGCCCCTCAGCGTGGAGGAGCTCAGCCGCGCCTACGAGTTGAACCTCTTCTCGCCGCGCGT

GCCCCCCAAGCGCCAGCCCAATGGCACCTGCGAGCCCAACCCGCGCCTCAACTTCTACCCGGTCTTCGCGGTG

CCCGAGGCCCTGGCCACCTACCACATCTTTTTCAAGAACCAAAAGATCCCCGTCTCCTGCCGCGCCAACCGCA

CCCGCGCCGACGCCCTTTTCAACCTGGGTCCCGGCGCCCGCCTACCTGATATCGCCTCCTTGGAAGAGGTTCC

CAAGATCTTCGAGGGTCTGGGCAGCGACGAGACTCGGGCCGCGAACGCTCTGCAAGGAGAAGGAGGAGAGC

ATGAGCACCACAGCGCCCTGGTCGAGTTGGAAGGCGACAACGCGCGGCTGGCGGTGCTCAAACGCACGGTCG

-continued

AGCTGACCCATTTCGCCTACCCGGCTCTGAACCTGCCCCCCAAAGTCATGAGCGCGGTCATGGACCAGGTGCT

CATCAAGCGCGCGTCGCCCATCTCCGAGGACGAGGGCATGCAAGACTCCGAGGAGGGCAAGCCCGTGGTCAG

CGACGAGCAGCTGGCCCGGTGGCTGGGTCCTAATGCTAGTCCCCAGAGTTTGGAAGAGCGGCGCAAACTCAT

GATGGCCGTGGTCCTGGTGACCGTGGAGCTGGAGTGCCTGCGCCGCTTCTTCGCCGACGCGGAGACCCTGCGC

AAGGTCGAGGAGAACCTGCACTACCTCTTCAGGCACGGGTTCGTGCGCCAGGCCTGCAAGATCTCCAACGTG

GAGCTGACCAACCTGGTCTCCTACATGGGCATCTTGCACGAGAACCGCCTGGGGCAGAACGTGCTGCACACC

ACCCTGCGCGGGGAGGCCCGGCGCGACTACATCCGCGACTGCGTCTACCTCTACCTCTGCCACACCTGGCAGA

CGGGCATGGGCGTGTGGCAGCAGTGTCTGGAGGAGCAGAACCTGAAAGAGCTCTGCAAGCTCCTGCAGAAG

AACCTCAAGGGTCTGTGGACCGGGTTCGACGAGCGCACCACCGCCTCGGACCTGGCCGACCTCATTTTCCCCG

AGCGCCTCAGGCTGACGCTGCGCAACGGCCTGCCCGACTTTATGAGCCAAAGCATGTTGCAAAACTTTCGCTC

TTTCATCCTCGAACGCTCCGGAATCCTGCCCGCCACCTGCTCCGCGCTGCCCTCGGACTTCGTGCCGCTGACCT

TCCGCGAGTGCCCCCCGCCGCTGTGGAGCCACTGCTACCTGCTGCGCCTGGCCAACTACCTGGCCTACCACTC

GGACGTGATCGAGGACGTCAGCGGCGAGGGCCTGCTCGAGTGCCACTGCCGCTGCAACCTCTGCACGCCGCA

CCGCTCCCTGGCCTGCAACCCCCAGCTGCTGAGCGAGACCCAGATCATCGGCACCTTCGAGTTGCAAGGGCCC

AGCGAAGGCGAGGGTTCAGCCGCCAAGGGGGGTCTGAAACTCACCCCGGGGCTGTGGACCTCGGCCTACTTG

CGCAAGTTCGTGCCCGAGGACTACCATCCCTTCGAGATCAGGTTCTACGAGGACCAATCCCATCCGCCCAAGG

CCGAGCTGTCGGCCTGCGTCATCACCCAGGGGGCGATCCTGGCCCAATTGCAAGCCATCCAGAAATCCCGCC

AAGAATTCTTGCTGAAAAAGGGCCGCGGGGTCTACCTCGACCCCCAGACCGGTGAGGAGCTCAACCCCGGCT

TCCCCCAGGATGCCCCGAGGAAACAAGAAGCTGAAAGTGGAGCTGCCGCCCGTGGAGGATTTGGAGGAAGA

CTGGGAGAACAGCAGTCAGGCAGAGGAGGAGGAGATGGAGGAAGACTGGGACAGCACTCAGGCAGAGGAG

GACAGCCTGCAAGACAGTCTGGAGGAAGACGAGGAGGAGGCAGAGGAGGAGGTGGAAGAAGCAGCCGCCG

CCAGACCGTCGTCCTCGGCGGGGGAGAAAGCAAGCAGCACGGATACCATCTCCGCTCCGGGTCGGGGTCCCG

CTCGACCACACAGTAGATGGGACGAGACCGGACGATTCCCGAACCCCACCACCCAGACCGGTAAGAAGGAG

CGGCAGGGATACAAGTCCTGGCGGGGGCACAAAAACGCCATCGTCTCCTGCTTGCAGGCCTGCGGGGGCAAC

ATCTCCTTCACCCGGCGCTACCTGCTCTTCCACCGCGGGGTGAACTTTCCCCGCAACATCTTGCATTACTACCG

TCACCTCCACAGCCCCTACTACTTCCAAGAAGAGGCAGCAGCAGCAGAAAAAGACCAGCAGAAAACCAGCA

GCTAGAAAATCCACAGCGGCGGCAGCAGGTGGACTGAGGATCGCGGCGAACGAGCCGGCGCAAACCCGGGA

GCTGAGGAACCGGATCTTTCCCACCCTCTATGCCATCTTCCAGCAGAGTCGGGGGCAGGAGCAGGAACTGAA

AGTCAAGAACCGTTCTCTGCGCTCGCTCACCCGCAGTTGTCTGTATCACAAGAGCGAAGACCAACTTCAGCGC

ACTCTCGAGGACGCCGAGGCTCTCTTCAACAAGTACTGCGCGCTCACTCTTAAAGAGTAGCCCGCGCCCGCCC

AGTCGCAGAAAAAGGCGGGAATTACGTCACCTGTGCCCTTCGCCCTAGCCGCCTCCACCCATCATCATGAGCA

AAGAGATTCCCACGCCTTACATGTGGAGCTACCAGCCCCAGATGGGCCTGGCCGCCGGTGCCGCCCAGGACT

ACTCCACCCGCATGAATTGGCTCAGCGCCGGGCCCGCGATGATCTCACGGGTGAATGACATCCGCGCCCACC

GAAACCAGATACTCCTAGAACAGTCAGCGCTCACCGCCACGCCCCGCAATCACCTCAATCCGCGTAATTGGC

CCGCCGCCCTGGTGTACCAGGAAATTCCCCAGCCCACGACCGTACTACTTCCGCGAGACGCCCAGGCCGAAG

TCCAGCTGACTAACTCAGGTGTCCAGCTGGCGGGCGGCGCCACCCTGTGTCGTCACCGCCCCGCTCAGGGTAT

AAAGCGGCTGGTGATCCGGGGCAGAGGCACACAGCTCAACGACGAGGTGGTGAGCTCTTCGCTGGGTCTGCG

ACCTGACGGAGTCTTCCAACTCGCCGGATCGGGGAGATCTTCCTTCACGCCTCGTCAGGCCGTCCTGACTTTG

GAGAGTTCGTCCTCGCAGCCCCGCTCGGGTGGCATCGGCACTCTCCAGTTCGTGGAGGAGTTCACTCCCTCGG

TCTACTTCAACCCCTTCTCCGGCTCCCCCGGCCACTACCCGGACGAGTTCATCCCGAACTTCGACGCCATCAG

-continued

CGAGTCGGTGGACGGCTACGATTGAAACTAATCACCCCCTTATCCAGTGAAATAAAGATCATATTGATGATG

ATTTTACAGAAATAAAAAATAATCATTTGATTTGAAATAAAGATACAATCATATTGATGATTTGAGTTTAACA

AAAAAATAAAGAATCACTTACTTGAAATCTGATACCAGGTCTCTGTCCATGTTTTCTGCCAACACCACTTCAC

TCCCCTCTTCCCAGCTCTGGTACTGCAGGCCCCGGCGGGCTGCAAACTTCCTCCACACGCTGAAGGGGATGTC

AAATTCCTCCTGTCCCTCAATCTTCATTTTATCTTCTATCAGATGTCCAAAAAGCGCGTCCGGGTGGATGATGA

CTTCGACCCCGTCTACCCCTACGATGCAGACAACGCACCGACCGTGCCCTTCATCAACCCCCCCTTCGTCTCTT

CAGATGGATTCCAAGAGAAGCCCCTGGGGGTGTTGTCCCTGCGACTGGCCGACCCCGTCACCACCAAGAACG

GGGAAATCACCCTCAAGCTGGGAGAGGGGGTGGACCTCGATTCCTCGGGAAAACTCATCTCCAACACGGCCA

CCAAGGCCGCCGCCCCTCTCAGTTTTTCCAACAACACCATTTCCCTTAACATGGATCACCCCTTTTACACTAAA

GATGGAAAATTATCCTTACAAGTTTCTCCACCATTAAATATACTGAGAACAAGCATTCTAAACACACTAGCTT

TAGGTTTTGGATCAGGTTTAGGACTCCGTGGCTCTGCCTTGGCAGTACAGTTAGTCTCTCCACTTACATTTGAT

ACTGATGGAAACATAAAGCTTACCTTAGACAGAGGTTTGCATGTTACAACAGGAGATGCAATTGAAAGCAAC

ATAAGCTGGGCTAAAGGTTTAAAATTTGAAGATGGAGCCATAGCAACCAACATTGGAAATGGGTTAGAGTTT

GGAAGCAGTAGTACAGAAACAGGTGTTGATGATGCTTACCCAATCCAAGTTAAACTTGGATCTGGCCTTAGCT

TTGACAGTACAGGAGCCATAATGGCTGGTAACAAAGAAGACGATAAACTCACTTTGTGGACAACACCTGATC

CATCACCAAACTGTCAAATACTCGCAGAAAATGATGCAAAACTAACACTTTGCTTGACTAAATGTGGTAGTCA

AATACTGGCCACTGTGTCAGTCTTAGTTGTAGGAAGTGGAAACCTAAACCCCATTACTGGCACCGTAAGCAGT

GCTCAGGTGTTTCTACGTTTTGATGCAAACGGTGTTCTTTTAACAGAACATTCTACACTAAAAAAATACTGGG

GGTATAGGCAGGGAGATAGCATAGATGGCACTCCATATACCAATGCTGTAGGATTCATGCCCAATTTAAAAG

CTTATCCAAAGTCACAAAGTTCTACTACTAAAAATAATATAGTAGGGCAAGTATACATGAATGGAGATGTTTC

AAAACCTATGCTTCTCACTATAACCCTCAATGGTACTGATGACAGCAACAGTACATATTCAATGTCATTTTCA

TACACCTGGACTAATGGAAGCTATGTTGGAGCAACATTTGGGGCTAACTCTTATACCTTCTCATACATCGCCC

AAGAATGAACACTGTATCCCACCCTGCATGCCAACCCTTCCCACCCCACTCTGTGGAACAAACTCTGAAACAC

AAAATAAAATAAAGTTCAAGTGTTTTATTGATTCAACAGTTTTACAGGATTCGAGCAGTTATTTTTCCTCCACC

CTCCCAGGACATGGAATACACCACCCTCTCCCCCCGCACAGCCTTGAACATCTGAATGCCATTGGTGATGGAC

ATGCTTTTGGTCTCCACGTTCCACACAGTTTCAGAGCGAGCCAGTCTCGGGTCGGTCAGGGAGATGAAACCCT

CCGGGCACTCCCGCATCTGCACCTCACAGCTCAACAGCTGAGGATTGTCCTCGGTGGTCGGGATCACGGTTAT

CTGGAAGAAGCAGAAGAGCGGCGGTGGGAATCATAGTCCGCGAACGGGATCGGCCGGTGGTGTCGCATCAG

GCCCCGCAGCAGTCGCTGCCGCCGCCGCTCCGTCAAGCTGCTGCTCAGGGGGTCCGGGTCCAGGGACTCCCTC

AGCATGATGCCCACGGCCCTCAGCATCAGTCGTCTGGTGCGGCGGGCGCAGCAGCGCATGCGGATCTCGCTC

AGGTCGCTGCAGTACGTGCAACACAGAACCACCAGGTTGTTCAACAGTCCATAGTTCAACACGCTCCAGCCG

AAACTCATCGCGGGAAGGATGCTACCCACGTGGCCGTCGTACCAGATCCTCAGGTAAATCAAGTGGTGCCCC

CTCCAGAACACGCTGCCCACGTACATGATCTCCTTGGGCATGTGGCGGTTCACCACCTCCCGGTACCACATCA

CCCTCTGGTTGAACATGCAGCCCCGGATGATCCTGCGGAACCACAGGGCCAGCACCGCCCCGCCCGCCATGC

AGCGAAGAGACCCCGGGTCCCGGCAATGGCAATGGAGGACCCACCGCTCGTACCCGTGGATCATCTGGGAGC

TGAACAAGTCTATGTTGGCACAGCACAGGCATATGCTCATGCATCTCTTCAGCACTCTCAACTCCTCGGGGGT

CAAAACCATATCCCAGGGCACGGGGAACTCTTGCAGGACAGCGAACCCCGCAGAACAGGGCAATCCTCGCAC

AGAACTTACATTGTGCATGGACAGGGTATCGCAATCAGGCAGCACCGGGTGATCCTCCACCAGAGAAGCGCG

GGTCTCGGTCTCCTCACAGCGTGGTAAGGGGGCCGGCCGATACGGGTGATGGCGGGACGCGGCTGATCGTGT

TCGCGACCGTGTCATGATGCAGTTGCTTTCGGACATTTTCGTACTTGCTGTAGCAGAACCTGGTCCGGGCGCT

GCACACCGATCGCCGGCGGCGGTCTCGGCGCTTGGAACGCTCGGTGTTGAAATTGTAAAACAGCCACTCTCTC

-continued

AGACCGTGCAGCAGATCTAGGGCCTCAGGAGTGATGAAGATCCCATCATGCCTGATGGCTCTGATCACATCG

ACCACCGTGGAATGGGCCAGACCCAGCCAGATGATGCAATTTTGTTGGGTTTCGGTGACGGCGAGCCTCGGG

AACAACGATGAAGTAAATGCAAGCGGTGCGTTCCAGCATGGTTAGTTAGCTGATCTGTAGAAAAAACAAAAA

TGAACATTAAACCATGCTAGCCTGGCGAACAGGTGGGTAAATCGTTCTCTCCAGCACCAGGCAGGCCACGGG

GTCTCCGGCGCGACCCTCGTAAAAATTGTCGCTATGATTGAAAACCATCACAGAGAGACGTTCCCGGTGGCC

GGCGTGAATGATTCGACAAGATGAATACACCCCCGGAACATTGGCGTCCGCGAGTGAAAAAAAGCGCCCGA

GGAAGCAATAAGGCACTACAATGCTCAGTCTCAAGTCCAGCAAAGCGATGCCATGCGGATGAAGCACAAAAT

TCTCAGGTGCGTACAAAATGTAATTACTCCCCTCCTGCACAGGCAGCAAAGCCCCCGATCCCTCCAGGTACAC

ATACAAAGCCTCAGCGTCCATAGCTTACCGAGCAGCAGCACACAACAGGCGCAAGAGTCAGAGAAAGGCTG

AGCTCTAACCTGTCCACCCGCTCTCTGCTCAATATATAGCCCAGATCTACACTGACGTAAAGGCCAAAGTCTA

AAAATACCCGCCAAATAATCACACACGCCCAGCACACGCCCAGAAACCGGTGACACACTCAAAAAAATACG

CGCACTTCCTCAAACGCCCAAAACTGCCGTCATTTCCGGGTTCCCACGCTACGTCATCAAAACACGACTTTCA

AATTCCGTCGACCGTTAAAAACGTCACCCGCCCCGCCCCTAACGGTCGCCCGTCTCTCAGCCAATCAGCGCCC

CGCATCCCCAAATTCAAACACCTCATTTGCATATTAACGCGCACAAAAAGTTTGAGGTATATTATTGATGATG

REFERENCES

1. Desrichard, A., Snyder, A. & Chan, T. A. Cancer Neoantigens and Applications for Immunotherapy. *Clin. Cancer Res. Off. J. Am. Assoc. Cancer Res*. (2015). doi: 10.1158/1078-0432. CCR-14-3175
2. Schumacher, T. N. & Schreiber, R. D. Neoantigens in cancer immunotherapy. *Science* 348, 69-74 (2015).
3. Gubin, M. M., Artyomov, M. N., Mardis, E. R. & Schreiber, R. D. Tumor neoantigens: building a framework for personalized cancer immunotherapy. *J. Clin. Invest*. 125, 3413-3421 (2015).
4. Rizvi, N. A. et al. Cancer immunology. Mutational landscape determines sensitivity to PD-1 blockade in non-small cell lung cancer. *Science* 348, 124-128 (2015).
5. Snyder, A. et al. Genetic basis for clinical response to CTLA-4 blockade in melanoma. *N Engl. J. Med*. 371, 2189-2199 (2014).
6. Carreno, B. M. et al. Cancer immunotherapy. A dendritic cell vaccine increases the breadth and diversity of melanoma neoantigen-specific T cells. *Science* 348, 803-808 (2015).
7. Tran, E. et al. Cancer immunotherapy based on mutation-specific CD4+ T cells in a patient with epithelial cancer. *Science* 344, 641-645 (2014).
8. Hacohen, N. & Wu, C. J.-Y. United States Patent Application: 20110293637-COMPOSITIONS AND METHODS OF IDENTIFYING TUMOR SPECIFIC NEOANTIGENS. (A1). at <appft1.uspto.gov/netacgi/nph-Parser?Sect1=PTO1&Sect2=HITOFF&d=PG01&p=1&u=/netahtml/PTO/srchnum.html&r=1&f=G&l=50&s1=20110293637.PGNR.>
9. Lundegaard, C., Hoof, I., Lund, O. & Nielsen, M. State of the art and challenges in sequence based T-cell epitope prediction. *Immunome Res*. 6 Suppl 2, S3 (2010).
10. Yadav, M. et al. Predicting immunogenic tumour mutations by combining mass spectrometry and exome sequencing. *Nature* 515, 572-576 (2014).
11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics MCP* 14, 658-673 (2015).
12. Van Allen, E. M. et al. Genomic correlates of response to CTLA-4 blockade in metastatic melanoma. *Science* 350, 207-211 (2015).
13. Yoshida, K. & Ogawa, S. Splicing factor mutations and cancer. *Wiley Interdiscip. Rev. RNA* 5, 445-459 (2014).
14. Cancer Genome Atlas Research Network. Comprehensive molecular profiling of lung adenocarcinoma. *Nature* 511, 543-550 (2014).
15. Rajasagi, M. et al. Systematic identification of personal tumor-specific neoantigens in chronic lymphocytic leukemia. *Blood* 124, 453-462 (2014).
16. Downing, S. R. et al. U.S. patent application Ser. No. 0120208706-OPTIMIZATION OF MULTIGENE ANALYSIS OF TUMOR SAMPLES. (A1). at <appft1.uspto.gov/netacgi/nph-Parser?Sect1=PT01&Sect2=HITOFF&d=PG01&p=1&u=/netahtml/PTO/srchnum.html&r=1&f=G&1=50&s1=20120208706.PGNR.>
17. Target Capture for NextGen Sequencing—IDT. at www.idtdna.com/pages/products/nextgen/target-capture
18. Shukla, S. A. et al. Comprehensive analysis of cancer-associated somatic mutations in class I HLA genes. *Nat. Biotechnol*. 33, 1152-1158 (2015).
19. Cieslik, M. et al. The use of exome capture RNA-seq for highly degraded RNA with application to clinical cancer sequencing. *Genome Res*. 25, 1372-1381 (2015).
20. Bodini, M. et al. The hidden genomic landscape of acute myeloid leukemia: subclonal structure revealed by undetected mutations. *Blood* 125, 600-605 (2015).
21. Saunders, C. T. et al. Strelka: accurate somatic small-variant calling from sequenced tumor-normal sample pairs. *Bioinforma. Oxf. Engl*. 28, 1811-1817 (2012).
22. Cibulskis, K. et al. Sensitive detection of somatic point mutations in impure and heterogeneous cancer samples. *Nat. Biotechnol*. 31, 213-219 (2013).
23. Wilkerson, M. D. et al. Integrated RNA and DNA sequencing improves mutation detection in low purity tumors. *Nucleic Acids Res*. 42, e107 (2014).
24. Mose, L. E., Wilkerson, M. D., Hayes, D. N., Perou, C. M. & Parker, J. S. ABRA: improved coding indel detection via assembly-based realignment. *Bioinforma. Oxf. Engl.* 30, 2813-2815 (2014).

25. Ye, K., Schulz, M. H., Long, Q., Apweiler, R. & Ning, Z. Pindel: a pattern growth approach to detect break points of large deletions and medium sized insertions from paired-end short reads. *Bioinforma. Oxf. Engl.* 25, 2865-2871 (2009).
26. Lam, H. Y. K. et al. Nucleotide-resolution analysis of structural variants using BreakSeq and a breakpoint library. *Nat. Biotechnol.* 28, 47-55 (2010).
27. Frampton, G. M. et al. Development and validation of a clinical cancer genomic profiling test based on massively parallel DNA sequencing. *Nat. Biotechnol.* 31, 1023-1031 (2013).
28. Boegel, S. et al. HLA typing from RNA-Seq sequence reads. *Genome Med.* 4, 102 (2012).
29. Liu, C. et al. ATHLATES: accurate typing of human leukocyte antigen through exome sequencing. *Nucleic Acids Res.* 41, e142 (2013).
30. Mayor, N. P. et al. HLA Typing for the Next Generation. *PloS One* 10, e0127153 (2015).
31. Roy, C. K., Olson, S., Graveley, B. R., Zamore, P. D. & Moore, M. J. Assessing long-distance RNA sequence connectivity via RNA-templated DNA-DNA ligation. *eLife* 4, (2015).
32. Song, L. & Florea, L. CLASS: constrained transcript assembly of RNA-seq reads. *BMC Bioinformatics* 14 Suppl 5, S14 (2013).
33. Maretty, L., Sibbesen, J. A. & Krogh, A. Bayesian transcriptome assembly. *Genome Biol.* 15, 501 (2014).
34. Pertea, M. et al. StringTie enables improved reconstruction of a transcriptome from RNA-seq reads. *Nat. Biotechnol.* 33, 290-295 (2015).
35. Roberts, A., Pimentel, H., Trapnell, C. & Pachter, L. Identification of novel transcripts in annotated genomes using RNA-Seq. *Bioinforma. Oxf. Engl.* (2011). doi:10.1093/bioinformatics/btr355
36. Vitting-Seerup, K., Porse, B. T., Sandelin, A. & Waage, J. spliceR: an R package for classification of alternative splicing and prediction of coding potential from RNA-seq data. *BMC Bioinformatics* 15, 81 (2014).
37. Rivas, M. A. et al. Human genomics. Effect of predicted protein-truncating genetic variants on the human transcriptome. *Science* 348, 666-669 (2015).
38. Skelly, D. A., Johansson, M., Madeoy, J., Wakefield, J. & Akey, J. M. A powerful and flexible statistical framework for testing hypotheses of allele-specific gene expression from RNA-seq data. *Genome Res.* 21, 1728-1737 (2011).
39. Anders, S., Pyl, P. T. & Huber, W. HTSeq—a Python framework to work with high-throughput sequencing data. *Bioinforma. Oxf. Engl.* 31, 166-169 (2015).
40. Furney, S. J. et al. SF3B1 mutations are associated with alternative splicing in uveal melanoma. *Cancer Discov.* (2013). doi:10.1158/2159-8290.CD-13-0330
41. Zhou, Q. et al. A chemical genetics approach for the functional assessment of novel cancer genes. *Cancer Res.* (2015). doi:10.1158/0008-5472.CAN-14-2930
42. Maguire, S. L. et al. SF3B1 mutations constitute a novel therapeutic target in breast cancer. *J. Pathol.* 235, 571-580 (2015).
43. Carithers, L. J. et al. A Novel Approach to High-Quality Postmortem Tissue Procurement: The GTEx Project. *Biopreservation Biobanking* 13, 311-319 (2015).
44. Xu, G. et al. RNA CoMPASS: a dual approach for pathogen and host transcriptome analysis of RNA-seq datasets. *PloS One* 9, e89445 (2014).
45. Andreatta, M. & Nielsen, M. Gapped sequence alignment using artificial neural networks: application to the MHC class I system. *Bioinforma. Oxf. Engl.* (2015). doi:10.1093/bioinformatics/btv639
46. Jorgensen, K. W., Rasmussen, M., Buus, S. & Nielsen, M. NetMHCstab-predicting stability of peptide-MHC-I complexes; impacts for cytotoxic T lymphocyte epitope discovery. *Immunology* 141, 18-26 (2014).
47. Larsen, M. V. et al. An integrative approach to CTL epitope prediction: a combined algorithm integrating MHC class I binding, TAP transport efficiency, and proteasomal cleavage predictions. *Eur. J. Immunol.* 35, 2295-2303 (2005).
48. Nielsen, M., Lundegaard, C., Lund, 0. & Keşmir, C. The role of the proteasome in generating cytotoxic T-cell epitopes: insights obtained from improved predictions of proteasomal cleavage. Immunogenetics 57, 33-41 (2005).
49. Boisvert, F.-M. et al. A Quantitative Spatial Proteomics Analysis of Proteome Turnover in Human Cells. *Mol. Cell*. Proteomics 11, M111.011429-M111.011429 (2012).
50. Duan, F. et al. Genomic and bioinformatic profiling of mutational neoepitopes reveals new rules to predict anticancer immunogenicity. *J. Exp. Med.* 211, 2231-2248 (2014).
51. Janeway's Immunobiology: 9780815345312: Medicine & Health Science Books @ Amazon.com. at www.amazon.com/Janeways-Immunobiology-Kenneth-Murphy/dp/0815345313
52. Calis, J. J. A. et al. Properties of MHC Class I Presented Peptides That Enhance Immunogenicity. *PLoS Comput. Biol.* 9, e1003266 (2013).
53. Zhang, J. et al. Intratumor heterogeneity in localized lung adenocarcinomas delineated by multiregion sequencing. *Science* 346, 256-259 (2014)
54. Walter, M. J. et al. Clonal architecture of secondary acute myeloid leukemia. *N Engl. J. Med.* 366, 1090-1098 (2012).
55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. *Science* 1992. 255: 1261-1263.
56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.
57. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.
58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9):1308-18. doi: 10.1038/nprot.2015.086. Epub 2015 Aug. 6
59. Barnstable C J, Bodmer W F, Brown G, Galfre G, Milstein C, Williams A F, Ziegler A. Production of monoclonal antibodies to group A erythrocytes, HLA and other human cell surface antigens-new tools for genetic analysis. Cell. 1978 May; 14(1):9-20.
60. Goldman J M, Hibbin J, Kearney L, Orchard K, Th'ng K H. HLA-D R monoclonal antibodies inhibit the proliferation of normal and chronic granulocytic leukaemia myeloid progenitor cells. Br J Haematol. 1982 November; 52(3):411-20.

61. Eng J K, Jahan T A, Hoopmann M R. Comet: an open-source M S/M S sequence database search tool. Proteomics. 2013 January; 13(1):22-4. doi: 10.1002/pmic.201200439. Epub 2012 Dec. 4.

62. Eng J K, Hoopmann M R, Jahan T A, Egertson J D, Noble W S, MacCoss M J. A deeper look into Comet—implementation and features. J Am Soc Mass Spectrom. 2015 November; 26(11):1865-74. doi: 10.1007/s13361-015-1179-x. Epub 2015 Jun. 27.

63. Lukas Kall, Jesse Canterbury, Jason Weston, William Stafford Noble and Michael J. MacCoss. Semi-supervised learning for peptide identification from shotgun proteomics datasets. Nature Methods 4:923-925, November 2007

64. Lukas Kall, John D. Storey, Michael J. MacCoss and William Stafford Noble. Assigning confidence measures to peptides identified by tandem mass spectrometry. Journal of Proteome Research, 7(1):29-34, January 2008

65. Lukas Kall, John D. Storey and William Stafford Noble. Nonparametric estimation of posterior error probabilities associated with peptides identified by tandem mass spectrometry. Bioinformatics, 24(16):i42-i48, August 2008

66. Kinney R M, B J Johnson, V L Brown, D W Trent. Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. 1986 Jul. 30.

67. Jill E Slansky, Frederique M Rattis, Lisa F Boyd, Tarek Fahmy, Elizabeth M Jaffee, Jonathan P Schneck, David H Margulies, Drew M Pardoll. Enhanced Antigen-Specific Antitumor Immunity with Altered Peptide Ligands that Stabilize the MHC-Peptide-TCR Complex. Immunity, Volume 13, Issue 4, 1 Oct. 2000, Pages 529-538.

68. A Y Huang, P H Gulden, A S Woods, M C Thomas, C D Tong, W Wang, V H Engelhard, G Pasternack, R Cotter, D Hunt, D M Pardoll, and E M Jaffee. The immunodominant major histocompatibility complex class I-restricted antigen of a murine colon tumor derives from an endogenous retroviral gene product. Proc Natl Acad Sci USA.; 93(18): 9730-9735, 1996 Sep. 3.

69. JOHNSON, BARBARA J. B., RICHARD M. KINNEY, CRYSTLE L. KOST AND DENNIS W. TRENT. Molecular Determinants of Alphavirus Neurovirulence: Nucleotide and Deduced Protein Sequence Changes during Attenuation of Venezuelan Equine Encephalitis Virus. J Gen Virol 67:1951-1960, 1986.

70. Aarnoudse, C. A., Kruse, M., Konopitzky, R., Brouwenstijn, N., and Schrier, P. I. (2002). TCR reconstitution in Jurkat reporter cells facilitates the identification of novel tumor antigens by cDNA expression cloning. Int J Cancer 99, 7-13.

71. Alexander, J., Sidney, J., Southwood, S., Ruppert, J., Oseroff, C., Maewal, A., Snoke, K., Serra, H. M., Kubo, R. T., and Sette, A. (1994). Development of high potency universal D R-restricted helper epitopes by modification of high affinity D R-blocking peptides. Immunity 1, 751-761.

72. Banu, N., Chia, A., Ho, Z. Z., Garcia, A. T., Paravasivam, K., Grotenbreg, G. M., Bertoletti, A., and Gehring, A. J. (2014). Building and optimizing a virus-specific T cell receptor library for targeted immunotherapy in viral infections. Scientific Reports 4, 4166.

73. Cornet, S., Miconnet, I., Menez, J., Lemonnier, F., and Kosmatopoulos, K. (2006). Optimal organization of a polypeptide-based candidate cancer vaccine composed of cryptic tumor peptides with enhanced immunogenicity. Vaccine 24, 2102-2109.

74. Depla, E., van der Aa, A., Livingston, B. D., Crimi, C., Allosery, K., de Brabandere, V., Krakover, J., Murthy, S., Huang, M., Power, S., et al. (2008). Rational design of a multiepitope vaccine encoding T-lymphocyte epitopes for treatment of chronic hepatitis B virus infections. Journal of Virology 82, 435-450.

75. Ishioka, G. Y., Fikes, J., Hermanson, G., Livingston, B., Crimi, C., Qin, M., del Guercio, M. F., Oseroff, C., Dahlberg, C., Alexander, J., et al. (1999). Utilization of MHC class I transgenic mice for development of minigene DNA vaccines encoding multiple HLA-restricted CTL epitopes. J Immunol 162, 3915-3925.

76. Janetzki, S., Price, L., Schroeder, H., Britten, C. M., Welters, M. J. P., and Hoos, A. (2015). Guidelines for the automated evaluation of Elispot assays. Nat Protoc 10, 1098-1115.

77. Lyons, G. E., Moore, T., Brasic, N., Li, M., Roszkowski, J. J., and Nishimura, M. I. (2006). Influence of human CD8 on antigen recognition by T-cell receptor-transduced cells. Cancer Res 66, 11455-11461.

78. Nagai, K., Ochi, T., Fujiwara, H., An, J., Shirakata, T., Mineno, J., Kuzushima, K., Shiku, H., Melenhorst, J. J., Gostick, E., et al. (2012). Aurora kinase A-specific T-cell receptor gene transfer redirects T lymphocytes to display effective antileukemia reactivity. Blood 119, 368-376.

79. Panina-Bordignon, P., Tan, A., Termijtelen, A., Demotz, S., Corradin, G., and Lanzavecchia, A. (1989). Universally immunogenic T cell epitopes: promiscuous binding to human MHC class II and promiscuous recognition by T cells. Eur J Immunol 19, 2237-2242.

80. Vitiello, A., Marchesini, D., Furze, J., Sherman, L. A., and Chesnut, R. W. (1991). Analysis of the HLA-restricted influenza-specific cytotoxic T lymphocyte response in transgenic mice carrying a chimeric human-mouse class I major histocompatibility complex. J Exp Med 173, 1007-1015.

81. Yachi, P. P., Ampudia, J., Zal, T., and Gascoigne, N. R. J. (2006). Altered peptide ligands induce delayed CD8-T cell receptor interaction—a role for CD8 in distinguishing antigen quality. Immunity 25, 203-211.

82. Pushko P, Parker M, Ludwig G V, Davis N L, Johnston R E, Smith J F. Replicon-helper systems from attenuated Venezuelan equine encephalitis virus: expression of heterologous genes in vitro and immunization against heterologous pathogens in vivo. Virology. 1997 Dec. 22; 239(2):389-401.

83. Strauss, J H and E G Strauss. The alphaviruses: gene expression, replication, and evolution. Microbiol Rev. 1994 September; 58(3): 491-562.

84. Rhême C, Ehrengruber M U, Grandgirard D. Alphaviral cytotoxicity and its implication in vector development. Exp Physiol. 2005 January; 90(1):45-52. Epub 2004 Nov. 12.

85. Riley, Michael K. II, and Wilfred Vermerris. Recent Advances in Nanomaterials for Gene Delivery—A Review. Nanomaterials 2017, 7(5), 94.

86. Frolov I, Hardy R, Rice C M. Cis-acting RNA elements at the 5' end of Sindbis virus genome RNA regulate minus- and plus-strand RNA synthesis. RNA. 2001 November; 7(11):1638-51.

87. Jose J, Snyder J E, Kuhn R J. A structural and functional perspective of alphavirus replication and assembly. Future Microbiol. 2009 September; 4(7):837-56.

88. Bo Li and C. olin N. Dewey. RSEM: accurate transcript quantification from RNA-Seq data with or without a referenfe genome. BMC Bioinformatics, 12:323, August 2011

89. Hillary Pearson, Tariq Daouda, Diana Paola Granados, Chantal Durette, Eric Bonneil, Mathieu Courcelles, Anja Rodenbrock, Jean-Philippe Laverdure, Caroline Cote, Sylvie Mader, Sébastien Lemieux, Pierre Thibault, and Claude Perreault. MHC class I-associated peptides derive from selective regions of the human genome. The Journal of Clinical Investigation, 2016, 90. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, October 2016.

91. Mommen G P., Marino, F., Meiring H D., Poelen, M C., van Gaans-van den Brink, J A., Mohammed S., Heck A J., and van Els C A. Sampling From the Proteome to the Human Leukocyte Antigen-D R (HLA-D R) Ligandome Proceeds Via High Specificity. Mol Cell Proteomics 15(4): 1412-1423, April 2016.

92. Sebastian Kreiter, Mathias Vormehr, Niels van de Roemer, Mustafa Diken, Martin Lower, Jan Diekmann, Sebastian Boegel, Barbara Schrors, Fulvia Vascotto, John C. Castle, Arbel D. Tadmor, Stephen P. Schoenberger, Christoph Huber, Ozlem Tureci, and Ugur Sahin. Mutant MHC class II epitopes drive therapeutic immune responses to caner. Nature 520, 692-696, April 2015.

93. Tran E., Turcotte S., Gros A., Robbins P. F., Lu Y. C., Dudley M. E., Wunderlich J. R., Somerville R. P., Hogan K., Hinrichs C. S., Parkhurst M. R., Yang J. C., Rosenberg S. A. Cancer immunotherapy based on mutation-specific CD4+ T cells in a patient with epithelial cancer. Science 344(6184) 641-645, May 2014.

94. Andreatta M., Karosiene E., Rasmussen M., Stryhn A., Buus S., Nielsen M. Accurate pan-specific prediction of peptide-MHC class II binding affinity with improved binding core identification. Immunogenetics 67(11-12) 641-650, November 2015.

95. Nielsen, M., Lund, O. N N-align. An artificial neural network-based alignment algorithm for MHC class II peptide binding prediction. BMC Bioinformatics 10:296, September 2009.

96. Nielsen, M., Lundegaard, C., Lund, O. Prediction of MHC class II binding affinity using SMM-align, a novel stabilization matrix alignment method. BMC Bioinformatics 8:238, July 2007.

97. Zhang, J., et al. PEAKS D B: de novo sequencing assisted database search for sensitive and accurate peptide identification. Molecular & Cellular Proteomics. 11(4):1-8. Jan. 2, 2012.

98. Jensen, Kamilla Kjaergaard, et al. "Improved Methods for Prediting Peptide Binding Affinity to MHC Class II Molecules." Immunology, 2018, doi:10.1111/imm.12889.

99. Carter, S. L., Cibulskis, K., Helman, E., McKenna, A., Shen, H., Zack, T., Laird, P. W., Onofrio, R. C., Winckler, W., Weir, B. A., et al. (2012). Absolute quantification of somatic DNA alterations in human cancer. Nat. Biotechnol. 30, 413-421

100. McGranahan, N., Rosenthal, R., Hiley, C. T., Rowan, A. J., Watkins, T. B. K., Wilson, G. A., Birkbak, N. J., Veeriah, S., Van Loo, P., Herrero, J., et al. (2017). Allele-Specific HLA Loss and Immune Escape in Lung Cancer Evolution. Cell 171, 1259-1271.e11.

101. Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. Nat. Biotechnol. 33, 1152-1158.

102. Van Loo, P., Nordgard, S. H., Lingjxrde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

103. Van Loo, P., Nordgard, S. H., Lingjxrde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

What is claimed is:

1. A method for treating a subject with cancer, the method comprising administering to the subject an immunotherapy comprising an adenovirus vector comprising:

an adenoviral backbone comprising one or more genes or regulatory sequences of an adenovirus genome, wherein the adenoviral backbone comprises a partially deleted E4 gene with reference to the adenovirus genome, wherein the partially deleted E4 gene comprises a partially-deleted E4orf2 region, a deleted E4orf3 region, and a partially-deleted E4orf4 region, and wherein the adenovirus vector further comprises a cassette, the cassette comprising:

(1) at least one payload nucleic acid sequence, optionally wherein the at least one payload nucleic acid sequence encodes a polypeptide, optionally wherein the polypeptide comprises an antigen, optionally wherein the antigen comprises:
(a) a MHC class I epitope,
(b) a MHC class II epitope,
(c) an epitope capable of stimulating a B cell response, or
(d) a combination thereof, and optionally wherein the at least one payload nucleic acid sequence further comprises a 5' linker sequence and/or a 3' linker sequence, and optionally wherein;
(2) at least one promoter sequence operably linked to the at least one payload nucleic acid sequence,
(3) optionally, at least one universal MHC class II antigen-encoding nucleic acid sequence;
(4) optionally, at least one GPGPG-encoding linker sequence (SEQ ID NO:56); and
(5) optionally, at least one polyadenylation sequence.

2. The method of claim 1, wherein:
(a) the partially deleted E4 gene comprises the E4 gene sequence shown in SEQ ID NO:1 except for lacking the partially-deleted E4orf2 region, the deleted E4orf3 region, and the partially-deleted E4orf4 region; and
(b) the one or more genes or regulatory sequences of the adenovirus genome comprise one or more genes or regulatory sequences of the ChAdV68 sequence shown in SEQ ID NO:1, optionally wherein the one or more genes or regulatory sequences comprise at least one of the chimpanzee adenovirus inverted terminal repeat (ITR), E1A, E1B, E2A, E2B, E3, L1, L2, L3, L4, and L5 genes of the sequence shown in SEQ ID NO:1.

3. The method of claim 2, wherein the one or more genes or regulatory sequences of the ChAdV68 sequence shown in SEQ ID NO:1 comprise:
A) nucleotides 2 to 34,915 of the sequence shown in SEQ ID NO:1, or
B) nucleotides 2 to 34,915 of the sequence shown in SEQ ID NO:1 except for lacking:
(i) nucleotides corresponding to a deletion in the E1 gene shown in SEQ ID NO:1; and/or
(ii) nucleotides corresponding to a deletion in the E3 gene shown in SEQ ID NO:1.

4. The method of claim 2, wherein the partially-deleted E4orf2 region, the deleted E4orf3 region, and the partially-deleted E4orf4 region is a deletion of nucleotides about in the range of 34,916 to 35,642 of the sequence shown in SEQ ID NO:1.

5. The method of claim 2, wherein the partially-deleted E4orf2 region, the deleted E4orf3 region, and the partially-deleted E4orf4 region is a deletion of nucleotides 34,916 to 35,642 of the sequence shown in SEQ ID NO:1.

6. The method of claim 2, wherein the adenoviral backbone comprises:
A) at least nucleotides 2 to 36,518 of the sequence shown in SEQ ID NO:1, except for lacking nucleotides 34,916 to 35,642 of the sequence shown in SEQ ID NO:1 corresponding to the partially deleted E4 gene,
B) at least nucleotides 2 to 36,518 of the sequence shown in SEQ ID NO:1, except for lacking nucleotides 34,916 to 35,642 corresponding to the partially deleted E4 gene and lacking nucleotides 577 to 3403 of the sequence shown in SEQ ID NO:1,
C) at least nucleotides 2 to 36,518 of the sequence shown in SEQ ID NO:1, except for lacking nucleotides 34,916 to 35,642 corresponding to the partially deleted E4 gene and lacking nucleotides 27,125 to 31,825 of the sequence shown in SEQ ID NO:1, or
D) at least nucleotides 2 to 36,518 of the sequence shown in SEQ ID NO:1, except for lacking nucleotides 34,916 to 35,642 corresponding to the partially deleted E4 gene, lacking nucleotides 577 to 3403, and lacking nucleotides 27,125 to 31,825 of the sequence shown in SEQ ID NO:1.

7. The method of claim 1, wherein the cassette is inserted in the vector at the E1 region, E3 region, and/or any deleted AdV region that allows incorporation of the cassette.

8. The method of claim 1, wherein at least one of the at least one payload nucleic acid sequences encodes a polypeptide sequence capable of undergoing antigen processing into an epitope, wherein the epitope is known or suspected to be presented by MHC class I on a surface of a cell, and wherein the surface of the cell is a tumor cell surface.

9. The method of claim 1, wherein at least one of the at least one payload nucleic acid sequences encodes an epitope with at least one alteration that makes the encoded epitope sequence distinct from the corresponding peptide sequence encoded by a wild-type nucleic acid sequence, optionally wherein the at least one alteration comprises a point mutation, a frameshift mutation, a non-frameshift mutation, a deletion mutation, an insertion mutation, a splice variant, a genomic rearrangement, or a proteasome-generated spliced antigen.

10. The method of claim 1, wherein one or more of the at least one payload nucleic acid sequences encode an MHC I epitope-encoding nucleic acid sequence inclusive of the optional 5' linker sequence and the optional 3' linker sequences that encodes a peptide 25 amino acids in length.

11. The method of claim 1, wherein at least one of the at least one payload nucleic acid sequences is linked to a distinct payload nucleic acid sequence with a nucleic acid sequence encoding a linker.

12. The method of claim 11, wherein the linker comprises one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length.

13. The method of claim 1, wherein the method further comprises administering to the subject a second vaccine composition.

14. The method of claim 13, wherein the second vaccine composition comprises a self-amplifying RNA (samRNA) vector encoding at least one payload nucleic acid sequence.

15. The method of claim 13, wherein the at least one payload nucleic acid sequence encoded by the samRNA vector is the same as at least one of the at least one payload nucleic acid sequence of claim 1.

16. The method of claim 1, wherein the adenovirus vector comprises:
A) a modified ChAdV68 sequence, wherein the modified ChAdV68 sequence comprises:
(i) the partially deleted E4 gene comprising the E4 gene sequence shown in SEQ ID NO:1 except for lacking nucleotides 34,916 to 35,642 of the sequence shown in SEQ ID NO:1;
(ii) (1) nucleotides 2 to 34,915 of the sequence shown in SEQ ID NO:1 or
(ii) (2) nucleotides 2 to 34,915 of the sequence shown in SEQ ID NO:1 except for lacking,
a) nucleotides 577 to 3403 of the sequence shown in SEQ ID NO:1 corresponding to an E1 deletion; and/or
b) nucleotides 27,125 to 31,825 of the sequence shown in SEQ ID NO:1 corresponding to an E3 deletion wherein the partially deleted E4 gene is 3' of the nucleotide 34,915 of the sequence shown in SEQ ID NO:1; and (iii) nucleotides 35,643 to 36,518 of the sequence shown in SEQ ID NO:1, wherein the partially deleted E4 gene is 5' of the nucleotide 35,643 of the sequence shown in SEQ ID NO:1;

B) a CMV-derived promoter sequence;

C) an SV40 polyadenylation signal nucleotide sequence; and

D) a cassette, the cassette comprising at least one at least one payload nucleic acid sequence encoding:

(i) at least one MHC class I epitope, optionally wherein the at least one MHC class I epitope comprises at least 2 distinct MHC class I epitopes linearly linked to each other and each optionally comprising:

(A) at least one alteration that makes the encoded peptide sequence distinct from the corresponding peptide sequence encoded by a wild-type nucleic acid sequence, wherein the distinct MHC I epitope is 7-15 amino acids in length, (B) a native 5' linker sequence that encodes a native N-terminal amino acid sequence of the epitope, and wherein the 5' linker sequence encodes a peptide that is between 2-20 amino acids in length, (C) a native 3' linker sequence that encodes a native C-terminal amino acid sequence of the epitope, and wherein the 3' linker sequence encodes a peptide that is between 2-20 amino acids in length, or (D) combinations thereof, (ii) at least one MHC class II epitope, optionally wherein the at least one MHC class II epitope comprises at least 2 distinct MHC class II epitopes, (iii) at least one an epitope capable of stimulating a B cell response, or (iv) combinations thereof, and wherein the cassette is inserted within a deleted region of ChAdV68 and the CMV-derived promoter sequence is operably linked to the cassette.

17. An adenovirus vector comprising:

an adenoviral backbone comprising one or more genes or regulatory sequences of an adenovirus genome, wherein the adenoviral backbone comprises a partially deleted E4 gene with reference to the adenovirus genome, wherein the partially deleted E4 gene comprises a partially-deleted E4orf2 region, a deleted E4orf3 region, and a partially-deleted E4orf4 region, and optionally, wherein the adenovirus vector further comprises a cassette, the cassette comprising:

(1) at least one payload nucleic acid sequence, optionally wherein the at least one payload nucleic acid sequence encodes a polypeptide, optionally wherein the polypeptide comprises an antigen, optionally wherein the antigen comprises:

(a) a MHC class I epitope, (b) a MHC class II epitope, (c) an epitope capable of stimulating a B cell response, or (d) a combination thereof, and optionally wherein the at least one payload nucleic acid sequence further comprises a 5' linker sequence and/or a 3' linker sequence, and optionally wherein;

(2) at least one promoter sequence operably linked to the at least one payload nucleic acid sequence, (3) optionally, at least one universal MHC class II antigen-encoding nucleic acid sequence;

(4) optionally, at least one GPGPG-encoding linker sequence (SEQ ID NO:56); and (5) optionally, at least one polyadenylation sequence.

18. The vector of claim 17, wherein:

(a) the partially deleted E4 gene comprises the E4 gene sequence shown in SEQ ID NO:1 except for lacking the partially-deleted E4orf2 region, the deleted E4orf3 region, and the partially-deleted E4orf4 region; and (b) the one or more genes or regulatory sequences of the adenovirus genome comprise one or more genes or regulatory sequences of the ChAdV68 sequence shown in SEQ ID NO:1, optionally wherein the one or more genes or regulatory sequences comprise at least one of the chimpanzee adenovirus inverted terminal repeat (ITR), E1A, E1B, E2A, E2B, E3, L1, L2, L3, L4, and L5 genes of the sequence shown in SEQ ID NO:1.

19. The vector of claim 17, wherein at least one of the at least one payload nucleic acid sequences encodes:

(a) an infectious disease organism peptide selected from the group consisting of: a pathogen-derived peptide, a virus-derived peptide, a bacteria-derived peptide, a fungus-derived peptide, and a parasite-derived peptide;

(b) an epitope with at least one alteration that makes the encoded epitope sequence distinct from the corresponding peptide sequence encoded by a wild-type nucleic acid sequence; and/or (c) a polypeptide sequence or portion thereof comprising an epitope capable of stimulating a B cell response, wherein the polypeptide sequence or portion thereof comprises a full-length protein, a protein domain, a protein subunit, or an antigenic fragment predicted or known to be capable of being bound by an antibody.

20. A chimpanzee adenovirus vector comprising a modified ChAdV68 sequence, wherein the modified ChAdV68 sequence comprises:

(a) a partially deleted E4 gene comprises the E4 gene sequence shown in SEQ ID NO:1 except for lacking a partially-deleted E4orf2 region, a deleted E4orf3 region, and a partially-deleted E4orf4 region; and (b) one or more genes or regulatory sequences of the adenovirus genome comprising one or more genes or regulatory sequences of the ChAdV68 sequence shown in SEQ ID NO:1, optionally wherein the one or more genes or regulatory sequences comprise at least one of the chimpanzee adenovirus inverted terminal repeat (ITR), E1A, E1B, E2A, E2B, E3, L1, L2, L3, L4, and L5 genes of the sequence shown in SEQ ID NO:1; and optionally, wherein the chimpanzee adenovirus vector further comprises a cassette, wherein the cassette comprises at least one payload nucleic acid sequence, and wherein the cassette comprises at least one promoter sequence operably linked to the at least one payload nucleic acid sequence.

21. The vector of claim 18, wherein the one or more genes or regulatory sequences of the ChAdV68 sequence shown in SEQ ID NO:1 comprise:

A) nucleotides 2 to 34,915 of the sequence shown in SEQ ID NO:1, or

B) nucleotides 2 to 34915 of the sequence shown in SEQ ID NO:1 except for lacking:

(i) nucleotides corresponding to a deletion in the E1 gene shown in SEQ ID NO:1; and/or (ii) nucleotides corresponding to a deletion in the E3 gene shown in SEQ ID NO:1.

22. The vector of claim 18, wherein the partially-deleted E4orf2 region, the deleted E4orf3 region, and the partially-deleted E4orf4 region is a deletion of nucleotides about in the range of 34,916 to 35,642 of the sequence shown in SEQ ID NO:1.

23. The vector of claim 18, wherein the partially-deleted E4orf2 region, the deleted E4orf3 region, and the partially-deleted E4orf4 region is a deletion of nucleotides 34,916 to 35,642 of the sequence shown in SEQ ID NO:1.

24. The vector of claim 18, wherein the adenoviral backbone comprises:

A) at least nucleotides 2 to 36,518 of the sequence shown in SEQ ID NO:1, except for lacking nucleotides 34,916 to 35,642 of the sequence shown in SEQ ID NO:1 corresponding to the partially deleted E4 gene, B) at least nucleotides 2 to 36,518 of the sequence shown in SEQ ID NO:1, except for lacking nucleotides 34,916 to 35,642 corresponding to the partially deleted E4 gene and lacking nucleotides 577 to 3403 of the sequence shown in SEQ ID NO:1, C) at least nucleotides 2 to 36,518 of the sequence shown in SEQ ID NO:1, except for lacking nucleotides 34,916 to 35,642 corresponding to the partially deleted E4 gene and lacking nucleotides 27,125 to 31,825 of the sequence shown in SEQ ID NO:1, or D) at least nucleotides 2 to 36,518 of the sequence shown in SEQ ID NO:1, except for lacking nucleotides 34,916 to 35,642 corresponding to the partially deleted E4 gene, lacking nucleotides 577 to 3403, and lacking nucleotides 27,125 to 31,825 of the sequence shown in SEQ ID NO:1.

25. The vector of claim 17, wherein the cassette is inserted in the vector at the E1 region, E3 region, and/or any deleted AdV region that allows incorporation of the cassette.

26. The vector of claim 17, wherein at least one of the at least one payload nucleic acid sequences encodes a polypeptide sequence capable of undergoing antigen processing into an epitope, wherein the epitope is known or suspected to be presented by MHC class I on a surface of a cell, and wherein the surface of the cell is a tumor cell surface.

27. The vector of claim 17, wherein one or more of the at least one payload nucleic acid sequences encode an MHC I epitope-encoding nucleic acid sequence inclusive of the optional 5' linker sequence and the optional 3' linker sequences that encodes a peptide 25 amino acids in length.

28. The vector of claim 17, wherein at least one of the at least one payload nucleic acid sequences is linked to a distinct payload nucleic acid sequence with a nucleic acid sequence encoding a linker.

29. The vector of claim 28, wherein the linker comprises one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length.

30. The vector of claim 17, wherein the adenovirus vector comprises:

A) a modified ChAdV68 sequence, wherein the modified ChAdV68 sequence comprises:

(i) the partially deleted E4 gene comprising the E4 gene sequence shown in SEQ ID NO:1 except for lacking nucleotides 34,916 to 35,642 of the sequence shown in SEQ ID NO:1;

(ii) (1) nucleotides 2 to 34,915 of the sequence shown in SEQ ID NO:1 or (ii) (2) nucleotides 2 to 34,915 of the sequence shown in SEQ ID NO:1 except for lacking, a) nucleotides 577 to 3403 of the sequence shown in SEQ ID NO:1 corresponding to an E1 deletion; and/or b) nucleotides 27,125 to 31,825 of the sequence shown in SEQ ID NO:1 corresponding to an E3 deletion wherein the partially deleted E4 gene is 3' of the nucleotide 34,915 of the sequence shown in SEQ ID NO:1; and (iii) nucleotides 35,643 to 36,518 of the sequence shown in SEQ ID NO:1, wherein the partially deleted E4 gene is 5' of the nucleotide 35,643 of the sequence shown in SEQ ID NO: 1;

B) a CMV-derived promoter sequence;

C) an SV40 polyadenylation signal nucleotide sequence; and

D) a cassette, the cassette comprising at least one at least one payload nucleic acid sequence encoding:

(i) at least one MHC class I epitope, optionally wherein the at least one MHC class I epitope comprises at least 2 distinct MHC class I epitopes linearly linked to each other and each optionally comprising:

(A) at least one alteration that makes the encoded peptide sequence distinct from the corresponding peptide sequence encoded by a wild-type nucleic acid sequence, wherein the distinct MHC I epitope is 7-15 amino acids in length, (B) a native 5' linker sequence that encodes a native N-terminal amino acid sequence of the epitope, and wherein the 5' linker sequence encodes a peptide that is between 2-20 amino acids in length, (C) a native 3' linker sequence that encodes a native C-terminal amino acid sequence of the epitope, and wherein the 3' linker sequence encodes a peptide that is between 2-20 amino acids in length, or (D) combinations thereof, (ii) at least one MHC class II epitope, optionally wherein the at least one MHC class II epitope comprises at least 2 distinct MHC class II epitopes, (iii) at least one an epitope capable of stimulating a B cell response, or (iv) combinations thereof, and wherein the cassette is inserted within a deleted region of ChAdV68 and the CMV-derived promoter sequence is operably linked to the cassette.

31. The vector claim 20, wherein the one or more genes or regulatory sequences of the ChAdV68 sequence shown in SEQ ID NO:1 comprise:

A) nucleotides 2 to 34,915 of the sequence shown in SEQ ID NO:1, or

B) nucleotides 2 to 34,915 of the sequence shown in SEQ ID NO:1 except for lacking:

(i) nucleotides corresponding to a deletion in the E1 gene shown in SEQ ID NO:1; and/or (ii) nucleotides corresponding to a deletion in the E3 gene shown in SEQ ID NO:1.

32. The vector of claim 20, wherein the partially-deleted E4orf2 region, the deleted E4orf3 region, and the partially-deleted E4orf4 region is a deletion of nucleotides about in the range of 34,916 to 35,642 of the sequence shown in SEQ ID NO:1.

33. The vector of claim 20, wherein the partially-deleted E4orf2 region, the deleted E4orf3 region, and the partially-deleted E4orf4 region is a deletion of nucleotides 34,916 to 35,642 of the sequence shown in SEQ ID NO:1.

34. The vector of claim 20, wherein the adenoviral backbone comprises:

A) at least nucleotides 2 to 36,518 of the sequence shown in SEQ ID NO:1, except for lacking nucleotides 34,916 to 35,642 of the sequence shown in SEQ ID NO:1 corresponding to the partially deleted E4 gene, B) at least nucleotides 2 to 36,518 of the sequence shown in SEQ ID NO:1, except for lacking nucleotides 34,916 to 35,642 corresponding to the partially deleted E4 gene and lacking nucleotides 577 to 3403 of the sequence shown in SEQ ID NO:1, C) at least nucleotides 2 to 36,518 of the sequence shown in SEQ ID NO:1, except for lacking nucleotides 34,916 to 35,642 corresponding to the partially deleted E4 gene and lacking nucleotides 27,125 to 31,825 of the sequence shown in SEQ ID NO:1, or D) at least nucleotides 2 to 36,518 of the sequence shown in SEQ ID NO:1, except for lacking nucleotides 34,916 to 35,642 corresponding to the partially deleted E4 gene, lacking nucleotides 577 to 3403, and lacking nucleotides 27,125 to 31,825 of the sequence shown in SEQ ID NO:1.

35. The vector of claim 20, wherein the cassette is inserted in the vector at the E1 region, E3 region, and/or any deleted AdV region that allows incorporation of the cassette.

36. The vector of claim 20, wherein at least one of the at least one payload nucleic acid sequences encodes a polypeptide sequence capable of undergoing antigen processing into an epitope, wherein the epitope is known or suspected to be presented by MHC class I on a surface of a cell, and wherein the surface of the cell is a tumor cell surface.

37. The vector of claim 20, wherein one or more of the at least one payload nucleic acid sequences encode an MHC I epitope-encoding nucleic acid sequence inclusive of the optional 5' linker sequence and the optional 3' linker sequences that encodes a peptide 25 amino acids in length.

38. The vector of claim 20, wherein at least one of the at least one payload nucleic acid sequences is linked to a distinct payload nucleic acid sequence with a nucleic acid sequence encoding a linker.

39. The vector of claim 38, wherein the linker comprises one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length.

40. The vector of claim 20, wherein the adenovirus vector comprises:

A) a modified ChAdV68 sequence, wherein the modified ChAdV68 sequence comprises:

(i) the partially deleted E4 gene comprising the E4 gene sequence shown in SEQ ID NO:1 except for lacking nucleotides 34,916 to 35,642 of the sequence shown in SEQ ID NO:1;

(ii) (1) nucleotides 2 to 34,915 of the sequence shown in SEQ ID NO:1 or (ii) (2) nucleotides 2 to 34,915 of the sequence shown in SEQ ID NO:1 except for lacking, a) nucleotides 577 to 3403 of the sequence shown in SEQ ID NO:1 corresponding to an E1 deletion; and/or b) nucleotides 27,125 to 31,825 of the sequence shown in SEQ ID NO:1 corresponding to an E3 deletion wherein the partially deleted E4 gene is 3' of the nucleotide 34,915 of the sequence shown in SEQ ID NO:1; and (iii) nucleotides 35,643 to 36,518 of the sequence shown in SEQ ID NO:1, wherein the partially deleted E4 gene is 5' of the nucleotide 35,643 of the sequence shown in SEQ ID NO: 1;

B) a CMV-derived promoter sequence;

C) an SV40 polyadenylation signal nucleotide sequence; and

D) a cassette, the cassette comprising at least one at least one payload nucleic acid sequence encoding:

(i) at least one MHC class I epitope, optionally wherein the at least one MHC class I epitope comprises at least 2 distinct MHC class I epitopes linearly linked to each other and each optionally comprising:

(A) at least one alteration that makes the encoded peptide sequence distinct from the corresponding peptide sequence encoded by a wild-type nucleic acid sequence, wherein the distinct MHC I epitope is 7-15 amino acids in length, (B) a native 5' linker sequence that encodes a native N-terminal amino acid sequence of the epitope, and wherein the 5' linker sequence encodes a peptide that is between 2-20 amino acids in length, (C) a native 3' linker sequence that encodes a native C-terminal amino acid sequence of the epitope, and wherein the 3' linker sequence encodes a peptide that is between 2-20 amino acids in length, or (D) combinations thereof, (ii) at least one MHC class II epitope, optionally wherein the at least one MHC class II epitope comprises at least 2 distinct MHC class II epitopes, (iii) at least one an epitope capable of stimulating a B cell response, or (iv) combinations thereof, and wherein the cassette is inserted within a deleted region of ChAdV68 and the CMV-derived promoter sequence is operably linked to the cassette.

41. The vector of claim 20, wherein at least one of the at least one payload nucleic acid sequences encodes:

(a) an infectious disease organism peptide selected from the group consisting of: a pathogen-derived peptide, a virus-derived peptide, a bacteria-derived peptide, a fungus-derived peptide, and a parasite-derived peptide;

(b) an epitope with at least one alteration that makes the encoded epitope sequence distinct from the corresponding peptide sequence encoded by a wild-type nucleic acid sequence; and/or (c) a polypeptide sequence or portion thereof comprising an epitope capable of stimulating a B cell response, wherein the polypeptide sequence or portion thereof comprises a full-length protein, a protein domain, a protein subunit, or an antigenic fragment predicted or known to be capable of being bound by an antibody.

* * * * *